US011926632B2

(12) United States Patent
Vu et al.

(10) Patent No.: US 11,926,632 B2
(45) Date of Patent: Mar. 12, 2024

(54) METHODS AND COMPOUNDS FOR RESTORING MUTANT P53 FUNCTION

(71) Applicant: PMV Pharmaceuticals, Inc., Cranbury, NJ (US)

(72) Inventors: Binh Vu, North Caldwell, NJ (US); Romyr Dominique, East Brunswick, NJ (US); Hongju Li, Edison, NJ (US); Bruce Fahr, East Windsor, NJ (US); Yi Chen, Nutley, NJ (US)

(73) Assignee: PMV Pharmaceuticals, Inc., Princeton, NJ (US)

( * ) Notice: Subject to any disclaimer, the term of this patent is extended or adjusted under 35 U.S.C. 154(b) by 0 days.

(21) Appl. No.: 17/353,199

(22) Filed: Jun. 21, 2021

(65) Prior Publication Data
US 2023/0046427 A1 Feb. 16, 2023

Related U.S. Application Data

(60) Provisional application No. 63/042,252, filed on Jun. 22, 2020.

(51) Int. Cl.
| | | |
|---|---|---|
| C07D 487/10 | (2006.01) | |
| C07C 237/40 | (2006.01) | |
| C07D 213/36 | (2006.01) | |
| C07D 213/38 | (2006.01) | |
| C07D 213/73 | (2006.01) | |
| C07D 213/81 | (2006.01) | |
| C07D 215/12 | (2006.01) | |
| C07D 231/56 | (2006.01) | |
| C07D 239/42 | (2006.01) | |
| C07D 401/04 | (2006.01) | |
| C07D 401/12 | (2006.01) | |
| C07D 405/12 | (2006.01) | |
| C07D 413/12 | (2006.01) | |
| C07D 417/12 | (2006.01) | |
| C07D 487/08 | (2006.01) | |
| C07D 491/107 | (2006.01) | |

(52) U.S. Cl.
CPC ......... *C07D 487/10* (2013.01); *C07C 237/40* (2013.01); *C07D 213/36* (2013.01); *C07D 213/38* (2013.01); *C07D 213/73* (2013.01); *C07D 213/81* (2013.01); *C07D 215/12* (2013.01); *C07D 231/56* (2013.01); *C07D 239/42* (2013.01); *C07D 401/04* (2013.01); *C07D 401/12* (2013.01); *C07D 405/12* (2013.01); *C07D 413/12* (2013.01); *C07D 417/12* (2013.01); *C07D 487/08* (2013.01); *C07D 491/107* (2013.01)

(58) Field of Classification Search
CPC ... C07D 213/38; C07D 401/04; C07D 215/12
See application file for complete search history.

(56) References Cited

U.S. PATENT DOCUMENTS

| | | | |
|---|---|---|---|
| 6,159,677 A | 12/2000 | Haraguchi | |
| 9,120,749 B2 * | 9/2015 | Matsuo | ............... C07D 471/04 |
| 2013/0165458 A1 | 6/2013 | Huang et al. | |
| 2014/0256717 A1 | 9/2014 | Fernández et al. | |
| 2023/0056253 A1 | 2/2023 | Vu et al. | |

FOREIGN PATENT DOCUMENTS

| | | | |
|---|---|---|---|
| CN | 103044446 A * | 4/2013 | |
| CN | 108373462 A | 8/2018 | |
| WO | WO-2005120509 A1 | 12/2005 | |
| WO | WO-2007022241 A2 * | 2/2007 | ............... A61P 1/18 |
| WO | WO-2009155121 A2 | 12/2009 | |
| WO | WO-2012016082 A1 | 2/2012 | |
| WO | WO-2012156756 A2 | 11/2012 | |
| WO | WO-2016077656 A2 | 5/2016 | |
| WO | WO-2017023905 A1 | 2/2017 | |
| WO | WO-2017097182 A1 | 6/2017 | |
| WO | WO-2019018584 A1 | 1/2019 | |
| WO | WO-2019192954 A1 * | 10/2019 | ........... C07D 209/86 |
| WO | WO-2019229765 A1 | 12/2019 | |
| WO | WO-2020051235 A1 | 3/2020 | |
| WO | WO-2020215037 A1 | 10/2020 | |
| WO | WO-2021165346 A1 | 8/2021 | |

OTHER PUBLICATIONS

Shao et al., European Journal of Medicinal Chemistry, 2014, 75, pp. 96-105. (Year: 2014).*
Chemical Abstracts Registry No. 2127059-67-8, indexed in the Registry file on STN CAS Online Sep. 13, 2017. (Year: 2017).*
Chemical Abstracts Registry No. 2127239-78-3, indexed in the Registry file on STN CAS Online Sep. 14, 2017. (Year: 2017).*
A machine generated English translation of CN 103044446 A, 2013 (Year: 2013).*
Eldar et al., Structural studies of p53 inactivation by DNA-contact mutations and its rescue by suppressor mutations via alternative protein-DNA interactions. Nucleic Acids Res. Oct. 2013;41(18):8748-59.
International Search Report and Written Opinion Issued in PCT/US2021/038249 dated Nov. 10, 2021.
PubChem SID: 128196206 Deposit Date: Dec. 4, 2011 pp. 1-7.
PubChem CID: 10376659 Deposit Date: Dec. 18, 2015 pp. 1-6.
PubChem SID: 374412121 Deposit Date: Jun. 23, 2018 pp. 1-8.

(Continued)

*Primary Examiner* — Laura L Stockton
(74) *Attorney, Agent, or Firm* — Wilson Sonsini Goodrich & Rosati

(57) ABSTRACT

Mutations in oncogenes and tumor suppressors contribute to the development and progression of cancer. The present disclosure describes compounds and methods that restore DNA binding affinity of p53 mutants. The compounds of the present disclosure can bind to mutant p53 and restore the ability of the p53 mutant to bind DNA and activate downstream effectors involved in tumor suppression. The disclosed compounds can be used to reduce the progression of cancers that contain a p53 mutation.

12 Claims, No Drawings

(56) References Cited

OTHER PUBLICATIONS

Hei, Y. et al., "Alkylsulfonamide-containing quinazoline derivatives as potent and orally bioavailable PI3Ks inhibitors," Bioorganic & Medicinal Chemistry, 2019, vol. 27, pp. 1-11.

Kundu, B. et al., "Development of a metabolically stable topoisomerase I poison as anticancer agent," European Journal of Medicinal Chemistry, 2020, vol. 202, 112551.

Nishimura, N. et al., "Phospshoinositide 3-Kinase (PI3K)/Mammalian Target of Rapamycin (mTOR) Dual Inhibitors: Discovery and Structure-Activity Relationships of a Series of Quinoline and Quinoxaline Derivatives," Journal of Medicinal Chemistry, 2011, vol. 54, No. 13, pp. 4735-4751.

Xiao, H. et al., "Biologic-like In Vivo Efficacy with Small Molecule Inhibitors of TNFα Identified Using Scaffold Hopping and Structure-Based Drug Design Approaches," Journal of Medicinal Chemistry, 2020, vol. 63, No. 23, pp. 15050-15071.

Yang, W. et al., "3D-QSAR and docking studies of 3-Pyridine heterocyclic derivatives as potent PI3K/mTOR inhibitors," Journal of Molecular Structure, 2013, vol. 1054-1055, pp. 107-116.

Degorce et al.: Discovery of Novel 3-Quinoline Carboxamides as Potent, Selective, and Orally Bioavailable Inhibitors of Ataxia Telangiectasia Mutated (ATM) Kinase. J. Med. Chem. 59(13):6281-6292 (2016).

Hoffer et al.: Antifertility, spermicidal and ultrastructural effects of gossypol and derivatives administered orally and by intratesticular injections. Contraception. 37(3):301-331 (1988).

Venkateswarlu et al.: 4-(N-Phenyl-N'-substituted benzenesulfonyl)-6-(4-hydroxyphenyl)quinolines as inhibitors of mammalian target of rapamycin. Bioorganic & Medicinal Chemistry. 23(15):4237-4247 (2015).

Zhang et al.: Rhodium-Catalyzed Oxidative Benzannulation of N-Pivaloylanilines with Internal Alkynes through Dual C—H Bond Activation: Synthesis of Highly Substituted Naphthalenes. Chemistry. 11(22):3241-3250 (2016).

\* cited by examiner

METHODS AND COMPOUNDS FOR RESTORING MUTANT P53 FUNCTION

CROSS-REFERENCE

This application claims the benefit of U.S. Provisional Application No. 63/042,252, filed Jun. 22, 2020, which is incorporated herein by reference.

BACKGROUND

Cancer, an uncontrolled proliferation of cells, is a multifactorial disease characterized by tumor formation, growth, and in some instances, metastasis. Cells carrying an activated oncogene, damaged genome, or other cancer-promoting alterations can be prevented from replicating through an elaborate tumor suppression network. A central component of this tumor suppression network is p53, one of the most potent tumor suppressors in the cell. Both the wild type and mutant conformations of p53 are implicated in the progression of cancer.

INCORPORATION BY REFERENCE

All publications, patents, and patent applications mentioned in this specification are herein incorporated by reference to the same extent as if each individual publication, patent, or patent application was specifically and individually indicated to be incorporated by reference.

SUMMARY OF THE INVENTION

In some embodiments, described herein is a compound of formula:

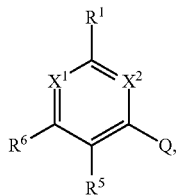

wherein:
$X^1$ is $CR^7$ or N;
$X^2$ is $CR^2$ or N;
each of $R^1$ and $R^2$ is independently alkyl, $-NR^8R^9$, $-C(O)NR^8R^9$, $-NR^8C(O)R^9$, $-OR^{10}$, $-SR^{11}$, $-C(O)R^{12}$, $-C(O)OR^{12}$, $-S(O)_2R^{13}$, CN, each of which is unsubstituted or substituted, or hydrogen or halogen;
Q is

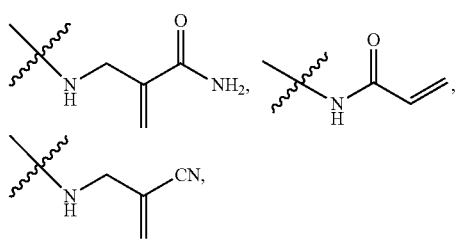

or $NR^3R^4$, wherein each of $R^3$ and $R^4$ is independently alkyl, cycloalkyl, alkenyl, $-C(O)R^{13}$, $-C(O)OR^{13}$, $-S(O)_2R^{13}$, $-S(O)_2R^{13}$, each of which is unsubstituted or substituted; or hydrogen, or $R^3$ and $R^4$ together with the nitrogen atom to which $R^3$ and $R^4$ are bound form a ring, wherein the ring is unsubstituted or substituted;
$R^7$ is alkyl, alkenyl, cycloalkyl, aryl, heteroaryl or heterocyclyl, each of which is unsubstituted or substituted, or hydrogen or halogen;
each of $R^8$ and $R^9$ is alkyl, alkenyl, cycloalkyl, aryl, heterocyclyl, heteroaryl, each of which is unsubstituted or substituted, or hydrogen; or $R^8$ and $R^9$ together with the nitrogen atom to which $R^8$ and $R^9$ are bound form a ring, wherein the ring is unsubstituted or substituted; and
each of $R^{10}$, $R^{11}$, $R^{12}$, and $R^{13}$ is independently is alkyl, alkenyl, cycloalkyl, aryl, heteroaryl or heterocyclyl, each of which is unsubstituted or substituted, or hydrogen or halogen;
provided that:
(i) when Q is

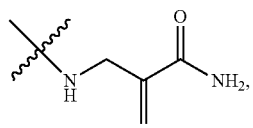 [SMILES: *NCC(=C)C(N)=O]

then each of $R^5$ and $R^6$ is independently aryl or heteroaryl, each of which is unsubstituted or substituted, or hydrogen or halogen; or $R^5$ and $R^6$ together with the carbon atoms to which $R^5$ and $R^6$ are bound form a ring, wherein the ring is unsubstituted or substituted;
(ii) when Q is

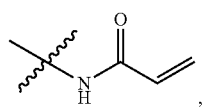

then $R^5$ and $R^6$ together with the carbon atoms to which $R^5$ and $R^6$ are bound form a ring, wherein the ring is unsubstituted or substituted;
(iii) when Q is

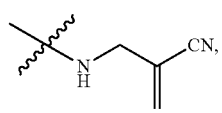 [SMILES: *NCC(=C)C#N]

then:
(a) $R^5$ is hydrogen or halogen, and $R^6$ is

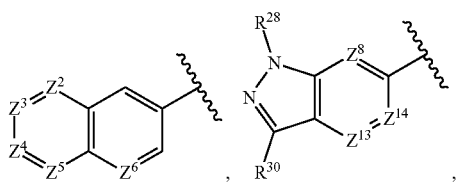

-continued

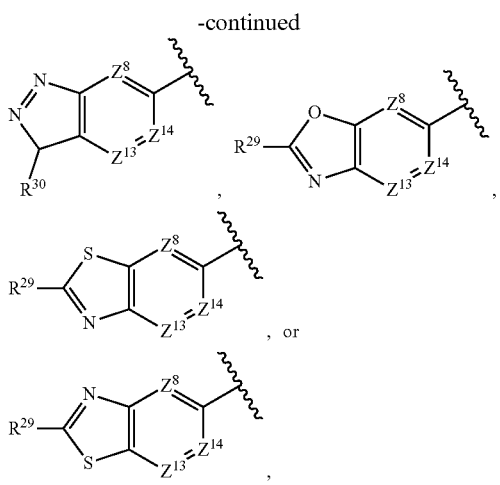

wherein
Z² is N or CH;
Z³ is N or CR²²;
Z⁴ is N or CR²³;
Z⁵ is N or CR²⁴;
Z⁶ is N or CR²⁵;
Z⁸ is N or CR²⁷;
Z¹³ is N or CR³²; and
Z¹⁴ is N or CR³³,
wherein each of $R^{22}$, $R^{23}$, $R^{24}$, $R^{25}$, $R^{27}$, $R^{28}$, $R^{29}$, $R^{30}$, $R^{32}$, and $R^{33}$ is independently, alkyl, heteroaryl, —$NR^{14}R^{15}$, —$C(O)NR^{14}R^{15}$, —$NR^{14}C(O)R^{15}$, —$OR^{16}$, —$SR^{17}$, —$C(O)R^{18}$, —$C(O)OR^{18}$, —$S(O)_2R^{19}$, or —CN, each of which is unsubstituted or substituted, or hydrogen or halogen; or (b) $R^5$ and $R^6$ together with the carbon atoms to which $R^5$ and $R^6$ are bound form a ring, and the compound has the structure:

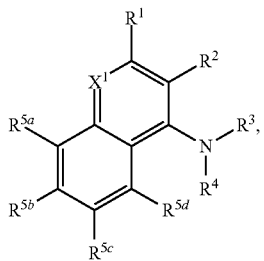

wherein
$R^{5a}$, $R^{5b}$, and $R^{5d}$ are each independently aryl or heteroaryl, each of which is substituted or unsubstituted, or hydrogen or halogen, and
$R^{5c}$ is

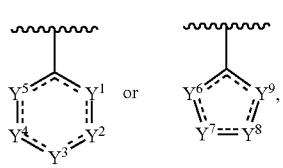

wherein
each ----- is independently a single bond or a double bond;
$Y^1$ is $CR^{6a}$, N, $NR^{6a}$, O or S;
$Y^2$ is $CR^{6b}$, N, $NR^{6b}$, O or S;
$Y^3$ is $CR^{6c}$, N, $NR^{6c}$, O or S;
$Y^4$ is $CR^{6d}$, N, $NR^{6d}$, O or S;
$Y^5$ is $CR^{6e}$, N, $NR^{6e}$, O or S;
$Y^6$ is $CR^{6f}$, N, $NR^{6f}$, O or S;
$Y^7$ is $CR^{6g}$, N, $NR^{6g}$, O or S;
$Y^8$ is $CR^{6h}$, N, $NR^{6h}$, O or S; and
$Y^9$ is $CR^{6i}$, N, $NR^{6i}$, O or S,
wherein
each of $R^{6a}$, $R^{6b}$, $R^{6c}$, $R^{6d}$, $R^{6e}$, $R^{6f}$, $R^{6g}$, $R^{6h}$, and $R^{6i}$ is independently alkyl, cycloalkyl, —$NR^{14}R^{15}$, —$OR^{16}$, —$SR^{17}$, —$C(O)NR^{14}R^{15}$, —$NHC(O)R^{14}R^{15}$, —CN, —$C(O)OR^{18}$, —$S(O)_2R^{19}$, —$NHS(O)_2R^{19}$, each of which is unsubstituted or substituted, or hydrogen or halogen; or $R^{6a}$ and $R^{6b}$ together with the carbon atoms to which $R^{6a}$ and $R^{6b}$ are bound form a ring, wherein the ring is unsubstituted or substituted, and each of $R^{6c}$, $R^{6d}$, $R^{6e}$, $R^{6f}$, $R^{6g}$, $R^{6h}$, and $R^{6i}$ is independently alkyl, cycloalkyl, —$NR^{14}R^{15}$, —$OR^{16}$, —$SR^{17}$, —$C(O)NR^{14}R^{15}$, —$NHC(O)R^{14}R^{15}$, —CN, —$C(O)OR^{18}$, —$S(O)_2R^{19}$, —$NHS(O)_2R^{19}$, each of which is unsubstituted or substituted, or hydrogen or halogen; or $R^{6b}$ and $R^{6c}$ together with the carbon atoms to which $R^{6b}$ and $R^{6c}$ are bound form a ring, wherein the ring is unsubstituted or substituted, and each of $R^{6a}$, $R^{6d}$, $R^{6e}$, $R^{6f}$, $R^{6g}$, $R^{6h}$, and $R^{6i}$ is independently alkyl, cycloalkyl, —$NR^{14}R^{15}$, —$OR^{16}$, —$SR^{17}$, —$C(O)NR^{14}R^{15}$, —$NHC(O)R^{14}R^{15}$, —CN, —$C(O)OR^{18}$, —$S(O)_2R^{19}$, —$NHS(O)_2R^{19}$, each of which is unsubstituted or substituted, or hydrogen or halogen; or $R^{6c}$ and $R^{6d}$ together with the carbon atoms to which $R^{6c}$ and $R^{6d}$ are bound form a ring, wherein the ring is unsubstituted or substituted, and each of $R^{6a}$, $R^{6b}$, $R^{6e}$, $R^{6f}$, $R^{6g}$, $R^{6h}$, and $R^{6i}$ is independently alkyl, cycloalkyl, —$NR^{14}R^{15}$, —$OR^{16}$, —$SR^{17}$, —$C(O)NR^{14}R^{15}$, —$NHC(O)R^{14}R^{15}$, —CN, —$C(O)OR^{18}$, —$S(O)_2R^{19}$, —$NHS(O)_2R^{19}$, each of which is unsubstituted or substituted, or hydrogen or halogen; or $R^{6d}$ and $R^{6e}$ together with the carbon atoms to which $R^{6d}$ and $R^{6e}$ are bound form a ring, wherein the ring is unsubstituted or substituted, and each of $R^{6a}$, $R^{6b}$, $R^{6c}$, $R^{6f}$, $R^{6g}$, $R^{6h}$, and $R^{6i}$ is independently alkyl, cycloalkyl, —$NR^{14}R^{15}$, —$OR^{16}$, —$SR^{17}$, —$C(O)NR^{14}R^{15}$, —$NHC(O)R^{14}R^{15}$, —CN, —$C(O)OR^{18}$, —$S(O)_2R^{19}$, —$NHS(O)_2R^{19}$, each of which is unsubstituted or substituted, or hydrogen or halogen; or $R^{6f}$ and $R^{6g}$ together with the carbon atoms to which $R^{6f}$ and $R^{6g}$ are bound form a ring, wherein the ring is unsubstituted or substituted, and each of $R^{6a}$, $R^{6b}$, $R^{6c}$, $R^{6d}$, $R^{6e}$, $R^{6h}$ and $R^{6i}$ is independently alkyl, cycloalkyl, —$NR^{14}R^{15}$, —$OR^{16}$, —$SR^{17}$, —$C(O)NR^{14}R^{15}$, —$NHC(O)R^{14}R^{15}$, —CN, —$C(O)OR^{18}$, —$S(O)_2R^{19}$, —$NHS(O)_2R^{19}$, each of which is unsubstituted or substituted, or hydrogen or halogen; or $R^{6g}$ and $R^{6h}$ together with the carbon atoms to which $R^{6g}$ and $R^{6h}$ are bound form a ring, wherein the ring is unsubstituted or substituted, and each of $R^{6a}$, $R^{6b}$, $R^{6c}$, $R^{6d}$, $R^{6e}$, $R^{6f}$, and $R^{6i}$ is independently alkyl, cycloalkyl, —$NR^{14}R^{15}$, —OR$^{16}$, —SR$^{17}$, —C(O)NR$^{14}$R$^{15}$, —NHC(O)R$^{14}$R$^{15}$, —CN, —C(O)OR$^{18}$, —S(O)$_2$R$^{19}$, —NHS(O)$_2$R$^{19}$, each of which is unsubstituted or substituted, or hydrogen or halogen; or R$^{6h}$ and R$^{6i}$ together with the carbon atoms to which R$^{6h}$ and R$^{6i}$ are bound form a ring, wherein the ring is unsubstituted or substituted, and each of R$^{6a}$, R$^{6b}$, R$^{6c}$, R$^{6d}$, R$^{6e}$, R$^{6f}$, and R$^{6g}$ is independently alkyl, cycloalkyl, —NR$^{14}$R$^{15}$, —OR$^{16}$, —SR$^{17}$, —C(O)NR$^{14}$R$^{15}$, —NHC(O)R$^{14}$R$^{15}$, —CN, —C(O)OR$^{18}$, —S(O)$_2$R$^{19}$, —NHS(O)$_2$R$^{19}$, each of which is unsubstituted or substituted, or hydrogen or halogen, and (iv) when Q is not

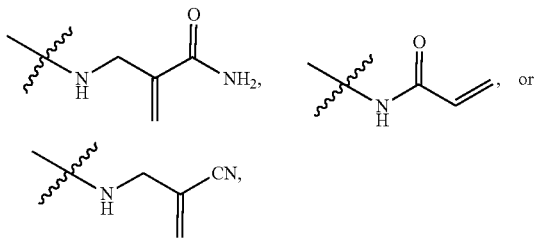

then R$^5$ and R$^6$ together with the carbon atoms to which R$^5$ and R$^6$ are bound form a ring, and compound has the structure:

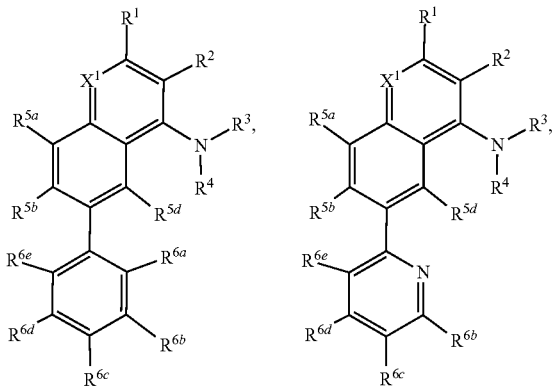

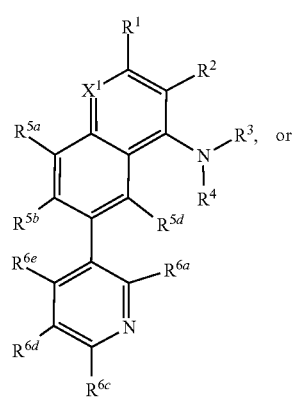

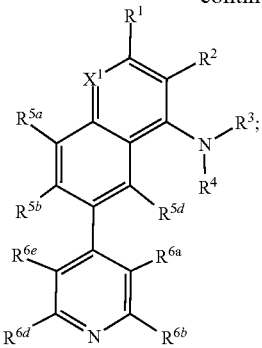

wherein:
R$^{5a}$, R$^{5b}$, and R$^{5d}$ are each independently aryl or heteroaryl, each of which is substituted or unsubstituted, or hydrogen or halogen; and each of R$^{6a}$, R$^{6b}$, R$^{6c}$, R$^{6d}$, and R$^{6e}$ is independently alkyl, cycloalkyl, —NR$^{14}$R$^{15}$, —OR$^{16}$, —SR$^{17}$, —C(O)NR$^{14}$R$^{15}$, —NHC(O)R$^{14}$R$^{15}$, —CN, —C(O)OR$^{18}$, —S(O)$_2$R$^{19}$, —NHS(O)$_2$R$^{19}$, each of which is unsubstituted or substituted, or hydrogen or halogen; wherein at least one of R$^{6a}$, R$^{6b}$, R$^{6c}$, R$^{6d}$, and R$^{6e}$ is —C(O)NR$^{14}$R$^{15}$, NR$^{14}$R$^{15}$, or NR$^{14}$C(O)R$^{15}$, and each of R$^{14}$ and R$^{15}$ is alkyl, alkenyl, cycloalkyl, aryl, heterocyclyl, or heteroaryl, each of which is unsubstituted or substituted, or hydrogen; or R$^{14}$ and R$^{15}$ together with the nitrogen atom to which R$^{14}$ and R$^{15}$ are bound form a ring, wherein the ring is unsubstituted or substituted; and each of R$^{16}$, R$^{17}$, R$^{18}$, and R$^{19}$ is independently is alkyl, alkenyl, cycloalkyl, aryl, heteroaryl or heterocyclyl, each of which is unsubstituted or substituted, or hydrogen or halogen;

or a pharmaceutically-acceptable salt thereof.

In some embodiments, described herein is as pharmaceutical composition comprising a compound of the disclosure and a pharmaceutically-acceptable excipient.

In some embodiments, described herein is a method of inducing apoptosis in a cell, the method comprising contacting the cell with a therapeutically-effective amount of a compound of the disclosure that binds a p53 mutant, wherein the compound increases the ability of the p53 mutant to bind DNA, wherein the cell expresses the p53 mutant. In some embodiments, described herein is a method of treating a cancer, the method comprising administering to a subject in need thereof a therapeutically-effective amount of a compound of the disclosure.

DETAILED DESCRIPTION

The present invention provides compounds and methods for restoring wild-type function to mutant p53. The compounds of the present invention can bind to mutant p53 and restore the ability of the p53 mutant to bind DNA. The restoration of activity of the p53 mutant can allow for the activation of downstream effectors of p53 leading to inhibition of cancer progression. The invention further provides methods of treatment of a cancerous lesion or a tumor harboring a p53 mutation.

Cancer is a collection of related diseases characterized by uncontrolled proliferation of cells with the potential to metastasize throughout the body. Cancer can be classified into five broad categories including, for example: carcinomas, which can arise from cells that cover internal and external parts of the body such as the lung, breast, and colon; sarcomas, which can arise from cells that are located in bone, cartilage, fat, connective tissue, muscle, and other supportive tissues; lymphomas, which can arise in the lymph nodes and immune system tissues; leukemia, which can arise in the bone marrow and accumulate in the bloodstream; and adenomas, which can arise in the thyroid, the pituitary gland, the adrenal gland, and other glandular tissues.

Although different cancers can develop in virtually any of the body's tissues, and contain unique features, the basic processes that cause cancer can be similar in all forms of the disease. Cancer begins when a cell breaks free from the normal restraints on cell division and begins to grow and divide out of control. Genetic mutations in the cell can preclude the ability of the cell to repair damaged DNA or initiate apoptosis, and can result in uncontrolled growth and division of cells.

The ability of tumor cell populations to multiply is determined not only by the rate of cell proliferation but also by the rate of cell attrition. Programmed cell death, or apoptosis, represents a major mechanism of cellular attrition. Cancer cells can evade apoptosis through a variety of strategies, for example, through the suppression of p53 function, thereby suppressing expression of pro-apoptotic proteins.

Oncogenes and tumor suppressor genes can regulate the proliferation of cells. Genetic mutations can affect oncogenes and tumor suppressors, potentially activating or suppressing activity abnormally, further facilitating uncontrolled cell division. Whereas oncogenes assist in cellular growth, tumor suppressor genes slow cell division by repairing damaged DNA and activating apoptosis. Cellular oncogenes that can be mutated in cancer include, for example, Cdk1, Cdk2, Cdk3, Cdk4, Cdk6, EGFR, PDGFR, VEGF, HER2, Raf kinase, K-Ras, and myc. Tumor suppressor genes that can be mutated in cancer include, for example, BRCA1, BRCA2, cyclin-dependent kinase inhibitor 1C, Retinoblastoma protein (pRb), PTEN, p16, p27, p53, and p73.

The tumor suppressor p53 acts as a DNA sequence-specific transcription factor regulating and activating the expression of a range of target genes in response to genotoxic stress. Activation of target genes by p53 initiates a cascade of signal transduction pathways, which leads to different cellular responses including cell-cycle arrest and apoptosis that prevent cancer development. p53 binds as a tetramer to specific response elements consisting mainly of two decameric half-sites separated by a variable number of base pairs. Mutations in the p53 gene that lead to inactivation of the protein are observed in ~50% of human cancers. The majority of tumor-related p53 mutations, particularly those defined as mutational 'hotspots', occur within the DNA-binding core domain of p53. The top hotspot mutations are located at or near the protein-DNA interface and can be divided into two major groups: DNA-contact mutations affecting residues involved directly in DNA contacts without altering p53 conformation; and structural mutations that cause a conformational change in the core domain.

R273, a DNA-contact amino acid, is one of the most frequently altered residues in human cancer (6.4% of all somatic mutations), with mutations to histidine (46.6%) and to cysteine (39.1%) being most common. Crystal structures of the p53 core-domain bound to DNA show that the positively charged guanidinium groups of R273 residues interact with the negatively charged DNA backbone at the center of each DNA half-site, supported by salt-bridge and hydrogen-bond interactions. R273 residues play a pivotal role in docking p53 to the DNA backbone at the central region of each half-site where no direct base-mediated contacts exist. Substitution of R273 by histidine (R273H) or cysteine (R273C) lead to dramatic reduction in the DNA binding affinity, even through the protein retains wild-type stability.

Tumor Suppressor p53.

The tumor suppressor protein p53 is a 393 amino acid transcription factor that can regulate cell growth in response to cellular stresses including, for example, UV radiation, hypoxia, oncogene activation, and DNA damage. p53 has various mechanisms for inhibiting the progression of cancer including, for example, initiation of apoptosis, maintenance of genomic stability, cell cycle arrest, induction of senescence, and inhibition of angiogenesis. Due to the critical role of p53 in tumor suppression, p53 is inactivated in almost all cancers either by direct mutation or through perturbation of associated signaling pathways involved in tumor suppression. Homozygous loss of the p53 gene occurs in almost all types of cancer, including carcinomas of the breast, colon, and lung. The presence of certain p53 mutations in several types of human cancer can correlate with less favorable patient prognosis.

In the absence of stress signals, p53 levels are maintained at low levels via the interaction of p53 with Mdm2, an E3 ubiquitin ligase. In an unstressed cell, Mdm2 can target p53 for degradation by the proteasome. Under stress conditions, the interaction between Mdm2 and p53 is disrupted, and p53 accumulates. The critical event leading to the activation of p53 is phosphorylation of the N-terminal domain of p53 by protein kinases, thereby transducing upstream stress signals. The phosphorylation of p53 leads to a conformational change, which can promote DNA binding by p53 and allow transcription of downstream effectors. The activation of p53 can induce, for example, the intrinsic apoptotic pathway, the extrinsic apoptotic pathway, cell cycle arrest, senescence, and DNA repair. p53 can activate proteins involved in the above pathways including, for example, Fas/Apo1, KILLER/DR5, Bax, Puma, Noxa, Bid, caspase-3, caspase-6, caspase-7, caspase-8, caspase-9, and p21 (WAF1). Additionally, p53 can repress the transcription of a variety of genes including, for example, c-MYC, Cyclin B, VEGF, RAD51, and hTERT.

Each chain of the p53 tetramer is composed of several functional domains including the transactivation domain (amino acids 1-100), the DNA-binding domain (amino acids 101-306), and the tetramerization domain (amino acids 307-355), which are highly mobile and largely unstructured. Most p53 cancer mutations are located in the DNA-binding core domain of the protein, which contains a central β-sandwich of anti-parallel β-sheets that serves as a basic scaffold for the DNA-binding surface. The DNA-binding surface is composed of two β-turn loops, L2 and L3, which are stabilized by a zinc ion, for example, at Arg175 and Arg248, and a loop-sheet-helix motif. Altogether, these structural elements form an extended DNA-binding surface that is rich in positively-charged amino acids, and makes specific contact with various p53 response elements.

Due to the prevalence of p53 mutations in virtually every type of cancer, the reactivation of wild type p53 function in a cancerous cell can be an effective therapy. Mutations in p53 located in the DNA-binding domain of the protein or periphery of the DNA-binding surface can result in aberrant protein folding required for DNA recognition and binding or reduction in DNA binding affinity. Mutations in p53 can occur, for example, at amino acids Val143, His168, Arg175, Tyr220, Gly245, Arg248, Arg249, Phe270, Arg273, and Arg282. p53 mutations that can abrogate the activity of p53 include, for example, R175H, Y220C, G245S, R248Q, R248W, R273C, R273H, and R282H. p53 mutations can distort the structure of the DNA-binding site, thermodynamically destabilize the folded protein at body temperature, or weaken consensus DNA binding. Wild-type function of p53 mutants can be recovered by binding of the p53 mutant to a compound that can shift the folding-unfolding equilibrium towards the folded state, thereby reducing the rate of unfolding and destabilization; or by conjugating a small molecule to the DNA binding interface to restore consensus DNA binding.

Non-limiting examples of amino acids include: alanine (A, Ala); arginine (R, Arg); asparagine (N, Asn); aspartic acid (D, Asp); cysteine (C, Cys); glutamic acid (E, Glu); glutamine (Q, Gin); glycine (G, Gly); histidine (H, His); isoleucine (I, lie); leucine (L, Leu); lysine (K, Lys); methionine (M, Met); phenylalanine (F, Phe); proline (P, Pro); serine (S, Ser); threonine (T, Thr); tryptophan (W, Trp); tyrosine (Y, Tyr); and valine (V, Val).

Mechanism of Compounds of the Disclosure.

The compounds of the present disclosure can selectively bind to a p53 mutant and can recover wild-type activity of the p53 mutant including, for example, DNA binding function and activation of downstream targets involved in tumor suppression. In some embodiments, a compound of the disclosure selectively binds to a p53 R248 mutant. In some embodiments, a compound of the disclosure selectively binds to a p53 R248Q mutant. In some embodiments, a compound of the disclosure selectively binds to a p53 R248W mutant. In some embodiments, a compound of the disclosure selectively binds to a p53 R273 mutant. In some embodiments, a compound of the disclosure selectively binds to a p53 R273C mutant. In some embodiments, a compound of the disclosure selectively binds to a p53 R273H mutant.

A compound of the disclosure can bind or conjugate to an amino acid in the DNA binding interface. In some embodiments, a compound of the disclosure can conjugate to C277. In some embodiments, a compound of the disclosure can conjugate to C182.

Assays can be employed to determine the ability of a compound of the disclosure to bind to p53 and restore DNA binding affinity. Examples of assays include differential scanning fluorimetry (DSF), isothermal titration calorimetry (ITC), nuclear magnetic resonance spectrometry (NMR), X-ray crystallography, immunoprecipitation (IP), immunofluorescence (IF), or immunoblotting.

Methods used to detect the ability of the p53 mutant to bind DNA can include, for example, DNA affinity immunoblotting, modified enzyme-linked immunosorbent assay (ELISA), electrophoretic mobility shift assay (EMSA), fluorescence resonance energy transfer (FRET), homogeneous time-resolved fluorescence (HTRF), and a chromatin immunoprecipitation (ChIP) assay.

A compound of the disclosure can increase the ability of a p53 mutant to bind DNA by at least or up to about 0.1%, at least or up to about 0.2%, at least or up to about 0.3%, at least or up to about 0.4%, at least or up to about 0.5%, at least or up to about 0.6%, at least or up to about 0.7%, at least or up to about 0.8%, at least or up to about 0.9%, at least or up to about 1%, at least or up to about 2%, at least or up to about 3%, at least or up to about 4%, at least or up to about 5%, at least or up to about 6%, at least or up to about 7%, at least or up to about 8%, at least or up to about 9%, at least or up to about 10%, at least or up to about 11%, at least or up to about 12%, at least or up to about 13%, at least or up to about 14%, at least or up to about 15%, at least or up to about 16%, at least or up to about 17%, at least or up to about 18%, at least or up to about 19%, at least or up to about 20%, at least or up to about 21%, at least or up to about 22%, at least or up to about 23%, at least or up to about 24%, at least or up to about 25%, at least or up to about 26%, at least or up to about 27%, at least or up to about 28%, at least or up to about 29%, at least or up to about 30%, at least or up to about 31%, at least or up to about 32%, at least or up to about 33%, at least or up to about 34%, at least or up to about 35%, at least or up to about 36%, at least or up to about 37%, at least or up to about 38%, at least or up to about 39%, at least or up to about 40%, at least or up to about 41%, at least or up to about 42%, at least or up to about 43%, at least or up to about 44%, at least or up to about 45%, at least or up to about 46%, at least or up to about 47%, at least or up to about 48%, at least or up to about 49%, at least or up to about 50%, at least or up to about 51%, at least or up to about 52%, at least or up to about 53%, at least or up to about 54%, at least or up to about 55%, at least or up to about 56%, at least or up to about 57%, at least or up to about 58%, at least or up to about 59%, at least or up to about 60%, at least or up to about 61%, at least or up to about 62%, at least or up to about 63%, at least or up to about 64%, at least or up to about 65%, at least or up to about 66%, at least or up to about 67%, at least or up to about 68%, at least or up to about 69%, at least or up to about 70%, at least or up to about 71%, at least or up to about 72%, at least or up to about 73%, at least or up to about 74%, at least or up to about 75%, at least or up to about 76%, at least or up to about 77%, at least or up to about 78%, at least or up to about 79%, at least or up to about 80%, at least or up to about 81%, at least or up to about 82%, at least or up to about 83%, at least or up to about 84%, at least or up to about 85%, at least or up to about 86%, at least or up to about 87%, at least or up to about 88%, at least or up to about 89%, at least or up to about 90%, at least or up to about 91%, at least or up to about 92%, at least or up to about 93%, at least or up to about 94%, at least or up to about 95%, at least or up to about 96%, at least or up to about 97%, at least or up to about 98%, at least or up to about 99%, at least or up to about 100%, at least or up to about 125%, at least or up to about 150%, at least or up to about 175%, at least or up to about 200%, at least or up to about 225%, or at least or up to about 250% as compared to the ability of the p53 mutant to bind DNA in the absence of a compound of the disclosure.

A compound described herein can increase the activity of the p53 mutant that is, for example, at least or up to about 2-fold, at least or up to about 3-fold, at least or up to about 4-fold, at least or up to about 5-fold, at least or up to about 6-fold, at least or up to about 7-fold, at least or up to about 8-fold, at least or up to about 9-fold, at least or up to about 10-fold, at least or up to about 11-fold, at least or up to about 12-fold, at least or up to about 13-fold, at least or up to about 14-fold, at least or up to about 15-fold, at least or up to about 16-fold, at least or up to about 17-fold, at least or up to about 18-fold, at least or up to about 19-fold, at least or up to about 20-fold, at least or up to about 25-fold, at least or up to about 30-fold, at least or up to about 35-fold, at least or up to about 40-fold, at least or up to about 45-fold, at least or up to about 50-fold, at least or up to about 55-fold, at least or up to about 60-fold, at least or up to about 65-fold, at least or up to about 70-fold, at least or up to about 75-fold, at least or up to about 80-fold, at least or up to about 85-fold, at least or up to about 90-fold, at least or up to about 95-fold, at least or up to about 100-fold, at least or up to about 110-fold, at least or up to about 120-fold, at least or up to about 130-fold, at least or up to about 140-fold, at least or up to about 150-fold, at least or up to about 160-fold, at least or up to about 170-fold, at least or up to about 180-fold, at least or up to about 190-fold, at least or up to about 200-fold, at least or up to about 250-fold, at least or up to about 300-fold, at least or up to about 350-fold, at least or up to about 400-fold, at least or up to about 450-fold, at least or up to about 500-fold, at least or up to about 550-fold, at least or up to about 600-fold, at least or up to about 650-fold, at least or up to about 700-fold, at least or up to about 750-fold, at least or up to about 800-fold, at least or up to about 850-fold, at least or up to about 900-fold, at least or up to about 950-fold, at least or up to about 1,000-fold, at least or up to about 1,500-fold, at least or up to about 2,000-fold, at least or up to about 3,000-fold, at least or up to about 4,000-fold, at least or up to about 5,000-fold, at least or up to about 6,000-fold, at least or up to about 7,000-fold, at least or up to about 8,000-fold, at least or up to about 9,000-fold, or at least or up to about 10,000-fold greater than the activity of the p53 mutant in the absence of the compound.

A compound of the disclosure can be used, for example, to induce apoptosis, cell cycle arrest, or senescence in a cell. In some embodiments, the cell is a cancer cell. In some embodiments, the cell carries a mutation in p53.

Compounds of the Disclosure.

In some embodiments, the present disclosure provides a compound of the formula:

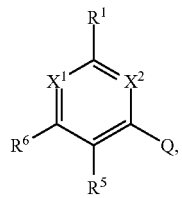

wherein:

$X^1$ is $CR^7$ or N;

$X^2$ is $CR^2$ or N;

each of $R^1$ and $R^2$ is independently alkyl, —$NR^8R^9$, —$C(O)NR^8R^9$, —$NR^8C(O)R^9$, —$OR^{10}$, —$SR^{11}$, —$C(O)R^{12}$, —$C(O)OR^{12}$, —$S(O)_2R^{13}$, CN, each of which is unsubstituted or substituted, or hydrogen or halogen;

Q is

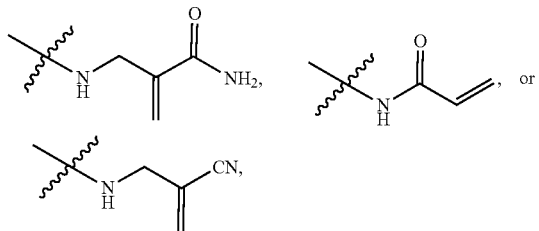

or $NR^3R^4$, wherein each of $R^3$ and $R^4$ is independently alkyl, cycloalkyl, alkenyl, —$C(O)R^{13}$, —$C(O)OR^{13}$, —$S(O)_2R^{13}$, —$S(O)_2R^{13}$, each of which is unsubstituted or substituted; or hydrogen, or $R^3$ and $R^4$ together with the nitrogen atom to which $R^3$ and $R^4$ are bound form a ring, wherein the ring is unsubstituted or substituted;

each of $R^5$ and $R^6$ is independently aryl or heteroaryl, each of which is unsubstituted or substituted, or hydrogen or halogen; or $R^5$ and $R^6$ together with the carbon atoms to which $R^5$ and $R^6$ are bound form a ring, wherein the ring is unsubstituted or substituted;

$R^7$ is alkyl, alkenyl, cycloalkyl, aryl, heteroaryl or heterocyclyl, each of which is unsubstituted or substituted, or hydrogen or halogen;

each of $R^8$ and $R^9$ is alkyl, alkenyl, cycloalkyl, aryl, heterocyclyl, heteroaryl, each of which is unsubstituted or substituted, or hydrogen; or $R^8$ and $R^9$ together with the nitrogen atom to which $R^8$ and $R^9$ are bound form a ring, wherein the ring is unsubstituted or substituted; and each of $R^{10}$, $R^{11}$, $R^{12}$ and $R^{13}$ is independently is alkyl, alkenyl, cycloalkyl, aryl, heteroaryl or heterocyclyl, each of which is unsubstituted or substituted, or hydrogen or halogen.

In some embodiments, $R^5$ is halogen or hydrogen, and $R^6$ is aryl and heteroaryl. In some embodiments, $R^5$ is aryl or heteroaryl, and $R^6$ is halogen or hydrogen. In some embodiments, $R^5$ is hydrogen.

In some embodiments, $R^6$ is pyridinyl, pyrazinyl, pyrimidinyl, each of which is unsubstituted or substituted. In some embodiments, $R^6$ is pyridinyl that is substituted or unsubstituted. In some embodiments, $R^6$ is pyridin-2-yl, pyridin-3-yl, or pyridin-4-yl, each of which is substituted or unsubstituted. In some embodiments, $R^6$ is pyrimidin-2-yl, pyrimidin-4-yl, or pyrimidin-5-yl, each of which is substituted or unsubstituted. In some embodiments, $R^6$ is pyridin-2-yl, which is substituted or unsubstituted. In some embodiments, $R^6$ is oxazolyl or imidazolyl, each of which is substituted or unsubstituted. In some embodiments, $R^6$ is oxazolyl that is substituted or unsubstituted. In some embodiments, $R^6$ is oxazol-2-yl that is substituted or unsubstituted.

In some embodiments, $R^6$ is quinolinyl, isoquinolinyl, quinazolinyl, or phthalazinyl, each of which is substituted or unsubstituted. In some embodiments, $R^6$ is quinolyl that is substituted or unsubstituted. In some embodiments, $R^6$ is quinolin-2-yl, quinolin-3-yl, quinolin-4-yl, quinolin-5-yl, quinolin-6-yl, quinolin-7-yl, or quinolin-8-yl, each of which is substituted or unsubstituted. In some embodiments, $R^6$ is quinolin-6-yl, or quinolin-7-yl, each of which is substituted or unsubstituted.

In some embodiments, $R^6$ is quinazolinlyl that is substituted or unsubstituted. In some embodiments, $R^6$ is quinazolin-2-yl, quinazolin-4-yl, quinazolin-5-yl, quinazolin-6-yl, quinazolin-7-yl, or quinazolin-8-yl, each of which is substituted or substituted. In some embodiments, $R^6$ is quinazolin-7-yl, which is substituted or unsubstituted.

In some embodiments, $R^6$ is isoquinolyl that is substituted or unsubstituted. In some embodiments, $R^6$ is isoquinolin-1-yl, isoquinolin-3-yl, isoquinolin-4-yl, isoquinolin-5-yl, isoquinolin-6-yl, isoquinolin-7-yl, or isoquinolin-8-yl, each of which is substituted or unsubstituted. In some embodiments, $R^6$ is isoquinolyl that is substituted or unsubstituted. In some embodiments, $R^6$ is isoquinolin-3-yl, isoquinolin-5-yl, isoquinolin-6-yl, or isoquinolin-7-yl, each of which is substituted or unsubstituted.

In some embodiments, $R^6$ is indolyl, isoindolyl, indazolyl, benzimidazolyl, benzoxazolyl, benzisoxazolyl, benzofuranyl, or benzothiophenyl, or benzthiazolyl, each of which is substituted or unsubstituted. In some embodiments, $R^6$ is indolyl that is substituted or unsubstituted. In some embodiments, $R^6$ is 1H-indol-1-yl, 1H-indol-2-yl, 1H-indol-3-yl, 1H-indol-4-yl, 1H-indol-5-yl, 1H-indol-6-yl, or 1H-indol-7- yl, each of which is substituted or unsubstituted. In some embodiments, R⁶ is indazolyl that is substituted or unsubstituted. In some embodiments, R⁶ is 1H-indazol-1-yl, 1H-indazol-3-yl, 1H-indazol-4-yl, 1H-indazol-5-yl, 1H-indazol-6-yl, or 1H-indazol-7-yl, each of which is substituted or unsubstituted. In some embodiments, R⁶ is 1H-indazol-3-yl that is substituted or unsubstituted. In some embodiments, R⁶ is 1H-indazol-5-yl that is substituted or unsubstituted. In some embodiments, R⁶ is 1H-indazol-6-yl that is substituted or unsubstituted.

In some embodiments, R⁶ is 1H-pyrazolo[3,4-c]pyridinyl that is substituted or unsubstituted. In some embodiments, R⁶ is 1H-pyrazolo[3,4-c]pyridin-5-yl that is substituted or unsubstituted. In some embodiments, R⁶ is 7H-pyrrolo[2,3-d]pyrimidinyl that is substituted or unsubstituted. In some embodiments, R⁶ is 7H-pyrrolo[2,3-d]pyrimidin-2-yl that is substituted or unsubstituted.

In some embodiments, R⁶ is

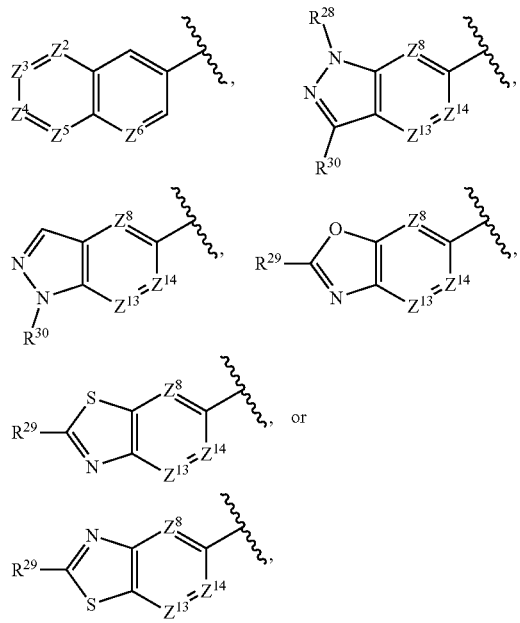

wherein
  $Z^2$ is N or CH;
  $Z^3$ is N or $CR^{22}$;
  $Z^4$ is N or $CR^{23}$;
  $Z^5$ is N or $CR^{24}$;
  $Z^6$ is N or $CR^{25}$;
  $Z^8$ is N or $CR^{27}$;
  $Z^{13}$ is N or $CR^{32}$; and
  $Z^{14}$ is N or $CR^{33}$,
  wherein each of $R^{22}$, $R^{23}$, $R^{24}$, $R^{25}$, $R^{27}$, $R^{28}$, $R^{29}$, $R^{30}$, $R^{32}$, and $R^{33}$ is independently, alkyl, heteroaryl, —NR¹⁴R¹⁵, —C(O)NR¹⁴R¹⁵, —NR¹⁴C(O)R¹⁵, —OR¹⁶, —SR¹⁷, —C(O)R¹⁸, —C(O)OR¹⁸, —S(O)₂R¹⁹, or —CN, each of which is unsubstituted or substituted, or hydrogen or halogen.

In some embodiments, Q is

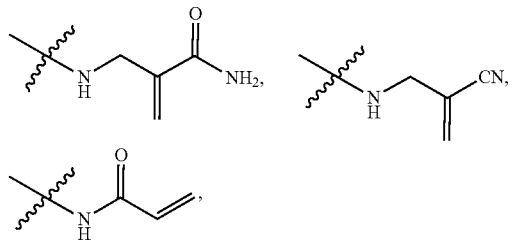

In some embodiments, Q is

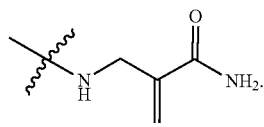 [SMILES: *NCC(=C)C(N)=O]

In some embodiments, when Q is

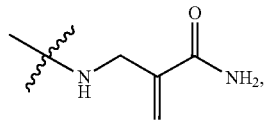 [SMILES: *NCC(=C)C(N)=O]

then each of R⁵ and R⁶ is independently aryl or heteroaryl, each of which is unsubstituted or substituted, or hydrogen or halogen; or R⁵ and R⁶ together with the carbon atoms to which R⁵ and R⁶ are bound form a ring, wherein the ring is unsubstituted or substituted.

In some embodiments, Q is

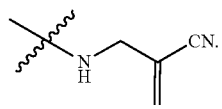 [SMILES: *NCC(=C)C#N]

In some embodiments, when Q is

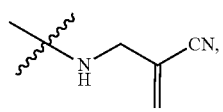 [SMILES: *NCC(=C)C#N]

then R⁵ and R⁶ together with the carbon atoms to which R⁵ and R⁶ are bound form the ring, wherein the ring is unsubstituted or substituted.

In some embodiments, Q is

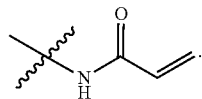 [SMILES: *NC(=O)C=C]

In some embodiments, when Q is

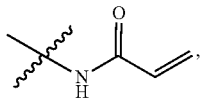 [SMILES: *NC(=O)C=C]

then $R^5$ is hydrogen or halogen, and $R^6$ is aryl or heteroaryl, which is unsubstituted or substituted.

In some embodiments, when Q is

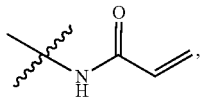 [SMILES: *NC(=O)C=C]

then $R^5$ and $R^6$ together with the carbon atoms to which $R^5$ and $R^6$ are bound form the ring, and the compound has the structure:

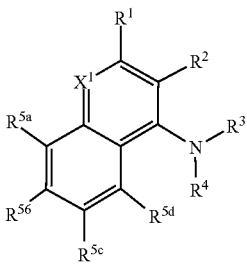

wherein
$R^{5a}$, $R^{5b}$ and $R^{5d}$ are each independently aryl or heteroaryl, each of which is substituted or unsubstituted, or hydrogen or halogen, and
$R^{5c}$ is

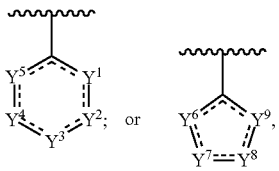

wherein
each of ------ is independently a single bond or a double bond;
$Y^1$ is $CR^{6a}$, N, $NR^{6a}$, O or S;
$Y^2$ is $CR^{6b}$, N, $NR^{6b}$, O or S;
$Y^3$ is $CR^{6c}$, N, $NR^{6c}$, O or S;
$Y^4$ is $CR^{6d}$, N, $NR^{6d}$, O or S;
$Y^5$ is $CR^{6e}$, N, $NR^{6e}$, O or S;
$Y^6$ is $CR^{6f}$, N, $NR^{6f}$, O or S;
$Y^7$ is $CR^{6g}$, N, $NR^{6g}$, O or S;
$Y^8$ is $CR^{6h}$, N, $NR^{6h}$, O or S; and
$Y^9$ is $CR^{6i}$, N, $NR^{6i}$, O or S,
wherein
each of $R^{6a}$, $R^{6b}$, $R^{6c}$, $R^{6d}$, $R^{6e}$, $R^{6f}$, $R^{6g}$, $R^{6h}$ and $R^{6i}$ is independently alkyl, cycloalkyl, —$N^{14}R^{15}$, —$OR^{16}$, —$SR^{17}$, —$C(O)NR^{14}R^{15}$, —$NHC(O)R^{14}R^{15}$, —CN, —$C(O)OR^{18}$, —$S(O)_2R^{19}$, —$NHS(O)_2R^{19}$, each of which is unsubstituted or substituted, or hydrogen or halogen; or $R^{6a}$ and $R^{6b}$ together with the carbon atoms to which $R^{6a}$ and $R^{6b}$ are bound form a ring, wherein the ring is unsubstituted or substituted, and each of $R^{6c}$, $R^{6d}$, $R^{6e}$, $R^{6f}$, $R^{6g}$, $R^{6h}$ and $R^{6i}$ is independently alkyl, cycloalkyl, —$N^{14}R^{15}$, —$OR^{16}$, —$SR^{17}$, —$C(O)NR^{14}R^{15}$, —$NHC(O)R^{14}R^{15}$, —CN, —$C(O)OR^{18}$, —$S(O)_2R^{19}$, —$NHS(O)_2R^{19}$, each of which is unsubstituted or substituted, or hydrogen or halogen; or $R^{6b}$ and $R^{6c}$ together with the carbon atoms to which $R^{6b}$ and $R^{6c}$ are bound form a ring, wherein the ring is unsubstituted or substituted, and each of $R^{6a}$, $R^{6d}$, $R^{6e}$, $R^{6f}$, $R^{6g}$, $R^{6h}$ and $R^{6i}$ is independently alkyl, cycloalkyl, —$N^{14}R^{15}$, —$OR^{16}$, —$SR^{17}$, —$C(O)NR^{14}R^{15}$, —$NHC(O)R^{14}R^{15}$, —CN, —$C(O)OR^{18}$, —$S(O)_2R^{19}$, —$NHS(O)_2R^{19}$, each of which is unsubstituted or substituted, or hydrogen or halogen; or $R^{6c}$ and $R^{6d}$ together with the carbon atoms to which $R^{6c}$ and $R^{6d}$ are bound form a ring, wherein the ring is unsubstituted or substituted, and each of $R^{6a}$, $R^{6b}$, $R^{6e}$, $R^{6f}$, $R^{6g}$, $R^{6h}$ and $R^{6i}$ is independently alkyl, cycloalkyl, —$N^{14}R^{15}$, —$OR^{16}$, —$SR^{17}$, —$C(O)NR^{14}R^{15}$, —$NHC(O)R^{14}R^{15}$, —CN, —$C(O)OR^{18}$, —$S(O)_2R^{19}$, —$NHS(O)_2R^{19}$, each of which is unsubstituted or substituted, or hydrogen or halogen; or $R^{6d}$ and $R^{6e}$ together with the carbon atoms to which $R^{6d}$ and $R^{6e}$ are bound form a ring, wherein the ring is unsubstituted or substituted, and each of $R^{6a}$, $R^{6b}$, $R^{6c}$, $R^{6f}$, $R^{6g}$, $R^{6h}$ and $R^{6i}$ is independently alkyl, cycloalkyl, —$N^{14}R^{15}$, —$OR^{16}$, —$SR^{17}$, —$C(O)NR^{14}R^{15}$, —$NHC(O)R^{14}R^{15}$, —CN, —$C(O)OR^{18}$, —$S(O)_2R^{19}$, —$NHS(O)_2R^{19}$, each of which is unsubstituted or substituted, or hydrogen or halogen; or $R^{6f}$ and $R^{6g}$ together with the carbon atoms to which $R^{6f}$ and $R^{6g}$ are bound form a ring, wherein the ring is unsubstituted or substituted, and each of $R^{6a}$, $R^{6b}$, $R^{6c}$, $R^{6d}$, $R^{6e}$, $R^{6h}$ and $R^{6i}$ is independently alkyl, cycloalkyl, —$N^{14}R^{15}$, —$OR^{16}$, —$SR^{17}$, —$C(O)NR^{14}R^{15}$, —$NHC(O)R^{14}R^{15}$, —CN, —$C(O)OR^{18}$, —$S(O)_2R^{19}$, —$NHS(O)_2R^{19}$, each of which is unsubstituted or substituted, or hydrogen or halogen; or $R^{6g}$ and $R^{6h}$ together with the carbon atoms to which $R^{6g}$ and $R^{6h}$ are bound form a ring, wherein the ring is unsubstituted or substituted, and each of $R^{6a}$, $R^{6b}$, $R^{6c}$, $R^{6d}$, $R^{6e}$, $R^{6f}$, and $R^{6i}$ is independently alkyl, cycloalkyl, —$N^{14}R^{15}$, —$OR^{16}$, —$SR^{17}$, —$C(O)NR^{14}R^{15}$, —$NHC(O)R^{14}R^{15}$, —CN, —$C(O)OR^{18}$, —$S(O)_2R^{19}$, —$NHS(O)_2R^{19}$, each of which is unsubstituted or substituted, or hydrogen or halogen; or $R^{6h}$ and $R^{6i}$ together with the carbon atoms to which $R^{6h}$ and $R^{6i}$ are bound form a ring, wherein the ring is unsubstituted or substituted, and each of $R^{6a}$, $R^{6b}$, $R^{6c}$, $R^{6d}$, $R^{6e}$, $R^{6f}$, and $R^{6g}$ is independently alkyl, cycloalkyl, —$N^{14}R^{15}$, —$OR^{16}$, —$SR^{17}$, —$C(O)NR^{14}R^{15}$, —$NHC(O)R^{14}R^{15}$, —CN, —$C(O)OR^{18}$, —$S(O)_2R^{19}$, —$NHS(O)_2R^{19}$, each of which is unsubstituted or substituted, or hydrogen or halogen.

In some embodiments, when Q is not

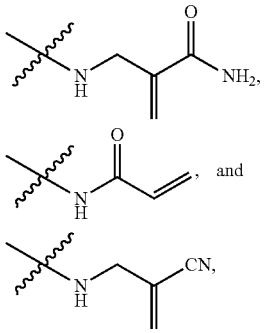

then R⁵ and R⁶ together with the carbon atoms to which R⁵ and R⁶ are bound form the ring, and compound has the structure:

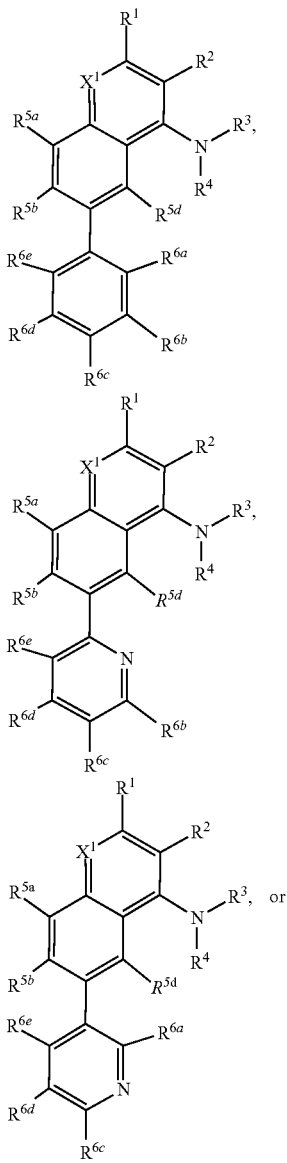

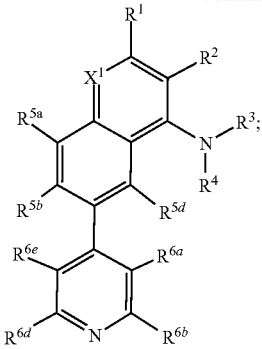

wherein:

$R^{5a}$, $R^{5b}$ and $R^{5d}$ are each independently aryl or heteroaryl, each of which is substituted or unsubstituted, or hydrogen or halogen; and each of $R^{6a}$, $R^{6b}$, $R^{6c}$, $R^{6d}$, and $R^{6e}$ is independently alkyl, cycloalkyl, —$N^{14}R^{15}$, —$OR^{16}$, —$SR^{17}$, —$C(O)NR^{14}R^{15}$, —$NHC(O)R^{14}R^{15}$, —CN, —C(O)$OR^{18}$, —$S(O)_2R^{19}$, —$NHS(O)_2R^{19}$, each of which is unsubstituted or substituted, or hydrogen or halogen; wherein at least one of $R^{6a}$, $R^{6b}$, $R^{6c}$, $R^{6d}$, and $R^{6e}$ is —$C(O)NR^{14}R^{15}$, $NR^{14}R^{15}$, or $NR^{14}C(O)R^{15}$, and each of $R^{14}$ and $R^{15}$ is alkyl, alkenyl, cycloalkyl, aryl, heterocyclyl, or heteroaryl, each of which is unsubstituted or substituted, or hydrogen; or $R^{14}$ and $R^{15}$ together with the nitrogen atom to which $R^{14}$ and $R^{15}$ are bound form a ring, wherein the ring is unsubstituted or substituted; and each of $R^{16}$, $R^{17}$, $R^{18}$ and $R^{19}$ is independently is alkyl, alkenyl, cycloalkyl, aryl, heteroaryl or heterocyclyl, each of which is unsubstituted or substituted, or hydrogen or halogen;

or a pharmaceutically-acceptable salt thereof.

In some embodiments, $X^1$ is $CR^7$. In some embodiments, $X^1$ is N. In some embodiments, $R^7$ is H.

In some embodiments, $R^1$ is H. In some embodiments, $R^1$ is —$C(O)NR^8R^9$, —$OR^{10}$, or CN, each of which is unsubstituted or substituted.

In some embodiments, $R^2$ is H. In some embodiments, $R^2$ is —$OR^{10}$. In some embodiments, $R^2$ is halogen. In some embodiments, $R^2$ is —$C(O)NH_2$.

In some embodiments, Q is $NR^3R^4$, wherein $R^3$ is hydrogen.

In some embodiments, Q is $NR^3R^4$, wherein one or both of $R^3$ and $R^4$ is

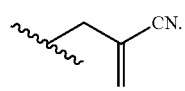 [SMILES: *CC(=C)C#N]

In some embodiments, the present disclosure provides a compound of the formula:

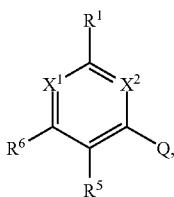

wherein:
X$^1$ is CR$^7$ or N;
X$^2$ is CR$^2$ or N;
each of R$^1$ and R$^2$ is independently alkyl, —NR$^8$R$^9$, —C(O)NR$^8$R$^9$, —NR$^8$C(O)R$^9$, —OR$^{10}$, —SR$^{11}$, —C(O)R$^{12}$, —C(O)OR$^{12}$, —S(O)$_2$R$^{13}$, CN, each of which is unsubstituted or substituted, or hydrogen or halogen;
Q is

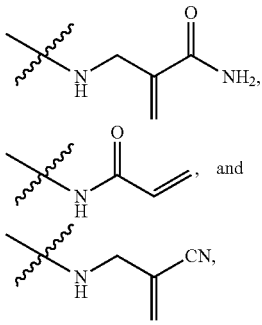

or NR$^3$R$^4$, wherein each of R$^3$ and R$^4$ is independently alkyl, cycloalkyl, alkenyl, —C(O)R$^{13}$, —C(O)OR$^{13}$, —S(O)$_2$R$^{13}$, —S(O)$_2$R$^{13}$, each of which is unsubstituted or substituted; or hydrogen, or R$^3$ and R$^4$ together with the nitrogen atom to which R$^3$ and R$^4$ are bound form a ring, wherein the ring is unsubstituted or substituted;
R$^7$ is alkyl, alkenyl, cycloalkyl, aryl, heteroaryl or heterocyclyl, each of which is unsubstituted or substituted, or hydrogen or halogen;
each of R$^8$ and R$^9$ is alkyl, alkenyl, cycloalkyl, aryl, heterocyclyl, heteroaryl, each of which is unsubstituted or substituted, or hydrogen; or R$^8$ and R$^9$ together with the nitrogen atom to which R$^8$ and R$^9$ are bound form a ring, wherein the ring is unsubstituted or substituted;
each of R$^{10}$, R$^{11}$, R$^{12}$ and R$^{13}$ is independently is alkyl, alkenyl, cycloalkyl, aryl, heteroaryl or heterocyclyl, each of which is unsubstituted or substituted, or hydrogen or halogen;
provided that:
(i) when Q is

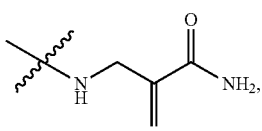 [SMILES: *NCC(=C)C(N)=O]

then each of R$^5$ and R$^6$ is independently aryl or heteroaryl, each of which is unsubstituted or substituted, or hydrogen or halogen; or R$^5$ and R$^6$ together with the carbon atoms to which R$^5$ and R$^6$ are bound form a ring, wherein the ring is unsubstituted or substituted;

(ii) when Q is

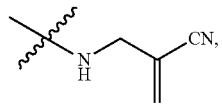 [SMILES: *NCC(=C)C#N]

then R$^5$ and R$^6$ together with the carbon atoms to which R$^5$ and R$^6$ are bound form the ring, wherein the ring is unsubstituted or substituted;

(iii) when Q is

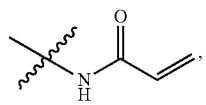

then:
(a) R$^5$ is hydrogen or halogen, and R$^6$ is

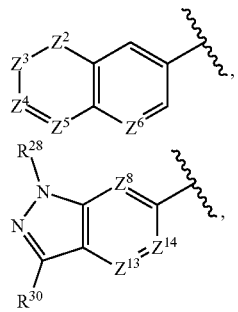

wherein
Z$^2$ is N or CH;
Z$^3$ is N or CR$^{22}$;
Z$^4$ is N or CR$^{23}$;
Z$^5$ is N or CR$^{24}$;
Z$^6$ is N or CR$^{25}$;
Z$^8$ is N or CR$^{27}$;
Z$^{13}$ is N or CR$^{32}$; and
Z$^{14}$ is N or CR$^{33}$,
wherein each of R$^{22}$, R$^{23}$, R$^{24}$, R$^{25}$, R$^{27}$, R$^{28}$, R$^{29}$, R$^{30}$, R$^{32}$, and R$^{33}$ is independently, alkyl, heteroaryl, —NR$^{14}$R$^{15}$, —C(O)NR$^{14}$R$^{15}$, —NR$^{14}$C(O)R$^{15}$, —OR$^{16}$, —SR$^{17}$, —C(O)R$^{18}$, —C(O)OR$^{18}$, —S(O)$_2$R$^{19}$, or —CN, each of which is unsubstituted or substituted, or hydrogen or halogen; or (b) R$^5$ and R$^6$ together with the carbon atoms to which R$^5$ and R$^6$ are bound form the ring, and the compound has the structure:

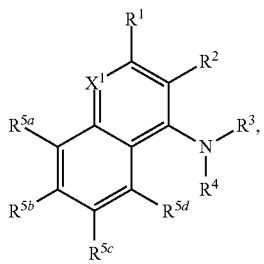

wherein $R^{5a}$, $R^{5b}$ and $R^{5d}$ are each independently aryl or heteroaryl, each of which is substituted or unsubstituted, or hydrogen or halogen, and $R^{5c}$ is

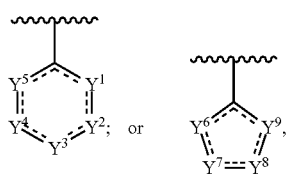

wherein each of ------ is independently a single bond or a double bond;

$Y^1$ is $CR^{6a}$, N, $NR^{6a}$, O or S;
$Y^2$ is $CR^{6b}$, N, $NR^{6b}$, O or S;
$Y^3$ is $CR^{6c}$, N, $NR^{6c}$, O or S;
$Y^4$ is $CR^{6d}$, N, $NR^{6d}$, O or S;
$Y^5$ is $CR^{6e}$, N, $NR^{6e}$, O or S;
$Y^6$ is $CR^{6f}$, N, $NR^{6f}$, O or S;
$Y^7$ is $CR^{6g}$, N, $NR^{6g}$, O or S;
$Y^8$ is $CR^{6h}$, N, $NR^{6h}$, O or S; and
$Y^9$ is $CR^{6i}$, N, $NR^{6i}$, O or S, wherein each of $R^{6a}$, $R^{6b}$, $R^{6c}$, $R^{6d}$, $R^{6e}$, $R^{6f}$, $R^{6g}$, $R^{6h}$ and $R^{6i}$ is independently alkyl, cycloalkyl, $-N^{14}R^{15}$, $-OR^{16}$, $-SR^{17}$, $-C(O)NR^{14}R^{15}$, $-NHC(O)R^{14}R^{15}$, $-CN$, $-C(O)OR^{18}$, $-S(O)_2R^{19}$, $-NHS(O)_2R^{19}$, each of which is unsubstituted or substituted, or hydrogen or halogen; or $R^{6a}$ and $R^{6b}$ together with the carbon atoms to which $R^{6a}$ and $R^{6b}$ are bound form a ring, wherein the ring is unsubstituted or substituted, and each of $R^{6c}$, $R^{6d}$, $R^{6e}$, $R^{6f}$, $R^{6g}$, $R^{6h}$ and $R^{6i}$ is independently alkyl, cycloalkyl, $-N^{14}R^{15}$, $-OR^{16}$, $-SR^{17}$, $-C(O)NR^{14}R^{15}$, $-NHC(O)R^{14}R^{15}$, $-CN$, $-C(O)OR^{18}$, $-S(O)_2R^{19}$, $-NHS(O)_2R^{19}$, each of which is unsubstituted or substituted, or hydrogen or halogen; or $R^{6b}$ and $R^{6c}$ together with the carbon atoms to which $R^{6b}$ and $R^{6c}$ are bound form a ring, wherein the ring is unsubstituted or substituted, and each of $R^{6a}$, $R^{6d}$, $R^{6e}$, $R^{6f}$, $R^{6g}$, $R^{6h}$ and $R^{6i}$ is independently alkyl, cycloalkyl, $-N^{14}R^{15}$, $-OR^{16}$, $-SR^{17}$, $-C(O)NR^{14}R^{15}$, $-NHC(O)R^{14}R^{15}$, $-CN$, $-C(O)OR^{18}$, $-S(O)_2R^{19}$, $-NHS(O)_2R^{19}$, each of which is unsubstituted or substituted, or hydrogen or halogen; or $R^{6c}$ and $R^{6d}$ together with the carbon atoms to which $R^{6c}$ and $R^{6d}$ are bound form a ring, wherein the ring is unsubstituted or substituted, and each of $R^{6a}$, $R^{6b}$, $R^{6e}$, $R^{6f}$, $R^{6g}$, $R^{6h}$ and $R^{6i}$ is independently alkyl, cycloalkyl, $-N^{14}R^{15}$, $-OR^{16}$, $-SR^{17}$, $-C(O)NR^{14}R^{15}$, $-NHC(O)R^{14}R^{15}$, $-CN$, $-C(O)OR^{18}$, $-S(O)_2R^{19}$, $-NHS(O)_2R^{19}$, each of which is unsubstituted or substituted, or hydrogen or halogen; or $R^{6d}$ and $R^{6e}$ together with the carbon atoms to which $R^{6d}$ and $R^{6e}$ are bound form a ring, wherein the ring is unsubstituted or substituted, and each of $R^{6a}$, $R^{6b}$, $R^{6c}$, $R^{6f}$, $R^{6g}$, $R^{6h}$ and $R^{6i}$ is independently alkyl, cycloalkyl, $-N^{14}R^{15}$, $-OR^{16}$, $-SR^{17}$, $-C(O)NR^{14}R^{15}$, $-NHC(O)R^{14}R^{15}$, $-CN$, $-C(O)OR^{18}$, $-S(O)_2R^{19}$, $-NHS(O)_2R^{19}$, each of which is unsubstituted or substituted, or hydrogen or halogen; or $R^{6f}$ and $R^{6g}$ together with the carbon atoms to which $R^{6f}$ and $R^{6g}$ are bound form a ring, wherein the ring is unsubstituted or substituted, and each of $R^{6a}$, $R^{6b}$, $R^{6c}$, $R^{6d}$, $R^{6e}$, $R^{6h}$ and $R^{6i}$ is independently alkyl, cycloalkyl, $-N^{14}R^{15}$, $-OR^{16}$, $-SR^{17}$, $-C(O)NR^{14}R^{15}$, $-NHC(O)R^{14}R^{15}$, $-CN$, $-C(O)OR^{18}$, $-S(O)_2R^{19}$, $-NHS(O)_2R^{19}$, each of which is unsubstituted or substituted, or hydrogen or halogen; or $R^{6g}$ and $R^{6h}$ together with the carbon atoms to which $R^{6g}$ and $R^{6h}$ are bound form a ring, wherein the ring is unsubstituted or substituted, and each of $R^{6a}$, $R^{6b}$, $R^{6c}$, $R^{6d}$, $R^{6e}$, $R^{6f}$, and $R^{6i}$ is independently alkyl, cycloalkyl, $-N^{14}R^{15}$, $-OR^{16}$, $-SR^{17}$, $-C(O)NR^{14}R^{15}$, $-NHC(O)R^{14}R^{15}$, $-CN$, $-C(O)OR^{18}$, $-S(O)_2R^{19}$, $-NHS(O)_2R^{19}$, each of which is unsubstituted or substituted, or hydrogen or halogen; or $R^{6h}$ and $R^{6i}$ together with the carbon atoms to which $R^{6h}$ and $R^{6i}$ are bound form a ring, wherein the ring is unsubstituted or substituted, and each of $R^{6a}$, $R^{6b}$, $R^{6c}$, $R^{6d}$, $R^{6e}$, $R^{6f}$, and $R^{6g}$ is independently alkyl, cycloalkyl, $-N^{14}R^{15}$, $-OR^{16}$, $-SR^{17}$, $-C(O)NR^{14}R^{15}$, $-NHC(O)R^{14}R^{15}$, $-CN$, $-C(O)OR^{18}$, $-S(O)_2R^{19}$, $-NHS(O)_2R^{19}$, each of which is unsubstituted or substituted, or hydrogen or halogen, and (iv) when Q is not

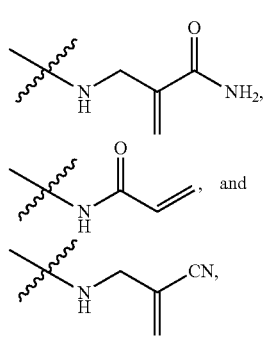

then $R^5$ and $R^6$ together with the carbon atoms to which $R^5$ and $R^6$ are bound form the ring, and compound has the structure:

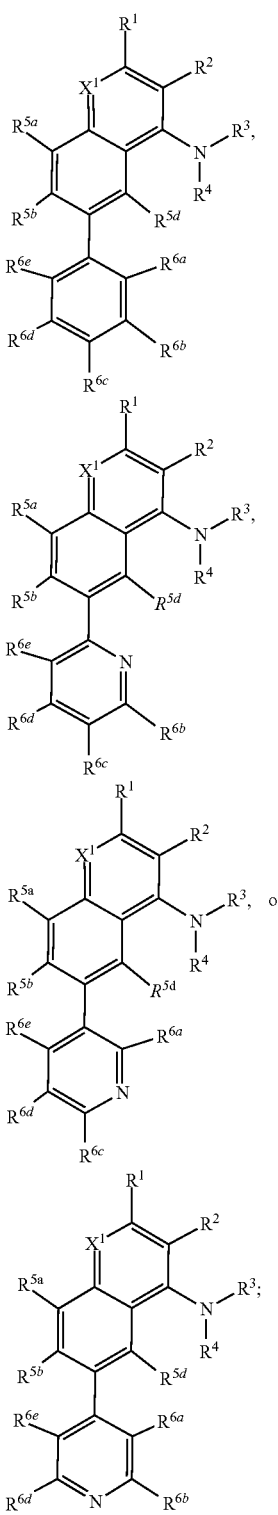

wherein:
R$^{5a}$, R$^{5b}$ and R$^{5d}$ are each independently aryl or heteroaryl, each of which is substituted or unsubstituted, or hydrogen or halogen; and
each of R$^{6a}$, R$^{6b}$, R$^{6c}$, R$^{6d}$, and R$^{6e}$ is independently alkyl, cycloalkyl, —N$^{14}$R$^{15}$, —OR$^{16}$, —SR$^{17}$, —C(O)NR$^{14}$R$^{15}$, —NHC(O)R$^{14}$R$^{15}$, —CN, —C(O)OR$^{18}$, —S(O)$_2$R$^{19}$, —NHS(O)$_2$R$^{19}$, each of which is unsubstituted or substituted, or hydrogen or halogen; wherein at least one of R$^{6a}$, R$^{6b}$, R$^{6c}$, R$^{6d}$, and R$^{6e}$ is —C(O)NR$^{14}$R$^{15}$, NR$^{14}$R$^{15}$, or NR$^{14}$C(O)R$^{15}$, and each of R$^{14}$ and R$^{15}$ is alkyl, alkenyl, cycloalkyl, aryl, heterocyclyl, or heteroaryl, each of which is unsubstituted or substituted, or hydrogen; or R$^{14}$ and R$^{15}$ together with the nitrogen atom to which R$^{14}$ and R$^{15}$ are bound form a ring, wherein the ring is unsubstituted or substituted; and each of R$^{16}$, R$^{17}$, R$^{18}$ and R$^{19}$ is independently is alkyl, alkenyl, cycloalkyl, aryl, heteroaryl or heterocyclyl, each of which is unsubstituted or substituted, or hydrogen or halogen;

or a pharmaceutically-acceptable salt thereof.

In some embodiments, the compound has the formula:

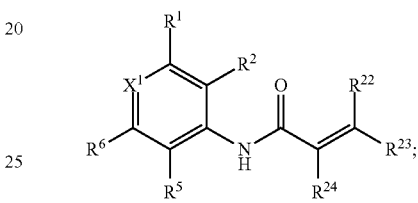

wherein each of R$^{22}$, R$^{23}$, and R$^{24}$ is independently alkyl, which is unsubstituted or substituted, or hydrogen, or halogen.

In some embodiments, the compound has the formula:

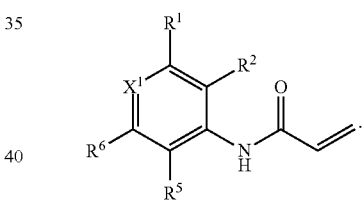

In some embodiments, the compound has the formula:

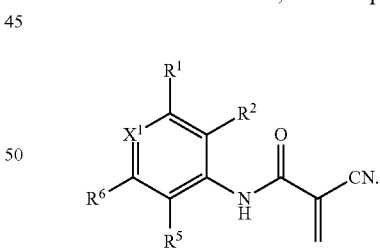

In some embodiments, the compound has the formula:

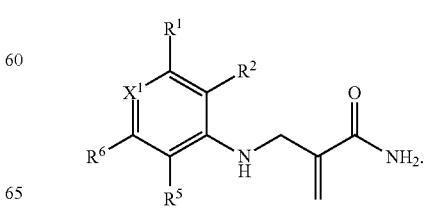

In some embodiments, the compound has the formula:

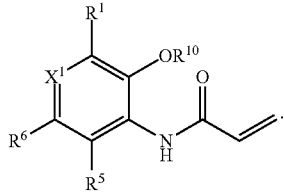

In some embodiments, the compound has the formula:

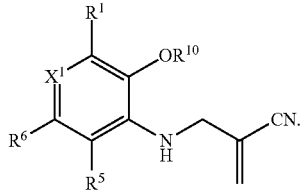

In some embodiments, the compound has the formula:

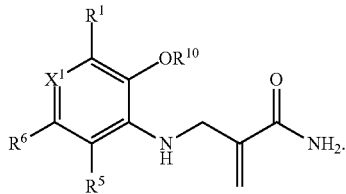

In some embodiments, the compound has the formula:

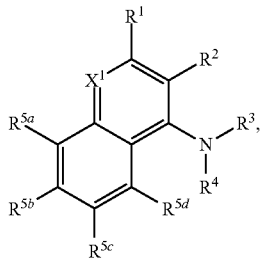

wherein
$R^{5a}$, $R^{5b}$, $R^{5c}$, and $R^{5d}$ are each independently aryl or heteroaryl, each of which is substituted or unsubstituted, or hydrogen or halogen.

In some embodiments, at least one of $R^{5a}$, $R^{5b}$, $R^{5c}$, and $R^{5d}$ is

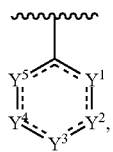

wherein
each of ====== is independently a single bond or a double bond;
$Y^1$ is $CR^{6a}$, N, $NR^{6a}$, O or S;
$Y^2$ is $CR^{6b}$, N, $NR^{6b}$, O or S;
$Y^3$ is $CR^{6c}$, N, $NR^{6c}$, O or S;
$Y^4$ is $CR^{6d}$, N, $NR^{6d}$, O or S;
$Y^5$ is $CR^{6e}$, N, $NR^{6e}$, O or S;
wherein
each of $R^{6a}$, $R^{6b}$, $R^{6c}$, $R^{6d}$, and $R^{6e}$ is independently alkyl, cycloalkyl, —$NR^{14}R^{15}$, —$OR^{16}$, —$SR^{17}$, —$C(O)NR^{14}R^{15}$, —$NHC(O)R^{14}R^{15}$, —CN, —$C(O)OR^{18}$, —$S(O)_2R^{19}$, —$NHS(O)_2R^{19}$, each of which is unsubstituted or substituted, or hydrogen or halogen; or $R^{6a}$ and $R^{6b}$ together with the carbon atoms to which $R^{6a}$ and $R^{6b}$ are bound form a ring, wherein the ring is unsubstituted or substituted, and each of $R^{6c}$, $R^{6d}$, and $R^{6e}$ is independently alkyl, cycloalkyl, —$NR^{14}R^{15}$, —$OR^{16}$, —$SR^{17}$, —$C(O)NR^{14}R^{15}$, —$NHC(O)R^{14}R^{15}$, —CN, —$C(O)OR^{18}$, —$S(O)_2R^{19}$, —$NHS(O)_2R^{19}$, each of which is unsubstituted or substituted, or hydrogen or halogen; or $R^{6b}$ and $R^{6c}$ together with the carbon atoms to which $R^{6b}$ and $R^{6c}$ are bound form a ring, wherein the ring is unsubstituted or substituted; and each of $R^{6a}$, $R^{6d}$, and $R^{6e}$ is independently alkyl, cycloalkyl, —$NR^{14}R^{15}$, —$OR^{16}$, —$SR^{17}$, —$C(O)NR^{14}R^{15}$, —$NHC(O)R^{14}R^{15}$, —CN, —$C(O)OR^{18}$, —$S(O)_2R^{19}$, —$NHS(O)_2R^{19}$, each of which is unsubstituted or substituted, or hydrogen or halogen; or $R^{6c}$ and $R^{6d}$ together with the carbon atoms to which $R^{6c}$ and $R^{6d}$ are bound form a ring, wherein the ring is unsubstituted or substituted, and each of $R^{6a}$, $R^{6b}$, $R^{6d}$, and $R^{6e}$ is independently alkyl, cycloalkyl, —$NR^{14}R^{15}$, —$OR^{16}$, —$SR^{17}$, —$C(O)NR^{14}R^{15}$, —$NHC(O)R^{14}R^{15}$, —CN, —$C(O)OR^{18}$, —$S(O)_2R^{19}$, —$NHS(O)_2R^{19}$, each of which is unsubstituted or substituted, or hydrogen or halogen; or $R^{6d}$ and $R^{6e}$ together with the carbon atoms to which $R^{6d}$ and $R^{6e}$ are bound form a ring, wherein the ring is unsubstituted or substituted, and each of $R^{6a}$, $R^{6b}$, $R^{6c}$, and $R^{6d}$ is independently alkyl, cycloalkyl, —$NR^{14}R^{15}$, —$OR^{16}$, —$SR^{17}$, —$C(O)NR^{14}R^{15}$, —$NHC(O)R^{14}R^{15}$, —CN, —$C(O)OR^{18}$, —$S(O)_2R^{19}$, —$NHS(O)_2R^{19}$, each of which is unsubstituted or substituted, or hydrogen or halogen.

In some embodiments, at least one of $R^{5a}$, $R^{5b}$, $R^{5c}$, and $R^{5d}$ is

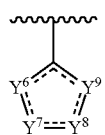

wherein
each of ====== is independently a single bond or a double bond;
$Y^6$ is $CR^{6f}$, N, $NR^{6f}$, O or S;
$Y^7$ is $CR^{6g}$, N, $NR^{6ga}$, O or S;
$Y^8$ is $CR^{6h}$, N, $NR^{6h}$, O or S; and
$Y^9$ is $CR^{6i}$, N, $NR^{6i}$, O or S;

wherein
each of $R^{6f}$, $R^{6g}$, $R^{6h}$, and $R^{6i}$ is independently alkyl, cycloalkyl, —$NR^{14}R^{15}$, —$OR^{16}$, —$SR^{17}$, —$C(O)NR^{14}R^{15}$, —$NHC(O)R^{14}R^{15}$, —CN, —$C(O)OR^{18}$, —$S(O)_2R^{19}$, —$NHS(O)_2R^{19}$, each of which is unsubstituted or substituted, or hydrogen or halogen; or $R^{6f}$ and $R^{6g}$ together with the carbon atoms to which $R^{6f}$ and $R^{6g}$ are bound form a ring, wherein the ring is unsubstituted or substituted, and each of $R^{6h}$ and $R^{6i}$ is independently alkyl, cycloalkyl, —$NR^{14}R^{15}$, —$OR^{16}$, —$SR^{17}$, —$C(O)NR^{14}R^{15}$, —$NHC(O)R^{14}R^{15}$, —CN, —$C(O)OR^{18}$, —$S(O)_2R^{19}$, —$NHS(O)_2R^{19}$, each of which is unsubstituted or substituted, or hydrogen or halogen; or $R^{6g}$ and $R^{6h}$ together with the carbon atoms to which $R^{6g}$ and $R^{6h}$ are bound form a ring, wherein the ring is unsubstituted or substituted, and each of $R^{6f}$ and $R^{6i}$ is independently alkyl, cycloalkyl, —$NR^{14}R^{15}$, —$OR^{16}$, —$SR^{17}$, —$C(O)NR^{14}R^{15}$, —$NHC(O)R^{14}R^{15}$, —CN, —$C(O)OR^{18}$, —$S(O)_2R^{19}$, —$NHS(O)_2R^{19}$, each of which is unsubstituted or substituted, or hydrogen or halogen; or $R^{6h}$ and $R^{6i}$ together with the carbon atoms to which $R^{6h}$ and $R^{6i}$ are bound form a ring, wherein the ring is unsubstituted or substituted, and each of $R^{6f}$, and $R^{6g}$ is independently alkyl, cycloalkyl, —$NR^{14}R^{15}$, —$OR^{16}$, —$SR^{17}$, —$C(O)NR^{14}R^{15}$, —$NHC(O)R^{14}R^{15}$, —CN, —$C(O)OR^{18}$, —$S(O)_2R^{19}$, —$NHS(O)_2R^{19}$, each of which is unsubstituted or substituted, or hydrogen or halogen.

In some embodiments, the compound has the formula:

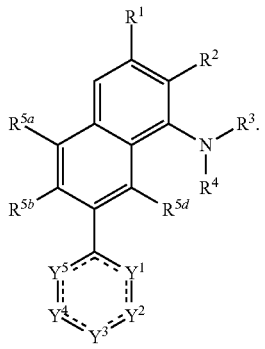

In some embodiments, the compound has the formula:

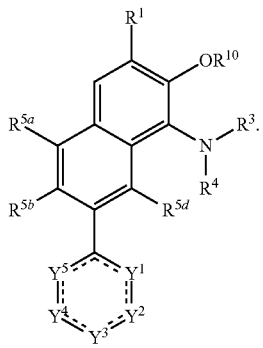

In some embodiments, the compound has the formula:

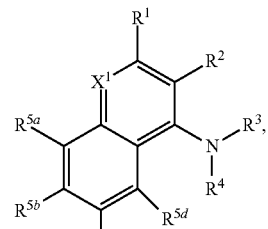

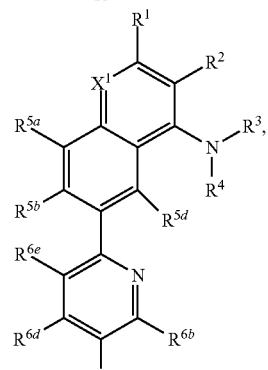

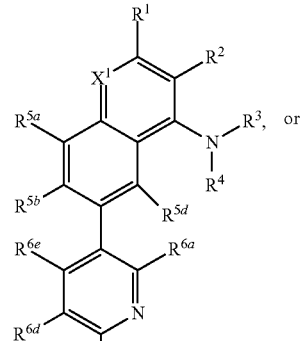, or

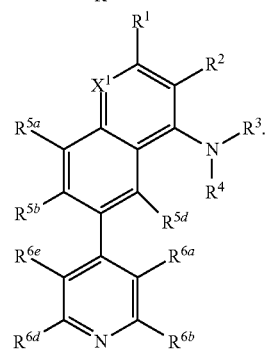

In some embodiments, at least one of $R^{6a}$, $R^{6b}$, $R^{6c}$, $R^{6d}$ and $R^{6e}$ is —$C(O)NR^{14}R^{15}$, —$NR^{14}C(O)R^{15}$, or —$NR^{14}R^{15}$. In some embodiments, $R^{6b}$ is —$C(O)NR^{14}R^{15}$. In some embodiments, $R^{6b}$ is —$NR^{14}R^{15}$. In some embodiments, $R^{6b}$ is —$NR^{14}C(O)R^{15}$.

In some embodiments, the compound has the formula:

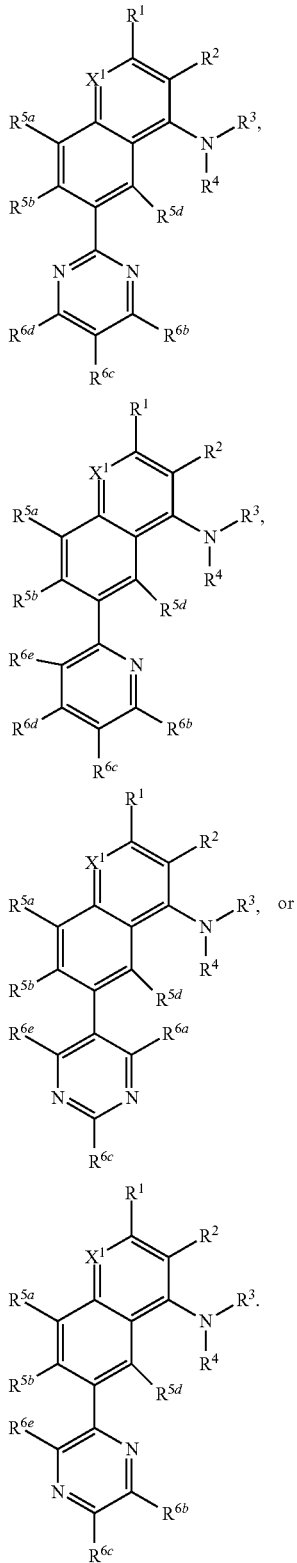

In some embodiments, at least one of $R^{6a}$, $R^{6b}$, $R^{6c}$, $R^{6d}$ and $R^{6e}$ is —C(O)NR$^{14}$R$^{15}$, —NR$^{14}$C(O)R$^{15}$, or —NR$^{14}$R$^{15}$. In some embodiments, $R^{6b}$ is —C(O)NR$^{14}$R$^{15}$.

In some embodiments, $R^{6b}$ is —NR$^{14}$R$^{15}$. In some embodiments, $R^{6b}$ is —NR$^{14}$C(O)R$^{15}$.

In some embodiments, the compound has the formula:

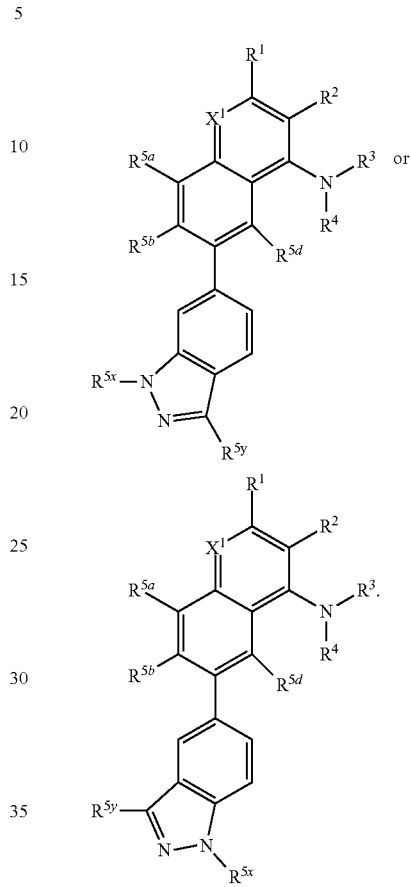

wherein each of $R^{5x}$ and $R^{5y}$ is each independently alkyl, alkyl, cycloalkyl, —N$^{14}$R$^{15}$, —OR$^{16}$, —SR$^{17}$, —C(O)NR$^{14}$R$^{15}$, —NHC(O)R$^{14}$R$^{15}$, —CN, —C(O)OR$^{18}$, —S(O)$_2$R$^{19}$, —NHS(O)$_2$R$^{19}$, each of which is unsubstituted or substituted, or hydrogen or halogen. In some embodiments, $R^{5x}$ or $R^{5y}$ is —C(O)NR$^{14}$R$^{15}$. In some embodiments, $R^{5x}$ or $R^{5y}$ is —NR$^{14}$R$^{15}$. In some embodiments, $R^{5x}$ or $R^{5y}$ is —NR$^{14}$C(O)R$^{15}$.

In some embodiments, the compound has the structure:

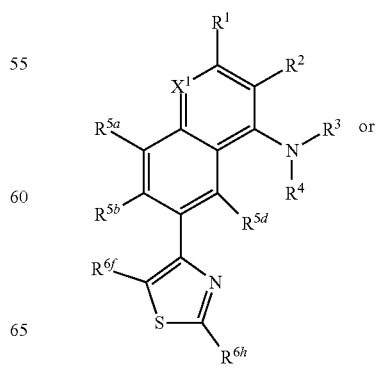

-continued

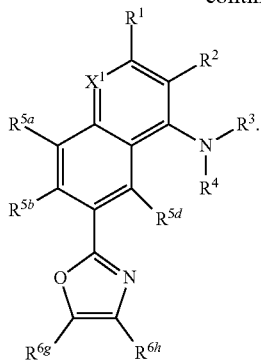

In some embodiments, $R^{6f}$, $R^{6g}$, or $R^{6h}$ is —C(O)NR$^{14}$R$^{15}$. In some embodiments, $R^{6f}$, $R^{6g}$, or $R^{6h}$ is —NR$^{14}$R$^{15}$. In some embodiments, $R^{6f}$, $R^{6g}$, or $R^{6h}$ is —NR$^{14}$C(O)R$^{15}$.

In some embodiments, the compound has the formula:

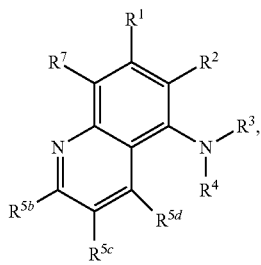

wherein $R^{5b}$, $R^{5c}$, and $R^{5d}$ are each independently aryl, heteroaryl, each of which is substituted or unsubstituted, or hydrogen or halogen.

In some embodiments, the compound has the formula:

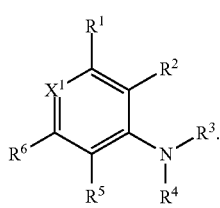

In some embodiments, at least one of $R^{5a}$, $R^{5b}$, $R^{5c}$, and $R^{5d}$ is

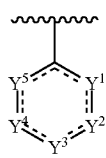

wherein
each of ====== is independently a single bond or a double bond;
$Y^1$ is CR$^{6a}$, N, NR$^{6a}$, O or S;
$Y^2$ is CR$^{6b}$, N, NR$^{6b}$, O or S;
$Y^3$ is CR$^{6c}$, N, NR$^{6c}$, O or S;
$Y^4$ is CR$^{6d}$, N, NR$^{6d}$, O or S;
$Y^5$ is CR$^{6e}$, N, NR$^{6e}$, O or S;
wherein
each of $R^{6a}$, $R^{6b}$, $R^{6c}$, $R^{6d}$, and $R^{6e}$ is independently alkyl, cycloalkyl, —NR$^{14}$R$^{15}$, —OR$^{16}$, —SR$^{17}$, —C(O)NR$^{14}$R$^{15}$, —NHC(O)R$^{14}$R$^{15}$, —CN, —C(O)OR$^{18}$, —S(O)$_2$R$^{19}$, —NHS(O)$_2$R$^{19}$, each of which is unsubstituted or substituted, or hydrogen or halogen; or $R^{6a}$ and $R^{6b}$ together with the carbon atoms to which $R^{6a}$ and $R^{6b}$ are bound form a ring, wherein the ring is unsubstituted or substituted, and each of $R^{6c}$, $R^{6d}$, and $R^{6e}$ is independently alkyl, cycloalkyl, —NR$^{14}$R$^{15}$, —OR$^{16}$, —SR$^{17}$, —C(O)NR$^{14}$R$^{15}$, —NHC(O)R$^{14}$R$^{15}$, —CN, —C(O)OR$^{18}$, —S(O)$_2$R$^{19}$, —NHS(O)$_2$R$^{19}$, each of which is unsubstituted or substituted, or hydrogen or halogen; or $R^{6b}$ and $R^{6c}$ together with the carbon atoms to which $R^{6b}$ and $R^{6c}$ are bound form a ring, wherein the ring is unsubstituted or substituted; and each of $R^{6a}$, $R^{6d}$, and $R^{6e}$ is independently alkyl, cycloalkyl, —NR$^{14}$R$^{15}$, —OR$^{16}$, —SR$^{17}$, —C(O)NR$^{14}$R$^{15}$, —NHC(O)R$^{14}$R$^{15}$, —CN, —C(O)OR$^{18}$, —S(O)$_2$R$^{19}$, —NHS(O)$_2$R$^{19}$, each of which is unsubstituted or substituted, or hydrogen or halogen; or $R^{6c}$ and $R^{6d}$ together with the carbon atoms to which $R^{6c}$ and $R^{6d}$ are bound form a ring, wherein the ring is unsubstituted or substituted, and each of $R^{6a}$, $R^{6b}$, and $R^{6e}$ is independently alkyl, cycloalkyl, —NR$^{14}$R$^{15}$, —OR$^{16}$, —SR$^{17}$, —C(O)NR$^{14}$R$^{15}$, —NHC(O)R$^{14}$R$^{15}$, —CN, —C(O)OR$^{18}$, —S(O)$_2$R$^{19}$, —NHS(O)$_2$R$^{19}$, each of which is unsubstituted or substituted, or hydrogen or halogen; or $R^{6d}$ and $R^{6e}$ together with the carbon atoms to which $R^{6d}$ and $R^{6e}$ are bound form a ring, wherein the ring is unsubstituted or substituted, and each of $R^{6a}$, $R^{6b}$, and $R^{6c}$ is independently alkyl, cycloalkyl, —NR$^{14}$R$^{15}$, —OR$^{16}$, —SR$^{17}$, —C(O)NR$^{14}$R$^{15}$, —NHC(O)R$^{14}$R$^{15}$, —CN, —C(O)OR$^{18}$, —S(O)$_2$R$^{19}$, —NHS(O)$_2$R$^{19}$, each of which is unsubstituted or substituted, or hydrogen or halogen.

In some embodiments, at least one of $R^{5a}$, $R^{5b}$, $R^{5c}$, and $R^{5d}$ is

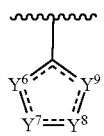

wherein
each of ====== is independently a single bond or a double bond;
$Y^6$ is CR$^{6f}$, N, NR$^{6f}$, O or S;
$Y^7$ is CR$^{6g}$, N, NR$^{6ga}$, O or S;
$Y^8$ is CR$^{6h}$, N, NR$^{6h}$, O or S; and
$Y^9$ is CR$^{6i}$, N, NR$^{6i}$, O or S;
wherein
each of $R^{6f}$, $R^{6g}$, $R^{6h}$, and $R^{6i}$ is independently alkyl, cycloalkyl, —NR$^{14}$R$^{15}$, —OR$^{16}$, —SR$^{17}$, —C(O)NR$^{14}$R$^{15}$, —NHC(O)R$^{14}$R$^{15}$, —CN, —C(O)

OR$^{18}$, —S(O)$_2$R$^{19}$, —NHS(O)$_2$R$^{19}$, each of which is unsubstituted or substituted, or hydrogen or halogen; or R$^{6f}$ and R$^{6g}$ together with the carbon atoms to which R$^{6f}$ and R$^{6g}$ are bound form a ring, wherein the ring is unsubstituted or substituted, and each of R$^{6h}$ and R$^{6i}$ is independently alkyl, cycloalkyl, —NR$^{14}$R$^{15}$, —OR$^{16}$, —SR$^{17}$, —C(O)NR$^{14}$R$^{15}$, —NHC(O)R$^{14}$R$^{15}$, —CN, —C(O)OR$^{18}$, —S(O)$_2$R$^{19}$, —NHS(O)$_2$R$^{19}$, each of which is unsubstituted or substituted, or hydrogen or halogen; or R$^{6g}$ and R$^{6h}$ together with the carbon atoms to which R$^{6g}$ and R$^{6h}$ are bound form a ring, wherein the ring is unsubstituted or substituted, and each of R$^{6f}$ and R$^{6i}$ is independently alkyl, cycloalkyl, —NR$^{14}$R$^{15}$, —OR$^{16}$, —SR$^{17}$, —C(O)NR$^{14}$R$^{15}$, —NHC(O)R$^{14}$R$^{15}$, —CN, —C(O)OR$^{18}$, —S(O)$_2$R$^{19}$, —NHS(O)$_2$R$^{19}$, each of which is unsubstituted or substituted, or hydrogen or halogen; or R$^{6h}$ and R$^{6i}$ together with the carbon atoms to which R$^{6h}$ and R$^{6i}$ are bound form a ring, wherein the ring is unsubstituted or substituted, and each of R$^{6f}$, and R$^{6g}$ is independently alkyl, cycloalkyl, —NR$^{14}$R$^{15}$, —OR$^{16}$, —SR$^{17}$, —C(O)NR$^{14}$R$^{15}$, —NHC(O)R$^{14}$R$^{15}$, —CN, —C(O)OR$^{18}$, —S(O)$_2$R$^{19}$, —NHS(O)$_2$R$^{19}$, each of which is unsubstituted or substituted, or hydrogen or halogen.

In some embodiments, the compound has the formula:

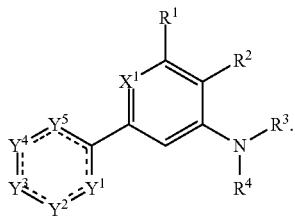

In some embodiments, the compound has the formula:

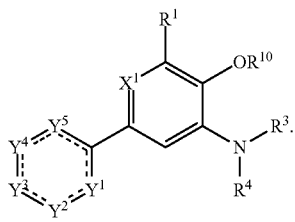

In some embodiments, the compound has the formula:

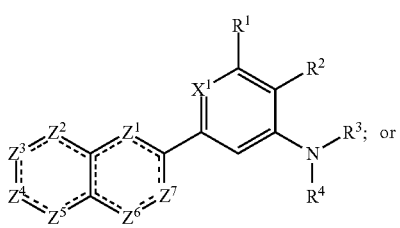

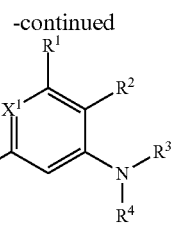

wherein
each of ------ is independently a single bond or a double bond;
Z$^1$ is N, NR$^{20}$, O, S or CR$^{20}$;
Z$^2$ is N, NR$^{21}$, O, S or CR$^{21}$;
Z$^3$ is N, NR$^{22}$, O, S or CR$^{22}$;
Z$^4$ is N, NR$^{23}$, O, S or CR$^{23}$;
Z$^5$ is N, NR$^{24}$, O, S or CR$^{24}$;
Z$^6$ is N, NR$^{25}$, O, S or CR$^{25}$;
Z$^7$ is N, NR$^{26}$, O, S or CR$^{26}$;
Z$^8$ is N, NR$^{27}$, O, S or CR$^{27}$;
Z$^9$ is N, NR$^{28}$, O, S or CR$^{28}$;
Z$^{10}$ is N, NR$^{29}$, O, S or CR$^{29}$;
Z$^{11}$ is N, NR$^{30}$, O, S or CR$^{30}$;
Z$^{12}$ is N, NR$^{31}$, O, S or CR$^{31}$;
Z$^{13}$ is N, NR$^{32}$, O, S or CR$^{32}$; and
Z$^{14}$ is N, NR$^{33}$, O, S or CR$^{33}$;
wherein each of R$^{20}$, R$^{21}$, R$^{22}$, R$^{23}$, R$^{24}$, R$^{25}$, R$^{26}$, R$^{27}$, R$^{28}$, R$^{29}$, R$^{30}$, R$^{31}$, R$^{32}$, and R$^{33}$, is independently, alkyl, heteroaryl, —NR$^{14}$R$^{15}$, —C(O)NR$^{14}$R$^{15}$, —NR$^{14}$C(O)R$^{15}$, —OR$^{16}$, —SR$^{17}$, —C(O)R$^{18}$, —C(O)OR$^{18}$, —S(O)$_2$R$^{19}$, or —CN, each of which is unsubstituted or substituted, or hydrogen or halogen.

In some embodiments, the compound has the formula:

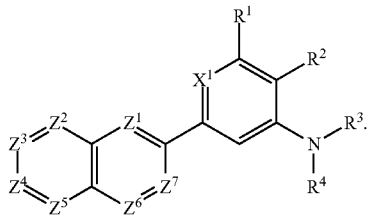

wherein
Z$^1$ is N or CR$^{20}$;
Z$^2$ is N or CR$^{21}$;
Z$^3$ is N or CR$^{22}$;
Z$^4$ is N or CR$^{23}$;
Z$^5$ is N or CR$^{24}$;
Z$^6$ is N or CR$^{25}$; and
Z$^7$ is N or CR$^{26}$.

In some embodiments, the compound has the formula:

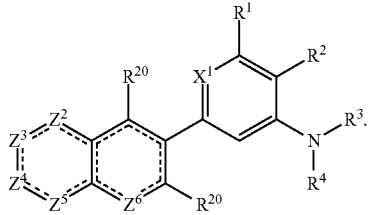

In some embodiments, $Z^1$ is $CR^{20}$, wherein $R^{20}$ is —C(O)NR$^{14}$R$^{15}$, —NR$^{14}$C(O)R$^{15}$, or —NR$^{14}$R$^{15}$. In some embodiments, $Z^2$ is $CR^{21}$, wherein $R^{21}$ is —C(O)NR$^{14}$R$^{15}$, —NR$^{14}$C(O)R$^{15}$, or —NR$^{14}$R$^{15}$. In some embodiments, $Z^3$ is $CR^{22}$, wherein $R^{22}$ is —C(O)NR$^{14}$R$^{15}$, —NR$^{14}$C(O)R$^{15}$, or —NR$^{14}$R$^{15}$. In some embodiments, $Z^4$ is $CR^{23}$, wherein $R^{23}$ is —C(O)NR$^{14}$R$^{15}$, —NR$^{14}$C(O)R$^{15}$, or —NR$^{14}$R$^{15}$. In some embodiments, $Z^5$ is $CR^{24}$, wherein $R^{24}$ is —C(O)NR$^{14}$R$^{15}$, —NR$^{14}$C(O)R$^{15}$, or —NR$^{14}$R$^{15}$. In some embodiments, $Z^3$ is N or $CR^{22}$, wherein $R^{22}$ is —C(O)NR$^{14}$R$^{15}$, —NR$^{14}$C(O)R$^{15}$, or —NR$^{14}$R$^{15}$. In some embodiments, $R^{20}$ is hydrogen. In some embodiments, $R^{26}$ is hydrogen.

In some embodiments, the compound has the formula:

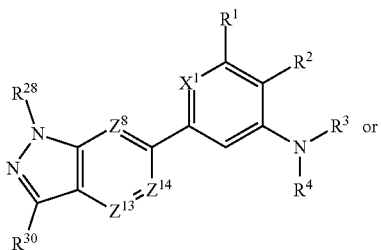 or

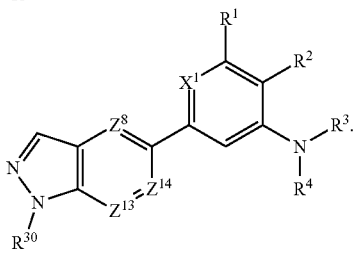

In some embodiments, $R^{27}$, $R^{28}$, $R^{29}$, $R^{30}$, $R^{32}$, or $R^{33}$ is —C(O)NR$^{14}$R$^{15}$. In some embodiments, $R^{27}$, $R^{28}$, $R^{29}$, $R^{30}$, $R^{32}$, or $R^{33}$ is —NR$^{14}$R$^{15}$. In some embodiments, $R^{27}$, $R^{28}$, $R^{29}$, $R^{30}$, $R^{32}$, or $R^{33}$ is —NR$^{14}$C(O)R$^{15}$.

In some embodiments, the compound has the formula:

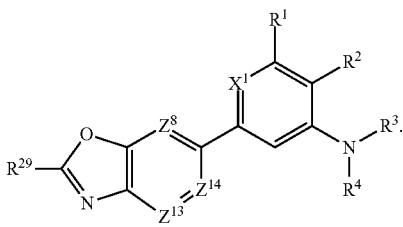

In some embodiments, the compound has the formula:

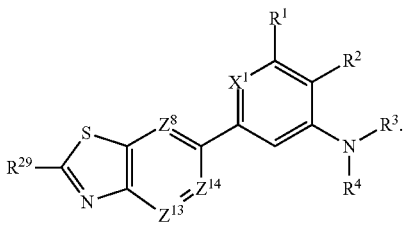

In some embodiments, the compound has the formula:

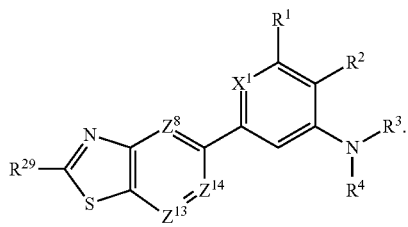

In some embodiments, $Z^8$ is $CR^{27}$, $Z^{13}$ is $CR^{32}$, and $Z^{14}$ is $CR^{33}$. In some embodiments, $Z^8$ is $CR^{27}$, $Z^{13}$ is $CR^{32}$, and $Z^{14}$ is N. In some embodiments, $Z^8$ is N, $Z^{13}$ is $CR^{32}$, and $Z^{14}$ is $CR^{33}$. In some embodiments, $Z^8$ is $CR^{27}$, $Z^{13}$ is N, and $Z^{14}$ is $CR^{33}$. In some embodiments, $Z^8$ is N, $Z^{13}$ is $CR^{32}$, and $Z^{14}$ is NR$^{33}$. In some embodiments, $Z^8$ is $CR^{27}$, $Z^{13}$ is N, and $Z^{14}$ is N. In some embodiments, $R^{27}$, $R^{29}$, $R^{32}$, or $R^{33}$ is —C(O)NR$^{14}$R$^{15}$. In some embodiments, $R^{27}$, $R^{29}$, $R^{32}$, or $R^{33}$ is —NR$^{14}$R$^{15}$. In some embodiments, $R^{27}$, $R^{29}$, $R^{32}$, or $R^{33}$ is —NR$^{14}$C(O)R$^{15}$.

In some embodiments, the compound has the formula:

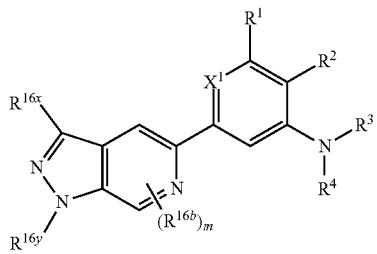

wherein
each $R^{16b}$ is independently alkyl, which is unsubstituted or substituted, or hydrogen or halogen;
each of $R^{16x}$ and $R^{16y}$ is independently alkyl, —NR$^{14}$R$^{15}$, —C(O)NR$^{14}$R$^{15}$, —NR$^{14}$C(O)R$^{15}$, or —R$^{16}$, each of which is unsubstituted or substituted, or hydrogen or halogen; and
m is independently 0, 1, or 2.

In some embodiments, the compound has the formula:

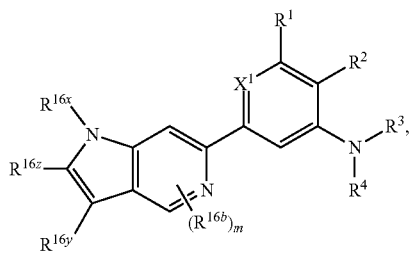

wherein
each $R^{16b}$ is independently alkyl, which is unsubstituted or substituted, or hydrogen or halogen;
each of $R^{16x}$, $R^{16y}$, and $R^{16z}$ is independently alkyl, —NR$^{14}$R$^{15}$, —C(O)NR$^{14}$R$^{15}$, —NR$^{14}$C(O)R$^{15}$, —OR$^{16}$, each of which is unsubstituted or substituted, or hydrogen or halogen; and
m is independently 0, 1, or 2.

In some embodiments, the compound has the formula:

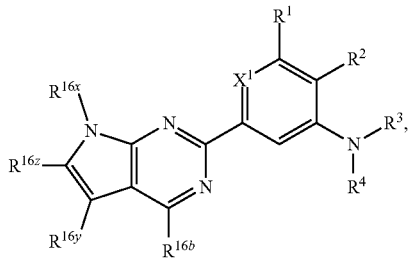

wherein
$R^{16b}$ is alkyl, which is unsubstituted or substituted, or hydrogen or halogen; and
each of $R^{16x}$, $R^{16y}$, and $R^{16z}$ is independently alkyl, —$NR^{14}R^{15}$, —$C(O)NR^{14}R^{15}$, —$NR^{14}C(O)R^{15}$, or —$OR^{16}$, each of which is unsubstituted or substituted, or hydrogen or halogen.

In some embodiments, the compound has the formula:

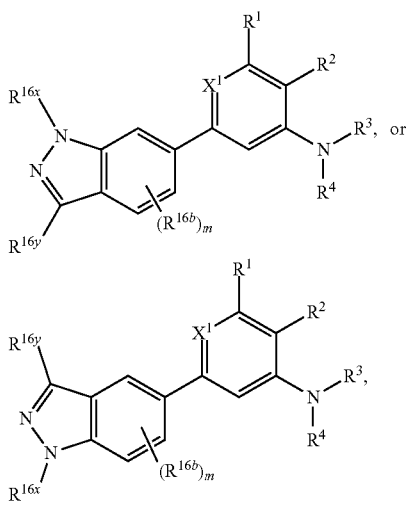

wherein
each of $R^{16a}$ and $R^{16b}$ is independently alkyl, which is unsubstituted or substituted, or hydrogen or halogen;
each of $R^{16x}$ and $R^{16y}$ is each independently alkyl, —$NR^{14}R^{15}$, —$C(O)NR^{14}R^{15}$, —$NR^{14}C(O)R^{15}$, —$OR^{16}$, each of which is unsubstituted or substituted, or hydrogen or halogen; and
m is independently 0, 1, 2, or 3; and
n is independently 0, 1, 2, or 3.

In some embodiments, the compound has the formula:

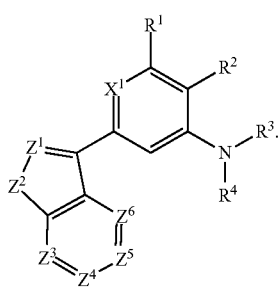

wherein
$Z^1$ is N or $CR^{20}$;
$Z^2$ is N, $NR^{21}$, O, S or $CR^{21}$;
$Z^3$ is N or $CR^{22}$;
$Z^4$ is N or $CR^{23}$;
$Z^5$ is N or $CR^{24}$; and
$Z^6$ is N or $CR^{25}$;
wherein each of $R^{20}$, $R^{21}$, $R^{22}$, $R^{23}$, $R^{24}$, and $R^{25}$ is independently, alkyl, heteroaryl, —$NR^{14}R^{15}$, —$C(O)NR^{14}R^{15}$, —$NR^{14}C(O)R^{15}$, —$OR^{16}$, —$SR^{17}$, —$C(O)R^{18}$, —$C(O)OR^{18}$, —$S(O)_2R^{19}$, or —CN, each of which is unsubstituted or substituted, or hydrogen or halogen.

In some embodiments, the compound has the formula:

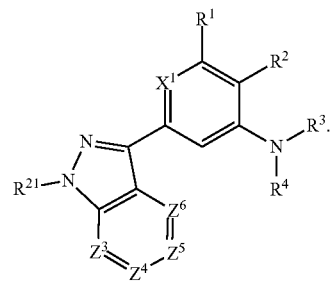

In some embodiments, the compound has the formula:

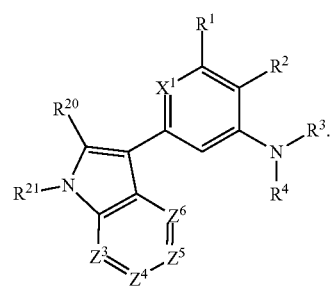

In some embodiments, $R^{21}$, $R^{22}$, $R^{23}$, $R^{24}$, or $R^{25}$ is —$C(O)NR^{14}R^{15}$. In some embodiments, $R^{21}$, $R^{22}$, $R^{23}$, $R^{24}$, or $R^{25}$ is —$NR^{14}R^{15}$. In some embodiments, $R^{21}$, $R^{22}$, $R^{23}$, $R^{24}$, or $R^{25}$ is —$NR^{14}C(O)R^{15}$. In some embodiments, $R^{20}$, $R^{21}$, $R^{22}$, $R^{23}$, $R^{24}$, or $R^{25}$ is —$C(O)NR^{14}R^{15}$. In some embodiments, $R^{20}$, $R^{21}$, $R^{22}$, $R^{23}$, $R^{24}$, or $R^{25}$ is —$NR^{14}R^{15}$. In some embodiments, $R^{20}$, $R^{21}$, $R^{22}$, $R^{23}$, $R^{24}$, or $R^{25}$ is —$NR^{14}C(O)R^{15}$. In some embodiments, 81-83, wherein $Z^3$ is $CR^{22}$, $Z^4$ is $CR^{23}$, $Z^5$ is $CR^{24}$, and $Z^6$ is $CR^{25}$. In some embodiments, $Z^3$ is N, $Z^4$ is $CR^{23}$, $Z^5$ is $CR^{24}$, and $Z^6$ is $CR^{25}$. In some embodiments, $Z^3$ is $CR^{22}$, $Z^4$ is N, $Z^5$ is $CR^{24}$, and $Z^6$ is $CR^{25}$. In some embodiments, $Z^3$ is $CR^{22}$, $Z^4$ is $CR^{23}$, $Z^5$ is N, and $Z^6$ is $CR^{25}$. In some embodiments, $Z^3$ is $CR^{22}$, $Z^4$ is $CR^{23}$, $Z^5$ is $CR^{24}$, and $Z^6$ is N. In some embodiments, $Z^3$ is N, $Z^4$ is $CR^{23}$, $Z^5$ is N, and $Z^6$ is $CR^{25}$. In some embodiments, $Z^3$ is N, $Z^4$ is $CR^{23}$, $Z^5$ is $CR^{24}$, and $Z^6$ is N. In some embodiments, $R^{14}$ is hydrogen. In some embodiments, —$NR^{14}C(O)R^{15}$ is

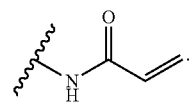

In some embodiments, $R^{15}$ is cycloalkyl which is unsubstituted or substituted. In some embodiments, $R^{15}$ is cycloalkyl substituted by —C(O)NR$^{20}$R$^{21}$, —NR$^{20}$C(O)R$^{21}$, or —NR$^{20}$R$^{21}$, wherein each of R$^{20}$ and R$^{21}$ is alkyl, alkenyl, cycloalkyl, aryl, heterocyclyl, heteroaryl, each of which is unsubstituted or substituted, or hydrogen; or R$^{20}$ and R$^{21}$ together with the nitrogen atom to which R$^{20}$ and R$^{21}$ are bound form a ring, wherein the ring is unsubstituted or substituted.

In some embodiments, $R^{15}$ is heteroaryl which is unsubstituted or substituted. In some embodiments, $R^{15}$ is heteroaryl substituted by —C(O)NR$^{20}$R$^{21}$, —NR$^{20}$C(O)R$^{21}$, or —NR$^{20}$R$^{21}$, wherein each of R$^{20}$ and R$^{21}$ is alkyl, alkenyl, cycloalkyl, aryl, heterocyclyl, heteroaryl, each of which is unsubstituted or substituted, or hydrogen; or R$^{20}$ and R$^{21}$ together with the nitrogen atom to which R$^{20}$ and R$^{21}$ are bound form a ring, wherein the ring is unsubstituted or substituted.

In some embodiments, $R^{15}$ is heterocyclyl which is unsubstituted or substituted. In some embodiments, $R^{15}$ is heterocyclyl substituted by —C(O)NR$^{20}$R$^{21}$, —NR$^{20}$C(O)R$^{21}$, or —NR$^{20}$R$^{21}$, wherein each of R$^{20}$ and R$^{21}$ is alkyl, alkenyl, cycloalkyl, aryl, heterocyclyl, heteroaryl, each of which is unsubstituted or substituted, or hydrogen; or R$^{20}$ and R$^{21}$ together with the nitrogen atom to which R$^{20}$ and R$^{21}$ are bound form a ring, wherein the ring is unsubstituted or substituted.

In some embodiments, $R^{15}$ is piperidinyl which is unsubstituted or substituted. In some embodiments, $R^{15}$ is

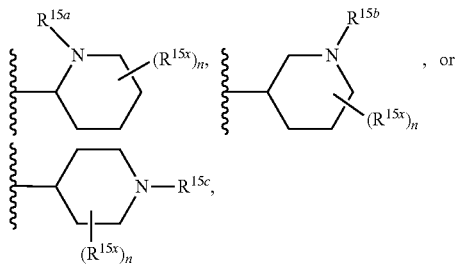

wherein
each of R$^{15a}$ R$^{15b}$, or R$^{15c}$ is independently alkyl which is unsubstituted or substituted, or hydrogen or halogen;
each of R$^{15x}$ is independently halogen or hydrogen; and
n is independently 0, 1, 2, 3, 4, 5, 6, 7, or 8.

In some embodiments, $R^6$ is aryl or heteroaryl substituted by $R^{15}$, wherein $R^{15}$ is piperidinyl which is unsubstituted or substituted. In some embodiments, $R^{15}$ is

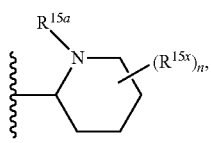

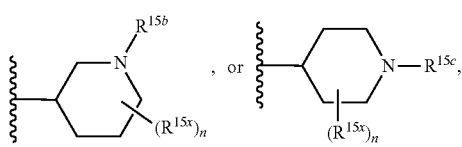

wherein
each of R$^{15a}$ R$^{15b}$, or R$^{15c}$ is independently alkyl which is unsubstituted or substituted, or hydrogen or halogen;
each of R$^{15x}$ is independently halogen or hydrogen; and
n is independently 0, 1, 2, 3, 4, 5, 6, 7, or 8.

In some embodiments, R$^{15a}$, R$^{15b}$, and R$^{15c}$ is methyl. In some embodiments, $R^{15}$ is an alkyl which is unsubstituted or substituted. In some embodiments, $R^{15}$ is an alkyl which is substituted with a heterocyclyl. In some embodiments, $R^{15}$ is an alkyl which is substituted with a morpholinyl or piperidinyl, each of which is substituted or unsubstituted. In some embodiments, $R^{15}$ is an alkyl which is substituted with an unsubstituted or substituted heteroaryl. In some embodiments, $R^{15}$ is an alkyl which is substituted with an unsubstituted or substituted imidazolyl.

In some embodiments, $R^{15}$ is piperidinyl that is unsubstituted or substituted. In some embodiments, $R^{15}$ is

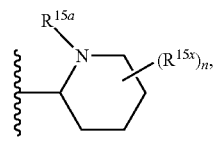

wherein R$^{15a}$ is independently alkyl that is unsubstituted or substituted, or hydrogen or halogen; each R$^{15x}$ is independently halogen or hydrogen; and n is independently 0, 1, 2, 3, 4, 5, 6, 7, or 8. In some embodiments, R$^{15b}$ is methyl. In some embodiments, $R^{15}$ is

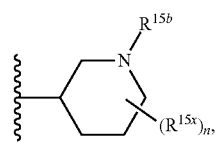

wherein each of R$^{15b}$ is independently alkyl that is unsubstituted or substituted, or hydrogen or halogen; each R$^{15x}$ is independently halogen or hydrogen; and n is independently 0, 1, 2, 3, 4, 5, 6, 7, or 8. In some embodiments, R$^{15b}$ is methyl. In some embodiments, $R^{15}$ is

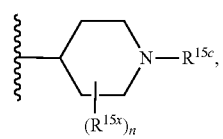

wherein each R$^{15c}$ is independently alkyl that is unsubstituted or substituted, or hydrogen or halogen; each R$^{15x}$ is independently halogen or hydrogen; and n is independently 0, 1, 2, 3, 4, 5, 6, 7, or 8. In some embodiments, R$^{15c}$ is methyl.

In some embodiments, $R^{15}$ is alkyl that is unsubstituted or substituted. In some embodiments, $R^{15}$ is alkyl that is substituted with a heterocyclyl group. In some embodiments, $R^{15}$ is alkyl that is substituted with a morpholinyl or piperidinyl group, each of which is substituted or unsubstituted. In some embodiments, $R^{15}$ is alkyl that is substituted with an unsubstituted or substituted heteroaryl group. In some embodiments, $R^{15}$ is alkyl that is substituted with an unsubstituted or substituted imidazolyl group.

In some embodiments, Q is $NR^3R^4$,
wherein $NR^3R^4$ is

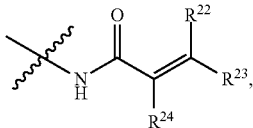

wherein each of $R^{22}$, $R^{23}$, and $R^{24}$ is independently alkyl, which is unsubstituted or substituted, or hydrogen, or halogen. In some embodiments, $NR^3R^4$ is

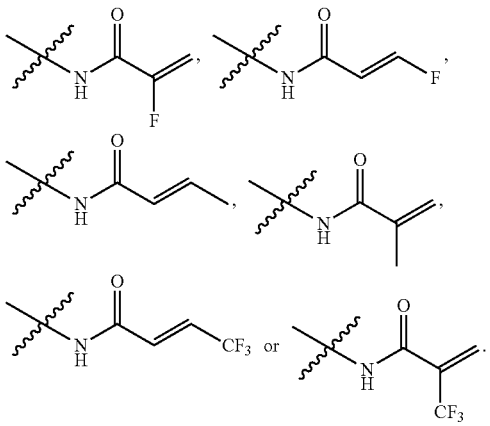

Several moieties described herein may be substituted or unsubstituted. Non-limiting examples of optional substituents include hydroxyl groups, sulfhydryl groups, halogens, amino groups, nitro groups, nitroso groups, cyano groups, azido groups, sulfoxide groups, sulfone groups, sulfonamide groups, carboxyl groups, carboxaldehyde groups, imine groups, alkyl groups, halo-alkyl groups, alkenyl groups, halo-alkenyl groups, alkynyl groups, halo-alkynyl groups, alkoxy groups, aryl groups, aryloxy groups, aralkyl groups, arylalkoxy groups, heterocyclyl groups, acyl groups, acyloxy groups, carbamate groups, amide groups, ureido groups, epoxy groups, and ester groups.

Non-limiting examples of alkyl and alkylene groups include straight, branched, and cyclic alkyl and alkylene groups. An alkyl or alkylene group can be, for example, a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ group that is substituted or unsubstituted.

Non-limiting examples of straight alkyl groups include methyl, ethyl, propyl, butyl, pentyl, hexyl, heptyl, octyl, nonyl, and decyl.

Branched alkyl groups include any straight alkyl group substituted with any number of alkyl groups. Non-limiting examples of branched alkyl groups include isopropyl, isobutyl, sec-butyl, and t-butyl.

Non-limiting examples of substituted alkyl groups includes hydroxymethyl, chloromethyl, trifluoromethyl, aminomethyl, 1-chloroethyl, 2-hydroxy ethyl, 1,2-difluoroethyl, and 3-carboxypropyl.

Non-limiting examples of cyclic alkyl groups include cyclopropyl, cyclobutyl, cyclopentyl, cyclohexyl, cycloheptlyl, and cyclooctyl groups. Cyclic alkyl groups also include fused-, bridged-, and spiro-bicycles and higher fused-, bridged-, and spiro-systems. A cyclic alkyl group can be substituted with any number of straight, branched, or cyclic alkyl groups. Non-limiting examples of cyclic alkyl groups include cyclopropyl, 2-methyl-cycloprop-1-yl, cycloprop-2-en-1-yl, cyclobutyl, 2,3-dihydroxycyclobut-1-yl, cyclobut-2-en-1-yl, cyclopentyl, cyclopent-2-en-1-yl, cyclopenta-2,4-dien-1-yl, cyclohexyl, cyclohex-2-en-1-yl, cycloheptyl, cyclooctanyl, 2,5-dimethylcyclopent-1-yl, 3,5-dichlorocyclohex-1-yl, 4-hydroxycyclohex-1-yl, 3,3,5-trimethylcyclohex-1-yl, octahydropentalenyl, octahydro-1H-indenyl, 3a,4,5,6,7,7a-hexahydro-3H-inden-4-yl, decahydroazulenyl, bicyclo-[2.1.1]hexanyl, bicyclo[2.2.1]heptanyl, bicyclo [3.1.1]heptanyl, 1,3-dimethyl[2.2.1]heptan-2-yl, bicyclo [2.2.2]octanyl, and bicyclo[3.3.3]undecanyl.

Non-limiting examples of alkenyl and alkenylene groups include straight, branched, and cyclic alkenyl groups. The olefin or olefins of an alkenyl group can be, for example, E, Z, cis, trans, terminal, or exo-methylene. An alkenyl or alkenylene group can be, for example, a $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ group that is substituted or unsubstituted. Non-limiting examples of alkenyl and alkenylene groups include ethenyl, prop-1-en-1-yl, isopropenyl, but-1-en-4-yl; 2-chloroethenyl, 4-hydroxybuten-1-yl, 7-hydroxy-7-methyloct-4-en-2-yl, and 7-hydroxy-7-methyl-oct-3,5-dien-2-yl.

Non-limiting examples of alkynyl or alkynylene groups include straight, branched, and cyclic alkynyl groups. The triple bond of an alkylnyl or alkynylene group can be internal or terminal. An alkylnyl or alkynylene group can be, for example, a $C_2$, $C_3$, $C_4$, $C_5$, $C_6$, $C_7$, $C_8$, $C9$, $C_{10}$, $Cn$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ group that is substituted or unsubstituted. Non-limiting examples of alkynyl or alkynylene groups include ethynyl, prop-2-yn-1-yl, prop-1-yn-1-yl, and 2-methyl-hex-4-yn-1-yl; 5-hydroxy-5-methylhex-3-yn-1-yl, 6-hydroxy-6-methylhept-3-yn-2-yl, and 5-hydroxy-5-ethylhept-3-yn-1-yl.

A halo-alkyl group can be any alkyl group substituted with any number of halogen atoms, for example, fluorine, chlorine, bromine, and iodine atoms. A halo-alkenyl group can be any alkenyl group substituted with any number of halogen atoms. A halo-alkynyl group can be any alkynyl group substituted with any number of halogen atoms.

An alkoxy group can be, for example, an oxygen atom substituted with any alkyl, alkenyl, or alkynyl group. An ether or an ether group comprises an alkoxy group. Non-limiting examples of alkoxy groups include methoxy, ethoxy, propoxy, isopropoxy, and isobutoxy.

An aryl group can be heterocyclic or non-heterocyclic. An aryl group can be monocyclic or polycyclic. An aryl group can be substituted with any number of substituents described herein, for example, hydrocarbyl groups, alkyl groups, alkoxy groups, and halogen atoms. Non-limiting examples of aryl groups include phenyl, toluyl, naphthyl, pyrrolyl, pyridyl, imidazolyl, thiophenyl, and furyl. Non-limiting examples of substituted aryl groups include 3,4-dimethylphenyl, 4-tert-butylphenyl, 4-cyclopropylphenyl, 4-diethylaminophenyl, 4-(trifluoromethyl)phenyl, 4-(difluoromethoxy)-phenyl, 4-(trifluoromethoxy)phenyl, 3-chlorophenyl, 4-chlorophenyl, 3,4-dichlorophenyl, 2-fluorophenyl, 2-chlorophenyl, 2-iodophenyl, 3-iodophenyl, 4-iodophenyl, 2-methylphenyl, 3-fluorophenyl, 3-methylphenyl, 3-methoxyphenyl, 4-fluorophenyl, 4-methylphenyl, 4-methoxyphenyl, 2,3-difluorophenyl, 3,4-difluorophenyl, 3,5-difluorophenyl, 2,3-dichlorophenyl, 3,4-dichlorophenyl, 3,5-dichlorophenyl, 2-hydroxyphenyl, 3-hydroxyphenyl, 4-hydroxyphenyl, 2-methoxyphenyl, 3-methoxyphenyl, 4-methoxyphenyl, 2,3-dimethoxyphenyl, 3,4-dimethoxyphenyl, 3,5-dimethoxyphenyl, 2,4-difluorophenyl, 2,5-difluorophenyl, 2,6-difluorophenyl, 2,3,4-trifluorophenyl, 2,3,5-trifluorophenyl, 2,3,6-trifluorophenyl, 2,4,5-trifluorophenyl, 2,4,6-trifluorophenyl, 2,4-dichlorophenyl, 2,5-dichlorophenyl, 2,6-dichlorophenyl, 3,4-dichlorophenyl, 2,3,4-trichlorophenyl, 2,3,5-trichlorophenyl, 2,3,6-trichlorophenyl, 2,4,5-trichlorophenyl, 3,4,5-trichlorophenyl, 2,4,6-trichlorophenyl, 2,3-dimethylphenyl, 2,4-dimethylphenyl, 2,5-dimethylphenyl, 2,6-dimethylphenyl, 2,3,4-trimethylphenyl, 2,3,5-trimethylphenyl, 2,3,6-trimethylphenyl, 2,4,5-trimethylphenyl, 2,4,6-trimethylphenyl, 2-ethylphenyl, 3-ethylphenyl, 4-ethylphenyl, 2,3-diethylphenyl, 2,4-diethylphenyl, 2,5-diethylphenyl, 2,6-diethylphenyl, 3,4-diethylphenyl, 2,3,4-triethylphenyl, 2,3,5-triethylphenyl, 2,3,6-triethylphenyl, 2,4,5-triethylphenyl, 2,4,6-triethylphenyl, 2-isopropylphenyl, 3-isopropylphenyl, and 4-isopropylphenyl, Non-limiting examples of substituted aryl groups include 2-aminophenyl, 2-(N-methylamino)phenyl, 2-(N,N-dimethylamino)phenyl, 2-(N-ethylamino)phenyl, 2-(N,N-diethylamino)phenyl, 3-aminophenyl, 3-(N-methylamino)phenyl, 3-(N,N-dimethylamino)phenyl, 3-(N-ethylamino)phenyl, 3-(N,N-diethylamino)phenyl, 4-aminophenyl, 4-(N-methylamino)phenyl, 4-(N,N-dimethylamino)phenyl, 4-(N-ethylamino)phenyl, and 4-(N,N-diethylamino)phenyl.

A heterocycle can be any ring containing a ring atom that is not carbon, for example, N, O, S, P, Si, B, or any other heteroatom. A heterocycle can be substituted with any number of substituents, for example, alkyl groups and halogen atoms. A heterocycle can be aromatic (heteroaryl) or non-aromatic. Non-limiting examples of heterocycles include pyrrole, pyrrolidine, pyridine, piperidine, succinamide, maleimide, morpholine, imidazole, thiophene, furan, tetrahydrofuran, pyran, and tetrahydropyran.

Non-limiting examples of heterocycles include: heterocyclic units having a single ring containing one or more heteroatoms, non-limiting examples of which include, diazirinyl, aziridinyl, azetidinyl, pyrazolidinyl, imidazolidinyl, oxazolidinyl, isoxazolinyl, thiazolidinyl, isothiazolinyl, oxathiazolidinonyl, oxazolidinonyl, hydantoinyl, tetrahydrofuranyl, pyrrolidinyl, morpholinyl, piperazinyl, piperidinyl, dihydropyranyl, tetrahydropyranyl, piperidin-2-onyl, 2,3,4,5-tetrahydro-1H-azepinyl, 2,3-dihydro-1H-indole, and 1,2,3,4-tetrahydroquinoline; and ii) heterocyclic units having 2 or more rings one of which is a heterocyclic ring, non-limiting examples of which include hexahydro-1H-pyrrolizinyl, 3a,4,5,6,7,7a-hexahydro-1H-benzo[d]imidazolyl, 3a,4,5,6,7,7a-hexahydro-1H-indolyl, 1,2,3,4-tetrahydroquinolinyl, and decahydro-1H-cycloocta[b]pyrrolyl.

Non-limiting examples of heteroaryl include: i) heteroaryl rings containing a single ring, non-limiting examples of which include, 1,2,3,4-tetrazolyl, [1,2,3]triazolyl, [1,2,4]triazolyl, triazinyl, thiazolyl, 1H-imidazolyl, oxazolyl, isoxazolyl, isothiazolyl, furanyl, thiophenyl, pyrimidinyl, 2-phenylpyrimidinyl, pyridinyl, 3-methylpyridinyl, and 4-dimethylaminopyridinyl; and ii) heteroaryl rings containing 2 or more fused rings one of which is a heteroaryl ring, non-limiting examples of which include: 7H-purinyl, 9H-purinyl, 6-amino-9H-purinyl, 5H-pyrrolo[3,2-d]pyrimidinyl, 7H-pyrrolo[2,3-d]pyrimidinyl, pyrido[2,3-d]pyrimidinyl, 4,5,6,7-tetrahydro-1H-indolyl, quinoxalinyl, quinazolinyl, quinolinyl, 8-hydroxy-quinolinyl, and isoquinolinyl.

Any compound herein can be purified. A compound herein can be least 1% pure, at least 2% pure, at least 3% pure, at least 4% pure, at least 5% pure, at least 6% pure, at least 7% pure, at least 8% pure, at least 9% pure, at least 10% pure, at least 11% pure, at least 12% pure, at least 13% pure, at least 14% pure, at least 15% pure, at least 16% pure, at least 17% pure, at least 18% pure, at least 19% pure, at least 20% pure, at least 21% pure, at least 22% pure, at least 23% pure, at least 24% pure, at least 25% pure, at least 26% pure, at least 27% pure, at least 28% pure, at least 29% pure, at least 30% pure, at least 31% pure, at least 32% pure, at least 33% pure, at least 34% pure, at least 35% pure, at least 36% pure, at least 37% pure, at least 38% pure, at least 39% pure, at least 40% pure, at least 41% pure, at least 42% pure, at least 43% pure, at least 44% pure, at least 45% pure, at least 46% pure, at least 47% pure, at least 48% pure, at least 49% pure, at least 50% pure, at least 51% pure, at least 52% pure, at least 53% pure, at least 54% pure, at least 55% pure, at least 56% pure, at least 57% pure, at least 58% pure, at least 59% pure, at least 60% pure, at least 61% pure, at least 62% pure, at least 63% pure, at least 64% pure, at least 65% pure, at least 66% pure, at least 67% pure, at least 68% pure, at least 69% pure, at least 70% pure, at least 71% pure, at least 72% pure, at least 73% pure, at least 74% pure, at least 75% pure, at least 76% pure, at least 77% pure, at least 78% pure, at least 79% pure, at least 80% pure, at least 81% pure, at least 82% pure, at least 83% pure, at least 84% pure, at least 85% pure, at least 86% pure, at least 87% pure, at least 88% pure, at least 89% pure, at least 90% pure, at least 91% pure, at least 92% pure, at least 93% pure, at least 94% pure, at least 95% pure, at least 96% pure, at least 97% pure, at least 98% pure, at least 99% pure, at least 99.1% pure, at least 99.2% pure, at least 99.3% pure, at least 99.4% pure, at least 99.5% pure, at least 99.6% pure, at least 99.7% pure, at least 99.8% pure, or at least 99.9% pure.

Pharmaceutical Compositions of the Disclosure.

A pharmaceutical composition of the disclosure can be used, for example, before, during, or after treatment of a subject with, for example, another pharmaceutical agent.

Subjects can be, for example, elderly adults, adults, adolescents, pre-adolescents, children, toddlers, infants, neonates, and non-human animals. In some embodiments, a subject is a patient.

A pharmaceutical composition of the disclosure can be a combination of any pharmaceutical compounds described herein with other chemical components, such as carriers, stabilizers, diluents, dispersing agents, suspending agents, thickening agents, and/or excipients. The pharmaceutical composition facilitates administration of the compound to an organism. Pharmaceutical compositions can be administered in therapeutically-effective amounts as pharmaceutical compositions by various forms and routes including, for example, intravenous, subcutaneous, intramuscular, oral, parenteral, ophthalmic, subcutaneous, transdermal, nasal, vaginal, and topical administration.

A pharmaceutical composition can be administered in a local manner, for example, via injection of the compound directly into an organ, optionally in a depot or sustained release formulation or implant. Pharmaceutical compositions can be provided in the form of a rapid release formulation, in the form of an extended release formulation, or in the form of an intermediate release formulation. A rapid release form can provide an immediate release. An extended release formulation can provide a controlled release or a sustained delayed release.

For oral administration, pharmaceutical compositions can be formulated by combining the active compounds with pharmaceutically-acceptable carriers or excipients. Such carriers can be used to formulate liquids, gels, syrups, elixirs, slurries, or suspensions, for oral ingestion by a subject. Non-limiting examples of solvents used in an oral dissolvable formulation can include water, ethanol, isopropanol, saline, physiological saline, DMSO, dimethylformamide, potassium phosphate buffer, phosphate buffer saline (PBS), sodium phosphate buffer, 4-2-hydroxyethyl-1-piperazineethanesulfonic acid buffer (HEPES), 3-(N-morpholino)propanesulfonic acid buffer (MOPS), piperazine-N, N'-bis(2-ethanesulfonic acid) buffer (PIPES), and saline sodium citrate buffer (SSC). Non-limiting examples of co-solvents used in an oral dissolvable formulation can include sucrose, urea, cremaphor, DMSO, and potassium phosphate buffer.

Pharmaceutical preparations can be formulated for intravenous administration. The pharmaceutical compositions can be in a form suitable for parenteral injection as a sterile suspension, solution or emulsion in oily or aqueous vehicles, and can contain formulatory agents such as suspending, stabilizing and/or dispersing agents. Pharmaceutical formulations for parenteral administration include aqueous solutions of the active compounds in water-soluble form. Suspensions of the active compounds can be prepared as oily injection suspensions. Suitable lipophilic solvents or vehicles include fatty oils such as sesame oil, or synthetic fatty acid esters, such as ethyl oleate or triglycerides, or liposomes. The suspension can also contain suitable stabilizers or agents which increase the solubility of the compounds to allow for the preparation of highly concentrated solutions. Alternatively, the active ingredient can be in powder form for constitution with a suitable vehicle, e.g., sterile pyrogen-free water, before use.

The active compounds can be administered topically and can be formulated into a variety of topically administrable compositions, such as solutions, suspensions, lotions, gels, pastes, medicated sticks, balms, creams, and ointments. Such pharmaceutical compositions can contain solubilizers, stabilizers, tonicity enhancing agents, buffers and preservatives.

The compounds of the disclosure can be applied topically to the skin, or a body cavity, for example, oral, vaginal, bladder, cranial, spinal, thoracic, or pelvic cavity of a subject. The compounds of the disclosure can be applied to an accessible body cavity.

The compounds can also be formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, and PEG. In suppository forms of the compositions, a low-melting wax such as a mixture of fatty acid glycerides, optionally in combination with cocoa butter, can be melted.

In practicing the methods of treatment or use provided herein, therapeutically-effective amounts of the compounds described herein are administered in pharmaceutical compositions to a subject having a disease or condition to be treated. In some embodiments, the subject is a mammal such as a human. A therapeutically-effective amount can vary widely depending on the severity of the disease, the age and relative health of the subject, the potency of the compounds used, and other factors. The compounds can be used singly or in combination with one or more therapeutic agents as components of mixtures.

Pharmaceutical compositions can be formulated using one or more physiologically-acceptable carriers comprising excipients and auxiliaries, which facilitate processing of the active compounds into preparations that can be used pharmaceutically. Formulations can be modified depending upon the route of administration chosen. Pharmaceutical compositions comprising a compound described herein can be manufactured, for example, by mixing, dissolving, emulsifying, encapsulating, entrapping, or compression processes.

The pharmaceutical compositions can include at least one pharmaceutically-acceptable carrier, diluent, or excipient and compounds described herein as free-base or pharmaceutically-acceptable salt form. Pharmaceutical compositions can contain solubilizers, stabilizers, tonicity enhancing agents, buffers and preservatives.

Methods for the preparation of compositions comprising the compounds described herein include formulating the compounds with one or more inert, pharmaceutically-acceptable excipients or carriers to form a solid, semi-solid, or liquid composition. Solid compositions include, for example, powders, tablets, dispersible granules, capsules, and cachets. Liquid compositions include, for example, solutions in which a compound is dissolved, emulsions comprising a compound, or a solution containing liposomes, micelles, or nanoparticles comprising a compound as disclosed herein. Semi-solid compositions include, for example, gels, suspensions and creams. The compositions can be in liquid solutions or suspensions, solid forms suitable for solution or suspension in a liquid prior to use, or as emulsions. These compositions can also contain minor amounts of nontoxic, auxiliary substances, such as wetting or emulsifying agents, pH buffering agents, and other pharmaceutically-acceptable additives.

Non-limiting examples of dosage forms suitable for use in the disclosure include liquid, powder, gel, nanosuspension, nanoparticle, microgel, aqueous or oily suspensions, emulsion, and any combination thereof.

Non-limiting examples of pharmaceutically-acceptable excipients suitable for use in the disclosure include binding agents, disintegrating agents, anti-adherents, anti-static agents, surfactants, anti-oxidants, coating agents, coloring agents, plasticizers, preservatives, suspending agents, emulsifying agents, anti-microbial agents, spheronization agents, and any combination thereof.

A composition of the disclosure can be, for example, an immediate release form or a controlled release formulation. An immediate release formulation can be formulated to allow the compounds to act rapidly. Non-limiting examples of immediate release formulations include readily dissolvable formulations. A controlled release formulation can be a pharmaceutical formulation that has been adapted such that release rates and release profiles of the active agent can be matched to physiological and chronotherapeutic requirements or, alternatively, has been formulated to effect release of an active agent at a programmed rate. Non-limiting examples of controlled release formulations include granules, delayed release granules, hydrogels (e.g., of synthetic or natural origin), other gelling agents (e.g., gel-forming dietary fibers), matrix-based formulations (e.g., formulations comprising a polymeric material having at least one active ingredient dispersed through), granules within a matrix, polymeric mixtures, and granular masses.

In some, a controlled release formulation is a delayed release form. A delayed release form can be formulated to delay a compound's action for an extended period of time. A delayed release form can be formulated to delay the release of an effective dose of one or more compounds, for example, for about 4, about 8, about 12, about 16, or about 24 h.

A controlled release formulation can be a sustained release form. A sustained release form can be formulated to sustain, for example, the compound's action over an extended period of time. A sustained release form can be formulated to provide an effective dose of any compound described herein (e.g., provide a physiologically-effective blood profile) over about 4, about 8, about 12, about 16 or about 24 h.

Non-limiting examples of pharmaceutically-acceptable excipients can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), each which is incorporated by reference in its entirety.

Multiple therapeutic agents can be administered in any order or simultaneously. In some embodiments, a compound of the disclosure is administered in combination with, before, or after treatment with another therapeutic agent. If simultaneously, the multiple therapeutic agents can be provided in a single, unified form, or in multiple forms, for example, as multiple separate pills. The agents can be packed together or separately, in a single package or in a plurality of packages. One or all of the therapeutic agents can be given in multiple doses. If not simultaneous, the timing between the multiple doses can vary to as much as about a month.

Therapeutic agents described herein can be administered before, during, or after the occurrence of a disease or condition, and the timing of administering the composition containing a therapeutic agent can vary. For example, the compositions can be used as a prophylactic and can be administered continuously to subjects with a propensity to conditions or diseases in order to lessen a likelihood of the occurrence of the disease or condition. The compositions can be administered to a subject during or as soon as possible after the onset of the symptoms. The administration of the therapeutic agents can be initiated within the first 48 h of the onset of the symptoms, within the first 24 h of the onset of the symptoms, within the first 6 h of the onset of the symptoms, or within 3 h of the onset of the symptoms. The initial administration can be via any route practical, such as by any route described herein using any formulation described herein.

A compound can be administered as soon as is practical after the onset of a disease or condition is detected or suspected, and for a length of time necessary for the treatment of the disease, such as, for example, from about 1 month to about 3 months. In some embodiments, the length of time a compound can be administered can be about 1 day, about 2 days, about 3 days, about 4 days, about 5 days, about 6 days, about 1 week, about 2 weeks, about 3 weeks, about 4 weeks, about 1 month, about 5 weeks, about 6 weeks, about 7 weeks, about 8 weeks, about 2 months, about 9 weeks, about 10 weeks, about 11 weeks, about 12 weeks, about 3 months, about 13 weeks, about 14 weeks, about 15 weeks, about 16 weeks, about 4 months, about 17 weeks, about 18 weeks, about 19 weeks, about 20 weeks, about 5 months, about 21 weeks, about 22 weeks, about 23 weeks, about 24 weeks, about 6 months, about 7 months, about 8 months, about 9 months, about 10 months, about 11 months, about 1 year, about 13 months, about 14 months, about 15 months, about 16 months, about 17 months, about 18 months, about 19 months, about 20 months, about 21 months, about 22 months about 23 months, about 2 years, about 2.5 years, about 3 years, about 3.5 years, about 4 years, about 4.5 years, about 5 years, about 6 years, about 7 years, about 8 years, about 9 years, or about 10 years. The length of treatment can vary for each subject.

Pharmaceutical compositions described herein can be in unit dosage forms suitable for single administration of precise dosages. In unit dosage form, the formulation is divided into unit doses containing appropriate quantities of one or more compounds. The unit dosage can be in the form of a package containing discrete quantities of the formulation. Non-limiting examples are packaged injectables, vials, or ampoules. Aqueous suspension compositions can be packaged in single-dose non-reclosable containers. Multiple-dose reclosable containers can be used, for example, in combination with or without a preservative. Formulations for injection can be presented in unit dosage form, for example, in ampoules, or in multi-dose containers with a preservative.

Pharmaceutical compositions provided herein, can be administered in conjunction with other therapies, for example, chemotherapy, radiation, surgery, anti-inflammatory agents, and selected vitamins. The other agents can be administered prior to, after, or concomitantly with the pharmaceutical compositions.

Depending on the intended mode of administration, the pharmaceutical compositions can be in the form of solid, semi-solid or liquid dosage forms, such as, for example, tablets, suppositories, pills, capsules, powders, liquids, suspensions, lotions, creams, or gels, for example, in unit dosage form suitable for single administration of a precise dosage.

For solid compositions, nontoxic solid carriers include, for example, pharmaceutical grades of mannitol, lactose, starch, magnesium stearate, sodium saccharin, talc, cellulose, glucose, sucrose, and magnesium carbonate.

Non-limiting examples of pharmaceutically active agents suitable for combination with compositions of the disclosure include anti-infectives, i.e., aminoglycosides, antiviral agents, antimicrobials, anticholinergics/antispasmotics, antidiabetic agents, antihypertensive agents, antineoplastics, cardiovascular agents, central nervous system agents, coagulation modifiers, hormones, immunologic agents, immunosuppressive agents, and ophthalmic preparations.

Compounds can be delivered via liposomal technology. The use of liposomes as drug carriers can increase the therapeutic index of the compounds. Liposomes are composed of natural phospholipids, and can contain mixed lipid chains with surfactant properties (e.g., egg phosphatidylethanolamine). A liposome design can employ surface ligands for attaching to unhealthy tissue. Non-limiting examples of liposomes include the multilamellar vesicle (MLV), the small unilamellar vesicle (SUV), and the large unilamellar vesicle (LUV). Liposomal physicochemical properties can be modulated to optimize penetration through biological barriers and retention at the site of administration, and to reduce a likelihood of developing premature degradation and toxicity to non-target tissues. Optimal liposomal properties depend on the administration route: large-sized liposomes show good retention upon local injection, small-sized liposomes are better suited to achieve passive targeting. PEGylation reduces the uptake of the liposomes by the liver and spleen, and increases the circulation time, resulting in increased localization at the inflamed site due to the enhanced permeability and retention (EPR) effect. Additionally, liposomal surfaces can be modified to achieve selective delivery of the encapsulated drug to specific target cells. Non-limiting examples of targeting ligands include monoclonal antibodies, vitamins, peptides, and polysaccharides specific for receptors concentrated on the surface of cells associated with the disease.

Non-limiting examples of dosage forms suitable for use in the disclosure include liquid, elixir, nanosuspension, aqueous or oily suspensions, drops, syrups, and any combination thereof. Non-limiting examples of pharmaceutically-acceptable excipients suitable for use in the disclosure include granulating agents, binding agents, lubricating agents, disintegrating agents, sweetening agents, glidants, anti-adherents, anti-static agents, surfactants, anti-oxidants, gums, coating agents, coloring agents, flavoring agents, coating agents, plasticizers, preservatives, suspending agents, emulsifying agents, plant cellulosic material and spheronization agents, and any combination thereof.

Compositions of the disclosure can be packaged as a kit. In some embodiments, a kit includes written instructions on the administration/use of the composition. The written material can be, for example, a label. The written material can suggest conditions methods of administration. The instructions provide the subject and the supervising physician with the best guidance for achieving the optimal clinical outcome from the administration of the therapy. The written material can be a label. In some embodiments, the label can be approved by a regulatory agency, for example the U.S. Food and Drug Administration (FDA), the European Medicines Agency (EMA), or other regulatory agencies.

Dosing.

Pharmaceutical compositions described herein can be in unit dosage forms suitable for single administration of precise dosages. In unit dosage form, the formulation is divided into unit doses containing appropriate quantities of one or more compounds. The unit dosage can be in the form of a package containing discrete quantities of the formulation. Non-limiting examples are liquids in vials or ampoules. Aqueous suspension compositions can be packaged in single-dose non-reclosable containers. Multiple-dose reclosable containers can be used, for example, in combination with a preservative. Formulations for parenteral injection can be presented in unit dosage form, for example, in ampoules, or in multi-dose containers with a preservative.

A dose can be expressed in terms of an amount of the drug divided by the mass of the subject, for example, milligrams of drug per kilograms of subject body mass. A compound described herein can be present in a composition in a range of from about 1 mg to about 2000 mg; from about 100 mg to about 2000 mg; from about 10 mg to about 2000 mg; from about 5 mg to about 1000 mg, from about 10 mg to about 500 mg, from about 50 mg to about 250 mg, from about 100 mg to about 200 mg, from about 1 mg to about 50 mg, from about 50 mg to about 100 mg, from about 100 mg to about 150 mg, from about 150 mg to about 200 mg, from about 200 mg to about 250 mg, from about 250 mg to about 300 mg, from about 300 mg to about 350 mg, from about 350 mg to about 400 mg, from about 400 mg to about 450 mg, from about 450 mg to about 500 mg, from about 500 mg to about 550 mg, from about 550 mg to about 600 mg, from about 600 mg to about 650 mg, from about 650 mg to about 700 mg, from about 700 mg to about 750 mg, from about 750 mg to about 800 mg, from about 800 mg to about 850 mg, from about 850 mg to about 900 mg, from about 900 mg to about 950 mg, or from about 950 mg to about 1000 mg.

In some embodiments, a compound is administered in an amount ranging from about 5 mg/kg to about 50 mg/kg, 250 mg/kg to about 2000 mg/kg, about 10 mg/kg to about 800 mg/kg, about 50 mg/kg to about 400 mg/kg, about 100 mg/kg to about 300 mg/kg, or about 150 mg/kg to about 200 mg/kg. In some embodiments, a compound described herein can be present in a composition in a range of from about 20 mg/kg to about 400 mg/kg. In some embodiments, a compound described herein can be present in a composition in a range of from about 20 mg/kg to about 240 mg/kg. In some embodiments, a compound described herein can be present in a composition in a range of from about 75 mg/kg to about 150 mg/kg. In some embodiments, a compound described herein can be present in a composition in a range of from about 75 mg/kg to about 150 mg/kg. In some embodiments, a compound described herein can be present in a composition in a range of from about 100 mg/kg to about 150 mg/kg.

In some embodiments, a compound described herein can be present in a composition in an amount of about 75 mg/kg. In some embodiments, a compound described herein can be present in a composition in an amount of about 100 mg/kg. In some embodiments, a compound described herein can be present in a composition in an amount of about 150 mg/kg. In some embodiments, a compound described herein can be present in a composition in an amount of about 200 mg/kg. In some embodiments, a compound described herein can be present in a composition in an amount of about 250 mg/kg. In some embodiments, a compound described herein can be present in a composition in an amount of about 400 mg/kg.

A compound described herein can be present in a composition in an amount of about 1 mg, about 2 mg, about 3 mg, about 4 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 125 mg, about 150 mg, about 175 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, about 1800 mg, about 1850 mg, about 1900 mg, about 1950 mg, or about 2000 mg.

In some embodiments, a compound described herein can be present in a composition in an amount of about 100 mg, about 120 mg, about 140 mg, about 160 mg, about 180 mg, about 200 mg, about 220 mg, about 240 mg, about 260 mg, about 280 mg, or about 300 mg. In some embodiments, a compound described herein can be present in a composition in an amount of about 150 mg. In some embodiments, a compound described herein can be present in a composition in an amount of about 170 mg. In some embodiments, a compound described herein can be present in a composition in an amount of about 280 mg. In some embodiments, a compound described herein can be present in a composition in an amount of about 300 mg.

Methods of Use

In some embodiments, compounds of the invention can be used to treat cancer in a subject. A compound of the invention can, for example, slow the proliferation of cancer cell lines, or kill cancer cells. Non-limiting examples of cancer that can be treated by a compound of the invention include: acute lymphoblastic leukemia, acute myeloid leukemia, adrenocortical carcinoma, AIDS-related cancers, AIDS-related lymphoma, anal cancer, appendix cancer, astrocytomas, basal cell carcinoma, bile duct cancer, bladder cancer, bone cancers, brain tumors, such as cerebellar astrocytoma, cerebral astrocytoma/malignant glioma, ependymoma, medulloblastoma, supratentorial primitive neuroectodermal tumors, visual pathway and hypothalamic glioma, breast cancer, bronchial adenomas, Burkitt lymphoma, carcinoma of unknown primary origin, central nervous system lymphoma, cerebellar astrocytoma, cervical cancer, childhood cancers, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, Ewing's sarcoma, germ cell tumors, gallbladder cancer, gastric cancer, gastrointestinal carcinoid tumor, gastrointestinal stromal tumor, gliomas, hairy cell leukemia, head and neck cancer, heart cancer, hepatocellular (liver) cancer, Hodgkin lymphoma, Hypopharyngeal cancer, intraocular melanoma, islet cell carcinoma, Kaposi sarcoma, kidney cancer, laryngeal cancer, lip and oral cavity cancer, liposarcoma, liver cancer, lung cancers, such as non-small cell and small cell lung cancer, lymphomas, leukemias, macroglobulinemia, malignant fibrous histiocytoma of bone/osteosarcoma, medulloblastoma, melanomas, mesothelioma, metastatic squamous neck cancer with occult primary, mouth cancer, multiple endocrine neoplasia syndrome, myelodysplastic syndromes, myeloid leukemia, nasal cavity and paranasal sinus cancer, nasopharyngeal carcinoma, neuroblastoma, non-Hodgkin lymphoma, non-small cell lung cancer, oral cancer, oropharyngeal cancer, osteosarcoma/malignant fibrous histiocytoma of bone, ovarian cancer, ovarian epithelial cancer, ovarian germ cell tumor, pancreatic cancer, pancreatic cancer islet cell, paranasal sinus and nasal cavity cancer, parathyroid cancer, penile cancer, pharyngeal cancer, pheochromocytoma, pineal astrocytoma, pineal germinoma, pituitary adenoma, pleuropulmonary blastoma, plasma cell neoplasia, primary central nervous system lymphoma, prostate cancer, rectal cancer, renal cell carcinoma, renal pelvis and ureter transitional cell cancer, retinoblastoma, rhabdomyosarcoma, salivary gland cancer, sarcomas, skin cancers, skin carcinoma merkel cell, small intestine cancer, soft tissue sarcoma, squamous cell carcinoma, stomach cancer, T-cell lymphoma, throat cancer, thymoma, thymic carcinoma, thyroid cancer, trophoblastic tumor (gestational), cancers of unknown primary site, urethral cancer, uterine sarcoma, vaginal cancer, vulvar cancer, Waldenstrom macroglobulinemia, and Wilms tumor.

In some embodiments, the cancer is ovarian cancer. In some embodiments, the cancer is breast cancer. In some embodiments, the cancer is lung cancer. In some embodiments, the compounds of the invention show non-lethal toxicity.

Disclosed herein is a method of inducing apoptosis in a cell, the method comprising contacting the cell with a therapeutically-effective amount of a compound of the disclosure that binds a p53 mutant. Further disclosed herein is a method of inducing apoptosis in a cell, the method comprising contacting the cell with a therapeutically-effective amount of a compound of the disclosure that binds a p53 mutant.

In some embodiments, the compound increases the ability of the p53 mutant to bind DNA. In some embodiments, the cell expresses the p53. In some embodiments, the p53 mutant has a mutation at amino acid R248. In some embodiments, the p53 mutant is p53 R248Q. In some embodiments, the p53 mutant is p53 R248W. In some embodiments, the p53 mutant has a mutation at amino acid R273. In some embodiments, the p53 mutant is p53 R273C. In some embodiments, the p53 mutant is p53 R273H. In some embodiments, the compound selectively binds the p53 mutant as compared to a wild type p53.

In some embodiments, the compound increases the ability of the p53 mutant to bind DNA. In some embodiments, the compound increases a stability of a biologically-active conformation of a p53 mutant relative to a stability of the biologically-active conformation of the p53 mutant in an absence of the compound. In some embodiments, the compound selectively binds a p53 mutant as compared to a wild type p53.

In some embodiments, the therapeutically-effective amount is from about 50 mg to about 3000 mg. In some embodiments, the therapeutically-effective amount is about 600 mg. In some embodiments, the therapeutically-effective amount is about 1200 mg.

In some embodiments, the cancer is ovarian cancer. In some embodiments, the cancer is breast cancer. In some embodiments, the cancer is lung cancer. In some embodiments, the cancer is pancreatic cancer.

In some embodiments, the administration is oral. In some embodiments, the administration is intravenous. In some embodiments, the administration is subcutaneous. In some embodiments, the administration is topical.

EXAMPLES

Example 1: Method A

Route 1: General Scheme

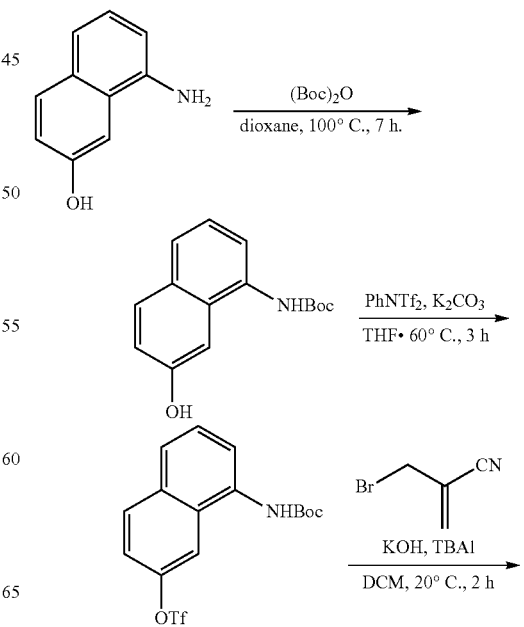

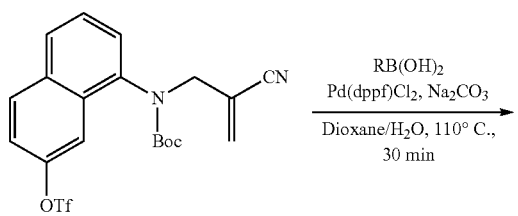

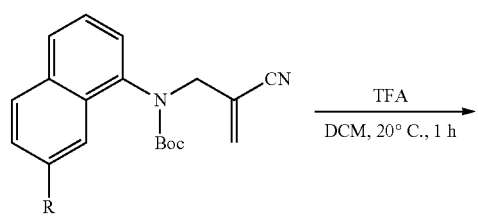

Preparation of tert-butyl N-(7-hydroxy-1-naphthyl)carbamate

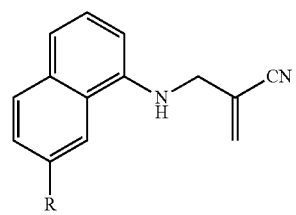

A mixture of 8-aminonaphthalen-2-ol (8 g, 25.13 mmol, 1 eq) and Boc₂O (5.48 g, 25.13 mmol, 5.77 mL, 1 eq) in dioxane (60 mL) was stirred at 100° C. for 7 hrs. The reaction mixture was concentrated. The residue was purified by column chromatography (SiO₂, PE:EtOAc=6:1 to 4:1) to afford the title compound (11 g, 84.4% yield) as an off-white solid.

Preparation of [8-(tert-butoxycarbonylamino)-2-naphthyl]trifluoromethanesulfonate

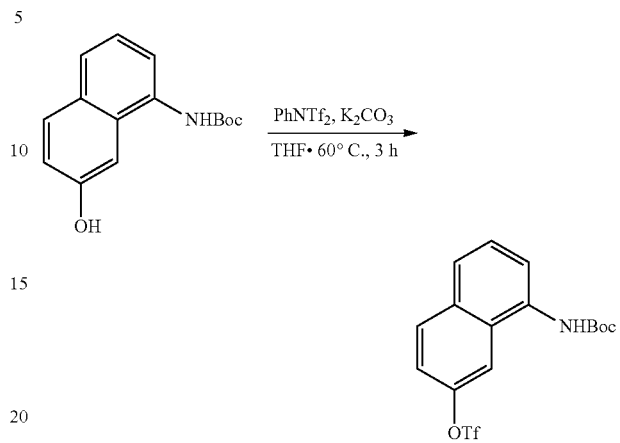

To a solution of tert-butyl N-(7-hydroxy-1-naphthyl)carbamate (2 g, 7.71 mmol, 1 eq) in THF (40 mL) were added K₂CO₃ (2.13 g, 15.43 mmol, 2 eq) and 1,1,1-trifluoro-N-phenyl-N-(trifluoro methylsulfonyl)methanesulfonamide (3.31 g, 9.26 mmol, 1.2 eq). The reaction was stirred at 60° C. for 3 hours. The reaction mixture was diluted with 30 mL of water and extracted with EtOAc (2×30 mL). The combined organic layer was washed with brine (2×25 mL), dried over anhydrous Na₂SO₄, filtered, and concentrated. The residue was purified by column chromatography (SiO₂, PE:EtOAc=8/1 to 6:1) to afford the title compound (1.8 g, 59.6% yield) as a white solid.

Preparation of [8-[tert-butoxycarbonyl(2-cyanoallyl)amino]-2-naphthyl]trifluoro methane sulfonate

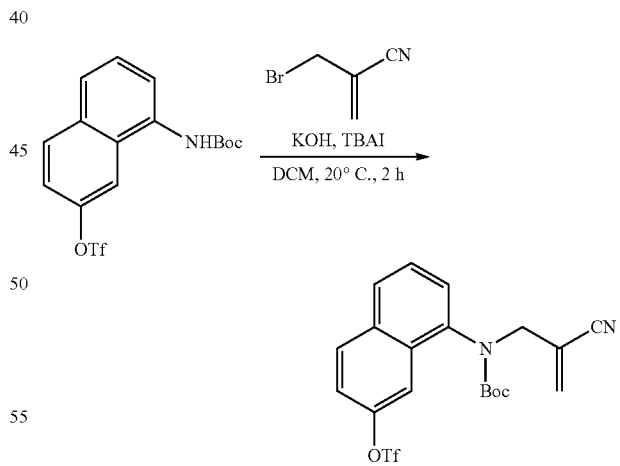

To a solution of [8-(tert-butoxycarbonylamino)-2-naphthyl]trifluoromethanesulfonate (300 mg, 766.55 μmol, 1 eq) in DCM (10 mL) were added KOH (129 mg, 2.3 mmol, 3 eq), TBAI (141.5 mg, 383.28 μmol, 0.5 eq) and 2-(bromomethyl)prop-2-enenitrile (134.3 mg, 919.87 μmol, 1.2 eq) at 20° C. under N₂. The mixture was stirred at 20° C. for 2 hrs. The reaction was filtered, and concentrated. The residue was purified by prep-TLC (SiO₂, PE:EtOAc=4:1) to afford the title compound (270 mg, 77.2% yield) as a colorless gum.

Preparation of tert-butyl N-(2-cyanoallyl)-N-[7-(3-pyridyl)-1-naphthyl]carbamate

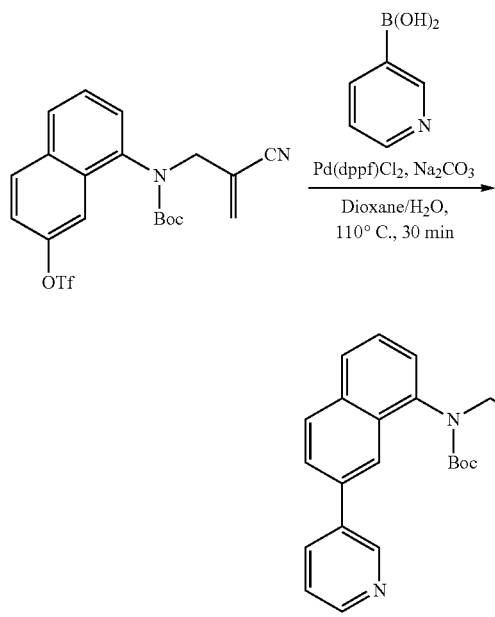

To a mixture of [8-[tert-butoxycarbonyl(2-cyanoallyl)amino]-2-naphthyl]trifluoromethane-sulfonate (120 mg, 262.91 µmol, 1 eq) and 3-pyridylboronic acid (38.8 mg, 315.49 µmol, 1.2 eq) in dioxane (2 mL) and H$_2$O (0.5 mL) were added Na$_2$CO$_3$ (83.6 mg, 788.72 µmol, 3 eq) and Pd(dppf)Cl$_2$ (76.9 mg, 105.16 µmol, 0.4 eq) under N$_2$. The mixture was stirred at 110° C. for 30 min. The mixture was poured into saturated EDTA solution (30 mL) and diluted with 20 mL of EtOAc. The mixture was stirred at 25° C. for 1 h. The aqueous phase was extracted with EtOAc (3×20 mL). The combined organic phase was washed with brine (3×30 mL), dried with anhydrous Na$_2$SO$_4$, filtered, and concentrated in vacuo. The residue was purified by prep-TLC (SiO$_2$, PE:EtOAc=1:1) to afford the title compound (60 mg, 59.2% yield) as a yellow gum.

Compound 1: Preparation of 2-({[7-(pyridin-3-yl)naphthalen-1-yl]amino}methyl)prop-2-enenitrile

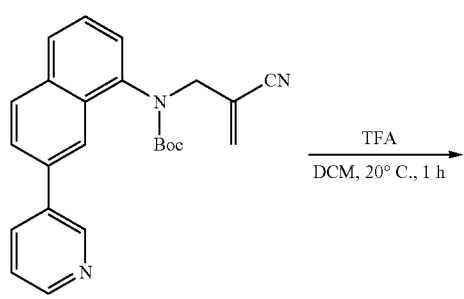

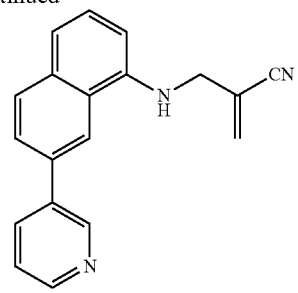

To a solution of tert-butyl N-(2-cyanoallyl)-N-[7-(3-pyridyl)-1-naphthyl]carbamate (50 mg, 129.72 µmol, 1 eq) in DCM (5 mL) was added TFA (1.54 g, 13.51 mmol, 1 mL, 104.12 eq). The mixture was stirred at 20° C. for 1 h. The reaction was adjusted to pH=9 with saturated Na$_2$CO$_3$ and extracted with EtOAc (3×20 mL). The combined organic layer was washed with brine (2×20 mL), dried over Na$_2$SO$_4$, filtered, and concentrated in vacuo. The residue was purified by prep-HPLC to afford the title compound (16.1 mg, 43.4% yield) as a white solid. 286.1 [(M+H)$^+$].

Route 2: General Scheme

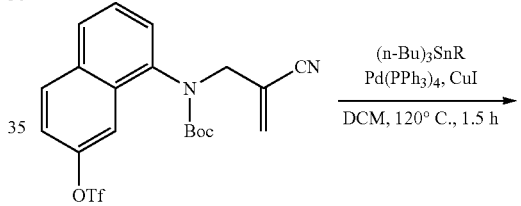

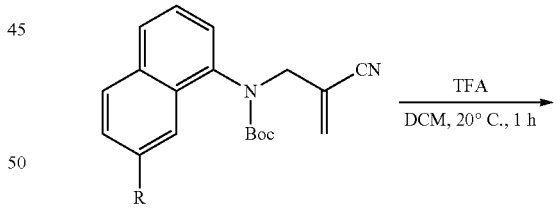

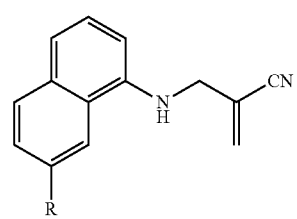

Preparation of tert-butyl N-(2-cyanoallyl)-N-[7-(2-pyridyl)-1-naphthyl]carbamate

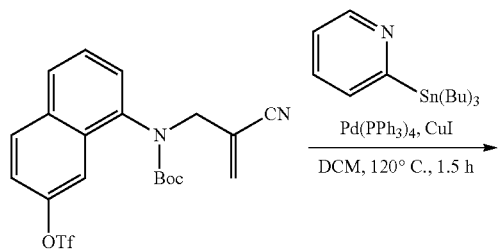

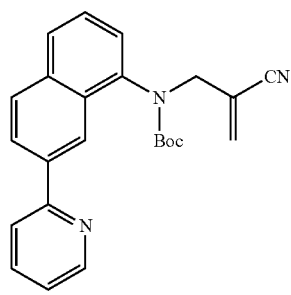

To a solution of [8-[tert-butoxycarbonyl(2-cyanoallyl)amino]-2-naphthyl]trifluoromethane-sulfonate (100 mg, 219.09 μmol, 1 eq) in DMF (3 mL) were added CuI (41.7 mg, 219.09 μmol, 1 eq), tributyl(2-pyridyl)stannane (806.6 mg, 2.19 mmol, 10 eq) and Pd(PPh₃)₄ (50.6 mg, 43.82 μmol, 0.2 eq). The mixture was stirred at 120° C. for 90 min. The mixture was poured into saturated EDTA solution (30 mL) and diluted with 20 mL of EtOAc. The mixture was stirred for 1 h. The aqueous phase was extracted with EtOAc (3×20 mL). The combined organic phase was washed with brine (3×30 mL), dried with anhydrous Na₂SO₄ and concentrated in vacuo. The residue was purified by prep-TLC (PE:EtOAc=1:1) to afford the title compound (60 mg, 71.1% yield) as a yellow oil.

Compound 2: Preparation of 2-({[7-(pyridin-2-yl)naphthalen-1-yl]amino}methyl)prop-2-enenitrile

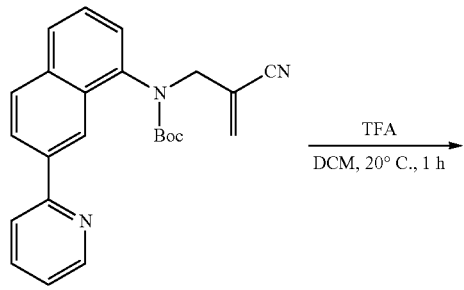

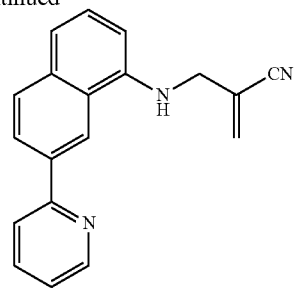

To a solution of tert-butyl N-(2-cyanoallyl)-N-[7-(2-pyridyl)-1-naphthyl]carbamate (50 mg, 129.72 μmol, 1 eq) in DCM (5 mL) was added TFA (1.54 g, 13.51 mmol, 1 mL, 104.12 eq). The mixture was stirred at 20° C. for 1 h. The reaction was adjusted to pH=9 with saturated Na₂CO₃ and extracted with EtOAc (2×20 mL). The combined organic layer was washed with brine (2×20 mL), dried over Na₂SO₄, filtered, and concentrated in vacuo. The residue was purified by prep-TLC (SiO₂, DCM:Methanol=20:1) and prep-HPLC to afford the title compound (7.4 mg, 20% yield) as a colorless oil. LC-MS (ES+, m/z) 286.1 [(M+H)⁺].

Preparation of tert-butyl N-(2-cyano-2-methylidene-ethyl)-N-[7-(4-acetamidopyridin-2-yl)naphthalen-1-yl]carbamate

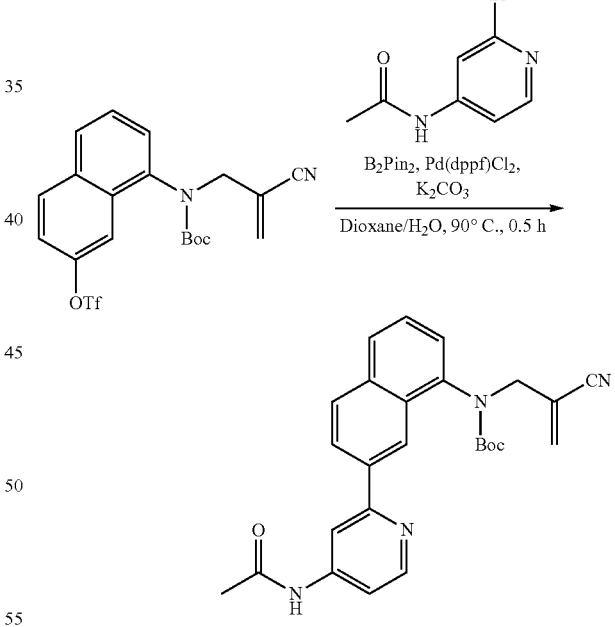

[8-[tert-butoxycarbonyl(2-cyanoallyl)amino]-2-naphthyl]trifluoromethane-sulfonate (150 mg, 328.63 μmol, 1 eq), N-(2-bromopyridin-4-yl)acetamide (91.87 mg, 427.22 μmol, 1.3 eq), K₂CO₃ (90.84 mg, 657.27 μmol, 2 eq), Pd(dppf)Cl₂ (48.09 mg, 65.73 μmol, 0.2 eq), and Pin₂B₂ (125.18 mg, 492.95 μmol, 1.5 eq) were added to a microwave tube in dioxane (2 mL) and H₂O (0.5 mL). The sealed tube was heated at 90° C. for 30 min. LCMS showed that the reaction was complete. 20 mL of EtOAc was poured into the mixture, which was then poured into a 2 N EDTA solution (30 mL) and stirred for 1 h. The aqueous phase was extracted with EtOAc (20 mL×3). The combined organic phase was washed with brine (30 mL×3), dried with anhydrous Na$_2$SO$_4$ and concentrated in vacuo. The residue was purified by prep-TLC (SiO$_2$, DCM:MeOH=20:1) to afford the title compound (40 mg, 54.24 μmol, 16.50% yield, 60% purity) as a yellow gum.

TABLE 1 shows compounds prepared using the methods of EXAMPLE 1.

TABLE 1

| Cpd. No. | Structure | IUPAC | LC-MS (ES+, m/z) |
|---|---|---|---|
| 1 | 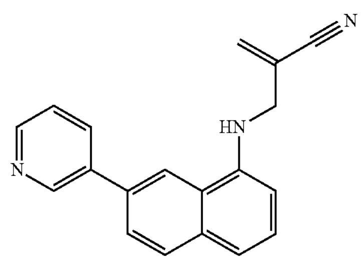 [SMILES: C=C(C#N)CNc1cccc2ccc(-c3cccnc3)cc12] | 2-({[7-(pyridin-3-yl)naphthalen-1-yl]amino}methyl)prop-2-enenitrile | 286.1 |
| 2 | 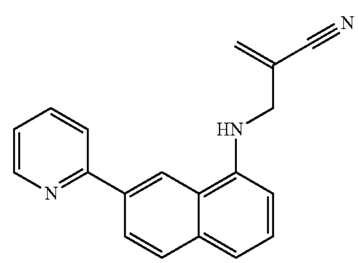 [SMILES: C=C(C#N)CNc1cccc2ccc(-c3ccccn3)cc12] | 2-({[7-(pyridin-2-yl)naphthalen-1-yl]amino}methyl)prop-2-enenitrile | 286.1 |
| 3 | 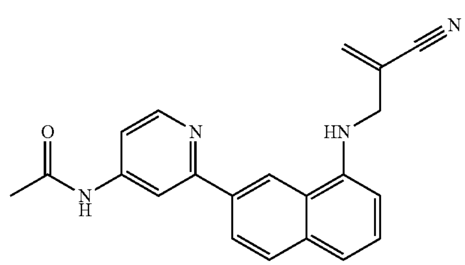 [SMILES: C=C(C#N)CNc1cccc2ccc(-c3cc(NC(C)=O)ccn3)cc12] | N-(2-{8-[(2-cyano-2-methylideneethyl)amino]naphthalen-2-yl}pyridin-4-yl) acetamide | 343.1 |
| 4 | 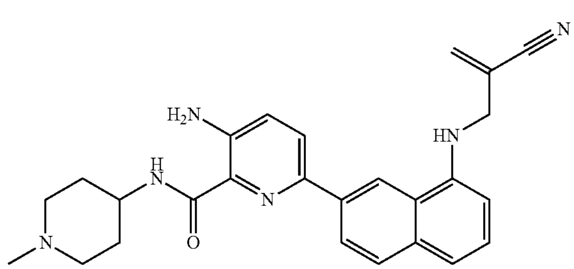 [SMILES: C=C(C#N)CNc1cccc2ccc(-c3ccc(N)c(C(=O)NC4CCN(C)CC4)n3)cc12] | 3-amino-6-{8-[(2-cyano-2-methylideneethyl)amino]naphthalen-2-yl}-N-(1-methylpiperidin-4-yl)pyridine-2-carboxamide | 441.2 |

TABLE 1-continued

| Cpd. No. | Structure | IUPAC | LC-MS (ES+, m/z) |
|---|---|---|---|
| 5 | 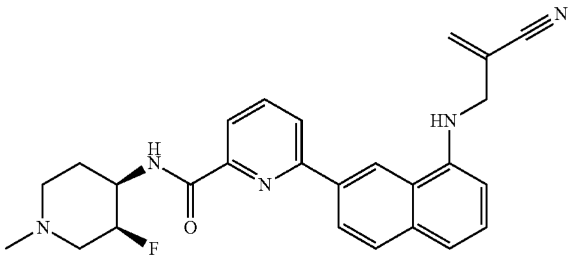 [SMILES: C=C(C#N)CNc1cccc2ccc(-c3cccc(C(=O)N[C@@H]4CCN(C)C[C@@H]4F)n3)cc12] | 6-{8-[(2-cyano-2-methylideneethyl)amino]naphthalen-2-yl}-N-[(3S,4R)-3-fluoro-1-methylpiperidin-4-yl]pyridine-2-carboxamide | 444.2 |
| 6 | 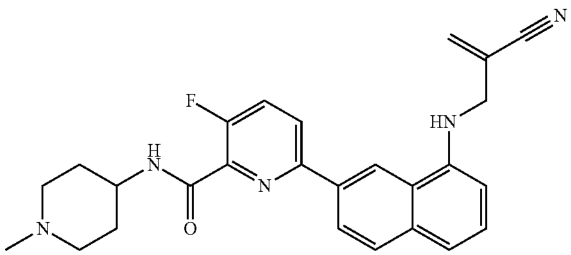 [SMILES: C=C(C#N)CNc1cccc2ccc(-c3ccc(F)c(C(=O)NC4CCN(C)CC4)n3)cc12] | 6-{8-[(2-cyano-2-methylideneethyl)amino]naphthalen-2-yl}-3-fluoro-N-(1-methylpiperidin-4-yl)pyridine-2-carboxamide | 444.2 |
| 7 | 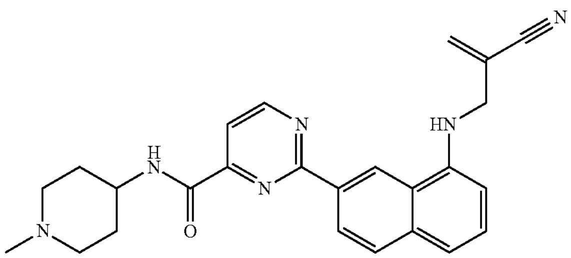 [SMILES: C=C(C#N)CNc1cccc2ccc(-c3nccc(C(=O)NC4CCN(C)CC4)n3)cc12] | 2-{8-[(2-cyano-2-methylideneethyl)amino]naphthalen-2-yl}-N-(1-methylpiperidin-4-yl)pyrimidine-4-carboxamide | 427.2 |

Example 2: Method B

Route 1: General Scheme

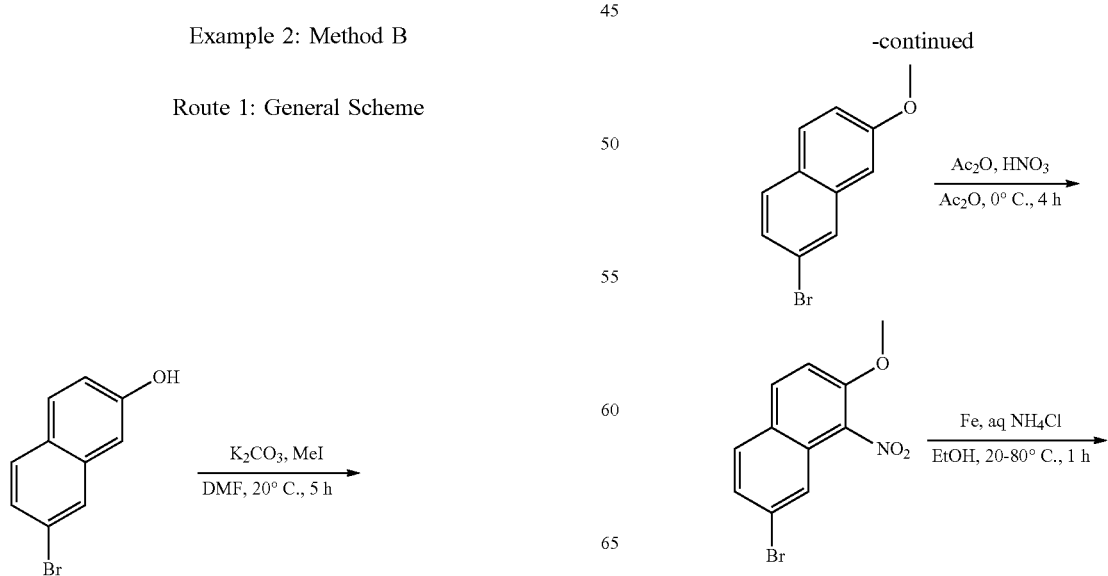

-continued

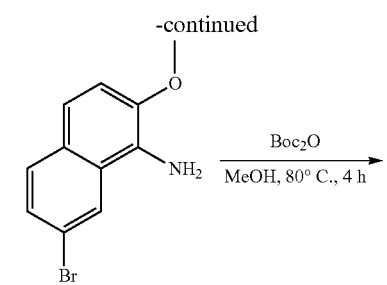

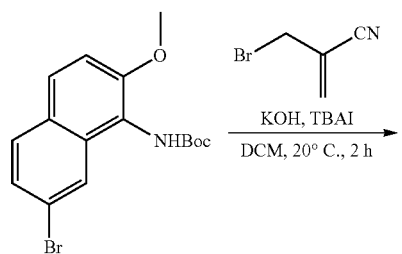

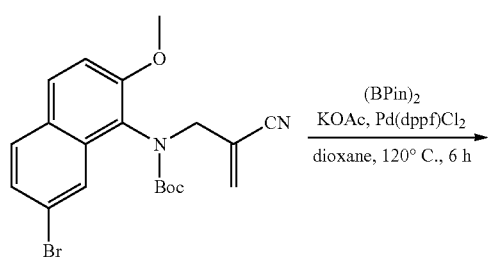

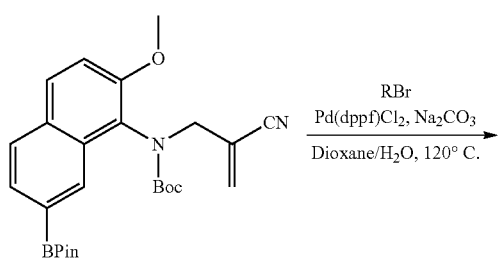

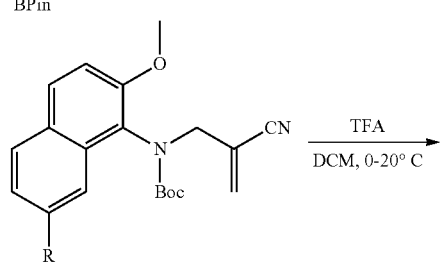

Preparation of 2-bromo-7-methoxy-naphthalene

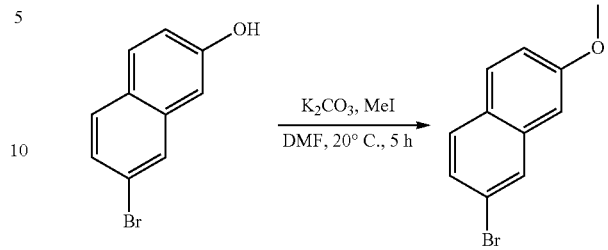

To a mixture of 7-bromonaphthalen-2-ol (1 g, 44.83 mmol, 1 eq) in DMF (100 mL) was added K$_2$CO$_3$ (12.39 g, 89.66 mmol, 2 eq). Then MeI (7.64 g, 53.8 mmol, 3.35 mL, 1.2 eq) was added to the mixture. The mixture was stirred at 20° C. for 5 h. The reaction mixture was poured into ice-water (200 mL). The aqueous phase was extracted with EtOAc (3×100 mL). The combined organic phase was washed with brine (3×100 mL), dried with anhydrous Na$_2$SO$_4$, filtered, and concentrated in vacuo. The crude was used directly in the next step without further purification. 2-bromo-7-methoxy-naphthalene (10.6 g, crude) was obtained as a white solid.

Preparation of 7-bromo-2-methoxy-1-nitronaphthalene

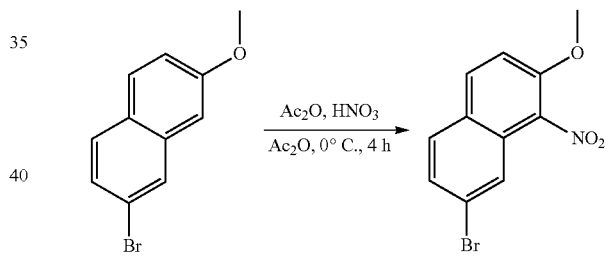

To a mixture of 2-bromo-7-methoxy-naphthalene (7 g, 1 eq) in Ac$_2$O (70 mL, 50.63 eq) was added HNO$_3$ (3.41 g, 1.57 mL, 1.1 eq) at 0° C. The mixture was stirred at 0° C. for 4 h. The product was obtained by filtration. The title compound was obtained (7 g, crude) as a yellow solid, which was used directly without any purification. (80% yield).

Preparation of 7-bromo-2-methoxy-naphthalen-1-amine

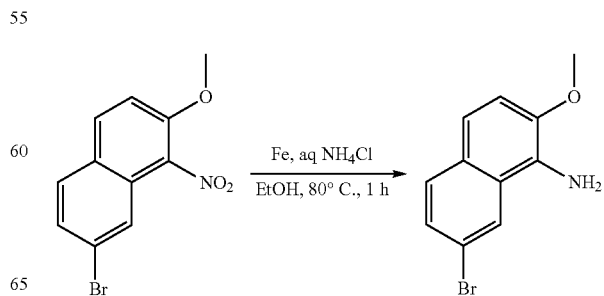

To 7-bromo-2-methoxy-1-nitro-naphthalene (7 g, 1 eq) in EtOH (40 mL) and H$_2$O (10 mL) was added NH$_4$Cl (1.26 g, 1 eq). Then Fe (6.58 g, 5 eq) was added to the mixture at 80° C. and stirred at 80° C. for 1 h. The reaction was filtered, and the liquid was poured into ice-water (300 mL). The aqueous phase was extracted with EtOAc (3×100 mL). The combined organic phase was washed with brine (3×100 mL), dried with anhydrous Na$_2$SO$_4$, filtered, and concentrated in vacuo. The crude was without purification, crude used directly. The title compound was obtained (6 g, crude) as a brown solid.

Preparation of tert-butyl N-(7-bromo-2-methoxynaphthalen-1-yl)carbamate

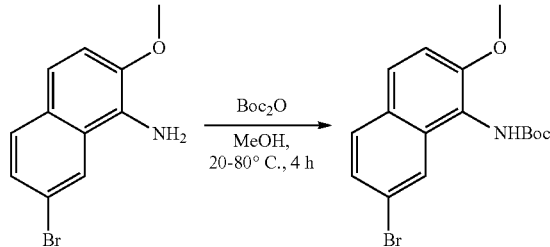 [SMILES: "Boc2O" ; COc1ccc2ccc(Br)cc2c1N ; COc1ccc2ccc(Br)cc2c1NC(=O)OC(C)(C)C]

To 7-bromo-2-methoxy-naphthalen-1-amine (2 g, 1 eq) in MeOH (20 mL, 62.30 eq) was added Boc$_2$O (17.31 g, 10 eq) at 20° C. The mixture was stirred at 80° C. for 4 h. The reaction was concentrated in vacuo, and the resulting solid was the desired product. The residue was purified by silica gel chromatography (PE:EtOAc=3:1). The title compound was obtained as a brown solid. (2.3 g, 82%).

Preparation of tert-butyl N-(7-bromo-2-methoxynaphthalen-1-yl)-N-(2-cyano-2-methyl deneethyl)carbamate

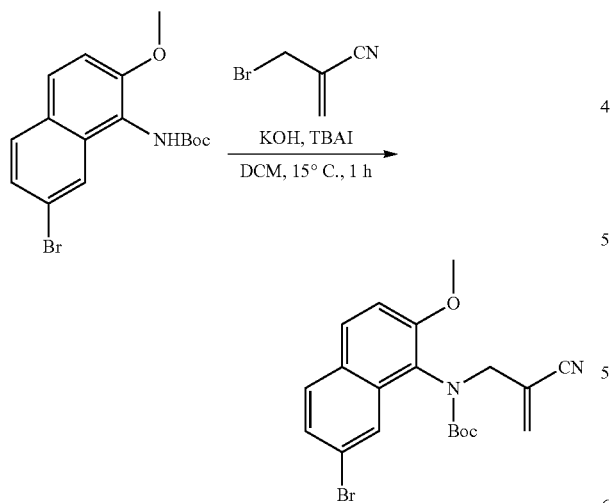

To a solution of tert-butyl (7-bromo-2-methoxynaphthalen-1-yl)carbamate (1.9 g, 5.39 mmol, 1 eq) in DCM (19 mL) were added KOH (605.3 mg, 10.79 mmol, 2 eq) and TBAI (398.5 mg, 1.08 mmol, 0.2 eq). Then, 2-(bromomethyl)prop-2-enenitrile (866.2 mg, 5.93 mmol, 1.1 eq) was added to the reaction. The reaction was stirred at 15° C. for 1 h. The reaction was poured into ice-water (30 mL). The aqueous phase was extracted with DCM (3×40 mL). The combined organic phase was washed with water (3×40 mL) and brine (3×30 mL), dried with anhydrous Na$_2$SO$_4$, filtered, and concentrated in vacuo. The crude was washed with PE:EtOAc=30:1 (40 mL) and filtered. The filter cake was obtained as an off-white solid (1.9 g, 4.55 mmol, 84.41% yield).

Preparation of tert-butyl N-(2-cyano-2-methylideneethyl)-N-[2-methoxy-7-(4,4,5,5-tetramethyl-1,3,2-dioxaborolan-2-yl)naphthalen-1-yl]carbamate

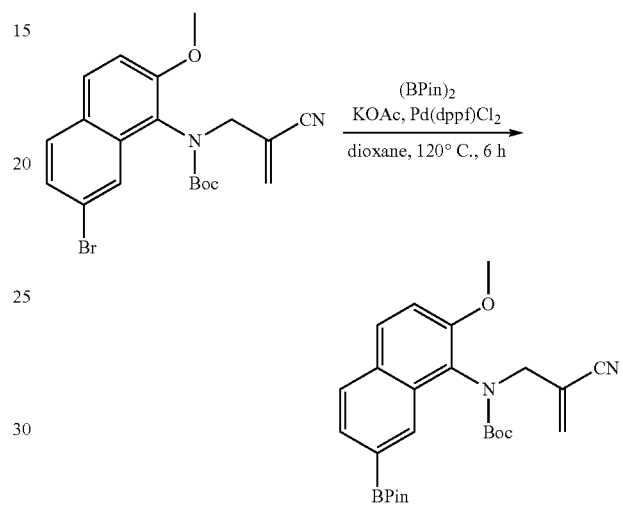

To a mixture of (BPin)$_2$ (5.48 g, 21.57 mmol, 3 eq) and tert-butyl N-(7-bromo-2-methoxy naphthalen-1-yl)-N-(2-cyano-2-methylideneethyl)carbamate (3. g, 7.19 mmol, 1 eq) in dioxane (50 mL) were added KOAc (2.12 g, 21.57 mmol, 3 eq) and Pd(dppf)Cl$_2$ (454.6 mg, 621.21 μmol, 8.64 eq). The mixture was heated to 120° C. and stirred for 6 hours under N$_2$ atmosphere. The reaction was filtered, and concentrated in vacuo. The residue was purified by silica gel chromatography (PE:EtOAc=4:1). The title compound was obtained as a white solid (2.8 g, 6.03 mmol, 83.87% yield).

General Procedure for Suzuki Coupling:

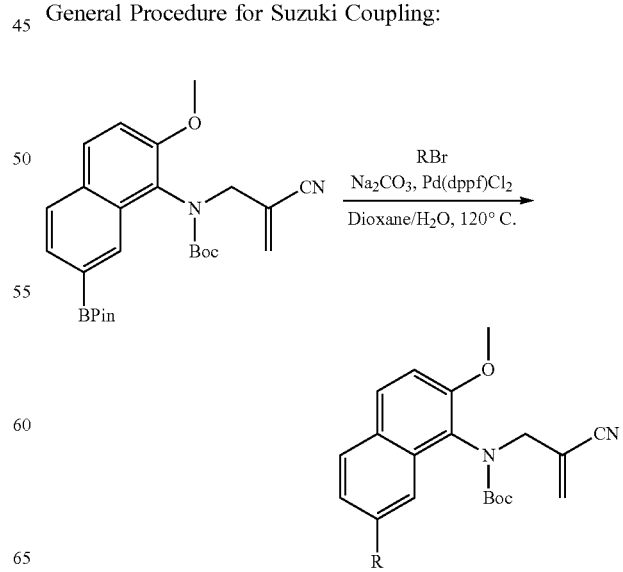

To a mixture of tert-butyl N-(2-cyano-2-methylidene-ethyl)-N-[2-methoxy-7-(4,4,5,5-tetramethyl-1,3,2-dioxaborolan-2-yl)naphthalen-1-yl]carbamate (73 mg, 157 μmol), aryl bromide (1.2 eq) in dioxane (1 mL) and H$_2$O (0.25 mL) were added Na$_2$CO$_3$ (50.1 mg, 472.92 μmol, 3 eq) and Pd(dppf)Cl$_2$ (5.8 mg, 7.88 μmol, 0.05 eq) under N$_2$. The mixture was stirred for 0.5 h at 120° C. under N$_2$. The reaction was poured into saturated EDTA (50 mL) and stirred for 2 h. The aqueous phase was extracted with EtOAc (3×30 mL). The combined organic phase was washed with brine (3×30 mL), dried with anhydrous Na$_2$SO$_4$, filtered, and concentrated in vacuo. The crude was purified by prep-HPLC (basic) and purified by prep-TLC (SiO$_2$, PE:EtOAc=1:1) to afford the title compound in yields ranging from 8-79%.

General Procedure for Boc Deprotection

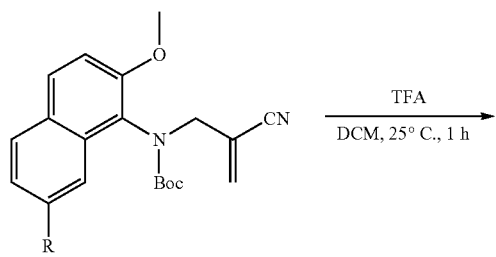

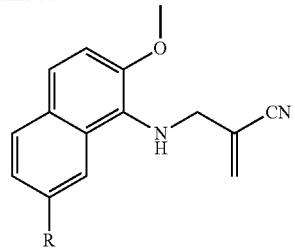

The Boc derivative (30 mg, 1 eq) was dissolved in DCM (2 mL), and TFA (0.4 mL) was added at 25° C. The mixture was stirred at 25° C. for 1 h. Upon completion of the reaction as indicated by HPLC, the mixture was poured into a saturated Na$_2$CO$_3$ solution (20 mL, pH>8), and the aqueous phase was extracted with DCM (3×30 mL). The combined organic phase was washed with brine (3×30 mL), dried with anhydrous Na$_2$SO$_4$. Then concentrated in vacuo. The residue was purified by prep-HPLC and lyophilized to afford the product.

Route 2: General Scheme

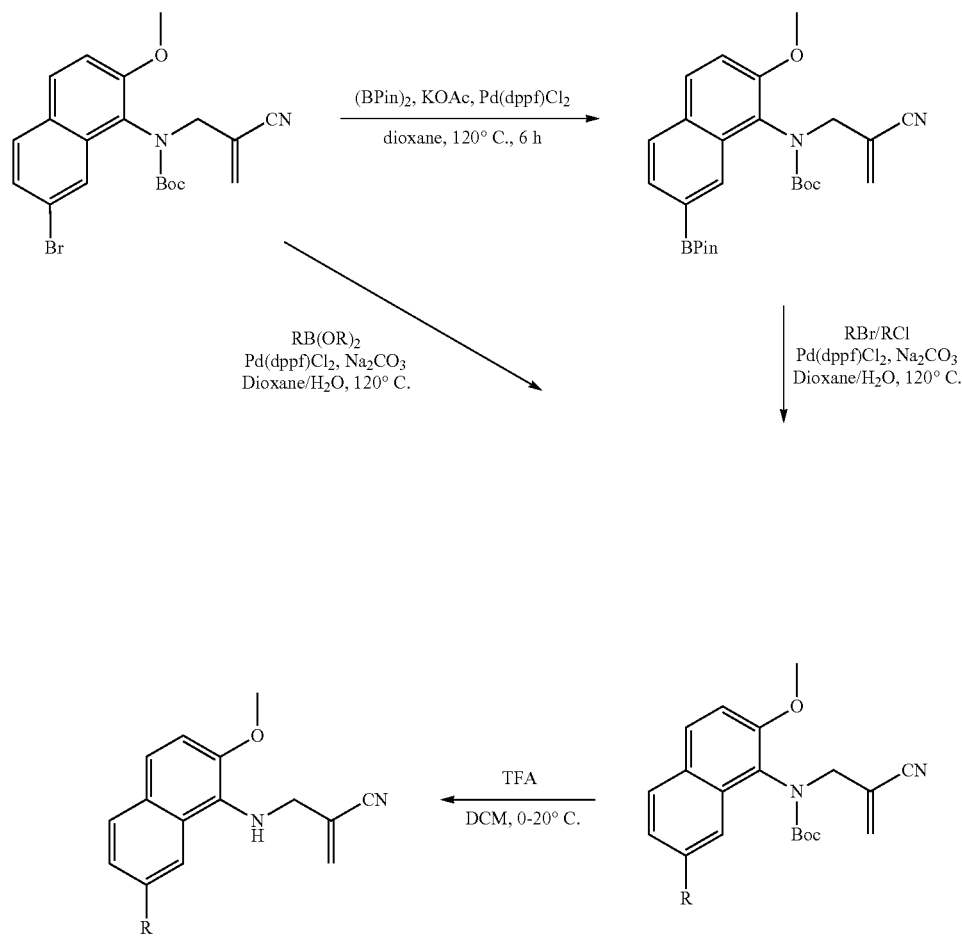

69
Preparation of tert-butyl N-[7-(5-amino-6-chloro-2-pyridyl)-2-methoxy-1-naphthyl]-N-(2-cyanoallyl) carbamate

70
Compound 12: Preparation of 2-[[[7-(5-amino-6-chloro-2-pyridyl)-2-methoxy-1-naphthyl]amino]methyl]prop-2-enenitrile

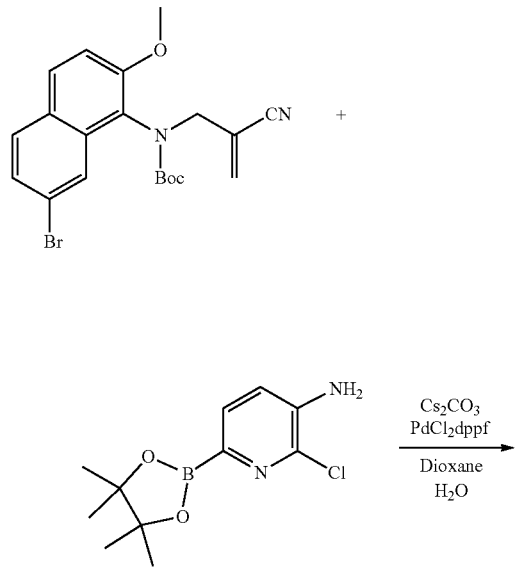

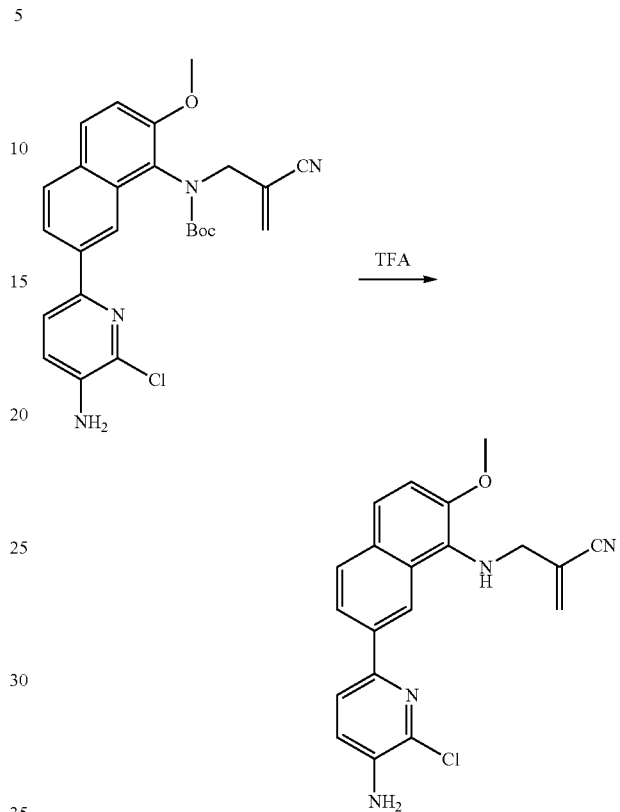

To a solution of tert-butyl N-(7-bromo-2-methoxy-1-naphthyl)-N-(2-cyanoallyl) carbamate (60 mg, 144 μmol) in dioxane (2 mL) and water (0.4 mL) were added 2-chloro-6-(4,4,5,5-tetramethyl-1,3,2-dioxaborolan-2-yl)pyridin-3-amine (54.9 mg, 216 μmol), $Cs_2CO_3$ (140.4 mg, 432 μmol) and $PdCl_2dppf$ (20 mg, 24.51 μmol). The reaction was heated at 100° C. for 40 min in a microwave. The reaction mixture was passed through a celite pad, and 2 mL of 0.5M EDTA was added. The resulting solution was stirred at r.t. for 30 minutes. The solution was washed with brine, dried over anhydrous sodium sulfate and the solvent was removed in vacuo. The residue was purified by chromatography on silica gel eluting with 0-60% EtOAc/Hexane to afford the title compound (67 mg, Yield 100%).

To a solution of tert-butyl N-[7-(5-amino-6-chloro-2-pyridyl)-2-methoxy-1-naphthyl]-N-(2-cyanoallyl) carbamate (67 mg, 144.1 μmol) in DCM (2 mL) was added TFA (0.5 mL) at 0° C. The resulting solution was stirred at 0° C. for 1 hour and at r.t. for 1 h. The reaction mixture was concentrated in vacuo and the residue was diluted with DCM, washed with saturated $NaHCO_3$ and brine, dried over anhydrous sodium sulfate, filtered, and concentrated. The residue was purified by reverse phase HPLC using a gradient of water 0.1% FA/acetonitrile 0.1% FA to afford the title compound (12.7 mg, Yield 24%). LC-MS ($ES^+$, m/z): 364.9 $[(M+H)^+]$ Preparation of 6-{8-[(2-cyano-2-methylideneethyl)amino]-7-methoxynaphthalen-2-yl}-4-acetamido-N-methylpyridine-2-carboxamide

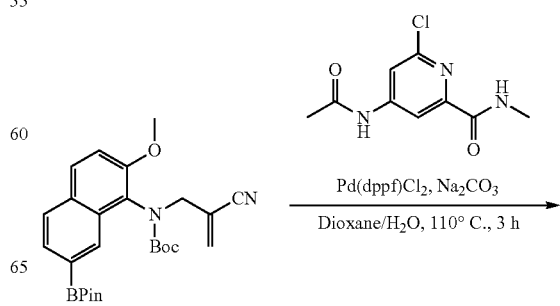

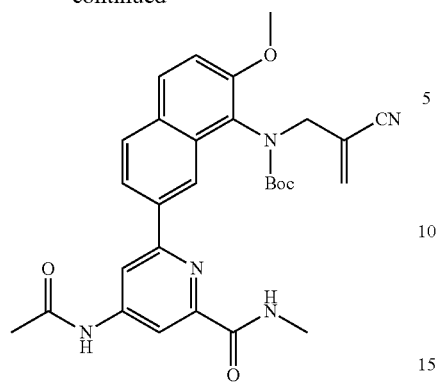

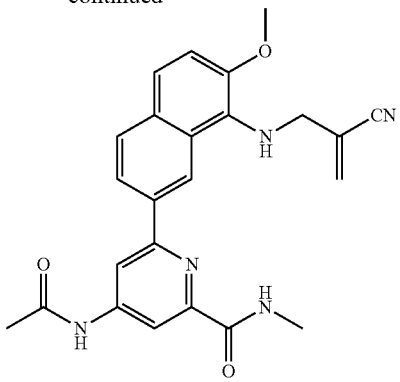

To a mixture of 6-chloro-4-acetamido-N-methylpyridine-2-carboxamide (50.9 mg, 223.96 μmol, 1.3 eq), tert-butyl N-(2-cyano-2-methylideneethyl)-N-[2-methoxy-7-(4,4,5,5-tetramethyl-1,3,2-dioxaborolan-2-yl)naphthalen-1-yl]carbamate (80 mg, 172.28 μmol, 1 eq) in dioxane (3 mL), H$_2$O (0.75 mL) was added Na$_2$CO$_3$ (36.5 mg, 344.56 μmol, 2 eq), Pd(dppf)Cl$_2$ (12.6 mg, 17.23 μmol, 0.1 eq) at 25° C. The mixture was stirred at 110° C. for 3 h. Upon completion of the reaction as indicated by LCMS, 20 mL of EtOAc was poured into the mixture. The mixture was poured into saturated EDTA solution (20 mL) and stirred for 1 h. The aqueous phase was extracted with EtOAc (3×30 mL). The combined organic phase was washed with brine (3×30 mL), dried with anhydrous Na$_2$SO$_4$. Then concentrated in vacuo. The residue was purified by prep-TLC (EtOAc). The title compound was obtained (50 mg, 84.97 μmol, 49.32% yield, 90% purity) as a colorless oil.

Compound 51: Preparation of 6-{8-[(2-cyano-2-methylideneethyl)amino]-7-Methoxynaphthalen-2-yl}-4-acetamido-N-Methylpyridine-2-carboxamide

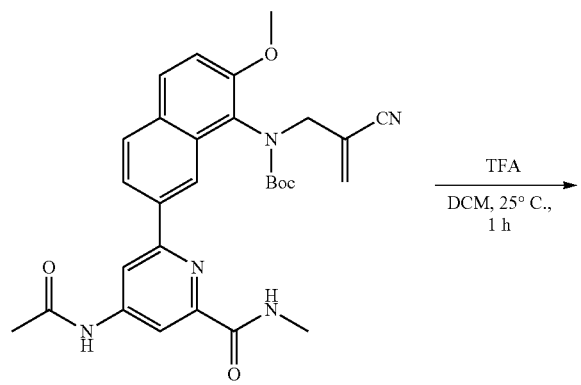

Tert-butyl N-(2-cyano-2-methylideneethyl)-N-{7-[4-acetamido-6-(methylcarbamoyl)pyridin-2-yl]-2-methoxynaphthalen-1-yl}carbamate (30 mg, 50.98 μmol, 1 eq) was dissolved in DCM (2 mL). Then TFA (0.4 mL) was added at 25° C. The mixture was stirred at 25° C. for 1 h. HPLC showed that the reaction was complete. The mixture was poured into saturated Na$_2$CO$_3$ solution (20 mL) and adjusted to pH>8, and the aqueous phase was extracted with DCM (3×30 mL). The combined organic phase was washed with brine (3×30 mL), dried with anhydrous Na$_2$SO$_4$, filtered, and concentrated in vacuo. The residue was purified by prep-HPLC to afford the title compound (12.2 mg, 28 μmol, 54.93% yield, 98.584% purity) as a yellow solid.

Preparation of 3-bromo-N-methyl-5-(trifluoromethoxy)benzamide

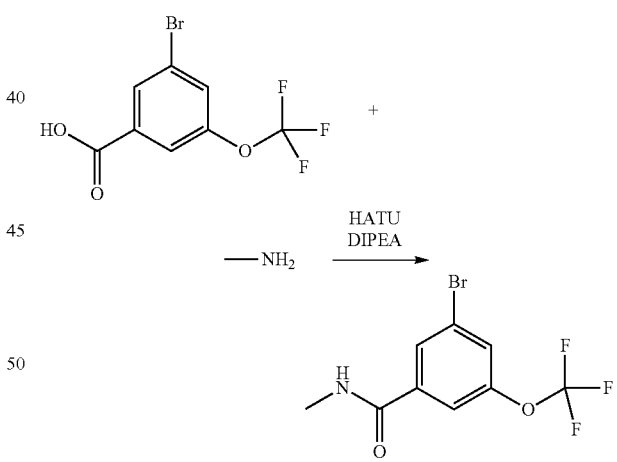

A mixture of 3-bromo-5-(trifluoromethoxy)benzoic acid (500 mg, 1.953 mmol), HATU (1.33 g, 3.506 mmol) and DIPEA (1.13 g, 8.77 mmol) in DMF (8 mL) was stirred at r.t. for 30 min. Methylamine (2 M, 4.39 mL, 8.77 mmol) was then added, and the resulting mixture was stirred at r.t. for 18 h and partitioned between EtOAc and water. The aqueous phase was extracted with EtOAc (3×). The combined organic phase was washed with saturated NaHCO$_3$ and brine, dried over (MgSO$_4$), filtered, and concentrated in vacuo. The residue was purified by chromatography on silica gel eluting with 0-50% EtOAc/Hexane to afford the title compound (0.331 g, Yield 63%).

73

Preparation of N-methyl-3-(4,4,5,5-tetramethyl-1,3,2-dioxaborolan-2-yl)-5-(trifluoromethoxy)benzamide

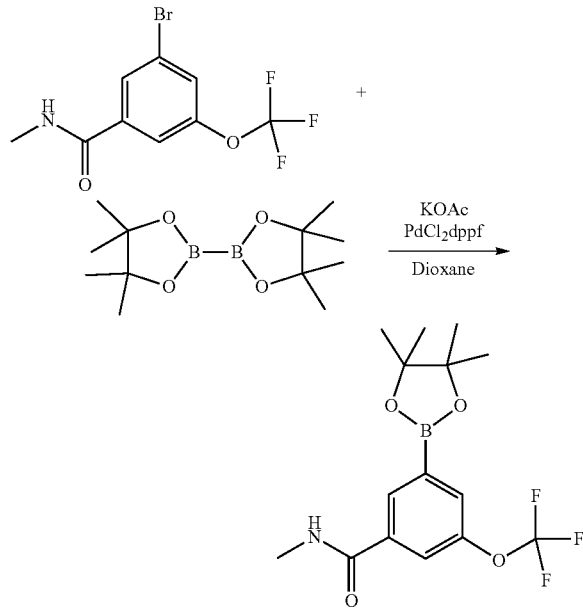

To a solution of 3-bromo-N-methyl-5-(trifluoromethoxy)benzamide (100 mg, 335.51 μmol) in dioxane (2 mL) were added 4,4,5,5-tetramethyl-2-(4,4,5,5-tetramethyl-1,3,2-dioxaborolan-2-yl)-1,3,2-dioxaborolane (128 mg, 503 μmol), KOAc (99 mg, 1.008 mmol) and PdCl₂dppf (40 mg, 49.02 μmol). The reaction was heated at 100° C. for 30 min in a microwave. The reaction mixture was passed through a celite pad, and the solvent was removed in vacuo. The residue was purified by chromatography on silica gel eluting with 0-20% MeOH/DCM to afford the title compound (73.7 mg, Yield 100%).

Preparation of tert-butyl N-(2-cyanoallyl)-N-[2-methoxy-7-[3-(methyl-carbamoyl)-5-(trifluoromethoxy)phenyl]-1-naphthyl]carbamate

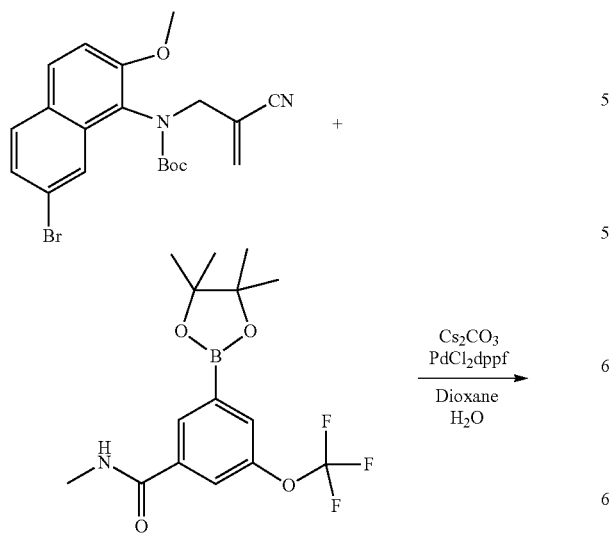

74

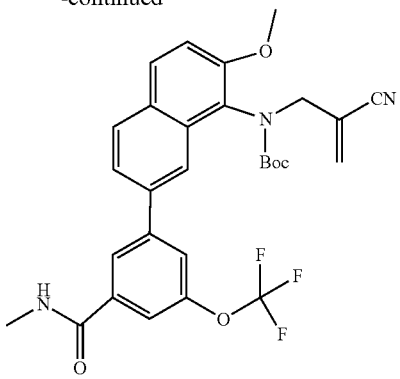

To a solution of tert-butyl N-(7-bromo-2-methoxy-1-naphthyl)-N-(2-cyanoallyl) carbamate (60 mg, 144 μmol) in dioxane (2 mL) and water (0.4 mL) were added N-methyl-3-(4,4,5,5-tetramethyl-1,3,2-dioxaborolan-2-yl)-5-(trifluoromethoxy)benzamide (42.9 mg, 124.3 μmol), Cs₂CO₃ (0.14 g, 430.77 μmol), and PdCl₂dppf (20 mg, 24.51 μmol). The reaction was heated at 100° C. for 40 min in a microwave. The reaction mixture was passed through a celite pad, and 2 mL of 0.5M EDTA was added. The resulting solution was stirred at r.t. for 40 min. The solution was washed with brine, dried over anhydrous sodium sulfate, filtered, and concentrated in vacuo. The residue was purified by chromatography on silica gel eluting with 0-60% EtOAc/Hexane to afford the title compound (36.7 mg, Yield 46%).

Compound 13: Preparation of 3-{8-[(2-cyano-2-methylideneethyl)amino]-7-methoxynaphthalen-2-yl}-N-methyl-5-(trifluoromethoxy)benzamide

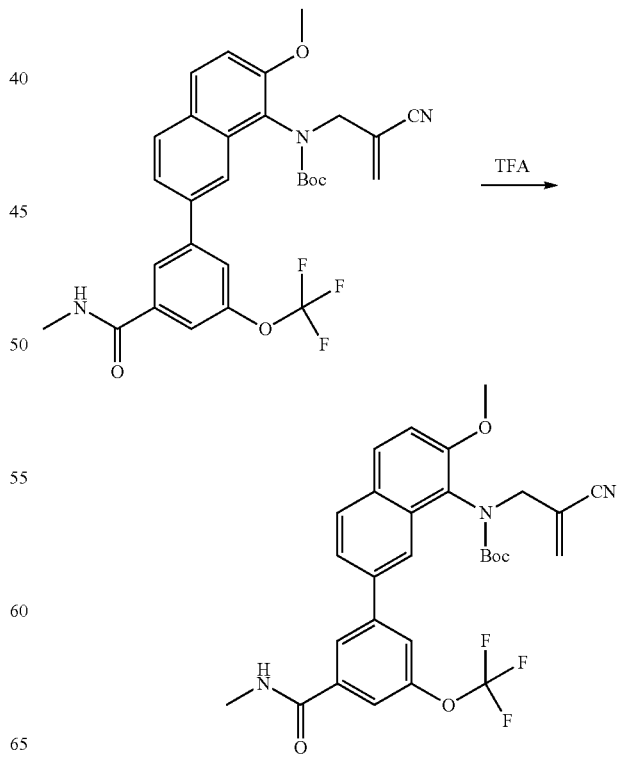

To a solution of tert-butyl N-(2-cyanoallyl)-N-[2-methoxy-7-[3-(methylcarbamoyl)-5-(trifluoromethoxy)phenyl]-1-naphthyl]carbamate (36.7 mg, 66 μmol) in DCM (2 mL) was added TFA (0.5 mL) at 0° C. The resulting solution was stirred at 0° C. for 1 hour and at r.t. for 1 h. The reaction mixture was concentrated in vacuo, and the residue was diluted with DCM, washed with saturated NaHCO₃ and brine, dried over anhydrous sodium sulfate, filtered, and concentrated. The residue was purified by reverse phase HPLC using a gradient of water 0.1% FA/acetonitrile 0.1% FA to afford the title compound (23.6 mg, Yield 78%). LC-MS (ES⁺, m/z): 455.9 [(M+H)⁺].

Preparation of tert-butyl N-(2-cyanoallyl)-N-[2-methoxy-7-(1-methyl-pyrazol-4-yl)-1-naphthyl]carbamate

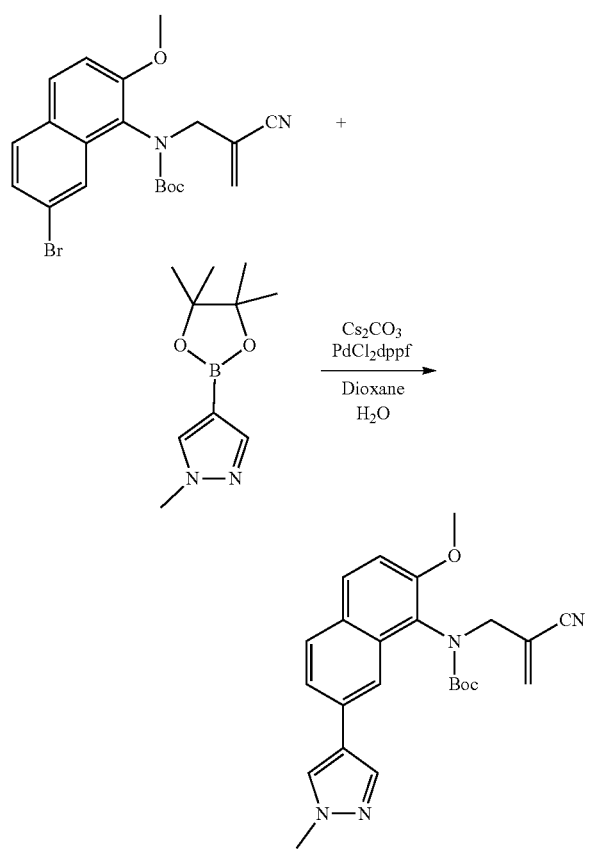

To a solution of tert-butyl N-(7-bromo-2-methoxy-1-naphthyl)-N-(2-cyanoallyl)carbamate (50 mg, 119.82 μmol) in dioxane (2 mL) and water (0.4 mL) were added 1-methyl-4-(4,4,5,5-tetramethyl-1,3,2-dioxaborolan-2-yl)pyrazole (37.4 mg, 179.75 μmol), Cs₂CO₃ (0.117 g, 36 μmol) and PdCl₂dppf (18 mg, 119.82 μmol). The reaction was heated at 100° C. for 40 min in a microwave. The reaction mixture was passed through a celite pad, and 2 mL of 0.5M EDTA was added. The resulting solution was stirred at r.t. for 40 min. The solution was washed with brine, dried over anhydrous sodium sulfate, filtered, and concentrated in vacuo. The residue was purified by chromatography on silica gel eluting with 0-80% EtOAc/Hexane to afford the title compound (50.2 mg, Yield 100%).

Compound 21: Preparation of 2-[[[2-methoxy-7-(1-methylpyrazol-4-yl)-1-naphthyl]amino]methyl]prop-2-enenitrile

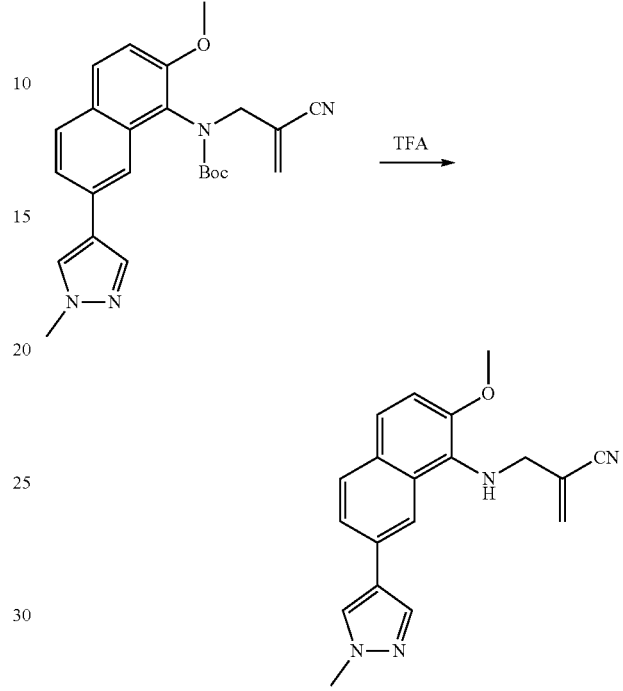

To a solution of tert-butyl N-(2-cyanoallyl)-N-[2-methoxy-7-(1-methylpyrazol-4-yl)-1-naphthyl]carbamate (50.2 mg, 12 μmol) in DCM (2 mL) was added TFA (0.5 mL) at 0° C. The resulting solution was stirred at 0° C. for 1 hour and r.t. for 1 h. The reaction mixture was concentrated in vacuo, and the residue was diluted with DCM. The solution was washed with saturated NaHCO₃ and brine, dried over anhydrous sodium sulfate, filtered, and concentrated. The residue was purified by chromatography on silica gel eluting with 40-90% EtOAc/Hexane to afford the title compound (11 mg, Yield 29%). LC-MS (ES⁺, m/z): 319 [(M+H)⁺].

Preparation of tert-butyl N-(2-cyanoallyl)-N-[2-methoxy-7-(3-methyl-1H-indazol-5-yl)-1-naphthyl] carbamate

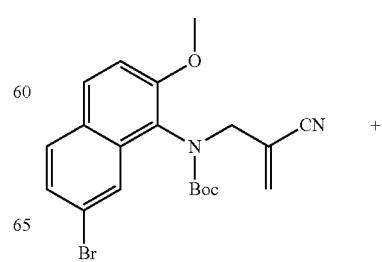

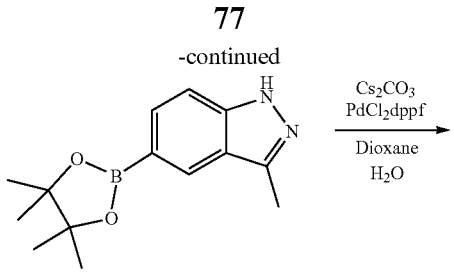

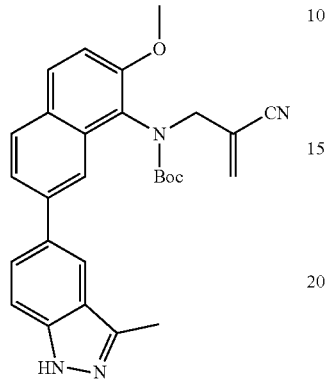

To a solution of tert-butyl N-(7-bromo-2-methoxy-1-naphthyl)-N-(2-cyanoallyl)carbamate (50 mg, 119.82 μmol) in dioxane (2 mL) and water (0.4 mL) were added 3-methyl-5-(4,4,5,5-tetramethyl-1,3,2-dioxaborolan-2-yl)-1H-indazole (45.9 mg, 177.82 μmol), Cs$_2$CO$_3$ (0.117 g, 36 μmol), and PdCl$_2$dppf (18 mg, 119.82 μmol). The reaction was heated at 100° C. for 40 min in a microwave. The reaction mixture was passed through a celite pad, and 2 mL of 0.5M EDTA was added. The resulting solution was stirred at r.t. for 40 min and washed with brine, dried over anhydrous sodium sulfate, filtered, and concentrated in vacuo. The residue was purified by chromatography on silica gel eluting with 0-70% EtOAc/Hexane to afford the title compound (35 mg, Yield 62%).

Compound 22: Preparation of 2-[[[2-methoxy-7-(3-methyl-1H-indazol-5-yl)-1-naphthyl]amino]methyl]prop-2-enenitrile

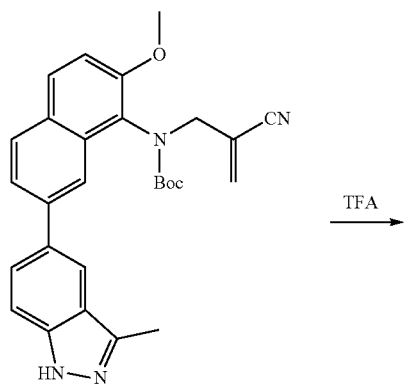

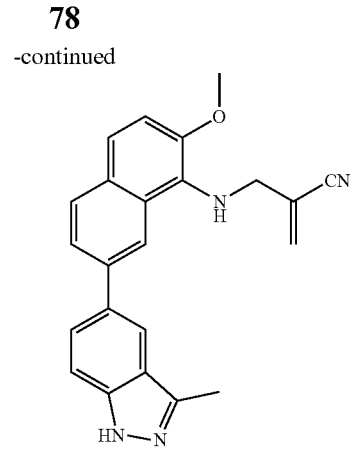

To a solution of tert-butyl N-(2-cyanoallyl)-N-[2-methoxy-7-(3-methyl-1H-indazol-5-yl)-1-naphthyl]carbamate (35 mg, 75 μmol) in DCM (2 mL) was added TFA (0.5 mL) at 0° C. The resulting solution was stirred at 0° C. for 1 hour and r.t. for 1 h. The reaction mixture was concentrated in vacuo, and the residue was diluted with DCM. The solution was washed with saturated NaHCO$_3$ and brine, dried over anhydrous sodium sulfate, filtered, and concentrated. The residue was purified by chromatography on silica gel eluting with 20-80% EtOAc/Hexane to afford the title compound (13.9 mg, Yield 50%). LC-MS (ES$^+$, m/z): 369 [(M+H)$^+$].

Preparation of 5-bromo-N-methyl-pyridine-3-carboxamide

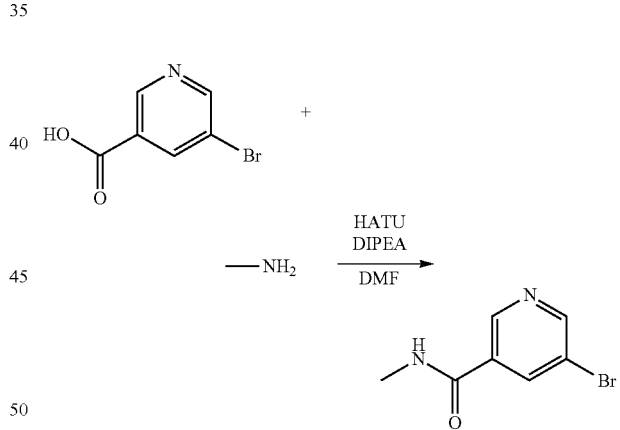

A mixture of 5-bromopyridine-3-carboxylic acid (200 mg, 990.07 μmol), HATU (0.564 g, 1.48 mmol) and DIPEA (0.51 g, 3.95 mmol) in DMF (4 mL) was stirred at r.t. for 30 min. Methylamine (2 M, 0.99 mL, 1.98 mmol) was added. The resulting mixture was stirred at r.t. for 18 h and partitioned between EtOAc and water. The aqueous phase was extracted with EtOAc (3×). The combined organic phase was washed with saturated NaHCO$_3$ and brine, dried over (MgSO$_4$), filtered, and concentrated in vacuo. The residue was purified by chromatography on silica gel eluting with 20-100% EtOAc/Hexane to afford the title compound (0.12 g, Yield 57%).

Preparation of tert-butyl N-(2-cyanoallyl)-N-[2-methoxy-7-[5-(methylcarbamoyl)-3-pyridyl]-1-naphthyl]carbamate Compound 45: Preparation of 5-[8-(2-cyanoallylamino)-7-methoxy-2-naphthyl]-N-methyl-pyridine-3-carboxamide

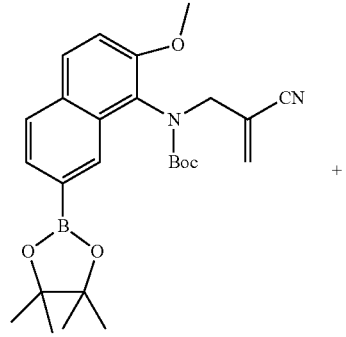
+
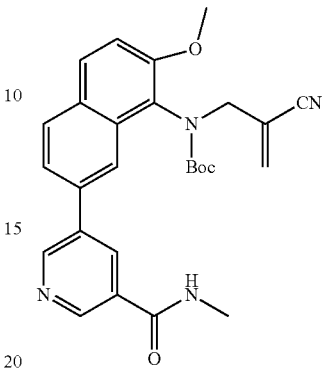

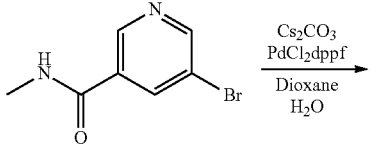

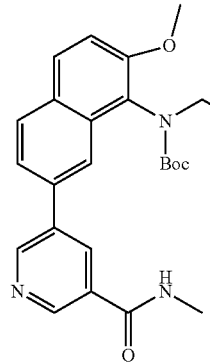

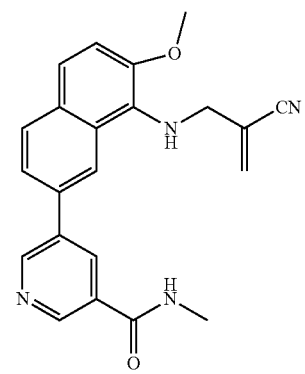

To a solution of tert-butyl N-(2-cyanoallyl)-N-[2-methoxy-7-(4,4,5,5-tetramethyl-1,3,2-dioxaborolan-2-yl)-1-naphthyl]carbamate (60 mg, 129.21 µmol) in dioxane (2 mL) and water (0.4 mL) were added 5-bromo-N-methyl-pyridine-3-carboxamide (41.9 mg, 194.84 µmol), Cs$_2$CO$_3$ (0.125 g, 384.62 µmol), and PdCl$_2$dppf (18 mg, 22.06 µmol). The reaction was heated at 100° C. for 30 min in a microwave. The reaction mixture was passed through a celite pad, and 2 mL of 0.5M EDTA was added. The resulting solution was stirred at r.t. for 40 min. The solution was washed with brine, dried over anhydrous sodium sulfate, filtered, and concentrated in vacuo. The residue was purified by chromatography on silica gel eluting with 20-100% EtOAc/Hexane to afford the title compound (60 mg, Yield 98%).

To a solution of tert-butyl N-(2-cyanoallyl)-N-[2-methoxy-7-[5-(methylcarbamoyl)-3-pyridyl]-1-naphthyl]carbamate (57.7 mg, 122 µmol) in DCM (2 mL) was added TFA (0.5 mL) at 0° C. The resulting solution was stirred at 0° C. for 1 hour and r.t. for 1 h. The reaction mixture was concentrated in vacuo and the residue was diluted with DCM. The solution was washed with saturated NaHCO$_3$ and brine, dried over anhydrous sodium sulfate, filtered, and concentrated. The residue was purified by reverse phase HPLC using a gradient of water 0.1% FA/acetonitrile 0.1% FA to afford the title compound (5 mg, Yield 11%). FC-MS (ES$^+$, m/z): 373 [(M+H)$^+$].

Preparation of 6-bromo-N-tetrahydropyran-4-yl-pyridine-2-carboxamide

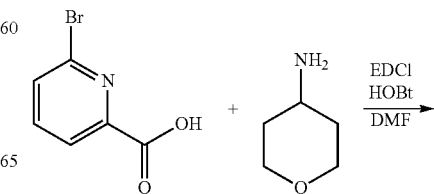

-continued

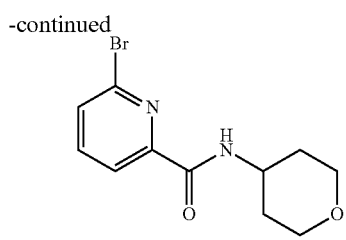

A mixture of 6-bromopyridine-2-carboxylic acid (200 mg, 990.07 µmol), EDCI (228 mg, 1.19 mmol) and HOBt (160.60 mg, 1.19 mmol) in DMF (4 mL) was stirred at r.t. for 30 min. Tetrahydropyran-4-amine (150.20 mg, 1.48 mmol) was added. The resulting mixture was stirred at r.t. for 18 h and partitioned between EtOAc and water. The aqueous phase was extracted with EtOAc (3×). The combined organic phase was washed with saturated NaHCO$_3$ and brine, dried over (MgSO$_4$), filtered, and concentrated in vacuo. The residue was purified by chromatography on silica gel eluting with 0-20% MeOH/EtOAc to afford the title compound (0.217 g, Yield 75%).

Preparation of tert-butyl N-(2-cyanoallyl)-N-[2-methoxy-7-[6-(tetrahydropyran-4-ylcarbamoyl)-2-pyridyl]-1-naphthyl]carbamate

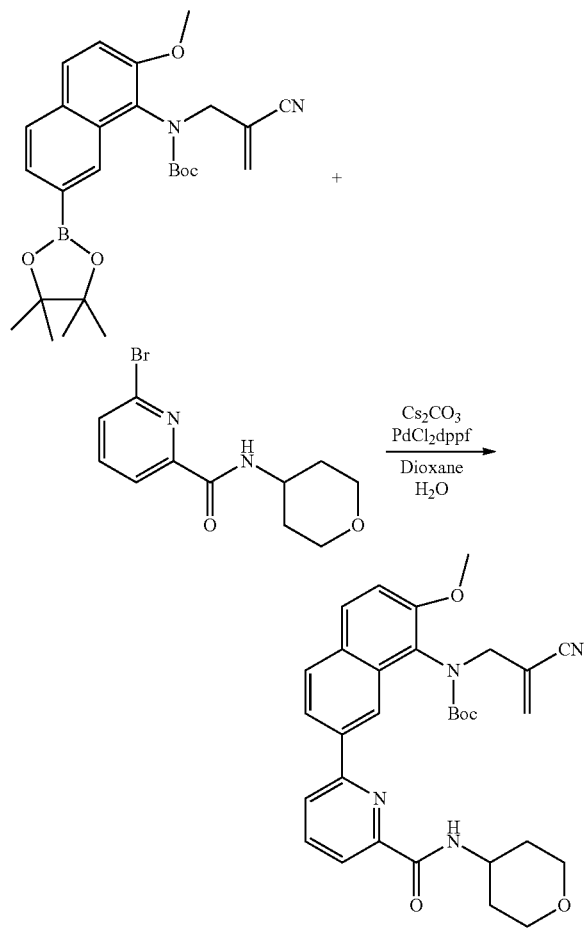

To a solution of tert-butyl N-(2-cyanoallyl)-N-[2-methoxy-7-(4,4,5,5-tetramethyl-1,3,2-dioxaborolan-2-yl)-1-naphthyl]carbamate (50 mg, 108 µmol) in dioxane (2 mL) and water (0.4 mL) were added 6-bromo-N-tetrahydropyran-4-yl-pyridine-2-carboxamide (46 mg, 162 µmol), Cs$_2$CO$_3$ (105 mg, 324 µmol) and PdCl$_2$dppf (18 mg, 22.06 µmol). The reaction was heated at 100° C. for 30 min in a microwave. The reaction mixture was passed through a celite pad, and 2 mL of 0.5M EDTA was added. The resulting solution was stirred at r.t. for 40 min. The solution was washed with brine, dried over anhydrous sodium sulfate, filtered, and concentrated in vacuo. The residue was purified by chromatography on silica gel eluting with 10-100% EtOAc/Hexane to afford the title compound (55.6 mg, Yield 97%).

Compound 69: Preparation of 6-[8-(2-cyanoallylamino)-7-methoxy-2-naphthyl]-N-tetrahydropyran-4-yl-pyridine-2-carboxamide

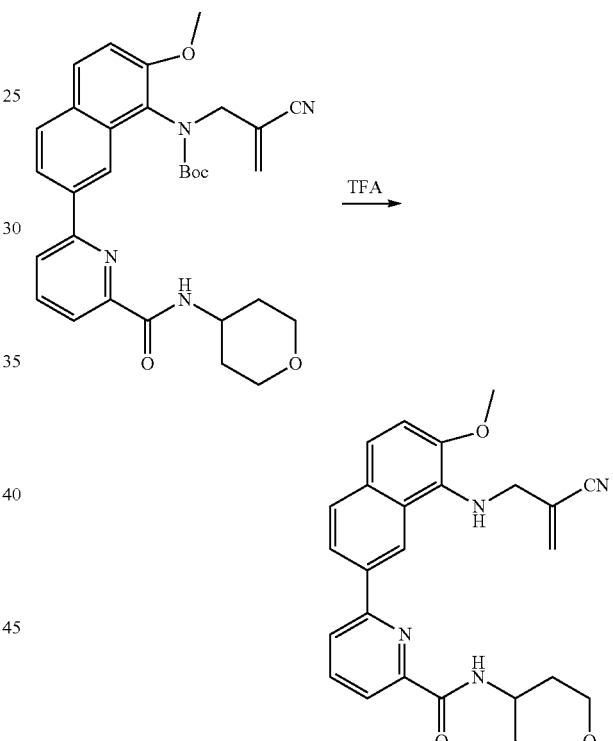

To a solution of tert-butyl N-(2-cyanoallyl)-N-[2-methoxy-7-[6-(tetrahydropyran-4-ylcarbamoyl)-2-pyridyl]-1-naphthyl]carbamate (55.6 mg, 102.47 µmol) in DCM (2 mL) was added TFA (0.5 mL) at 0° C. The resulting solution was stirred at 0° C. for 1 hour and r.t. for 1 h. The reaction mixture was concentrated in vacuo and the residue was diluted with DCM. The solution was washed with saturated NaHCO$_3$ and brine, dried over anhydrous sodium sulfate, filtered, and concentrated. The residue was purified by chromatography on silica gel eluting with 10-80% EtOAc/Hexane to afford the title compound (37.8 mg, Yield 83%). LC-MS (ES$^+$, m/z): 443 [(M+H)$^+$].

Preparation of 6-bromo-N-cyclopentyl-pyridine-2-carboxamide

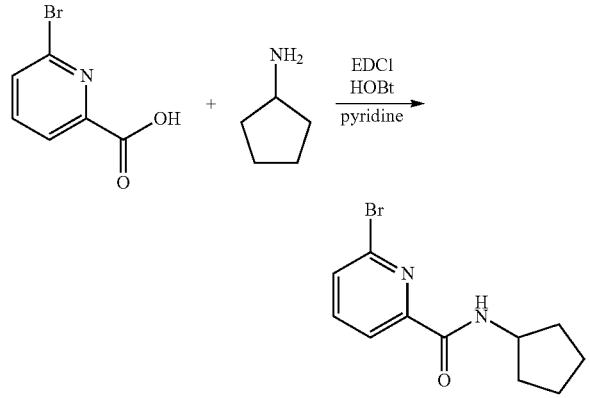

A mixture of 6-bromopyridine-2-carboxylic acid (200 mg, 990.07 µmol), EDCI (380 mg, 1.98 mmol), HOBt (268 mg, 1.98 mmol), and pyridine (235 mg, 2.97 mmol) in DMF (4 mL) was stirred at r.t. for 30 min. Cyclopentanamine (169 mg, 1.98 mmol) was added. The resulting mixture was stirred at r.t. for 18 h and partitioned between EtOAc and water. The aqueous phase was extracted with EtOAc (3×). The combined organic phase was washed with saturated NaHCO₃ and brine, dried over (MgSO₄), filtered, and concentrated in vacuo. The residue was purified by chromatography on silica gel eluting with 0-80% EtOAc/Hexane to afford the title compound (0.242 g, Yield 91%).

Preparation of tert-butyl N-(2-cyanoallyl)-N-[7-[6-(cyclopentyl-carbamoyl)-2-pyridyl]-2-methoxy-1-naphthyl]carbamate

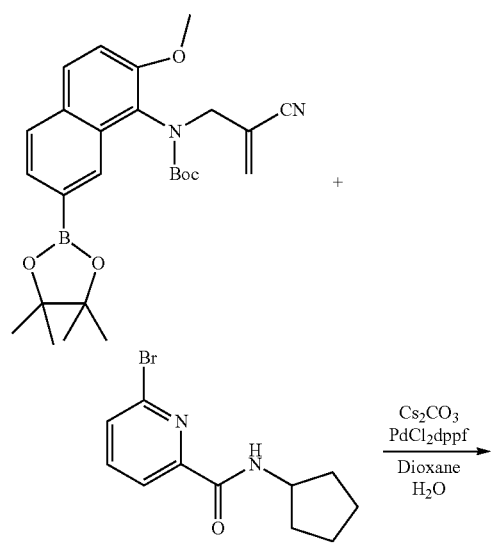

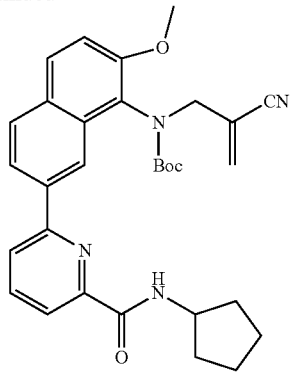

To a solution of tert-butyl N-(2-cyanoallyl)-N-[2-methoxy-7-(4,4,5,5-tetramethyl-1,3,2-dioxaborolan-2-yl)-1-naphthyl]carbamate (50 mg, 107.68 µmol) in dioxane (2 mL) and water (0.4 mL) were added 6-bromo-N-cyclopentyl-pyridine-2-carboxamide (43.6 mg, 162 µmol), Cs₂CO₃ (105.3 mg, 324 µmol), and PdCl₂dppf (18 mg, 22.06 µmol). The reaction was heated at 100° C. for 30 min in a microwave. The reaction mixture was passed through a celite pad, and 2 mL of 0.5M EDTA was added. The resulting solution was stirred at r.t. for 40 min. The solution was washed with brine, dried over anhydrous sodium sulfate and the solvent was removed in vacuo. The residue was purified by chromatography on silica gel eluting with 0-40% EtOAc/Hexane to afford the title compound (56.8 mg, Yield 100%).

Compound 70: Preparation of 6-[8-(2-cyanoallylamino)-7-methoxy-2-naphthyl]-N-cyclopentyl-pyridine-2-carboxamide

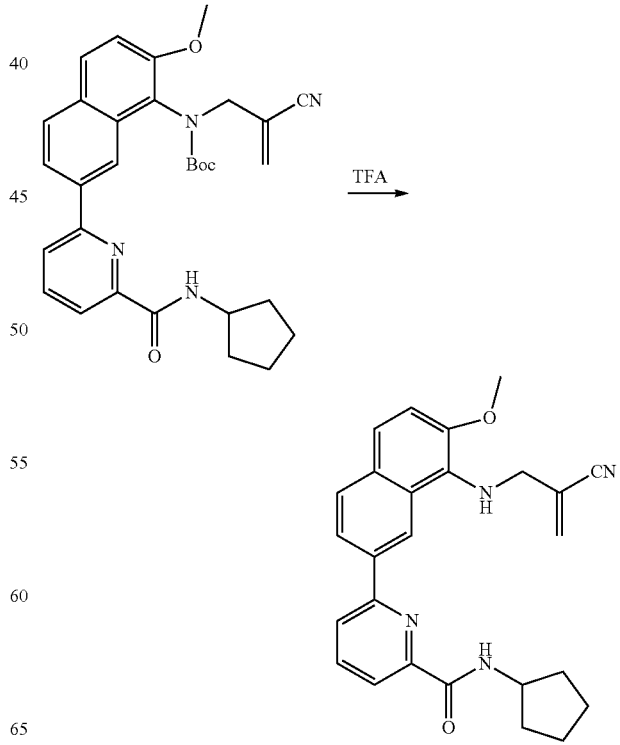

To a solution of tert-butyl N-(2-cyanoallyl)-N-[7-[6-(cyclopentylcarbamoyl)-2-pyridyl]-2-methoxy-1-naphthyl]carbamate (56.8 mg, 107.86 µmol) in DCM (2 mL) was added TFA (0.5 mL) at 0° C. The resulting solution was stirred at 0° C. for 1 hour and r.t. for 1 h. The reaction mixture was concentrated in vacuo and the residue was diluted with DCM. The solution was washed with saturated NaHCO$_3$ and brine, dried over anhydrous sodium sulfate, filtered, and concentrated. The residue was purified by chromatography on silica gel eluting with 0-40% EtOAc/Hexane to afford the title compound (24.1 mg, Yield 52%). LC-MS (ES$^+$, m/z): 427 [(M+H)$^+$].

Preparation of N-(2-bromo-4-pyridyl)-1-methyl-piperidine-3-carboxamide

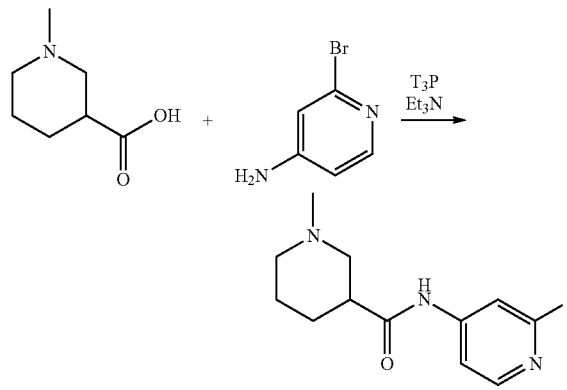

To a mixture of 1-methylpiperidine-3-carboxylic acid (222 mg, 1.55 mmol), 2-bromopyridin-4-amine (402 mg, 2.32 mmol) and Et$_3$N (0.78 g, 7.72 mmol) in DMF (4 mL) was added propanephosphonic acid anhydride (T$_3$P, 50 wt % in EtOAc, 2.06 mL, 2.32 mmol). The resulting mixture was stirred at r.t. for 18 h and partitioned between EtOAc and water. The aqueous phase was extracted with EtOAc (3×). The combined organic phase was washed with saturated NaHCO$_3$ and brine, dried over (MgSO$_4$), filtered, and concentrated in vacuo. The residue was purified by reverse phase HPLC using a gradient of water 0.1% FA/acetonitrile 0.1% FA to afford the title compound (0.182 g, Yield 39%).

Preparation of tert-butyl N-(2-cyanoallyl)-N-[2-methoxy-7-[4-[(l-methylpiperidine-3-carbonyl)amino]-2-pyridyl]-1-naphthyl]carbamate

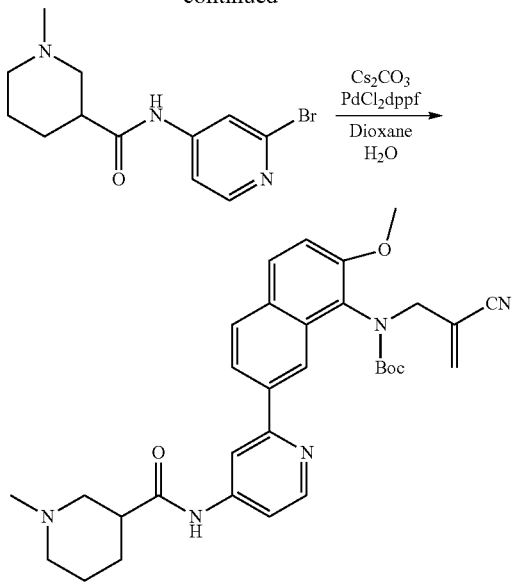

To a solution of tert-butyl N-(2-cyanoallyl)-N-[2-methoxy-7-(4,4,5,5-tetramethyl-1,3,2-dioxaborolan-2-yl)-1-naphthyl]carbamate (50 mg, 107.68 µmol) in dioxane (2 mL) and water (0.4 mL) were added N-(2-bromo-4-pyridyl)-1-methyl-piperidine-3-carboxamide (48.2 mg, 161.65 µmol), Cs$_2$CO$_3$ (105 mg, 323.08 µmol), and PdCl$_2$dppf (18 mg, 22.06 µmol). The reaction was heated at 100° C. for 30 min in a microwave. The reaction mixture was passed through a celite pad, and 2 mL of 0.5M EDTA was added. The resulting solution was stirred at r.t. for 30 min. The solution was washed with brine, dried over anhydrous sodium sulfate, filtered, and concentrated in vacuo. The residue was purified by chromatography on silica gel eluting with 0-40% MeOH/EtOAc/3% Et$_3$N to afford the title compound (35 mg, Yield 58%).

Compound 112: Preparation of N-[2-[8-(2-cyanoallylamino)-7-methoxy-2-naphthyl]-4-pyridyl]-1-methyl-piperidine-3-carboxamide

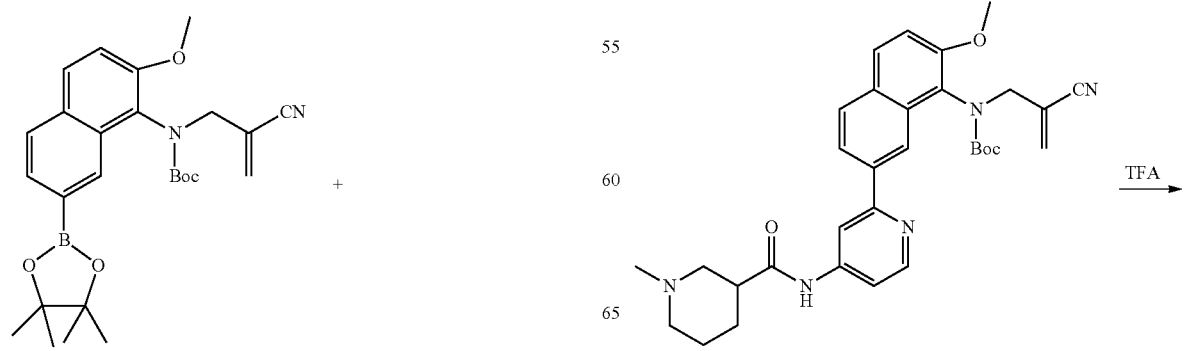

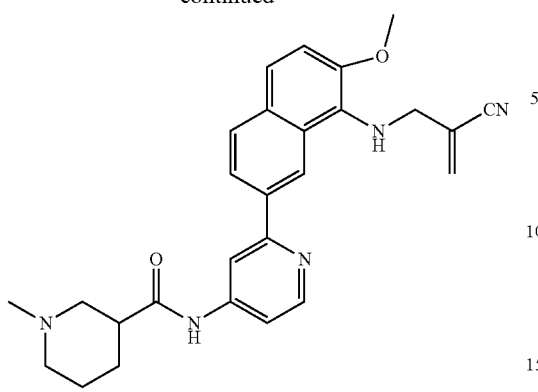

To a solution of tert-butyl N-(2-cyanoallyl)-N-[2-methoxy-7-[4-[(1-methylpiperidine-3-carbonyl)amino]-2-pyridyl]-1-naphthyl]carbamate (35 mg, 63 μmol) in DCM (2 mL) was added TFA (0.5 mL) at 0° C. The resulting solution was stirred at 0° C. for 1 hour and r.t. for 1 h. The reaction mixture was concentrated in vacuo, and the residue was diluted with DCM. The solution was washed with saturated NaHCO$_3$ and brine, dried over anhydrous sodium sulfate, filtered, and concentrated. The residue was purified by reverse phase HPLC using a gradient of water 0.1% FA/acetonitrile 0.1% FA to afford the title compound (20 mg, Yield 70%). LC-MS (ES$^+$, m/z): 456.2 [(M+H)$^+$].

Preparation of tert-butyl (3R)-3-[(6-bromopyridine-2-carbonyl)amino]piperidine-1-carboxylate

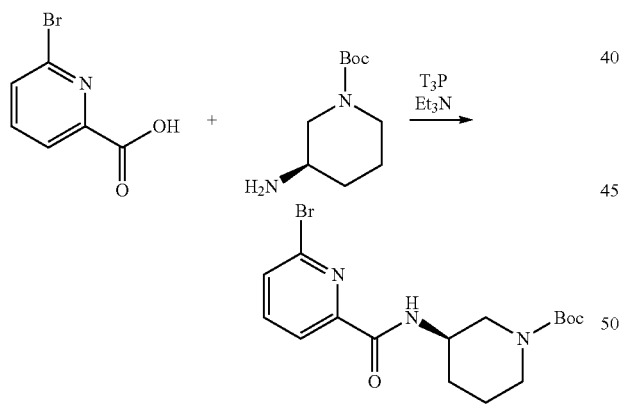

A mixture of 6-bromopyridine-2-carboxylic acid (300 mg, 1.49 mmol), tert-butyl (3R)-3-aminopiperidine-1-carboxylate (595 mg, 2.97 mmol) and Et$_3$N (450 mg, 4.46 mmol) in DMF (4 mL) was added T$_3$P (50 wt % in EtOAc, 1.98 mL, 2.97 mmol). The resulting mixture was stirred at r.t. for 18 h and partitioned between EtOAc and water. The aqueous phase was extracted with EtOAc (3×). The combined organic phase was washed with saturated NaHCO$_3$ and brine, dried over (MgSO$_4$), filtered, and concentrated in vacuo. The residue was purified by chromatography on silica gel eluting with 0-60% EtOAc/Hexane to afford the title compound (571 mg, Yield 100%).

Preparation of 6-bromo-N-[(3R)-3-piperidyl]pyridine-2-carboxamide

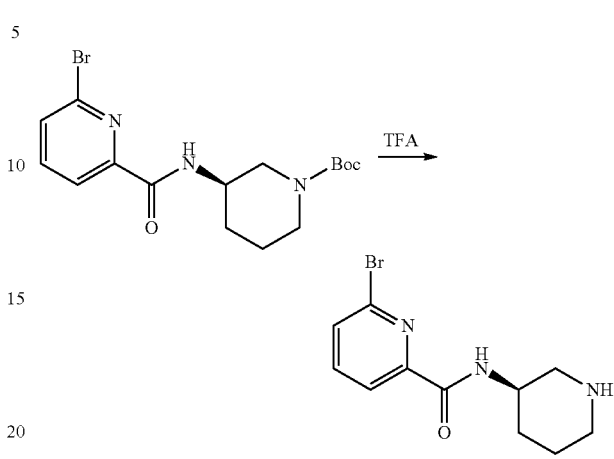

To a solution of tert-butyl (3R)-3-[(6-bromopyridine-2-carbonyl)amino]piperidine-1-carboxylate (571 mg, 1.486 mmol) in DCM (10 mL) was added TFA (2 mL) at 0° C. The resulting solution was stirred at 0° C. for 1 hour and r.t. for 1 h. The reaction mixture was concentrated in vacuo and the residue was diluted with DCM, washed with saturated NaHCO$_3$ and brine, dried over anhydrous sodium sulfate, filtered, and concentrated. The crude residue (0.2 g, 47%) was used in the next step without further purification.

Preparation of N-[(3R)-1-acetyl-3-piperidyl]-6-bromo-pyridine-2-carboxamide

To a mixture of 6-bromo-N-[(3R)-3-piperidyl]pyridine-2-carboxamide (200 mg, 703.85 μmol) and Et$_3$N (142 mg, 1.41 mmol) in DCM (5 mL) at 0° C. was added a solution of acetyl chloride (60.7 mg, 773.27 μmol) in DCM (1 mL). The resulting mixture was stirred at r.t. for 2 h. The reaction mixture was concentrated in vacuo and the residue was diluted with EtOAc, washed with saturated NaHCO$_3$ and brine, dried over anhydrous sodium sulfate, filtered, and concentrated. The residue was purified by chromatography on silica gel eluting with 0-20% MeOH/EtOAc to afford the title compound (0.147 g, Yield 64%).

Preparation of tert-butyl N-[7-[6-[[(3R)-1-acetyl-3-piperidyl]carbamoyl]-2-pyridyl]-2-methoxy-1-naphthyl]-N-(2-cyanoallyl) carbamate Compound 113: Preparation of N-[(3R)-1-acetyl-3-piperidyl]-6-[8-(2-cyanoallylamino)-7-methoxy-2-naphthyl]pyridine-2-carboxamide

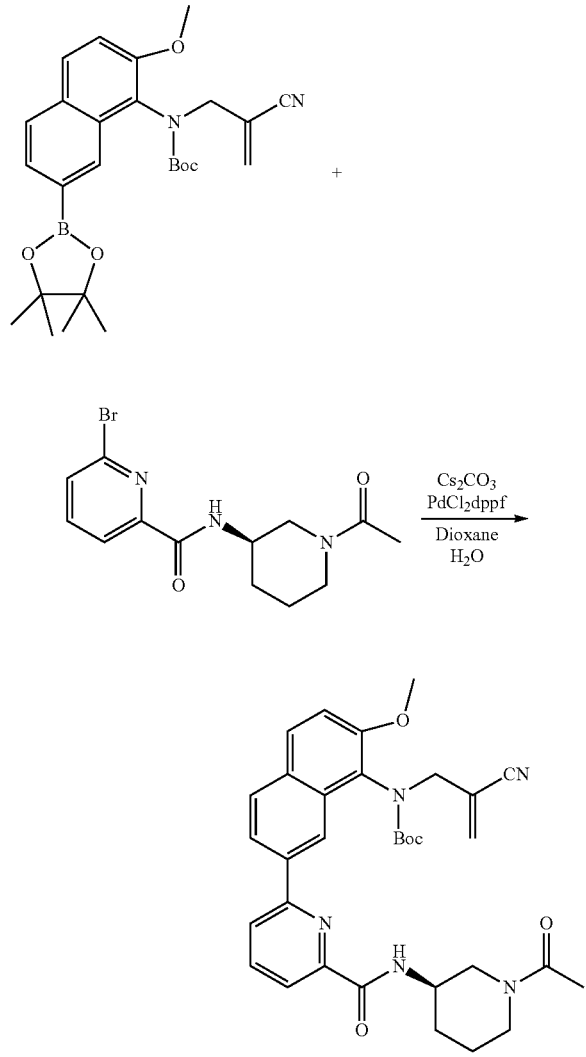

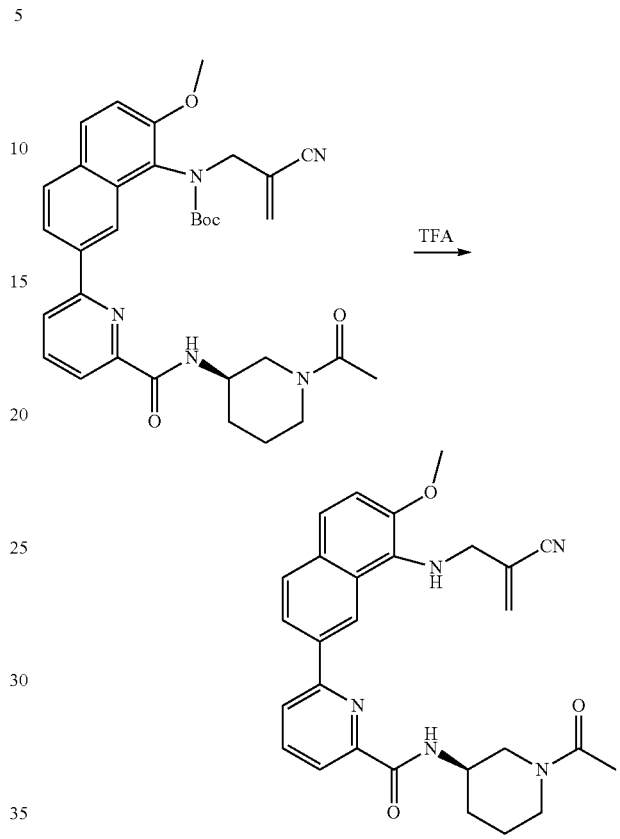

To a solution of tert-butyl N-(2-cyanoallyl)-N-[2-methoxy-7-(4,4,5,5-tetramethyl-1,3,2-dioxaborolan-2-yl)-1-naphthyl]carbamate (40 mg, 86.14 μmol) in dioxane (2 mL) and water (0.4 mL) were added N-[(3R)-1-acetyl-3-piperidyl]-6-bromo-pyridine-2-carboxamide (42.2 mg, 129.37 μmol), Cs$_2$CO$_3$ (83.99 mg, 258.42 μmol) and PdCl$_2$dppf (18 mg, 22.06 μmol). The reaction was heated at 100° C. for 30 min in a microwave. The reaction mixture was passed through a celite pad, and 2 mL of 0.5M EDTA was added. The resulting solution was stirred at r.t. for 30 min. The solution was then washed with brine, dried over anhydrous sodium sulfate, filtered, and concentrated in vacuo. The residue was purified by chromatography on silica gel eluting with 0-30% MeOH/EtOAc to afford the title compound (41.6 mg, Yield 100%).

To a solution of tert-butyl N-[7-[6-[[(3R)-1-acetyl-3-piperidyl]carbamoyl]-2-pyridyl]-2-methoxy-1-naphthyl]-N-(2-cyanoallyl)carbamate (41.6 mg, 71 μmol) in DCM (2 mL) was added TFA (0.5 mL) at 0° C. The resulting solution was stirred at 0° C. for 1 hour and r.t. for 1 h. The reaction mixture was concentrated in vacuo and the residue was diluted with DCM. The solution was washed with saturated NaHCO$_3$ and brine, dried over anhydrous sodium sulfate, filtered, and concentrated. The residue was purified by reverse phase HPLC using a gradient of water 0.1% LA/acetonitrile 0.1% PA to afford the title compound (10 mg, Yield 29%). (ES$^+$, m/z): 484.2.

Preparation of N-(2-bromo-4-pyridyl)-1-methylpyrrolidine-3-carboxamide

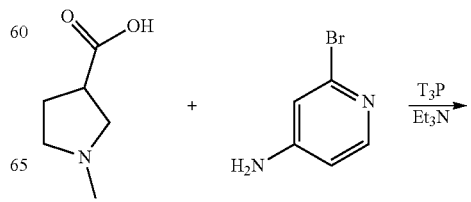

-continued

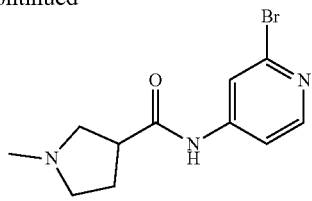

To a mixture of 1-methylpyrrolidine-3-carboxylic acid (200 mg, 1.548 mmol), 2-bromo-pyridin-4-amine (402 mg, 2.32 mmol) and Et₃N (391 mg, 7.74 mmol) in DMF (4 mL) was added T₃P (50 wt %, 2.06 mL, 2.32 mmol). The resulting mixture was stirred at r.t. for 18 h and partitioned between EtOAc and water. The aqueous phase was extracted with EtOAc (3×). The combined organic phase was washed with saturated NaHCO₃ and brine, dried over (MgSO₄), filtered, and concentrated in vacuo. The residue was purified by chromatography on C₁₋₈ column eluting a gradient of water 0.1% FA/acetonitrile 0.1% FA to afford the title compound (163 mg, Yield 37%).

Preparation of tert-butyl N-(2-cyanoallyl)-N-[2-methoxy-7-[4-[(1-methylpyrrolidine-3-carbonyl) amino]-2-pyridyl]-1-naphthyl]carbamate

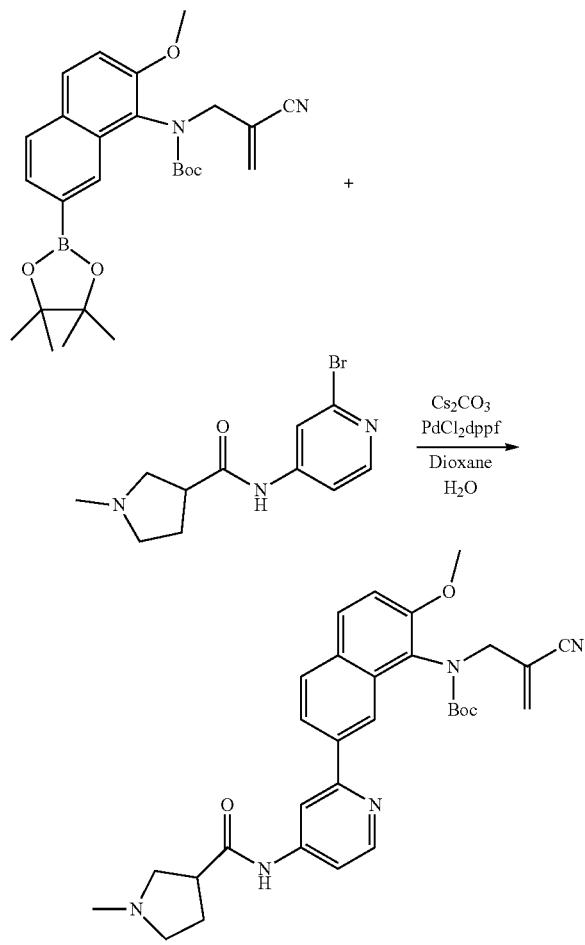

To a solution of tert-butyl N-(2-cyanoallyl)-N-[2-methoxy-7-(4,4,5,5-tetramethyl-1,3,2-dioxaborolan-2-yl)-1-naphthyl]carbamate (40 mg, 86.14 μmol) in dioxane (2 mL) and water (0.4 mL) were added N-(2-bromo-4-pyridyl)-1-methyl-pyrrolidine-3-carboxamide (36.7 mg, 129.16 μmol), Cs₂CO₃ (84 mg, 258.46 μmol) and PdCl₂dppf (18 mg, 22.06 μmol). The reaction was heated at 100° C. for 30 min in a microwave. The reaction mixture was passed through a celite pad, and 2 mL of 0.5M EDTA was added. The resulting solution was stirred at r.t. for 30 min. The solution was washed with brine, dried over anhydrous sodium sulfate, filtered, and concentrated in vacuo. The residue was purified by chromatography on silica gel eluting with 0-30% MeOH/EtOAc/5% Et₃N to afford the title compound (34.3 mg, Yield 74%).

Compound 114: Preparation of N-[2-[8-(2-cyanoallylamino)-7-methoxy-2-naphthyl]-4-pyridyl]-1-methyl-pyrrolidine-3-carboxamide

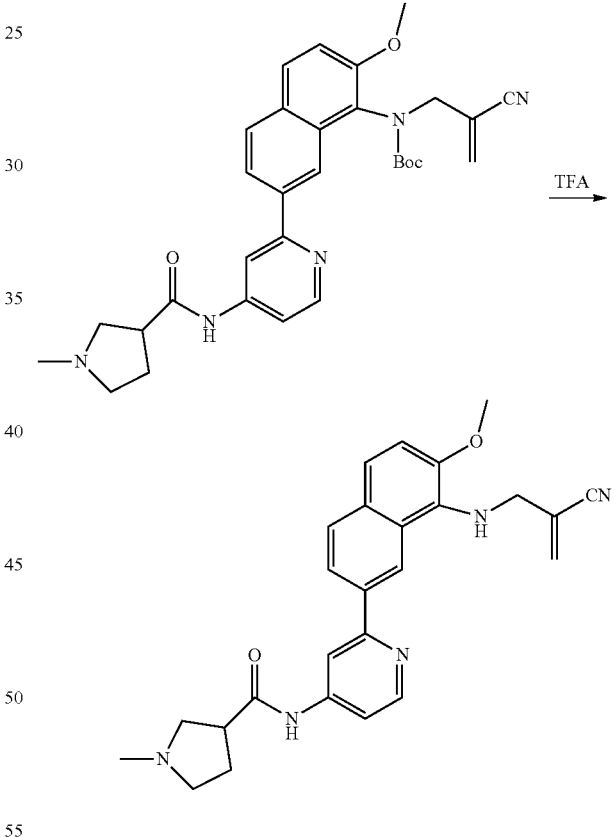

To a solution of tert-butyl N-(2-cyanoallyl)-N-[2-methoxy-7-[4-[(1-methylpyrrolidine-3-carbonyl)amino]-2-pyridyl]-1-naphthyl]carbamate (34.3 mg, 63 μmol) in DCM (2 mL) was added TFA (0.5 mL) at 0° C. The resulting solution was stirred at 0° C. for 1 hour and r.t. for 1 h. The reaction mixture was concentrated in vacuo, and the residue was diluted with DCM, washed with saturated NaHCO₃ and brine, dried over anhydrous sodium sulfate, filtered, and concentrated. The residue was purified by reverse phase HPLC using a gradient of water 0.1% FA/acetonitrile 0.1% FA to afford the title compound (5 mg, Yield 17.9%). (ES⁺, m/z): 442.2.

Preparation of 6-bromo-N-[1-(2-hydroxyethyl)piperidin-4-yl]pyridine-2-carboxamide

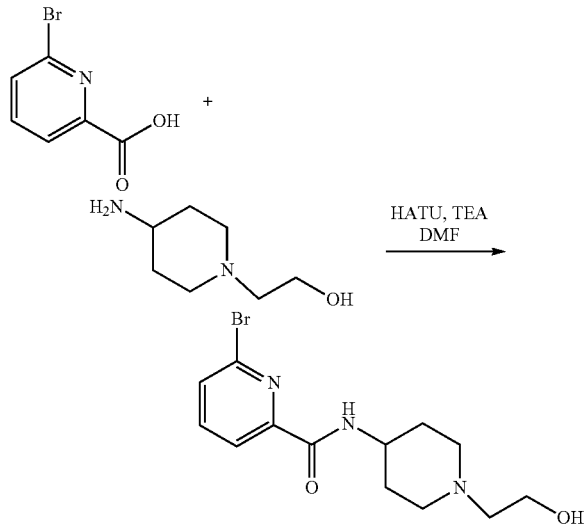

To a solution of 6-bromopyridine-2-carboxylic acid (0.5 g, 2.49 mmol) in DMF (5 mL) were added HATU (1.04 g, 2.74 mmol) and triethylamine (0.7 mL, 5 mmol). The solution was stirred for 5 minutes at r.t. Then, 2-(4-aminopiperidin-1-yl)ethan-1-ol (334 mg, 2.74 mmol) in DMF (5 mL) was added, and the reaction mixture was stirred at r.t. for 4 hours. The resulting solution was diluted with water and extracted with EtOAc (2x). The combined organic phase was washed with brine, dried over anhydrous sodium sulfate, filtered, and concentrated in vacuo. The crude material was purified by column chromatography. The desired product was eluted with 30% MeOH-65% EtOAc-5% TEA to afford an oil (220 mg, 27% yield).

Preparation of tert-butyl N-(2-cyanoallyl)-N-[7-[6-[[1-(2-hydroxyethyl)-4-piperidyl]carbamoyl]-2-pyridyl]-2-methoxy-1-naphthyl]carbamate

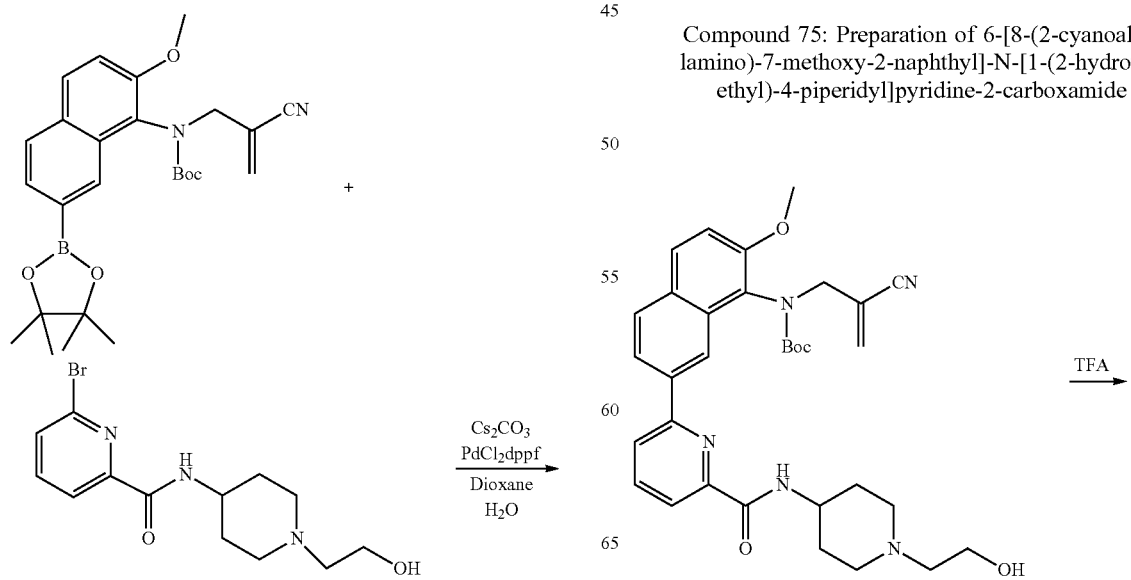

To a solution of tert-butyl N-(2-cyanoallyl)-N-[2-methoxy-7-(4,4,5,5-tetramethyl-1,3,2-dioxaborolan-2-yl)-1-naphthyl]carbamate (40 mg, 86.14 µmol) in dioxane (2 mL) and water (0.4 mL) were added 6-bromo-N-[1-(2-hydroxyethyl)-4-piperidyl]pyridine-2-carboxamide (42.4 mg, 129.19 µmol), Cs₂CO₃ (84 mg, 258.46 µmol) and PdCl₂dppf (18 mg, 22.06 µmol). The reaction was heated at 100° C. for 30 min in a microwave. The reaction mixture was passed through a celite pad, and 2 mL of 0.5M EDTA was added. The resulting solution was stirred at r.t. for 40 min. The solution was washed with brine, dried over anhydrous sodium sulfate, filtered, and concentrated in vacuo. The residue was purified by chromatography on silica gel eluting with 10-50% MeOH/EtOAc/2.5% Et₃N to afford the title compound (40.7 mg, Yield 81%).

Compound 75: Preparation of 6-[8-(2-cyanoallylamino)-7-methoxy-2-naphthyl]-N-[1-(2-hydroxyethyl)-4-piperidyl]pyridine-2-carboxamide

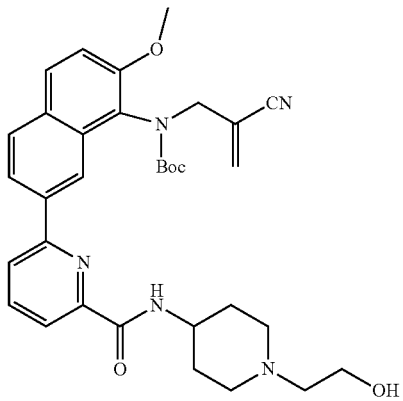

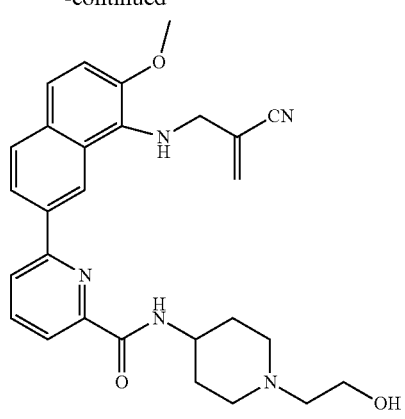

To a solution of tert-butyl N-(2-cyanoallyl)-N-[7-[6-[[1-(2-hydroxyethyl)-4-piperidyl]carbamoyl]-2-pyridyl]-2-methoxy-1-naphthyl]carbamate (40.7 mg, 69.49 µmol) in DCM (2 mL) was added TFA (0.5 mL) at 0° C. The resulting solution was stirred at 0° C. for 1 hour and r.t. for 1 h. The reaction mixture was concentrated in vacuo and the residue was diluted with DCM, washed with saturated NaHCO$_3$ and brine, dried over anhydrous sodium sulfate, filtered, and concentrated. The residue was purified by reverse phase HPLC using a gradient of water 0.1% FA/acetonitrile 0.1% FA to afford the title compound (21.2 mg, Yield 63%). LC-MS (ES$^+$, m/z): 486 [(M+H)$^+$]. Preparation of 6-bromo-N-[1-(2-methoxyethyl)piperidin-4-yl]pyridine-2-carboxamide

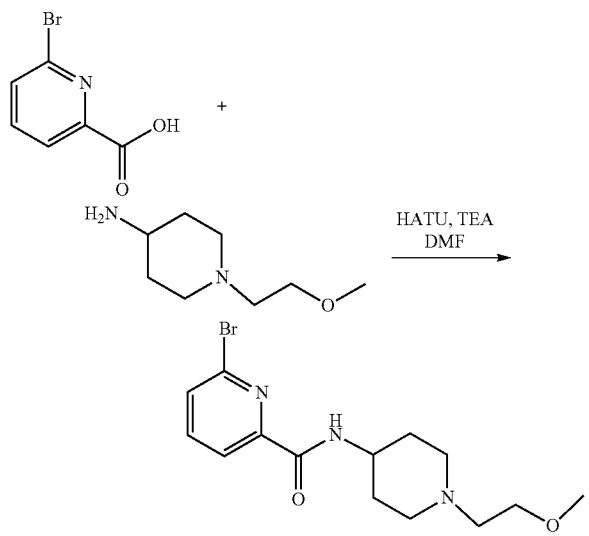

To a solution of 6-bromopyridine-2-carboxylic acid (0.5 g, 2.49 mmol) in DMF (5 mL) were added HATU (1.04 g, 2.74 mmol) and triethylamine (0.7 mL, 5 mmol). The solution was stirred for 5 minutes at r.t. Then, 1-(2-methoxyethyl)piperidin-4-amine (433 mg, 2.74 mmol) in DMF (5 mL) was added, and the reaction mixture was stirred at r.t. for 4 hours. The resulting solution was diluted with water and extracted with EtOAc (2×). The combined organic phase was washed with brine, dried over anhydrous sodium sulfate, and concentrated in vacuo. The crude material was purified by column chromatography. The desired product was eluted with 30% MeOH-65% EtOAc-5% TEA to afford an oil (810 mg, 95% yield).

Preparation of tert-butyl N-(2-cyanoallyl)-N-[2-methoxy-7-[6-[[1-(2-methoxyethyl)-4-piperidyl]carbamoyl]-2-pyridyl]-1-naphthyl]carbamate

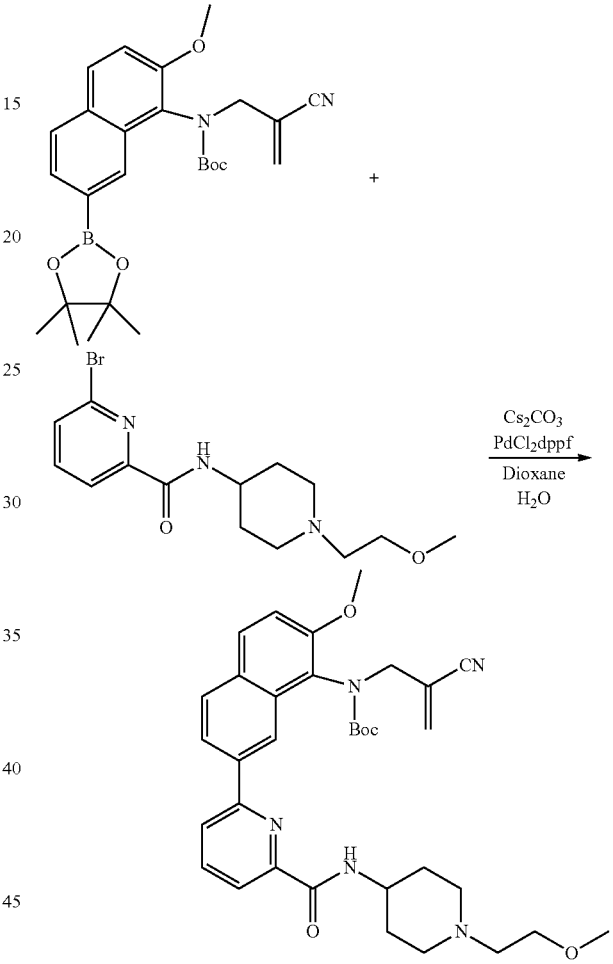

To a solution of tert-butyl N-(2-cyanoallyl)-N-[2-methoxy-7-(4,4,5,5-tetramethyl-1,3,2-dioxaborolan-2-yl)-1-naphthyl]carbamate (40 mg, 86.14 µmol) in dioxane (2 mL) and water (0.4 mL) were added 6-bromo-N-[1-(2-methoxyethyl)-4-piperidyl]pyridine-2-carboxamide (44.1 g, 128.86 mmol), Cs$_2$CO$_3$ (84 mg, 258.46 µmol), and PdCl$_2$dppf (18 mg, 22.06 µmol). The reaction was heated at 100° C. for 30 min in a microwave. The reaction mixture was passed through a celite pad, and 2 mL of 0.5M EDTA was added. The resulting solution was stirred at r.t. for 40 min. The solution was washed with brine, dried over anhydrous sodium sulfate, filtered, and concentrated in vacuo. The residue was purified by chromatography on silica gel eluting with 0-20% MeOH/EtOAc to afford the title compound (51.5 mg, Yield 100%).

Compound 82: Preparation of 6-[8-(2-cyanoallylamino)-7-methoxy-2-naphthyl]-N-[1-(2-methoxyethyl)-4-piperidyl]pyridine-2-carboxamide

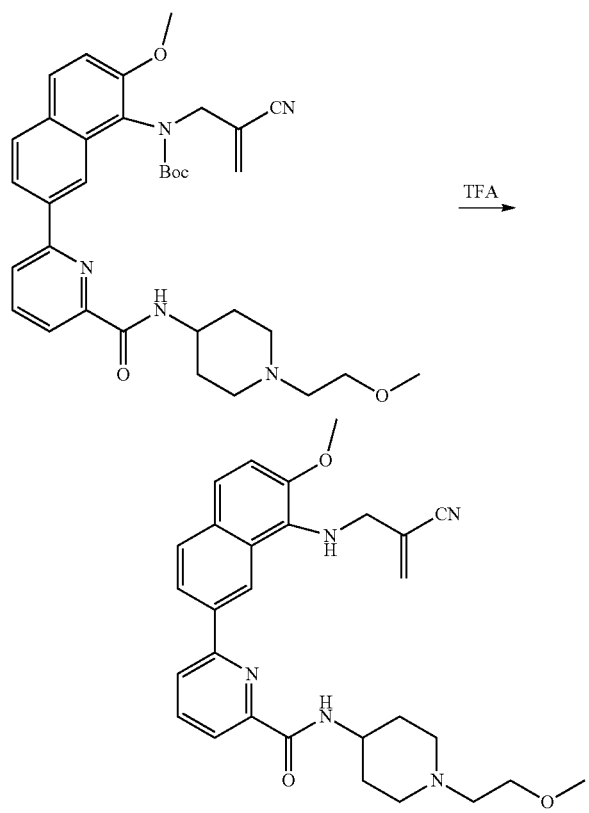

To a solution of tert-butyl N-(2-cyanoallyl)-N-[2-methoxy-7-[6-[[1-(2-methoxyethyl)-4-piperidyl]carbamoyl]-2-pyridyl]-1-naphthyl]carbamate (51.5 mg, 85.9 μmol) in DCM (2 mL) was added TFA (0.5 mL) at 0° C. The resulting solution was stirred at 0° C. for 1 hour and r.t. for 1 h. The reaction mixture was concentrated in vacuo, and the residue was diluted with DCM, washed with saturated NaHCO₃ and brine, dried over anhydrous sodium sulfate, filtered, and concentrated. The residue was purified by reverse phase HPLC using a gradient of water 0.1% FA/acetonitrile 0.1% FA to afford the title compound (13 mg, Yield 31%). %). FC-MS (ES$^+$, m/z): 500 [(M+H)$^+$].

Route 3: General Scheme

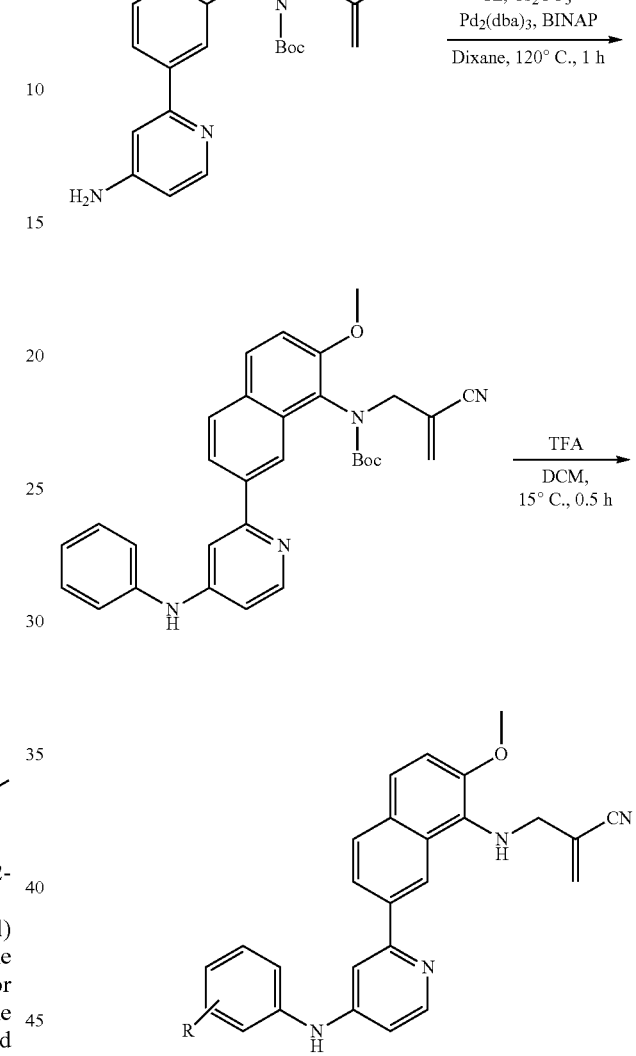

Example 61, 62, 155

Preparation of tert-butyl N-[7-(4-aminopyridin-2-yl)-2-Methoxynaphthalen-1-yl]-N-(2-cyano-2-methylideneethyl)carbamate

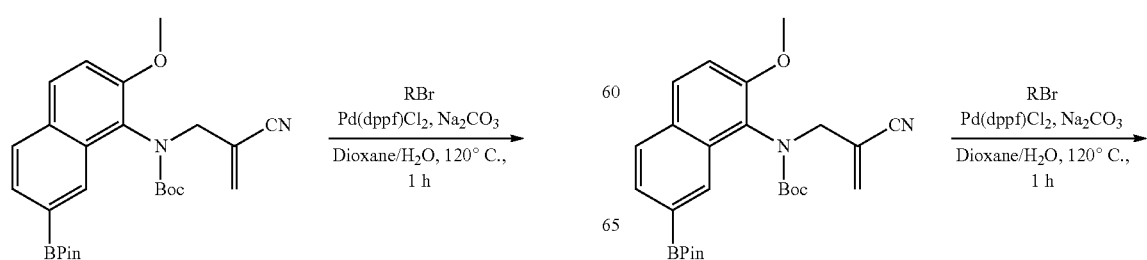

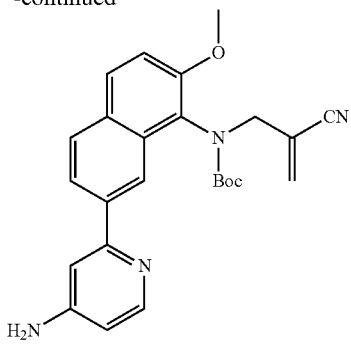

To a solution of tert-butyl N-(2-cyano-2-methylideneethyl)-N-[2-methoxy-7-(4,4,5,5-tetramethyl-1,3,2-dioxaborolan-2-yl)naphthalen-1-yl]carbamate (130 mg, 279.96 μmol, 1 eq), 2-bromopyridin-4-amine (65 mg, 375.7 μmol, 1.34 eq) in dioxane (4 mL) and H₂O (1 mL) were added Pd(dppf)Cl₂ (20.5 mg, 28 μmol, 0.1 eq) and Na₂CO₃ (89 mg, 839.87 μmol, 3 eq). The reaction was then stirred at 120° C. for 60 min under N₂ atmosphere. The reaction was extracted with DCM:MeOH=10:1 (5×20 mL). The combined organic layer was washed with brine (2×10 mL), dried over Na₂SO₄, filtered, and concentrated. The crude was purified by prep-TLC (SiO₂, DCM/MeOH=10:1, Rf=0.1). The title compound was obtained as a yellow oil (80 mg, 185.83 μmol, 66.38% yield).

Preparation of tert-butyl N-(2-cyano-2-methylideneethyl)-N-{2-Methoxy-7-[4-(phenylamino)pyridine-2-yl]naphthalen-1-yl}carbamate

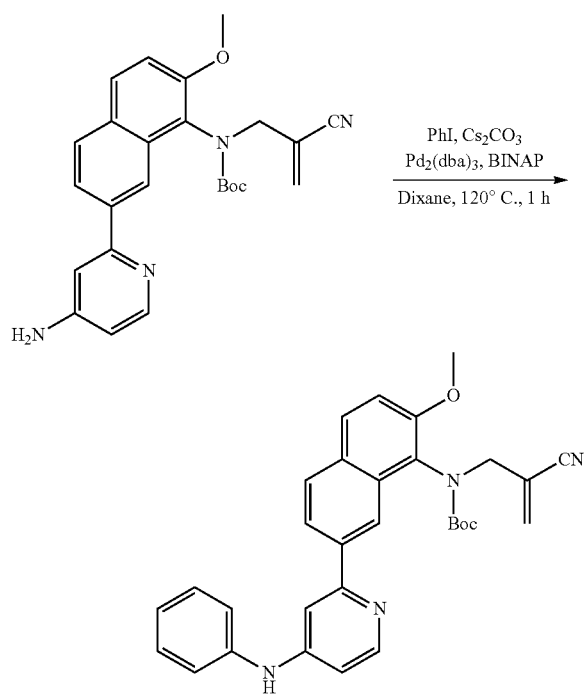

To a solution of tert-butyl N-[7-(4-aminopyridin-2-yl)-2-Methoxynaphthalen-1-yl]-N-(2-cyano-2-methylideneethyl)carbamate (150 mg, 348.43 μmol, 1 eq), iodobenzene (138.5 mg, 678.71 μmol, 75.66 μL, 1.95 eq) in dioxane (4.5 mL) was added Cs₂CO₃ (340.6 mg, 1.05 mmol, 3 eq). BINAP (43.4 mg, 69.69 μmol, 0.2 eq) and Pd₂(dba)₃ (31.9 mg, 34.84 μmol, 0.1 eq) were then added to the reaction. The reaction was stirred at 120° C. for 1 h under N₂ atmosphere. Upon completion of the reaction as indicated by TLC, 30 mL saturated EDTA and 20 mL DCM were added to the reaction. Then the reaction was stirred at 15° C. for 1 h, and the reaction mixture was then extracted with DCM (3×20 mL). The combined organic layer was washed with brine (3×20 mL), dried over Na₂SO₄, filtered, and concentrated. The crude was purified by prep-TLC (SiO₂, DCM:MeOH=15:1, Rf=0.5) to afford the title compound as a yellow oil (40 mg, 67.11 μmol, 19.26% yield, 85% purity).

Compound 155: Preparation of 2-[({2-methoxy-7-[4-(phenylamino)pyridin-2-yl]naphthalen-1-yl}amino)methyl]prop-2-enenitrile

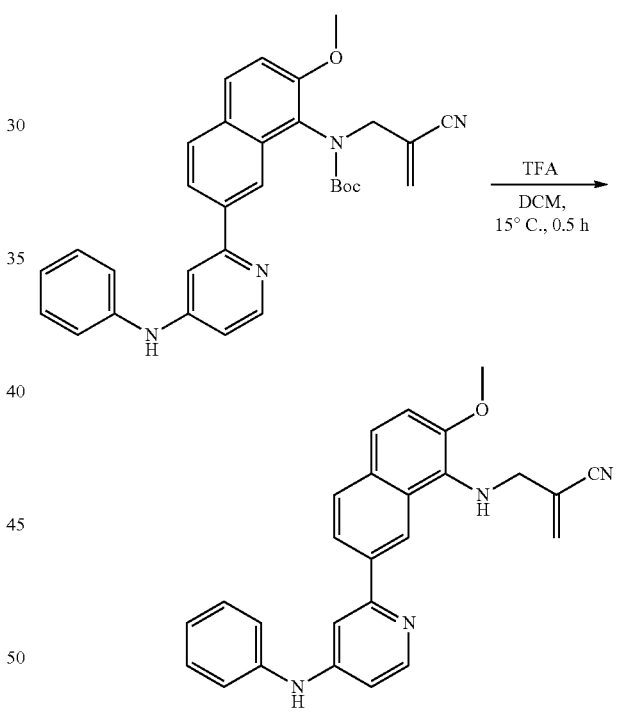

To a solution of tert-butyl N-(2-cyano-2-methylideneethyl)-N-{2-Methoxy-7-[4-(phenylamino)pyridine-2-yl]naphthalen-1-yl}carbamate (40 mg, 78.96 μmol, 1 eq) in DCM (3 mL) was added TFA (0.6 mL). Then the reaction was stirred at 15° C. for 0.5 h. Upon completion of the reaction as indicated by LCMS and TLC. The reaction was poured into saturated NaHCO₃ (30 mL) to adjust PH to 8-9, and extracted with DCM (4×10 mL). The combined organic layer was washed with brine (3×10 mL), dried over Na₂SO₄, filtrated, and concentrated to afford crude product. The crude was purified by prep-HPLC to obtain the title compound was obtained as a yellow solid (7.1 mg, 17.17 μmol, 21.75% yield). LC-MS (ES⁺, m/z): 407.1 [(M+H)⁺].

101

Route 4: General Scheme

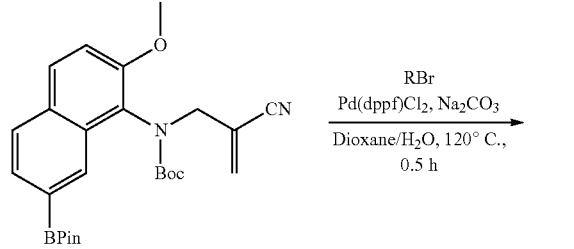

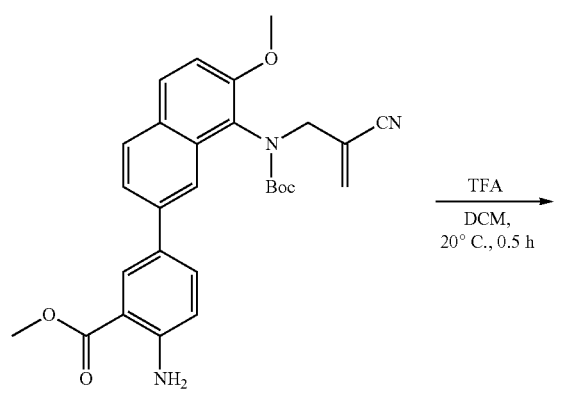

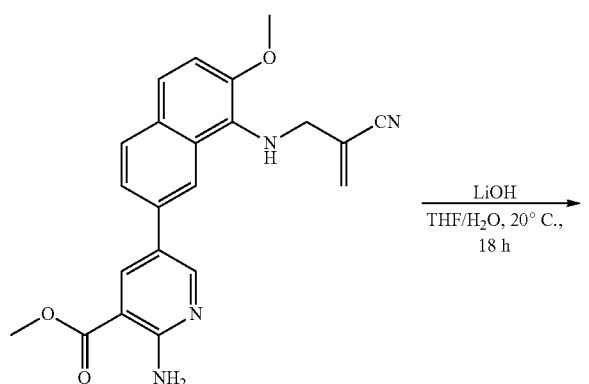

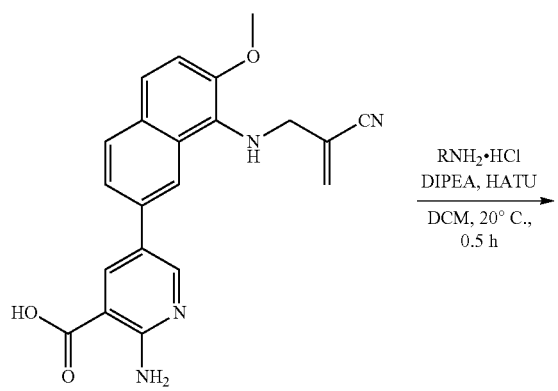

102

-continued

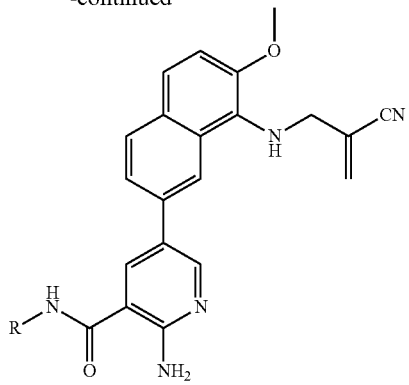

Preparation of methyl 2-amino-5-(8-{[(tert-butoxy)carbonyl](2-Cyano-2-methylideneethyl)amino}-7-Methoxynaphthalen-2-yl)pyridine-3-carboxylate

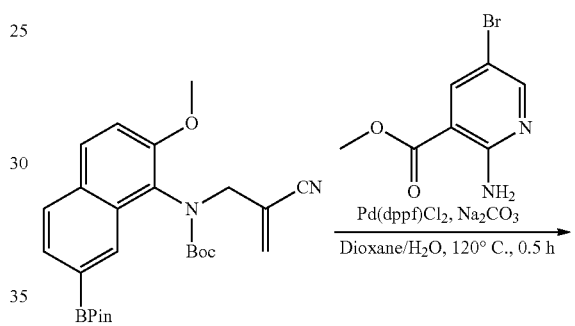

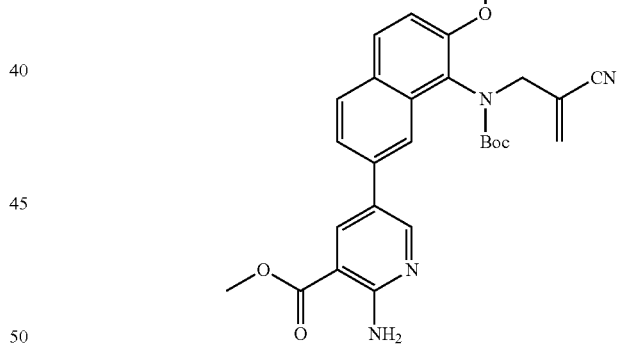

To a mixture of tert-butyl N-(2-cyano-2-methylideneethyl)-N-[2-methoxy-7-(4,4,5,5-tetramethyl-1,3,2-dioxaborolan-2-yl)naphthalen-1-yl]carbamate (1 g, 2.15 mmol, 1 eq) and methyl 2-amino-5-bromo-pyridine-3-carboxylate (547.3 mg, 2.37 mmol, 1.1 eq) in dioxane (8 mL) and H$_2$O (2 mL) were added Na$_2$CO$_3$ (684.8 mg, 6.46 mmol, 3 eq) and Pd(dppf)Cl$_2$ (78.8 mg, 107.68 μmol, 0.05 eq) under N$_2$, and the mixture was stirred for 0.5 h at 120° C. The reaction was poured into saturated EDTA (200 mL) and stirred for 2 h. The aqueous phase was extracted with EtOAc (3×50 mL). The combined organic phase was washed with brine (3×50 mL), dried with anhydrous Na$_2$SO$_4$, filtered, and concentrated in vacuo. The crude was purified by silica gel chromatography to afford the title compound (560 mg, 1.15 mmol, 53.23% yield) as a white solid.

103
Preparation of methyl 2-amino-5-{8-[(2-cyano-2-methylideneethyl)amino]-7-methoxy naphthalen-2-yl}pyridine-3-carboxylate

104
Preparation of 2-amino-5-[8-(2-cyanoallylamino)-7-methoxy-2-naphthyl]pyridine-3-carboxylic acid

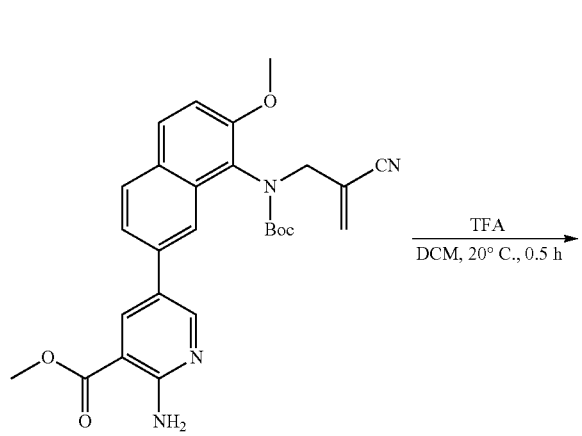

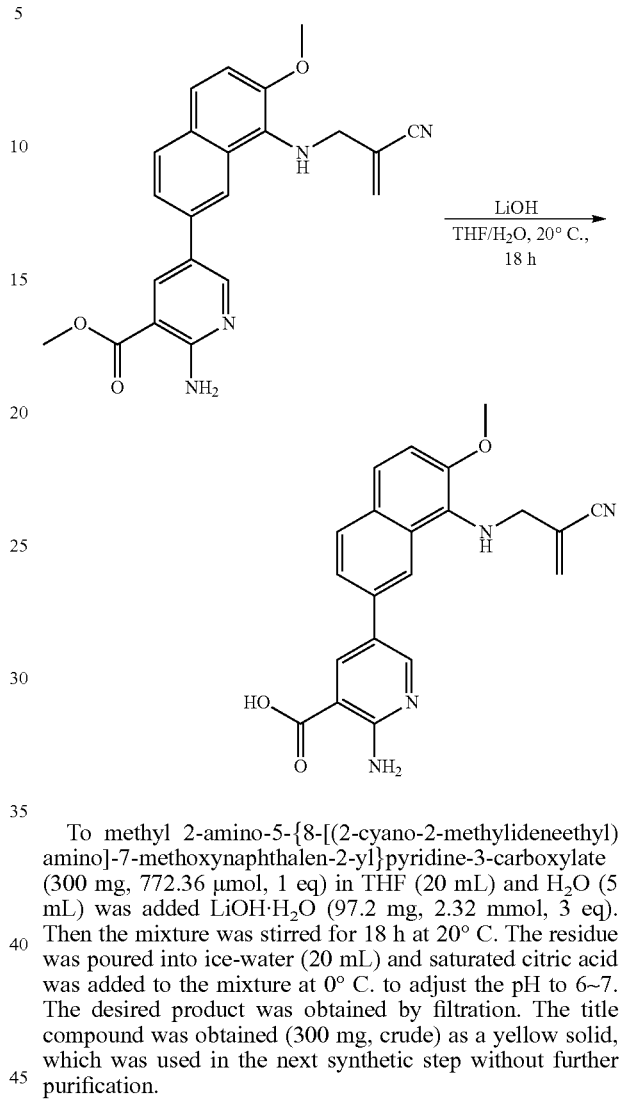

To TFA (5 mL) and DCM (5 mL) was added methyl 2-amino-5-(8-{[(tert-butoxy)carbonyl] (2-Cyano-2-methylideneethyl)amino}-7-Methoxynaphthalen-2-yl)pyridine-3-carboxylate (500 mg, 1.02 mmol, 1 eq). Then the mixture was stirred for 0.5 h at 20° C. Upon completion of the reaction as indicated by LCMS and TLC. The residue was poured into ice-water (100 mL) and saturated Na₂CO₃ was added to the mixture at 0° C. to adjust the pH to 8~9. The aqueous phase was extracted with DCM (3×50 mL), and the combined organic phase was washed with brine (3×50 mL), dried with anhydrous Na₂SO₄, filtered, and concentrated in vacuo. The crude was purified by silica gel chromatography to afford the title compound (350 mg, 901.09 μmol, 88.04% yield) as a brown oil.

To methyl 2-amino-5-{8-[(2-cyano-2-methylideneethyl)amino]-7-methoxynaphthalen-2-yl}pyridine-3-carboxylate (300 mg, 772.36 μmol, 1 eq) in THF (20 mL) and H₂O (5 mL) was added LiOH·H₂O (97.2 mg, 2.32 mmol, 3 eq). Then the mixture was stirred for 18 h at 20° C. The residue was poured into ice-water (20 mL) and saturated citric acid was added to the mixture at 0° C. to adjust the pH to 6~7. The desired product was obtained by filtration. The title compound was obtained (300 mg, crude) as a yellow solid, which was used in the next synthetic step without further purification.

Compound 153: Preparation of 2-amino-5-[8-(2-cyanoallylamino)-7-methoxy-2-naphthyl]-N-(1-methyl-4-piperidyl)pyridine-3-carboxamide

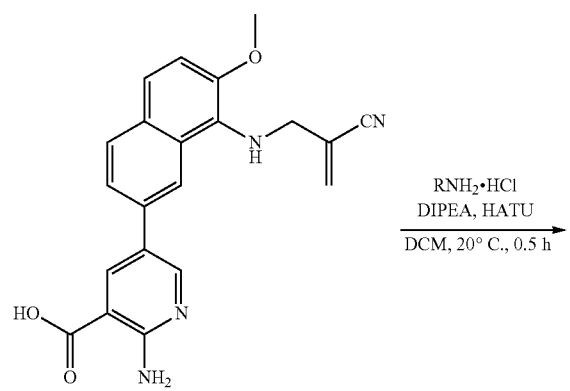

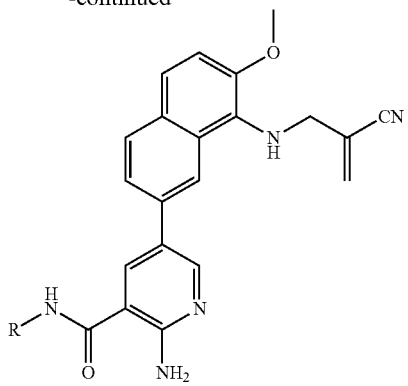

To a mixture of RNH₂ (30.5 mg, 267.1 μmol, 2 eq) and 2-amino-5-[8-(2-cyanoallylamino)-7-methoxy-2-naphthyl]pyridine-3-carboxylic acid (50 mg, 133.55 μmol, 1 eq) in DCM (5 mL) was added DIPEA (51.8 mg, 400.65 μmol, 69.78 μL, 3 eq). Then HATU (76.2 mg, 200.32 μmol, 1.5 eq) was added to the mixture. The mixture was stirred at 20° C. for 0.5 h. Upon completion of the reaction as indicated by LCMS and TLC. The reaction was slowly quenched by ice water (50 mL) and extracted with DCM (3×20 mL). The combined organic phase was washed with brine (3×20 mL), dried over anhydrous Na₂SO₄, filtered, and concentrated in vacuo. The crude was purified by prep-HPLC to afford the title compound (14.1 mg, 29.96 μmol, 22.44% yield) as a yellow solid. LC-MS (ES⁺, m/z): 471.2 [(M+H)⁺].

Preparation of tert-butyl N-(7-{4-amino-6-[(2-hydroxyethyl)carbamoyl]pyridin-2-yl}-2-methoxynaphthalen-1-yl)-N-(2-cyano-2-methylideneethyl)carbamate

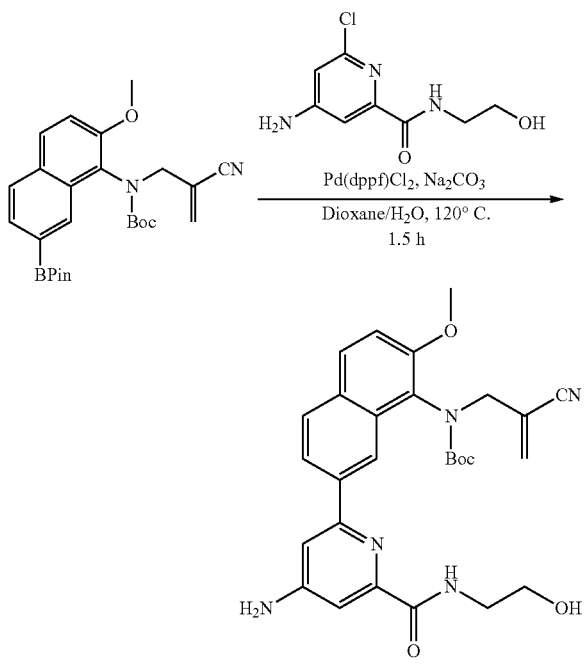

To a mixture of tert-butyl N-(2-cyanoallyl)-N-[2-methoxy-7-(4,4,5,5-tetramethyl-1,3,2-dioxaborolan-2-yl)-1-naphthyl]carbamate (100 mg, 215.35 μmol, 1 eq) and 4-amino-6-chloro-N-(2-hydroxyethyl)pyridine-2-carboxamide (55.7 mg, 258.4 μmol, 1.2 eq) in dioxane (2 mL) and H₂O (0.5 mL) were added Na₂CO₃ (68.5 mg, 646.05 μmol, 3 eq), Pd(dppf)Cl₂ (78.8 mg, 107.68 μmol, 0.5 eq) in one portion under N₂. The mixture was stirred at 120° C. for 1.5 hours. Upon completion of the reaction as indicated by TLC, 20 mL of EtOAc was poured into the mixture. The mixture was poured into saturated EDTA solution (30 mL) and stirred for 1 h. The aqueous phase was extracted with EtOAc (3×20 mL). The combined organic phase was washed with brine (3×30 mL), dried with anhydrous Na₂SO₄ and active carbon to remove color, and filtered and concentrated in vacuo. The residue was purified by prep-TLC (SiO₂, DCM:MeOH=10:1) to afford the title compound (30 mg, 57.96 μmol, 26.9% yield) as a yellow gum.

Compound 81: Preparation of 4-amino-6-(8-((2-cyanoallyl)amino)-7-methoxynaphthalen-2-yl)-N-(2-hydroxy ethyl)picolinamide

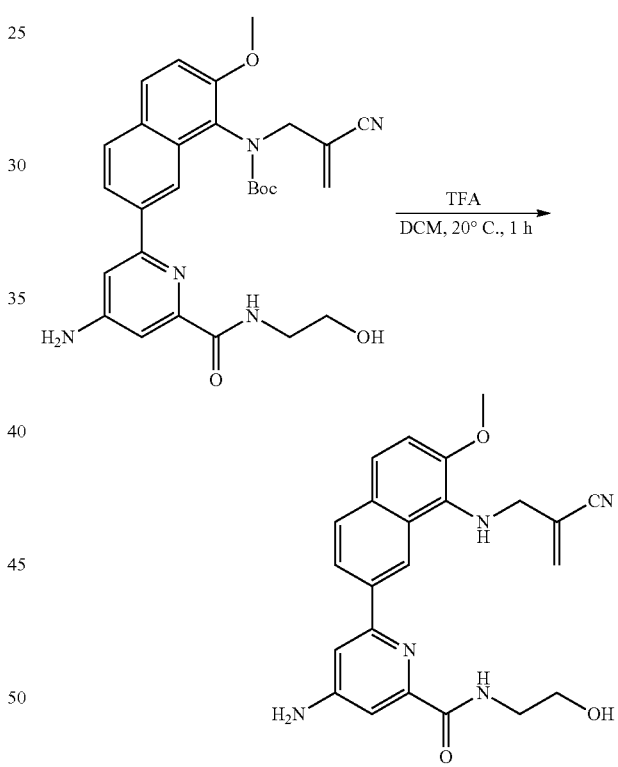

To a mixture of tert-butyl N-(7-{4-amino-6-[(2-hydroxy ethyl)carbamoyl]pyridin-2-yl}-2-methoxynaphthalen-1-yl)-N-(2-cyano-2-methylideneethyl)carbamate (30 mg, 96.6 μmol, 1 eq) in DCM (3 mL) was added TFA (1.54 g, 13.51 mmol, 1 mL, 139.81 eq), and the reaction was stirred at 20° C. for 1 hour. The reaction was adjusted to pH=9 with saturated aq. Na₂CO₃. The mixture was extracted with EtOAc (3×20 mL). The combined organic layer was washed with brine (2×20 mL), dried over Na₂SO₄, filtered, and concentrated in vacuo. The residue was purified by prep-HPLC to afford the title compound (5.5 mg, 12.6 μmol, 13% yield, 95.6% purity) as a yellow solid. LC-MS (ES⁺, m/z): 418.1 [(M+H)⁺].

107

Preparation of tert-butyl N-(2-cyanoallyl)-N-[7-[2-[[(2S,4R)-1,2-dimethyl-4-piperidyl]carbamoyl]thiazol-4-yl]-2-methoxy-1-naphthyl]carbamate

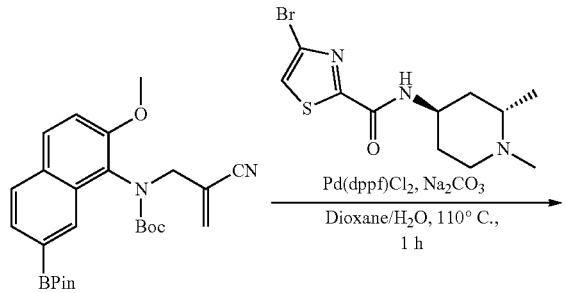

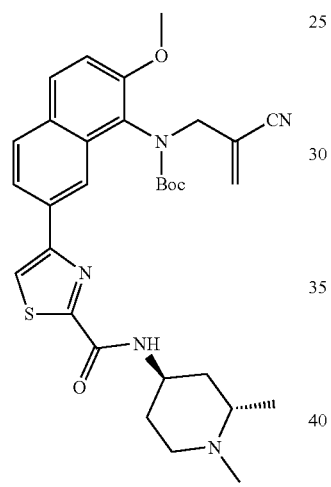

To a mixture of tert-butyl N-(2-cyanoallyl)-N-[2-methoxy-7-(4,4,5,5-tetramethyl-1,3,2-dioxaborolan-2-yl)-1-naphthyl]carbamate (150 mg, 323.03 μmol, 1 eq) and 4-bromo-N-[(2S,4R)-1,2-dimethyl-4-piperidyl]thiazole-2-carboxamide (113.1 mg, 355.33 μmol, 1.1 eq) in dioxane (2 mL), H₂O (0.5 mL) were added Na₂CO₃ (171.2 mg, 1.62 mmol, 5 eq), Pd(dppf)Cl₂ (94.5 mg, 129.21 μmol, 0.4 eq) in one portion under N₂. The mixture was stirred at 110° C. for 1 hour. The reaction was diluted with 30 mL water and extracted with EtOAc (2×30 mL). The combined organic layer was washed with brine (2×20 mL), dried over Na₂SO₄, filtered, and concentrated in vacuo. The residue was purified by prep-TLC (SiO₂, DCM:MeOH=5:1) to afford tert-butyl N-(2-cyanoallyl)-N-[7-[2-[[(2S,4R)-1,2-dimethyl-4-piperidyl]carbamoyl]thiazol-4-yl]-2-methoxy-1-naphthyl]carbamate (60 mg, 104.22 μmol, 32.26% yield) as a yellow gum. LC-MS (ES$^+$, m/z): 576.2 [(M+H)$^+$].

108

Compound 143: Preparation of 4-[8-(2-cyanoallylamino)-7-methoxy-2-naphthyl]-N-[(2S,4R)-1,2-dimethyl-4-piperidyl]thiazole-2-carboxamide

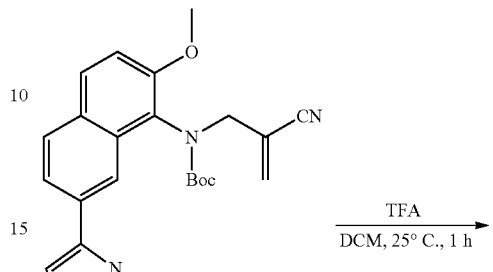

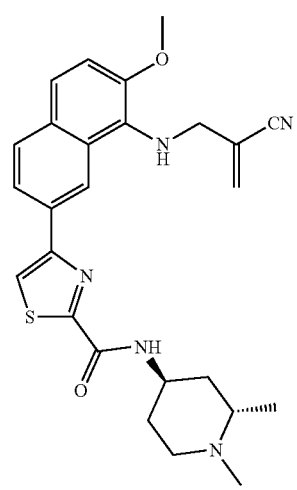

To a mixture of tert-butyl N-(2-cyanoallyl)-N-[7-[2-[[(2S,4R)-1,2-dimethyl-4-piperidyl]carbamoyl]thiazol-4-yl]-2-methoxy-1-naphthyl]carbamate (60 mg, 104.22 μmol, 1 eq) in DCM (3 mL) was added TFA (1.54 g, 13.51 mmol, 1 mL, 129.60 eq). The reaction was stirred at 25° C. for 1 hour. The reaction was diluted with 30 mL water, and the pH was adjusted to 9 with saturated aq. Na₂CO₃. The mixture was extracted with DCM (2×15 mL), and the combined organic layer was washed with brine (3×15 mL), dried over Na₂SO₄, filtered, and concentrated in vacuo. The residue was purified by prep-HPLC to afford 4-[8-(2-cyanoallylamino)-7-methoxy-2-naphthyl]-N-[(2S,4R)-1,2-dimethyl-4-piperidyl]thiazole-2-carboxamide (11.6 mg, 24.29 μmol, 23.31% yield, 99.6% purity) as a yellow solid. LC-MS (ES$^+$, m/z): 476.2 [(M+H)$^+$] $^1$H NMR (400 MHz, DMSO-d₆) δ=8.83 (s, 1H), 8.51 (d, J=8.4 Hz, 1H), 8.46 (s, 1H), 8.06 (dd, J=1.6, 8.8 Hz, 1H), 7.90 (d, J=8.8 Hz, 1H), 7.55 (d, J=8.8 Hz, 1H), 7.40 (d, J=8.8 Hz, 1H), 6.04 (s, 1H), 5.99 (s, 1H), 5.31 (t, J=7.6 Hz, 1H), 4.06 (d, J=7.6 Hz, 2H), 3.91 (s, 3H), 3.87-3.79 (m, 1H), 2.87-2.79 (m, 1H), 2.17 (s, 3H), 2.10-2.02 (m, 1H), 1.94 (br dd, J=6.4, 8.8 Hz, 1H), 1.84-1.67 (m, 3H), 1.44 (q, J=12.0 Hz, 1H), 1.04 (d, J=6.0 Hz, 3H).

Preparation of tert-butyl N-[7-[5-amino-6-[[4-(dimethylamino)cyclohexyl]carbamoyl]-2-pyridyl]-2-methoxy-1-naphthyl]-N-(2-cyanoallyl)carbamate Route 5: General Scheme

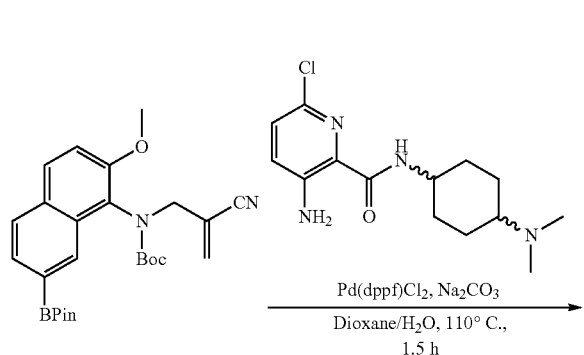

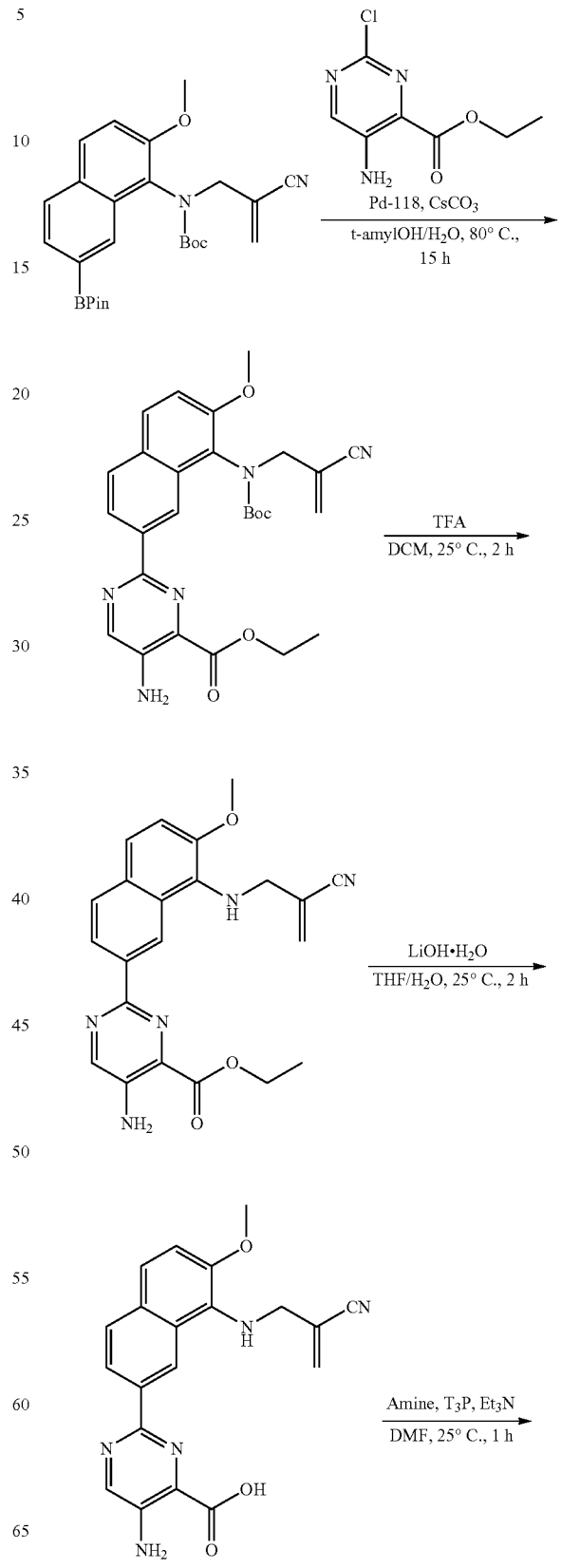

To a mixture of tert-butyl N-(2-cyanoallyl)-N-[2-methoxy-7-(4,4,5,5-tetramethyl-1,3,2-dioxaborolan-2-yl)-1-naphthyl]carbamate (300 mg, 646.05 µmol, 1 eq) and 3-amino-6-chloro-N-[4-(dimethylamino)cyclohexyl]pyridine-2-carboxamide (210.9 mg, 710.66 µmol, 1.1 eq) in dioxane (4 mL) and H$_2$O (1 mL) were added Na$_2$CO$_3$ (205.4 mg, 1.94 mmol, 3 eq), Pd(dppf)Cl$_2$ (47.27 mg, 64.61 µmol, 0.1 eq) in one portion under N$_2$. The mixture was stirred at 110° C. for 1.5 hour. The reaction mixture was poured into 50 mL saturated EDTA and stirred at 25° C. for 1 h. Then the aqueous phase was extracted with EtOAc (3×30 mL), and the combined organic layer was washed with brine (3×30 mL), dried over Na$_2$SO$_4$, filtered, and concentrated in vacuo. The residue was purified by column chromatography (SiO$_2$, DCM:MeOH=5:1) to afford tert-butyl N-[7-[5-amino-6-[[4-(dimethylamino)cyclohexyl]carbamoyl]-2-pyridyl]-2-methoxy-1-naphthyl]-N-(2-cyanoallyl)carbamate (50 mg, 83.51 µmol, 12.93% yield) as a yellow oil. LC-MS (ES$^+$, m/z): 599.4 [(M+H)$^+$].

-continued

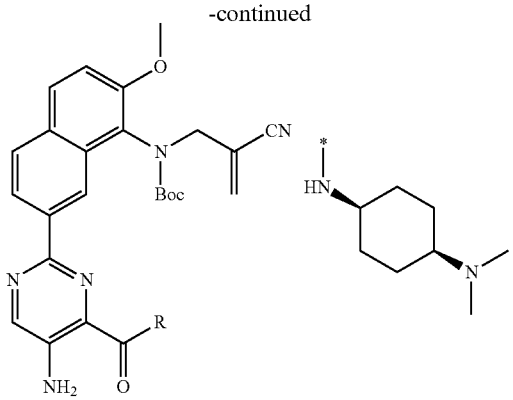

Preparation of ethyl 5-amino-2-[8-[tert-butoxycarbonyl(2-cyanoallyl)amino]-7-methoxy-2-naphthyl]pyrimidine-4-carboxylate

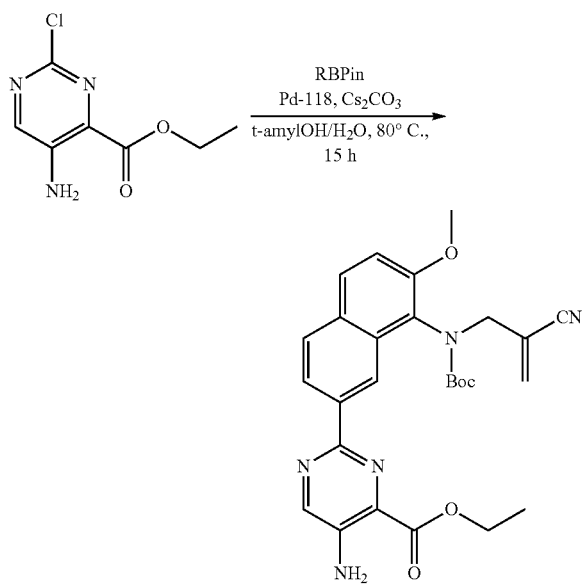

To a mixture of ethyl 5-amino-2-chloro-pyrimidine-4-carboxylate (500 mg, 2.48 mmol, 1 eq) and tert-butyl N-(2-cyanoallyl)-N-[2-methoxy-7-(4,4,5,5-tetramethyl-1,3,2-dioxaborolan-2-yl)-1-naphthyl]carbamate (1.27 g, 2.73 mmol, 1.1 eq) and tert-amyl alcohol (10 mL) in H$_2$O (2.5 mL) were added Cs$_2$CO$_3$ (1.62 g, 4.96 mmol, 2 eq) and ditert butyl(cyclopentyl)phosphane; dichloro palladium; iron (161.6 mg, 248 μmol, 0.1 eq) in one portion under N$_2$. The mixture was stirred at 80° C. for 15 hours. The reaction mixture was poured into 30 mL saturated EDTA and stirred at 25° C. for 1 h. Then the aqueous phase was extracted with EtOAc (3×30 mL), and the combined organic layer was washed with brine (2×30 mL), dried over Na$_2$SO$_4$, filtered, and concentrated in vacuo. The residue was purified by column chromatography (SiO$_2$, PE:EtOAc=1/1) to afford ethyl 5-amino-2-[8-[tert-butoxycarbonyl(2-cyanoallyl)amino]-7-methoxy-2-naphthyl]pyrimidine-4-carboxylate (1.g, 1.99 mmol, 80.08% yield) as a yellow gum. LC-MS (ES$^+$, m/z): 504.1 [(M+H)$^+$].

Preparation of ethyl 5-amino-2-[8-(2-cyanoallylamino)-7-methoxy-2-naphthyl]pyrimidine-4-carboxylate

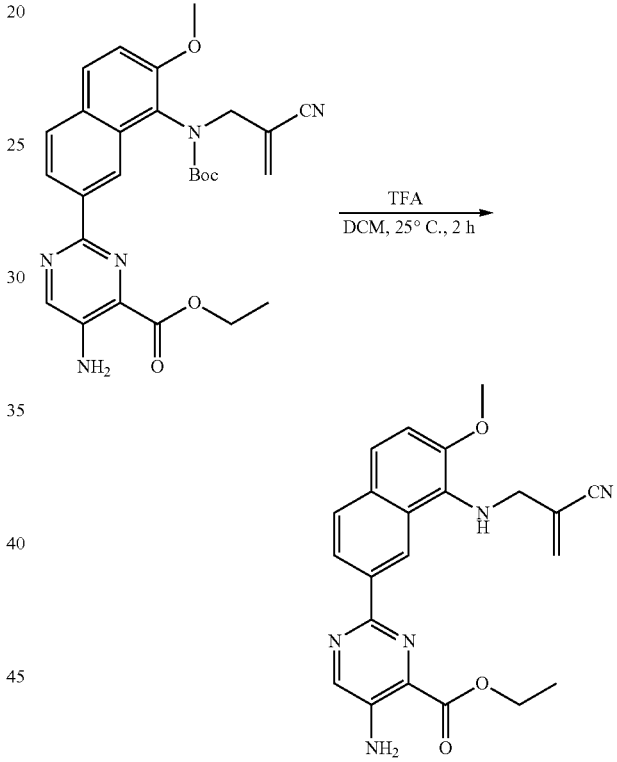

To a mixture of ethyl 5-amino-2-[8-[tert-butoxycarbonyl(2-cyanoallyl)amino]-7-methoxy-2-naphthyl]pyrimidine-4-carboxylate (350 mg, 695.07 μmol, 1 eq) in DCM (8 mL) was added TFA (2.31 g, 20.26 mmol, 1.5 mL, 29.15 eq) in one portion, and the reaction was stirred at 25° C. for 2 hour. The reaction was diluted with 20 mL ice water, and the pH was adjusted to 8 with saturated aq. Na$_2$CO$_3$. The mixture was extracted with DCM (3×20 mL), and the combined organic layer was washed with brine (3×20 mL), dried over Na$_2$SO$_4$, filtered, and concentrated in vacuo. The residue was purified by prep-TLC (SiO$_2$, PE:EtOAc=1:1) to afford ethyl 5-amino-2-[8-(2-cyanoallylamino)-7-methoxy-2-naphthyl]pyrimidine-4-carboxylate (200 mg, 495.75 μmol, 71.32% yield) as a yellow gum. LC-MS (ES$^+$, m/z): 404.1 [(M+H)$^+$].

Preparation of 5-amino-2-[8-(2-cyanoallylamino)-7-methoxy-2-naphthyl]pyrimidine-4-carboxylic acid

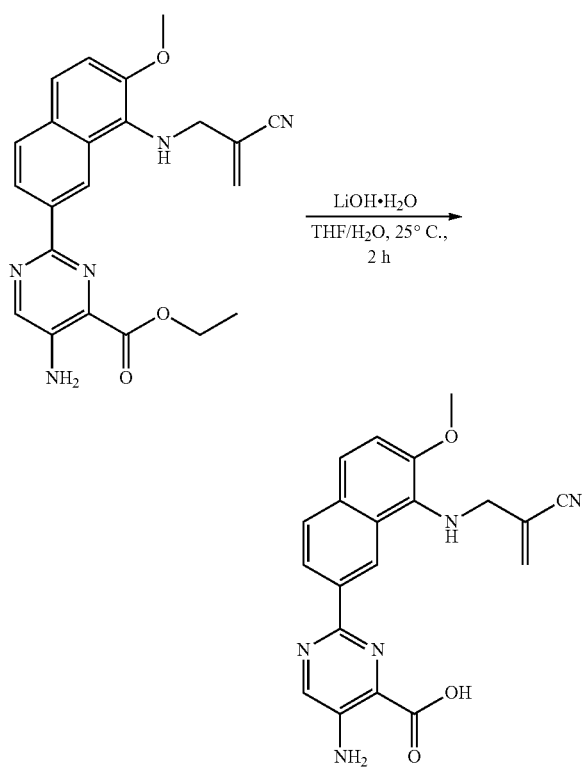

To a mixture of ethyl 5-amino-2-[8-(2-cyanoallylamino)-7-methoxy-2-naphthyl]pyrimidine-4-carboxylate (200 mg, 495.75 μmol, 1 eq) in THF (4 mL), H$_2$O (1 mL) was added LiOH·H$_2$O (312 mg, 7.44 mmol, 15 eq) in one portion under N$_2$. The mixture was stirred at 25° C. for 2 hours. The reaction was diluted with 30 mL water, and the pH was adjusted to 6 with saturated citric acid. The mixture was extracted with EtOAc (2×30 mL), and the combined organic layer was washed with brine (2×30 mL), dried over Na$_2$SO$_4$, filtered, and concentrated in vacuo. 5-amino-2-[8-(2-cyanoallylamino)-7-methoxy-2-naphthyl]pyrimidine-4-carboxylic acid (160 mg, crude) was obtained as a yellow gum. LC-MS (ES$^+$, m/z): 376.1 [(M+H)$^+$]

Preparation of 5-amino-2-[8-(2-cyanoallylamino)-7-methoxy-2-naphthyl]-N-(1-methyl-4-piperidyl)pyrimidine-4-carboxamide

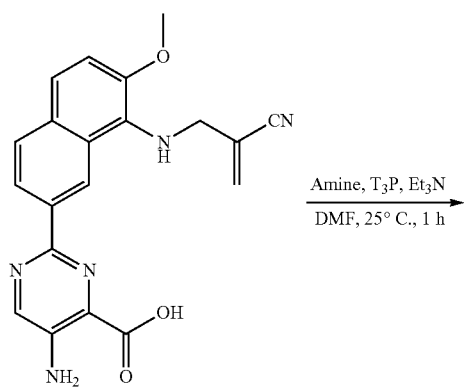

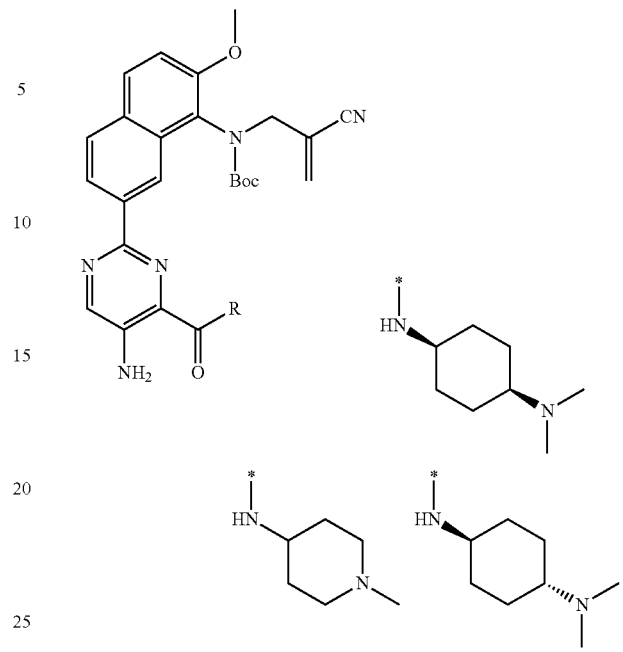

To a mixture of 5-amino-2-[8-(2-cyanoallylamino)-7-methoxy-2-naphthyl]pyrimidine-4-carboxylic acid (60 mg, 159.84 μmol, 1 eq) and 1-methylpiperidin-4-amine (27.4 mg, 239.76 μmol, 1.5 eq) in DMF (2 mL) were added Et$_3$N (80.9 mg, 799.19 μmol, 111.24 μL, 5 eq) and T$_3$P (152.6 mg, 239.76 μmol, 142.59 μL, 50% purity, 1.5 eq) in one portion under N$_2$. The mixture was stirred at 25° C. for 60 min. The reaction was diluted with 20 mL water, and the pH was adjusted to 9 with saturated aq. Na$_2$CO$_3$. The mixture was extracted with EtOAc (2×20 mL), and the combined organic layer was washed with brine (2×20 mL), dried over Na$_2$SO$_4$, filtered, and concentrated in vacuo. The residue was purified by prep-HPLC to afford 5-amino-2-[8-(2-cyanoallylamino)-7-methoxy-2-naphthyl]-N-(1-methyl-4-piperidyl)pyrimidine-4-carboxamide (11.1 mg, 23.4 μmol, 14.64% yield, 99.4% purity) as a yellow solid.

Route 6: General Scheme

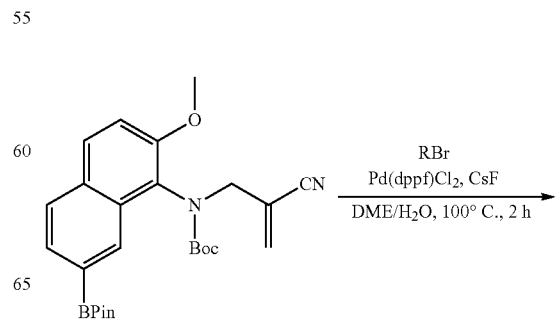

Preparation of methyl 6-(8-((tert-butoxycarbonyl)(2-cyanoallyl)amino)-7-methoxynaphthalen-2-yl)picolinate

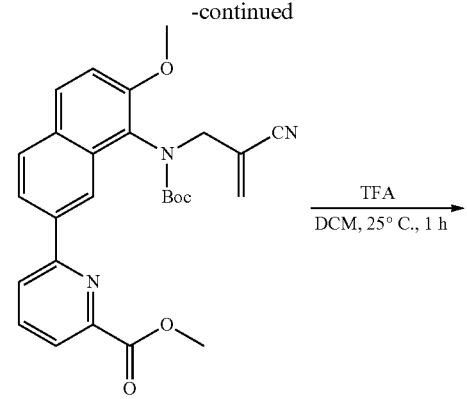

To a mixture of tert-butyl (2-cyanoallyl)(2-methoxy-7-(4,4,5,5-tetramethyl-1,3,2-dioxaborolan-2-yl)naphthalen-1-yl)carbamate (2.5 g, 4.31 mmol, 1 eq) and methyl 6-bromopyridine-2-carboxylate (2.79 g, 12.92 mmol, 3 eq) in DME (20 mL), H₂O (5 mL) were added CsF (3.27 g, 21.54 mmol, 794 μL, 5 eq), Pd(dppf)Cl₂ (630.3 mg, 861.4 μmol, 0.2 eq) in one portion. The mixture was stirred at 100° C. for 2 hours. The reaction mixture was poured into 30 mL saturated EDTA and stirred at 25° C. for 1 h. Then the aqueous phase was extracted with EtOAc (2×30 mL), and the combined organic layer was washed with brine (2×30 mL), dried over Na₂SO₄, filtered, and concentrated in vacuo. The residue was purified by column chromatography (SiO₂, PE:EtOAc=6:1 to 3:1). Methyl 6-(8-((tert-butoxycarbonyl)(2-cyanoallyl)amino)-7-methoxynaphthalen-2-yl)picolinate (1.5 g, 3.17 mmol, 73.6% yield) was obtained as a brown solid. LC-MS (ES⁺, m/z): 474.2 [(M+H)⁺].

Preparation of methyl 6-(8-((2-cyanoallyl)amino)-7-methoxynaphthalen-2-yl)picolinate 117
-continued

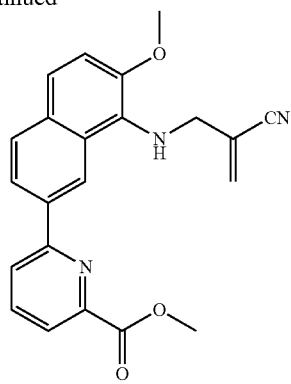

To a mixture of methyl 6-(8-((tert-butoxycarbonyl)(2-cyanoallyl)amino)-7-methoxynaphthalen-2-yl)picolinate (1.2 g, 2.53 mmol, 1 eq) in DCM (9 mL) was added TFA (4.62 g, 40.52 mmol, 3 mL, 15.99 eq) in one portion, and the reaction mixture was stirred at 20° C. for 1 hour. The mixture was adjusted to pH=8 with saturated Na$_2$CO$_3$. Then the mixture was extracted with EtOAc (2×30 mL). The combined organic layer was washed with brine (2×20 mL), dried over Na$_2$SO$_4$, filtered, and concentrated in vacuo. The residue was purified by column chromatography (SiO$_2$, PE:EtOAc=8/1 to 3:1). Methyl 6-(8-((2-cyanoallyl)amino)-7-methoxynaphthalen-2-yl)picolinate (1. g, 2.68 mmol) was obtained as a yellow solid. LC-MS (ES$^+$, m/z): 374.1 [(M+H)$^+$].

Preparation of compound 6-(8-((2-cyanoallyl)amino)-7-methoxynaphthalen-2-yl)picolinic acid

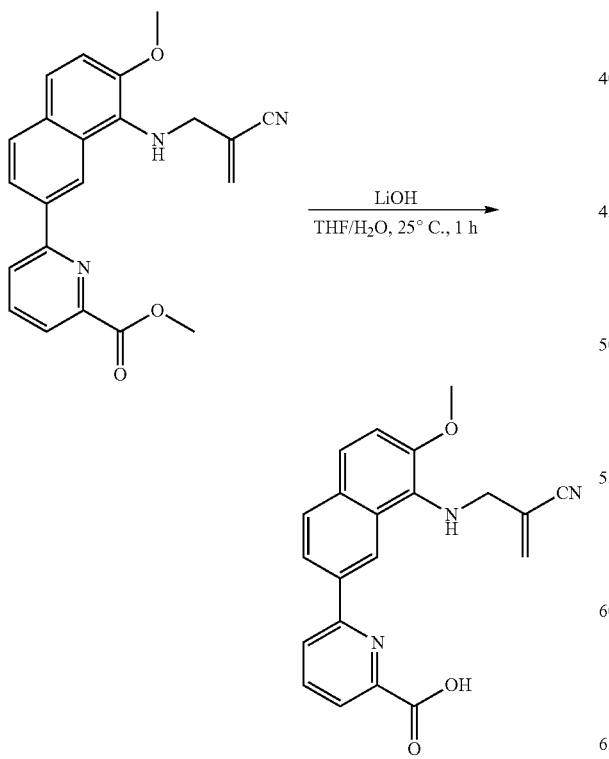

118

To a mixture of methyl 6-(8-((2-cyanoallyl)amino)-7-methoxynaphthalen-2-yl)picolinate (400 mg, 1.07 mmol, 1 eq) in THF (6 mL) H$_2$O (1.5 mL) was added LiOH·H$_2$O (449.5 mg, 10.71 mmol, 10 eq) in one portion. The mixture was stirred at 25° C. for 60 min. The reaction was diluted with 20 mL water, adjust to pH=5 with saturated citric acid. The mixture was extracted with EtOAc (2×20 mL), and the combined organic layer was washed with brine (2×30 mL), dried over Na$_2$SO$_4$, filtered, and concentrated in vacuo to give afford crude 6-(8-((2-cyanoallyl)amino)-7-methoxy naphthalen-2-yl)picolinic acid (400 mg, crude) as a brown gum. LC-MS (ES$^+$, m/z): 360.1 [(M+H)$^+$].

Compound 193: Preparation of 6-[8-(2-cyanoallylamino)-7-methoxy-2-naphthyl]-N-(4-pyrrolidin-1-ylcyclohexyl)pyridine-2-carboxamide

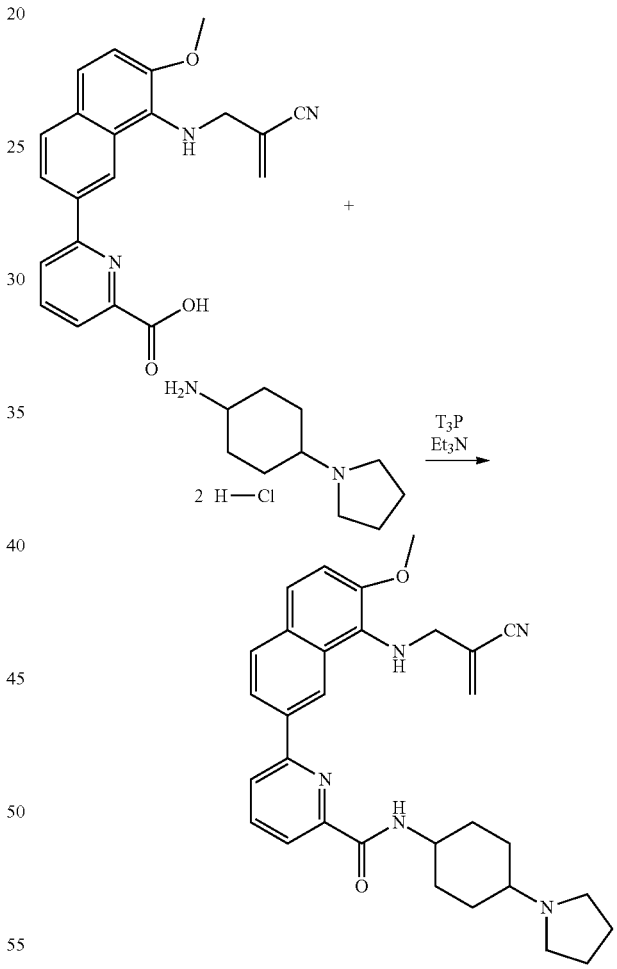

To a mixture of 6-[8-(2-cyanoallylamino)-7-methoxy-2-naphthyl]pyridine-2-carboxylic acid (75 mg, 208.69 µmol), 4-pyrrolidin-1-ylcyclohexanamine (75 mg, 313.07 µmol) and Et$_3$N (211.09 mg, 2.09 mmol) in DMF (2 mL) was added T$_3$P (50 wt % in EtOAc, 0.27 mL, 313.07 µmol). The resulting mixture was stirred at r.t. for 18 h and partitioned between EtOAc and water. The aqueous phase was extracted with EtOAc (3×). The combined organic phase was washed with saturated NaHCO$_3$ and brine, dried over (MgSO$_4$), filtered, and concentrated in vacuo. The residue was purified by chromatography on silica gel eluting with 0-60% EtOAc/Hexane to afford the title compound (20 mg, Yield 19%). LC-MS (ES+, m/z): 510.3 [(M+H)+]

Compound 194: Preparation of 6-[8-(2-cyanoallylamino)-7-methoxy-2-naphthyl]-N-[(2R)-2-hydroxypropyl]pyridine-2-carboxamide Compound 195: Preparation of 6-[8-(2-cyanoallylamino)-7-methoxy-2-naphthyl]-N-(1,4-dioxaspiro[4.5]decan-8-yl)pyridine-2-carboxamide

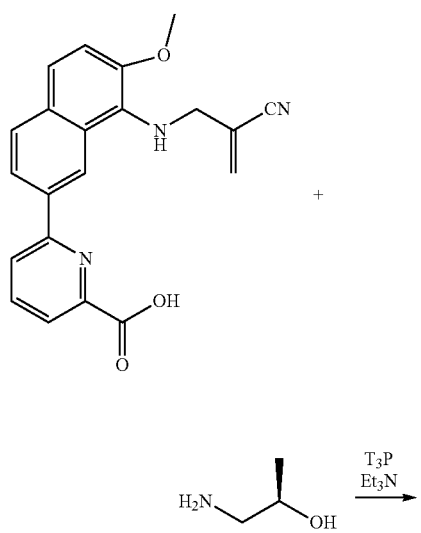

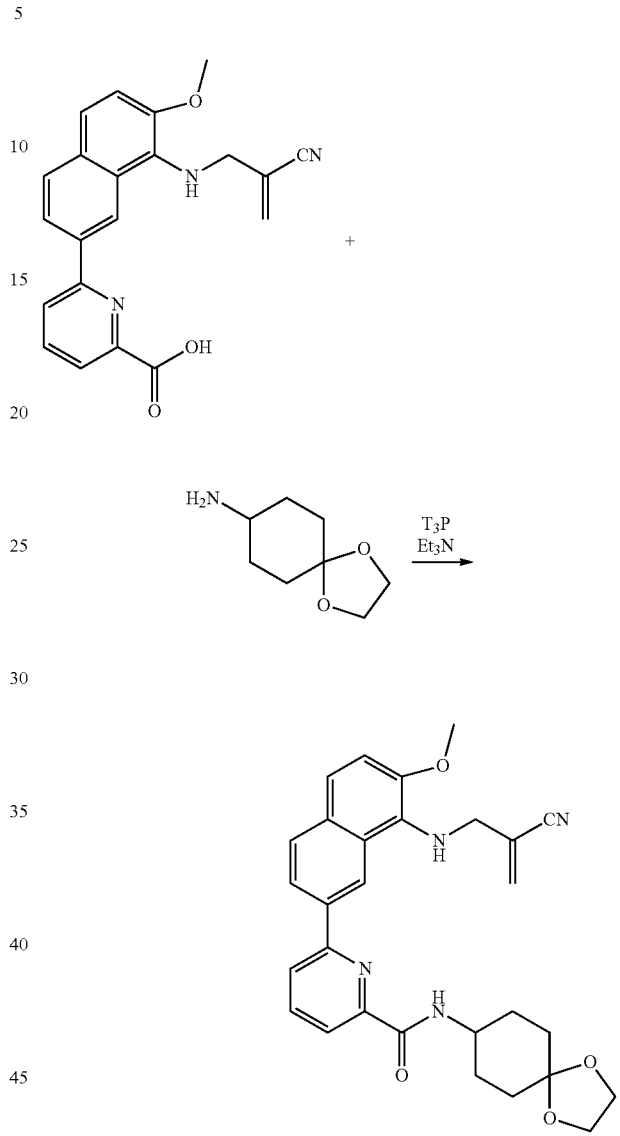

To a mixture of 6-[8-(2-cyanoallylamino)-7-methoxy-2-naphthyl]pyridine-2-carboxylic acid (75 mg, 208.69 μmol), (2R)-1-aminopropan-2-ol (23.5 mg, 313 μmol) and Et$_3$N (211.09 mg, 2.09 mmol) in DMF (2 mL) was added T$_3$P (50 wt % in EtOAc, 0.27 mL, 313 μmol). The resulting mixture was stirred at r.t. for 18 h and partitioned between EtOAc and water. The aqueous phase was extracted with EtOAc (3×). The combined organic phase was washed with saturated NaHCO$_3$ and brine, dried over (MgSO$_4$), filtered, and concentrated in vacuo. The residue was purified by chromatography on silica gel eluting with 30-100% EtOAc/Hexane to afford the title compound (20 mg, Yield 23%). (ES+, m/z): 417.2.

To a mixture of 6-[8-(2-cyanoallylamino)-7-methoxy-2-naphthyl]pyridine-2-carboxylic acid (75 mg, 208.69 μmol), 1,4-dioxaspiro[4.5]decan-8-amine (53.6 mg, 313 μmol) and Et$_3$N (211.09 mg, 2.09 mmol) in DMF (2 mL) was added T$_3$P (50 wt % in EtOAc, 0.27 mL, 313 μmol). The resulting mixture was stirred at r.t. for 18 h and partitioned between EtOAc and water. The aqueous phase was extracted with EtOAc (3×). The combined organic phase was washed with saturated NaHCO$_3$ and brine, dried over (MgSO$_4$), filtered, and concentrated in vacuo. The residue was purified by chromatography on silica gel eluting with 0-60% EtOAc/Hexane to afford the title compound (54 mg, Yield 52%). LC-MS (ES+, m/z): 499.2 [(M+H)+].

Compound 197: Preparation of 6-[8-(2-cyanoallylamino)-7-methoxy-2-naphthyl]-N-(4-oxocyclohexyl)pyridine-2-carboxamide

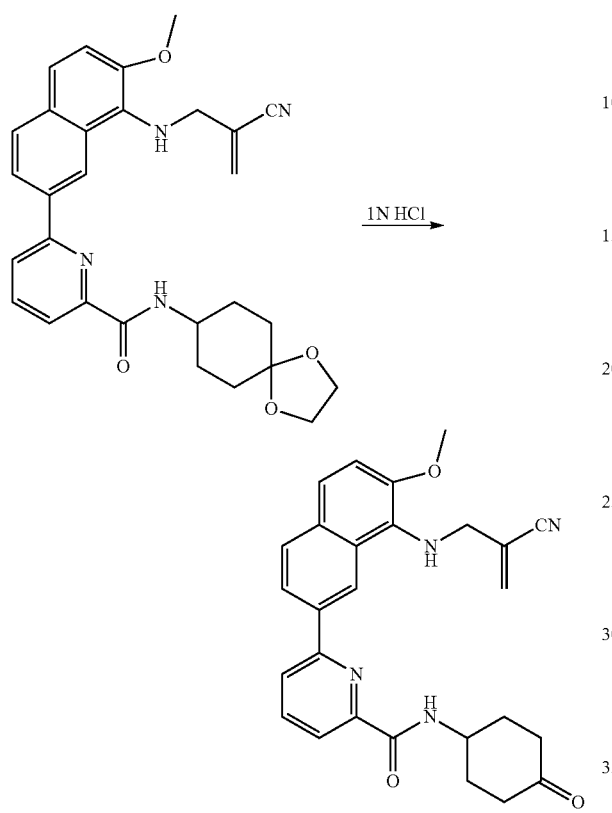

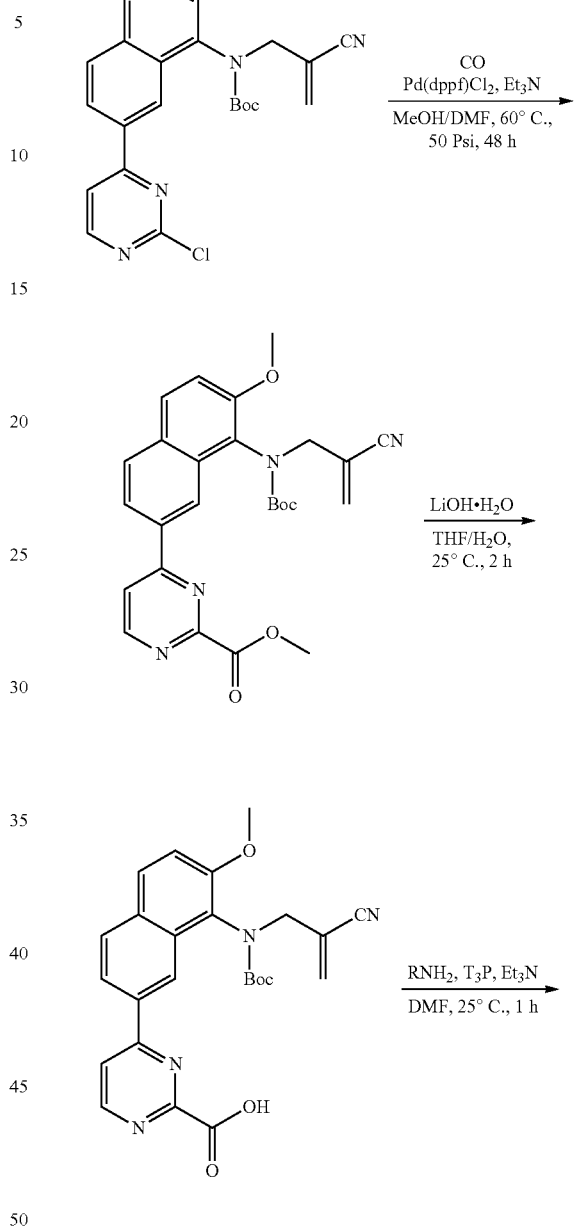

To a solution of 6-[8-(2-cyanoallylamino)-7-methoxy-2-naphthyl]-N-(1,4-dioxaspiro[4.5]decan-8-yl)pyridine-2-carboxamide (37 mg, 74 µmol) in MeCN (4 mL) was added 0.37 mL of 1N HCl. The resulting mixture was stirred at r.t. for 18 h. The reaction mixture was concentrated in vacuo and the residue was purified by reverse phase HPLC using a gradient of water 0.1% FA/acetonitrile 0.1% FA to afford the title compound (2.5 mg, Yield 8%). LC-MS (ES$^+$, m/z): 455.2 [(M+H)$^+$].

Route 7: General Scheme

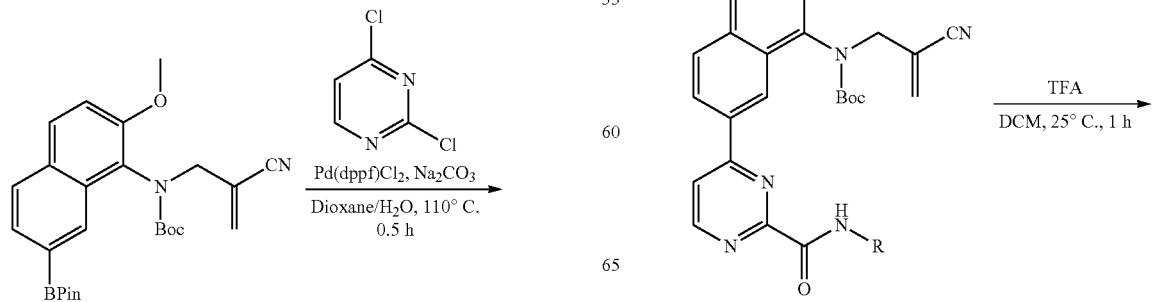

-continued

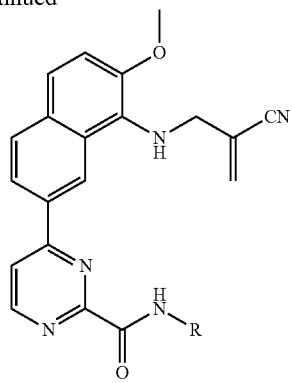

which was purified by column chromatography (PE: EtOAc=1:0 to 0:1) to afford the title compound (3. g, 6.65 mmol, 88.3% yield) as a yellow solid. NMR (400 MHz, DMSO-d$_6$) δ=8.87 (d, J=5.25 Hz, 1H) 8.55-8.58 (m, 1H) 8.16-8.26 (m, 1H) 7.99-8.15 (m, 3H) 7.64-7.67 (m, 1H) 5.97-5.99 (m, 1H) 5.82-5.86 (m, 1H) 4.35-4.45 (m, 2H) 3.91-4.02 (m, 3H) 1.55 (s, 3H) 1.17 (s, 6H).

Preparation of methyl 4-[8-[tert-butoxycarbonyl(2-cyanoallyl)amino]-7-methoxy-2-naphthyl]pyrimidine-2-carboxylate Preparation of tert-butyl N-[7-(2-chloropyrimidin-4-yl)-2-Methoxynaphthalen-1-yl]-N-(2-cyano-2-methylideneethyl)carbamate

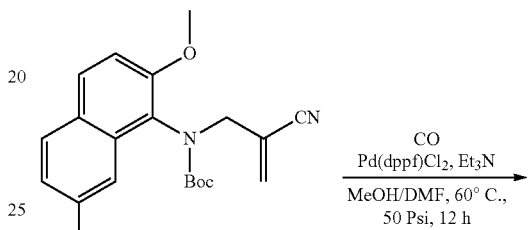

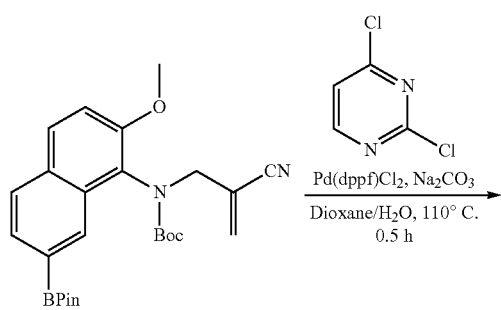

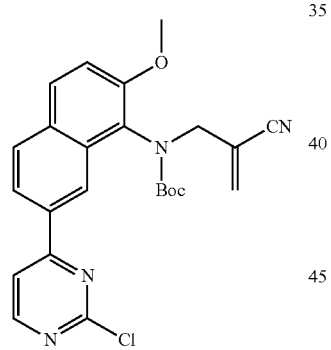

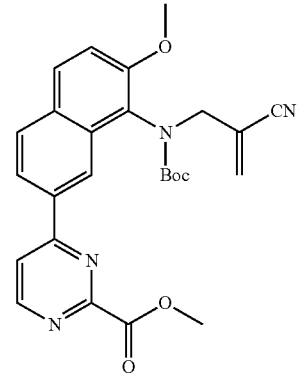

A solution of compound tert-butyl N-(2-cyanoallyl)-N-[2-methoxy-7-(4,4,5,5-tetramethyl-1,3,2-dioxaborolan-2-yl)-1-naphthyl]carbamate (3.5 g, 7.54 mmol, 1 eq) and 2,4-dichloropyrimidine (1.35 g, 9.04 mmol, 1.2 eq) in dioxane (30.0 mL) and H$_2$O (7.5 mL) were added Na$_2$CO$_3$ (2.4 g, 22.61 mmol, 3 eq) and Pd(dppf)Cl$_2$ (500 mg, 683.33 μmol, 0.091 eq). The resulting reaction mixture was stirred at 110° C. for 0.5 hr. TLC showed that the reaction was complete. To the reaction mixture was added (100 mL) saturated EDTA, and the solution was stirred for 1 h. The mixture was extracted with EtOAc (3×50 mL). The combined organic layer was washed with brine (2×60 mL), dried over Na$_2$SO$_4$, filtered, and concentrated to give the residue To a solution of tert-butyl N-[7-(2-chloropyrimidin-4-yl)-2-Methoxynaphthalen-1-yl]-N-(2-cyano-2-methylideneethyl)carbamate (310 mg, 687.49 μmol, 1 eq) in MeOH (5 mL) and DMF (5 mL) were added Et$_3$N (208.7 mg, 2.06 mmol, 287 μL, 3 eq; dropwise) and Pd(dppf)Cl$_2$ (50.3 mg, 68.75 μmol, 0.1 eq). Then to the mixture was bubbled in carbon monoxide (192.6 mg, 6.87 mmol, 10 eq). The reaction mixture was heated to 60° C. for 12 h under CO atmosphere. TLC showed that the reaction was complete. To the reaction mixture was added (30 mL) saturated EDTA. The solution was stirred for 1 h, and extracted with EtOAc (3×30 mL). The combined organic layer was washed with brine (40 mL), dried over Na$_2$SO$_4$, filtered, and concentrated to give the residue which was purified by prep-TLC (PE: EtOAc=1:1) to afford the title compound (60 mg, 126.45 μmol, 18.4% yield) as a yellow oil.

125

Preparation of 4-[8-[tert-butoxycarbonyl(2-cyanoallyl)amino]-7-methoxy-2-naphthyl]pyrimidine-2-carboxylic acid

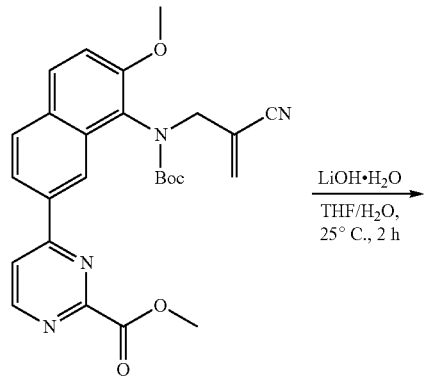

LiOH·H₂O
THF/H₂O,
25° C., 2 h

To a solution of compound methyl 4-[8-[tert-butoxycarbonyl(2-cyanoallyl)amino]-7-methoxy-2-naphthyl]pyrimidine-2-carboxylate (60 mg, 126.45 μmol, 1 eq) in THF (2 mL) and H₂O (0.5 mL) was added LiOH·H₂O (53.1 mg, 1.26 mmol, 10 eq) in one portion. The reaction mixture was stirred at 25° C. for 120 min. TLC showed that the reaction was complete. The reaction mixture was diluted with H₂O (30 mL) and EtOAc (30 mL), and saturated citric acid was added to adjust the pH to 6. The organic layer was extracted with EtOAc (2×20 mL), and the combined organic layer was washed with brine (30 mL), dried over Na₂SO₄, filtered, and concentrated to afford the title compound (50 mg, crude) as a yellow oil.

Preparation of tert-butyl N-(2-cyanoallyl)-N-[2-methoxy-7-[2-(methylcarbamoyl)pyrimidin-4-yl]-1-naphthyl]carbamate RNH₂, T₃P, Et₃N
DMF, 25° C., 1 h

126

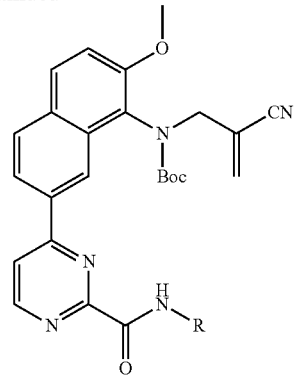

To a solution of 4-[8-[tert-butoxycarbonyl(2-cyanoallyl)amino]-7-methoxy-2-naphthyl]pyrimidine-2-carboxylic acid (50 mg, 108.58 μmol, 1 eq) in DMF (2 mL) were drop-wise methanamine; hydrochloride (14.7 mg, 217.16 μmol, 2 eq; dropwise) and Et₃N (32.9 mg, 325.75 μmol, 45.34 μL, 3 eq) and T₃P (103.6 mg, 162.87 μmol, 96.7 μL, 50% purity, 1.5 eq). The reaction mixture was stirred at 25° C. for 1 hr. TLC showed that the reaction was complete. The reaction mixture was quenched by adding H₂O (20 mL), and extracted with EtOAc (3×20 mL). The combined organic layer was washed with brine (2×20 mL), dried over Na₂SO₄, filtered, and concentrated to give the residue which was purified by prep-TLC (DCM:MeOH=10:1) to afford the title compound tert-butyl N-(2-cyanoallyl)-N-[2-methoxy-7-[2-(methylcarbamoyl)pyrimidin-4-yl]-1-naphthyl]carbamate (40 mg, 84.47 μmol, 77.8% yield) as a yellow oil.

Compound 218: Preparation of 4-[8-(2-cyanoallylamino)-7-methoxy-2-naphthyl]-N-methyl-pyrimidine-2-carboxamide TFA
DCM, 25° C., 1 h To a solution of compound tert-butyl N-(2-cyanoallyl)-N-[2-methoxy-7-[2-(methylcarbamoyl)pyrimidin-4-yl]-1-naphthyl]carbamate (40 mg, 84.47 μmol, 1 eq) in DCM (3 mL) was added TFA (1.23 g, 10.8 mmol, 0.8 mL, 127.91 eq; dropwise). Then the mixture was stirred at 25° C. for 1 h. LCMS showed that the reaction was complete. The reaction mixture was quenched by adding saturated Na$_2$CO$_3$ (30 mL) to adjust pH>8, and extracted with EtOAc (3×20 mL). The combined organic layer was washed with brine (30 mL), dried over Na$_2$SO$_4$, filtered, and concentrated to give a residue which was purified by prep-HPLC to afford the title compound (17.5 mg, 46.49 μmol, 55.04% yield) as a yellow solid. LC-MS (ES$^+$, m/z): 374 [(M+H)$^+$]

Route 8A: General Scheme

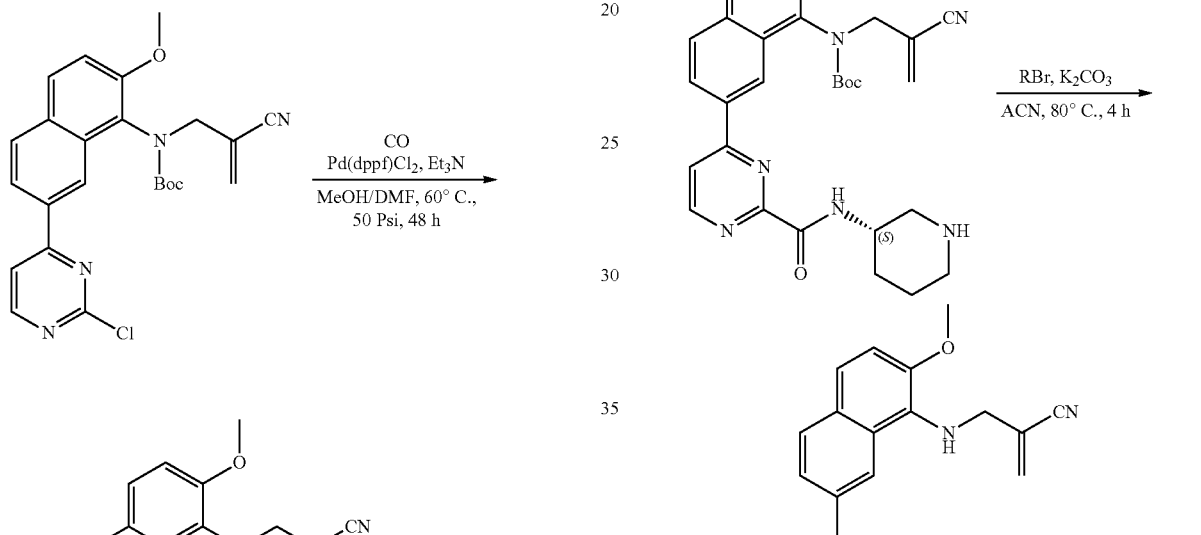

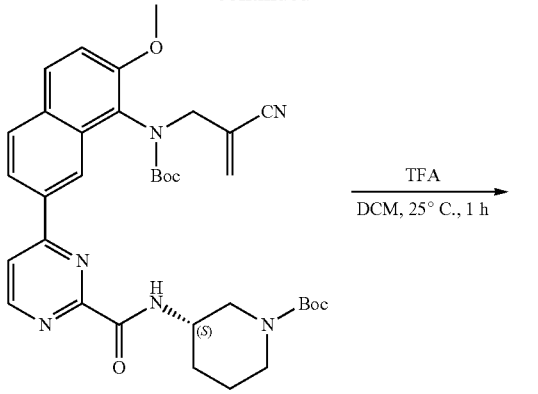

-continued

Preparation of tert-butyl (3S)-3-[[4-[8-[tert-butoxycarbonyl(2-cyanoallyl)amino]-7-methoxy-2-naphthyl]pyrimidine-2-carbonyl]amino]piperidine-1-carboxylate

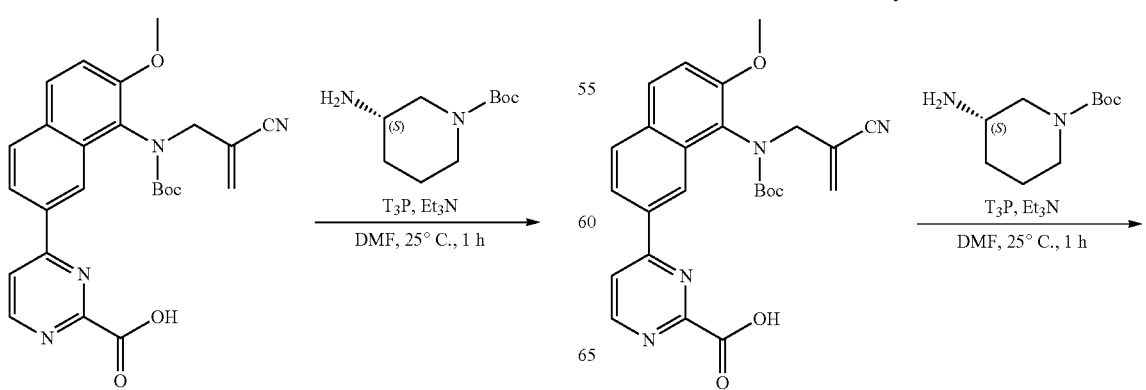

-continued

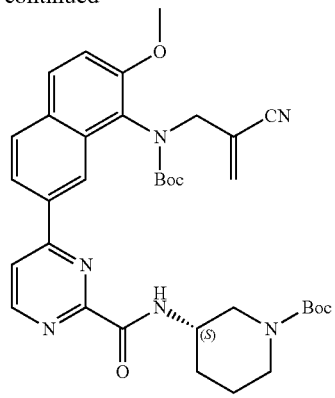

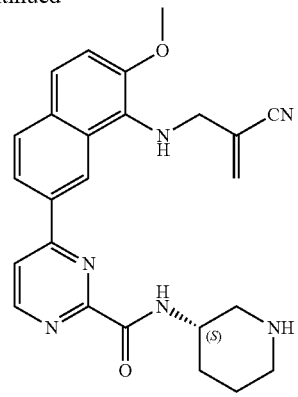

To a mixture of 4-[8-[tert-butoxycarbonyl(2-cyanoallyl)amino]-7-methoxy-2-naphthyl]pyrimidine-2-carboxylic acid (220 mg, 477.76 μmol, 1 eq) and tert-butyl (3S)-3-amino piperidine-1-carboxylate (114.8 mg, 573.31 μmol, 1.2 eq) in DMF (3 mL) was added T₃P (456 mg, 716.64 μmol, 426.21 μL, 50% purity, 1.5 eq) and Et₃N (241.7 mg, 2.39 mmol, 332.49 μL, 5 eq) in one portion. The reaction mixture was stirred at 25° C. for 1 hour. The reaction was diluted with 20 mL water and adjusted to pH=9 with saturated aq. Na₂CO₃. The mixture was extracted with EtOAc (4×20 mL), and the combined organic layer was washed with brine (2×20 mL), dried over Na₂SO₄, filtered, and concentrated in vacuo. The residue was purified by prep-TLC (SiO₂, DCM:MeOH=15:1) to afford the title compound (160 mg, 248.93 μmol, 52.10% yield) as a yellow oil. (SiO₂, PE:EtOAc=15:1, SM Rf=0.06, TM Rf=0.30).

Preparation of 4-[8-(2-cyanoallylamino)-7-methoxy-2-naphthyl]-N-[(3S)-3-piperidyl]pyrimidine-2-carboxamide To a mixture of tert-butyl (3S)-3-[[4-[8-[tert-butoxycarbonyl(2-cyanoallyl)amino]-7-methoxy-2-naphthyl]pyrimidine-2-carbonyl]amino]piperidine-1-carboxylate (160 mg, 248.93 μmol, 1 eq) in DCM (3 mL) was added TFA (1.54 g, 13.51 mmol, 1 mL, 54.26 eq). The reaction mixture was stirred at 25° C. for 1 hour. The reaction was diluted with 20 mL water and adjusted to pH=9 with saturated aq. Na₂CO₃. The mixture was extracted with DCM (4×20 mL), and the combined organic layer was washed with brine (2×20 mL), dried over Na₂SO₄, filtered, and concentrated in vacuo. The residue was purified by prep-TLC (SiO₂, DCM:MeOH=6:1) to afford the title compound 4-[8-(2-cyanoallylamino)-7-methoxy-2-naphthyl]-N-[(3S)-3-piperidyl]pyrimidine-2-carboxamide (80 mg, 180.79 μmol, 72.62% yield) as a yellow oil. LC-MS (ES⁺, m/z): 443.2 [(M+H)⁺].

Compound 206: Preparation of 4-[8-(2-cyanoallylamino)-7-methoxy-2-naphthyl]-N-[(3S)-1-(2-methoxyethyl)-3-piperidyl]pyrimidine-2-carboxamide

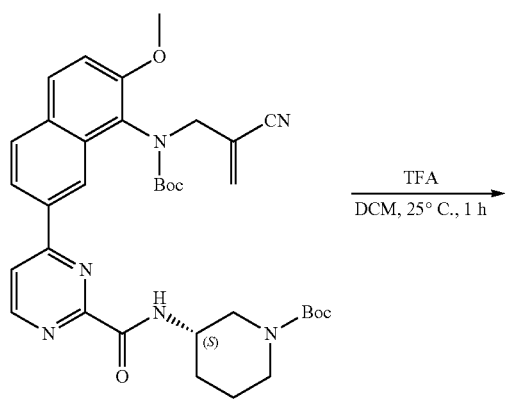

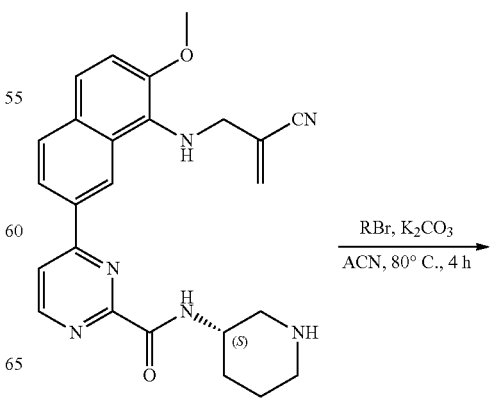

131
-continued

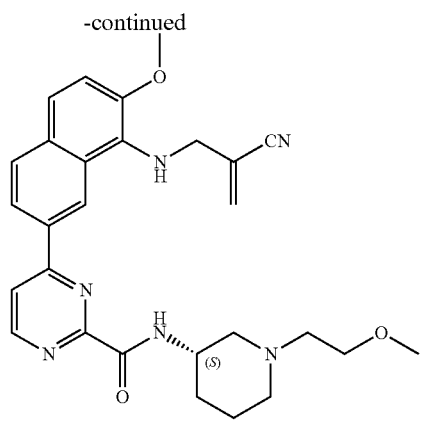

132
-continued

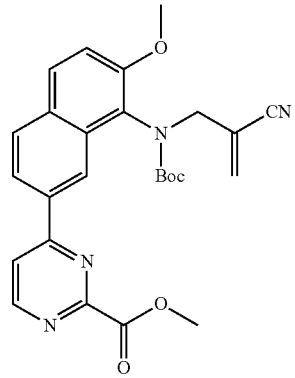

To a mixture of 4-[8-(2-cyanoallylamino)-7-methoxy-2-naphthyl]-N-[(3S)-3-piperidyl]pyrimidine-2-carboxamide (70 mg, 158.19 µmol, 1 eq) in ACN (2 mL) were added $K_2CO_3$ (65.6 mg, 474.56 µmol, 3 eq) and 1-bromo-2-methoxy-ethane (109.9 mg, 790.94 µmol, 74.28 µL, 5 eq) in one portion. The reaction mixture was stirred at 80° C. for 4 hours. The reaction was diluted with 30 mL water and extracted with EtOAc (3×20 mL). The combined organic layer was washed with brine (2×20 mL), dried over $Na_2SO_4$, filtered, and concentrated in vacuo. The residue was purified by prep-HPLC (basic condition) to afford the title compound (6.5 mg, 12.85 µmol, 8.13% yield, 99.0% purity) as a yellow gum. LC-MS (ES$^+$, m/z): 501.3 [(M+H)$^+$], $^1$H NMR (400 MHz, DMSO-de) δ=9.06 (s, 1H), 9.04 (d, J=5.6 Hz, 1H), 8.72 (br d, J=8.4 Hz, 1H), 8.41 (d, J=5.2 Hz, 1H), 8.26 (br d, J=8.8 Hz, 1H), 7.98 (d, J=8.4 Hz, 1H), 7.60-7.52 (m, 1H), 7.50-7.43 (m, 1H), 6.01 (s, 1H), 5.97 (s, 1H), 5.86 (br t, J=7.0 Hz, 1H), 4.20 (br d, J=7.6 Hz, 2H), 4.02 (br s, 1H), 3.91 (s, 3H), 3.46 (br t, J=5.4 Hz, 2H), 3.24 (s, 3H), 2.79 (br d, J=8.8 Hz, 1H), 2.63-2.55 (m, 3H), 2.29 (br d, J=8.4 Hz, 2H), 1.81-1.76 (m, 1H), 1.71 (br s, 1H), 1.61-1.48 (m, 2H)

Route 8B: General Scheme

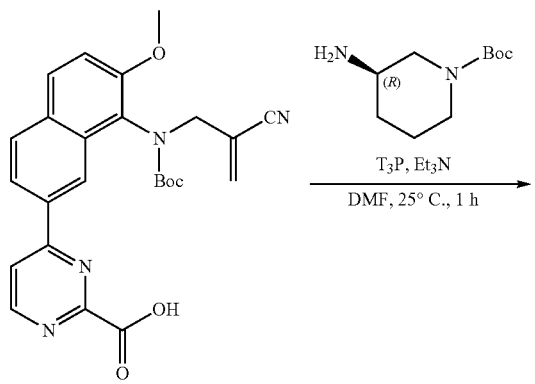

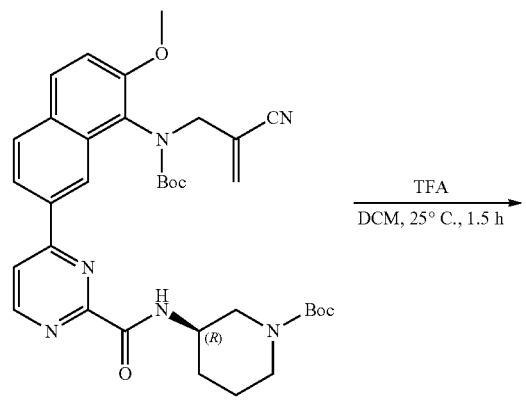

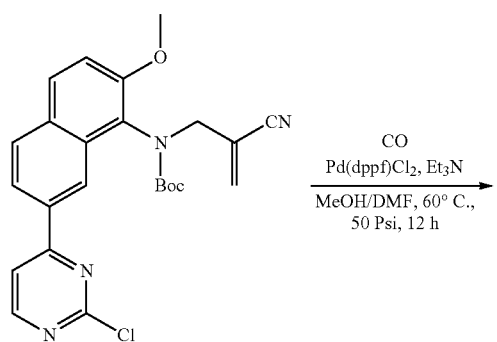

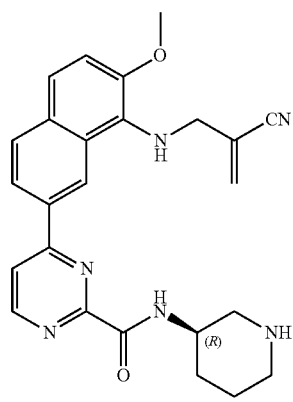

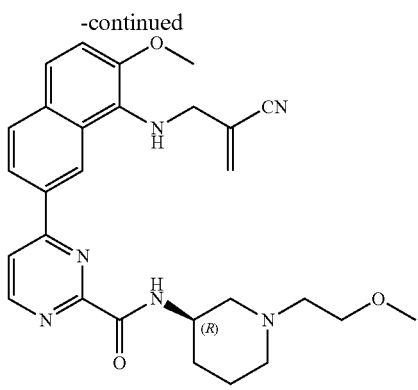

Preparation of tert-butyl (3R)-3-[[4-[8-[tert-butoxycarbonyl (2-cyanoallyl)amino]-7-methoxy-2-naphthyl]pyrimidine-2-carbonyl]amino]piperidine-1-carboxylate

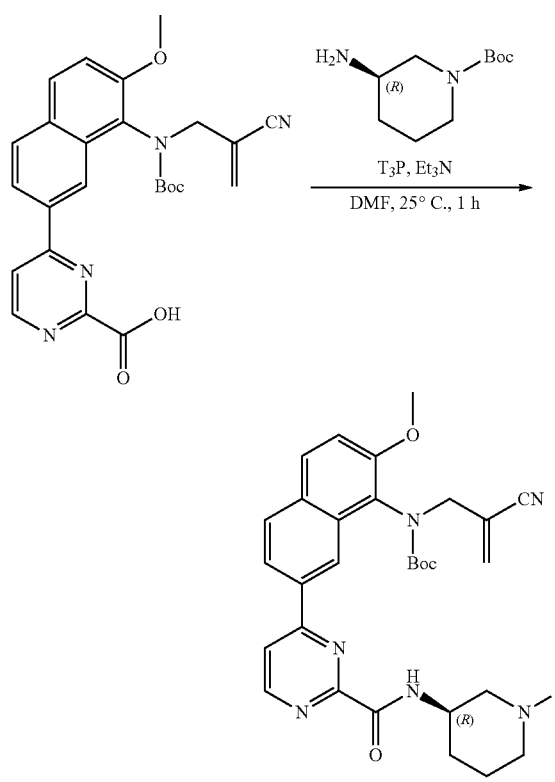

To a mixture of 4-[8-[tert-butoxycarbonyl(2-cyanoallyl) amino]-7-methoxy-2-naphthyl]pyrimidine-2-carboxylic acid (110 mg, 238.88 μmol, 1 eq) and tert-butyl (3R)-3-aminopiperidine-1-carboxylate (95.7 mg, 477.76 μmol, 2 eq) in DMF (3 mL) were added Et₃N (120.9 mg, 1.19 mmol, 166 μL, 5 eq) and T₃P (228 mg, 358.32 μmol, 213 μL, 50% purity, 1.5 eq) in one portion. The mixture was stirred at 25° C. for 60 min. The reaction was diluted with 15 mL water and adjusted to pH=9 with saturated aq.Na₂CO₃. The mixture was extracted with EtOAc (3×25 mL), and the combined organic layer was washed with brine (2×25 mL), dried over Na₂SO₄, filtered, and concentrated in vacuo. The residue was purified by prep-TLC (SiO₂, DCM:MeOH=15:1) to afford the title compound (110 mg, 171.14 μmol, 71.6% yield) as a yellow oil.

Preparation of 4-[8-(2-cyanoallylamino)-7-methoxy-2-naphthyl]-N-[(3R)-3-piperidyl]pyrimidine-2-carboxamide

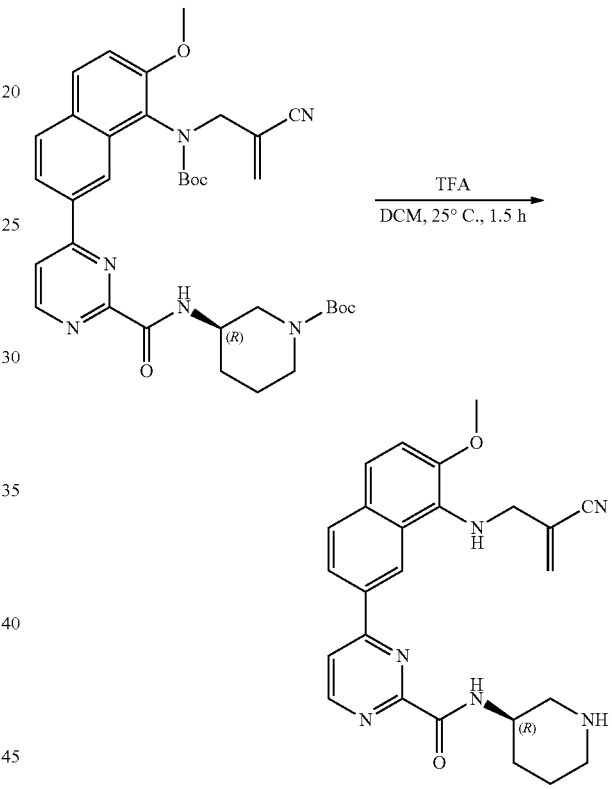

To a mixture of tert-butyl (3R)-3-[[4-[8-[tert-butoxycarbonyl(2-cyanoallyl)amino]-7-methoxy-2-naphthyl]pyrimidine-2-carbonyl]amino]piperidine-1-carboxylate (110 mg, 171.14 μmol, 1 eq) in DCM (3 mL) was added TFA (1.54 g, 13.51 mmol, 1 mL, 78.92 eq). The reaction mixture was stirred at 25° C. for 1 hour. TLC showed that most of the starting material was consumed. The reaction was stirred at 25° C. for another 0.5 hour. The reaction mixture was diluted with 15 mL DCM, poured into 15 mL ice water, and adjust to pH=8 with saturated aq.Na₂CO₃. The mixture was extracted with DCM (3×15 mL), and the combined organic layer was washed with brine (3×15 mL), dried over Na₂SO₄, filtered, and concentrated in vacuo. The residue was purified by prep-TLC (SiO₂, DCM:MeOH=7:1) to afford the title compound (70 mg, 158.19 μmol, 92.4% yield) as a yellow gum. LC-MS (ES⁺, m/z): 443.2 [(M+H)⁺].

Compound 205: Preparation of 4-[8-(2-cyanoallylamino)-7-methoxy-2-naphthyl]-N-[(3R)-1-(2-methoxyethyl)-3-piperidyl]pyrimidine-2-carboxamide

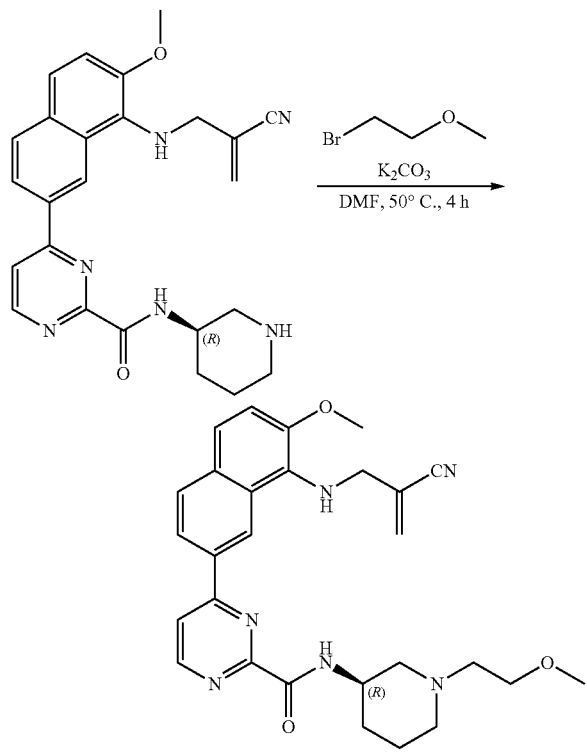

To a mixture of 4-[8-(2-cyanoallylamino)-7-methoxy-2-naphthyl]-N-[(3R)-3-piperidyl]pyrimidine-2-carboxamide (40 mg, 90.39 μmol, 1 eq) in DMF (1.5 mL) was added K$_2$CO$_3$ (37.5 mg, 271.18 μmol, 3 eq) and 1-bromo-2-methoxy-ethane (62.8 mg, 451.97 μmol, 42.45 μL, 5 eq) in one portion. The reaction mixture was stirred at 50° C. for 4 hours. LCMS showed ~40% desired product. The reaction was diluted with 20 mL water and extracted with EtOAc (3×20 mL). The combined organic layer was washed with brine (2×20 mL), dried over Na$_2$SO$_4$, filtered, and concentrated in vacuo. The residue was purified by prep-HPLC to afford the title compound (2.5 mg, 4.86 μmol, 5.38% yield, 97.4% purity) as a yellow solid. LC-MS (ES$^+$, m/z): 501.3 [(M+H)$^+$].

$^1$H NMR (400 MHz, DMSO-d6) δ ppm 9.06 (s, 1H) 9.04 (d, J=5.38 Hz, 1H) 8.72 (br d, J=8.68 Hz, 1H) 8.41 (d, J=5.50 Hz, 1H) 8.27 (d, J=8.80 Hz, 1H) 8.20 (s, 1H) 7.98 (d, J=8.68 Hz, 1H) 7.56 (d, J=8.93 Hz, 1H) 7.47 (d, J=8.93 Hz, 1H) 6.01 (s, 1H) 5.97 (s, 1H) 5.86 (br t, J=7.15 Hz, 1H) 4.20 (br d, J=6.97 Hz, 2H) 4.02 (br d, J=7.83 Hz, 1H) 3.91 (s, 3H) 3.59 (br s, 2H) 3.44-3.53 (m, 2H) 3.24 (s, 3H) 2.74-2.87 (m, 1H) 2.57-2.64 (m, 1H) 2.55-2.64 (m, 3H) 2.28 (br d, J=10.27 Hz, 2H) 1.71 (br s, 2H) 1.49-1.65 (m, 2H)

TABLE 2 shows compounds synthesized using method B of EXAMPLE 2 described above.

TABLE 2

| Cmp. No. | Structure | IUPAC | LC-MS (ES+, m/z) |
|---|---|---|---|
| 8 | 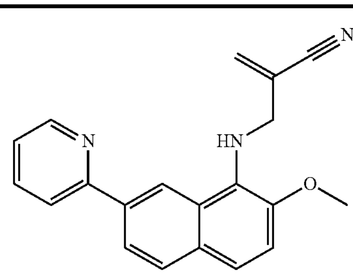 | 2-({[2-methoxy-7-(pyridin-2-yl)naphthalen-1-yl]amino}methyl)prop-2-enenitrile | 316.1 |

TABLE 2-continued

| Cmp. No. | Structure | IUPAC | LC-MS (ES+, m/z) |
|---|---|---|---|
| 9 | 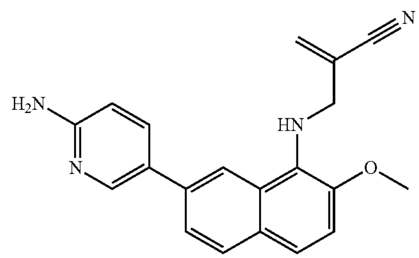 [SMILES: C=C(C#N)CNc1c(OC)ccc2ccc(-c3ccc(N)nc3)cc12] | 2-({[7-(6-aminopyridin-3-yl)-2-methoxynaphthalen-1-yl]amino}methyl)prop-2-enenitrile | 331.1 |
| 10 | 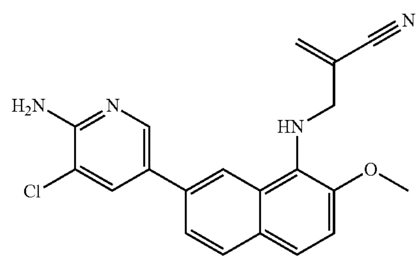 [SMILES: C=C(C#N)CNc1c(OC)ccc2ccc(-c3cnc(N)c(Cl)c3)cc12] | 2-({[7-(6-amino-5-chloropyridin-3-yl)-2-methoxynaphthalen-1-yl]amino}methyl)prop-2-enenitrile | 365.1 |
| 11 | 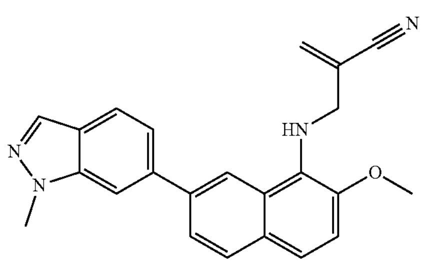 [SMILES: C=C(C#N)CNc1c(OC)ccc2ccc(-c3ccc4cnn(C)c4c3)cc12] | 2-({[2-methoxy-7-(1-methyl-1H-indazol-6-yl)naphthalen-1-yl]amino}methyl)prop-2-enenitrile | 369.2 |
| 12 | 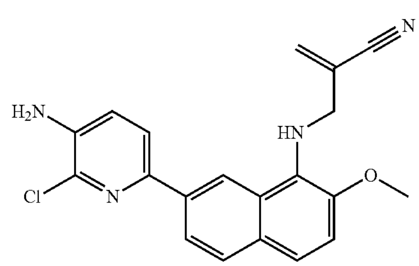 [SMILES: C=C(C#N)CNc1c(OC)ccc2ccc(-c3ccc(N)c(Cl)n3)cc12] | 2-({[7-(5-amino-6-chloropyridin-2-yl)-2-methoxynaphthalen-1-yl]amino}methyl)prop-2-enenitrile | 364.9 |

TABLE 2-continued

| Cmp. No. | Structure | IUPAC | LC-MS (ES+, m/z) |
|---|---|---|---|
| 13 | 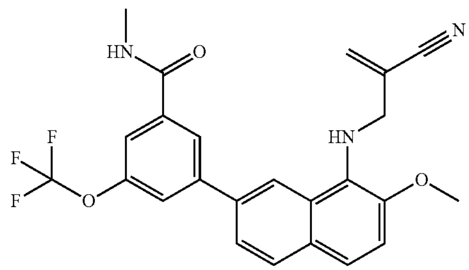 [SMILES: C=C(C#N)CNc1c(OC)ccc2ccc(-c3cc(OC(F)(F)F)cc(C(=O)NC)c3)cc12] | 3-{8-[(2-cyano-2-methylideneethyl)amino]-7-methoxynaphthalen-2-yl}-N-methyl-5-(trifluoromethoxy)benzamide | 455.9 |
| 14 | 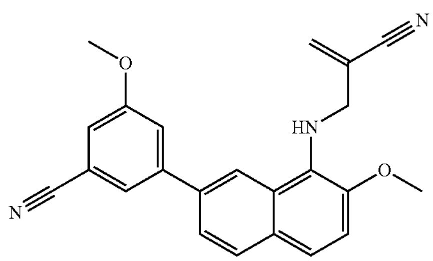 [SMILES: C=C(C#N)CNc1c(OC)ccc2ccc(-c3cc(C#N)cc(OC)c3)cc12] | 3-{8-[(2-cyano-2-methylideneethyl)amino]-7-methoxynaphthalen-2-yl}-5-methoxybenzonitrile | 370 |
| 15 | 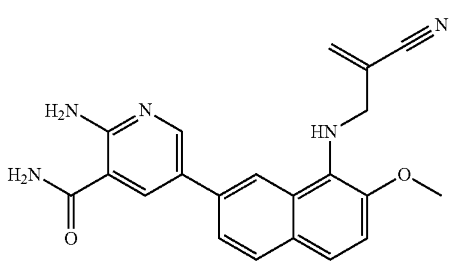 [SMILES: C=C(C#N)CNc1c(OC)ccc2ccc(-c3cnc(N)c(C(N)=O)c3)cc12] | 2-amino-5-{8-[(2-cyano-2-methylideneethyl)amino]-7-methoxynaphthalen-2-yl}pyridine-3-carboxamide | 374.2 |
| 16 | 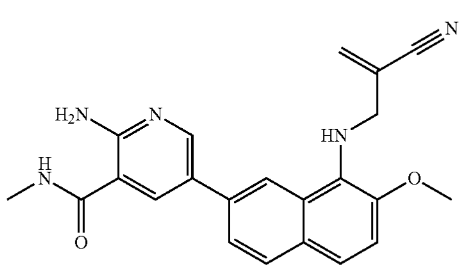 | 2-amino-5-{8-[(2-cyano-2-methylideneethyl)amino]-7-methoxynaphthalen-2-yl}-N-methylpyridine-3-carboxamide | 388.2 |

TABLE 2-continued

| Cmp. No. | Structure | IUPAC | LC-MS (ES+, m/z) |
|---|---|---|---|
| 17 | 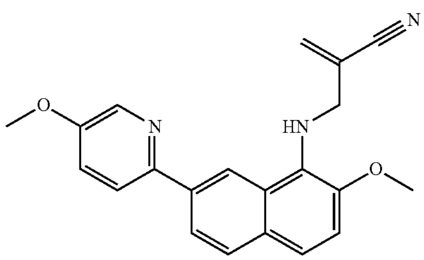 | 2-({[2-methoxy-7-(5-methoxypyridin-2-yl)naphthalen-1-yl]amino}methyl)prop-2-enenitrile | 346.2 |
| 18 | 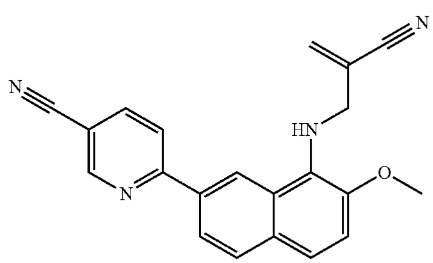 [SMILES: C=C(C#N)CNc1c(OC)ccc2ccc(-c3ccc(C#N)cn3)cc12] | 6-{8-[(2-cyano-2-methylideneethyl)amino]-7-methoxynaphthalen-2-yl}pyridine-3-carbonitrile | 341.1 |
| 19 | 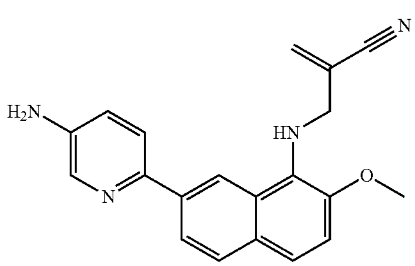 [SMILES: C=C(C#N)CNc1c(OC)ccc2ccc(-c3ccc(N)cn3)cc12] | 2-({[7-(5-aminopyridin-2-yl)-2-methoxynaphthalen-1-yl]amino}methyl)prop-2-enenitrile | 331.1 |
| 20 | 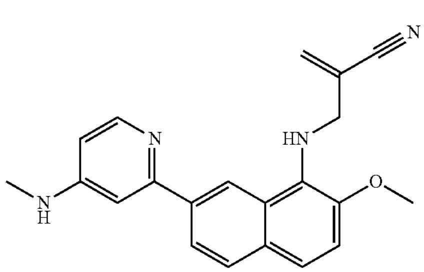 | 2-[({2-methoxy-7-[4-(methylamino)pyridin-2-yl]naphthalen-1-yl}amino)methyl]prop-2-enenitrile | 345.1 |

TABLE 2-continued

| Cmp. No. | Structure | IUPAC | LC-MS (ES+, m/z) |
|---|---|---|---|
| 21 | 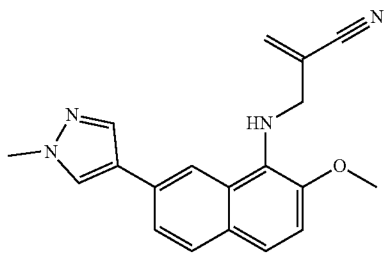 | 2-({[2-methoxy-7-(1-methyl-1H-pyrazol-4-yl)naphthalen-1-yl]amino}methyl)prop-2-enenitrile | 319 |
| 22 | 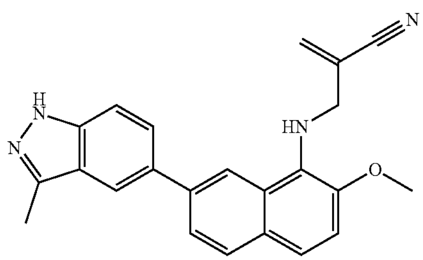 [SMILES: C=C(C#N)CNc1c(OC)ccc2ccc(-c3ccc4[nH]nc(C)c4c3)cc12] | 2-({[2-methoxy-7-(3-methyl-1H-indazol-5-yl)naphthalen-1-yl]amino}methyl)prop-2-enenitrile | 369 |
| 23 | 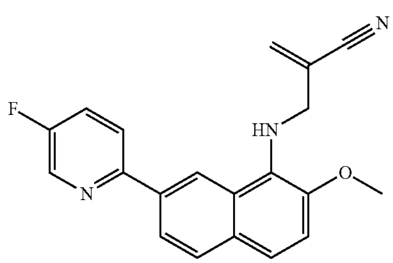 [SMILES: C=C(C#N)CNc1c(OC)ccc2ccc(-c3ccc(F)cn3)cc12] | 2-({[7-(5-fluoropyridin-2-yl)-2-methoxynaphthalen-1-yl]amino}methyl)prop-2-enenitrile | 334.1 |
| 24 | 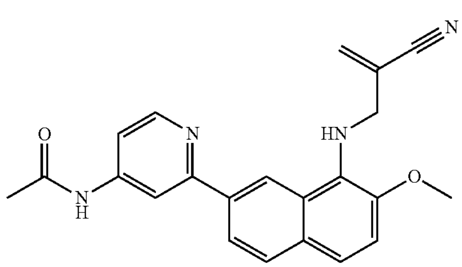 [SMILES: C=C(C#N)CNc1c(OC)ccc2ccc(-c3cc(NC(C)=O)ccn3)cc12] | N-(2-{8-[(2-cyano-2-methylideneethyl)amino]-7-methoxynaphthalen-2-yl}pyridin-4-yl)acetamide | 373.1 |

TABLE 2-continued

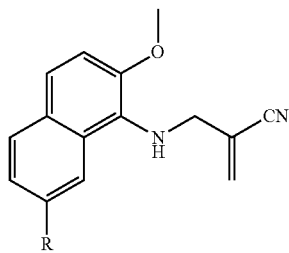

| Cmp. No. | Structure | IUPAC | LC-MS (ES+, m/z) |
|---|---|---|---|
| 25 | 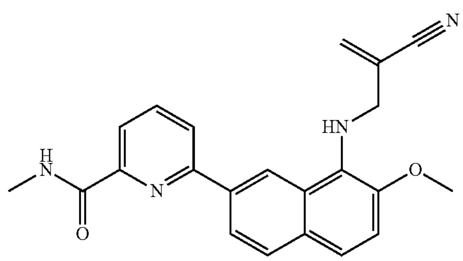 | 6-{8-[(2-cyano-2-methylideneethyl)amino]-7-methoxynaphthalen-2-yl}-N-methylpyridine-2-carboxamide | 373.2 |
| 26 | 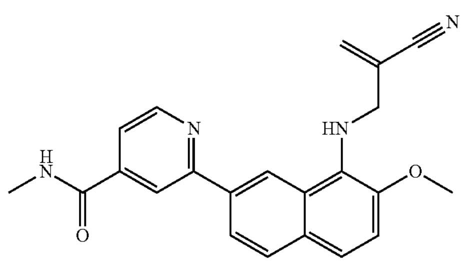 | 2-{8-[(2-cyano-2-methylideneethyl)amino]-7-methoxynaphthalen-2-yl}-N-methylpyridine-4-carboxamide | 373.1 |
| 27 | 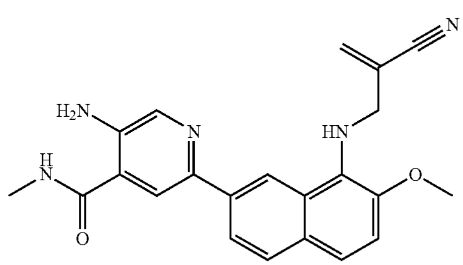 | 5-amino-2-{8-[(2-cyano-2-methylideneethyl)amino]-7-methoxynaphthalen-2-yl}-N-methylpyridine-4-carboxamide | 388.2 |
| 28 | 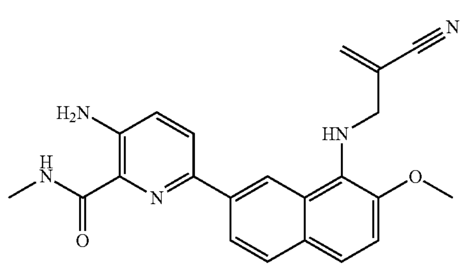 | 3-amino-6-{8-[(2-cyano-2-methylideneethyl)amino]-7-methoxynaphthalen-2-yl}-N-methylpyridine-2-carboxamide | 388.2 |

TABLE 2-continued

| Cmp. No. | Structure | IUPAC | LC-MS (ES+, m/z) |
|---|---|---|---|
| 29 | 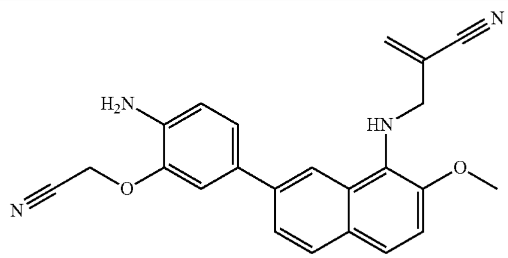 [SMILES: C=C(C#N)CNc1c(OC)ccc2ccc(-c3ccc(N)c(OCC#N)c3)cc12] | 2-[({7-[4-amino-3-(cyanomethoxy)phenyl]-2-methoxynaphthalen-1-yl}amino)methyl]prop-2-enenitrile | 385.1 |
| 30 | 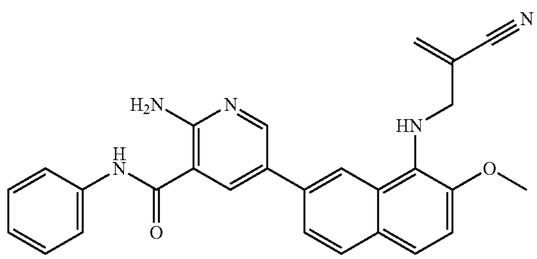 [SMILES: C=C(C#N)CNc1c(OC)ccc2ccc(-c3cnc(N)c(C(=O)Nc4ccccc4)c3)cc12] | 2-amino-5-{8-[(2-cyano-2-methylideneethyl)amino]-7-methoxynaphthalen-2-yl}-N-phenylpyridine-3-carboxamide | 450.2 |
| 31 | 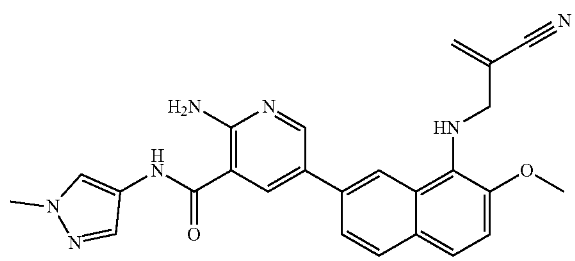 | 2-amino-5-{8-[(2-cyano-2-methylideneethyl)amino]-7-methoxynaphthalen-2-yl}-N-(1-methyl-1H-pyrazol-4-yl)pyridine-3-carboxamide | 454.2 |
| 32 | 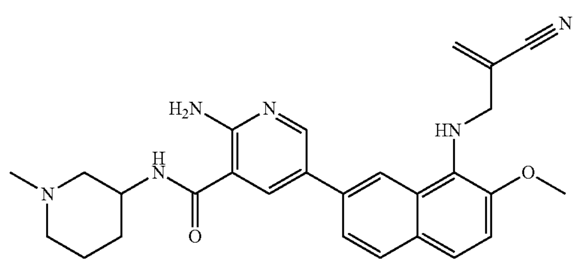 | 2-amino-5-{8-[(2-cyano-2-methylideneethyl)amino]-7-methoxynaphthalen-2-yl}-N-(1-methylpiperidin-3-yl)pyridine-3-carboxamide | 471.3 |
| 33 | 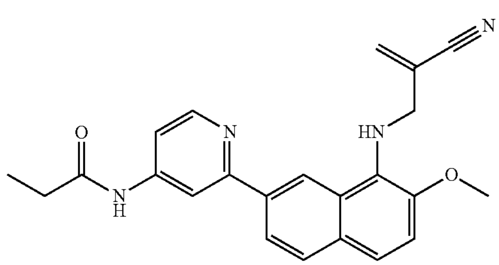 [SMILES: C=C(C#N)CNc1c(OC)ccc2ccc(-c3cc(NC(=O)CC)ccn3)cc12] | N-(2-{8-[(2-cyano-2-methylideneethyl)amino]-7-methoxynaphthalen-2-yl}pyridin-4-yl)propanamide | 387.2 |

TABLE 2-continued

| Cmp. No. | Structure | IUPAC | LC-MS (ES+, m/z) |
|---|---|---|---|
| 34 | 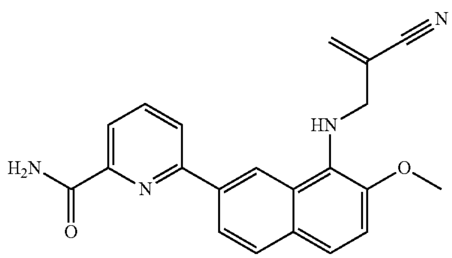 [SMILES: C=C(C#N)CNc1c(OC)ccc2ccc(-c3cccc(C(N)=O)n3)cc12] | 6-{8-[(2-cyano-2-methylideneethyl)amino]-7-methoxynaphthalen-2-yl}pyridine-2-carboxamide | 359.1 |
| 35 | 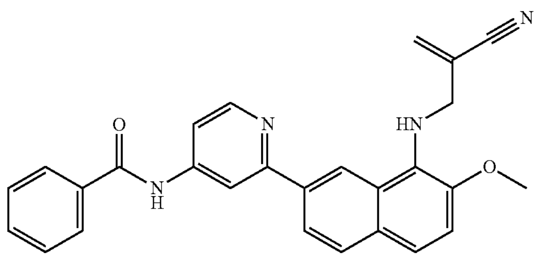 [SMILES: C=C(C#N)CNc1c(OC)ccc2ccc(-c3cc(NC(=O)c4ccccc4)ccn3)cc12] | N-(2-{8-[(2-cyano-2-methylideneethyl)amino]-7-methoxynaphthalen-2-yl}pyridin-4-yl)benzamide | 435.2 |
| 36 | 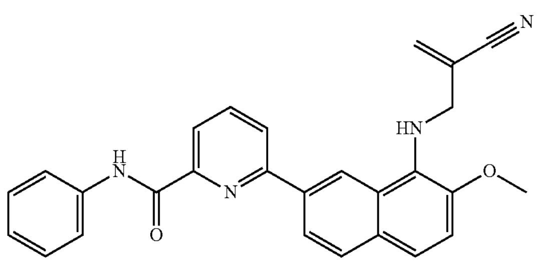 [SMILES: C=C(C#N)CNc1c(OC)ccc2ccc(-c3cccc(C(=O)Nc4ccccc4)n3)cc12] | 6-{8-[(2-cyano-2-methylideneethyl)amino]-7-methoxynaphthalen-2-yl}-N-phenylpyridine-2-carboxamide | 435.1 |
| 37 | 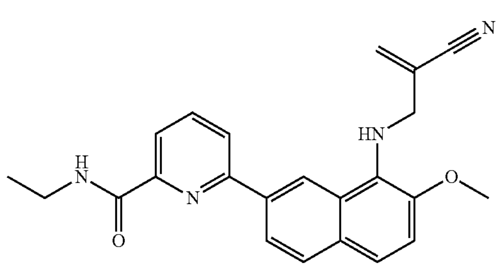 [SMILES: C=C(C#N)CNc1c(OC)ccc2ccc(-c3cccc(C(=O)NCC)n3)cc12] | 6-{8-[(2-cyano-2-methylideneethyl)amino]-7-methoxynaphthalen-2-yl}-N-ethylpyridine-2-carboxamide | 387.2 |

TABLE 2-continued

| Cmp. No. | Structure | IUPAC | LC-MS (ES+, m/z) |
|---|---|---|---|
| 38 | 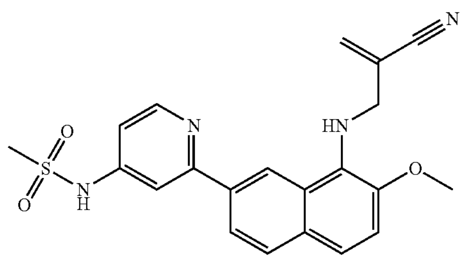 | N-(2-{8-[(2-cyano-2-methylideneethyl)amino]-7-methoxynaphthalen-2-yl}pyridin-4-yl)methanesulfonamide | 409.1 |
| 39 | 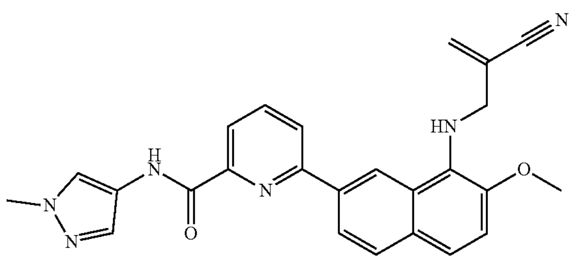 | 6-{8-[(2-cyano-2-methylideneethyl)amino]-7-methoxynaphthalen-2-yl}-N-(1-methyl-1H-pyrazol-4-yl)pyridine-2-carboxamide | 439.2 |
| 40 | 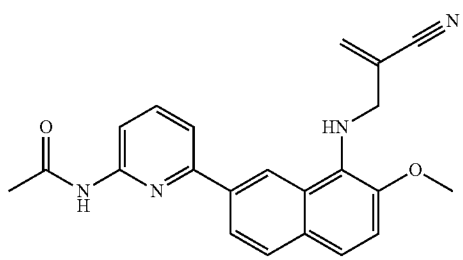 [SMILES: C=C(C#N)CNc1c(OC)ccc2ccc(-c3cccc(NC(C)=O)n3)cc12] | N-(6-{8-[(2-cyano-2-methylideneethyl)amino]-7-methoxynaphthalen-2-yl}pyridin-2-yl)acetamide | 373.2 |
| 41 | 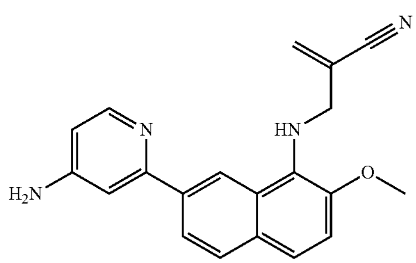 [SMILES: C=C(C#N)CNc1c(OC)ccc2ccc(-c3cc(N)ccn3)cc12] | 2-({[7-(4-aminopyridin-2-yl)-2-methoxynaphthalen-1-yl]amino}methyl)prop-2-enenitrile | 331 |
| 42 | 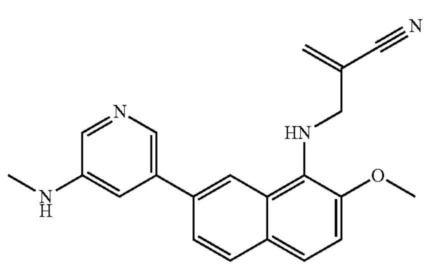 [SMILES: C=C(C#N)CNc1c(OC)ccc2ccc(-c3cncc(NC)c3)cc12] | 2-[({2-methoxy-7-[5-(methylamino)pyridin-3-yl]naphthalen-1-yl}amino)methyl]prop-2-enenitrile | 345.1 |

TABLE 2-continued

| Cmp. No. | Structure | IUPAC | LC-MS (ES+, m/z) |
|---|---|---|---|
| 43 | 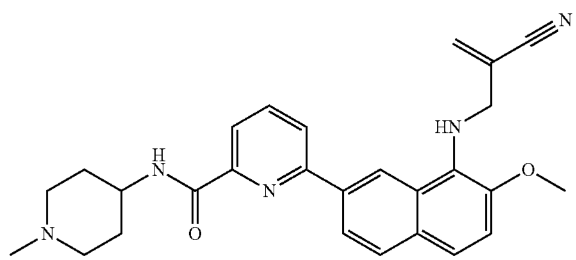 | 6-{8-[(2-cyano-2-methylideneethyl)amino]-7-methoxynaphthalen-2-yl}-N-(1-methylpiperidin-4-yl)pyridine-2-carboxamide | 456.2 |
| 44 | 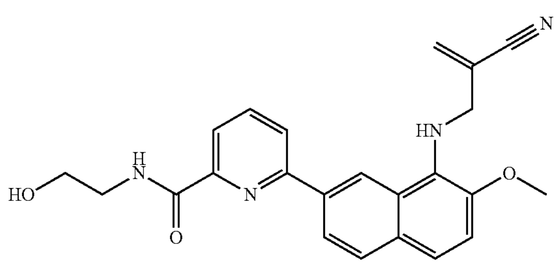 [SMILES: C=C(C#N)CNc1c(OC)ccc2ccc(-c3cccc(C(=O)NCCO)n3)cc12] | 6-{8-[(2-cyano-2-methylideneethyl)amino]-7-methoxynaphthalen-2-yl}-N-(2-hydroxyethyl)pyridine-2-carboxamide | 403.1 |
| 45 | 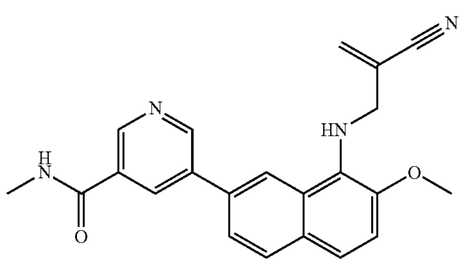 | 5-{8-[(2-cyano-2-methylideneethyl)amino]-7-methoxynaphthalen-2-yl}-N-methylpyridine-3-carboxamide | 373 |
| 46 | 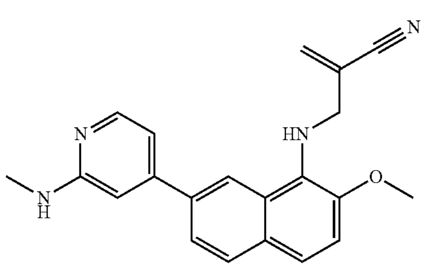 | 2-[({2-methoxy-7-[2-(methylamino)pyridin-4-yl]naphthalen-1-yl}amino)methyl]prop-2-enenitrile | 345.1 |

TABLE 2-continued

| Cmp. No. | Structure | IUPAC | LC-MS (ES+, m/z) |
|---|---|---|---|
| 47 | 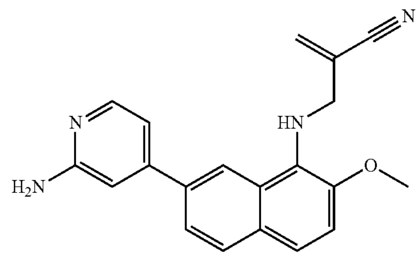 [SMILES: C=C(C#N)CNc1c(OC)ccc2ccc(-c3ccnc(N)c3)cc12] | 2-({[7-(2-aminopyridin-4-yl)-2-methoxynaphthalen-1-yl]amino}methyl)prop-2-enenitrile | 331.2 |
| 48 | 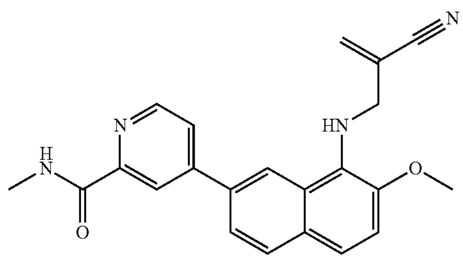 | 4-{8-[(2-cyano-2-methylideneethyl)amino]-7-methoxynaphthalen-2-yl}-N-methylpyridine-2-carboxamide | 373.1 |
| 49 | 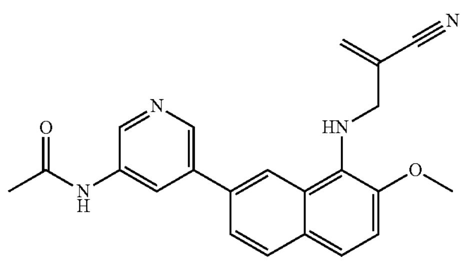 [SMILES: C=C(C#N)CNc1c(OC)ccc2ccc(-c3cncc(NC(C)=O)c3)cc12] | N-(5-{8-[(2-cyano-2-methylideneethyl)amino]-7-methoxynaphthalen-2-yl}pyridin-3-yl)acetamide | 373.1 |
| 50 | 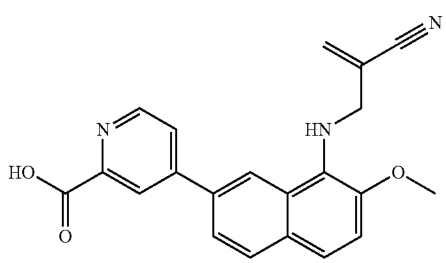 [SMILES: C=C(C#N)CNc1c(OC)ccc2ccc(-c3ccnc(C(=O)O)c3)cc12] | 4-{8-[(2-cyano-2-methylideneethyl)amino]-7-methoxynaphthalen-2-yl}pyridine-2-carboxylic acid | 360.1 |

TABLE 2-continued

| Cmp. No. | Structure | IUPAC | LC-MS (ES+, m/z) |
|---|---|---|---|
| 51 | 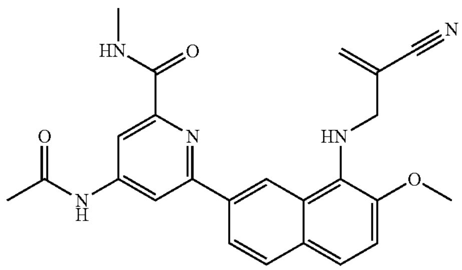 [SMILES: C=C(C#N)CNc1c(OC)ccc2ccc(-c3cc(NC(C)=O)cc(C(=O)NC)n3)cc12] | 6-{8-[(2-cyano-2-methylideneethyl)amino]-7-methoxynaphthalen-2-yl}-4-acetamido-N-methylpyridine-2-carboxamide | 430.1 |
| 52 | 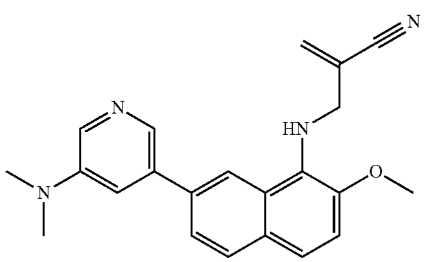 [SMILES: C=C(C#N)CNc1c(OC)ccc2ccc(-c3cncc(N(C)C)c3)cc12] | 2-[({7-[5-(dimethylamino)pyridin-3-yl]-2-methoxynaphthalen-1-yl}amino)methyl]prop-2-enenitrile | 359.2 |
| 53 | 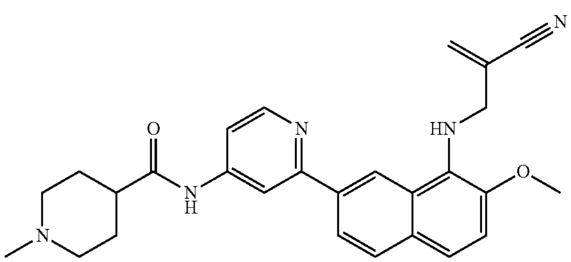 | N-(2-{8-[(2-cyano-2-methylideneethyl)amino]-7-methoxynaphthalen-2-yl}pyridin-4-yl)-1-methylpiperidine-4-carboxamide | 456.3 |
| 54 | 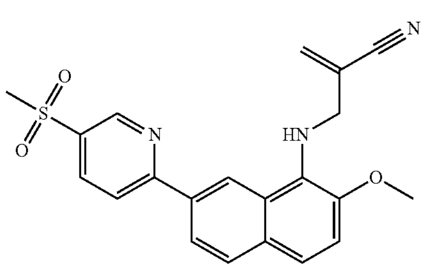 [SMILES: C=C(C#N)CNc1c(OC)ccc2ccc(-c3ccc(S(C)(=O)=O)cn3)cc12] | 2-({[7-(5-methanesulfonylpyridin-2-yl)-2-methoxynaphthalen-1-yl]amino}methyl)prop-2-enenitrile | 393.9 |

TABLE 2-continued

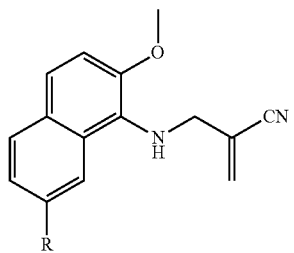

| Cmp. No. | Structure | IUPAC | LC-MS (ES+, m/z) |
|---|---|---|---|
| 55 | 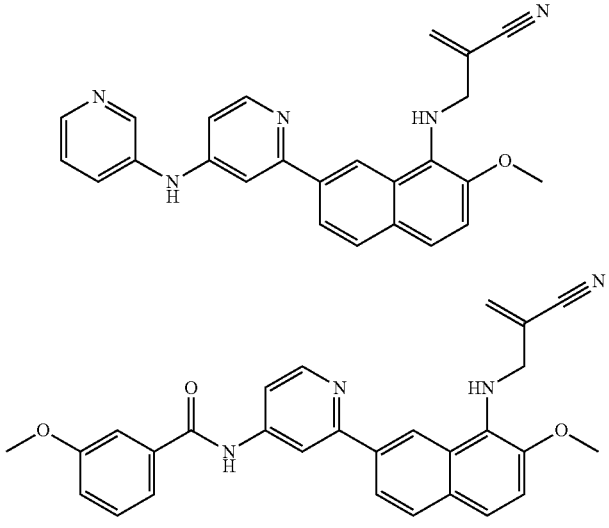 | 2-{[(2-methoxy-7-{4-[(pyridin-3-yl)amino]pyridin-2-yl}naphthalen-1-yl)amino]methyl}prop-2-enenitrile | 408.2 |
| 56 | 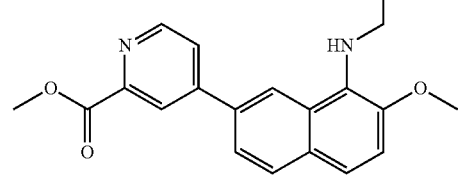 | N-(2-{8-[(2-cyano-2-methylideneethyl)amino]-7-methoxynaphthalen-2-yl}pyridin-4-yl)-3-methoxybenzamide | 465.2 |
| 57 | 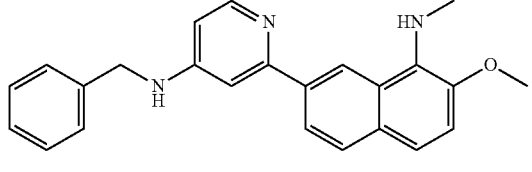 | methyl 4-{8-[(2-cyano-2-methylideneethyl)amino]-7-methoxynaphthalen-2-yl}pyridine-2-carboxylate | 374.1 |
| 58 | 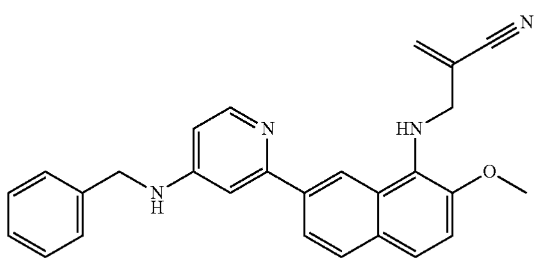 [SMILES: C=C(C#N)CNc1c(OC)ccc2ccc(-c3cc(NCc4ccccc4)ccn3)cc12] | 2-[({7-[4-(benzylamino)pyridin-2-yl]-2-methoxynaphthalen-1-yl}amino)methyl]prop-2-enenitrile | 421 |
| 59 | 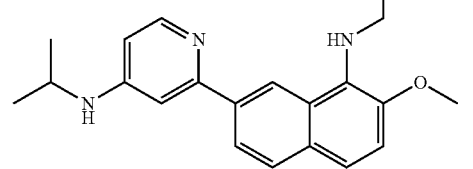 | 2-{[(2-methoxy-7-{4-[(propan-2-yl)amino]pyridin-2-yl}naphthalen-1-yl)amino]methyl}prop-2-enenitrile | 373 |

TABLE 2-continued

| Cmp. No. | Structure | IUPAC | LC-MS (ES+, m/z) |
|---|---|---|---|
| 60 | 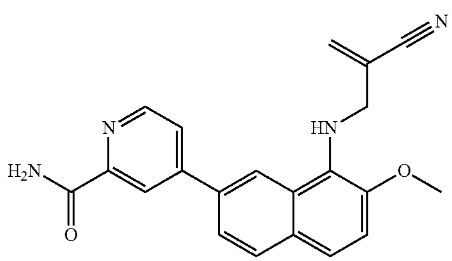 [SMILES: C=C(C#N)CNc1c(OC)ccc2ccc(-c3ccnc(C(N)=O)c3)cc12] | 4-{8-[(2-cyano-2-methylideneethyl)amino]-7-methoxynaphthalen-2-yl}pyridine-2-carboxamide | 359.1 |
| 61 | 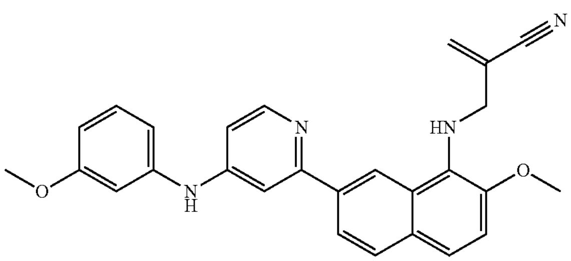 | 2-{[(2-methoxy-7-{4-[(3-methoxyphenyl)amino]pyridin-2-yl}naphthalen-1-yl)amino]methyl}prop-2-enenitrile | 437.1 |
| 62 | 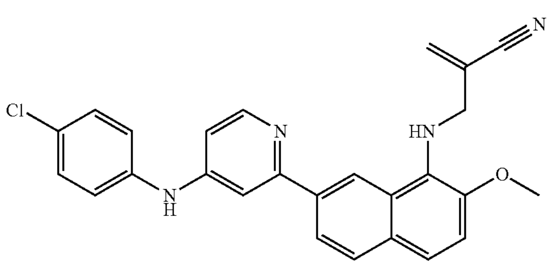 [SMILES: C=C(C#N)CNc1c(OC)ccc2ccc(-c3cc(Nc4ccc(Cl)cc4)ccn3)cc12] | 2-{[(7-{4-[(4-chlorophenyl)amino]pyridin-2-yl}-2-methoxynaphthalen-1-yl)amino]methyl}prop-2-enenitrile | 441.1 |
| 63 | 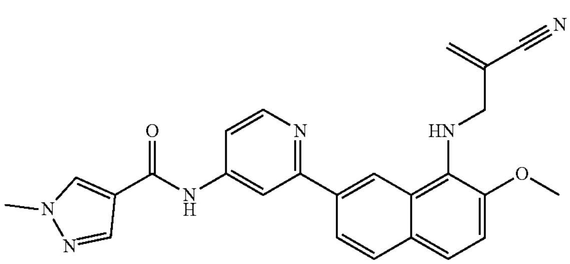 | N-(2-{8-[(2-cyano-2-methylideneethyl)amino]-7-methoxynaphthalen-2-yl}pyridin-4-yl)-1-methyl-1H-pyrazole-4-carboxamide | 439.2 |

TABLE 2-continued

| Cmp. No. | Structure | IUPAC | LC-MS (ES+, m/z) |
|---|---|---|---|
| 64 | 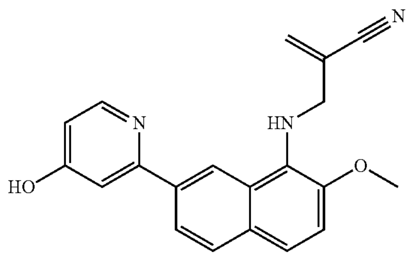 [SMILES: C=C(C#N)CNc1c(OC)ccc2ccc(-c3cc(O)ccn3)cc12] | 2-({[7-(4-hydroxypyridin-2-yl)-2-methoxynaphthalen-1-yl]amino}methyl)prop-2-enenitrile | 332.2 |
| 65 | 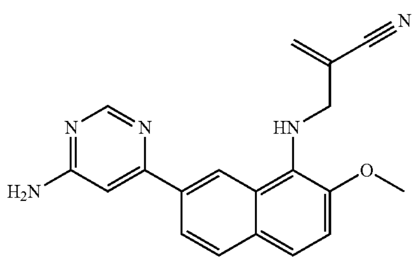 [SMILES: C=C(C#N)CNc1c(OC)ccc2ccc(-c3cc(N)ncn3)cc12] | 2-({[7-(6-aminopyrimidin-4-yl)-2-methoxynaphthalen-1-yl]amino}methyl)prop-2-enenitrile | 332.2 |
| 66 | 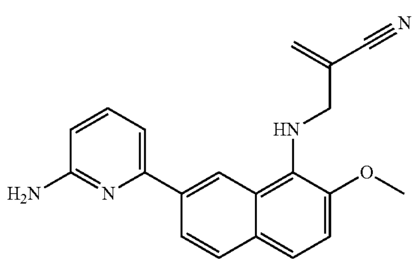 [SMILES: C=C(C#N)CNc1c(OC)ccc2ccc(-c3cccc(N)n3)cc12] | 2-({[7-(6-aminopyridin-2-yl)-2-methoxynaphthalen-1-yl]amino}methyl)prop-2-enenitrile | 331.1 |
| 67 | 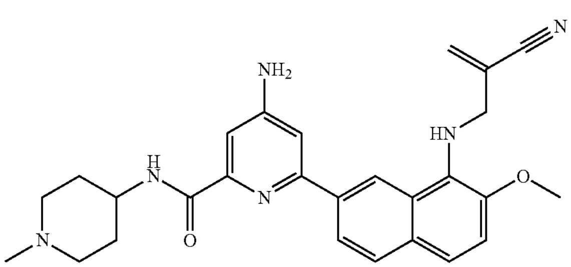 | 4-amino-6-{8-[(2-cyano-2-methylideneethyl)amino]-7-methoxynaphthalen-2-yl}-N-(1-methylpiperidin-4-yl)pyridine-2-carboxamide | 471.2 |

TABLE 2-continued

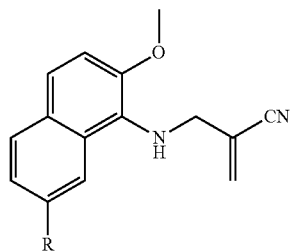

| Cmp. No. | Structure | IUPAC | LC-MS (ES+, m/z) |
|---|---|---|---|
| 68 | 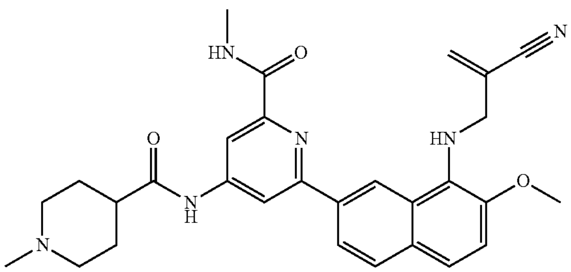 | 6-{8-[(2-cyano-2-methylideneethyl)amino]-7-methoxynaphthalen-2-yl}-N-methyl-4-(1-methylpiperidine-4-amido)pyridine-2-carboxamide | 513.1 |
| 69 | 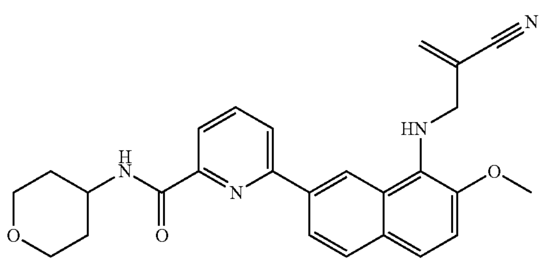 [SMILES: C=C(C#N)CNc1c(OC)ccc2ccc(-c3cccc(C(=O)NC4CCOCC4)n3)cc12] | 6-{8-[(2-cyano-2-methylideneethyl)amino]-7-methoxynaphthalen-2-yl}-N-(oxan-4-yl)pyridine-2-carboxamide | 443 |
| 70 | 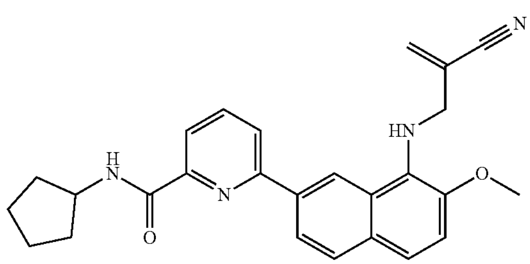 [SMILES: C=C(C#N)CNc1c(OC)ccc2ccc(-c3cccc(C(=O)NC4CCCC4)n3)cc12] | 6-{8-[(2-cyano-2-methylideneethyl)amino]-7-methoxynaphthalen-2-yl}-N-cyclopentylpyridine-2-carboxamide | 427 |
| 71 | 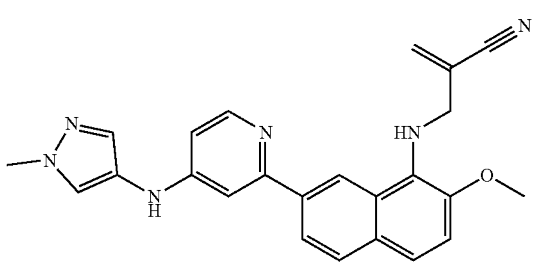 | 2-{[(2-methoxy-7-{4-[(1-methyl-1H-pyrazol-4-yl)amino]pyridin-2-yl}naphthalen-1-yl)amino]methyl}prop-2-enenitrile | 411.2 |

TABLE 2-continued

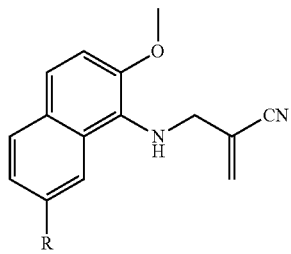

| Cmp. No. | Structure | IUPAC | LC-MS (ES+, m/z) |
|---|---|---|---|
| 72 | 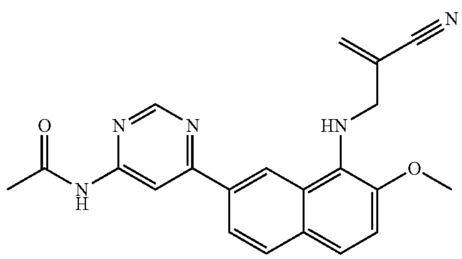 [SMILES: C=C(C#N)CNc1c(OC)ccc2ccc(-c3cc(NC(C)=O)ncn3)cc12] | N-(6-{8-[(2-cyano-2-methylideneethyl)amino]-7-methoxynaphthalen-2-yl}pyrimidin-4-yl)acetamide | 374.1 |
| 73 | 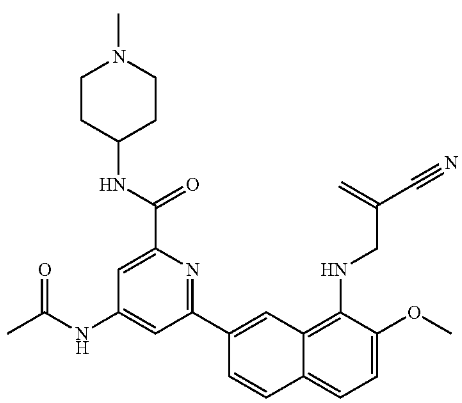 [SMILES: C=C(C#N)CNc1c(OC)ccc2ccc(-c3cc(NC(C)=O)cc(C(=O)NC4CCN(C)CC4)n3)cc12] | 6-{8-[(2-cyano-2-methylideneethyl)amino]-7-methoxynaphthalen-2-yl}-4-acetamido-N-(1-methylpiperidin-4-yl)pyridine-2-carboxamide | 513.3 |
| 74 | 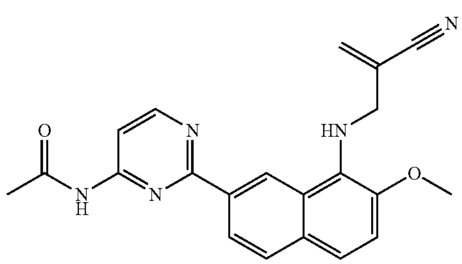 [SMILES: C=C(C#N)CNc1c(OC)ccc2ccc(-c3nccc(NC(C)=O)n3)cc12] | N-(2-{8-[(2-cyano-2-methylideneethyl)amino]-7-methoxynaphthalen-2-yl}pyrimidin-4-yl)acetamide | 374.2 |
| 75 | 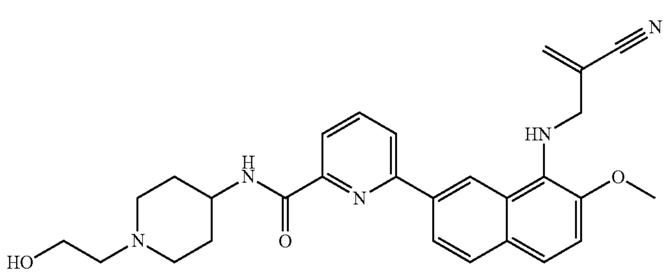 [SMILES: C=C(C#N)CNc1c(OC)ccc2ccc(-c3cccc(C(=O)NC4CCN(CCO)CC4)n3)cc12] | 6-{8-[(2-cyano-2-methylideneethyl)amino]-7-methoxynaphthalen-2-yl}-N-[1-(2-hydroxyethyl)piperidin-4-yl]pyridine-2-carboxamide | 486 |

TABLE 2-continued

| Cmp. No. | Structure | IUPAC | LC-MS (ES+, m/z) |
|---|---|---|---|
| 76 | 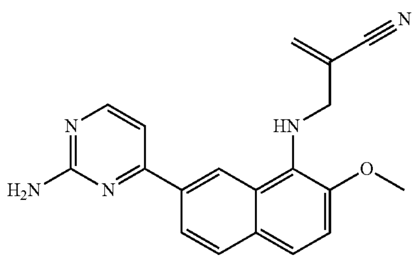 [SMILES: C=C(C#N)CNc1c(OC)ccc2ccc(-c3ccnc(N)n3)cc12] | 2-({[7-(2-aminopyrimidin-4-yl)-2-methoxynaphthalen-1-yl]amino}methyl)prop-2-enenitrile | 332 |
| 77 | 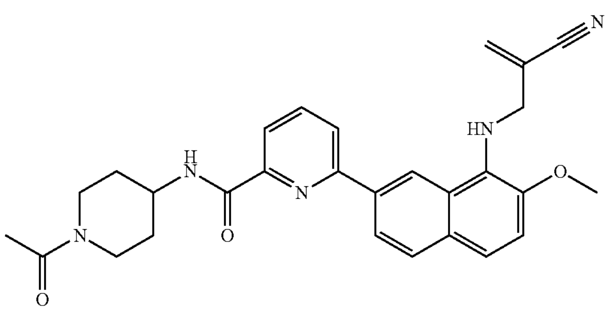 [SMILES: C=C(C#N)CNc1c(OC)ccc2ccc(-c3cccc(C(=O)NC4CCN(C(C)=O)CC4)n3)cc12] | N-(1-acetylpiperidin-4-yl)-6-{8-[(2-cyano-2-methylideneethyl)amino]-7-methoxynaphthalen-2-yl}pyridine-2-carboxamide | 484.2 |
| 78 | 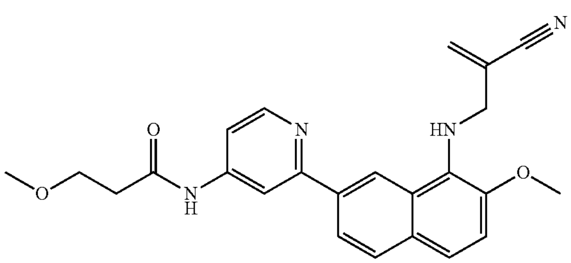 | N-(2-{8-[(2-cyano-2-methylideneethyl)amino]-7-methoxynaphthalen-2-yl}pyridin-4-yl)-3-methoxypropanamide | 417 |
| 79 | 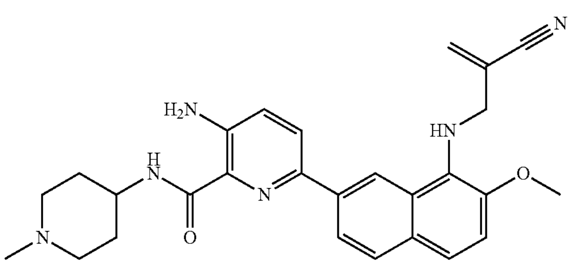 | 3-amino-6-{8-[(2-cyano-2-methylideneethyl)amino]-7-methoxynaphthalen-2-yl}-N-(1-methylpiperidin-4-yl)pyridine-2-carboxamide | 471.3 |

TABLE 2-continued

| Cmp. No. | Structure | IUPAC | LC-MS (ES+, m/z) |
|---|---|---|---|
| 80 | 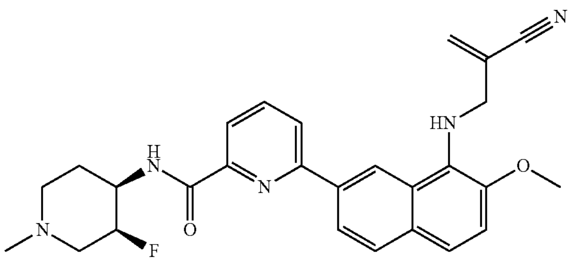 | 6-{8-[(2-cyano-2-methylideneethyl)amino]-7-methoxynaphthalen-2-yl}-N-[(3S,4R)-3-fluoro-1-methylpiperidin-4-yl]pyridine-2-carboxamide | 474.1 |
| 81 | 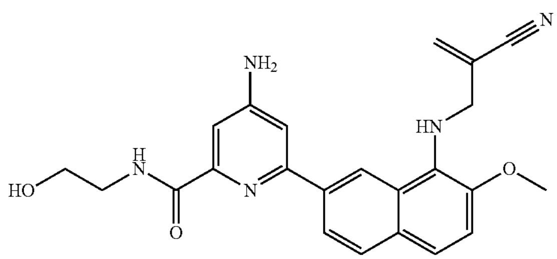 [SMILES: C=C(C#N)CNc1c(OC)ccc2ccc(-c3cc(N)cc(C(=O)NCCO)n3)cc12] | 4-amino-6-{8-[(2-cyano-2-methylideneethyl)amino]-7-methoxynaphthalen-2-yl}-N-(2-hydroxyethyl)pyridine-2-carboxamide | 418.1 |
| 82 | 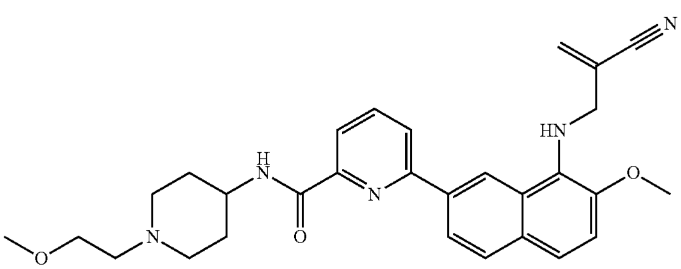 | 6-{8-[(2-cyano-2-methylideneethyl)amino]-7-methoxynaphthalen-2-yl}-N-[1-(2-methoxyethyl)piperidin-4-yl]pyridine-2-carboxamide | 500 |
| 83 | 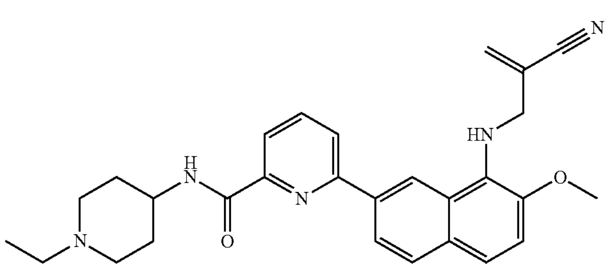 [SMILES: C=C(C#N)CNc1c(OC)ccc2ccc(-c3cccc(C(=O)NC4CCN(CC)CC4)n3)cc12] | 6-{8-[(2-cyano-2-methylideneethyl)amino]-7-methoxynaphthalen-2-yl}-N-(1-ethylpiperidin-4-yl)pyridine-2-carboxamide | 470 |

TABLE 2-continued

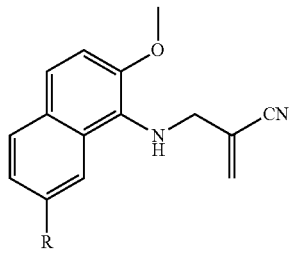

| Cmp. No. | Structure | IUPAC | LC-MS (ES+, m/z) |
|---|---|---|---|
| 84 | 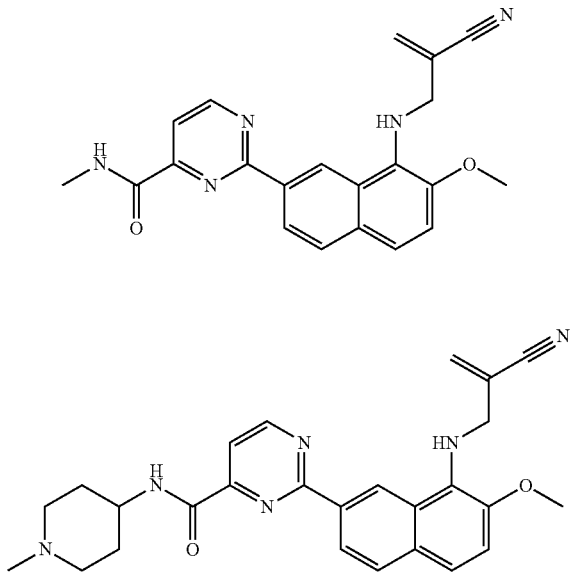 | 2-{8-[(2-cyano-2-methylideneethyl)amino]-7-methoxynaphthalen-2-yl}-N-methylpyrimidine-4-carboxamide | 374.2 |
| 85 | 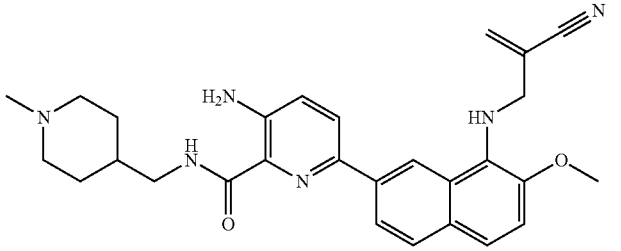 | 2-{8-[(2-cyano-2-methylideneethyl)amino]-7-methoxynaphthalen-2-yl}-N-(1-methylpiperidin-4-yl)pyrimidine-4-carboxamide | 457.2 |
| 86 | 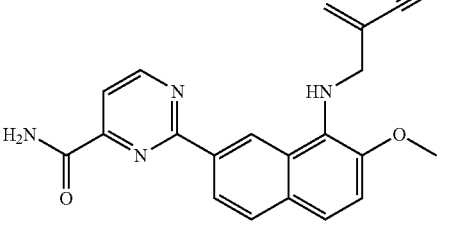 | 3-amino-6-{8-[(2-cyano-2-methylideneethyl)amino]-7-methoxynaphthalen-2-yl}-N-[(1-methylpiperidin-4-yl)methyl]pyridine-2-carboxamide | 485.1 |
| 87 | 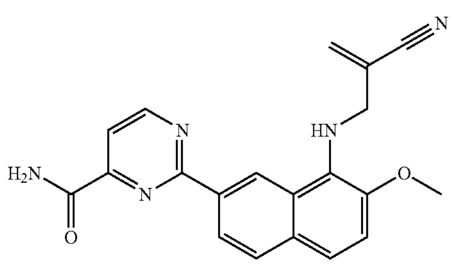 [SMILES: C=C(C#N)CNc1c(OC)ccc2ccc(-c3nccc(C(N)=O)n3)cc12] | 2-{8-[(2-cyano-2-methylideneethyl)amino]-7-methoxynaphthalen-2-yl}pyrimidine-4-carboxamide | 360 |

TABLE 2-continued

| Cmp. No. | Structure | IUPAC | LC-MS (ES+, m/z) |
|---|---|---|---|
| 88 | 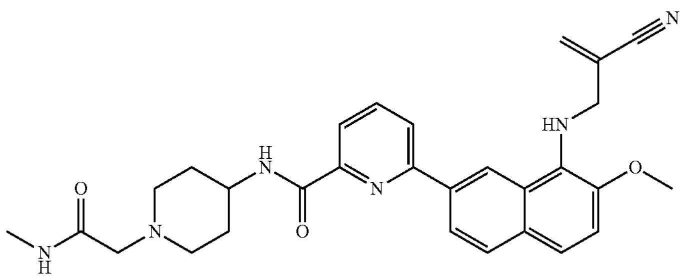 | 6-{8-[(2-cyano-2-methylideneethyl)amino]-7-methoxynaphthalen-2-yl}-N-{1-[(methylcarbamoyl)methyl]piperidin-4-yl}pyridine-2-carboxamide | 492.2 |
| 89 | 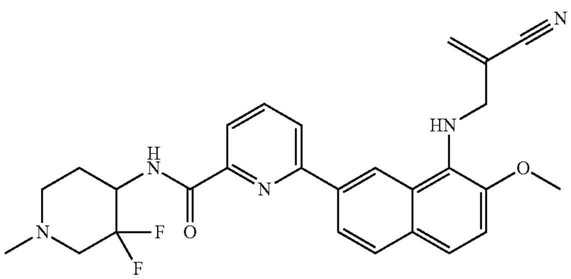 | 6-{8-[(2-cyano-2-methylideneethyl)amino]-7-methoxynaphthalen-2-yl}-N-(3,3-difluoro-1-methylpiperidin-4-yl)pyridine-2-carboxamide | 492.1 |
| 90 | 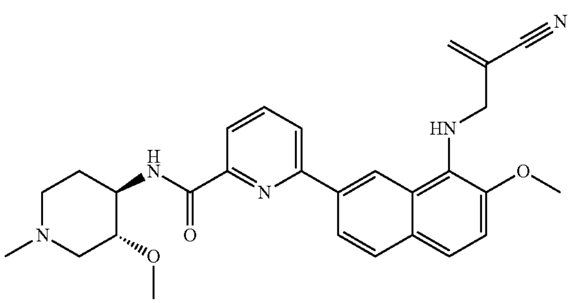 | 6-{8-[(2-cyano-2-methylideneethyl)amino]-7-methoxynaphthalen-2-yl}-N-[(3R,4R)-3-methoxy-1-methylpiperidin-4-yl]pyridine-2-carboxamide | 486.1 |
| 91 | 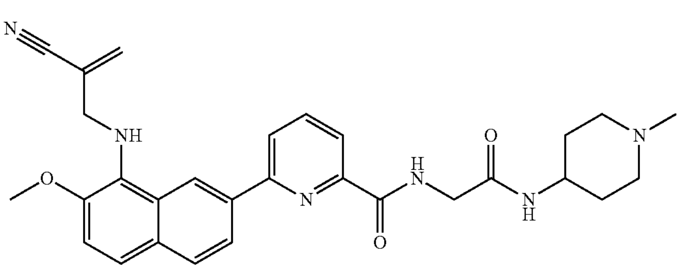 [SMILES: C=C(C#N)CNc1c(OC)ccc2ccc(-c3cccc(C(=O)NCC(=O)NC4CCN(C)CC4)n3)cc12] | 2-[(6-{8-[(2-cyano-2-methylideneethyl)amino]-7-methoxynaphthalen-2-yl}pyridin-2-yl)formamido]-N-(1-methylpiperidin-4-yl)acetamide | 513.1 |

US 11,926,632 B2

TABLE 2-continued

| Cmp. No. | Structure | IUPAC | LC-MS (ES+, m/z) |
|---|---|---|---|
| 92 | 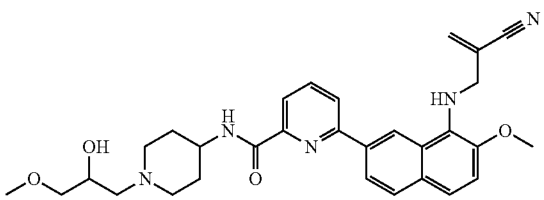 | 6-{8-[(2-cyano-2-methylideneethyl)amino]-7-methoxynaphthalen-2-yl}-N-[1-(2-hydroxy-3-methoxypropyl)piperidin-4-yl]pyridine-2-carboxamide | 530.1 |
| 93 | 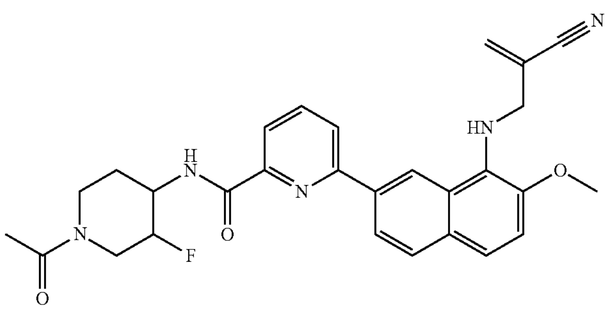 [SMILES: C=C(C#N)CNc1c(OC)ccc2ccc(-c3cccc(C(=O)NC4CCN(C(C)=O)CC4F)n3)cc12] | N-(1-acetyl-3-fluoropiperidin-4-yl)-6-{8-[(2-cyano-2-methylideneethyl)amino]-7-methoxynaphthalen-2-yl}pyridine-2-carboxamide | 502 |
| 94 | 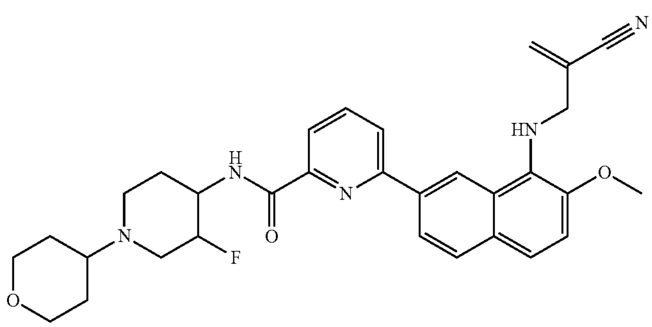 [SMILES: C=C(C#N)CNc1c(OC)ccc2ccc(-c3cccc(C(=O)NC4CCN(C5CCOCC5)CC4F)n3)cc12] | 6-{8-[(2-cyano-2-methylideneethyl)amino]-7-methoxynaphthalen-2-yl}-N-[3-fluoro-1-(oxan-4-yl)piperidin-4-yl]pyridine-2-carboxamide | 544 |
| 95 | 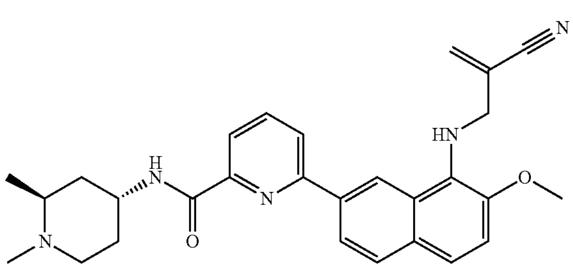 | 6-{8-[(2-cyano-2-methylideneethyl)amino]-7-methoxynaphthalen-2-yl}-N-[(2S,4R)-1,2-dimethylpiperidin-4-yl]pyridine-2-carboxamide | 470.1 |

TABLE 2-continued

| Cmp. No. | Structure | IUPAC | LC-MS (ES+, m/z) |
|---|---|---|---|
| 96 | 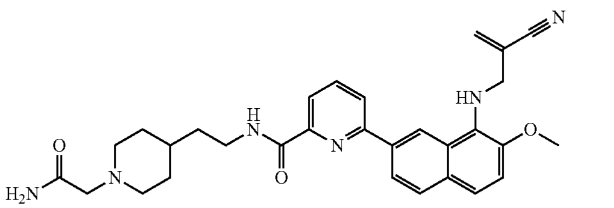 [SMILES: C=C(C#N)CNc1c(OC)ccc2ccc(-c3cccc(C(=O)NCCC4CCN(CC(N)=O)CC4)n3)cc12] | N-{2-[1-(carbamoylmethyl)piperidin-4-yl]ethyl}-6-{8-[(2-cyano-2-methylideneethyl)amino]-7-methoxynaphthalen-2-yl}pyridine-2-carboxamide | 527 |
| 97 | 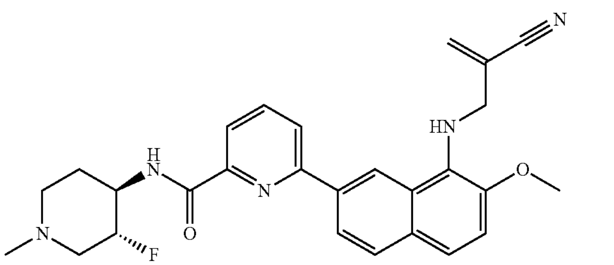 | 6-{8-[(2-cyano-2-methylideneethyl)amino]-7-methoxynaphthalen-2-yl}-N-[(3R,4R)-3-fluoro-1-methylpiperidin-4-yl]pyridine-2-carboxamide | 474.2 |
| 98 | 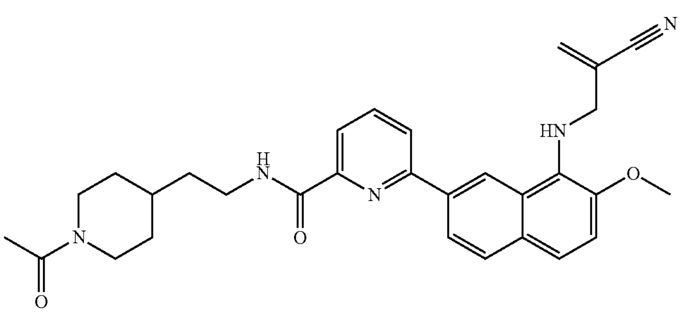 [SMILES: C=C(C#N)CNc1c(OC)ccc2ccc(-c3cccc(C(=O)NCCC4CCN(C(C)=O)CC4)n3)cc12] | N-[2-(1-acetylpiperidin-4-yl)ethyl]-6-{8-[(2-cyano-2-methylideneethyl)amino]-7-methoxynaphthalen-2-yl}pyridine-2-carboxamide | 512.3 |
| 99 | 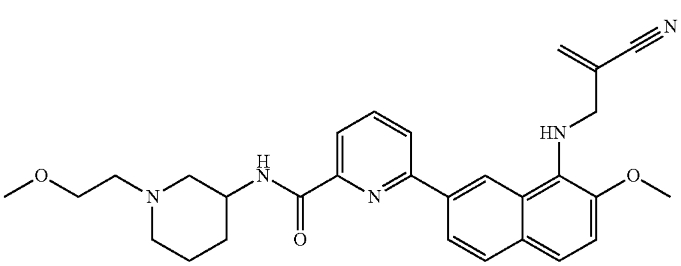 | 6-{8-[(2-cyano-2-methylideneethyl)amino]-7-methoxynaphthalen-2-yl}-N-[1-(2-methoxyethyl)piperidin-3-yl]pyridine-2-carboxamide | 500.1 |

TABLE 2-continued

| Cmp. No. | Structure | IUPAC | LC-MS (ES+, m/z) |
|---|---|---|---|
| 100 | 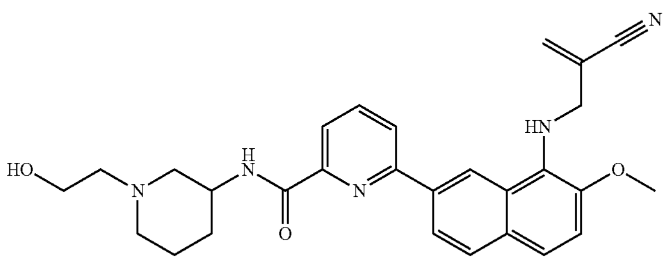 [SMILES: C=C(C#N)CNc1c(OC)ccc2ccc(-c3cccc(C(=O)NC4CCCN(CCO)C4)n3)cc12] | 6-{8-[(2-cyano-2-methylideneethyl)amino]-7-methoxynaphthalen-2-yl}-N-[1-(2-hydroxyethyl)piperidin-3-yl]pyridine-2-carboxamide | 486.1 |
| 101 | 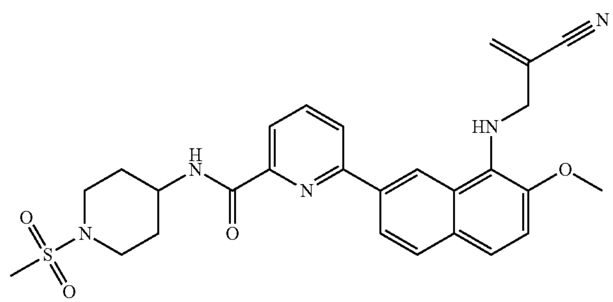 | 6-{8-[(2-cyano-2-methylideneethyl)amino]-7-methoxynaphthalen-2-yl}-N-(1-methanesulfonylpiperidin-4-yl)pyridine-2-carboxamide | 520.1 |
| 102 | 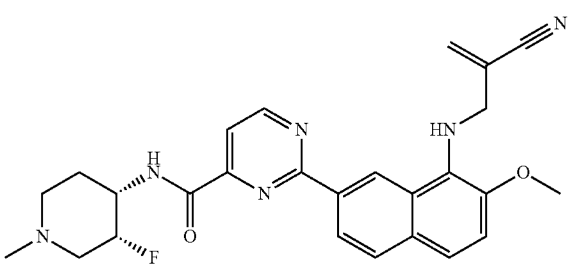 | 2-{8-[(2-cyano-2-methylideneethyl)amino]-7-methoxynaphthalen-2-yl}-N-[(3R,4S)-3-fluoro-1-methylpiperidin-4-yl]pyrimidine-4-carboxamide | 475.1 |
| 103 | 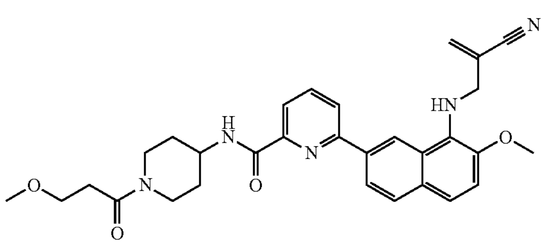 | 6-{8-[(2-cyano-2-methylideneethyl)amino]-7-methoxynaphthalen-2-yl}-N-[1-(3-methoxypropanoyl)piperidin-4-yl]pyridine-2-carboxamide | 528.3 |

TABLE 2-continued

| Cmp. No. | Structure | IUPAC | LC-MS (ES+, m/z) |
|---|---|---|---|
| 104 | 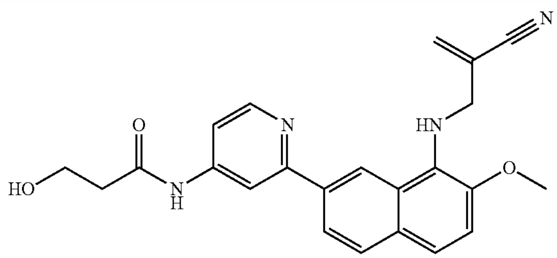 [SMILES: C=C(C#N)CNc1c(OC)ccc2ccc(-c3cc(NC(=O)CCO)ccn3)cc12] | N-(2-{8-[(2-cyano-2-methylideneethyl)amino]-7-methoxynaphthalen-2-yl}pyridin-4-yl)-3-hydroxypropanamide | 403 |
| 105 | 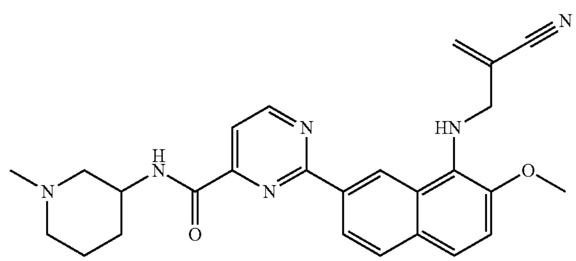 | 2-{8-[(2-cyano-2-methylideneethyl)amino]-7-methoxynaphthalen-2-yl}-N-(1-methylpiperidin-3-yl)pyrimidine-4-carboxamide | 457.3 |
| 106 | 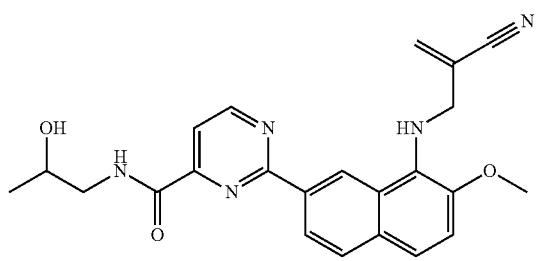 | 2-{8-[(2-cyano-2-methylideneethyl)amino]-7-methoxynaphthalen-2-yl}-N-(2-hydroxypropyl)pyrimidine-4-carboxamide | 418.2 |
| 107 | 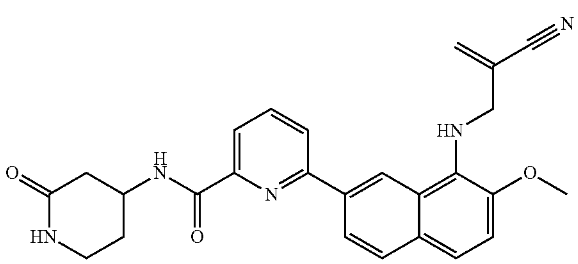 [SMILES: C=C(C#N)CNc1c(OC)ccc2ccc(-c3cccc(C(=O)NC4CCNC(=O)C4)n3)cc12] | 6-{8-[(2-cyano-2-methylideneethyl)amino]-7-methoxynaphthalen-2-yl}-N-(2-oxopiperidin-4-yl)pyridine-2-carboxamide | 456 |
| 108 | 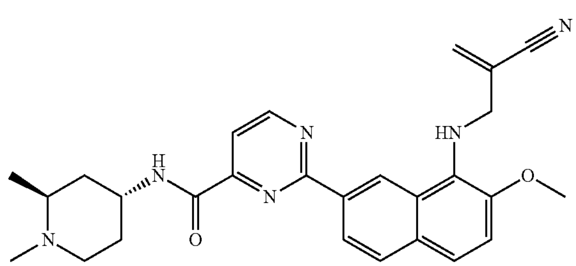 | 2-{8-[(2-cyano-2-methylideneethyl)amino]-7-methoxynaphthalen-2-yl}-N-[(2S,4R)-1,2-dimethylpiperidin-4-yl]pyrimidine-4-carboxamide | 471.1 |

TABLE 2-continued

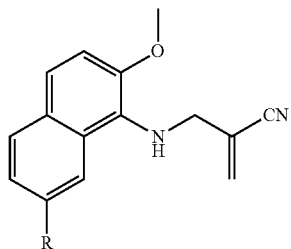

| Cmp. No. | Structure | IUPAC | LC-MS (ES+, m/z) |
|---|---|---|---|
| 109 | 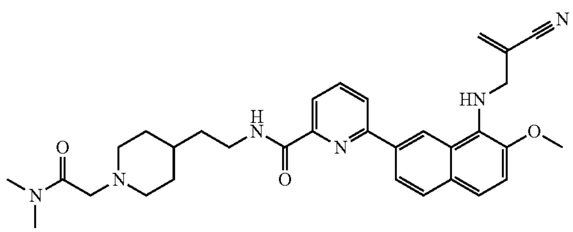 | 6-{8-[(2-cyano-2-methylideneethyl)amino]-7-methoxynaphthalen-2-yl}-N-(2-{1-[(dimethylcarbamoyl)methyl]piperidin-4-yl}ethyl)pyridine-2-carboxamide | 555.1 |
| 110 | 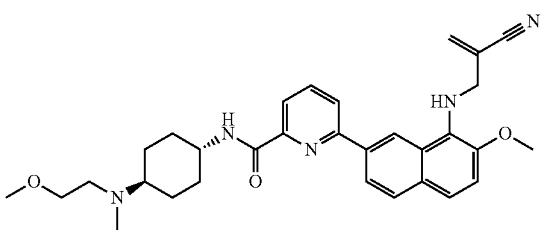 | 6-{8-[(2-cyano-2-methylideneethyl)amino]-7-methoxynaphthalen-2-yl}-N-[(1r,4r)-4-[(2-methoxyethyl)(methyl)amino]cyclohexyl]pyridine-2-carboxamide | 528.3 |
| 111 | 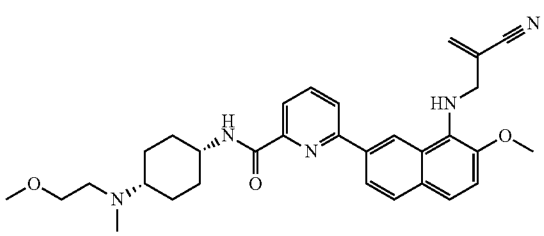 | 6-{8-[(2-cyano-2-methylideneethyl)amino]-7-methoxynaphthalen-2-yl}-N-[(1s,4s)-4-[(2-methoxyethyl)(methyl)amino]cyclohexyl]pyridine-2-carboxamide | 528.3 |
| 112 | 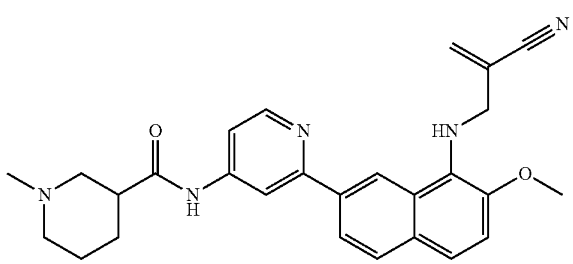 | N-(2-{8-[(2-cyano-2-methylideneethyl)amino]-7-methoxynaphthalen-2-yl}pyridin-4-yl)-1-methylpiperidine-3-carboxamide | 456.2 |
| 113 | 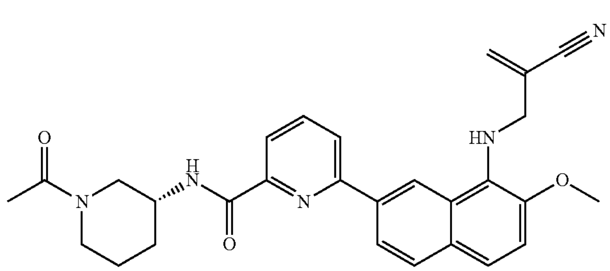 [SMILES: C=C(C#N)CNc1c(OC)ccc2ccc(-c3cccc(C(=O)N[C@@H]4CCCN(C(C)=O)C4)n3)cc12] | N-[(3R)-1-acetylpiperidin-3-yl]-6-{8-[(2-cyano-2-methylideneethyl)amino]-7-methoxynaphthalen-2-yl}pyridine-2-carboxamide | 484.2 |

TABLE 2-continued

| Cmp. No. | Structure | IUPAC | LC-MS (ES+, m/z) |
|---|---|---|---|
| 114 | 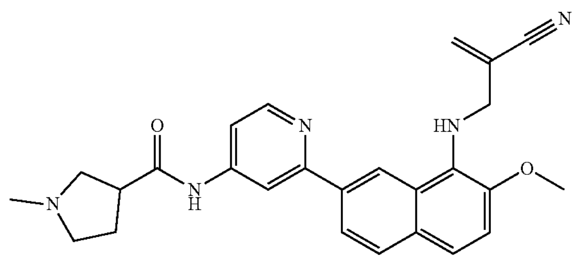 | N-(2-{8-[(2-cyano-2-methylideneethyl)amino]-7-methoxynaphthalen-2-yl}pyridin-4-yl)-1-methylpyrrolidine-3-carboxamide | 442.2 |
| 115 | 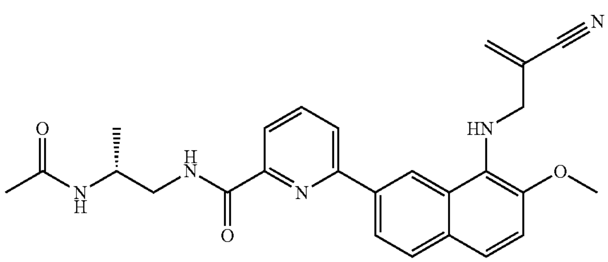 [SMILES: C=C(C#N)CNc1c(OC)ccc2ccc(-c3cccc(C(=O)NC[C@@H](C)NC(C)=O)n3)cc12] | N-[(2R)-1-[(6-{8-[(2-cyano-2-methylideneethyl)amino]-7-methoxynaphthalen-2-yl}pyridin-2-yl)formamido]propan-2-yl]acetamide | 458.2 |
| 116 | 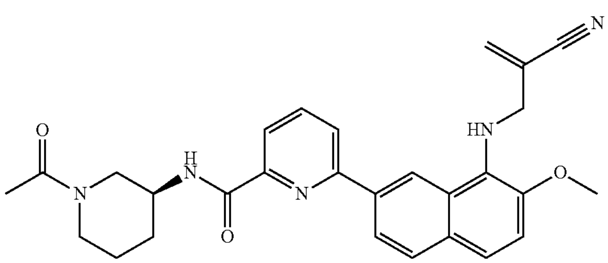 [SMILES: C=C(C#N)CNc1c(OC)ccc2ccc(-c3cccc(C(=O)N[C@H]4CCCN(C(C)=O)C4)n3)cc12] | N-[(3S)-1-acetylpiperidin-3-yl]-6-{8-[(2-cyano-2-methylideneethyl)amino]-7-methoxynaphthalen-2-yl}pyridine-2-carboxamide | 484.2 |
| 117 | 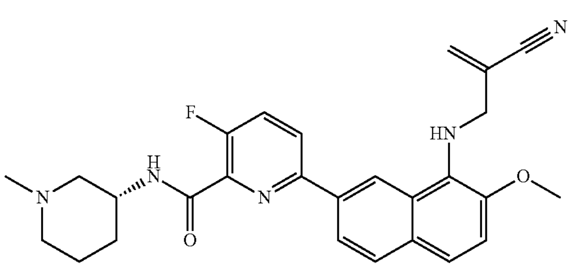 | 6-{8-[(2-cyano-2-methylideneethyl)amino]-7-methoxynaphthalen-2-yl}-3-fluoro-N-[(3R)-1-methylpiperidin-3-yl]pyridine-2-carboxamide | 474.2 |

TABLE 2-continued

| Cmp. No. | Structure | IUPAC | LC-MS (ES+, m/z) |
|---|---|---|---|
| 118 | 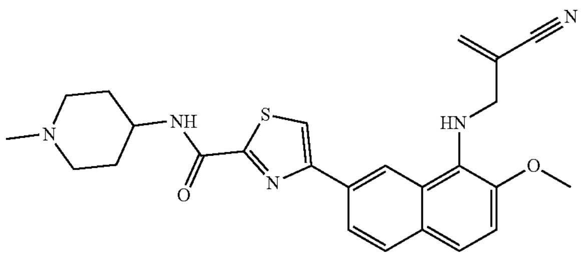 | 4-{8-[(2-cyano-2-methylideneethyl)amino]-7-methoxynaphthalen-2-yl}-N-(1-methylpiperidin-4-yl)-1,3-thiazole-2-carboxamide | 462.1 |
| 119 | 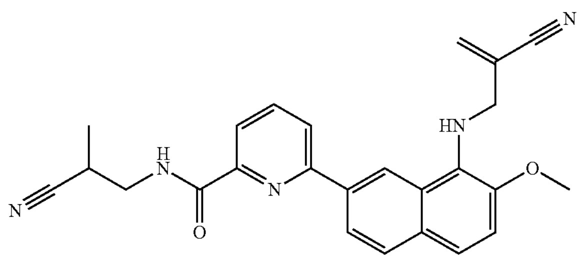 [SMILES: C=C(C#N)CNc1c(OC)ccc2ccc(-c3cccc(C(=O)NCC(C)C#N)n3)cc12] | N-(2-cyano-2-methylethyl)-6-{8-[(2-cyano-2-methylideneethyl)amino]-7-methoxynaphthalen-2-yl}pyridine-2-carboxamide | 426.2 |
| 120 | 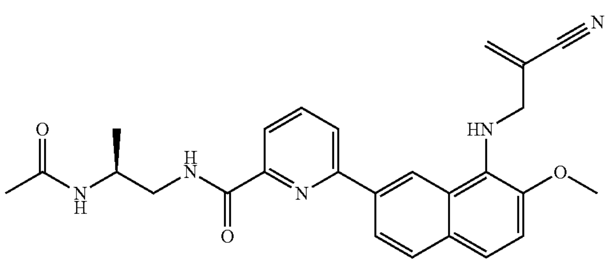 [SMILES: C=C(C#N)CNc1c(OC)ccc2ccc(-c3cccc(C(=O)NC[C@H](C)NC(C)=O)n3)cc12] | N-[(2S)-1-[(6-{8-[(2-cyano-2-methylideneethyl)amino]-7-methoxynaphthalen-2-yl}pyridin-2-yl)formamido]propan-2-yl]acetamide | 458.2 |
| 121 | 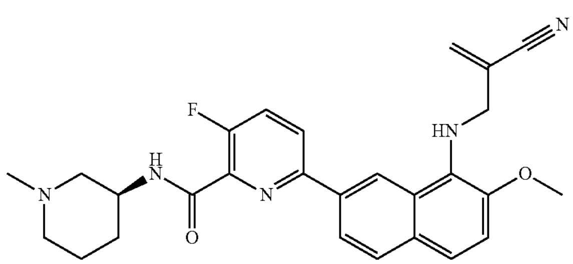 | 6-{8-[(2-cyano-2-methylideneethyl)amino]-7-methoxynaphthalen-2-yl}-3-fluoro-N-[(3S)-1-methylpiperidin-3-yl]pyridine-2-carboxamide | 474.2 |

TABLE 2-continued

| Cmp. No. | Structure | IUPAC | LC-MS (ES+, m/z) |
|---|---|---|---|
| 122 | 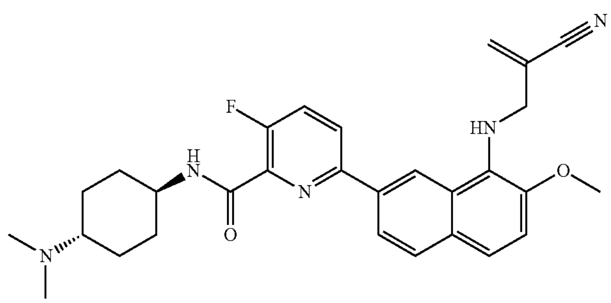 | 6-{8-[(2-cyano-2-methylideneethyl)amino]-7-methoxynaphthalen-2-yl}-3-fluoro-N-[(1r,4r)-4-(dimethylamino)cyclohexyl]pyridine-2-carboxamide | 502.3 |
| 123 | 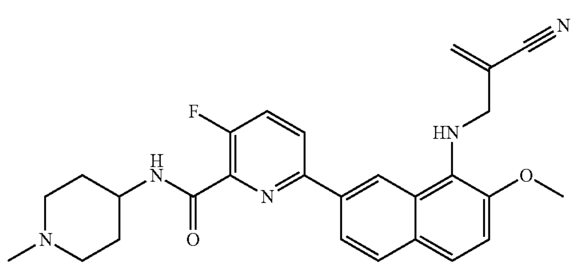 | 6-{8-[(2-cyano-2-methylideneethyl)amino]-7-methoxynaphthalen-2-yl}-3-fluoro-N-(1-methylpiperidin-4-yl)pyridine-2-carboxamide | 474.2 |
| 124 | 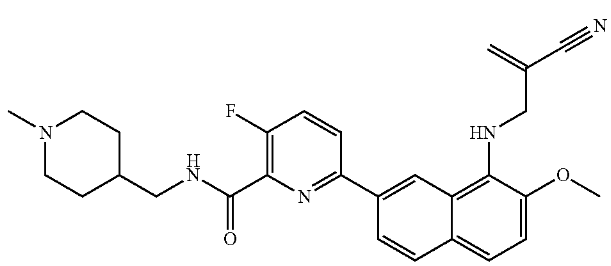 | 6-{8-[(2-cyano-2-methylideneethyl)amino]-7-methoxynaphthalen-2-yl}-3-fluoro-N-[(1-methylpiperidin-4-yl)methyl]pyridine-2-carboxamide | 488.3 |
| 125 | 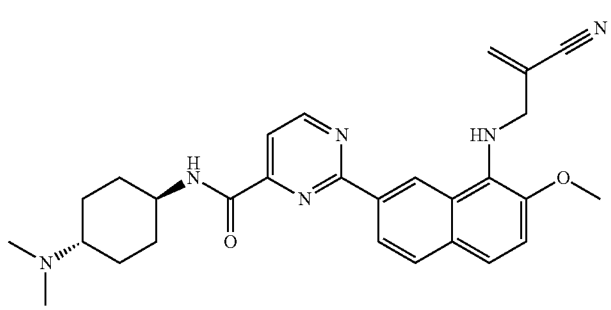 | 2-{8-[(2-cyano-2-methylideneethyl)amino]-7-methoxynaphthalen-2-yl}-N-[(1r,4r)-4-(dimethylamino)cyclohexyl]pyrimidine-4-carboxamide | 485.3 |

TABLE 2-continued

| Cmp. No. | Structure | IUPAC | LC-MS (ES+, m/z) |
|---|---|---|---|
| 126 | 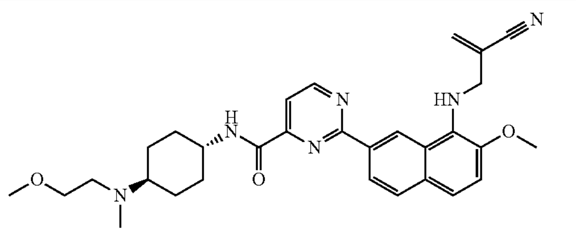 | 2-{8-[(2-cyano-2-methylideneethyl)amino]-7-methoxynaphthalen-2-yl}-N-[(1r,4r)-4-[(2-methoxyethyl)(methyl)amino]cyclohexyl]pyrimidine-4-carboxamide | 529.3 |
| 127 | 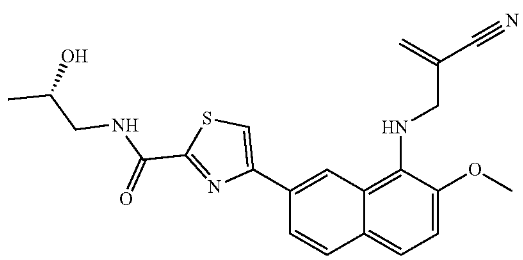 [SMILES: C=C(C#N)CNc1c(OC)ccc2ccc(-c3csc(C(=O)NC[C@H](C)O)n3)cc12] | 4-{8-[(2-cyano-2-methylideneethyl)amino]-7-methoxynaphthalen-2-yl}-N-[(2S)-2-hydroxypropyl]-1,3-thiazole-2-carboxamide | 423.1 |
| 128 | 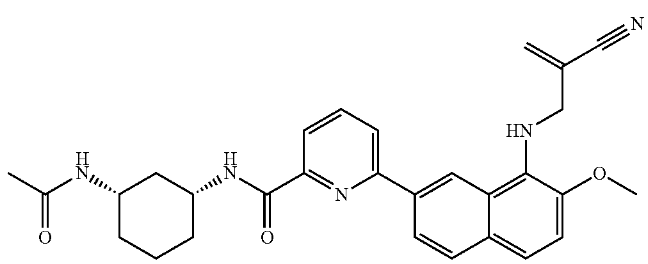 [SMILES: C=C(C#N)CNc1c(OC)ccc2ccc(-c3cccc(C(=O)N[C@@H]4CCC[C@H](NC(C)=O)C4)n3)cc12] | 6-{8-[(2-cyano-2-methylideneethyl)amino]-7-methoxynaphthalen-2-yl}-N-[(1R,3S)-3-acetamidocyclohexyl]pyridine-2-carboxamide | 498.2 |
| 129 | 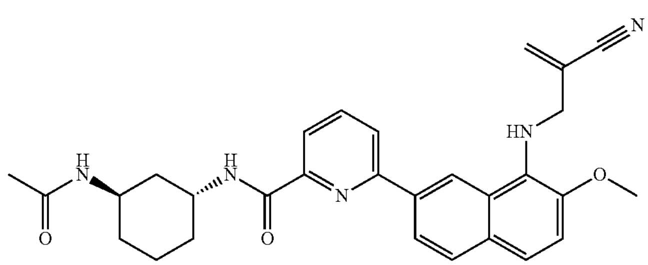 [SMILES: C=C(C#N)CNc1c(OC)ccc2ccc(-c3cccc(C(=O)N[C@@H]4CCC[C@@H](NC(C)=O)C4)n3)cc12] | 6-{8-[(2-cyano-2-methylideneethyl)amino]-7-methoxynaphthalen-2-yl}-N-[(1R,3R)-3-acetamidocyclohexyl]pyridine-2-carboxamide | 498.2 |
| 130 | 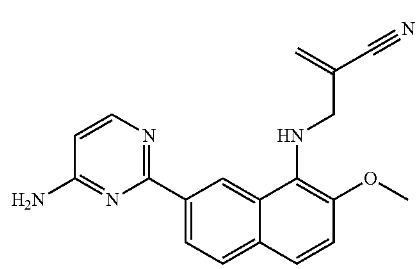 [SMILES: C=C(C#N)CNc1c(OC)ccc2ccc(-c3nccc(N)n3)cc12] | 2-({[7-(4-aminopyrimidin-2-yl)-2-methoxynaphthalen-1-yl]amino}methyl)prop-2-enenitrile | 332.1 |

TABLE 2-continued


| Cmp. No. | Structure | IUPAC | LC-MS (ES+, m/z) |
|---|---|---|---|
| 131 | 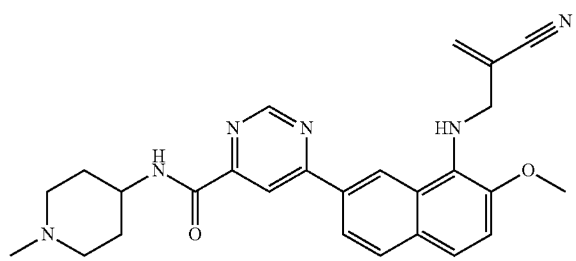 | 6-{8-[(2-cyano-2-methylideneethyl)amino]-7-methoxynaphthalen-2-yl}-N-(1-methylpiperidin-4-yl)pyrimidine-4-carboxamide | 457.2 |
| 132 | 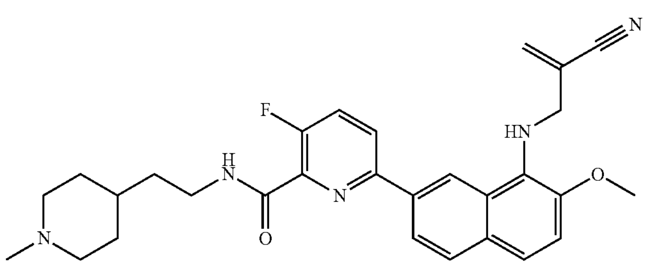 | 6-{8-[(2-cyano-2-methylideneethyl)amino]-7-methoxynaphthalen-2-yl}-3-fluoro-N-[2-(1-methylpiperidin-4-yl)ethyl]pyridine-2-carboxamide | 502.3 |
| 133 | 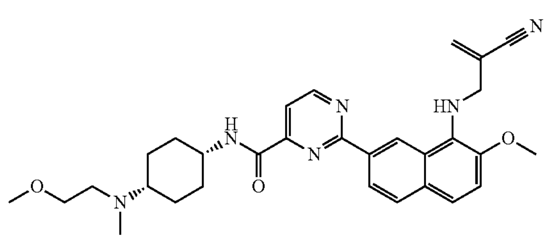 | 2-{8-[(2-cyano-2-methylideneethyl)amino]-7-methoxynaphthalen-2-yl}-N-[(1s,4s)-4-[(2-methoxyethyl)(methyl)amino]cyclohexyl]pyrimidine-4-carboxamide | 529.3 |
| 134 | 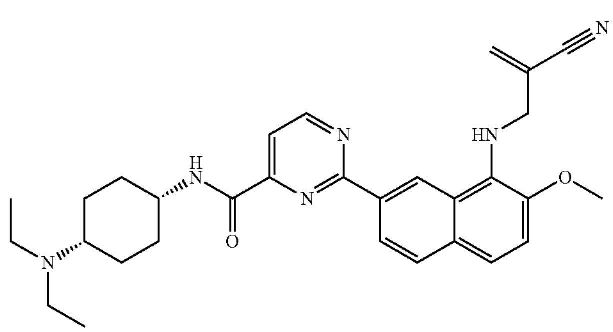 [SMILES: C=C(C#N)CNc1c(OC)ccc2ccc(-c3nccc(C(=O)N[C@H]4CC[C@@H](N(CC)CC)CC4)n3)cc12] | 2-{8-[(2-cyano-2-methylideneethyl)amino]-7-methoxynaphthalen-2-yl}-N-[(1s,4s)-4-(diethylamino)cyclohexyl]pyrimidine-4-carboxamide | 513.3 |

TABLE 2-continued

| Cmp. No. | Structure | IUPAC | LC-MS (ES+, m/z) |
|---|---|---|---|
| 135 | 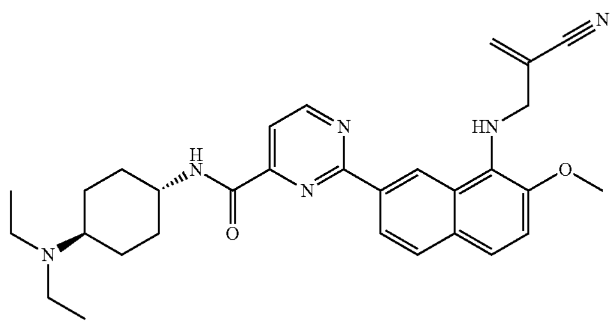 [SMILES: C=C(C#N)CNc1c(OC)ccc2ccc(-c3nccc(C(=O)N[C@H]4CC[C@H](N(CC)CC)CC4)n3)cc12] | 2-{8-[(2-cyano-2-methylideneethyl)amino]-7-methoxynaphthalen-2-yl}-N-[(1r,4r)-4-(diethylamino)cyclohexyl]pyrimidine-4-carboxamide | 513.3 |
| 136 | 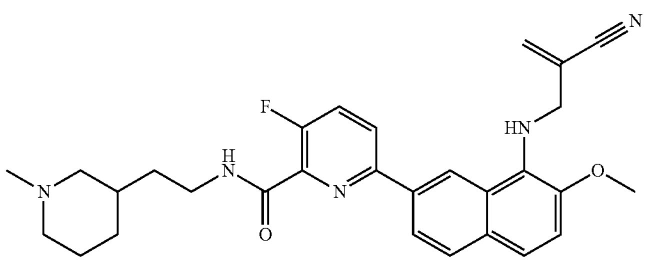 | 6-{8-[(2-cyano-2-methylideneethyl)amino]-7-methoxynaphthalen-2-yl}-3-fluoro-N-[2-(1-methylpiperidin-3-yl)ethyl]pyridine-2-carboxamide | 502.3 |
| 137 | 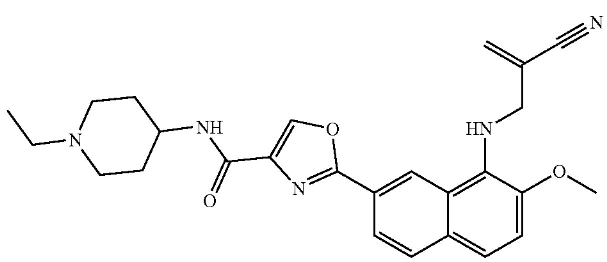 [SMILES: C=C(C#N)CNc1c(OC)ccc2ccc(-c3nc(C(=O)NC4CCN(CC)CC4)co3)cc12] | 2-{8-[(2-cyano-2-methylideneethyl)amino]-7-methoxynaphthalen-2-yl}-N-(1-ethylpiperidin-4-yl)-1,3-oxazole-4-carboxamide | 460.2 |
| 138 | 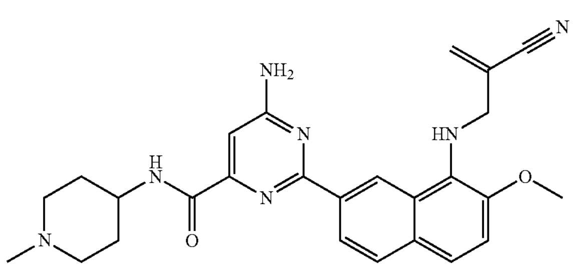 | 6-amino-2-{8-[(2-cyano-2-methylideneethyl)amino]-7-methoxynaphthalen-2-yl}-N-(1-methylpiperidin-4-yl)pyrimidine-4-carboxamide | 472.3 |

TABLE 2-continued

| Cmp. No. | Structure | IUPAC | LC-MS (ES+, m/z) |
|---|---|---|---|
| 139 | 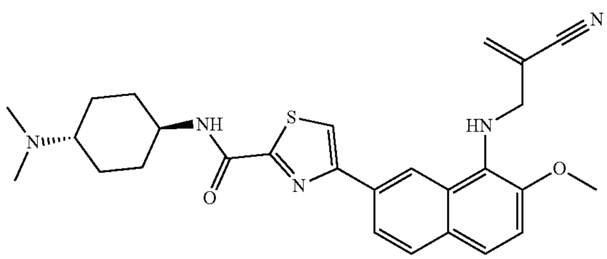 | 4-{8-[(2-cyano-2-methylideneethyl)amino]-7-methoxynaphthalen-2-yl}-N-[(1r,4r)-4-(dimethylamino)cyclohexyl]-1,3-thiazole-2-carboxamide | 490.3 |
| 140 | 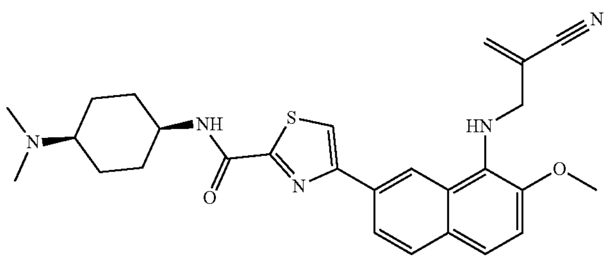 | 4-{8-[(2-cyano-2-methylideneethyl)amino]-7-methoxynaphthalen-2-yl}-N-[(1s,4s)-4-(dimethylamino)cyclohexyl]-1,3-thiazole-2-carboxamide | 490.2 |
| 141 | 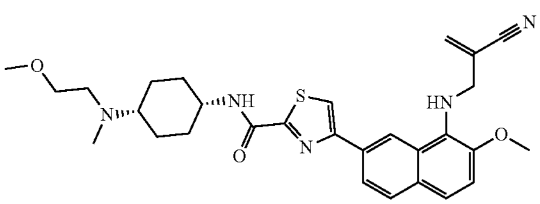 | 4-{8-[(2-cyano-2-methylideneethyl)amino]-7-methoxynaphthalen-2-yl}-N-[(1s,4s)-4-[(2-methoxyethyl)(methyl)amino]cyclohexyl]-1,3-thiazole-2-carboxamide | 534.3 |
| 142 | 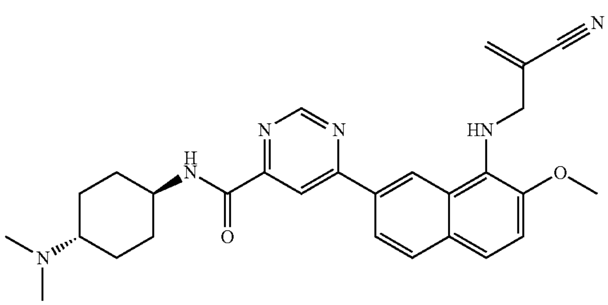 | 6-{8-[(2-cyano-2-methylideneethyl)amino]-7-methoxynaphthalen-2-yl}-N-[(1r,4r)-4-(dimethylamino)cyclohexyl]pyrimidine-4-carboxamide | 485.3 |
| 143 | 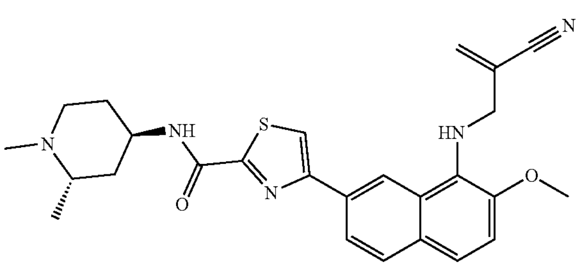 | 4-{8-[(2-cyano-2-methylideneethyl)amino]-7-methoxynaphthalen-2-yl}-N-[(2S,4R)-1,2-dimethylpiperidin-4-yl]-1,3-thiazole-2-carboxamide | 476.2 |

TABLE 2-continued

| Cmp. No. | Structure | IUPAC | LC-MS (ES+, m/z) |
|---|---|---|---|
| 144 | 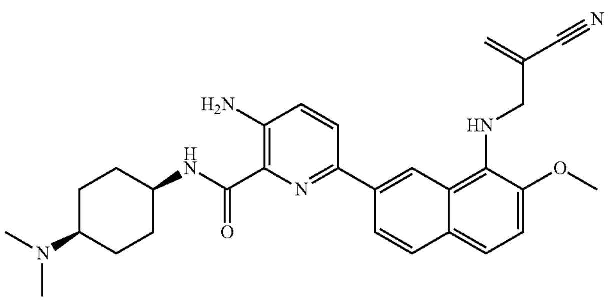 | 3-amino-6-{8-[(2-cyano-2-methylideneethyl)amino]-7-methoxynaphthalen-2-yl}-N-[(1s,4s)-4-(dimethylamino)cyclohexyl]pyridine-2-carboxamide | 499.3 |
| 145 | 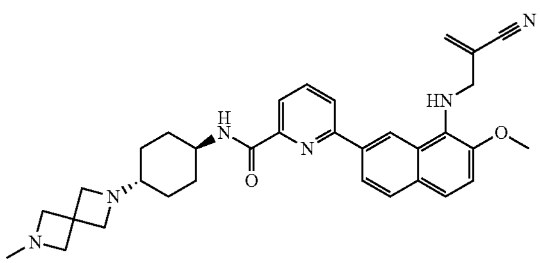 | 6-{8-[(2-cyano-2-methylideneethyl)amino]-7-methoxynaphthalen-2-yl}-N-[(1r,4r)-4-{6-methyl-2,6-diazaspiro[3.3]heptan-2-yl}cyclohexyl]pyridine-2-carboxamide | 551.3 |
| 146 | 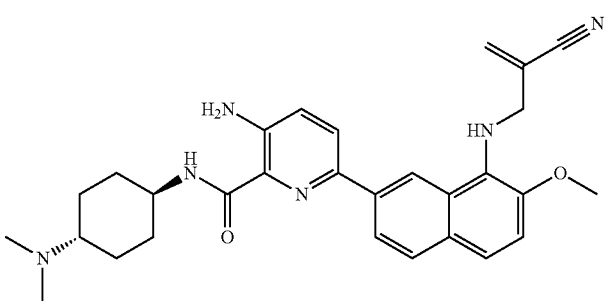 | 3-amino-6-{8-[(2-cyano-2-methylideneethyl)amino]-7-methoxynaphthalen-2-yl}-N-[(1r,4r)-4-(dimethylamino)cyclohexyl]pyridine-2-carboxamide | 499.3 |
| 147 | 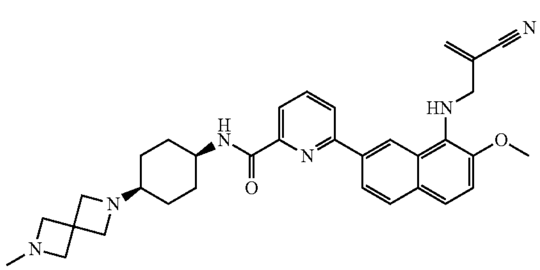 | 6-{8-[(2-cyano-2-methylideneethyl)amino]-7-methoxynaphthalen-2-yl}-N-[(1s,4s)-4-{6-methyl-2,6-diazaspiro[3.3]heptan-2-yl}cyclohexyl]pyridine-2-carboxamide | 551.3 |

TABLE 2-continued

| Cmp. No. | Structure | IUPAC | LC-MS (ES+, m/z) |
|---|---|---|---|
| 148 | 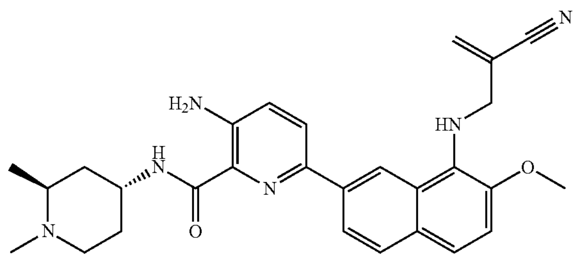 | 3-amino-6-{8-[(2-cyano-2-methylideneethyl)amino]-7-methoxynaphthal-en-2-yl}-N-[(2S,4R)-1,2-dimethylpiperidin-4-yl]pyridine-2-carboxamide | 485.3 |
| 149 | 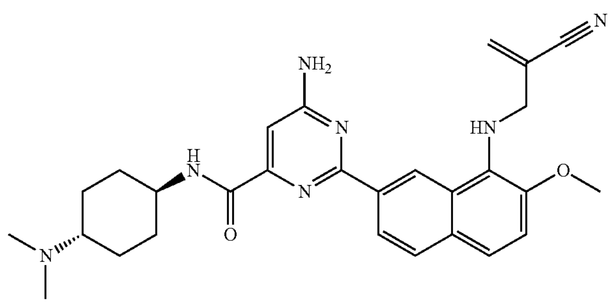 | 6-amino-2-{8-[(2-cyano-2-methylideneethyl)amino]-7-methoxynaphthalen-2-yl}-N-[(1r,4r)-4-(dimethylamino)cyclohexyl]pyrimidine-4-carboxamide | 500.3 |
| 150 | 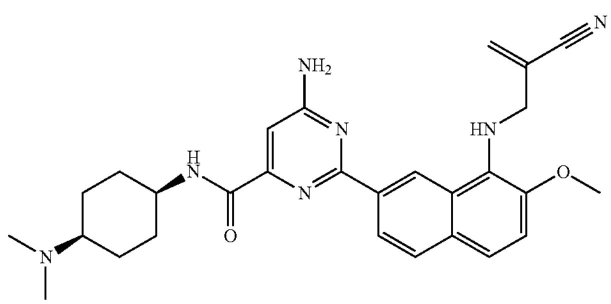 | 6-amino-2-{8-[(2-cyano-2-methylideneethyl)amino]-7-methoxynaphthalen-2-yl}-N-[(1s,4s)-4-(dimethylamino)cyclohexyl]pyrimidine-4-carboxamide | 500.3 |
| 151 | 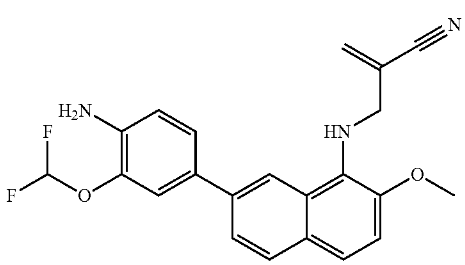 [SMILES: C=C(C#N)CNc1c(OC)ccc2ccc(-c3ccc(N)c(OC(F)F)c3)cc12] | 2-[({7-[4-amino-3-(difluoromethoxy)phenyl]-2-methoxynaphthalen-1-yl}amino)methyl]prop-2-enenitrile | 396.2 |

TABLE 2-continued

| Cmp. No. | Structure | IUPAC | LC-MS (ES+, m/z) |
|---|---|---|---|
| 152 | 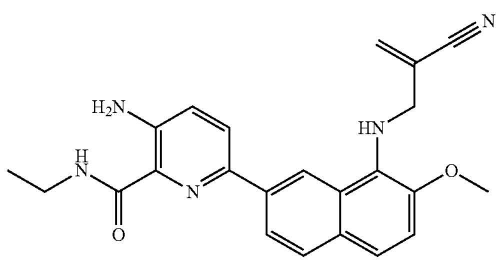 [SMILES: C=C(C#N)CNc1c(OC)ccc2ccc(-c3ccc(N)c(C(=O)NCC)n3)cc12] | 3-amino-6-{8-[(2-cyano-2-methylideneethyl)amino]-7-methoxynaphthalen-2-yl}-N-ethylpyridine-2-carboxamide | 402.2 |
| 153 | 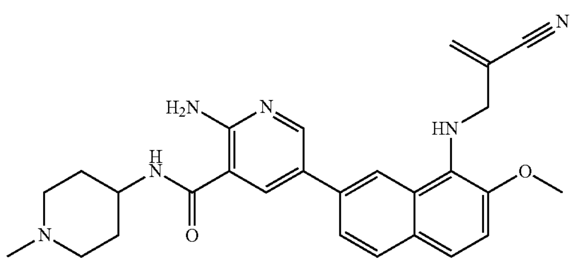 | 2-amino-5-{8-[(2-cyano-2-methylideneethyl)amino]-7-methoxynaphthalen-2-yl}-N-(1-methylpiperidin-4-yl)pyridine-3-carboxamide | 471.2 |
| 154 | 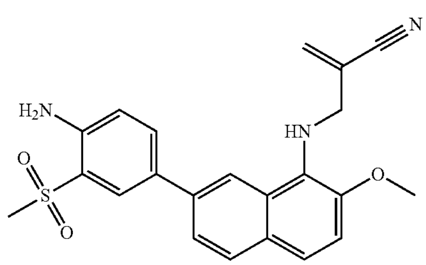 | 2-({[7-(4-amino-3-methanesulfonylphenyl)-2-methoxynaphthalen-1-yl]amino}methyl)prop-2-enenitrile | 408.1 |
| 155 | 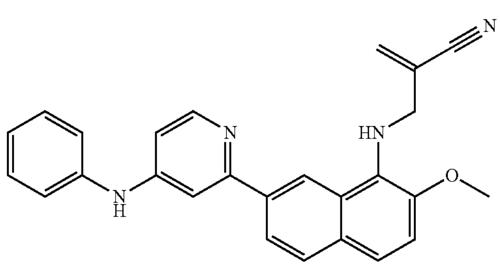 [SMILES: C=C(C#N)CNc1c(OC)ccc2ccc(-c3cc(Nc4ccccc4)ccn3)cc12] | 2-[({2-methoxy-7-[4-(phenylamino)pyridin-2-yl]naphthalen-1-yl}amino)methyl]prop-2-enenitrile | 407.1 |

TABLE 2-continued

| Cmp. No. | Structure | IUPAC | LC-MS (ES+, m/z) |
|---|---|---|---|
| 156 | 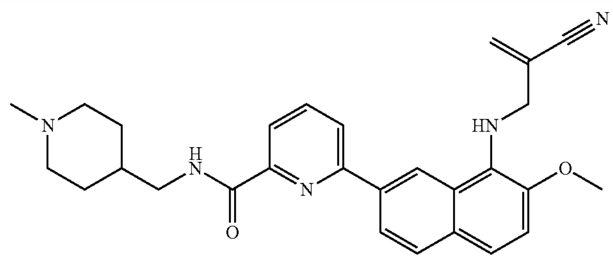 | 6-{8-[(2-cyano-2-methylideneethyl)amino]-7-methoxynaphthalen-2-yl}-N-[(1-methylpiperidin-4-yl)methyl]pyridine-2-carboxamide | 470.2 |
| 157 | 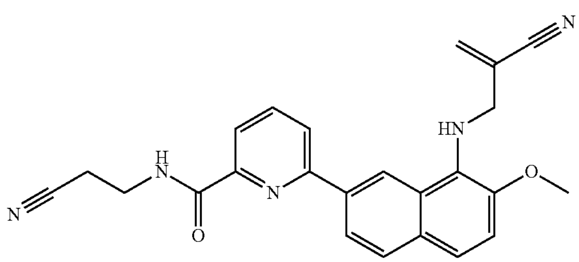 [SMILES: C=C(C#N)CNc1c(OC)ccc2ccc(-c3cccc(C(=O)NCCC#N)n3)cc12] | 6-{8-[(2-cyano-2-methylideneethyl)amino]-7-methoxynaphthalen-2-yl}-N-(2-cyanoethyl)pyridine-2-carboxamide | 412.1 |
| 158 | 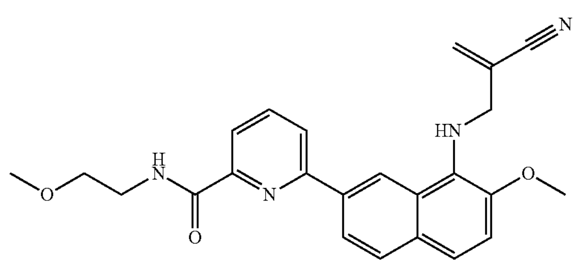 | 6-{8-[(2-cyano-2-methylideneethyl)amino]-7-methoxynaphthalen-2-yl}-N-(2-methoxyethyl)pyridine-2-carboxamide | 417.1 |
| 159 | 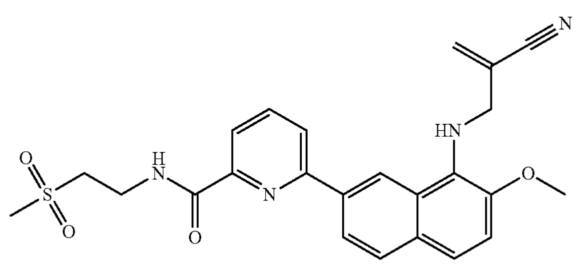 | 6-{8-[(2-cyano-2-methylideneethyl)amino]-7-methoxynaphthalen-2-yl}-N-(2-methanesulfonylethyl)pyridine-2-carboxamide | 465.1 |
| 160 | 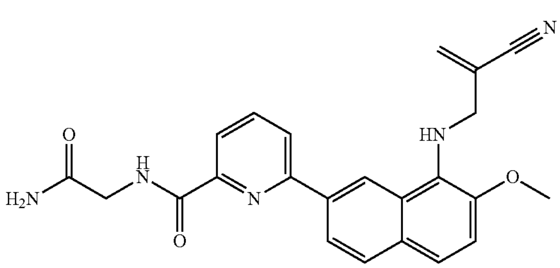 [SMILES: C=C(C#N)CNc1c(OC)ccc2ccc(-c3cccc(C(=O)NCC(N)=O)n3)cc12] | 2-[(6-{8-[(2-cyano-2-methylideneethyl)amino]-7-methoxynaphthalen-2-yl}pyridin-2-yl)formamido]acetamide | 416.2 |

TABLE 2-continued

| Cmp. No. | Structure | IUPAC | LC-MS (ES+, m/z) |
|---|---|---|---|
| 161 | 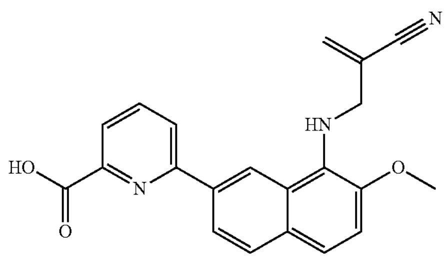 [SMILES: C=C(C#N)CNc1c(OC)ccc2ccc(-c3cccc(C(=O)O)n3)cc12] | 6-{8-[(2-cyano-2-methylideneethyl)amino]-7-methoxynaphthalen-2-yl}pyridine-2-carboxylic acid | 360 |
| 162 | 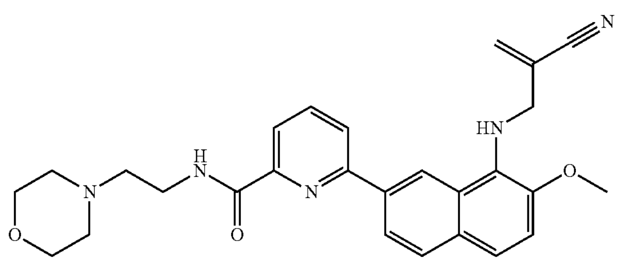 | 6-{8-[(2-cyano-2-methylideneethyl)amino]-7-methoxynaphthalen-2-yl}-N-[2-(morpholin-4-yl)ethyl]pyridine-2-carboxamide | 472.1 |
| 163 | 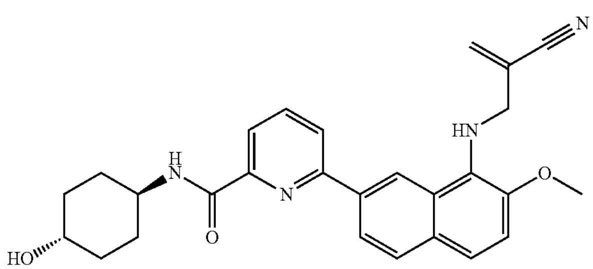 [SMILES: C=C(C#N)CNc1c(OC)ccc2ccc(-c3cccc(C(=O)N[C@H]4CC[C@H](O)CC4)n3)cc12] | 6-{8-[(2-cyano-2-methylideneethyl)amino]-7-methoxynaphthalen-2-yl}-N-[(1r,4r)-4-hydroxycyclohexyl]pyridine-2-carboxamide | 457.1 |
| 164 | 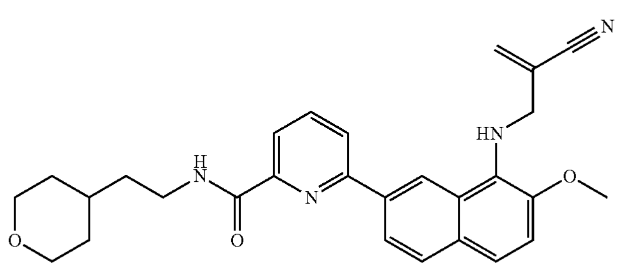 [SMILES: C=C(C#N)CNc1c(OC)ccc2ccc(-c3cccc(C(=O)NCCC4CCOCC4)n3)cc12] | 6-{8-[(2-cyano-2-methylideneethyl)amino]-7-methoxynaphthalen-2-yl}-N-[2-(oxan-4-yl)ethyl]pyridine-2-carboxamide | 471.1 |

TABLE 2-continued

| Cmp. No. | Structure | IUPAC | LC-MS (ES+, m/z) |
|---|---|---|---|
| 165 | 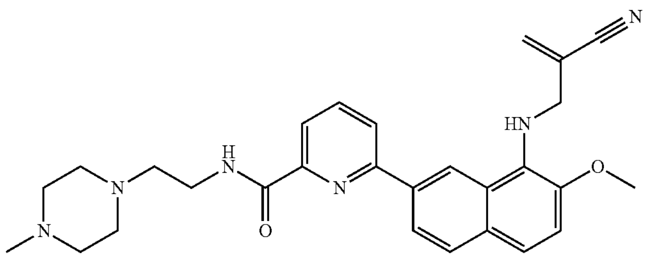 [SMILES: C=C(C#N)CNc1c(OC)ccc2ccc(-c3cccc(C(=O)NCCN4CCN(C)CC4)n3)cc12] | 6-{8-[(2-cyano-2-methylideneethyl)amino]-7-methoxynaphthalen-2-yl}-N-[2-(4-methylpiperazin-1-yl)ethyl]pyridine-2-carboxamide | 485.1 |
| 166 | 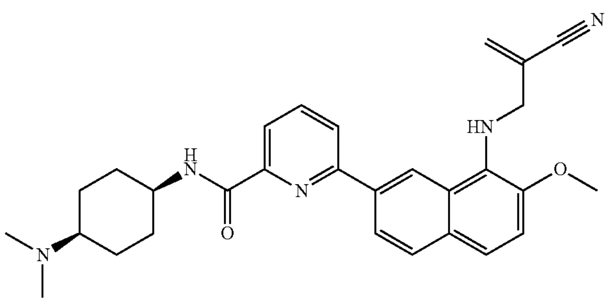 | 6-{8-[(2-cyano-2-methylideneethyl)amino]-7-methoxynaphthalen-2-yl}-N-[(1s,4s)-4-(dimethylamino)cyclohexyl]pyridine-2-carboxamide | 484.2 |
| 167 | 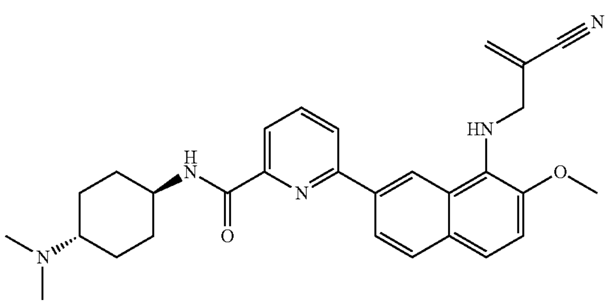 | 6-{8-[(2-cyano-2-methylideneethyl)amino]-7-methoxynaphthalen-2-yl}-N-[(1r,4r)-4-(dimethylamino)cyclohexyl]pyridine-2-carboxamide | 484.1 |
| 168 | 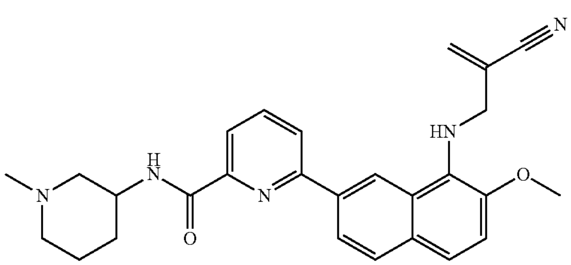 | 6-{8-[(2-cyano-2-methylideneethyl)amino]-7-methoxynaphthalen-2-yl}-N-(1-methylpiperidin-3-yl)pyridine-2-carboxamide | 456.1 |

TABLE 2-continued

| Cmp. No. | Structure | IUPAC | LC-MS (ES+, m/z) |
|---|---|---|---|
| 169 | 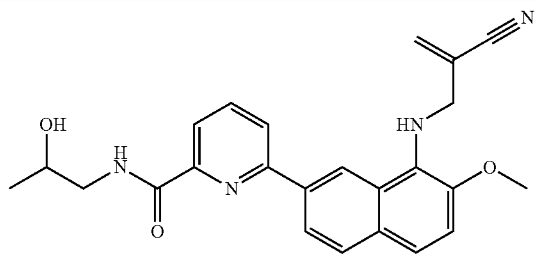 [SMILES: C=C(C#N)CNc1c(OC)ccc2ccc(-c3cccc(C(=O)NCC(C)O)n3)cc12] | 6-{8-[(2-cyano-2-methylideneethyl)amino]-7-methoxynaphthalen-2-yl}-N-(2-hydroxypropyl)pyridine-2-carboxamide | 417.1 |
| 170 | 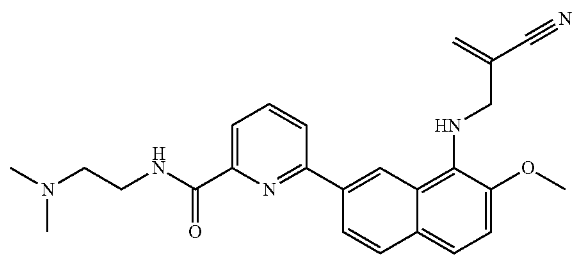 | 6-{8-[(2-cyano-2-methylideneethyl)amino]-7-methoxynaphthalen-2-yl}-N-[2-(dimethylamino)ethyl]pyridine-2-carboxamide | 430.1 |
| 171 | 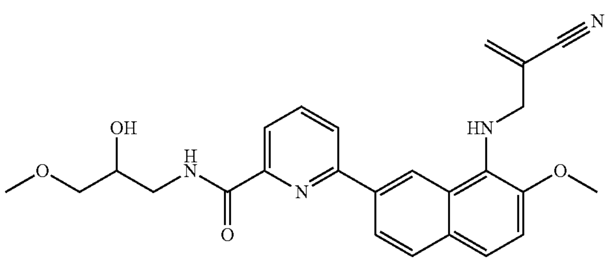 | 6-{8-[(2-cyano-2-methylideneethyl)amino]-7-methoxynaphthalen-2-yl}-N-(2-hydroxy-3-172methoxypropyl)pyridine-2-carboxamide | 447.1 |
| 172 | 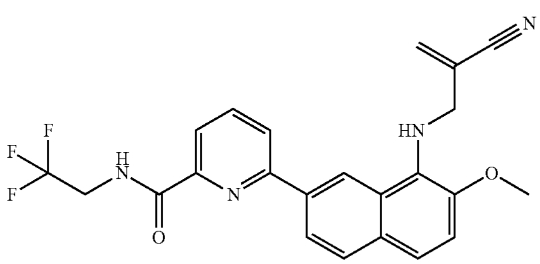 [SMILES: C=C(C#N)CNc1c(OC)ccc2ccc(-c3cccc(C(=O)NCC(F)(F)F)n3)cc12] | 6-{8-[(2-cyano-2-methylideneethyl)amino]-7-methoxynaphthalen-2-yl}-N-(2,2,2-trifluoro ethyl)pyridine-2-carboxamide | 441 |
| 173 | 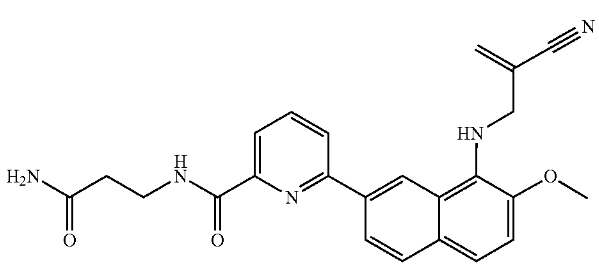 [SMILES: C=C(C#N)CNc1c(OC)ccc2ccc(-c3cccc(C(=O)NCCC(N)=O)n3)cc12] | 3-[(6-{8-[(2-cyano-2-methylideneethyl)amino]-7-methoxynaphthalen-2-yl}pyridin-2-yl)formamido]propanamide | 430.1 |

TABLE 2-continued

| Cmp. No. | Structure | IUPAC | LC-MS (ES+, m/z) |
|---|---|---|---|
| 174 | 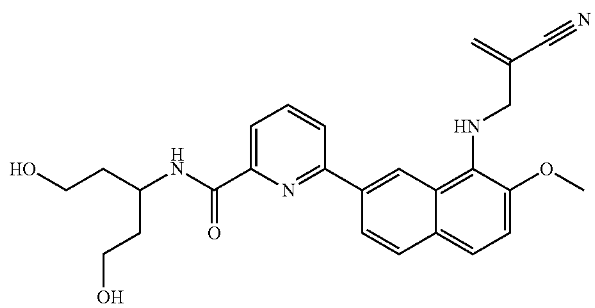 [SMILES: C=C(C#N)CNc1c(OC)ccc2ccc(-c3cccc(C(=O)NC(CCO)CCO)n3)cc12] | 6-{8-[(2-cyano-2-methylideneethyl)amino]-7-methoxynaphthalen-2-yl}-N-(1,5-dihydroxypentan-3-yl)pyridine-2-carboxamide | 461.1 |
| 175 | 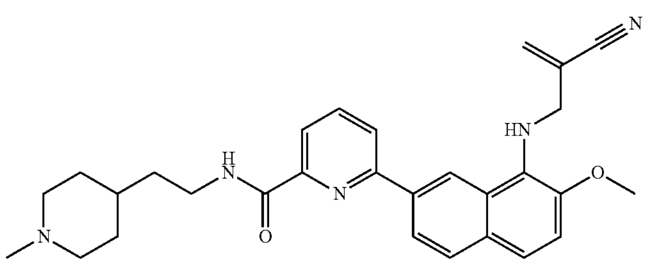 | 6-{8-[(2-cyano-2-methylideneethyl)amino]-7-methoxynaphthalen-2-yl}-N-[2-(1-methylpiperidin-4-yl)ethyl]pyridine-2-carboxamide | 484.1 |
| 176 | 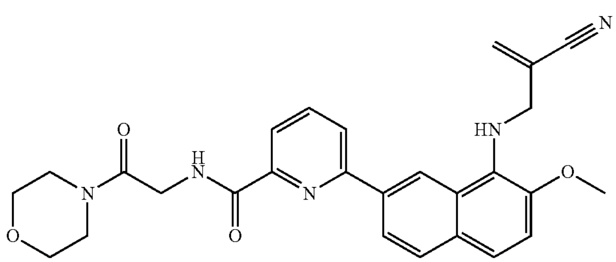 [SMILES: C=C(C#N)CNc1c(OC)ccc2ccc(-c3cccc(C(=O)NCC(=O)N4CCOCC4)n3)cc12] | 6-{8-[(2-cyano-2-methylideneethyl)amino]-7-methoxynaphthalen-2-yl}-N-[2-(morpholin-4-yl)-2-oxoethyl]pyridine-2-carboxamide | 486.1 |
| 177 | 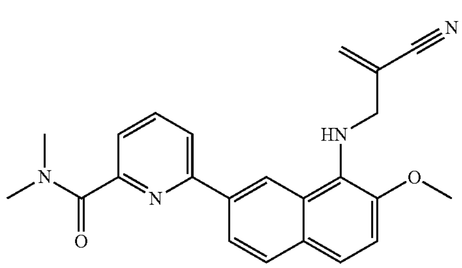 | 6-{8-[(2-cyano-2-methylideneethyl)amino]-7-methoxynaphthalen-2-yl}-N,N-dimethylpyridine-2-carboxamide | 387.1 |

TABLE 2-continued

| Cmp. No. | Structure | IUPAC | LC-MS (ES+, m/z) |
|---|---|---|---|
| 178 | 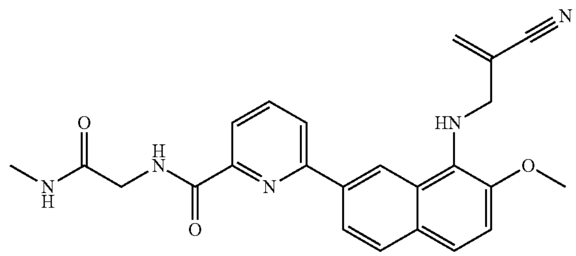 | 2-[(6-{8-[(2-cyano-2-methylideneethyl)amino]-7-methoxynaphthalen-2-yl}pyridin-2-yl)formamido]-N-methylacetamide | 430.1 |
| 179 | 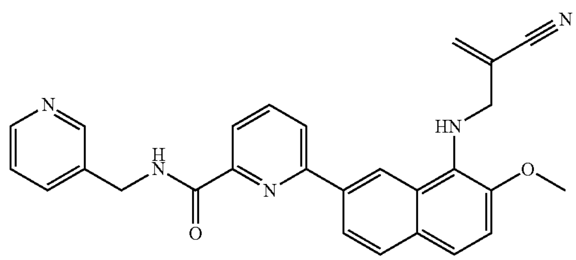 [SMILES: C=C(C#N)CNc1c(OC)ccc2ccc(-c3cccc(C(=O)NCc4cccnc4)n3)cc12] | 6-{8-[(2-cyano-2-methylideneethyl)amino]-7-methoxynaphthalen-2-yl}-N-[(pyridin-3-yl)methyl]pyridine-2-carboxamide | 450 |
| 180 | 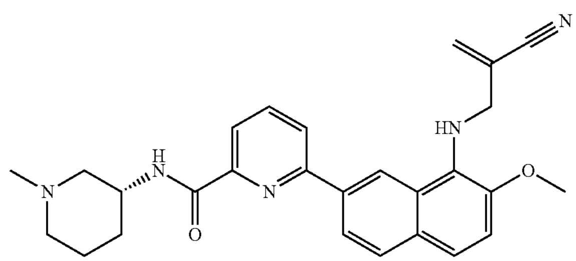 | 6-{8-[(2-cyano-2-methylideneethyl)amino]-7-methoxynaphthalen-2-yl}-N-[(3R)-1-methylpiperidin-3-yl]pyridine-2-carboxamide | 456.1 |
| 181 | 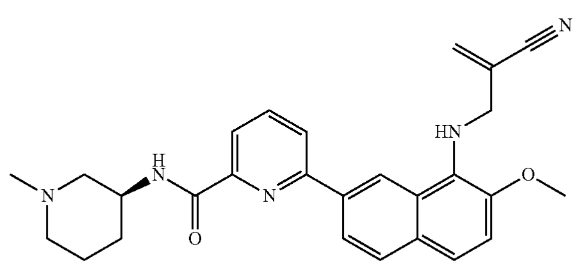 | 6-{8-[(2-cyano-2-methylideneethyl)amino]-7-methoxynaphthalen-2-yl}-N-[(3S)-1-methylpiperidin-3-yl]pyridine-2-carboxamide | 456.1 |

TABLE 2-continued

| Cmp. No. | Structure | IUPAC | LC-MS (ES+, m/z) |
|---|---|---|---|
| 182 | 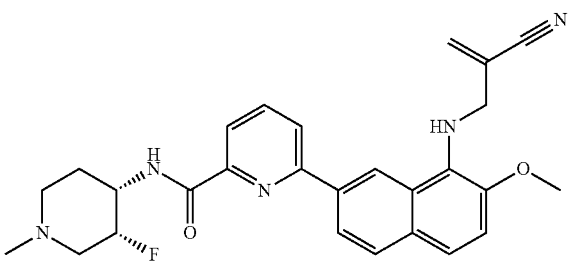 | 6-{8-[(2-cyano-2-methylideneethyl)amino]-7-methoxynaphthalen-2-yl}-N-[(3R,4S)-3-fluoro-1-methylpiperidin-4-yl]pyridine-2-carboxamide | 474.1 |
| 183 | 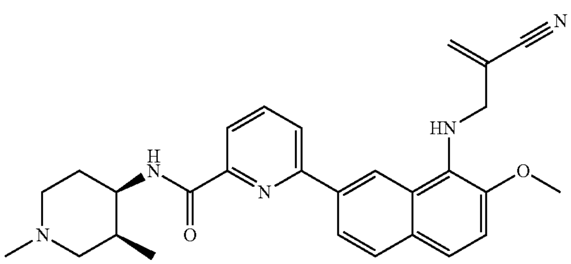 | 6-{8-[(2-cyano-2-methylideneethyl)amino]-7-methoxynaphthalen-2-yl}-N-[(3S,4R)-1,3-dimethylpiperidin-4-yl]pyridine-2-carboxamide | 470.1 |
| 184 | 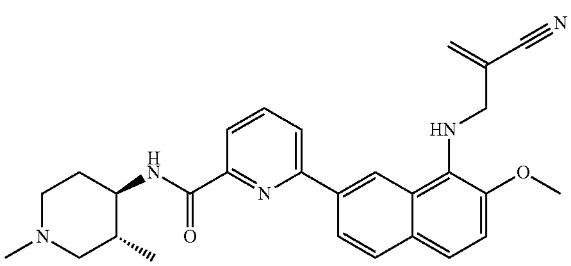 | 6-{8-[(2-cyano-2-methylideneethyl)amino]-7-methoxynaphthalen-2-yl}-N-[(3R,4R)-1,3-dimethylpiperidin-4-yl]pyridine-2-carboxamide | 470.1 |
| 185 | 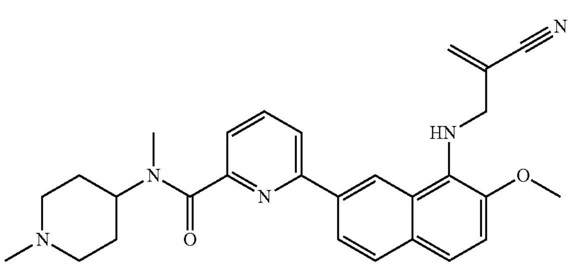 | 6-{8-[(2-cyano-2-methylideneethyl)amino]-7-methoxynaphthalen-2-yl}-N-methyl-N-(1-methylpiperidin-4-yl)pyridine-2-carboxamide | 470.1 |

TABLE 2-continued

| Cmp. No. | Structure | IUPAC | LC-MS (ES+, m/z) |
|---|---|---|---|
| 186 | 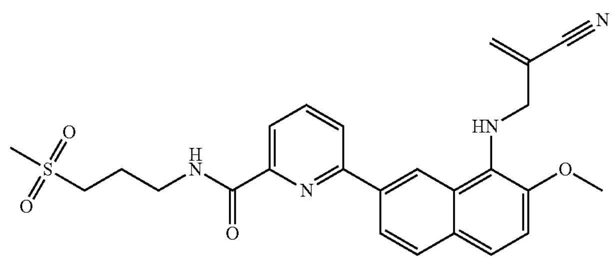 | 6-{8-[(2-cyano-2-methylideneethyl)amino]-7-methoxynaphthalen-2-yl}-N-(3-methanesulfonylpropyl)pyridine-2-carboxamide | 479 |
| 187 | 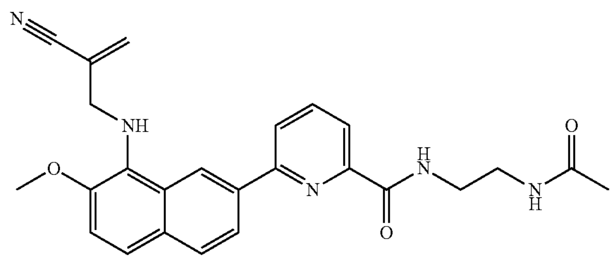 [SMILES: C=C(C#N)CNc1c(OC)ccc2ccc(-c3cccc(C(=O)NCCNC(C)=O)n3)cc12] | N-{2-[(6-{8-[(2-cyano-2-methylideneethyl)amino]-7-methoxynaphthalen-2-yl}pyridin-2-yl)formamido]ethyl}acetamide | 444.2 |
| 188 | 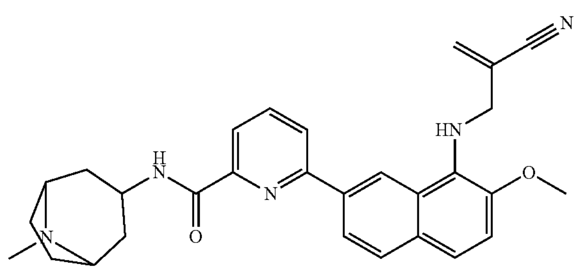 | 6-{8-[(2-cyano-2-methylideneethyl)amino]-7-methoxynaphthalen-2-yl}-N-{8-methyl-8-azabicyclo[3.2.1]octan-3-yl}pyridine-2-carboxamide | 482.3 |
| 189 | 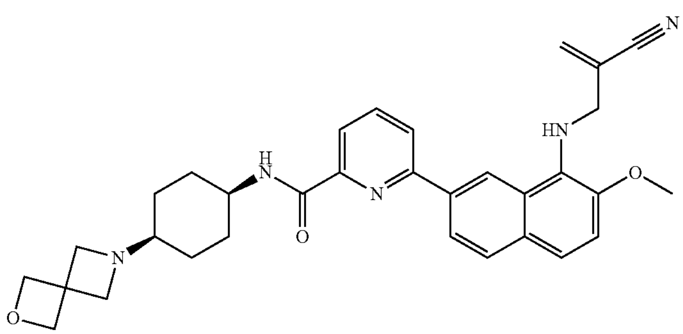 [SMILES: C=C(C#N)CNc1c(OC)ccc2ccc(-c3cccc(C(=O)N[C@H]4CC[C@@H](N5CC6(COC6)C5)CC4)n3)cc12] | 6-{8-[(2-cyano-2-methylideneethyl)amino]-7-methoxynaphthalen-2-yl}-N-[(1s,4s)-4-{2-oxa-6-azaspiro[3.3]heptan-6-yl}cyclohexyl]pyridine-2-carboxamide | 538.3 |

TABLE 2-continued

| Cmp. No. | Structure | IUPAC | LC-MS (ES+, m/z) |
|---|---|---|---|
| 190 | 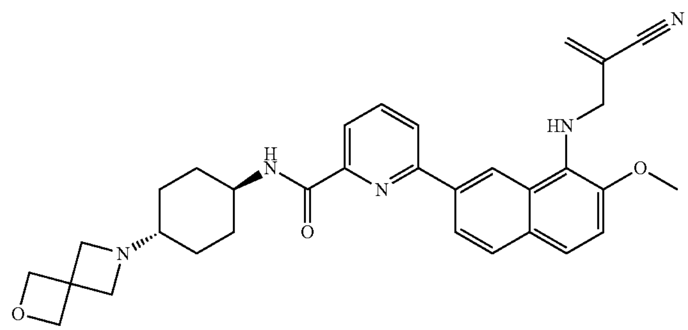 [SMILES: C=C(C#N)CNc1c(OC)ccc2ccc(-c3cccc(C(=O)N[C@H]4CC[C@H](N5CC6(COC6)C5)CC4)n3)cc12] | 6-{8-[(2-cyano-2-methylideneethyl)amino]-7-methoxynaphthalen-2-yl}-N-[(1r,4r)-4-{2-oxa-6-azaspiro[3.3]heptan-6-yl}cyclohexyl]pyridine-2-carboxamide | 538.3 |
| 191 | 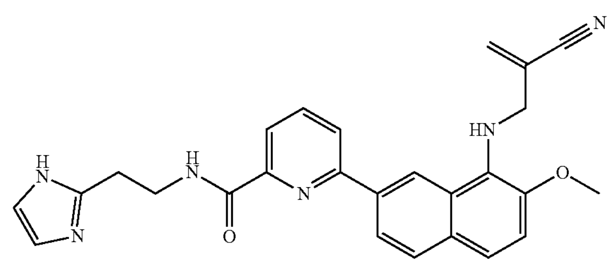 [SMILES: C=C(C#N)CNc1c(OC)ccc2ccc(-c3cccc(C(=O)NCCc4ncc[nH]4)n3)cc12] | 6-{8-[(2-cyano-2-methylideneethyl)amino]-7-methoxynaphthalen-2-yl}-N-[2-(1H-imidazol-2-yl)ethyl]pyridine-2-carboxamide | 453.2 |
| 192 | 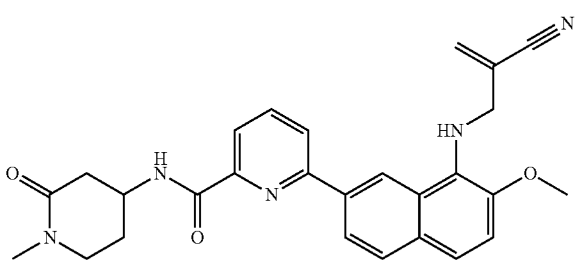 [SMILES: C=C(C#N)CNc1c(OC)ccc2ccc(-c3cccc(C(=O)NC4CCN(C)C(=O)C4)n3)cc12] | 6-{8-[(2-cyano-2-methylideneethyl)amino]-7-methoxynaphthalen-2-yl}-N-(1-methyl-2-oxopiperidin-4-yl)pyridine-2-carboxamide | 470.2 |
| 193 | 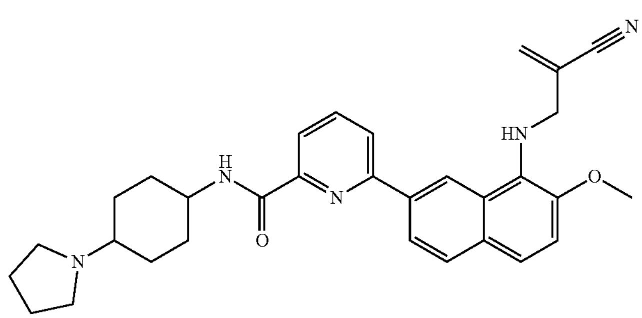 [SMILES: C=C(C#N)CNc1c(OC)ccc2ccc(-c3cccc(C(=O)NC4CCC(N5CCCC5)CC4)n3)cc12] | 6-{8-[(2-cyano-2-methylideneethyl)amino]-7-methoxynaphthalen-2-yl}-N-[4-(pyrrolidin-1-yl)cyclohexyl]pyridine-2-carboxamide | 510.3 |

TABLE 2-continued

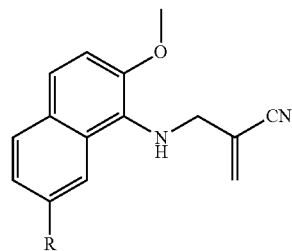

| Cmp. No. | Structure | IUPAC | LC-MS (ES+, m/z) |
|---|---|---|---|
| 194 | 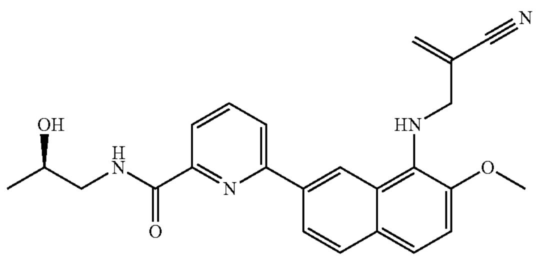 [SMILES: C=C(C#N)CNc1c(OC)ccc2ccc(-c3cccc(C(=O)NC[C@@H](C)O)n3)cc12] | 6-{8-[(2-cyano-2-methylideneethyl)amino]-7-methoxynaphthalen-2-yl}-N-[(2R)-2-hydroxypropyl]pyridine-2-carboxamide | 417.2 |
| 195 | 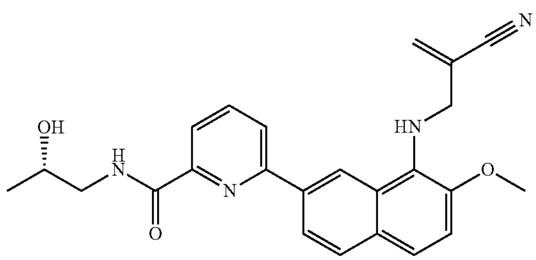 [SMILES: C=C(C#N)CNc1c(OC)ccc2ccc(-c3cccc(C(=O)NC[C@H](C)O)n3)cc12] | 6-{8-[(2-cyano-2-methylideneethyl)amino]-7-methoxynaphthalen-2-yl}-N-[(2S)-2-hydroxypropyl]pyridine-2-carboxamide | 417.1 |
| 196 | 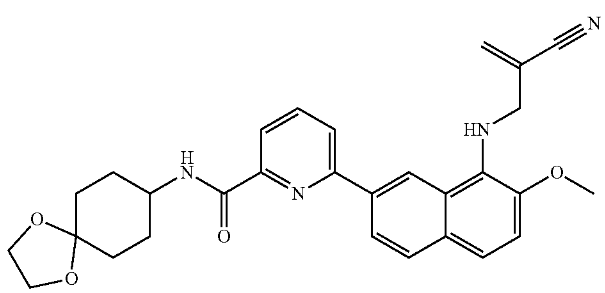 [SMILES: C=C(C#N)CNc1c(OC)ccc2ccc(-c3cccc(C(=O)NC4CCC5(CC4)OCCO5)n3)cc12] | 6-{8-[(2-cyano-2-methylideneethyl)amino]-7-methoxynaphthalen-2-yl}-N-{1,4-dioxaspiro[4.5]decan-8-yl}pyridine-2-carboxamide | 499.2 |
| 197 | 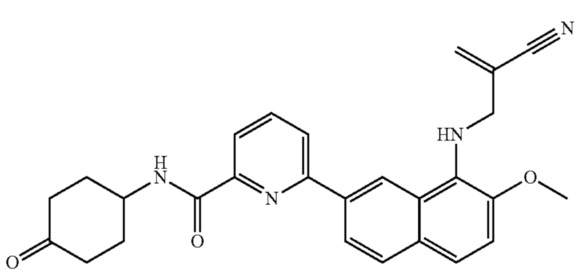 [SMILES: C=C(C#N)CNc1c(OC)ccc2ccc(-c3cccc(C(=O)NC4CCC(=O)CC4)n3)cc12] | 6-{8-[(2-cyano-2-methylideneethyl)amino]-7-methoxynaphthalen-2-yl}-N-(4-oxocyclohexyl)pyridine-2-carboxamide | 455.2 |

TABLE 2-continued

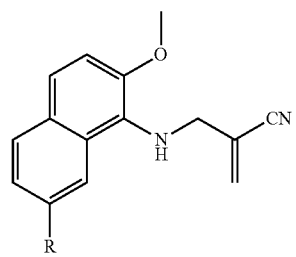

| Cmp. No. | Structure | IUPAC | LC-MS (ES+, m/z) |
|---|---|---|---|
| 198 | 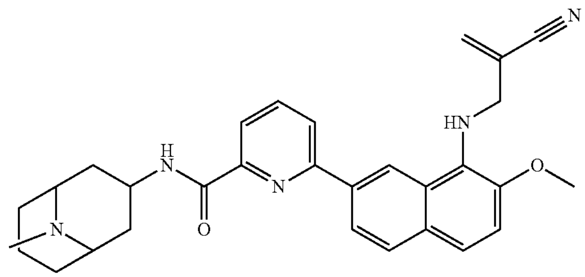 | 6-{8-[(2-cyano-2-methylideneethyl)amino]-7-methoxynaphthalen-2-yl}-N-{9-methyl-9-azabicyclo[3.3.1]nonan-3-yl}pyridine-2-carboxamide | 496.3 |
| 199 | 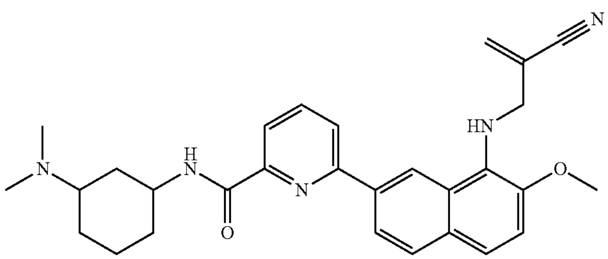 | 6-{8-[(2-cyano-2-methylideneethyl)amino]-7-methoxynaphthalen-2-yl}-N-[3-(dimethylamino)cyclohexyl]pyridine-2-carboxamide | 484.2 |
| 200 | 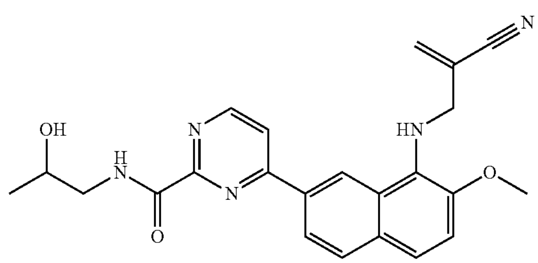 | 4-{8-[(2-cyano-2-methylideneethyl)amino]-7-methoxynaphthalen-2-yl}-N-(2-hydroxypropyl)pyrimidine-2-carboxamide | 418.1 |
| 201 | 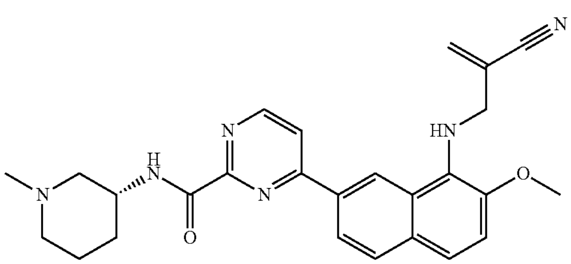 | 4-{8-[(2-cyano-2-methylideneethyl)amino]-7-methoxynaphthalen-2-yl}-N-[(3R)-1-methylpiperidin-3-yl]pyrimidine-2-carboxamide | 457.1 |

TABLE 2-continued

| Cmp. No. | Structure | IUPAC | LC-MS (ES+, m/z) |
|---|---|---|---|
| 202 | 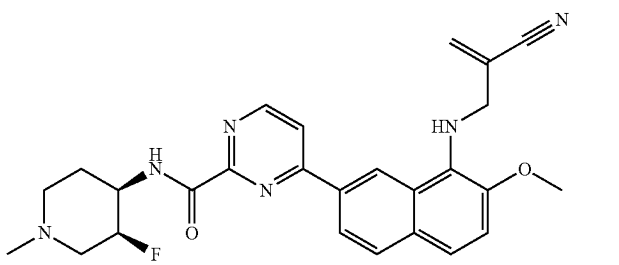 | 4-{8-[(2-cyano-2-methylideneethyl)amino]-7-methoxynaphthalen-2-yl}-N-[(3S,4R)-3-fluoro-1-methylpiperidin-4-yl]pyrimidine-2-carboxamide | 475.1 |
| 203 | 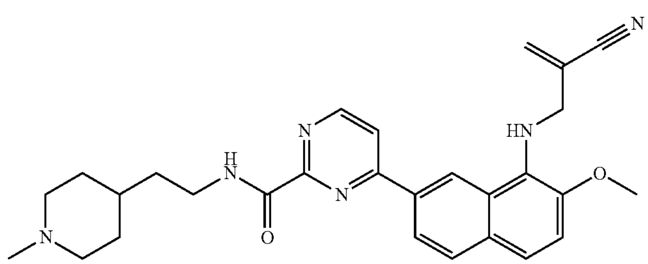 | 4-{8-[(2-cyano-2-methylideneethyl)amino]-7-methoxynaphthalen-2-yl}-N-[2-(1-methylpiperidin-4-yl)ethyl]pyrimidine-2-carboxamide | 485.1 |
| 204 | 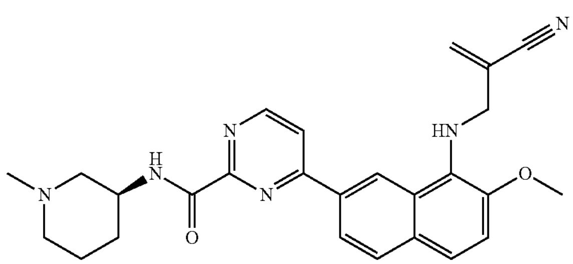 | 4-{8-[(2-cyano-2-methylideneethyl)amino]-7-methoxynaphthalen-2-yl}-N-[(3S)-1-methylpiperidin-3-yl]pyrimidine-2-carboxamide | 457.2 |
| 205 | 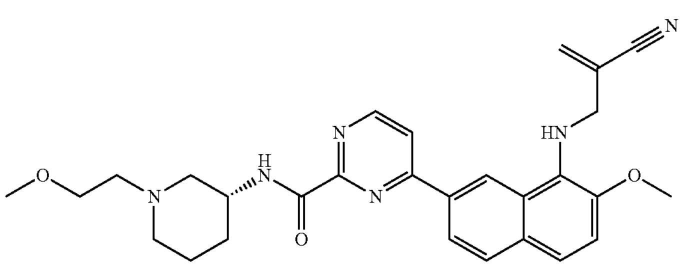 | 4-{8-[(2-cyano-2-methylideneethyl)amino]-7-methoxynaphthalen-2-yl}-N-[(3R)-1-(2-methoxyethyl)piperidin-3-yl]pyrimidine-2-carboxamide | 501.3 |

TABLE 2-continued

| Cmp. No. | Structure | IUPAC | LC-MS (ES+, m/z) |
|---|---|---|---|
| 206 | 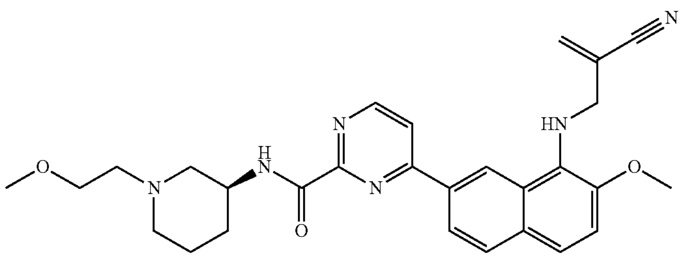 | 4-{8-[(2-cyano-2-methylideneethyl)amino]-7-methoxynaphthalen-2-yl}-N-[(3S)-1-(2-methoxyethyl)piperidin-3-yl]pyrimidine-2-carboxamide | 501.3 |
| 207 | 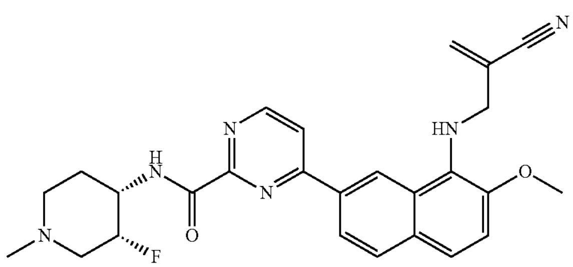 | 4-{8-[(2-cyano-2-methylideneethyl)amino]-7-methoxynaphthalen-2-yl}-N-[(3R,4S)-3-fluoro-1-methylpiperidin-4-yl]pyrimidine-2-carboxamide | 475.2 |
| 208 | 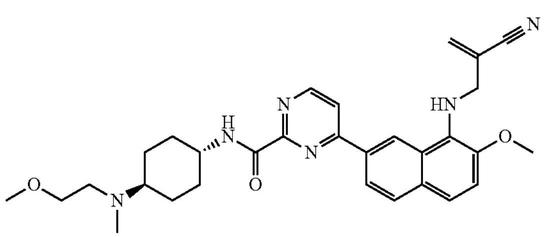 | 4-{8-[(2-cyano-2-methylideneethyl)amino]-7-methoxynaphthalen-2-yl}-N-[(1r,4r)-4-[(2-methoxyethyl)(methyl)amino]cyclohexyl]pyrimidine-2-carboxamide | 529.3 |
| 209 | 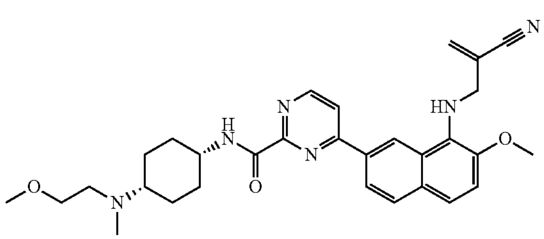 | 4-{8-[(2-cyano-2-methylideneethyl)amino]-7-methoxynaphthalen-2-yl}-N-[(1s,4s)-4-[(2-methoxyethyl)(methyl)amino]cyclohexyl]pyrimidine-2-carboxamide | 529.3 |
| 210 | 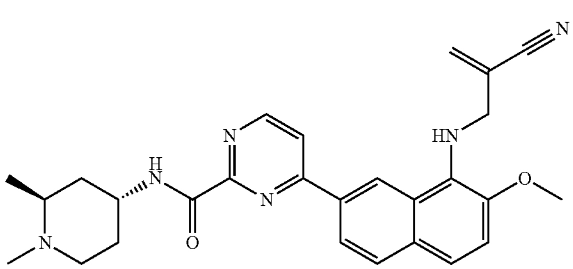 | 4-{8-[(2-cyano-2-methylideneethyl)amino]-7-methoxynaphthalen-2-yl}-N-[(2S,4R)-1,2-dimethylpiperidin-4-yl]pyrimidine-2-carboxamide | 471.2 |

TABLE 2-continued

| Cmp. No. | Structure | IUPAC | LC-MS (ES+, m/z) |
|---|---|---|---|
| 211 | 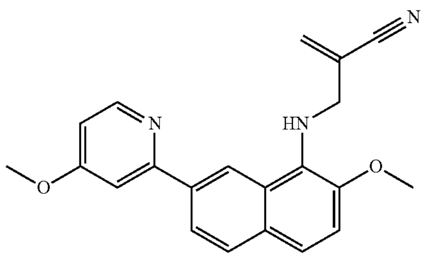 | 2-({[2-methoxy-7-(4-methoxypyridin-2-yl)naphthalen-1-yl]amino}methyl)prop-2-enenitrile | 346.1 |
| 212 | 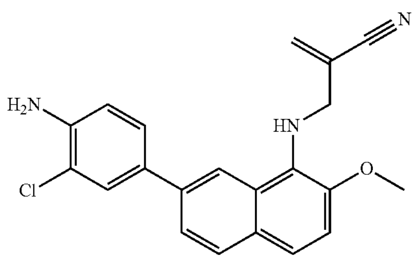 [SMILES: C=C(C#N)CNc1c(OC)ccc2ccc(-c3ccc(N)c(Cl)c3)cc12] | 2-({[7-(4-amino-3-chlorophenyl)-2-methoxynaphthalen-1-yl]amino}methyl)prop-2-enenitrile | 364.1 |
| 213 | 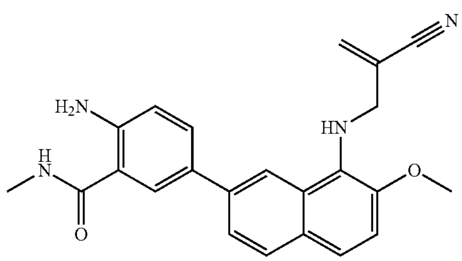 | 2-amino-5-{8-[(2-cyano-2-methylideneethyl)amino]-7-methoxynaphthalen-2-yl}-N-methylbenzamide | 387.1 |
| 214 | 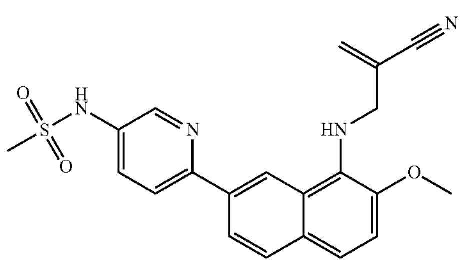 | N-(6-{8-[(2-cyano-2-methylideneethyl)amino]-7-methoxynaphthalen-2-yl}pyridin-3-yl)methanesulfonamide | 408.9 |
| 215 | 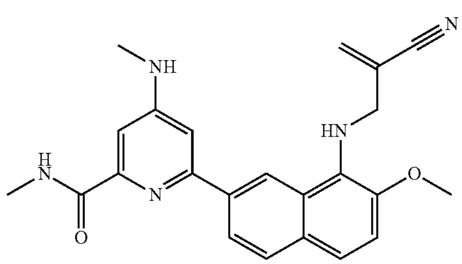 | 6-{8-[(2-cyano-2-methylideneethyl)amino]-7-methoxynaphthalen-2-yl}-N-methyl-4-(methylamino)pyridine-2-carboxamide | 402.1 |

TABLE 2-continued

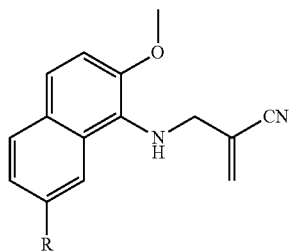

| Cmp. No. | Structure | IUPAC | LC-MS (ES+, m/z) |
|---|---|---|---|
| 216 | 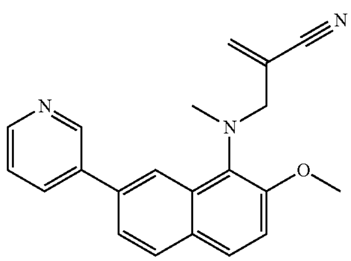 [SMILES: C=C(C#N)CN(C)c1c(OC)ccc2ccc(-c3cccnc3)cc12] | 2-({[2-methoxy-7-(pyridin-3-yl)naphthalen-1-yl](methyl)amino}methyl)prop-2-enenitrile | 330 |
| 217 | 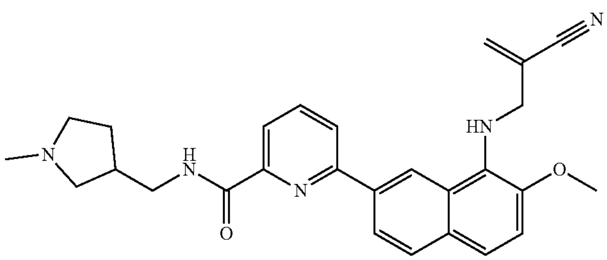 | 6-{8-[(2-cyano-2-methylideneethyl)amino]-7-methoxynaphthalen-2-yl}-N-[(1-methylpyrrolidin-3-yl)methyl]pyridine-2-carboxamide | 456.1 |
| 218 | 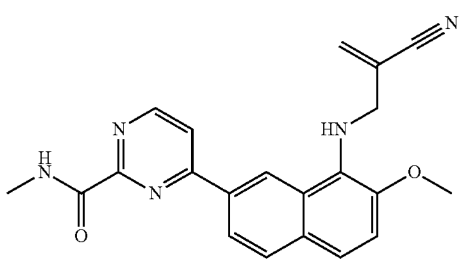 | 4-{8-[(2-cyano-2-methylideneethyl)amino]-7-methoxynaphthalen-2-yl}-N-methylpyrimidine-2-carboxamide | 374 |
| 219 | 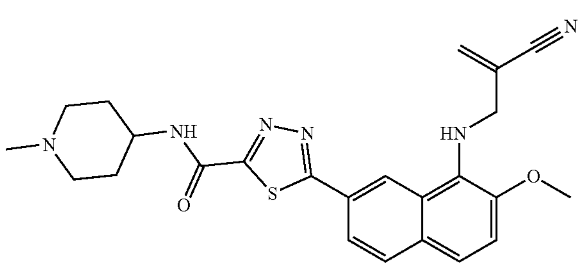 | 5-{8-[(2-cyano-2-methylideneethyl)amino]-7-methoxynaphthalen-2-yl}-N-(1-methylpiperidin-4-yl)-1,3,4-thiadiazole-2-carboxamide | 463.2 |
| 220 | 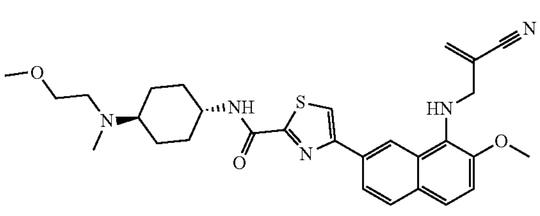 | 4-{8-[(2-cyano-2-methylideneethyl)amino]-7-methoxynaphthalen-2-yl}-N-[(1r,4r)-4-[(2-methoxyethyl)(methyl)amino]cyclohexyl]-1,3-thiazole-2-carboxamide | 534.3 |

TABLE 2-continued

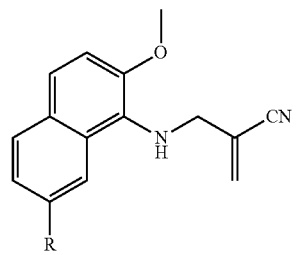

| Cmp. No. | Structure | IUPAC | LC-MS (ES+, m/z) |
|---|---|---|---|
| 221 | 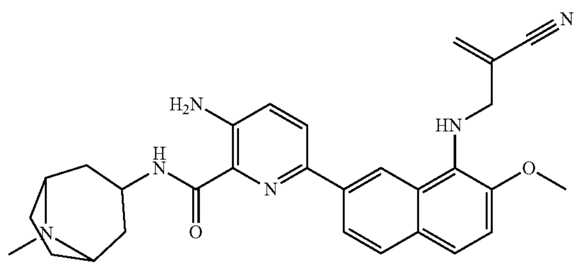 | 3-amino-6-{8-[(2-cyano-2-methylideneethyl)amino]-7-methoxynaphthalen-2-yl}-N-{8-methyl-8-azabicyclo[3.2.1]octan-3-yl}pyridine-2-carboxamide | 497.3 |
| 222 | 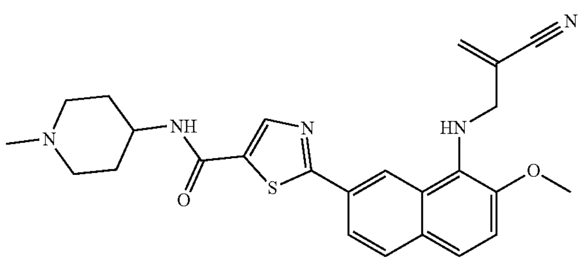 | 2-{8-[(2-cyano-2-methylideneethyl)amino]-7-methoxynaphthalen-2-yl}-N-(1-methylpiperidin-4-yl)-1,3-thiazole-5-carboxamide | 462.2 |
| 223 | 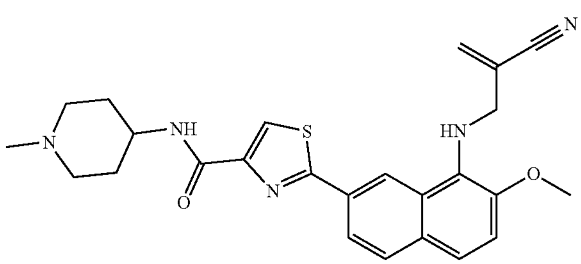 | 2-{8-[(2-cyano-2-methylideneethyl)amino]-7-methoxynaphthalen-2-yl}-N-(1-methylpiperidin-4-yl)-1,3-thiazole-4-carboxamide | 462.2 |
| 224 | 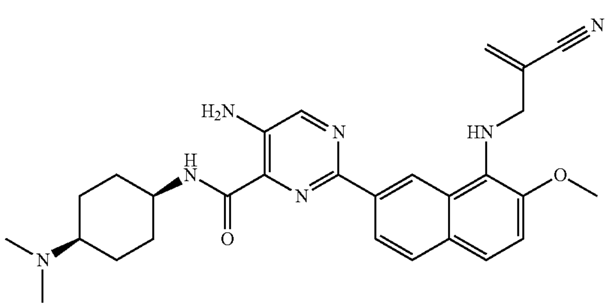 | 5-amino-2-{8-[(2-cyano-2-methylideneethyl)amino]-7-methoxynaphthalen-2-yl}-N-[(1s,4s)-4-(dimethylamino)cyclohexyl]pyrimidine-4-carboxamide | 500.3 |

TABLE 2-continued

| Cmp. No. | Structure | IUPAC | LC-MS (ES+, m/z) |
|---|---|---|---|
| 225 | 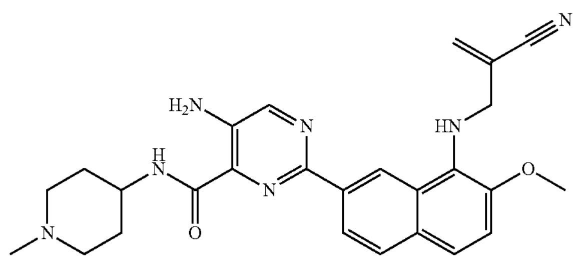 | 5-amino-2-{8-[(2-cyano-2-methylideneethyl)amino]-7-methoxynaphthalen-2-yl}-N-(1-methylpiperidin-4-yl)pyrimidine-4-carboxamide | 472.2 |
| 226 | 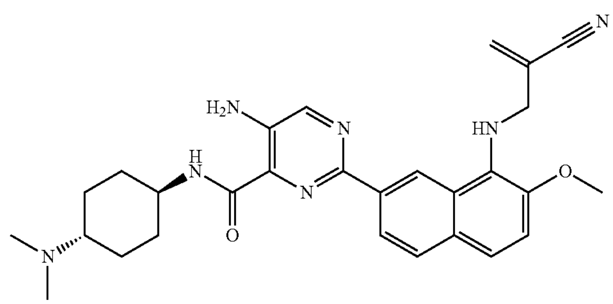 | 5-amino-2-{8-[(2-cyano-2-methylideneethyl)amino]-7-methoxynaphthalen-2-yl}-N-[(1r,4r)-4-(dimethylamino)cyclohexyl]pyrimidine-4-carboxamide | 500.3 |
| 227 | 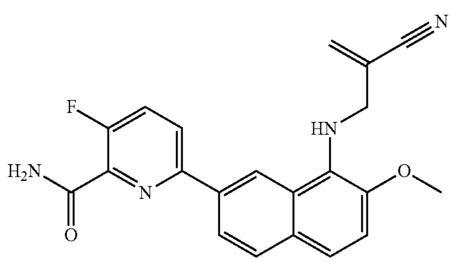 [SMILES: C=C(C#N)CNc1c(OC)ccc2ccc(-c3ccc(F)c(C(N)=O)n3)cc12] | 6-{8-[(2-cyano-2-methylideneethyl)amino]-7-methoxynaphthalen-2-yl}-3-fluoropyridine-2-carboxamide | 376.9 |
| 228 | 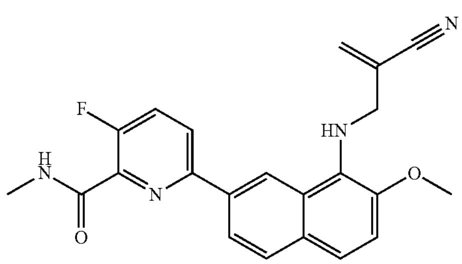 | 6-{8-[(2-cyano-2-methylideneethyl)amino]-7-methoxynaphthalen-2-yl}-3-fluoro-N-methylpyridine-2-carboxamide | 391.1 |

TABLE 2-continued
| Cmp. No. | Structure | IUPAC | LC-MS (ES+, m/z) |
|---|---|---|---|
| 229 | 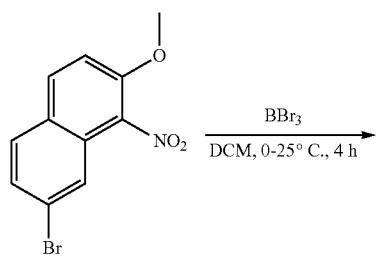 | 6-{8-[(2-cyano-2-methylideneethyl)amino]-7-methoxynaphthalen-2-yl}-3-fluoro-N-[(1s,4s)-4-(dimethylamino)cyclohexyl]pyridine-2-carboxamide | 502.3 |
| 230 | 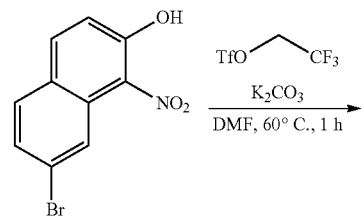 | 3-chloro-6-{8-[(2-cyano-2-methylideneethyl)amino]-7-methoxynaphthalen-2-yl}pyridine-2-carboxamide | 393.1 |
Example 3: Method C
Route 1: General Scheme
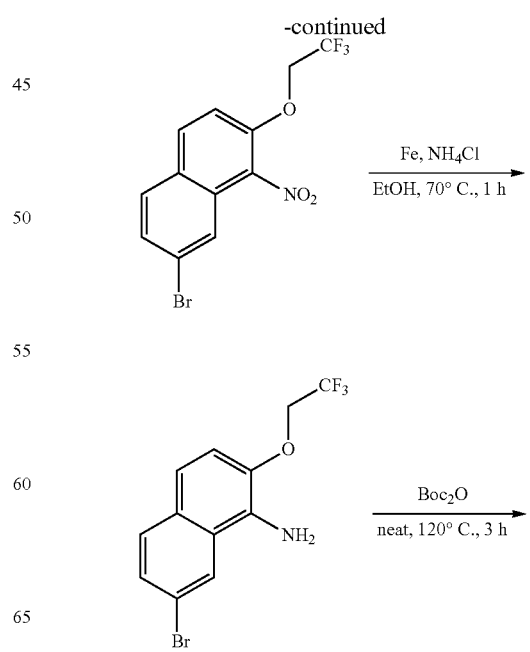

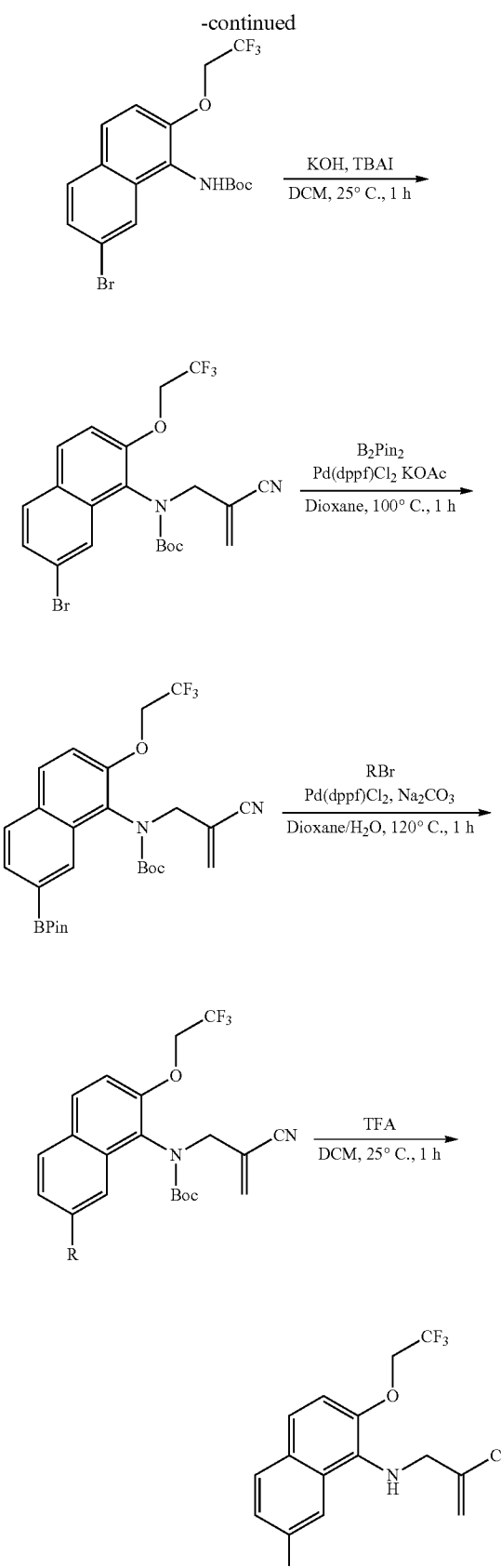

Examples 231-236

Preparation of 7-bromo-1-nitronaphthalen-2-ol

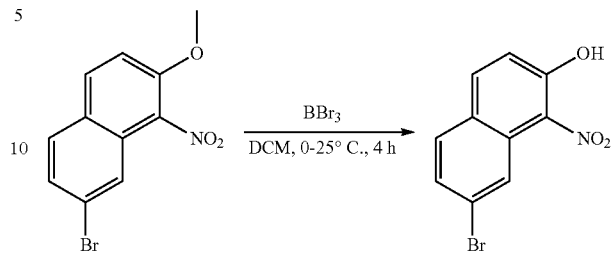

To a mixture of 7-bromo-2-methoxy-1-nitronaphthalene (8 g, 28.36 mmol, 1 eq) in DCM (80 mL) was added BBr$_3$ (35.52 g, 141.8 mmol, 13.66 mL, 5 eq) at 0° C. The mixture was stirred at 25° C. for 4 h. TLC showed that the reaction was complete. The reaction mixture was diluted with ice-water. The mixture was extracted with EtOAc (2×200 mL). The combined organic layers were washed with H$_2$O (2×100 mL) and brine (2×100 mL), dried over anhydrous Na$_2$SO$_4$, filtered, and concentrated in vacuo to give a residue. The crude product (7.8 g, crude) was obtained as a yellow solid, which was used without further purification.

Preparation of 7-bromo-1-nitro-2-(2,2,2-trifluoroethoxy)naphthalene

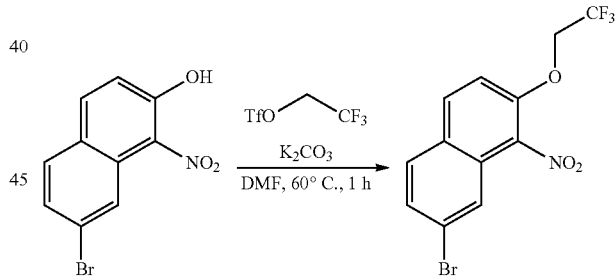

To a solution of 7-bromo-1-nitronaphthalen-2-ol (5.8 g, 21.64 mmol, 1 eq) in DMF (60 mL) was added K$_2$CO$_3$ (8.97 g, 64.91 mmol, 3 eq). Then, 2,2,2-Trifluoroethyl trifluoromethanesulfonate (7.53 g, 32.46 mmol, 1.5 eq) was added to the reaction and stirred at 60° C. for 1 h. TLC showed that the reaction was complete. The reaction mixture was diluted with H$_2$O. The mixture was extracted with EtOAc (2×200 mL). The combined organic layers were washed with H$_2$O (2×200 mL) and brine (2×200 mL), dried over anhydrous Na$_2$SO$_4$, filtered, and concentrated in vacuo to give a residue. The title compound was obtained as a yellow solid (7 g, crude) and used without purification.

Preparation of 7-bromo-2-(2,2,2-trifluoroethoxy)naphthalen-1-amine

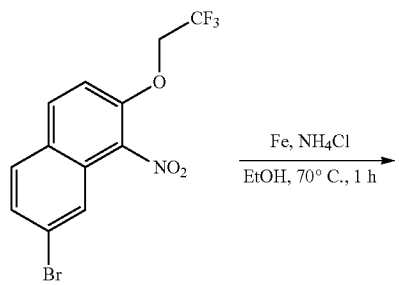

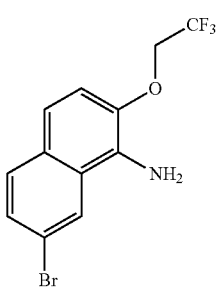

To a mixture of 7-bromo-1-nitro-2-(2,2,2-trifluoroethoxy)naphthalene (7 g, 19.99 mmol, 1 eq) in EtOH (60 mL) was added saturated NH₄Cl (1.07 g, 19.99 mmol, 15 mL, 1 eq), and the reaction mixture was heated to 70° C. Fe (3.35 g, 59.98 mmol, 3 eq) was added to the reaction and stirred for 1 hr. The reaction mixture was diluted with H₂O. The mixture was extracted with EtOAc (2×200 mL). The combined organic layers were washed with H₂O (2×100 mL) and brine (2×100 mL), dried over anhydrous Na₂SO₄, filtered, and concentrated in vacuo to give a residue. The residue was purified by column chromatography (SiO₂, PE:EtOAc=10:1 to 6:1) to afford the title compound (3.7 g, 11.56 mmol, 57.8% yield) as a yellow solid.

Preparation of tert-butyl N-[7-bromo-2-(2,2,2-trifluoroethoxy)naphthalen-1-yl]carbamate

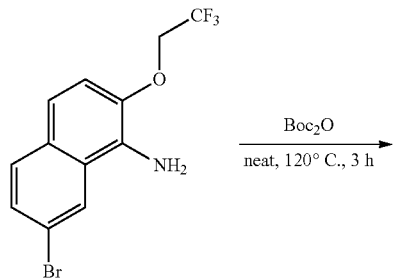

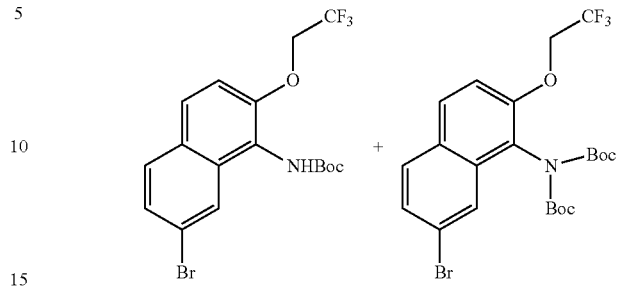

A solution of 7-bromo-2-(2,2,2-trifluoroethoxy)naphthalen-1-amine (1 g, 3.12 mmol, 1 eq) in Boc₂O (20.45 g, 93.72 mmol, 21.53 mL, 30 eq) was stirred at 120° C. for 3 h. TLC showed that the reaction was complete. The reaction mixture was diluted with H₂O (100 mL). The mixture was extracted with EtOAc (2×50 mL). The combined organic layers were washed with H₂O (2×50 mL) and brine (2×50 mL), dried over anhydrous Na₂SO₄, filtered, and concentrated in vacuo to give a residue. The residue was purified by column chromatography (SiO₂, PE:EtOAc=10:1 to 6:1) to afford the title compound (1.3 g, 2.5 mmol, 79.97% yield) as a yellow solid.

To a solution of tert-butyl N-[7-bromo-2-(2,2,2-trifluoroethoxy)-1-naphthyl]-N-tert-Butoxy carbonyl-carbamate (1.2 g, 2.31 mmol, 1 eq) in MeOH (12 mL) was added K₂CO₃ (1.27 g, 9.22 mmol, 4 eq). The reaction mixture was stirred at 25° C. for 15 h. LCMS showed that the reaction was complete. The reaction mixture was diluted with H₂O (100 mL). The mixture was extracted with EtOAc (2×50 mL). The combined organic layers were washed with H₂O (2×50 mL) and brine (2×50 mL), dried over anhydrous Na₂SO₄, filtered, and concentrated in vacuo to give a residue. The crude product (1 g, crude) was obtained as a white solid and used without purification. LC-MS (ES⁺, m/z): 363.0 [(M-tBu)⁺].

Preparation of tert-butyl N-[7-bromo-2-(2,2,2-trifluoroethoxy)naphthalen-1-yl]-N-(2-cyano-2-methylideneethyl)carbamate

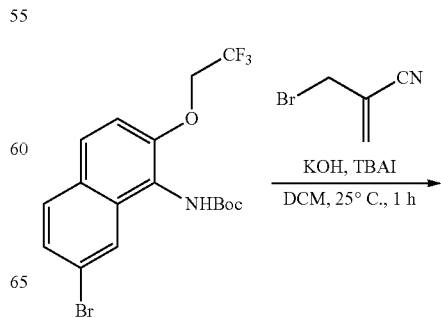

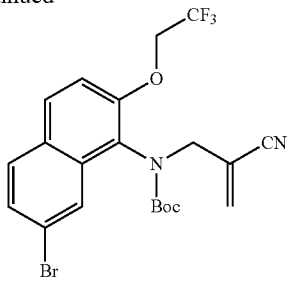

To a solution of tert-butyl N-[7-bromo-2-(2,2,2-trifluoroethoxy)naphthalen-1-yl]carbamate (1 g, 2.38 mmol, 1 eq) in DCM (10 mL) were added KOH (267.1 mg, 4.76 mmol, 2 eq) and TBAI (263.7 mg, 713.91 µmol, 0.3 eq). Then, 2-(bromomethyl)prop-2-enenitrile (521.1 mg, 3.57 mmol, 1.5 eq) was added and the mixture was stirred at 25° C. for 1 hr. LCMS showed that the reaction was complete. The reaction mixture was diluted with H₂O (100 mL). The mixture was extracted with EtOAc (2×50 mL). The combined organic layers were washed with H₂O (2×50 mL) and brine (2×50 mL), dried over anhydrous Na₂SO₄, filtered, and concentrated in vacuo to give a residue. The residue was purified by column chromatography (SiO₂, PE:EtOAc) to afford the title compound (0.9 g, 1.85 mmol) as a white solid.

Preparation of tert-butyl N-(2-cyano-2-methylideneethyl)-N-[7-(4,4,5,5-tetramethyl-1,3-dioxolan-2-yl)-2-(2,2,2-trifluoroethoxy)naphthalen-1-yl]carbamate

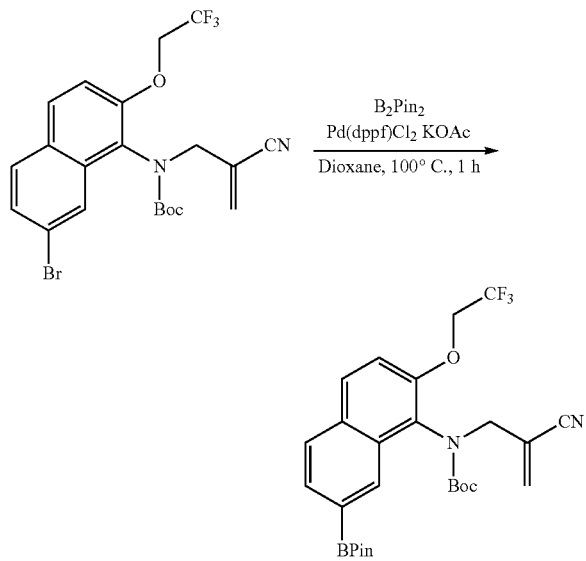

To a mixture of tert-butyl N-[7-bromo-2-(2,2,2-trifluoroethoxy)naphthalen-1-yl]-N-(2-cyano-2-methylideneethyl)carbamate (0.5 g, 1.03 mmol, 1 eq) and 4,4,5,5-tetramethyl-2-(4,4,5,5-tetramethyl-1,3,2-dioxaborolan-2-yl)-1,3,2-dioxaborolane (523.3 mg, 2.06 mmol, 2 eq) in dioxane (6 mL) were added KOAc (505.6 mg, 5.15 mmol, 5 eq) and Pd(dppf)Cl₂ (150.8 mg, 206.06 µmol, 0.2 eq). The reaction mixture was stirred at 100° C. for 1 hr. LCMS showed that the reaction was complete. The reaction mixture was diluted with H₂O (60 mL). The mixture was extracted with EtOAc (2×40 mL). The combined organic layers were washed with H₂O (2×50 mL) and brine (2×50 mL), dried over anhydrous Na₂SO₄, filtered, and concentrated in vacuo to give a residue. The residue was purified by column chromatography (SiO₂, PE:EtOAc) to afford the title compound (0.44 g, 826.51 µmol, 80.22% yield) as a yellow oil. LC-MS (ES⁺, m/z): 477.2 [(M-tBu)⁺]

Preparation of tert-butyl N-(2-cyanoallyl)-N-[7-(2-pyridyl)-2-(2,2,2-trifluoroethoxy)-1-naphthyl]carbamate

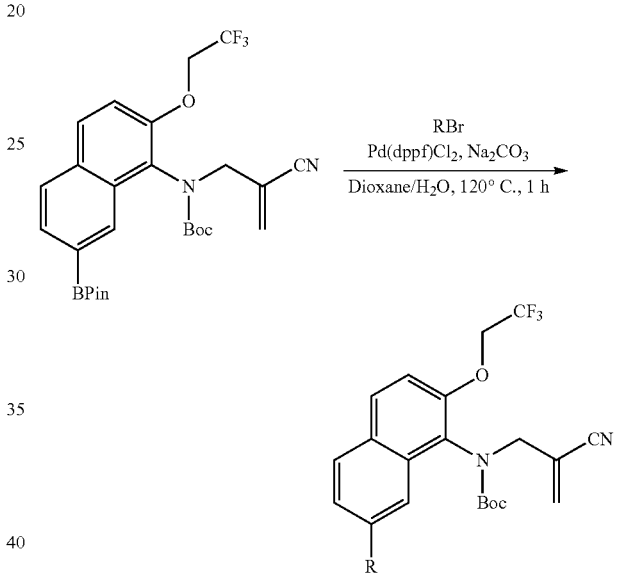

To a mixture of tert-butyl N-(2-cyanoallyl)-N-[7-(4,4,5,5-tetramethyl-1,3,2-dioxaborolan-2-yl)-2-(2,2,2-trifluoroethoxy)-1-naphthyl]carbamate (70 mg, 131.49 µmol, 1 eq) and 2-bromopyridine (41.6 mg, 262.98 µmol, 25.03 µL, 2 eq) in dioxane (2 mL) and H₂O (0.5 mL) were added Na₂CO₃ (41.8 mg, 394.47 µmol, 3 eq) and Pd(dppf)Cl₂ (9.6 mg, 13.15 µmol, 0.1 eq). The reaction was heated to 120° C. under N₂ and stirred for 1 h. TLC showed that the reaction was complete. The reaction mixture was stirred by adding saturated EDTA (50 mL) and EtOAc (50 mL) at 25° C. The mixture was extracted with EtOAc (2×50 mL). The combined organic phase was washed with H₂O (2×100 mL) and brine (2×100 mL), dried over anhydrous Na₂SO₄, filtered, and concentrated in vacuo to give a residue. The residue was purified by prep-TLC (SiO₂, PE:EtOAc=4:1) to afford the title compound tert-butyl N-(2-cyanoallyl)-N-[7-(2-pyridyl)-2-(2,2,2-trifluoroethoxy)-1-naphthyl]carbamate (50 mg, 103.42 µmol, 78.65% yield) as a yellow oil.

Preparation of 2-[[[7-(2-pyridyl)-2-(2,2,2-trifluoro-ethoxy)-1-naphthyl]amino]methyl]prop-2-enenitrile

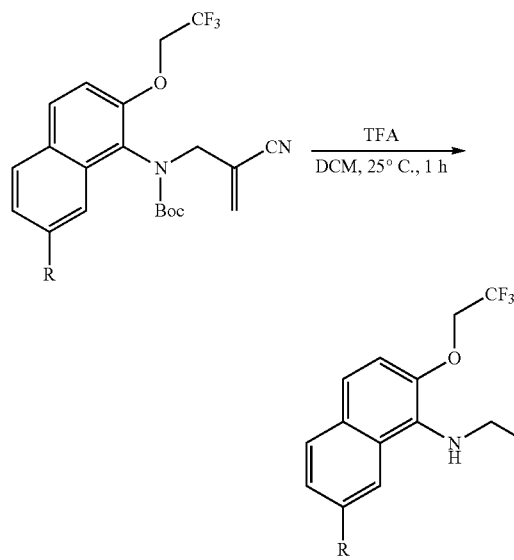

To a solution of tert-butyl N-(2-cyanoallyl)-N-[7-(2-pyridyl)-2-(2,2,2-trifluoroethoxy)-1-naphthyl]carbamate (50 mg, 103.42 μmol, 1 eq) in DCM (2 mL) was added TFA (616 mg, 5.4 mmol, 0.4 mL, 52.24 eq). The reaction mixture was stirred at 25° C. for 1 h. LCMS showed that the reaction was complete. The reaction mixture was adjusted to pH>8 with saturated NaHCO$_3$. The mixture was extracted with EtOAc (2×50 mL). The combined organic layers were washed with H$_2$O (2×50 mL) and brine (2×50 mL), dried over anhydrous Na$_2$SO$_4$, filtered, and concentrated in vacuo to give a residue. The residue was purified by prep-HPLC to afford the title compound 2-[[[7-(2-pyridyl)-2-(2,2,2-trifluoroethoxy)-1-naphthyl]amino]methyl]prop-2-enenitrile (5.3 mg, 13.73 μmol, 13.27% yield, 99.3% purity) as a white solid. LC-MS (ES$^+$, m/z): 384 [(M+H)$^+$]

Route 2: General Scheme (Compounds 237-240)

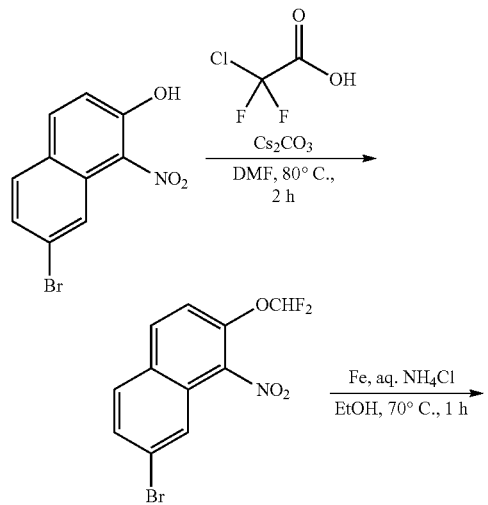

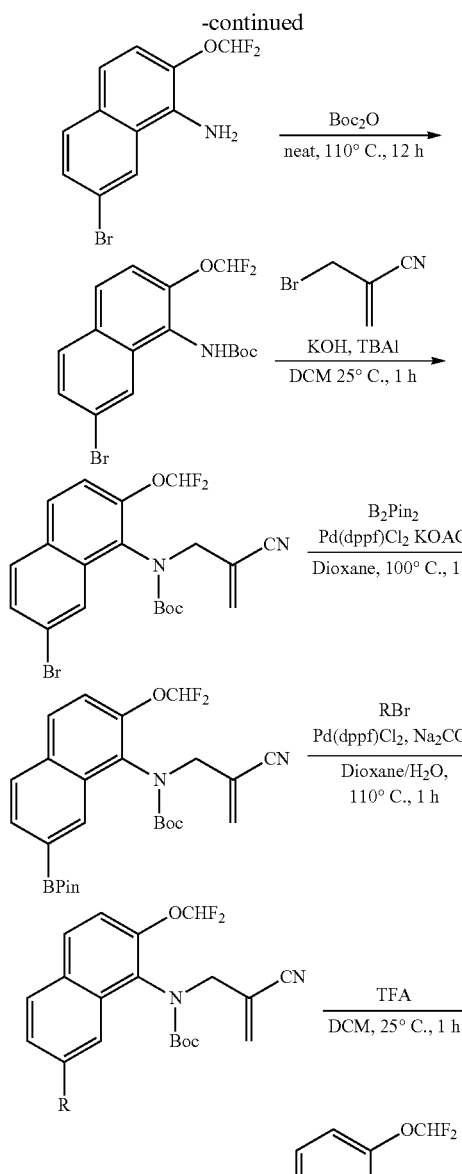

Preparation of 7-bromo-2-(difluoromethoxy)-1-nitro-naphthalene

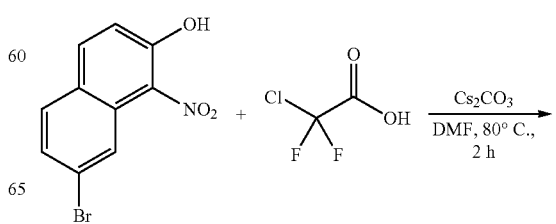

-continued

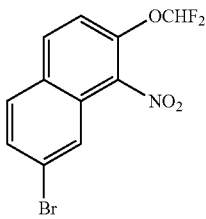

To a mixture of 2-chloro-2,2-difluoro-acetic acid (973.5 mg, 7.46 mmol, 632 μL, 2 eq) and 7-bromo-1-nitro-naphthalen-2-ol (1 g, 3.73 mmol, 1 eq) in DMF (15 mL) was added Cs$_2$CO$_3$ (6.08 g, 18.65 mmol, 5 eq). The mixture was stirred at 80° C. for 2 hrs. The reaction was diluted with 30 mL of water and extracted with EtOAc (2×30 mL). The combined organic layer was washed with brine (2×30 mL), dried over Na$_2$SO$_4$, filtered, and concentrated in vacuo. The residue was purified by column chromatography (SiO$_2$, PE:EtOAc=20/1 to 10:1) to afford the title compound (700 mg, 59% yield) as a yellow solid.

Preparation of
7-bromo-2-(difluoromethoxy)naphthalen-1-amine

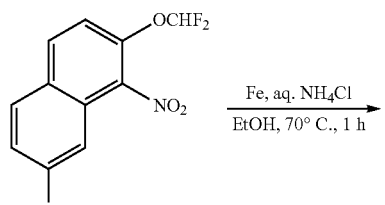

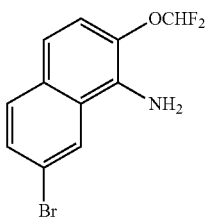

To a solution of 7-bromo-2-(difluoromethoxy)-1-nitronaphthalene (0.65 g, 2.04 mmol, 1 eq) in EtOH (6 mL) was added saturated NH$_4$Cl (2.04 mmol, 1.5 mL, 1 eq). Then the mixture was heated to 70° C. Fe (342.4 mg, 6.13 mmol, 3 eq) was added, and the mixture was stirred at 70° C. for 1 h. The reaction mixture was diluted with H$_2$O (100 mL) and extracted with EtOAc (3×50 mL). The combined organic layers were washed with H$_2$O (2×50 mL) and brine (2×50 mL), dried over anhydrous Na$_2$SO$_4$, filtered, and concentrated in vacuo. The residue was purified by column chromatography (SiO$_2$, PE:EtOAc=10:1 to 6:1) to afford the title compound (500 mg, 84.9% yield) as a yellow solid.

Preparation of tert-butyl N-[7-bromo-2-(difluoromethoxy)-1-naphthyl]carbamate

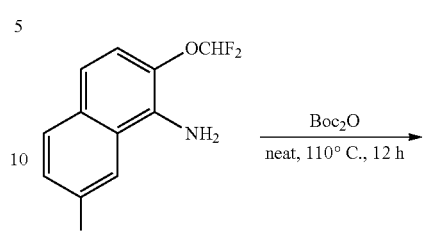

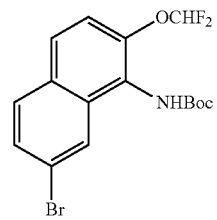

A mixture of 7-bromo-2-(difluoromethoxy)naphthalen-1-amine (460 mg, 1.6 mmol, 1 eq) and Boc$_2$O (17.42 g, 79.84 mmol, 18.34 mL, 50 eq) was stirred at 110° C. for 12 h. The mixture was partitioned between EtOAc and water. The aqueous phase was extracted with EtOAc (3×100 mL). The combined organic layers were washed with H$_2$O (2×50 mL) and brine (2×50 mL), dried over anhydrous Na$_2$SO$_4$, filtered, and concentrated in vacuo. The residue was purified by column chromatography (SiO$_2$, PE:EtOAc=10:1 to 6:1) to afford the title compound (0.57 g, 92% yield) as a yellow solid.

Preparation of tert-butyl N-[7-bromo-2-(difluoromethoxy)-1-naphthyl]-N-(2-cyanoallyl) carbamate

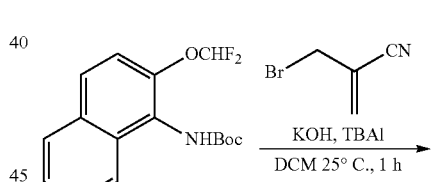

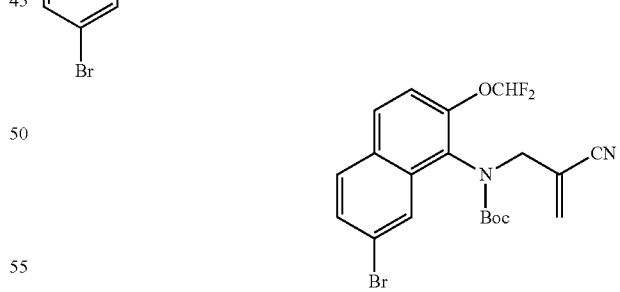

To a solution of tert-butyl N-[7-bromo-2-(difluoromethoxy)-1-naphthyl]carbamate (0.25 g, 643.99 μmol, 1 eq) in DCM (4 mL) were added KOH (72.3 mg, 1.29 mmol, 2 eq), TBAI (71.4 mg, 193.2 μmol, 0.3 eq) and 2-(bromomethyl)prop-2-enenitrile (141 mg, 965.99 μmol, 1.5 eq). The mixture was stirred at 25° C. for 1 h. The reaction mixture was partitioned between EtOAc and water. The aqueous phase was extracted with EtOAc (3×100 mL). The combined organic layers were washed with H$_2$O (2×50 mL) and brine (2×50 mL), dried over anhydrous Na$_2$SO$_4$, filtered, and concentrated in vacuo. The residue was purified by column chromatography (SiO$_2$, PE:EtOAc=10:1 to 4:1) to afford the title compound (0.27 g, 92.5% yield) as a colorless oil.

Preparation of tert-butyl N-(2-cyanoallyl)-N-[2-(difluoromethoxy)-7-(4,4,5,5-tetramethyl-1,3,2-dioxaborolan-2-yl)-1-naphthyl]carbamate

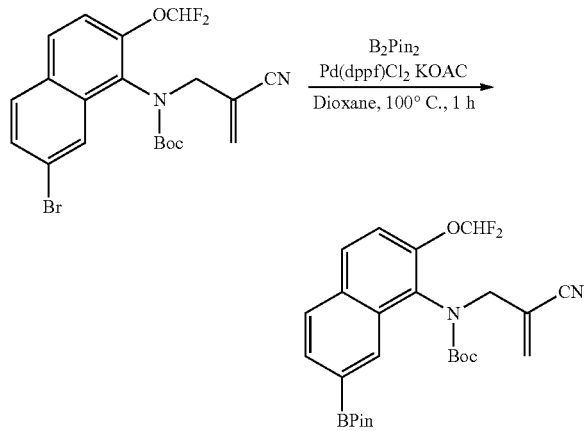

To a mixture of tert-butyl N-[7-bromo-2-(difluoromethoxy)-1-naphthyl]-N-(2-cyanoallyl) carbamate (220 mg, 485.35 μmol, 1 eq) and B$_2$Pin$_2$ (246.5 mg, 970.71 μmol, 2 eq) in dioxane (4 mL) were added KOAc (142.9 mg, 1.46 mmol, 3 eq) and Pd(dppf)Cl$_2$ (71 mg, 97.07 μmol, 0.2 eq). The mixture was stirred at 100° C. for 1 hr. The reaction mixture was concentrated in vacuo. The residue was washed with DCM (3×5 mL), filtered and dried with anhydrous Na$_2$SO$_4$. The title compound (0.2 g, crude) was used without further purification.

Preparation of tert-butyl N-(2-cyanoallyl)-N-[2-(difluoromethoxy)-7-[6-[(1-methyl-4-piperidyl)carbamoyl]-2-pyridyl]-1-naphthyl]carbamate

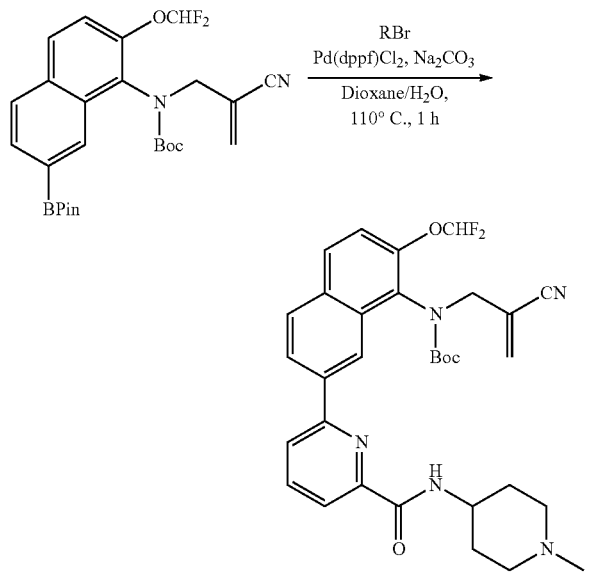

To a mixture of tert-butyl N-(2-cyanoallyl)-N-[2-(difluoromethoxy)-7-methyl-1-naphthyl]carbamate (0.2 g, 399.73 μmol, 1 eq) and 6-bromo-N-(1-methyl-4-piperidyl)pyridine-2-carboxamide (119.2 mg, 399.73 μmol, 1 eq) in dioxane (2 mL) and H$_2$O (0.5 mL) were added Na$_2$CO$_3$ (127.1 mg, 1.2 mmol, 3 eq) and Pd(dppf)Cl$_2$ (58.5 mg, 79.95 μmol, 0.2 eq). The mixture was stirred at 110° C. for 1 h. The reaction was diluted with 50 mL of saturated EDTA solution and EtOAc (50 mL). The mixture was stirred at r.t. for 1 h and extracted with EtOAc (5×50 mL). The combined organic layer was washed with H$_2$O (2×50 mL) and brine (2×50 mL), dried over anhydrous Na$_2$SO$_4$, filtered, and concentrated in vacuo. The residue was purified by prep-TLC (SiO$_2$, DCM:MeOH=10:1) to afford the title compound (0.1 g, 42.3% yield) as a yellow oil.

Compound 240: Preparation of 6-{8-[(2-cyano-2-methylideneethyl)amino]-7-(difluoromethoxy)naphthalen-2-yl}-N-(1-methylpiperidin-4-yl)pyridine-2-carboxamide

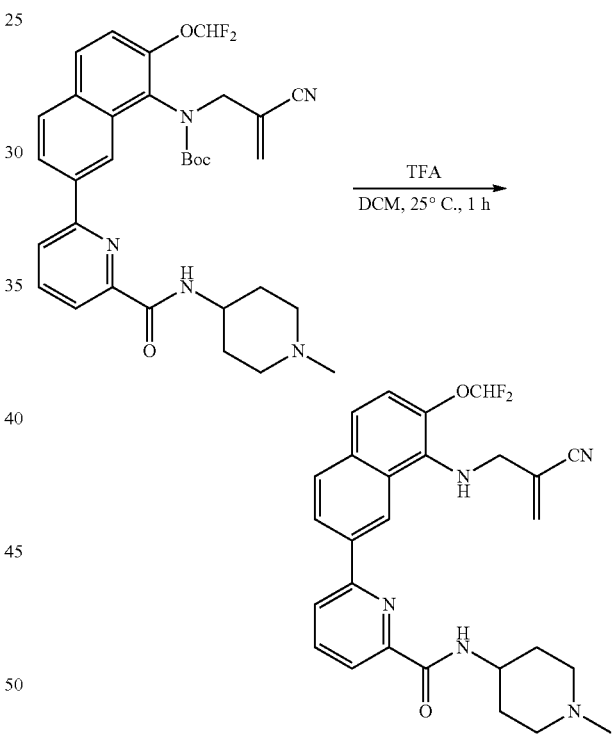

To a solution of tert-butyl N-(2-cyanoallyl)-N-[2-(difluoromethoxy)-7-[6-[(1-methyl-4-piperidyl)carbamoyl]-2-pyridyl]-1-naphthyl]carbamate (0.1 g, 169.02 μmol, 1 eq) in DCM (2 mL) was added TFA (616 mg, 5.4 mmol, 0.4 mL, 31.96 eq). The mixture was stirred at 25° C. for 1 h. The reaction mixture was adjusted to pH=8 with saturated NaHCO$_3$ solution and extracted with EtOAc (2×50 mL). The combined organic layer were washed with H$_2$O (2×50 mL) and brine (2×50 mL), dried over anhydrous Na$_2$SO$_4$, filtered, and concentrated in vacuo. The residue was purified by prep-HPLC (basic condition) to afford the title compound (19.4 mg, 23.2% yield) as a white solid. LC-MS (ES$^+$, m/z): 492.2 [(M+H)$^+$].

Route 3: General Scheme (Compounds 241-244)

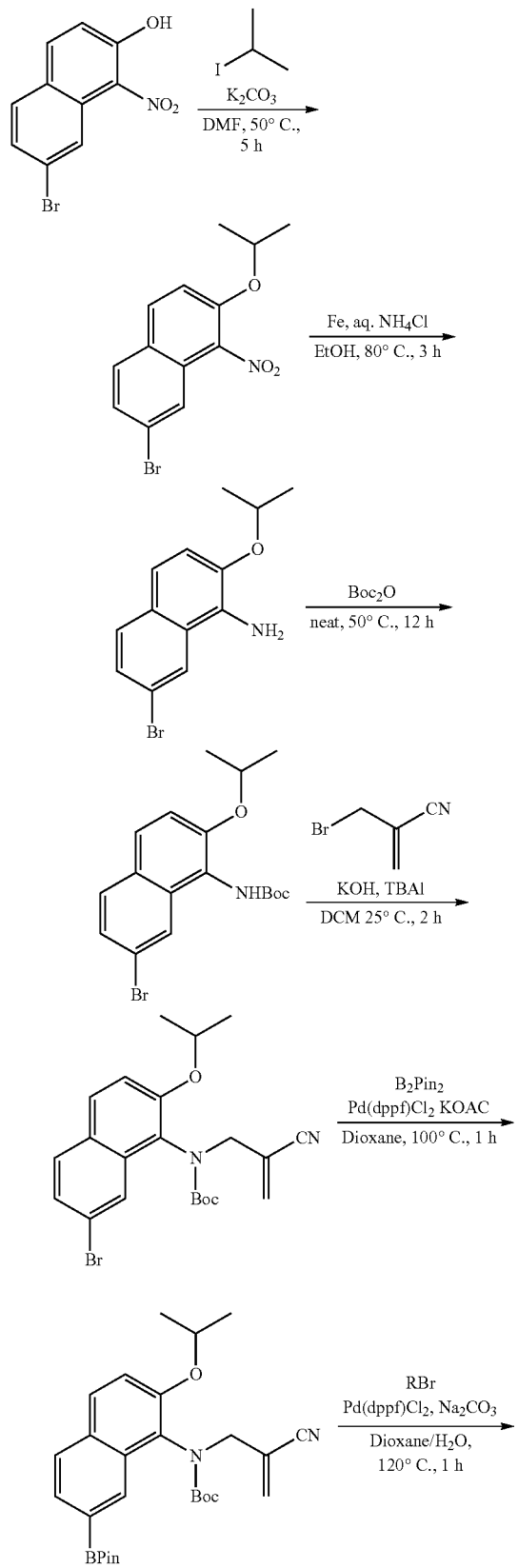

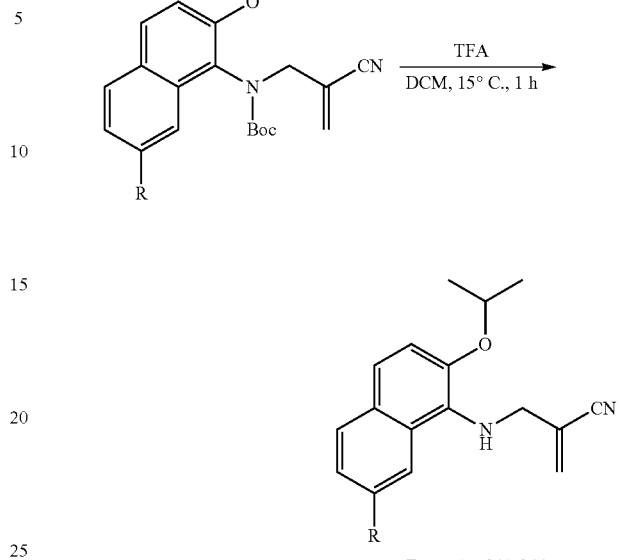

Examples 241-244

Preparation of
7-bromo-2-isopropoxy-1-nitro-naphthalene

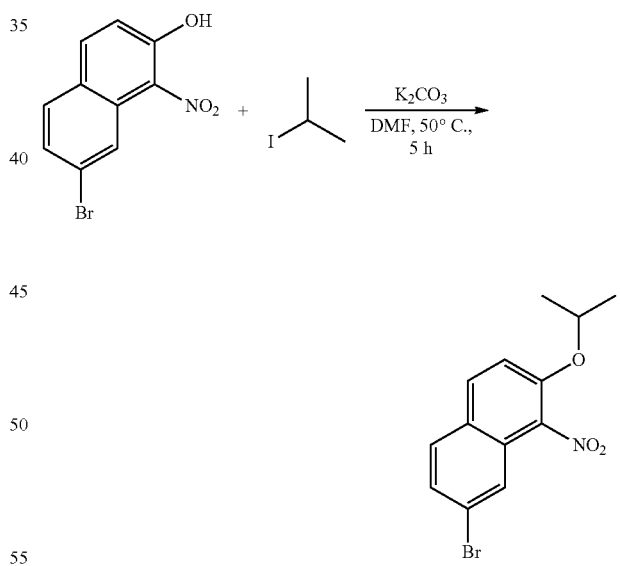

To a solution of 7-bromo-1-nitro-naphthalen-2-ol (2.5 g, 9.33 mmol, 1 eq) in DMF (50 mL) were added $K_2CO_3$ (2.58 g, 18.65 mmol, 2 eq) and 2-iodopropane (2.06 g, 12.12 mmol, 1.21 mL, 1.3 eq). The mixture was stirred at 50° C. for 5 hrs. The mixture was filtered to remove $K_2CO_3$. Then quenched with water (200 mL), extracted with EtOAc (3×100 mL). The combined organic layer was washed with brine (200 mL), dried over $Na_2SO_4$, filtered, and concentrated in vacuo. The title compound (2.5 g, crude) was used in the next step without further purification.

Preparation of 7-bromo-2-isopropoxy-naphthalen-1-amine

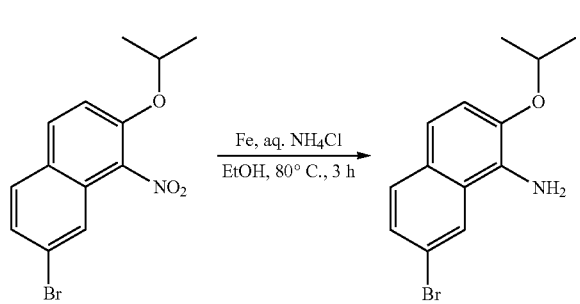 [SMILES: CC(C)Oc1ccc2ccc(Br)cc2c1[N+](=O)[O-] ; "Fe, aq. NH4Cl" ; CC(C)Oc1ccc2ccc(Br)cc2c1N]

To a solution of 7-bromo-2-isopropoxy-1-nitro-naphthalene (2 g, 6.45 mmol, 1 eq) in EtOH (40 mL) and $H_2O$ (8 mL) was added $NH_4Cl$ (1.72 g, 32.24 mmol, 5 eq) and the mixture was heated to 80° C. Fe (1.8 g, 32.24 mmol, 5 eq) was added in one portion. The mixture was stirred at 80° C. for 3 hrs. The mixture was filtered, and concentrated in reduced pressure. The residue was purified by column chromatography ($SiO_2$, PE:EtOAc=10:1 to 5:1) to afford the title compound (1.1 g, 60.9% yield) as a brown solid.

Preparation of tert-butyl N-(7-bromo-2-isopropoxy-1-naphthyl)carbamate

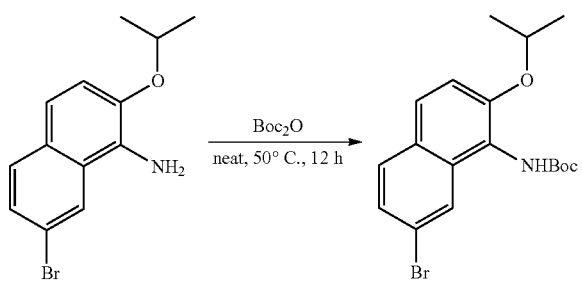 [SMILES: "Boc2O" ; CC(C)Oc1ccc2ccc(Br)cc2c1N ; CC(C)Oc1ccc2ccc(Br)cc2c1NC(=O)OC(C)(C)C]

A mixture of 7-bromo-2-isopropoxy-naphthalen-1-amine (1.1 g, 3.93 mmol, 1 eq) and $Boc_2O$ (31.35 g, 143.64 mmol, 33 mL, 36.58 eq) was stirred at 50° C. for 12 hrs. Upon completion of the reaction as indicated by TLC, to the reaction mixture was added 5 mL N1,N1-dimethylethane-1,2-diamine and stirred at 25° C. for 1 h. Then 60 mL water was added and extracted with EtOAc (3×30 mL). The combined organic layer was washed with brine (3×30 mL), dried over anhydrous $Na_2SO_4$, filtered, and concentrated in vacuo. The residue was purified by prep-TLC ($SiO_2$, PE:EtOAc=10:1) to afford the title compound (1.1 g, 73.7%) as a light yellow solid.

Preparation of tert-butyl N-(7-bromo-2-isopropoxy-1-naphthyl)-N-(2-cyanoallyl)carbamate

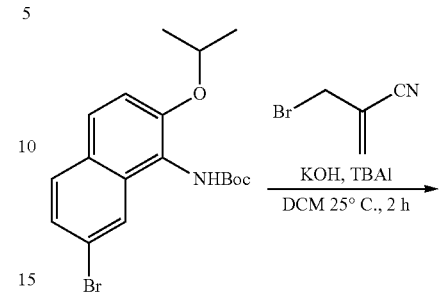

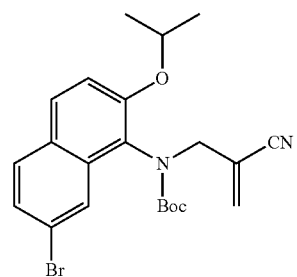

To a solution of tert-butyl N-(7-bromo-2-isopropoxy-1-naphthyl)carbamate (1.1 g, 2.84 mmol, 1 eq) in DCM (40 mL) were added KOH (318.7 mg, 5.68 mmol, 2 eq), TBAI (104.9 mg, 284 μmol, 0.1 eq) and 2-(bromomethyl)prop-2-enenitrile (456.1 mg, 3.12 mmol, 1.1 eq) in DCM (1 mL). The mixture was stirred at 25° C. for 2 hrs. The reaction mixture was quenched with ice water (100 mL), and extracted with DCM (3×50 mL). The combined organic layer was washed with brine (50 mL), dried over anhydrous $Na_2SO_4$, filtered, and concentrated in vacuo. The residue was purified by column chromatography ($SiO_2$, PE:EtOAc=20/1 to 10:1) to afford the title compound (1.1 g, 78.3%) as gray solid.

Preparation of tert-butyl N-(2-cyanoallyl)-N-[2-isopropoxy-7-(4,4,5,5-tetramethyl-1,3,2-dioxaborolan-2-yl)-1-naphthyl]carbamate

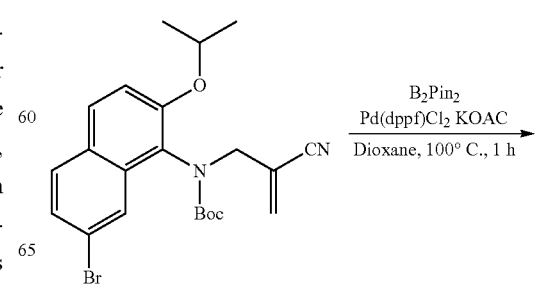

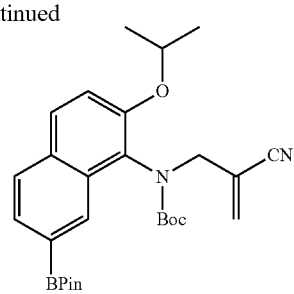

A mixture of tert-butyl N-(7-bromo-2-isopropoxy-1-naphthyl)-N-(2-cyanoallyl)carbamate (1 g, 2.25 mmol, 1 eq), 4,4,5,5-tetramethyl-2-(4,4,5,5-tetramethyl-1,3,2-dioxaborolan-2-yl)-1,3,2-dioxaborolane (1.14 g, 4.49 mmol, 2 eq), KOAc (661.1 mg, 6.74 mmol, 3 eq) and Pd(dppf)Cl₂ (164.3 mg, 224.54 μmol, 0.1 eq) in dioxane (50 mL) was degassed and purged with N₂ 3 times, and the mixture was stirred at 100° C. for 1 hr under N₂ atmosphere. The reaction mixture was filtered, and concentrated in vacuo to afford the title compound (2.2 g, crude), which was used in the next step without further purification.

Preparation of tert-butyl N-(2-cyanoallyl)-N-[2-isopropoxy-7-[6-[(1-methyl-4-piperidyl)carbamoyl]-2-pyridyl]-1-naphthyl]carbamate

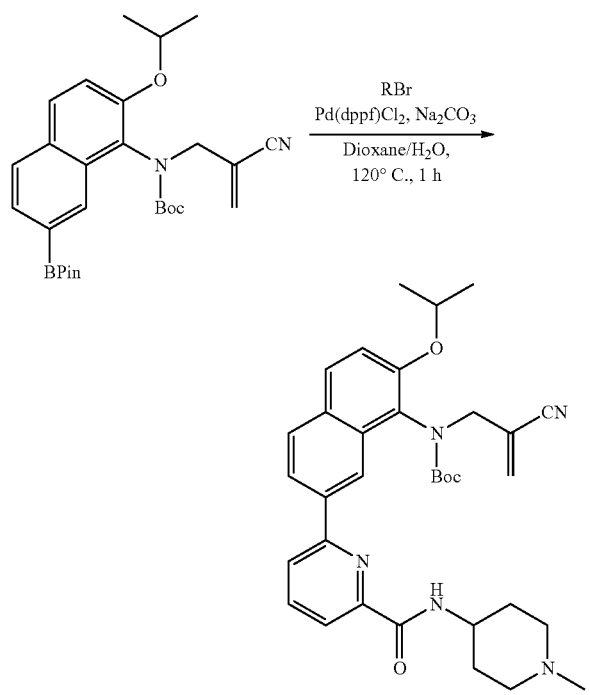

A mixture of tert-butyl N-(2-cyanoallyl)-N-[2-hydroxy-7-(4,4,5,5-tetramethyl-1,3,2-dioxaborolan-2-yl)-1-naphthyl]carbamate (100 mg, 222.06 μmol, 1 eq), 6-bromo-N-(1-methyl-4-piperidyl)pyridine-2-carboxamide (99.3 mg, 333.09 μmol, 1.5 eq), Na₂CO₃ (70.6 mg, 666.17 μmol, 3 eq), and Pd(dppf)Cl₂ (16.3 mg, 22.21 μmol, 0.1 eq) in dioxane (4 mL) and H₂O (1 mL) was degassed and purged with N₂ 3 times, and the mixture was stirred at 120° C. for 1 hr under N₂ atmosphere. TLC showed that the reaction was complete. The reaction mixture was poured into saturated EDTA (50 mL) and stirred at 25° C. for 1 h. Then the aqueous phase was extracted with EtOAc (3×50 mL). The combined organic layer were washed with H₂O (3×50 mL) and brine (3×50 mL), dried over anhydrous Na₂SO₄, filtered, and concentrated in vacuo to give a residue. The residue was purified by prep-TLC (SiO₂, DCM:MeOH=10:1) to afford the title compound (60 mg, 102.79 μmol, 46.29% yield) as a light yellow solid.

Compound 244: Preparation of 6-[8-(2-cyanoallylamino)-7-isopropoxy-2-naphthyl]-N-(1-methyl-4-piperidyl)pyridine-2-carboxamide

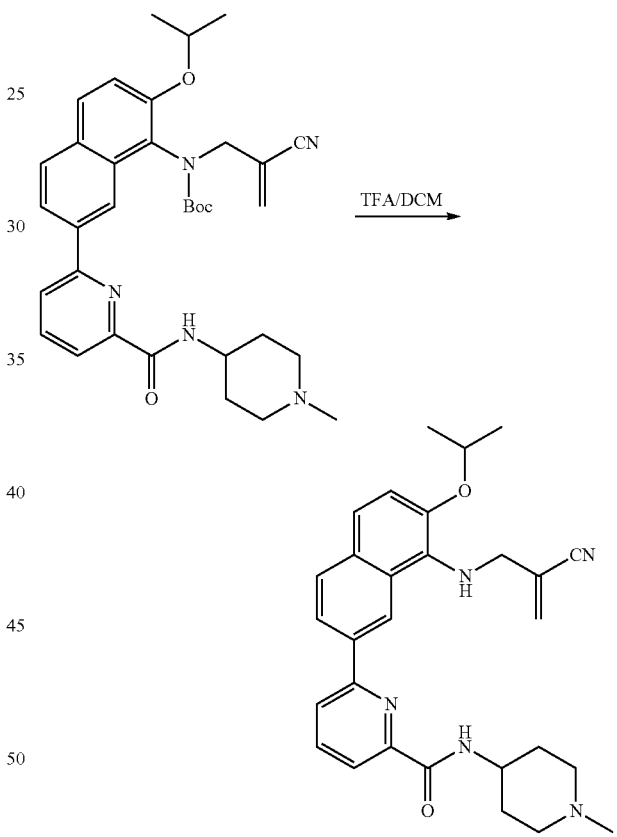

To a solution of tert-butyl N-(2-cyanoallyl)-N-[2-isopropoxy-7-[6-[(1-methyl-4-piperidyl)carbamoyl]-2-pyridyl]-1-naphthyl]carbamate (50 mg, 85.66 μmol, 1 eq) in DCM (5 mL) was added TFA (7.7 g, 67.53 mmol, 5 mL, 788.37 eq). The mixture was stirred at 25° C. for 1 hr. The reaction mixture was quenched with ice water (10 mL) and saturated Na₂CO₃ was add to adjust pH=8. The mixture was extracted with DCM (3×15 mL). The combined organic layer was washed with brine (10 mL), dried over anhydrous Na₂SO₄, filtered, and concentrated in vacuo. The residue was purified by prep-HPLC to afford the title compound (8.6 mg, 17.78 μmol, 20.76% yield, 100% purity) as a white solid.

Route 4: General Scheme (Examples 245-253)

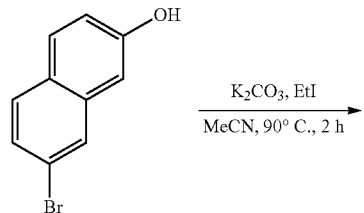

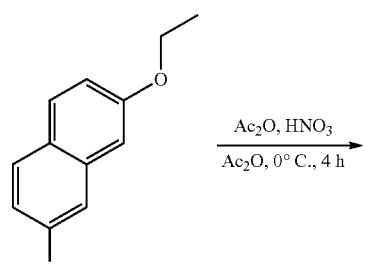

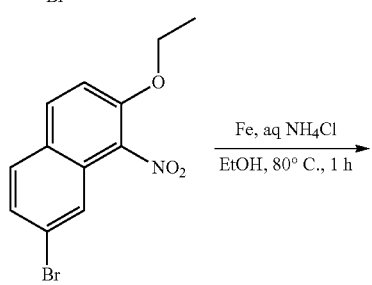

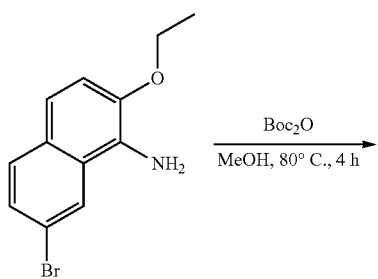

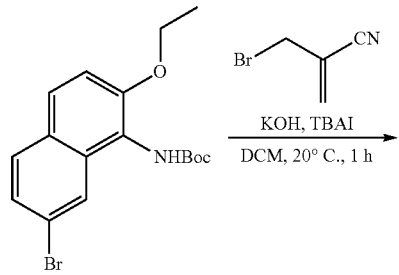

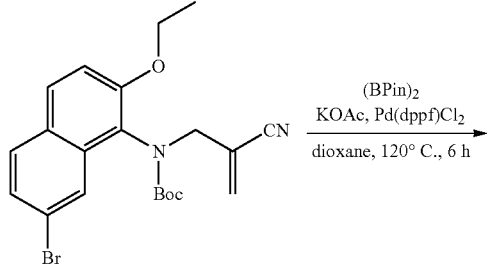

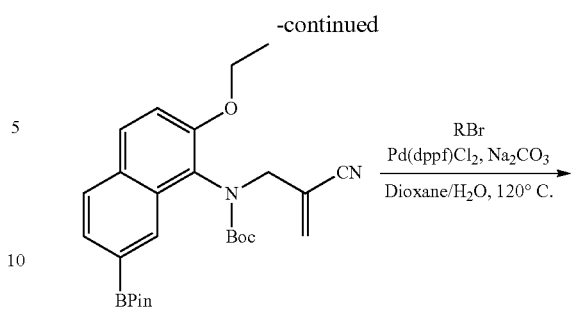

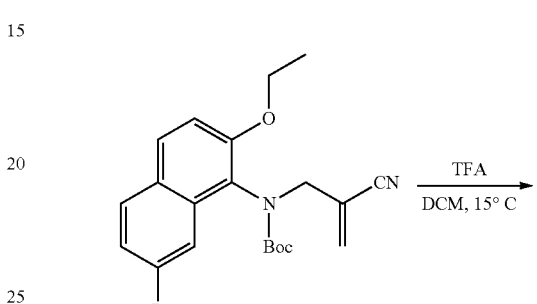

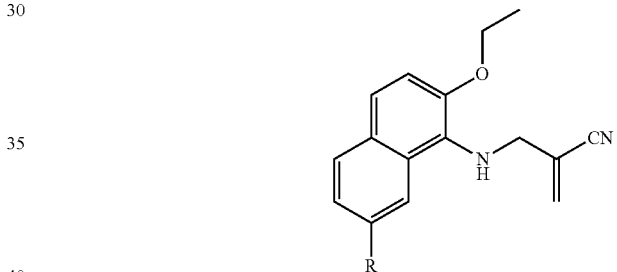

Preparation of 2-bromo-7-ethoxy-naphthalene

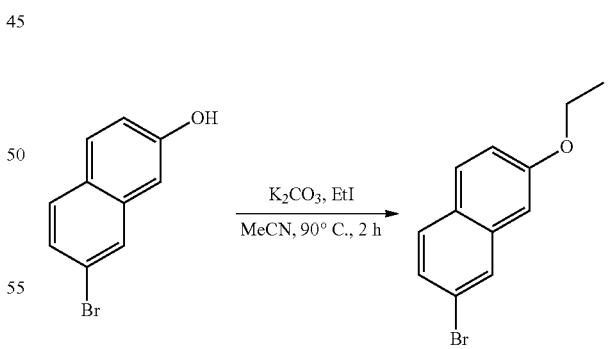

To a mixture of 7-bromonaphthalen-2-ol (5. g, 22.4 mmol, 1 eq), EtI (5.2 g, 33.6 mmol, 1.5 eq) and $K_2CO_3$ (9.3 g, 67.2 mmol, 3 eq) in MeCN (100 mL). Then the mixture was heated to 90° C. and stirred for 2 hours. Upon completion of the reaction as indicated by TLC, to the reaction mixture was added 30 mL $H_2O$. Then filtered, and concentrated in vacuo to afford the title compound (5.5 g, crude) as a light yellow solid.

Preparation of 7-bromo-2-ethoxy-1-nitro-naphthalene

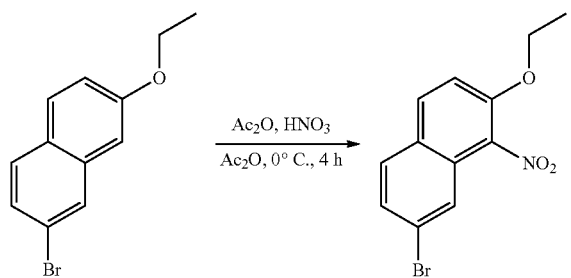 [SMILES: CCOc1ccc2ccc(Br)cc2c1 ; CCOc1ccc2ccc(Br)cc2c1[N+](=O)[O-]]

To a solution of 2-bromo-7-ethoxy-naphthalene (5. g, 19.9 mmol, 1 eq) in $Ac_2O$ (50 mL) was added $HNO_3$ (3.1 g, 29.9 mmol, 60% purity, 1.5 eq). The mixture was stirred at 0° C. for 4 hours. The reaction mixture was filtered, and concentrated in vacuo to give a residue. The residue was washed with PE (3×10 mL) to afford the title compound (3.6 g, 12.2 mmol, 61.1% yield) as a light yellow solid.

Preparation of 7-bromo-2-ethoxy-naphthalen-1-amine

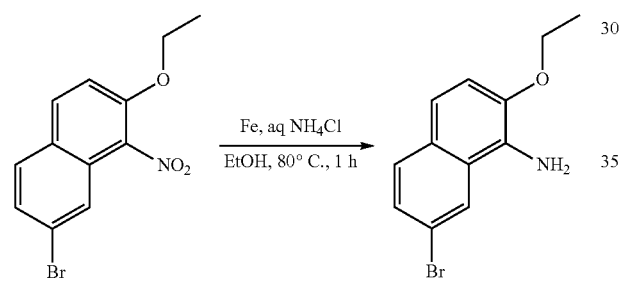

A mixture of 7-bromo-2-ethoxy-1-nitro-naphthalene (3.6 g, 12.2 mmol, 1 eq), $NH_4Cl$ (455.2 mg, 8.5 mmol, 0.7 eq) in EtOH (70 mL) and $H_2O$ (10 mL) was added Le (3.4 g, 60.8 mmol, 5 eq) in portions at 80° C. The mixture was stirred at 80° C. for 1 hour. The reaction mixture was filtered, and concentrated in vacuo to give a residue. The residue was purified by column chromatography ($SiO_2$, PE:EtOAc=50/1 to 20/1) to afford the title compound (2.8 g, 10.5 mmol, 86.5% yield) as a light yellow solid.

Preparation of tert-butyl N-(7-bromo-2-ethoxy-1-naphthyl)carbamate

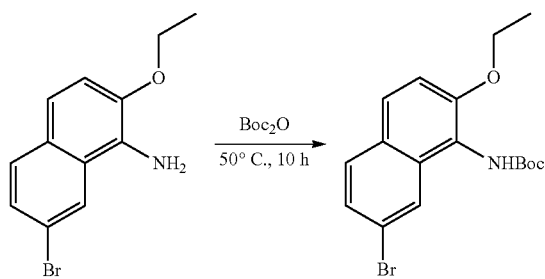 [SMILES: "Boc2O" ; CCOc1ccc2ccc(Br)cc2c1N ; CCOc1ccc2ccc(Br)cc2c1NC(=O)OC(C)(C)C]

A solution of 7-bromo-2-ethoxy-naphthalen-1-amine (2.8 g, 10.5 mmol, 1 eq) in $Boc_2O$ (50 mL) was stirred at 50° C. for 10 hours. The reaction mixture was added to 10 mL N',N'-dimethylethane-1,2-diamine and stirred for 1 hour. Then 50 mL $H_2O$ was added and extracted with EtOAc (3×30 mL). The organic phase was separated, washed with $H_2O$ (2×30 mL) and brine (2×30 mL), dried over anhydrous $Na_2SO_4$, filtered, and concentrated in vacuo to give a residue. The residue was purified by column chromatography ($SiO_2$, PE:EtOAc=30:1 to 10:1) to afford the title compound (2.9 g, 7.9 mmol, 75.3% yield) as a light yellow solid.

Preparation of tert-butyl N-(7-bromo-2-ethoxy-1-naphthyl)-N-(2-cyanoallyl)carbamate

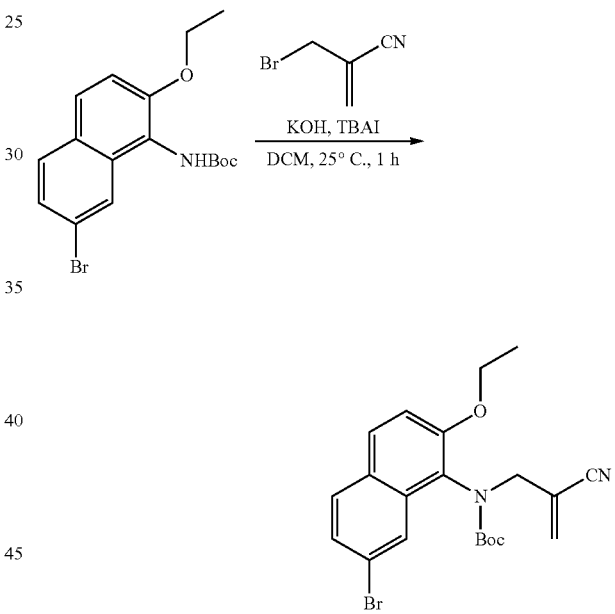

A mixture of tert-butyl N-(7-bromo-2-ethoxy-1-naphthyl)carbamate (2. g, 5.5 mmol, 1 eq), 2-(bromomethyl)prop-2-enenitrile (956.6 mg, 6.6 mmol, 1.2 eq), KOH (612.8 mg, 10.9 mmol, 2 eq), and TBAI (806.8 mg, 2.2 mmol, 0.4 eq) in DCM (20 mL) was stirred at 25° C. for 1 hour. The reaction mixture was poured into $H_2O$ (100 mL) and extracted with DCM (3×50 mL). The organic phase was separated, washed with $H_2O$ (2×30 mL) and brine (2×30 mL), dried over anhydrous $Na_2SO_4$, filtered, and concentrated in vacuo to give a residue. The residue was purified by column chromatography ($SiO_2$, PE:EtOAc=50:1 to 10:1) to afford the title compound (2. g, 4.6 mmol, 84.9% yield) as a light yellow solid.

Preparation of tert-butyl N-(2-cyanoallyl)-N-[2-ethoxy-7-(4,4,5,5-tetramethyl-1,3,2-dioxaborolan-2-yl)-1-naphthyl]carbamate

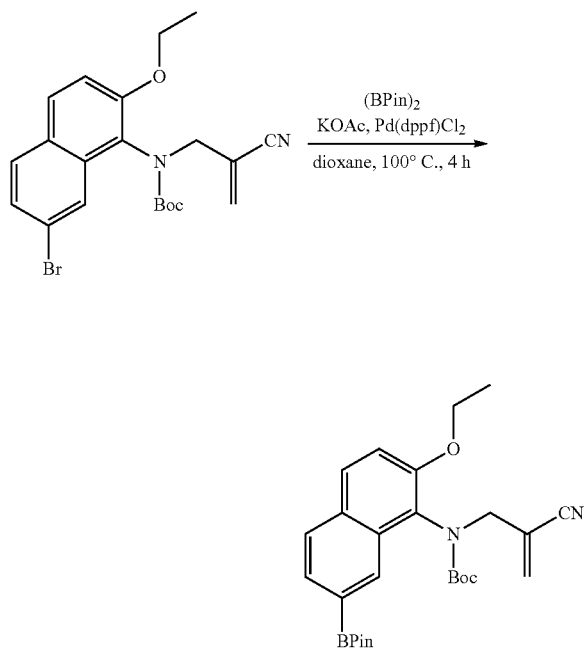

A mixture of tert-butyl N-(7-bromo-2-ethoxy-1-naphthyl)-N-(2-cyanoallyl)carbamate (2. g, 4.6 mmol, 1 eq), (BPin)$_2$ (5.9 g, 23.2 mmol, 5 eq), AcOK (2.3 g, 23.2 mmol, 5 eq), and Pd(dppf)Cl$_2$ (339.3 mg, 463.7 μmol, 0.1 eq) in dioxane (10 mL) was stirred at 100° C. for 4 hours. LCMS/TLC showed that the reaction was complete. The reaction mixture was filtered and concentrated in vacuo to give a residue. The residue was purified by column chromatography (SiO$_2$, PE:EtOAc=40:1 to 10:1) to afford the title compound (1.9 g, 3.9 mmol, 85.6% yield) as a light yellow solid. LC-MS (ES$^+$, m/z): 423.2 [(M-tBu)$^+$].

Preparation of tert-butyl N-(2-cyanoallyl)-N-[2-ethoxy-7-[4-[(1-methyl-4-piperidyl) carbamoyl]pyrimidin-2-yl]-1-naphthyl]carbamate

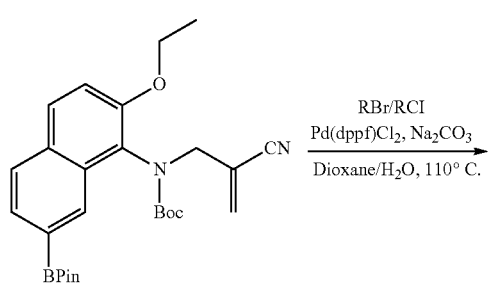

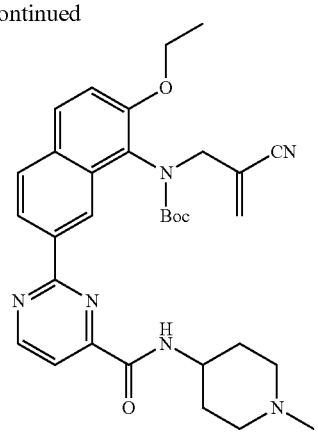

A mixture of tert-butyl N-(2-cyanoallyl)-N-[2-ethoxy-7-(4,4,5,5-tetramethyl-1,3,2-dioxaborolan-2-yl)-1-naphthyl]carbamate (100 mg, 209.04 μmol, 1 eq), 2-chloro-N-(1-methyl-4-piperidyl)pyrimidine-4-carboxamide (85.2 mg, 334.46 μmol, 1.6 eq), Na$_2$CO$_3$ (66.5 mg, 627.11 μmol, 3 eq), and Pd(dppf)Cl$_2$ (15.3 mg, 20.9 μmol, 0.1 eq) in dioxane (2 mL) and H$_2$O (0.5 mL) was degassed and purged with N$_2$ 3 times. The mixture was stirred at 110° C. for 2 hr under N$_2$ atmosphere. LCMS showed that the reaction was complete. To the reaction mixture was added 50 mL saturated EDTA and stirred for 1 h, and was then extracted with EtOAc (3×30 mL). The organic phase was separated, washed with H$_2$O (2×30 mL) and brine (2×30 mL), dried over anhydrous Na$_2$SO$_4$, filtered, and concentrated in vacuo to give a residue. The residue was purified by prep-TLC (SiO$_2$, DCM: MeOH=10:1) to afford the title compound tert-butyl N-(2-cyanoallyl)-N-[2-ethoxy-7-[4-[(1-methyl-4-piperidyl)carbamoyl]pyrimidin-2-yl]-1-naphthyl]carbamate (80 mg, 140.18 μmol, 67.06% yield) as a light yellow oil.

Compound 248: Preparation of 2-[8-(2-cyanoallylamino)-7-ethoxy-2-naphthyl]-N-(1-methyl-4-piperidyl)pyrimidine-4-carboxamide

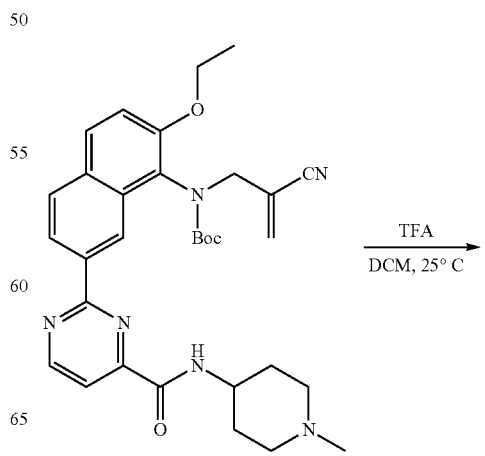

-continued

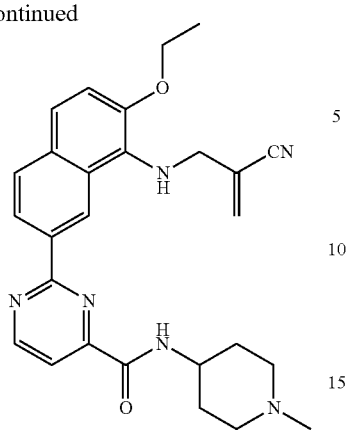

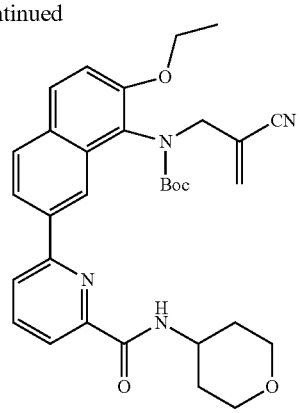

To a solution of tert-butyl N-(2-cyanoallyl)-N-[2-ethoxy-7-[4-[(1-methyl-4-piperidyl) carbamoyl]pyrimidin-2-yl]-1-naphthyl]carbamate (70 mg, 122.66 µmol, 1 eq) in DCM (3 mL) was added TFA (1 mL) dropwise. The mixture was stirred at 25° C. for 1 hr. LCMS showed the reaction was completed. The reaction mixture was poured into ice water (30 mL). Then saturated Na2CO3 was slowly added to adjust the solution to pH=8~9. The mixture was extracted with DCM (3×30 mL). The organic phase was separated, washed with H2O (2×30 mL) and brine (2×30 mL), dried over anhydrous Na2SO4, filtered, and concentrated in vacuo to give a residue. The residue was purified by prep-HPLC to afford the title compound 2-[8-(2-cyanoallylamino)-7-ethoxy-2-naphthyl]-N-(1-methyl-4-piperidyl)pyrimidine-4-carboxamide (11.4 mg, 24.23 µmol, 19.75% yield, 100% purity) as a light yellow solid.

Preparation of tert-butyl N-(2-cyanoallyl)-N-[2-ethoxy-7-[6-(tetrahydropyran-4-ylcarbamoyl)-2-pyridyl]-1-naphthyl]carbamate To a solution of tert-butyl N-(2-cyanoallyl)-N-[2-ethoxy-7-(4,4,5,5-tetramethyl-1,3,2-dioxaborolan-2-yl)-1-naphthyl]carbamate (50 mg, 105 µmol) in dioxane (2 mL) and water (0.4 mL) were added 6-bromo-N-tetrahydropyran-4-yl-pyridine-2-carboxamide (44.8 mg, 157 µmol), Cs2CO3 (102 mg, 315 µmol) and PdCl2dppf (18 mg, 22.06 µmol). The reaction was heated at 100° C. for 30 min in a microwave. The reaction mixture was passed through a celite pad, and 2 mL of 0.5M EDTA was added. The resulting solution was stirred at r.t. for 40 min. The solution was washed with brine, dried over anhydrous sodium sulfate, filtered, and concentrated in vacuo. The residue was purified by chromatography on silica gel eluting with 10-80% EtOAc/Hexane to afford the title compound (56.9 mg, Yield 97%).

Compound 245: Preparation of 6-[8-(2-cyanoallylamino)-7-ethoxy-2-naphthyl]-N-tetrahydropyran-4-yl-pyridine-2-carboxamide

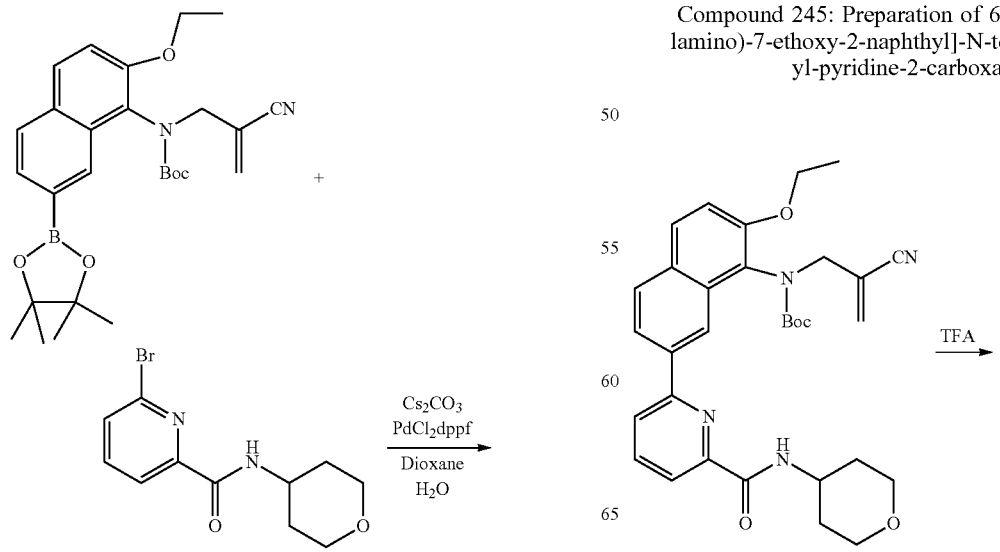

269
-continued

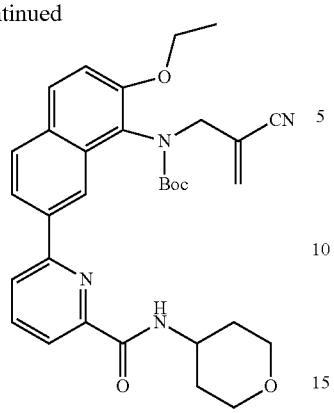

To a solution of tert-butyl N-(2-cyanoallyl)-N-[2-ethoxy-7-[6-(tetrahydropyran-4-ylcarbamoyl)-2-pyridyl]-1-naphthyl]carbamate (56.9 mg, 102. μmol) in DCM (2 mL) was added TFA (0.5 mL) at 0° C. The resulting solution was stirred at 0° C. for 1 hour and r.t. for 1 h. The reaction mixture was concentrated in vacuo and the residue was diluted with DCM. The solution was washed with saturated NaHCO$_3$ and brine, dried over anhydrous sodium sulfate, filtered, and concentrated. The residue was purified by chromatography on silica gel eluting with 10-90% EtOAc/Hexane to afford the title compound (15 mg, Yield 32%). LC-MS (ES$^+$, m/z): 457 [(M+H)$^+$].

Preparation of tert-butyl N-(2-cyanoallyl)-N-[2-ethoxy-7-[6-[[1-(2-methoxyethyl)-4-piperidyl]carbamoyl]-2-pyridyl]-1-naphthyl]carbamate

270
-continued

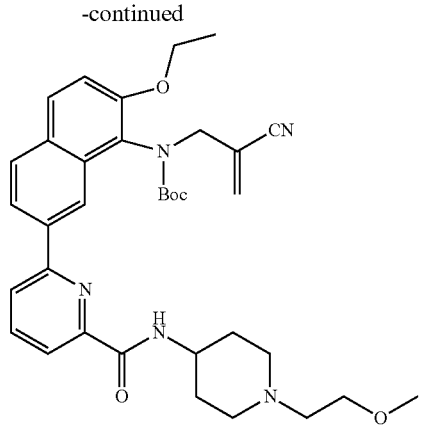

To a solution of tert-butyl N-(2-cyanoallyl)-N-[2-ethoxy-7-(4,4,5,5-tetramethyl-1,3,2-dioxaborolan-2-yl)-1-naphthyl]carbamate (50 mg, 105 μmol) in dioxane (2 mL) and water (0.4 mL) were added 6-bromo-N-[1-(2-methoxyethyl)-4-piperidyl]pyridine-2-carboxamide (53.7 g, 157 mmol), Cs$_2$CO$_3$ (102 mg, 314 μmol) and PdCl$_2$dppf (18 mg, 22.06 μmol). The reaction was heated at 100° C. for 30 min in a microwave. The reaction mixture was passed through a celite pad, and 2 mL of 0.5M EDTA was added. The resulting solution was stirred at r.t. for 40 min. The solution was washed with brine, dried over anhydrous sodium sulfate, filtered, and concentrated in vacuo. The residue was purified by chromatography on silica gel eluting with 0-20% MeOH/EtOAc to afford the title compound (46.4 mg, Yield 72%).

Compound 246: Preparation of 6-[8-(2-cyanoallylamino)-7-ethoxy-2-naphthyl]-N-[1-(2-methoxyethyl)-4-piperidyl]pyridine-2-carboxamide

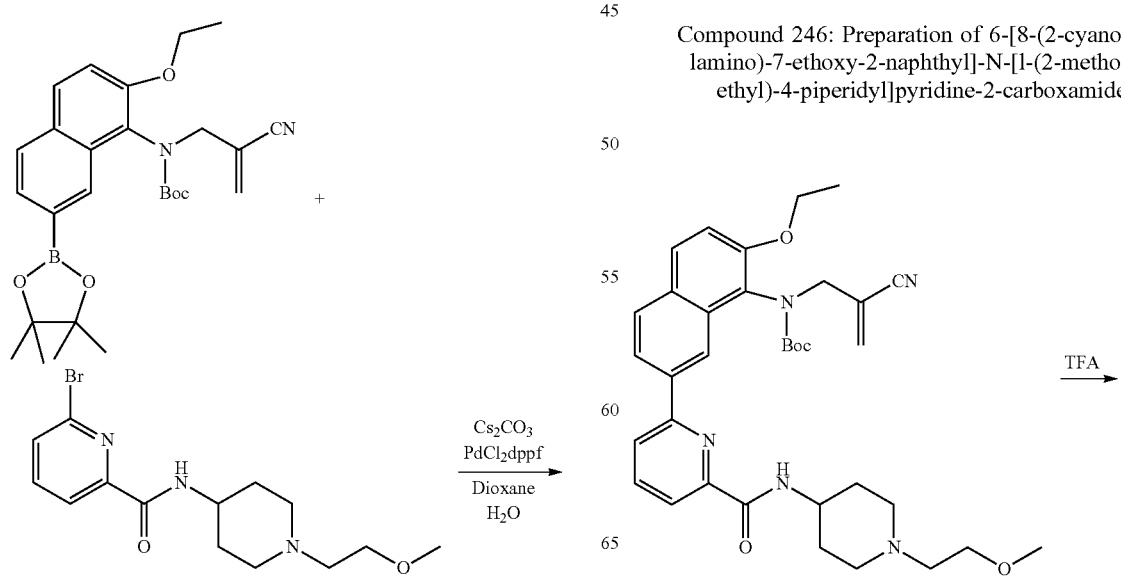

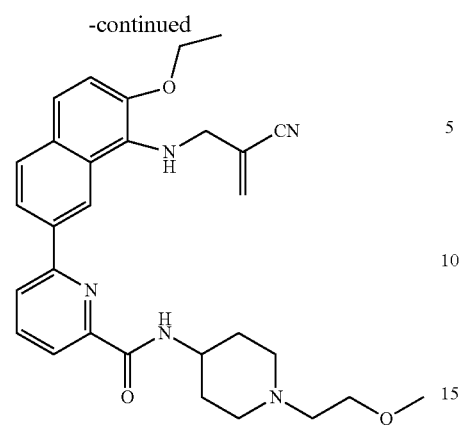

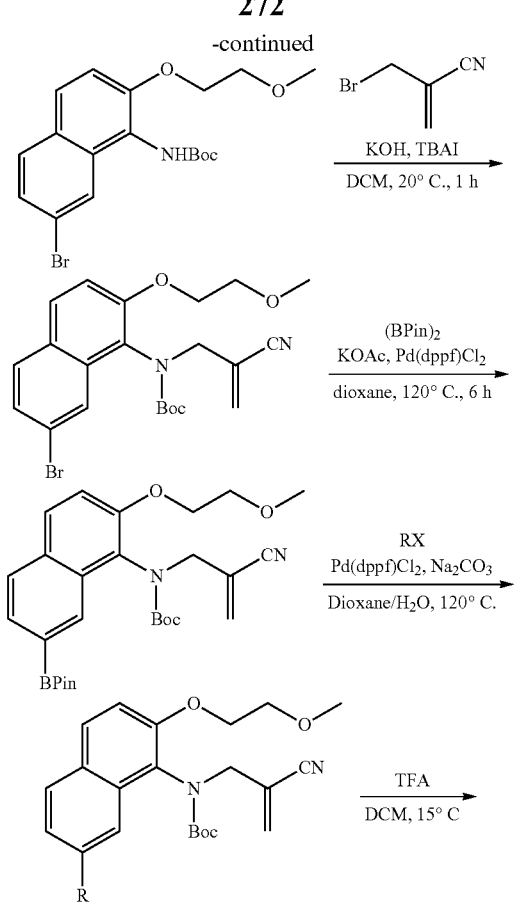

To a solution of tert-butyl N-(2-cyanoallyl)-N-[2-ethoxy-7-[6-[[1-(2-methoxyethyl)-4-piperidyl]carbamoyl]-2-pyridyl]-1-naphthyl]carbamate (46.4 mg, 75.7 μmol) in DCM (2 mL) was added TFA (0.5 mL) at 0° C. The resulting solution was stirred at 0° C. for 1 hour and r.t. for 1 h. The reaction mixture was concentrated in vacuo and the residue was diluted with DCM. The mixture was washed with saturated NaHCO$_3$ and brine, dried over anhydrous sodium sulfate, filtered, and concentrated. The residue was purified by reverse phase HPLC using a gradient of water 0.1% FA/acetonitrile 0.1% FA to afford the title compound (6 mg, Yield 15%). LC-MS (ES$^+$, m/z): 514 [(M+H)$^+$]

Route 5: General Scheme (Examples 254-256)

Preparation of 2-bromo-7-(2-methoxyethoxy)naphthalene

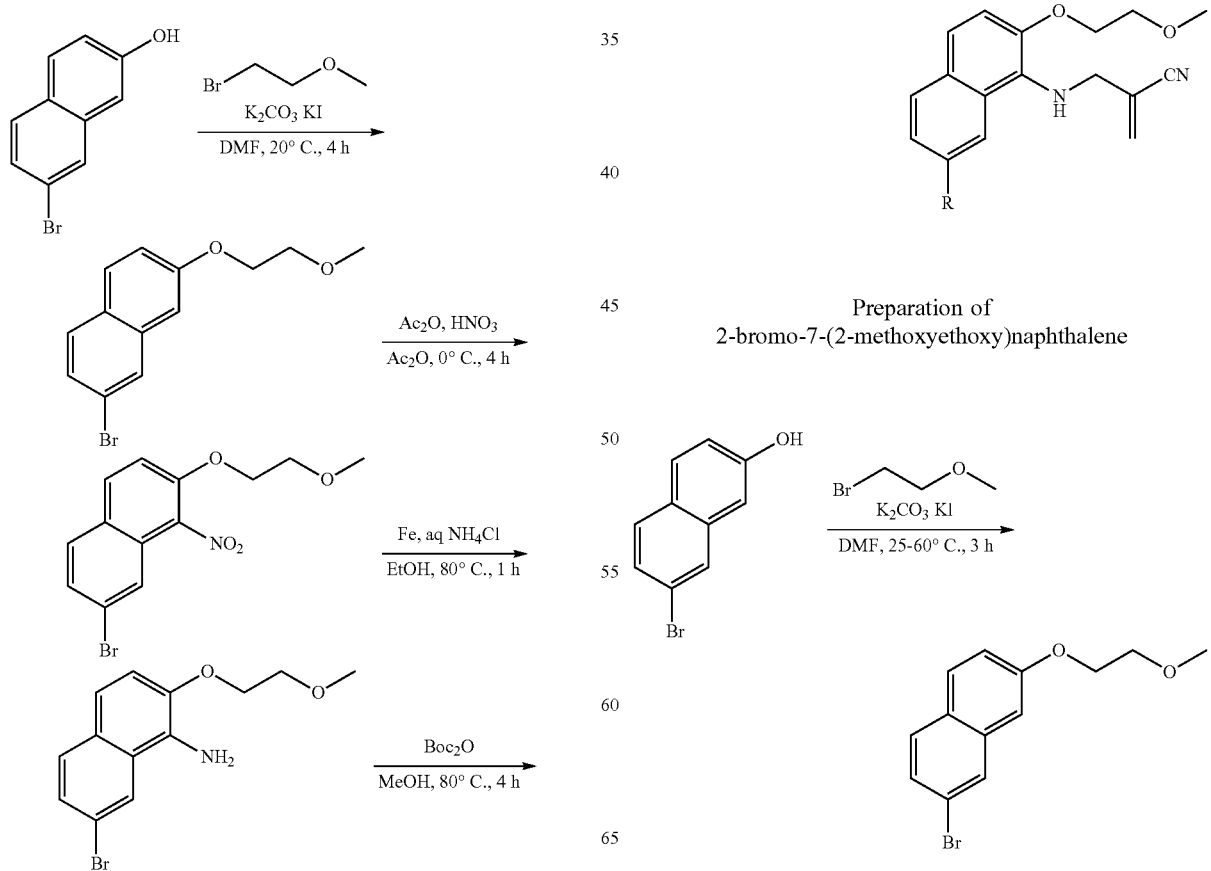

To a mixture of 7-bromonaphthalen-2-ol (1 g, 4.48 mmol, 1 eq) and 1-bromo-2-meth oxyethane (934.6 mg, 6.72 mmol, 631 μL, 1.5 eq) in DMF (25 mL) were added K$_2$CO$_3$ (1.86 g, 13.45 mmol, 3 eq) and KI (744.2 mg, 4.48 mmol, 1 eq) in one portion at 25° C. under N$_2$. Then, 1-bromo-2-methoxy-ethane (934.6 mg, 6.72 mmol, 631 μL, 1.5 eq) was added to the mixture. The mixture was stirred at 60° C. for 3 hours. The reaction was poured into ice water (100 mL) and extracted with EtOAc (3×100 mL). The combined organic layer was washed with brine (3×50 mL), dried over anhydrous Na$_2$SO$_4$ and concentrated in vacuo to afford the title compound (1 g, crude) as a yellow solid, which was used directly. LC-MS (ES$^+$, m/z): 377.2 [(M+H)$^+$].

Preparation of 7-bromo-2-(2-methoxyethoxy)-1-nitronaphthalene

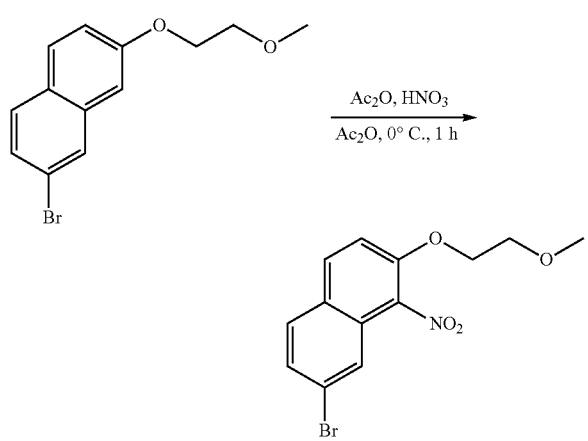

To a mixture of 2-bromo-7-(2-methoxyethoxy)naphthalene (1 g, 3.56 mmol, 1 eq) in Ac$_2$O (10 mL) was added HNO$_3$ (410.9 mg, 3.91 mmol, 293.50 μL, 60% purity, 1.1 eq) in one portion at 0° C. under N$_2$. The mixture was stirred at 0° C. for 1 hour. The reaction was filtered in vacuo to obtain crude product. The residue was washed with PE (3×50 mL) to afford the title compound as a yellow solid. (0.6 g, 1.84 mmol, 52% yield)

Preparation of 7-bromo-2-(2-methoxyethoxy)naphthalen-1-amine

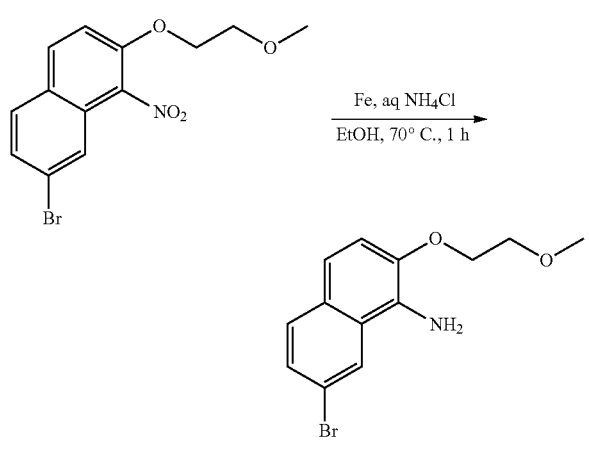

To a mixture of 7-bromo-2-(2-methoxyethoxy)-1-nitronaphthalene (0.6 g, 1.84 mmol, 1 eq) in EtOH (8 mL) was added saturated NH$_4$Cl (2 mL). Then the mixture was heated to 70° C. Le (513.7 mg, 9.2 mmol, 5 eq) was added in one portion at 70° C. The mixture was stirred at 70° C. for 1 hour. The reaction was filtered in vacuo and the filtrate was concentrated in vacuo. The residue was purified by column chromatography (SiO$_2$, PE:EtOAc=1:0 to 4:1) to afford the title compound as a yellow solid. (0.4 g, 1.35 mmol, 73% yield).

Preparation of tert-butyl N-[7-bromo-2-(2-methoxyethoxy)naphthalen-1-yl]carbamate

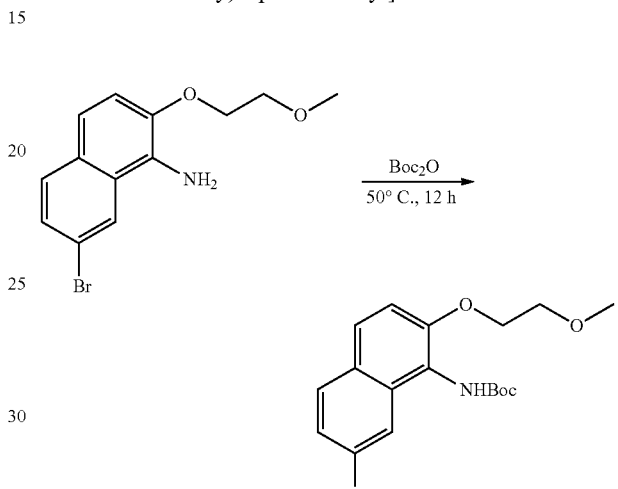

To a mixture of 7-bromo-2-(2-methoxyethoxy)naphthalen-1-amine (0.4 g, 1.35 mmol, 1 eq) was added (Boc)$_2$O (10 mL) in one portion at 50° C. under N$_2$. The mixture was stirred at 50° C. for 12 hours. LCMS showed that the reaction was complete. N1,N1-dimethyl ethane-1,2-diamine (4 mL) was added to the reaction mixture and stirred at 25° C. for 1 hour. Then the reaction was poured into water (100 mL) and extracted with EtOAc (3×30 mL). The combined organic layer was dried over anhydrous Na$_2$SO$_4$, concentrated in vacuo. The crude product was used directly without further purification to afford the title compound (0.5 g, crude) as a yellow solid. LC-MS (ES$^+$, m/z): 296.0 [(M+H)$^+$].

Preparation of tert-butyl N-[7-bromo-2-(2-methoxyethoxy)naphthalen-1-yl]-N-(2-cyano-2-methylideneethyl)carbamate

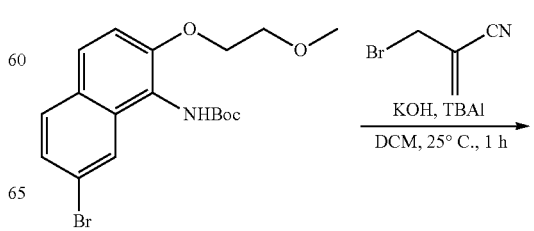

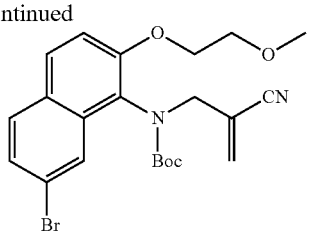

To a mixture of tert-butyl N-[7-bromo-2-(2-methoxyethoxy)naphthalen-1-yl]carbamate (0.45 g, 1.14 mmol, 1 eq) in DCM (20 mL) were added KOH (127.4 mg, 2.27 mmol, 2 eq) and TBAI (209.7 mg, 567.79 µmol, 0.5 eq) in one portion at 25° C. under $N_2$. Then, 2-(bromomethyl)prop-2-enenitrile (248.7 mg, 1.7 mmol, 1.5 eq) was added, and the mixture was stirred at 25° C. for 1 hour. The reaction was poured into ice water (100 mL) and extracted with DCM (3×50 mL). The combined organic layer was dried over anhydrous $Na_2SO_4$, filtered, and concentrated in vacuo. The residue was purified by prep-TLC ($SiO_2$, PE:EtOAc=3:1) to afford the title compound (0.45 g, 975.4 µmol, 86% yield) as a colorless oil. LC-MS ($ES^+$, m/z): 361.0.

Preparation of tert-butyl N-(2-cyano-2-methylideneethyl)-N-[2-(2-methoxyethoxy)-7-(4,4,5,5-tetramethyl-1,3-dioxolan-2-yl)naphthalen-1-yl]carbamate

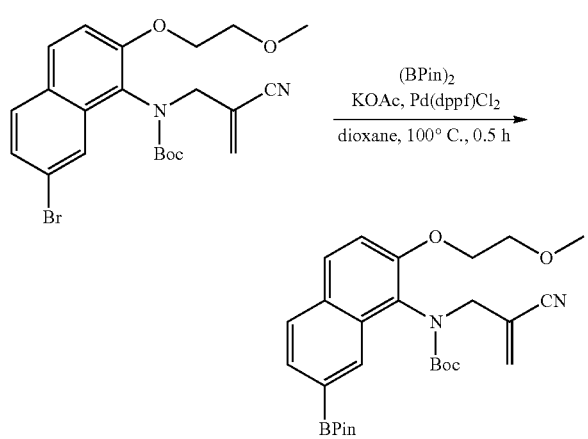

To a mixture of tert-butyl N-[7-bromo-2-(2-methoxyethoxy)naphthalen-1-yl]-N-(2-cyano-2-methylideneethyl) carbamate (0.2 g, 433.51 µmol, 1.0 eq) and $(BPin)_2$ (165.1 mg, 650.27 µmol, 1.5 eq) in dioxane (15 mL) were added KOAc (127.6 mg, 1.3 mmol, 3 eq) and $Pd(dppf)Cl_2$ (31.7 mg, 43.35 µmol, 0.1 eq) in one portion at 100° C. under $N_2$. The mixture was stirred at 100° C. for 0.5 hours. The reaction mixture was concentrated in vacuo. The residue was purified by prep-TLC ($SiO_2$, PE:EtOAc=2:1) to afford the title compound (0.2 g, 393.38 µmol, 91% yield) as a yellow oil.

Preparation of tert-butyl N-(2-cyano-2-methylideneethyl)-N-[2-(2-methoxyethoxy)-7-(4-{[(1r,4r)-4-(dimethylamino)cyclohexyl]carbamoyl}pyrimidin-2-yl)naphthalen-1-yl]carbamate and tert-butyl N-(2-cyano-2-methylideneethyl)-N-[2-(2-methoxyethoxy)-7-(4-{[(1s,4s)-4-(dimethylamino)cyclohexyl]carbamoyl}pyrimidin-2-yl)naphthalen-1-yl]carbamate

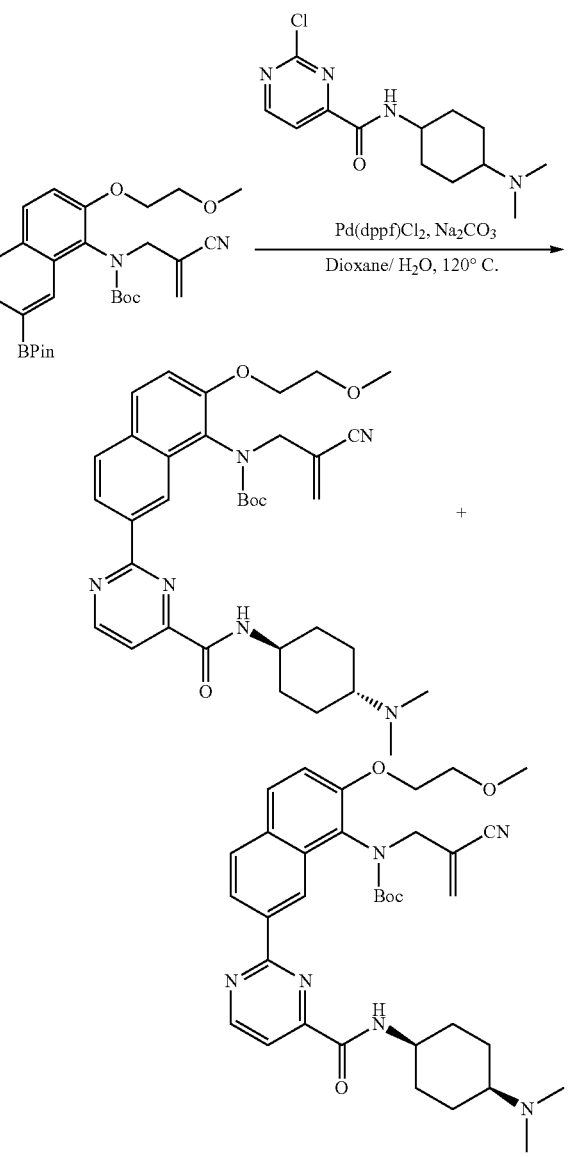

To a mixture of tert-butyl N-(2-cyanoallyl)-N-[2-(2-methoxyethoxy)-7-(4,4,5,5-tetramethyl-1,3,2-dioxaborolan-2-yl)-1-naphthyl]carbamate (0.2 g, 393.38 µmol, 1 eq) and 2-chloro-N-[4-(dimethylamino)cyclohexyl]pyrimidine-4-carboxamide (222.5 mg, 786.76 µmol, 2 eq) in dioxane (4 mL) and $H_2O$ (1 mL). Then added $Na_2CO_3$ (125.1 mg, 1.18 mmol, 3 eq) and $Pd(dppf)Cl_2$ (28.8 mg, 39.34 µmol, 0.1 eq). The reaction was heated to 120° C. under $N_2$ and stirred for 1 h. LCMS showed that the reaction was complete. To the reaction mixture was added saturated EDTA (50 mL) and EtOAc (50 mL) at 25° C. Then stirred at 25° C. for 1 h. Then the mixture was extracted with EtOAc (2×50 mL), washed with H$_2$O (2×50 mL) and brine (2×50 mL), dried over anhydrous Na$_2$SO$_4$, filtered, and concentrated in vacuo to give a residue. The residue was purified by prep-TLC (SiO$_2$, DCM:MeOH=6:1) to afford tert-butyl N-(2-cyano-2-methylideneethyl)-N-[2-(2-methoxyethoxy)-7-(4-{[(1r,4r)-4-(dimethylamino)cyclohexyl]carbamoyl}pyrimidin-2-yl)naphthalen-1-yl]carbamate (80 mg, 127.23 μmol, 32.34% yield) as a yellow oil. LC-MS (ES$^+$, m/z): 629.3 [(M+H)$^+$]; and tert-butyl N-(2-cyano-2-methylideneethyl)-N-[2-(2-methoxyethoxy)-7-(4-{[(1s,4s)-4-(dimethylamino)cyclohexyl]carbamoyl}pyrimidin-2-yl)naphthalen-1-yl]carbamate (60 mg, 95.43 μmol, 24.26% yield) as a yellow oil. LC-MS (ES$^+$, m/z): 629.3 [(M+H)$^+$].

Compound 255: Preparation of 2-{8-[(2-cyano-2-methylideneethyl)amino]-7-(2-methoxyethoxy)naphthalen-2-yl}-N-[(1r,4r)-4-(dimethylamino)cyclohexyl]pyrimidine-4-carboxamide

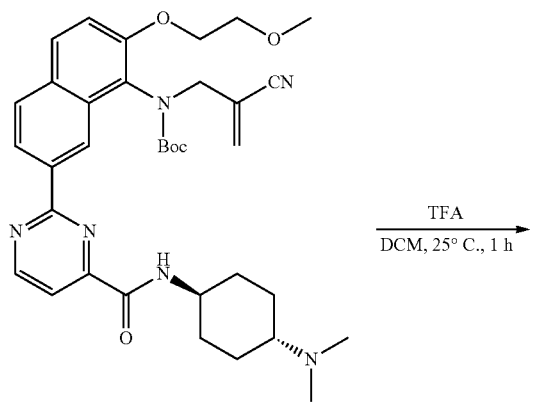

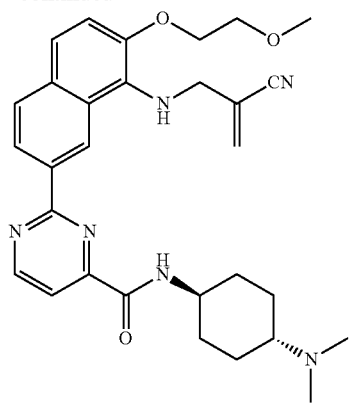

To a solution of tert-butyl N-(2-cyano-2-methylideneethyl)-N-[2-(2-methoxyethoxy)-7-(4-{[(1r,4r)-4-(dimethylamino)cyclohexyl]carbamoyl}pyrimidin-2-yl)naphthalen-1-yl]carbamate (80 mg, 127.23 μmol, 1 eq) in DCM (2 mL) was added TFA (770 mg, 6.75 mmol, 0.5 mL, 53.08 eq). The mixture was stirred at 25° C. for 1 h. LCMS showed that the reaction was complete. The reaction mixture was adjusted to pH=8 with saturated NaHCO$_3$. The mixture was extracted with DCM (2×30 mL). The combined organic layers were washed with H$_2$O (2×30 mL) and brine (2×30 mL), dried over anhydrous Na$_2$SO$_4$, filtered, and concentrated in vacuo to give a residue. The residue was purified by prep-HPLC to afford the title compound (7.5 mg, 13.41 μmol, 10% yield) as a white solid. LC-MS (ES$^+$, m/z): 529.3 [(M+H)$^+$].

TABLE 3 shows compounds synthesized using method C described in EXAMPLE 3 above.

TABLE 3

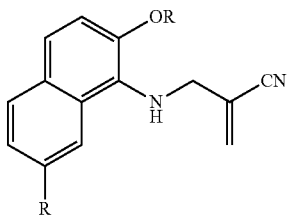

| Cpd. No. | Structure | IUPAC | LC-MS (ES+, m/z) |
|---|---|---|---|
| 231 | ![structure] | 2-({[7-(pyridin-2-yl)-2-(2,2,2-trifluoroethoxy)naphthalen-1-yl]amino}methyl)prop-2-enenitrile | 384 |

TABLE 3-continued

| Cpd. No. | Structure | IUPAC | LC-MS (ES+, m/z) |
|---|---|---|---|
| 232 | 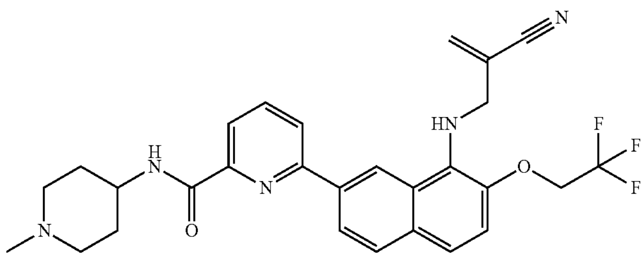 [SMILES: C=C(C#N)CNc1c(OCC(F)(F)F)ccc2ccc(-c3cccc(C(=O)NC4CCN(C)CC4)n3)cc12] | 6-{8-[(2-cyano-2-methylideneethyl)amino]-7-(2,2,2-trifluoroethoxy)naphthalen-2-yl}-N-(1-methylpiperidin-4-yl)pyridine-2-carboxamide | 524.1 |
| 233 | 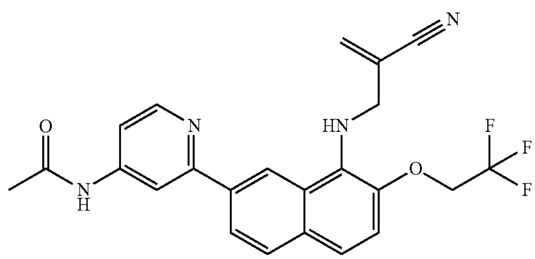 [SMILES: C=C(C#N)CNc1c(OCC(F)(F)F)ccc2ccc(-c3cc(NC(C)=O)ccn3)cc12] | N-(2-{8-[(2-cyano-2-methylideneethyl)amino]-7-(2,2,2-trifluoroethoxy)naphthalen-2-yl}pyridin-4-yl)acetamide | 441 |
| 234 | 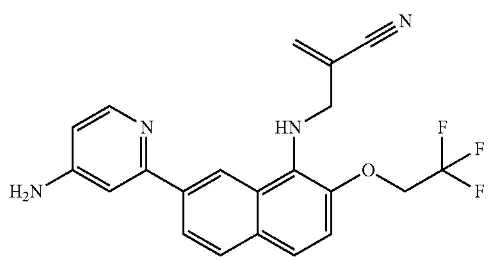 [SMILES: C=C(C#N)CNc1c(OCC(F)(F)F)ccc2ccc(-c3cc(N)ccn3)cc12] | 2-(({[7-(4-aminopyridin-2-yl)-2-(2,2,2-trifluoroethoxy)naphthalen-1-yl]amino}methyl)prop-2-enenitrile | 399 |
| 235 | 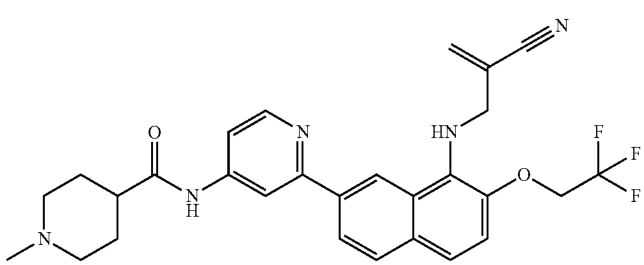 [SMILES: C=C(C#N)CNc1c(OCC(F)(F)F)ccc2ccc(-c3cc(NC(=O)C4CCN(C)CC4)ccn3)cc12] | N-(2-{8-[(2-cyano-2-methylideneethyl)amino]-7-(2,2,2-trifluoroethoxy)naphthalen-2-yl}pyridin-4-yl)-1-methylpiperidine-4-carboxamide | 524.1 |
| 236 | 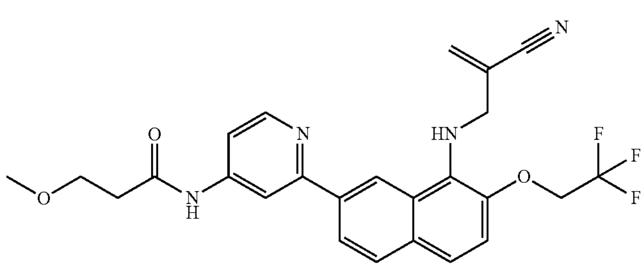 [SMILES: C=C(C#N)CNc1c(OCC(F)(F)F)ccc2ccc(-c3cc(NC(=O)CCOC)ccn3)cc12] | N-(2-{8-[(2-cyano-2-methylideneethyl)amino]-7-(2,2,2-trifluoroethoxy)naphthalen-2-yl}pyridin-4-yl)-3-methoxypropanamide | 485.2 |

TABLE 3-continued

| Cpd. No. | Structure | IUPAC | LC-MS (ES+, m/z) |
|---|---|---|---|
| 237 | 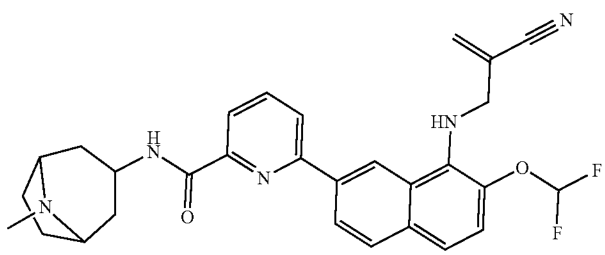 [SMILES: C=C(C#N)CNc1c(OC(F)F)ccc2ccc(-c3cccc(C(=O)NC4CC5CCC(C4)N5C)n3)cc12] | 6-{8-[(2-cyano-2-methylideneethyl)amino]-7-(difluoromethoxy)naphthalen-2-yl}-N-{8-methyl-8-azabicyclo[3.2.1]octan-3-yl}pyridine-2-carboxamide | 518.3 |
| 238 | 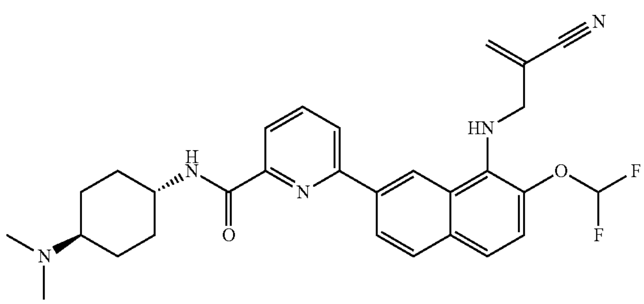 [SMILES: C=C(C#N)CNc1c(OC(F)F)ccc2ccc(-c3cccc(C(=O)N[C@H]4CC[C@H](N(C)C)CC4)n3)cc12] | 6-{8-[(2-cyano-2-methylideneethyl)amino]-7-(difluoromethoxy)naphthalen-2-yl}-N-[(1r,4r)-4-(dimethylamino)cyclohexyl]pyridine-2-carboxamide | 520.3 |
| 239 | 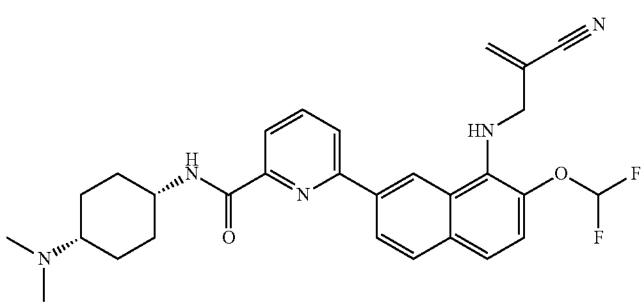 [SMILES: C=C(C#N)CNc1c(OC(F)F)ccc2ccc(-c3cccc(C(=O)N[C@H]4CC[C@@H](N(C)C)CC4)n3)cc12] | 6-{8-[(2-cyano-2-methylideneethyl)amino]-7-(difluoromethoxy)naphthalen-2-yl}-N-[(1s,4s)-4-(dimethylamino)cyclohexyl]pyridine-2-carboxamide | 520.3 |
| 240 | 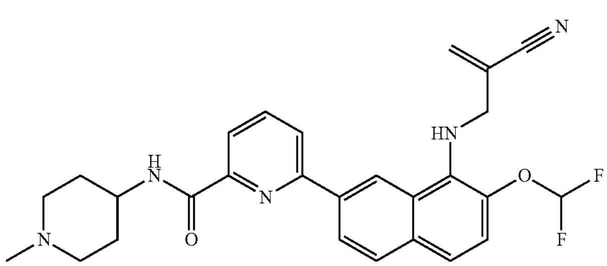 [SMILES: C=C(C#N)CNc1c(OC(F)F)ccc2ccc(-c3cccc(C(=O)NC4CCN(C)CC4)n3)cc12] | 6-{8-[(2-cyano-2-methylideneethyl)amino]-7-(difluoromethoxy)naphthalen-2-yl}-N-(1-methylpiperidin-4-yl)pyridine-2-carboxamide | 492.2 |

TABLE 3-continued

| Cpd. No. | Structure | IUPAC | LC-MS (ES+, m/z) |
|---|---|---|---|
| 241 | 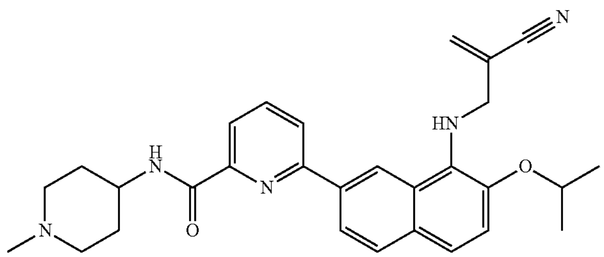 [SMILES: C=C(C#N)CNc1c(OC(C)C)ccc2ccc(-c3cccc(C(=O)NC4CCN(C)CC4)n3)cc12] | 6-{8-[(2-cyano-2-methylideneethyl)amino]-7-(propan-2-yloxy)naphthalen-2-yl}-N-(1-methylpiperidin-4-yl)pyridine-2-carboxamide | 484.3 |
| 242 | 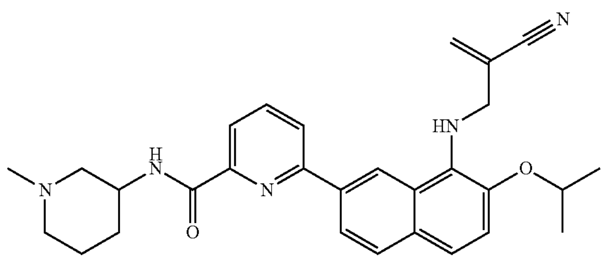 [SMILES: C=C(C#N)CNc1c(OC(C)C)ccc2ccc(-c3cccc(C(=O)NC4CCCN(C)C4)n3)cc12] | 6-{8-[(2-cyano-2-methylideneethyl)amino]-7-(propan-2-yloxy)naphthalen-2-yl}-N-(1-methylpiperidin-3-yl)pyridine-2-carboxamide | 484.3 |
| 243 | 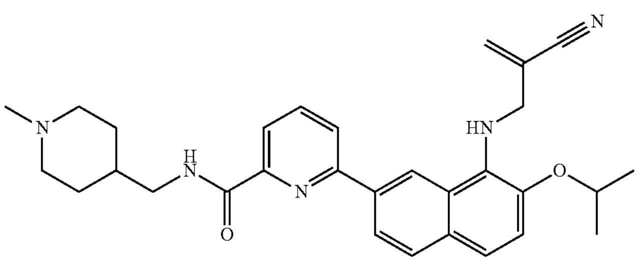 [SMILES: C=C(C#N)CNc1c(OC(C)C)ccc2ccc(-c3cccc(C(=O)NCC4CCN(C)CC4)n3)cc12] | 6-{8-[(2-cyano-2-methylideneethyl)amino]-7-(propan-2-yloxy)naphthalen-2-yl}-N-[(1-methylpiperidin-4-yl)methyl]pyridine-2-carboxamide | 498.3 |
| 244 | 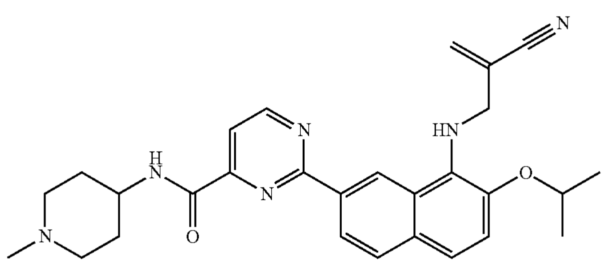 [SMILES: C=C(C#N)CNc1c(OC(C)C)ccc2ccc(-c3nccc(C(=O)NC4CCN(C)CC4)n3)cc12] | 2-{8-[(2-cyano-2-methylideneethyl)amino]-7-(propan-2-yloxy)naphthalen-2-yl}-N-(1-methylpiperidin-4-yl)pyrimidine-4-carboxamide | 485.1 |
| 245 | 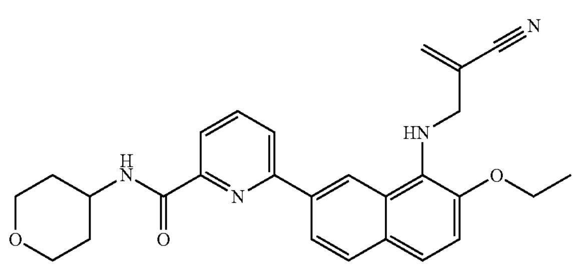 [SMILES: C=C(C#N)CNc1c(OCC)ccc2ccc(-c3cccc(C(=O)NC4CCOCC4)n3)cc12] | 6-{8-[(2-cyano-2-methylideneethyl)amino]-7-ethoxynaphthalen-2-yl}-N-(oxan-4-yl)pyridine-2-carboxamide | 457 |

TABLE 3-continued

| Cpd. No. | Structure | IUPAC | LC-MS (ES+, m/z) |
|---|---|---|---|
| 246 | 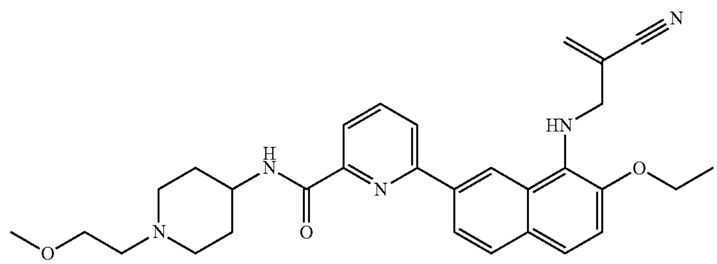 [SMILES: C=C(C#N)CNc1c(OCC)ccc2ccc(-c3cccc(C(=O)NC4CCN(CCOC)CC4)n3)cc12] | 6-{8-[(2-cyano-2-methylideneethyl)amino]-7-ethoxynaphthalen-2-yl}-N-[1-(2-methoxyethyl)piperidin-4-yl]pyridine-2-carboxamide | 514 |
| 247 | 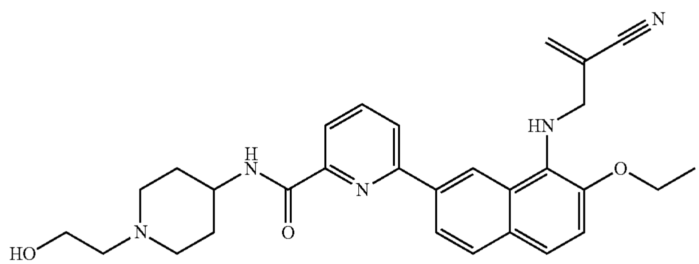 [SMILES: C=C(C#N)CNc1c(OCC)ccc2ccc(-c3cccc(C(=O)NC4CCN(CCO)CC4)n3)cc12] | 6-{8-[(2-cyano-2-methylideneethyl)amino]-7-ethoxynaphthalen-2-yl}-N-[1-(2-hydroxyethyl)piperidin-4-yl]pyridine-2-carboxamide | 500 |
| 248 | 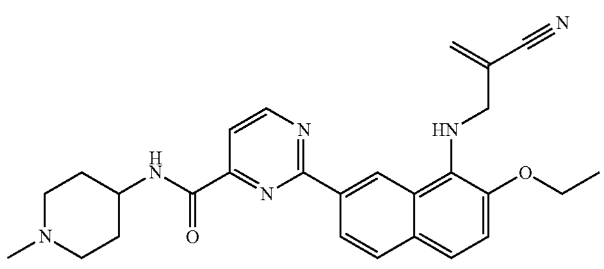 [SMILES: C=C(C#N)CNc1c(OCC)ccc2ccc(-c3nccc(C(=O)NC4CCN(C)CC4)n3)cc12] | 2-{8-[(2-cyano-2-methylideneethyl)amino]-7-ethoxynaphthalen-2-yl}-N-(1-methylpiperidin-4-yl)pyrimidine-4-carboxamide | 471.3 |
| 249 | 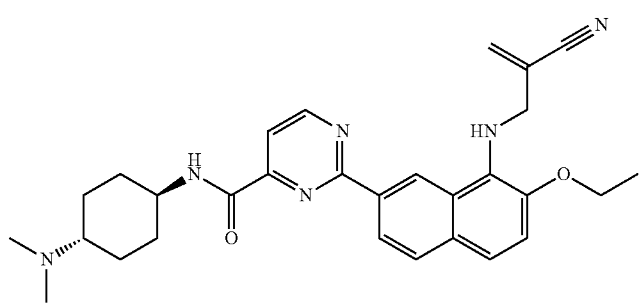 [SMILES: C=C(C#N)CNc1c(OCC)ccc2ccc(-c3nccc(C(=O)N[C@H]4CC[C@H](N(C)C)CC4)n3)cc12] | 2-{8-[(2-cyano-2-methylideneethyl)amino]-7-ethoxynaphthalen-2-yl}-N-[(1r,4r)-4-(dimethylamino)cyclohexyl]pyrimidine-4-carboxamide | 499.3 |

TABLE 3-continued

| Cpd. No. | Structure | IUPAC | LC-MS (ES+, m/z) |
|---|---|---|---|
| 250 | 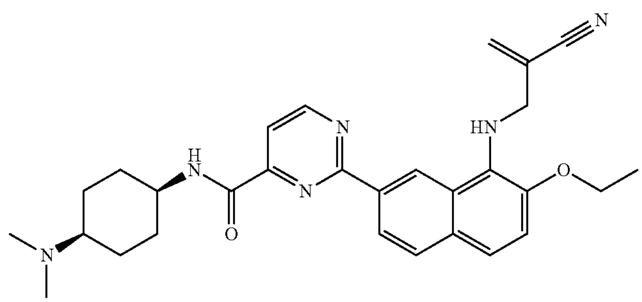 [SMILES: C=C(C#N)CNc1c(OCC)ccc2ccc(-c3nccc(C(=O)N[C@H]4CC[C@@H](N(C)C)CC4)n3)cc12] | 2-{8-[(2-cyano-2-methylideneethyl)amino]-7-ethoxynaphthalen-2-yl}-N-[(1s,4s)-4-(dimethylamino)cyclohexyl]pyrimidine-4-carboxamide | 499.3 |
| 251 | 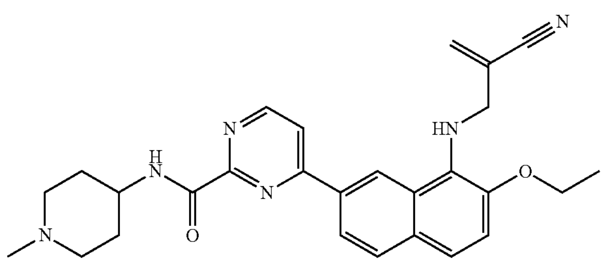 [SMILES: C=C(C#N)CNc1c(OCC)ccc2ccc(-c3ccnc(C(=O)NC4CCN(C)CC4)n3)cc12] | 4-{8-[(2-cyano-2-methylideneethyl)amino]-7-ethoxynaphthalen-2-yl}-N-(1-methylpiperidin-4-yl)pyrimidine-2-carboxamide | 471.3 |
| 252 | 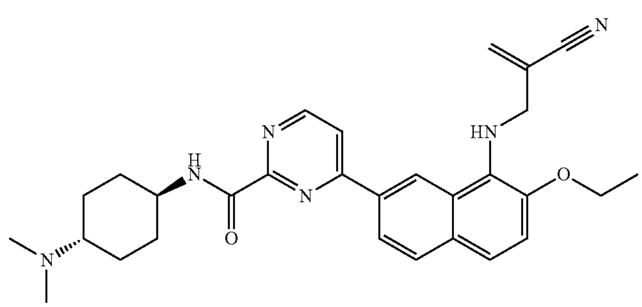 [SMILES: C=C(C#N)CNc1c(OCC)ccc2ccc(-c3ccnc(C(=O)N[C@H]4CC[C@H](N(C)C)CC4)n3)cc12] | 4-{8-[(2-cyano-2-methylideneethyl)amino]-7-ethoxynaphthalen-2-yl}-N-[(1r,4r)-4-(dimethylamino)cyclohexyl]pyrimidine-2-carboxamide | 499.4 |
| 253 | 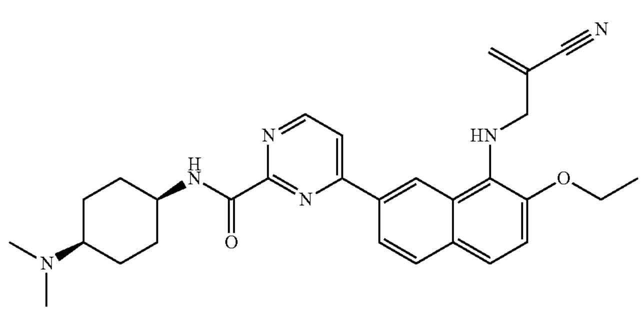 [SMILES: C=C(C#N)CNc1c(OCC)ccc2ccc(-c3ccnc(C(=O)N[C@H]4CC[C@@H](N(C)C)CC4)n3)cc12] | 4-{8-[(2-cyano-2-methylideneethyl)amino]-7-ethoxynaphthalen-2-yl}-N-[(1s,4s)-4-(dimethylamino)cyclohexyl]pyrimidine-2-carboxamide | 499.3 |

TABLE 3-continued

| Cpd. No. | Structure | IUPAC | LC-MS (ES+, m/z) |
|---|---|---|---|
| 254 | 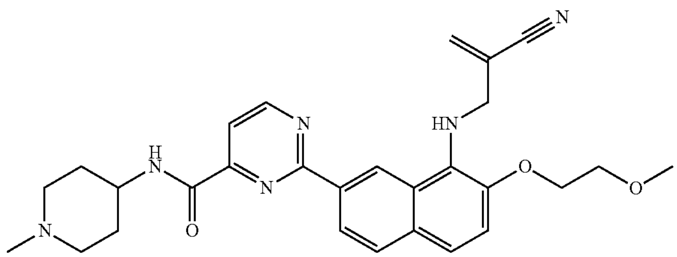 | 2-{8-[(2-cyano-2-methylideneethyl)amino]-7-(2-methoxyethoxy)naphthalen-2-yl}-N-(1-methylpiperidin-4-yl)pyrimidine-4-carboxamide | 501.3 |
| 255 | 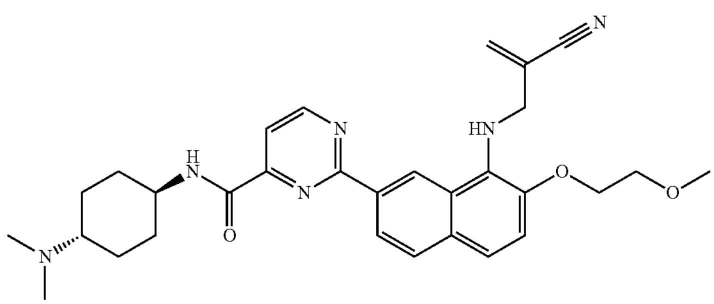 | 2-{8-[(2-cyano-2-methylideneethyl)amino]-7-(2-methoxyethoxy)naphthalen-2-yl}-N-[(1r,4r)-4-(dimethylamino)cyclohexyl]pyrimidine-4-carboxamide | 529.3 |
| 256 | 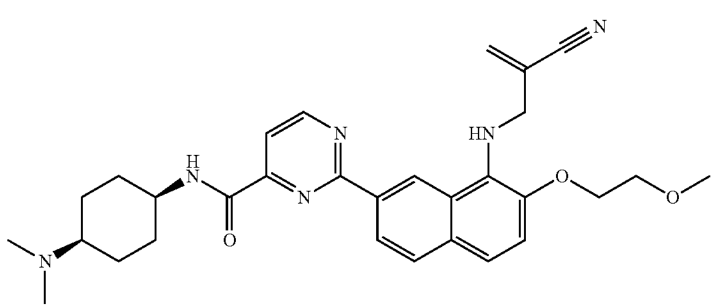 | 2-{8-[(2-cyano-2-methylideneethyl)amino]-7-(2-methoxyethoxy)naphthalen-2-yl}-N-[(1s,4s)-4-(dimethylamino)cyclohexyl]pyrimidine-4-carboxamide | 529.3 |

Example 4: Method D
Route 1: General Scheme
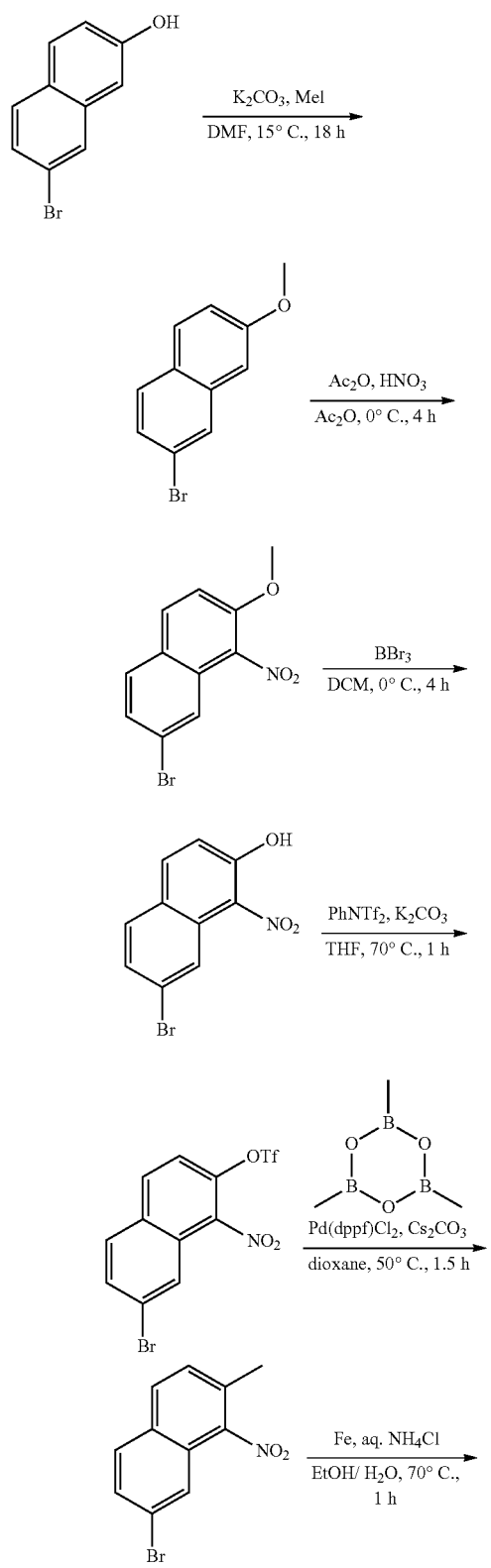
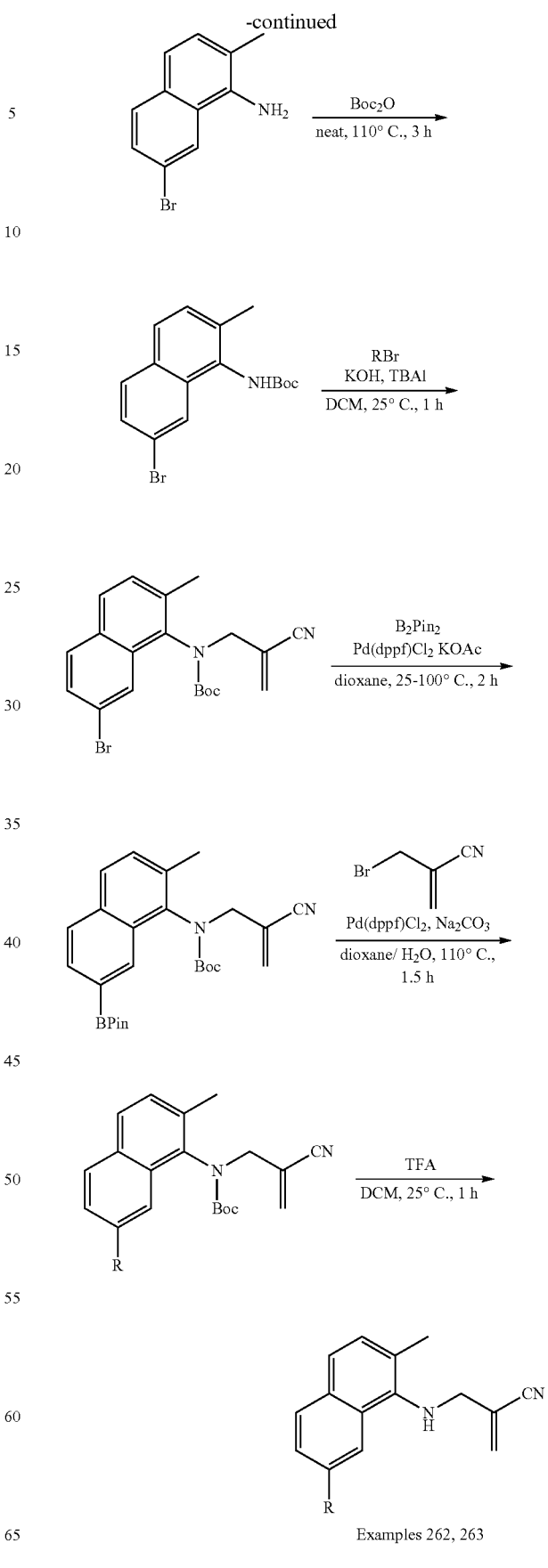
Examples 262, 263

Route 1

Preparation of 2-bromo-7-methoxynaphthalene

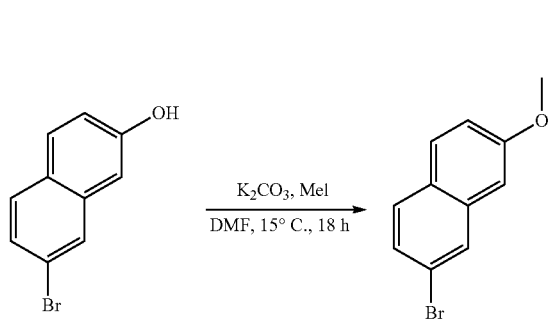

To a mixture of 7-bromonaphthalen-2-ol (2 g, 89.66 mmol, 1 eq) in DMF (200 mL) were added $K_2CO_3$ (24.78 g, 179.32 mmol, 2 eq) and MeI (15.27 g, 107.59 mmol, 6.70 mL, 1.2 eq) at 15° C. The mixture was stirred at 15° C. for 18 h. TLC showed that the stating material was consumed. The residue was poured into saturated $NH_4Cl$ (300 mL), and the aqueous phase was extracted with EtOAc (3×200 mL). The combined organic phase was washed with brine (3×250 mL), dried with anhydrous $Na_2SO_4$, filtered, and concentrated in vacuo to afford the title compound (2 g, crude) as a white solid.

Preparation of 7-bromo-2-methoxy-1-nitronaphthalene

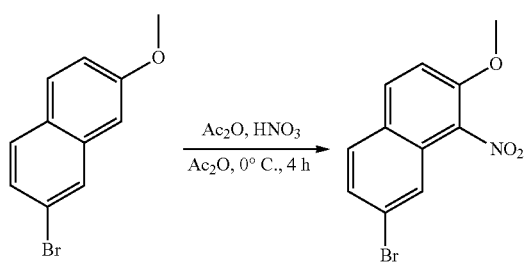 [SMILES: COc1ccc2ccc(Br)cc2c1 ; COc1ccc2ccc(Br)cc2c1[N+](=O)[O-]]

To a solution of 2-bromo-7-methoxynaphthalene (2 g, 84.36 mmol, 1 eq) in $Ac_2O$ (200 mL) was added $HNO_3$ (9.75 g, 92.79 mmol, 6.96 mL, 60% purity, 1.1 eq) at 0° C. The mixture was stirred at 0° C. for 4 h. A yellow solid formed. TLC showed that the stating material was consumed. The reaction mixture was filtered. The filter cake was washed with PE (50 mL) and concentrated to afford the title compound (17 g, crude) as a yellow solid. $^1$H NMR (400 MHz, DMSO-$d_6$) δ=8.28-8.26 (d, J=9.2 Hz, 1H), 8.05-8.02 (d, J=8.8 Hz, 1H), 7.76-7.74 (d, J=9.2 Hz, 1H), 7.69 (s, 1H), 7.69-7.67 (d, J=7.2 Hz, 1H), 4.05 (s, 1H).

Preparation of 7-bromo-1-nitronaphthalen-2-ol

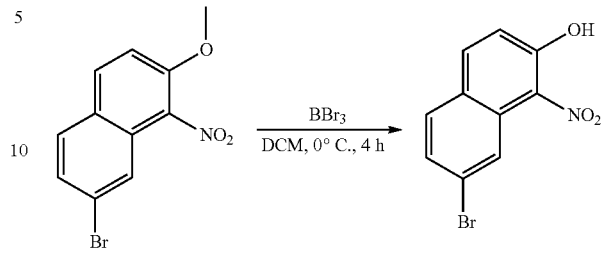

To a mixture of 7-bromo-2-methoxy-1-nitronaphthalene (8 g, 28.36 mmol, 1 eq) in DCM (80 mL) was added $BBr_3$ (35.52 g, 141.8 mmol, 13.7 mL, 5 eq) at 0° C. The mixture was stirred at 0° C. for 4 h. TLC showed no starting material remained. The residue was poured into ice-water (150 mL), and the aqueous phase was extracted with DCM (3×100 mL). The combined organic phase was washed with brine (3×100 mL), dried with anhydrous $Na_2SO_4$, filtered, and concentrated in vacuo to afford the title compound (8 g, crude) as a yellow solid. $^1$H NMR (400 MHz, DMSO-$d_6$) δ=11.72 (s, 1H), 8.08-8.06 (d, J=9.2 Hz, 1H), 7.96-7.94 (d, 7=8.4 Hz, 1H), 7.75 (s, 1H), 7.62-7.60 (d, 7=8.8 Hz, 1H), 7.38-7.36 (d, 7=9.2 Hz, 1H).

Preparation of 7-bromo-1-nitronaphthalen-2-yltrifluoromethanesulfonate

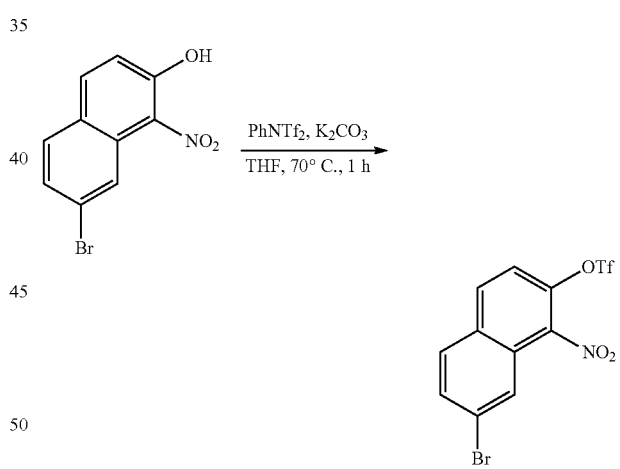

To a mixture of 7-bromo-1-nitronaphthalen-2-ol (850 mg, 3.17 mmol, 1 eq) in THF (10 mL) were added $K_2CO_3$ (876.5 mg, 6.34 mmol, 2 eq) and $PhNTf_2$ (1.36 g, 3.81 mmol, 1.2 eq) at 25° C. The mixture was stirred at 70° C. for 1 h. The residue was poured into water (50 mL), and the aqueous phase was extracted with EtOAc (3×20 mL). The combined organic phase was washed with brine (3×20 mL), dried with anhydrous $Na_2SO_4$, filtered, and concentrated in vacuo. The residue was purified by silica gel chromatography (PE:EtOAc=1/0, 10:1) to afford the title compound (1.3 g, 2.92 mmol, 92.22% yield, 90% purity) as a yellow solid. $^1$H NMR (400 MHz, DMSO-A) 5=8.56-8.54 (d, 7=9.2 Hz, 1H), 8.26-8.23 (d, 7=8.8 Hz, 1H), 8.20 (s, 1H), 8.02-7.9 (d, 7=8.4 Hz, 1H), 7.94-7.91 (d, 7=9.2 Hz, 1H).

Preparation of 7-bromo-2-methyl-1-nitronaphthalene

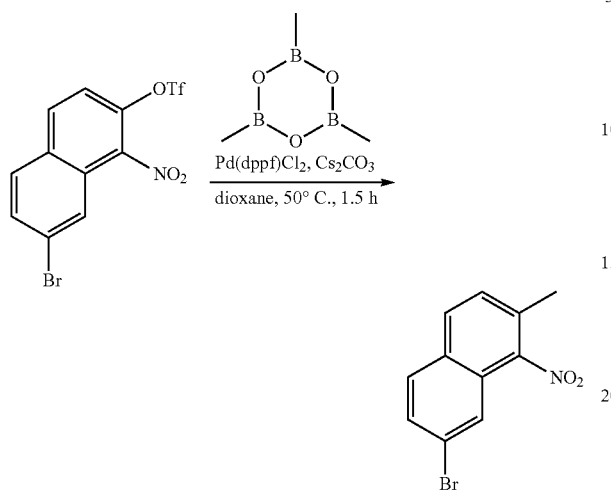

To a mixture of 7-bromo-1-nitronaphthalen-2-yl trifluoromethanesulfonate (1 g, 2.37 mmol, 1 eq) in dioxane (10 mL) were added trimethyl boroxine (894.2 mg, 3.56 mmol, 995.72 μL, 1.5 eq), Cs$_2$CO$_3$ (1.55 g, 4.75 mmol, 2 eq), and Pd(dppf)Cl$_2$ (173.7 mg, 237.43 μmol, 0.1 eq) at 25° C. under N$_2$. The mixture was stirred at 50° C. for 1.5 h. The residue was poured into saturated EDTA (60 mL) and stirred for 60 min. The aqueous phase was extracted with EtOAc (3×30 mL). The combined organic phase was washed with brine (3×30 mL×3), dried with anhydrous Na$_2$SO$_4$, filtered, and concentrated in vacuo. The residue was purified by silica gel chromatography (PE:EtOAc=1:0, 20:1) to afford the title compound (330 mg, 1.24 mmol, 52.23% yield) as a light yellow solid.

Preparation of 7-bromo-2-methylnaphthalen-1-amine

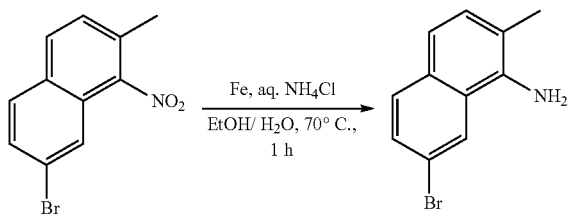

To a solution of 7-bromo-2-methyl-1-nitronaphthalene (370 mg, 1.39 mmol, 1 eq) in EtOH (5 mL) and saturated NH$_4$Cl (0.5 mL) was added Fe (776.5 mg, 13.91 mmol, 10 eq) at 70° C. The mixture was stirred at 70° C. for 1 h. Upon completion of the reaction as indicated by LCMS and TLC. The residue was poured into water (40 mL). The aqueous phase was filtered with diatomite, and extracted with EtOAc (3×20 mL). The combined organic phase was washed with brine (3×20 mL), dried with anhydrous Na$_2$SO$_4$, filtered, and concentrated in vacuo. The residue was purified by silica gel chromatography (PE:EtOAc=1/0, 10:1) to afford the title compound (300 mg, 1.21 mmol, 86.8% yield, 95% purity) as a red solid. LC-MS (ES$^+$, m/z): 236.0, 238.0 [(M+H)$^+$].

Preparation of tert-butyl N-(7-bromo-2-methylnaphthalen-1-yl)carbamate

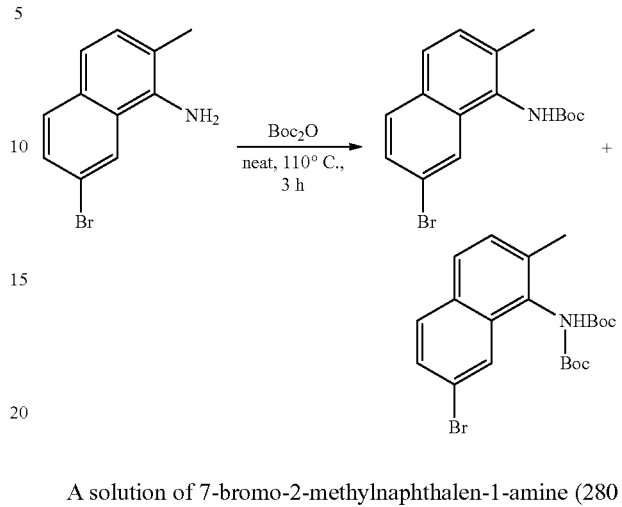

A solution of 7-bromo-2-methylnaphthalen-1-amine (280 mg, 1.13 mmol, 1 eq) dissolved in Boc$_2$O (10 mL) was prepared at 25° C. under N$_2$. The mixture was stirred at 110° C. for 3 h. TLC showed no starting material remained. The mixture was concentrated in vacuo. The residue was purified by silica gel chromatography (PE:EtOAc=1/0, 10:1) to afford the title compound (360 mg, 910.11 μmol, 80.8% yield, 85% purity) and di-Boc product (360 mg, 107.26 μmol, 9.52% yield, 13% purity) as a white solid. LC-MS (ES$^+$, m/z): 279.9, 281.9 [(M+H)$^+$].

Preparation of tert-butyl (7-bromo-2-methylnaphthalen-1-yl)(2-cyanoallyl)carbamate

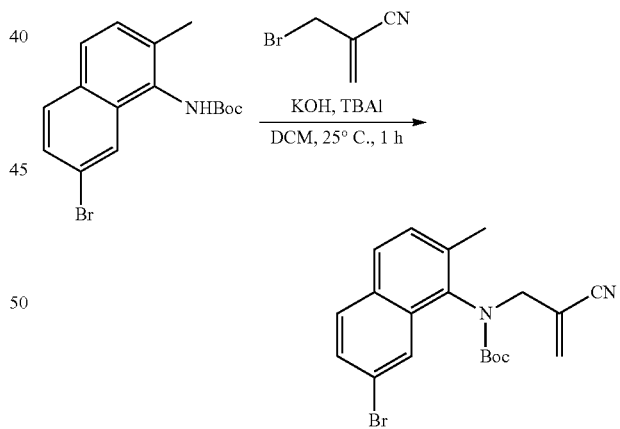

To a mixture of ten-butyl N-(7-bromo-2-methylnaphthalen-1-yl)carbamate (240 mg, 713.81 μmol, 1 eq) in DCM (10 mL) were added KOH (80.1 mg, 1.43 mmol, 2 eq), TBAI (131.8 mg, 356.91 μmol, 0.5 eq), and 2-(bromomethyl)prop-2-enenitrile (114.6 mg, 785.19 μmol, 1.1 eq) at 25° C. under N$_2$. The mixture was stirred at 25° C. for 1 h. The residue was poured into H$_2$O (30 mL). The aqueous phase was extracted with DCM (3×15 mL). The combined organic phase was washed with brine (3×15 mL), dried with anhydrous Na$_2$SO$_4$, filtered, and concentrated in vacuo. The residue was purified by silica gel chromatography (PE:

EtOAc=1:0, 10:1) to afford the title compound (260 mg, 637.58 μmol, 89.32% yield, 98.407% purity) as a white solid. LC-MS (ES+, m/z): 345.0, 347.0 [(M+H)+]

Preparation of tert-butyl N-(2-cyano-2-methylideneethyl)-N-[2-methyl-7-(4,4,5,5-tetramethyl-1,3,2-dioxaborolan-2-yl)naphthalen-1-yl]carbamate

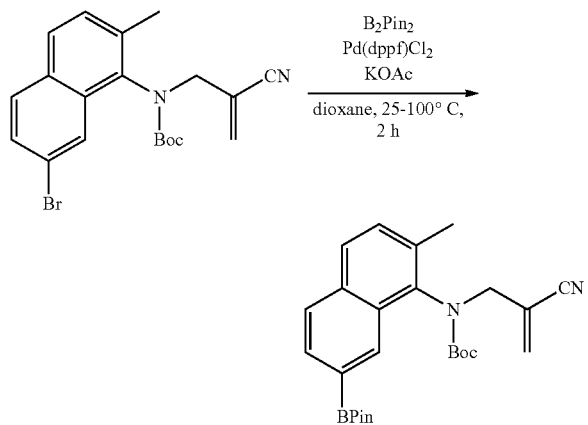

To a mixture of ten-butyl (7-bromo-2-methylnaphthalen-1-yl)(2-cyanoallyl)carbamate (210 mg, 514.97 μmol, 1 eq) in dioxane (10 mL) were added Pin₂B₂ (392.3 mg, 1.54 mmol, 3 eq), KOAc (252.7 mg, 2.57 mmol, 5 eq), and a Pd(dppf)Cl₂ (37.7 mg, 51.5 μmol, 0.1 eq) at 25° C. under N₂. The mixture was stirred at 100° C. for 2 h. Upon completion of the reaction as indicated by LCMS and TLC. The residue was poured into saturated EDTA (30 mL) and stirred for 60 min. The aqueous phase was extracted with EtOAc (3×30 mL). The combined organic phase was washed with brine (3×30 mL), dried with anhydrous Na₂SO₄, filtered, and concentrated in vacuo. The residue was purified by silica gel chromatography (PE:EtOAc=1:0, 10:1). The product was purified by prep-TLC to afford the title compound (180 mg, 361.32 μmol, 70.2% yield, 90% purity) as a colourless oil. LC-MS (ES+, m/z): 393.2 [(M+H)+], ¹H NMR (400 MHz, DMSO-A) 5=8.11 (s, 1H), 7.91-7.83 (m, 2H), 7.70-7.68 (d, J=8.4 Hz, 1H), 7.50-7.48 (d, J=8.4 Hz, 1H), 6.03 (s, 1H), 5.87-5.75 (m, 1H), 4.62-4.49 (d, J=14.8, 1H), 4.26-4.19 (d, J=7.6, 1H), 2.38-2.36 (d, 3H), 1.13 (d, 12H), 1.18-1.07 (d, 9H).

Preparation of tert-butyl N-(2-cyano-2-methylideneethyl)-N-[7-(4-acetamido pyridin-2-yl)-2-methyl-naphthalen-1-yl]carbamate

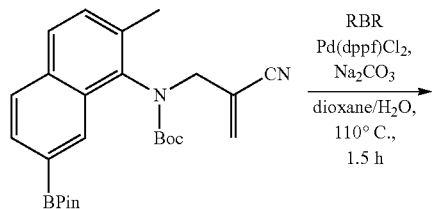

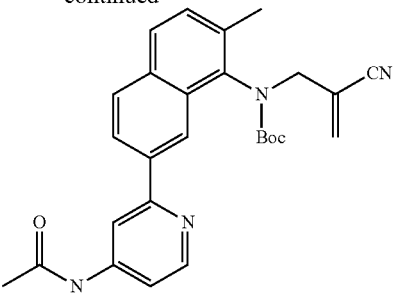

To a mixture of N-(2-bromopyridin-4-yl)acetamide (41.1 mg, 240.88 μmol, 2 eq) and ten-butyl N-(2-cyano-2-methylideneethyl)-N-[2-methyl-7-(4,4,5,5-tetramethyl-1,3,2-dioxaborolan-2-yl) naphthalen-1-yl]carbamate (60 mg, 120.44 μmol, 1 eq) in dioxane (3 mL), H₂O (0.75 mL) were added Na₂CO₃ (25.5 mg, 240.88 μmol, 2 eq), Pd(dppf)Cl₂ (8.8 mg, 12.04 μmol, 0.1 eq) at 25° C. The mixture was stirred at 110° C. for 1.5 h. TLC showed no starting material remained. The residue was poured into saturated EDTA (30 mL) and stirred for 60 min. The aqueous phase was extracted with EtOAc (3×30 mL). The combined organic phase was washed with brine (3×30 mL), dried with anhydrous Na₂SO₄, filtered, and concentrated in vacuo. The residue was purified by prep-TLC to afford the title compound (50 mg, 98.57 μmol, 81.8% yield, 90% purity) as a colourless oil.

Compound 263: Preparation of N-(2-{8-[(2-cyano-2-methylideneethyl)amino]-7-methylnaphthalen-2-yl}pyridin-4-yl) acetamide

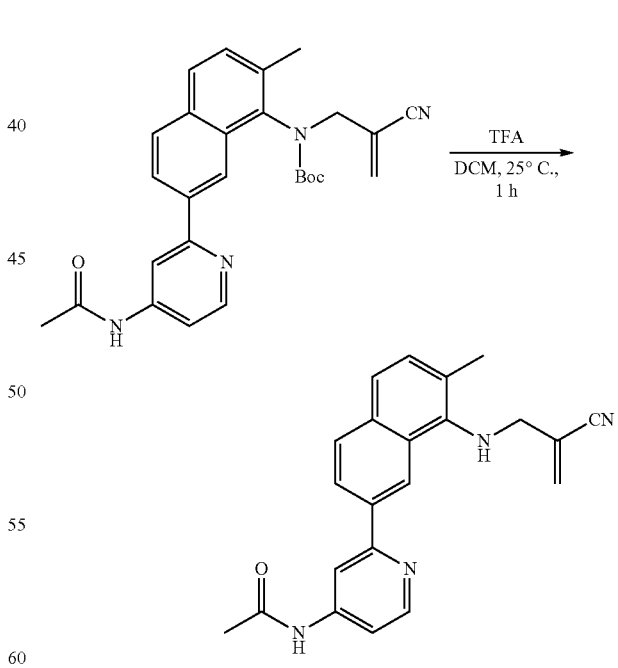

To a mixture of tert-butyl N-(2-cyano-2-methylideneethyl)-N-[7-(4-acetamidopyridin-2-yl)-2-methylnaphthalen-1-yl]carbamate (50 mg, 98.57 μmol, 1 eq) in DCM (4 mL) was added TFA (1 mL) at 25° C. under N₂. The mixture was stirred at 25° C. for 1 h. The mixture was poured into saturated Na₂CO₃ (20 mL), and the aqueous phase was extracted with EtOAc (3×30 mL). The combined organic phase was washed with brine (3×30 mL), dried with anhydrous Na$_2$SO$_4$. Then concentrated in vacuo. The residue was purified by prep-HPLC to afford the title compound (4.1 mg, 11.38 μmol, 11.55% yield, 98.967% purity) as a light yellow solid. LC-MS (ES$^+$, m/z): 356.1 [(M+H)$^+$].
Route 2: General Scheme
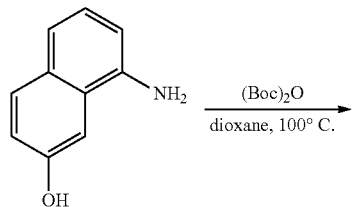
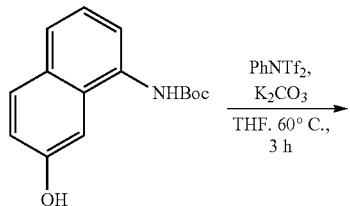
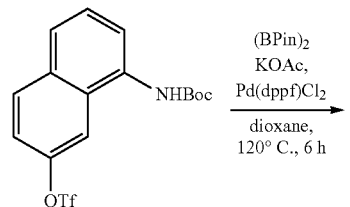
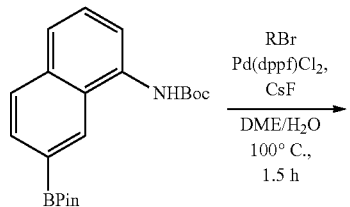
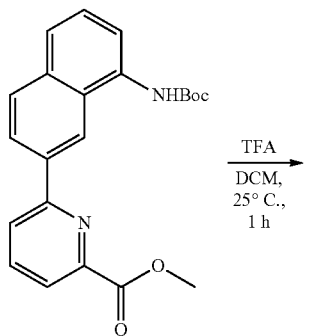
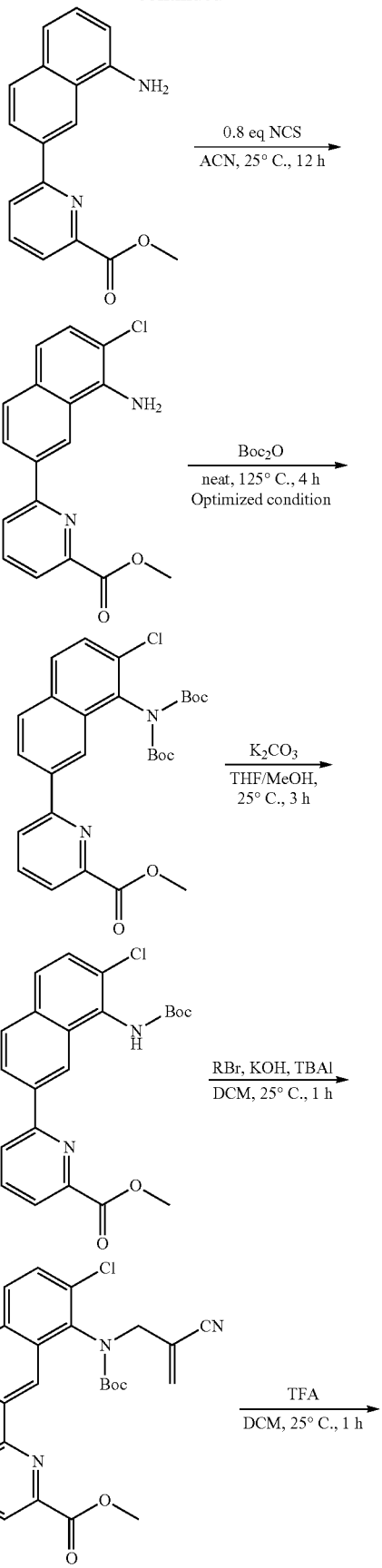

-continued

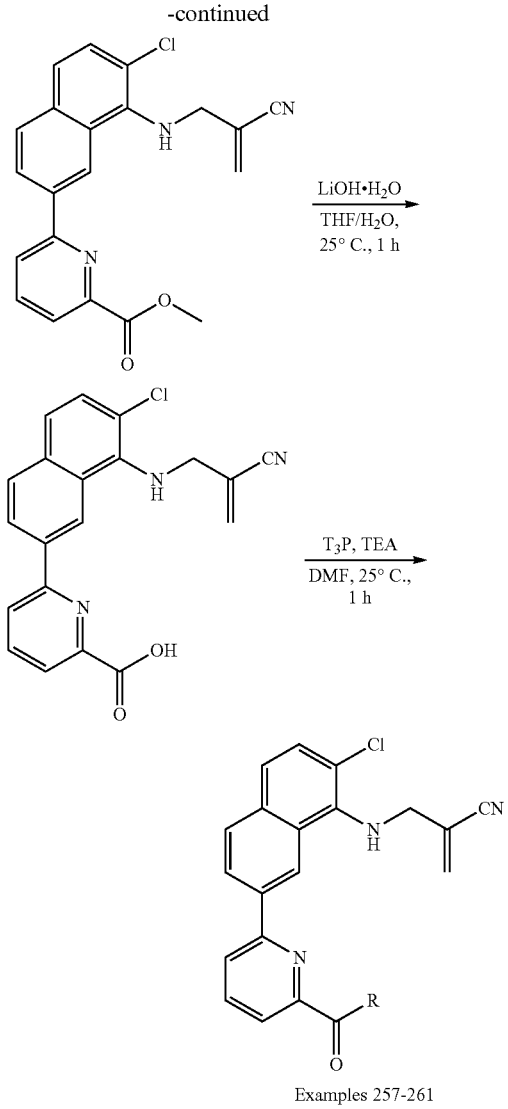

Examples 257-261

Preparation of tert-butyl N-(7-hydroxy-1-naphthyl)carbamate

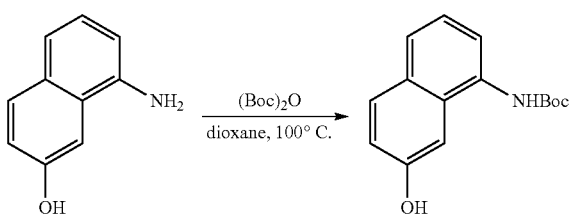 [SMILES: "(Boc)2O" ; Nc1cccc2ccc(O)cc12 ; CC(C)(C)OC(=O)Nc1cccc2ccc(O)cc12]

A mixture of 8-aminonaphthalen-2-ol (1 g, 62.82 mmol, 1 eq) and Boc₂O (15.08 g, 69.1 mmol, 15.88 mL, 1.1 eq) in dioxane (150 mL) was stirred at 100° C. for 7 hours. The reaction was concentrated directly to give crude material. The residue was purified by column chromatography (SiO$_2$, PE:EtOAc=6:1 to 4:1) to afford the title compound (12 g, 46.28 mmol, 73.67% yield) as an off-white solid.

Preparation of 8-(tert-butoxycarbonylamino)-2-naphthyl]trifluoromethanesulfonate

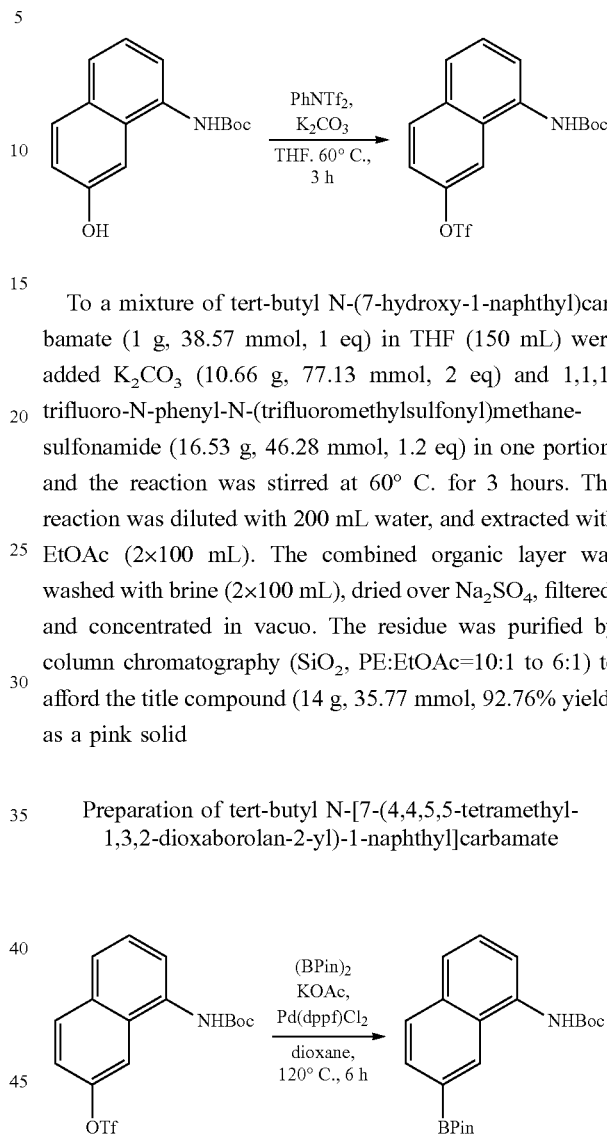

To a mixture of tert-butyl N-(7-hydroxy-1-naphthyl)carbamate (1 g, 38.57 mmol, 1 eq) in THF (150 mL) were added K$_2$CO$_3$ (10.66 g, 77.13 mmol, 2 eq) and 1,1,1-trifluoro-N-phenyl-N-(trifluoromethylsulfonyl)methanesulfonamide (16.53 g, 46.28 mmol, 1.2 eq) in one portion, and the reaction was stirred at 60° C. for 3 hours. The reaction was diluted with 200 mL water, and extracted with EtOAc (2×100 mL). The combined organic layer was washed with brine (2×100 mL), dried over Na$_2$SO$_4$, filtered, and concentrated in vacuo. The residue was purified by column chromatography (SiO$_2$, PE:EtOAc=10:1 to 6:1) to afford the title compound (14 g, 35.77 mmol, 92.76% yield) as a pink solid Preparation of tert-butyl N-[7-(4,4,5,5-tetramethyl-1,3,2-dioxaborolan-2-yl)-1-naphthyl]carbamate To a mixture of [8-(tert-butoxycarbonylamino)-2-naphthyl]trifluoro methane sulfonate (14 g, 35.77 mmol, 1 eq) and 4,4,5,5-tetramethyl-2-(4,4,5,5-tetramethyl-1,3,2-dioxaborolan-2-yl)-1,3,2-dioxaborolane (18.17 g, 71.55 mmol, 2 eq) in dioxane (200 mL) were added KOAc (10.53 g, 107.32 mmol, 3 eq) and Pd(dppf)Cl$_2$ (2.09 g, 2.86 mmol, 0.08 eq) in one portion. The reaction was stirred at 120° C. for 6 hours under N$_2$. The reaction was diluted with 100 mL water, extracted with EtOAc (2×100 mL), and the combined organic layer was washed with brine (2×100 mL), dried over Na$_2$SO$_4$, filtered, and concentrated in vacuo. The residue was purified by column chromatography (SiO$_2$, PE:EtOAc=8/1 to 4:1) to afford the title compound (9.4 g, 25.46 mmol, 71.16% yield) as an off-white solid. LC-MS (ES$^+$, m/z): 314.1 [(M+H)$^+$].

Preparation of methyl 6-[8-(tert-butoxycarbonylamino)-2-naphthyl]pyridine-2-carboxylate

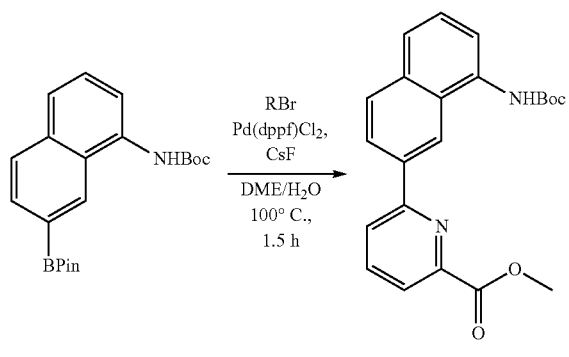

To a mixture of tert-butyl N-[7-(4,4,5,5-tetramethyl-1,3,2-dioxaborolan-2-yl)-1-naphthyl]carbamate (9.4 g, 25.46 mmol, 1 eq) and methyl 6-bromopyridine-2-carboxylate (6.05 g, 28 mmol, 1.1 eq) in DME (100 mL) and H$_2$O (25 mL) were added CsF (11.6 g, 76.37 mmol, 2.82 mL, 3 eq), Pd(dppf)Cl$_2$ (1.86 g, 2.55 mmol, 0.10 eq) in one portion, and the reaction mixture was stirred at 100° C. for 1.5 hours. TLC and LCMS showed that the reaction was complete. The reaction mixture was poured into saturated EDTA (200 mL) and stirred at 25° C. for 1 h. Then. The mixture was extracted with EtOAc (2×100 mL), washed with brine (2×100 mL), dried over Na$_2$SO$_4$ filtered, and concentrated in vacuo to give a crude residue. The crude material was purified by column chromatography (SiO$_2$, PE:EtOAc=6:1 to 1/1) to afford the title compound (5.5 g, 14.53 mmol, 57.09% yield) as a white solid. LC-MS (ES$^+$, m/z): 379.2 [(M+H)$^+$].

Preparation of methyl 6-(8-amino-2-naphthyl)pyridine-2-carboxylate

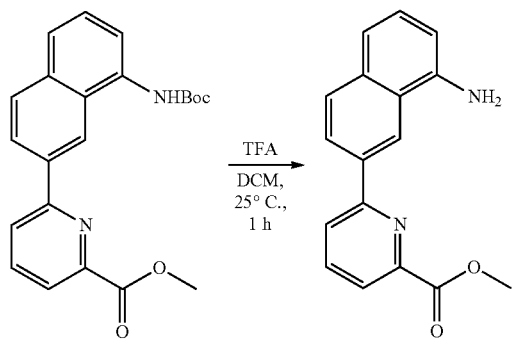 [SMILES: COC(=O)c1cccc(-c2ccc3cccc(NC(=O)OC(C)(C)C)c3c2)n1 ; COC(=O)c1cccc(-c2ccc3cccc(N)c3c2)n1]

To a mixture of methyl 6-[8-(tert-butoxycarbonylamino)-2-naphthyl]pyridine-2-carboxylate (5.5 g, 14.53 mmol, 1 eq) in DCM (80 mL) was added TFA (26.06 g, 228.56 mmol, 16 mL, 15 eq) in one portion, and the reaction mixture was stirred at 25° C. for 1 hours. The reaction mixture was adjusted to pH=8 with saturated aq. Na$_2$CO$_3$. The mixture was extracted with EtOAc (2×100 mL). The combined organic layer was washed with brine (2×100 mL), dried over Na$_2$SO$_4$, filtered, and concentrated in vacuo. The residue was purified by column chromatography (SiO$_2$, PE:EtOAc=6:1 to 4:1) to afford the title compound (3.5 g, 12.58 mmol, 86.53% yield) as a yellow solid. LC-MS (ES$^+$, m/z): 279.1 [(M+H)$^+$].

Preparation of methyl 6-(8-amino-7-chloro-2-naphthyl)pyridine-2-carboxylate

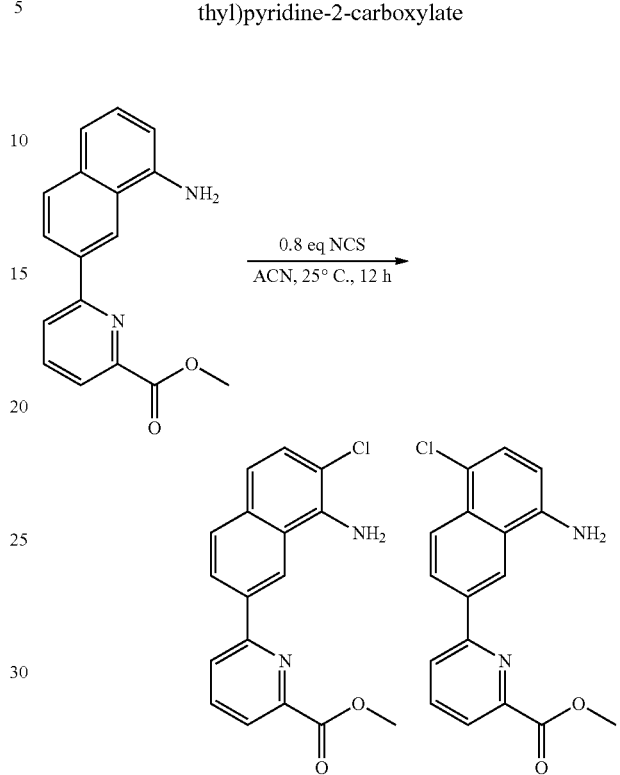

To a mixture of methyl 6-(8-amino-2-naphthyl)pyridine-2-carboxylate (3 g, 10.78 mmol, 1 eq) in ACN (8 mL) was added NCS (1.15 g, 8.62 mmol, 0.8 eq) in one portion under N$_2$. The mixture was stirred at 25° C. for 12 hours. LCMS showed that the reaction was complete. The reaction was diluted with 100 mL water and extracted with EtOAc (2×50 mL). The combined organic layer was washed with brine (2×50 mL), dried over Na$_2$SO$_4$, filtered, and concentrated in vacuo. The residue was purified by column chromatography (SiO$_2$, PE:EtOAc=8/1 to 4:1) to afford the title compound (1.9 g, 6.08 mmol, 56.36% yield) as an off-white solid and the byproduct (1. g, 3.2 mmol, 29.66% yield) as a yellow solid. LC-MS (ES$^+$, m/z): 313.0 [(M+H)$^+$].

Preparation of methyl 6-[8-[bis(tert-butoxycarbonyl)amino]-7-chloro-2-naphthyl]pyridine-2-carboxylate

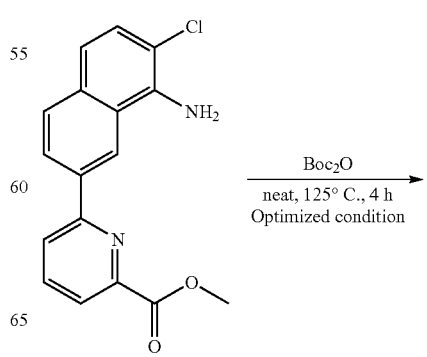

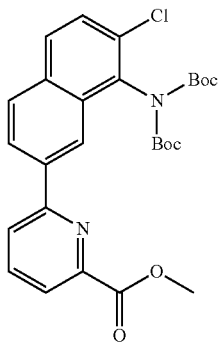

To a mixture of methyl 6-(8-amino-7-chloro-2-naphthyl)pyridine-2-carboxylate (900 mg, 2.88 mmol, 1 eq) in Boc$_2$O (14.25 g, 65.29 mmol, 15 mL, 22.69 eq) was stirred at 125° C. for 4 hours. The reaction was concentrated directly. The crude residue was purified by column chromatography (SiO$_2$, PE:EtOAc=8/1 to 6:1) to obtain 1.2 g of the desired product (~80% purity). Then purified by prep-HPLC (TFA condition) to afford the title compound (900 mg, 1.75 mmol, 60.97% yield) as an off-white solid.

Preparation of methyl 6-[8-(tert-butoxycarbonylamino)-7-chloro-2-naphthyl]pyridine-2-carboxylate

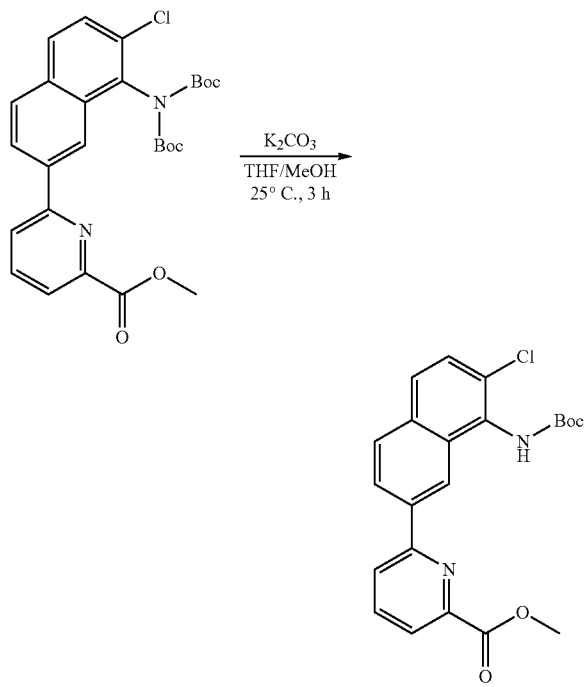

To a mixture of methyl 6-[8-[bis(tert-butoxycarbonyl)amino]-7-chloro-2-naphthyl]pyridine-2-carboxylate (700 mg, 1.36 mmol, 1 eq) in THF (10 mL), MeOH (5 mL) was added K$_2$CO$_3$ (188.6 mg, 1.36 mmol, 1 eq) in one portion under N$_2$. The mixture was stirred at 25° C. for 3 hours. The reaction mixture was filtered to give filtrate and concentrated in vacuo to afford the title compound (550 mg, crude) as an off-white solid.

To a mixture of methyl 6-[8-[bis(tert-butoxycarbonyl)amino]-7-chloro-2-naphthyl]pyridine-2-carboxylate (350 mg, 682.29 μmol, 1 eq) in THF (5 mL) and MeOH (2.5 mL) was added K$_2$CO$_3$ (94.3 mg, 682.29 μmol, 1 eq) in one portion under N$_2$. The mixture was stirred at 25° C. for 3 hours. The reaction mixture was filtered to give filtrate and concentrated in vacuo to give crude to afford the title compound (200 mg, 484.42 μmol, 71.00% yield) as an off-white solid.

Preparation of methyl 6-[8-[tert-butoxycarbonyl(2-cyanoallyl)amino]-7-chloro-2-naphthyl]pyridine-2-carboxylate

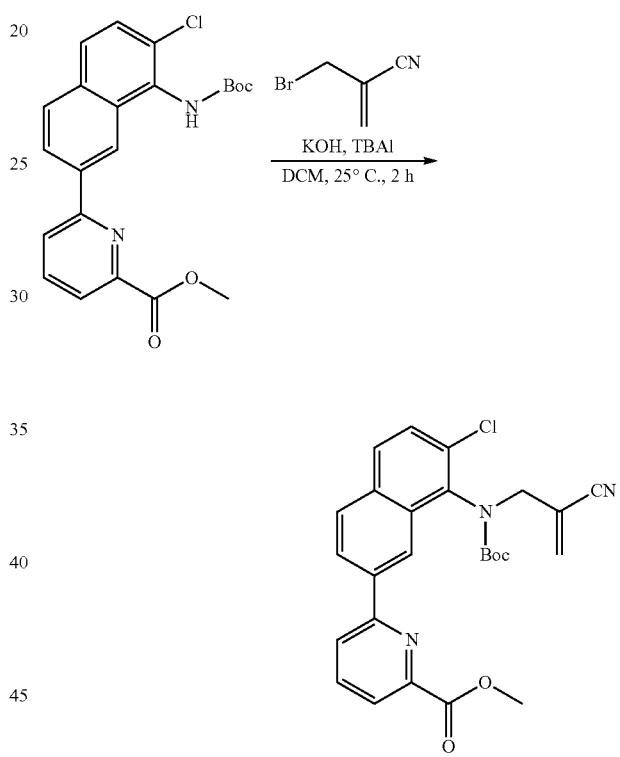

To a mixture of methyl 6-[8-(tert-butoxycarbonylamino)-7-chloro-2-naphthyl]pyridine-2-carboxylate (150 mg, 363.31 μmol, 1 eq) in DCM (4 mL) were added KOH (40.8 mg, 726.63 μmol, 2 eq), TBAI (40.3 mg, 108.99 μmol, 0.3 eq) and 2-(bromomethyl)prop-2-enenitrile (68.9 mg, 472.31 μmol, 1.3 eq) in one portion under N$_2$. The mixture was stirred at 25° C. for 60 min. TLC showed that ~40% of the desired product was formed. The reaction was stirred for another 1 hour. TLC showed ~60% desired product. The reaction was diluted with 30 mL water and extracted with EtOAc (2×30 mL). The combined organic layer was washed with brine (2×25 mL), dried over Na$_2$SO$_4$, filtered, and concentrated in vacuo. The residue was purified by prep-TLC twice (SiO$_2$, PE:EtOAc=4:1) to afford the title compound (90 mg, 188.31 μmol, 51.8% yield) as a yellow solid.

307

Preparation of methyl 6-[7-chloro-8-(2-cyanoally-lamino)-2-naphthyl]pyridine-2-carboxylate

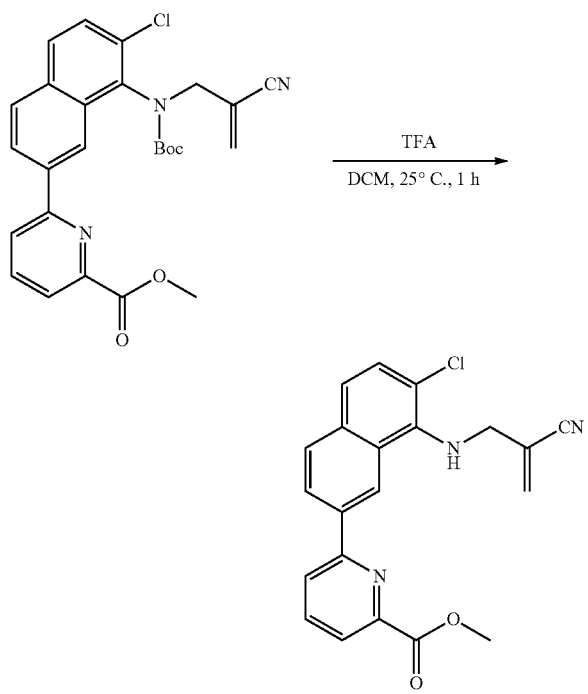

To a mixture of methyl 6-[8-[tert-butoxycarbonyl(2-cyanoallyl)amino]-7-chloro-2-naphthyl]pyridine-2-carboxylate (90 mg, 188.7 μmol, 1 eq) in DCM (3 mL) was added TFA (1.54 g, 13.51 mmol, 1 mL, 71.57 eq) in one portion. The mixture was stirred at 25° C. for 60 min. The reaction was diluted with 20 mL water and extracted with EtOAc (2×20 mL). The combined organic layer was washed with brine (2×20 mL), dried over Na$_2$SO$_4$, filtered, and concentrated in vacuo. The residue was purified by prep-TLC (SiO$_2$, PE:EtOAc=4:1) to afford the title compound (60 mg, 158.8 μmol, 84.16% yield) as a yellow solid.

Preparation of 6-[7-chloro-8-(2-cyanoallylamino)-2-naphthyl]pyridine-2-carboxylic acid

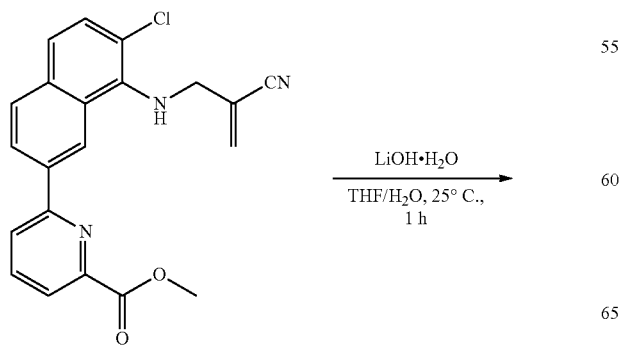

308

-continued

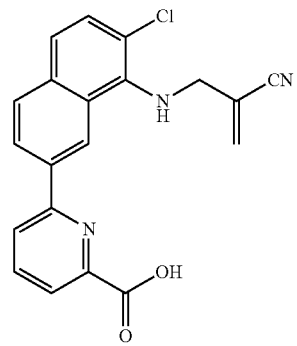

To a mixture of methyl 6-[7-chloro-8-(2-cyanoallylamino)-2-naphthyl]pyridine-2-carboxylate (60 mg, 158.8 μmol, 1 eq) in THF (4 mL) H$_2$O (1 mL) was added LiOH·H$_2$O (66.6 mg, 1.59 mmol, 10 eq) in one portion. The mixture was stirred at 25° C. for 60 min. The reaction mixture was adjusted to pH=6 with saturated citric acid and extracted with EtOAc (2×20 mL). The combined organic layer was washed with brine (2×20 mL), dried over Na$_2$SO$_4$, filtered, and concentrated in vacuo to afford the title compound (50 mg, crude) as a yellow gum.

Compound 258: Preparation of 6-[7-chloro-8-(2-cyanoallylamino)-2-naphthyl]-N-(1-methyl-4-piperidyl)pyridine-2-carboxamide

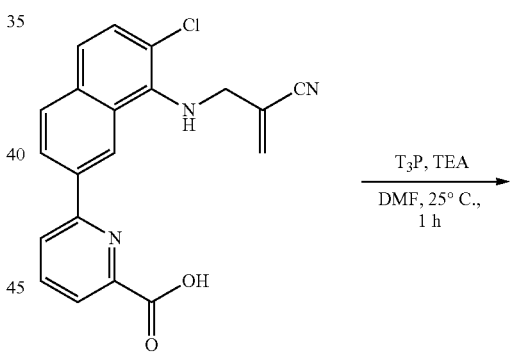

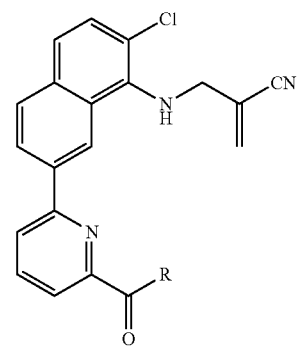

-continued

R = 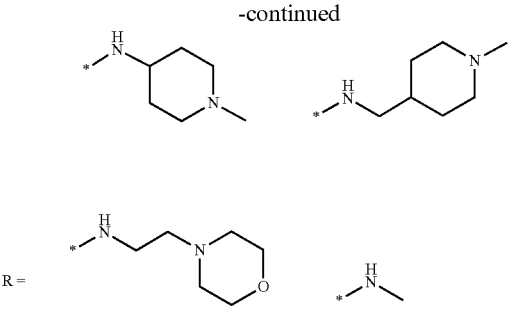

To a mixture of 6-[7-chloro-8-(2-cyanoallylamino)-2-naphthyl]pyridine-2-carboxylic acid (50 mg, 137.44 μmol, 1 eq) and 1-methylpiperidin-4-amine (31.4 mg, 274.88 μmol, 2 eq) in DMF (5 mL) were added $Et_3N$ (41.7 mg, 412.32 μmol, 57.39 μL, 3 eq), $T_3P$ (131.2 mg, 206.16 μmol, 122.61 μL, 50% purity, 1.5 eq) in one portion, and the reaction was stirred at 25° C. for 1 hours. LCMS showed that the reaction was complete. The reaction was diluted with 30 mL water and extracted with EtOAc (2×30 mL). The combined organic layer was washed with brine (2×25 mL), dried over $Na_2SO_4$, filtered, and concentrated in vacuo. The residue was purified by prep-HPLC to afford the title compound 6-[7-chloro-8-(2-cyanoallylamino)-2-naphthyl]-N-(1-methyl-4-piperidyl)pyridine-2-carboxamide (11.8 mg, 25.65 μmol, 18.67% yield, 100.0% purity) as an off-white solid. LC-MS ($ES^+$, m/z): 286.1 [$(M+H)^+$].

TABLE 4 shows compounds synthesized using methods described in EXAMPLE 4 described above.

TABLE 4

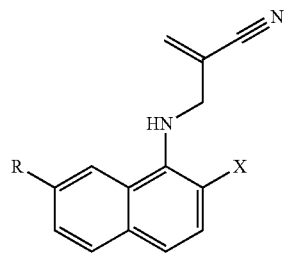

| Cpd. No. | Structure | IUPAC | LC-MS (ES+, m/z) |
|---|---|---|---|
| 257 | 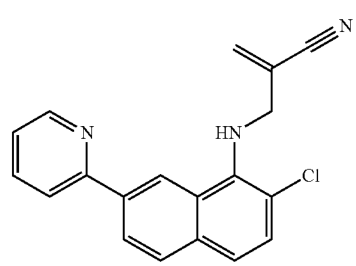 [SMILES: C=C(C#N)CNc1c(Cl)ccc2ccc(-c3ccccn3)cc12] | 2-({[2-chloro-7-(pyridin-2-yl)naphthalen-1-yl]amino}methyl)prop-2-enenitrile | 319.9 |
| 258 | 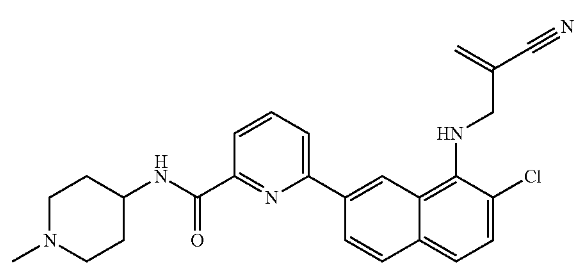 [SMILES: C=C(C#N)CNc1c(Cl)ccc2ccc(-c3cccc(C(=O)NC4CCN(C)CC4)n3)cc12] | 6-{7-chloro-8-[(2-cyano-2-methylideneethyl)amino]naphthalen-2-yl}-N-(1-methylpiperidin-4-yl)pyridine-2-carboxamide | 460 |
| 259 | 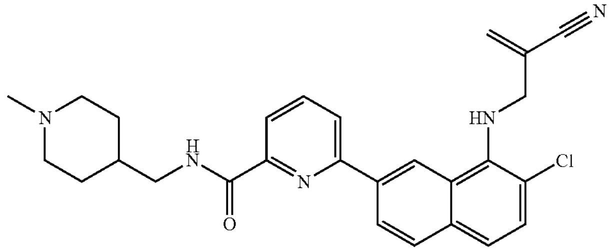 [SMILES: C=C(C#N)CNc1c(Cl)ccc2ccc(-c3cccc(C(=O)NCC4CCN(C)CC4)n3)cc12] | 6-{7-chloro-8-[(2-cyano-2-methylideneethyl)amino]naphthalen-2-yl}-N-[(1-methylpiperidin-4-yl)methyl]pyridine-2-carboxamide | 475 |

TABLE 4-continued

| Cpd. No. | Structure | IUPAC | LC-MS (ES+, m/z) |
|---|---|---|---|
| 260 | 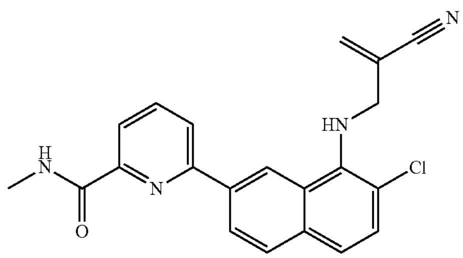 [SMILES: C=C(C#N)CNc1c(Cl)ccc2ccc(-c3cccc(C(=O)NC)n3)cc12] | 6-{7-chloro-8-[(2-cyano-2-methylideneethyl)amino]naphthalen-2-yl}-N-methylpyridine-2-carboxamide | 377 |
| 261 | 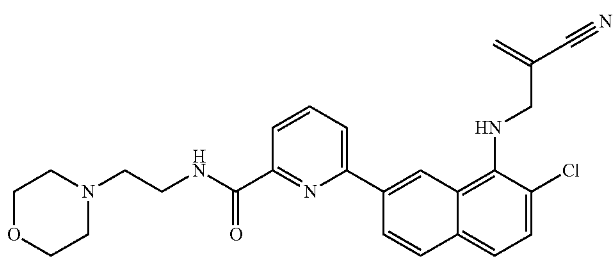 [SMILES: C=C(C#N)CNc1c(Cl)ccc2ccc(-c3cccc(C(=O)NCCN4CCOCC4)n3)cc12] | 6-{7-chloro-8-[(2-cyano-2-methylideneethyl)amino]naphthalen-2-yl}-N-[2-(morpholin-4-yl)ethyl]pyridine-2-carboxamide | 476 |
| 262 | 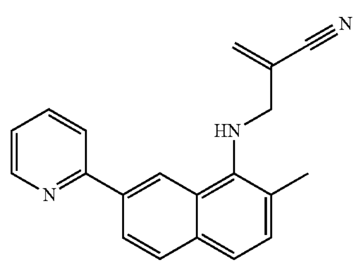 [SMILES: C=C(C#N)CNc1c(C)ccc2ccc(-c3ccccn3)cc12] | 2-({[2-methyl-7-(pyridin-2-yl)naphthalen-1-yl]amino}methyl)prop-2-enenitrile | 299.377 |
| 263 | 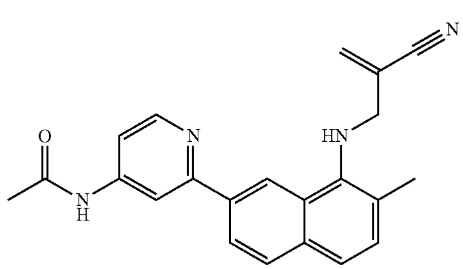 [SMILES: C=C(C#N)CNc1c(C)ccc2ccc(-c3cc(NC(C)=O)ccn3)cc12] | N-(2-{8-[(2-cyano-2-methylideneethyl)amino]-7-methylnaphthalen-2-yl}pyridin-4-yl)acetamide | 356.429 |

Example 5: Method E
Route 1: General Scheme
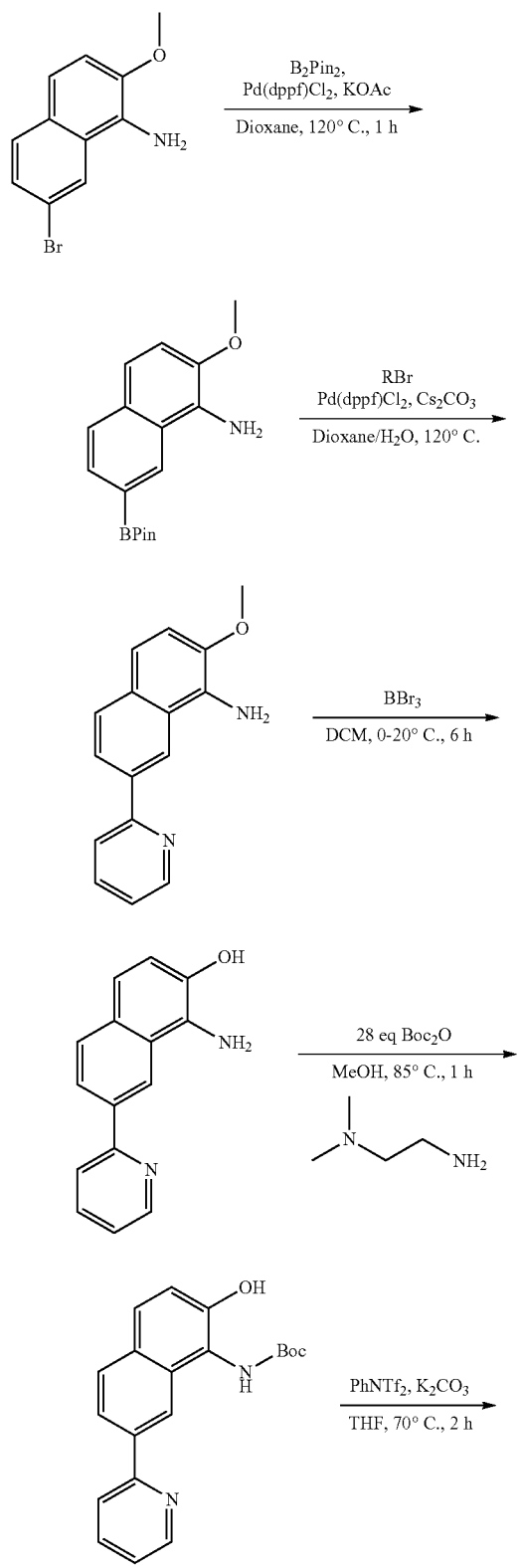
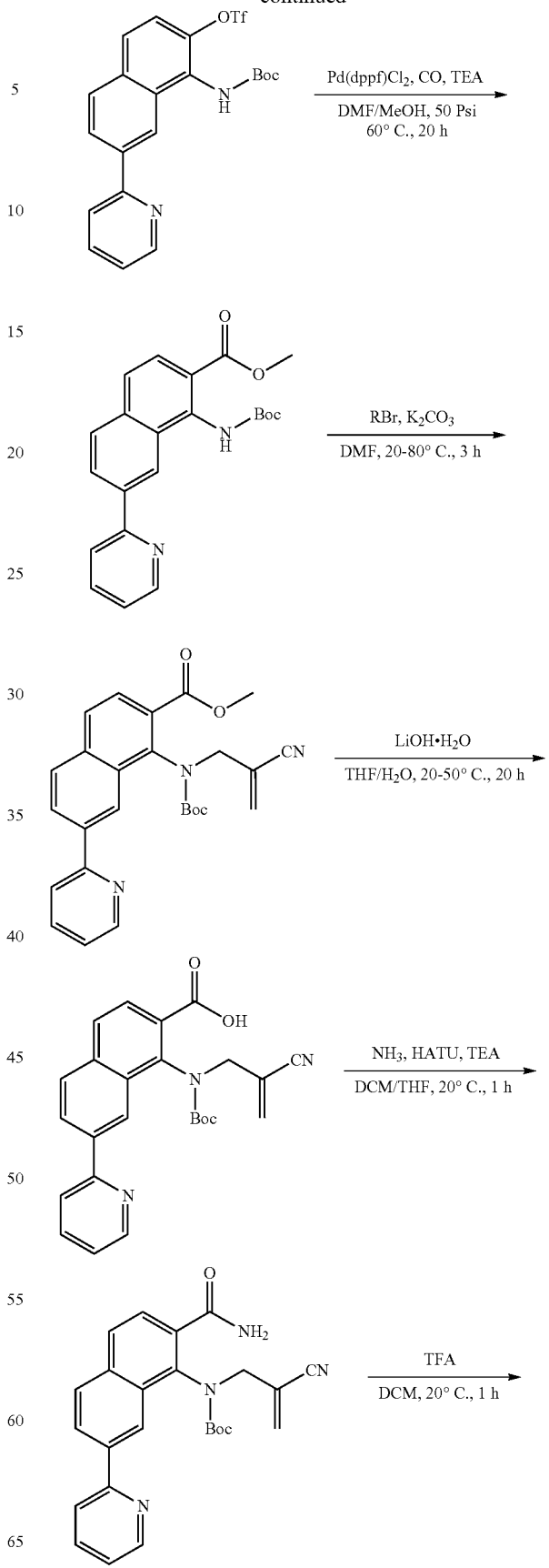

-continued

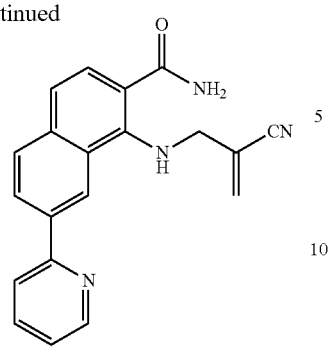

Step 1) Preparation of 2-methoxy-7-(4,4,5,5-tetramethyl-1,3,2-dioxaborolan-2-yl)naphthalen-1-amine

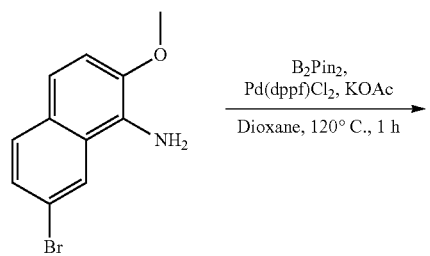

To a solution of 7-bromo-2-methoxy-naphthalen-1-amine (1 g, 39.67 mmol, 1 eq) and 4,4,5,5-tetramethyl-2-(4,4,5,5-tetramethyl-1,3,2-dioxaborolan-2-yl)-1,3,2-dioxaborolane (30.22 g, 119 mmol, 3 eq) in dioxane (150 mL) were added Pd(dppf)Cl₂ (1.45 g, 1.98 mmol, 0.05 eq) and KOAc (11.68 g, 119 mmol, 3 eq). Then the reaction was stirred at 120° C. for 1 h under N₂ atmosphere. The reaction mixture was filtered and the filtrated cake was washed with DCM (3×80 mL). The combined filtrate was concentrated. The residue was purified by silica gel chromatography (PE:EtOAc=5/1) and washed with 100 mL PE to afford the title compound (13.8 g, 93.03% yield) as a light yellow solid.

Step 2) Preparation of 2-methoxy-7-(2-pyridyl)naphthalen-1-amine

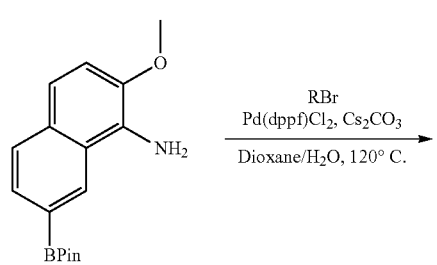

-continued

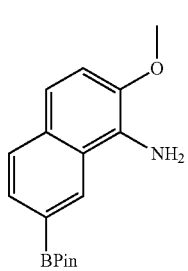

To a solution of 2-methoxy-7-(4,4,5,5-tetramethyl-1,3,2-dioxaborolan-2-yl)naphthalen-1-amine (5 g, 16.71 mmol, 1 eq) and 2-bromopyridine (3.96 g, 25.07 mmol, 2.39 mL, 1.5 eq) in dioxane (40 mL) and H₂O (10 mL) were added Cs₂CO₃ (16.34 g, 50.14 mmol, 3 eq) and Pd(dppf)Cl₂ (122.3 mg, 167.13 µmol, 0.01 eq). The reaction was stirred at 120° C. for 3 h under N₂ atmosphere. The reaction mixture was poured into saturated EDTA (200 mL) and stirred at 25° C. for 1 h. Then the mixture was extracted with EtOAc (3×100 mL). The combined organic layer was washed with brine (3×100 mL), dried over Na₂SO₄, filtered, and concentrated. The residue was purified by silica gel chromatography (PE:EtOAc/DCM=3:1/1) to afford the title compound (3.6 g, 86.06% yield) as a yellow oil.

Step 3) Preparation of 1-amino-7-(2-pyridyl)naphthalen-2-ol

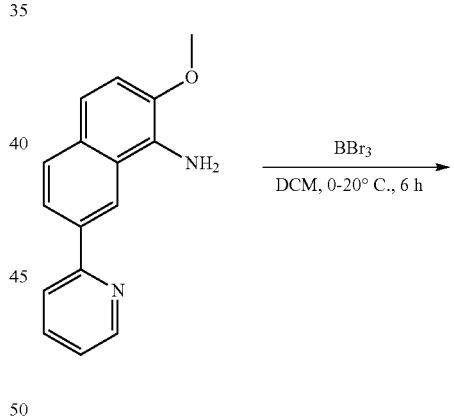

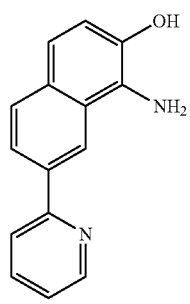

To a solution of 2-methoxy-7-(2-pyridyl)naphthalen-1-amine (3. g, 11.99 mmol, 1 eq) in DCM (30 mL) was added BBr₃ (46.84 g, 186.98 mmol, 18.02 mL, 15.6 eq) at 0° C. Then the reaction was stirred at 20° C. for 6 h. The reaction was poured into ice-water (300 mL) and adjusted to pH=8 with solid Na₂CO₃. The reaction was filtered, and the filter cake was washed with water (50 mL) and concentrated to afford the title compound (2. g) as a brown solid, which was used directly in the next step. The filtrate was extracted with DCM (3×50 mL). The combined organic layer was washed with brine (3×40 mL), dried over Na₂SO₄, filtered, and concentrated to give 600 mg of crude product. Total yield of crude product was 92%.

Step 4) Preparation of tert-butyl N-[2-hydroxy-7-(2-pyridyl)-1-naphthyl]carbamate

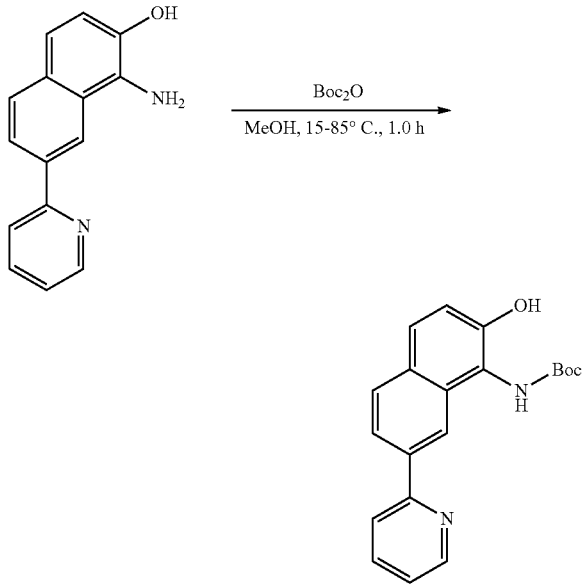

To a solution of 1-amino-7-(2-pyridyl)naphthalen-2-ol (2. g, 8.46 mmol, 1 eq) in MeOH (20 mL) was added Boc₂O (36.95 g, 169.3 mmol, 38.89 mL, 20 eq) at 15° C. The reaction was stirred at 85° C. for 1 h. TLC showed the desired product. 20 mL of N,N-dimethylethane-1,2-diamine was added, and the reaction was stirred at 20° C. for 18 h. LCMS showed 70% of desired compound. The reaction was quenched with water (50 mL) and extracted with DCM (3×30 mL). The combined organic layer was washed with water (3×20 mL) and brine (3×20 mL), dried over Na₂SO₄, filtered, and concentrated. The residue was purified by silica gel chromatography (PE:EtOAc=1/1) to afford the title compound (2.3 g, 68.66% yield) as a yellow solid.

Step 5) Preparation of [1-(tert-butoxycarbonylamino)-7-(2-pyridyl)-2-naphthyl]trifluoromethane sulfonate

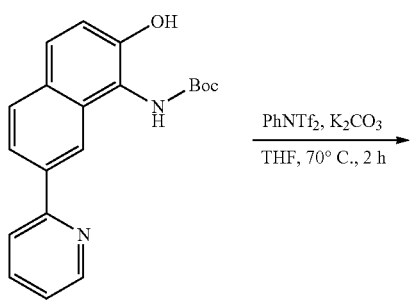

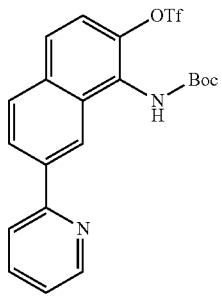

To a solution of tert-butyl N-[2-hydroxy-7-(2-pyridyl)-1-naphthyl]carbamate (1.3 g, 3.28 mmol, 1 eq) in THF (20 mL) were added K₂CO₃ (1.3 g, 9.41 mmol, 2.86 eq) and PhNTf₂ (1.52 g, 4.25 mmol, 1.30 eq). The reaction was stirred at 70° C. for 2 h. The reaction mixture was concentrated to remove the THF. The residue was quenched with water (100 mL) at 0° C. and extracted with EtOAc (3×30 mL). The combined organic layer was washed with water (3×30 mL) and brine (3×30 mL), dried over Na₂SO₄, filtered, and concentrated. The residue was purified by silica gel chromatography (PE:EtOAc=4:1) to afford the title compound (1.3 g, 71% yield) as a yellow oil.

Step 6) Preparation of methyl 1-(tert-butoxycarbonylamino)-7-(2-pyridyl)naphthalene-2-carboxylate

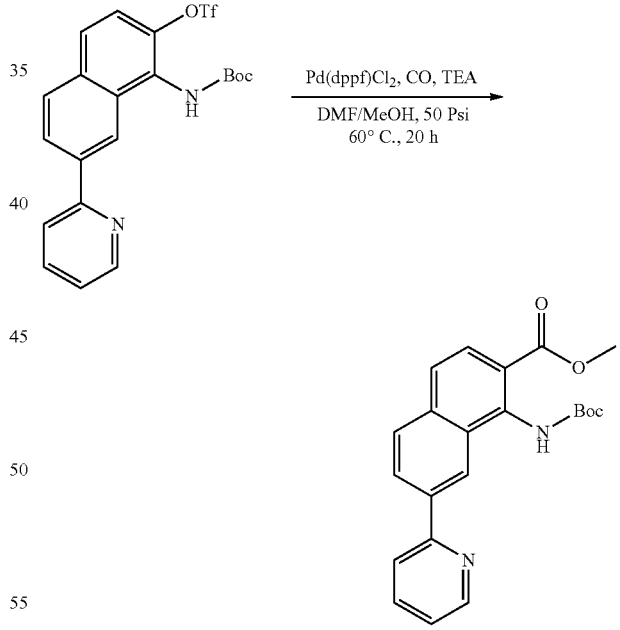

To a sealed tube were added [1-(tert-butoxycarbonylamino)-7-(2-pyridyl)-2-naphthyl]trifluoromethanesulfonate (570 mg, 973.43 μmol, 1 eq), Pd(dppf)Cl₂ (71.2 mg, 97.34 μmol, 0.1 eq) and TEA (610.7 mg, 6.03 mmol, 840.00 μL, 6.20 eq) in DMF (4 mL) and MeOH (4 mL). The reaction was stirred at 60° C. for 20 h under CO (50 Psi) atmosphere. LCMS showed 80% desired compound. The reaction mixture was concentrated to remove MeOH. Then 50 mL Saturated EDTA and 50 mL DCM were added. The mixture was stirred at 20° C. for 1 h. The mixture was extracted with DCM (3×30 mL). The combined organic layer was washed with water (3×30 mL) and brine (3×30 mL), dried over Na₂SO₄, filtered, and concentrated. The residue was purified by silica gel chromatography (PE: EtOAc=4:1) to afford the title compound (300 mg, 65.15% yield) as a yellow solid.

Step 7) Preparation of methyl 1-[tert-butoxycarbonyl(2-cyanoallyl)amino]-7-(2-pyridyl)naphthalene-2-carboxylate

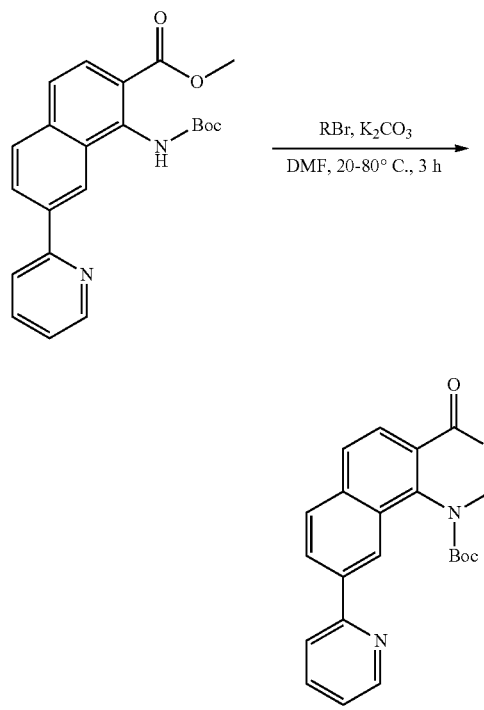

To a solution of methyl 1-(tert-butoxycarbonylamino)-7-(2-pyridyl)naphthalene-2-carboxylate (270 mg, 713.49 μmol, 1 eq) in DMF (5 mL) were added K₂CO₃ (247.5 mg, 1.79 mmol, 2.51 eq) and 2-(bromomethyl)prop-2-enenitrile (192.9 mg, 1.32 mmol, 1.85 eq) in 0.5 mL of DMF. The reaction mixture was stirred at 80° C. for 2 h. A solution of 2-(bromomethyl)prop-2-enenitrile (52.1 mg, 356.75 μmol, 0.5 eq) in 0.5 L DMF was added, and the reaction was heated at 80° C. for another 1 h. TLC showed 80% desired compound. The reaction was poured into saturated NH₄Cl (50 mL) at 0° C. and extracted with EtOAc (3×30 mL). The combined organic layer was washed with water (3×30 mL) and brine (3×30 mL), dried over Na₂SO₄, filtered, and concentrated. The residue was purified by silica gel chromatography (PE:EtOAc=4:1) to afford the title compound (250 mg, 79.01% yield) as a light yellow oil.

Step 8) Preparation of 1-[tert-butoxycarbonyl(2-cyanoallyl)amino]-7-(2-pyridyl)naphthalene-2-carboxylic acid

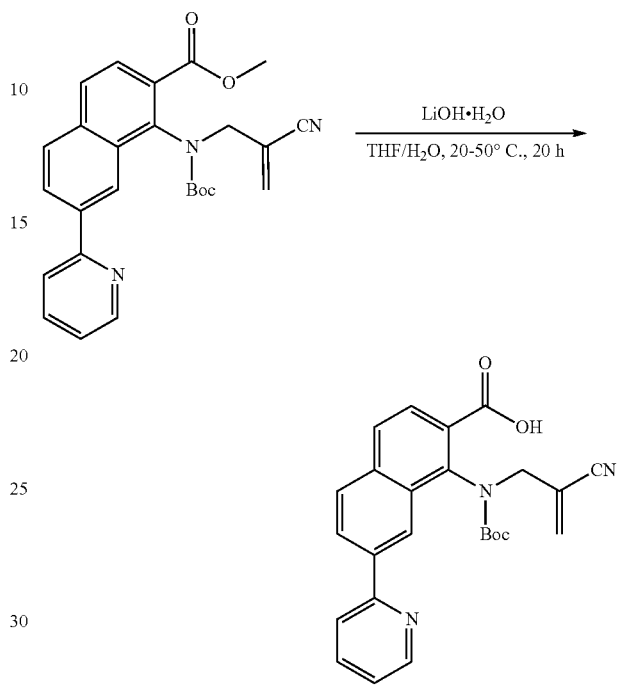

To a solution of methyl 1-[tert-butoxycarbonyl(2-cyanoallyl)amino]-7-(2-pyridyl)naphthalene-2-carboxylate (170 mg, 383.32 μmol, 1 eq) in THF (4 mL) and H₂O (1 mL) was added LiOH·H₂O (170 mg, 4.05 mmol, 10.57 eq). Then the reaction was stirred at 20° C. for 18 h and at 50° C. for 2 h. The reaction mixture was adjusted pH=5 with 1M HCl and extracted with DCM (3×30 mL). The combined organic layer was washed with brine (3×30 mL), dried over Na₂SO₄, filtered, and concentrated. The residue was purified by prep-TLC (SiO₂, DCM/MeOH=18/1, Rf=0.4) to afford the title compound (120 mg, 72.89% yield) as a light yellow solid.

Step 9) Preparation of tert-butyl N-[2-carbamoyl-7-(2-pyridyl)-1-naphthyl]-N-(2-cyanoallyl) carbamate

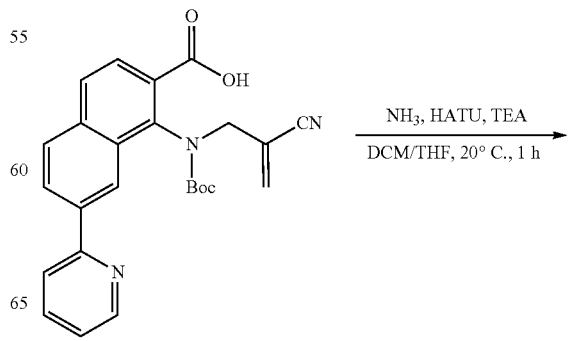

-continued

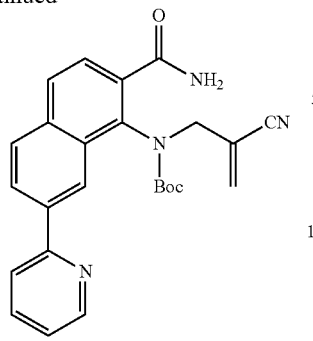

To a solution of 1-[tert-butoxycarbonyl(2-cyanoallyl)amino]-7-(2-pyridyl)naphthalene-2-carboxylic acid (100 mg, 232.85 µmol, 1 eq) in DCM (6 mL) were added TEA (203.6 mg, 2.01 mmol, 280.00 µL, 8.64 eq) and HATU (200 mg, 526 µmol, 2.26 eq). Then, NH$_3$ (3.57 mL, 61.35 eq) (4M in THF) was added at 0° C. The reaction mixture was stirred at 20° C. for 1 h. The reaction was quenched with water (30 mL) at 0° C. and extracted with DCM (3×10 mL). The combined organic layer was washed with brine (3×10 mL), dried over Na$_2$SO$_4$, filtered, and concentrated. The residue was purified by prep-TLC (SiO$_2$, DCM/MeOH=20/1) to afford the title compound (69 mg, 69.16% yield) as a light yellow solid.

Step 10) Compound 265: Preparation of 1-(2-cyanoallylamino)-7-(2-pyridyl)naphthalene-2-carboxamide To a solution of tert-butyl N-[2-carbamoyl-7-(2-pyridyl)-1-naphthyl]-N-(2-cyanoallyl)carbamate (50 mg, 116.69 µmol, 1 eq) in DCM (3 mL) was added TFA (0.6 mL). The reaction mixture was stirred at 20° C. for 1 h. The reaction was poured into Saturated NaHCO$_3$ (30 mL) and extracted with DCM (4×10 mL). The combined organic layer was washed with brine (3×10 mL), dried over Na$_2$SO$_4$, filtered, and concentrated. The residue was purified by prep-TLC (SiO$_2$, DCM/MeOH=18/1, Rf=0.6) to afford the title compound (20 mg, 52.20% yield) as a light yellow solid. LC-MS (ES$^+$, m/z): 329.1 [(M+H)$^+$]

Route 2: General Scheme

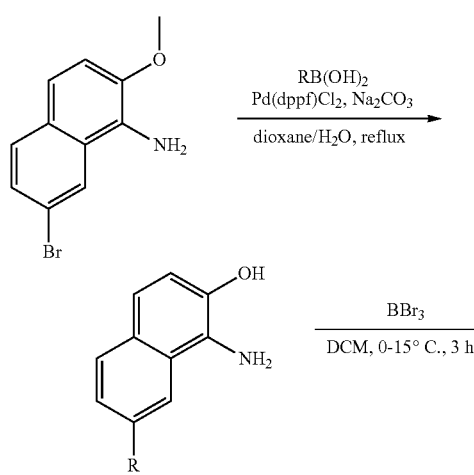

-continued

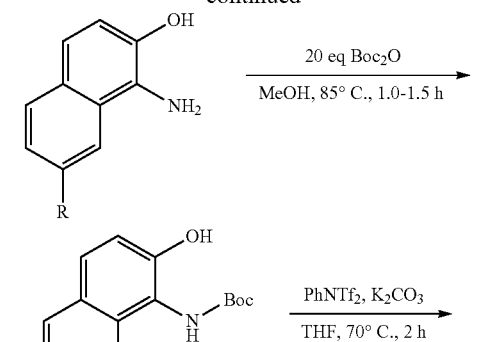

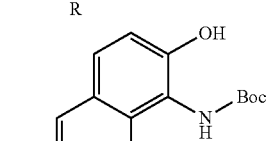

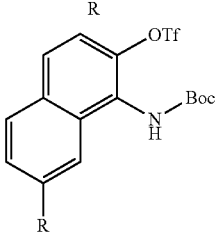

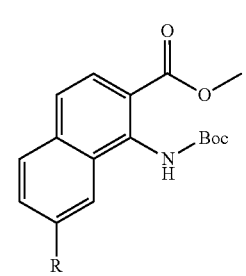

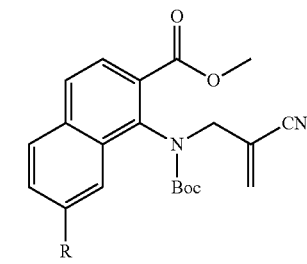

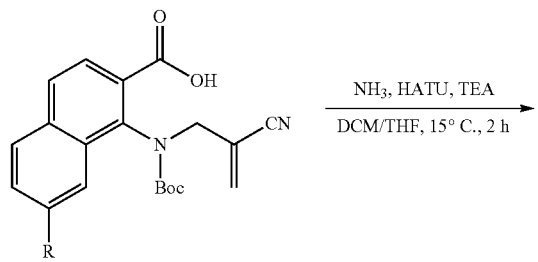

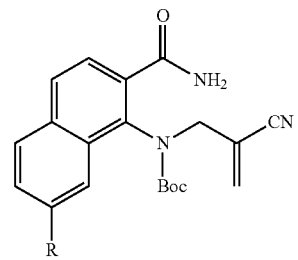

323

-continued

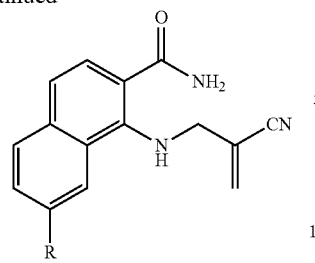

Step 1) Preparation of 2-methoxy-7-(3-pyridyl)naphthalen-1-amine

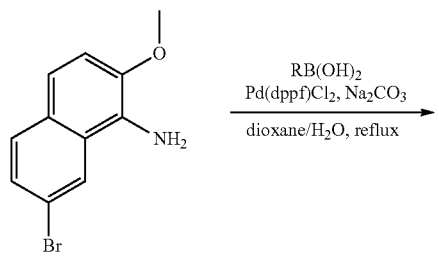

To a solution of 7-bromo-2-methoxy-naphthalen-1-amine (5. g, 19.83 mmol, 1 eq) and 3-pyridylboronic acid (3.66 g, 29.75 mmol, 1.5 eq) in dioxane (60 mL) and H₂O (15 mL) were added Na₂CO₃ (6.31 g, 59.5 mmol, 3 eq) and Pd(dppf)Cl₂ (1.45 g, 1.98 mmol, 0.1 eq). The reaction mixture was stirred at 120° C. for 1 h under N₂ atmosphere. TLC showed that the reaction was complete. 100 mL of EtOAc and 200 mL of saturated EDTA were added. The reaction mixture was stirred at 15° C. for 1 h and extracted with EtOAc (3×200 mL). The combined organic layer was washed with brine (3×100 mL), dried over Na₂SO₄, filtered, and concentrated. The residue was purified by silica gel chromatography (PE/EtOAc=1/1 to 100% EtOAc) to afford the title compound (4.5 g, 90.65% yield) as a yellow solid.

324

Step 2) Preparation of 1-amino-7-(3-pyridyl)naphthalen-2-ol

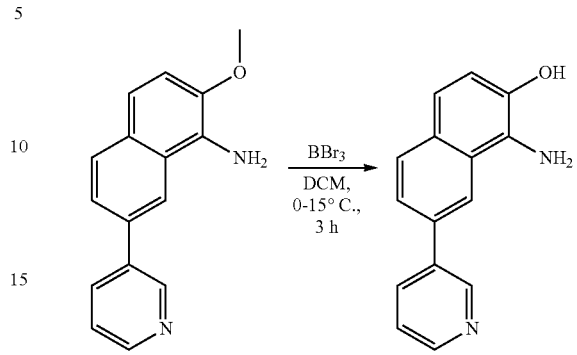

To a solution of 2-methoxy-7-(3-pyridyl)naphthalen-1-amine (2.8 g, 11.19 mmol, 1 eq) in DCM (28 mL) was added BBr₃ (14.56 g, 58.12 mmol, 5.60 mL, 5.20 eq) in 1 mL DCM at 0° C. The reaction mixture was stirred at 15° C. for 3 h. The reaction mixture was poured into water (200 mL). The solution was adjusted to pH=8 with solid NaHCO₃. A yellow solid formed, and the precipitate was filtered. The filter cake was washed with water (3×150 mL) and dried to afford the title compound (2.5 g, 94% yield) as a yellow solid.

Step 3) Preparation of tert-butyl N-[2-hydroxy-7-(3-pyridyl)-1-naphthyl]carbamate

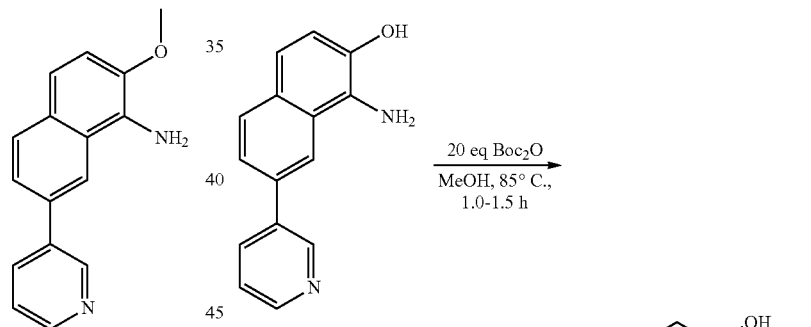

To a solution of 1-amino-7-(3-pyridyl)naphthalen-2-ol (2.2 g, 8.38 mmol, 1 eq) in MeOH (146 mL) was added Boc₂O (36.58 g, 167.61 mmol, 38.50 mL, 20 eq). The reaction mixture was stirred at 85° C. for 1.0 h. LCMS showed the desired product. 14.6 mL of N,N-dimethyl-ethane-1,2-diamine was added, and the reaction was stirred at 15° C. for 1d. The reaction was concentrated. The residue was diluted with 20 mL of DCM, washed with water (3×40 mL) and brine (3×40 mL), dried over Na₂SO₄, filtered, and concentrated. The residue was purified by silica gel chromatography (PE/EtOAc/DCM=50/50/20) to afford the title compound (2.1 g, 74.5% yield) as a light yellow solid.

Step 4) Preparation of [1-(tert-butoxycarbonylamino)-7-(3-pyridyl)-2-naphthyl]trifluoromethane sulfonate

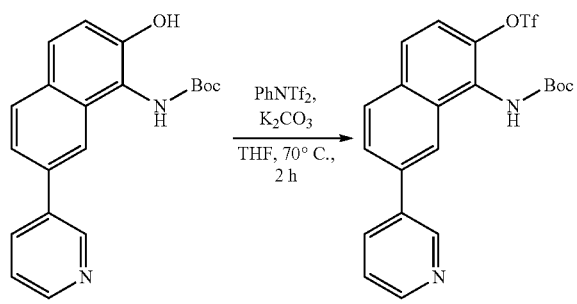 [SMILES: CC(C)(C)OC(=O)Nc1c(O)ccc2ccc(-c3cccnc3)cc12 ; CC(C)(C)OC(=O)Nc1c(OS(=O)(=O)C(F)(F)F)ccc2ccc(-c3cccnc3)cc12]

To a solution of tert-butyl N-[2-hydroxy-7-(3-pyridyl)-1-naphthyl]carbamate (1.86 g, 5.53 mmol, 1 eq) and 1,1,1-trifluoro-N-phenyl-N-(trifluoromethylsulfonyl) methanesulfonamide (2.37 g, 6.64 mmol, 1.2 eq) in THF (30 mL) was added $K_2CO_3$ (1.53 g, 11.06 mmol, 2 eq). The reaction mixture was stirred at 70° C. for 2 h. The reaction was quenched with water (100 mL) at 0° C. and extracted with EtOAc (3×50 mL). The combined organic layer was washed with water (3×50 mL) and brine (3×50 mL), dried over $Na_2SO_4$, filtered, and concentrated. The residue was purified by silica gel chromatography (DCM/MeOH=20/1) to afford the title compound (2.15 g, 83% yield) as a yellow oil.

Step 5) Preparation of methyl 1-(tert-butoxycarbonylamino)-7-(3-pyridyl)naphthalene-2-carboxylate

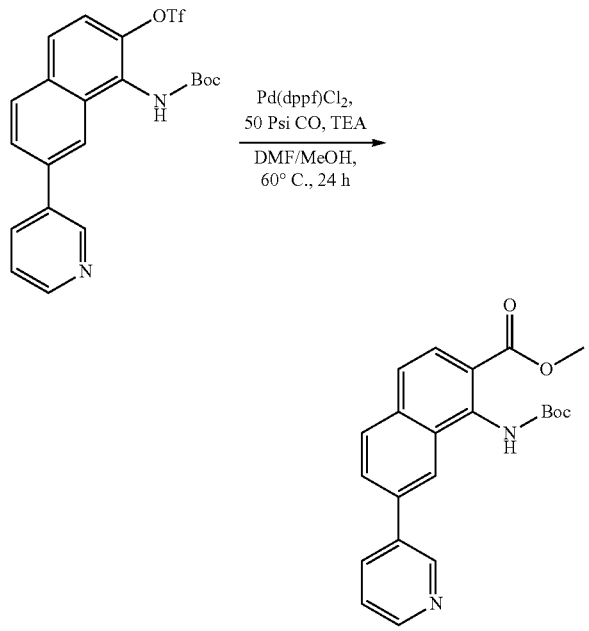

To a solution of [1-(tert-butoxycarbonylamino)-7-(3-pyridyl)-2-naphthyl]trifluoromethane-sulfonate (1. g, 2.13 mmol, 1 eq) in DMF (8.3 mL) and MeOH (8.3 mL) were added TEA (1.08 g, 10.67 mmol, 1.49 mL, 5 eq) and Pd(dppf)Cl$_2$ (156.2 mg, 213.47 μmol, 0.1 eq). The reaction mixture was stirred at 60° C. for 24 h under CO (50 Psi) atmosphere. The reaction was concentrated. 50 mL of Saturated EDTA and 20 mL of DCM were added to the mixture. The reaction mixture was stirred at 15° C. for 1 h. Then. The mixture was extracted with DCM/MeOH=10:1 (3×30 mL). The combined organic layer was washed with water (3×30 mL), dried over $Na_2SO_4$, filtered, and concentrated. The residue was purified by silica gel chromatography (DCM/MeOH=20/1) to afford the title compound (640 mg, 79.2% yield) as a light yellow solid.

Step 6) Preparation of methyl 1-[tert-butoxycarbonyl(2-cyanoallyl)amino]-7-(3-pyridyl)naphthalene-2-carboxylate

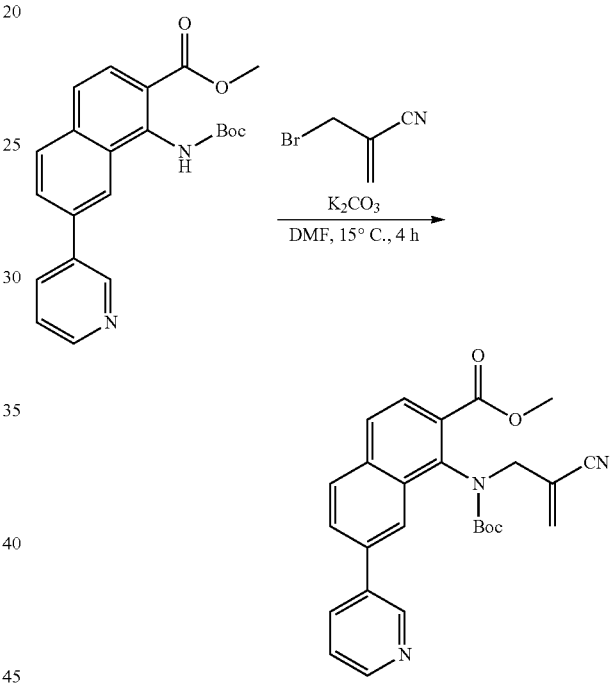

To a solution of methyl 1-(tert-butoxycarbonylamino)-7-(3-pyridyl)naphthalene-2-carboxylate (640 mg, 1.69 mmol, 1 eq) in DMF (10 mL) were added $K_2CO_3$ (640 mg, 4.63 mmol, 2.74 eq) and 2-(bromomethyl)prop-2-enenitrile (314 mg, 2.15 mmol, 1.27 eq) in 2 mL of DMF. The reaction mixture was stirred at 15° C. for 2 h. Then, a solution of 2-(bromomethyl)prop-2-enenitrile (170 mg, 1.16 mmol, 0.69 eq) in 0.5 mL of DMF was added, and the reaction was stirred at 15° C. for another 2 h. The reaction was poured into Saturated NH$_4$Cl (50 mL) at 0° C. and the mixture was extracted with EtOAc (3×30 mL). The combined organic layer was washed with water (3×30 mL) and brine (3×10 mL), dried over $Na_2SO_4$, filtered, and concentrated. The residue was purified by prep-TLC (SiO$_2$, PE/EtOAc=1/1) to afford the title compound (300 mg, 40% yield) as a light yellow oil. Methyl 1-(tert-butoxycarbonylamino)-7-(3-pyridyl)naphthalene-2-carboxylate (180 mg) was recovered.

327

Step 7) Preparation of 1-[tert-butoxycarbonyl(2-cyanoallyl)amino]-7-(3-pyridyl)naphthalene-2-carboxylic acid

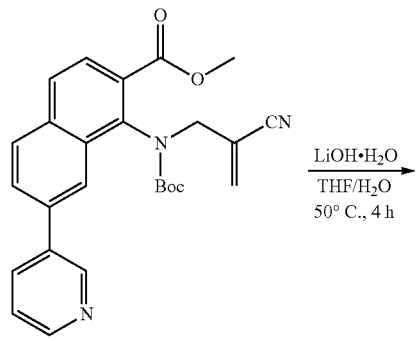

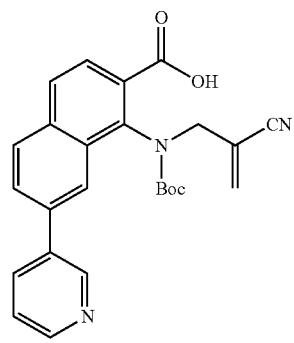

To a solution of methyl 1-[tert-butoxycarbonyl(2-cyanoallyl)amino]-7-(3-pyridyl)naphthalene-2-carboxylate (260 mg, 586.25 μmol, 1 eq) in THF (11.2 mL) and H$_2$O (2.8 mL) was added LiOH·H$_2$O (272.8 mg, 6.5 mmol, 11.09 eq). The reaction mixture was stirred at 50° C. for 4 h. The reaction was adjusted pH=3 with Saturated citric acid (3 mL) and extracted with DCM/MeOH=10:1 (3×50 mL). The combined organic layer was washed with brine (3×30 mL), dried over Na$_2$SO$_4$, filtered, and concentrated. The residue was washed with DCM/MeOH=10:1 (8 mL) to give the desired compound (140 mg). The filtrate was purified by prep-TLC (SiO$_2$, DCM/MeOH=10:1) to afford the title compound (70 mg). The total yield was 83%.

Step 8) Preparation of tert-butyl N-[2-carbamoyl-7-[4-[(1-methyl-4-piperidyl)carbamoyl]pyrimidin-2-yl]-1-naphthyl]-N-(2-cyanoallyl)carbamate

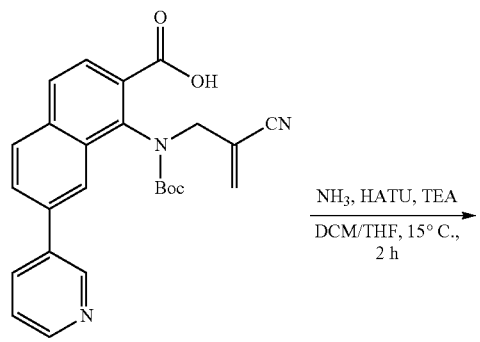

328

-continued

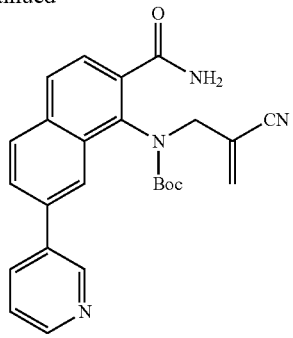

To a solution of 1-[tert-butoxycarbonyl(2-cyanoallyl)amino]-7-(3-pyridyl)naphthalene-2-carboxylic acid (210 mg, 415.63 μmol, 1 eq) in DCM (6 mL) were added TEA (762 mg, 7.53 mmol, 1.05 mL, 18.12 eq), HATU (316.1 mg, 831.26 μmol, 2 eq) and NH$_3$ (4M NH$_3$ in THF, 6 mL, 57.74 eq). The reaction mixture was stirred at 15° C. for 2 h. The reaction was quenched with ice-water (30 mL) and extracted with DCM (3×15 mL). The combined organic layer was washed with brine (3×15 mL), dried over Na$_2$SO$_4$, filtered, and concentrated. The residue was purified by prep-TLC (SiO$_2$, DCM/MeOH=20/1, Rf=0.4) to afford the title compound (160 mg, 89.8% yield) as a light yellow oil.

Step 9) Compound 264: Preparation of 1-((2-cyanoallyl)amino)-7-(pyridin-3-yl)-2-naphthamide

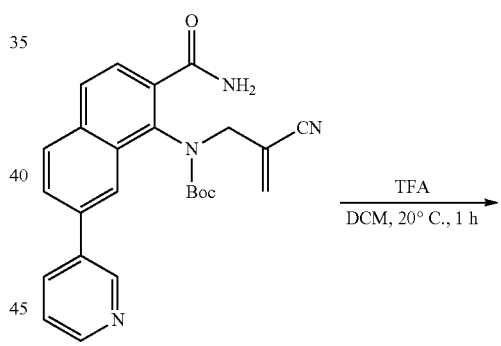

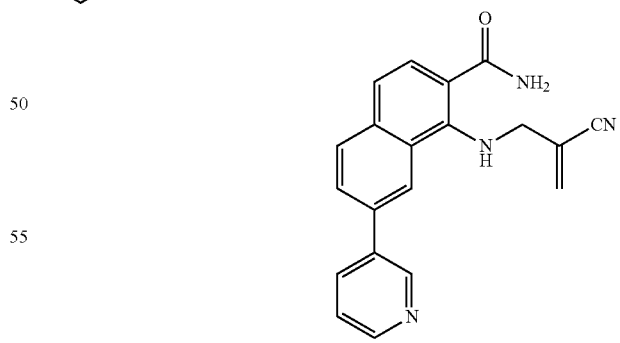

To a solution of tert-butyl N-[2-carbamoyl-7-[4-[(1-methyl-4-piperidyl)carbamoyl]pyrimidin-2-yl]-1-naphthyl]-N-(2-cyanoallyl)carbamate (50 mg, 116.69 μmol, 1 eq) in DCM (3 mL) was added TFA (0.5 mL) at 20° C. The reaction mixture was stirred at 20° C. for 1 h. The reaction was poured into Saturated NaHCO$_3$ (30 mL) and extracted with DCM (4×10 mL). The combined organic layer was washed with brine (3×10 mL), dried over Na₂SO₄, filtered, and concentrated. The residue was purified by HPLC to afford the title compound (15 mg, 38% yield) as a white solid. LC-MS (ES⁺, m/z): 329.1 [(M+H)⁺].
Route 3: General Scheme
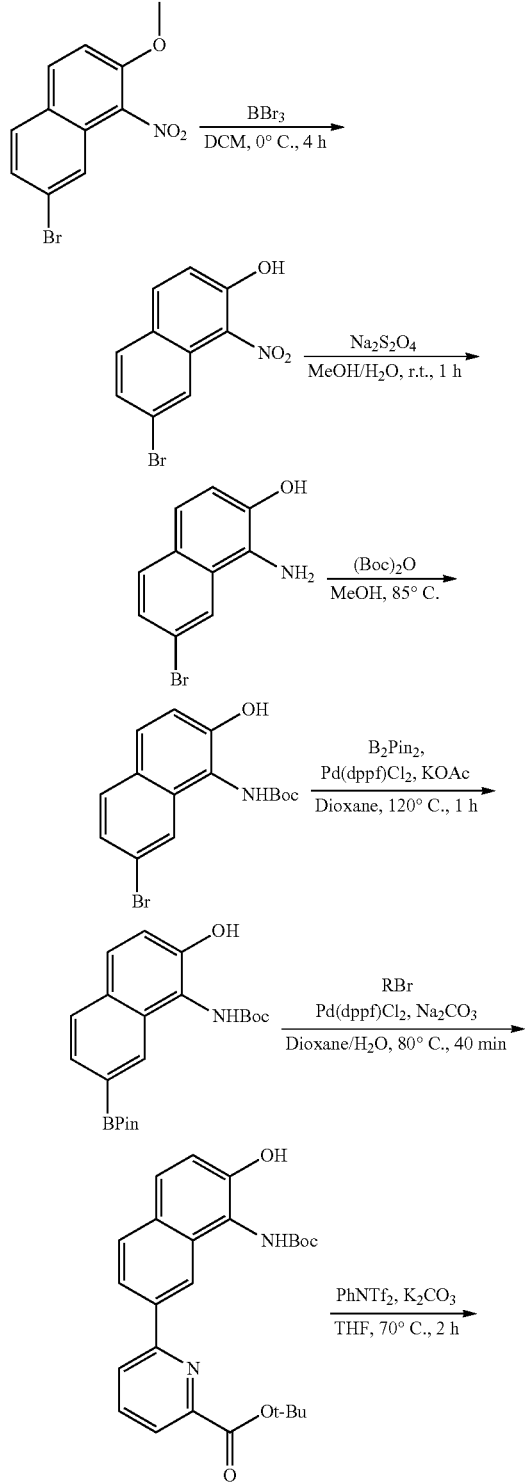
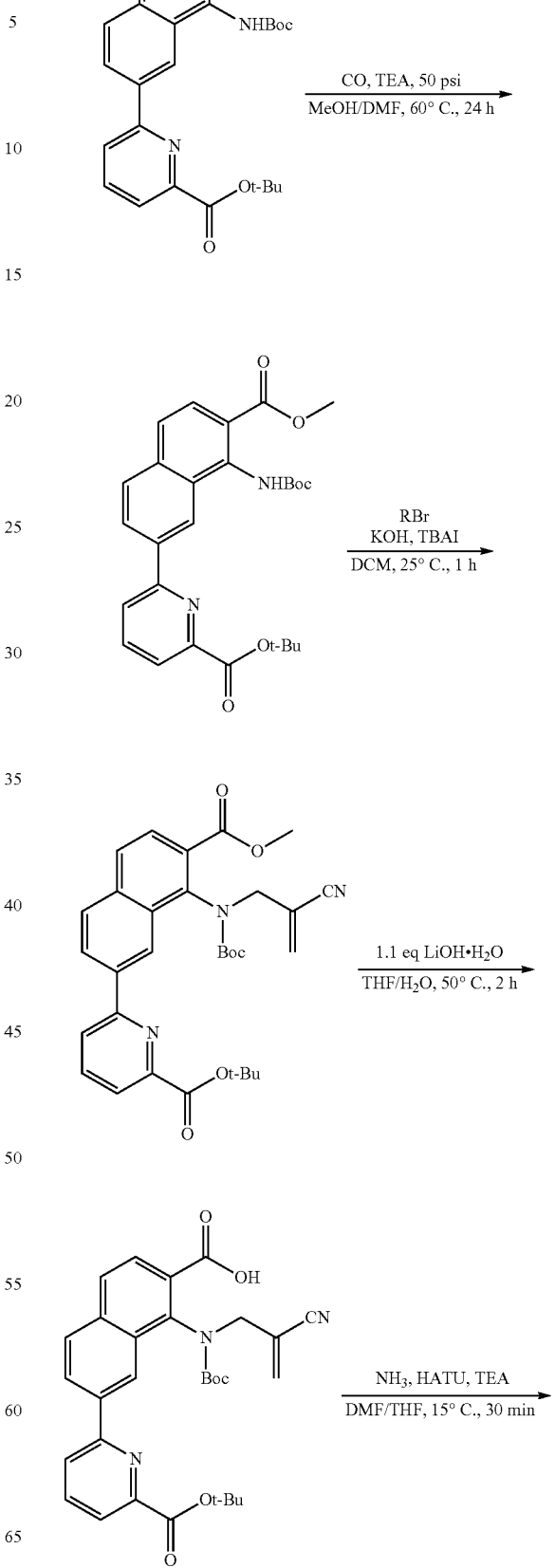

-continued

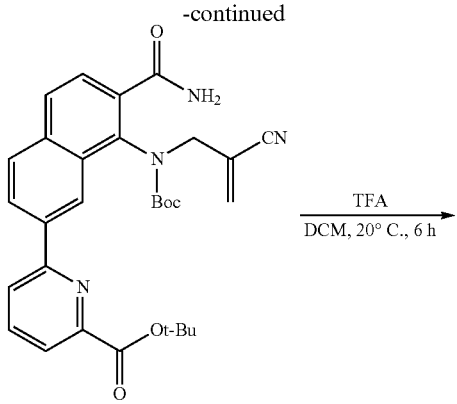

TFA
DCM, 20° C., 6 h
→

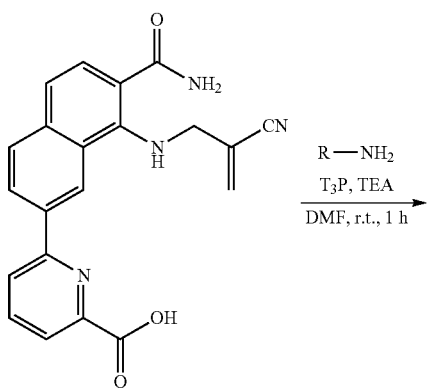

R—NH$_2$
T$_3$P, TEA
DMF, r.t., 1 h
→

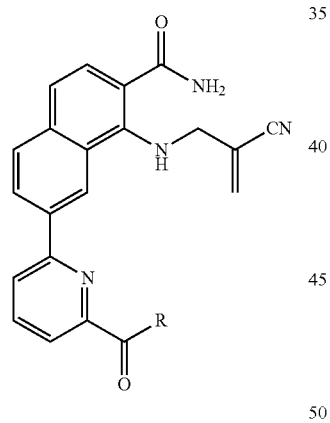

Step 1) Preparation of
7-bromo-1-nitro-naphthalen-2-ol

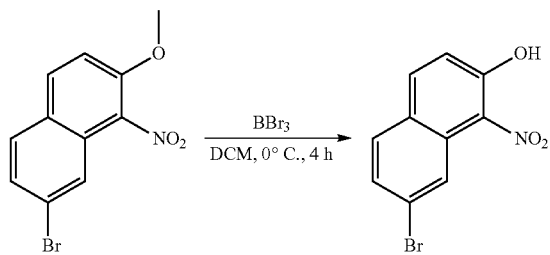 [SMILES: COc1ccc2ccc(Br)cc2c1[N+](=O)[O-] ; "BBr3" ; O=[N+]([O-])c1c(O)ccc2ccc(Br)cc12]

To a solution of 7-bromo-2-methoxy-1-nitro-naphthalene (23 g, 81.53 mmol, 1 eq) in DCM (230 mL) was added BBr$_3$ (61.28 g, 244.6 mmol, 23.57 mL, 3 eq) at 0° C. The mixture was stirred at 0° C. for 4 h. The mixture was poured into ice-water (500 mL) and the aqueous phase was extracted with EtOAc (3×200 mL). The combined organic phase was washed with brine (3×200 mL), dried with anhydrous Na$_2$SO$_4$, filtered, and concentrated in vacuo to afford the title compound (22 g, 99% yield) as a light yellow solid, which was used in the next step without further purification.

Step 2) Preparation of
1-amino-7-bromo-naphthalen-2-ol

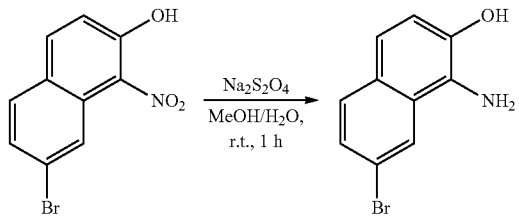

To a solution of 7-bromo-1-nitro-naphthalen-2-ol (5 g, 18.65 mmol, 1 eq) in MeOH (18 mL) and H$_2$O (6 mL) was added sodium dithionite (25.98 g, 149.22 mmol, 32.47 mL, 8 eq). The mixture was stirred at 25° C. for 1 hr. The solid was filtered, washed with water (3×300 mL) to afford the title compound (5 g, crude) as a white solid.

Step 3) Preparation of tert-butyl
N-(7-bromo-2-hydroxy-1-naphthyl)carbamate

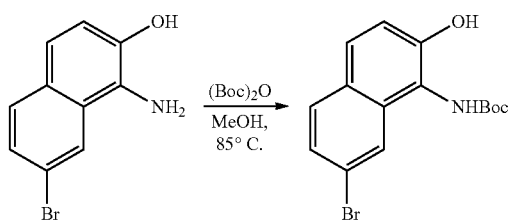 [SMILES: "(Boc)2O" ; Nc1c(O)ccc2ccc(Br)cc12 ; CC(C)(C)OC(=O)Nc1c(O)ccc2ccc(Br)cc12]

To a solution of 1-amino-7-bromo-naphthalen-2-ol (4.4 g, 18.48 mmol, 1 eq) in MeOH (350 mL) was added Boc$_2$O (32.27 g, 147.85 mmol, 33.97 mL, 8 eq). The reaction mixture was stirred at 85° C. for 14 hrs. LCMS showed di-Boc product was detected. 34 mL of N,N-dimethylethane-1,2-diamine was added and the reaction was stirred at 25° C. for 12 hrs. The reaction mixture was concentrated. The residue was diluted with 20 mL of DCM and washed with water (3×40 mL) and brine (3×40 mL), dried over Na$_2$SO$_4$, filtered, and concentrated. The residue was purified by silica gel chromatography (PE:EtOAc=10:1 to 4:1) to afford the title compound (4.7 g, 58.0% yield) as a light yellow solid.

Step 4) Preparation of tert-butyl N-[2-hydroxy-7-(4,4,5,5-tetramethyl-1,3,2-dioxaborolan-2-yl)-1-naphthyl]carbamate

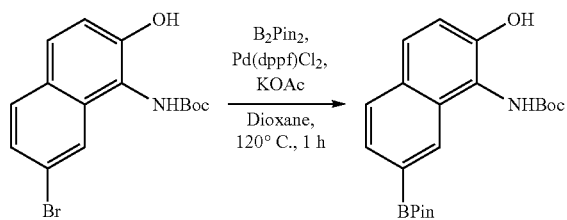

To a solution of 4,4,5,5-tetramethyl-2-(4,4,5,5-tetramethyl-1,3,2-dioxaborolan-2-yl)-1,3,2-dioxaborolane (5.56 g, 21.88 mmol, 2 eq) and tert-butyl N-(7-bromo-2-hydroxy-1-naphthyl) carbamate (3.7 g, 10.94 mmol, 1 eq) in dioxane (40 mL) were added KOAc (3.22 g, 32.82 mmol, 3 eq) and Pd (dppf)Cl$_2$ (400 mg, 546.67 µmol, 0.05 eq). The mixture was stirred at 120° C. for 1 h under N$_2$. TLC showed that the reaction as completed. The reaction was poured into 150 mL of water and extracted with EtOAc (3×150 mL), washed with brine (3×150 mL), dried over by anhydrous Na$_2$SO$_4$, filtered, and concentrated in vacuo. The residue was purified by silica gel chromatography (PE:EtOAc=10:1 to 4:1) and washed with PE (3×150 mL) to afford the title compound (3.8 g, 90.2% yield) as a white solid.

Step 5) Preparation of tert-butyl 6-/8-(tert-butoxycarbonylamino)-7-hydroxy-2-naphthyl/pyridine-2-carboxylate

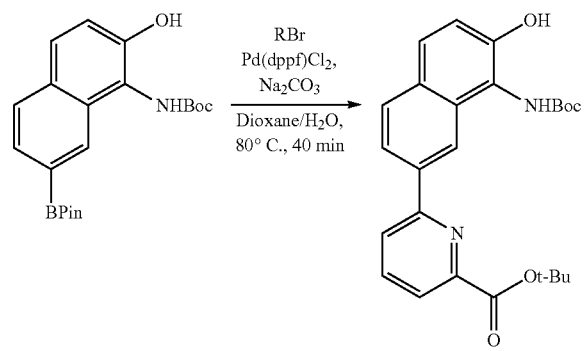

To a solution of tert-butyl N-[2-hydroxy-7-(4,4,5,5-tetramethyl-1,3,2-dioxaborolan-2-yl)-1-naphthyl]carbamate (2.8 g, 7.27 mmol, 1 eq) and tert-butyl 6-bromopyridine-2-carboxylate (2.06 g, 7.99 mmol, 1.1 eq) in dioxane (40 mL) and H$_2$O (10 mL) were added Na$_2$CO$_3$ (2.31 g, 21.8 mmol, 3 eq) and Pd(dppf)Cl$_2$ (531.8 mg, 726.78 µmol, 0.1 eq). The mixture was stirred at 80° C. for 40 min under N$_2$. The reaction was diluted with 30 mL of EtOAc and 60 mL of Saturated EDTA. The reaction mixture was stirred at 15° C. for 1 h and extracted with EtOAc (3×30 mL). The combined organic layer was washed with brine (3×30 mL), dried over Na$_2$SO$_4$, filtered, and concentrated. The residue was purified by silica gel chromatography (PE:EtOAc=10:1 to 4:1) to afford the title compound (2.5 g, 78.8% yield) as an orange solid.

Step 6) Preparation of tert-butyl 6-[8-(tert-butoxycarbonylamino)-7-(trifluoromethylsulfonyloxy)-2-naphthyl]pyridine-2-carboxylate

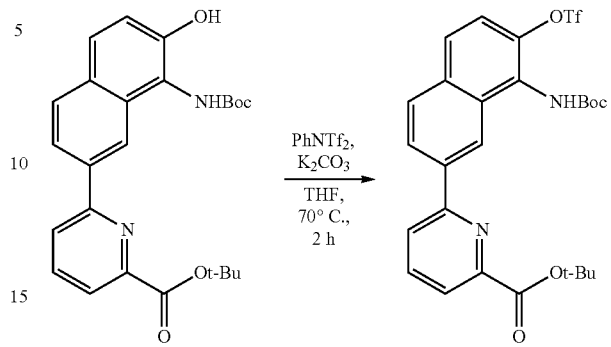

To a solution of tert-butyl 6-[8-(tert-butoxycarbonylamino)-7-hydroxy-2-naphthyl]pyridine-2-carboxylate (2.5 g, 5.73 mmol, 1 eq) in THF (50 mL) were added K$_2$CO$_3$ (1.58 g, 11.45 mmol, 2 eq) and 1,1,1-trifluoro-N-phenyl-N-(trifluoromethylsulfonyl)methanesulfonamide (2.46 g, 6.87 mmol, 1.2 eq). The mixture was stirred at 70° C. for 2 hr. The reaction was poured into 150 mL of water and extracted with EtOAc (3×150 mL). The combined organic layer was washed with brine (3×150 mL), dried over Na$_2$SO$_4$, filtered, and concentrated. The residue was purified by silica gel chromatography (PE:EtOAc=10:1 to 4:1) to afford the title compound (2. g, 61.4% yield) as a yellow solid.

Step 7) Preparation of tert-butyl 6-[8-(tert-butoxycarbonylamino)-7-methoxycarbonyl-2-naphthyl]pyridine-2-carboxylate

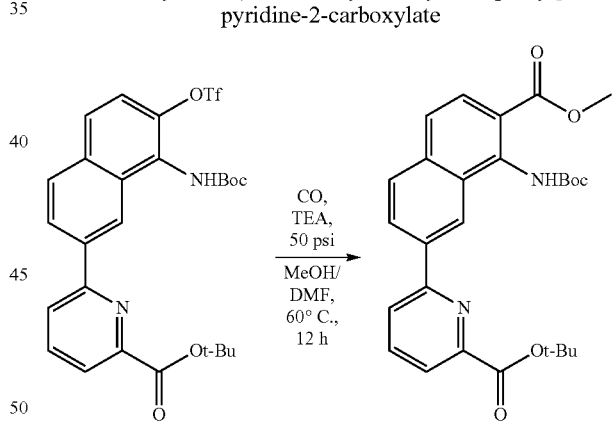

To a solution of tert-butyl 6-[8-(tert-butoxycarbonylamino)-7-(trifluoromethyl-sulfonyloxy)-2-naphthyl]pyridine-2-carboxylate (0.9 g, 1.58 mmol, 1 eq) in DMF (12 mL) and MeOH (12 mL) were added TEA (480.5 mg, 4.75 mmol, 660.98 µL, 3 eq) and Pd(dppf)Cl$_2$ (115.8 mg, 158.29 µmol, 0.1 eq). The reaction mixture was stirred at 60° C. for 12 h under CO (50 Psi) atmosphere. LCMS showed that the reaction was complete. 50 mL of Saturated EDTA and 20 mL of EtOAc were added. The reaction mixture was stirred at 25° C. for 1 h. Then the mixture was extracted with EtOAc (3×30 mL). The combined organic layer was washed with brine (3×30 mL), dried over Na$_2$SO$_4$, filtered, and concentrated. The residue was purified by prep-TLC (SiO$_2$, DCM/MeOH=20/1) to afford the title compound (580 mg, 76.6% yield) as a yellow solid.

Step 8) Preparation of tert-butyl 6-[8-[tert-butoxycarbonyl(2-cyanoallyl)amino]-7-methoxycarbonyl-2-naphthyl]pyridine-2-carboxylate

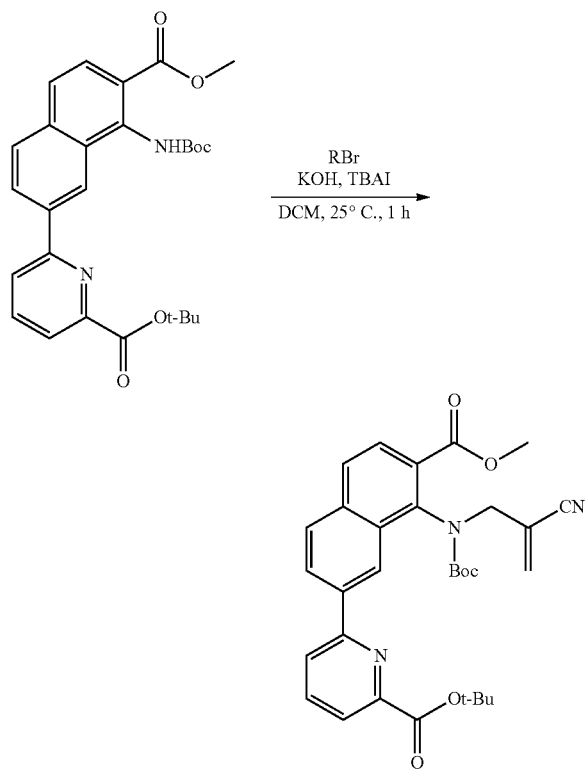

To a solution of tert-butyl 6-[8-(tert-butoxycarbonylamino)-7-methoxycarbonyl-2-naphthyl]pyridine-2-carboxylate (0.48 g, 1 mmol, 1 eq) in DCM (4 mL) were added KOH (112.6 mg, 2.01 mmol, 2 eq), TBAI (185.3 mg, 501.53 µmol, 0.5 eq) and 2-(bromomethyl)prop-2-enenitrile (175.7 mg, 1.2 mmol, 1.2 eq). The reaction mixture was stirred at 25° C. for 1 h. The reaction was poured into water (30 mL) and extracted with DCM (3×20 mL). The combined organic layer was washed with brine (3×20 mL), dried over Na$_2$SO$_4$, filtered, and concentrated. The residue was purified by prep-TLC (SiO$_2$, PE:EtOAc=3.5:1) to afford the title compound (290 mg, 53.2% yield) as a yellow solid.

Step 9) Preparation of 1-[tert-butoxycarbonyl(2-cyanoallyl)amino]-7-(6-tert-butoxycarbonyl-2-pyridyl)naphthalene-2-carboxylic acid

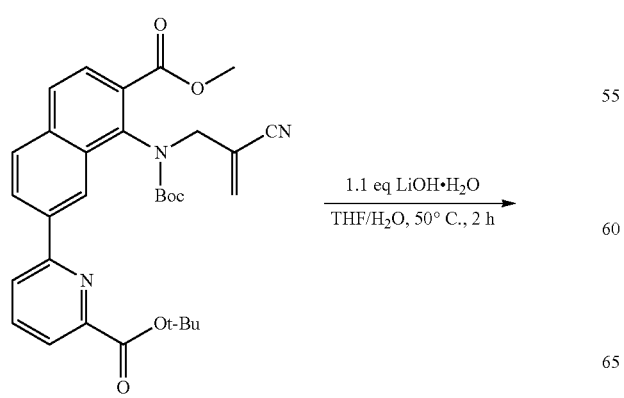

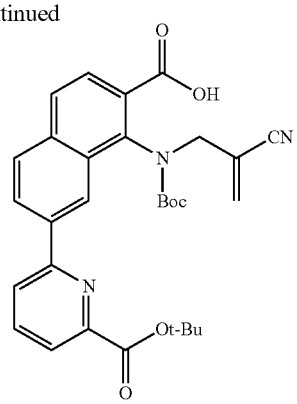

To a solution of tert-butyl 6-[8-[tert-butoxycarbonyl(2-cyanoallyl)amino]-7-methoxy carbonyl-2-naphthyl]pyridine-2-carboxylate (0.29 g, 533.47 µmol, 1 eq) in THF (13 mL) and H$_2$O (3.2 mL) was added LiOH·H$_2$O (22.4 mg, 533.47 µmol, 1.1 eq). The mixture was stirred at 50° C. for 1 h. Then LiOH·H$_2$O (4.5 mg, 106.69 µmol, 0.2 eq) was added and the reaction mixture was stirred at 50° C. for another 1 h. The reaction was poured into 50 mL of ice water and washed with PE (3×20 mL). The aqueous layer was adjusted to pH=7 with Saturated citric acid. The mixture was extracted with EtOAc (3×20 mL). The combined organic phase was washed with 20 mL of brine, dried over Na$_2$SO$_4$, filtered, and concentrated. The residue was purified by prep-TLC (SiO$_2$, DCM/MeOH=10:1) to afford the title compound (0.2 g, 70.8% yield) as a colorless oil.

Step 10) Preparation of tert-butyl 6-[8-[tert-butoxycarbonyl (2-cyanoallyl)amino]-7-carbamoyl-2-naphthyl]pyridine-2-carboxylate

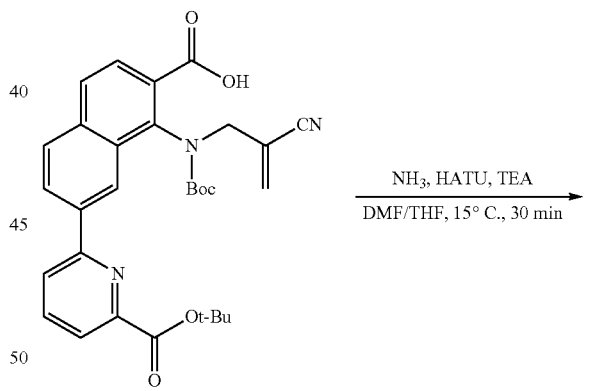

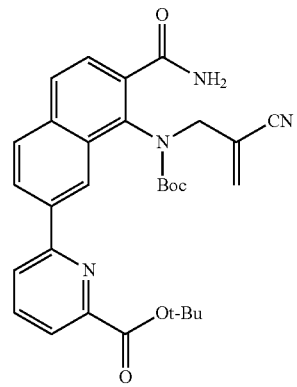

To a solution of 1-[tert-butoxycarbonyl(2-cyanoallyl)amino]-7-(3-pyridyl) naphthalene-2-carboxylic acid (0.35 g, 660.9 µmol, 1 eq) in DMF (10 mL) were added TEA (2.1 g, 20.75 mmol, 2.89 mL, 31.40 eq) and HATU (502.6 mg, 1.32 mmol, 2 eq). The mixture was stirred at 25° C. for 10 min. After cooling to 0° C., NH₃ (4 M NH₃ in THF, 6 mL, 36.4 eq) was added. The reaction mixture was stirred at 0° C. for 20 min. The reaction was quenched with water (15 mL) and extracted with EtOAc (3×15 mL). The combined organic layer was washed with brine (3×15 mL), dried over Na₂SO₄, filtered, and concentrated. The residue was purified by prep-TLC (SiO₂, PE:EtOAc=1/2) to afford the title compound (200 mg, 57.3% yield) as a white solid.

Step 11) Preparation of 6-(7-carbamoyl-8-((2-cyanoallyl)amino)naphthalen-2-yl)picolinic acid

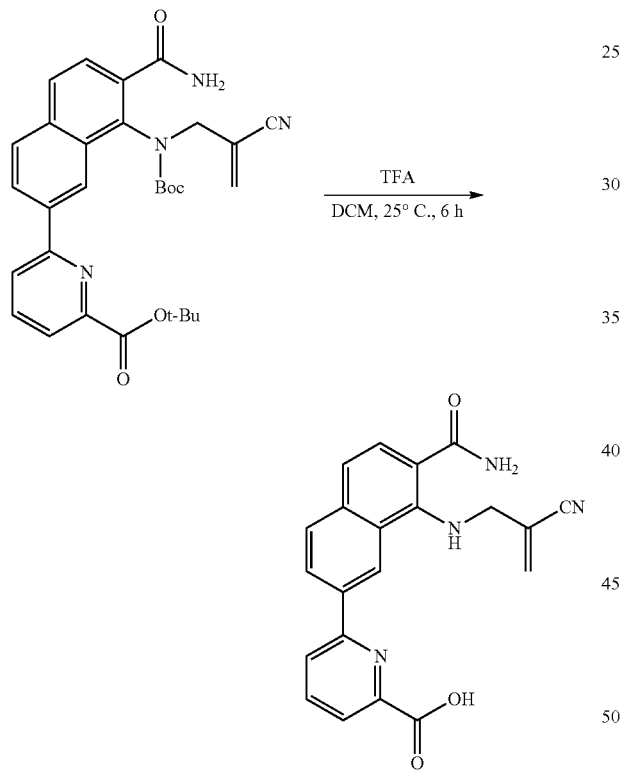

To a solution of tert-butyl 6-[8-[tert-butoxycarbonyl(2-cyanoallyl)amino]-7-carbamoyl-2-naphthyl]pyridine-2-carboxylate (0.25 g, 472.95 µmol, 1 eq) in DCM (3 mL) was added TFA (1 mL) The reaction mixture was stirred at 25° C. for 6 h. The reaction was poured into 50 mL of ice water and adjusted to pH=6 with Saturated Na₂CO₃. The mixture was extracted with DCM (3×30 mL). The combined organic layer was washed with brine (3×30 mL), dried over Na₂SO₄, filtered, and concentrated to afford the title compound (0.16 g, 90% yield) as a yellow solid, which was used in the next step without further purification.

Step 12) Compound 271 and 273: Preparation of 6-{7-carbamoyl-8-[(2-cyano-2-methylideneethyl)amino]naphthalen-2-yl}-N-[(1R,4R)-4-(dimethylamino)cyclohexyl]pyridine-2-carboxamide (P1) and 6-{7-carbamoyl-8-[(2-cyano-2-methylideneethyl)amino]naphthalen-2-yl}-N-[(1S,4S)-4-(dimethylamino)cyclohexyl]pyridine-2-carboxamide

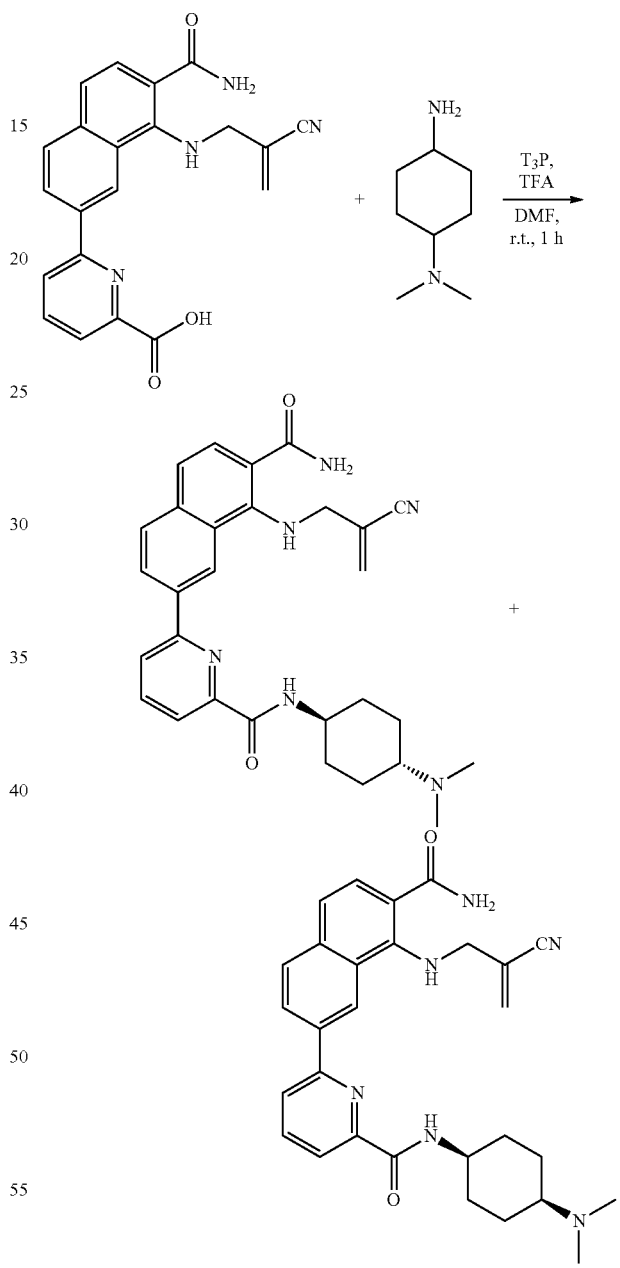

To a solution of 6-[7-carbamoyl-8-(2-cyanoallylamino)-2-naphthyl]pyridine-2-carboxylic acid (0.1 g, 268.55 µmol, 1 eq) in DMF (3 mL) were added TEA (135.9 mg, 1.34 mmol, 186.89 µL, 5 eq) and N₄,N₄-dimethylcyclohexane-1,4-diamine (76.4 mg, 537.09 µmol, 2 eq). Then, T₃P (256.3 mg, 402.82 µmol, 239.57 µL, 50% purity, 1.5 eq) was added, and the reaction was stirred at 25° C. for 1 h. LCMS showed that the reaction was complete. The reaction mixture was diluted with H₂O (50 mL) and extracted with EtOAc (2×30 mL). The combined organic layers were washed with H₂O (2×30 mL) and brine (2×30 mL), dried over Na₂SO₄, filtered, and concentrated in vacuo. The residue was purified by prep-HPLC to afford Compound 271 as a white solid (7.3 mg, 5.07% yield). LC-MS (ES⁺, m/z): 497.3 [(M+H)⁺] and Compound 273 (9.5 mg, 7.12% yield) as a white solid. LC-MS (ES⁺, m/z): 497.3 [(M+H)⁺].
Route 4: General Scheme
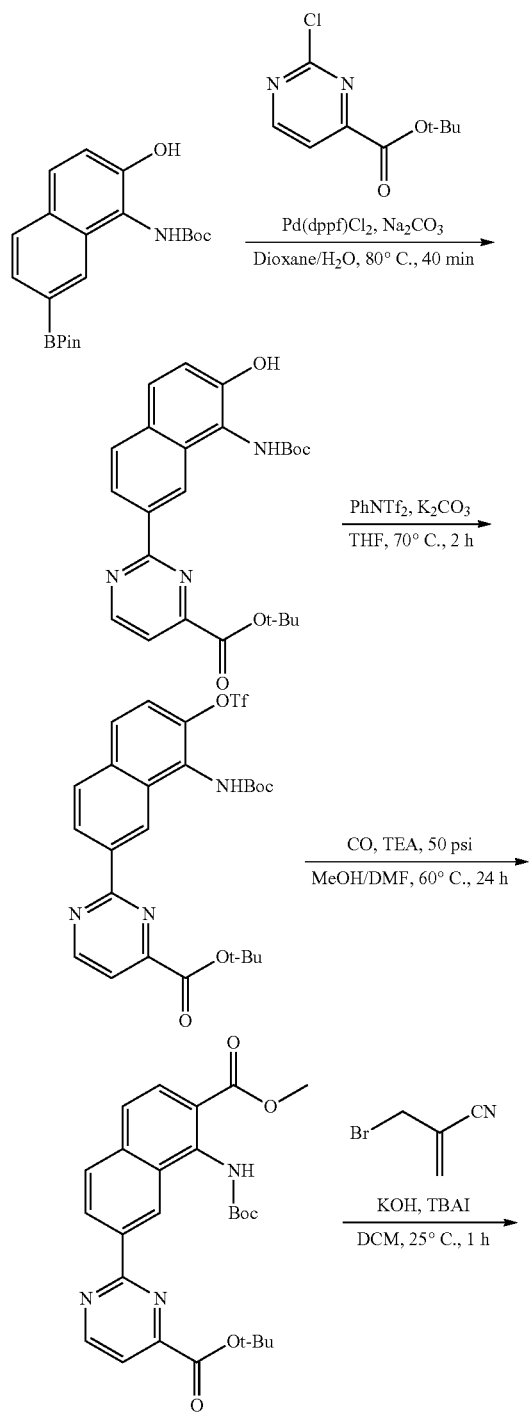
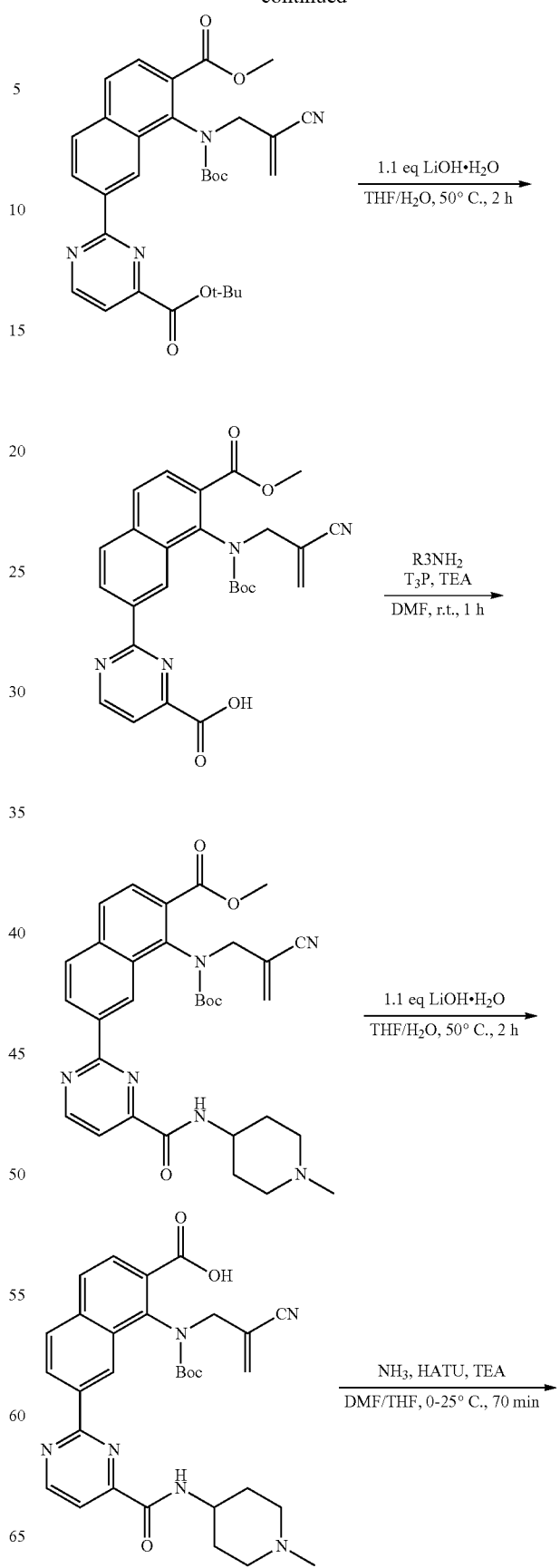

-continued

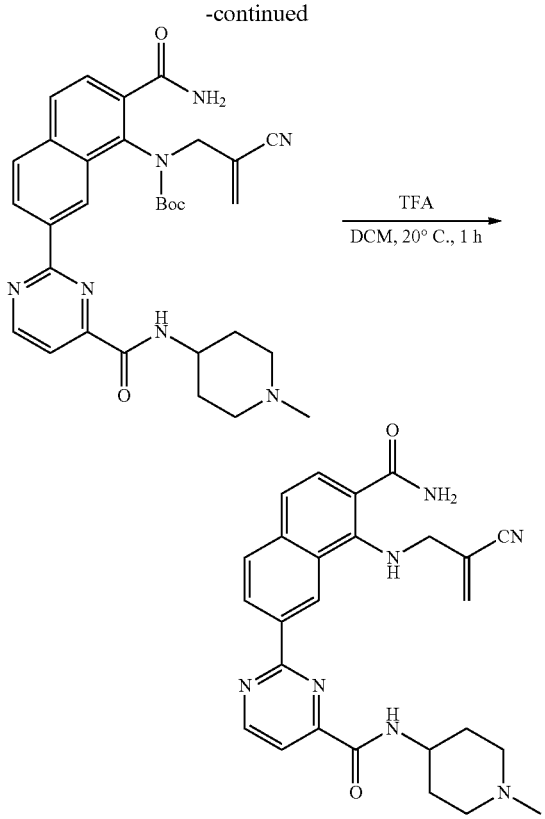

Step 1) Preparation of tert-butyl 2-[8-(tert-butoxy-carbonylamino)-7-hydroxy-2-naphthyl]pyrimidine-4-carboxylate

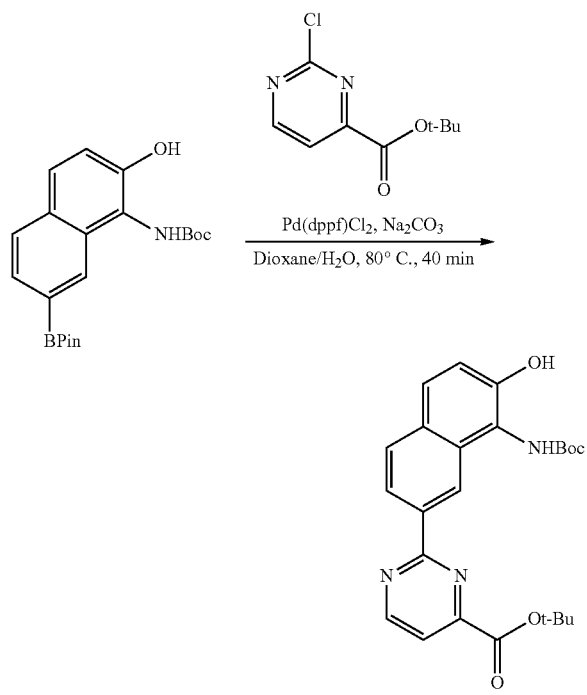

To a solution of tert-butyl N-[2-hydroxy-7-(4,4,5,5-tetramethyl-1,3,2-dioxaborolan-2-yl)-1-naphthyl]carbamate (3 g, 7.79 mmol, 1 eq) in dioxane (78 mL) and $H_2O$ (3 mL) were added tert-butyl 2-chloropyrimidine-4-carboxylate (1.84 g, 8.57 mmol, 1.1 eq), $Na_2CO_3$ (2.48 g, 23.36 mmol, 3 eq) and Pd (dppf)$Cl_2$ (569.8 mg, 778.69 μmol, 0.1 eq). The mixture was stirred at 80° C. for 40 min under $N_2$. The reaction mixture was poured into saturated EDTA (100 mL) and stirred at 25° C. for 1 h. The mixture was extracted with EtOAc (3×50 mL), washed with brine (3×50 mL), dried over $Na_2SO_4$, filtered, and concentrated in vacuo. The residue was purified by column chromatography ($SiO_2$, PE:EtOAc=1:0 to 10:1) to afford the title compound (2.5 g, 73.39% yield) as a white solid.

Step 2) Preparation of 6-tert-butyl 2-[8-(tert-butoxycarbonylamino)-7-(trifluoromethylsulfonyloxy)-2-naphthyl]pyrimidine-4-carboxylate

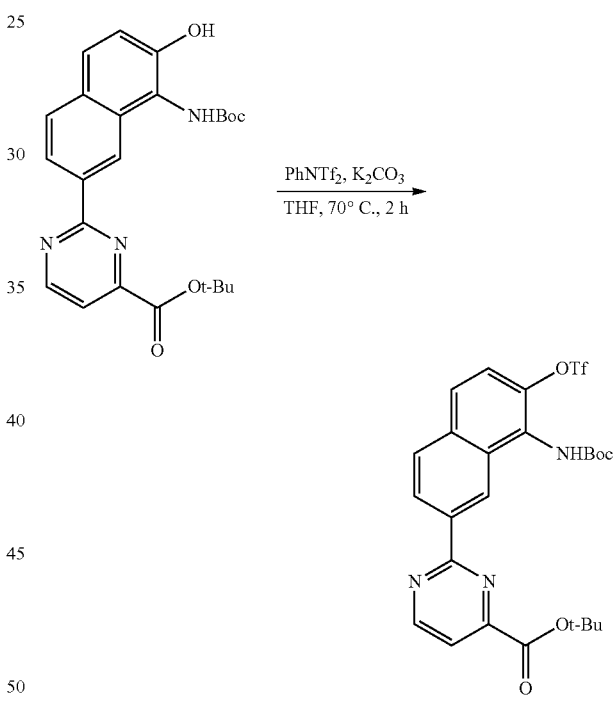

To a solution of tert-butyl 2-[8-(tert-butoxycarbonylamino)-7-hydroxy-2-naphthyl]pyrimidine-4-carboxylate (2.5 g, 5.71 mmol, 1 eq) in THF (50 mL) were added $K_2CO_3$ (1.58 g, 11.43 mmol, 2 eq) and 1,1,1-trifluoro-N-phenyl-N-(trifluoromethylsulfonyl)methanesulfonamide (2.65 g, 7.43 mmol, 1.3 eq). The mixture was stirred at 70° C. for 2 hr. The reaction was poured into 300 mL of water and extracted with EtOAc (3×300 mL). The combined organic phase was washed with brine (3×300 mL), dried over $Na_2SO_4$, filtered, and concentrated in vacuo. The residue was purified by column chromatography ($SiO_2$, PE:EtOAc=10:1 to 4:1) to afford the title compound (3 g, 92.18% yield) as a light yellow solid.

Step 3) Preparation of 7-tert-butyl 2-[8-(tert-butoxycarbonylamino)-7-methoxycarbonyl-2-naphthyl]pyrimidine-4-carboxylate

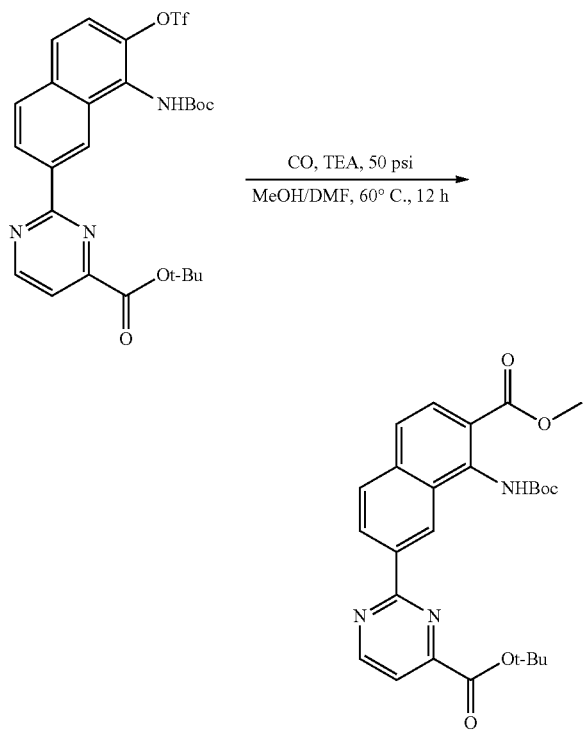

To a solution of tert-butyl 2-[8-(tert-butoxycarbonylamino)-7-(trifluoromethyl sulfonyloxy)-2-naphthyl]pyrimidine-4-carboxylate (3 g, 5.27 mmol, 1 eq) in DMF (60 mL) and MeOH (60 mL) were added TEA (1.6 g, 15.8 mmol, 2.20 mL, 3 eq) and Pd(dppf)Cl$_2$ (385.4 mg, 526.73 μmol, 0.1 eq). The reaction was stirred at 60° C. for 12 h under CO (50 psi). TLC (PE:EtOAc=4:1) showed that the reaction was complete. 300 mL of saturated EDTA was added and diluted with 150 mL of EtOAc. The mixture was stirred at 25° C. for 1 h and extracted with EtOAc (3×150 mL), and the combined organic phase was washed with brine (3×300 mL), dried over Na$_2$SO$_4$, filtered, and concentrated in vacuo. The residue was purified by column chromatography (SiO$_2$, PE:EtOAc=10:1 to 4:1) to afford the title compound (2.1 g, 83.14% yield) as a light yellow solid.

Step 4) Preparation of tert-butyl 2-[8-[tert-butoxycarbonyl(2-cyanoallyl)amino]-7-methoxy carbonyl-2-naphthyl]pyrimidine-4-carboxylate

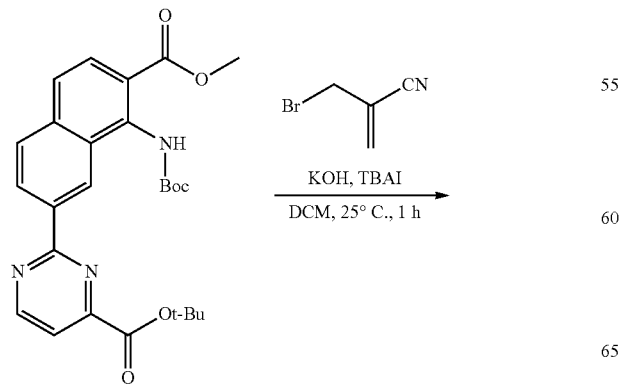

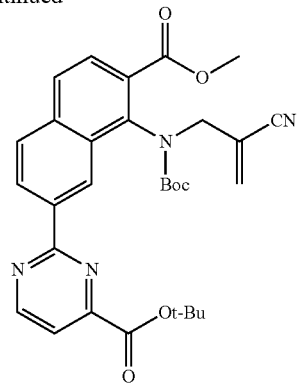

To a solution of tert-butyl 2-[8-(tert-butoxycarbonylamino)-7-methoxycarbonyl-2-naphthyl]pyrimidine-4-carboxylate (2.1 g, 4.38 mmol, 1 eq) in DCM (210 mL) were added KOH (491.5 mg, 8.76 mmol, 2 eq), TBAI (808.8 mg, 2.19 mmol, 0.5 eq) and 2-(bromomethyl)prop-2-enenitrile (767.2 mg, 5.26 mmol, 1.2 eq). The mixture was stirred at 25° C. for 1 hr. The reaction was poured into 150 mL of water and extracted with EtOAc (3×70 mL). The combined organic phase was washed with brine (3×70 mL), dried over Na$_2$SO$_4$, filtered, and concentrated in vacuo. The residue was purified by column chromatography (SiO$_2$, PE:EtOAc=10:1 to 4:1) to afford the title compound (1.4 g, 58.70% yield) as a yellow oil.

Step 5) Preparation of 2-[8-[tert-butoxycarbonyl(2-cyanoallyl)amino]-7-methoxycarbonyl-2-naphthyl]pyrimidine-4-carboxylic acid

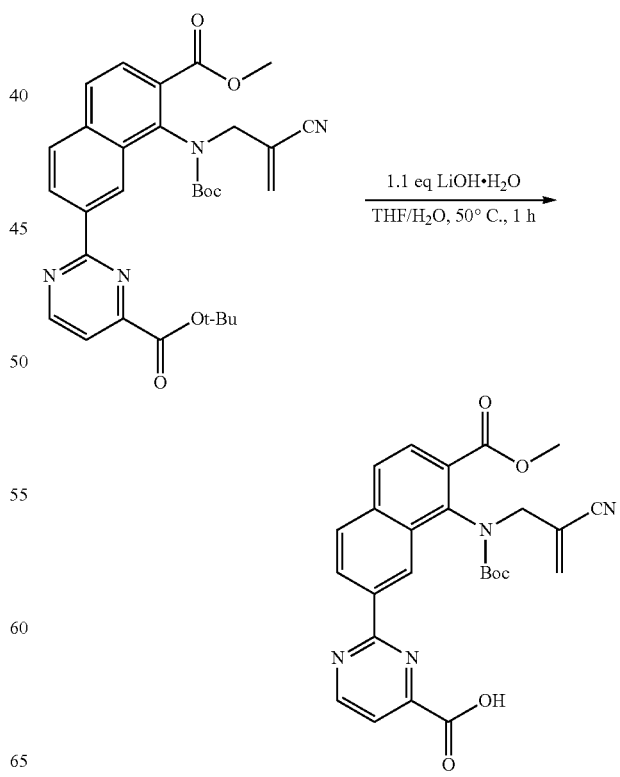

To a solution of tert-butyl 2-[8-[tert-butoxycarbonyl(2-cyanoallyl)amino]-7-methoxycarbonyl-2-naphthyl]pyrimidine-4-carboxylate (0.54 g, 991.56 μmol, 1 eq) in THF (24 mL) and H₂O (6 mL) was added LiOH·H₂O (41.6 mg, 991.56 μmol, 1 eq). The mixture was stirred at 50° C. for 1 hr. HPLC showed that the reaction was complete. The reaction was poured into 100 mL of ice water and washed with PE (3×50 mL). To the aqueous phase was added saturated citric acid until pH=7, and the mixture was filtered. The filtrate was extracted with EtOAc (3×50 mL), dried with anhydrous Na₂SO₄, filtered, and concentrated in vacuo. The residue was purified by prep-TLC (SiO₂, DCM:MeOH=10:1) to afford the title compound (0.2 g, 41.29% yield) as a white solid.

Step 6) Preparation of Methyl 1-[tert-butoxycarbonyl(2-cyanoallyl)amino]-7-[4-[(1-methyl-4-piperidyl)carbamoyl]pyrimidin-2-yl]naphthalene-2-carboxylate

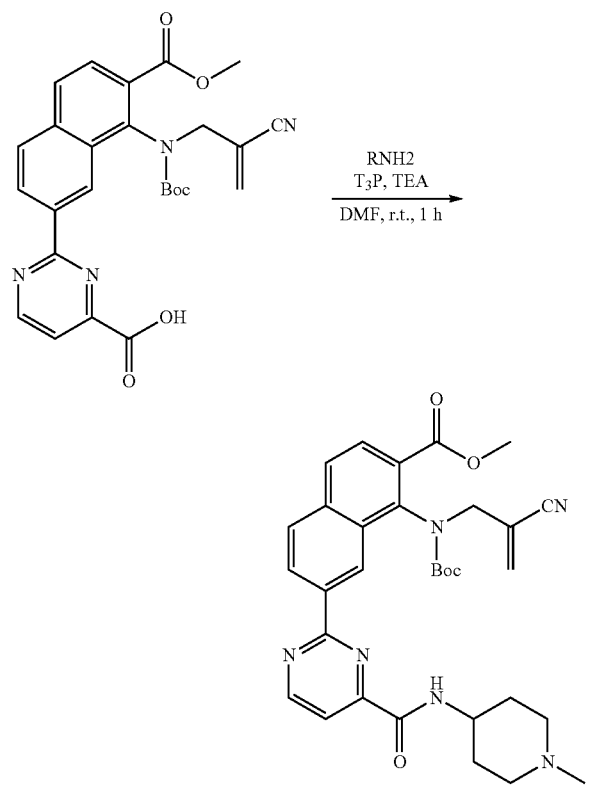

To a solution of 2-[8-[tert-butoxycarbonyl(2-cyanoallyl)amino]-7-methoxycarbonyl-2-naphthyl]pyrimidine-4-carboxylic acid (0.2 g, 409.42 μmol, 1 eq) and 1-methylpiperidin-4-amine (70.1 mg, 614.14 μmol, 1.5 eq) in DMF (2 mL) were added Et₃N (207.2 mg, 2.05 mmol, 284.94 μL, 5 eq) and T₃P (390.8 mg, 614.14 μmol, 365.24 μL, 50% purity, 1.5 eq). The mixture was stirred at 25° C. for 1 hr. The reaction was poured into 50 mL water and extracted with DCM (3×50 mL). The combined organic phase was washed with brine (3×50 mL), dried over Na₂SO₄, filtered, and concentrated in vacuo to afford the title compound (0.24 g, crude) as a yellow solid, which was used in the next step without further purification.

Step 7) Preparation of 1-[tert-butoxycarbonyl(2-cyanoallyl)amino]-7-[4-[(1-methyl-4-piperidyl) carbamoyl]pyrimidin-2-yl]naphthalene-2-carboxylic acid

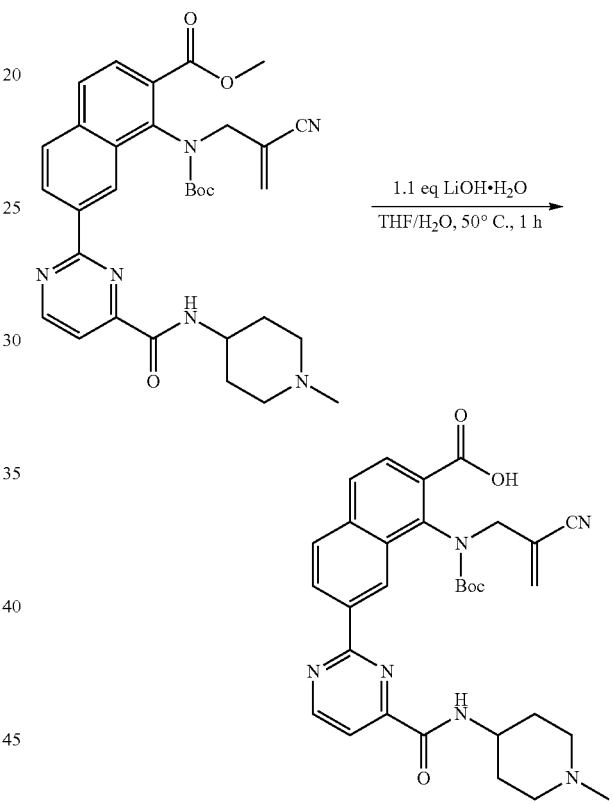

To a solution of methyl 1-[tert-butoxycarbonyl(2-cyanoallyl)amino]-7-[4-[(1-methyl-4-piperidyl)carbamoyl]pyrimidin-2-yl]naphthalene-2-carboxylate (0.19 g, 324.97 μmol, 1 eq) in THF (7.6 mL) and H₂O (1.9 mL) was added LiOH·H₂O (27.3 mg, 649.95 μmol, 2 eq). The mixture was stirred at 50° C. for 1 hr. HPLC showed that the reaction was complete. The reaction was poured into 100 mL of ice water and washed with PE (3×50 mL). To the aqueous phase was added saturated citric acid until pH=7. The mixture was filtered, and the filtrate was extracted with EtOAc (3×50 mL). The combined organic phase was dried with anhydrous Na₂SO₄, filtered, and concentrated in vacuo. The residue was purified by prep-HPLC to afford the title compound (0.04 g, 26.67% yield) as a white solid.

347

Step 8) Preparation of Tert-butyl N-[2-carbamoyl-7-[4-[(1-methyl-4-piperidyl) carbamoyl]pyrimidin-2-yl]-1-naphthyl]-N-(2-cyanoallyl)carbamate

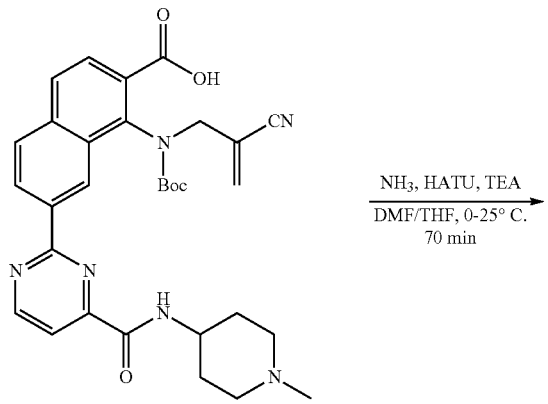

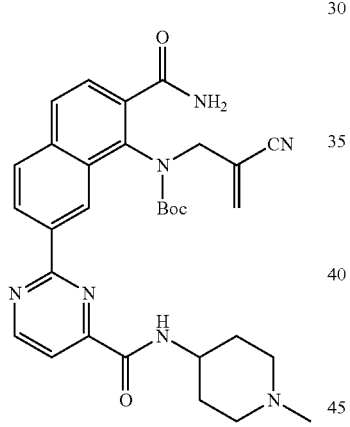

To a solution of 1-[tert-butoxycarbonyl(2-cyanoallyl) amino]-7-[4-[(1-methyl-4-piperidyl) carbamoyl]pyrimidin-2-yl]naphthalene-2-carboxylic acid (0.01 g, 17.52 μmol, 1 eq) in DMF (2 mL) were added TEA (55.7 mg, 550.26 μmol, 76.59 μL, 31.4 eq) and HATU (13.3 mg, 35.05 μmol, 2 eq). The mixture was stirred at 25° C. for 10 min. Then NH$_3$ (4 M NH$_3$ in THF, 0.5 mL, 117 eq) was added at 0° C. The mixture was stirred at 25° C. for 1 hr. The reaction was poured into 10 mL of water. The mixture was extracted with EtOAc (3×10 mL). The organic phase was washed with brine (3×10 mL), dried over Na$_2$SO$_4$, filtered, and concentrated in vacuo. The residue was purified by prep-TLC (SiO$_2$, DCM:MeOH=10:1) to afford the title compound (0.015 g, 75.13% yield) as a yellow solid.

348

Step 9) Compound 274: Preparation of 2-{7-carbamoyl-8-[(2-cyano-2-methylideneethyl)amino]naphthalen-2-yl}-N-(1-methylpiperidin-4-yl)pyrimidine-4-carboxamide

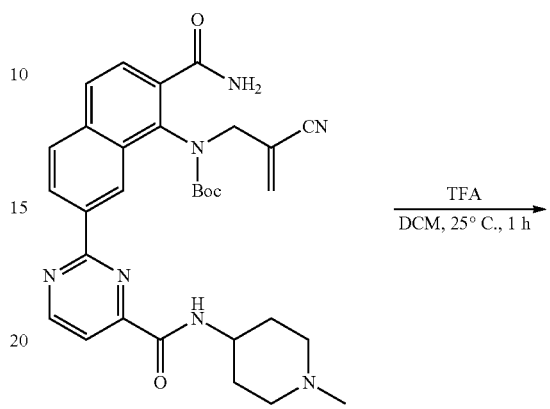

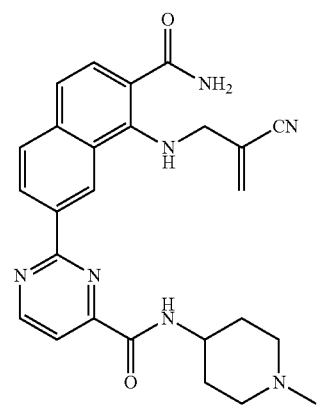

To a solution of tert-butyl N-[2-carbamoyl-7-[4-[(1-methyl-4-piperidyl) carbamoyl]pyrimidin-2-yl]-1-naphthyl]-N-(2-cyanoallyl)carbamate (0.015 g, 26.33 μmol, 1 eq) in DCM (2 mL) was added TFA (1.08 g, 9.45 mmol, 0.7 mL, 359.04 eq). The mixture was stirred at 25° C. for 1 hr. The reaction was poured into 10 mL of ice water and 10 mL of DCM. Then to the mixture was added saturated Na$_2$CO$_3$ until pH=8, and the mixture was extracted with DCM (3×10 mL). The combined organic phase was washed with 10 mL of brine, dried over Na$_2$SO$_4$, filtered, and concentrated in vacuo. The residue was purified by prep-HPLC to afford the title compound (3.2 mg, 25.88% yield) as a yellow solid. LC-MS (ES$^+$, m/z): 470.2 [(M+H)$^+$].

TABLE 5 shows compounds synthesized using methods described in EXAMPLE 5.

TABLE 5

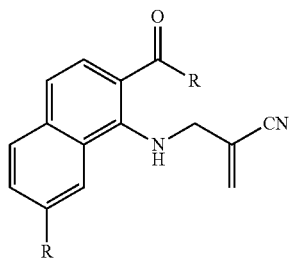

| Cpd. No. | Structure | IUPAC | LC-MS (ES+, m/z) |
|---|---|---|---|
| 264 | 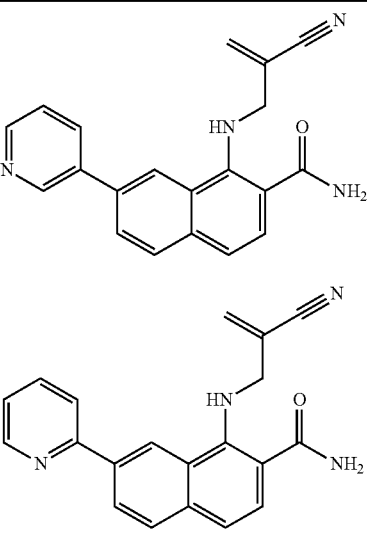 | 1-[(2-cyano-2-methylideneethyl)amino]-7-(pyridin-3-yl)naphthalene-2-carboxamide | 329.1 |
| 265 | 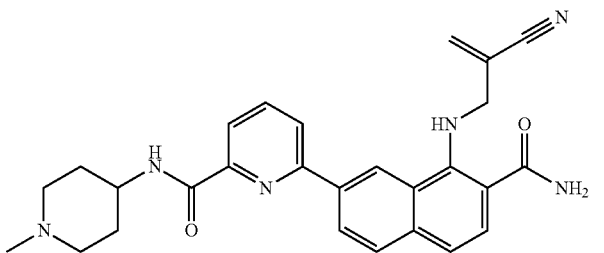 [SMILES: C=C(C#N)CNc1c(C(N)=O)ccc2ccc(-c3cccc(C(=O)NC4CCN(C)CC4)n3)cc12] | 1-[(2-cyano-2-methylideneethyl)amino]-7-(pyridin-2-yl)naphthalene-2-carboxamide | 329.1 |
| 266 | 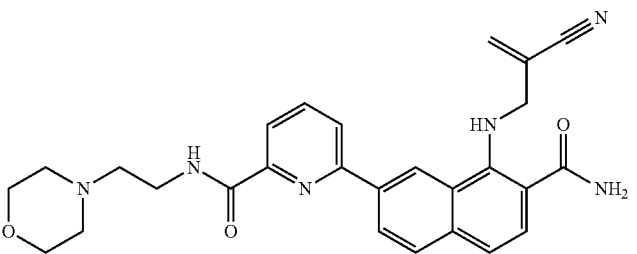 [SMILES: C=C(C#N)CNc1c(C(N)=O)ccc2ccc(-c3cccc(C(=O)NCCN4CCOCC4)n3)cc12] | 6-{7-carbamoyl-8-[(2-cyano-2-methylideneethyl)amino]naphthalen-2-yl}-N-(1-methylpiperidin-4-yl)pyridine-2-carboxamide | 469.1 |
| 267 | 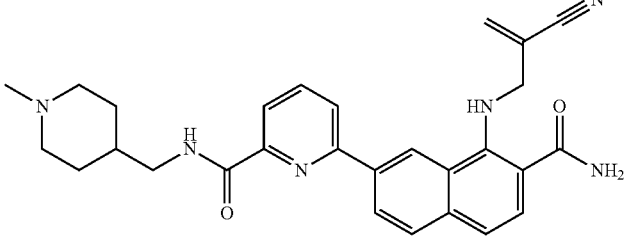 | 6-{7-carbamoyl-8-[(2-cyano-2-methylideneethyl)amino]naphthalen-2-yl}-N-[2-(morpholin-4-yl)ethyl]pyridine-2-carboxamide | 485.1 |
| 268 | 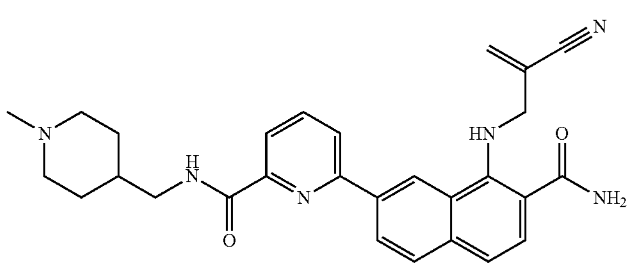 [SMILES: C=C(C#N)CNc1c(C(N)=O)ccc2ccc(-c3cccc(C(=O)NCC4CCN(C)CC4)n3)cc12] | 6-{7-carbamoyl-8-[(2-cyano-2-methylideneethyl)amino]naphthalen-2-yl}-N-[(1-methylpiperidin-4-yl)methyl]pyridine-2-carboxamide | 483.2 |

TABLE 5-continued

| Cpd. No. | Structure | IUPAC | LC-MS (ES+, m/z) |
|---|---|---|---|
| 269 | 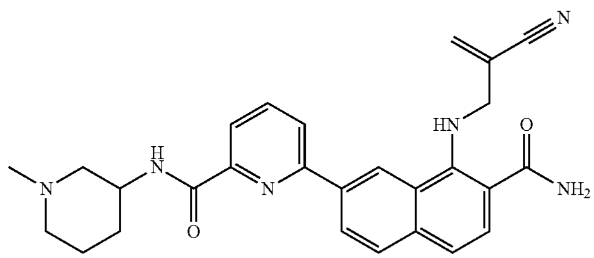 [SMILES: C=C(C#N)CNc1c(C(N)=O)ccc2ccc(-c3cccc(C(=O)NC4CCCN(C)C4)n3)cc12] | 6-{7-carbamoyl-8-[(2-cyano-2-methylideneethyl)amino]naphthalen-2-yl}-N-(1-methylpiperidin-3-yl)pyridine-2-carboxamide | 469.3 |
| 270 | 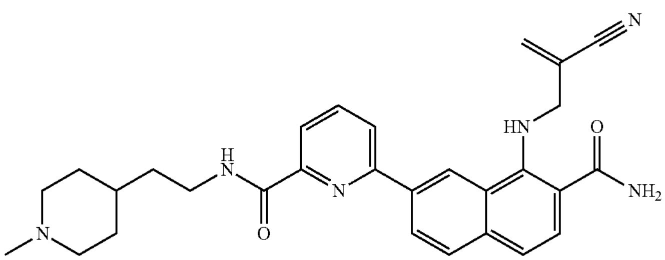 [SMILES: C=C(C#N)CNc1c(C(N)=O)ccc2ccc(-c3cccc(C(=O)NCCC4CCN(C)CC4)n3)cc12] | 6-{7-carbamoyl-8-[(2-cyano-2-methylideneethyl)amino]naphthalen-2-yl}-N-[2-(1-methylpiperidin-4-yl)ethyl]pyridine-2-carboxamide | 497.3 |
| 271 | 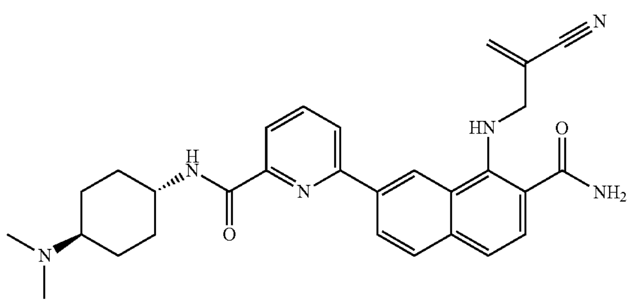 [SMILES: C=C(C#N)CNc1c(C(N)=O)ccc2ccc(-c3cccc(C(=O)N[C@H]4CC[C@H](N(C)C)CC4)n3)cc12] | 6-{7-carbamoyl-8-[(2-cyano-2-methylideneethyl)amino]naphthalen-2-yl}-N-[(1r,4r)-4-(dimethylamino)cyclohexyl]pyridine-2-carboxamide | 497.3 |
| 272 | 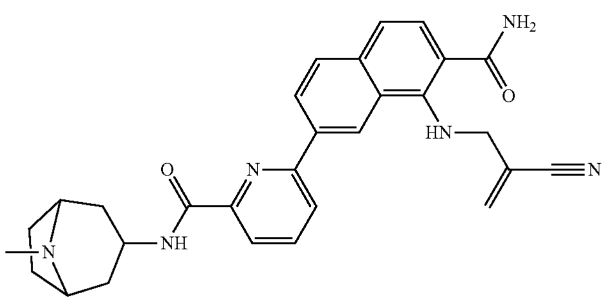 [SMILES: C=C(C#N)CNc1c(C(N)=O)ccc2ccc(-c3cccc(C(=O)NC4CC5CCC(C4)N5C)n3)cc12] | 6-{7-carbamoyl-8-[(2-cyano-2-methylideneethyl)amino]naphthalen-2-yl}-N-{8-methyl-8-azabicyclo[3.2.1]octan-3-yl}pyridine-2-carboxamide | 495.1 |

TABLE 5-continued

| Cpd. No. | Structure | IUPAC | LC-MS (ES+, m/z) |
|---|---|---|---|
| 273 | 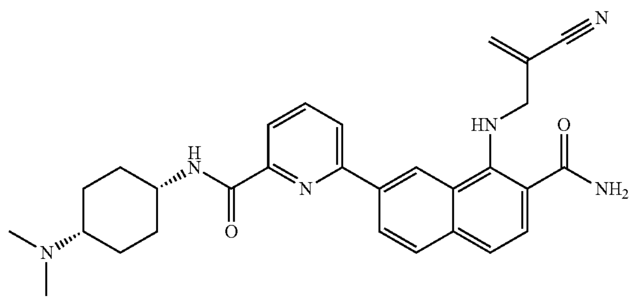 [SMILES: C=C(C#N)CNc1c(C(N)=O)ccc2ccc(-c3cccc(C(=O)N[C@H]4CC[C@@H](N(C)C)CC4)n3)cc12] | 6-{7-carbamoyl-8-[(2-cyano-2-methylideneethyl)amino]naphthalen-2-yl}-N-[(1s,4s)-4-(dimethylamino)cyclohexyl]pyridine-2-carboxamide | 497.3 |
| 274 | 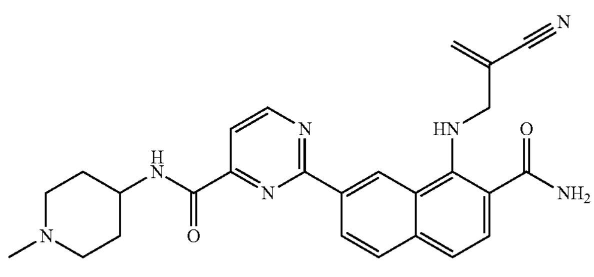 | 2-{7-carbamoyl-8-[(2-cyano-2-methylideneethyl)amino]naphthalen-2-yl}-N-(1-methylpiperidin-4-yl)pyrimidine-4-carboxamide | 470.2 |
| 275 | 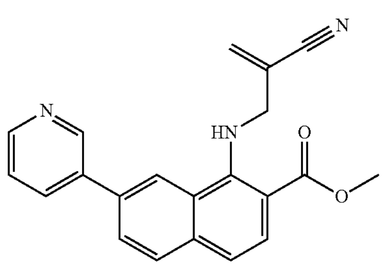 [SMILES: C=C(C#N)CNc1c(C(=O)OC)ccc2ccc(-c3cccnc3)cc12] | methyl 1-[(2-cyano-2-methylideneethyl)amino]-7-(pyridin-3-yl)naphthalene-2-carboxylate | 344.1 |
| 276 | 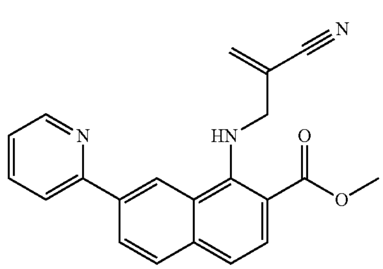 [SMILES: C=C(C#N)CNc1c(C(=O)OC)ccc2ccc(-c3ccccn3)cc12] | methyl 1-[(2-cyano-2-methylideneethyl)amino]-7-(pyridin-2-yl)naphthalene-2-carboxylate | 344 |

TABLE 5-continued
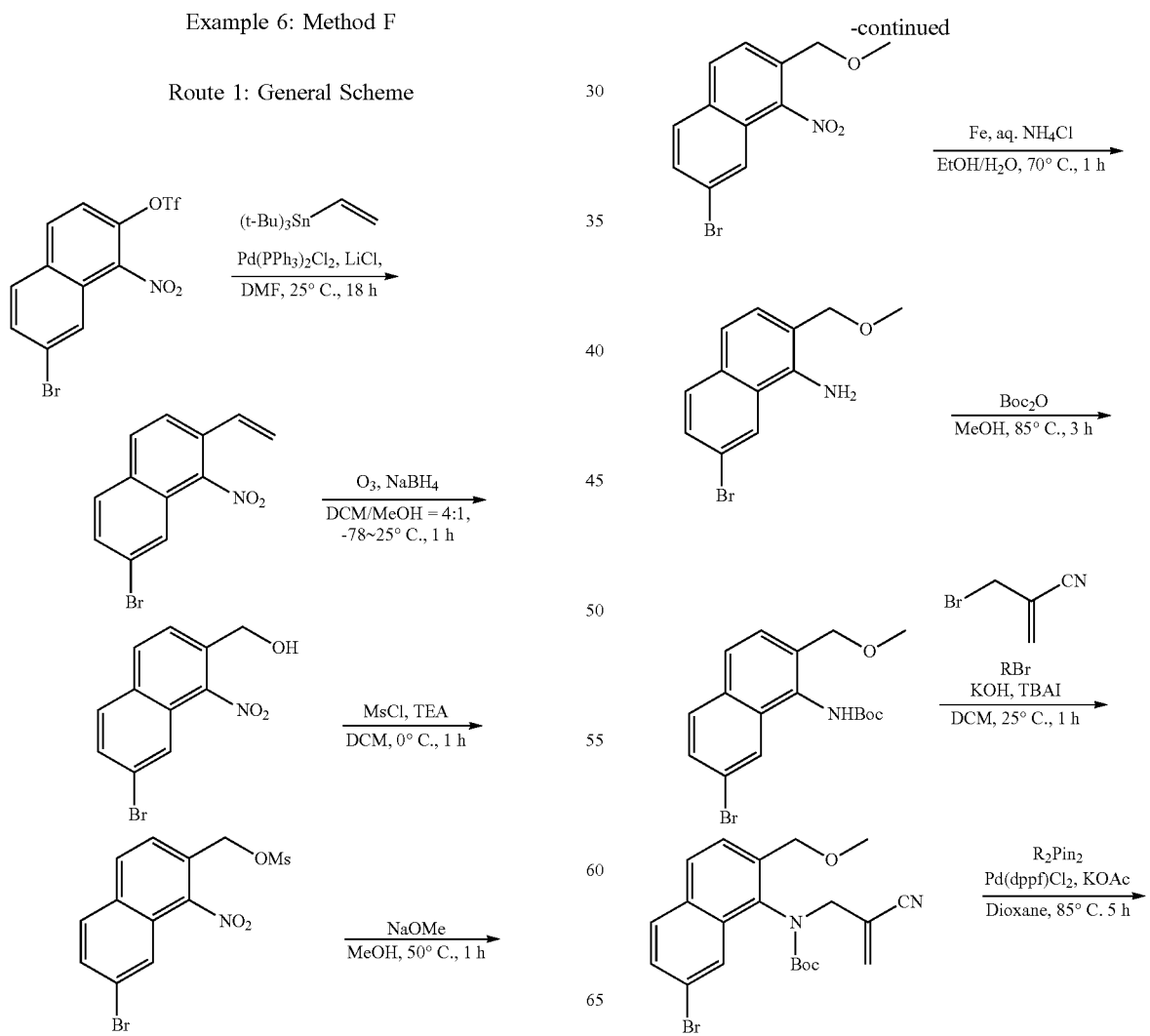
| Cpd. No. | Structure | IUPAC | LC-MS (ES+, m/z) |
|---|---|---|---|
| 277 | 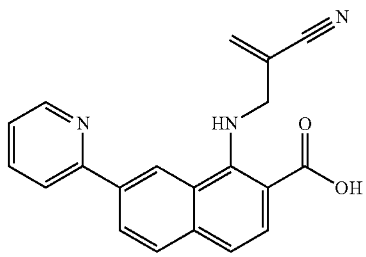 [SMILES: C=C(C#N)CNc1c(C(=O)O)ccc2ccc(-c3ccccn3)cc12] | 1-[(2-cyano-2-methylideneethyl)amino]-7-(pyridin-2-yl)naphthalene-2-carboxylic acid | 330.1 |
Example 6: Method F
Route 1: General Scheme -continued

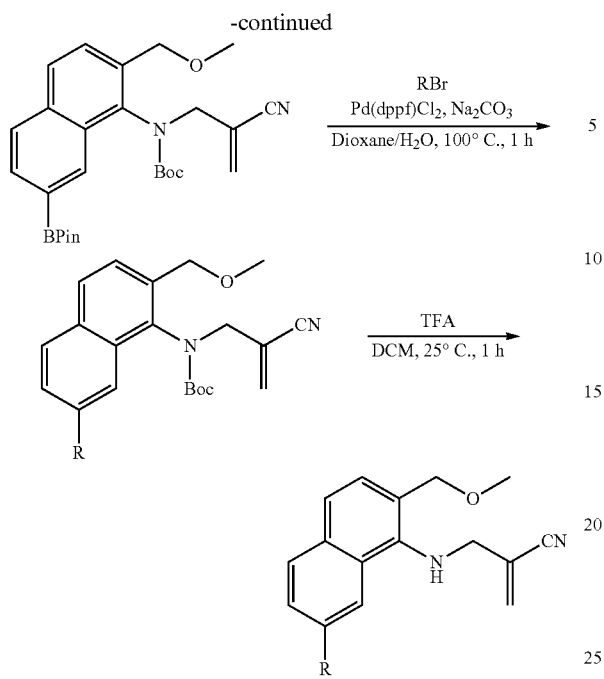

Step 1) Preparation of 7-bromo-1-nitro-2-vinyl-naphthalene

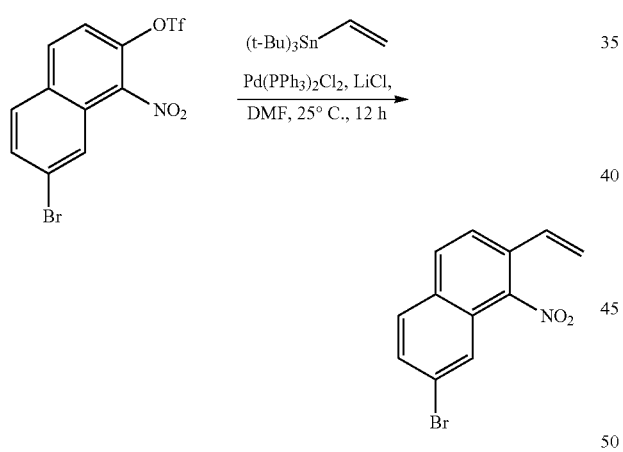

To a mixture of (7-bromo-1-nitro-2-naphthyl)trifluoromethanesulfonate (5.2 g, 12.5 mmol, 1 eq) and tributyl(vinyl)stannane (4.16 g, 13.12 mmol, 3.82 mL, 1.05 eq) in DMF (130 mL) were added LiCl (1.59 g, 37.49 mmol, 3 eq) and Pd(PPh$_3$)$_2$Cl$_2$ (877.1 mg, 1.25 mmol, 0.1 eq). The reaction was stirred at 25° C. for 12 h under N$_2$. The reaction mixture was diluted with H$_2$O (300 mL). The mixture was extracted with EtOAc (3×200 mL). The combined organic layer was washed with H$_2$O (2×200 mL) and brine (2×200 mL), dried over anhydrous Na$_2$SO$_4$, filtered, and concentrated in vacuo. The residue was purified by column chromatography (SiO$_2$, PE:EtOAc) to afford the title compound (4.4 g, 63.3% yield) as a yellow solid.

Step 2) Preparation of (7-bromo-1-nitro-2-naphthyl)methanol

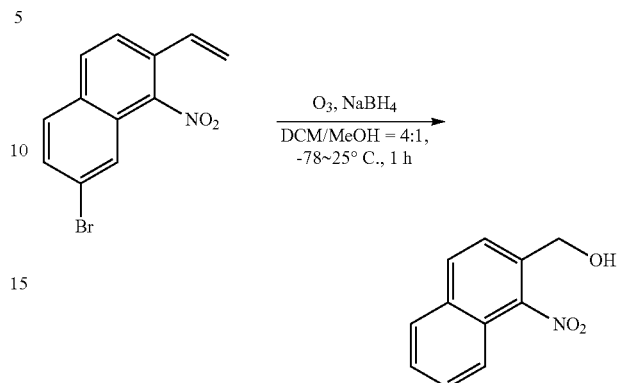

To a mixture of 7-bromo-1-nitro-2-vinyl-naphthalene (5.8 g, 20.86 mmol, 1 eq) in DCM (200 mL) and MeOH (50 mL) was added ozone (1 g, 20.86 mmol, 1 eq). The mixture was stirred at −78° C. for 0.5 h. Then NaBH$_4$ (2.37 g, 62.57 mmol, 3 eq) was added. The mixture was stirred at 25° C. for another 0.5 h. The reaction mixture was diluted with H$_2$O (200 mL). The mixture was extracted with EtOAc (2×100 mL). The combined organic layer was washed with H$_2$O (2×100 mL) and brine (2×100 mL), dried over anhydrous Na$_2$SO$_4$, filtered, and concentrated in vacuo. The residue was purified by column chromatography (SiO$_2$, PE:EtOAc=10:1 to 4:1) to afford the title compound (4.4 g, 74.8% yield) as a white solid.

Step 3) Preparation of (7-bromo-1-nitro-2-naphthyl)methyl methanesulfonate

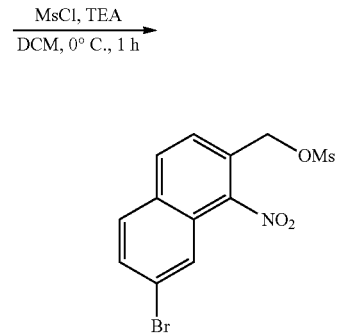

To a solution of (7-bromo-1-nitro-2-naphthyl)methanol (4.4 g, 15.6 mmol, 1 eq) in DCM (50 mL) were added TEA (7.89 g, 77.99 mmol, 10.86 mL, 5 eq) and methanesulfonyl chloride (2.68 g, 23.4 mmol, 1.81 mL, 1.5 eq). The mixture was stirred at 0° C. for 1 h. The reaction mixture was diluted with H$_2$O (200 mL) and extracted with EtOAc (2×100 mL). The combined organic layer was washed with H$_2$O (2×100 mL) and brine (2×100 mL), dried over anhydrous Na$_2$SO$_4$,

Step 4) Preparation of 7-bromo-2-(methoxymethyl)-1-nitro-naphthalene

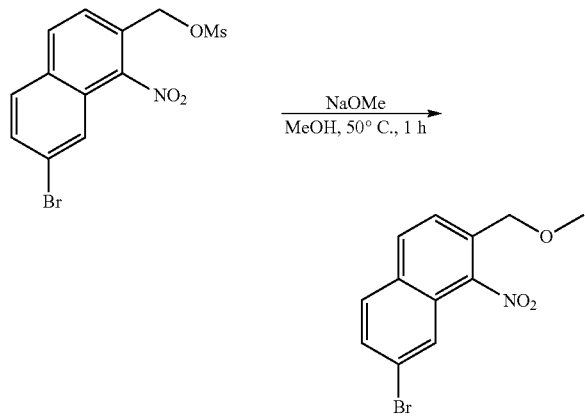

To a solution of (7-bromo-1-nitro-2-naphthyl)methyl methanesulfonate (4 g, 11.11 mmol, 1 eq) in MeOH (60 mL) was added CH$_3$ONa (1.8 g, 33.32 mmol, 3 eq), and the mixture was stirred at 50° C. for 1 h. The reaction mixture was diluted with H$_2$O (200 mL) and extracted with EtOAc (2×100 mL). The combined organic layer was washed with H$_2$O (2×50 mL) and brine (2×50 mL), dried over anhydrous Na$_2$SO$_4$, filtered, and concentrated in vacuo. The residue was purified by column chromatography (SiO$_2$, PE:EtOAc=10:1 to 6:1) to afford the title compound (1.5 g, 45.6% yield) as a yellow solid.

Step 5) Preparation of 7-bromo-2-(methoxymethyl)naphthalen-1-amine

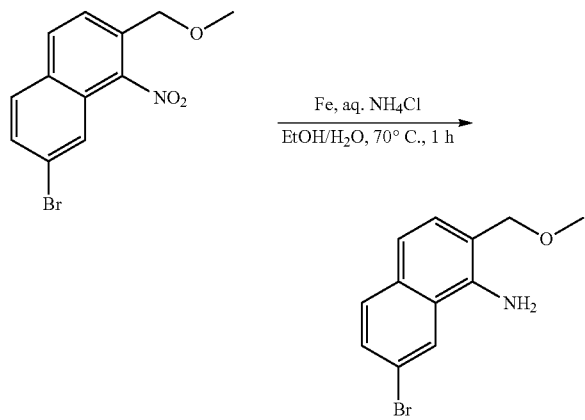

To a solution of 7-bromo-2-(methoxymethyl)-1-nitro-naphthalene (1.9 g, 6.42 mmol, 1 eq) in EtOH (16 mL) were added saturated NH$_4$Cl (6.42 mmol, 4 mL, 1 eq) and Fe (1.07 g, 19.25 mmol, 3 eq) at 70° C. The mixture was stirred at 70° C. for 1 h. The reaction mixture was diluted with H$_2$O (100 mL) and extracted with EtOAc (3×50 mL). The combined organic layer was washed with H$_2$O (2×50 mL) and brine (2×50 mL), dried over anhydrous Na$_2$SO$_4$, filtered, and concentrated in vacuo. The residue was purified by column chromatography (SiO$_2$, PE:EtOAc=20:1 to 8:1) to afford the title compound (1.35 g, 79.1% yield) as a yellow solid.

Step 6) Preparation of tert-butyl N-[7-bromo-2-(methoxymethyl)-1-naphthyl]carbamate

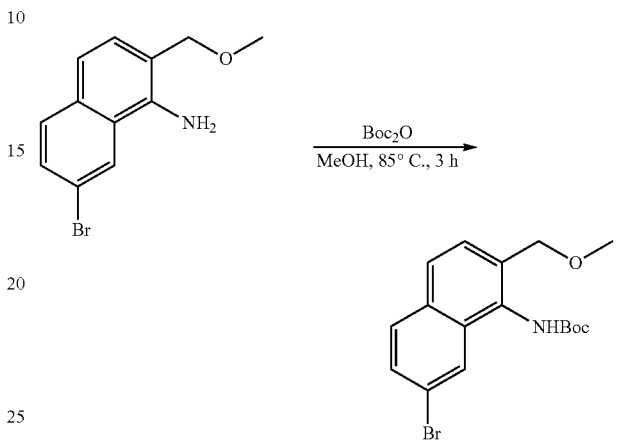

To a solution of 7-bromo-2-(methoxymethyl)naphthalen-1-amine (0.3 g, 1.13 mmol, 1 eq) in MeOH (5 mL) was added Boc$_2$O (4.92 g, 22.55 mmol, 5.18 mL, 20 eq). The reaction mixture was stirred at 85° C. for 3 h. The reaction mixture was diluted with H$_2$O (50 mL) and extracted with EtOAc (3×30 mL). The combined organic layer was washed with H$_2$O (2×30 mL) and brine (2×30 mL), dried over anhydrous Na$_2$SO$_4$, filtered, and concentrated in vacuo. The residue was purified by column chromatography (SiO$_2$, PE:EtOAc=20/1 to 8/1) to afford the title compound (0.3 g, 819.12 μmol, 72.66% yield) as a white solid.

Step 7) Preparation of tert-butyl N-[7-bromo-2-(methoxymethyl)-1-naphthyl]-N-(2-cyanoallyl) carbamate

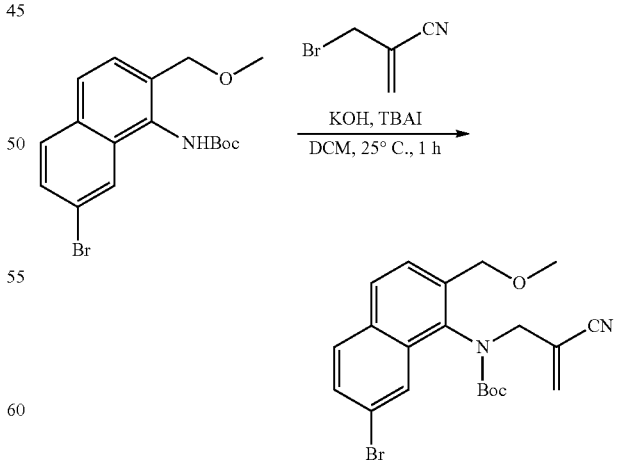

To a solution of tert-butyl N-[7-bromo-2-(methoxymethyl)-1-naphthyl]carbamate (0.28 g, 764.51 μmol, 1 eq) in DCM (4 mL) were added KOH (85.8 mg, 1.53 mmol, 2 eq), TBAI (84.7 mg, 229.35 μmol, 0.3 eq) and 2-(bromomethyl)

prop-2-enenitrile (167.4 mg, 1.15 mmol, 1.5 eq). The mixture was stirred at 25° C. for 1 hr. The reaction mixture was diluted with H₂O (50 mL) and extracted with EtOAc (2×30 mL). The combined organic layer was washed with H₂O (2×30 mL) and brine (2×30 mL), dried over anhydrous Na₂SO₄, filtered, and concentrated in vacuo. The residue was purified by prep-TLC (SiO₂, PE:EtOAc=6:1) to afford the title compound (0.3 g, 695.54 µmol, 90.98% yield) as a yellow oil.

Step 8) Preparation of tert-butyl N-(2-cyanoallyl)-N-[2-(methoxymethyl)-7-(4,4,5,5-tetramethyl-1,3,2-(dioxaborolan-2-yl)-1-naphthyl]carbamate

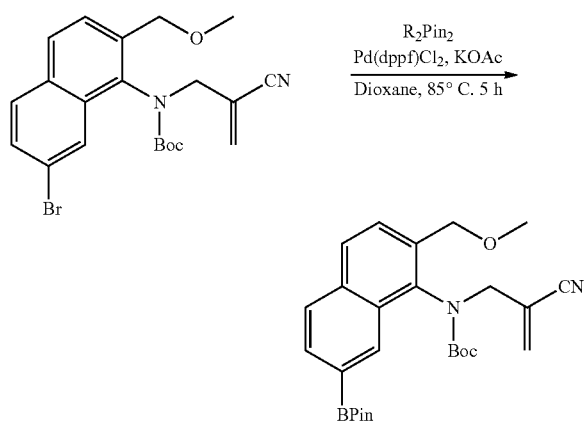

To a mixture of tert-butyl N-[7-bromo-2-(methoxymethyl)-1-naphthyl]-N-(2-cyanoallyl) carbamate (0.26 g, 602.8 µmol, 1 eq) and 4,4,5,5-tetramethyl-2-(4,4,5,5-tetramethyl-1,3,2-dioxaborolan-2-yl)-1,3,2-dioxaborolane (459.2 mg, 1.81 mmol, 3 eq in dioxane (5 mL) were added KOAc (473.3 mg, 4.82 mmol, 8 eq) and Pd(dppf)Cl₂ (88.2 mg, 120.56 µmol, 0.2 eq). The reaction mixture was stirred at 85° C. for 5 hr. The mixture was concentrated in vacuo. The residue was washed with DCM (3×5 mL), filtered, and concentrated in vacuo to afford the title compound (0.5 g, crude) as a black brown oil, which was used in the next step without further purification.

Step 9) Preparation of tert-butyl N-(2-cyanoallyl)-N-[2-(methoxymethyl)-7-(2-pyridyl)-1-naphthyl]carbamate

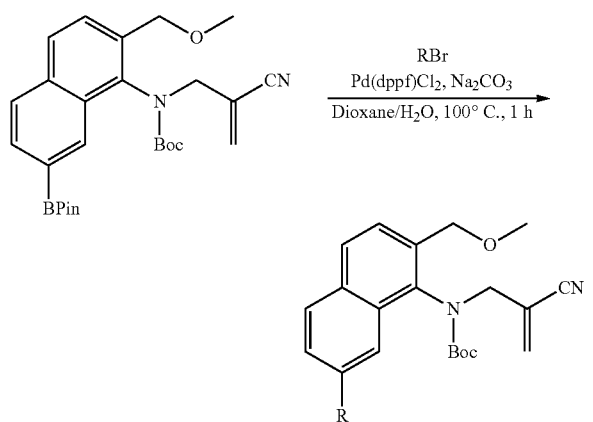

R = 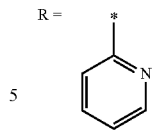

To a mixture of tert-butyl N-(2-cyanoallyl)-N-[2-(methoxymethyl)-7-(4,4,5,5-tetramethyl-1,3,2-dioxaborolan-2-yl)-1-naphthyl]carbamate (130 mg, 271.75 µmol, 1 eq) and RBr (64.4 mg, 407.62 µmol, 38.80 µL, 1.5 eq) in dioxane (4 mL) and H₂O (1 mL) were added Na₂CO₃ (86.4 mg, 815.24 µmol, 3 eq) and Pd(dppf)Cl₂ (19.9 mg, 27.17 µmol, 0.1 eq). The mixture was stirred at 100° C. for 1 h. TLC showed that the reaction was complete. Saturated EDTA solution (50 mL) and EtOAc (30 mL) were added and the mixture was stirred at r.t. for 1 h. The mixture was filtered and extracted with EtOAc (2×30 mL). The combined organic layer was washed with H₂O (2×30 mL) and brine (2×30 mL), dried over anhydrous Na₂SO₄, filtered, and concentrated in vacuo. The residue was purified by prep-TLC (SiO₂, DCM:MeOH=10:1) to afford the title compound (50 mg, 116.41 µmol, 42.84% yield) as a yellow oil.

Step 10) Compound 278: Preparation of 2-[[[2-(methoxymethyl)-7-(2-pyridyl)-1-naphthyl]amino]methyl]prop-2-enenitrile

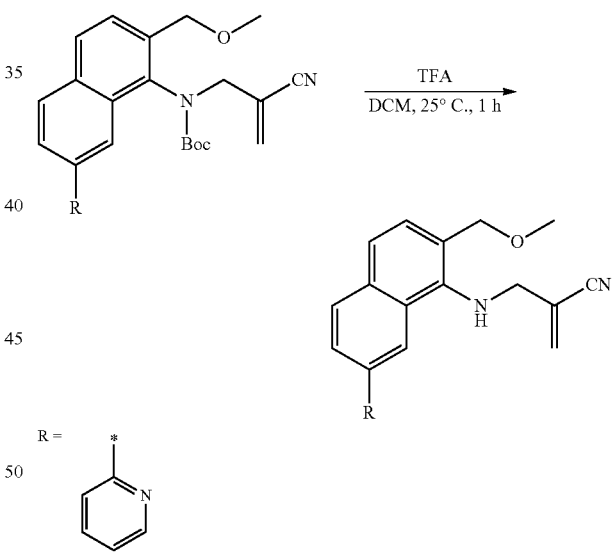

To a solution of tert-butyl N-(2-cyanoallyl)-N-[2-(methoxymethyl)-7-(2-pyridyl)-1-naphthyl]carbamate (50 mg, 116.41 µmol, 1 eq) in DCM (3 mL) was added TFA (1.54 g, 13.51 mmol, 1 mL, 116.02 eq) (DCM:TFA=3:1). The mixture was stirred at 25° C. for 1 h. The reaction mixture was adjusted with saturated NaHCO₃ to pH=8 and extracted with EtOAc (2×30 mL). The combined organic layer was washed with H₂O (2×30 mL) and brine (2×30 mL), dried over anhydrous Na₂SO₄, filtered, and concentrated in vacuo. The residue was purified by prep-HPLC to afford the title compound (2 mg, 6.07 µmol, 5.22% yield) as a white solid. LC-MS (ES⁺, m/z): 330 [(M+H)⁺].

363
Route 2: General Scheme
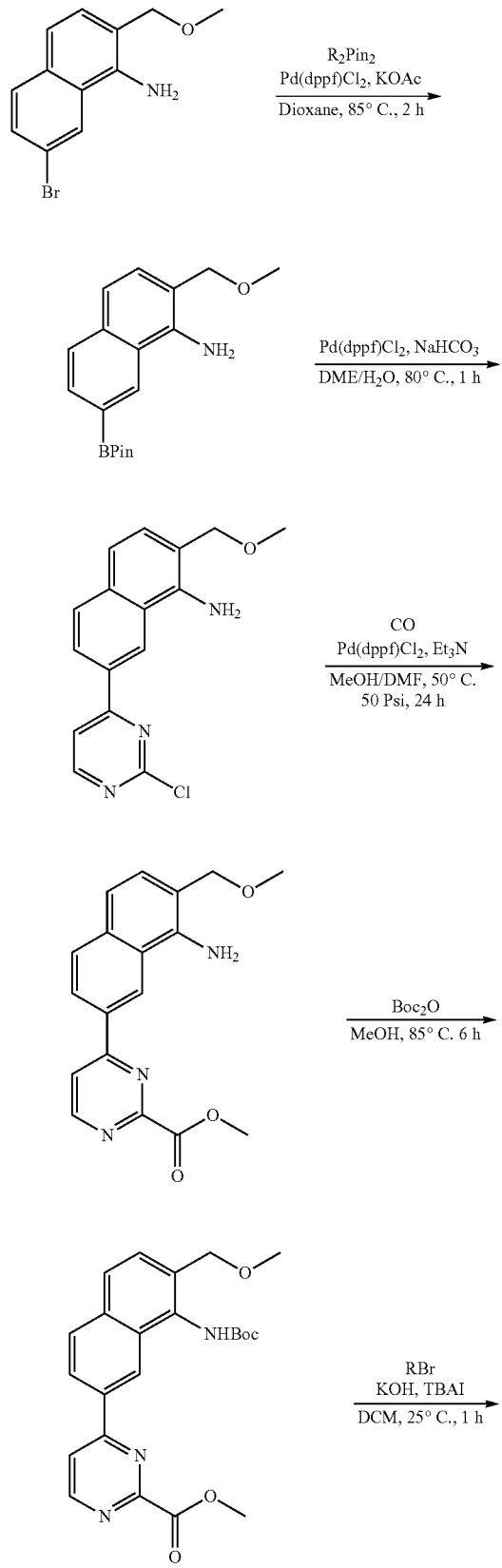
364
-continued
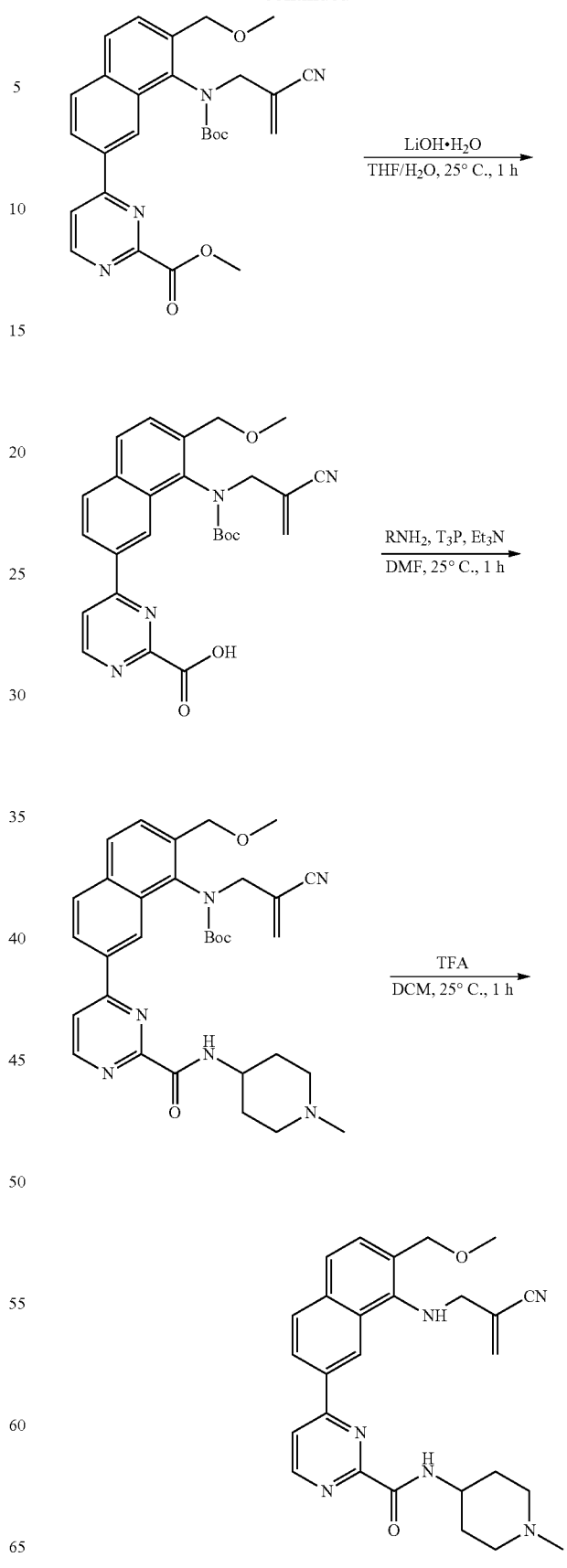

Step 1) Preparation of 2-(methoxymethyl)-7-(4,4,5,5-tetramethyl-1,3,2-dioxaborolan-2-yl)naphthalen-1-amine

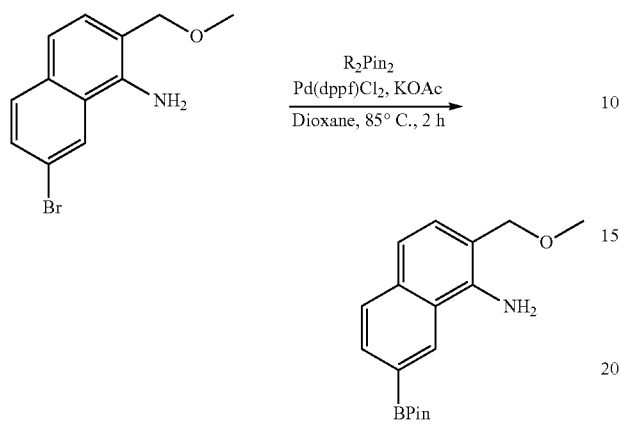

To a mixture of 7-bromo-2-(methoxymethyl)naphthalen-1-amine (1.1 g, 4.13 mmol, 1 eq) and 4,4,5,5-tetramethyl-2-(4,4,5,5-tetramethyl-1,3,2-dioxaborolan-2-yl)-1,3,2-dioxaborolane (3.15 g, 12.4 mmol, 3 eq) in dioxane (20 mL) were added KOAc (3.25 g, 33.07 mmol, 8 eq) and Pd(dppf)Cl$_2$ (604.87 mg, 826.65 µmol, 0.2 eq) and the mixture was stirred at 85° C. for 2 h under N$_2$. The reaction mixture was concentrated in vacuo. The residue was purified by column chromatography (SiO$_2$, PE:EtOAc=10:1 to 4:1) to afford the title compound (1.2 g, 92.7% yield) as a yellow oil.

Step 2) Preparation of 7-(2-chloropyrimidin-4-yl)-2-(methoxymethyl)naphthalen-1-amine

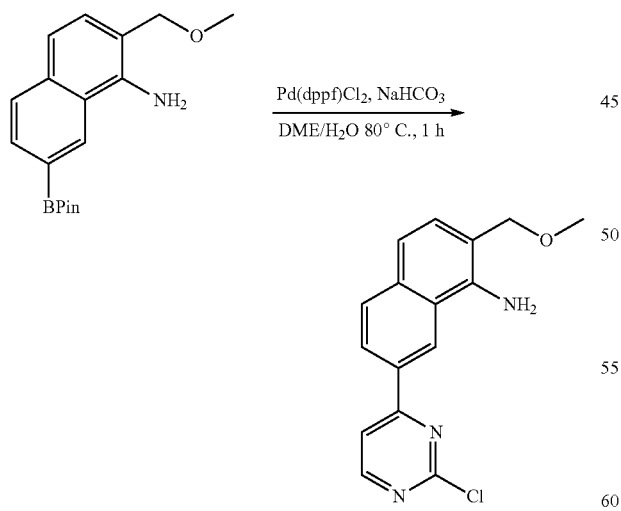

To a mixture of 2-(methoxymethyl)-7-(4,4,5,5-tetramethyl-1,3,2-dioxaborolan-2-yl)naphthalen-1-amine (1.2 g, 3.83 mmol, 1 eq) and 2,4-dichloropyrimidine (1.71 g, 11.49 mmol, 3 eq) in DME (12 mL) and H$_2$O (3 mL) were added NaHCO$_3$ (965.6 mg, 11.49 mmol, 3 eq) and Pd(dppf)Cl$_2$ (280.4 mg, 383.14 µmol, 0.1 eq) and the mixture was stirred at 80° C. for 1 h under N$_2$. TLC showed that the reaction was complete. 50 mL of saturated EDTA solution and EtOAc (50 mL) were added and the mixture was stirred at 25° C. for 1 h. The mixture was extracted with EtOAc (3×50 mL). The combined organic layer was washed with H$_2$O (2×50 mL) and brine (2×50 mL), dried over anhydrous Na$_2$SO$_4$, filtered, and concentrated in vacuo. The residue was purified by column chromatography (SiO$_2$, PE:EtOAc=10:1 to 1:1) to afford the title compound (1 g, 87.1% yield) as a yellow solid.

Step 3) Preparation of methyl 4-[8-amino-7-(methoxymethyl)-2-naphthyl]pyrimidine-2-carboxylate

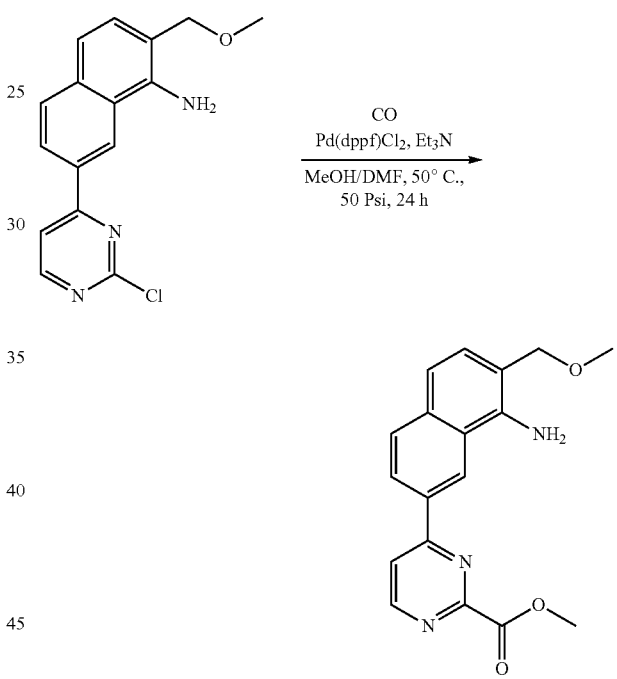

To a mixture of 7-(2-chloropyrimidin-4-yl)-2-(methoxymethyl)naphthalen-1-amine (0.8 g, 2.67 mmol, 1 eq) in MeOH (26 mL) and DMF (26 mL) were added TEA (810.2 mg, 8.01 mmol, 1.11 mL, 3 eq) and Pd(dppf)Cl$_2$ (195.3 mg, 266.89 µmol, 0.1 eq). The mixture was stirred at 50° C. for 1 d under CO (50 psi). TLC showed that the reaction was complete. 50 mL of saturated EDTA solution and EtOAc (50 mL) were added and the mixture was stirred at 25° C. for 1 h. The mixture was extracted with EtOAc (2×50 mL). The combined organic layer was washed with H$_2$O (2×50 mL) and brine (2×50 mL), dried over anhydrous Na$_2$SO$_4$, filtered, and concentrated in vacuo. The residue was purified by column chromatography (SiO$_2$, PE:EtOAc=8:1 to 4:1) to afford to the title compound (0.33 g, 38.2% yield) as a yellow oil.

Step 4) Preparation of methyl 4-[8-(tert-butoxycarbonylamino)-7-(methoxymethyl)-2-naphthyl]pyrimidine-2-carboxylate

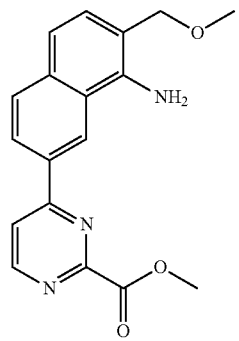

To a solution of methyl 4-[8-amino-7-(methoxymethyl)-2-naphthyl]pyrimidine-2-carboxylate (0.33 g, 1.02 mmol, 1 eq) in MeOH (5 mL) was added Boc$_2$O (4.45 g, 20.41 mmol, 4.69 mL, 20 eq). The reaction mixture was stirred at 85° C. for 6 h. The reaction mixture was concentrated in vacuo. The residue was purified by column chromatography (SiO$_2$, PE:EtOAc=4:1 to 1:1) to afford the title compound (0.38 g, 87.9% yield) as a yellow oil.

Step 5) Preparation of methyl 4-[8-[tert-butoxycarbonyl(2-cyanoallyl)amino]-7-(methoxymethyl)-2-naphthyl]pyrimidine-2-carboxylate

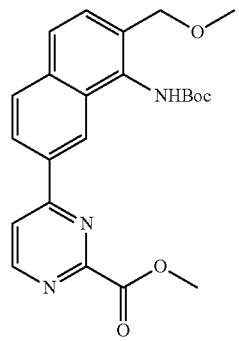

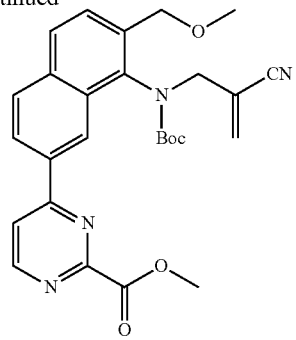

To a solution of methyl 4-[8-(tert-butoxycarbonylamino)-7-(methoxymethyl)-2-naphthyl]pyrimidine-2-carboxylate (0.33 g, 779.29 µmol, 1 eq) in DCM (4 mL) were added KOH (131.2 mg, 2.34 mmol, 3 eq), TBAI (57.6 mg, 155.86 µmol, 0.2 eq) and 2-(bromomethyl)prop-2-enenitrile (136.5 mg, 935.15 µmol, 1.2 eq), and the mixture was stirred at 25° C. for 1 hr. The reaction mixture was diluted with H$_2$O (50 mL) and extracted with EtOAc (2×30 mL). The combined organic layers were washed with H$_2$O (2×30 mL) and brine (2×30 mL), dried over anhydrous Na$_2$SO$_4$, filtered, and concentrated in vacuo. The residue was purified by prep-TLC (SiO$_2$, PE:EtOAc=1:2) to afford the title compound (0.32 g, 84.1% yield) as a yellow oil.

Step 6) Preparation of 4-[8-[tert-butoxycarbonyl(2-cyanoallyl)amino]-7-(methoxymethyl)-2-naphthyl]pyrimidine-2-carboxylic acid

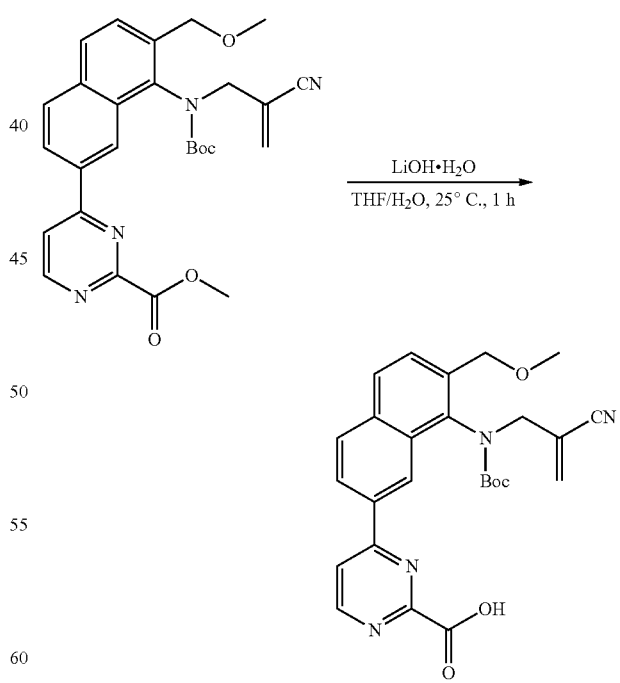

To a mixture of methyl 4-[8-[tert-butoxycarbonyl(2-cyanoallyl)amino]-7-(methoxymethyl)-2-naphthyl]pyrimidine-2-carboxylate (0.27 g, 552.67 µmol, 1 eq) in THF (4 mL) and H$_2$O (1 mL) was added LiOH·H$_2$O (231.9 mg, 5.53 mmol, 10 eq). The mixture was stirred at 25° C. for 1 h. The Step 7) Preparation of tert-butyl N-(2-cyanoallyl)-N-[2-(methoxymethyl)-7-[2-[(1-methyl-4-piperidyl)carbamoyl]pyrimidin-4-yl]-1-naphthyl]carbamate

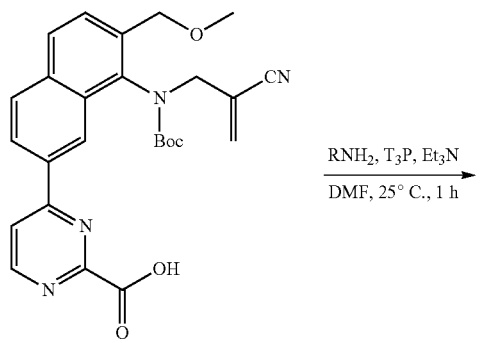

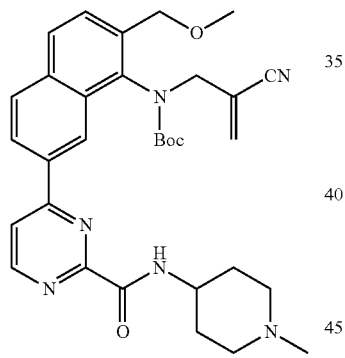

To a solution of 4-[8-[tert-butoxycarbonyl(2-cyanoallyl)amino]-7-(methoxymethyl)-2-naphthyl]pyrimidine-2-carboxylic acid (0.25 g, 526.86 μmol, 1 eq) in DMF (4 mL) were added TEA (266.6 mg, 2.63 mmol, 366.67 μL, 5 eq), 1-methylpiperidin-4-amine (90.2 mg, 790.29 μmol, 1.5 eq), and T$_3$P (502.9 mg, 790.29 μmol, 470.01 μL, 50% purity, 1.5 eq). The reaction was stirred at 25° C. for 1 h. The reaction mixture was diluted with H$_2$O (50 mL) and extracted with EtOAc (2×30 mL). The combined organic layer was washed with H$_2$O (2×30 mL) and brine (2×30 mL), dried over anhydrous Na$_2$SO$_4$, filtered, and concentrated in vacuo. The residue was purified by prep-TLC (SiO$_2$, DCM:MeOH=10:1) to afford the title compound (0.22 g, 73.2% yield) as a yellow solid.

Step 8) Compound 283: Preparation of 4-{8-[(2-cyano-2-methylideneethyl)amino]-7-(methoxymethyl)naphthalen-2-yl}-N-(1-methylpiperidin-4-yl)pyrimidine-2-carboxamide

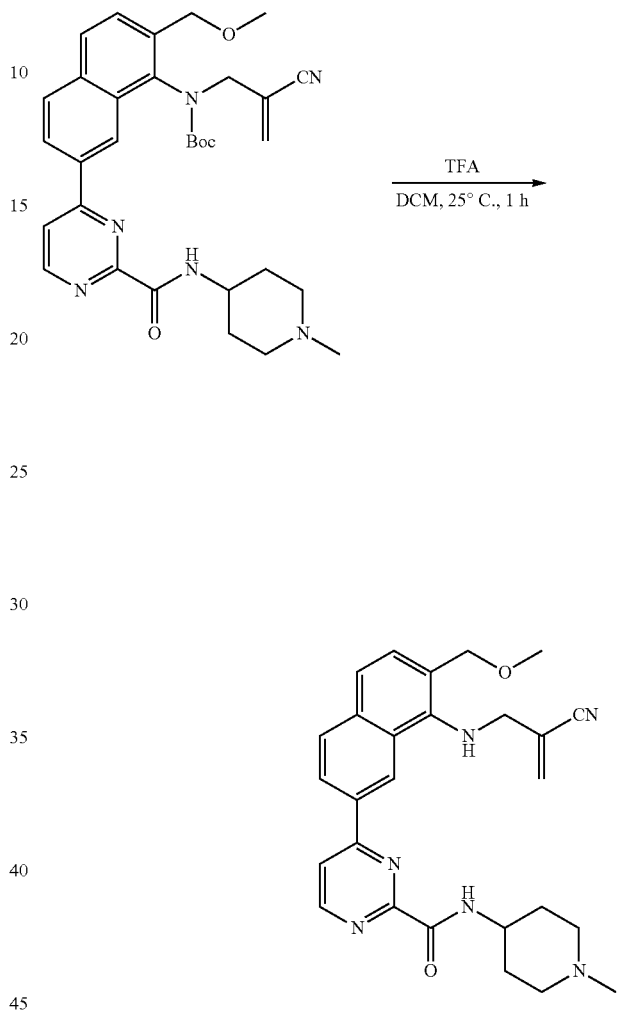

To a solution of tert-butyl N-(2-cyanoallyl)-N-[2-(methoxymethyl)-7-[2-[(1-methyl-4-piperidyl) carbamoyl]pyrimidin-4-yl]-1-naphthyl]carbamate (0.1 g, 175.23 μmol, 1 eq) in DCM (2 mL) was added TFA (770 mg, 6.75 mmol, 0.5 mL, 38.54 eq). The mixture was stirred at 25° C. for 1 h. The reaction mixture was adjusted to pH=8 with saturated NaHCO$_3$ and extracted with EtOAc (2×30 mL). The combined organic layer was washed with H$_2$O (2×30 mL) and brine (2×30 mL), dried over anhydrous Na$_2$SO$_4$, filtered, and concentrated in vacuo. The residue was purified by prep-HPLC to afford the title compound (16.6 mg, 20.1% yield) as a white solid. LC-MS (ES$^+$, m/z): 471.2 [(M+H)$^+$].

TABLE 6 shows compounds synthesized using the methods described in EXAMPLE 6 above.

TABLE 6

| Cpd. No. | Structure | IUPAC | LC-MS (ES+, m/z) |
|---|---|---|---|
| 278 | 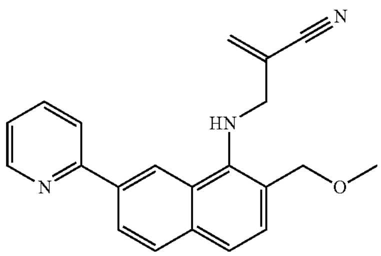 [SMILES: C=C(C#N)CNc1c(COC)ccc2ccc(-c3ccccn3)cc12] | 2-({[2-(methoxymethyl)-7-(pyridin-2-yl)naphthalen-1-yl]amino}methyl)prop-2-enenitrile | 330 |
| 279 | 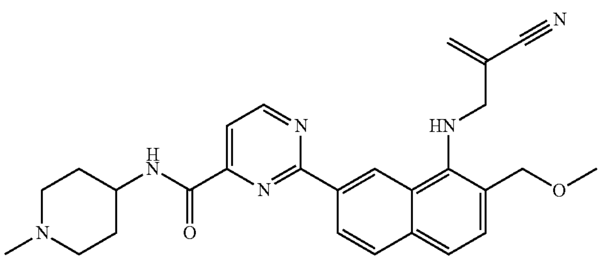 | 2-{8-[(2-cyano-2-methylideneethyl)amino]-7-(methoxymethyl)naphthalen-2-yl}-N-(1-methylpiperidin-4-yl)pyrimidine-4-carboxamide | 471.3 |
| 280 | 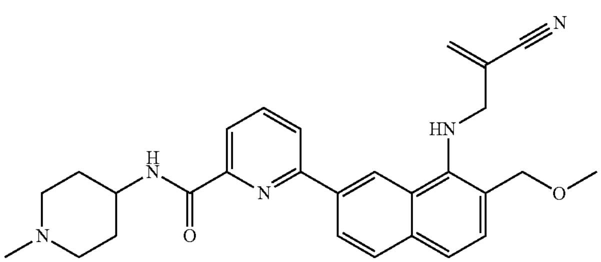 | 6-{8-[(2-cyano-2-methylideneethyl)amino]-7-(methoxymethyl)naphthalen-2-yl}-N-(1-methylpiperidin-4-yl)pyridine-2-carboxamide | 470.3 |
| 281 | 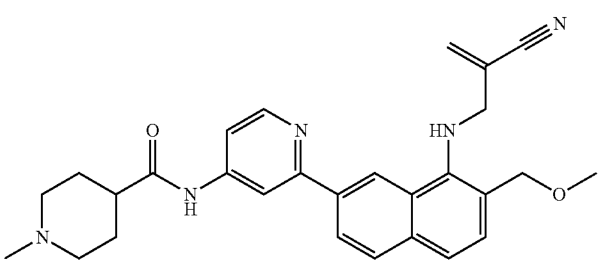 | N-(2-{8-[(2-cyano-2-methylideneethyl)amino]-7-(methoxymethyl)naphthalen-2-yl}pyridin-4-yl)-1-methylpiperidine-4-carboxamide | 470.3 |
| 282 | 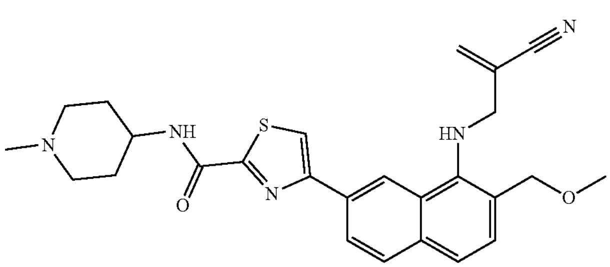 | 4-{8-[(2-cyano-2-methylideneethyl)amino]-7-(methoxymethyl)naphthalen-2-yl}-N-(1-methylpiperidin-4-yl)-1,3-thiazole-2-carboxamide | 476.2 |

TABLE 6-continued

| Cpd. No. | Structure | IUPAC | LC-MS (ES+, m/z) |
|---|---|---|---|
| 283 | 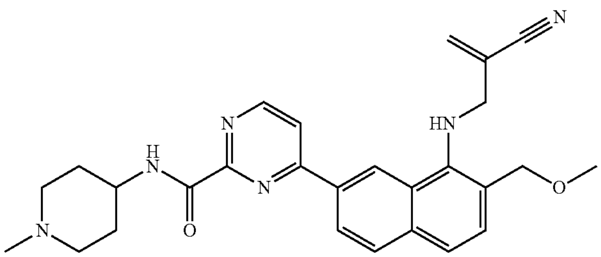 | 4-{8-[(2-cyano-2-methylideneethyl)amino]-7-(methoxymethyl)naphthalen-2-yl}-N-(1-methylpiperidin-4-yl)pyrimidine-2-carboxamide | 471.2 |
| 284 | 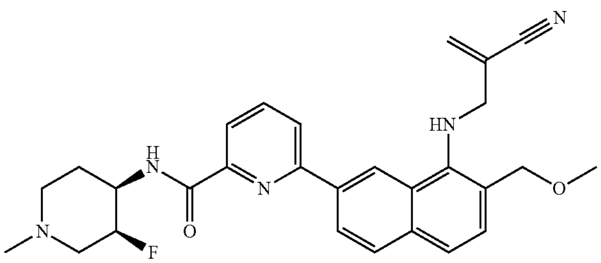 | 6-{8-[(2-cyano-2-methylideneethyl)amino]-7-(methoxymethyl)naphthalen-2-yl}-N-[(3S,4R)-3-fluoro-1-methylpiperidin-4-yl]pyridine-2-carboxamide | 488.3 |
| 285 | 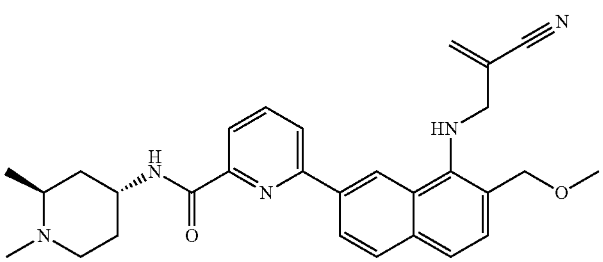 | 6-{8-[(2-cyano-2-methylideneethyl)amino]-7-(methoxymethyl)naphthalen-2-yl}-N-[(2S,4R)-1,2-dimethylpiperidin-4-yl]pyridine-2-carboxamide | 484.3 |

Example 7: Method G

Route 1: General Method

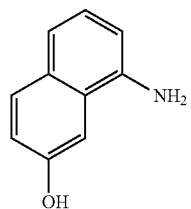

PhNTf₂, K₂CO₃
―――――――→
THF, 70° C.

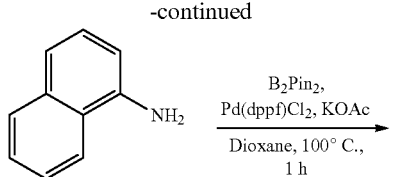

B₂Pin₂, Pd(dppf)Cl₂, KOAc
―――――――→
Dioxane, 100° C., 1 h

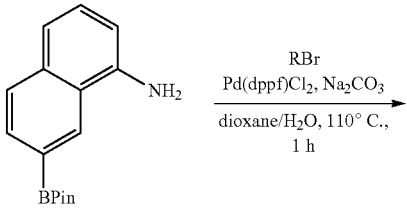

RBr
Pd(dppf)Cl₂, Na₂CO₃
―――――――→
dioxane/H₂O, 110° C., 1 h

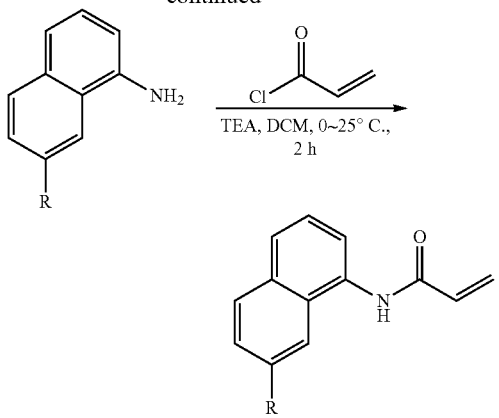

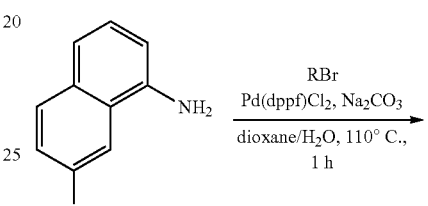

reaction mixture was stirred at 100° C. for 1 hr under N₂. TLC showed that the reaction mixture was completed. The reaction mixture was filtered, and the filtrate was concentrated in vacuo to give a residue. The residue was purified by column chromatography (SiO₂, PE:EtOAc=20/1 to 10:1) to afford the title compound 7-(4,4,5,5-tetramethyl-1,3,2-dioxaborolan-2-yl)naphthalen-1-amine (1. g, 3.34 mmol, 19.48% yield, 90% purity) as a pink solid. LC-MS (ES⁺, m/z): 270.1 [(M+H)⁺], ¹H NMR (400 MHz, DMSO-d6) δ=8.42 (s, 1H), 7.68 (d, J=8.2 Hz, 1H), 7.61 (d, J=7.9 Hz, 1H), 7.23 (t, J=7.8 Hz, 1H), 7.05 (d, J=8.1 Hz, 1H), 6.68 (d, J=7.3 Hz, 1H), 5.81 (br s, 2H), 1.34 (s, 12H), 1.25-1.07 (m, 2H).

Step 3) General Procedure for Suzuki Coupling

Step 1) (8-amino-2-naphthyl)trifluoromethanesulfonate

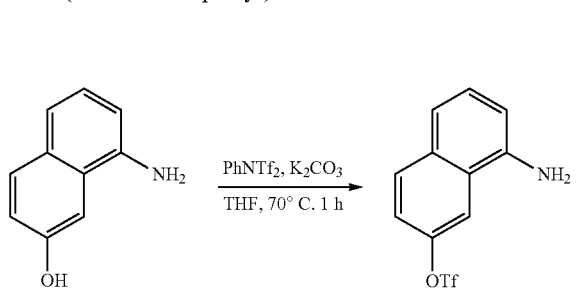

To a solution of 8-aminonaphthalen-2-ol (5 g, 31.41 mmol, 1 eq) in THF (50 mL) were added K₂CO₃ (8.68 g, 62.82 mmol, 2 eq) and 1,1,1-trifluoro-N-phenyl-N-(trifluoromethylsulfonyl) methanesulfonamide (14.59 g, 40.83 mmol, 1.3 eq). The reaction mixture was stirred at 70° C. for 1 hr. TLC (PE:EtOAc=4:1, SM Rf=0.38, SM Rf=0.59) showed that the reaction mixture was completed. The reaction mixture was concentrated to remove the solvent in vacuo to give a residue which was purified by column chromatography (SiO₂, PE:EtOAc=10:1 to 4:1) to afford the title compound (8-amino-2-naphthyl)trifluoromethanesulfonate (7 g, 24.03 mmol, 76.52% yield) as a brown solid.

Step 2) 7-(4,4,5,5-tetramethyl-1,3,2-dioxaborolan-2-yl)naphthalen-1-amine

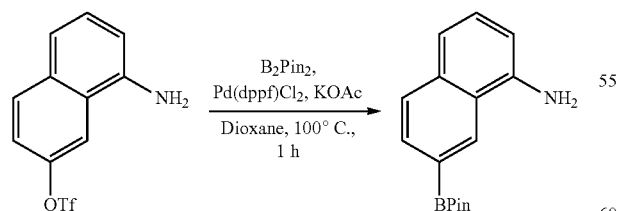

To a solution of (8-amino-2-naphthyl)trifluoromethanesulfonate (5 g, 17.17 mmol, 1 eq) and 4,4,5,5-tetramethyl-2-(4,4,5,5-tetramethyl-1,3,2-dioxaborolan-2-yl)-1,3,2-dioxaborolane (6.54 g, 25.75 mmol, 1.5 eq) in dioxane (60 mL) was added KOAc (5.05 g, 51.5 mmol, 3 eq) and Pd(dppf)Cl₂ (1.26 g, 1.72 mmol, 0.1 eq). The resulting To a mixture of 7-(4,4,5,5-tetramethyl-1,3,2-dioxaborolan-2-yl)naphthalen-1-amine (300 mg, 1.11 μmol, 1 eq), bromo derivative (1.34 mmol, 1.2 eq) and Na₂CO₃ (354.4 mg, 3.34 μmol 3 eq) in dioxane (2 mL) H₂O (0.5 mL) was added Pd(dppf)Cl₂ (81.6 mg, 111.46 μmol 0.1 eq). The reaction was heated to 110° C. and stirred for 1 h. Upon completion of the reaction as indicated by LCMS, 30 mL saturated EDTA was added to the solution stirred for 1 hour. The mixture was extracted with EtOAc (3×30 mL). The organic phase was separated, washed with H₂O (2×30 mL) and brine (2×30 mL), dried over anhydrous Na₂SO₄, filtered, and concentrated in vacuo to give a residue. The residue was purified by prep-TLC (SiO₂, DCM:MeOH=10:1) to afford the desired product.

Step 4) General Procedure for Acylation with Acryloyl Chloride

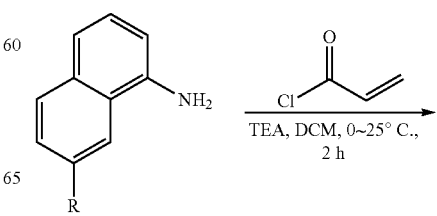

377

-continued

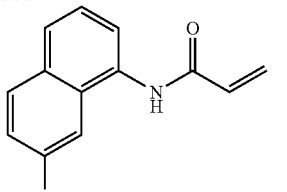

A Mixture of Naphthalene Amine Derivative (100 mg, 253.46 μMol, 1 Eq), Prop-2-Enoyl Chloride (22.9 mg, 253.46 μmol, 1 eq), and TEA (76.9 mg, 760.38 μmol, 3 eq) in DCM (2 mL) at 0° C., and the mixture was stirred at 25° C. for 2 hours. The reaction mixture was poured into H₂O (50 mL) and extracted with DCM (3×30 mL). The organic phase was separated, washed with H₂O (2×30 mL) and brine (2×30 mL), dried over anhydrous Na₂SO₄, filtered, and concentrated in vacuo to give a residue. The residue was purified by prep-HPLC to afford the desired compound.

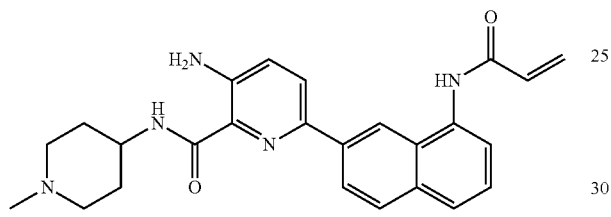

Preparation of 3-amino-N-(1-methylpiperidin-4-yl)-6-[8-(prop-2-enamido)naphthalen-2-yl]pyridine-2-carboxamide (Compound 295)

To a solution of 3-amino-6-(8-amino-2-naphthyl)-N-(1-methyl-4-piperidyl)pyridine-2-carboxamide (0.1 g, 266.34 μmol, 1 eq) in DCM (5 mL) was added TEA (13.5 mg, 133.17 μmol, 18.54 μL, 0.5 eq), prop-2-enoyl chloride (12.1 mg, 133.17 μmol, 10.86 μL, 0.5 eq) was added to the solution at −60° C. Then stirred at −60° C. for 1 hr. HPLC and LCMS showed that the reaction was complete. The reaction was poured into ~10 mL ice water and extracted with DCM (3×10 mL. The combined organic phase was washed with brine (3×10 mL), dried over with anhydrous Na₂SO₄, filtered, and concentrated in vacuo. The residue was purified by prep-TLC (SiO₂, DCM:MeOH=10:1). The residue was purified by prep-HPLC (basic condition) to afford the title compound (0.0166 g, 37.99 μmol, 14.26% yield, 98.3% purity) as a light yellow solid. LC-MS (ES⁺, m/z): 430.2 [(M+H)⁺]

Route 2: General Scheme

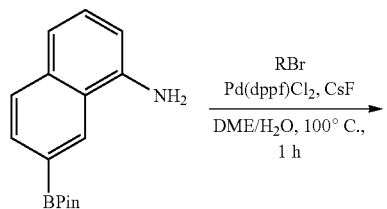

378

-continued

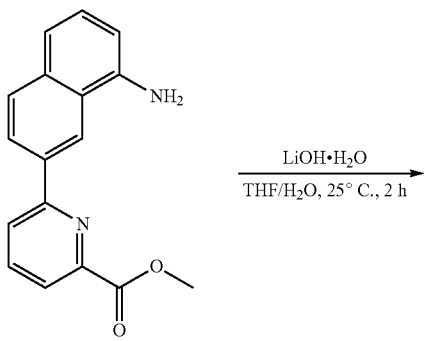

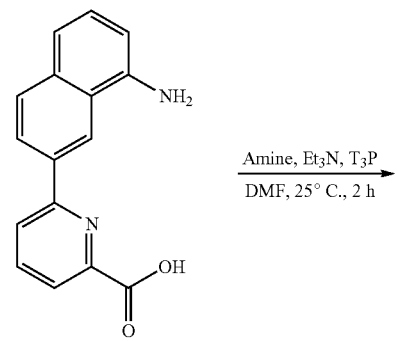

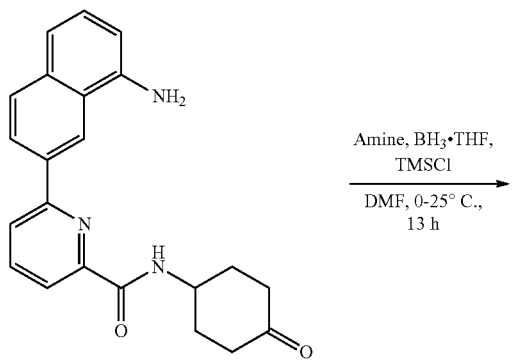

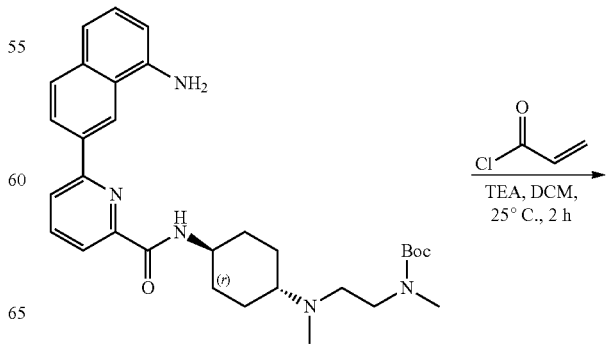

-continued

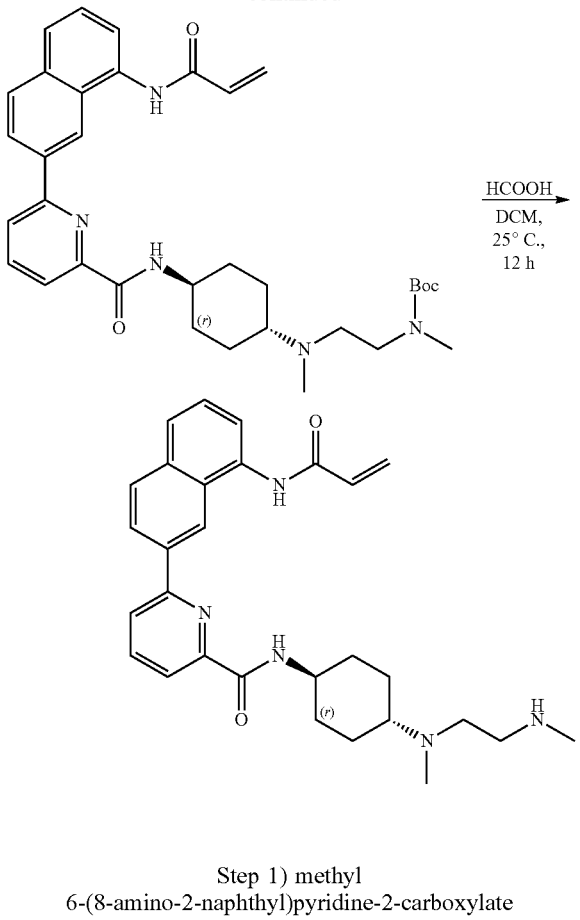

Step 1) methyl 6-(8-amino-2-naphthyl)pyridine-2-carboxylate

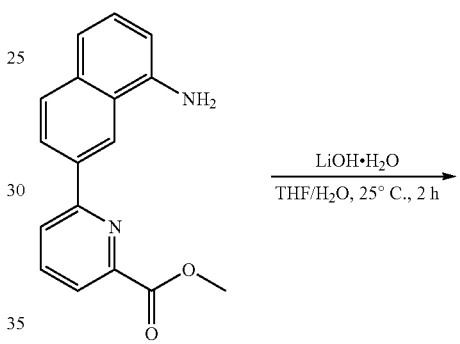

A mixture of 7-(4,4,5,5-tetramethyl-1,3,2-dioxaborolan-2-yl)naphthalen-1-amine (5 g, 18.58 mmol, 1 eq), methyl 6-bromopyridine-2-carboxylate (4.82 g, 22.29 mmol, 1.2 eq), CsF (8.47 g, 55.73 mmol, 2.05 mL, 3 eq), and Pd(dppf)Cl₂ (1.36 g, 1.86 mmol, 0.1 eq) in DME (40 mL) and H₂O (10 mL) was stirred at 100° C. for 1 hour. Upon completion of the reaction as indicated by LCMS, to the reaction mixture was added 30 mL saturated EDTA solution stirred for 1 hour. The mixture was extracted with EtOAc (3×30 mL). The organic phase was separated, washed with H₂O (2×30 mL) and brine (2×30 mL), dried over anhydrous Na₂SO₄, filtered, and concentrated in vacuo to give crude product. The residue was purified by column chromatography (SiO₂, PE:EtOAc=5:1 to 1:1) to afford the title compound (3.2 g, 11.5 mmol, 61.89% yield) as a light yellow gum. LC-MS (ES$^+$, m/z): 279.2 [(M+H)$^+$].

Step 2) 6-(8-amino-2-naphthyl)pyridine-2-carboxylic acid

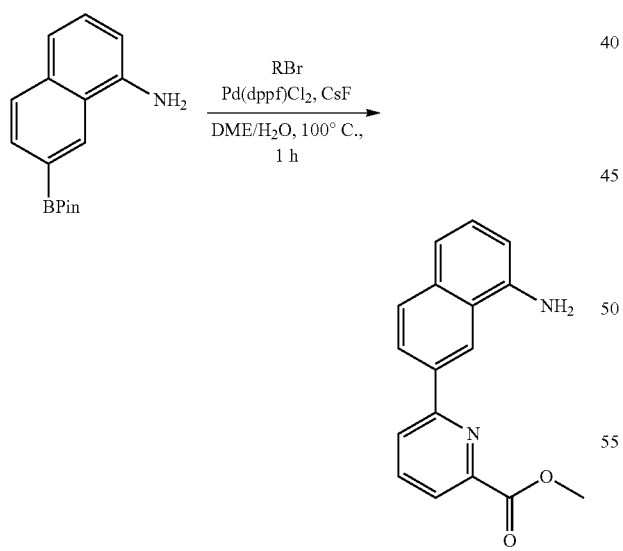

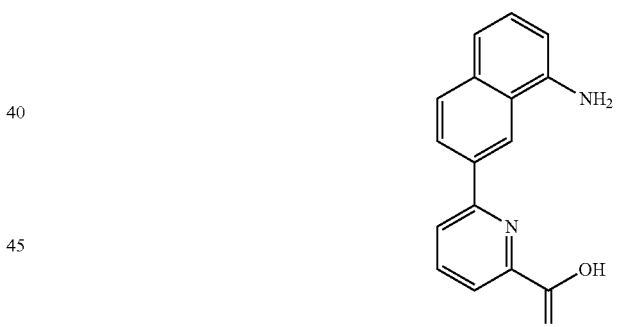

To a solution of methyl 6-(8-amino-2-naphthyl)pyridine-2-carboxylate (3.2 g, 11.5 mmol, 1 eq) in THF (60 mL) and H₂O (12 mL) was added LiOH·H₂O (2.41 g, 57.49 mmol, 5 eq). The mixture was stirred at 25° C. for 2 hours. LCMS showed that the reaction was complete. Add the reaction mixture to ice water (100 mL). Then slowly saturated citric acid was added to adjust pH=5~6. The mixture was extracted with PE (3×30 mL). The organic phase was separated, washed with H₂O (2×30 mL) and brine (2×30 mL), dried over anhydrous Na₂SO₄, filtered, and concentrated in vacuo to afford the title compound (3.5 g, crude) as a light yellow solid. LC-MS (ES$^+$, m/z): 265.2 [(M+H)$^+$].

Step 3) N-(4-oxocyclohexyl)-6-[8-(prop-2-enoylamino)-2-naphthyl]pyridine-2-carboxamide

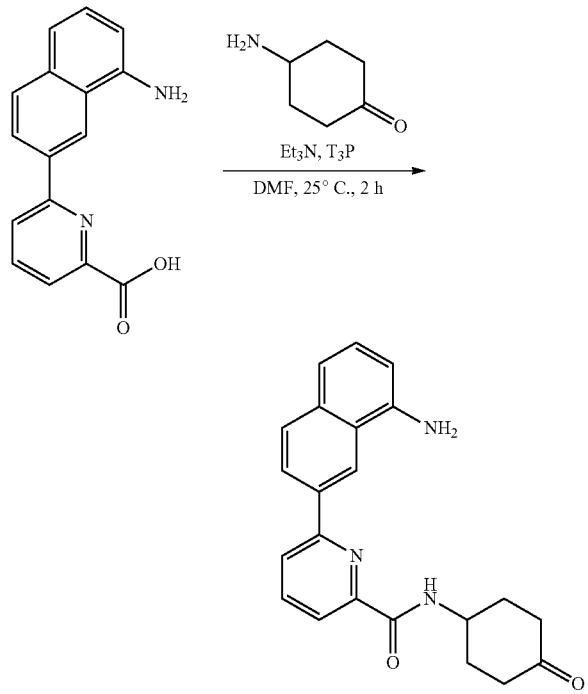

A mixture of-6-(8-amino-2-naphthyl)pyridine-2-carboxylic acid (3 g, 9.42 mmol, 1 eq), 4-aminocyclohexanone (1.41 g, 9.42 mmol, 1 eq, HCl), T₃P (9 g, 14.14 mmol, 1.5 eq), and TEA (5.72 g, 56.55 mmol, 6 eq) in DMF (30 mL) was stirred at 25° C. for 2 hours. The reaction mixture was added to water (100 mL) and extracted with EtOAc (3×30 mL). The organic phase was separated, washed with H₂O (2×30 mL) and brine (2×30 mL), dried over anhydrous Na₂SO₄, filtered, and concentrated in vacuo. The crude residue was purified by column chromatography (SiO₂, PE:EtOAc=40:1 to 10:1) to afford the title compound (700 mg, 1.69 mmol, 17.96% yield) as a light yellow oil. LC-MS (ES⁺, m/z): 360.1 [(M+H)⁺].

Step 4) tert-butyl N-[2-[[4-[[6-(8-amino-2-naphthyl)pyridine-2-carbonyl]amino]cyclohexyl]-methylamino]ethyl]-N-methyl-carbamate

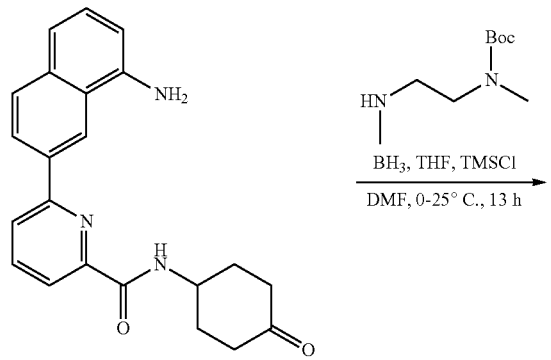

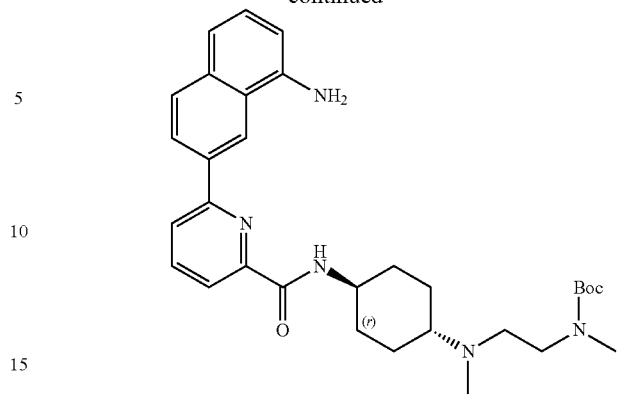

To a mixture of 6-(8-amino-2-naphthyl)-N-(4-oxocyclohexyl)pyridine-2-carboxamide (700 mg, 1.95 mmol, 1 eq) in DMF (10 mL) were added TMSCl (528.97 mg, 4.87 mmol, 2.5 eq) and tert-butyl N-methyl-N-[2-(methylamino)ethyl]carbamate (1.83 g, 9.74 mmol, 5 eq). The mixture was stirred at 0° C. for 1 hour. Then, BH₃·THF (1 M, 5.84 mL, 3 eq) was added and the mixture was stirred at 0° C. for another 12 hours. The reaction mixture was poured into ice-water (50 mL) and extracted with EtOAc (3×30 mL). The organic phase was separated, washed with H₂O (2×30 mL) and brine (2×30 mL), dried over anhydrous Na₂SO₄, filtered, and concentrated in vacuo to give crude product. The residue was purified by prep-TLC (SiO₂, DCM:MeOH=10:1) to afford the title compound (360 mg, 677.09 µmol, 34.77% yield) as a light yellow oil. LC-MS (ES⁺, m/z): 532.3 [(M+H)⁺].

Step 5) tert-butyl N-methyl-N-[2-[methyl-[4-[[6-[8-(prop-2-enoylamino)-2-naphthyl]pyridine-2-carbonyl]amino]cyclohexyl]amino]ethyl]carbamate

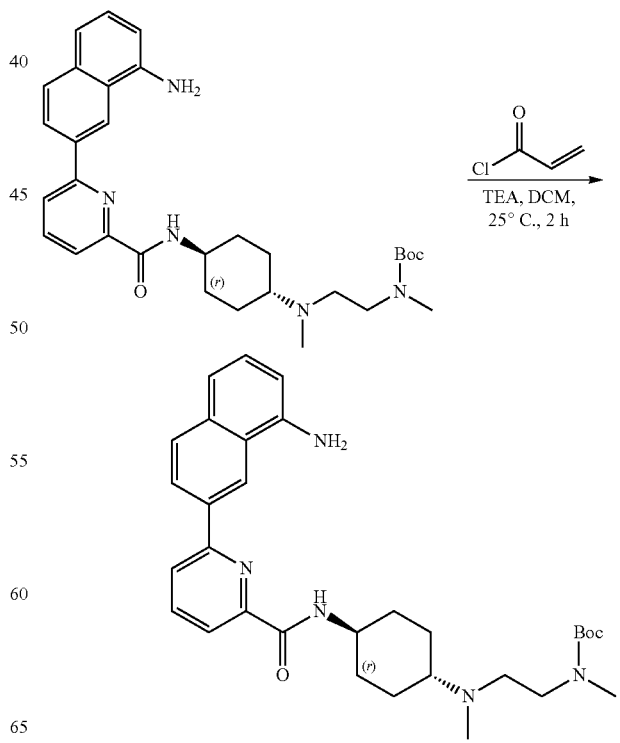

To a solution of tert-butyl N-[2-[[4-[[6-(8-amino-2-naphthyl)pyridine-2-carbonyl]amino]cyclohexyl]-methylamino]ethyl]-N-methyl-carbamate (360 mg, 677.09 µmol, 1 eq) in DCM (2 mL) was added TEA (205.5 mg, 2.03 mmol, 3 eq) and prop-2-enoyl chloride (61.3 mg, 677.09 µmol, 1 eq) at 0° C. The mixture was stirred at 25° C. for 2 hours. LCMS showed that the reaction was complete. Add the reaction mixture to ice water (50 mL) and extracted with DCM (3×30 mL). The organic phase was separated, washed with H₂O (2×30 mL) and brine (2×30 mL), dried over anhydrous Na₂SO₄, filtered, and concentrated in vacuo to give crude product. The residue was purified by prep-TLC (SiO₂, DCM:MeOH=10:1) to afford the title compound-(200 mg, 341.45 µmol, 50.43% yield) as a light yellow oil. LC-MS (ES⁺, m/z): 586.4 [(M+H)⁺].

Step 6) Compound 320: N-[4-[methyl-[2-(methylamino)ethyl]amino]cyclohexyl]-6-[8-(prop-2-enoylamino)-2-naphthyl]pyridine-2-carboxamide

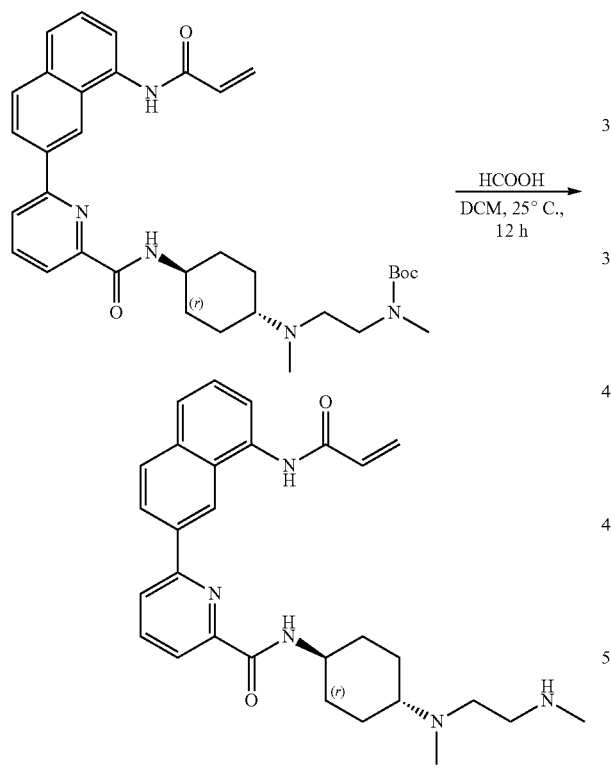

To a solution of tert-butyl N-methyl-N-[2-[methyl-[4-[[6-[8-(prop-2-enoylamino)-2-naphthyl]pyridine-2-carbonyl]amino]cyclohexyl]amino]ethyl]carbamate (100 mg, 170.73 µmol, 1 eq) in DCM (1 mL) was added HCOOH (2 mL). The mixture was stirred at 25° C. for 12 hours. The reaction mixture was dried by N₂ for 1 hour and concentrated in vacuo to give crude product. The residue was purified by prep-HPLC to afford the title compound (15.9 mg, 30.46 µmol, 17.84% yield, 100% purity, HCl) as a light yellow solid. LC-MS (ES⁺, m/z): 486.3 [(M+H)⁺], ¹H NMR (400 MHz, DMSO-d₆) δ=10.97-10.92 (m, 1H), 10.54 (s, 1H), 9.23 (s, 2H), 9.13 (s, 1H), 8.73-8.72 (d, J=8.60 Hz, 1H), 8.47-8.45 (d, J=8.60 Hz, 1H), 8.42-8.40 (d, J=7.50 Hz, 1H), 8.15 (m, 1H), 8.11-8.09 (d, J=8.80 Hz, 1H), 8.03-8.02 (d, J=7.30 Hz, 1H), 8.01-7.96 (d, J=7.50 Hz, 1H), 7.84-7.82 (d, J=7.90 Hz, 1H), 7.59 (s, 1H), 6.88-6.85 (d, J=16.70 Hz, 1H), 6.39-6.34 (dd, J=18.8 Hz, 1H), 5.91-5.88 (d, J=11.60 Hz, 1H), 3.91 (s, 1H), 3.60 (s, 1H) 3.38 (s, 3H), 2.81 (s, 3H), 2.62 (m, 3H) 2.54 (s, 1H), 2.10-2.08 (m, 4H), 1.71-1.68 (m, 4H).

Route 3: General Scheme

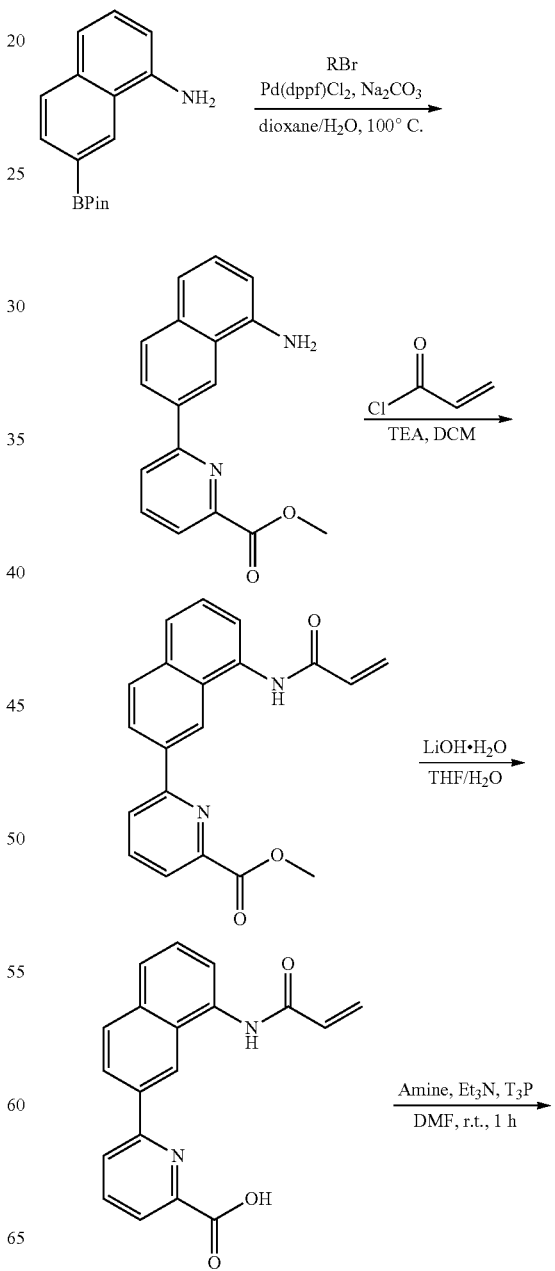

-continued

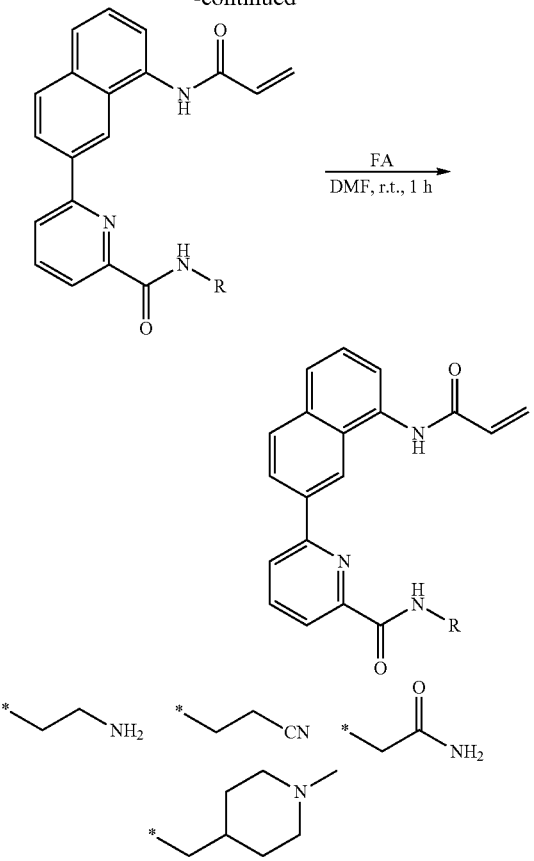

Preparation of Methyl 6-[8-(prop-2-enoylamino)-2-naphthyl]pyridine-2-carboxylate

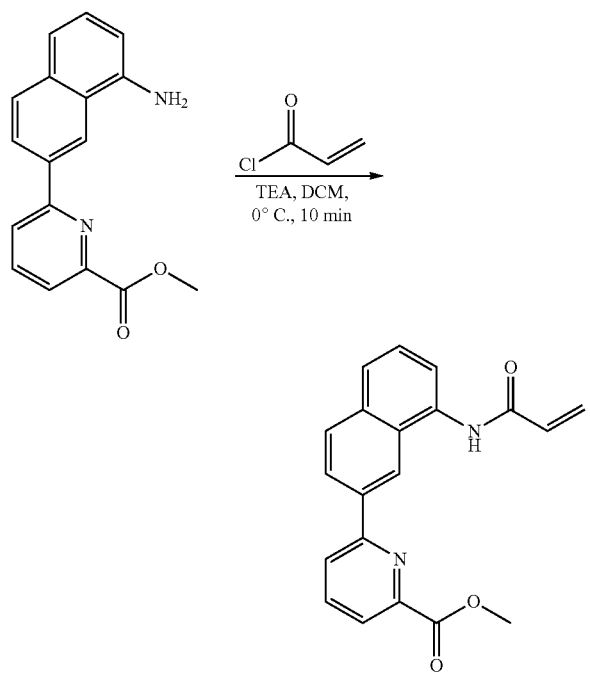

To a solution of methyl 6-(8-amino-2-naphthyl)pyridine-2-carboxylate (0.6 g, 2.16 mmol, 1 eq) in DCM (10 mL) were added TEA (654.5 mg, 6.47 mmol, 900.22 μL, 3 eq) and prop-2-enoyl chloride (195.1 mg, 2.16 mmol, 175.79 μL, 1 eq) at 0° C. The reaction was stirred at 0° C. for 10 min. The reaction was poured into ~50 mL ice water and extracted with DCM (3×100 mL). The organic phase was washed with brine (3×100 mL), dried over by anhydrous Na$_2$SO$_4$, filtered, and concentrated in vacuo. The residue was purified by column chromatography (SiO$_2$, PE:EtOAc=10:1 to 4:1) to afford the title compound (0.32 g, 962.83 μmol, 44.66% yield) as a yellow solid. LC-MS (ES$^+$, m/z): 333.0 [(M+H)$^+$].

Preparation of 6-[8-(prop-2-enoylamino)-2-naphthyl]pyridine-2-carboxylic acid

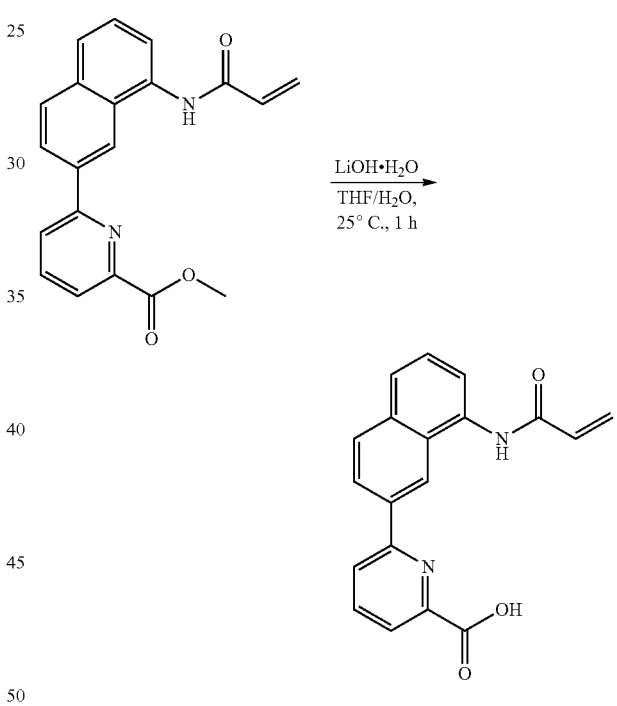

To a solution of methyl 6-[8-(prop-2-enoylamino)-2-naphthyl]pyridine-2-carboxylate (0.1 g, 300.89 μmol, 1 eq) in THF (2 mL) and H$_2$O (0.5 mL) was added LiOH·H$_2$O (25.3 mg, 601.77 μmol, 2 eq) and stirred at 25° C. for 1 hr. The reaction was poured into ~15 mL ice water and washed with EtOAc (3×10 mL). The aqueous phase was adjusted to pH=8 with saturated citric acid and extracted with EtOAc (3×10 mL). The organic phase was washed with brine (3×10 mL), dried over by anhydrous Na$_2$SO$_4$, filtered, and concentrated in vacuo to afford the title compound (0.07 g, crude) as a yellow solid. LC-MS (ES$^+$, m/z): 319.0 [(M+H)$^+$].

General Procedure for Amide Coupling

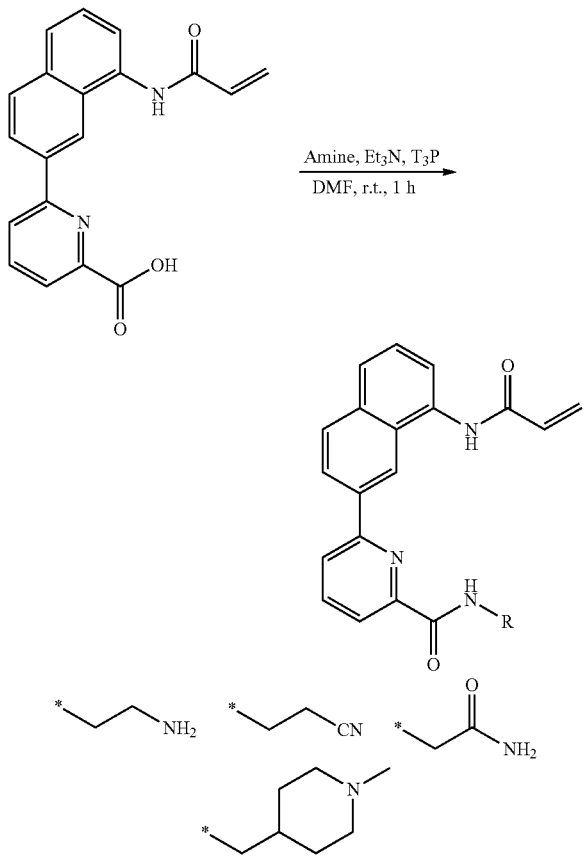

To a solution of 6-[8-(prop-2-enoylamino)-2-naphthyl]pyridine-2-carboxylic acid (0.06 g, 188.49 μmol, 1 eq) and amine derivative (17.2 mg, 245.03 μmol, 18.08 μL, 1.3 eq) in DMF (2 mL) were added Et₃N (95.4 mg, 942.43 μmol, 131.17 μL, 5 eq) and T₃P (179.9 mg, 282.73 μmol, 168.15 μL, 50% purity, 1.5 eq). The reaction was stirred at 25° C. for 1 hr. The reaction was poured into water (30 mL) and extracted with EtOAc (3×15 mL). The combined organic phase was washed with brine (3×15 mL), dried over by anhydrous Na₂SO₄, filtered, and concentrated in vacuo. The residue was purified by prep-HPLC (basic condition) to afford the desired compound as a white solid

Compound 318: Preparation of 6-(8-acrylamidonaphthalen-2-yl)-N—R-picolinamide

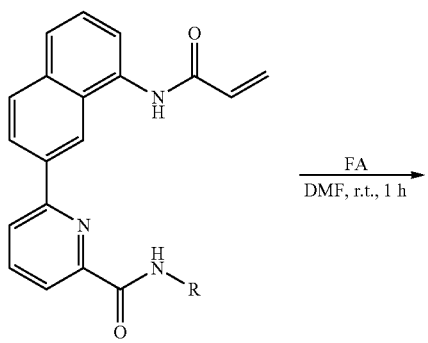

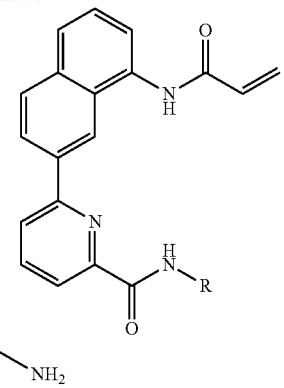

To a solution of tert-butyl N-[2-[[6-[8-(prop-2-enoylamino)-2-naphthyl]pyridine-2-carbonyl]amino]ethyl]carbamate (0.047 g, 102.06 μmol, 1 eq) in DCM (1 mL) was added formic acid (1.83 g, 39.76 mmol, 1.5 mL, 389.59 eq) and stirred at 25° C. for 1 hr. LCMS showed that the reaction was complete. The reaction was concentrated under N₂. The residue was purified by prep-HPLC (FA condition) to afford the title compound (0.0188 g, 50.39 μmol, 49.37% yield, 96.6% purity) as a light yellow solid. LC-MS (ES⁺, m/z): 361.2 [(M+H)⁺], 1H NMR (400 MHz, DMSO-d6) Shift=10.91 (br s, 1H), 9.38 (br t, J=5.6 Hz, 1H), 9.18 (s, 1H), 8.49 (d, J=8.6 Hz, 1H), 8.39 (s, 1H), 8.37 (s, 1H), 8.15 (t, J=7.7 Hz, 1H), 8.09 (d, J=8.6 Hz, 1H), 8.03 (br d, J=7.5 Hz, 2H), 7.81 (d, J=8.2 Hz, 1H), 7.57 (t, J=7.9 Hz, 1H), 6.85 (br dd, J=10.1, 17.0 Hz, 1H), 6.36 (dd, J=1.8, 17.0 Hz, 1H), 5.88-5.80 (m, 1H), 3.61 (q, J=5.7 Hz, 2H), 3.03 (br t, J=5.8 Hz, 2H).

Route 4: General Scheme

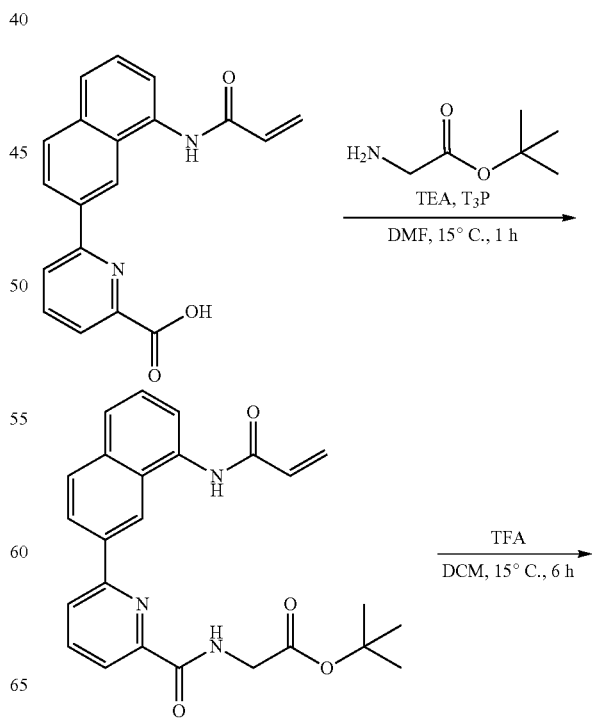

389
-continued

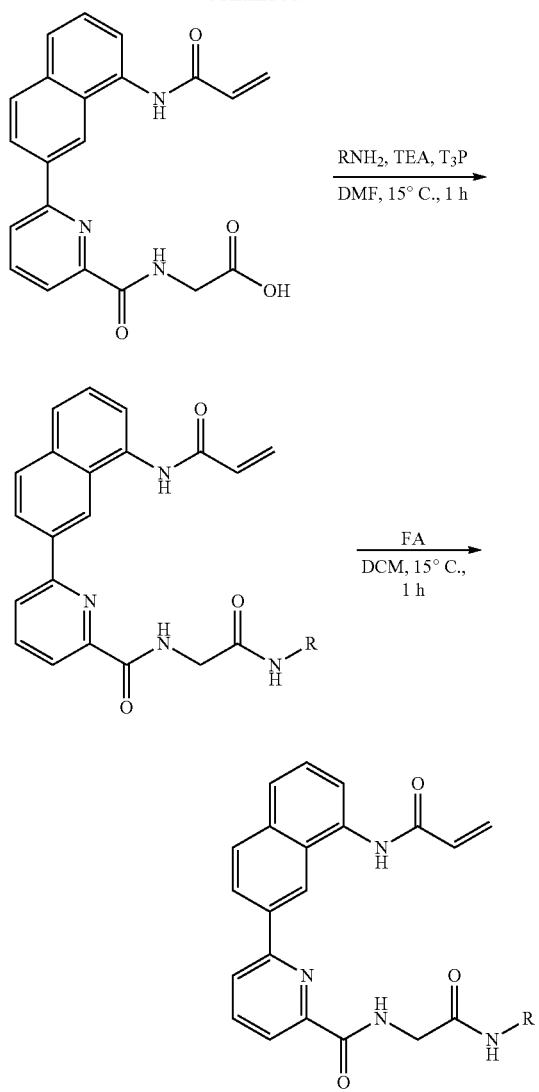

R =

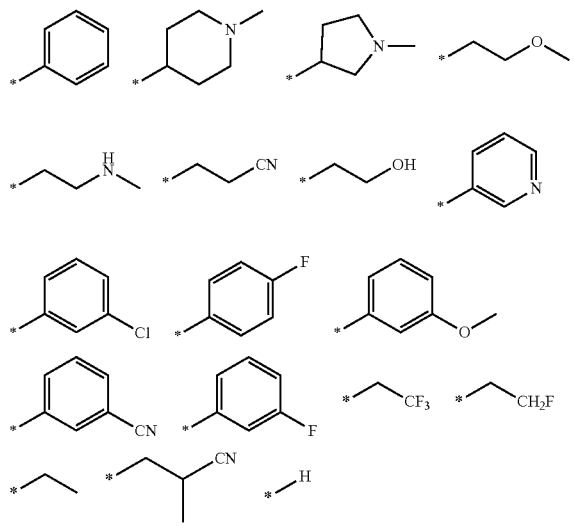

390

6 tert-butyl 2-(6-(8-acrylamidonaphthalen-2-yl)picolinamido)acetate

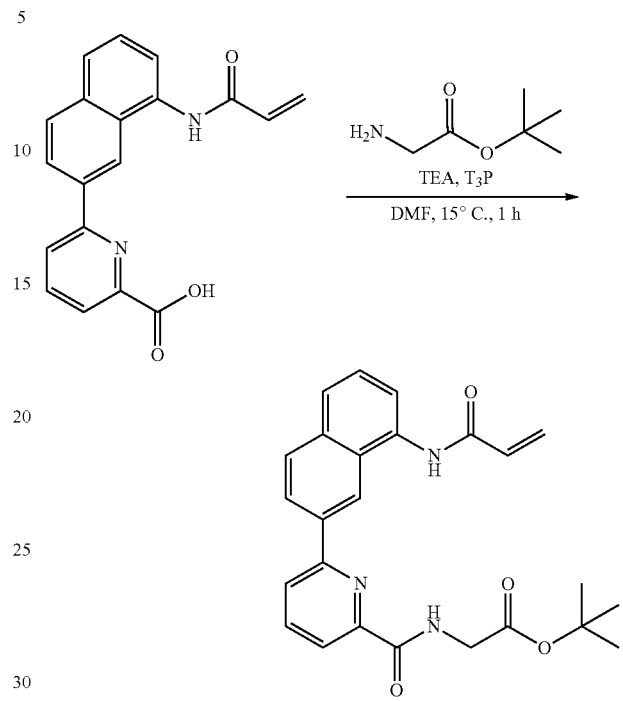

To a solution of 6-[8-(prop-2-enoylamino)-2-naphthyl]pyridine-2-carboxylic acid (0.6 g, 1.88 mmol, 1 eq) in DMF (10 mL) were added tert-butyl 2-aminoacetate (494.5 mg, 3.77 mmol, 2 eq), TEA (572.2 mg, 5.65 mmol, 787.05 μL, 3 eq) and T₃P (2.4 g, 3.77 mmol, 2.24 mL, 50% purity, 2 eq). The reaction mixture was stirred for 1 hr at 15° C. under N₂. TLC (PE:EtOAc=1:1 SM=0.0, Rf=0.33) showed that the reaction was complete. The reaction mixture was poured into H₂O (30 mL) and extracted with EtOAc (3×20 mL). The combined organic layer was washed with brine (2×30 mL), dried over anhydrous Na₂SO₄, filtered, and concentrated in vacuo to give a residue. The residue was purified by prep-TLC (SiO₂, PE:EtOAc=1:1) to afford the title compound (0.5 g, 1.16 mmol, 61.48% yield) as a yellow solid. LC-MS (ES⁺, m/z): 432.2 [(M+H)⁺].

2-(6-(8-acrylamidonaphthalen-2-yl)picolinamido) acetic acid

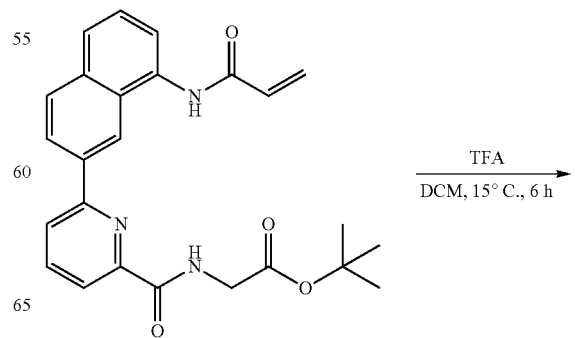

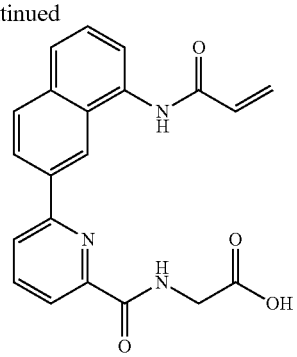

To a solution of tert-butyl 2-[[6-[8-(prop-2-enoylamino)-2-naphthyl]pyridine-2-carbonyl]amino]acetate (0.4 g, 927.04 µmol, 1 eq) in DCM (10 mL) was added TFA (15.4 g, 135.06 mmol, 10 mL, 145.69 eq). The reaction mixture was stirred for 6 hr at 15° C. under $N_2$. TLC (PE:EtOAc=1:1 SM=0.41, Rf=0.0) showed that the reaction was complete. The reaction mixture was poured into $H_2O$ (100 mL), and the aqueous phase was extracted with DCM:THF=1:2 (3×100 mL). The combined organic layer was washed with brine (2×200 mL), dried over anhydrous $Na_2SO_4$, filtered, and concentrated in vacuo to afford the title compound (0.45 g, crude) as a yellow solid. LC-MS (ES+, m/z): 376.2 [(M+H)+].

General Procedure for Amide Coupling

N-(2-anilino-2-oxo-ethyl)-6-[8-(prop-2-enoylamino)-2-naphthyl]pyridine-2-carboxamide

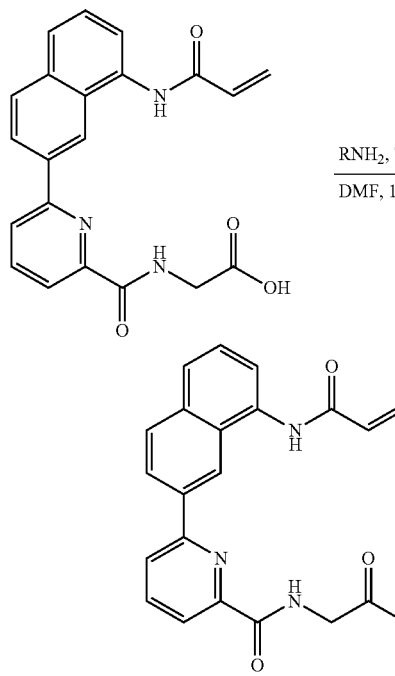

To a solution of 2-[[6-[8-(prop-2-enoylamino)-2-naphthyl]pyridine-2-carbonyl]amino]acetic acid (0.06 g, 159.84 µmol, 1 eq) in DMF (2 mL) were added amine (RNH2) (319.68 µmol, 29.19 µL, 2 eq), TEA (48.5 mg, 479.52 µmol, 66.74 µL, 3 eq) and $T_3P$ (203.4 mg, 319.68 µmol, 190.12 µL, 50% purity, 2 eq). The reaction mixture was stirred for 1 hr at 15° C. under $N_2$. The reaction mixture was poured into $H_2O$ (20 mL) and extracted with EtOAc (3×20 mL). The combined organic layer was washed with brine (2×30 mL), dried over anhydrous $Na_2SO_4$, filtered, and concentrated in vacuo to afford a residue. The residue was purified by prep-HPLC to afford the desired compound.

Route 5: General Scheme

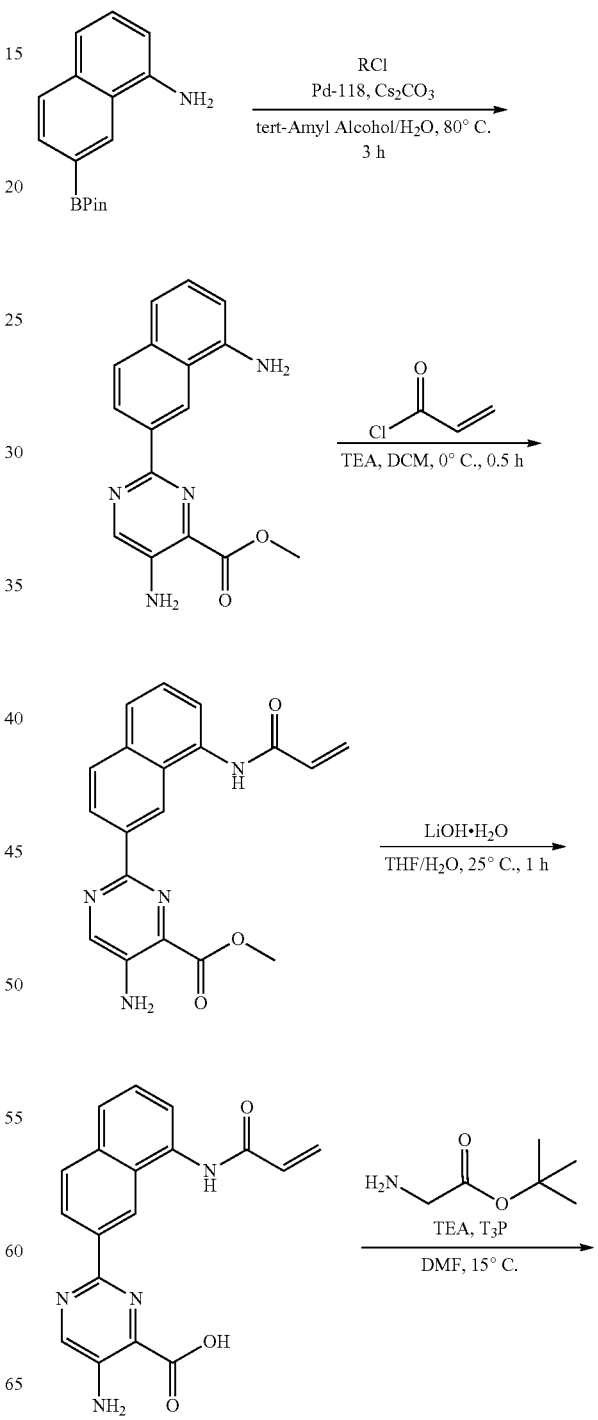

393
-continued

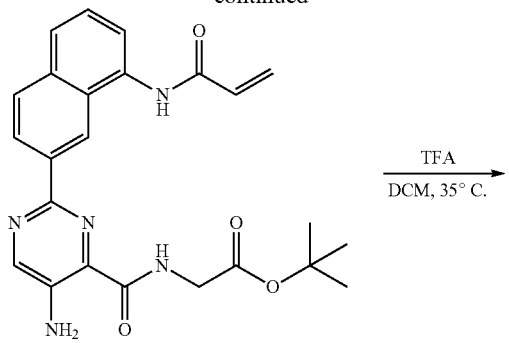

TFA
DCM, 35° C.

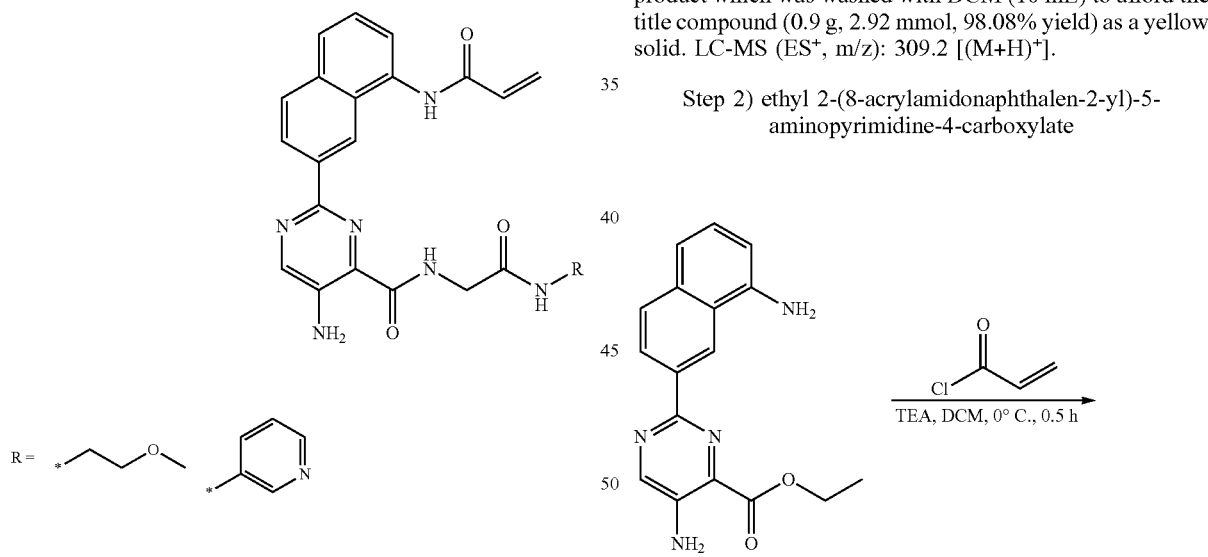

R = *~~O~ , *~(3-pyridyl)

Step 1) ethyl 5-amino-2-(8-aminonaphthalen-2-yl)pyrimidine-4-carboxylate

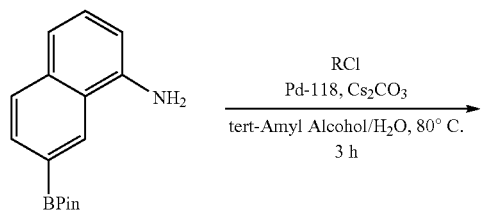

RCl
Pd-118, Cs₂CO₃
tert-Amyl Alcohol/H₂O, 80° C.
3 h

394
-continued

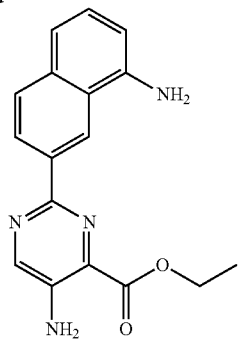

To a solution of 7-(4,4,5,5-tetramethyl-1,3,2-dioxaborolan-2-yl)naphthalen-1-amine (1.2 g, 4.46 mmol, 1.5 eq) in 2-methylbutan-2-ol (12 mL) and H₂O (3 mL) were added ethyl 5-amino-2-chloro-pyrimidine-4-carboxylate (0.6 g, 2.98 mmol, 1 eq), Cs₂CO₃ (2.91 g, 8.93 mmol, 3 eq) and ditert-butyl(cyclopentyl)phosphane; dichloro palladium; iron (194.0 mg, 297.6 μmol, 0.1 eq). The reaction mixture was stirred for 3 hr at 80° C. under N₂. TLC (PE:EtOAc=1:1; SM=0.63, Rf=0.28) showed that the reaction was complete. The reaction mixture was poured into 50 mL saturated EDTA, and 50 mL EtOAc was added. The solution was stirred at 20° C. for 1 hr. Then the aqueous phase was separated and extracted with EtOAc (3×50 mL). The combined organic layer was washed with 100 mL brine, dried over Na₂SO₄ and concentrated in vacuo to give a crude product which was washed with DCM (10 mL) to afford the title compound (0.9 g, 2.92 mmol, 98.08% yield) as a yellow solid. LC-MS (ES⁺, m/z): 309.2 [(M+H)⁺].

Step 2) ethyl 2-(8-acrylamidonaphthalen-2-yl)-5-aminopyrimidine-4-carboxylate

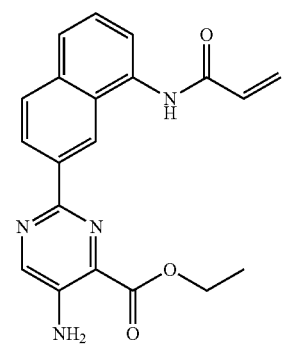

To a solution of ethyl 5-amino-2-(8-amino-2-naphthyl)pyrimidine-4-carboxylate (0.8 g, 2.59 mmol, 1 eq) in DCM (20 mL) were added TEA (787.6 mg, 7.78 mmol, 1.08 mL, 3 eq) and prop-2-enoyl chloride (352.3 mg, 3.89 mmol, 317.34 µL, 1.5 eq). The reaction mixture was stirred for 0.5 hr at 0° C. under $N_2$. LCMS showed that the reaction was complete. The reaction mixture was poured into $H_2O$ (50 mL), and the aqueous phase was extracted with DCM (3×50 mL). The combined organic layer was washed with brine (2×50 mL), dried over anhydrous $Na_2SO_4$, filtered, and concentrated in vacuo to afford a residue. The residue was washed with EtOAc (10 mL) to afford the title compound (0.75 g, 2.07 mmol, 79.77% yield) as a yellow solid. LC-MS (ES$^+$, m/z): 363.1 [(M+H)$^+$].

Step 3) 2-(8-acrylamidonaphthalen-2-yl)-5-amino-pyrimidine-4-carboxylic acid

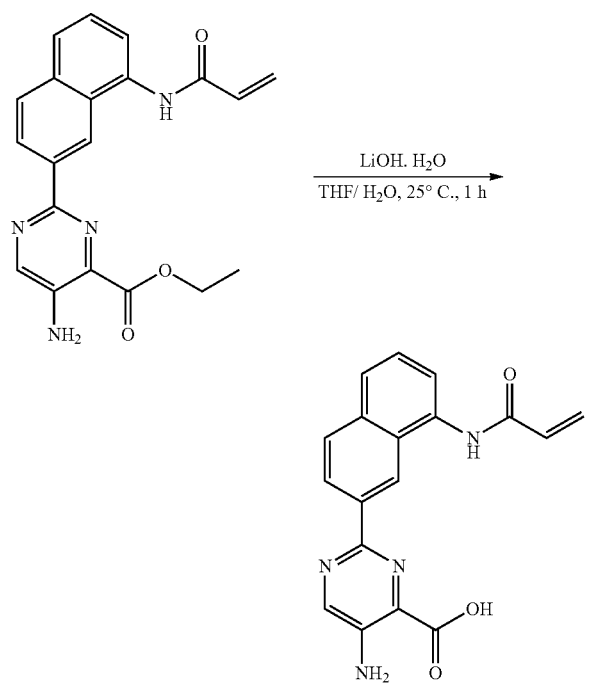

Step 4) 2 tert-butyl 2-[[5-amino-2-[8-(prop-2-enoylamino)-2-naphthyl]pyrimidine-4-carbonyl]amino]acetate

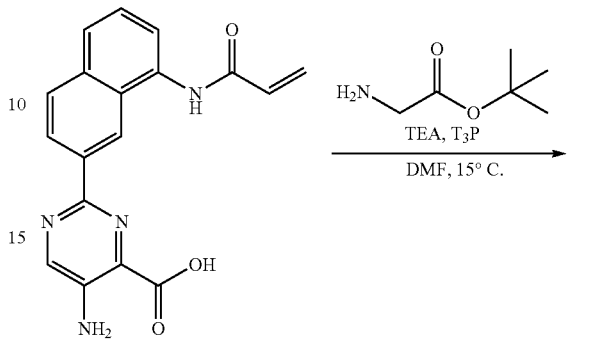

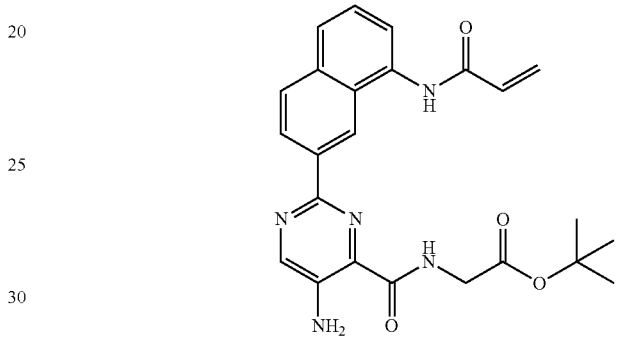

To a solution of 5-amino-2-[8-(prop-2-enoylamino)-2-naphthyl]pyrimidine-4-carboxylic acid (0.5 g, 1.5 mmol, 1 eq) in DMF (2 mL) were added tert-butyl 2-aminoacetate (392.4 mg, 2.99 mmol, 2 eq), TEA (454 mg, 4.49 mmol, 624.48 µL, 3 eq) and $T_3P$ (1.9 g, 2.99 mmol, 1.78 mL, 50% purity, 2 eq), and the reaction mixture was stirred for 1 hr at 15° C. under $N_2$. TLC (DCM:MeOH=30:1; SM=0.0, Rf=0.32) showed that the reaction was complete. The reaction mixture was poured into $H_2O$ (50 mL), and the aqueous phase was extracted with EtOAc (3×50 mL). The combined organic layer was washed with brine (2×50 mL), dried over anhydrous $Na_2SO_4$, filtered, and concentrated in vacuo to afford the title compound tert-butyl 2-[[5-amino-2-[8-(prop-2-enoylamino)-2-naphthyl]pyrimidine-4-carbonyl]amino]acetate (0.7 g, crude) as a yellow solid. LC-MS (ES$^+$, m/z): 448.1 [(M+H)$^+$].

Step 5) 2-[[5-amino-2-[8-(prop-2-enoylamino)-2-naphthyl]pyrimidine-4-carbonyl]amino]acetic acid To a solution of ethyl 5-amino-2-[8-(prop-2-enoylamino)-2-naphthyl]pyrimidine-4-carboxylate (0.65 g, 1.79 mmol, 1 eq) in THF (12 mL) and $H_2O$ (3 mL) was added LiOH·$H_2O$ (150.5 mg, 3.59 mmol, 2 eq), and the reaction was stirred for 1 hr at 25° C. TLC (PE:EtOAc=1:1; SM=0.45, Rf=0.0) showed that the reaction was complete. The reaction mixture was poured into $H_2O$ (30 mL) and adjusted to pH=6 with 1M HCl. The aqueous phase was extracted with EtOAc (3×50 mL). The combined organic layer was washed with brine (2×50 mL), dried over anhydrous $Na_2SO_4$, filtered, and concentrated in vacuo to afford the title compound (0.6 g, crude) as a yellow solid. LC-MS (ES$^+$, m/z): 335.1 [(M+H)$^+$].

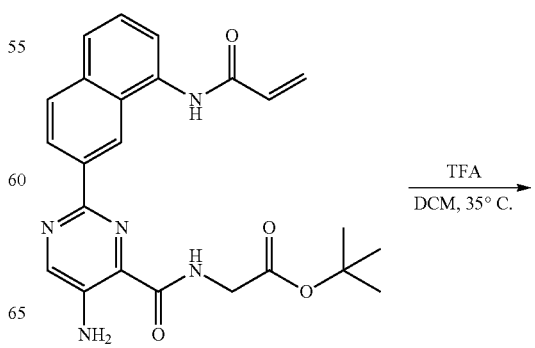

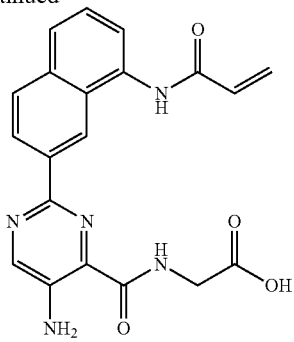

To a solution of tert-butyl 2-[[5-amino-2-[8-(prop-2-enoylamino)-2-naphthyl]pyrimidine-4-carbonyl]amino]acetate (0.6 g, 1.34 mmol, 1 eq) in DCM (6 mL) was added TFA (9.24 g, 81.04 mmol, 6 mL, 60.44 eq), and the reaction was stirred for 1.5 hr at 35° C. under $N_2$. TLC (DCM: MeOH=30:1; SM=0.35, Rf=0.0) showed that the reaction was complete. The reaction mixture was poured into $H_2O$ (50 mL). The precipitate was collected by filtration, and the filter cake was washed with DCM (5 mL) to afford the title compound 2-[[5-amino-2-[8-(prop-2-enoylamino)-2-naphthyl]pyrimidine-4-carbonyl]amino]acetic acid (0.45 g, 1.15 mmol, 85.75% yield) as a yellow solid. LC-MS (ES$^+$, m/z): 392.1 [(M+H)$^+$].

Step 6) Compound 334: N-{7-[5-amino-4-({[(2-methoxyethyl)carbamoyl]methyl}carbamoyl)pyrimidin-2-yl]naphthalen-1-yl}prop-2-enamide

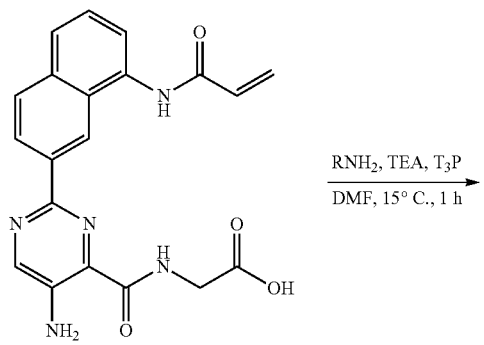

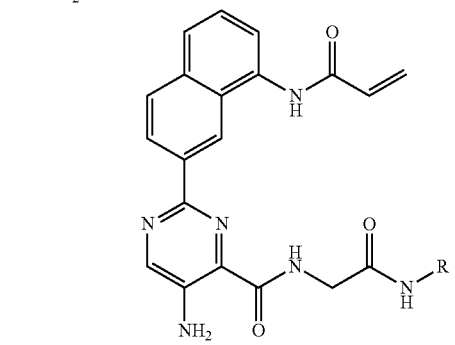

R=

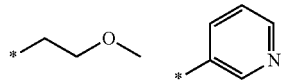

To a solution of 2-[[5-amino-2-[8-(prop-2-enoylamino)-2-naphthyl]pyrimidine-4-carbonyl]amino]acetic acid (0.06 g, 153.3 μmol, 1 eq) in DMF (2 mL) were added 2-methoxyethanamine (23 mg, 306.61 μmol, 26.65 μL, 2 eq), TEA (46.5 mg, 459.91 μmol, 64.01 μL, 3 eq) and T$_3$P (195.1 mg, 306.61 μmol, 182.35 μL, 50% purity, 2 eq), and the reaction was stirred for 1 hr at 15° C. under $N_2$. The reaction mixture was poured into $H_2O$ (20 mL). The aqueous phase was extracted with EtOAc (3×20 mL). The combined organic layer was washed with brine (2×30 mL), dried over anhydrous $Na_2SO_4$, filtered, and concentrated in vacuo to afford a residue. The residue was purified by prep-HPLC to afford the title compound 5-amino-N-[2-(2-methoxyethylamino)-2-oxo-ethyl]-2-[8-(prop-2-enoylamino)-2-naphthyl]pyrimidine-4-carboxamide (0.0123 g, 25.86 μmol, 16.87% yield, 94.3% purity) as a yellow solid. LC-MS (ES$^+$, m/z): 449.2 [(M+H)$^+$]

Route 6: General Scheme

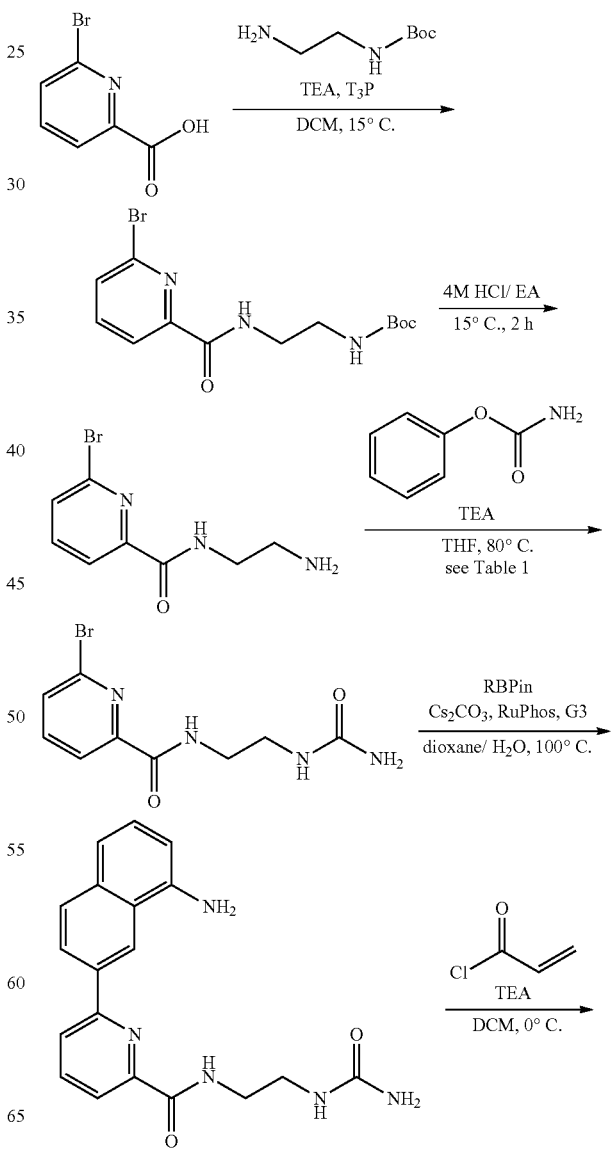

-continued

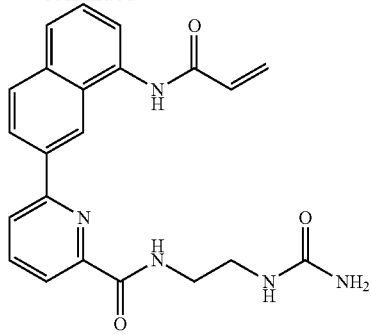

Step 1) tert-butyl N-[2-[(6-bromopyridine-2-carbonyl)amino]ethyl]carbamate

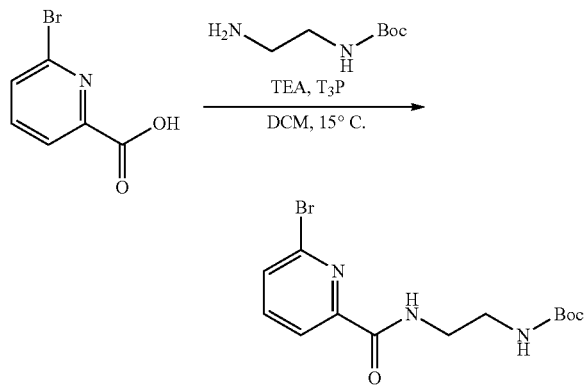

To a solution of 6-bromopyridine-2-carboxylic acid (2 g, 9.9 mmol, 1 eq) in DCM (10 mL) were added tert-butyl N-(2-aminoethyl)carbamate (3.17 g, 19.8 mmol, 3.11 mL, 2 eq), TEA (3.01 g, 29.7 mmol, 4.13 mL, 3 eq) and T$_3$P (9.45 g, 14.85 mmol, 8.83 mL, 50% purity, 1.5 eq), and the reaction was stirred for 1 hr at 15° C. under N$_2$. TLC (PE:EtOAc=1:1; SM=0.0, Rf=0.2) showed that the reaction was complete. The reaction mixture was poured into H$_2$O (30 mL). The aqueous phase was extracted with DCM (3×30 mL). The combined organic layer was washed with brine (2×30 mL), dried over anhydrous Na$_2$SO$_4$, filtered, and concentrated in vacuo to afford the title compound tert-butyl N-[2-[(6-bromopyridine-2-carbonyl)amino]ethyl]carbamate (4 g, crude) as a yellow oil.

Step 2) N-(2-aminoethyl)-6-bromo-pyridine-2-carboxamide

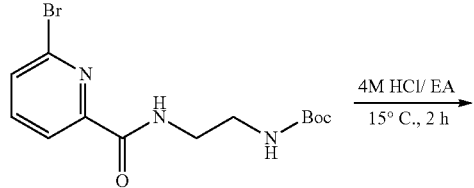

-continued

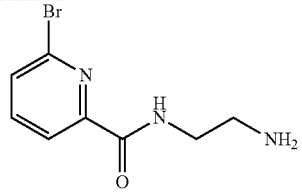

A solution of tert-butyl N-[2-[(6-bromopyridine-2-carbonyl)amino]ethyl]carbamate (0.5 g, 1.45 mmol, 1 eq) in HCl/EtOAc (4 M, 10 mL, 27.54 eq) was stirred for 2 hr at 15° C. under N$_2$. The solvent was removed in vacuo to afford the title compound N-(2-aminoethyl)-6-bromo-pyridine-2-carboxamide (0.35 g, crude) as a white solid. LC-MS (ES$^+$, m/z): 244.0&246.0 [(M+H)$^+$].

Step 3) 6-bromo-N-(2-ureidoethyl)pyridine-2-carboxamide

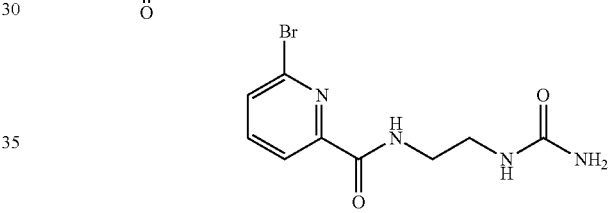

To a solution of N-(2-aminoethyl)-6-bromo-pyridine-2-carboxamide (0.35 g, 1.43 mmol, 1 eq) in THF (10 mL) were added phenyl carbamate (196.6 mg, 1.43 mmol, 1 eq) and TEA (725.5 mg, 7.17 mmol, 997.91 μL, 5 eq). The reaction mixture was stirred for 1 hr at 80° C. under N$_2$. TLC (DCM:MeOH=10:1; SM=0.0, RF=0.19) showed that the reaction was complete. The reaction mixture was poured into saturated Na$_2$CO$_3$ (30 mL). The aqueous phase was extracted with EtOAc (3×30 mL). The combined organic phase was washed with brine (2×30 mL), dried with anhydrous Na$_2$SO$_4$, filtered, and concentrated in vacuo to give a residue which was washed with 5 mL PE:EtOAc=3:1 to afford the title compound 6-bromo-N-(2-ureidoethyl)pyridine-2-carboxamide (0.2 g, 696.59 μmol, 48.58% yield) as a yellow solid. LC-MS (ES$^+$, m/z): 287.0&289.0 [(M+H)$^+$].

Step 4) 6-(8-amino-2-naphthyl)-N-(2-ureidoethyl)pyridine-2-carboxamide

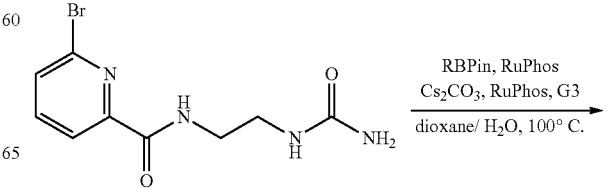

401

-continued

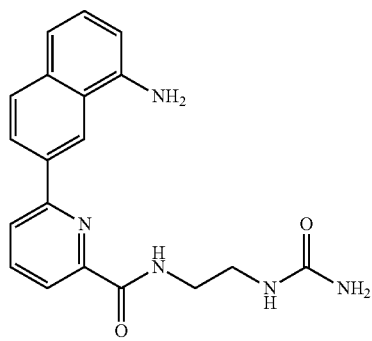

To a solution of 6-bromo-N-(2-ureidoethyl)pyridine-2-carboxamide (0.1 g, 348.29 μmol, 1 eq) in dioxane (2 mL) and H₂O (0.5 mL) were added 7-(4,4,5,5-tetramethyl-1,3,2-dioxaborolan-2-yl)naphthalen-1-amine (112.5 mg, 417.95 μmol, 1.2 eq), Cs₂CO₃ (340.4 mg, 1.04 mmol, 3 eq), dicyclohexyl-[2-(2,6-diisopropoxyphenyl)phenyl]phosphane (16.3 mg, 34.83 μmol, 0.1 eq) and [2-(2-aminophenyl)phenyl]-methylsulfonyloxy-palladium; dicyclohexyl-[2-(2,6-diisopropoxyphenyl)phenyl]phosphane (14.6 mg, 17.41 μmol, 0.05 eq). The reaction mixture was stirred for 1 hr at 100° C. under N₂. The reaction mixture was poured into 20 mL saturated EDTA and diluted with 20 mL EtOAc. The solution was stirred at 20° C. for 1 hr, and aqueous phase was separated and extracted with EtOAc (3×20 mL). The combined organic layer was washed with 30 mL brine, dried over Na₂SO₄ and concentrated in vacuo to give a crude product. The residue was purified by prep-TLC (SiO₂, DCM:MeOH=10:1). 6-(8-amino-2-naphthyl)-N-(2-ureidoethyl)pyridine-2-carboxamide (0.08 g, 228.97 μmol, 65.74% yield) was obtained as a yellow solid Step 5) Compound 342: 6-[8-(prop-2-enoylamino)-2-naphthyl]-N-(2-ureidoethyl)pyridine-2-carboxamide

402

-continued

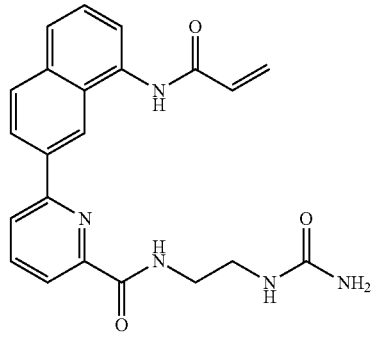

To a solution of 6-(8-amino-2-naphthyl)-N-(2-ureidoethyl)pyridine-2-carboxamide (0.06 g, 171.73 μmol, 1 eq) in DCM (2 mL) were added TEA (52.1 mg, 515.19 μmol, 71.71 μL, 3 eq) and prop-2-enoyl chloride (18.7 mg, 206.08 μmol, 16.80 μL, 1.2 eq) at 0° C., and the reaction mixture was stirred for 0.5 hr at 0° C. under N₂. The reaction mixture was poured into H₂O (20 mL). The aqueous phase was extracted with DCM (3×20 mL). The combined organic layer was washed with brine (2×30 mL), dried over anhydrous Na₂SO₄, filtered, and concentrated in vacuo to afford a residue. The residue was purified by prep-HPLC to afford the title compound 6-[8-(prop-2-enoylamino)-2-naphthyl]-N-(2-ureidoethyl)pyridine-2-carboxamide (5.10 mg, 12.64 μmol, 7.36% yield, 100.0% purity) as a white solid. LC-MS (ES⁺, m/z): 404.2 [(M+H)⁺]

Route 7: General Scheme

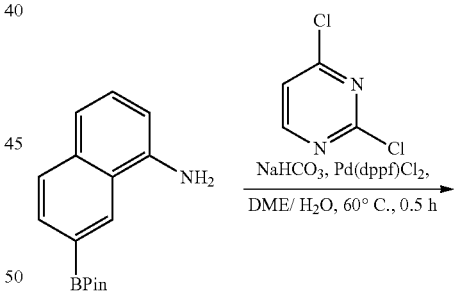

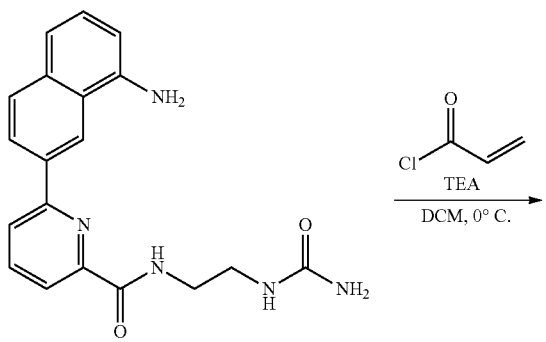

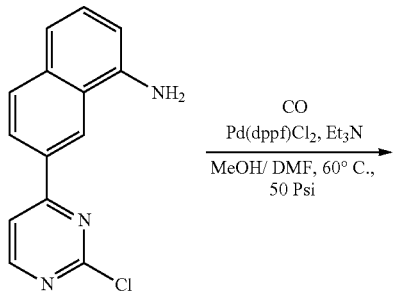

403
-continued

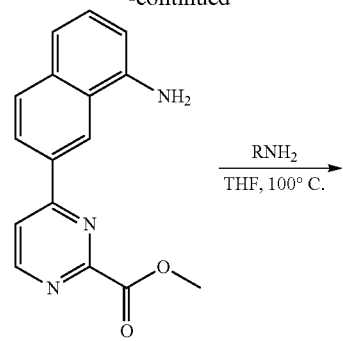

RNH₂
―――→
THF, 100° C.

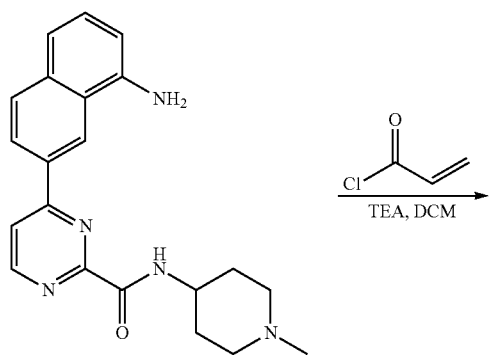

General Procedure for Preparation of
7-(2-chloropyrimidin-4-yl)naphthalen-1-amine

404
-continued

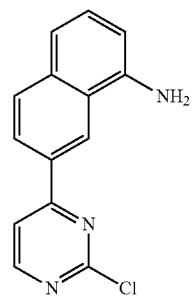

To a mixture of 2,4-dichloropyrimidine (0.5 g, 3.36 mmol, 1 eq) and 7-(4,4,5,5-tetramethyl-1,3,2-dioxaborolan-2-yl)naphthalen-1-amine (903.3 mg, 3.36 mmol, 1 eq) in DME (20 mL) H₂O (5 mL) were added NaHCO₃ (845.8 mg, 10.07 mmol, 391.59 μL, 3 eq) and Pd(dppf)Cl₂ (1.23 g, 1.68 mmol, 0.5 eq) in one portion at 25° C. under N₂. The mixture was stirred at 60° C. for 30 min. The reaction was poured into 20 mL saturated EDTA and diluted with 20 mL EtOAc. The mixture was stirred at 25° C. for 1 hr and extracted with EtOAc (3×20 mL). The combined organic layer was washed with brine 20 mL, dried with sodium sulfate, filtered, and concentrated in vacuo. The residue was purified by prep-TLC (SiO₂, PE:EtOAc=2:1) to afford the title compound (0.25 g, 977.7 μmol, 29.13% yield) as a yellow solid.

General Procedure for Preparation of methyl 4-(8-aminonaphthalen-2-yl)pyrimidine-2-carboxylate

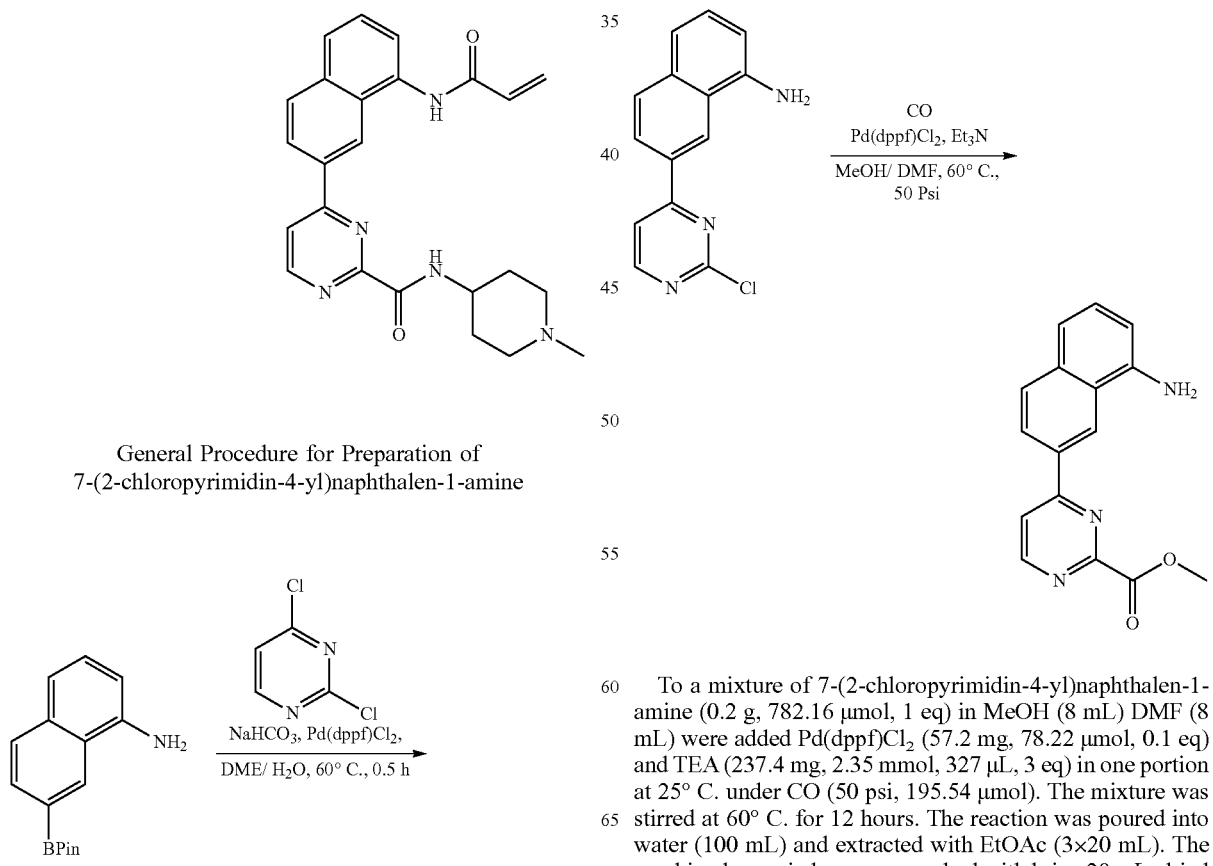

To a mixture of 7-(2-chloropyrimidin-4-yl)naphthalen-1-amine (0.2 g, 782.16 μmol, 1 eq) in MeOH (8 mL) DMF (8 mL) were added Pd(dppf)Cl₂ (57.2 mg, 78.22 μmol, 0.1 eq) and TEA (237.4 mg, 2.35 mmol, 327 μL, 3 eq) in one portion at 25° C. under CO (50 psi, 195.54 μmol). The mixture was stirred at 60° C. for 12 hours. The reaction was poured into water (100 mL) and extracted with EtOAc (3×20 mL). The combined organic layer was washed with brine 20 mL, dried over anhydrous sodium sulfate, filtered, and concentrated in vacuo. The residue was purified by prep-TLC (SiO$_2$, PE:EtOAc=1:2) to afford the title compound (0.18 g, 580.04 μmol, 74.2% yield, 90% purity) as a yellow oil.

General Procedure for Preparation of 4-(8-aminonaphthalen-2-yl)-N-(1-methylpiperidin-4-yl)pyrimidine-2-carboxamide

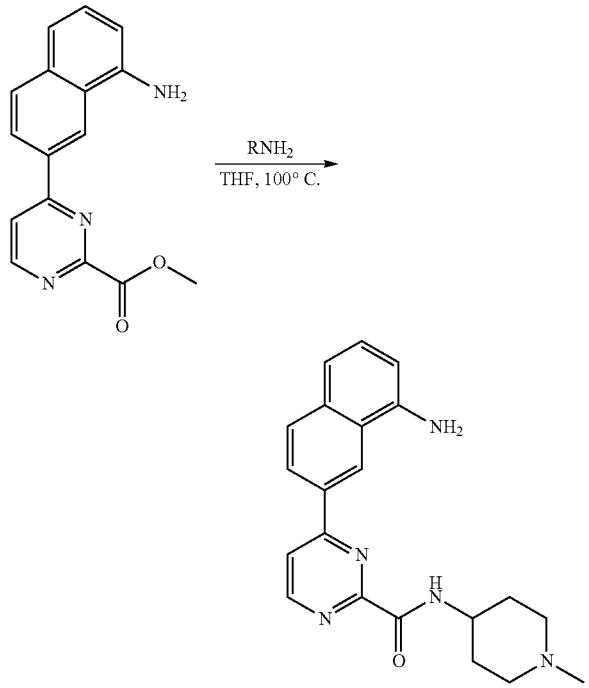

To a mixture of methyl 4-(8-aminonaphthalen-2-yl)pyrimidine-2-carboxylate (0.08 g, 286.44 μmol, 1 eq) in THF (3 mL) was added 1-Methylpiperidin-4-amine (3 mL) in one portion at 100° C. under N$_2$. The mixture was stirred at 100° C. for 6 hours. The reaction was poured into water (100 mL) and extracted with EtOAc (3×20 mL). The combined organic layer was washed with brine 20 mL, dried over anhydrous sodium sulfate, filtered, and concentrated in vacuo. The residue was purified by prep-TLC (SiO$_2$, DCM:MeOH=8:1) to afford the title compound (0.09 g, 249 μmol, 86.93% yield) as a yellow oil.

General Procedure for Preparation of 4-(8-acrylamidonaphthalen-2-yl)-N-(1-methylpiperidin-4-yl)pyrimidine-2-carboxamide (Compound 288)

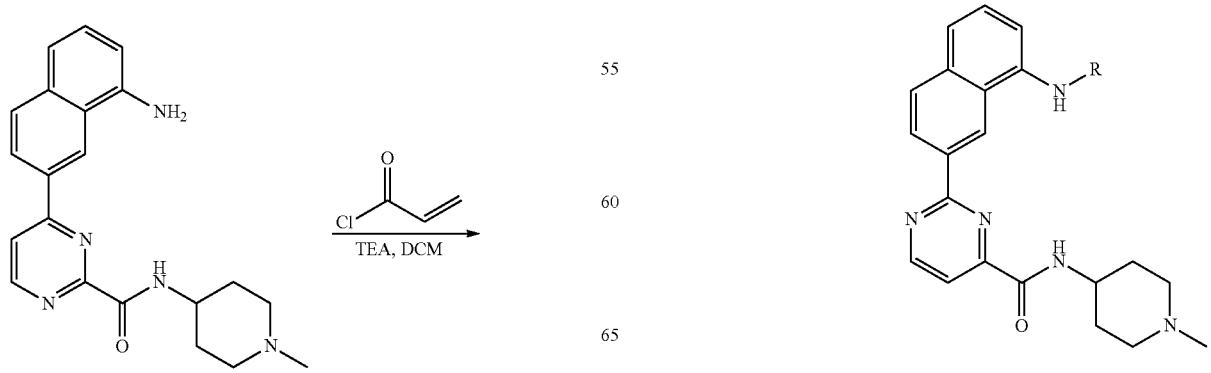

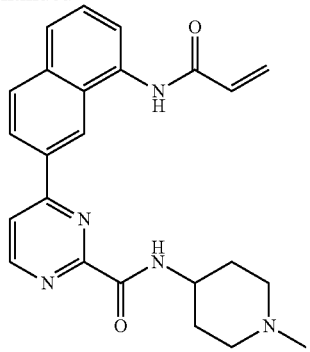 [SMILES: C=CC(=O)Nc1cccc2ccc(-c3ccnc(C(=O)NC4CCN(C)CC4)n3)cc12]

To a mixture of 4-(8-amino-2-naphthyl)-N-(1-methyl-4-piperidyl)pyrimidine-2-carboxamide (0.07 g, 193.67 μmol, 1 eq) in DCM (6 mL) was added TEA (58.8 mg, 581.01 μmol, 81 μL, 3 eq) in one portion at 0° C. under N$_2$. Then, prop-2-enoyl chloride (35.1 mg, 387.34 μmol, 32 μL, 2 eq) was added to the reaction, and the mixture was stirred at 0° C. for 1 hour. LCMS and showed that the reaction was complete. The reaction was poured into water (100 mL) and extracted with DCM (3×20 mL). The combined organic layer was washed with brine 20 mL, dried over sodium sulfate, filtered, and concentrated in vacuo. The residue was purified by prep-TLC (SiO$_2$, DCM:MeOH=8:1) to afford the title compound (0.01 g, 23.01 μmol, 11.88% yield, 95.6% purity) as a white solid. LC-MS (ES$^+$, m/z): 416.2 [(M+H)$^+$].

Route 8: General Scheme

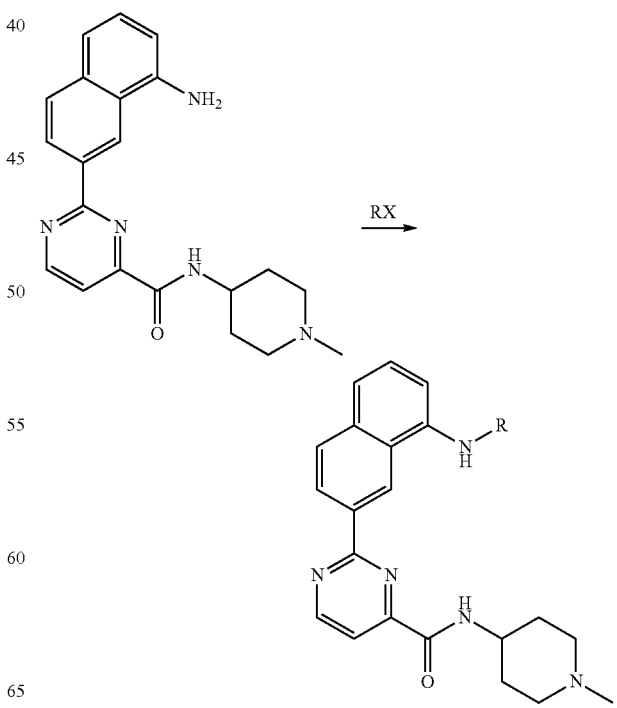

407

Preparation of 2-[8-(2-chloroacetamido)naphthalen-2-yl]-N-(1-methylpiperidin-4-yl)pyrimidine-4-carboxamide (Compound 345)

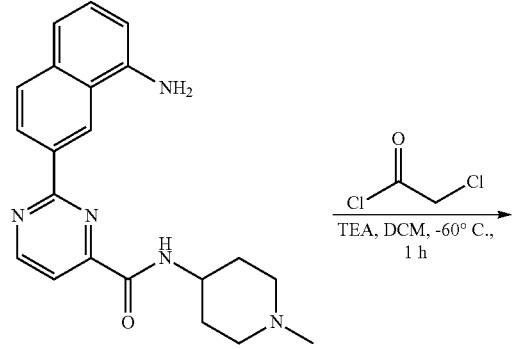

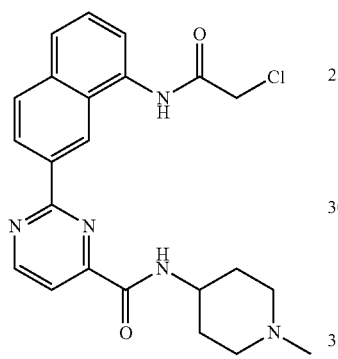

A mixture of 2-(8-amino-2-naphthyl)-N-(1-methyl-4-piperidyl)pyrimidine-4-carboxamide (100 mg, 276.67 μmol, 1 eq), 2-chloroacetyl chloride (62.5 mg, 553.34 μmol, 2 eq), and TEA (84 mg, 830.02 μmol, 3 eq) in DCM (2 mL) was stirred at −60° C. for 1 hour. LCMS showed that the reaction was complete. The reaction mixture was added to ice water (50 mL) and extracted with DCM (3×30 mL). The organic phase was separated, washed with H$_2$O (2×30 mL) and brine (2×30 mL), dried over anhydrous Na$_2$SO$_4$, filtered, and concentrated in vacuo to give crude product. The residue was purified by prep-TLC (SiO$_2$, DCM:MeOH=10:1) to afford the title compound (18.9 mg, 41.86 μmol, 15.13% yield, 97% purity) as a light yellow solid. LC-MS (ES$^+$, m/z): 438.2 [(M+H)$^+$], $^1$H NMR (400 MHz, DMSO-d$_6$) δ=10.59 (s, 1H), 9.39 (s, 1H), 9.21-9.20 (d, J=5.00 Hz, 1H), 8.91-8.90 (d, J=8.00 Hz, 1H), 8.76-8.74 (d, J=8.60 Hz, 1H), 8.14-8.12 (d, J=8.60 Hz, 1H), 7.96-7.95 (d, J=4.40 Hz, 1H), 7.90-7.88 (d, J=8.40 Hz, 1H), 7.84-7.82 (d, J=6.80 Hz, 1H), 7.65-7.63 (m, 1H), 4.53 (s, 2H), 3.86-3.84 (d, J=8.00 Hz, 1H), 2.87-2.84 (d, J=10.80 Hz, 2H), 2.23 (s, 3H), 2.05 (s, 2H). 1.86 (s, 2H), 1.20-1.81 (m, 2H).

408

Preparation of 2-{8-[(2E)-but-2-enamido]naphthalen-2-yl}-N-(1-methylpiperidin-4-yl)pyrimidine-4-carboxamide (Compound 344)

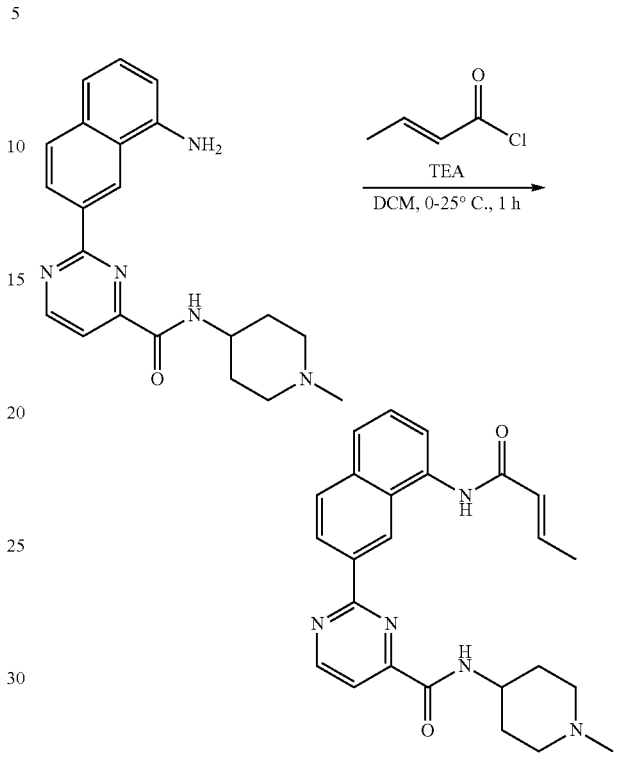

To a mixture of 2-(8-amino-2-naphthyl)-N-(1-methyl-4-piperidyl)pyrimidine-4-carboxamide (100 mg, 276.67 μmol, 1 eq), and TEA (84 mg, 830.01 μmol, 3 eq) in DCM (2 mL) was added (E)-but-2-enoyl chloride (28.9 mg, 276.67 μmol, 1 eq) at 0° C. The mixture was stirred at 25° C. for 1 hour. The reaction mixture was poured into water (50 mL) and extracted with DCM (3×30 mL). The organic phase was separated, washed with H$_2$O (2×30 mL) and brine (2×30 mL), dried over anhydrous Na$_2$SO$_4$, filtered, and concentrated in vacuo to give a residue. The residue was purified by prep-HPLC to afford the title compound (6.7 mg, 15.6 μmol, 5.64% yield, 100% purity) as a light yellow solid.

Preparation of 2-[8-(2-fluoroprop-2-enamido)naphthalen-2-yl]-N-(1-methylpiperidin-4-yl)pyrimidine-4-carboxamide (Compound 347)

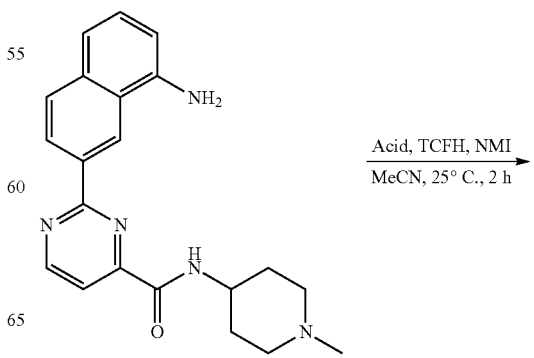

-continued

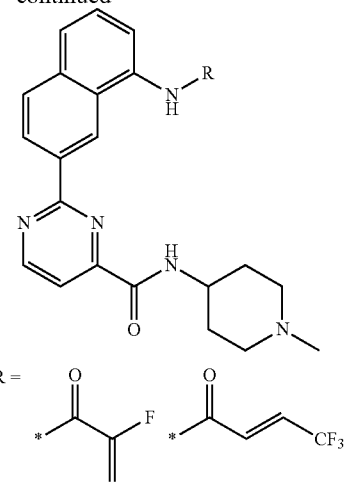

A mixture of 2-(8-amino-2-naphthyl)-N-(1-methyl-4-piperidyl)pyrimidine-4-carboxamide (100 mg, 276.67 µmol, 1 eq), 2-fluoroprop-2-enoic acid (37.4 mg, 415.01 µmol, 1.5 eq), 1-methylimidazole (295.3 mg, 3.6 mmol, 13 eq), [chloro(dimethylamino)methylene]-dimethyl-ammonium; hexafluorophosphate (776.3 mg, 2.77 mmol, 10 eq) in MeCN (2 mL) was stirred at 25° C. for 2 hours. The reaction mixture was poured into H₂O (50 mL) and extracted with EtOAc (3×30 mL). The organic phase was separated, washed with H₂O (2×30 mL) and brine (2×30 mL), dried over anhydrous Na₂SO₄, filtered, and concentrated in vacuo to give crude product. The residue was purified by prep-HPLC to afford the title compound (21.3 mg, 49.14 µmol, 17.76% yield, 100% purity) as a light yellow solid. LC-MS (ES⁺, m/z): 434.2 [(M+H)⁺].

Route 8: Genera Scheme

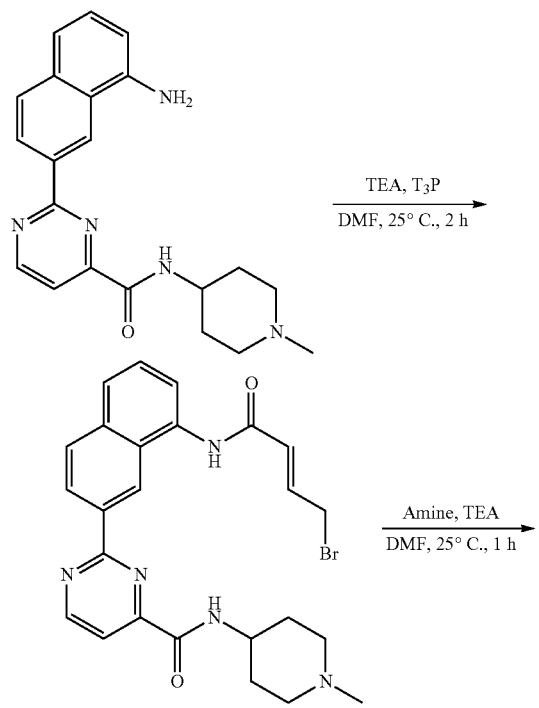

-continued

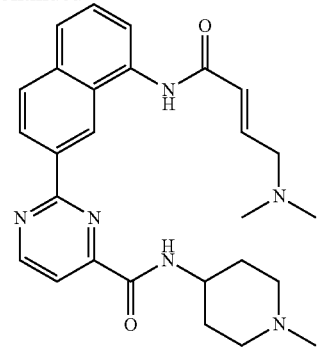

Step 1) 2-[8-[[(E)-4-bromobut-2-enoyl]amino]-2-naphthyl]-N-(1-methyl-4-piperidyl)pyrimidine-4-carboxamide

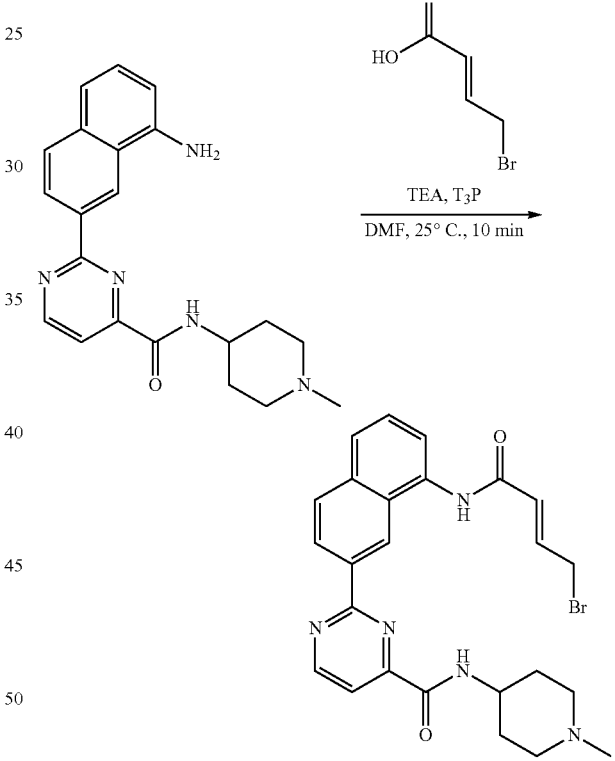

To a solution of 2-(8-amino-2-naphthyl)-N-(1-methyl-4-piperidyl)pyrimidine-4-carboxamide (0.1 g, 276.67 µmol, 1 eq) and (E)-4-bromobut-2-enoic acid (50.2 mg, 304.34 µmol, 1.1 eq) in DMF (1 mL) were added Et₃N (84 mg, 830.01 µmol, 115.53 µL, 3 eq) and T₃P (264.1 mg, 415.01 µmol, 246.82 µL, 50% purity, 1.5 eq), and the reaction was stirred at 25° C. for 10 min. The reaction was poured into 10 mL water and extracted with EtOAc (3×10 mL). The combined organic phase was washed with brine (3×10 mL), dried over by anhydrous Na₂SO₄, filtered, and concentrated in vacuo. The residue was purified by prep-TLC (SiO₂, DCM:MeOH=10:1) to afford the title compound 2-[8-[[(E)-4-bromobut-2-enoyl]amino]-2-naphthyl]-N-(1-methyl-4-piperidyl)pyrimidine-4-carboxamide (0.02 g, 39.34 µmol, 14.22% yield) as a white solid. LC-MS (ES+, m/z): 510.2 [(M+H)+]

Step 2) Compound 346: Preparation of 2-{8-[(2E)-4-(dimethylamino)but-2-enamido]naphthalen-2-yl}-N-(1-methylpiperidin-4-yl)pyrimidine-4-carboxamide

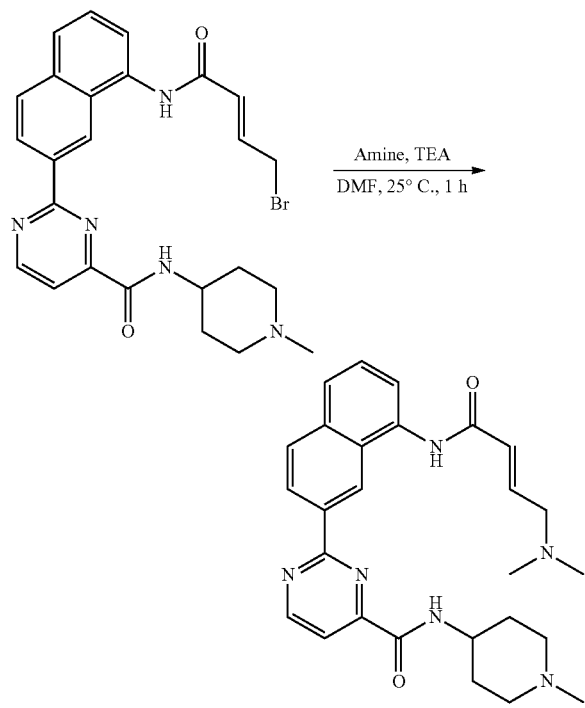

To a solution of 2-[8-[[(E)-4-bromobut-2-enoyl]amino]-2-naphthyl]-N-(1-methyl-4-piperidyl)pyrimidine-4-carboxamide (0.015 g, 29.5 µmol, 1 eq) and N-methylmethanamine (3.6 mg, 44.26 µmol, 4.05 µL, 1.5 eq, HCl) in DMF (2 mL) was added Et₃N (9 mg, 88.51 µmol, 12.32 µL, 3 eq), and the reaction was stirred at 25° C. for 1 hr. The reaction was poured into 10 mL water and extracted with EtOAc (3×10 mL). The combined organic phase was washed with brine (3×10 mL), dried over by anhydrous Na₂SO₄, filtered, and concentrated in vacuo. The residue was purified by prep-HPLC (basic condition) to afford the title compound 2-[8-[[(E)-4-(dimethylamino)but-2-enoyl]amino]-2-naphthyl]-N-(1-methyl-4-piperidyl)pyrimidine-4-carboxamide (0.004 g, 7.81 µmol, 26.48% yield, 92.3% purity) as a white solid. LC-MS (ES+, m/z): 473.2 [(M+H)+] 1H NMR (400 MHz, DMSO-d6) Shift=10.34 (s, 1H), 9.45 (s, 1H), 9.20 (d, J=4.9 Hz, 1H), 8.87 (br d, J=8.3 Hz, 1H), 8.71 (d, J=8.8 Hz, 1H), 8.12 (d, J=8.7 Hz, 1H), 8.00 (br d, J=7.8 Hz, 1H), 7.95 (d, J=4.9 Hz, 1H), 7.84 (d, J=8.3 Hz, 1H), 7.62 (t, J=7.9 Hz, 1H), 6.88-6.80 (m, 1H), 6.63 (br d, J=15.2 Hz, 1H), 3.85 (br s, 1H), 3.28-3.21 (m, 2H), 3.13 (br d, J=6.1 Hz, 2H), 2.89-2.79 (m, 2H), 2.22 (s, 9H), 2.03 (brt, J=10.3 Hz, 2H), 1.91-1.75 (m, 4H).

Preparation of 2-{8-[(2-chloroethyl)amino]naphthalen-2-yl}-N-(1-methylpiperidin-4-yl)pyrimidine-4-carboxamide (Compound 349)

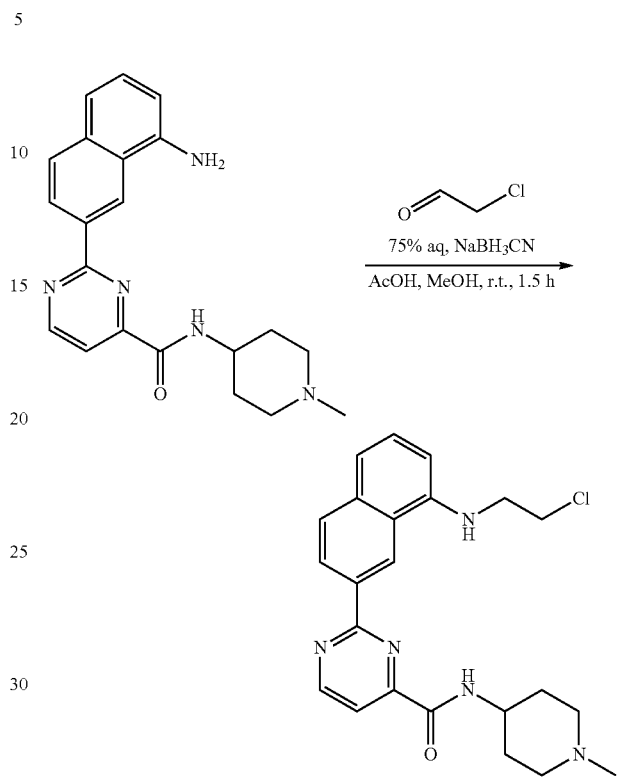

To a solution of 2-(8-amino-2-naphthyl)-N-(1-methyl-4-piperidyl)pyrimidine-4-carboxamide (0.05 g, 138.34 µmol, 1 eq) and 2-chloroacetaldehyde (54.3 mg, 276.67 µmol, 44.50 µL, 2 eq) in MeOH (3 mL) were added AcOH (83.1 ug, 1.38 µmol, 7.91e−2 µL, 0.01 eq) and NaBH₃CN (26.1 mg, 415.01 µmol, 3 eq) after 30 min. The reaction was stirred at 25° C. for 1 hr. The reaction was poured into 10 mL water and extracted with DCM (3×10 mL). The combined organic phase was washed with brine (3×10 mL), dried over by anhydrous Na₂SO₄, filtered, and concentrated in vacuo. The residue was purified by prep-TLC (SiO₂, DCM:MeOH=8:1). The residue was purified by prep-HPLC (FA condition) to afford the title compound 2-[8-(2-chloroethylamino)-2-naphthyl]-N-(1-methyl-4-piperidyl)pyrimidine-4-carboxamide (0.017 g, 39.3 µmol, 28.41% yield, 98.0% purity) as a yellow solid. LC-MS (ES+, m/z): 424.2 [(M+H)+], 1H NMR (400 MHz, DMSO-d6) Shift=9.40 (s, 1H), 9.16 (d, J=4.9 Hz, 1H), 8.94-8.87 (m, J=8.2 Hz, 1H), 8.64 (dd, J=1.3, 8.6 Hz, 1H), 8.18 (s, 1H), 7.95-7.89 (m, 2H), 7.40 (t, J=7.9 Hz, 1H), 7.25-7.20 (m, J=8.1 Hz, 1H), 6.77 (br t, J=5.5 Hz, 1H), 6.65 (d, J=7.6 Hz, 1H), 3.93 (t, J=6.4 Hz, 2H), 3.86 (br dd, J=7.2, 15.7 Hz, 1H), 3.66 (q, J=6.1 Hz, 2H), 3.34 (br s, 2H), 2.86 (br d, J=11.6 Hz, 2H), 2.24 (s, 3H), 2.18-2.00 (m, 2H), 1.91-1.79 (m, 4H).

Compound 350: Preparation of 2-[8-(4-chlorobutanamido)naphthalen-2-yl]-N-(1-methylpiperidin-4-yl)pyrimidine-4-carboxamide

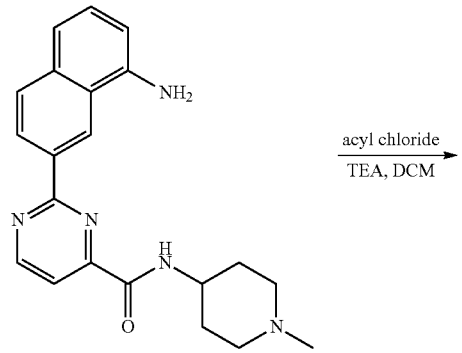

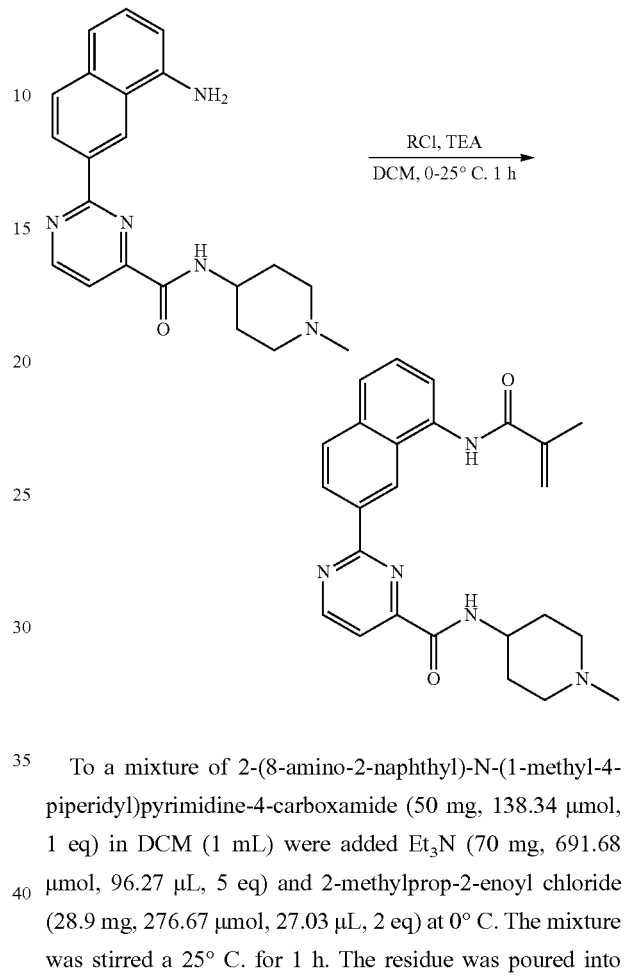

Compound 343: Preparation of N-(1-methylpiperidin-4-yl)-2-[8-(2-methylprop-2-enamido)naphthalen-2-yl]pyrimidine-4-carboxamide To a solution of 2-(8-amino-2-naphthyl)-N-(1-methyl-4-piperidyl)pyrimidine-4-carboxamide (0.1 g, 276.67 µmol, 1 eq) in DCM (2 mL) were added TEA (84 mg, 830.02 µmol, 115.53 µL, 3 eq) and 4-chlorobutanoyl chloride (39 mg, 276.67 µmol, 30.96 µL, 1 eq) at −60° C. dropwise. The reaction was stirred at −60° C. for 1 hr. LCMS and HPLC showed that the reaction was complete. The reaction was poured into ~10 mL ice water and extracted with DCM (3×10 mL). The combined organic phase was washed with brine (3×10 mL), dried over by anhydrous Na₂SO₄, filtered, and concentrated in vacuo. The residue was purified by prep-HPLC (FA condition) to afford the title compound 2-[8-(4-chlorobutanoylamino)-2-naphthyl]-N-(1-methyl-4-piperidyl)pyrimidine-4-carboxamide (0.015 g, 31.39 µmol, 48.75% yield, 97.5% purity) as a white solid. LC-MS (ES⁺, m/z): 466.2 [(M+H)⁺].

To a mixture of 2-(8-amino-2-naphthyl)-N-(1-methyl-4-piperidyl)pyrimidine-4-carboxamide (50 mg, 138.34 µmol, 1 eq) in DCM (1 mL) were added Et₃N (70 mg, 691.68 µmol, 96.27 µL, 5 eq) and 2-methylprop-2-enoyl chloride (28.9 mg, 276.67 µmol, 27.03 µL, 2 eq) at 0° C. The mixture was stirred a 25° C. for 1 h. The residue was poured into water (20 mL). The aqueous phase was extracted with DCM (2×20 mL). The combined organic phase was washed with brine (2×20 mL), dried with anhydrous Na₂SO₄, filtered, and concentrated in vacuo. The residue was purified by prep-HPLC to afford the title compound N-(1-methyl-4-piperidyl)-2-[8-(2-methylprop-2-enoylamino)-2-naphthyl]pyrimidine-4-carboxamide (18.7 mg, 43.54 µmol, 15.74% yield, 100% purity) as a white solid. LC-MS (ES⁺, m/z): 430.2 [(M+H)⁺], ¹H NMR (400 MHz, DMSO-d₆) δ=ppm 10.12 (s, 1H), 9.22 (s, 1H), 9.19 (d, J=5.2 Hz, 1H), 8.80 (br d, J=8.0 Hz, 1H), 8.74 (dd, J=8.8, 1.32 Hz, 1H), 8.13 (d, J=8.8 Hz, 1H), 7.89-7.96 (m, 2H), 7.60-7.69 (m, 2H), 6.09 (s, 1H), 5.62 (s, 1H), 3.83 (ddd, J=10.4, 4.35, 1.65 Hz, 1H), 2.78-2.85 (m, 2H), 2.20 (s, 3H), 2.07 (s, 3H), 1.95-2.04 (m, 2H), 1.73-1.86 (m, 4H).

TABLE 7 shows compounds synthesized using the methods described in EXAMPLE 7 above.

TABLE 7

| Cpd. No. | Structure | IUPAC | LC-MS (ES+, m/z) |
|---|---|---|---|
| 286 | 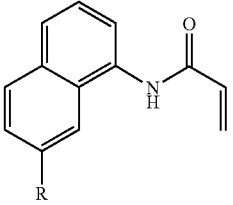 | N-(1-methylpiperidin-4-yl)-3-[8-(prop-2-enamido)naphthalen-2-yl]benzamide | 414.2 |
| 287 | 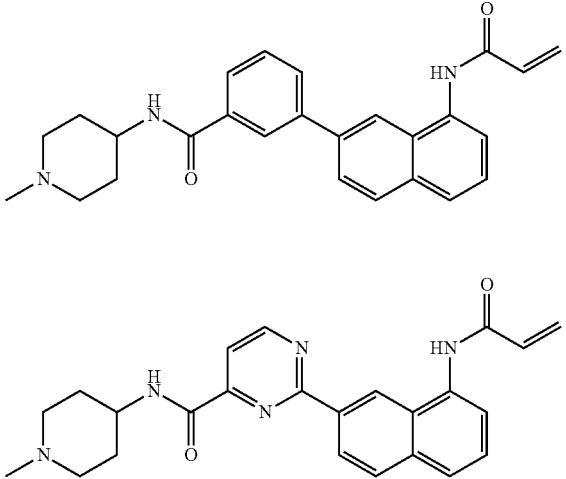 | N-(1-methylpiperidin-4-yl)-2-[8-(prop-2-enamido)naphthalen-2-yl]pyrimidine-4-carboxamide | 416.2 |
| 288 | 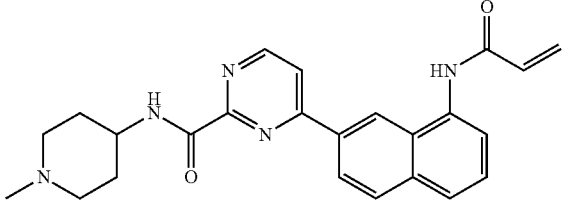 [SMILES: C=CC(=O)Nc1cccc2ccc(-c3nccc(C(=O)NC4CCN(C)CC4)n3)cc12] | N-(1-methylpiperidin-4-yl)-4-[8-(prop-2-enamido)naphthalen-2-yl]pyrimidine-2-carboxamide | 416.2 |
| 289 | 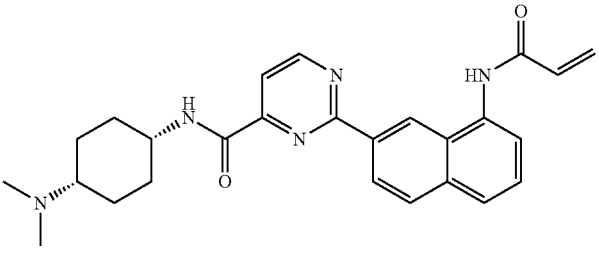 [SMILES: C=CC(=O)Nc1cccc2ccc(-c3nccc(C(=O)N[C@H]4CC[C@@H](N(C)C)CC4)n3)cc12] | 2-[8-(prop-2-enamido)naphthalen-2-yl]-N-[(1s,4s)-4-(dimethylamino)cyclohexyl]pyrimidine-4-carboxamide | 444.3 |
| 290 | 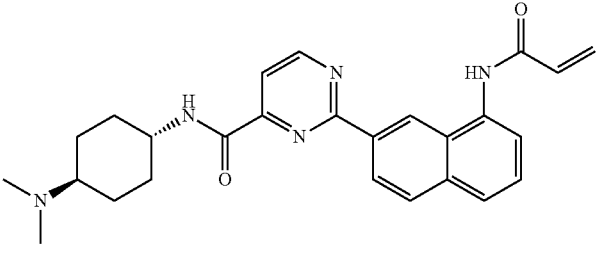 [SMILES: C=CC(=O)Nc1cccc2ccc(-c3nccc(C(=O)N[C@H]4CC[C@H](N(C)C)CC4)n3)cc12] | 2-[8-(prop-2-enamido)naphthalen-2-yl]-N-[(1r,4r)-4-(dimethylamino)cyclohexyl]pyrimidine-4-carboxamide | 444.2 |

TABLE 7-continued

| Cpd. No. | Structure | IUPAC | LC-MS (ES+, m/z) |
|---|---|---|---|
| 291 | 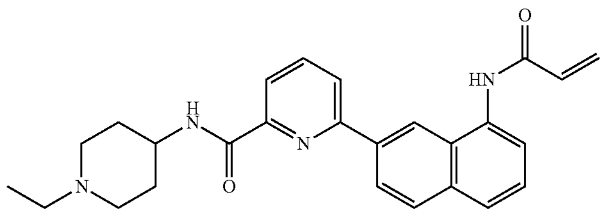 [SMILES: C=CC(=O)Nc1cccc2ccc(-c3cccc(C(=O)NC4CCN(CC)CC4)n3)cc12] | N-(1-ethylpiperidin-4-yl)-6-[8-(prop-2-enamido)naphthalen-2-yl]pyridine-2-carboxamide | 429.2 |
| 292 | 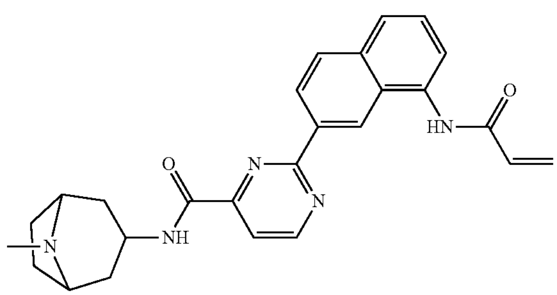 [SMILES: C=CC(=O)Nc1cccc2ccc(-c3nccc(C(=O)NC4CC5CCC(C4)N5C)n3)cc12] | N-{8-methyl-8-azabicyclo[3.2.1]octan-3-yl}-2-[8-(prop-2-enamido)naphthalen-2-yl]pyrimidine-4-carboxamide | 442.2 |
| 293 | 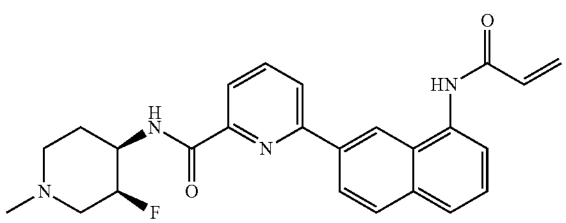 | N-[(3S,4R)-3-fluoro-1-methylpiperidin-4-yl]-6-[8-(prop-2-enamido)naphthalen-2-yl]pyridine-2-carboxamide | 433.2 |
| 294 | 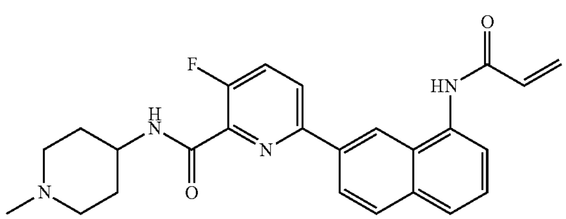 [SMILES: C=CC(=O)Nc1cccc2ccc(-c3ccc(F)c(C(=O)NC4CCN(C)CC4)n3)cc12] | 3-fluoro-N-(1-methylpiperidin-4-yl)-6-[8-(prop-2-enamido)naphthalen-2-yl]pyridine-2-carboxamide | 433.2 |
| 295 | 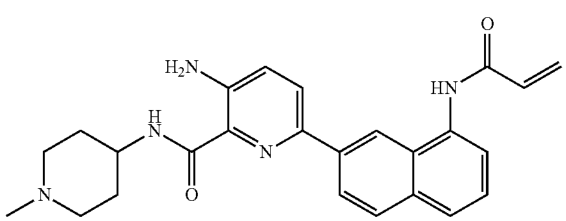 [SMILES: C=CC(=O)Nc1cccc2ccc(-c3ccc(N)c(C(=O)NC4CCN(C)CC4)n3)cc12] | 3-amino-N-(1-methylpiperidin-4-yl)-6-[8-(prop-2-enamido)naphthalen-2-yl]pyridine-2-carboxamide | 430.2 |

TABLE 7-continued

| Cpd. No. | Structure | IUPAC | LC-MS (ES+, m/z) |
|---|---|---|---|
| 296 | 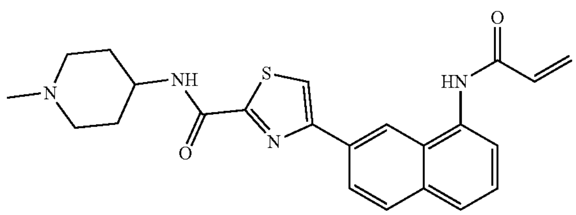 [SMILES: C=CC(=O)Nc1cccc2ccc(-c3csc(C(=O)NC4CCN(C)CC4)n3)cc12] | N-(1-methylpiperidin-4-yl)-4-[8-(prop-2-enamido)naphthalen-2-yl]-1,3-thiazole-2-carboxamide | 421.1 |
| 297 | 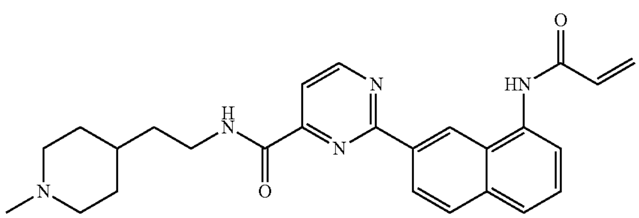 [SMILES: C=CC(=O)Nc1cccc2ccc(-c3nccc(C(=O)NCCC4CCN(C)CC4)n3)cc12] | N-[2-(1-methylpiperidin-4-yl)ethyl]-2-[8-(prop-2-enamido)naphthalen-2-yl]pyrimidine-4-carboxamide | 444.2 |
| 298 | 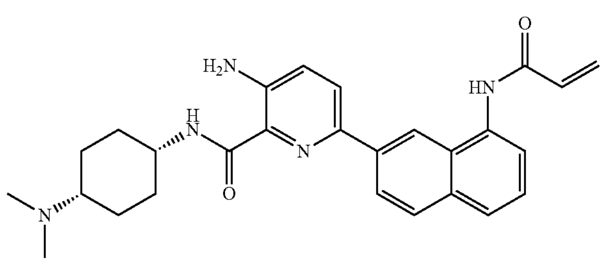 [SMILES: C=CC(=O)Nc1cccc2ccc(-c3ccc(N)c(C(=O)N[C@H]4CC[C@@H](N(C)C)CC4)n3)cc12] | 3-amino-6-[8-(prop-2-enamido)naphthalen-2-yl]-N-[(1s,4s)-4-(dimethylamino)cyclohexyl]pyridine-2-carboxamide | 458.2 |
| 299 | 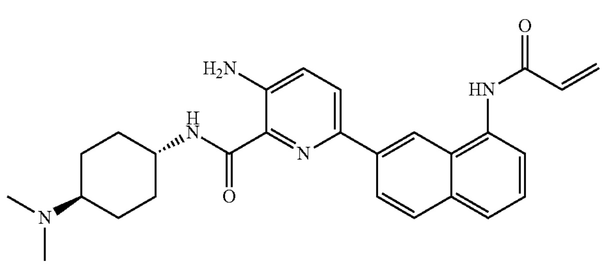 [SMILES: C=CC(=O)Nc1cccc2ccc(-c3ccc(N)c(C(=O)N[C@H]4CC[C@H](N(C)C)CC4)n3)cc12] | 3-amino-6-[8-(prop-2-enamido)naphthalen-2-yl]-N-[(1r,4r)-4-(dimethylamino)cyclohexyl]pyridine-2-carboxamide | 458.2 |
| 300 | 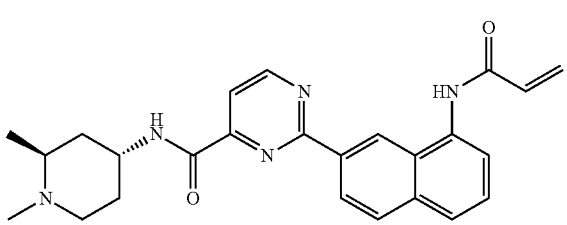 [SMILES: C=CC(=O)Nc1cccc2ccc(-c3nccc(C(=O)N[C@@H]4CCN(C)[C@@H](C)C4)n3)cc12] | N-[(2S,4R)-1,2-dimethylpiperidin-4-yl]-2-[8-(prop-2-enamido)naphthalen-2-yl]pyrimidine-4-carboxamide | 430.2 |

TABLE 7-continued

| Cpd. No. | Structure | IUPAC | LC-MS (ES+, m/z) |
|---|---|---|---|
| 301 | 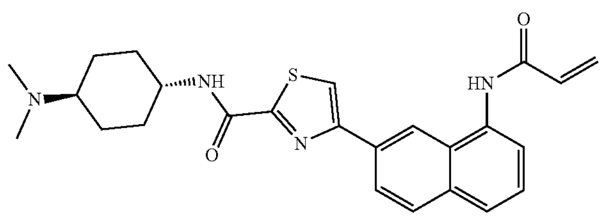 [SMILES: C=CC(=O)Nc1cccc2ccc(-c3csc(C(=O)N[C@H]4CC[C@H](N(C)C)CC4)n3)cc12] | 4-[8-(prop-2-enamido)naphthalen-2-yl]-N-[(1r,4r-4-(dimethylamino)cyclohexyl]-1,3-thiazole-2-carboxamide | 449.2 |
| 302 | 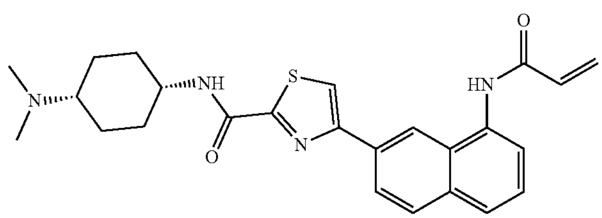 [SMILES: C=CC(=O)Nc1cccc2ccc(-c3csc(C(=O)N[C@H]4CC[C@@H](N(C)C)CC4)n3)cc12] | 4-[8-(prop-2-enamido)naphthalen-2-yl]-N-[(1s,4s)-4-(dimethylamino)cyclohexyl]-1,3-thiazole-2-carboxamide | 449.2 |
| 303 | 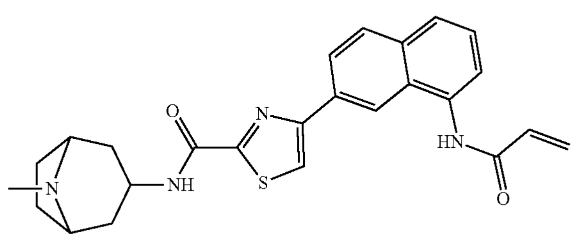 [SMILES: C=CC(=O)Nc1cccc2ccc(-c3csc(C(=O)NC4CC5CCC(C4)N5C)n3)cc12] | N-{8-methyl-8-azabicyclo[3.2.1]octan-3-yl}-4-[8-(prop-2-enamido)naphthalen-2-yl]-1,3-thiazole-2-carboxamide | 447.1 |
| 304 | 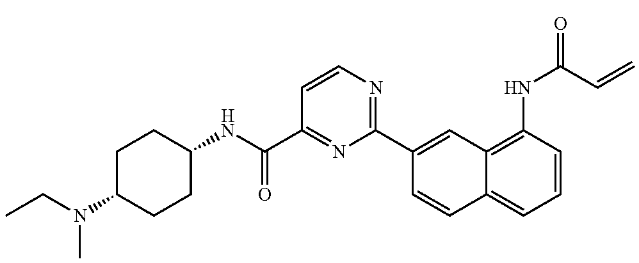 [SMILES: C=CC(=O)Nc1cccc2ccc(-c3nccc(C(=O)N[C@H]4CC[C@@H](N(C)CC)CC4)n3)cc12] | 2-[8-(prop-2-enamido)naphthalen-2-yl]-N-[(1s,4s)-4-[ethyl(methyl)amino]cyclohexyl]pyrimidine-4-carboxamide | 458.2 |
| 305 | 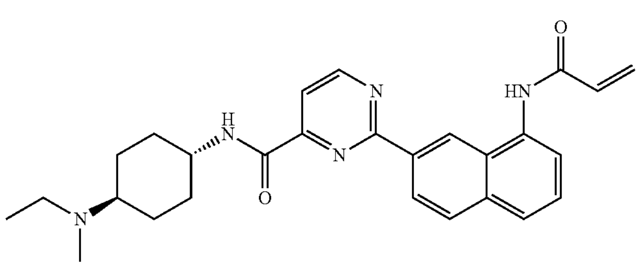 [SMILES: C=CC(=O)Nc1cccc2ccc(-c3nccc(C(=O)N[C@H]4CC[C@H](N(C)CC)CC4)n3)cc12] | 2-[8-(prop-2-enamido)naphthalen-2-yl]-N-[(1r,4r)-4-[ethyl(methyl)amino]cyclohexyl]pyrimidine-4-carboxamide | 458.2 |

TABLE 7-continued

| Cpd. No. | Structure | IUPAC | LC-MS (ES+, m/z) |
|---|---|---|---|
| 306 | 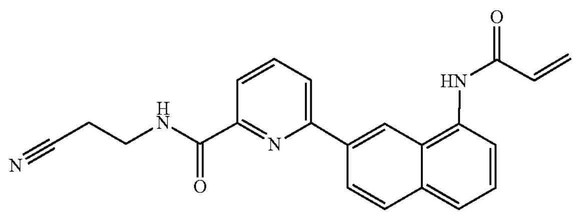 [SMILES: C=CC(=O)Nc1cccc2ccc(-c3cccc(C(=O)NCCC#N)n3)cc12] | N-(2-cyanoethyl)-6-[8-(prop-2-enamido)naphthalen-2-yl]pyridine-2-carboxamide | 371.1 |
| 307 | 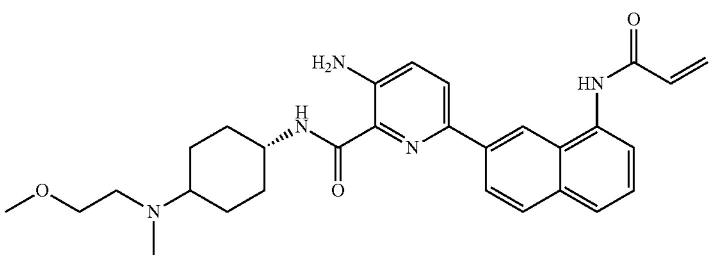 | 3-amino-6-[8-(prop-2-enamido)naphthalen-2-yl]-N-[(1r,4r)-4-[(2-methoxyethyl)(methyl)amino]cyclohexyl]pyridine-2-carboxamide | 502.3 |
| 308 | 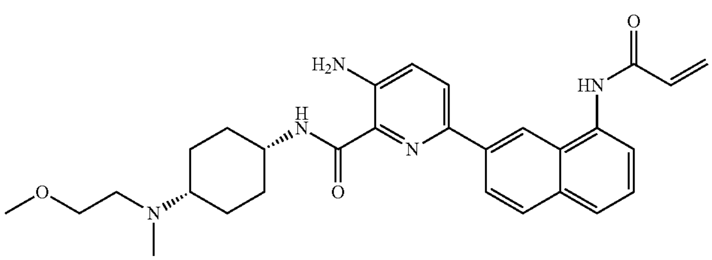 | 3-amino-6-[8-(prop-2-enamido)naphthalen-2-yl]-N-[(1s,4s)-4-[(2-methoxyethyl)(methyl)amino]cyclohexyl]pyridine-2-carboxamide | 502.3 |
| 309 | 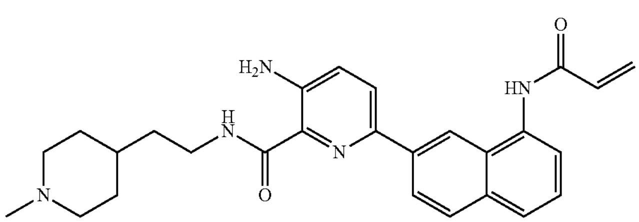 [SMILES: C=CC(=O)Nc1cccc2ccc(-c3ccc(N)c(C(=O)NCCC4CCN(C)CC4)n3)cc12] | 3-amino-N-[2-(1-methylpiperidin-4-yl)ethyl]-6-[8-(prop-2-enamido)naphthalen-2-yl]pyridine-2-carboxamide | 458.3 |
| 310 | 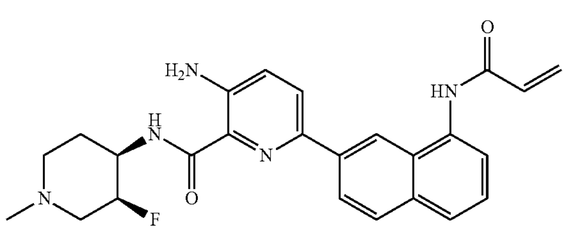 [SMILES: C=CC(=O)Nc1cccc2ccc(-c3ccc(N)c(C(=O)N[C@@H]4CCN(C)C[C@@H]4F)n3)cc12] | 3-amino-N-[(3S,4R)-3-fluoro-1-methylpiperidin-4-yl]-6-[8-(prop-2-enamido)naphthalen-2-yl]pyridine-2-carboxamide | 448.2 |

TABLE 7-continued

| Cpd. No. | Structure | IUPAC | LC-MS (ES+, m/z) |
|---|---|---|---|
| 311 | 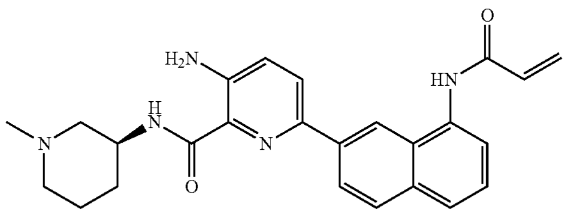 [SMILES: C=CC(=O)Nc1cccc2ccc(-c3ccc(N)c(C(=O)N[C@H]4CCCN(C)C4)n3)cc12] | 3-amino-N-[(3S)-1-methylpiperidin-3-yl]-6-[8-(prop-2-enamido)naphthalen-2-yl]pyridine-2-carboxamide | 430.2 |
| 312 | 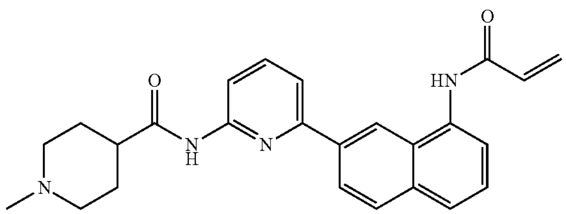 [SMILES: C=CC(=O)Nc1cccc2ccc(-c3cccc(NC(=O)C4CCN(C)CC4)n3)cc12] | 1-methyl-N-{6-[8-(prop-2-enamido)naphthalen-2-yl]pyridin-2-yl}piperidine-4-carboxamide | 415.3 |
| 313 | 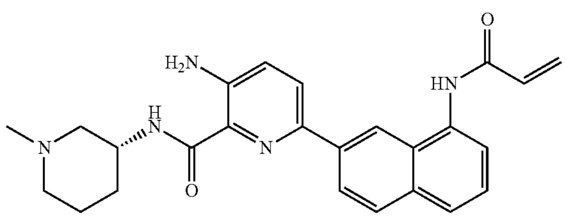 [SMILES: C=CC(=O)Nc1cccc2ccc(-c3ccc(N)c(C(=O)N[C@@H]4CCCN(C)C4)n3)cc12] | 3-amino-N-[(3R)-1-methylpiperidin-3-yl]-6-[8-(prop-2-enamido)naphthalen-2-yl]pyridine-2-carboxamide | 430.2 |
| 314 | 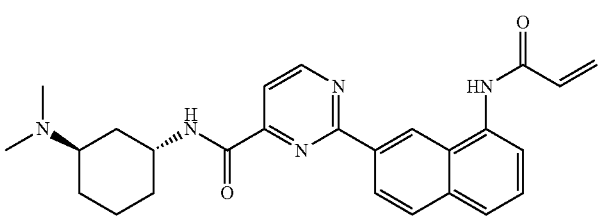 [SMILES: C=CC(=O)Nc1cccc2ccc(-c3nccc(C(=O)N[C@@H]4CCC[C@@H](N(C)C)C4)n3)cc12] | N-[(1R,3R)-3-(dimethylamino)cyclohexyl]-2-[8-(prop-2-enamido)naphthalen-2-yl]pyrimidine-4-carboxamide | 444.2 |
| 315 | 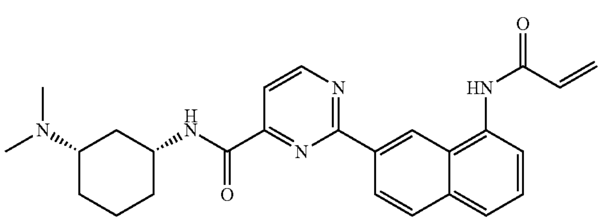 [SMILES: C=CC(=O)Nc1cccc2ccc(-c3nccc(C(=O)N[C@@H]4CCC[C@H](N(C)C)C4)n3)cc12] | N-[(1R,3S)-3-(dimethylamino)cyclohexyl]-2-[8-(prop-2-enamido)naphthalen-2-yl]pyrimidine-4-carboxamide | 444.2 |
| 316 | 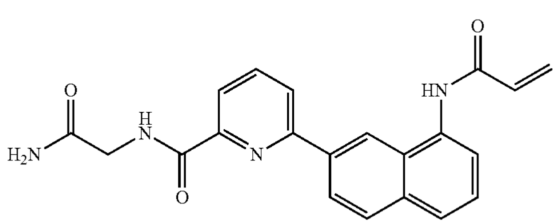 [SMILES: C=CC(=O)Nc1cccc2ccc(-c3cccc(C(=O)NCC(N)=O)n3)cc12] | N-(7-{6-[(carbamoylmethyl)carbamoyl]pyridin-2-yl}naphthalen-1-yl)prop-2-enamide | 375.1 |

TABLE 7-continued

| Cpd. No. | Structure | IUPAC | LC-MS (ES+, m/z) |
|---|---|---|---|
| 317 | 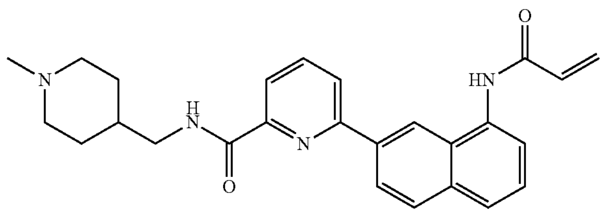 [SMILES: C=CC(=O)Nc1cccc2ccc(-c3cccc(C(=O)NCC4CCN(C)CC4)n3)cc12] | N-[(1-methylpiperidin-4-yl)methyl]-6-[8-(prop-2-enamido)naphthalen-2-yl]pyridine-2-carboxamide | 429.2 |
| 318 | 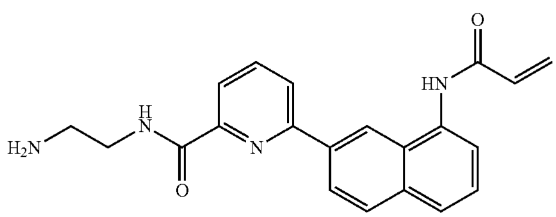 [SMILES: C=CC(=O)Nc1cccc2ccc(-c3cccc(C(=O)NCCN)n3)cc12] | N-(2-aminoethyl)-6-[8-(prop-2-enamido)naphthalen-2-yl]pyridine-2-carboxamide | 361.2 |
| 319 | 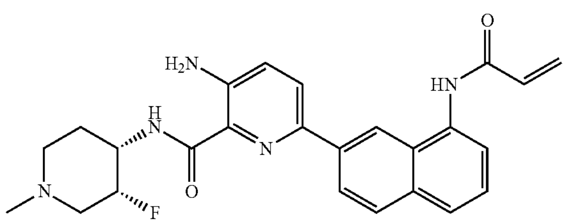 [SMILES: C=CC(=O)Nc1cccc2ccc(-c3ccc(N)c(C(=O)N[C@H]4CCN(C)C[C@H]4F)n3)cc12] | 3-amino-N-[(3R,4S)-3-fluoro-1-methylpiperidin-4-yl]-6-[8-(prop-2-enamido)naphthalen-2-yl]pyridine-2-carboxamide | 448.2 |
| 320 | 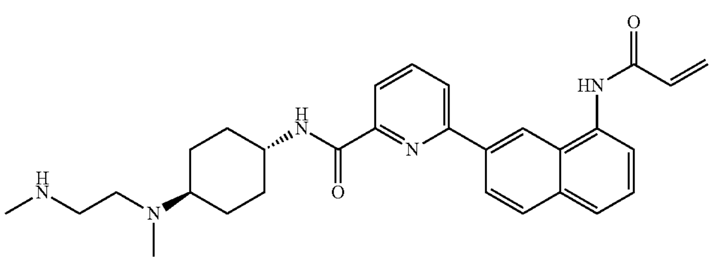 [SMILES: C=CC(=O)Nc1cccc2ccc(-c3cccc(C(=O)N[C@H]4CC[C@H](N(C)CCNC)CC4)n3)cc12] | 6-[8-(prop-2-enamido)naphthalen-2-yl]-N-[(1r,4r)-4-{methyl[2-(methylamino)ethyl]amino}cyclohexyl]pyridine-2-carboxamide | 486.3 |
| 321 | 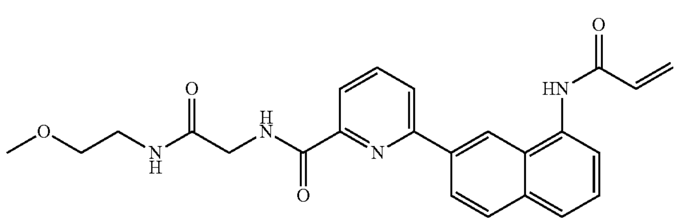 [SMILES: C=CC(=O)Nc1cccc2ccc(-c3cccc(C(=O)NCC(=O)NCCOC)n3)cc12] | N-{7-[6-({[(2-methoxyethyl)carbamoyl]methyl}carbamoyl)pyridin-2-yl]naphthalen-1-yl}prop-2-enamide | 433.2 |
| 322 | 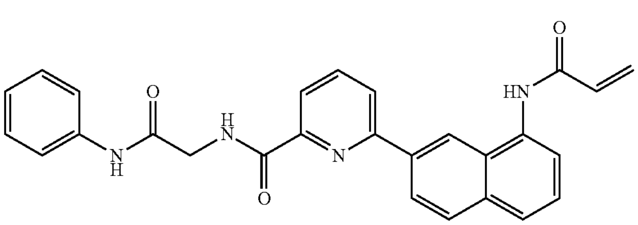 [SMILES: C=CC(=O)Nc1cccc2ccc(-c3cccc(C(=O)NCC(=O)Nc4ccccc4)n3)cc12] | N-[7-(6-{[(phenylcarbamoyl)methyl]carbamoyl}pyridin-2-yl)naphthalen-1-yl]prop-2-enamide | 451.2 |

TABLE 7-continued

| Cpd. No. | Structure | IUPAC | LC-MS (ES+, m/z) |
|---|---|---|---|
| 323 | 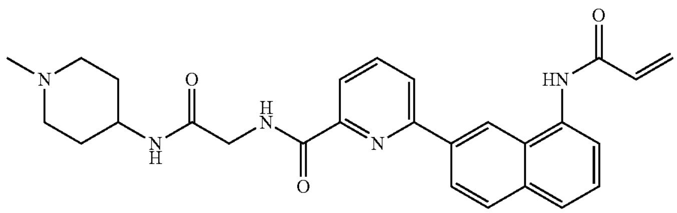 [SMILES: C=CC(=O)Nc1cccc2ccc(-c3cccc(C(=O)NCC(=O)NC4CCN(C)CC4)n3)cc12] | N-{7-[6-({[(1-methylpiperidin-4-yl)carbamoyl]methyl}carbamoyl)pyridin-2-yl]naphthalen-1-yl}prop-2-enamide | 472.2 |
| 324 | 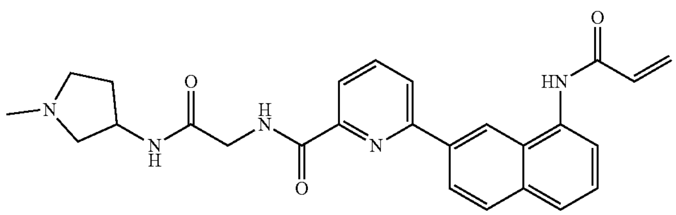 [SMILES: C=CC(=O)Nc1cccc2ccc(-c3cccc(C(=O)NCC(=O)NC4CCN(C)C4)n3)cc12] | N-{7-[6-({[(1-methylpyrrolidin-3-yl)carbamoyl]methyl}carbamoyl)pyridin-2-yl]naphthalen-1-yl}prop-2-enamide | 458.2 |
| 325 | 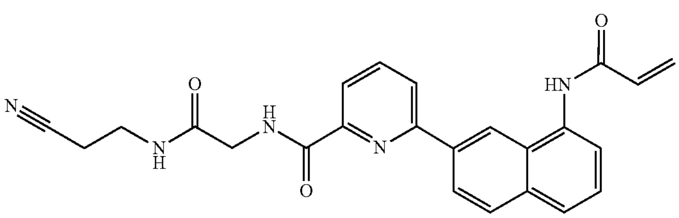 [SMILES: C=CC(=O)Nc1cccc2ccc(-c3cccc(C(=O)NCC(=O)NCCC#N)n3)cc12] | N-{7-[6-({[(2-cyanoethyl)carbamoyl]methyl}carbamoyl)pyridin-2-yl]naphthalen-1-yl}prop-2-enamide | 428.2 |
| 326 | 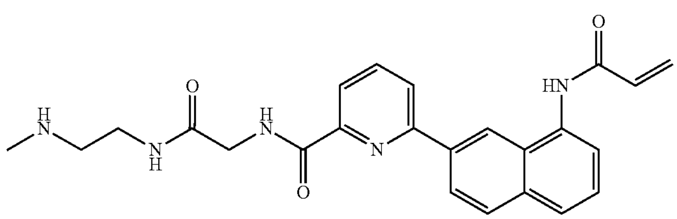 [SMILES: C=CC(=O)Nc1cccc2ccc(-c3cccc(C(=O)NCC(=O)NCCNC)n3)cc12] | N-(7-{6-[({2-(methylamino)ethyl]carbamoyl}methyl)carbamoyl]pyridin-2-yl}naphthalen-1-yl)prop-2-enamide | 432.2 |
| 327 | 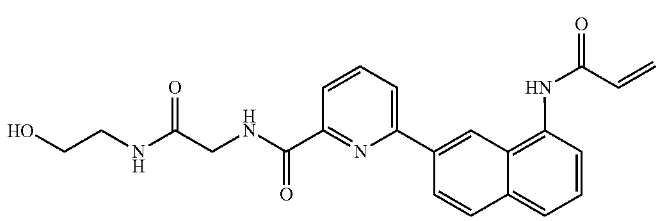 [SMILES: C=CC(=O)Nc1cccc2ccc(-c3cccc(C(=O)NCC(=O)NCCO)n3)cc12] | N-{7-[6-({[(2-hydroxyethyl)carbamoyl]methyl}carbamoyl)pyridin-2-yl]naphthalen-1-yl}prop-2-enamide | 419.2 |
| 328 | 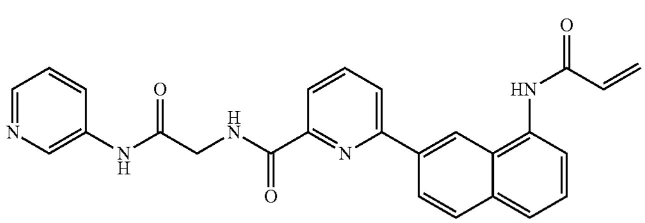 [SMILES: C=CC(=O)Nc1cccc2ccc(-c3cccc(C(=O)NCC(=O)Nc4cccnc4)n3)cc12] | N-{7-[6-({[(pyridin-3-yl)carbamoyl]methyl}carbamoyl)pyridin-2-yl]naphthalen-1-yl}prop-2-enamide | 452.2 |

TABLE 7-continued

| Cpd. No. | Structure | IUPAC | LC-MS (ES+, m/z) |
|---|---|---|---|
| 329 | 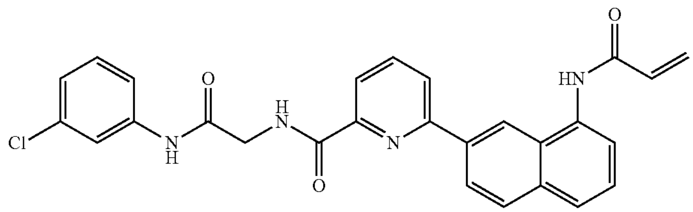 [SMILES: C=CC(=O)Nc1cccc2ccc(-c3cccc(C(=O)NCC(=O)Nc4cccc(Cl)c4)n3)cc12] | N-{7-[6-({[(3-chlorophenyl)carbamoyl]methyl}carbamoyl)pyridin-2-yl]naphthalen-1-yl}prop-2-enamide | 485.1 |
| 330 | 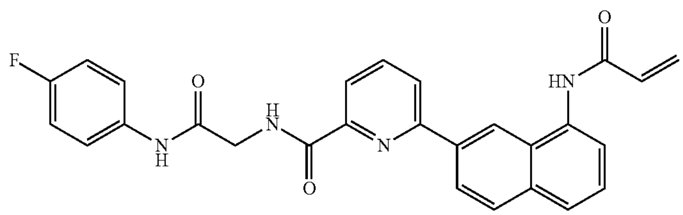 [SMILES: C=CC(=O)Nc1cccc2ccc(-c3cccc(C(=O)NCC(=O)Nc4ccc(F)cc4)n3)cc12] | N-{7-[6-({[(4-fluorophenyl)carbamoyl]methyl}carbamoyl)pyridin-2-yl]naphthalen-1-yl}prop-2-enamide | 469.2 |
| 331 | 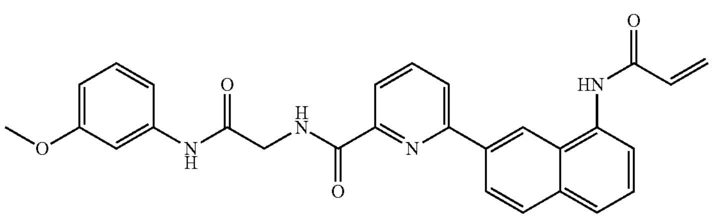 [SMILES: C=CC(=O)Nc1cccc2ccc(-c3cccc(C(=O)NCC(=O)Nc4cccc(OC)c4)n3)cc12] | N-{7-[6-({[(3-methoxyphenyl)carbamoyl]methyl}carbamoyl)pyridin-2-yl]naphthalen-1-yl}prop-2-enamide | 481.2 |
| 332 | 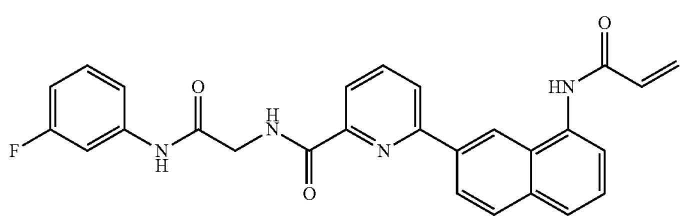 [SMILES: C=CC(=O)Nc1cccc2ccc(-c3cccc(C(=O)NCC(=O)Nc4cccc(F)c4)n3)cc12] | N-{7-[6-({[(3-fluorophenyl)carbamoyl]methyl}carbamoyl)pyridin-2-yl]naphthalen-1-yl}prop-2-enamide | 469.2 |
| 333 | 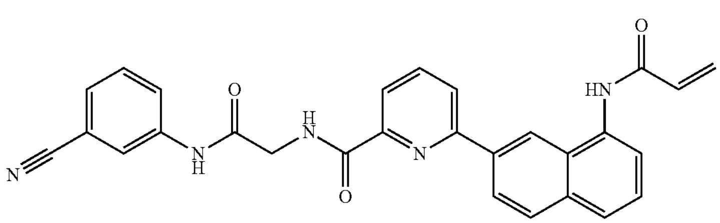 [SMILES: C=CC(=O)Nc1cccc2ccc(-c3cccc(C(=O)NCC(=O)Nc4cccc(C#N)c4)n3)cc12] | N-{7-[6-({[(3-cyanophenyl)carbamoyl]methyl}carbamoyl)pyridin-2-yl]naphthalen-1-yl}prop-2-enamide | 476.2 |
| 334 | 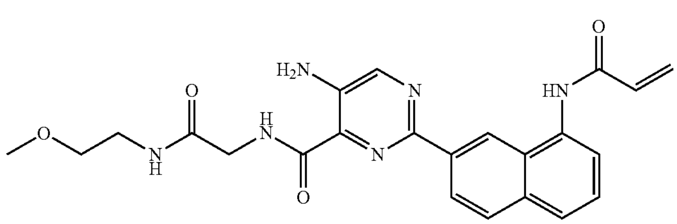 [SMILES: C=CC(=O)Nc1cccc2ccc(-c3ncc(N)c(C(=O)NCC(=O)NCCOC)n3)cc12] | N-{7-[5-amino-4-({[(2-methoxyethyl)carbamoyl]methyl}carbamoyl)pyrimidin-2-yl]naphthalen-1-yl}prop-2-enamide | 449.2 |

TABLE 7-continued

| Cpd. No. | Structure | IUPAC | LC-MS (ES+, m/z) |
|---|---|---|---|
| 335 | 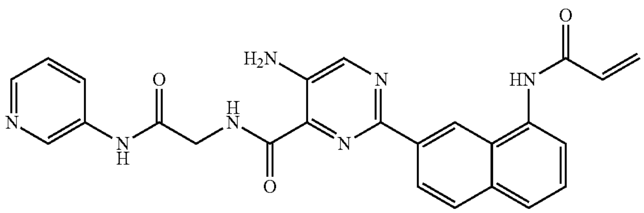 [SMILES: C=CC(=O)Nc1cccc2ccc(-c3ncc(N)c(C(=O)NCC(=O)Nc4cccnc4)n3)cc12] | N-{7-[5-amino-4-({[(pyridin-3-yl)carbamoyl]methyl}carbamoyl)pyrimidin-2-yl]naphthalen-1-yl}prop-2-enamide | 468.2 |
| 336 | 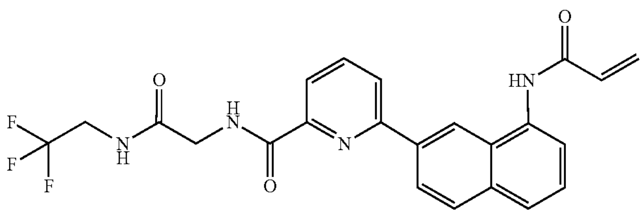 [SMILES: C=CC(=O)Nc1cccc2ccc(-c3cccc(C(=O)NCC(=O)NCC(F)(F)F)n3)cc12] | N-{7-[6-({[(2,2,2-trifluoroethyl)carbamoyl]methyl}carbamoyl)pyridin-2-yl]naphthalen-1-yl}prop-2-enamide | 457.2 |
| 337 | 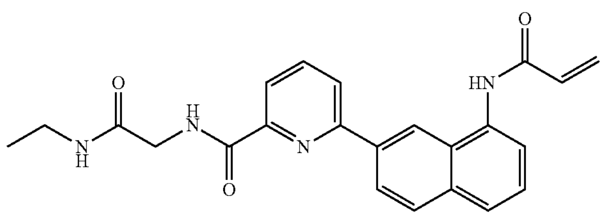 [SMILES: C=CC(=O)Nc1cccc2ccc(-c3cccc(C(=O)NCC(=O)NCC)n3)cc12] | N-[7-(6-{[(ethylcarbamoyl)methyl]carbamoyl}pyridin-2-yl)naphthalen-1-yl]prop-2-enamide | 403.2 |
| 338 | 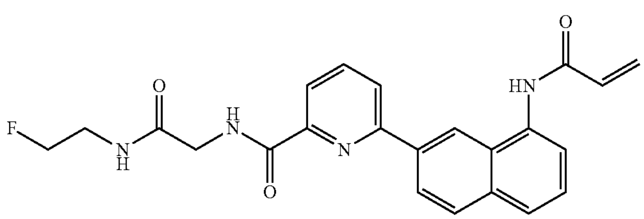 [SMILES: C=CC(=O)Nc1cccc2ccc(-c3cccc(C(=O)NCC(=O)NCCF)n3)cc12] | N-{7-[6-({[(2-fluoroethyl)carbamoyl]methyl}carbamoyl)pyridin-2-yl]naphthalen-1-yl}prop-2-enamide | 421.2 |
| 339 | 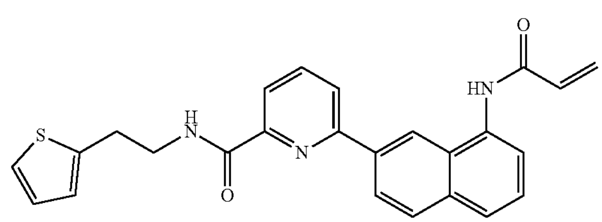 [SMILES: C=CC(=O)Nc1cccc2ccc(-c3cccc(C(=O)NCCc4cccs4)n3)cc12] | 6-[8-(prop-2-enamido)naphthalen-2-yl]-N-[2-(thiophen-2-yl)ethyl]pyridine-2-carboxamide | 428.1 |
| 340 | 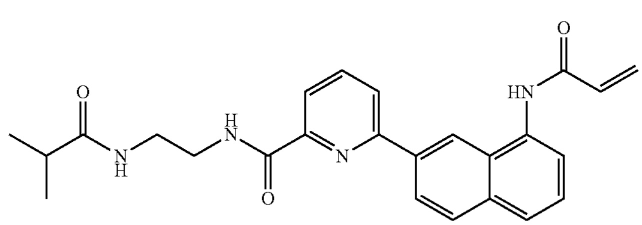 [SMILES: C=CC(=O)Nc1cccc2ccc(-c3cccc(C(=O)NCCNC(=O)C(C)C)n3)cc12] | N-[7-(6-{[2-(2-methylpropanamido)ethyl]carbamoyl}pyridin-2-yl)naphthalen-1-yl]prop-2-enamide | 431.2 |

TABLE 7-continued

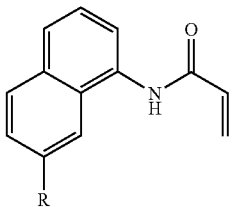

| Cpd. No. | Structure | IUPAC | LC-MS (ES+, m/z) |
|---|---|---|---|
| 341 | 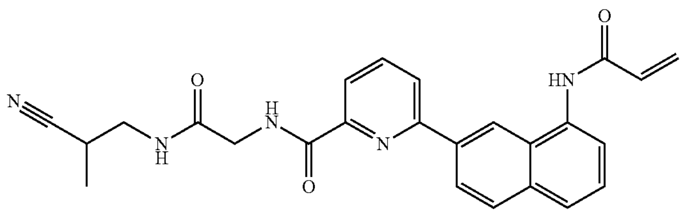 [SMILES: C=CC(=O)Nc1cccc2ccc(-c3cccc(C(=O)NCC(=O)NCC(C)C#N)n3)cc12] | N-{7-[6-({[(2-cyano-2-methylethyl)carbamoyl]methyl}carbamoyl)pyridin-2-yl]naphthalen-1-yl}prop-2-enamide | 442.2 |
| 342 | 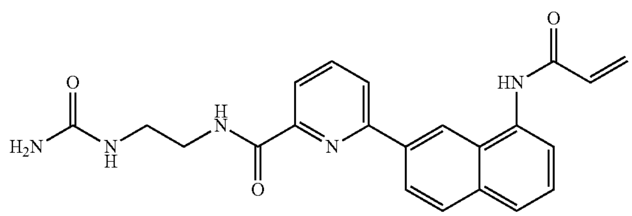 [SMILES: C=CC(=O)Nc1cccc2ccc(-c3cccc(C(=O)NCCNC(N)=O)n3)cc12] | N-[2-(carbamoylamino)ethyl]-6-[8-(prop-2-enamido)naphthalen-2-yl]pyridine-2-carboxamide | 404.2 |
| 343 | 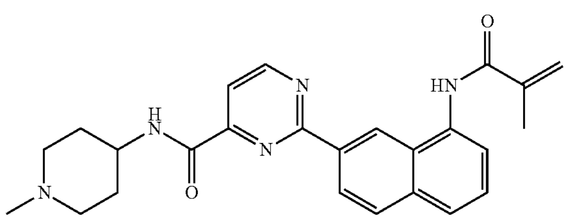 [SMILES: C=C(C)C(=O)Nc1cccc2ccc(-c3nccc(C(=O)NC4CCN(C)CC4)n3)cc12] | N-(1-methylpiperidin-4-yl)-2-[8-(2-methylprop-2-enamido)naphthalen-2-yl]pyrimidine-4-carboxamide | 430.2 |
| 344 | 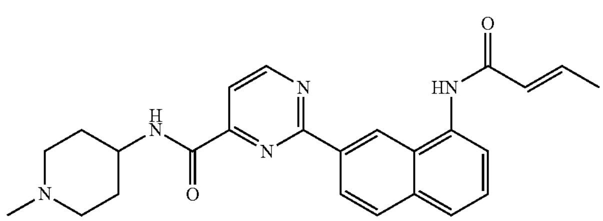 [SMILES: C/C=C/C(=O)Nc1cccc2ccc(-c3nccc(C(=O)NC4CCN(C)CC4)n3)cc12] | 2-{8-[(2E)-but-2-enamido]naphthalen-2-yl}-N-(1-methylpiperidin-4-yl)pyrimidine-4-carboxamide | 430.2 |
| 345 | 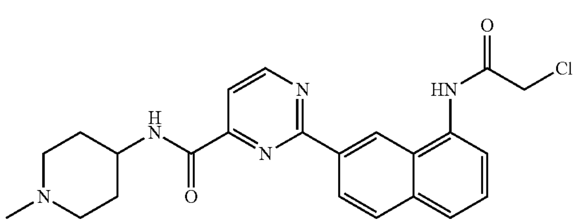 [SMILES: CN1CCC(NC(=O)c2ccnc(-c3ccc4cccc(NC(=O)CCl)c4c3)n2)CC1] | 2-[8-(2-chloroacetamido)naphthalen-2-yl]-N-(1-methylpiperidin-4-yl)pyrimidine-4-carboxamide | 438.2 |
| 346 | 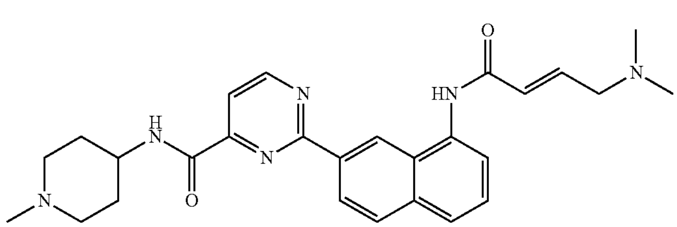 | 2-{8-[(2E)-4-(dimethylamino)but-2-enamido]naphthalen-2-yl}-N-(1-methylpiperidin-4-yl)pyrimidine-4-carboxamide | 473.2 |

TABLE 7-continued

| Cpd. No. | Structure | IUPAC | LC-MS (ES+, m/z) |
|---|---|---|---|
| 347 | 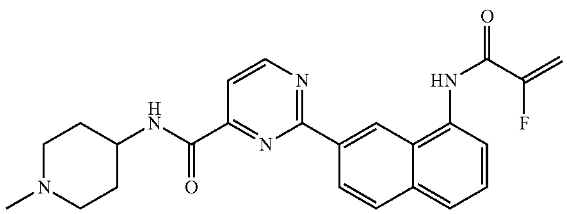 [SMILES: C=C(F)C(=O)Nc1cccc2ccc(-c3nccc(C(=O)NC4CCN(C)CC4)n3)cc12] | 2-[8-(2-fluoroprop-2-enamido)naphthalen-2-yl]-N-(1-methylpiperidin-4-yl)pyrimidine-4-carboxamide | 434.2 |
| 348 | 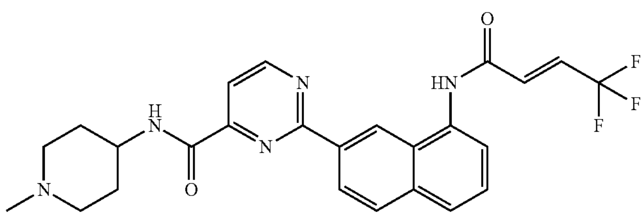 [SMILES: CN1CCC(NC(=O)c2ccnc(-c3ccc4cccc(NC(=O)/C=C/C(F)(F)F)c4c3)n2)CC1] | N-(1-methylpiperidin-4-yl)-2-{8-[(2E)-4,4,4-trifluorobut-2-enamido]naphthalen-2-yl}pyrimidine-4-carboxamide | 484.2 |
| 349 | 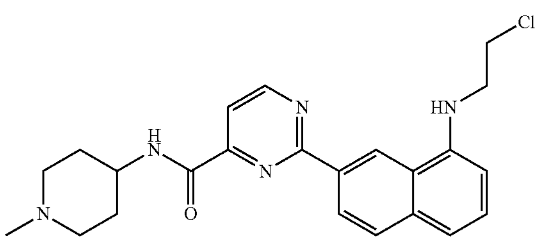 [SMILES: CN1CCC(NC(=O)c2ccnc(-c3ccc4cccc(NCCCl)c4c3)n2)CC1] | 2-{8-[(2-chloroethyl)amino]naphthalen-2-yl}-N-(1-methylpiperidin-4-yl)pyrimidine-4-carboxamide | 424.2 |
| 350 | 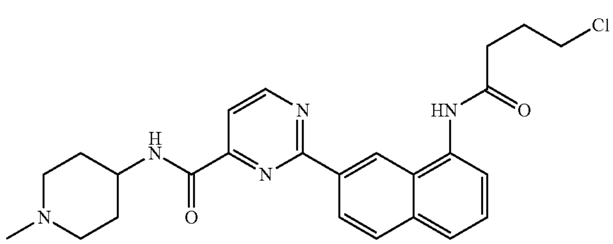 [SMILES: CN1CCC(NC(=O)c2ccnc(-c3ccc4cccc(NC(=O)CCCCl)c4c3)n2)CC1] | 2-[8-(4-chlorobutanamido)naphthalen-2-yl]-N-(1-methylpiperidin-4-yl)pyrimidine-4-carboxamide | 466.2 |

Example 8: Method H

Route 1: General Scheme

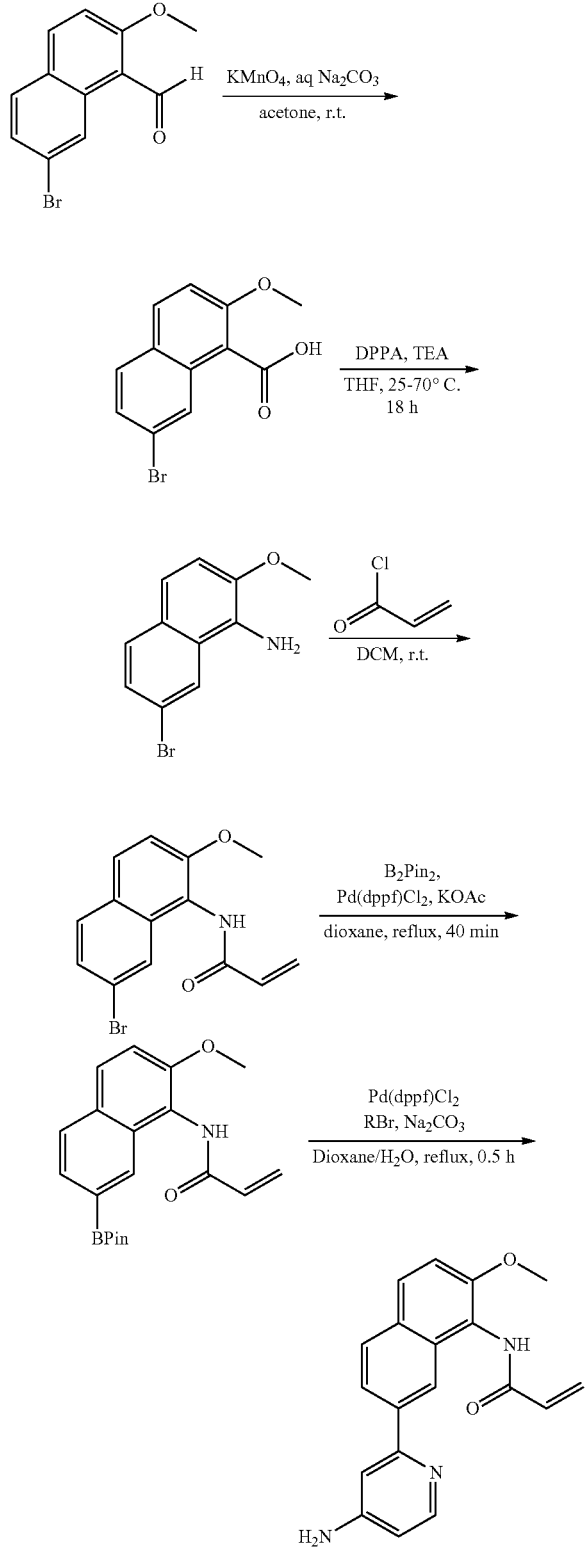

Step 1) Preparation of 7-bromanyl-2-methoxy-naphthalene-1-carboxylic acid

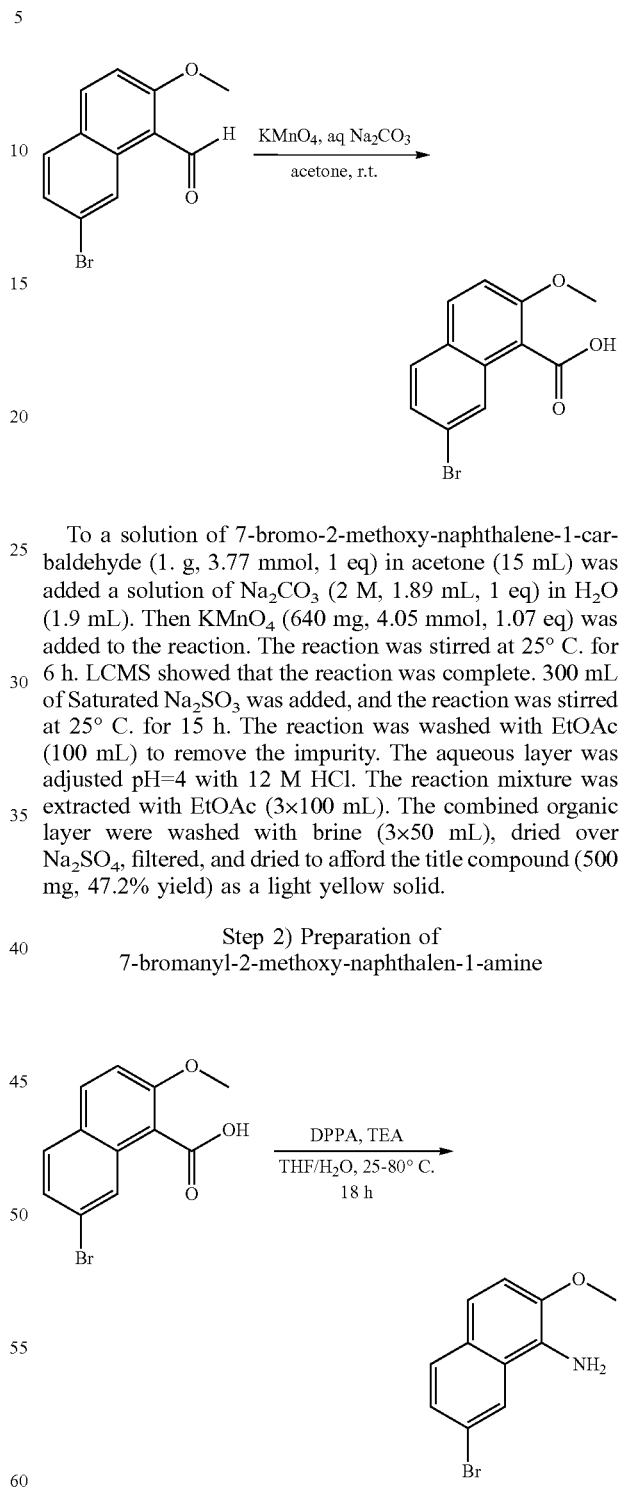

To a solution of 7-bromo-2-methoxy-naphthalene-1-carbaldehyde (1. g, 3.77 mmol, 1 eq) in acetone (15 mL) was added a solution of $Na_2CO_3$ (2 M, 1.89 mL, 1 eq) in $H_2O$ (1.9 mL). Then $KMnO_4$ (640 mg, 4.05 mmol, 1.07 eq) was added to the reaction. The reaction was stirred at 25° C. for 6 h. LCMS showed that the reaction was complete. 300 mL of Saturated $Na_2SO_3$ was added, and the reaction was stirred at 25° C. for 15 h. The reaction was washed with EtOAc (100 mL) to remove the impurity. The aqueous layer was adjusted pH=4 with 12 M HCl. The reaction mixture was extracted with EtOAc (3×100 mL). The combined organic layer were washed with brine (3×50 mL), dried over $Na_2SO_4$, filtered, and dried to afford the title compound (500 mg, 47.2% yield) as a light yellow solid.

Step 2) Preparation of 7-bromanyl-2-methoxy-naphthalen-1-amine

To a solution of 7-bromo-2-methoxy-naphthalene-1-carboxylic acid (430 mg, 1.53 mmol, 1 eq) in THF (10 mL) were added DPPA (442 mg, 1.61 mmol, 348.05 μL, 1.05 eq) and TEA (309.6 mg, 3.06 mmol, 425.83 μL, 2 eq). The reaction was stirred at 25° C. for 16 h. Water (1 mL) was added, and the reaction was stirred at 80° C. for 2 h. The reaction was quenched with ice-water (10 mL) and EtOAc (10 mL) at 0° C. The reaction was filtered and the filter cake was extracted with EtOAc (3×10 mL). The combined organic layer was washed with brine (3×10 mL), dried over Na₂SO₄, filtered, and dried to afford the title compound (340 mg, 88.2% yield) as a yellow solid.

Step 3) Preparation of N-(7-bromanyl-2-methoxy-1-naphthyl)prop-2-enamide

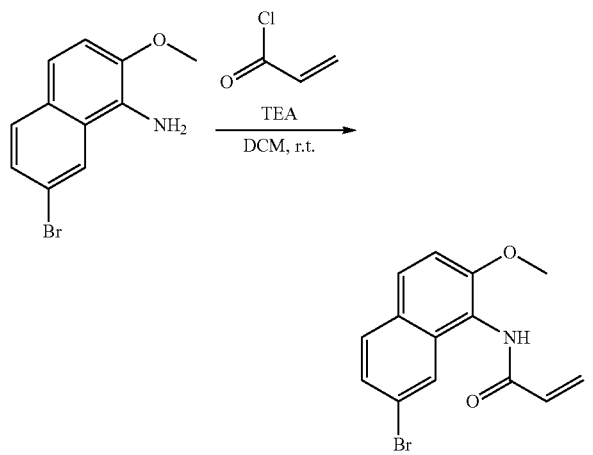

To a solution of 7-bromo-2-methoxy-naphthalen-1-amine (340 mg, 1.35 mmol, 1 eq) in DCM (10 mL) were added TEA (887 mg, 8.77 mmol, 1.22 mL, 6.5 eq) and prop-2-enoyl chloride (264.9 mg, 2.93 mmol, 238.63 μL, 2.17 eq) at 25° C. The reaction was stirred at 25° C. for 15 min. The reaction was quenched with water (5 mL) and extracted with EtOAc (3×20 mL). The combined organic layer were washed with brine (3×20 mL), dried over Na₂SO₄, filtered, and concentrated. The residue was purified by prep-TLC (SiO₂, DCM/MeOH=50/1, Rf=0.4) to afford the title compound (160 mg, 38.8% yield) as a light yellow solid.

Step 4) Preparation of N-[2-methoxy-7-[4,4,5,5-tetra(methyl)-1,3,2-dioxaborolan-2-yl]-1-naphthyl]prop-2-enamide

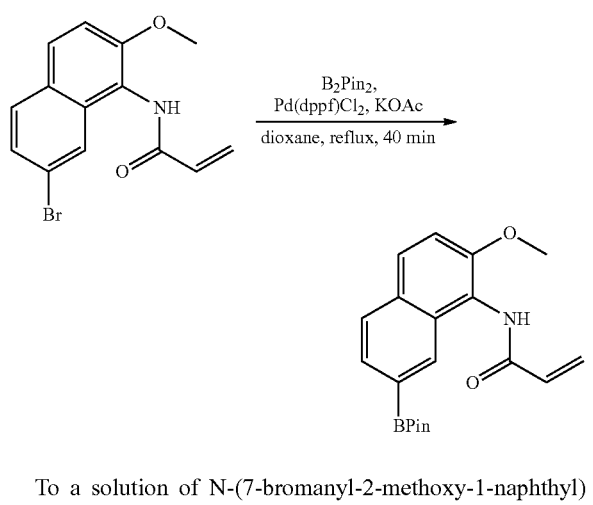

To a solution of N-(7-bromanyl-2-methoxy-1-naphthyl)prop-2-enamide (78 mg, 254.77 μmol, 1 eq) and 4,4,5,5-tetramethyl-2-(4,4,5,5-tetramethyl-1,3,2-dioxaborolan-2-yl)-1,3,2-dioxaborolane (327.6 mg, 1.29 mmol, 5.06 eq) in dioxane (5 mL) were added Pd(dppf)Cl₂·CH₂Cl₂ (20.8 mg, 25.48 μmol, 0.1 eq) and KOAc (125 mg, 1.27 mmol, 5 eq). The reaction was stirred at 120° C. for 40 min under N₂ atmosphere. The reaction was filtered, and concentrated. The residue was purified by prep-TLC (SiO₂, PE:EtOAc=1/1) to afford the title compound (160 mg, 43% purity, 76.4% yield) as black solid.

Step 5) Compound 351: Preparation of N-[7-(4-aminopyridin-2-yl)-2-methoxynaphthalen-1-yl]prop-2-enamide

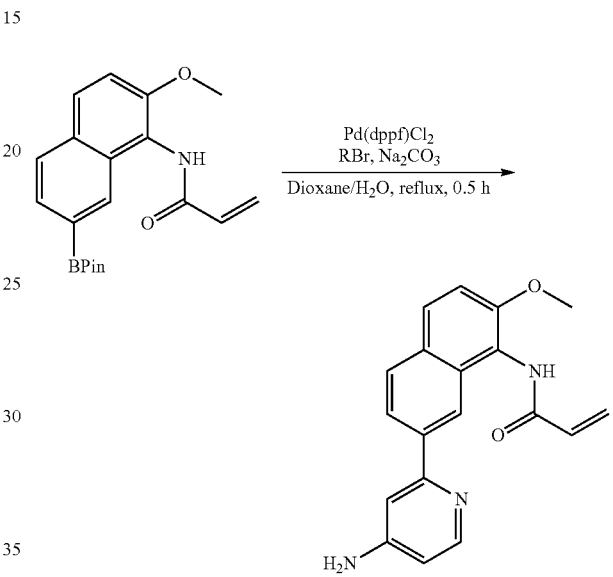

To a solution of N-[2-methoxy-7-[4,4,5,5-tetra(methyl)-1,3,2-dioxaborolan-2-yl]-1-naphthyl]prop-2-enamide (140 mg, 396.35 μmol, 1 eq) and 2-bromopyridin-4-amine (60 mg, 346.8 μmol, 0.88 eq) in dioxane (4 mL) and H₂O (1 mL) were added Pd(dppf)Cl₂ (29 mg, 39.64 μmol, 0.1 eq) and Na₂CO₃ (126 mg, 1.19 mmol, 3 eq). The reaction was stirred at 120° C. for 0.5 h under N₂ atmosphere. LCMS showed that the reaction was complete. 20 mL of Saturated EDTA was added, and the reaction was stirred at 25° C. for 1 h. The reaction was filtered and the filtrate was extracted with EtOAc (3×10 mL). The combined organic layer was washed with brine (3×10 mL), dried over Na₂SO₄, filtered, and concentrated. The residue was purified by prep-TLC (SiO₂, DCM/MeOH=8/1, Rf=0.3) and prep-HPLC to afford the title compound (5.6 mg, 4.4% yield) as a white solid. LC-MS (ES⁺, m/z): 320.1 [(M+H)⁺]

Route 2: General Scheme

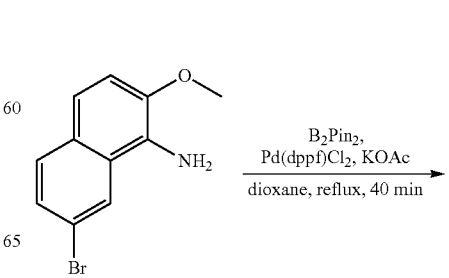

-continued

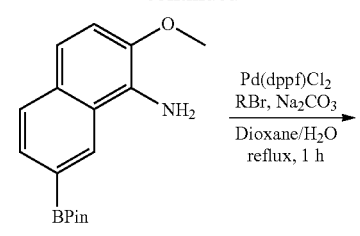

Step 2) Preparation of 2-methoxy-7-(2-pyridyl)naphthalen-1-amine

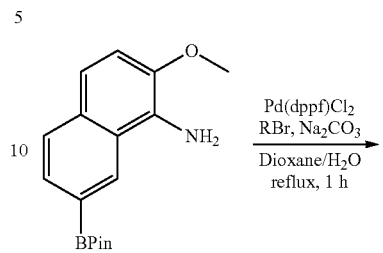

Step 1) Preparation of 2-methoxy-7-[4,4,5,5-tetra(methyl)-1,3,2-dioxaborolan-2-yl]naphthalen-1-amine

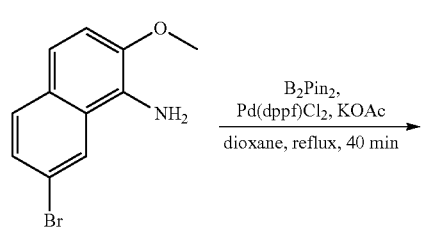

To a solution of 7-bromo-2-methoxy-naphthalen-1-amine (800 mg, 3.17 mmol, 1 eq) and 4,4,5,5-tetramethyl-2-(4,4,5,5-tetramethyl-1,3,2-dioxaborolan-2-yl)-1,3,2-dioxaborolane (960 mg, 3.78 mmol, 1.19 eq) in dioxane (20 mL) were added Pd(dppf)Cl$_2$ (232.2 mg, 317.33 µmol, 0.1 eq) and KOAc (934.3 mg, 9.52 mmol, 3 eq). The reaction was stirred at 120° C. for 0.5 h under N$_2$ atmosphere. The reaction was filtered. The filtrate was concentrated, and the residue was purified by silica gel chromatography (PE:EtOAc=3:1) to afford the title compound (800 mg, 84.3% yield) as a yellow solid.

To a solution of 2-methoxy-7-[4,4,5,5-tetra(methyl)-1,3,2-dioxaborolan-2-yl]naphthalen-1-amine (284 mg, 949.39 µmol, 1 eq) and 2-bromopyridine (150 mg, 949.39 µmol, 90.36 µL, 1 eq) in dioxane (2 mL) and H$_2$O (0.5 mL) were added Pd(dppf)Cl$_2$·CH$_2$Cl$_2$ (77.5 mg, 94.94 µmol, 0.1 eq) and Na$_2$CO$_3$ (301.9 mg, 2.85 mmol, 3 eq). The reaction was stirred at 120° C. for 1 h under N$_2$ atmosphere. LCMS showed that the reaction was complete. 20 mL Saturated EDTA was added, and the reaction was stirred at 25° C. for 1 h. The reaction was extracted with EtOAc (2×10 mL). The combined organic layer was washed with brine (3×10 mL), dried over Na$_2$SO$_4$ and concentrated. The residue was purified by prep-TLC (SiO$_2$, PE/EtOAc=2/1, Rf=0.4) to afford the title compound (100 mg, 42.1% yield) as a yellow oil.

Step 3) Compound 352: Preparation of N-[2-methoxy-7-(pyridin-2-yl)naphthalen-1-yl]prop-2-enamide

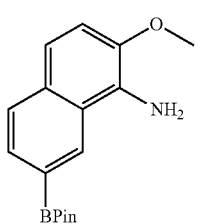

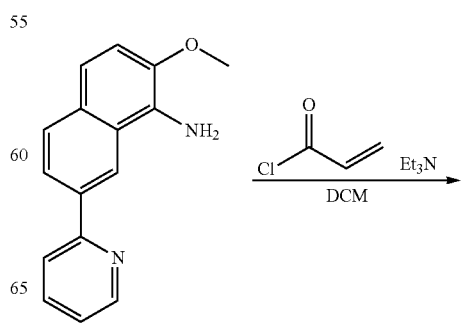

-continued

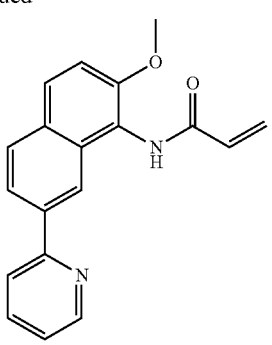

To a solution of 2-methoxy-7-(2-pyridyl)naphthalen-1-amine (40 mg, 159.81 μmol, 1 eq) in DCM (2.0 mL) were added TEA (48.5 mg, 479.44 μmol, 66.73 μL, 3 eq) and prop-2-enoyl chloride (14.5 mg, 159.81 μmol, 13.03 μL, 1 eq) in 0.3 mL DCM. The reaction was stirred at 25° C. for 1 h. The reaction was poured into ice-water (5 mL) and extracted with EtOAc (3×10 mL). The combined organic layer were washed with brine (3×10 mL), dried over Na$_2$SO$_4$, filtered, and concentrated. The residue was purified by pre-HPLC to afford the title compound (9 mg, 18.4% yield) as a white solid. LC-MS (ES$^+$, m/z): 305.1 [(M+H)$^+$].

Compound 358 and 359: General Procedure for Compound 3-(8-acrylamido-7-methoxynaphthalen-2-yl)-N-((3S,4R)-3-fluoro-1-methylpiperidin-4-yl)benzamide

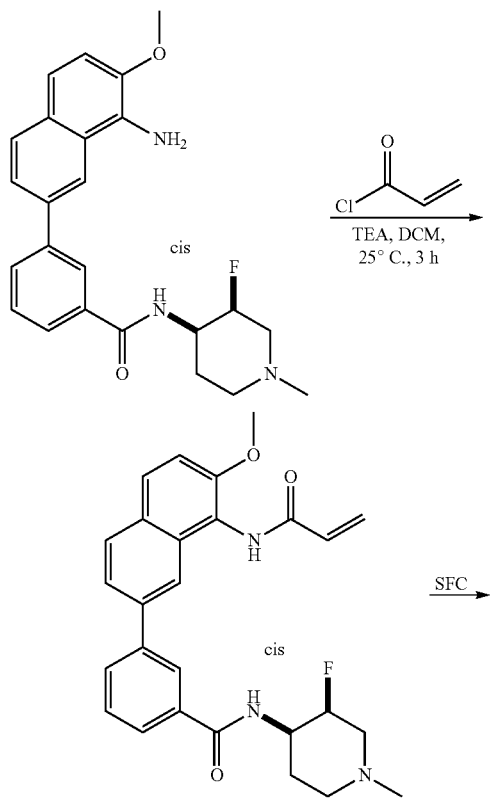

-continued

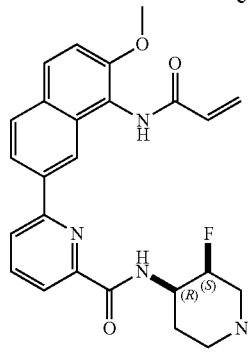

To a mixture of 6-(8-amino-7-methoxy-2-naphthyl)-N-[(3R,4S)-3-fluoro-1-methyl-4-piperidyl]pyridine-2-carboxamide (110 mg, 269.3 μmol, 1 eq) in DCM (3 mL) were added Et$_3$N (136.3 mg, 1.35 mmol, 187.4 μL, 5 eq) and prop-2-enoyl chloride (24.4 mg, 269.3 μmol, 21.95 μL, 1 eq) in one portion. The reaction mixture was stirred at 25° C. for 2 hours. TLC showed ~50% of the starting material remained. An additional portion of prop-2-enoyl chloride (24.4 mg, 269.3 μmol, 21.95 μL, 1 eq) was added to the reaction mixture and stirred at 25° C. for another 1 hour. TLC showed that the reaction was complete. The reaction was diluted with 30 mL water and extracted with EtOAc (2×30 mL). The combined organic layer was washed with brine (2×25 mL), dried over Na$_2$SO$_4$, filtered, and concentrated in vacuo. The residue was purified by prep-TLC (SiO$_2$, DCM:MeOH=10:1). then purified by chiral SFC to afford example 358 (28.5 mg, 60.82 μmol, 22.6% yield, 98.7% purity) as a white solid. LC-MS (ES$^+$, m/z): 463.2 [(M+H)$^+$], The other enantiomer (Compound 359) was also obtained (30.1 mg, 63.97 μmol, 23.76% yield, 98.3% purity) as a white solid. LC-MS (ES$^+$, m/z): 463.2 [(M+H)$^+$].

Route 3: General Scheme

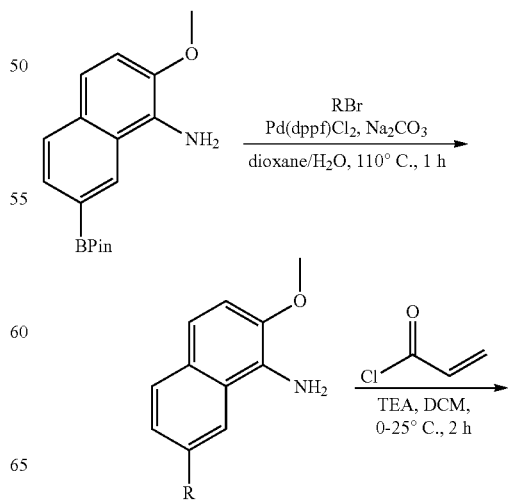

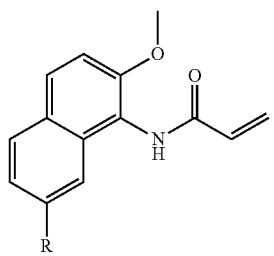

General Procedure for Suzuki Coupling

Preparation of 2-(8-amino-7-methoxy-2-naphthyl)-N-(1-methyl-4-piperidyl)pyrimidine-4-carboxamide

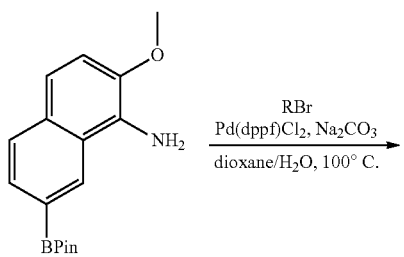

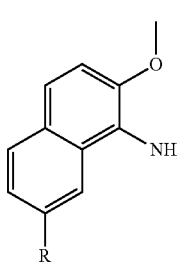

To a solution of 2-methoxy-7-(4,4,5,5-tetramethyl-1,3,2-dioxaborolan-2-yl)naphthalen-1-amine (0.5 g, 1.67 mmol, 1 eq) and RBr 2-chloro-N-(1-methyl-4-piperidyl)pyrimidine-4-carboxamide (510.8 mg, 2.01 mmol, 1.2 eq) in dioxane (6 mL) and H$_2$O (1.5 mL) were added Na$_2$CO$_3$ (531.4 mg, 5.01 mmol, 3 eq) and Pd(dppf)Cl$_2$ (122.3 mg, 167.13 μmol, 0.1 eq), and the reaction was stirred at 100° C. for 1 hr under N$_2$. The reaction was poured into ~20 mL saturated EDTA and stirred at 25° C. for 0.5 h. The mixture was extracted with EtOAc (3×20 mL). The combined organic phase was washed with brine (3×20 mL), dried over by anhydrous Na$_2$SO$_4$, filtered, and concentrated in vacuo. The residue was purified by prep-TLC (SiO$_2$, DCM:MeOH=10:1) to afford the title compound (0.3 g, 766.35 μmol, 45.8% yield) as a yellow solid. LC-MS (ES$^+$, m/z): 392.1 [(M+H)$^+$]

General Procedure for Acylation

Compound 357: Preparation of 2-[7-methoxy-8-(prop-2-enamido)naphthalen-2-yl]-N-(1-methylpiperidin-4-yl)pyrimidine-4-carboxamide

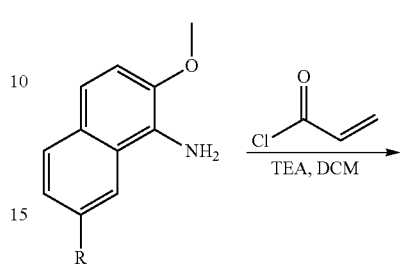

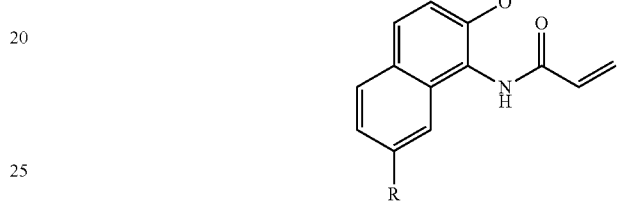

To a mixture of 2-(8-amino-7-methoxy-2-naphthyl)-N-(1-methyl-4-piperidyl)pyrimidine-4-carboxamide (0.03 g, 76.64 μmol, 1 eq) in DCM (2 mL) were added Et$_3$N (23.3 mg, 229.91 μmol, 32 μL, 3 eq) and prop-2-enoyl chloride (6.9 mg, 76.64 μmol, 6.25 μL, 1 eq), and the reaction was stirred at 25° C. for 1 hr. The reaction was poured into ~10 mL water and extracted with DCM (3×10 mL. The combined organic phase was washed with brine (3×10 mL), dried over by anhydrous Na$_2$SO$_4$, filtered, and concentrated in vacuo. The residue was purified by prep-HPVC (neutral condition) to afford the title compound (0.0065 g, 14.59 μmol, 19.04% yield, 100% purity) as a white solid. LC-MS (ES$^+$, m/z): 446.2 [(M+H)$^+$].

Preparation of 2-methoxy-7-(1-methylpyrazol-4-yl)naphthalen-1-amine

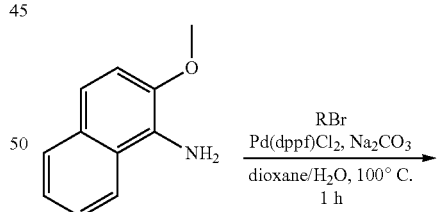

To a solution of 2-methoxy-7-(4,4,5,5-tetramethyl-1,3,2-dioxaborolan-2-yl) naphthalen-1-amine (200 mg, 668.51

µmol, 1 eq) in dioxane (2 mL) and H₂O (0.5 mL) was successively added 4-bromo-1-methyl-pyrazole (215.3 mg, 1.34 mmol, 2 eq), Na₂CO₃ (212.6 mg, 2.01 mmol, 3 eq) and Pd(dppf)Cl₂ (48.9 mg, 66.85 µmol, 0.1 eq) at 25° C. The resulting reaction mixture was stirred at 100° C. for 1 hour. LCMS showed that the reaction was complete. The reaction mixture was poured into 80 mL saturated EDTA and followed by 30 mL EtOAc. The solution was stirred at 20° C. for 2 hours. The aqueous phase was extracted with EtOAc (2×20 mL). The combined organic layer was washed successively with water (2×20 mL) and brine (1×20 mL), dried over anhydrous Na₂SO₄, filtered, and concentrated to give a residue. The residue was purified by prep-TLC (SiO₂, DCM:MeOH=30:1) to afford the title compound (100 mg, 394.79 µmol, 59.06% yield) as a yellow solid. LC-MS (ES⁺, m/z): 254.1 [(M+H)⁺].

Compound 377: Preparation of N-[2-methoxy-7-(1-methyl-1H-pyrazol-4-yl)naphthalen-1-yl]prop-2-enamide

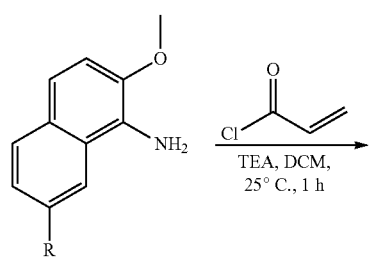

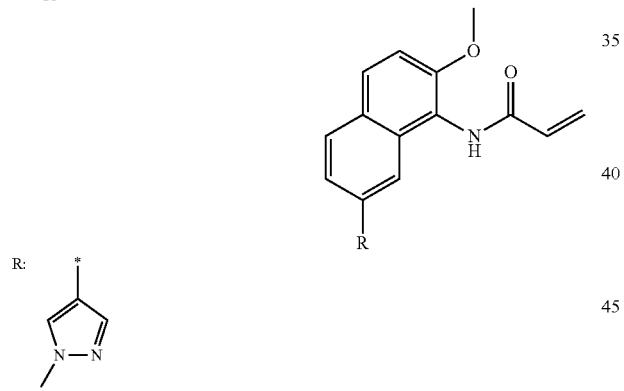

Route 4: General Scheme

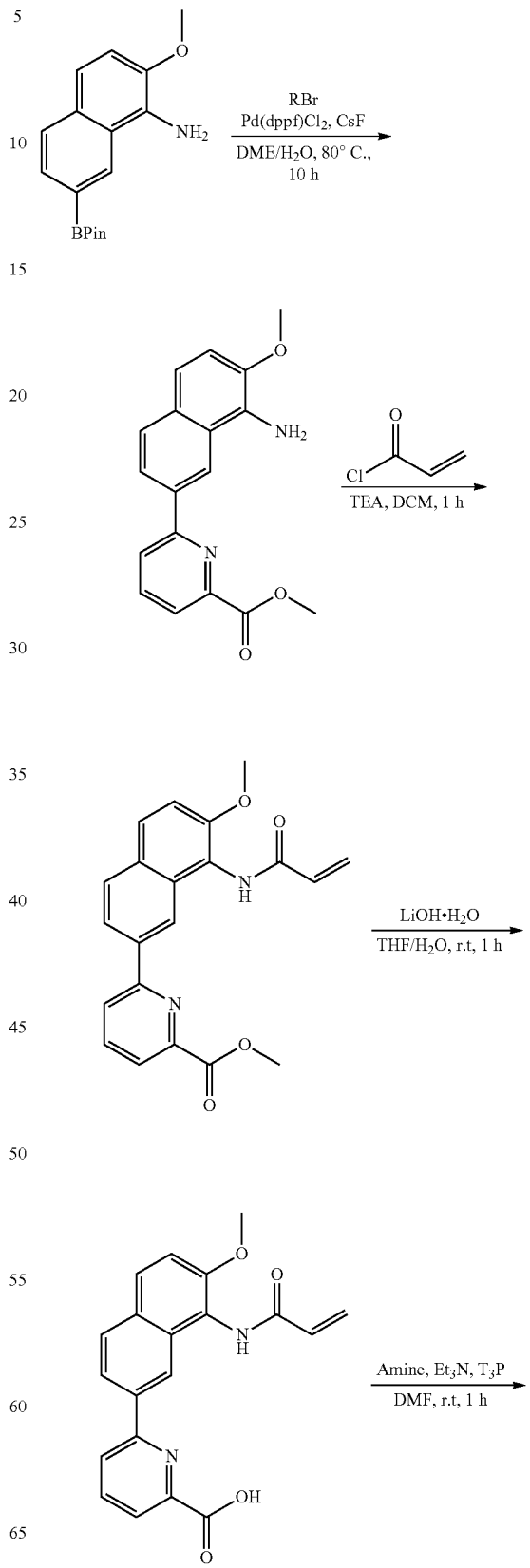

To a solution of 2-methoxy-7-(1-methylpyrazol-4-yl)naphthalen-1-amine (80 mg, 315.83 µmol, 1 eq) in DCM (4 mL) were added TEA (95.9 mg, 947.5 µmol, 3 eq) and prop-2-enoyl chloride (28.6 mg, 315.83 µmol, 1 eq) at 25° C. The mixture was stirred at 25° C. for 1 hour. The reaction mixture was poured into water (80 mL) and extracted with DCM (3×30 mL). The combined organic layer was washed with H₂O (2×30 mL) and brine (2×30 mL), dried over anhydrous Na₂SO₄, filtered, and concentrated in vacuo to give a residue. The residue was purified by prep-HPLC to afford the title compound (20.4 mg, 66.37 µmol, 21.02% yield, 100% purity) as a light yellow solid. LC-MS (ES⁺, m/z): 309.1 [(M+H)⁺], ¹H NMR (400 MHz, DMSO-d₆) =9.67 (s, 1H), 8.18 (s, 1H), 7.89-7.94 (m, 1H), 7.86 (s, 2H), 7.76 (s, 1H), 7.72-7.79 (m, 1H), 7.43 (d, J=9.04 Hz, 1H), 6.64 (dd, J=16.90, 1H), 6.25 (d, 0.7=17.20 Hz, 1H), 5.78 (d, J=10.10 Hz, 1H).

451

-continued

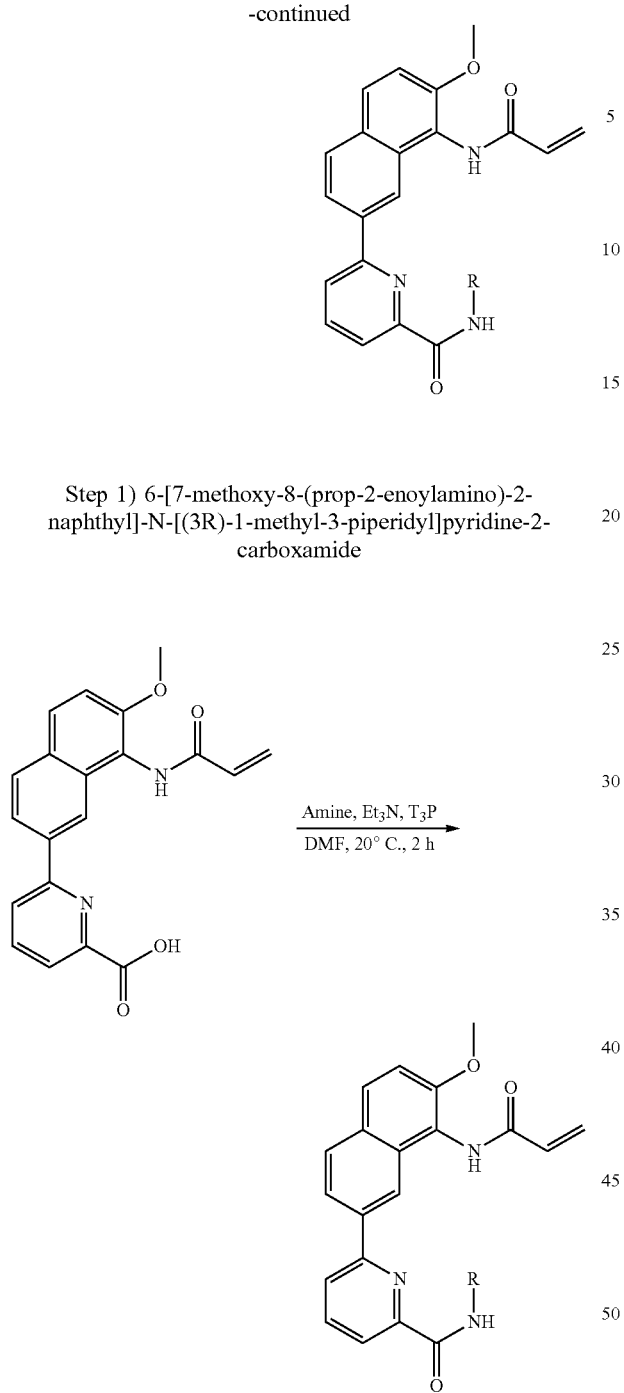

Step 1) 6-[7-methoxy-8-(prop-2-enoylamino)-2-naphthyl]-N-[(3R)-1-methyl-3-piperidyl]pyridine-2-carboxamide To a solution of 6-[7-methoxy-8-(prop-2-enoylamino)-2-naphthyl]pyridine-2-carboxylic acid (200 mg, 574.13 μmol, 1 eq) in DMF (2 mL) were added (3R)-1-methylpiperidin-3-amine (78.7 mg, 688.96 μmol, 1.2 eq), T₃P (548 mg, 861.2 μmol, 1.5 eq) and TEA (174.3 mg, 1.72 mmol, 3 eq). The mixture was stirred at 20° C. for 2 hours. The reaction mixture was poured into H₂O (50 mL) and extracted with EtOAc (3×30 mL). The organic phase was separated, washed with H₂O (2×30 mL) and brine (2×30 mL), dried over anhydrous Na₂SO₄, filtered, and concentrated in vacuo to give crude product. The residue was purified by prep-HPLC to afford the title compound 6-[7-methoxy-8-(prop-

452

2-enoylamino)-2-naphthyl]-N-[(3R)-1-methyl-3-piperidyl]pyridine-2-carboxamide (10.2 mg, 22.95 μmol, 4.00% yield) as a light yellow solid.

Route 4: General Scheme

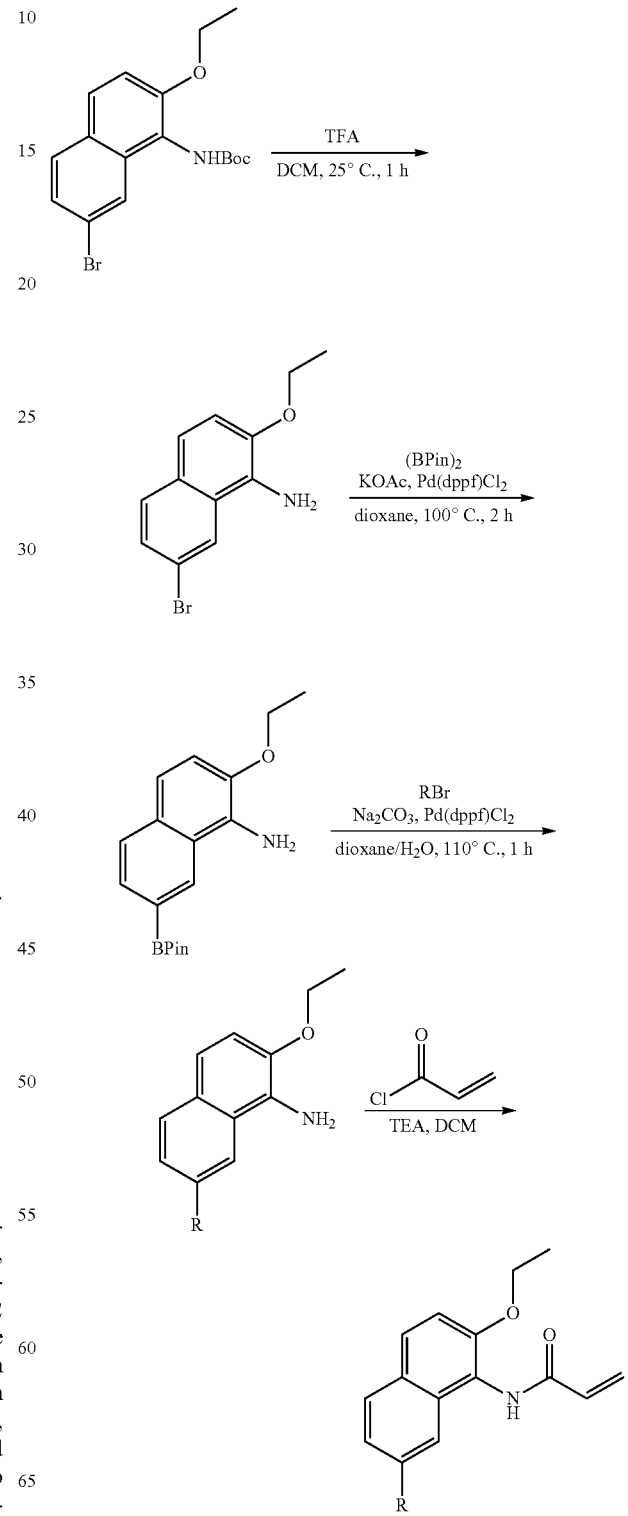

R:

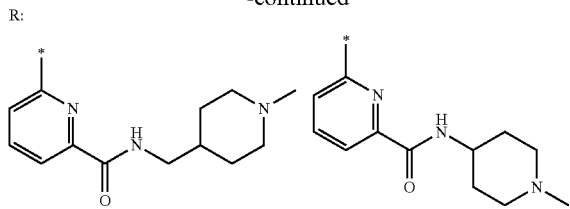

Step 1—7-Bromo-2-ethoxy-naphthalen-1-amine

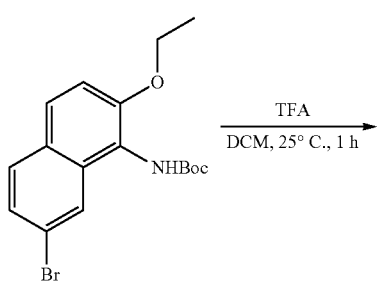

To a solution of tert-butyl N-(7-bromo-2-ethoxy-1-naphthyl)carbamate (1 g, 2.73 mmol, 1 eq) in DCM (10 mL) was added TFA (2 mL). The mixture was stirred at 25° C. for 1 hour. LCMS showed that the reaction was complete. The reaction mixture was added to ice water (100 mL). Then saturated $Na_2CO_3$ was slowly added to the mixture to adjust the mixture to pH=8~9. The mixture was extracted with DCM (3×30 mL). The organic phase was separated, washed with $H_2O$ (2×30 mL) and brine (2×30 mL), dried over anhydrous $Na_2SO_4$, filtered, and concentrated in vacuo to afford the title compound (700 mg, crude) as a light yellow solid. LC-MS ($ES^+$, m/z): 365.9 $[(M+H)^+]$.

Step 2—2-ethoxy-7-(4,4,5,5-tetramethyl-1,3,2-dioxaborolan-2-yl)naphthalen-1-amine

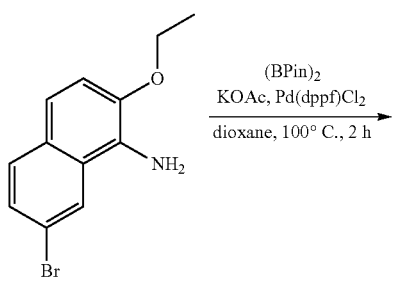

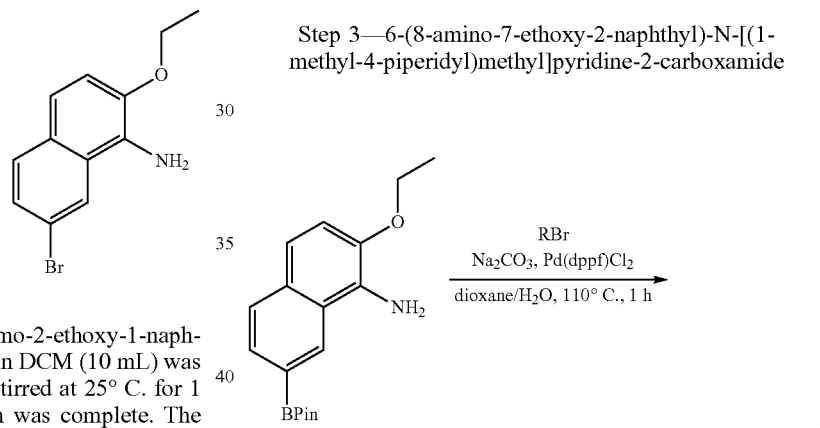

A mixture of 7-bromo-2-ethoxy-naphthalen-1-amine (700 mg, 2.63 mmol, 1 eq), 4,4,5,5-tetramethyl-2-(4,4,5,5-tetramethyl-1,3,2-dioxaborolan-2-yl)-1,3,2-dioxaborolane (1.34 g, 5.26 mmol, 2 eq), KOAc (1.29 g, 13.15 mmol, 5 eq), and $Pd(dppf)Cl_2$ (192.5 mg, 263.03 µmol, 0.1 eq) in dioxane (20 mL) was prepared. The mixture was stirred at 100° C. for 2 hours. The reaction mixture was filtered, and concentrated in vacuo to give crude product. The residue was purified by column chromatography ($SiO_2$, PE:EtOAc=10:0 to 8:1) to afford the title compound (800 mg, 2.55 mmol, 97.11% yield) as a light yellow solid. LC-MS ($ES^+$, m/z): 314.1 $[(M+H)^+]$.

Step 3—6-(8-amino-7-ethoxy-2-naphthyl)-N-[(1-methyl-4-piperidyl)methyl]pyridine-2-carboxamide A mixture of 6-bromo-N-[(1-methyl-4-piperidyl)methyl]pyridine-2-carboxamide (150 mg, 480.45 µmol, 1 eq), 2-ethoxy-7-(4,4,5,5-tetramethyl-1,3,2-dioxaborolan-2-yl)naphthalen-1-amine (180.6 mg, 576.54 µmol, 1.2 eq), $Na_2CO_3$ (152.8 mg, 1.44 mmol, 3 eq), and $Pd(dppf)Cl_2$ (35.2 mg, 48.05 µmol, 0.1 eq) in dioxane (2 mL) and $H_2O$ (0.5 mL) was heated to 110° C. and stirred for 1 hour. The reaction mixture was added to 30 mL saturated EDTA solution and stirred for 1 hour. The mixture was extracted with EtOAc (3×30 mL). The organic phase was separated, washed with $H_2O$ (2×30 mL) and brine (2×30 mL), dried over anhydrous $Na_2SO_4$, filtered, and concentrated in vacuo to give a residue. The residue was purified by prep-TLC ($SiO_2$, DCM:MeOH=10:1) to afford the title compound (180

Step 4—Compound 367: Preparation of 6-[7-ethoxy-8-(prop-2-enamido)naphthalen-2-yl]-N-(1-methylpiperidin-4-yl)pyridine-2-carboxamide

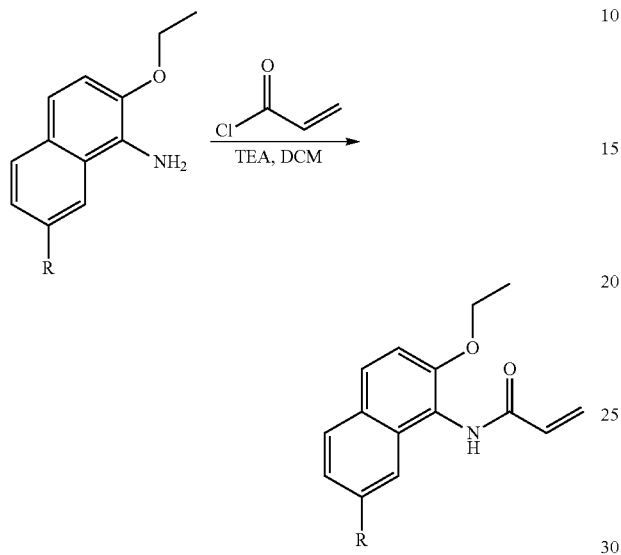

A mixture of 6-(8-amino-7-ethoxy-2-naphthyl)-N-[(1-methyl-4-piperidyl)methyl]pyridine-2-carboxamide (140 mg, 334.5 μmol, 1 eq), TEA (101.5 mg, 1 μmol, 3 eq) in DCM (2 mL), add prop-2-enoyl chloride (30.3 mg, 334.5 μmol, 1 eq) at 0° C., and the mixture was stirred at 25° C. for 2 hours. The reaction mixture was poured into $H_2O$ (50 mL) and the mixture was extracted with DCM (3×30 mL). The organic phase was separated, washed with $H_2O$ (2×30 mL) and brine (2×30 mL), dried over anhydrous $Na_2SO_4$, filtered, and concentrated in vacuo to give a residue. The residue was purified by prep-HPLC to afford the title compound (27.6 mg, 58.4 μmol, 17.46% yield, 100% purity) as a light yellow solid. LC-MS (ES+, m/z): 459.3 [(M+H)+]

Route 5: General Scheme

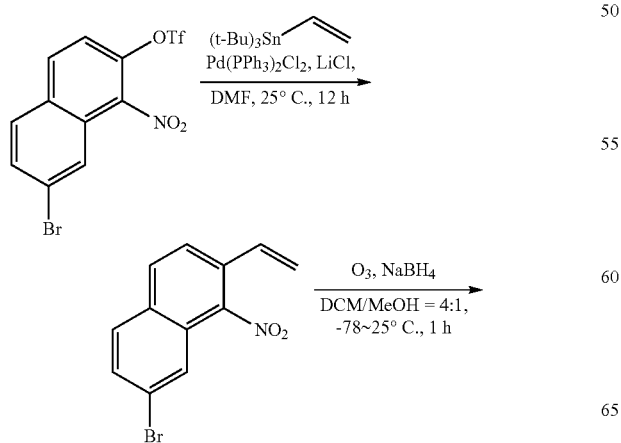

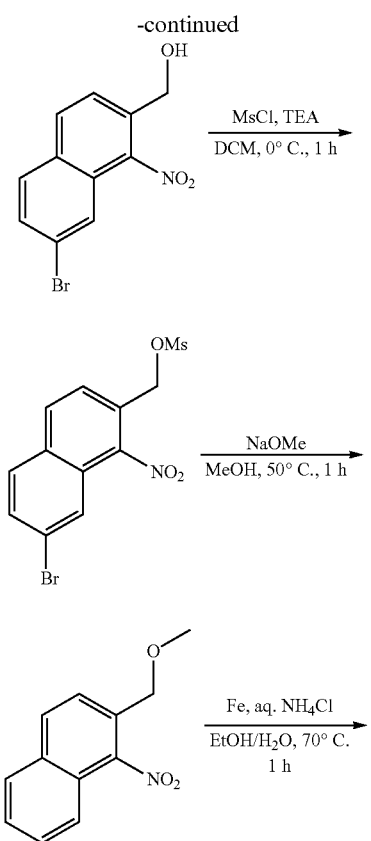

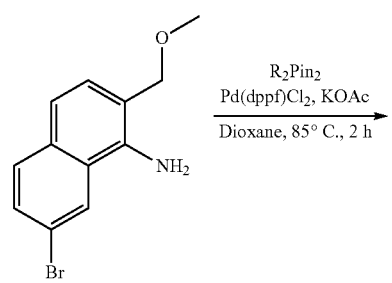

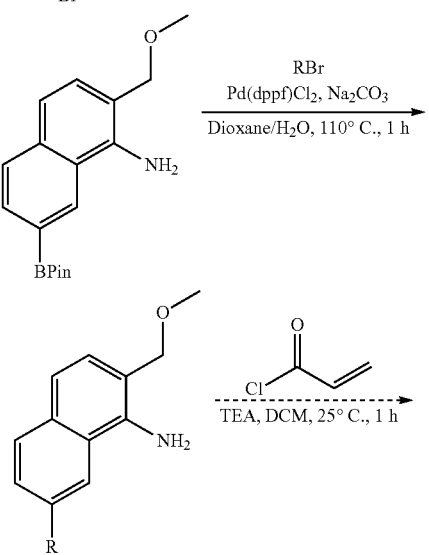

-continued

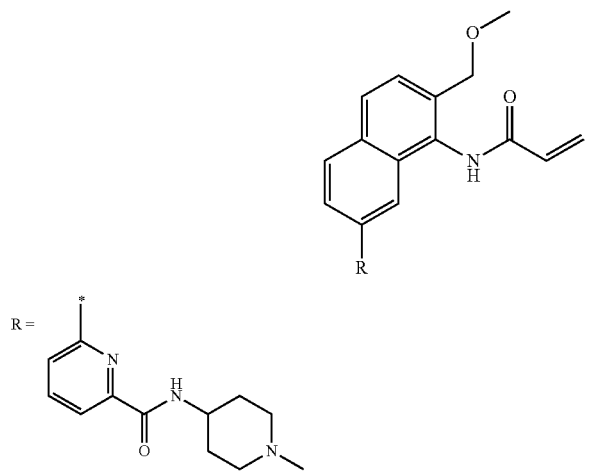

R =

Step 1—7-bromo-1-nitro-2-vinyl-naphthalene

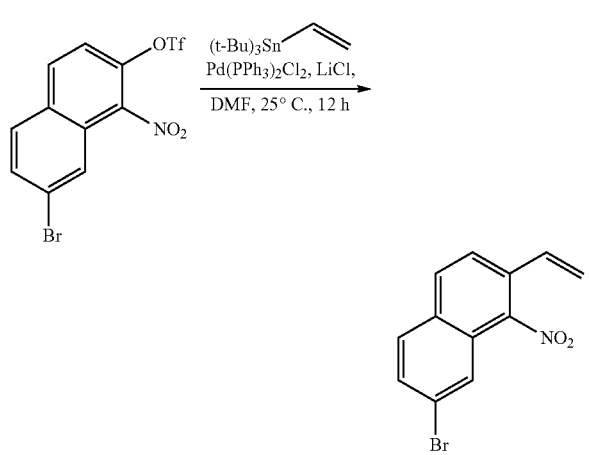

To a solution of (7-bromo-1-nitro-2-naphthyl)trifluoromethanesulfonate (6. g, 15 mmol, 1 eq) and tributyl(vinyl)stannane (4.99 g, 15.75 mmol, 1.05 eq) in DMF (100 mL) was added LiCl (1.91 g, 44.99 mmol, 3 eq) and Pd(PPh$_3$)$_2$Cl$_2$ (877.10 mg, 1.25 mmol, 0.1 eq). The reaction mixture was stirred at 25° C. for 12 hours under N$_2$. TLC (PE:EtOAc=10:1, SM/Rf=0.2, TM/Rf=0.4) showed that the reaction was complete. The reaction mixture was poured into H$_2$O (450 mL) and extracted with EtOAc (3×200 mL). The combined organic layers were washed with H$_2$O (2×200 mL) and brine (2×200 mL), dried over anhydrous Na$_2$SO$_4$, filtered, and concentrated in vacuo to give a residue. The residue was purified by column chromatography (SiO$_2$, PE:EtOAc=1:0 to 10:1) to afford the title compound 7-bromo-1-nitro-2-vinyl-naphthalene (4. g, 11.51 mmol, 76.73% yield) as a yellow solid.

Step 2—(7-bromo-1-nitro-2-naphthyl)methanol

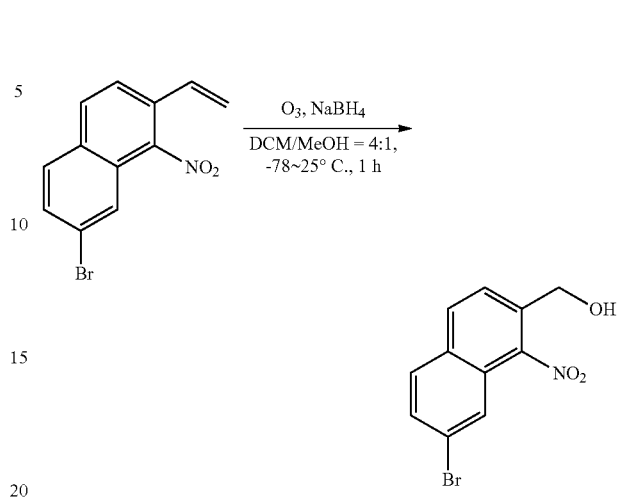

A solution of 7-bromo-1-nitro-2-vinyl-naphthalene (6. g, 17.26 mmol, 1 eq) in DCM (240 mL) and MeOH (60 mL) was cooled to −78° C. The reaction was bubbled with ozone (828.4 g, 17.26 mmol, 1 eq) at −78° C. for 0.5 h. After that, NaBH$_4$ (1.96 g, 51.78 mmol, 3 eq) was added. The resulting reaction mixture was warmed to 25° C. and stirred at 25° C. for 0.5 h. TLC (PE:EtOAc=4:1, SM/Rf=0.7, TM/Rf=0.3) showed that the reaction was complete. The reaction mixture was poured into H$_2$O (300 mL) and extracted with EtOAc (2×100 mL). The combined organic layers were washed with H$_2$O (2×100 mL) and brine (2×100 mL), dried over anhydrous Na$_2$SO$_4$, filtered, and concentrated in vacuo to give a residue. The residue was purified by column chromatography (SiO$_2$, PE:EtOAc=10:1 to 4:1) to afford the title compound (7-bromo-1-nitro-2-naphthyl)methanol (3.2 g, 11.34 mmol, 65.72% yield) as a white solid.

Step 3—(7-bromo-1-nitro-2-naphthyl)methyl methanesulfonate

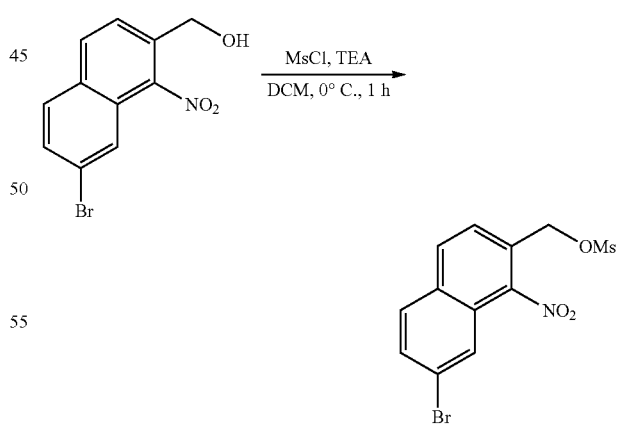

To a solution of (7-bromo-1-nitro-2-naphthyl)methanol (1.7 g, 6.03 mmol, 1 eq) in DCM (20 mL) was added TEA (3.05 g, 30.13 mmol, 5 eq) and methanesulfonyl chloride (1.04 g, 9.04 mmol, 1.5 eq) at 0° C. The resulting reaction mixture was stirred at 0° C. for 1 h. TLC (PE:EtOAc=3:1, SM/Rf=0.5, TM/Rf=0.4) showed that the reaction was complete. The reaction mixture was poured into H$_2$O (400 mL)

and extracted with EtOAc (2×200 mL). The combined organic layers were washed with H₂O (2×100 mL) and brine (2×100 mL), dried over anhydrous Na₂SO₄, filtered, and concentrated in vacuo to afford the title compound (7-bromo-1-nitro-2-naphthyl)methyl methanesulfonate (2. g, crude) as a white solid, which was used for the next step directly without further purification.

Step 4—7-bromo-2-(methoxymethyl)-1-nitro-naphthalene

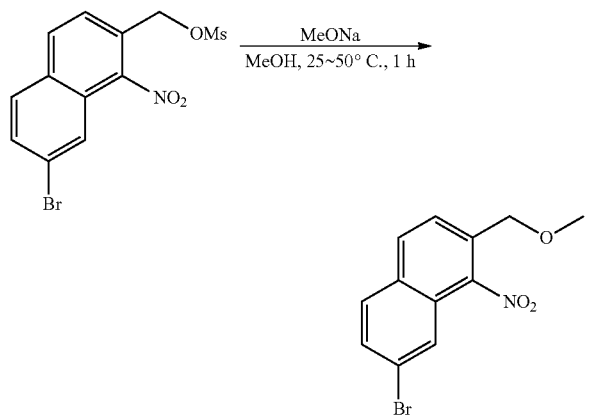

To a solution of (7-bromo-1-nitro-2-naphthyl)methyl methanesulfonate (1.7 g, 4.72 mmol, 1 eq) in MeOH (34 mL) was added CH₃ONa (0.76 g, 14.16 mmol, 3 eq) at 25° C. The mixture was stirred at 50° C. for 1 h. TLC (PE:EtOAc=4:1, SM/Rf=0.3, TM/Rf=0.7) showed that the reaction was complete. The reaction mixture was poured into H₂O (300 mL) and extracted with EtOAc (2×100 mL). The combined organic layers were washed with H₂O (2×50 mL) and brine (2×50 mL), dried over anhydrous Na₂SO₄, filtered, and concentrated in vacuo to give a residue. The residue was purified by column chromatography (SiO₂, PE:EtOAc=10:1 to 6:1) to afford the title compound 7-bromo-2-(methoxymethyl)-1-nitro-naphthalene (0.77 g, 2.6 mmol, 55.09% yield) as a yellow solid.

Step 5—7-bromo-2-(methoxymethyl)naphthalen-1-amine

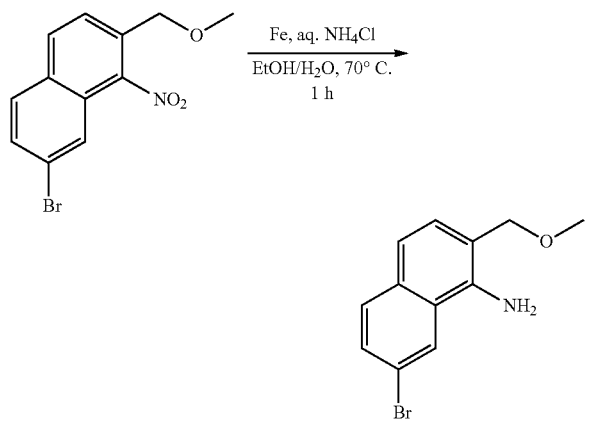

To a solution of 7-bromo-2-(methoxymethyl)-1-nitro-naphthalene (1.5 g, 5.07 mmol, 1 eq) in EtOH (30 mL) was added saturated NH₄Cl (4 mL) at 25° C. Then, Fe (1.41 g, 25.33 mmol, 3 eq) was added at 70° C., and the reaction mixture was stirred at 70° C. for 1 h. TLC (PE:EtOAc=4:1, SM/Rf=0.5, TM/Rf=0.3) showed that the reaction was complete. The reaction mixture was poured into H₂O (200 mL) and extracted with EtOAc (3×50 mL). The combined organic layers were washed with H₂O (2×50 mL) and brine (2×50 mL), dried over anhydrous Na₂SO₄, filtered, and concentrated in vacuo to give a residue. The residue was purified by column chromatography (SiO₂, PE:EtOAc=20:1 to 8:1) to afford the title compound 7-bromo-2-(methoxymethyl)naphthalen-1-amine (1.3 g, 4.88 mmol, 96.43% yield) as a yellow solid. LC-MS (ES⁺, m/z): 266.0 [(M+H)⁺]

Step 6—2-(methoxymethyl)-7-(4,4,5,5-tetramethyl-1,3,2-dioxaborolan-2-yl) Naphthalen-1-amine

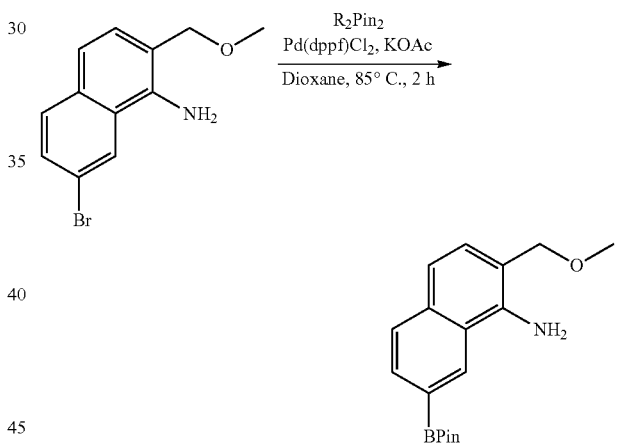

To a solution of 7-bromo-2-(methoxymethyl)naphthalen-1-amine (0.2 g, 0.75 mmol, 1 eq) and 4,4,5,5-tetramethyl-2-(4,4,5,5-tetramethyl-1,3,2-dioxaborolan-2-yl)-1,3,2-dioxaborolane (0.57 g, 2.25 mmol, 3 eq) in dioxane (15 mL) were added KOAc (0.59 g, 6.01 mmol, 8 eq) and Pd(dppf)Cl₂ (110 mg, 150.3 µmol, 0.2 eq) at 25° C. The resulting reaction mixture was stirred at 85° C. for 2 hours under N₂. LCMS showed that the reaction was complete. The reaction mixture was concentrated in vacuo to give a residue. The residue was purified by column chromatography (SiO₂, PE:EtOAc=10:1 to 4:1) to afford the title compound 2-(methoxymethyl)-7-(4,4,5,5-tetramethyl-1,3,2-dioxaborolan-2-yl) naphthalen-1-amine (1.2 g, 3.83 mmol, 92.70% yield) as a yellow oil. LC-MS (ES⁺, m/z): 314.1 [(M+H)⁺]

Step 7—6-[8-amino-7-(methoxymethyl)-2-naphthyl]-N-(1-methyl-4-piperidyl)pyridine-2-carboxamide

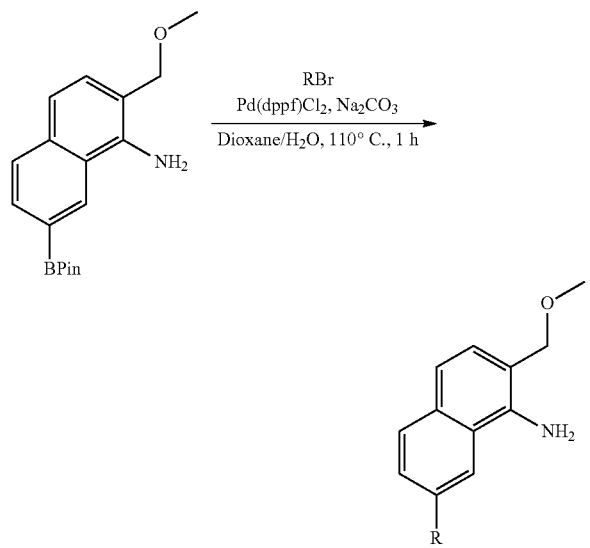

To a solution of 2-(methoxymethyl)-7-(4,4,5,5-tetramethyl-1,3,2-dioxaborolan-2-yl) naphthalen-1-amine (180 mg, 574.7 μmol, 1.2 eq) in dioxane (4 mL) and H₂O (1 mL) were successively added 6-bromo-N-(1-methyl-4-piperidyl) pyridine-2-carboxamide (142.8 mg, 478.93 μmol, 1 eq), Na₂CO₃ (152.3 mg, 1.44 mmol, 3 eq) and Pd(dppf)Cl₂ (35 mg, 47.9 μmol, 0.1 eq) at 25° C. The resulting reaction mixture was stirred at 110° C. for 1 hour. LCMS showed that the reaction was complete. The reaction mixture was poured into 80 mL saturated EDTA and followed by 30 mL EtOAc. The solution was stirred at 20° C. for 2 h. The organic phase was separated, and the aqueous phase was extracted with EtOAc (2×20 mL). The combined organic layer was washed successively with water (2×20 mL) and brine (1×20 mL), dried over anhydrous Na₂SO₄, filtered, and concentrated to give a residue. The residue was purified by prep-TLC (SiO₂, DCM:MeOH=10:1) to afford the title compound (160 mg, 395.55 μmol, 82.59% yield) as a light yellow solid. LC-MS (ES⁺, m/z): 405.3 [(M+H)⁺].

Step 8—Compound 380: Preparation of 6-[7-(methoxymethyl)-8-(prop-2-enamido)naphthalen-2-yl]-N-(1-methylpiperidin-4-yl)pyridine-2-carboxamide

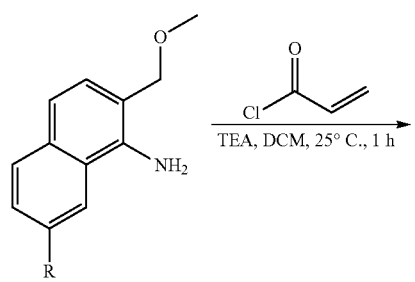

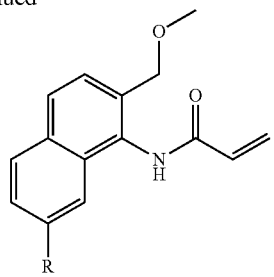

R =

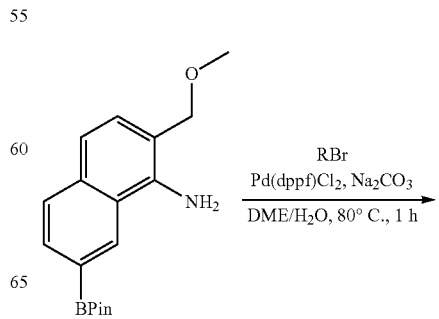

To a solution of 6-[8-amino-7-(methoxymethyl)-2-naphthyl]-N-(1-methyl-4-piperidyl)pyridine-2-carboxamide (140 mg, 346.1 μmol, 1 eq) in DCM (4 mL) were added TEA (105.1 mg, 1.04 mmol, 144.52 μL, 3 eq) and prop-2-enoyl chloride (62.7 mg, 692.21 μmol, 2 eq) at 25° C. The mixture was stirred at 25° C. for 1 h. Upon completion of the reaction as indicated by LCMS, the reaction mixture was poured into water and extracted with EtOAc (3×30 mL). The combined organic layer was washed with H₂O (2×30 mL) and brine (2×30 mL), dried over anhydrous Na₂SO₄, filtered, and concentrated in vacuo to give a residue. The residue was purified by prep-HPLC to afford the title compound (22.5 mg, 49.07 μmol, 14.18% yield, 100% purity) as a white solid. LC-MS (ES⁺, m/z): 459.3 [(M+H)+]. ¹H NMR (400 MHz, DMSO-d₆)=10.30 (s, 1H), 8.83 (s, 1H), 8.42 (d, J=8.50, 2H), 8.30 (d, J=7.30 Hz, 1H), 8.12-8.18 (m, 1H), 8.11 (d, J=4.20 Hz, 1H), 8.02 (d, J=6.970 Hz, 1H), 7.98 (d, J=8.60 Hz, 1H), 7.69 (d, J=8.40 Hz, 1H), 6.73 (d, J=17.00, 10.27 Hz, 1H), 6.34 (d, J=17.00, 1.71 Hz, 1H), 5.85 (d, J=10.20, 1.65 Hz, 1H), 4.49 (s, 2H), 3.72-3.91 (m, 1H), 3.29-3.32 (m, 2H), 2.81 (d, J=11.50 Hz, 2H), 2.21 (s, 3H), 1.94-2.09 (m, 2H), 1.80-1.90 (m, 2H), 1.67-1.80 (m, 2H).

Route 6: General Scheme

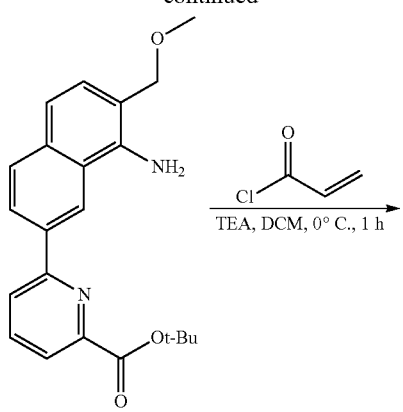
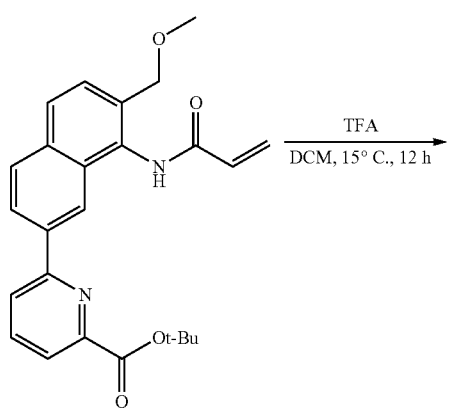
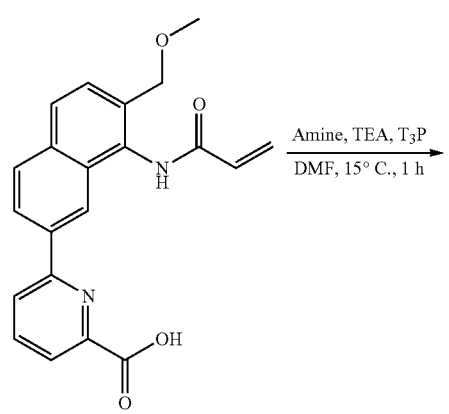
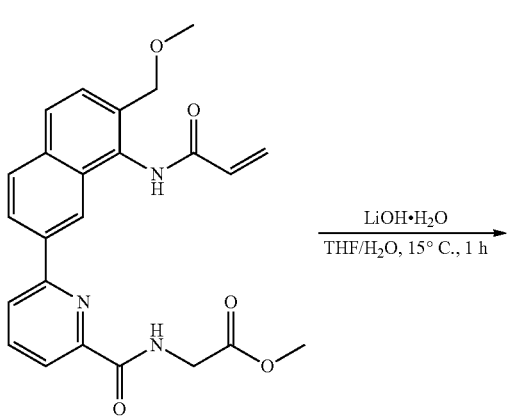
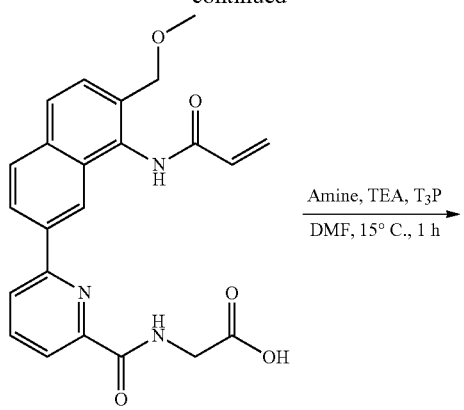
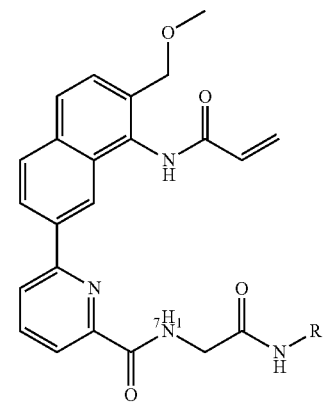
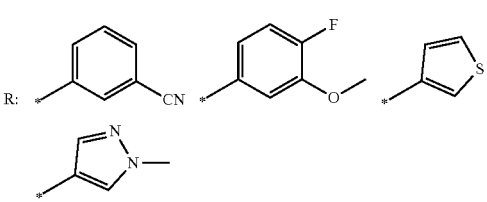
Step 1—tert-butyl 6-[8-amino-7-(methoxymethyl)-2-naphthyl]pyridine-2-carboxylate
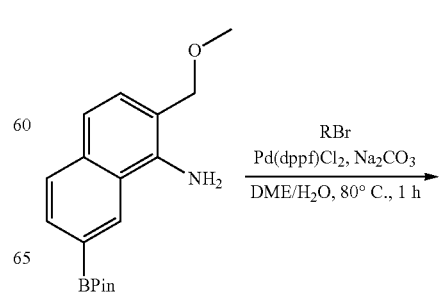

-continued

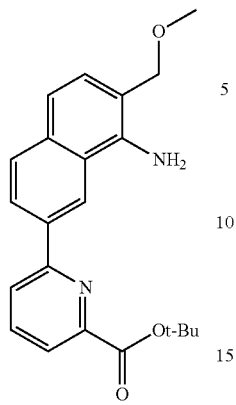

To a solution of tert-butyl 6-bromopyridine-2-carboxylate (725.2 mg, 2.81 mmol, 1.1 eq) and 2-(methoxymethyl)-7-(4,4,5,5-tetramethyl-1,3,2-dioxaborolan-2-yl)naphthalen-1-amine (0.8 g, 2.55 mmol, 1 eq) in DME (16 mL) and H$_2$O (4 mL) were added Na$_2$CO$_3$ (812.2 mg, 7.66 mmol, 3 eq) and Pd (dppf)Cl$_2$ (1.87 g, 2.55 mmol, 1 eq). The reaction mixture was stirred at 80° C. for 1 hr under N$_2$. TLC (PE:EtOAc=1:1, SM Rf=0.62, TM Rf=0.23) showed that the reaction was complete. The reaction was poured into ~10 mL saturated EDTA and stirred at 25° C. for 1 h. The mixture was extracted with EtOAc (3×10 mL), and the combined organic layer was washed with brine (3×10 mL), dried over anhydrous Na$_2$SO$_4$, filtered, and concentrated in vacuo to give a residue. The residue was purified by column chromatography (SiO$_2$, PE:EtOAc=20/1 to 1/1) to afford the title compound tert-butyl 6-[8-amino-7-(methoxymethyl)-2-naphthyl]pyridine-2-carboxylate (0.61 g, 1.67 mmol, 65.53% yield) as a yellow oil.

Step 2—tert-butyl 6-[7-(methoxymethyl)-8-(prop-2-enoylamino)-2-naphthyl]pyridine-2-carboxylate

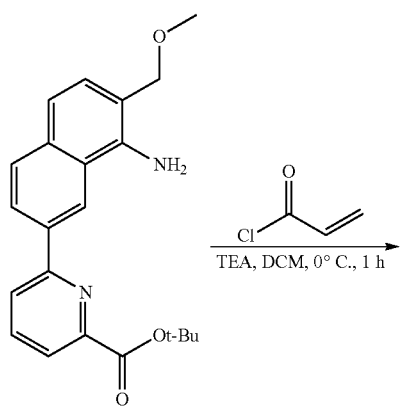

-continued

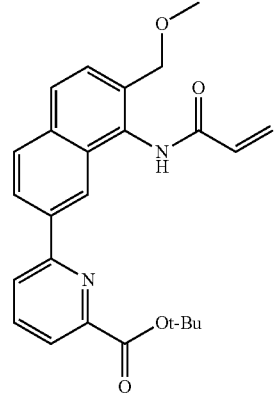

To a solution of tert-butyl 6-[8-amino-7-(methoxymethyl)-2-naphthyl]pyridine-2-carboxylate (0.55 g, 1.51 mmol, 1 eq) in DCM (2 mL) were added TEA (763.6 mg, 7.55 mmol, 1.05 mL, 5 eq) and prop-2-enoyl chloride (163.9 mg, 1.81 mmol, 147.67 µL, 1.2 eq). The reaction mixture was stirred at 0° C. for 1 h under N$_2$. TLC (PE:EtOAc=1:1, SM Rf=0.40, TM Rf=0.15) showed that the reaction was complete. The reaction mixture was poured into 50 mL H$_2$O and extracted with DCM (3×50 mL). The combined organic layers were washed with H$_2$O (2×50 mL) and brine (2×50 mL), dried over anhydrous Na$_2$SO$_4$, filtered, and concentrated in vacuo to give a residue. The residue was purified by prep-TLC (SiO$_2$, PE:EtOAc=1:1) to afford the title compound tert-butyl 6-[7-(methoxymethyl)-8-(prop-2-enoylamino)-2-naphthyl]pyridine-2-carboxylate (0.43 g, 1.03 mmol, 68.08% yield) as a yellow solid.

Step 3—6-[7-(methoxymethyl)-8-(prop-2-enoylamino)-2-naphthyl]pyridine-2-carboxylic acid

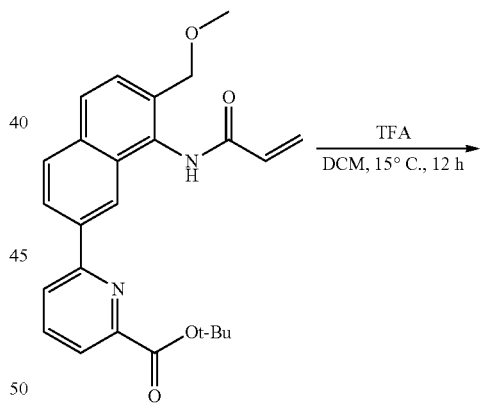

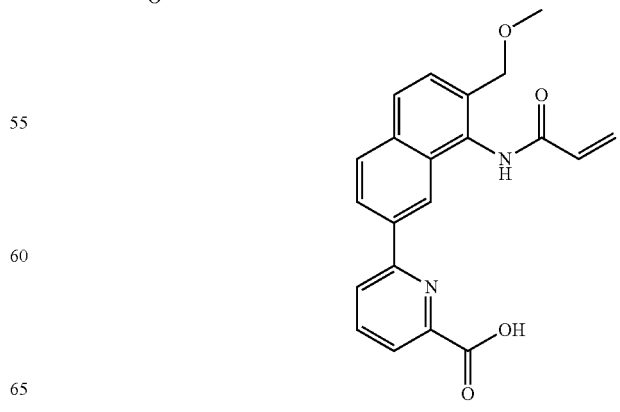

467

To a solution of tert-butyl 6-[7-(methoxymethyl)-8-(prop-2-enoylamino)-2-naphthyl]pyridine-2-carboxylate (0.38 g, 908.04 µmol, 1 eq) in DCM (6 mL) was added TFA (4.62 g, 40.52 mmol, 3 mL, 44.62 eq). The reaction mixture was stirred at 15° C. for 12 h. LCMS showed that the reaction was complete. The reaction mixture was concentrated in vacuo to afford the title compound 6-[7-(methoxy methyl)-8-(prop-2-enoylamino)-2-naphthyl]pyridine-2-carboxylic acid (0.5 g, crude, TFA) as a yellow oil, which was used for the next step directly without further purification. LC-MS (ES$^+$, m/z): 363.2 [(M+H)$^+$]

Step 4—methyl 2-[[6-[7-(methoxymethyl)-8-(prop-2-enoylamino)-2-naphthyl]pyridine-2-carbonyl]amino]acetate

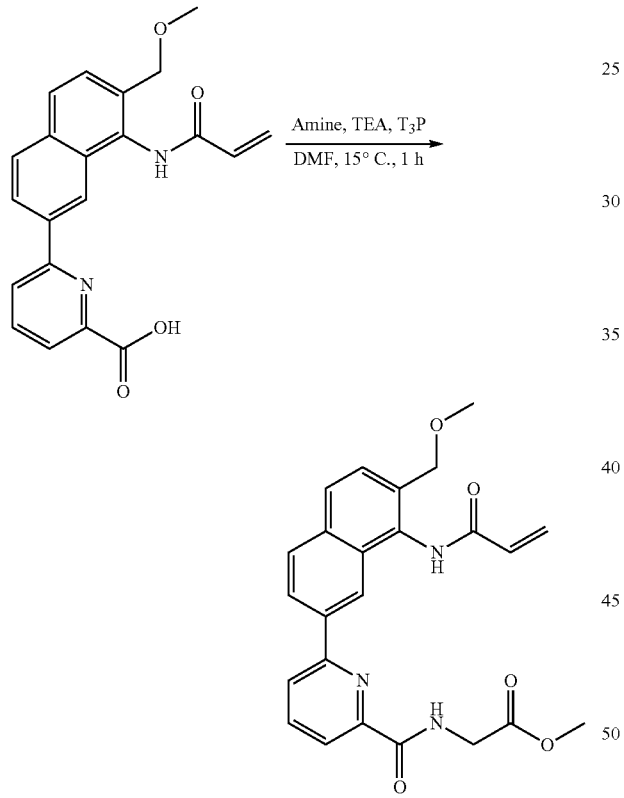

To a solution of 6-[7-(methoxymethyl)-8-(prop-2-enoylamino)-2-naphthyl]pyridine-2-carboxylic acid (0.5 g, 1.05 mmol, 1 eq, TFA) in DMF (8 mL) were added methyl 2-aminoacetate;hydrochloride (263.6 mg, 2.1 mmol, 2 eq) and TEA (531 mg, 5.25 mmol, 730.41 µL, 5 eq). Then, T$_3$P (1 g, 1.57 mmol, 936.29 µL, 50% purity, 1.5 eq) was added, and the resulting reaction mixture was stirred at 15° C. for 1 h. TLC (DCM:MeOH=10:1, SM Rf=0.00, TM Rf=0.28) showed that the reaction was complete. The reaction mixture was poured into 100 mL H$_2$O, extracted with EtOAc (3×100

468 mL). The combined organic layer was washed with H$_2$O (2×50 mL) and brine (2×50 mL), dried over anhydrous Na$_2$SO$_4$, filtered, and concentrated in vacuo to give a residue. The residue was purified by prep-TLC (SiO$_2$, DCM: MeOH=10:1) to afford the title compound methyl 2-[[6-[7-(methoxymethyl)-8-(prop-2-enoylamino)-2-naphthyl]pyridine-2-carbonyl]amino]acetate (0.35 g, 807.46 µmol, 76.94% yield) as a white solid.

Step 5—2-[[6-[7-(methoxymethyl)-8-(prop-2-enoylamino)-2-naphthyl]pyridine-2-carbonyl]amino]acetic acid

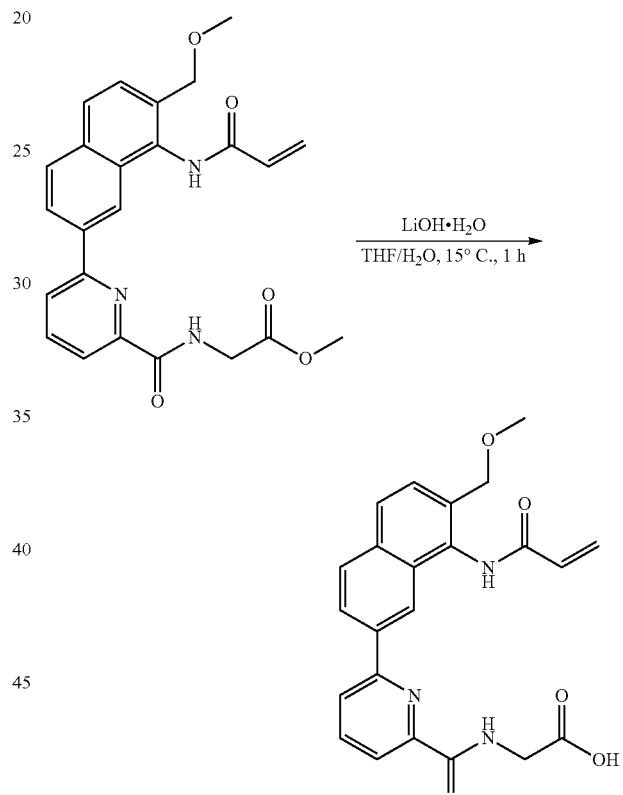

To a solution of methyl 2-[[6-[7-(methoxymethyl)-8-(prop-2-enoylamino)-2-naphthyl]pyridine-2-carbonyl]amino]acetate (0.3 g, 692.11 µmol, 1 eq) in THF (8 mL) and H$_2$O (2 mL) was added LiOH·H$_2$O (87.1 mg, 2.08 mmol, 3 eq). The reaction mixture was stirred at 15° C. for 1 h. TLC (DCM:MeOH=10:1, SM Rf=0.30, TM Rf=0.00) showed that the reaction was complete. The reaction mixture was poured into ~50 mL water, adjusted to pH=6 with saturated citric acid, and extracted with EtOAc (3×50 mL). The combined organic layer was dried over anhydrous Na$_2$SO$_4$, filtered, and concentrated in vacuo to afford the title compound 2-[[6-[7-(methoxymethyl)-8-(prop-2-enoylamino)-2-naphthyl]pyridine-2-carbonyl]amino]acetic acid (0.32 g, crude) as a yellow solid which was used for the next step directly without further purification.

Step 6—Compound 392: Preparation of N-{7-[6-({[(4-fluoro-3-methoxyphenyl) carbamoyl] methyl}carbamoyl)pyridin-2-yl]-2-(methoxymethyl) naphthalen-1-yl}prop-2-enamide Route 7: General Scheme

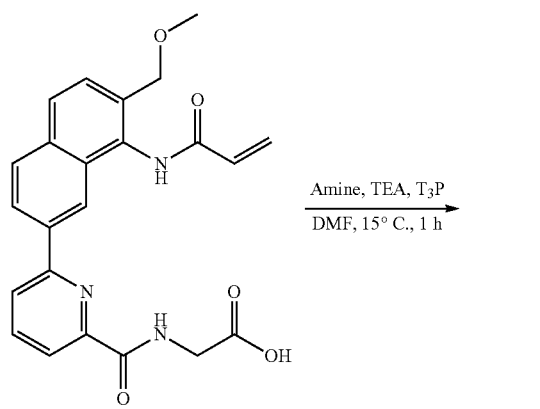

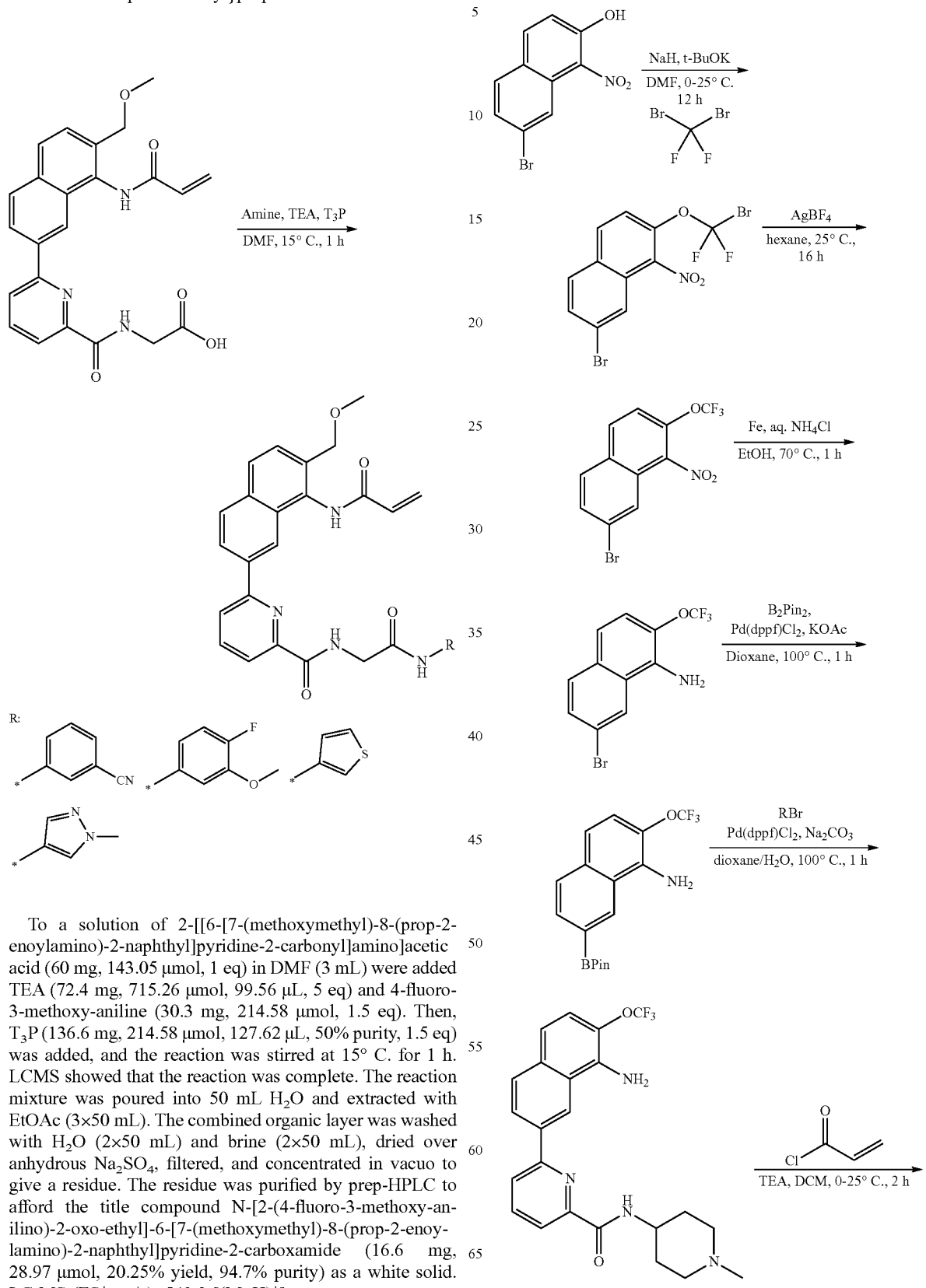

To a solution of 2-[[6-[7-(methoxymethyl)-8-(prop-2-enoylamino)-2-naphthyl]pyridine-2-carbonyl]amino]acetic acid (60 mg, 143.05 μmol, 1 eq) in DMF (3 mL) were added TEA (72.4 mg, 715.26 μmol, 99.56 μL, 5 eq) and 4-fluoro-3-methoxy-aniline (30.3 mg, 214.58 μmol, 1.5 eq). Then, T$_3$P (136.6 mg, 214.58 μmol, 127.62 μL, 50% purity, 1.5 eq) was added, and the reaction was stirred at 15° C. for 1 h. LCMS showed that the reaction was complete. The reaction mixture was poured into 50 mL H$_2$O and extracted with EtOAc (3×50 mL). The combined organic layer was washed with H$_2$O (2×50 mL) and brine (2×50 mL), dried over anhydrous Na$_2$SO$_4$, filtered, and concentrated in vacuo to give a residue. The residue was purified by prep-HPLC to afford the title compound N-[2-(4-fluoro-3-methoxy-anilino)-2-oxo-ethyl]-6-[7-(methoxymethyl)-8-(prop-2-enoylamino)-2-naphthyl]pyridine-2-carboxamide (16.6 mg, 28.97 μmol, 20.25% yield, 94.7% purity) as a white solid. LC-MS (ES$^+$, m/z): 543.2 [(M+H)$^+$]

471
-continued

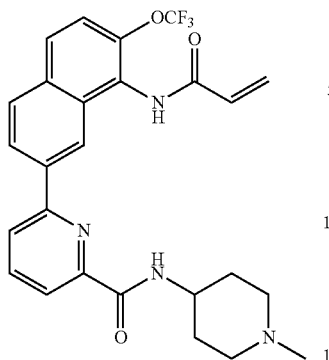

Route 2: Step 1—7-bromo-2-[bromo(difluoro)methoxy]-1-nitro-naphthalene

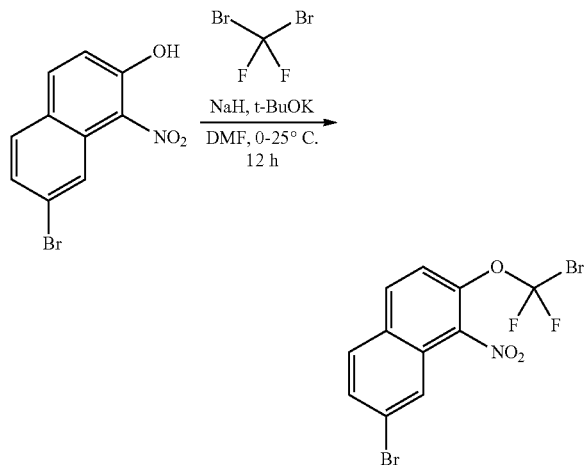

To a mixture of 7-bromo-1-nitro-naphthalen-2-ol (5 g, 18.65 mmol, 1 eq) in DMF (50 mL) was added NaH (2.24 g, 55.96 mmol, 60% purity, 3 eq) at 0° C. The mixture was stirred at 0° C. for 0.5 h, and KOtBu (2.3 g, 20.52 mmol, 1.1 eq) and dibromodifluoromethane (11.74 g, 55.96 mmol, 5.17 mL, 3 eq) in DMF (50 mL) were added at 0° C. The mixture was stirred at 25° C. for 12 h. HPLC showed ~30% reactant and ~60% product was detected. The residue was poured into saturated NH₄Cl (100 mL) and the aqueous phase was extracted with EtOAc (4×100 mL). The combined organic phase was washed with brine (4×100 mL), dried with anhydrous Na₂SO₄, filtered, and concentrated in vacuo. The residue was purified by silica gel chromatography (SiO₂, PE:EtOAc=1:0) to afford the title compound (1 g, 2.28 mmol, 12.22% yield, 90.455% purity) as a yellow solid. Some impure product (3 g, 4.53 mmol, 24.31% yield, 60% purity) was obtained as a yellow solid. $^1$H NMR (400 MHz, DMSO-$d_6$) δ=8.52 (d, J=8.8 Hz, 1H), 8.27 (d, J=8.8 Hz, 1H), 8.10 (s, 1H), 8.01 (dd, J=1.6, 8.8 Hz, 1H), 7.93 (d, J=9.2 Hz, 1H)

472

Step 2—7-bromo-1-nitro-2-(trifluoromethoxy)naphthalene

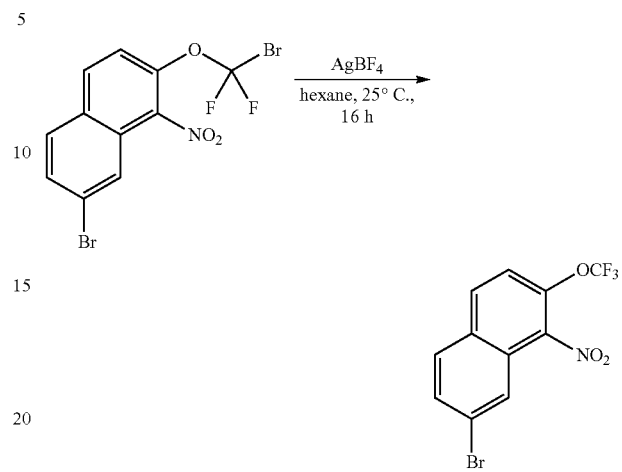

To a mixture of 7-bromo-2-[bromo(difluoro)methoxy]-1-nitro-naphthalene (500 mg, 1.26 mmol, 1 eq) in hexane (40 mL) was added AgBF₄ (1.47 g, 7.56 mmol, 6 eq) at 25° C. The mixture was stirred at 25° C. for 16 h. HPLC showed the starting material was consumed. The combined organic phase was concentrated in vacuo. The residue was purified by silica gel chromatography (SiO₂, PE:EtOAc=1:0 to 10:1) to afford the title compound (150 mg, 446.35 μmol, 35.44% yield) as a white solid. TLC (PE:EtOAc=1:0, SM=0.10, TM=0.14) $^1$H NMR (400 MHz, CDCl₃) δ=8.04 (d, J=9.2 Hz, 1H), 8.00 (s, 1H), 7.83 (d, J=8.8 Hz, 1H), 7.74 (dd, J=1.2, 8.8 Hz, 1H), 7.61-7.49 (d, J=9.2 Hz, 1H); F NMR (400 MHz, CDCl₃) δ=−56.96.

Step 3—7-bromo-2-(trifluoromethoxy)naphthalen-1-amine

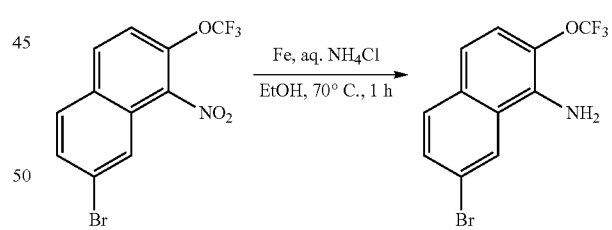

To a mixture of 7-bromo-1-nitro-2-(trifluoromethoxy)naphthalene (130 mg, 386.83 μmol, 1 eq) in EtOH (5 mL) and saturated NH₄Cl (1 mL) was added Fe (108 mg, 1.93 mmol, 5 eq) at 70° C. The mixture was stirred at 70° C. for 1 h. TLC showed no reactant was remained and product was detected. The residue was poured into H₂O (10 mL) and the aqueous phase was filtered with diatomite, and extracted with EtOAc (3×15 mL). The combined organic phase was washed with brine (3×15 mL), dried with anhydrous Na₂SO₄, filtered, and concentrated in vacuo. The residue was purified by prep-TLC to afford the title compound (100 mg, 326.71 μmol, 84.46% yield) as a white solid. TLC (PE:EtOAc=1:0, SM=0.14, TM=0.09)

Step 4—7-(4,4,5,5-tetramethyl-1,3,2-dioxaborolan-2-yl)-2-(trifluoromethoxy)naphthalene-1-amine

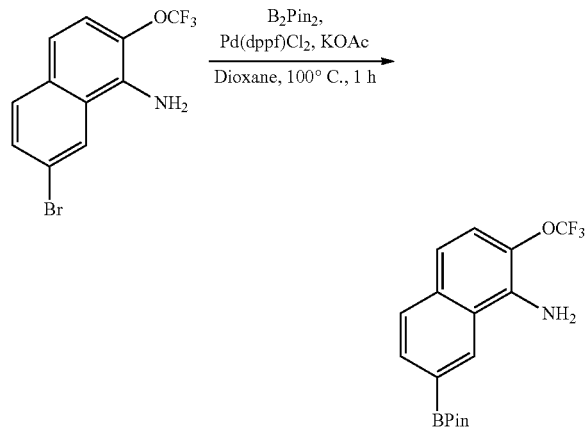

To a mixture of 7-bromo-2-(trifluoromethoxy)naphthalen-1-amine (80 mg, 261.37 µmol, 1 eq) and Pin₂B₂ (132.7 mg, 522.74 µmol, 2 eq) in dioxane (3 mL) were added KOAc (77 mg, 784.11 µmol, 3 eq), Pd(dppf)Cl₂ (38.3 mg, 52.27 µmol, 0.2 eq) under N₂. The mixture was stirred at 100° C. for 1 h. Upon completion of the reaction as indicated by TLC, the residue was poured into H₂O (20 mL) and the aqueous phase was extracted with EtOAc (3×20 mL). The combined organic phase was washed with brine (3×20 mL), dried with anhydrous Na₂SO₄, filtered, and concentrated in vacuo. The residue was purified by prep-TLC to afford the title compound (90 mg, 254.85 µmol, 97.51% yield) as a yellow oil.

Step 5—6-[8-amino-7-(trifluoromethoxy)-2-naphthyl]-N-(1-methyl-4-piperidyl)pyridine-2-carboxamide

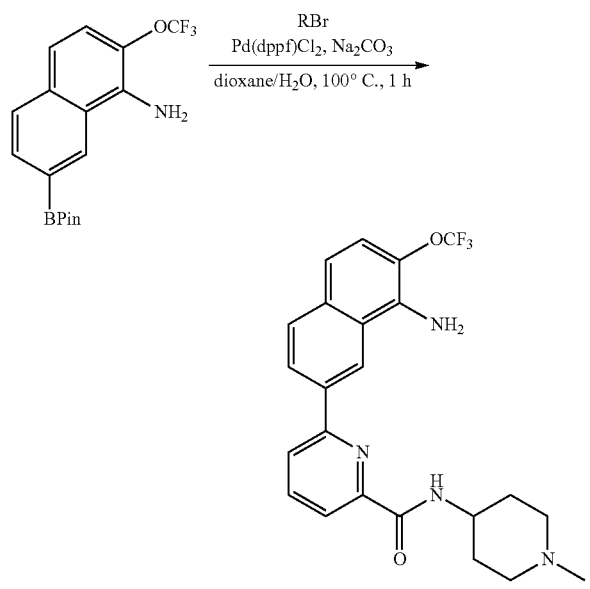

To a mixture of 7-(4,4,5,5-tetramethyl-1,3,2-dioxaborolan-2-yl)-2-(trifluoromethoxy) naphthalen-1-amine (80 mg, 226.54 µmol, 1 eq) and 6-bromo-N-(1-methyl-4-piperidyl)pyridine-2-carboxamide (101.3 mg, 339.81 µmol, 1.5 eq) in dioxane (3 mL) and H₂O (0.75 mL) were added Na₂CO₃ (48 mg, 453.07 µmol, 2 eq), Pd(dppf)Cl₂ (16.6 mg, 22.65 µmol, 0.1 eq) under N₂. The mixture was stirred at 100° C. for 1 h. The residue was poured into saturated EDTA (30 mL) and stirred for 60 min. The aqueous phase was extracted with EtOAc (3×30 mL). The combined organic phase was washed with brine (3×30 mL), dried with anhydrous Na₂SO₄, filtered, and concentrated in vacuo. The residue was purified by prep-TLC to afford the title compound (80 mg, 18 µmol, 79.46% yield) as a yellow oil. LCMS (ES⁺, m/z): 445.2 [(M+H)⁺].

Step 6—Compound 360: N-(1-methyl-4-piperidyl)-6-[8-(prop-2-enoylamino)-7-(trifluoromethoxy)-2-naphthyl]pyridine-2-carboxamide

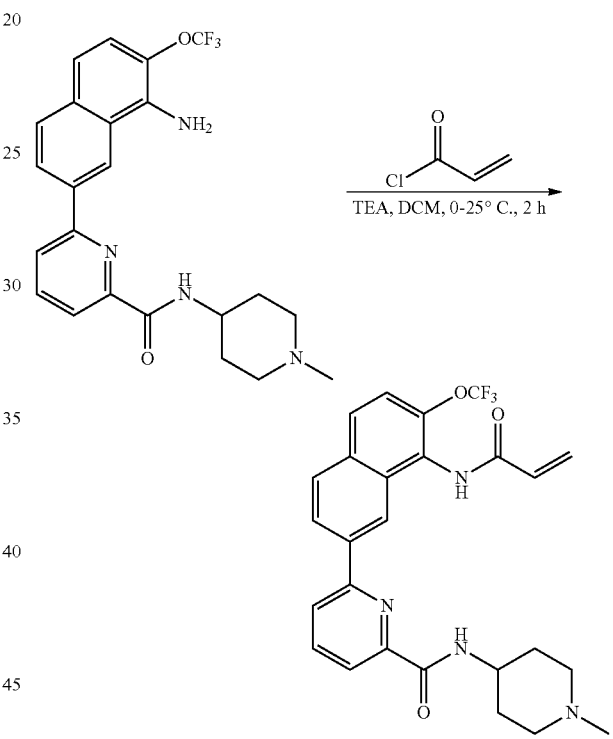

To a mixture of 6-[8-amino-7-(trifluoromethoxy)-2-naphthyl]-N-(1-methyl-4-piperidyl)pyridine-2-carboxamide (60 mg, 135 µmol, 1 eq) in DCM (3 mL) were added TEA (68.3 mg, 674.99 µmol, 93.95 µL, 5 eq) and prop-2-enoyl chloride (24.4 mg, 27 µmol, 22.02 µL, 2 eq) at 0° C. The mixture was stirred at 25° C. for 1 h. LCMS showed ~60% of the starting material remained. Then, prop-2-enoyl chloride (36.7 mg, 405 µmol, 33.02 µL, 3 eq) was added and the mixture was stirred at 25° C. for 1 h. Upon completion of the reaction as indicated by LCMS, the residue was poured into H₂O (15 mL) and the aqueous phase was extracted with EtOAc (3×10 mL). The combined organic phase was washed with brine (3×10 mL), dried with anhydrous Na₂SO₄, filtered, and concentrated in vacuo. The residue was purified by prep-HPLC to afford the title compound (24.8 mg, 49.4 µmol, 36.59% yield, 99.292% purity) as a white solid. LC-MS (ES⁺, m/z): 499.2 [(M+H)⁺] ¹H NMR (400 MHz, DMSO-d₆) δ=10.38 (s, 1H), 8.82 (s, 1H), 8.54 (d, J=8.4 Hz, 1H), 8.43 (br d, J=8.4 Hz, 1H), 8.33 (d, J=8.4 Hz, 1H), 8.22 (d, J=8.6

Hz, 1H), 8.18-8.10 (m, 2H), 8.04 (d, J=7.6 Hz, 1H), 7.67 (br d, J=9.2 Hz, 1H), 6.68 (br dd, J=10.8, 17.2 Hz, 1H), 6.34 (br d, J=16.4 Hz, 1H), 5.86 (br d, J=10.0 Hz, 1H), 3.87-3.77 (m, 1H), 2.86-2.73 (m, 2H), 2.21 (s, 3H), 2.09-1.96 (m, 2H), 1.88-1.80 (m, 2H), 1.79-1.66 (m, 2H).

Route 8: General Scheme

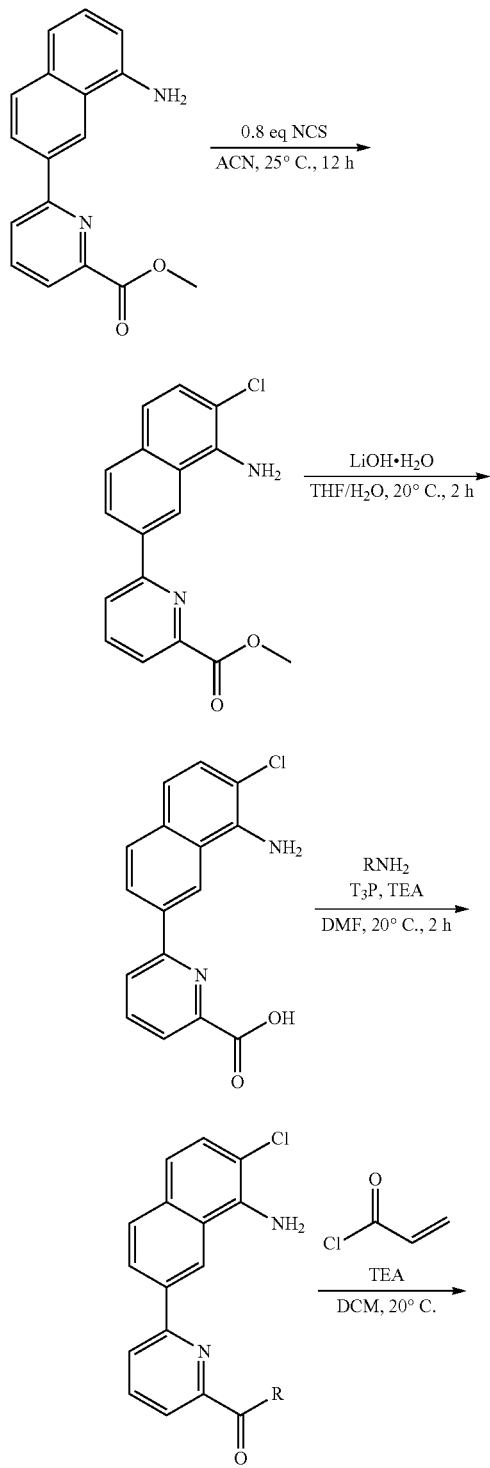

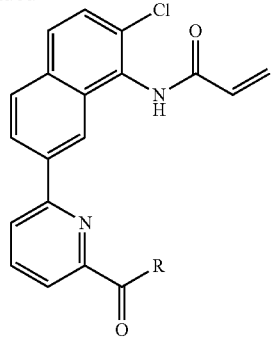

Step 1—methyl 6-(8-amino-7-chloronaphthalen-2-yl)picolinate

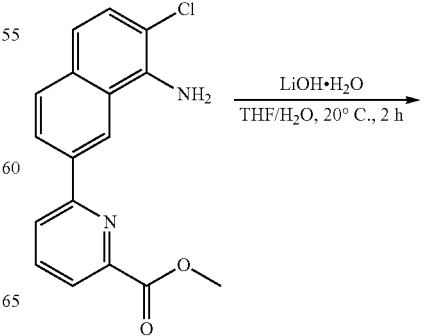

To a mixture of methyl 6-(8-amino-2-naphthyl)pyridine-2-carboxylate (400 mg, 1.44 mmol, 1 eq) in ACN (3 mL) was added NCS (153.5 mg, 1.15 mmol, 0.8 eq). The mixture was stirred at 25° C. for 12 hours. The reaction was diluted with H$_2$O (30 mL). The reaction was extracted with (3×10 mL) EtOAc. The combined organic phase was washed with brine (30 mL), dried over Na$_2$SO$_4$, dried over sodium sulfate, filtered, and concentrated in vacuo. The residue was purified by prep-TLC (SiO$_2$, PE:EtOAc=2:1) to afford the title compound (200 mg, 639.49 μmol, 44.5% yield) as a yellow solid. LC-MS (ES$^+$, m/z): 313.0 [(M+H)$^+$].

Step 2 6-(8-amino-7-chloronaphthalen-2-yl)picolinic acid

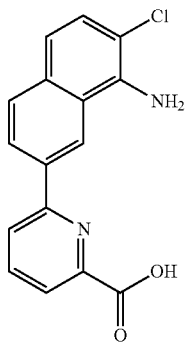

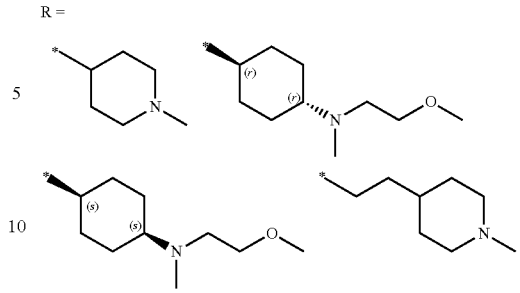

To a solution of methyl 6-(8-amino-7-chloro-2-naphthyl)pyridine-2-carboxylate (200 mg, 639.49 μmol, 1 eq) in THF (2 mL) and H$_2$O (0.5 mL) was added LiOH·H$_2$O (107.3 mg, 2.56 mmol, 4 eq). The mixture was stirred at 20° C. for 2 h. The reaction mixture was diluted with H$_2$O (30 mL) and EtOAc (30 mL), and saturated citric acid was added to adjust the mixture to pH~ 6. The mixture was extracted with EtOAc (2×20 mL), washed with brine (30 mL), dried over Na$_2$SO$_4$, dried over sodium sulfate, filtered, and concentrated in vacuo to afford the title compound (160 mg, crude) as a yellow solid. LC-MS (ES$^+$, m/z): 296.9 [(M−H)$^+$].

To a mixture of 6-(8-amino-7-chloro-2-naphthyl)pyridine-2-carboxylic acid (80 mg, 267.81 μmol, 1 eq) and 2-(1-methyl-4-piperidyl)ethanamine (76.2 mg, 535.61 μmol, 2 eq) in DMF (2 mL) were added Et$_3$N (81.3 mg, 803.42 μmol, 111.83 μL, 3 eq; drop-wise) and T$_3$P (255.6 mg, 401.71 μmol, 238.91 μL, 50% purity, 1.5 eq). The mixture was stirred at 20° C. for 2 h. The reaction was diluted with H$_2$O (30 mL) and extracted with EtOAc (3×20 mL). The combined organic phase was washed with brine (30 mL), dried over Na$_2$SO$_4$, filtered, and concentrated in vacuo to afford the title compound (60 mg, crude) as a yellow oil.

Step 3—6-(8-amino-7-chloronaphthalen-2-yl)picolinoyl

Step 4—6-(8-acrylamido-7-chloronaphthalen-2-yl)picolinoyl

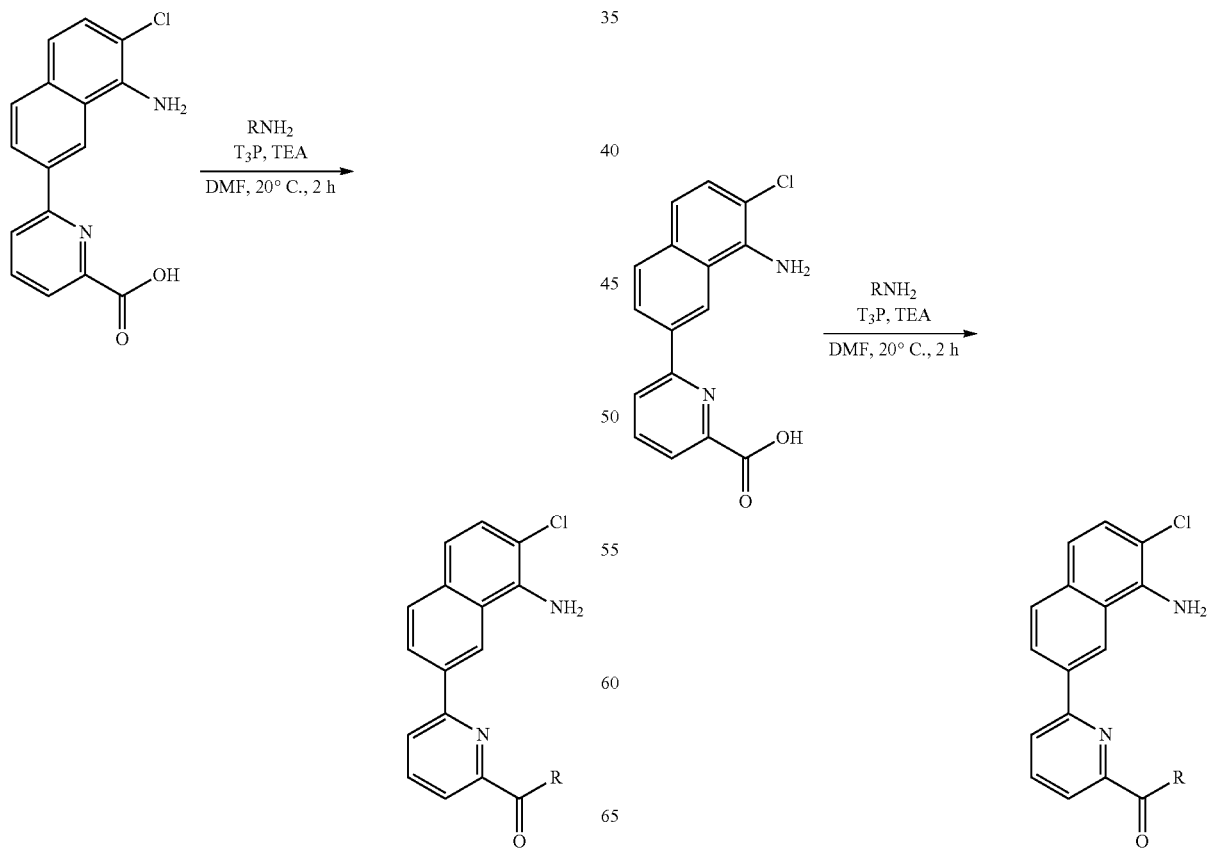

479

-continued

R =

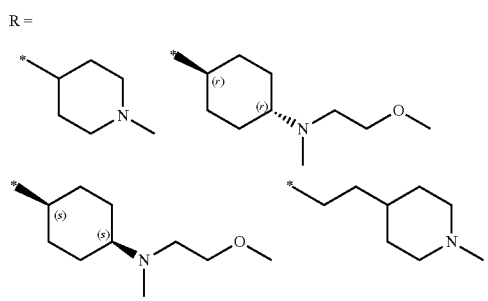

To a solution of 6-(8-amino-7-chloro-2-naphthyl)-N-(1-methyl-4-piperidyl)pyridine-2-carboxamide (60 mg, 151.94 μmol, 1 eq) in DCM (2 mL) was added drop-wise Et$_3$N (46.1 mg, 455.82 μmol, 63.44 μL, 3 eq) at 0° C. After about 5 min, prop-2-enoyl chloride (20.6 mg, 227.91 μmol, 18.58 μL, 1.5 eq) was added drop-wise at 0° C. The mixture was stirred at 20° C. for 115 min. Upon completion of the reaction as indicated by LCMS, the reaction was diluted with H$_2$O (20 mL). Then the reaction was extracted with (3×20 mL) DCM. The combined organic phase was washed with brine (30 mL), dried over Na$_2$SO$_4$ and concentrated in vacuo to give a residue. The residue was purified by prep-HPLC to afford the title compound 6-[7-chloro-8-(prop-2-enoylamino)-2-naphthyl]-N-(1-methyl-4-piperidyl)pyridine-2-carboxamide (5.1 mg, 11.36 μmol, 7.48% yield, 100% purity) as a white solid.

Route 9: General Scheme

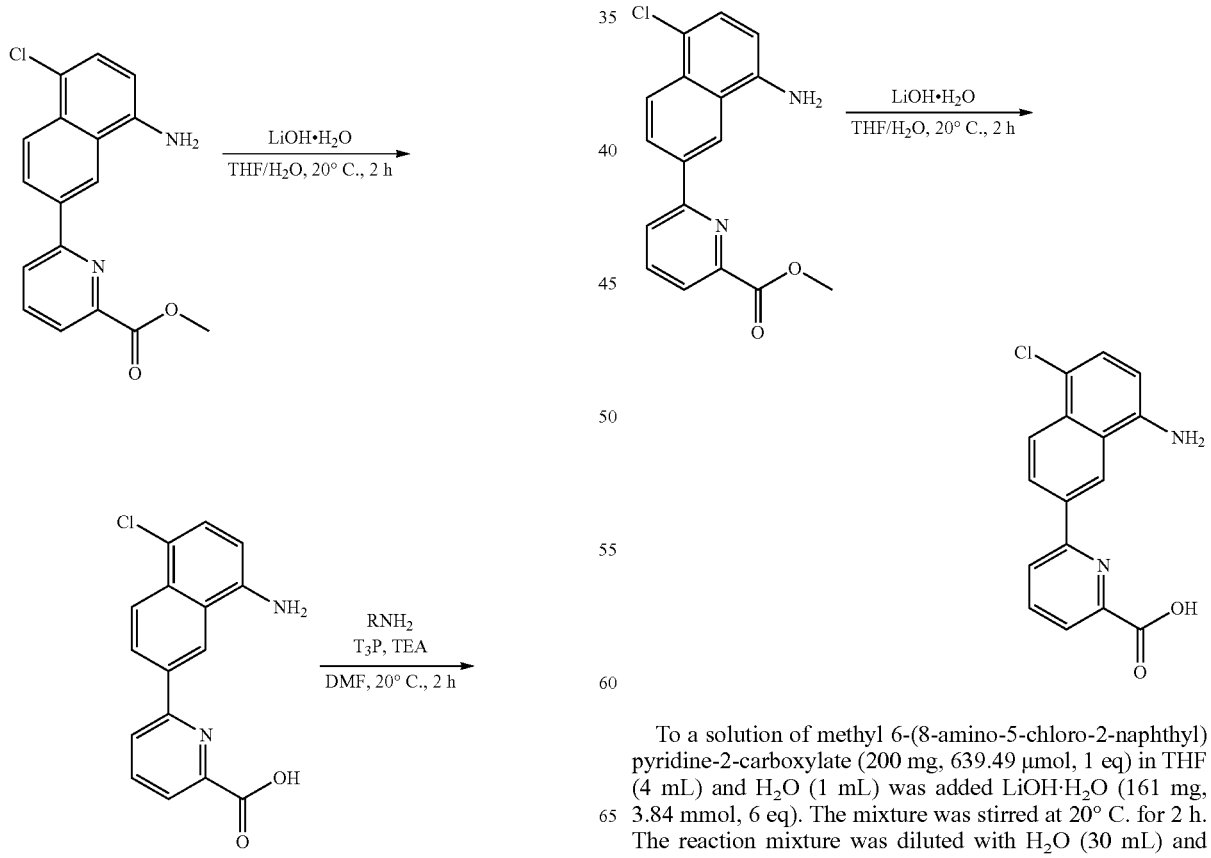

480

-continued

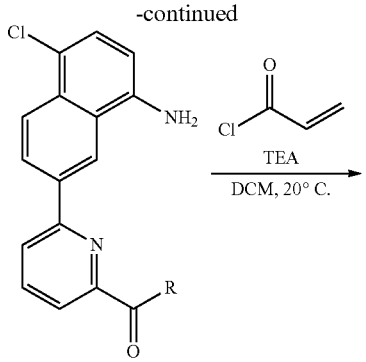

Step 1 methyl 6-(8-amino-5-chloronaphthalen-2-yl)picolinate

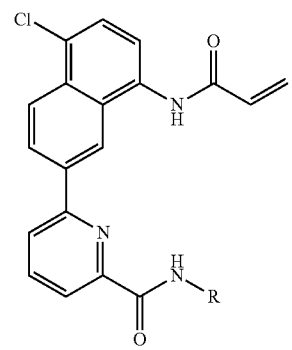

To a solution of methyl 6-(8-amino-5-chloro-2-naphthyl)pyridine-2-carboxylate (200 mg, 639.49 μmol, 1 eq) in THF (4 mL) and H$_2$O (1 mL) was added LiOH·H$_2$O (161 mg, 3.84 mmol, 6 eq). The mixture was stirred at 20° C. for 2 h. The reaction mixture was diluted with H$_2$O (30 mL) and EtOAc (30 mL). Then the mixture was adjusted to pH~6 using saturated citric acid. The organic layer was extracted with EtOAc (2×20 mL) and washed with brine (30 mL), dried over $Na_2SO_4$ and concentrated in vacuo to afford the title compound (160 mg, crude) as a yellow solid. LC-MS $(ES^+, m/z): 297.0 [(M–H)^+]$.

Step 3—6-(8-amino-5-chloronaphthalen-2-yl)picolinic

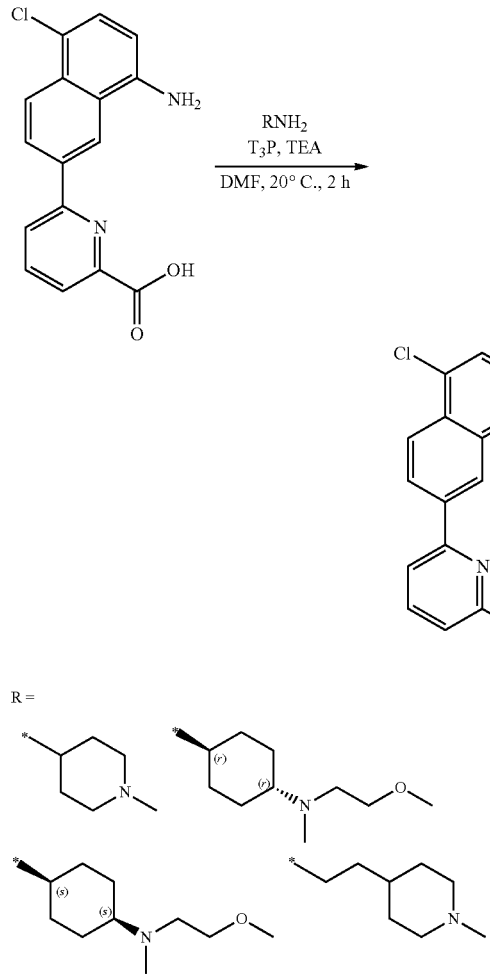

Step 4—Compound 401: Preparation of 6-[5-chloro-8-(prop-2-enamido)naphthalen-2-yl]-N-(1-methylpiperidin-4-yl)pyridine-2-carboxamide

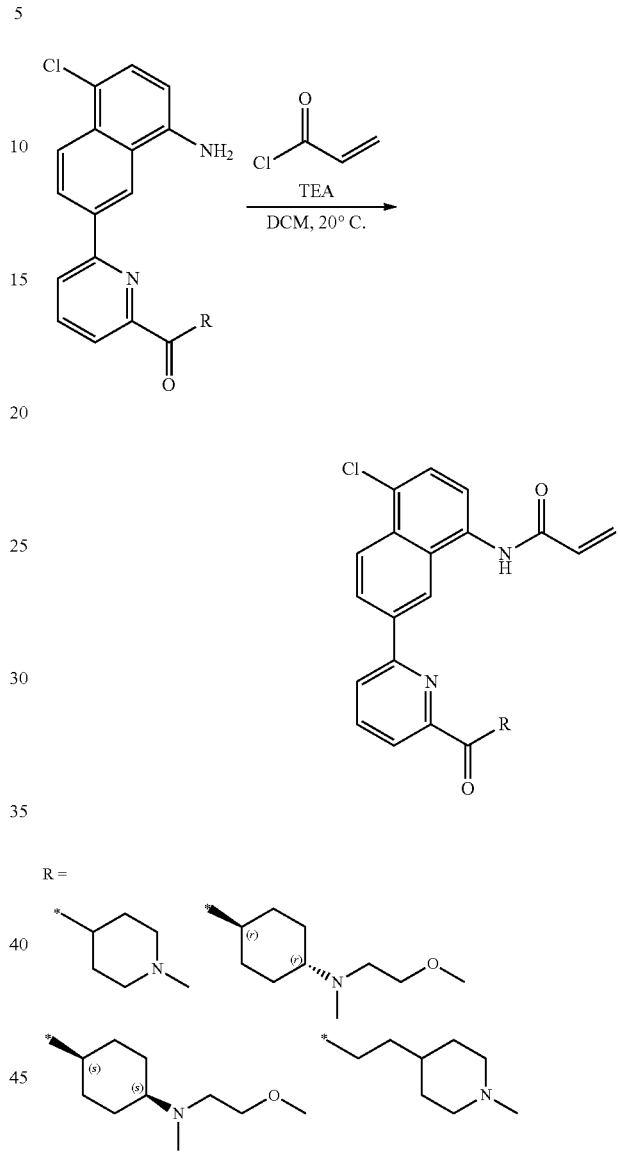

To a mixture of 6-(8-amino-5-chloro-2-naphthyl)pyridine-2-carboxylic acid (80 mg, 267.81 μmol, 1 eq) and 1-methylpiperidin-4-amine (91.7 mg, 803.42 μmol, 3 eq) in DMF (2 mL) were added $Et_3N$ (81.3 mg, 803.42 μmol, 111.83 μL, 3 eq; drop-wise) and $T_3P$ (255.6 mg, 401.71 μmol, 238.91 μL, 50% purity, 1.5 eq). The mixture was stirred at 20° C. for 2 h. Upon completion of the reaction as indicated by LCMS, the reaction was diluted with $H_2O$ (30 mL) and extracted with EtOAc (3×20 mL). The combined organic phase was washed with brine (30 mL), dried over $Na_2SO_4$, filtered, and concentrated in vacuo to give a residue. The residue was purified prep-TLC ($SiO_2$, DCM/MeOH=8:1 or 5:1) to afford the title compound 6-(8-amino-5-chloro-2-naphthyl)-N-(1-methyl-4-piperidyl)pyridine-2-carboxamide (60 mg, 151.94 μmol, 56.73% yield) as a yellow oil.

To a solution of 6-(8-amino-5-chloro-2-naphthyl)-N-(1-methyl-4-piperidyl)pyridine-2-carboxamide (60 mg, 151.94 μmol, 1 eq) in DCM (2 mL) was added $Et_3N$ (46.1 mg, 455.82 μmol, 63.44 μL, 3 eq; drop-wise) at 0° C. After about 5 min, prop-2-enoyl chloride (13.8 mg, 151.94 μmol, 12.39 μL, 1 eq) was added drop-wise at 0° C. The mixture was stirred at 20° C. for 115 min. The reaction was diluted with $H_2O$ (20 mL) and extracted with DCM (3×20 mL). The combined organic phase was washed with brine (30 mL), dried over $Na_2SO_4$ and concentrated in vacuo to give a residue. The residue was purified by prep-HPLC to afford the title compound 6-[5-chloro-8-(prop-2-enoylamino)-2-naphthyl]-N-(1-methyl-4-piperidyl)pyridine-2-carboxamide (13.1 mg, 29.09 μmol, 19.15% yield, 99.7% purity) as a white solid. LC-MS $(ES^+, m/z): 449.1 [(M+H)^+]$ TABLE 8 shows compounds synthesized using the methods described in EXAMPLE 8 above.

TABLE 8

| Cpd. No. | Structure | IUPAC | LC-MS (ES+, m/z) |
|---|---|---|---|
| 351 | 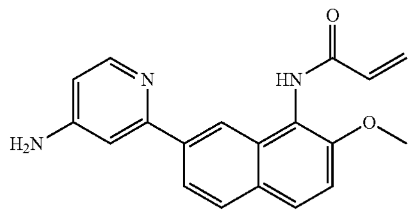 [SMILES: C=CC(=O)Nc1c(OC)ccc2ccc(-c3cc(N)ccn3)cc12] | N-[7-(4-aminopyridin-2-yl)-2-methoxynaphthalen-1-yl]prop-2-enamide | 320.1 |
| 352 | 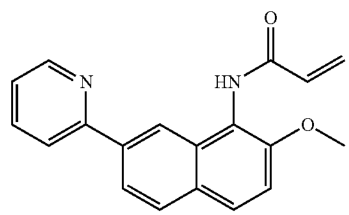 [SMILES: C=CC(=O)Nc1c(OC)ccc2ccc(-c3ccccn3)cc12] | N-[2-methoxy-7-(pyridin-2-yl)naphthalen-1-yl]prop-2-enamide | 305.1 |
| 353 | 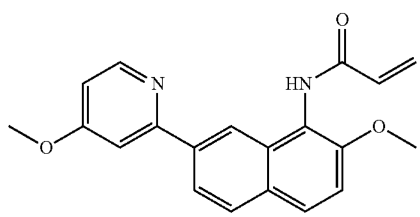 | N-[2-methoxy-7-(4-methoxypyridin-2-yl)naphthalen-1-yl]prop-2-enamide | 335.1 |
| 354 | 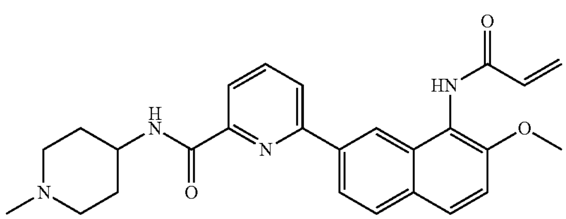 [SMILES: C=CC(=O)Nc1c(OC)ccc2ccc(-c3cccc(C(=O)NC4CCN(C)CC4)n3)cc12] | 6-[7-methoxy-8-(prop-2-enamido)naphthalen-2-yl]-N-(1-methylpiperidin-4-yl)pyridine-2-carboxamide | 445.2 |
| 355 | 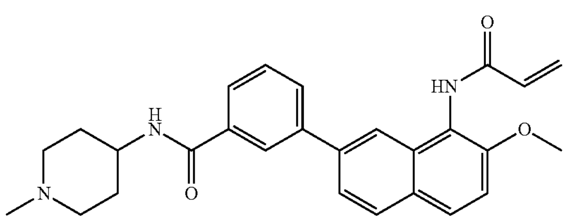 [SMILES: C=CC(=O)Nc1c(OC)ccc2ccc(-c3cccc(C(=O)NC4CCN(C)CC4)c3)cc12] | 3-[7-methoxy-8-(prop-2-enamido)naphthalen-2-yl]-N-(1-methylpiperidin-4-yl)benzamide | 444.1 |
| 356 | 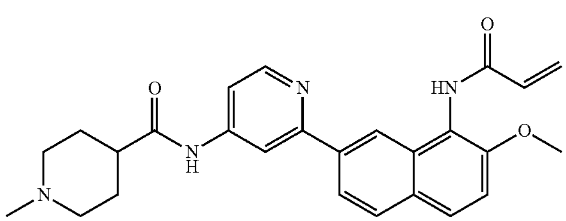 | N-{2-[7-methoxy-8-(prop-2-enamido)naphthalen-2-yl]pyridin-4-yl}-1-methylpiperidine-4-carboxamide | 445 |
| 357 | 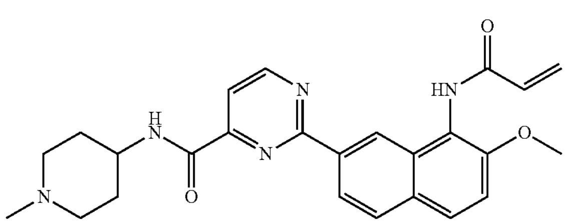 | 2-[7-methoxy-8-(prop-2-enamido)naphthalen-2-yl]-N-(1-methylpiperidin-4-yl)pyrimidine-4-carboxamide | 446.2 |

TABLE 8-continued

| Cpd. No. | Structure | IUPAC | LC-MS (ES+, m/z) |
|---|---|---|---|
| 358 | 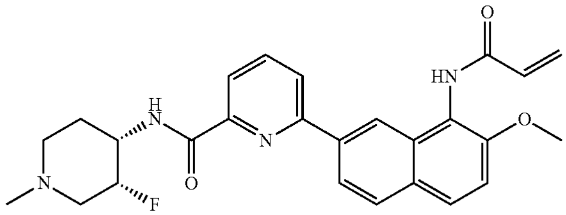 | N-[(3R,4S)-3-fluoro-1-methylpiperidin-4-yl]-6-[7-methoxy-8-(prop-2-enamido)naphthalen-2-yl]pyridine-2-carboxamide | 463.2 |
| 359 | 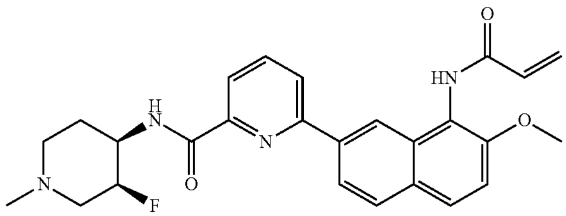 | N-[(3S,4R)-3-fluoro-1-methylpiperidin-4-yl]-6-[7-methoxy-8-(prop-2-enamido)naphthalen-2-yl]pyridine-2-carboxamide | 463.2 |
| 360 | 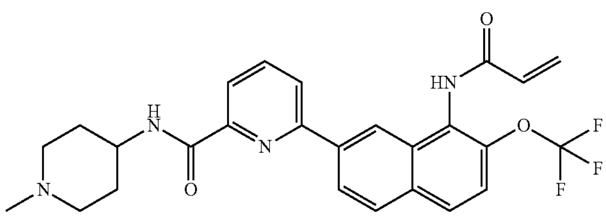 [SMILES: C=CC(=O)Nc1c(OC(F)(F)F)ccc2ccc(-c3cccc(C(=O)NC4CCN(C)CC4)n3)cc12] | N-(1-methylpiperidin-4-yl)-6-[8-(prop-2-enamido)-7-(trifluoromethoxy)naphthalen-2-yl]pyridine-2-carboxamide | 499.2 |
| 361 | 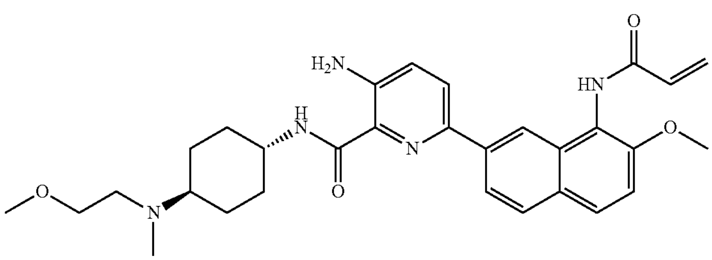 | 3-amino-6-[7-methoxy-8-(prop-2-enamido)naphthalen-2-yl]-N-[(1r,4r)-4-[(2-methoxyethyl)(methyl)amino]cyclohexyl]pyridine-2-carboxamide | 532.3 |
| 362 | 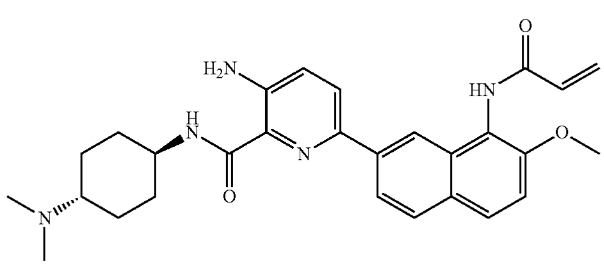 | 3-amino-6-[7-methoxy-8-(prop-2-enamido)naphthalen-2-yl]-N-[(1r,4r)-4-(dimethylamino)cyclohexyl]pyridine-2-carboxamide | 488.3 |
| 363 | 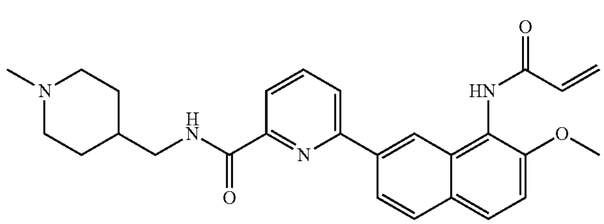 | 6-[7-methoxy-8-(prop-2-enamido)naphthalen-2-yl]-N-[(1-methylpiperidin-4-yl)methyl]pyridine-2-carboxamide | 459.2 |

TABLE 8-continued

| Cpd. No. | Structure | IUPAC | LC-MS (ES+, m/z) |
|---|---|---|---|
| 364 | 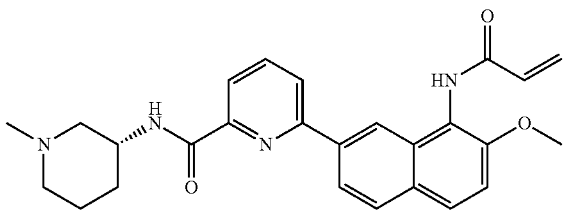 [SMILES: C=CC(=O)Nc1c(OC)ccc2ccc(-c3cccc(C(=O)N[C@@H]4CCCN(C)C4)n3)cc12] | 6-[7-methoxy-8-(prop-2-enamido)naphthalen-2-yl]-N-[(3R)-1-methylpiperidin-3-yl]pyridine-2-carboxamide | 445.2 |
| 365 | 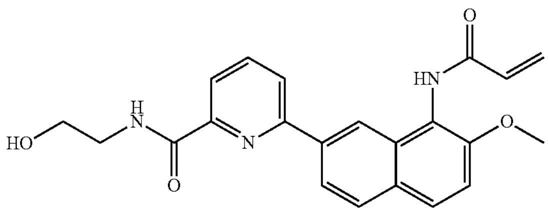 [SMILES: C=CC(=O)Nc1c(OC)ccc2ccc(-c3cccc(C(=O)NCCO)n3)cc12] | N-(2-hydroxyethyl)-6-[7-methoxy-8-(prop-2-enamido)naphthalen-2-yl]pyridine-2-carboxamide | 392.1 |
| 366 | 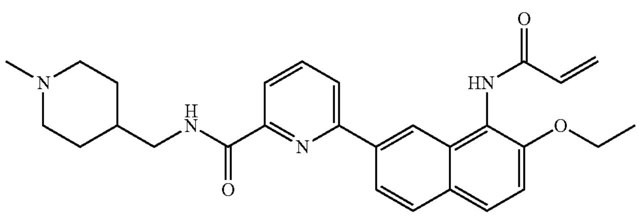 [SMILES: C=CC(=O)Nc1c(OCC)ccc2ccc(-c3cccc(C(=O)NCC4CCN(C)CC4)n3)cc12] | 6-[7-ethoxy-8-(prop-2-enamido)naphthalen-2-yl]-N-[(1-methylpiperidin-4-yl)methyl]pyridine-2-carboxamide | 473.3 |
| 367 | 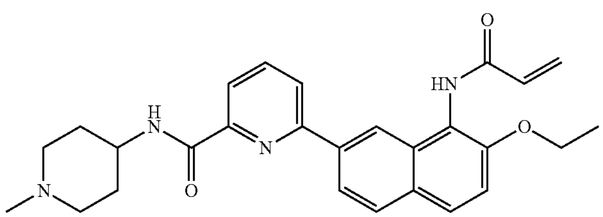 [SMILES: C=CC(=O)Nc1c(OCC)ccc2ccc(-c3cccc(C(=O)NC4CCN(C)CC4)n3)cc12] | 6-[7-ethoxy-8-(prop-2-enamido)naphthalen-2-yl]-N-(1-methylpiperidin-4-yl)pyridine-2-carboxamide | 459.3 |
| 368 | 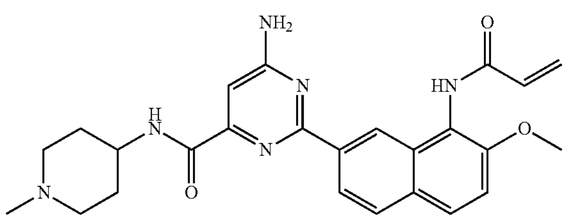 | 6-amino-2-[7-methoxy-8-(prop-2-enamido)naphthalen-2-yl]-N-(1-methylpiperidin-4-yl)pyrimidine-4-carboxamide | 461.2 |
| 369 | 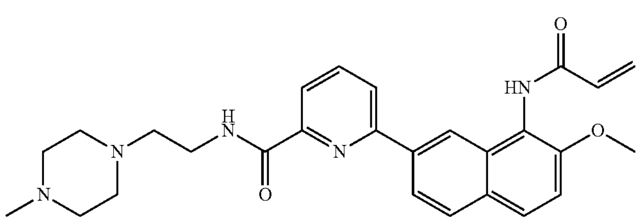 | 6-[7-methoxy-8-(prop-2-enamido)naphthalen-2-yl]-N-[2-(4-methylpiperazin-1-yl)ethyl]pyridine-2-carboxamide | 474.3 |
| 370 | 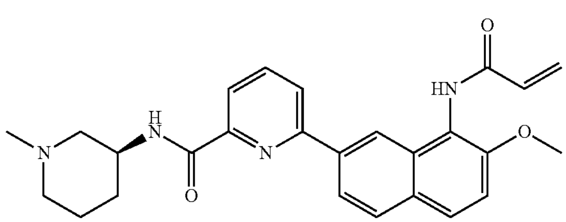 | 6-[7-methoxy-8-(prop-2-enamido)naphthalen-2-yl]-N-[(3S)-1-methylpiperidin-3-yl]pyridine-2-carboxamide | 445.2 |

TABLE 8-continued

| Cpd. No. | Structure | IUPAC | LC-MS (ES+, m/z) |
|---|---|---|---|
| 371 | 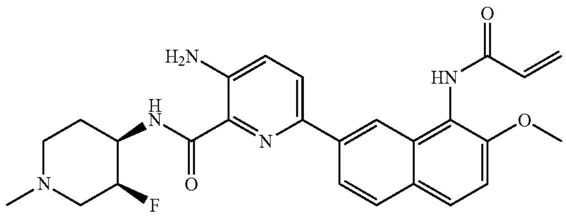 | 3-amino-N-[(3S,4R)-3-fluoro-1-methylpiperidin-4-yl]-6-[7-methoxy-8-(prop-2-enamido)naphthalen-2-yl]pyridine-2-carboxamide | 478.2 |
| 372 | 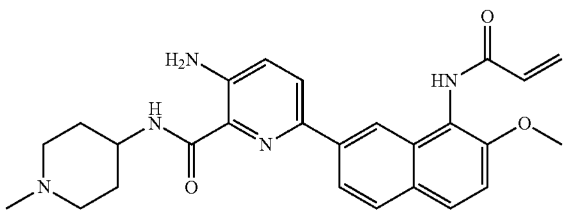 | 3-amino-6-[7-methoxy-8-(prop-2-enamido)naphthalen-2-yl]-N-(1-methylpiperidin-4-yl)pyridine-2-carboxamide | 460.2 |
| 373 | 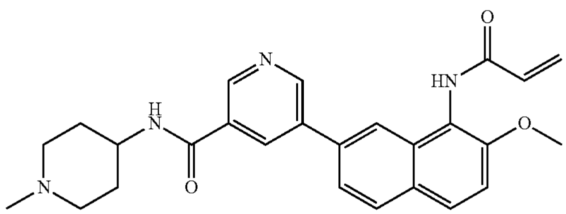 [SMILES: C=CC(=O)Nc1c(OC)ccc2ccc(-c3cncc(C(=O)NC4CCN(C)CC4)c3)cc12] | 5-[7-methoxy-8-(prop-2-enamido)naphthalen-2-yl]-N-(1-methylpiperidin-4-yl)pyridine-3-carboxamide | 445.2 |
| 374 | 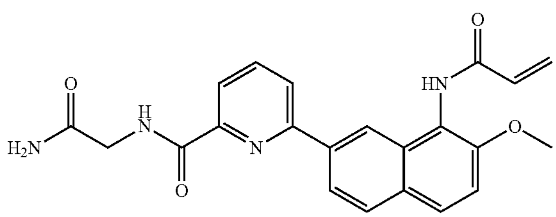 [SMILES: C=CC(=O)Nc1c(OC)ccc2ccc(-c3cccc(C(=O)NCC(N)=O)n3)cc12] | N-(7-{6-[(carbamoylmethyl)carbamoyl]pyridin-2-yl}-2-methoxynaphthalen-1-yl)prop-2-enamide | 405.1 |
| 375 | 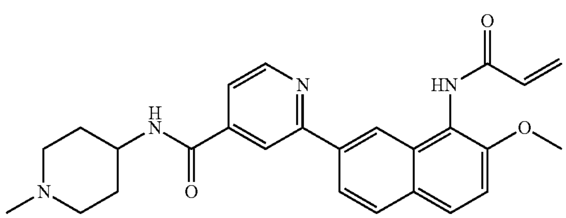 | 2-[7-methoxy-8-(prop-2-enamido)naphthalen-2-yl]-N-(1-methylpiperidin-4-yl)pyridine-4-carboxamide | 445.2 |
| 376 | 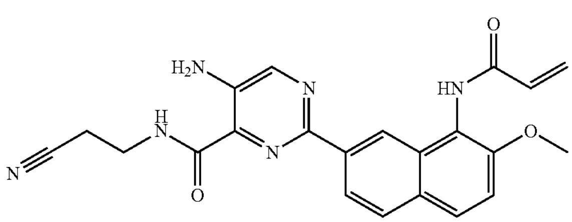 [SMILES: C=CC(=O)Nc1c(OC)ccc2ccc(-c3ncc(N)c(C(=O)NCCC#N)n3)cc12] | 5-amino-N-(2-cyanoethyl)-2-[7-methoxy-8-(prop-2-enamido)naphthalen-2-yl]pyrimidine-4-carboxamide | 417.1 |
| 377 | 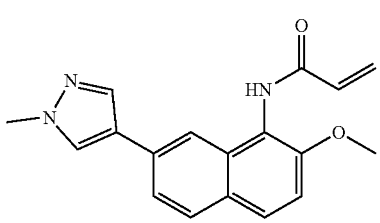 | N-[2-methoxy-7-(1-methyl-1H-pyrazol-4-yl)naphthalen-1-yl]prop-2-enamide | 308.1 |

TABLE 8-continued

| Cpd. No. | Structure | IUPAC | LC-MS (ES+, m/z) |
|---|---|---|---|
| 378 | 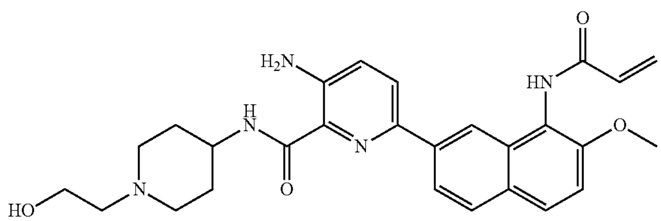 [SMILES: C=CC(=O)Nc1c(OC)ccc2ccc(-c3ccc(N)c(C(=O)NC4CCN(CCO)CC4)n3)cc12] | 3-amino-N-[1-(2-hydroxyethyl)piperidin-4-yl]-6-[7-methoxy-8-(prop-2-enamido)naphthalen-2-yl]pyridine-2-carboxamide | 490.3 |
| 379 | 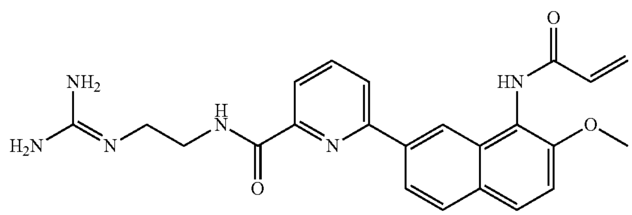 [SMILES: C=CC(=O)Nc1c(OC)ccc2ccc(-c3cccc(C(=O)NCCN=C(N)N)n3)cc12] | N-{2-[(diaminomethylidene)amino]ethyl}-6-[7-methoxy-8-(prop-2-enamido)naphthalen-2-yl]pyridine-2-carboxamide | 433.2 |
| 380 | 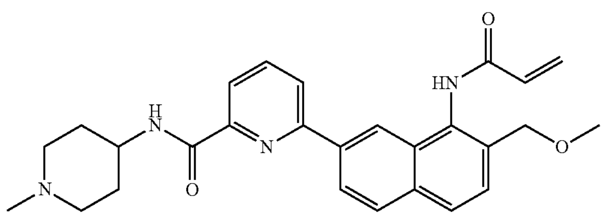 | 6-[7-(methoxymethyl)-8-(prop-2-enamido)naphthalen-2-yl]-N-(1-methylpiperidin-4-yl)pyridine-2-carboxamide | 459.3 |
| 381 | 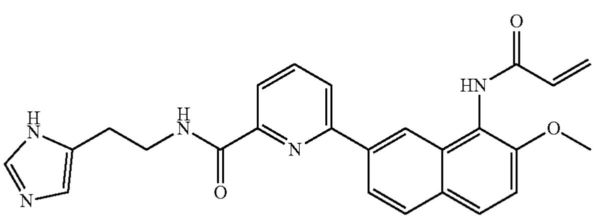 [SMILES: C=CC(=O)Nc1c(OC)ccc2ccc(-c3cccc(C(=O)NCCc4cnc[nH]4)n3)cc12] | N-[2-(1H-imidazol-5-yl)ethyl]-6-[7-methoxy-8-(prop-2-enamido)naphthalen-2-yl]pyridine-2-carboxamide | 442.2 |
| 382 | 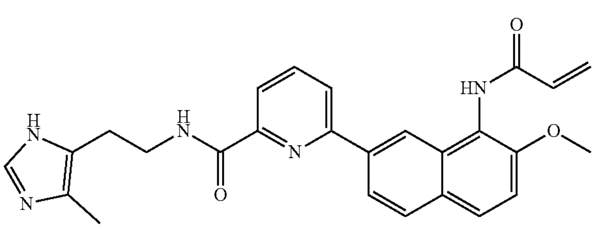 [SMILES: C=CC(=O)Nc1c(OC)ccc2ccc(-c3cccc(C(=O)NCCc4[nH]cnc4C)n3)cc12] | 6-[7-methoxy-8-(prop-2-enamido)naphthalen-2-yl]-N-[2-(4-methyl-1H-imidazol-5-yl)ethyl]pyridine-2-carboxamide | 456.2 |
| 383 | 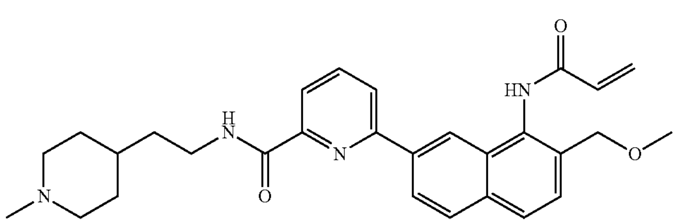 | 6-[7-(methoxymethyl)-8-(prop-2-enamido)naphthalen-2-yl]-N-[2-(1-methylpiperidin-4-yl)ethyl]pyridine-2-carboxamide | 487.3 |
| 384 | 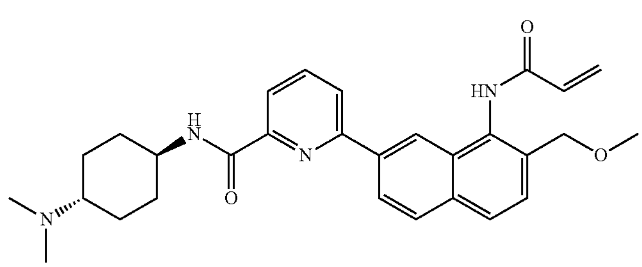 | 6-[7-(methoxymethyl)-8-(prop-2-enamido)naphthalen-2-yl]-N-[(1r,4r)-4-(dimethylamino)cyclohexyl]pyridine-2-carboxamide | 487.3 |

TABLE 8-continued

| Cpd. No. | Structure | IUPAC | LC-MS (ES+, m/z) |
|---|---|---|---|
| 385 | 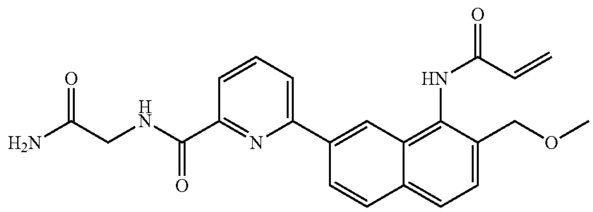 [SMILES: C=CC(=O)Nc1c(COC)ccc2ccc(-c3cccc(C(=O)NCC(N)=O)n3)cc12] | N-(7-{6-[(carbamoylmethyl)carbamoyl]pyridin-2-yl}-2-(methoxymethyl)naphthalen-1-yl)prop-2-enamide | 419.2 |
| 386 | 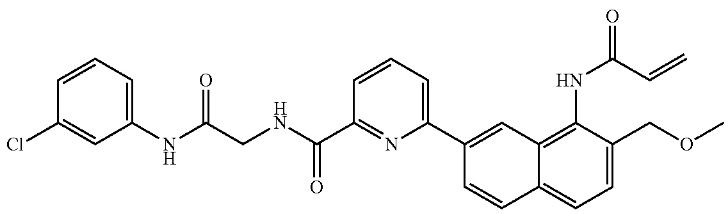 [SMILES: C=CC(=O)Nc1c(COC)ccc2ccc(-c3cccc(C(=O)NCC(=O)Nc4cccc(Cl)c4)n3)cc12] | N-{7-[6-({[(3-chlorophenyl)carbamoyl]methyl}carbamoyl)pyridin-2-yl]-2-(methoxymethyl)naphthalen-1-yl}prop-2-enamide | 529.2 |
| 387 | 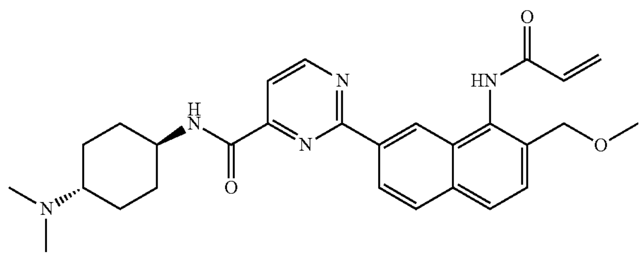 | 2-[7-(methoxymethyl)-8-(prop-2-enamido)naphthalen-2-yl]-N-[(1r,4r)-4-(dimethylamino)cyclohexyl]pyrimidine-4-carboxamide | 488.3 |
| 388 | 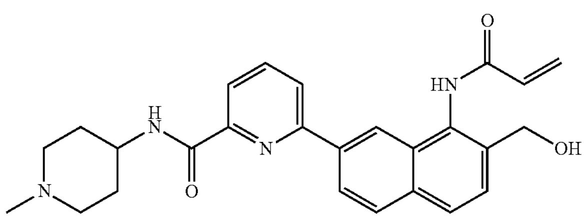 [SMILES: C=CC(=O)Nc1c(CO)ccc2ccc(-c3cccc(C(=O)NC4CCN(C)CC4)n3)cc12] | 6-[7-(hydroxymethyl)-8-(prop-2-enamido)naphthalen-2-yl]-N-(1-methylpiperidin-4-yl)pyridine-2-carboxamide | 445.2 |
| 389 | 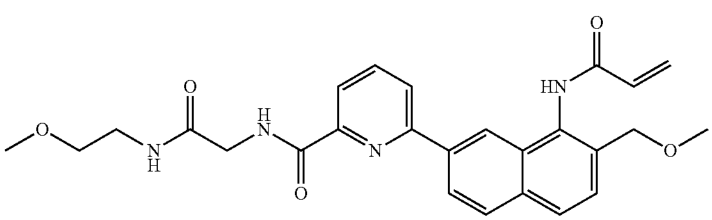 | N-{7-[6-({[(2-methoxyethyl)carbamoyl]methyl}carbamoyl)pyridin-2-yl]-2-(methoxymethyl)naphthalen-1-yl}prop-2-enamide | 477.2 |
| 390 | 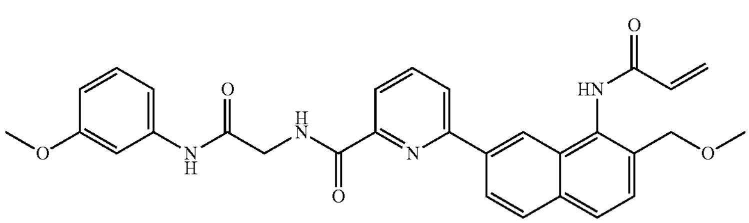 | N-[2-(methoxymethyl)-7-[6-({[(3-methoxyphenyl)carbamoyl]methyl}carbamoyl)pyridin-2-yl]naphthalen-1-yl]prop-2-enamide | 525.2 |
| 391 | 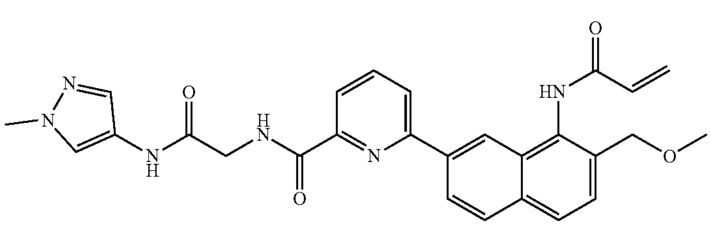 | N-[2-(methoxymethyl)-7-[6-({[(1-methyl-1H-pyrazol-4-yl)carbamoyl]methyl}carbamoyl)pyridin-2-yl]naphthalen-1-yl]prop-2-enamide | 499.1 |

TABLE 8-continued

| Cpd. No. | Structure | IUPAC | LC-MS (ES+, m/z) |
|---|---|---|---|
| 392 | 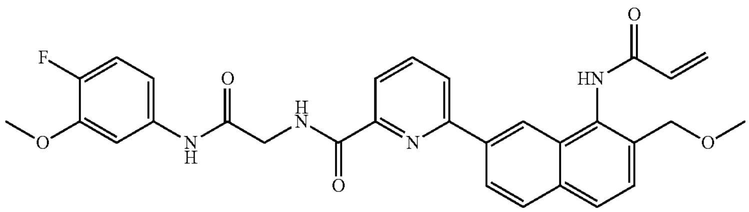 | N-{7-[6-({[(4-fluoro-3-methoxyphenyl)carbamoyl]methyl}carbamoyl)pyridin-2-yl]-2-(methoxymethyl)naphthalen-1-yl}prop-2-enamide | 543.2 |
| 393 | 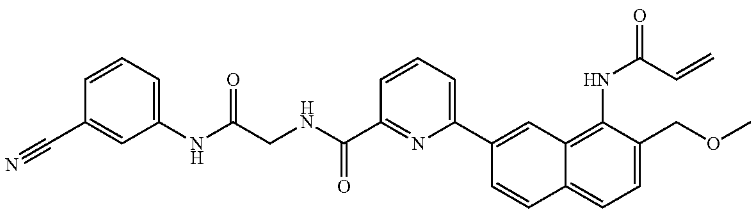 [SMILES: C=CC(=O)Nc1c(COC)ccc2ccc(-c3cccc(C(=O)NCC(=O)Nc4cccc(C#N)c4)n3)cc12] | N-{7-[6-({[(3-cyanophenyl)carbamoyl]methyl}carbamoyl)pyridin-2-yl]-2-(methoxymethyl)naphthalen-1-yl}prop-2-enamide | 520.1 |
| 394 | 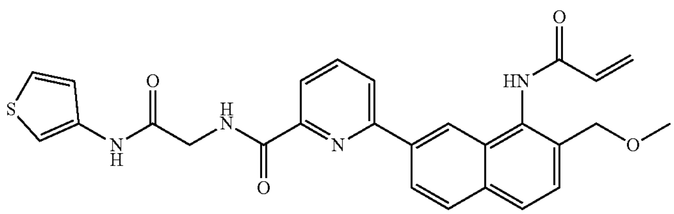 [SMILES: C=CC(=O)Nc1c(COC)ccc2ccc(-c3cccc(C(=O)NCC(=O)Nc4ccsc4)n3)cc12] | N-[2-(methoxymethyl)-7-[6-({[(thiophen-3-yl)carbamoyl]methyl}carbamoyl)pyridin-2-yl]naphthalen-1-yl]prop-2-enamide | 501.1 |
| 395 | 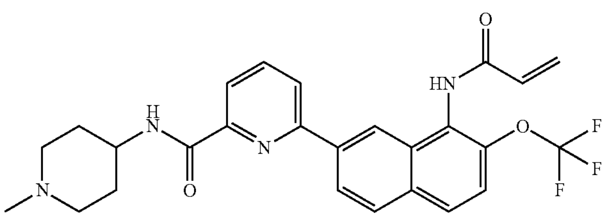 [SMILES: C=CC(=O)Nc1c(OC(F)(F)F)ccc2ccc(-c3cccc(C(=O)NC4CCN(C)CC4)n3)cc12] | N-(1-methylpiperidin-4-yl)-6-[8-(prop-2-enamido)-7-(trifluoromethoxy)naphthalen-2-yl]pyridine-2-carboxamide | 499.2 |
| 396 | 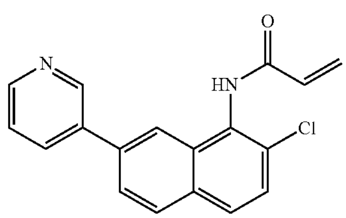 [SMILES: C=CC(=O)Nc1c(Cl)ccc2ccc(-c3cccnc3)cc12] | N-[2-chloro-7-(pyridin-3-yl)naphthalen-1-yl]prop-2-enamide | 308.9 |
| 397 | 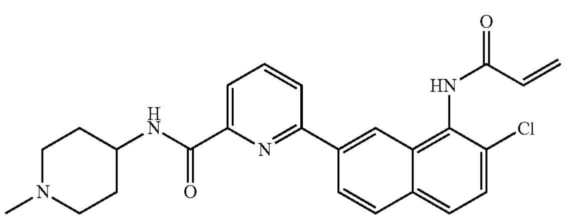 [SMILES: C=CC(=O)Nc1c(Cl)ccc2ccc(-c3cccc(C(=O)NC4CCN(C)CC4)n3)cc12] | 6-[7-chloro-8-(prop-2-enamido)naphthalen-2-yl]-N-(1-methylpiperidin-4-yl)pyridine-2-carboxamide | 449.1 |
| 398 | 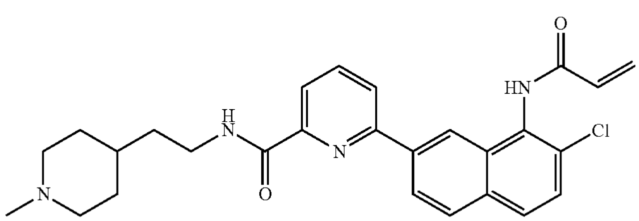 [SMILES: C=CC(=O)Nc1c(Cl)ccc2ccc(-c3cccc(C(=O)NCCC4CCN(C)CC4)n3)cc12] | 6-[7-chloro-8-(prop-2-enamido)naphthalen-2-yl]-N-[2-(1-methylpiperidin-4-yl)ethyl]pyridine-2-carboxamide | 477.2 |

TABLE 8-continued

| Cpd. No. | Structure | IUPAC | LC-MS (ES+, m/z) |
|---|---|---|---|
| 399 | 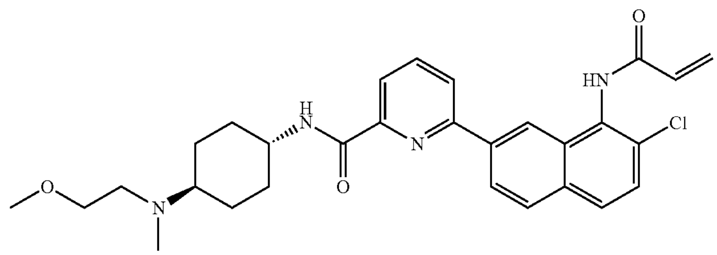 [SMILES: C=CC(=O)Nc1c(Cl)ccc2ccc(-c3cccc(C(=O)N[C@H]4CC[C@H](N(C)CCOC)CC4)n3)cc12] | 6-[7-chloro-8-(prop-2-enamido)naphthalen-2-yl]-N-[(1r,4r)-4-[(2-methoxyethyl)(methyl)amino]cyclohexyl]pyridine-2-carboxamide | 521.2 |
| 400 | 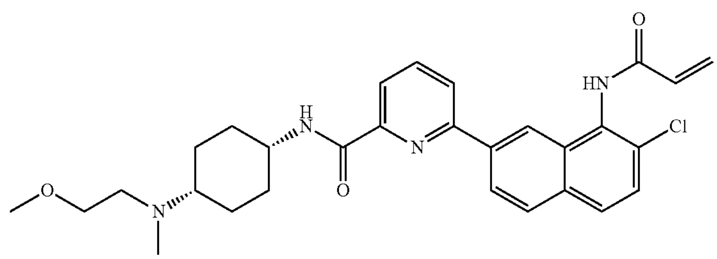 [SMILES: C=CC(=O)Nc1c(Cl)ccc2ccc(-c3cccc(C(=O)N[C@H]4CC[C@@H](N(C)CCOC)CC4)n3)cc12] | 6-[7-chloro-8-(prop-2-enamido)naphthalen-2-yl]-N-[(1s,4s)-4-[(2-methoxyethyl)(methyl)amino]cyclohexyl]pyridine-2-carboxamide | 521.2 |
| 401 | 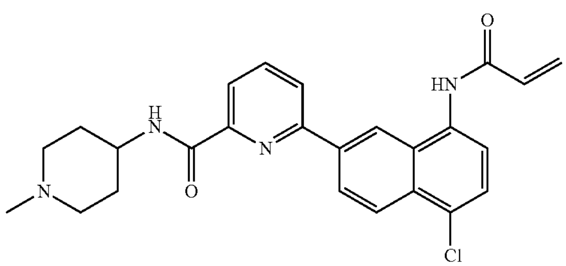 [SMILES: C=CC(=O)Nc1ccc(Cl)c2ccc(-c3cccc(C(=O)NC4CCN(C)CC4)n3)cc12] | 6-[5-chloro-8-(prop-2-enamido)naphthalen-2-yl]-N-(1-methylpiperidin-4-yl)pyridine-2-carboxamide | 449.1 |
| 402 | 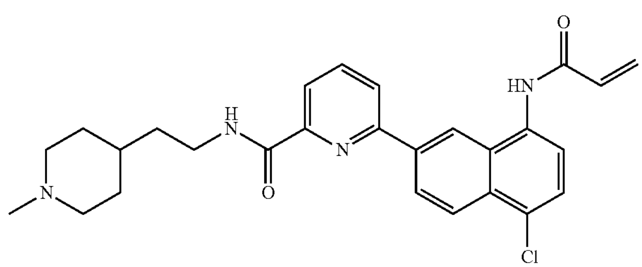 [SMILES: C=CC(=O)Nc1ccc(Cl)c2ccc(-c3cccc(C(=O)NCCC4CCN(C)CC4)n3)cc12] | 6-[5-chloro-8-(prop-2-enamido)naphthalen-2-yl]-N-[2-(1-methylpiperidin-4-yl)ethyl]pyridine-2-carboxamide | 477.2 |
| 403 | 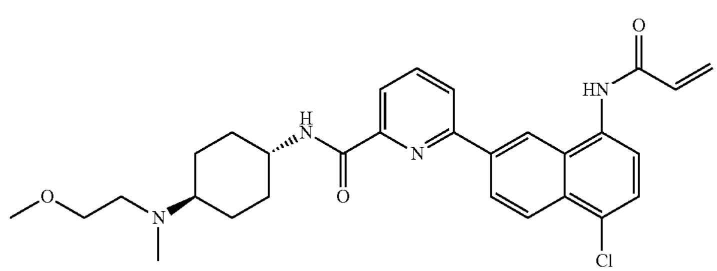 [SMILES: C=CC(=O)Nc1ccc(Cl)c2ccc(-c3cccc(C(=O)N[C@H]4CC[C@H](N(C)CCOC)CC4)n3)cc12] | 6-[5-chloro-8-(prop-2-enamido)naphthalen-2-yl]-N-[(1r,4r)-4-[(2-methoxyethyl)(methyl)amino]cyclohexyl]pyridine-2-carboxamide | 521.3 |

TABLE 8-continued
| Cpd. No. | Structure | IUPAC | LC-MS (ES+, m/z) |
|---|---|---|---|
| 404 | 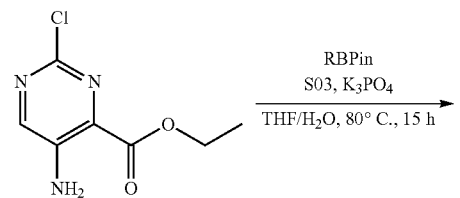 | 6-[5-chloro-8-(prop-2-enamido)naphthalen-2-yl]-N-[(1s,4s)-4-[(2-methoxyethyl)(methyl)amino]cyclohexyl]pyridine-2-carboxamide | 521.3 |
Example 9: Method I
Route 1: General Scheme
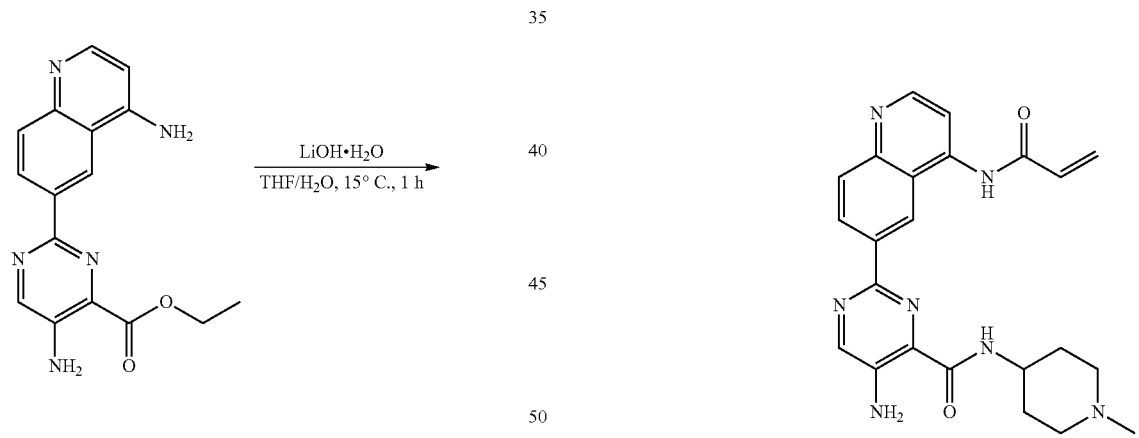
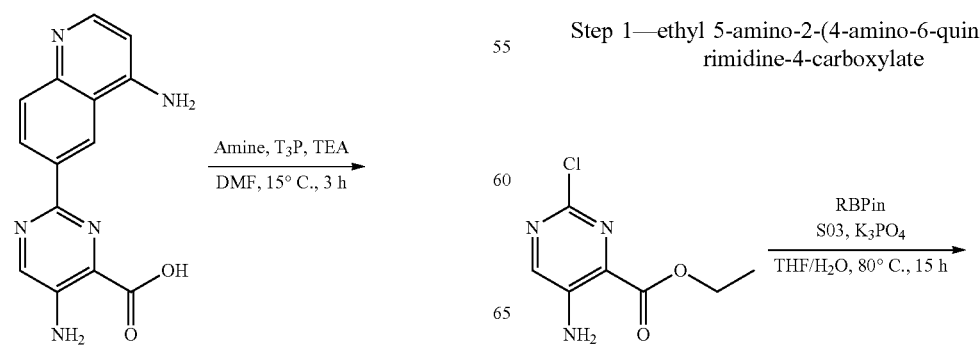
Step 1—ethyl 5-amino-2-(4-amino-6-quinolyl)pyrimidine-4-carboxylate
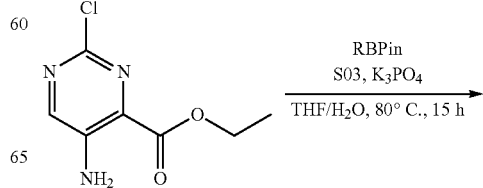

-continued

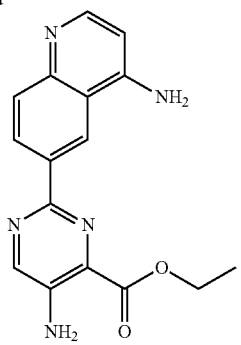

To a solution of (4-amino-6-quinolyl)boronic acid (150 mg, 797.91 μmol, 1 eq) and ethyl 5-amino-2-chloro-pyrimidine-4-carboxylate (193 mg, 957.49 μmol, 1.2 eq) in H₂O (1 mL) and THF (4 mL) were successively added K₃PO₄ (338.8 mg, 1.6 mmol, 2 eq) and [2-(2-aminophenyl)phenyl]-chloro-palladium;bis(1-adamantyl)-butyl-phosphane (53.4 mg, 79.79 μmol, 0.1 eq). The reaction mixture was heated to 80° C. under N₂ and stirred at 80° C. for 15 h. LCMS showed that the reaction was complete. The reaction mixture was poured into saturated EDTA (50 mL) and diluted with EtOAc (50 mL). The solution was stirred at 25° C. for another 1 h. The mixture was filtered, and the filtrate was washed with EtOAc (3×50 mL). The aqueous phase was concentrated in vacuo to give a residue. The residue was re-dissolved in DCM:MeOH=10:1 then filtered. The filtrate was concentrated to afford the title compound as a mixture of ethyl 5-amino-2-(4-amino-6-quinolyl)pyrimidine-4-carboxylate and 5-amino-2-(4-amino-6-quinolyl)pyrimidine-4-carboxylic acid (140 mg, crude) as a yellow solid. LC-MS (ES⁺, m/z): 310.1 [(M+H)⁺]

Step 2—5-amino-2-(4-amino-6-quinolyl)pyrimidine-4-carboxylic acid

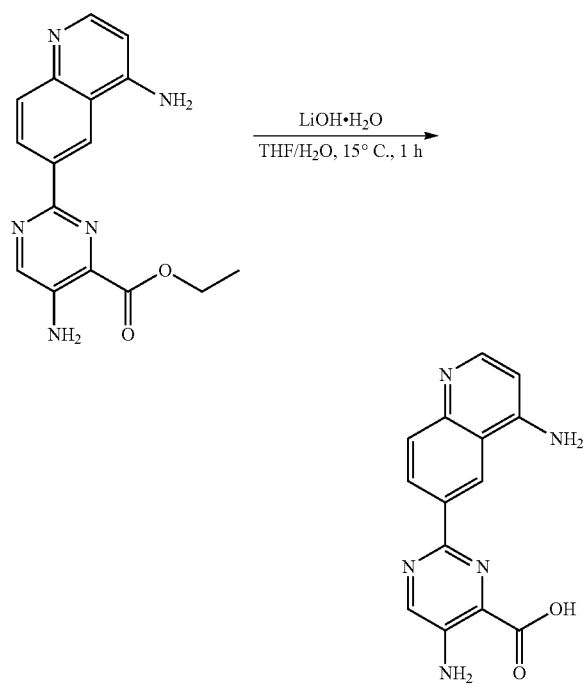

To a solution of ethyl 5-amino-2-(4-amino-6-quinolyl)pyrimidine-4-carboxylate (0.12 g, 387.95 μmol, 1 eq) in THF (4 mL) and H₂O (1 mL) was added LiOH·H₂O (48.8 mg, 1.16 mmol, 3 eq). The reaction mixture was stirred at 15° C. for 1 h. TLC (DCM:MeOH:TEA=10:1:0.1, SM Rf=0.35, TM Rf=0.06) showed that the reaction was complete. The reaction mixture was concentrated in vacuo to afford the title compound 5-amino-2-(4-amino-6-quinolyl)pyrimidine-4-carboxylic acid (0.2 g, crude) as a yellow solid, which was used for the next step directly without further purification.

Step 3—5-amino-2-(4-amino-6-quinolyl)-N-(1-methyl-4-piperidyl)pyrimidine-4-carboxamide

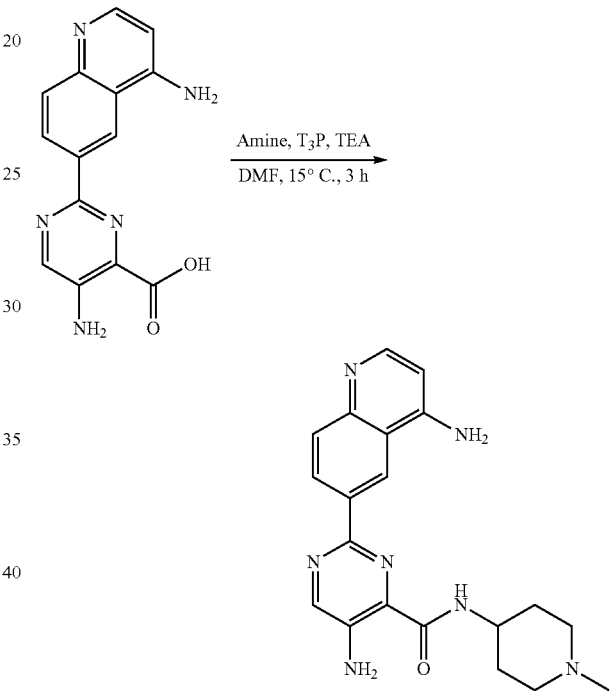

To a solution of 5-amino-2-(4-amino-6-quinolyl)pyrimidine-4-carboxylic acid (0.15 g, 533.3 μmol, 1 eq) in DMF (4 mL) were added TEA (269.8 mg, 2.67 mmol, 371.14 μL, 5 eq) and 1-methylpiperidin-4-amine (182.7 mg, 1.6 mmol, 3 eq). Then, T₃P (509.1 mg, 799.95 μmol, 475.75 μL, 50% purity, 1.5 eq) was added. The reaction mixture was stirred at 15° C. for 3 h. TLC showed that the reaction was complete. The reaction mixture was poured into 50 mL H₂O and extracted with EtOAc (2×50 mL). The combined organic layers were washed with H₂O (2×50 mL) and brine (2×50 mL), dried over anhydrous Na₂SO₄, filtered, and concentrated in vacuo to give a residue. The residue was purified by prep-TLC (SiO₂, DCM:MeOH:TEA=6:1:0.1) to afford the title compound 5-amino-2-(4-amino-6-quinolyl)-N-(1-methyl-4-piperidyl)pyrimidine-4-carboxamide (50 mg, 132.47 μmol, 24.84% yield) as a yellow solid. LC-MS (ES⁺, m/z): 378.3 [(M+H)⁺]

Step 4) Compound 438: Preparation of 5-amino-N-(1-methylpiperidin-4-yl)-2-[4-(prop-2-enamido)quinolin-6-yl]pyrimidine-4-carboxamide

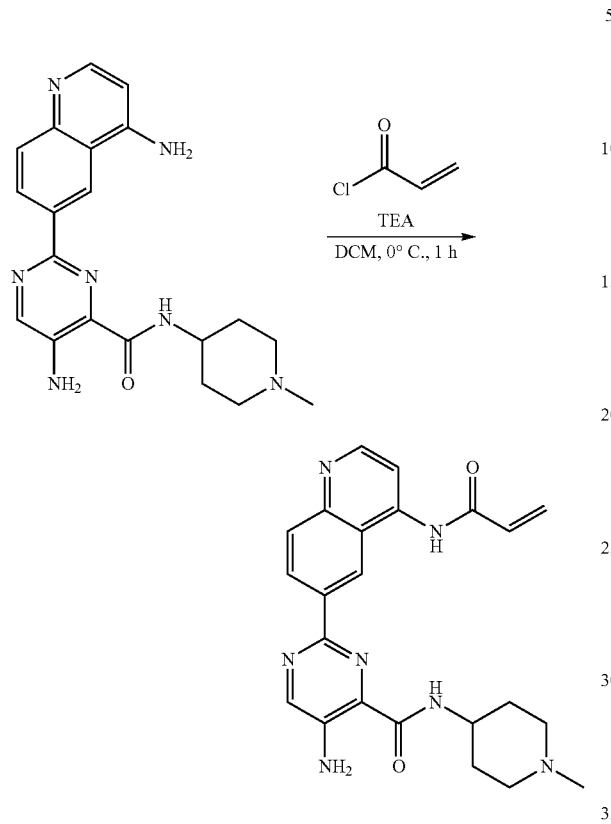

To a solution of 5-amino-2-(4-amino-6-quinolyl)-N-(1-methyl-4-piperidyl)pyrimidine-4-carboxamide (40 mg, 105.98 μmol, 1 eq) in DCM (2 mL) were added TEA (53.6 mg, 529.88 μmol, 73.75 μL, 5 eq) and prop-2-enoyl chloride (28.8 mg, 317.93 μmol, 25.92 μL, 3 eq). The reaction mixture was stirred at 0° C. for 1 h under $N_2$. LCMS showed that the reaction was complete. The reaction mixture was poured into 50 mL $H_2O$ and extracted with EtOAc (50 mL). The combined organic layers were washed with $H_2O$ (2×50 mL) and brine (2×50 mL), dried over anhydrous $Na_2SO_4$, filtered, and concentrated in vacuo to give a residue. The residue was purified by prep-HPLC to afford the title compound 5-amino-N-(1-methyl-4-piperidyl)-2-[4-(prop-2-enoylamino)-6-quinolyl]pyrimidine-4-carboxamide (5.1 mg, 11.37 μmol, 10.73% yield, 96.2% purity) as a white solid. LC-MS (ES$^+$, m/z): 432.2 [(M+H)$^+$]$^1$H NMR (400 MHz, DMSO-d$_6$) δ=10.70 (s, 1H), 9.30 (d, J=1.76 Hz, 1H), 8.76-8.85 (m, 2H), 8.70 (d, 7=7.90 Hz, 1H), 8.64 (s, 1H), 8.16 (d, 7=5.26 Hz, 1H), 8.07 (d, 7=8.78 Hz, 1H), 7.08 (s, 2H), 6.84-6.92 (m, 1H), 6.40-6.44 (m, 1H), 5.88-5.92 (m, 1H), 3.79-3.81 (m, 1H), 2.80 (br d, J=11.84 Hz, 2H), 2.20 (s, 3H), 1.93-2.06 (m, 2H), 1.75-1.89 (m, 4H).

Route 2: General Scheme

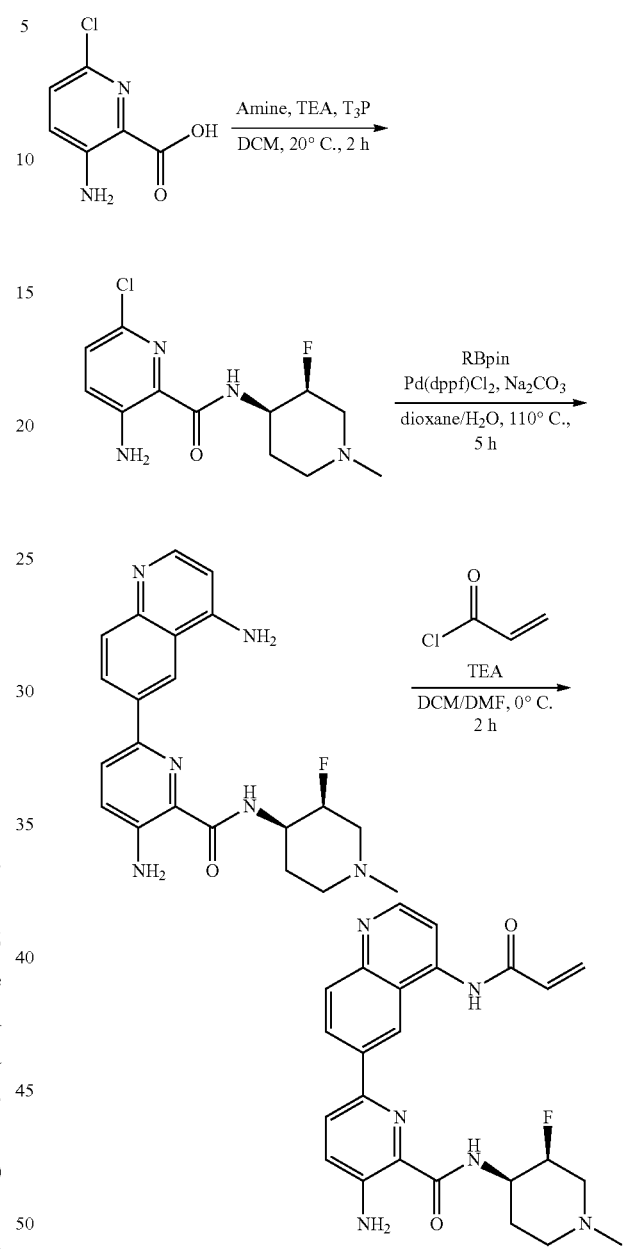

Step 1—3-amino-6-chloro-N-(3-fluoro-1-methyl-4-piperidyl)pyridine-2-carboxamide

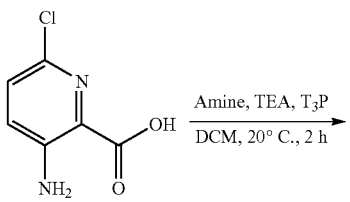

505

-continued

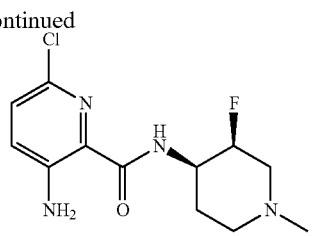

To a solution of 3-amino-6-chloro-pyridine-2-carboxylic acid (1 g, 5.79 mmol, 1 eq) and 3-fluoro-1-methyl-piperidin-4-amine (918.4 mg, 6.95 mmol, 1.2 eq, 2HCl) in DCM (15 mL) were added TEA (1.76 g, 17.37 mmol, 2.42 mL, 3 eq) and T₃P (5.53 g, 8.68 mmol, 5.17 mL, 50% purity, 1.5 eq) under N₂. The reaction mixture was stirred at 20° C. for 2 hours under N₂. The reaction mixture was concentrated directly to give a residue. The residue was purified by column chromatography (SiO₂, EtOAc:MeOH=30:1 to 20:1) to afford the title compound 3-amino-6-chloro-N-(3-fluoro-1-methyl-4-piperidyl)pyridine-2-carboxamide (1.25 g, 4.36 mmol, 75.29% yield) as a yellow solid.

Step 2—3-amino-6-(4-amino-6-quinolyl)-N-(3-fluoro-1-methyl-4-piperidyl)pyridine-2-carboxamide

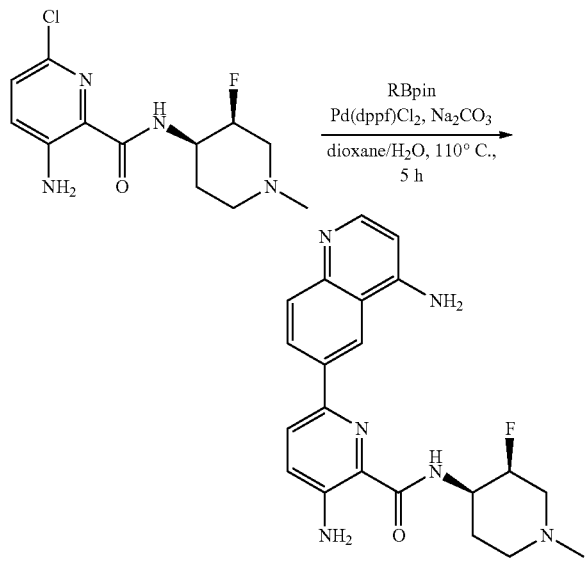

To a solution of 6-(4,4,5,5-tetramethyl-1,3,2-dioxaborolan-2-yl)quinolin-4-amine (471.06 mg, 1.74 mmol, 2.5 eq) and 3-amino-6-chloro-N-(3-fluoro-1-methyl-4-piperidyl)pyridine-2-carboxamide (200 mg, 697.51 μmol, 1 eq) in dioxane (2 mL) and H₂O (0.5 mL) were added Na₂CO₃ (221.8 mg, 2.09 mmol, 3 eq) Pd(dppf)Cl₂ (51 mg, 69.75 μmol, 0.1 eq) under N₂. The reaction mixture was stirred at 110° C. for 5 hours under N₂. The reaction mixture was poured into saturated EDTA (50 mL) and 20 mL EtOAc. The mixture was stirred for 1 h, and the aqueous phase was separated and extracted with EtOAc (3×20 mL). The combined organic phase was washed with brine (3×30 mL), dried over anhydrous Na₂SO₄, filtered, concentrated in vacuo to give a residue. The residue was purified by prep-TLC (SiO₂, DCM:MeOH:Et₃N=10:1:0.1) to afford the title compound 3-amino-6-(4-amino-6-quinolyl)-N-(3-fluoro-1-

506 methyl-4-piperidyl)pyridine-2-carboxamide (70 mg, 177.46 μmol, 25.44% yield) as a yellow gum. LC-MS (ES⁺, m/z): 395.1 [(M+H)⁺]

Preparation of 3-amino-N-[(3S,4R)-3-fluoro-1-methylpiperidin-4-yl]-6-[4-(prop-2-enamido)quinolin-6-yl]pyridine-2-carboxamide (Compound 436)

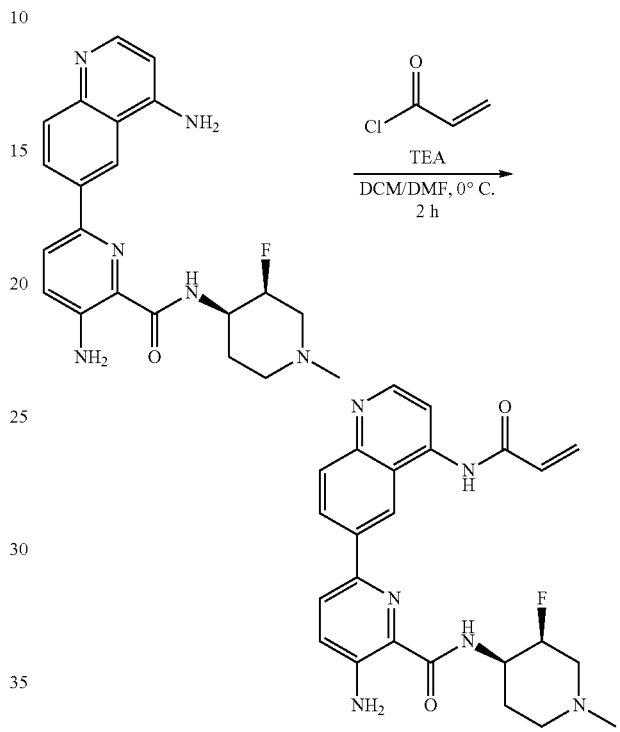

To a mixture of 3-amino-6-(4-amino-6-quinolyl)-N-(3-fluoro-1-methyl-4-piperidyl)pyridine-2-carboxamide (50 mg, 126.76 μmol, 1 eq) and TEA (15.4 mg, 152.11 μmol, 21.17 μL, 3 eq) in DCM (1 mL) and DMF (1 mL) was added prop-2-enoyl chloride (11.5 mg, 126.76 μmol, 10.34 μL, 1 eq) in one portion at 0° C. The reaction mixture was stirred at 0° C. for 1 hour. LCMS showed that the conversion was ~50%. Additional prop-2-enoyl chloride (11.5 mg, 126.76 μmol, 10.34 μL, 1 eq) was added at 0° C. The resulting reaction mixture was stirred at 0° C. for another 1 hour. The reaction was poured into 20 mL water and extracted with DCM (3×20 mL). The combined organic layer was washed with brine (2×20 mL), dried over Na₂SO₄, filtered, and concentrated in vacuo to give a residue. The residue was purified by prep-HPLC (basic condition) to afford the title compound 3-amino-N-(3-fluoro-1-methyl-4-piperidyl)-6-[4-(prop-2-enoylamino)-6-quinolyl]pyridine-2-carboxamide (11.4 mg, 24.17 μmol, 19.07% yield, 95.1% purity) as a white solid. LC-MS (ES⁺, m/z): 449.2 [(M+H)⁺]¹H NMR (400 MHz, DMSO-de) δ=10.59 (br s, 1H), 8.97 (d, J=1.6 Hz, 1H), 8.79 (d, J=5.2 Hz, 1H), 8.55 (br d, J=8.0 Hz, 1H), 8.44 (dd, J=2.0, 8.8 Hz, 1H), 8.21 (d, J=5.2 Hz, 1H), 8.17 (d, J=8.8 Hz, 1H), 8.06 (d, J=8.8 Hz, 1H), 7.38 (d, J=8.8 Hz, 1H), 7.09 (br s, 2H), 6.86 (dd, J=10.4, 17.2 Hz, 1H), 6.41 (dd, J=1.6, 17.2 Hz, 1H), 5.93-5.84 (m, 1H), 4.96-4.76 (m, 1H), 4.09-3.89 (m, 1H), 3.11-3.00 (m, 1H), 2.82 (br d, J=9.6 Hz, 1H), 2.22 (s, 4H), 2.16-2.01 (m, 2H), 1.77 (br d, J=12.4 Hz, 1H).

Route 3: General Scheme

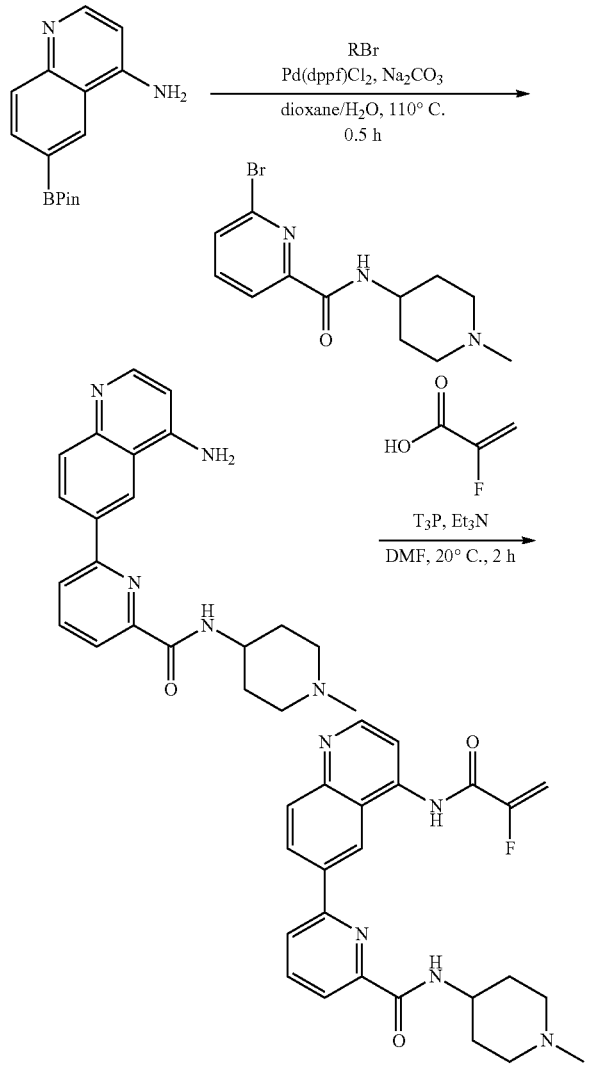

Step 1—6-(4-amino-6-quinolyl)-N-(1-methyl-4-piperidyl)pyridine-2-carboxamide

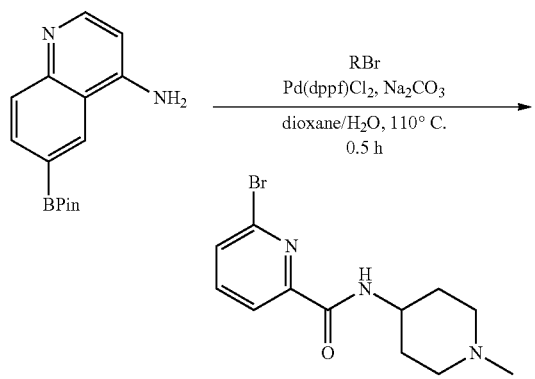

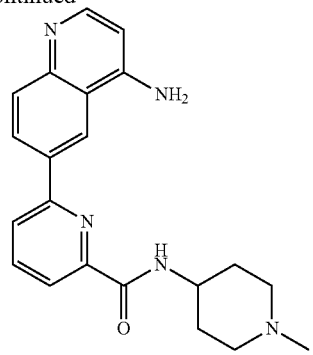

To a solution of 6-(4,4,5,5-tetramethyl-1,3,2-dioxaborolan-2-yl)quinolin-4-amine (906 mg, 3.35 mmol, 2.5 eq) and 6-bromo-N-(1-methyl-4-piperidyl)pyridine-2-carboxamide (400 mg, 1.34 mmol, 1 eq) in dioxane (8 mL) and H₂O (2 mL) were added Na₂CO₃ (426.6 mg, 4.02 mmol, 3 eq) and Pd(dppf)Cl₂ (98.2 mg, 134.15 µmol, 0.1 eq) in one portion under N₂. The reaction mixture was heated to 110° C. and stirred at 110° C. for 30 min under N₂. The reaction mixture was poured into saturated EDTA aqueous solution (50 mL) and 20 mL EtOAc. The mixture was stirred for 1 h, and the aqueous phase was separated and extracted with EtOAc (3×20 mL). The combined organic phase was washed with brine (3×20 mL), dried over anhydrous Na₂SO₄ and concentrated in vacuo to give a residue. The residue was purified by column chromatography (SiO₂, DCM:MeOH:Et₃N=10: 1:0 to 10:1:0.1) to afford the title compound 6-(4-amino-6-quinolyl)-N-(1-methyl-4-piperidyl)pyridine-2-carboxamide (300 mg, 830.01 µmol, 61.87% yield) as a yellow solid. LC-MS (ES⁺, m/z): 362.1 [(M+H)⁺].

Step 2—6-[4-(2-fluoroprop-2-enoylamino)-6-quinolyl]-N-(1-methyl-4-piperidyl)pyridine-2-carboxamide (Compound 437)

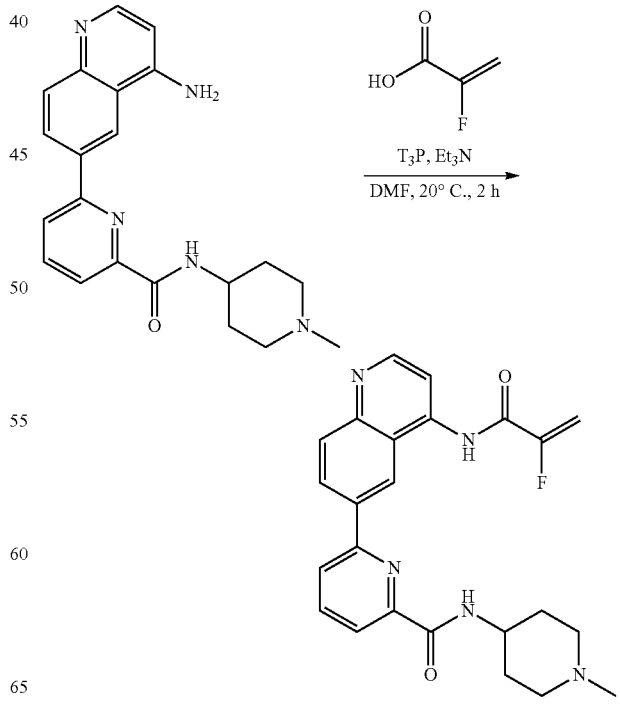

To a mixture of 6-(4-amino-6-quinolyl)-N-(1-methyl-4-piperidyl)pyridine-2-carboxamide (80 mg, 221.34 µmol, 1 eq) and 2-fluoroprop-2-enoic acid (39.9 mg, 442.0.67 µmol, 2 eq) in DMF (2 mL) were added Et₃N (112 mg, 1.11 mmol, 154.04 µL, 5 eq) and T₃P (281.7 mg, 442.67 µmol, 263.27 µL, 50% purity, 2 eq) in one portion under N₂. The reaction mixture was stirred at 20° C. for 2 hours. The reaction was poured into 20 mL water, extracted with EtOAc (3×20 mL). The combined organic layer was washed with brine (2×20 mL), dried over Na₂SO₄, filtered, and concentrated in vacuo to afford a residue. The residue was purified by prep-HPLC to afford the title compound 6-[4-(2-fluoroprop-2-enoylamino)-6-quinolyl]-N-(1-methyl-4-piperidyl)pyridine-2-carboxamide (19.1 mg, 43.05 µmol, 19.45% yield, 97.7% purity) as a white solid. LC-MS (ES⁺, m/z): 434.2 [(M+H)⁺], ¹H NMR (400 MHz, DMSO-d₆) δ=10.83 (br s, 1H), 9.01 (d, J=1.6 Hz, 1H), 8.93 (d, J=4.8 Hz, 1H), 8.72 (dd, J=2.0, 8.8 Hz, 1H), 8.63 (br d, J=8.4 Hz, 1H), 8.42 (d, J=7.6 Hz, 1H), 8.20-8.13 (m, 2H), 8.05 (d, J=7.6 Hz, 1H), 7.89 (d, J=4.8 Hz, 1H), 5.85 (d, J=4.0 Hz, 1H), 5.97 (d, J=4.0 Hz, 1H), 5.57 (dd, J=4.0, 15.6 Hz, 1H), 3.92-3.78 (m, 1H), 2.82 (br d, J=11.2 Hz, 2H), 2.21 (s, 3H), 2.03 (br t, J=10.8 Hz, 2H), 1.88-1.72 (m, 4H).

Route 4: General Scheme

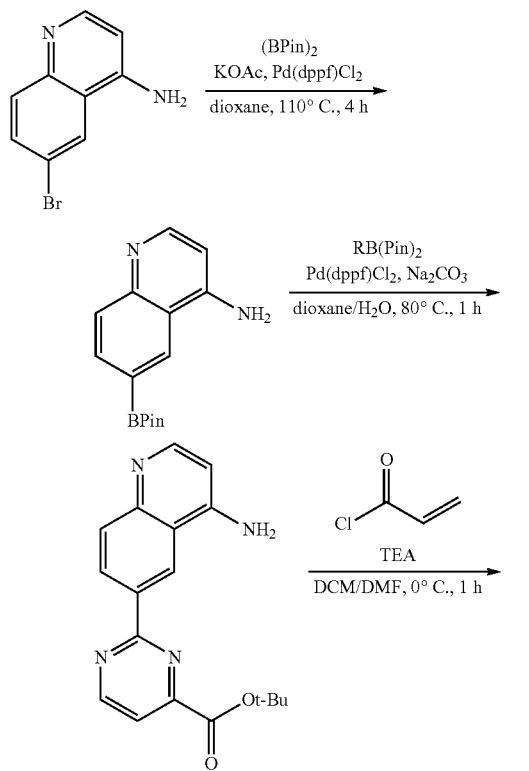

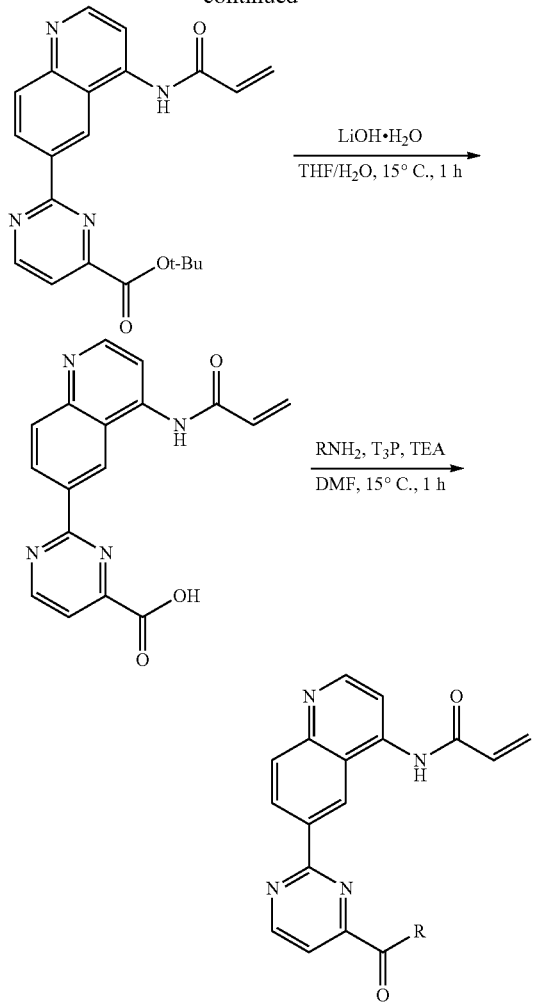

Step 1—6-(4,4,5,5-tetramethyl-1,3,2-dioxaborolan-2-yl)quinolin-4-amine

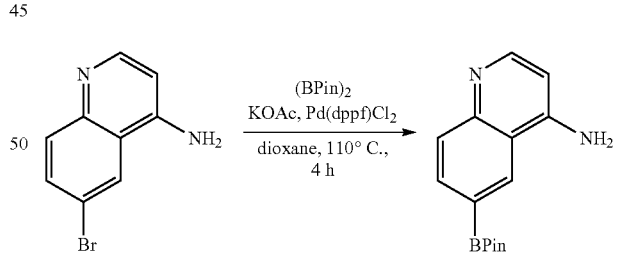

To a mixture of 6-bromoquinolin-4-amine (2 g, 8.97 mmol, 1 eq) and 4,4,5,5-tetramethyl-2-(4,4,5,5-tetramethyl-1,3,2-dioxaborolan-2-yl)-1,3,2-dioxaborolane (3.42 g, 13.45 mmol, 1.5 eq) in dioxane (20 mL) were added KOAc (2.64 g, 26.9 mmol, 3 eq) and Pd(dppf)Cl₂ (656 mg, 896.58 µmol, 0.1 eq). The reaction was stirred at 110° C. for 4 hr under N₂. LCMS showed that the reaction was complete. The reaction mixture was concentrated in vacuo to give a residue. The residue was washed with DCM and PE to afford the title compound 6-(4,4,5,5-tetramethyl-1,3,2-dioxaborolan-2-yl)quinolin-4-amine (3.8 g, crude) as a black brown solid. LC-MS (ES⁺, m/z): 189.0, 271.1 [(M+H)⁺]

Step 2—tert-butyl 2-(4-amino-6-quinolyl)pyrimidine-4-carboxylate

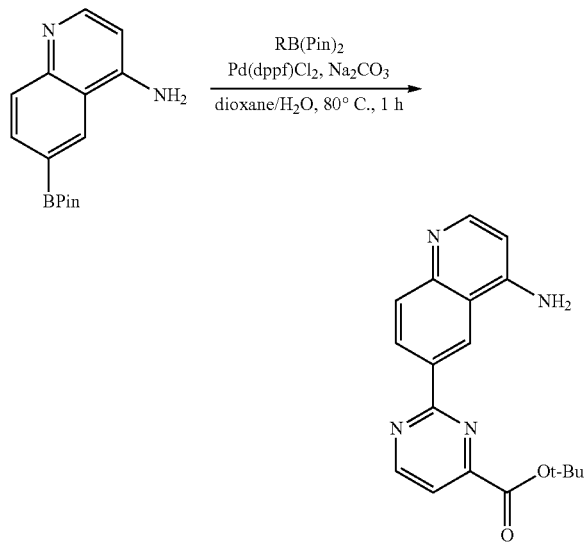

To a mixture of tert-butyl 2-chloropyrimidine-4-carboxylate (1 g, 4.66 mmol, 1 eq) and 6-(4,4,5,5-tetramethyl-1,3,2-dioxaborolan-2-yl)quinolin-4-amine (2.52 g, 9.32 mmol, 2 eq) in dioxane (8 mL) and H$_2$O (2 mL) were added Na$_2$CO$_3$ (1.48 g, 13.98 mmol, 3 eq) and Pd(dppf)Cl$_2$ (340.9 mg, 465.88 μmol, 0.1 eq). The reaction heated to 80° C. under N$_2$ and stirred for 1 h. TLC showed that the reaction was complete. The reaction mixture was stirred by adding saturated EDTA (50 mL) and EtOAc (50 mL) at 25° C. for 1 h. The combined organic phase was washed with H$_2$O (2×50 mL) and brine (2×50 mL), dried over anhydrous Na$_2$SO$_4$, filtered, and concentrated in vacuo to give a residue. The residue was purified by column chromatography (SiO$_2$, PE:EtOAc=1/1 to I/O) to afford the title compound tert-butyl 2-(4-amino-6-quinolyl)pyrimidine-4-carboxylate (1 g, 3.1 mmol, 66.59% yield) as a yellow solid. LC-MS (ES$^+$, m/z): 323.1 [(M+H)$^+$]

Step 3—tert-butyl 2-[4-(prop-2-enoylamino)-6-quinolyl]pyrimidine-4-carboxylate

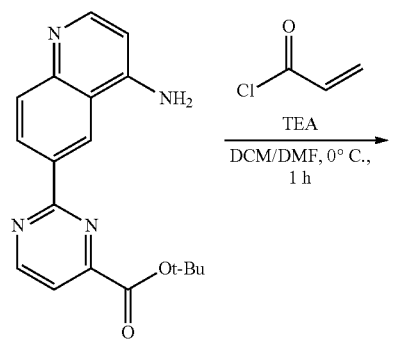 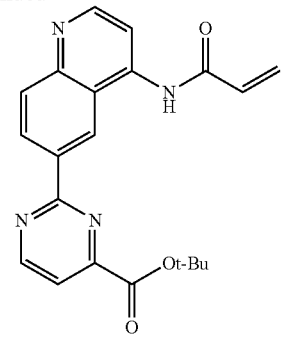

To a mixture of tert-butyl 2-(4-amino-6-quinolyl)pyrimidine-4-carboxylate (0.9 g, 2.79 mmol, 1 eq) in DCM (18 mL) and DMF (18 mL) were added TEA (565 mg, 5.58 mmol, 777.19 μL, 2 eq) and prop-2-enoyl chloride (379 mg, 4.19 mmol, 341.47 μL, 1.5 eq). The reaction mixture was stirred at 0° C. for 1 h under N$_2$. TLC showed that the reaction was complete. The reaction mixture was diluted with H$_2$O and extracted with EtOAc (3×50 mL). The combined organic layers were washed with H$_2$O (2×50 mL) and brine (2×50 mL), dried over anhydrous Na$_2$SO$_4$, filtered, and concentrated in vacuo to give a residue. The residue was purified by column chromatography (SiO$_2$, PE:EtOAc=3:1 to 1/3) to afford the title compound tert-butyl 2-[4-(prop-2-enoylamino)-6-quinolyl]pyrimidine-4-carboxylate (0.9 g, 2.39 mmol, 85.64% yield) as a yellow solid.

Step 4—2-[4-(prop-2-enoylamino)-6-quinolyl]pyrimidine-4-carboxylic acid

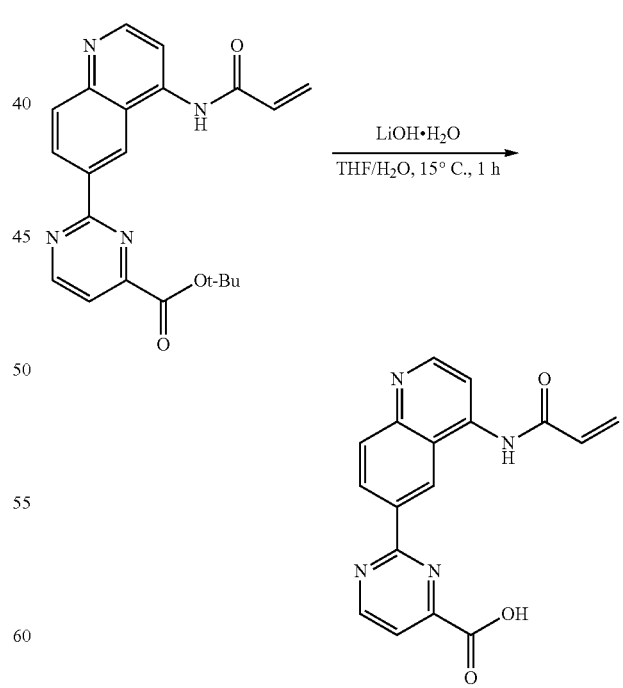

To a mixture of tert-butyl 2-[4-(prop-2-enoylamino)-6-quinolyl]pyrimidine-4-carboxylate (0.4 g, 1.06 mmol, 1 eq) in THF (8 mL) and H$_2$O (2 mL) was added LiOH·H$_2$O (223 mg, 5.31 mmol, 5 eq). The reaction was stirred at 15° C. for 1 h. TLC showed that the reaction was complete. The reaction was poured into ~100 mL ice water and adjusted to pH=7 with saturated citric acid. The mixture was extracted with EtOAc (3×50 mL), and the aqueous layer was lyophilized. The residue was washed with DCM:MeOH=10:1, filtered, and concentrated in vacuo to give a residue. The title compound 2-[4-(prop-2-enoylamino)-6-quinolyl]pyrimidine-4-carboxylic acid (550 mg, crude) was obtained as a yellow solid. LC-MS (ES$^+$, m/z): 321.0 [(M+H)$^+$]

Step 5—N-(8-methyl-8-azabicyclo[3.2.1]octan-3-yl)-2-[4-(prop-2-enoylamino)-6-quinolyl]pyrimidine-4-carboxamide To a solution of 2-[4-(prop-2-enoylamino)-6-quinolyl]pyrimidine-4-carboxylic acid (0.1 g, 312.21 μmol, 1 eq) in DMF (2 mL) were added TEA (58.01 mg, 1.56 mmol, 217.27 μL, 5 eq) and 8-methyl-8-azabicyclo[3.2.1]octan-3-amine (87.6 mg, 624.42 μmol, 2 eq). Then, T$_3$P (298 mg, 468.32 μmol, 278.52 μL, 50% purity, 1.5 eq) was added to the reaction, and the reaction was stirred at 15° C. for 1 h. LCMS showed that the reaction was complete. The reaction mixture was diluted with H$_2$O (50 mL) and extracted with EtOAc (2×50 mL). The combined organic layers were washed with H$_2$O (2×50 mL) and brine (2×50 mL), dried over anhydrous Na$_2$SO$_4$, filtered, and concentrated in vacuo to give a residue. The residue was purified by prep-HPLC to afford the title compound N-(8-methyl-8-azabicyclo[3.2.1]octan-3-yl)-2-[4-(prop-2-enoylamino)-6-quinolyl]pyrimidine-4-carboxamide (12.2 mg, 27.13 μmol, 8.69% yield, 98.4% purity) as a white solid.

Route 5: General Scheme

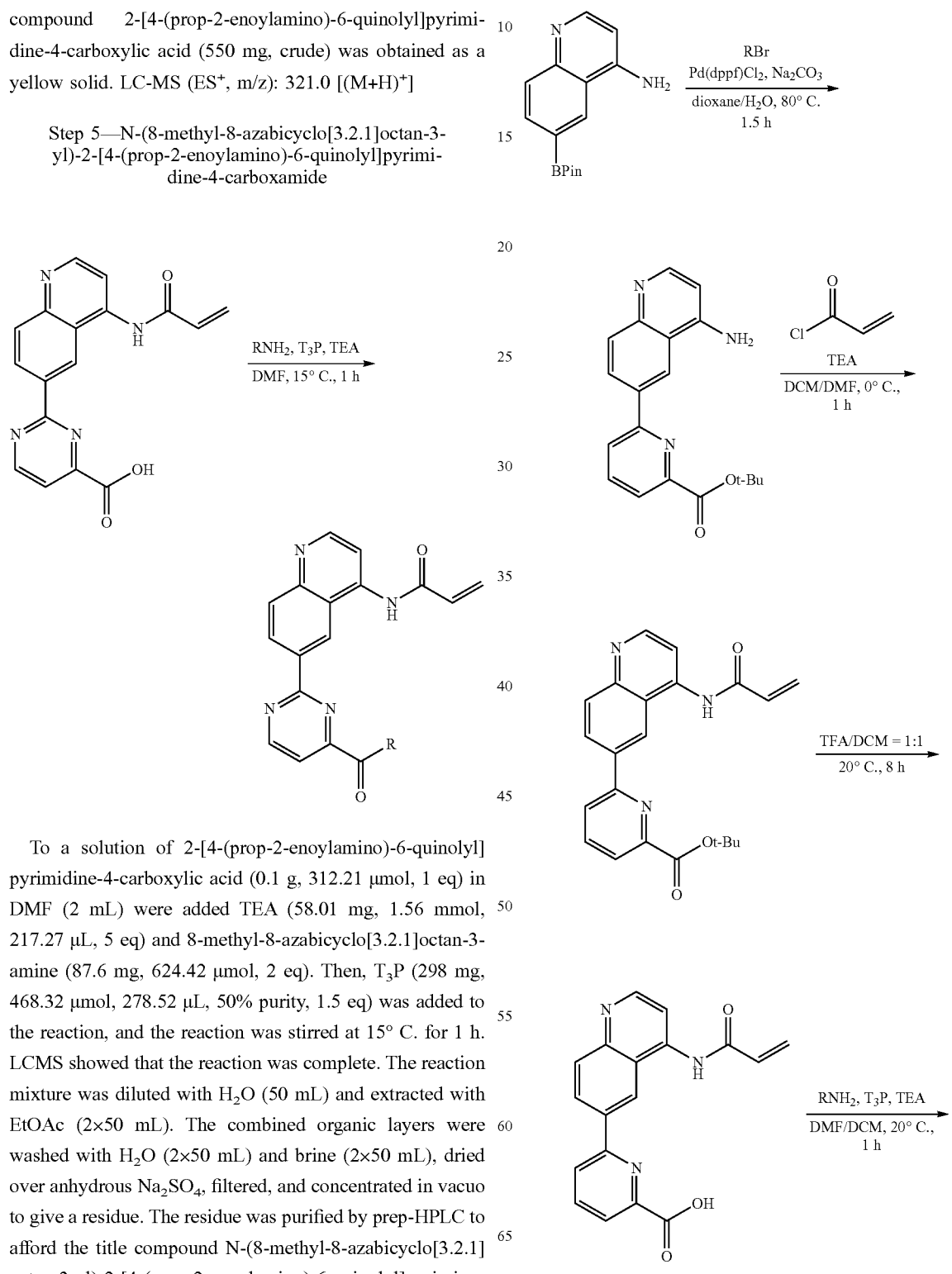

515
-continued

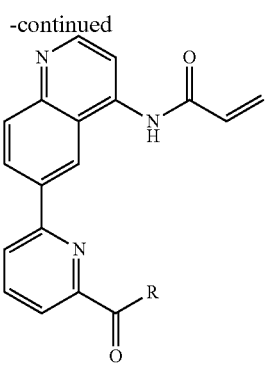

R =

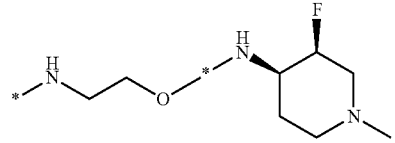

Step 2—tert-butyl 6-(4-amino-6-quinolyl)pyridine-2-carboxylate

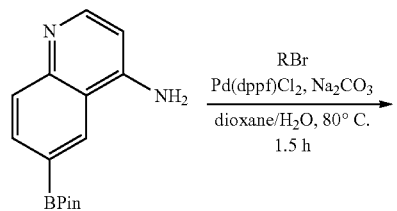

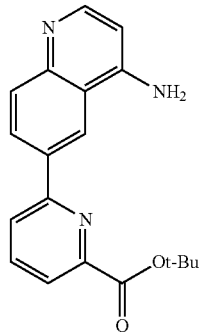

To a mixture of 6-(4,4,5,5-tetramethyl-1,3,2-dioxaborolan-2-yl)quinolin-4-amine (2.3 g, 8.52 mmol, 2.2 eq) and tert-butyl 6-bromopyridine-2-carboxylate (1 g, 3.87 mmol, 1 eq) in dioxane (20 mL) and H$_2$O (5 mL) were added Na$_2$CO$_3$ (1.23 g, 11.62 mmol, 3 eq), Pd(dppf)Cl$_2$ (283.5 mg, 387.43 µmol, 0.1 eq) in one portion under N$_2$. The mixture was stirred at 80° C. for 1.5 hours. The reaction was diluted with 20 mL water and extracted with EtOAc (2×20 mL). The combined organic layer was washed with brine (2×20 mL), dried over Na$_2$SO$_4$, filtered, and concentrated in vacuo. The residue was purified by column chromatography (SiO$_2$, DCM:MeOH=15:1 to 8:1) to afford the title compound tert-butyl 6-(4-amino-6-quinolyl)pyridine-2-carboxylate (0.9 g, 2.8 mmol, 72.28% yield) as a yellow solid. LC-MS (ES$^+$, m/z): 322.2 [(M+H)$^+$]

516

Step 3—tert-butyl 6-[4-(prop-2-enoylamino)-6-quinolyl]pyridine-2-carboxylate

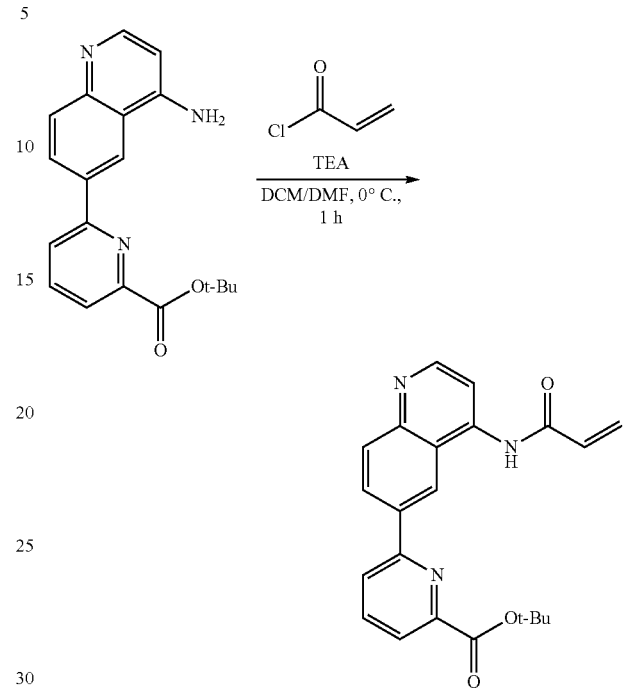

To a mixture of tert-butyl 6-(4-amino-6-quinolyl)pyridine-2-carboxylate (800 mg, 2.49 mmol, 1 eq) in DCM (8 mL) and DMF (8 mL) were added Et$_3$N (755.7 mg, 7.47 mmol, 1.04 mL, 3 eq) and prop-2-enamide (265.4 mg, 3.73 mmol, 257.67 µL, 1.5 eq) in one portion at 0° C. under N$_2$. The mixture was stirred at 0° C. for 60 min. The reaction was diluted with 30 mL water and extracted with EtOAc (3×30 mL). The combined organic layer was washed with brine (2×30 mL), dried over Na$_2$SO$_4$, filtered, and concentrated in vacuo. The residue was purified by column chromatography (SiO$_2$, DCM:MeOH=1:0) and purified by prep-TLC (SiO$_2$, DCM:MeOH=15:1) to afford the title compound tert-butyl 6-[4-(prop-2-enoylamino)-6-quinolyl]pyridine-2-carboxylate (600 mg, 1.6 mmol, 64.20% yield) as a yellow gum. LC-MS (ES$^+$, m/z): 376.1 [(M+H)$^+$]

Step 4—6-[4-(prop-2-enoylamino)-6-quinolyl]pyridine-2-carboxylic acid

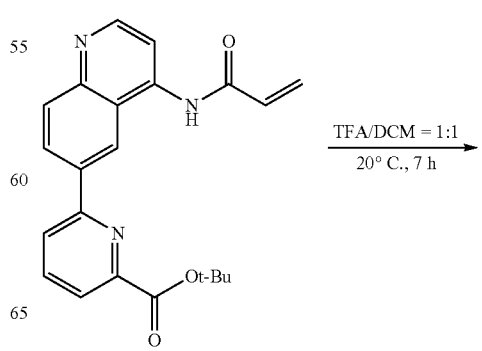

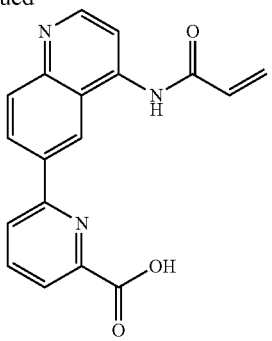

To a mixture of tert-butyl 6-[4-(prop-2-enoylamino)-6-quinolyl]pyridine-2-carboxylate (200 mg, 532.74 μmol, 1 eq) in DCM (3 mL) was added TFA (4.62 g, 40.52 mmol, 3 mL, 76.06 eq) in one portion. The mixture was stirred at 20° C. for 7 hours. The reaction was concentrated directly, and the crude material was lyophilized to afford the title compound 6-[4-(prop-2-enoylamino)-6-quinolyl]pyridine-2-carboxylic acid (160 mg, crude) as an off-white solid. LC-MS (ES$^+$, m/z): 320.2 [(M+H)$^+$].

Step 5—N-(2-methoxyethyl)-6-/4-(prop-2-enoylamino)-6-quinolyl/pyridine-2-carboxamide

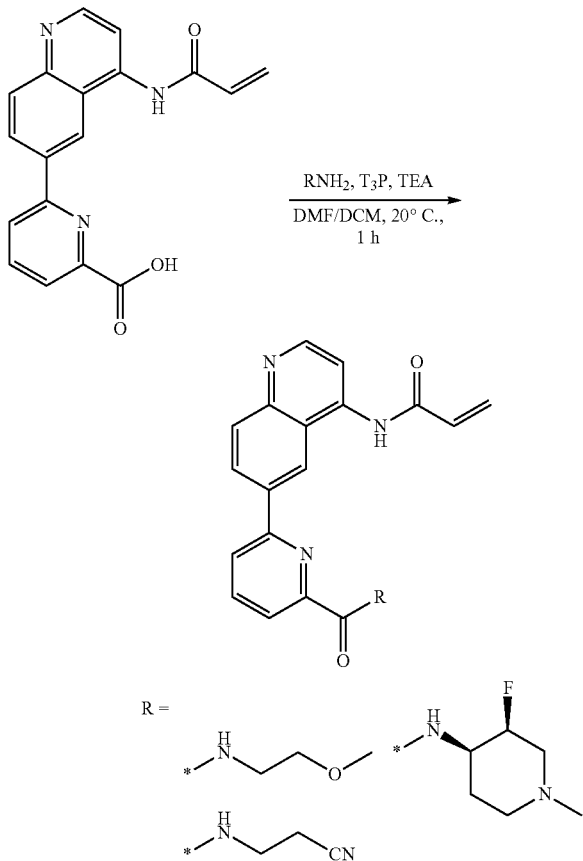

To a mixture of 6-[4-(prop-2-enoylamino)-6-quinolyl] pyridine-2-carboxylic acid (40 mg, 125.27 μmol, 1 eq) and 2-methoxyethanamine (14.1 mg, 187.9 μmol, 16.33 μL, 1.5 eq) in DCM (1.5 mL) and DMF (0.5 mL) were added Et$_3$N (63.4 mg, 626.34 μmol, 87.18 μL, 5 eq) and T$_3$P (119.6 mg, 187.9 μmol, 111.75 μL, 50% purity, 1.5 eq) in one portion. The mixture was stirred at 20° C. for 60 min. The reaction mixture was adjusted to pH=9 with saturated aq. Na$_2$CO$_3$ and extracted with EtOAc (4×15 mL). The combined organic layer was washed with brine (2×15 mL), dried over Na$_2$SO$_4$, filtered, and concentrated in vacuo. The residue was purified by prep-TLC (SiO$_2$, DCM:MeOH=10:1) and by prep-HPLC (neutral condition) to afford the title compound N-(2-methoxyethyl)-6-[4-(prop-2-enoylamino)-6-quinolyl]pyridine-2-carboxamide (5.7 mg, 15.14 μmol, 12.09% yield, 100.0% purity) as a white solid.

Step 6—N-(2-cyanoethyl)-6-[4-(prop-2-enoylamino)-6-quinolyl]pyridine-2-carboxamide

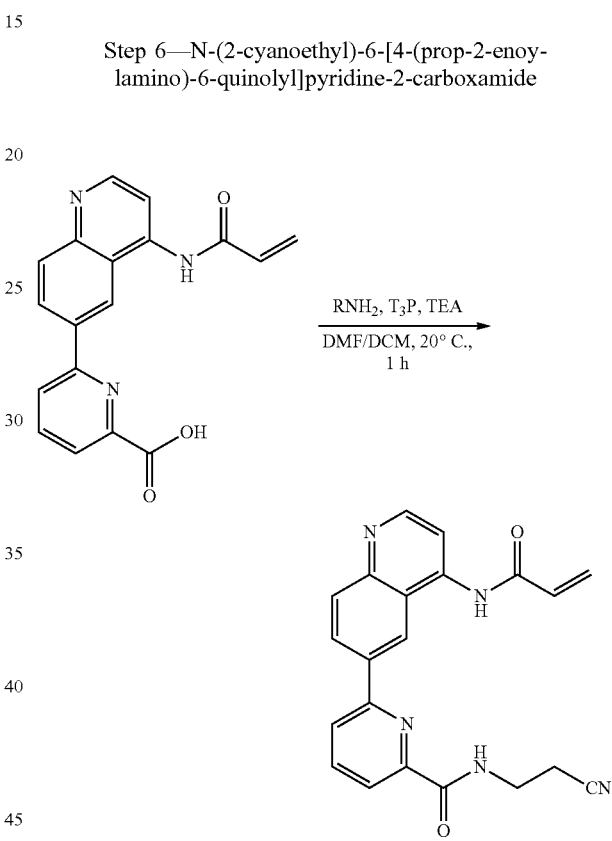

To a mixture of 6-[4-(prop-2-enoylamino)-6-quinolyl] pyridine-2-carboxylic acid (50 mg, 156.59 μmol, 1 eq) and 3-aminopropanenitrile (13.2 mg, 187.9 μmol, 13.86 μL, 1.2 eq) in DCM (1.5 mL) and DMF (0.5 mL) were added Et$_3$N (79.2 mg, 782.93 μmol, 108.97 μL, 5 eq) and T$_3$P (149.5 mg, 234.88 μmol, 139.69 μL, 50% purity, 1.5 eq) in one portion. The mixture was stirred at 20° C. for 60 min. The reaction was adjusted to pH=9 with saturated aq. Na$_2$CO$_3$ and extracted with EtOAc (4×15 mL). The combined organic layer was washed with brine (2×15 mL), dried over Na$_2$SO$_4$, filtered, and concentrated in vacuo. The residue was purified by prep-HPLC (basic condition) to afford the title compound N-(2-cyanoethyl)-6-[4-(prop-2-enoylamino)-6-quinolyl] pyridine-2-carboxamide (6 mg, 15.67 μmol, 10.01% yield, 97.0% purity) as a white solid. LC-MS (ES$^+$, m/z): 372.1 [(M+H)$^+$] $^1$H NMR (400 MHz, DMSO-d$_6$) δ=10.55 (s, 1H), 9.33 (br t, J=6.0 Hz, 1H), 9.16 (s, 1H), 8.90-8.82 (m, 2H), 8.50 (d, J=8.0 Hz, 1H), 8.31 (d, J=5.2 Hz, 1H), 8.21 (t, J=7.8 Hz, 1H), 8.15 (d, J=9.2 Hz, 1H), 8.08 (d, J=7.6 Hz, 1H), 6.89

(dd, J=10.4, 16.8 Hz, 1H), 6.43 (br d, J=16.8 Hz, 1H), 5.94 (br d, J=9.6 Hz, 1H), 3.67 (q, J=6.2 Hz, 2H), 2.90 (t, J=6.5 Hz, 2H).

Route 7: General Scheme

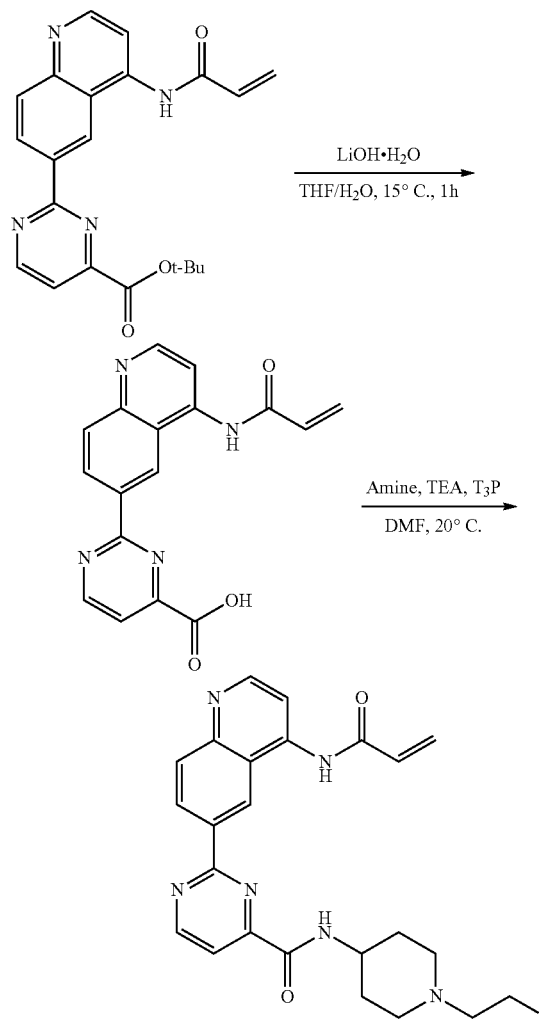

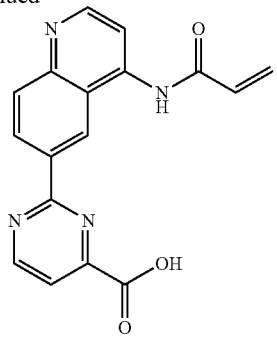

To a mixture of tert-butyl 2-[4-(prop-2-enoylamino)-6-quinolyl]pyrimidine-4-carboxylate (0.5 g, 1.33 mmol, 1 eq) in THF (6 mL) and H₂O (1.5 mL) was added LiOH·H₂O (278.7 mg, 6.64 mmol, 5 eq). The reaction was stirred at 15° C. for 1 h. TLC showed that the reaction was complete. The reaction was poured into ~50 mL ice water and washed with EtOAc (3×50 mL). The aqueous layers were concentrated by lyophilization to afford the title compound 2-[4-(prop-2-enoylamino)-6-quinolyl]pyrimidine-4-carboxylic acid (0.7 g, crude) as a yellow solid.

Step 2—N-[1-(2-methoxyethyl)-4-piperidyl]-2-[4-(prop-2-enoylamino)-6-quinolyl]pyrimidine-4-carboxamide Step 1—2-[4-(prop-2-enoylamino)-6-quinolyl]pyrimidine-4-carboxylic acid

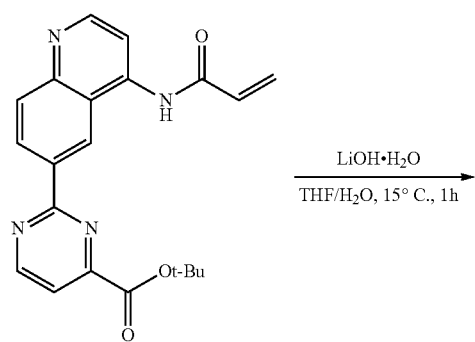

To a mixture of 2-[4-(prop-2-enoylamino)-6-quinolyl]pyrimidine-4-carboxylic acid (200 mg, 624.41 μmol, 1 eq) and 1-(2-methoxyethyl)piperidin-4-amine (182.4 mg, 936.62 μmol, 1.5 eq, HCl) in DCM (2 mL) were added Et₃N (315.9 mg, 3.12 mmol, 434.55 μL, 5 eq) and T₃P (596 mg, 936.62 μmol, 557.03 μL, 50% purity, 1.5 eq) in one portion under N₂. The mixture was stirred at 20° C. for 60 min. The reaction was diluted with 20 mL water and extracted with EtOAc (3×20 mL). The combined organic layer was washed with brine (3×20 mL), dried over Na$_2$SO$_4$, filtered, and concentrated in vacuo. The residue was purified by prep-HPLC (basic condition) to afford the title compound N-[1-(2-methoxyethyl)-4-piperidyl]-2-[4-(prop-2-enoylamino)-6-quinolyl]pyrimidine-4-carboxamide (20 mg, 43.43 μmol, 6.96% yield, 100.0% purity) as a white solid. LC-MS (ES$^+$, m/z): 461.3 [(M+H)$^+$], 1H NMR (400 MHz, DMSO-d6) Shift=10.78 (s, 1H), 9.59 (d, J=1.3 Hz, 1H), 9.23 (d, J=5.1 Hz, 1H), 8.99 (dd, J=1.7, 8.9 Hz, 1H), 8.94-8.89 (m, 2H), 8.22 (d, J=5.1 Hz, 1H), 8.16 (d, J=8.8 Hz, 1H), 7.98 (d, J=5.1 Hz, 1H), 6.90 (dd, J=10.3, 17.1 Hz, 1H), 6.43 (dd, J=1.7, 17.1 Hz, 1H), 6.01-5.84 (m, 1H), 3.99-3.79 (m, 1H), 3.45 (t, J=5.8 Hz, 2H), 3.25 (s, 3H), 2.93 (br d, J=11.9 Hz, 2H), 2.52 (br s, 2H), 2.18-2.07 (m, 2H), 1.89-1.77 (m, 4H).

Route 8: General Scheme

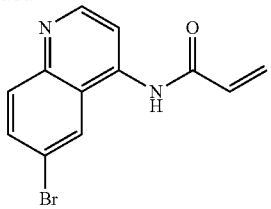

To a mixture of 6-bromoquinolin-4-amine (300 mg, 1.345 mmol) and Et$_3$N (679 mg, 6.725 mmol) in DCM (10 mL) at 0° C. was added a solution of prop-2-enoyl chloride (154 mg, 1.614 mmol) in DCM (1 mL). The resulting mixture was stirred at r.t. for 18 h. The reaction mixture was concentrated in vacuo and the residue was diluted with DCM. The mixture were washed with saturated NaHCO$_3$ and brine, dried over anhydrous sodium sulfate, filtered, and concentrated. The residue was purified by chromatography on silica gel eluting with 30-100% EtOAc/Hexane to afford the title compound (0.25 g, Yield 66%).

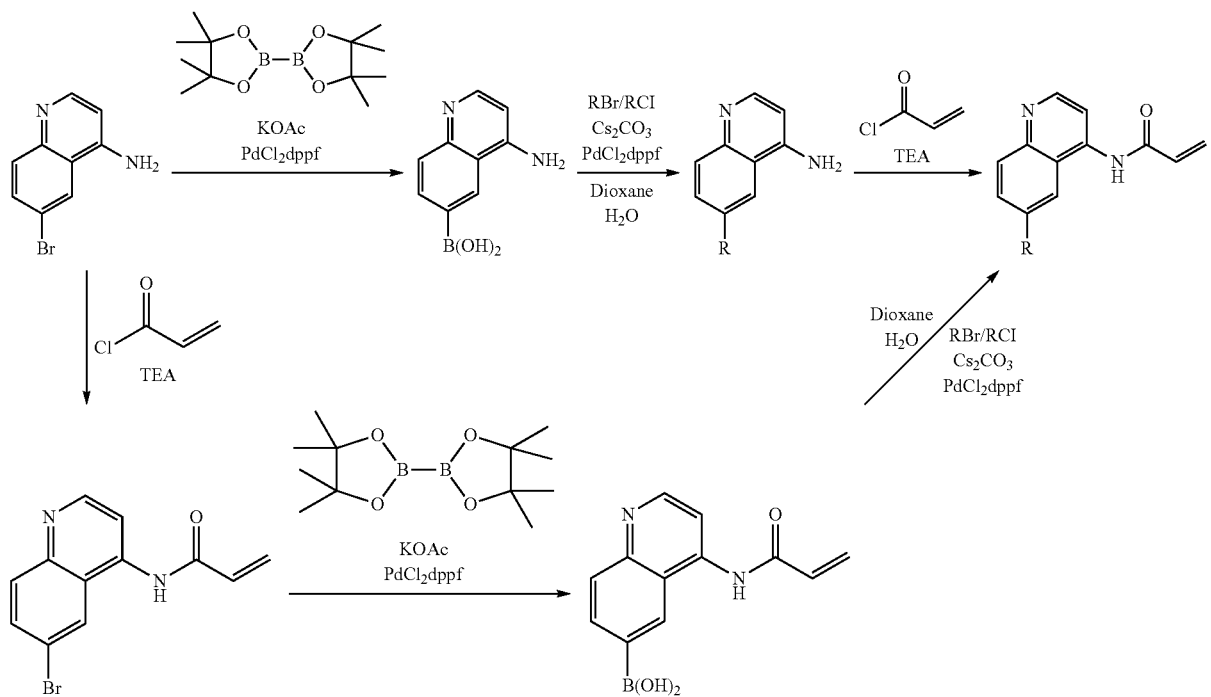

Preparation of N-(1-methyl-4-piperidyl)-6-[4-(prop-2-enoylamino)-6-quinolyl]pyridine-2-carboxamide (Compound 405)

Step 1) Preparation of N-(6-bromo-4-quinolyl)prop-2-enamide

Step 2) Preparation of [4-(prop-2-enoylamino)-6-quinolyl]boronic acid

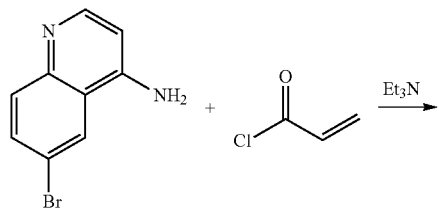 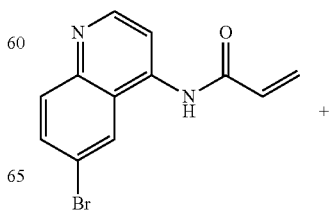

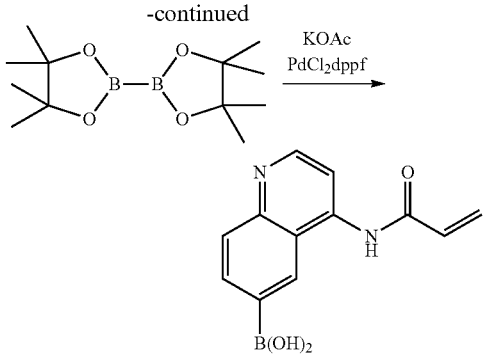

To a solution of N-(6-bromo-4-quinolyl)prop-2-enamide (74.9 mg, 27 μmol) in dioxane (3 mL) were added 4,4,5,5-tetramethyl-2-(4,4,5,5-tetramethyl-1,3,2-dioxaborolan-2-yl)-1,3,2-dioxaborolane (205 mg, 81 μmol), KOAc (133 mg, 1.35 mmol) and PdCl$_2$dppf (40 mg, 49 μmol). The reaction was heated at 100° C. for 1 h in a microwave. The reaction mixture was passed through a celite pad, and the solvent was removed in vacuo. The residue was purified by reverse phase HPLC using a gradient of water 0.1% FA/acetonitrile 0.1% FA to afford the title compound (16.9 mg, Yield 26%).

Step 3) Preparation of N-(1-methyl-4-piperidyl)-6-[4-(prop-2-enoylamino)-6-quinolyl]pyridine-2-carboxamide

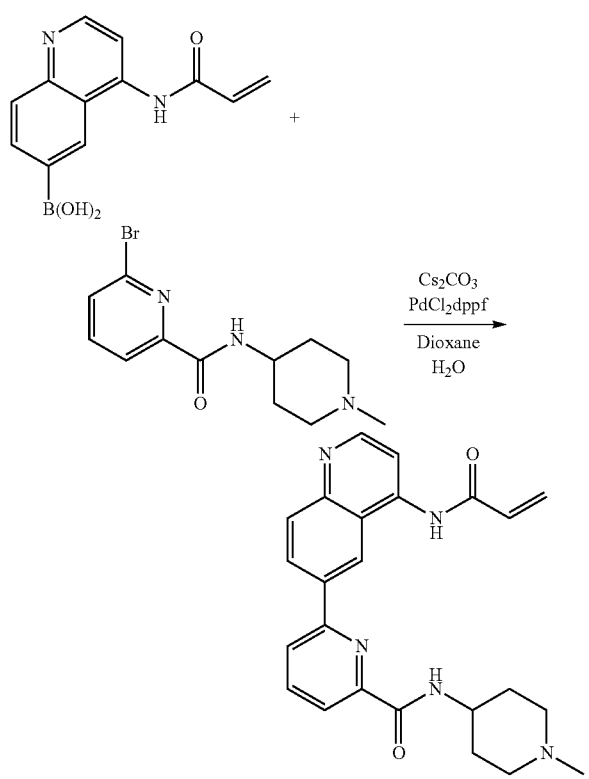

To a solution of [4-(prop-2-enoylamino)-6-quinolyl]boronic acid (16.9 mg, 7 μmol) in dioxane (1 mL) and water (0.2 mL) were added 6-bromo-N-(1-methyl-4-piperidyl)pyridine-2-carboxamide (31.3 mg, 105 μmol), Cs$_2$CO$_3$ (68.3 mg, 21 μmol) and PdCl$_2$dppf (15 mg, 18.5 μmol). The reaction was heated at 100° C. for 30 min in a microwave. The reaction mixture was passed through a celite pad, and 2 mL of 0.5M EDTA was added. The resulting solution was stirred at r.t. for 30 min. The solution was washed with brine, dried over anhydrous sodium sulfate, filtered, and concentrated in vacuo. The residue was purified by reverse phase HPLC using a gradient of water 0.1% FA/acetonitrile 0.1% FA to afford the title compound (6 mg, Yield 21%). LC-MS: [M+H]$^+$ 416.

Preparation of N-[6-(4-amino-3-cyano-phenyl)-4-quinolyl]prop-2-enamide (Compound 407)

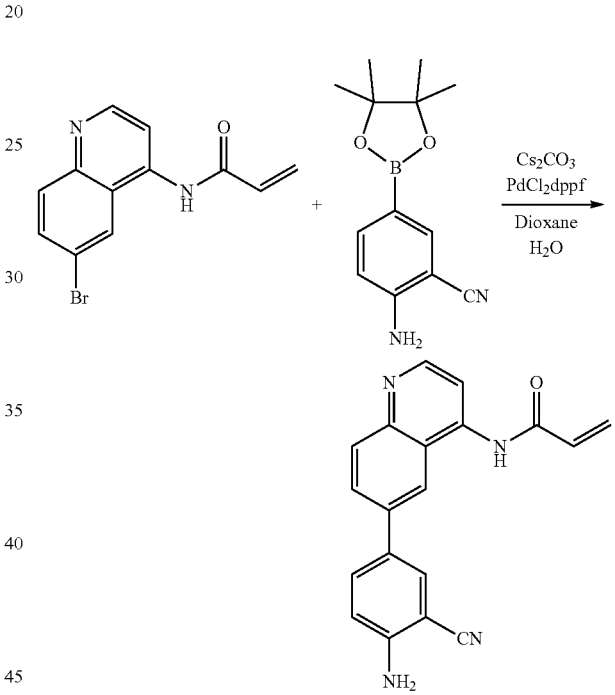

To a solution of N-(6-bromo-4-quinolyl)prop-2-enamide (40 mg, 144 μmol) in dioxane (1 mL) and water (0.2 mL) were added 2-amino-5-(4,4,5,5-tetramethyl-1,3,2-dioxaborolan-2-yl)benzonitrile (52.9 mg, 271 μmol), Cs$_2$CO$_3$ (140 mg, 432 μmol) and PdCl$_2$dppf (18 mg, 22.4 μmol). The reaction was heated at 100° C. for 30 min in a microwave. The reaction mixture was passed through a celite pad, and 2 mL of 0.5M EDTA was added. The resulting solution was stirred at r.t. for 30 min. The solution was washed with brine, dried over anhydrous sodium sulfate, filtered, and concentrated in vacuo. The residue was purified by reverse phase HPLC using a gradient of water 0.1% FA/acetonitrile 0.1% FA to afford the title compound (15 mg, Yield 30%). LC-MS: [M+H]$^+$ 315.

525

Preparation of N-methyl-5-[4-(prop-2-enoylamino)-6-quinolyl]pyridine-3-carboxamide (Compound 408)

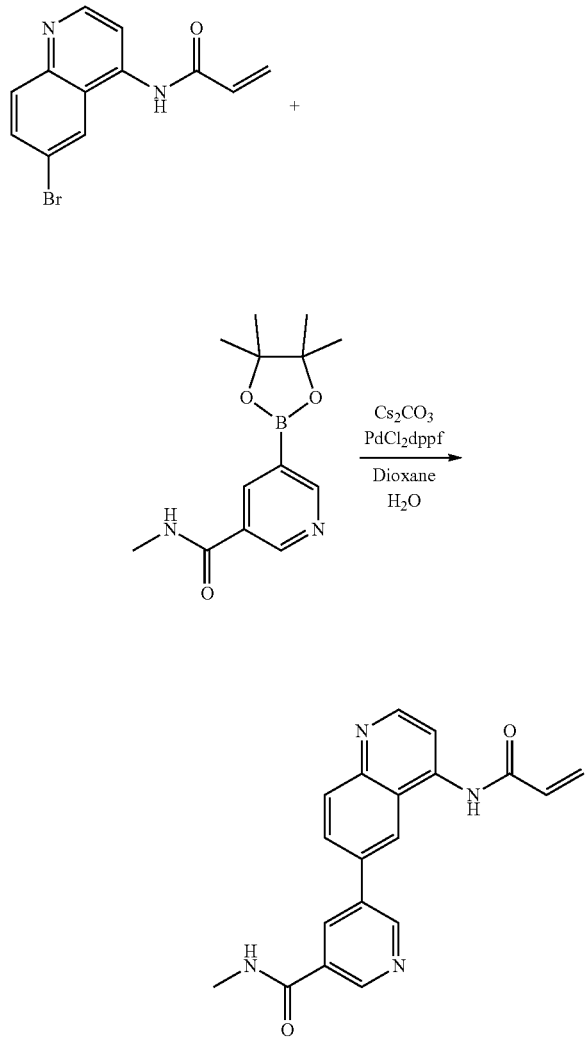

To a solution of N-(6-bromo-4-quinolyl)prop-2-enamide (40 mg, 144 µmol) in dioxane (1 mL) and water (0.2 mL) were added N-methyl-5-(4,4,5,5-tetramethyl-1,3,2-dioxaborolanyl)pyridine-3-carboxamide (71 mg, 271 µmol), $Cs_2CO_3$ (140 mg, 432 µmol) and $PdCl_2dppf$ (18 mg, 22.4 µmol). The reaction was heated at 100° C. for 30 min in a microwave. The reaction mixture was passed through a celite pad, and 2 mL of 0.5M EDTA was added. The resulting solution was stirred at r.t. for 30 min. The solution was washed with brine, dried over anhydrous sodium sulfate, filtered, and concentrated in vacuo. The residue was purified by reverse phase HPLC using a gradient of water 0.1% FA/acetonitrile 0.1% FA to afford the title compound (8 mg, Yield 16%). LC-MS: [M+H]$^+$ 333.

526

Preparation of N-[6-(5-amino-6-chloro-2-pyridyl)-4-quinolyl]prop-2-enamide (Compound 409)

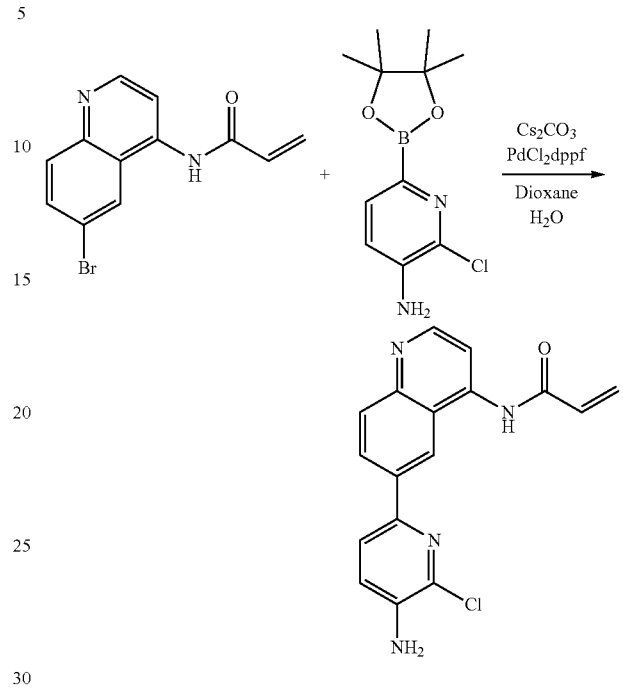

To a solution of N-(6-bromo-4-quinolyl)prop-2-enamide (40 mg, 144 µmol) in dioxane (1 mL) and water (0.2 mL) were added 2-chloro-6-(4,4,5,5-tetramethyl-1,3,2-dioxaborolan-2-yl)pyridin-3-amine (69 mg, 271 µmol), $Cs_2CO_3$ (140 mg, 432 µmol) and $PdCl_2dppf$ (18 mg, 22.4 µmol). The reaction was heated at 100° C. for 30 min in a microwave. The reaction mixture was passed through a celite pad, and 2 mL of 0.5M EDTA was added. The resulting solution was stirred at r.t. for 30 min. The solution was washed with brine, dried over anhydrous sodium sulfate, filtered, and concentrated in vacuo. The residue was purified by reverse phase HPLC using a gradient of water 0.1% FA/acetonitrile 0.1% FA to afford the title compound (5 mg, Yield 11%). FC-MS: [M+H]$^+$ 325.

Preparation of N-[6-(6-amino-5-chloro-3-pyridyl)-4-quinolyl]prop-2-enamide (Compound 411)

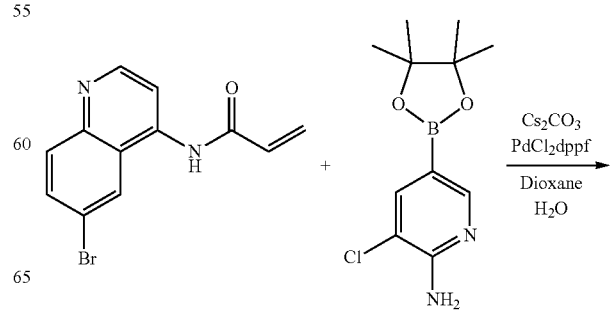

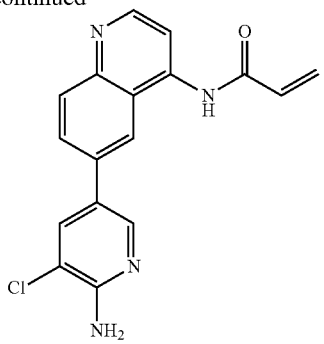

To a solution of N-(6-bromo-4-quinolyl)prop-2-enamide (40 mg, 144 µmol) in dioxane (1 mF) and water (0.2 mF) were added 3-chloro-5-(4,4,5,5-tetramethyl-1,3,2-dioxaborolan-2-yl)pyridin-2-amine (69 mg, 271 µmol), Cs₂CO₃ (140 mg, 432 µmol) and PdCl₂dppf (18 mg, 22.4 µmol). The reaction was heated at 100° C. for 30 min in a microwave. The reaction mixture was passed through a celite pad, and 2 mF of 0.5M EDTA was added. The resulting solution was stirred at r.t. for 30 min. The solution was washed with brine, dried over anhydrous sodium sulfate, filtered, and concentrated in vacuo. The residue was purified by reverse phase HPLC using a gradient of water 0.1% FA/acetonitrile 0.1% FA to afford the title compound (46.8 mg, Yield 100%). FC-MS: [M+H]⁺ 325.

Preparation of N-[6-(3-chlorophenyl)-4-quinolyl]prop-2-enamide (Compound 414)

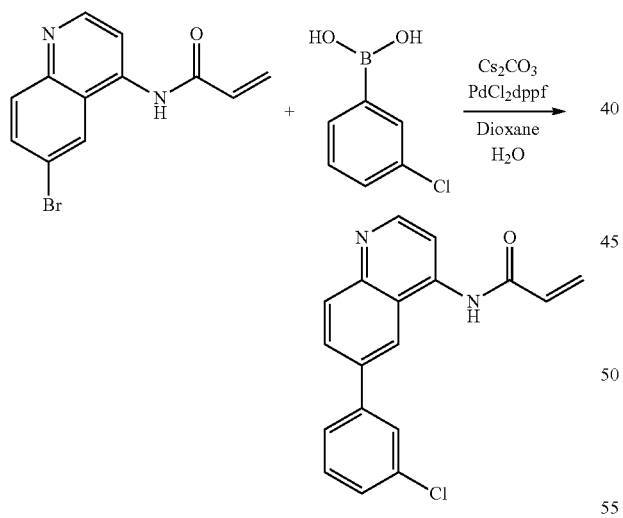

To a solution of N-(6-bromo-4-quinolyl)prop-2-enamide (50 mg, 18 µmol) in dioxane (1.5 mF) and water (0.3 mF) were added (3-chlorophenyl)boronic acid (42.3 mg, 271 µmol), Cs₂CO₃ (176 mg, 54 µmol) and PdCl₂dppf (20 mg, 24.3 µmol). The reaction was heated at 100° C. for 30 min in a microwave. The reaction mixture was passed through a celite pad, and 2 mF of 0.5M EDTA was added. The resulting solution was stirred at r.t. for 30 min. The solution was washed with brine, dried over anhydrous sodium sulfate, filtered, and concentrated in vacuo. The residue was purified by reverse phase HPLC using a gradient of water 0.1% FA/acetonitrile 0.1% FA to afford the title compound (4 mg, Yield 7%). LC-MS: [M+H]⁺ 309.

Preparation of N-[3-(dimethylamino)cyclohexyl]-6-[4-(prop-2-enoylamino)-6-quinolyl]pyridine-2-carboxamide (Compound 415)

Step 1) Preparation of 6-(4-amino-6-quinolyl)-N-[3-(dimethylamino)cyclohexyl]pyridine-2-carboxamide

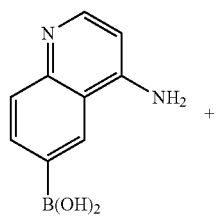

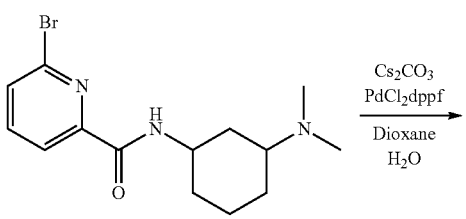

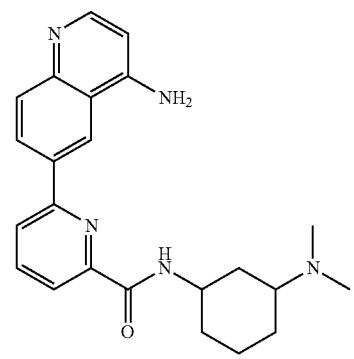

To a solution (4-amino-6-quinolyl)boronic acid (124 mg, 459 µmol) in dioxane (2 mL) and water (0.4 mL) were added 6-bromo-N-[3-(dimethylamino)cyclohexyl]pyridine-2-carboxamide (100 mg, 306 µmol), Cs₂CO₃ (298 mg, 0.918 mmol) and PdCl₂dppf (40 mg, 50.5 µmol). The reaction was heated at 100° C. for 35 min in a microwave. The reaction mixture was passed through a celite pad, and 2 mL of 0.5M EDTA was added. The resulting solution was stirred at r.t. for 30 min. The solution was washed with brine, dried over anhydrous sodium sulfate, filtered, and concentrated in vacuo. The residue was purified by chromatography on silica gel eluting with 0-60% MeOH/EtOAc/5% Et₃N to afford the title compound (81.9 mg, Yield 69%).

Step 2) Preparation of N-[3-(dimethylamino)cyclohexyl]-6-[4-(prop-2-enoylamino)-6-quinolyl]pyridine-2-carboxamide

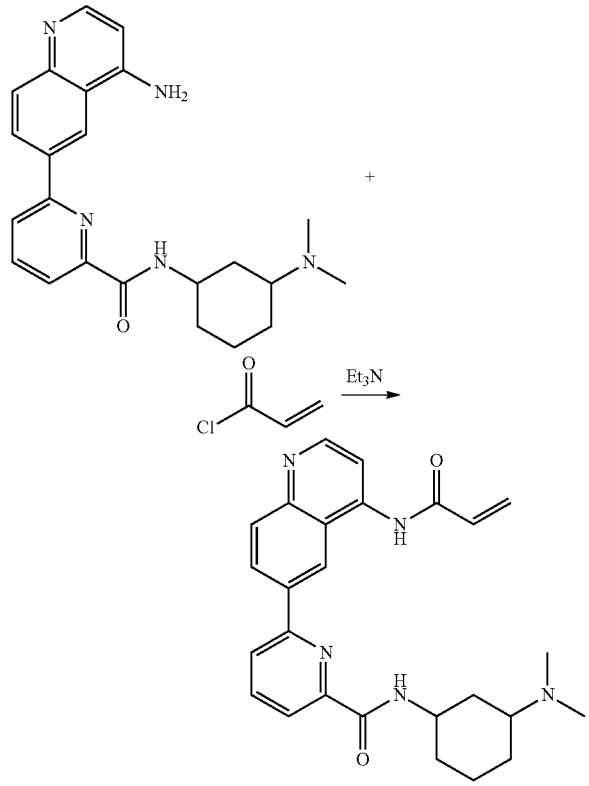

To a mixture of 6-(4-amino-6-quinolyl)-N-[3-(dimethylamino)cyclohexyl]pyridine-2-carboxamide (81.9 mg, 21 μmol) and Et₃N (106 mg, 1.05 mmol) in DCM (5 mL) at 0° C. was added a solution of prop-2-enoyl chloride (26.1 mg, 273 μmol) in DCM (0.5 mL). The resulting mixture was stirred at r.t. for 18 h. The reaction mixture was concentrated in vacuo, and the residue was diluted with DCM. The mixture was washed with saturated NaHCO₃ and brine, dried over anhydrous sodium sulfate, filtered, and concentrated. The residue was purified by reverse phase HPLC using a gradient of water 0.1% FA/acetonitrile 0.1% FA to afford the title compound (4 mg, Yield 4%). LC-MS: [M+H]⁺ 444.

Preparation of N-(8-methyl-8-azabicyclo[3.2.1]octan-3-yl)-6-[4-(prop-2-enoylamino)-6-quinolyl]pyridine-2-carboxamide (Compound 416)

Step 1) Preparation of 6-bromo-N-(8-methyl-8-azabicyclo[3.2.1]octan-3-yl)pyridine-2-carboxamide

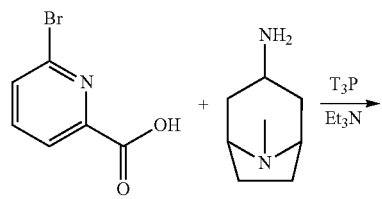

-continued

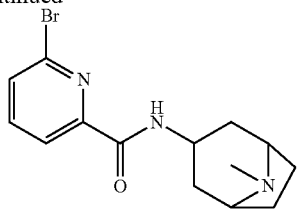

To a mixture of 6-bromopyridine-2-carboxylic acid (500 mg, 2.475 mmol), 8-methyl-8-azabicyclo[3.2.1]octan-3-amine (521 mg, 3.713 mmol) and Et₃N (1.25 g, 3.713 mmol) in DMF (6 mL) was added T₃P (50 wt % in EtOAc, 3.2 mL, 3.713 mmol). The resulting mixture was stirred at r.t. for 18 h and partitioned between EtOAc and water. The aqueous phase was extracted with EtOAc (3×). The combined organic phase was washed with saturated NaHCO₃ and brine, dried over (MgSO₄), filtered, and concentrated in vacuo. The residue was purified by chromatography on silica gel eluting with 0-20% MeOH/EtOAc/5% Et₃N to afford the title compound (442 mg, Yield 55%).

Step 2) Preparation of 6-(4-amino-6-quinolyl)-N-(8-methyl-8-azabicyclo[3.2.1]octan-3-yl)pyridine-2-carboxamide

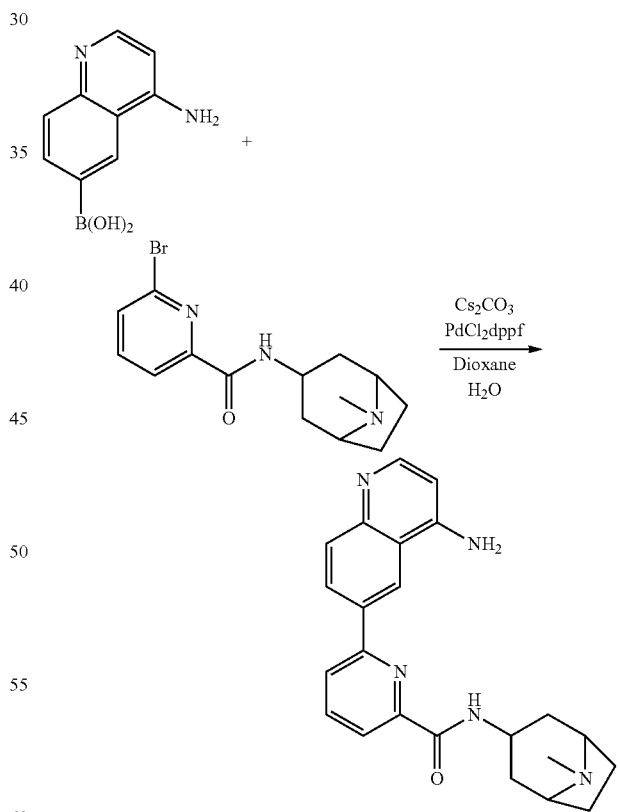

To a solution (4-amino-6-quinolyl)boronic acid (125 mg, 463 μmol) in dioxane (2 mL) and water (0.4 mL) were added 6-bromo-N-(8-methyl-8-azabicyclo[3.2.1]octan-3-yl)pyridine-2-carboxamide (100 mg, 308 μmol), Cs₂CO₃ (298 mg, 0.918 mmol) and PdCl₂dppf (40 mg, 50.5 μmol). The reaction was heated at 100° C. for 35 min in a microwave.

The reaction mixture was passed through a celite pad, and 2 mL of 0.5M EDTA was added. The resulting solution was stirred at r.t. for 30 min. The solution was washed with brine, dried over anhydrous sodium sulfate, filtered, and concentrated in vacuo. The residue was purified by chromatography on silica gel eluting with 0-60% MeOH/EtOAc/5% Et$_3$N to afford the title compound (52.1 mg, Yield 44%).

Step 3) Preparation of N-(8-methyl-8-azabicyclo[3.2.1]octan-3-yl)-6-[4-(prop-2-enoylamino)-6-quinolyl]pyridine-2-carboxamide

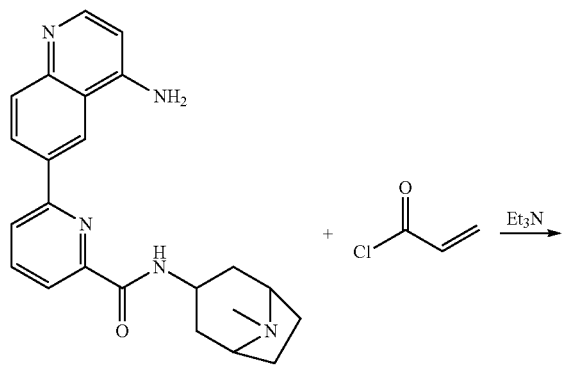

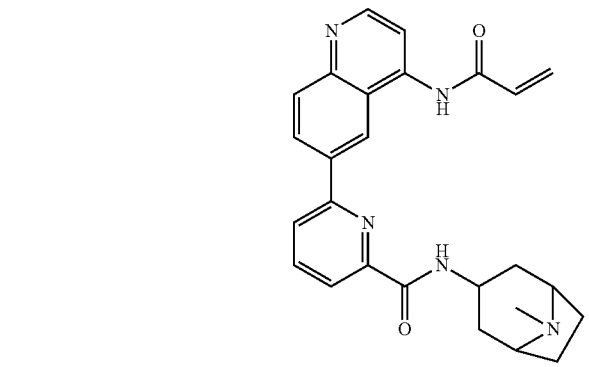

To a mixture of 6-(4-amino-6-quinolyl)-N-(8-methyl-8-azabicyclo[3.2.1]octan-3-yl)pyridine-2-carboxamide (52.1 mg, 134 µmol) and Et$_3$N (67 mg, 67 mmol) in DCM (5 mL) at 0° C. was added a solution of prop-2-enoyl chloride (16.7 mg, 175 µmol) in DCM (0.5 mL). The resulting mixture was stirred at r.t. for 18 h. The reaction mixture was concentrated in vacuo, and the residue was diluted with DCM. The mixture was washed with saturated NaHCO$_3$ and brine, dried over anhydrous sodium sulfate, filtered, and concentrated. The residue was purified by reverse phase HPLC using a gradient of water 0.1% FA/acetonitrile 0.1% FA to afford the title compound (11 mg, Yield 19%). LC-MS: [M+H]$^+$ 442.

Preparation of N-(8-methyl-8-azabicyclo[3.2.1]octan-3-yl)-6-[4-(prop-2-enoylamino)-6-quinolyl]pyridine-2-carboxamide (Compound 421)

Step 1) Preparation of 6-bromo-N-[2-(1-methyl-4-piperidyl)ethyl]pyridine-2-carboxamide

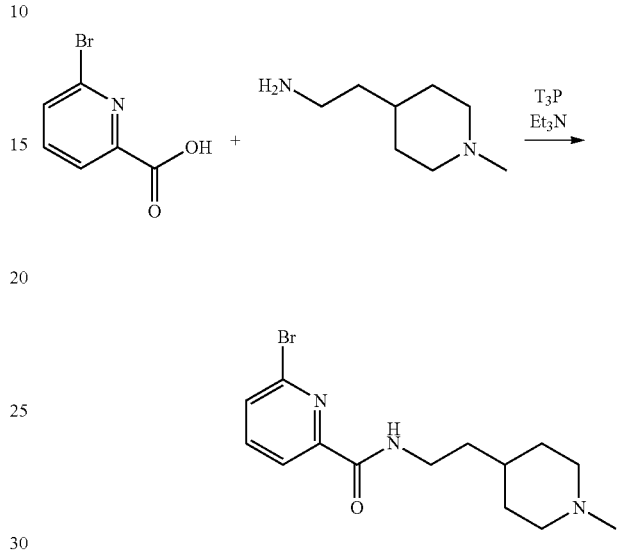

To a mixture of 6-bromopyridine-2-carboxylic acid (500 mg, 3.713 mmol), 2-(1-methyl-4-piperidyl) ethanamine (528 mg, 3.713 mmol) and Et$_3$N (1.279 g, 12.375 mmol) in DMF (5 mL) was added T$_3$P (50 wt % in EtOAc, 3.2 mL, 3.713 mmol). The resulting mixture was stirred at r.t. for 18 h and partitioned between EtOAc and water. The aqueous phase was extracted with EtOAc (3×). The combined organic phase was washed with saturated NaHCO$_3$ and brine, dried over (MgSO$_4$), filtered, and concentrated in vacuo. The residue was purified by chromatography on silica gel eluting with 0-60% MeOH/EtOAc/5% Et$_3$N to afford the title compound (531 mg, Yield 66%).

Step 2) Preparation of 6-(4-amino-6-quinolyl)-N-[2-(1-methyl-4-piperidyl)ethyl]pyridine-2-carboxamide

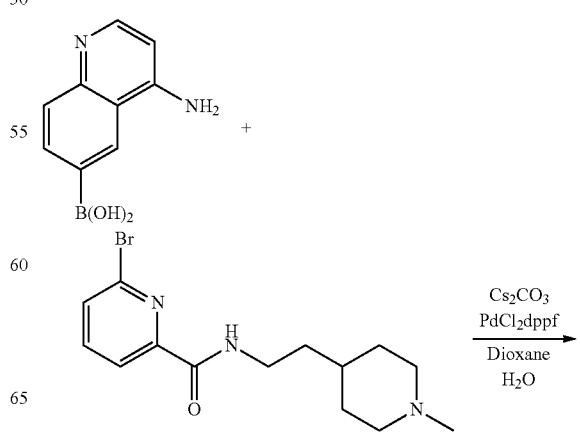

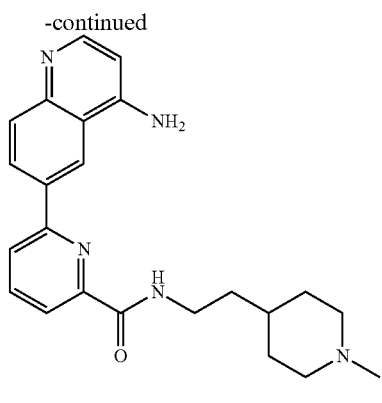

To a solution (4-amino-6-quinolyl)boronic acid (124 mg, 46 µmol) in dioxane (2 mL) and water (0.4 mL) were added 6-bromo-N-[2-(1-methyl-4-piperidyl)ethyl]pyridine-2-carboxamide (100 mg, 306 µmol), Cs₂CO₃ (298 mg, 0.918 mmol) and PdCl₂dppf (20 mg, 25 µmol). The reaction was heated at 100° C. for 35 min in a microwave. The reaction mixture was passed through a celite pad, and 2 mL of 0.5M EDTA was added. The resulting solution was stirred at r.t. for 30 min. The solution was washed with brine, dried over anhydrous sodium sulfate, filtered, and concentrated in vacuo. The residue was purified by chromatography on silica gel eluting with 0-60% MeOH/EtOAc/5% Et₃N to afford the title compound (53.4 mg, Yield 45%).

Step 3) Preparation of N-(8-methyl-8-azabicyclo[3.2.1]octan-3-yl)-6-[4-(prop-2-enoylamino)-6-quinolyl]pyridine-2-carboxamide

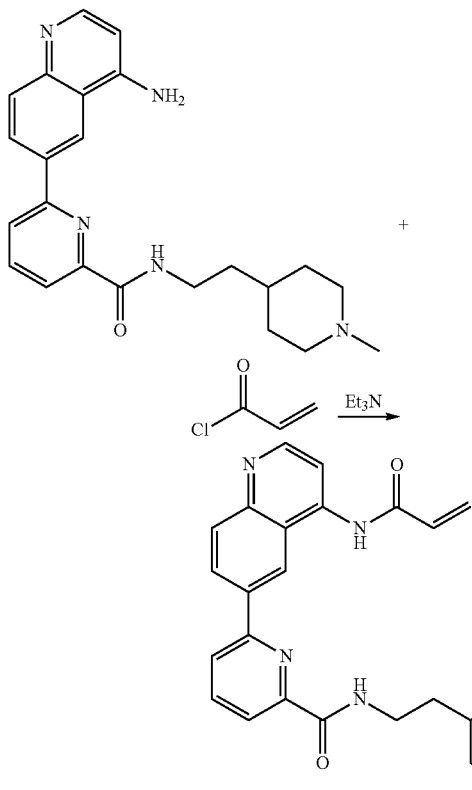

To a mixture of 6-(4-amino-6-quinolyl)-N-[2-(1-methyl-4-piperidyl)ethyl]pyridine-2-carboxamide (53 mg, 136 µmol) and Et₃N (68.7 mg, 68 mmol) in DCM (5 mL) at 0° C. was added a solution of prop-2-enoyl chloride (16.9 mg, 177 µmol) in DCM (0.5 mL). The resulting mixture was stirred at r.t. for 18 h. The reaction mixture was concentrated in vacuo and the residue was diluted with DCM, washed with saturated NaHCO₃ and brine, dried over anhydrous sodium sulfate, filtered, and concentrated. The residue was purified by reverse phase HPLC using a gradient of water 0.1% FA/acetonitrile 0.1% FA to afford the title compound (4 mg, Yield 6%). LC-MS: [M+H]⁺ 444.

Preparation of N-(1-methylazepan-3-yl)-6-[4-(prop-2-enoylamino)-6-quinolyl]pyridine-2-carboxamide (Compound 423)

Step 1) Preparation of 6-bromo-N-(1-methylazepan-4-yl)pyridine-2-carboxamide

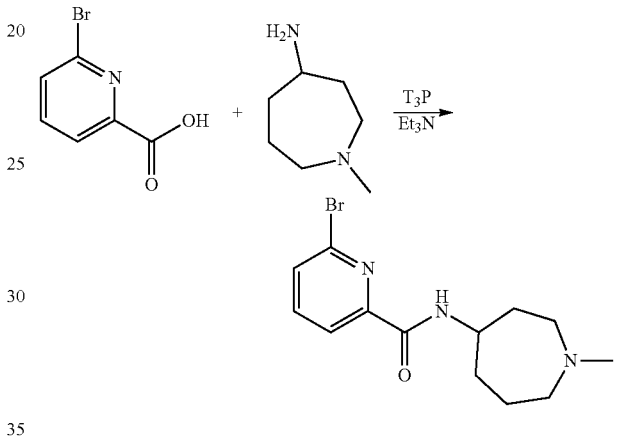

To a mixture of 6-bromopyridine-2-carboxylic acid (500 mg, 2.475 mmol), 1-methylazepan-4-amine (476 mg, 3.713 mmol) and Et₃N (1.279 g, 12.375 mmol) in DMF (5 mL) was added T₃P (50 wt % in EtOAc, 3.2 mL, 3.713 mmol). The resulting mixture was stirred at r.t. for 18 h and partitioned between EtOAc and water. The aqueous phase was extracted with EtOAc (3×). The combined organic phase was washed with saturated NaHCO₃ and brine, dried over (MgSO₄), filtered, and concentrated in vacuo. The residue was purified by chromatography on silica gel eluting with 0-60% MeOH/EtOAc/5% Et₃N to afford the title compound (350 mg, Yield 45%).

Step 2) Preparation of 6-(4-amino-6-quinolyl)-N-(1-methylazepan-3-yl)pyridine-2-carboxamide

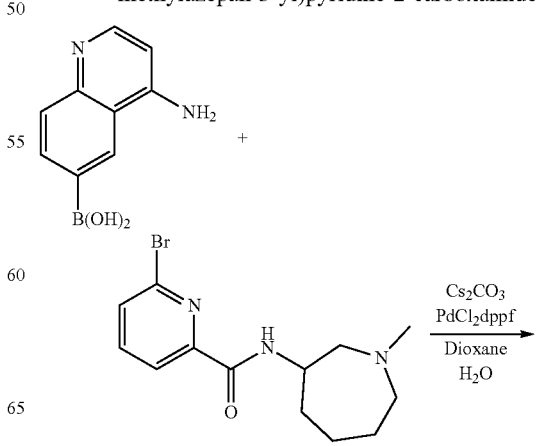

-continued

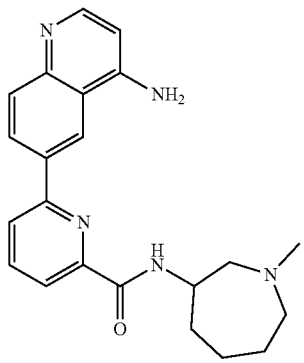

To a solution (4-amino-6-quinolyl)boronic acid (130 mg, 48 µmol) in dioxane (2 mL) and water (0.4 mL) were added 6-bromo-N-(1-methylazepan-3-yl)pyridine-2-carboxamide (100 mg, 32 µmol), Cs$_2$CO$_3$ (312 mg, 0.96 mmol) and PdCl$_2$dppf (40 mg, 5 µmol). The reaction was heated at 100° C. for 35 min in a microwave. The reaction mixture was passed through a celite pad, and 2 mL of 0.5M EDTA was added. The resulting solution was stirred at r.t. for 30 min. The solution was washed with brine, dried over anhydrous sodium sulfate, filtered, and concentrated in vacuo. The residue was purified by chromatography on silica gel eluting with 0-60% MeOH/EtOAc/5% Et$_3$N to afford the title compound (65.1 mg, Yield 54%).

Step 3) Preparation of N-(1-methylazepan-3-yl)-6-[4-(prop-2-enoylamino)-6-quinolyl]pyridine-2-carboxamide To a mixture of 6-(4-amino-6-quinolyl)-N-(1-methylazepan-3-yl)pyridine-2-carboxamide (65.1 mg, 173 µmol) and Et$_3$N (87.4 mg, 865 µmol) in DCM (5 mL) at 0° C. was added a solution of prop-2-enoyl chloride (21.5 mg, 225 µmol) in DCM (0.5 mL). The resulting mixture was stirred at r.t. for 18 h. The reaction mixture was concentrated in vacuo and the residue was diluted with DCM, washed with saturated NaHCO$_3$ and brine, dried over anhydrous sodium sulfate, filtered, and concentrated. The residue was purified by reverse phase HPLC using a gradient of water 0.1% FA/acetonitrile 0.1% FA to afford the title compound (4 mg, Yield 5%). LC-MS: [M+H]$^+$ 430.

Preparation of 3-amino-N-(1-methyl-4-piperidyl)-6-[4-(prop-2-enoylamino)-6-quinolyl]pyridine-2-carboxamide (Compound 426)

Step 1) Preparation of 3-amino-6-(4-amino-6-quinolyl)-N-(1-methyl-4-piperidyl)pyridine-2-carboxamide

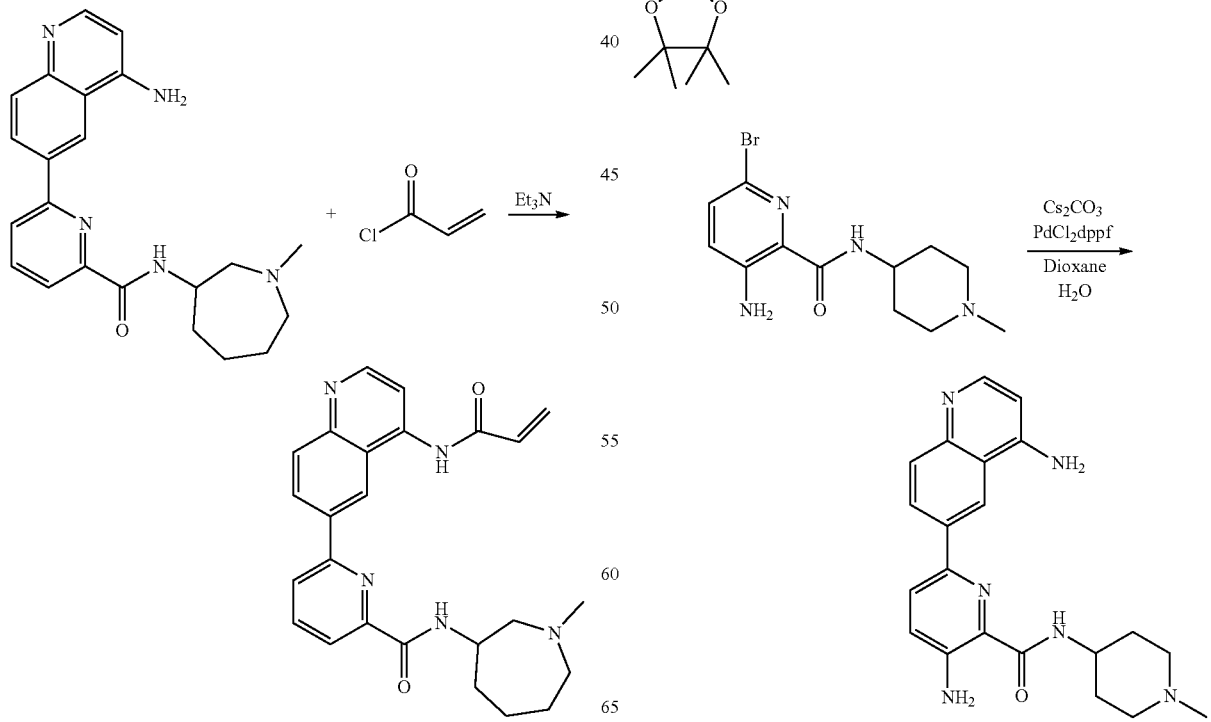

To a solution 6-(4,4,5,5-tetramethyl-1,3,2-dioxaborolan-2-yl)quinolin-4-amine (129 mg, 479 μmol) in dioxane (2 mL) and water (0.4 mL) were added 3-amino-6-bromo-N-(1-methyl-4-piperidyl)pyridine-2-carboxamide (100 mg, 319 μmol), $Cs_2CO_3$ (311 mg, 0.957 mmol) and $PdCl_2dppf$ (26 mg, 31.9 μmol). The reaction was heated at 100° C. for 35 min in a microwave. The reaction mixture was passed through a celite pad, and 2 mL of 0.5M EDTA was added. The resulting solution was stirred at r.t. for 30 min. The solution was washed with brine, dried over anhydrous sodium sulfate, filtered, and concentrated in vacuo. The residue was purified by chromatography on silica gel eluting with 0-60% MeOH/EtOAc/5% $Et_3N$ to afford the title compound (82.9 mg, Yield 69%).

Step 2) Preparation of 3-amino-N-(1-methyl-4-piperidyl)-6-[4-(prop-2-enoylamino)-6-quinolyl]pyridine-2-carboxamide

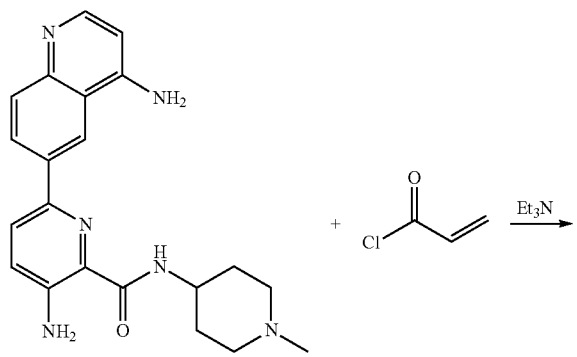

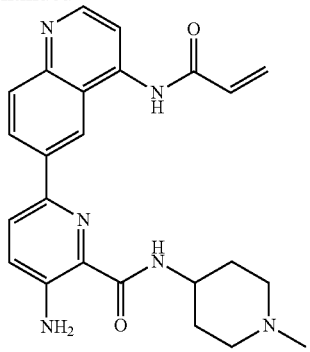

To a mixture of tert-butyl 3-amino-6-(4-amino-6-quinolyl)-N-(1-methyl-4-piperidyl)pyridine-2-carboxamide (82.9 mg, 22 μmol) and $Et_3N$ (111 mg, 1.1 mmol) in DCM (5 mL) at 0° C. was added a solution of prop-2-enoyl chloride (27.3 mg, 286 μmol) in DCM (0.5 mL). The resulting mixture was stirred at r.t. for 18 h. The reaction mixture was concentrated in vacuo and the residue was diluted with DCM, washed with saturated $NaHCO_3$ and brine, dried over anhydrous sodium sulfate, filtered, and concentrated. The residue was purified by reverse phase HPLC using a gradient of water 0.1% FA/acetonitrile 0.1% FA to afford the title compound (4 mg, Yield 4%). LC-MS: $[M+H]^+$ 431.

TABLE 9 shows compounds synthesized using the methods described in EXAMPLE 9 above.

TABLE 9

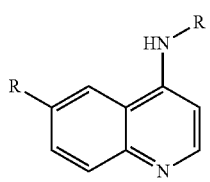

| Cpd. No. | Structure | IUPAC | LC-MS (ES+, m/z) |
|---|---|---|---|
| 405 | 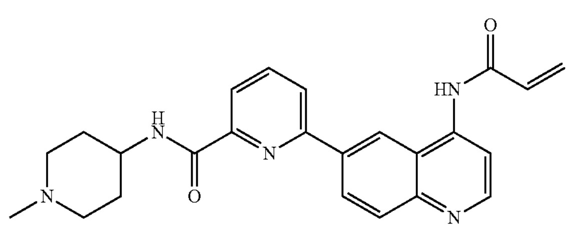 [SMILES: C=CC(=O)Nc1ccnc2ccc(-c3cccc(C(=O)NC4CCN(C)CC4)n3)cc12] | N-(1-methylpiperidin-4-yl)-6-[4-(prop-2-enamido)quinolin-6-yl]pyridine-2-carboxamide | 416.2 |
| 406 | 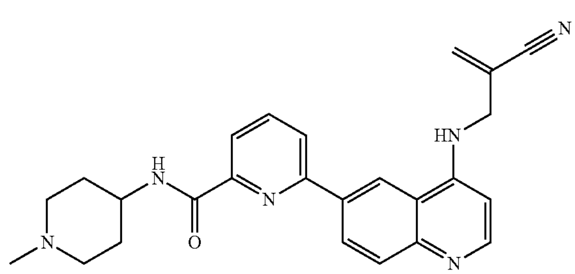 [SMILES: C=C(C#N)CNc1ccnc2ccc(-c3cccc(C(=O)NC4CCN(C)CC4)n3)cc12] | 6-{4-[(2-cyano-2-methylideneethyl)amino]quinolin-6-yl}-N-(1-methylpiperidin-4-yl)pyridine-2-carboxamide | 427.2 |

TABLE 9-continued

| Cpd. No. | Structure | IUPAC | LC-MS (ES+, m/z) |
|---|---|---|---|
| 407 | 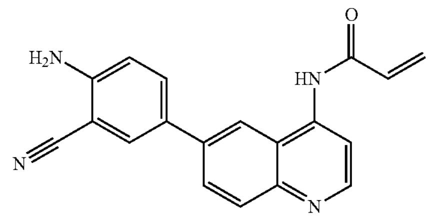 [SMILES: C=CC(=O)Nc1ccnc2ccc(-c3ccc(N)c(C#N)c3)cc12] | N-[6-(4-amino-3-cyanophenyl)quinolin-4-yl]prop-2-enamide | 315.1 |
| 408 | 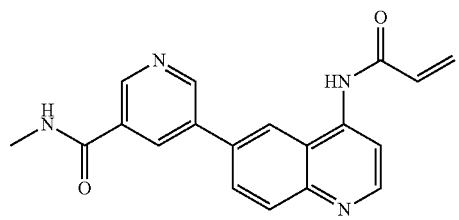 [SMILES: C=CC(=O)Nc1ccnc2ccc(-c3cncc(C(=O)NC)c3)cc12] | N-methyl-5-[4-(prop-2-enamido)quinolin-6-yl]pyridine-3-carboxamide | 333.1 |
| 409 | 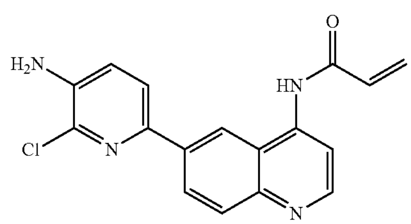 [SMILES: C=CC(=O)Nc1ccnc2ccc(-c3ccc(N)c(Cl)n3)cc12] | N-[6-(5-amino-6-chloropyridin-2-yl)quinolin-4-yl]prop-2-enamide | 325.1 |
| 410 | 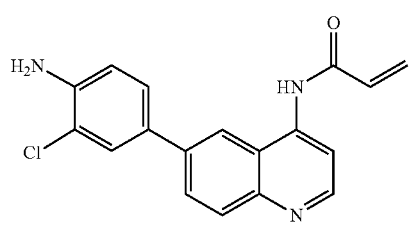 [SMILES: C=CC(=O)Nc1ccnc2ccc(-c3ccc(N)c(Cl)c3)cc12] | N-[6-(4-amino-3-chlorophenyl)quinolin-4-yl]prop-2-enamide | 324.1 |
| 411 | 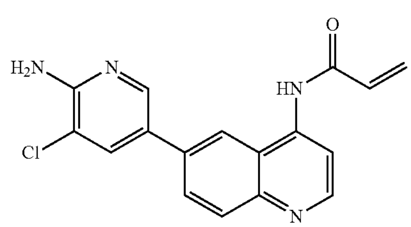 [SMILES: C=CC(=O)Nc1ccnc2ccc(-c3cnc(N)c(Cl)c3)cc12] | N-[6-(6-amino-5-chloropyridin-3-yl)quinolin-4-yl]prop-2-enamide | 325.1 |
| 412 | 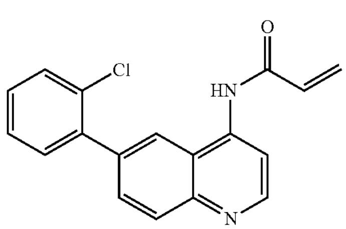 [SMILES: C=CC(=O)Nc1ccnc2ccc(-c3ccccc3Cl)cc12] | N-[6-(2-chlorophenyl)quinolin-4-yl]prop-2-enamide | 309.1 |

TABLE 9-continued

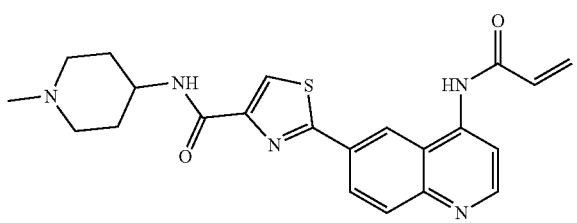 [SMILES: C=CC(=O)Nc1ccnc2ccc(-c3nc(C(=O)NC4CCN(C)CC4)cs3)cc12]

| Cpd. No. | Structure | IUPAC | LC-MS (ES+, m/z) |
|---|---|---|---|
| 413 | 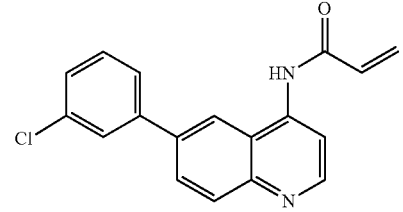 [SMILES: C=CC(=O)Nc1ccnc2ccc(-c3cccc(Cl)c3)cc12] | N-(1-methylpiperidin-4-yl)-2-[4-(prop-2-enamido)quinolin-6-yl]-1,3-thiazole-4-carboxamide | 422.2 |
| 414 | 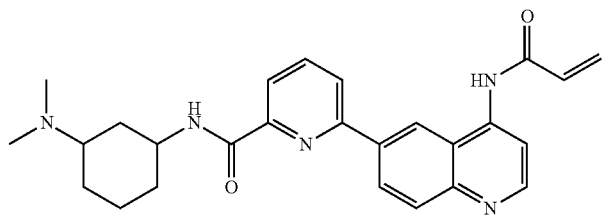 [SMILES: C=CC(=O)Nc1ccnc2ccc(-c3cccc(C(=O)NC4CCCC(N(C)C)C4)n3)cc12] | N-[6-(3-chlorophenyl)quinolin-4-yl]prop-2-enamide | 309.1 |
| 415 | 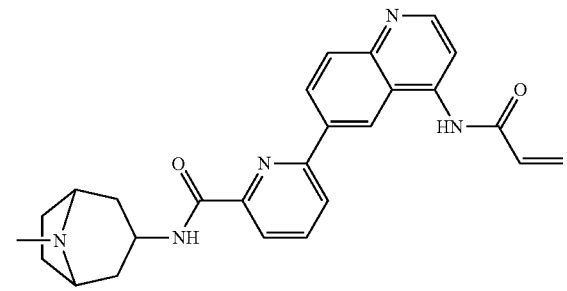 [SMILES: C=CC(=O)Nc1ccnc2ccc(-c3cccc(C(=O)NC4CC5CCC(C4)N5C)n3)cc12] | N-[3-(dimethylamino)cyclohexyl]-6-[4-(prop-2-enamido)quinolin-6-yl]pyridine-2-carboxamide | 444.2 |
| 416 | 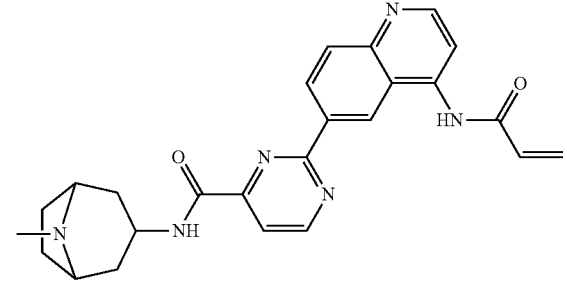 [SMILES: C=CC(=O)Nc1ccnc2ccc(-c3nccc(C(=O)NC4CC5CCC(C4)N5C)n3)cc12] | N-{8-methyl-8-azabicyclo[3.2.1]octan-3-yl}-6-[4-(prop-2-enamido)quinolin-6-yl]pyridine-2-carboxamide | 442.2 |
| 417 | 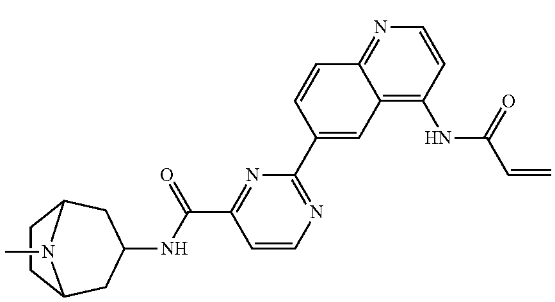 | N-{8-methyl-8-azabicyclo[3.2.1]octan-3-yl}-2-[4-(prop-2-enamido)quinolin-6-yl]pyrimidine-4-carboxamide | 443.2 |

TABLE 9-continued

| Cpd. No. | Structure | IUPAC | LC-MS (ES+, m/z) |
|---|---|---|---|
| 418 | 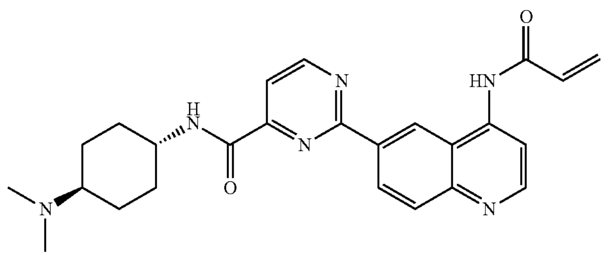 [SMILES: C=CC(=O)Nc1ccnc2ccc(-c3nccc(C(=O)N[C@H]4CC[C@H](N(C)C)CC4)n3)cc12] | 2-[4-(prop-2-enamido)quinolin-6-yl]-N-[(1r,4r)-4-(dimethylamino)cyclohexyl]pyrimidine-4-carboxamide | 445.2 |
| 419 | 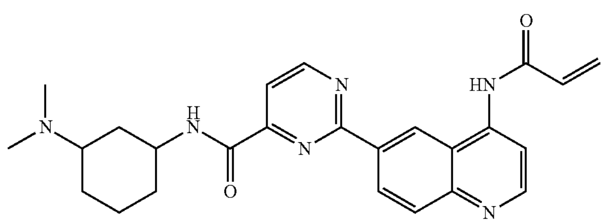 | N-[3-(dimethylamino)cyclohexyl]-2-[4-(prop-2-enamido)quinolin-6-yl]pyrimidine-4-carboxamide | 445.2 |
| 420 | 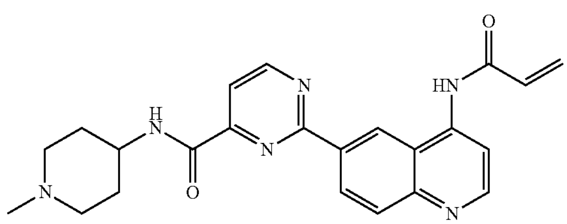 [SMILES: C=CC(=O)Nc1ccnc2ccc(-c3nccc(C(=O)NC4CCN(C)CC4)n3)cc12] | N-(1-methylpiperidin-4-yl)-2-[4-(prop-2-enamido)quinolin-6-yl]pyrimidine-4-carboxamide | 417.2 |
| 421 | 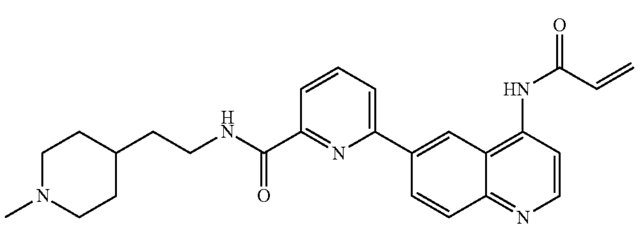 [SMILES: C=CC(=O)Nc1ccnc2ccc(-c3cccc(C(=O)NCCC4CCN(C)CC4)n3)cc12] | N-[2-(1-methylpiperidin-4-yl)ethyl]-6-[4-(prop-2-enamido)quinolin-6-yl]pyridine-2-carboxamide | 444.2 |
| 422 | 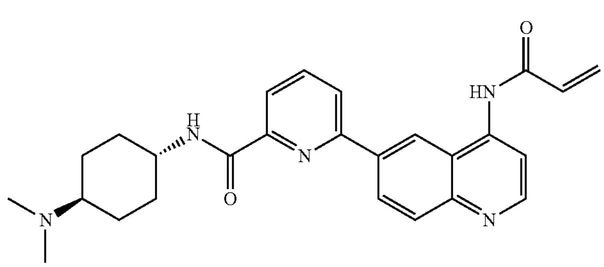 [SMILES: C=CC(=O)Nc1ccnc2ccc(-c3cccc(C(=O)N[C@H]4CC[C@H](N(C)C)CC4)n3)cc12] | 6-[4-(prop-2-enamido)quinolin-6-yl]-N-[(1r,4r)-4-(dimethylamino)cyclohexyl]pyridine-2-carboxamide | 444.3 |

TABLE 9-continued

| Cpd. No. | Structure | IUPAC | LC-MS (ES+, m/z) |
|---|---|---|---|
| 423 | 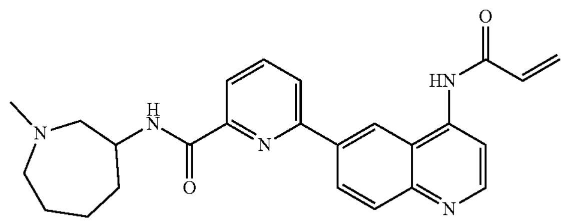 [SMILES: C=CC(=O)Nc1ccnc2ccc(-c3cccc(C(=O)NC4CCCCN(C)C4)n3)cc12] | N-(1-methylazepan-3-yl)-6-[4-(prop-2-enamido)quinolin-6-yl]pyridine-2-carboxamide | 430.2 |
| 424 | 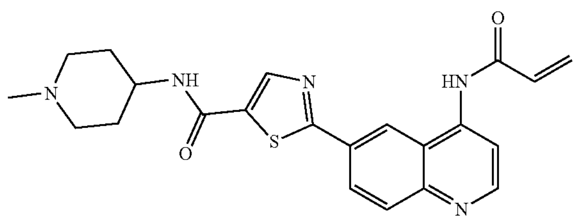 [SMILES: C=CC(=O)Nc1ccnc2ccc(-c3ncc(C(=O)NC4CCN(C)CC4)s3)cc12] | N-(1-methylpiperidin-4-yl)-2-[4-(prop-2-enamido)quinolin-6-yl]-1,3-thiazole-5-carboxamide | 422.1 |
| 425 | 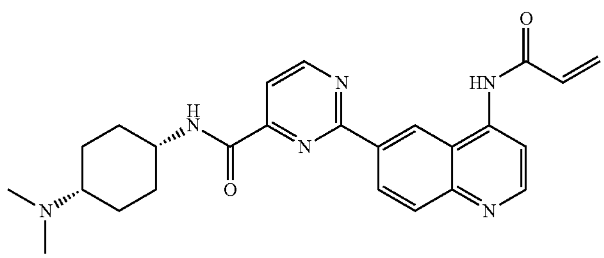 [SMILES: C=CC(=O)Nc1ccnc2ccc(-c3nccc(C(=O)N[C@H]4CC[C@@H](N(C)C)CC4)n3)cc12] | 2-[4-(prop-2-enamido)quinolin-6-yl]-N-[(1s,4s)-4-(dimethylamino)cyclohexyl]pyrimidine-4-carboxamide | 445.2 |
| 426 | 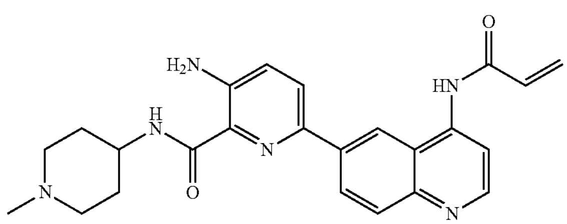 [SMILES: C=CC(=O)Nc1ccnc2ccc(-c3ccc(N)c(C(=O)NC4CCN(C)CC4)n3)cc12] | 3-amino-N-(1-methylpiperidin-4-yl)-6-[4-(prop-2-enamido)quinolin-6-yl]pyridine-2-carboxamide | 431.2 |
| 427 | 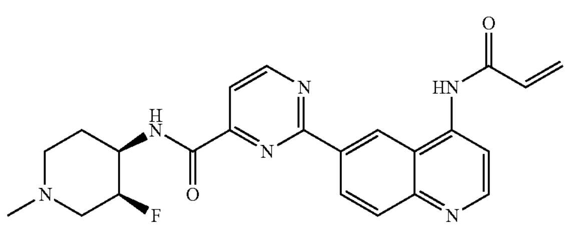 [SMILES: C=CC(=O)Nc1ccnc2ccc(-c3nccc(C(=O)N[C@@H]4CCN(C)C[C@@H]4F)n3)cc12] | N-[(3S,4R)-3-fluoro-1-methylpiperidin-4-yl]-2-[4-(prop-2-enamido)quinolin-6-yl]pyrimidine-4-carboxamide | 435.2 |
| 428 | 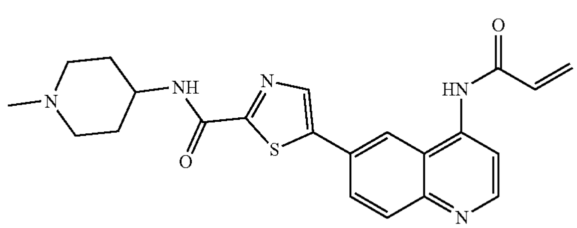 [SMILES: C=CC(=O)Nc1ccnc2ccc(-c3cnc(C(=O)NC4CCN(C)CC4)s3)cc12] | N-(1-methylpiperidin-4-yl)-5-[4-(prop-2-enamido)quinolin-6-yl]-1,3-thiazole-2-carboxamide | 422.2 |

TABLE 9-continued

| Cpd. No. | Structure | IUPAC | LC-MS (ES+, m/z) |
|---|---|---|---|
| 429 | 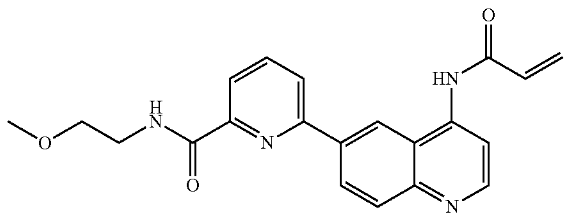 [SMILES: C=CC(=O)Nc1ccnc2ccc(-c3cccc(C(=O)NCCOC)n3)cc12] | N-(2-methoxyethyl)-6-[4-(prop-2-enamido)quinolin-6-yl]pyridine-2-carboxamide | 377.2 |
| 430 | 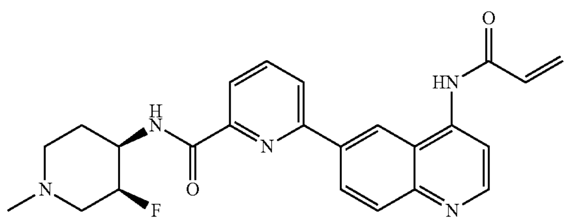 [SMILES: C=CC(=O)Nc1ccnc2ccc(-c3cccc(C(=O)N[C@@H]4CCN(C)C[C@@H]4F)n3)cc12] | N-[(3S,4R)-3-fluoro-1-methylpiperidin-4-yl]-6-[4-(prop-2-enamido)quinolin-6-yl]pyridine-2-carboxamide | 434.2 |
| 431 | 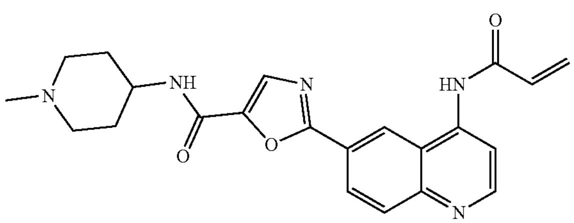 | N-(1-methylpiperidin-4-yl)-2-[4-(prop-2-enamido)quinolin-6-yl]-1,3-oxazole-5-carboxamide | 406.2 |
| 432 | 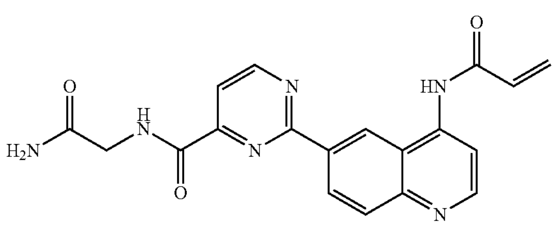 [SMILES: C=CC(=O)Nc1ccnc2ccc(-c3nccc(C(=O)NCC(N)=O)n3)cc12] | N-(6-{4-[(carbamoylmethyl)carbamoyl]pyrimidin-2-yl}quinolin-4-yl)prop-2-enamide | 377.1 |
| 433 | 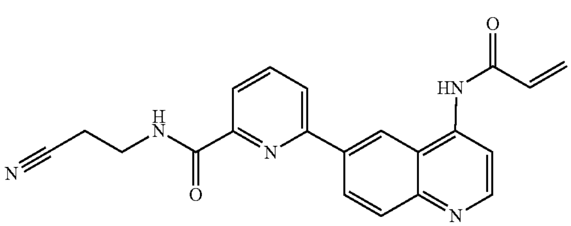 [SMILES: C=CC(=O)Nc1ccnc2ccc(-c3cccc(C(=O)NCCC#N)n3)cc12] | N-(2-cyanoethyl)-6-[4-(prop-2-enamido)quinolin-6-yl]pyridine-2-carboxamide | 372.1 |
| 434 | 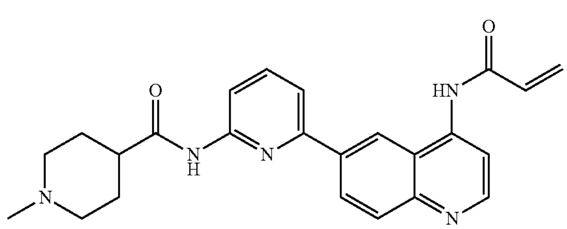 [SMILES: C=CC(=O)Nc1ccnc2ccc(-c3cccc(NC(=O)C4CCN(C)CC4)n3)cc12] | 1-methyl-N-{6-[4-(prop-2-enamido)quinolin-6-yl]pyridin-2-yl}piperidine-4-carboxamide | 416.2 |

TABLE 9-continued

| Cpd. No. | Structure | IUPAC | LC-MS (ES+, m/z) |
|---|---|---|---|
| 435 | 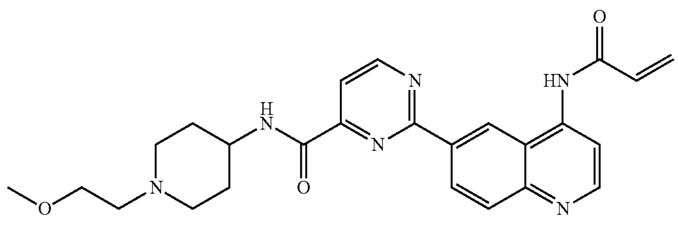 [SMILES: C=CC(=O)Nc1ccnc2ccc(-c3nccc(C(=O)NC4CCN(CCOC)CC4)n3)cc12] | N-[1-(2-methoxyethyl)piperidin-4-yl]-2-[4-(prop-2-enamido)quinolin-6-yl]pyrimidine-4-carboxamide | 461.3 |
| 436 | 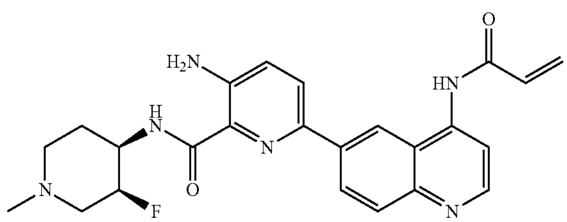 | 3-amino-N-[(3S,4R)-3-fluoro-1-methylpiperidin-4-yl]-6-[4-(prop-2-enamido)quinolin-6-yl]pyridine-2-carboxamide | 449.2 |
| 437 | 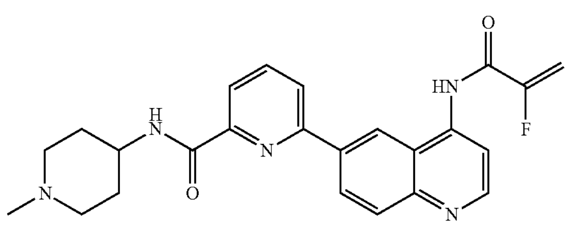 [SMILES: C=C(F)C(=O)Nc1ccnc2ccc(-c3cccc(C(=O)NC4CCN(C)CC4)n3)cc12] | 6-[4-(2-fluoroprop-2-enamido)quinolin-6-yl]-N-(1-methylpiperidin-4-yl)pyridine-2-carboxamide | 434.2 |
| 438 | 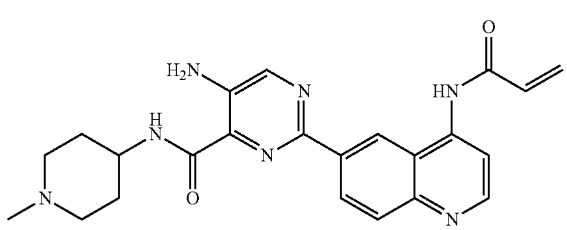 [SMILES: C=CC(=O)Nc1ccnc2ccc(-c3ncc(N)c(C(=O)NC4CCN(C)CC4)n3)cc12] | 5-amino-N-(1-methylpiperidin-4-yl)-2-[4-(prop-2-enamido)quinolin-6-yl]pyrimidine-4-carboxamide | 432.2 |

Example 10: Method J

Preparation of N-(1-methyl-4-piperidyl)-6-[5-(prop-2-enoylamino)-3-quinolyl]pyridine-2-carboxamide (Compound 441)

Step 1) Preparation of N-(3-bromo-5-quinolyl)prop-2-enamide

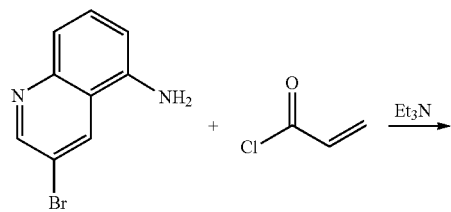

To a mixture of 3-bromoquinolin-5-amine (300 mg, 1.345 mmol) and Et$_3$N (679 mg, 6.725 mmol) in DCM (10 mL) at 0° C. was added a solution of prop-2-enoyl chloride (154 mg, 1.614 mmol) in DCM (1 mL). The resulting mixture was stirred at r.t. for 18 h. The reaction mixture was concentrated in vacuo and the residue was diluted with DCM, washed with saturated NaHCO$_3$ and brine, dried over anhydrous sodium sulfate, filtered, and concentrated. The residue was purified by chromatography on silica gel eluting with 30-100% EtOAc/Hexane to afford the title compound (0.25 g, Yield 66%).

Step 2) Preparation of [5-(prop-2-enoylamino)-3-quinolyl]boronic acid

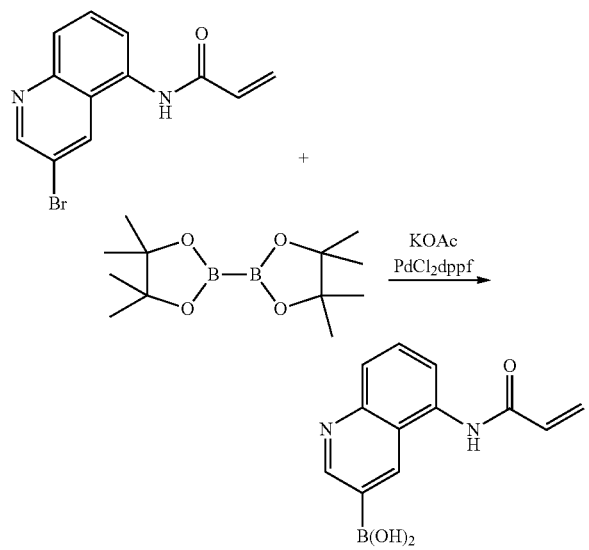

To a solution of N-(3-bromo-5-quinolyl)prop-2-enamide (108 mg, 39 μmol) in dioxane (3 mL) were added 4,4,5,5-tetramethyl-2-(4,4,5,5-tetramethyl-1,3,2-dioxaborolan-2-yl)-1,3,2-dioxaborolane (297 mg, 1.169 mmol), KOAc (191 mg, 1.95 mmol) and PdCl$_2$dppf (40 mg, 49 μmol). The reaction was heated at 100° C. for 1 h in a microwave. The reaction mixture was passed through a celite pad, and the solvent was removed in vacuo. The residue was purified by reverse phase HPLC using a gradient of water 0.1% FA/acetonitrile 0.1% FA to afford the title compound (46.1 mg, Yield 49%).

Step 3) Preparation of N-(1-methyl-4-piperidyl)-6-[5-(prop-2-enoylamino)-3-quinolyl]pyridine-2-carboxamide

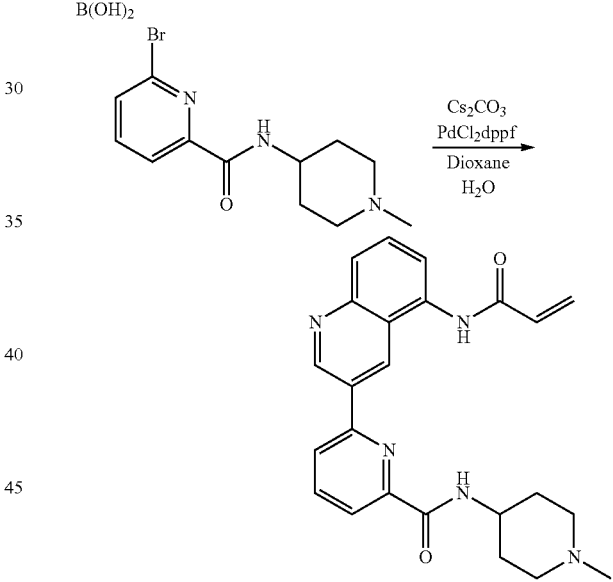

To a solution of [5-(prop-2-enoylamino)-3-quinolyl]boronic acid (40 mg, 165 μmol) in dioxane (2 mL) and water (0.4 mL) were added 6-bromo-N-(1-methyl-4-piperidyl)pyridine-2-carboxamide (73.9 mg, 248 μmol), Cs$_2$CO$_3$ (161 mg, 495 μmol) and PdCl$_2$dppf (18 mg, 22.1 μmol). The reaction was heated at 100° C. for 30 min in a microwave. The reaction mixture was passed through a celite pad, and 2 mL of 0.5M EDTA was added. The resulting solution was stirred at r.t. for 30 min. The solution was washed with brine, dried over anhydrous sodium sulfate, filtered, and concentrated in vacuo. The residue was purified by reverse phase HPLC using a gradient of water 0.1% FA/acetonitrile 0.1% FA to afford the title compound (10 mg, Yield 15%). LC-MS: [M+H]$^+$ 416.

TABLE 10 shows compounds synthesized using methods described in EXAMPLE 10 above.

TABLE 10
| Cpd. No. | Structure | IUPAC | LC-MS (ES+, m/z) |
|---|---|---|---|
| 439 | 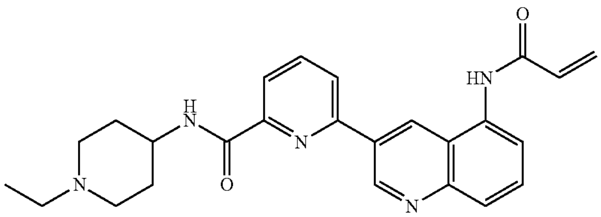 [SMILES: C=CC(=O)Nc1cccc2ncc(-c3cccc(C(=O)NC4CCN(CC)CC4)n3)cc12] | N-(1-ethylpiperidin-4-yl)-6-[5-(prop-2-enamido)quinolin-3-yl]pyridine-2-carboxamide | 430.2 |
| 440 | 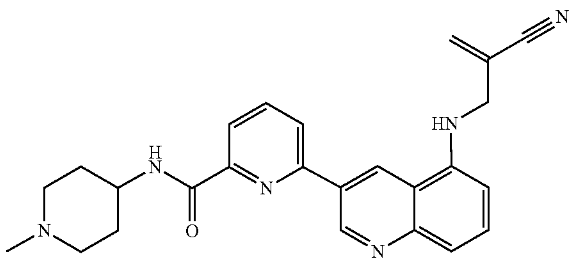 [SMILES: C=C(C#N)CNc1cccc2ncc(-c3cccc(C(=O)NC4CCN(C)CC4)n3)cc12] | 6-{5-[(2-cyano-2-methylideneethyl)amino]quinolin-3-yl}-N-(1-methylpiperidin-4-yl)pyridine-2-carboxamide | 427.2 |
| 441 | 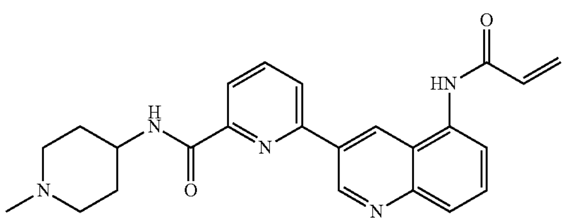 [SMILES: C=CC(=O)Nc1cccc2ncc(-c3cccc(C(=O)NC4CCN(C)CC4)n3)cc12] | N-(1-methylpiperidin-4-yl)-6-[5-(prop-2-enamido)quinolin-3-yl]pyridine-2-carboxamide | 416.2 |
Example 11: Method K
Route 1: General Scheme
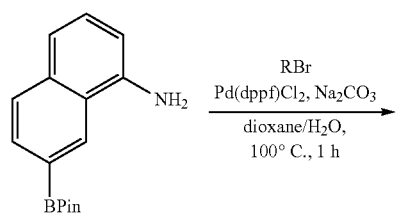
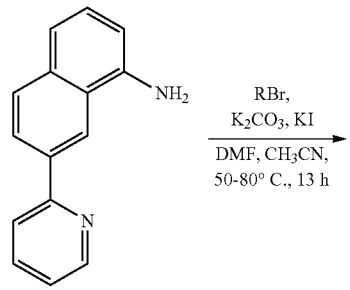
-continued
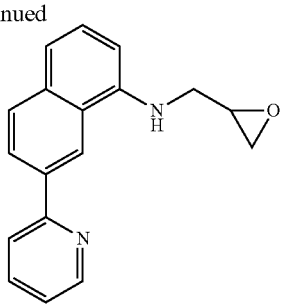
Step 1—7-(2-pyridyl)naphthalen-1-amine
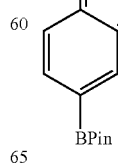
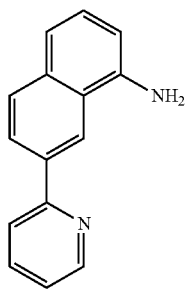

To a solution of 2-bromopyridine (915.8 mg, 5.8 mmol, 551.66 µL, 1.3 eq) and 7-(4,4,5,5-tetramethyl-1,3,2-dioxaborolan-2-yl)naphthalen-1-amine (1.2 g, 4.46 mmol, 1 eq) in dioxane (20 mL) and H$_2$O (5 mL) were added Na$_2$CO$_3$ (1.42 g, 13.38 mmol, 3 eq) and Pd(dppf)Cl$_2$ (3.26 g, 4.46 mmol, 1 eq). The reaction mixture was stirred at 100° C. for 1 hr under N$_2$. TLC (PE:EtOAc=1:1, SM Rf=0.47, TM Rf=0.34) showed that the reaction was complete. The reaction mixture was poured into ~20 mL water and extracted with EtOAc (3×20 mL). The combined organic layer was washed with brine (3×20 mL), dried over anhydrous Na$_2$SO$_4$, filtered, and concentrated in vacuo to give the residue. The residue was purified by column chromatography (SiO$_2$, PE:EtOAc=10:1 to 4:1) to afford the title compound 7-(2-pyridyl)naphthalen-1-amine (0.52 g, 2.36 mmol, 52.95% yield) as a brown solid.

Step 2—N-(oxiran-2-ylmethyl)-7-(2-pyridyl)naphthalen-1-amine

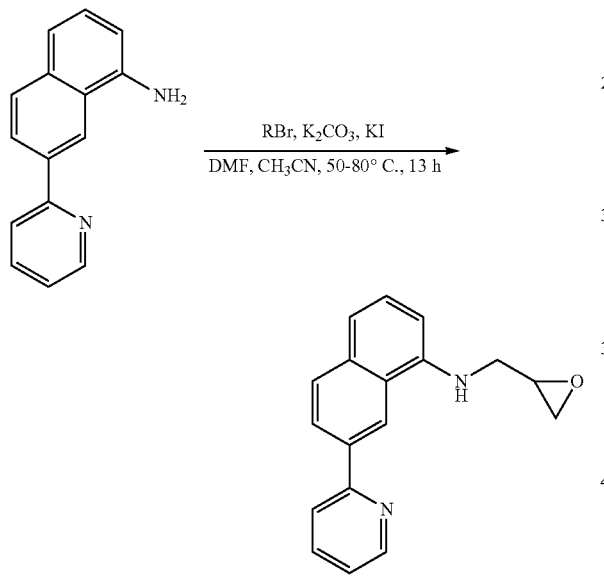

To a solution of 7-(2-pyridyl)naphthalen-1-amine (0.02 g, 90.8 µmol, 1 eq) and 2-(bromomethyl)oxirane (10 mg, 72.64 µmol, 5.99 µL, 0.8 eq) in CH$_3$CN (3 mL) was added K$_2$CO$_3$ (37.7 mg, 272.39 µmol, 3 eq). The reaction mixture was stirred at 50° C. for 1 hr. Then, KI (1.5 mg, 9.08 µmol, 0.1 eq) and additional solution of 2-(bromomethyl)oxirane (49.8 mg, 363.19 µmol, 29.97 µL, 4 eq) in DMF (0.3 mL) were successively added. The resulting reaction mixture was stirred at 80° C. for 12 hr, LCMS showed that the reaction was complete. The reaction mixture was poured into 10 mL water and extracted with EtOAc (3×10 mL). The combined organic layer was washed with brine (3×10 mL), dried over anhydrous Na$_2$SO$_4$, filtered, and concentrated in vacuo to give the residue. The residue was purified by prep-HPLC (neutral condition) to afford the title compound N-(oxiran-2-ylmethyl)-7-(2-pyridyl) naphthalen-1-amine (4.20 mg, 15.08 µmol, 16.61% yield, 99.2% purity) as a yellow solid. LC-MS (ES$^+$, m/z): 277.1 [(M+H)$^+$] 1H NMR (400 MHz, DMSO-d6) Shift=8.85 (s, 1H), 8.71 (dd, J=0.9, 4.9 Hz, 1H), 8.23 (s, 1H), 8.21 (s, 1H), 7.94 (dt, J=1.9, 7.8 Hz, 1H), 7.86 (d, J=8.6 Hz, 1H), 7.38-7.34 (m, 1H), 7.33-7.28 (m, 1H), 7.15 (d, J=7.9 Hz, 1H), 6.73 (t, J=5.5 Hz, 1H), 6.65 (d, J=7.7 Hz, 1H), 3.60 (dd, J=3.4, 5.6 Hz, 1H), 3.56 (dd, J=3.4, 5.4 Hz, 1H), 3.39-3.34 (m, 1H), 3.28-3.22 (m, 1H), 2.82 (s, 1H), 2.80 (d, J=4.2 Hz, 1H), 2.67 (d, J=2.4 Hz, 1H), 2.65 (br d, J=2.6 Hz, 1H)

Route 3

Step 1—1-chloro-3-[[7-(2-pyridyl)-1-naphthyl]amino]propan-2-ol

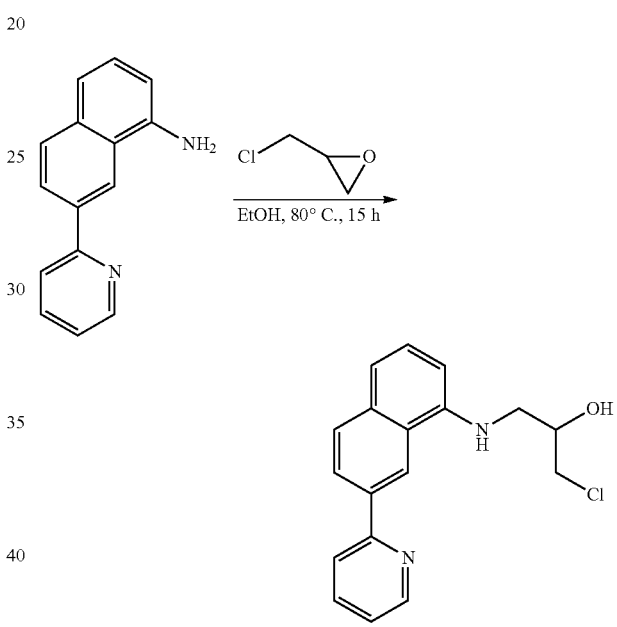

To a solution of 7-(2-pyridyl)naphthalen-1-amine (0.03 g, 136.2 µmol, 1 eq) in EtOH (2.0 mL) was added 2-(chloromethyl)oxirane (12.6 mg, 136.2 µmol, 10.68 µL, 1 eq). The reaction mixture was stirred at 80° C. for 15 hr. The reaction mixture was concentrated in vacuo to give the residue. The residue was purified by prep-HPLC (FA condition) to afford the title compound 1-chloro-3-[[7-(2-pyridyl)-1-naphthyl]amino]propan-2-ol (0.0058 g, 18.54 µmol, 13.61% yield, 100.0% purity) as a brown solid. LC-MS (ES$^+$, m/z): 313.1 [(M+H)$^+$], 1H NMR (400 MHz, DMSO-d6) Shift=8.83 (s, 1H), 8.72 (td, J=0.9, 4.9 Hz, 1H), 8.25-8.22 (m, 1H), 8.20 (s, 1H), 7.95 (dt, J=1.8, 7.7 Hz, 1H), 7.86 (d, J=8.6 Hz, 1H), 7.41-7.35 (m, 1H), 7.35-7.30 (m, 1H), 7.16 (d, J=7.9 Hz, 1H), 6.62 (d, J=7.5 Hz, 1H), 6.48 (t, J=5.7 Hz, 1H), 5.47 (d, J=5.3 Hz, 1H), 4.14-4.05 (m, 1H), 3.85-3.78 (m, 1H), 3.74-3.66 (m, 1H), 3.51 (s, 1H), 3.47-3.40 (m, 1H), 3.30-3.25 (m, 1H).

TABLE 11 shows compounds synthesized methods described in EXAMPLE 11 above.

TABLE 11
| Cpd No. | Structure | IUPAC | LC-MS (ES+, m/z) |
|---|---|---|---|
| 442 | 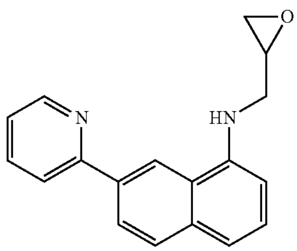 [SMILES: c1ccc(-c2ccc3cccc(NCC4CO4)c3c2)nc1] | N-[(oxiran-2-yl)methyl]-7-(pyridin-2-yl)naphthalen-1-amine | 277.1 |
| 443 | 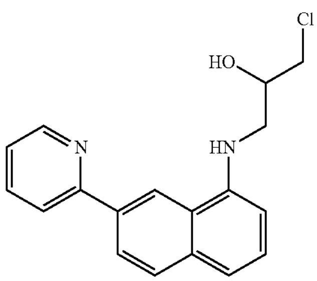 [SMILES: OC(CCl)CNc1cccc2ccc(-c3ccccn3)cc12] | 1-chloro-3-{[7-(pyridin-2-yl)naphthalen-1-yl]amino}propan-2-ol | 313.1 |
| 444 | 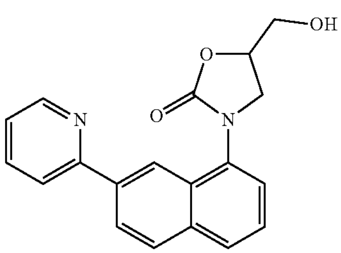 [SMILES: O=C1OC(CO)CN1c1cccc2ccc(-c3ccccn3)cc12] | 5-(hydroxymethyl)-3-[7-(pyridin-2-yl)naphthalen-1-yl]-1,3-oxazolidin-2-one | 321.1 |
Example 12: Method L
Route 1: General Scheme
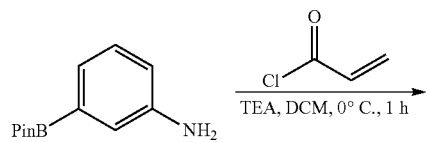
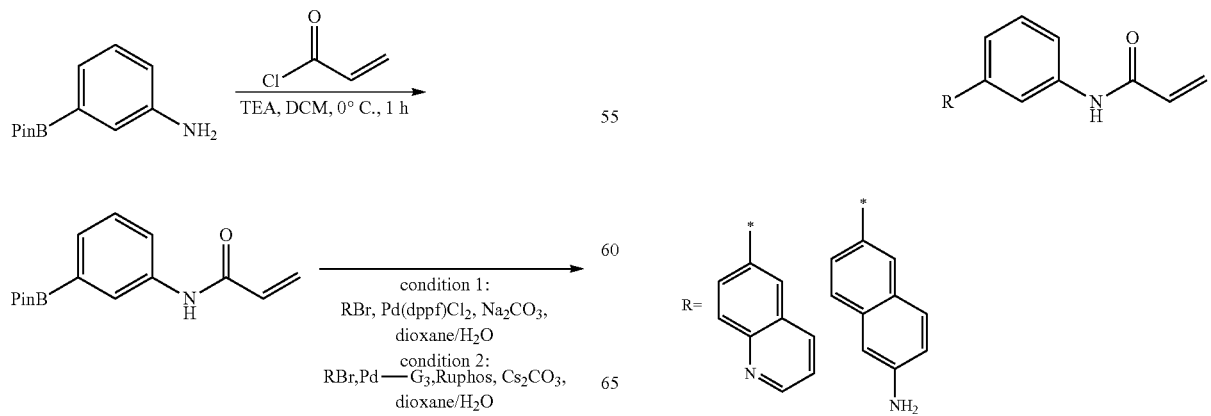

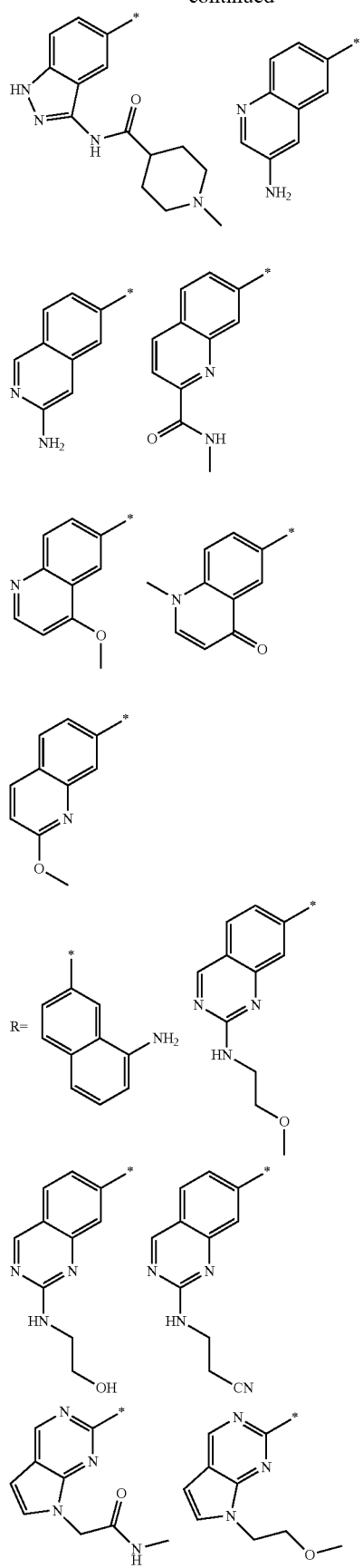
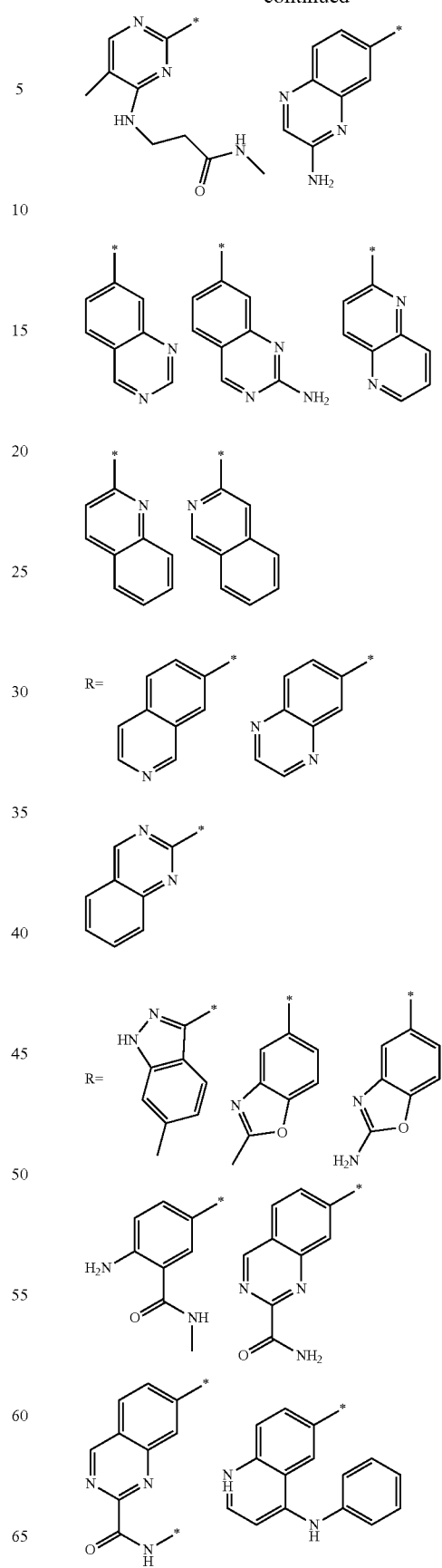

561
-continued

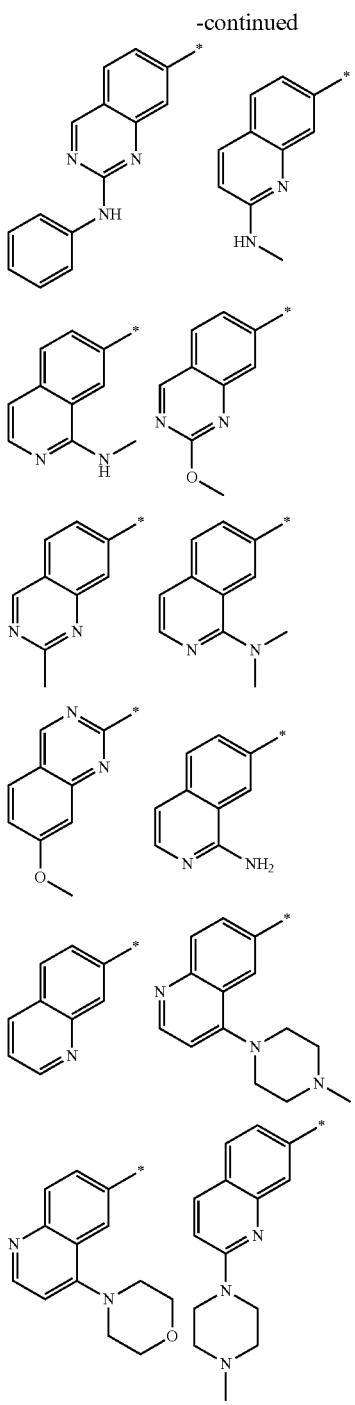

Step 1) 5-N-[3-(4,4,5,5-tetramethyl-1,3,2-dioxaborolan-2-yl)phenyl]prop-2-enamide

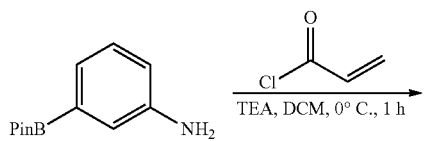

562
-continued

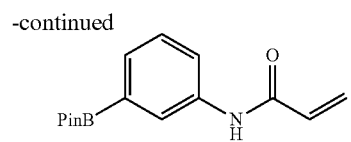

To a solution of 3-(4,4,5,5-tetramethyl-1,3,2-dioxaborolan-2-yl)aniline (2 g, 91.29 mmol, 1 eq) in DCM (200 mL) was added TEA (27.71 g, 273.86 mmol, 38.12 mL, 3 eq), prop-2-enoyl chloride (12.39 g, 136.93 mmol, 11.17 mL, 1.5 eq) was added to the solution at 0° C. The reaction was stirred at 0° C. for 1 hr under N$_2$. The reaction was poured into 300 mL water and extracted with DCM (3×150 mL). The combined organic phase was dried over anhydrous Na$_2$SO$_4$, filtered, and concentrated in vacuo. The residue was purified by column chromatography (SiO$_2$, PE:EtOAc=10:1 to 4:1) to afford the title compound N-[3-(4,4,5,5-tetramethyl-1,3,2-dioxaborolan-2-yl)phenyl]prop-2-enamide (14.7 g, 53.82 mmol, 58.96% yield) as a white solid. LC-MS (ES$^+$, m/z): 274.1 [(M+H)$^+$], 1H NMR (400 MHz, DMSO-d6) Shift=10.14 (s, 1H), 7.98 (s, 1H), 7.85 (br d, J=7.5 Hz, 1H), 7.40-7.28 (m, 2H), 6.48-6.34 (m, 1H), 6.31-6.17 (m, 1H), 5.75 (dd, J=1.9, 10.0 Hz, 1H), 1.30 (s, 12H).

Step 2—N-[3-[2-(2-methoxyethylamino)quinazolin-7-yl]phenyl]prop-2-enamide

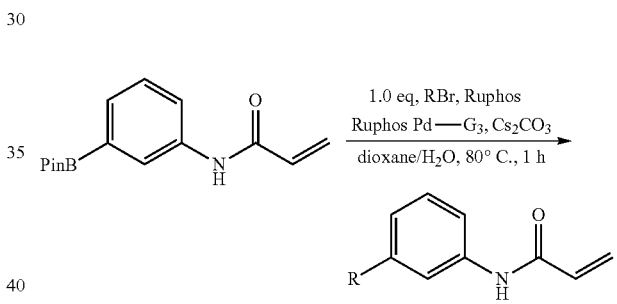

To the solution of 7-bromo-N-(2-methoxyethyl)quinazolin-2-amine (100 mg, 354.4 μmol, 1 eq) in dioxane (4 mL) and H$_2$O (1 mL) were successively added N-[3-(4,4,5,5-tetramethyl-1,3,2-dioxaborolan-2-yl)phenyl]prop-2-enamide (145.2 mg, 531.6 μmol, 1.5 eq), Cs$_2$CO$_3$ (231 mg, 708.88 μmol, 2 eq), RuPhos (16.5 mg, 35.44 μmol, 0.1 eq) and [2-(2-aminophenyl)phenyl]-methylsulfonyloxy-palladium; dicyclohexyl-[2-(2,6-diisopropoxyphenyl)phenyl]phosphane (14.8 mg, 17.72 μmol, 0.05 eq) at 25° C. The resulting reaction mixture was stirred at 80° C. for 1 hour. LCMS showed that the reaction was complete. The reaction mixture was poured into 80 mL saturated EDTA and followed by 30 mL EtOAc. The solution was stirred at 20° C. for 2 hours. The aqueous phase was separated and extracted with EtOAc (2×20 mL). The combined organic layer was washed successively with water (2×20 mL) and brine (1×20 mL), dried over anhydrous Na$_2$SO$_4$, filtered, and concentrated to give a residue. The residue was purified by prep-HPLC to afford the title compound (11.5 mg, 33.01 μmol, 9.31% yield, 100% purity) as a light yellow solid. 349.2 [(M+H)$^+$], 1H NMR (400 MHz, DMSO-d6) δ=10.28 (s, 1H), 9.13 (s, 1H), 8.45-8.01 (m, 1H), 7.89 (d, J=8.30 Hz, 1H), 7.71 (d, J=7.70 Hz, 1H), 7.66 (s, 1H), 7.52 (d, J=8.00 Hz, 2H), 7.56-7.50 (m, 1H), 7.40 (s, 1H), 6.56-6.39 (m, 1H), 6.36-6.22 (m, 1H), 5.91-5.56 (m, 1H), 3.70-3.45 (m, 4H), 3.29 (s, 3H).

Step 3—N-[3-(8-amino-2-naphthyl)phenyl]prop-2-enamide

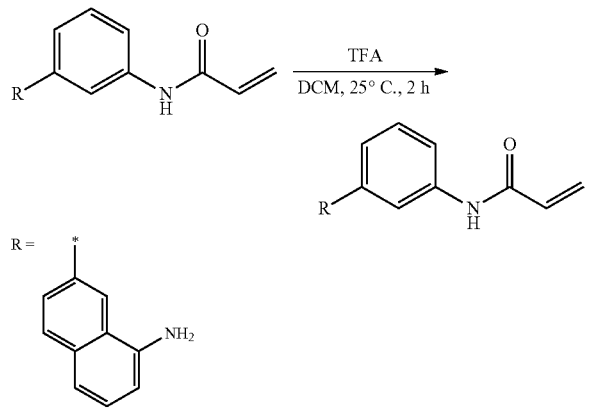

To a solution of tert-butyl N-[7-[3-(prop-2-enoylamino)phenyl]-1-naphthyl]carbamate (100 mg, 257.43 µmol, 1 eq) in DCM (4 mL) was added TFA (2 mL). The mixture was stirred at 25° C. for 2 hours. LCMS showed that the reaction was complete. The reaction mixture was poured into 50 mL ice water and adjusted to pH=8~9 with saturated $Na_2CO_3$. The solution was extracted with DCM (3×30 mL). The combined organic layer was washed with $H_2O$ (2×30 mL) and brine (2×30 mL), dried over anhydrous $Na_2SO_4$, filtered, and concentrated in vacuo to give a residue. The residue was purified by prep-HPLC to afford the title compound (9.4 mg, 32.6 µmol, 12.66% yield, 100% purity) as a light yellow solid. LC-MS ($ES^+$, m/z): 289.1 [(M+H)$^+$], $^1$H NMR (400 MHz, DMSO-$d_6$) δ=10.26 (s, 1H), 8.33 (s, 1H), 8.05 (s, 1H), 7.82 (d, J=8.60 Hz, 1H), 7.71 (d, J=8.20 Hz, 1H), 7.66 (d, J=8.50 Hz, 1H), 7.56 (d, J=8.00 Hz, 1H), 7.50-7.41 (m, 1H), 7.26-7.17 (m, 1H), 7.10 (d, J=8.00 Hz, 1H), 6.70 (d, J=7.30 Hz, 1H), 6.58-6.43 (m, 1H), 6.33-6.24 (m, 1H), 5.84 (s, 2H), 5.78 (d, J=10.00 Hz, 1H).

Preparation of N-[3-(4-oxo-3H-quinazolin-7-yl)phenyl]prop-2-enamide

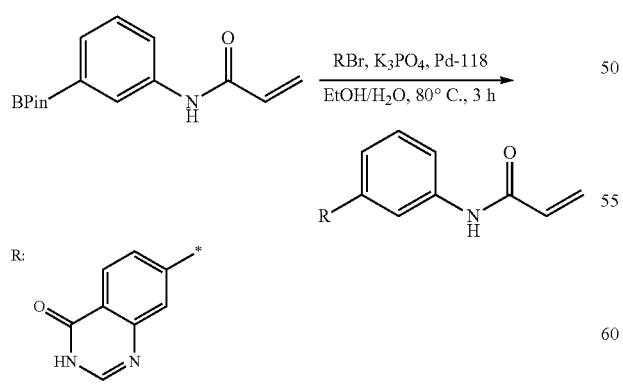

To the solution of 7-bromo-3H-quinazolin-4-one (100 mg, 444.36 µmol, 1 eq) in EtOH (4 mL) and $H_2O$ (1 mL) were successively added N-[3-(4,4,5,5-tetramethyl-1,3,2-dioxaborolan-2-yl)phenyl]prop-2-enamide (133.5 mg, 488.8 µmol, 1.1 eq), $K_3PO_4$ (188.7 mg, 888.72 µmol, 2 eq) and ditert-butyl(cyclopentyl)phosphane;dichloropalladium;iron (29 mg, 44.44 µmol, 0.1 eq) at 25° C. The reaction mixture was stirred at 80° C. for 3 hours. The reaction mixture was poured into 80 mL saturated EDTA and followed by 30 mL EtOAc. The solution was stirred at 20° C. for 2 hours. The aqueous phase was separated and extracted with EtOAc (2×20 mL). The combined organic layer was washed successively with water (2×20 mL) and brine (1×20 mL), dried over anhydrous $Na_2SO_4$, filtered, and concentrated to give a residue. The residue was purified by prep-HPLC to afford the title compound (9.4 mg, 32.27 µmol, 7.26% yield, 100% purity) as a light yellow solid. LC-MS ($ES^+$, m/z): 486.3 [(M+H)$^+$]. $^1$H NMR (400 MHz, DMSO-$d_6$) δ=12.29 (s, 1H), 10.33 (s, 1H), 8.21 (d, J=8.40 Hz, 1H), 8.14 (s, 2H), 7.86 (s, 1H), 7.79 (d, J=8.00 Hz, 1H), 7.73 (d, J=6.60 Hz, 1H), 7.43-7.56 (m, 2H), 6.38-6.62 (m, 1H), 6.21-6.36 (m, 1H), 5.80 (d, J=9.70 Hz, 1H).

Route 2: General Scheme

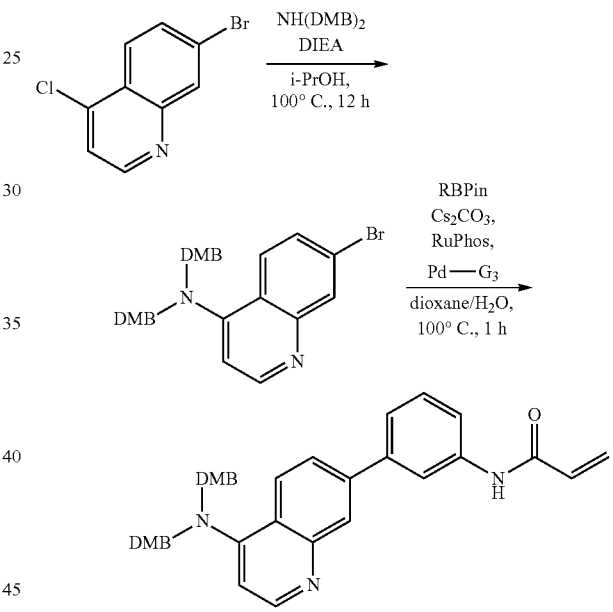

Step 1 7-bromo-N,N-bis[(2,4-dimethoxyphenyl)methyl]quinolin-4-amine

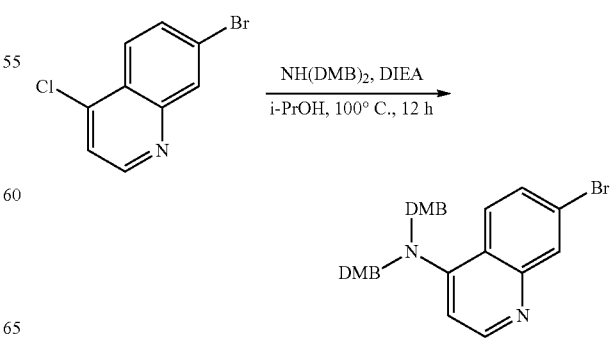

To a solution of 7-bromo-4-chloro-quinoline (0.3 g, 1.24 mmol, 1 eq) in i-PrOH (3 mL) was added DIPEA (479.7 mg, 3.71 mmol, 646.45 μL, 3 eq) and 1-(2,4-dimethoxyphenyl)-N-[(2,4-dimethoxyphenyl)methyl]methanamine (1.96 g, 6.19 mmol, 5 eq). Then, the mixture was stirred at 100° C. for 12 hr. LCMS showed half of the starting material remained. The reaction was concentrated in vacuo. The residue was purified by prep-TLC (SiO$_2$, PE; EtOAc=1:1) to afford the title compound 7-bromo-N,N-bis[(2,4-dimethoxyphenyl)methyl]quinolin-4-amine (0.1 g, 191.05 μmol, 15.44% yield) as a yellow oil. LC-MS (ES$^+$, m/z): 523.2/525.2 [(M+H)$^+$].

Step 2 7N-[3-[4-[bis[(2,4-dimethoxyphenyl)methyl]amino]-7-quinolyl]phenyl]prop-2-enamide

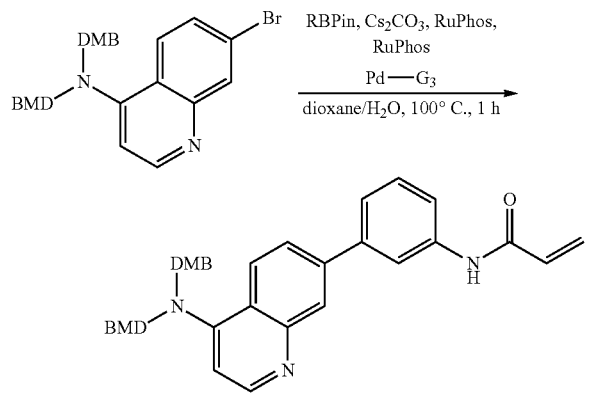

To a solution of 7-bromo-N,N-bis[(2,4-dimethoxyphenyl)methyl]quinolin-4-amine (0.1 g, 191.05 μmol, 1 eq) and N-[3-(4,4,5,5-tetramethyl-1,3,2-dioxaborolan-2-yl)phenyl]prop-2-enamide (52.2 mg, 191.05 μmol, 1 eq) in dioxane (2 mL) and H$_2$O (0.5 mL) were added Cs$_2$CO$_3$ (186.8 mg, 573.16 μmol, 3 eq), RuPhos (8.9 mg, 19.11 μmol, 0.1 eq) and RuPhos Pd G3 (8 mg, 9.55 μmol, 0.05 eq). The mixture was heated to 100° C. for 1 h under N$_2$. LCMS showed that the reaction was complete. The reaction mixture was poured into ~15 mL saturated EDTA and stirred at 25° C. for 1 h. The mixture was extracted with EtOAc (3×10 mL), washed with brine (3×20 mL), dried over anhydrous Na$_2$SO$_4$, filtered, and concentrated in vacuo. The residue was purified by prep-TLC (SiO$_2$, DCM:MeOH=10:1) to afford the title compound N-[3-[4-[bis[(2,4-dimethoxyphenyl)methyl]amino]-7-quinolyl]phenyl]prop-2-enamide (0.1 g, 169.58 μmol, 88.76% yield) as a brown oil. LC-MS (ES$^+$, m/z): 590.4 [(M+H)$^+$].

Step 3 N-[3-(4-amino-7-quinolyl)phenyl]prop-2-enamide

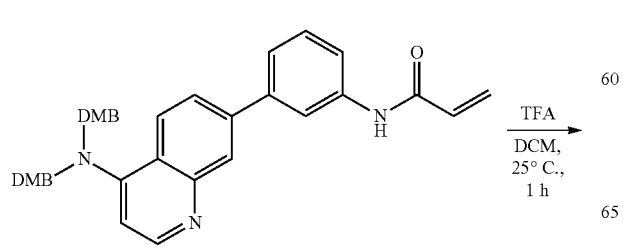

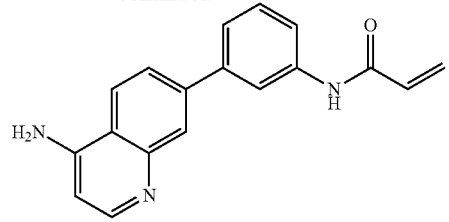

To a solution of N-[3-[4-[bis[(2,4-dimethoxyphenyl)methyl]amino]-7-quinolyl]phenyl]prop-2-enamide (0.12 g, 203.5 μmol, 1 eq) in DCM (4 mL) was added TFA (2.31 g, 20.26 mmol, 1.5 mL, 99.55 eq), and the mixture was stirred at 25° C. for 1 hr. HPLC showed that the reaction was complete. The reaction mixture was poured into ~10 mL ice water and adjusted to pH=7 using saturated NaHCO$_3$. The mixture was extracted with EtOAc (3×10 mL), washed with brine (3×30 mL), dried over anhydrous Na$_2$SO$_4$, filtered, and concentrated in vacuo. The residue was purified by prep-HPLC (basic condition) to afford the title compound N-[3-(4-amino-7-quinolyl)phenyl]prop-2-enamide (10.20 mg, 32.57 μmol, 16.01% yield, 92.4% purity) as a white solid. LC-MS (ES$^+$, m/z): 290.0 [(M+H)$^+$], 1H NMR (400 MHz, DMSO-d6) Shift=10.29 (s, 1H), 8.33 (d, J=5.3 Hz, 1H), 8.24 (d, J=8.8 Hz, 1H), 8.14 (s, 1H), 7.96 (d, J=1.6 Hz, 1H), 7.69-7.68 (m, 1H), 7.71 (br d, J=7.6 Hz, 1H), 7.66 (dd, J=1.9, 8.4 Hz, 1H), 7.56-7.50 (m, 1H), 7.49-7.41 (m, 1H), 6.82 (s, 2H), 6.54 (d, J=5.0 Hz, 1H), 6.52-6.41 (m, 1H), 6.35-6.22 (m, 1H), 5.83-5.75 (m, 1H).

Route 3: General Scheme

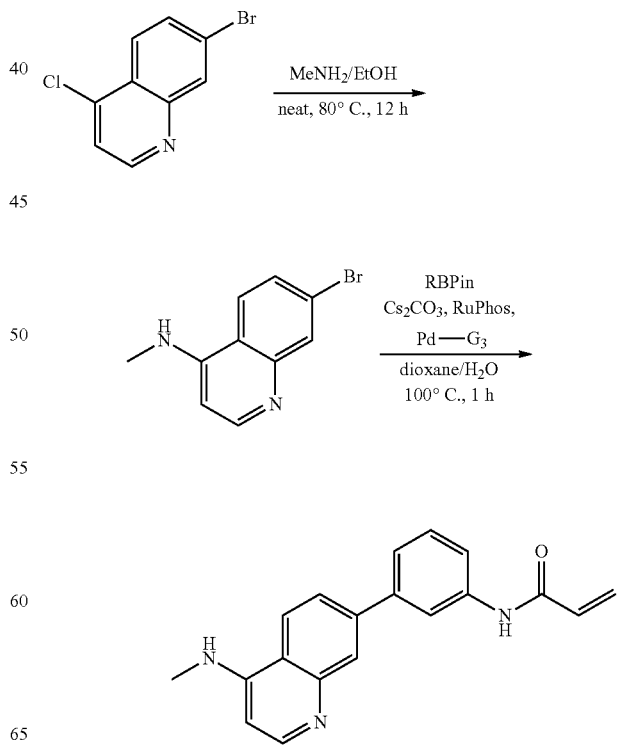

Step 1 7-bromo-N-methyl-quinolin-4-amine

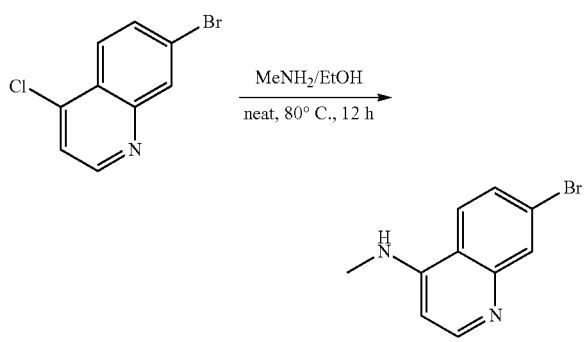

A solution of 7-bromo-4-chloro-quinoline (0.3 g, 1.24 mmol, 1 eq) in MeNH₂ (1 M in EtOH, 5 mL, 4.04 eq) was stirred at 80° C. for 12 hr. The reaction was concentrated in vacuo. The crude product was washed with PE (3×10 mL) to afford the title compound 7-bromo-N-methyl-quinolin-4-amine (0.25 g, crude) as a light yellow solid. LC-MS (ES⁺, m/z): 237.2/239.1 [(M+H)⁺].

Step 2 N-[3-[4-(methylamino)-7-quinolyl]phenyl]prop-2-enamide

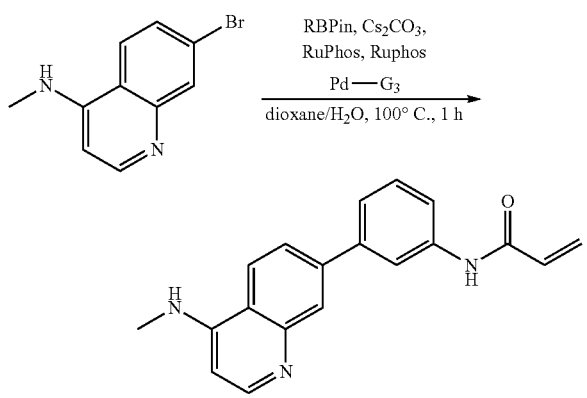

To a solution of 7-bromo-N-methyl-quinolin-4-amine (0.1 g, 421.77 μmol, 1 eq) and N-[3-(4,4,5,5-tetramethyl-1,3,2-dioxaborolan-2-yl)phenyl]prop-2-enamide (115.2 mg, 421.77 μmol, 1 eq) in dioxane (2 mL) and H₂O (0.5 mL) were added Cs₂CO₃ (412.3 mg, 1.27 mmol, 3 eq), RuPhos (19.7 mg, 42.18 μmol, 0.1 eq) and RuPhos Pd G3 (17.6 mg, 21.09 μmol, 0.05 eq). Then the mixture was heated to 100° C. for 1 h under N₂. The reaction was poured into ~15 mL saturated EDTA and stirred at 25° C. for 1 h. The mixture was extracted with EtOAc (3×15 mL). The organic phase was washed with brine (3×30 mL), dried over anhydrous Na₂SO₄, filtered, and concentrated in vacuo. The residue was purified by prep-HPLC (neutral condition) to afford the title compound N-[3-[4-(methylamino)-7-quinolyl]phenyl]prop-2-enamide (0.0161 g, 49.09 μmol, 11.64% yield, 92.5% purity) as a white solid. LC-MS (ES⁺, m/z): 304.1 [(M+H)⁺]. 1H NMR (400 MHz, DMSO-d6) Shift=10.29 (s, 1H), 8.44 (d, J=5.3 Hz, 1H), 8.24 (d, J=8.6 Hz, 1H), 8.15 (s, 1H), 7.99 (d, J=1.5 Hz, 1H), 7.70 (br d, J=7.3 Hz, 2H), 7.57-7.50 (m, 1H), 7.50-7.42 (m, 1H), 7.37 (br d, J=4.4 Hz, 1H), 6.57-6.43 (m, 1H), 6.39 (d, J=5.3 Hz, 1H), 6.34-6.19 (m, 1H), 5.86-5.72 (m, 1H), 2.91 (d, J=4.6 Hz, 3H).

Step 3—1-methyl-N-[5-[3-(prop-2-enoylamino)phenyl]-2H-indazol-3-yl]piperidine-4-carboxamide

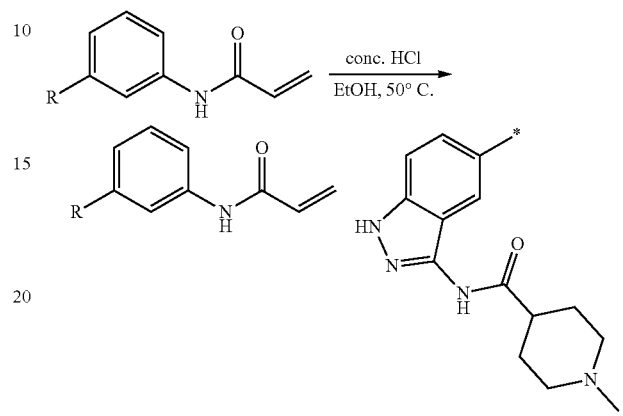

The solution of 1-methyl-N-[5-[3-(prop-2-enoylamino)phenyl]-2-(2-trimethylsilylethoxymethyl) indazol-3-yl]-N-(2-trimethylsilylethoxymethyl)piperidine-4-carboxamide (80 mg, 120.48 μmol, 1 eq) in EtOH (4 mL) was added concentrated HCl (37%, 2 mL). The reaction mixture was stirred at 50° C. for 3 h. The reaction mixture was poured into H₂O (10 mL) then adjusted to pH=7 with saturated NaHCO₃. The aqueous phase was extracted with EtOAc (3×20 mL). The combined organic layer was washed with brine (3×20 mL), dried over anhydrous Na₂SO₄, filtered, and concentrated in vacuo to afford a residue. The residue was purified by prep-TLC (SiO₂, DCM:MeOH=10:1, Rf=0.1) then further purified by prep-HPLC to afford the title compound 1-methyl-N-[5-[3-(prop-2-enoylamino)phenyl]-2H-indazol-3-yl]piperidine-4-carboxamide (3.6 mg, 8.7 μmol, 7.22% yield, 97.5% purity) as a white solid. 404.2 [(M+H)⁺], 1H NMR (400 MHz, DMSO-d6) δ=12.71 (s, 1H), 10.31 (br s, 1H), 10.25 (s, 1H), 7.96 (s, 1H), 7.92 (br s, 1H), 7.68 (br d, J=8.4 Hz, 1H), 7.62 (d, J=8.8 Hz, 1H), 7.55 (d, J=8.8 Hz, 1H), 7.42 (t, J=7.6 Hz, 1H), 7.32 (br d, J=7.6 Hz, 1H), 6.47 (dd, J=10.0, 17.2 Hz, 1H), 6.28 (dd, J=1.6, 17.2 Hz, 1H), 5.80 (dd, J=1.6, 10.0 Hz, 1H), 2.83 (br d, J=11.2 Hz, 2H), 2.45-2.39 (m, 1H), 2.16 (s, 3H), 1.93-1.78 (m, 4H), 1.78-1.65 (m, 2H).

Preparation of N-[3-(4-hydroxy-6-quinolyl)phenyl]prop-2-enamide

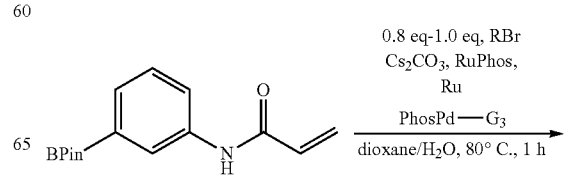

-continued

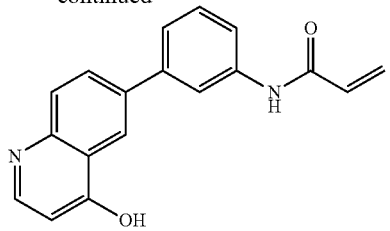

To a solution of N-[3-(4,4,5,5-tetramethyl-1,3,2-dioxaborolan-2-yl)phenyl]prop-2-enamide (0.25 g, 915.3 μmol, 1 eq) and 6-bromoquinolin-4-ol (164.1 mg, 732.24 μmol, 0.8 eq) in dioxane (4 mL) and H$_2$O (1 mL) were added Cs$_2$CO$_3$ (596.4 mg, 1.83 mmol, 2 eq), dicyclohexyl-[2-(2,6-diisopropoxyphenyl)phenyl]phosphane (42.7 mg, 91.53 μmol, 0.1 eq), and [2-(2-aminophenyl)phenyl]-methylsulfonyloxypalladium;dicyclohexyl-[2-(2,6-diisopropoxyphenyl)phenyl]phosphane (38.3 mg, 45.77 μmol, 0.05 eq). The reaction mixture was stirred at 80° C. for 1 hr under N$_2$. LCMS showed that the reaction was complete. The reaction mixture was poured into ~15 mL water and extracted with EtOAc (3×15 mL). The combined organic layer was washed with brine (3×15 mL), dried over anhydrous Na$_2$SO$_4$, filtered, and concentrated in vacuo to give the residue. The residue was purified by prep-TLC (SiO$_2$, DCM:MeOH=8:1) then further purified by prep-HPLC (FA condition) to afford the title compound N-[3-(4-hydroxy-6-quinolyl)phenyl]prop-2-enamide (0.005 g, 17.22 μmol, 1.88% yield, 100% purity) as a white solid. LC-MS (ES$^+$, m/z): 291.1 [(M+H)$^+$], 1H NMR (400 MHz, DMSO-d6) Shift=11.86 (br s, 1H), 10.28 (s, 1H), 8.34 (d, J=2.1 Hz, 1H), 8.22 (s, 1H), 8.09 (s, 1H), 7.96 (dd, J=2.2, 8.7 Hz, 1H), 7.93 (br s, 1H), 7.71 (dt, J=2.0, 4.6 Hz, 1H), 7.65 (d, J=8.7 Hz, 1H), 7.44 (d, J=5.1 Hz, 2H), 6.52-6.38 (m, 1H), 6.34-6.24 (m, 1H), 6.07 (d, J=7.3 Hz, 1H), 5.83-5.74 (m, 1H)

Preparation of N-[3-[5-[(1-methyl-4-piperidyl)methylamino]-3-isoquinolyl]phenyl]prop-2-enamide

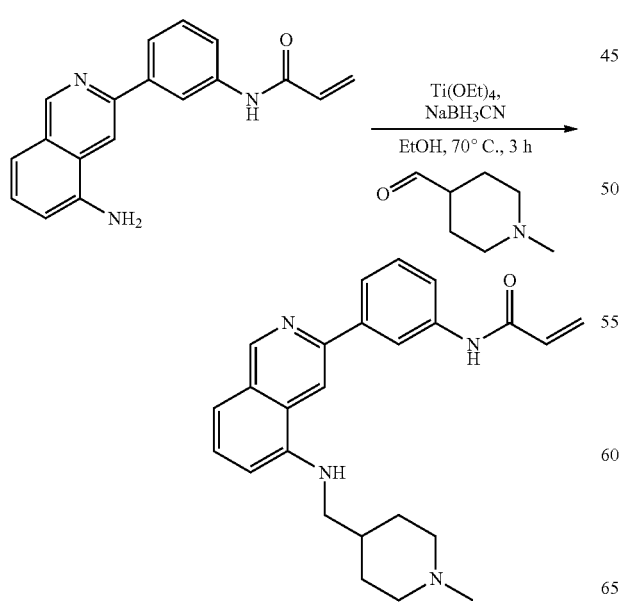

To a solution of N-[3-(5-amino-3-isoquinolyl)phenyl]prop-2-enamide (0.08 g, 276.5 μmol, 1 eq) and 1-methylpiperidine-4-carbaldehyde (1.76 g, 1.38 mmol, 10% purity, 5 eq) in EtOH (5 mL) was added Ti(OEt)$_4$ (315.4 mg, 1.38 mmol, 286.69 μL, 5 eq). The reaction mixture was stirred at 70° C. for 1 hr, and NaBH$_3$CN (86.9 mg, 1.38 mmol, 5 eq) was added. The resulting reaction mixture was stirred at 70° C. for further 2 hr. The reaction was poured into ~50 mL water then 50 mL EtOAc was added. The solution was filtered and the filtrate was extracted with EtOAc (3×50 mL). The combined organic layer was washed with brine (3×50 mL), dried over anhydrous Na$_2$SO$_4$, filtered, and concentrated in vacuo to give the residue. The residue was purified by prep-HPLC (FA condition) to afford the title compound N-[3-[5-[(1-methyl-4-piperidyl)methylamino]-3-isoquinolyl]phenyl]prop-2-enamide (0.0162 g, 40.45 μmol, 14.63% yield, 100% purity) as a pink solid. LC-MS (ES$^+$, m/z): 401.2 [(M+H)$^+$], 1H NMR (400 MHz, DMSO-d6) Shift=10.36 (s, 1H), 9.19 (s, 1H), 8.63 (s, 1H), 8.48 (s, 1H), 8.24 (s, 1H), 7.94 (d, J=7.9 Hz, 1H), 7.86 (br d, J=7.9 Hz, 1H), 7.48 (t, J=7.8 Hz, 1H), 7.45-7.45 (m, 1H), 7.44-7.39 (m, 1H), 7.25 (d, J=7.9 Hz, 1H), 6.76 (br t, J=5.5 Hz, 1H), 6.71 (d, J=7.9 Hz, 1H), 6.50 (dd, J=10.0, 16.9 Hz, 1H), 6.29 (dd, J=2.0, 17.0 Hz, 1H), 5.80-5.75 (m, 1H), 3.24-3.08 (m, 2H), 2.93 (brd, J=11.5 Hz, 2H), 2.28 (s, 3H), 2.10 (br t, J=11.6 Hz, 2H), 1.88-1.82 (m, 2H), 1.81-1.73 (m, 1H), 1.38-1.26 (m, 2H).

Preparation of 7-[3-(prop-2-enoylamino)phenyl]quinoline-2-carboxamide

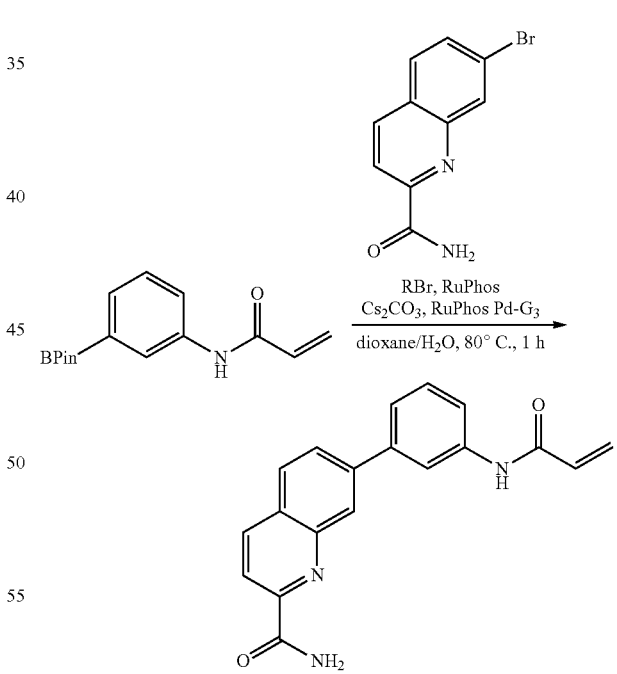

To a solution of N-[3-(4,4,5,5-tetramethyl-1,3,2-dioxaborolan-2-yl)phenyl]prop-2-en amide (60 mg, 219.67 μmol, 1 eq) in dioxane (2 mL) and H$_2$O (0.5 mL) were successively added 7-bromoquinoline-2-carboxamide (44.1 mg, 175.74 μmol, 0.8 eq), Cs$_2$CO$_3$ (143.2 mg, 439.34 μmol, 2 eq), RuPhos (10.3 mg, 21.97 μmol, 0.1 eq) and [2-(2-aminophenyl)phenyl]-methylsulfonyloxy-palladium; dicyclohexyl-[2-(2,6-diisopropoxyphenyl)phenyl]phosphane (9.2 mg, 10.98 µmol, 0.05 eq). The reaction mixture was stirred at 80° C. for 1 hr under $N_2$. LCMS showed that the reaction was complete. The reaction mixture was poured into saturated EDTA (50 mL) and EtOAc (50 mL) was added. The solution was stirred at 25° C. for 1 h. The mixture was extracted with EtOAc (3×100 mL). The combined organic layer was washed with $H_2O$ (2×50 mL) and brine (2×50 mL), dried over anhydrous $Na_2SO_4$, filtered, and concentrated in vacuo to give a residue. The residue was purified by prep-HPLC (PA condition) to afford the title compound 7-[3-(prop-2-enoylamino)phenyl]quinoline-2-carboxamide (11.6 mg, 36.55 µmol, 16.64% yield, 100.0% purity) as a white solid. LC-MS (ES+, m/z): 318.1 [(M+H)+]$^1$H NMR (400 MHz, DMSO-$d_6$) δ=10.37 (s, 1H), 8.59 (d, J=8.50 Hz, 1H), 8.39 (br s, 1H), 8.34 (s, 2H), 8.19 (d, J=8.64 Hz, 1H), 8.16 (d, J=8.50 Hz, 1H), 8.03 (dd, J=8.50, 1.76 Hz, 1H), 7.81 (br s, 1H), 7.49-7.68 (m, 3H), 6.49 (dd, J=16.96, 10.08 Hz, 1H), 6.30 (dd, J=16.96, 1.94 Hz, 1H), 5.78-5.84 (m, 1H).

Preparation of-N-[3-(2-amino-7-quinolyl)phenyl]prop-2-enamide

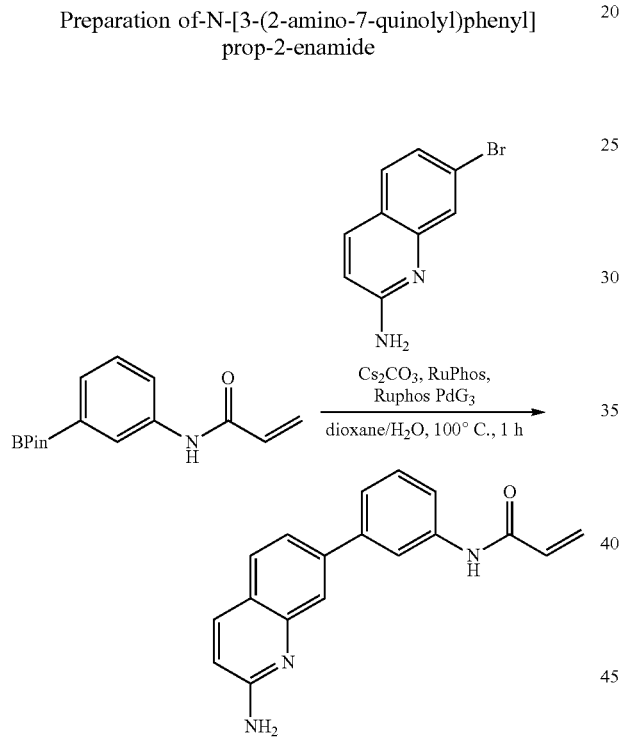

To a solution of N-[3-(4,4,5,5-tetramethyl-1,3,2-dioxaborolan-2-yl)phenyl]prop-2-enamide (60 mg, 219.67 µmol, 1 eq) and 7-bromoquinolin-2-amine (44.1 mg, 197.7 µmol, 0.9 eq) in dioxane (2 mL) and $H_2O$ (0.5 mL) was added $Cs_2CO_3$ (143.2 mg, 439.34 µmol, 2 eq) dicyclohexyl-[2-(2,6-diisopropoxyphenyl)phenyl]phosphane (15.4 mg, 32.95 µmol, 0.15 eq) [2-(2-aminophenyl)phenyl]-methylsulfonyloxy-palladium; dicyclohexyl-[2-(2,6-diisopropoxyphenyl)phenyl]phosphane (18.4 mg, 21.97 µmol, 0.1 eq) under $N_2$. The reaction mixture was stirred at 100° C. for 1 h. LCMS showed that the reaction was complete. The reaction mixture was poured into saturated EDTA (40 mL) and 20 mL EtOAc was added. The solution was stirred for 1 h. After that the aqueous phase was extracted with EtOAc (3×20 mL). The combined organic layer was washed with brine (3×30 mL), dried over anhydrous $Na_2SO_4$, filtered, and concentrated in vacuo to afford a residue. The residue was purified by prep-HPLC (neutral condition) to afford the title compound N-[3-(2-amino-7-quinolyl)phenyl]prop-2-enamide (23.6 mg, 81.57 µmol, 37.13% yield, 100.0% purity) as a white solid. LC-MS (ES+, m/z): 290.1 [(M+H)+], 1H NMR (400 MHz, DMSO-d6) 5=10.27 (s, 1H), 8.09 (s, 1H), 7.91 (d, J=9.2 Hz, 1H), 7.71 (d, J=8.4 Hz, 1H), 7.68 (td, J=2.8, 5.6 Hz, 1H), 7.65 (d, J=1.6 Hz, 1H), 7.46-7.43 (m, 2H), 7.43-7.39 (m, 1H), 6.76 (d, J=8.8 Hz, 1H), 6.52-6.42 (m, 3H), 6.33-6.26 (m, 1H), 5.82-5.77 (m, 1H).

Route 4: General Scheme

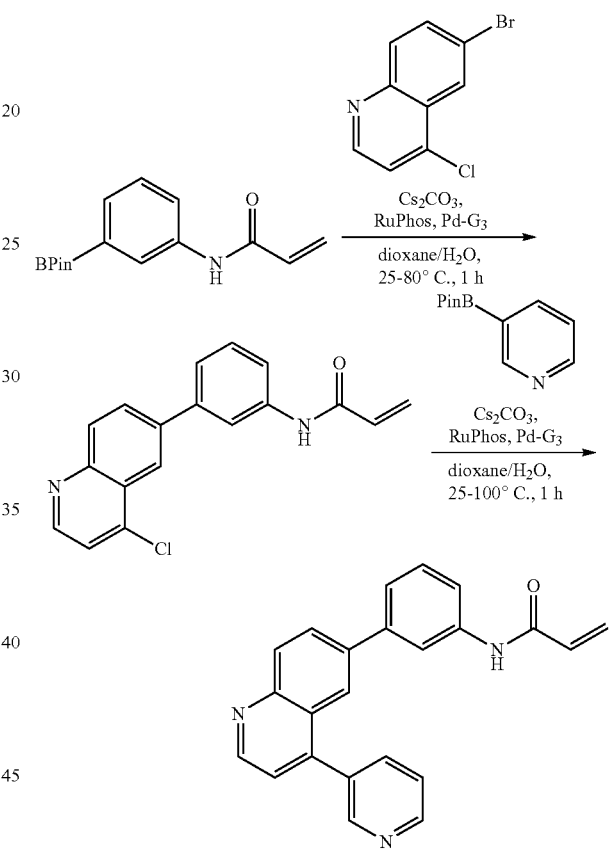

Step 1 N-[3-(4-chloro-6-quinolyl)phenyl]prop-2-enamide

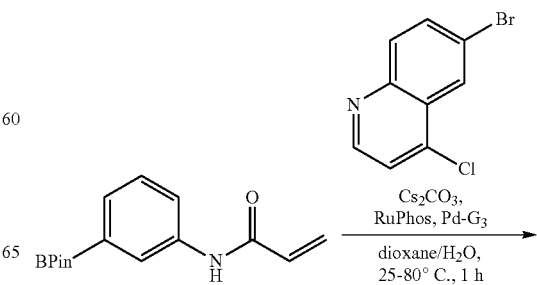

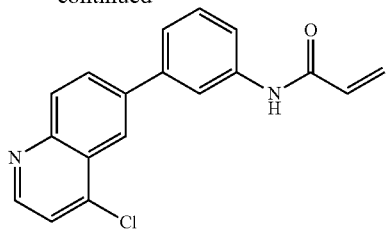

To a solution of 6-bromo-4-chloro-quinoline (0.5 g, 2.06 mmol, 1 eq) and N-[3-(4,4,5,5-tetramethyl-1,3,2-dioxaborolan-2-yl)phenyl]prop-2-enamide (563.2 mg, 2.06 mmol, 1 eq) in dioxane (2 mL) and H$_2$O (0.5 mL) were added Cs$_2$CO$_3$ (2.02 g, 6.19 mmol, 3 eq), RuPhos (96.2 mg, 206.19 μmol, 0.1 eq) and RuPhos Pd G̀b (86.2 mg, 103.09 μmol, 0.05 eq) at 25° C. The reaction was stirred at 80° C. for 1 hr under N$_2$. Upon completion of the reaction as indicated by LCMS, to the reaction was added ~15 mL EtOAc and the mixture was poured into ~30 mL saturated EDTA and stirred at 25° C. for 1 h. The mixture was extracted with EtOAc (3×15 mL). The combined organic phase was washed with brine (3×10 mL), dried over anhydrous Na$_2$SO$_4$, filtered, and concentrated in vacuo. The residue was purified by prep-HPLC (PA condition) to afford the title compound N-[3-(4-chloro-6-quinolyl)phenyl]prop-2-enamide (0.0235 g, 75.27 μmol, 3.65% yield, 98.9% purity) as a white solid. LC-MS (ES$^+$, m/z): 309.0 [(M+H)$^+$], 1H NMR (400 MHz, DMSO-d6) Shift=10.36 (s, 1H), 8.87 (d, J=4.6 Hz, 1H), 8.36 (d, J=1.2 Hz, 1H), 8.24-8.19 (m, 1H), 8.18-8.15 (m, 2H), 7.83 (d, J=4.6 Hz, 1H), 7.79 (d, J=8.0 Hz, 1H), 7.59-7.55 (m, 1H), 7.54-7.48 (m, 1H), 6.54-6.41 (m, 1H), 6.36-6.25 (m, 1H), 5.80 (dd, J=1.6, 10.0 Hz, 1H).

Step 2—N-[3-[4-(3-pyridyl)-6-quinolyl]phenyl]prop-2-enamide

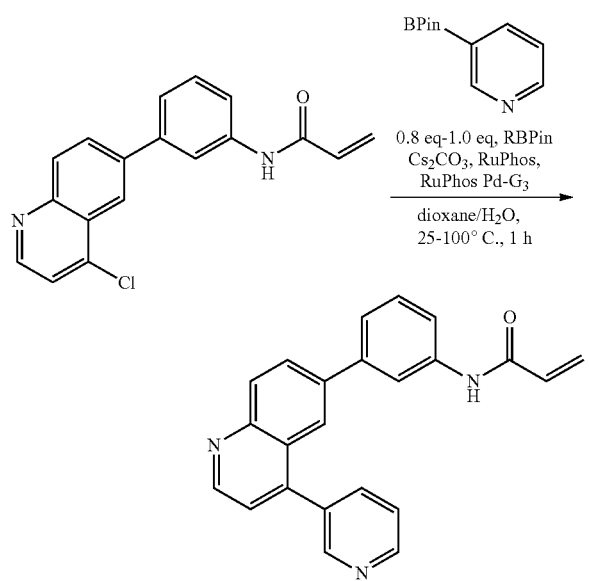

To a solution of N-[3-(4-chloro-6-quinolyl)phenyl]prop-2-enamide (0.14 g, 453.42 μmol, 1 eq) and 3-pyridylboronic acid (55.7 mg, 453.42 μmol, 1 eq) in dioxane (4 mL) and H$_2$O (1 mL) were added Cs$_2$CO$_3$ (443.2 mg, 1.36 mmol, 3 eq), RuPhos (21.2 mg, 45.34 μmol, 0.1 eq) and RuPhos Pd G3 (19 mg, 22.67 μmol, 0.05 eq) at 25° C. Then stirred at 100° C. for 1 hr under N$_2$. The reaction was diluted with 10 mL EtOAc and poured into 20 mL saturated EDTA and stirred at 25° C. for 1 h. The mixture was extracted with EtOAc (3×10 mL), washed with brine (3×10 mL), dried over anhydrous Na$_2$SO$_4$, filtered, and concentrated in vacuo. The residue was purified by prep-HPLC (FA condition) to afford the title compound N-[3-[4-(3-pyridyl)-6-quinolyl]phenyl]prop-2-enamide (0.0253 g, 72 μmol, 15.88% yield, 100.0% purity) as a white solid. LC-MS (ES$^+$, m/z): 352.1 [(M+H)$^+$], 1H NMR (400 MHz, DMSO-d6) Shift=10.26 (s, 1H), 9.01 (d, J=4.4 Hz, 1H), 8.84 (d, J=1.8 Hz, 1H), 8.79-8.75 (m, 1H), 8.25 (d, J=8.4 Hz, 1H), 8.15-8.06 (m, 2H), 7.98-7.90 (m, 2H), 7.75 (d, J=8.0 Hz, 1H), 7.65 (dd, J=5.0, 7.6 Hz, 1H), 7.59 (d, J=4.4 Hz, 1H), 7.48-7.43 (m, 1H), 7.41-7.35 (m, 1H), 6.52-6.39 (m, 1H), 6.36-6.21 (m, 1H), 5.77 (dd, J=1.8, 10.0 Hz, 1H)

Route 5: General Scheme

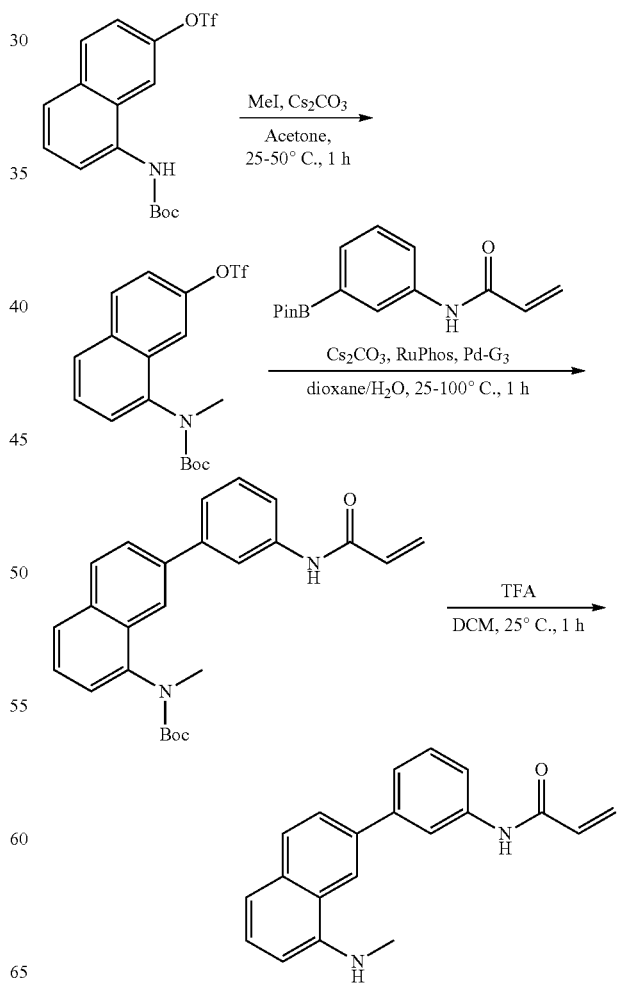

Step 1—[8-[tert-butoxycarbonyl(methyl)amino]-2-naphthyl]trifluoromethanesulfonate

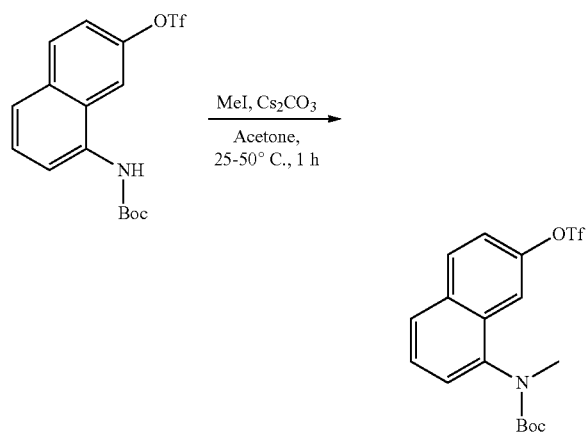

To a solution of [8-(tert-butoxycarbonylamino)-2-naphthyl]trifluoromethanesulfonate (0.8 g, 2.04 mmol, 1 eq) in acetone (8 mL) were added Cs₂CO₃ (2 g, 6.13 mmol, 3 eq) and MeI (435.2 mg, 3.07 mmol, 190.88 μL, 1.5 eq) at 25° C. The reaction was stirred at 50° C. for 1 hr. The reaction was filtered, and concentrated in vacuo. The residue was purified by column chromatography (SiO₂, PE:EtOAc=10:1 to 4:1) to afford the title compound [8-[tert-butoxycarbonyl(methyl)amino]-2-naphthyl]trifluoromethanesulfonate (0.8 g, 1.97 mmol, 96.54% yield) as a white solid. LC-MS (ES⁺, m/z): 350.1[(M-tBu)⁺].

Step 2—Tert-butyl N-methyl-N-[7-[3-(prop-2-enoylamino)phenyl]-1-naphthyl]carbamate

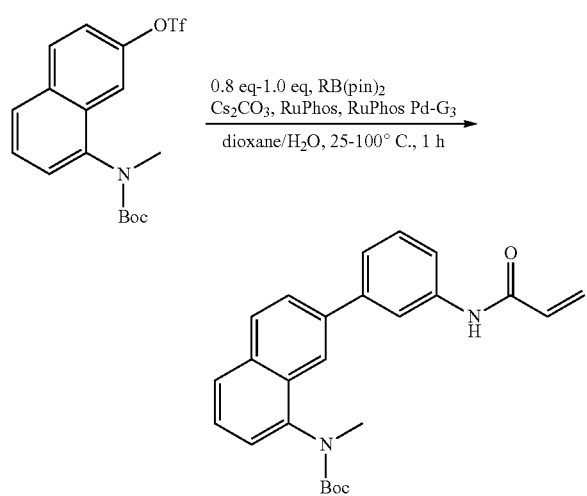 [SMILES: CN(C(=O)OC(C)(C)C)c1cccc2ccc(OS(=O)(=O)C(F)(F)F)cc12 ; C=CC(=O)Nc1cccc(-c2ccc3cccc(N(C)C(=O)OC(C)(C)C)c3c2)c1]

To a solution of [8-[tert-butoxycarbonyl(methyl)amino]-2-naphthyl]trifluoromethanesulfonate (0.3 g, 740.03 μmol, 1 eq) and N-[3-(4,4,5,5-tetramethyl-1,3,2-dioxaborolan-2-yl)phenyl]prop-2-enamide (202.1 mg, 740.03 μmol, 1 eq) in dioxane (2 mL) and H₂O (0.5 mL) were added Cs₂CO₃ (723.4 mg, 2.22 mmol, 3 eq), RuPhos (34.5 mg, 74 μmol, 0.1 eq) and RuPhos Pd G3 (31 mg, 37 μmol, 0.05 eq) at 25° C. The reaction was stirred at 100° C. for 1 hr under N₂. TLC (PE:EtOAc=1:1, SM Rf=0.74, TM Rf=0.33) showed that the reaction was complete. The reaction was diluted with 5 mL EtOAc and poured into ~30 mL saturated EDTA and stirred at 25° C. for 1 h. The aqueous phase was extracted with EtOAc (3×15 mL). The combined organic phase was washed with brine (3×15 mL), dried with anhydrous Na₂SO₄, filtered, and concentrated in vacuo. The residue was purified by prep-TLC (SiO₂, PE;EtOAc=1:1) to afford the title compound Tert-butyl N-methyl-N-[7-[3-(prop-2-enoylamino)phenyl]-1-naphthyl]carbamate (0.28 g, 695.68 μmol, 94.01% yield) as a yellow oil.

Step 3—N-[3-[8-(methylamino)-2-naphthyl]phenyl]prop-2-enamide

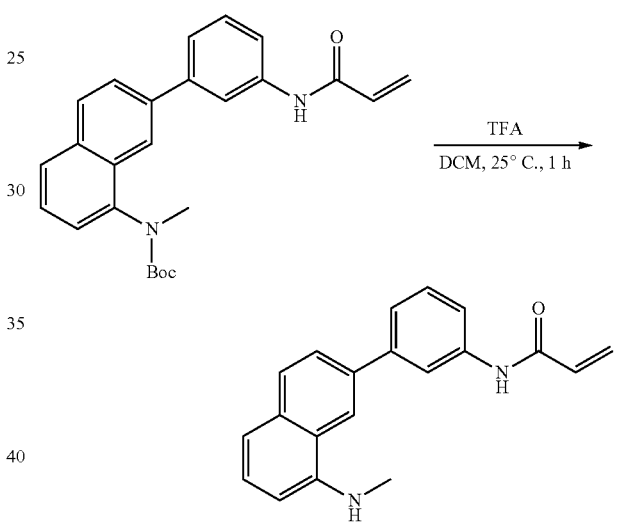

To a solution of tert-butyl N-methyl-N-[7-[3-(prop-2-enoylamino)phenyl]-1-naphthyl]carbamate (0.1 g, 248.46 μmol, 1 eq) in DCM (3 mL) was added TFA (1.08 g, 9.45 mmol, 0.7 mL, 38.05 eq). The reaction was stirred at 25° C. for 1 hr. The reaction was diluted with 10 mL DCM and the mixture was poured into 20 mL ice water. Then the mixture was adjusted to pH=7 with saturated Na₂CO₃, extracted with DCM (3×10 mL), washed with brine (3×20 mL), dried over by anhydrous Na₂SO₄, filtered, and concentrated in vacuo. The residue was purified by prep-HPLC to afford the title compound N-[3-[8-(methylamino)-2-naphthyl]phenyl]prop-2-enamide (0.0394 g, 130.3 μmol, 52.45% yield, 100.0% purity) as a white solid. LC-MS (ES⁺, m/z): 303.1 [(M+H)⁺], 1H NMR (400 MHz, DMSO-d6) Shift=10.26 (s, 1H), 8.37 (s, 1H), 8.05 (s, 1H), 7.85 (d, J=8.6 Hz, 1H), 7.75-7.64 (m, 2H), 7.59-7.52 (m, 1H), 7.50-7.41 (m, 1H), 7.35-7.27 (m, 1H), 7.12 (d, J=8.2 Hz, 1H), 6.54 (br d, J=4.6 Hz, 1H), 6.51-6.46 (m, 1H), 6.45 (s, 1H), 6.29 (dd, J=2.0, 17.0 Hz, 1H), 5.83-5.74 (m, 1H), 2.88 (d, J=4.6 Hz, 3H).

Preparation of N-[3-(7H-pyrrolo[2,3-d]pyrimidin-2-yl)phenyl]prop-2-enamide

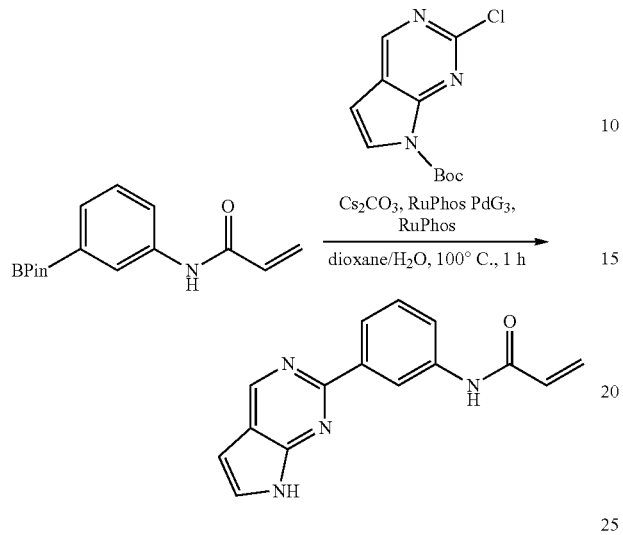

To a solution of N-[3-(4,4,5,5-tetramethyl-1,3,2-dioxaborolan-2-yl)phenyl]prop-2-enamide (200 mg, 732.24 μmol, 1 eq) and tert-butyl 2-chloropyrrolo[2,3-d]pyrimidine-7-carboxylate (185.8 mg, 732.24 μmol, 1 eq) in dioxane (4 mL) and H$_2$O (1 mL) were added Cs$_2$CO$_3$ (477.2 mg, 1.46 mmol, 2 eq) dicyclohexyl-[2-(2,6-diisopropoxyphenyl)phenyl]phosphane (34.2 mg, 73.22 μmol, 0.1 eq) and [2-(2-aminophenyl)phenyl]-methylsulfonyloxy-palladium;dicyclohexyl-[2-(2,6-diisopropoxyphenyl)phenyl]phosphane (49 mg, 58.58 μmol, 0.08 eq) under N$_2$. The reaction mixture was stirred at 100° C. for 1 h under N$_2$. LCMS and TLC showed that the starting material was consumed. The reaction mixture was poured into saturated EDTA (30 mL) and 20 mL of EtOAc was added. The solution was stirred for 1 h. After that the aqueous phase was extracted with EtOAc (3×20 mL). The combined organic layer was washed with brine (3×30 mL), dried over anhydrous Na$_2$SO$_4$, filtered, and concentrated in vacuo to afford a residue. The residue was purified by Prep-TLC (SiO$_2$, PE:EtOAc=1:1) and prep-HPLC to afford the title compound tert-butyl 2-[3-(prop-2-enoylamino)phenyl]pyrrolo[2,3-d]pyrimidine-7-carboxylate (60 mg, 164.66 μmol, 22.49% yield) as a yellow solid. N-[3-(7H-pyrrolo[2,3-d]pyrimidin-2-yl)phenyl]prop-2-enamide (5.2 mg, 100.0% purity) was obtained as a yellow solid. LC-MS (ES$^+$, m/z): 265.1 [(M+H)$^+$], $^1$H NMR (400 MHz, DMSO-d$_6$) δ=12.15 (br s, 1H), 10.31 (s, 1H), 9.10 (s, 1H), 8.76 (t, J=1.7 Hz, 1H), 8.15 (td, 7=1.2, 8.0 Hz, 1H), 7.82 (dd, J=1.1, 8.1 Hz, 1H), 7.59 (dd, J=2.1, 3.4 Hz, 1H), 7.45 (t, J=7.9 Hz, 1H), 6.62 (dd, J=1.2, 3.4 Hz, 1H), 6.53-6.44 (m, 1H), 6.34-6.24 (m, 1H), 5.81-5.75 (m, 1H).

Route 6: General Scheme

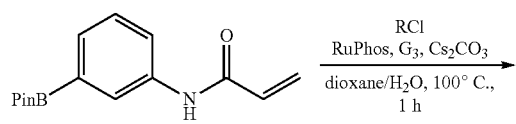

Step 1—N-[3-(5-amino-3-isoquinolyl)phenyl]prop-2-enamide

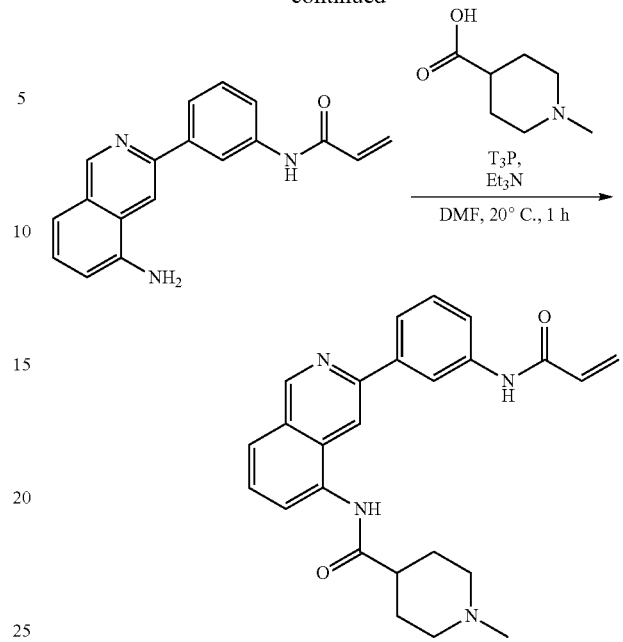

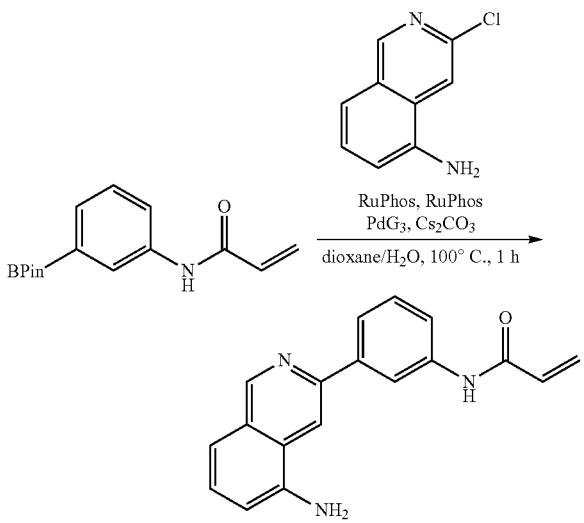

To a solution of N-[3-(4,4,5,5-tetramethyl-1,3,2-dioxaborolan-2-yl)phenyl]prop-2-enamide (50 mg, 183.06 μmol, 1 eq) and 3-chloroisoquinolin-5-amine (32.7 mg, 183.06 μmol, 1 eq) in dioxane (2 mL) and H$_2$O (0.5 mL) were added Cs$_2$CO$_3$ (119.3 mg, 366.12 μmol, 2 eq) dicyclohexyl-[2-(2,6-diisopropoxyphenyl)phenyl]phosphane (12.8 mg, 27.46 μmol, 0.15 eq) and [2-(2-aminophenyl)phenyl]-methylsulfonyloxy-palladium; dicyclohexyl-[2-(2,6-diisopropoxyphenyl)phenyl]phosphane (15.3 mg, 18.31 μmol, 0.1 eq) under N$_2$. The reaction mixture was stirred at 100° C. for 1 h. The reaction mixture was poured into saturated EDTA (40 mL) and 20 mL EtOAc was added. The solution was stirred for 1 h. After that the aqueous phase was extracted with EtOAc (3×20 mL). The combined organic layer was washed with brine (3×30 mL), dried over anhydrous Na₂SO₄ and concentrated in vacuo to give a residue. The residue was purified by prep-HPLC to afford the title compound N-[3-(5-amino-3-isoquinolyl)phenyl]prop-2-enamide (12.3 mg, 42.51 µmol, 23.22% yield) as a white solid. LC-MS (ES⁺, m/z): 290.1 [(M+H)⁺] 1H NMR (400 MHz, DMSO-d6) Shift=10.31 (s, 1H), 9.19 (s, 1H), 8.53 (s, 1H), 8.49 (t, J=2.0 Hz, 1H), 7.93 (d, J=8.4 Hz, 1H), 7.87-7.81 (m, 1H), 7.46 (t, J=8.0 Hz, 1H), 7.40-7.32 (m, 1H), 7.25 (d, J=8.0 Hz, 1H), 6.87 (dd, J=0.8, 7.6 Hz, 1H), 6.55-6.44 (m, 1H), 6.29 (dd, J=2.0, 17.2 Hz, 1H), 6.15 (s, 2H), 5.81-5.74 (m, 1H).

Step 2—1-methyl-N-[3-[3-(prop-2-enoylamino)phenyl]-5-isoquinolyl]piperidine-4-carboxamide

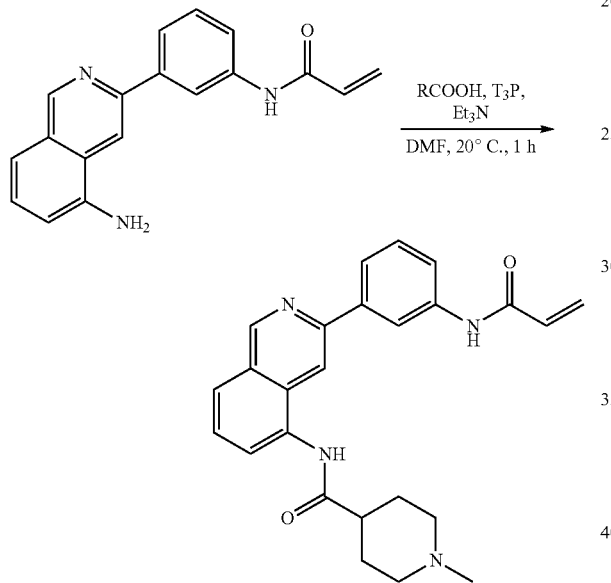

To a solution of N-[3-(5-amino-3-isoquinolyl)phenyl]prop-2-enamide (50 mg, 172.81 µmol, 1 eq) and 1-methylpiperidine-4-carboxylic acid (29.7 mg, 207.37 µmol, 1.2 eq) in DMF (1.5 mL) were added T₃P (82.5 mg, 259.22 µmol, 77.08 µL, 1.5 eq) and Et₃N (87.4 mg, 864.06 µmol, 120.27 µL, 5 eq) under N₂. The reaction mixture was stirred at 20° C. for 1 h. The reaction mixture was poured into 40 mL water and extracted with EtOAc (3×20 mL). The combined organic layer was washed with brine (3×20 mL), dried over anhydrous Na₂SO₄, filtered, and concentrated in vacuo to afford a residue. The residue was purified by prep-HPLC to afford the title compound 1-methyl-N-[3-[3-(prop-2-enoylamino)phenyl]-5-isoquinolyl]piperidine-4-carboxamide (19.8 mg, 47.77 µmol, 27.64% yield, 100.0% purity) as a white solid. LC-MS (ES⁺, m/z): 415.3 [(M+H)⁺] 1H NMR (400 MHz, DMSO-d6) 5=10.35 (s, 1H), 10.08 (s, 1H), 9.41 (s, 1H), 8.58 (s, 1H), 8.42 (s, 1H), 8.03 (d, J=7.5 Hz, 1H), 7.96 (d, J=8.2 Hz, 1H), 7.91 (d, J=8.2 Hz, 1H), 7.81 (br d, J=9.3 Hz, 1H), 7.65 (t, J=7.8 Hz, 1H), 7.51 (t, J=7.8 Hz, 1H), 6.54-6.44 (m, 1H), 6.30 (dd, J=2.0, 17.0 Hz, 1H), 5.82-5.77 (m, 1H), 2.87 (br d, J=11.0 Hz, 2H), 2.69-2.56 (m, 1H), 2.19 (s, 3H), 1.99-1.87 (m, 4H), 1.81-1.71 (m, 1H), 1.72-1.69 (m, 1H)

Preparation of-N-[3-[5-[(1-methyl-4-piperidyl)amino]-3-isoquinolyl]phenyl]prop-2-enamide

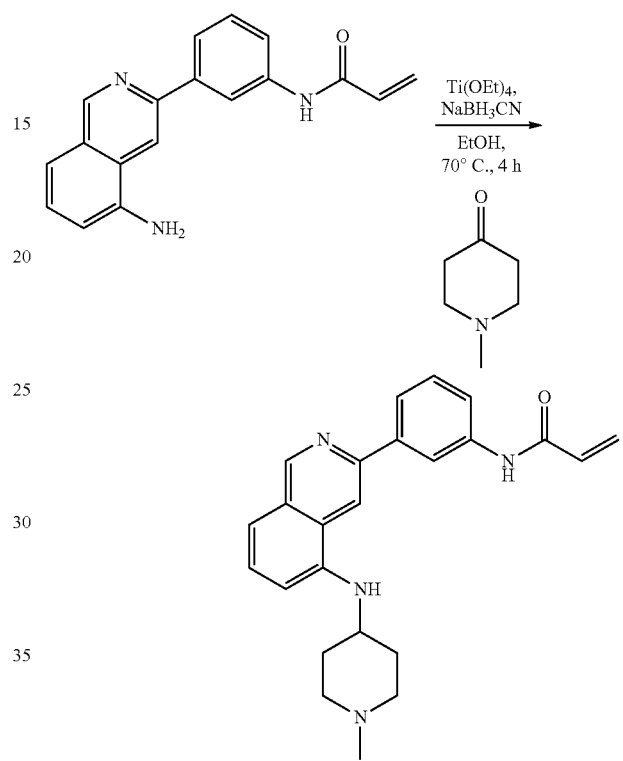

To a solution of N-[3-(5-amino-3-isoquinolyl)phenyl]prop-2-enamide (60 mg, 207.38 µmol, 1 eq) and 1-methylpiperidin-4-one (70.4 mg, 622.14 µmol, 72.35 µL, 3 eq) in EtOH (2 mL) was added Ti(OEt)₄ (236.5 mg, 1.04 mmol, 215.02 µL, 5 eq) under N₂. The reaction mixture was stirred at 70° C. for 1 hour. Then NaBH₃CN (65.2 mg, 1.04 mmol, 5 eq) was added at 70° C. The resulting reaction mixture was stirred at 70° C. for further 3 hours. The reaction mixture was poured into 40 mL saturated Na₂CO₃ and 20 mL EtOAc was added. The solution was stirred at 20° C. for 30 mins. The insoluble substance was removed by filtration. The filtrate was extracted with EtOAc (3×20 mL). The combined organic layer was washed with brine (2×20 mL), dried over anhydrous Na₂SO₄, filtered, and concentrated in vacuo to afford a residue. The residue was purified by prep-HPLC to afford the title compound N-[3-[5-[(1-methyl-4-piperidyl)amino]-3-isoquinolyl]phenyl]prop-2-enamide (5.1 mg, 12.68 µmol, 6.11% yield, 96.1% purity) as a white solid. LC-MS (ES⁺, m/z): 387.2 [(M+H)⁺], ¹H NMR (400 MHz, DMSO-d₆) δ=10.31 (br s, 1H), 9.19 (s, 1H), 8.61 (s, 1H), 8.45 (br s, 1H), 7.97 (br s, 1H), 7.88 (br d, 7=6.8 Hz, 1H), 7.52-7.36 (m, 2H), 7.25 (br d, 7=7.6 Hz, 1H), 6.78 (br d, 7=7.2 Hz, 1H), 6.57-6.42 (m, 1H), 6.29 (br d, 7=11.6 Hz, 2H), 5.78 (br d, 7=9.2 Hz, 1H), 3.42 (br s, 1H), 2.83 (br s, 2H), 2.21 (br s, 3H), 2.03 (br s, 4H), 1.64 (br d, 7=10.0 Hz, 2H)

581
Route 7: General Scheme

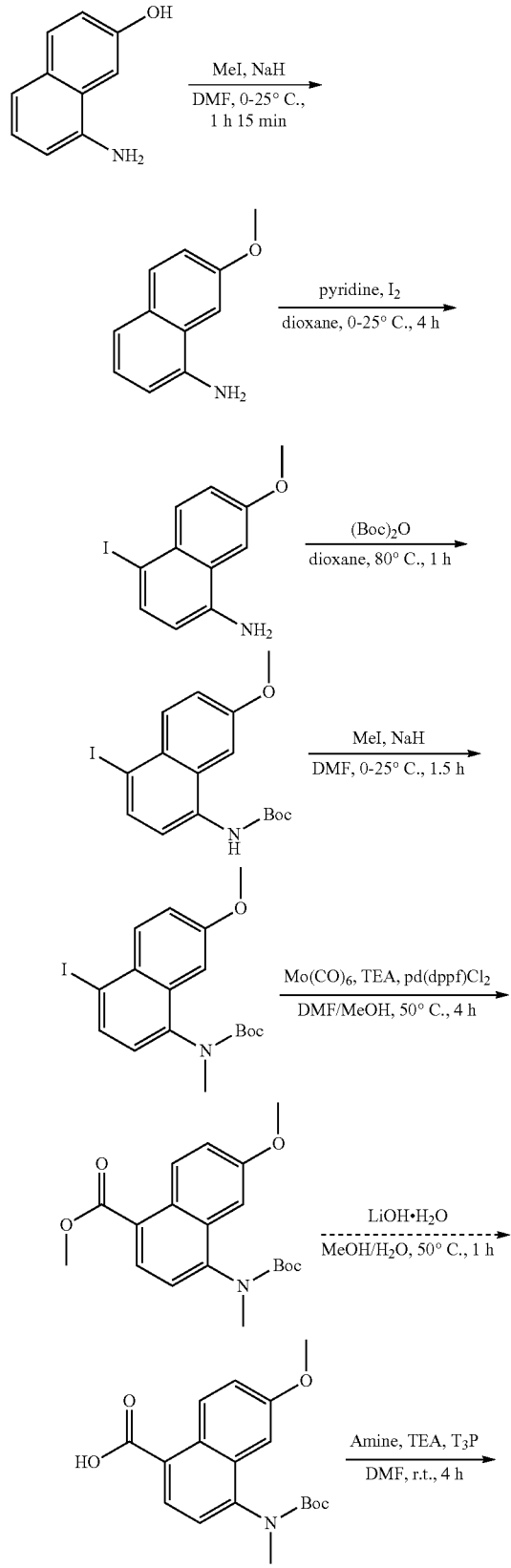

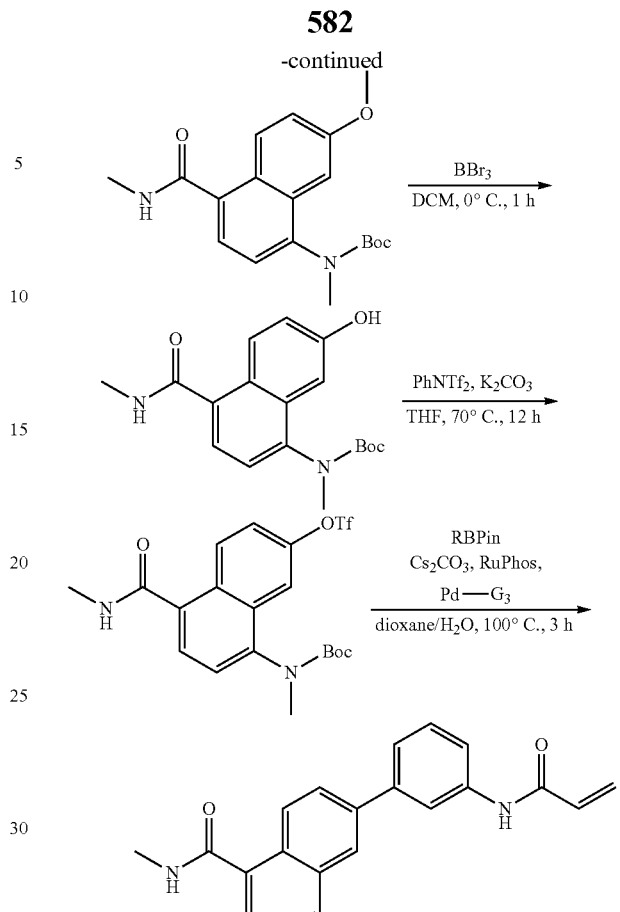

Step 1—7-Methoxynaphthalen-1-amine

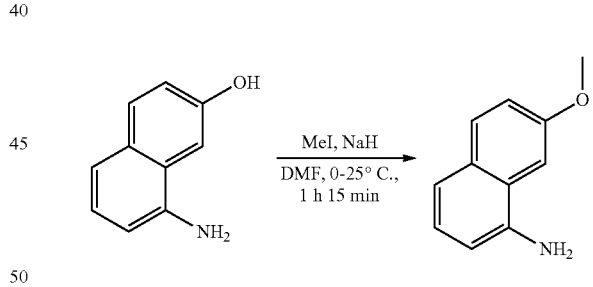

To a cold (0° C.) suspension of NaH (4.52 g, 113.08 mmol, 60% purity, 1.2 eq) in DMF (225 mL) was added 8-aminonaphthalen-2-ol (15 g, 94.23 mmol, 1 eq) in portions. The reaction was warmed to 25° C. and stirred for 15 min. Then the mixture was cooled to 0° C. MeI (13.37 g, 94.23 mmol, 5.87 mL, 1 eq) was added and the solution was warmed to 25° C. and stirred for 1 hr. TLC (PE:EtOAc=1:1, SM Rf=0.21, TM Rf=0.54) showed that the reaction was complete. The reaction was poured into ~500 mL saturated NH₄Cl slowly. Then, the mixture was extracted with EtOAc (3×300 mL), washed with brine (3×500 mL), dried over anhydrous Na₂SO₄, filtered, and concentrated in vacuo. The residue was purified by column chromatography (SiO₂, PE:EtOAc=10:1 to 4:1) to afford the title compound 7-Methoxynaphthalen-1-amine (1 g, 57.73 mmol, 61.27% yield) as a brown solid. 1H NMR (400 MHz, DMSO-d6)

=7.65 (d, J=8.9 Hz, 1H), 7.42 (s, 1H), 7.13-6.82 (m, 3H), 6.72-6.60 (m, 1H), 5.57 (br s, 2H), 3.88 (s, 3H).

Step 2—4-Iodo-7-methoxy-naphthalen-1-amine

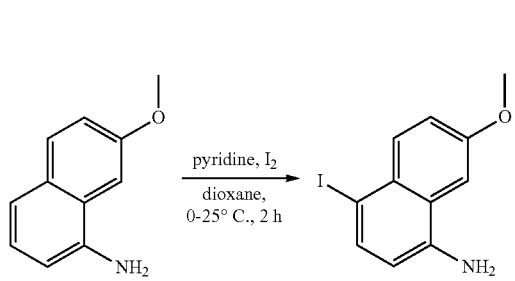

To a solution of 7-methoxynaphthalen-1-amine (5 g, 28.87 mmol, 1 eq) in dioxane (50 mL) was added pyridine (49 g, 619.47 mmol, 50 mL, 21.46 eq), $I_2$ (8.79 g, 34.64 mmol, 6.98 mL, 1.2 eq) at 0° C. Then the mixture was stirred at 25° C. for 2 hr. The reaction was poured into ~150 mL water and extracted with EtOAc (3×100 mL). The combined organic phase was washed with water (3×200 mL), dried over anhydrous $Na_2SO_4$, filtered, and concentrated in vacuo. The residue was purified by column chromatography ($SiO_2$, PE:EtOAc=10:1 to 4:1) to afford the title compound 4-iodo-7-methoxy-naphthalen-1-amine (5 g, 16.72 mmol, 57.91% yield) as a brown solid. LC-MS (ES$^+$, m/z): 300.0 [(M+H)$^+$], 1H NMR (400 MHz, DMSO-d6)=7.76 (d, J=9.2 Hz, 1H), 7.58 (d, J=8.0 Hz, 1H), 7.43 (d, J=2.4 Hz, 1H), 7.20 (dd, J=2.5, 9.2 Hz, 1H), 6.48 (d, J=8.0 Hz, 1H), 5.85 (br s, 2H), 3.94-3.83 (m, 3H)

Step 3—Tert-butyl N-(4-iodo-7-methoxy-1-naphthyl) carbamate

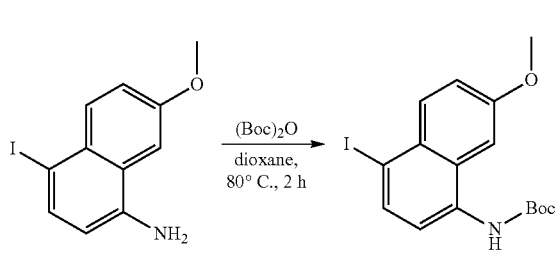 [SMILES: "(Boc)2O" ; COc1ccc2c(I)ccc(N)c2c1 ; COc1ccc2c(I)ccc(NC(=O)OC(C)(C)C)c2c1]

To a solution of 4-iodo-7-methoxy-naphthalen-1-amine (5 g, 16.72 mmol, 1 eq) in dioxane (50 mL) was added $Boc_2O$ (18.24 g, 83.58 mmol, 19.20 mL, 5 eq) and the mixture was stirred at 80° C. for 2 hr. LCMS showed that the reaction was complete. The reaction was poured into ~200 mL water and extracted with EtOAc (3×200 mL). The combined organic phase was washed with brine (3×300 mL), dried over by anhydrous $Na_2SO_4$, filtered, and concentrated in vacuo. The residue was purified by column chromatography ($SiO_2$, PE:EtOAc=10:1 to 4:1) to afford the title compound Tert-butyl N-(4-iodo-7-methoxy-1-naphthyl) carbamate (5.6 g, 14.03 mmol, 83.91% yield) as a brown solid. LC-MS (ES$^+$, m/z): 344.2 [(M-tBu)$^+$]. 1H NMR (400 MHz, DMSO-d6)= 9.33 (s, 1H), 7.99-7.84 (m, 2H), 7.41 (d, J=2.4 Hz, 1H), 7.38 (d, J=8.2 Hz, 1H), 7.29 (dd, J=2.5, 9.2 Hz, 1H), 3.92 (s, 3H), 1.51 (s, 9H).

Step 4—Tert-butyl N-(4-iodo-7-methoxy-1-naphthyl)-N-methyl-carbamate

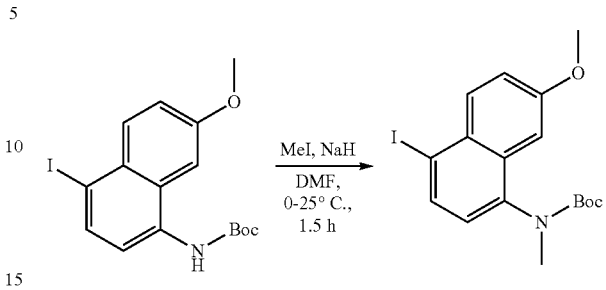

To a solution of tert-butyl N-(4-iodo-7-methoxy-1-naphthyl) carbamate (4.5 g, 11.27 mmol, 1 eq) in DMF (40 mL) was added NaH (676.3 mg, 16.91 mmol, 60% purity, 1.5 eq) at 0° C. Then the mixture was stirred at 0° C. for 30 min. $CH_3I$ (3.2 g, 22.54 mmol, 1.40 mL, 2 eq) was added to the solution at 0° C. Then the mixture was stirred at 25° C. for 1 hr. LCMS showed that the reaction was complete. The reaction was poured into ~100 mL saturated $NH_4Cl$ and extracted with EtOAc (3×100 mL). The combined organic phase was washed with brine (3×200 mL), dried over anhydrous $Na_2SO_4$, filtered, and concentrated in vacuo. The residue was purified by column chromatography ($SiO_2$, PE:EtOAc=10:1 to 4:1) to afford the title compound Tert-butyl N-(4-iodo-7-methoxy-1-naphthyl)-N-methyl-carbamate (4.5 g, 10.89 mmol, 96.61% yield) as a brown solid. LC-MS (ES$^+$, m/z): 358.0 [(M-tBu)$^+$]

Step 5—Methyl 4-[tert-butoxycarbonyl(methyl)amino]-6-methoxy-naphthalene-1-carboxylate

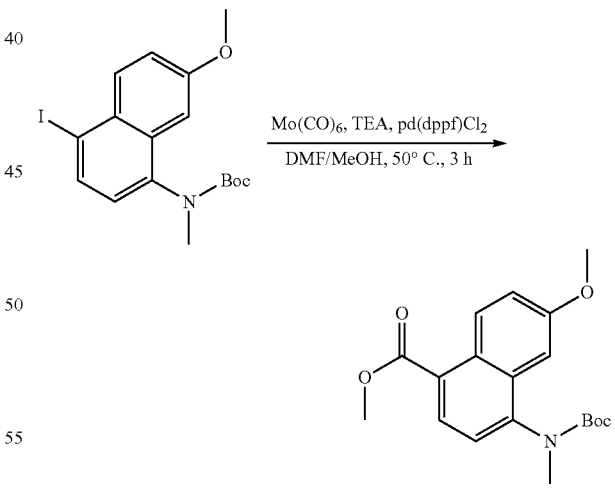

To a solution of tert-butyl N-(4-iodo-7-methoxy-1-naphthyl)-N-methyl-carbamate (3.5 g, 8.47 mmol, 1 eq) and $Mo(CO)_6$ (447.2 mg, 1.69 mmol, 228.16 μL, 0.2 eq) in DMSO (35 mL) and MeOH (35 mL) was added TEA (2.57 g, 25.41 mmol, 3.54 mL, 3 eq) and Pd (dppf) $Cl_2$ (619.7 mg, 846.95 μmol, 0.1 eq). Then the mixture was stirred at 50° C. for 3 hr under $N_2$. TLC (PE:EtOAc=4:1, SM Rf=0.36, TM Rf=0.41) showed that the reaction was complete. The reaction was poured into ~200 mL water and extracted with EtOAc (3×200 mL). The combined organic phase was washed with brine (3×300 mL), dried over anhydrous Na$_2$SO$_4$, filtered, and concentrated in vacuo. The residue was purified by column chromatography (SiO$_2$, PE:EtOAc=10:1 to 4:1) to afford the title compound Methyl 4-[tert-butoxycarbonyl(methyl)amino]-6-methoxy-naphthalene-1-carboxylate (3. g, 6.95 mmol, 82.04% yield, 80% purity) as a yellow solid.

Step 6—4-[Tert-butoxycarbonyl(methyl)amino]-6-methoxy-naphthalene-1-carboxylic acid

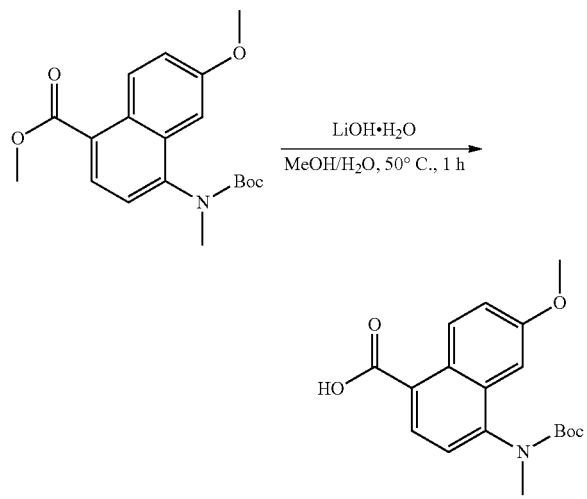

To a solution of methyl 4-[tert-butoxycarbonyl(methyl)amino]-6-methoxy-naphthalene-1-carboxylate (1.3 g, 3.76 mmol, 1 eq) in H$_2$O (16 mL) and MeOH (32 mL) was added LiOH·H$_2$O (1.58 g, 37.64 mmol, 10 eq), and the mixture was stirred at 50° C. for 1 hr. The reaction was poured into ~30 mL ice-water, adjusted to pH=8 with saturated citric acid. The mixture was extracted with EtOAc (3×100 mL), washed with brine (3×200 mL), dried over anhydrous Na$_2$SO$_4$, filtered, and concentrated in vacuo to afford the title compound 4-[Tert-butoxycarbonyl(methyl)amino]-6-methoxy-naphthalene-1-carboxylic acid (1 g, crude) as a yellow solid, which was used directly without further purification. LC-MS (ES$^+$, m/z): 276.2 [(M-tBu)$^+$].

Step 7—Tert-butyl N-[7-methoxy-4-(methylcarbamoyl)-1-naphthyl]-N-methyl-carbamate

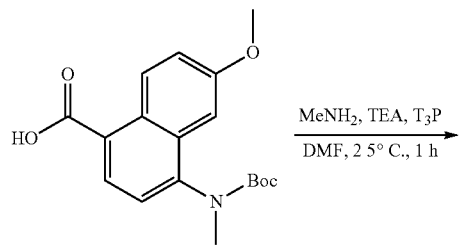

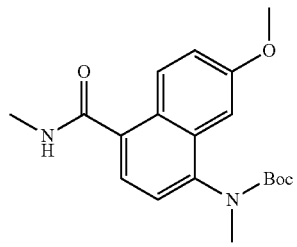

To a solution of 4-[tert-butoxycarbonyl(methyl)amino]-6-methoxy-naphthalene-1-carboxylic acid (0.4 g, 1.21 mmol, 1 eq) and methanamine; hydrochloride (163 mg, 2.41 mmol, 2 eq) in DMF (6 mL) were added TEA (610.8 mg, 6.04 mmol, 840.09 µL, 5 eq) and T$_3$P (1.15 g, 1.81 mmol, 1.08 mL, 50% purity, 1.5 eq). The mixture was stirred at 25° C. for 1 hr. The reaction mixture was quenched by adding 10 mL water and extracted with EtOAc (3×10 mL). The combined organic layers were washed with brine (3×20 mL), dried over anhydrous Na$_2$SO$_4$, filtered, and concentrated in vacuo to give a residue. The residue was purified by column chromatography (SiO$_2$, DCM/MeOH=1/0 to 10:1) to afford the title compound Tert-butyl N-[7-methoxy-4-(methylcarbamoyl)-1-naphthyl]-N-methyl-carbamate (0.8 g, 2.32 mmol, 96.21% yield) as a yellow oil. LC-MS (ES$^+$, m/z): 288.9 [(M-tBu)$^+$].

Step 8—Tert-butyl N-[7-hydroxy-4-(methylcarbamoyl)-1-naphthyl]-N-methyl-carbamate

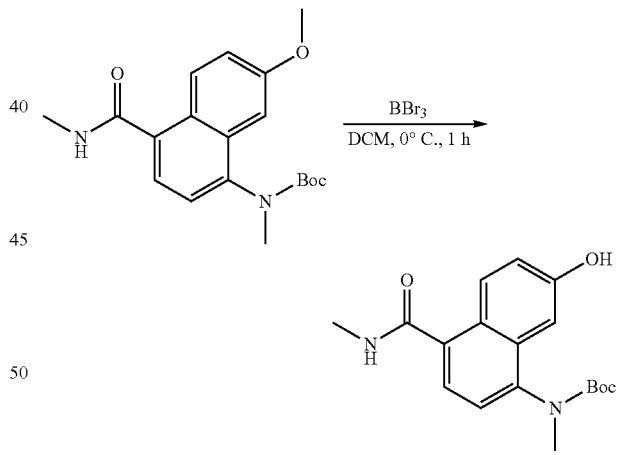

To a solution of tert-butyl N-[7-methoxy-4-(methylcarbamoyl)-1-naphthyl]-N-methyl-carbamate (0.5 g, 1.45 mmol, 1 eq) in DCM (5 mL) was added BBr$_3$ (1.49 g, 5.95 mmol, 573.08 µL, 4.10 eq) at 0° C. The mixture was stirred at 0° C. for 1 hr. LCMS showed that the reaction was complete. To the reaction was added ~3 mL MeOH at 0° C. Then concentrated under N$_2$. The residue was purified by column chromatography (SiO$_2$, DCM/MeOH=20/1 to 10:1) to afford the title compound Tert-butyl N-[7-hydroxy-4-(methylcarbamoyl)-1-naphthyl]-N-methyl-carbamate (0.35 g, 741.58 µmol, 51.08% yield, 70% purity) as a yellow solid. LC-MS (ES$^+$, m/z): 231.3[(M-tBu)$^+$].

Step 9. [8-(Methylamino)-5-(methylcarbamoyl)-2-naphthyl]trifluoromethanesulfonate

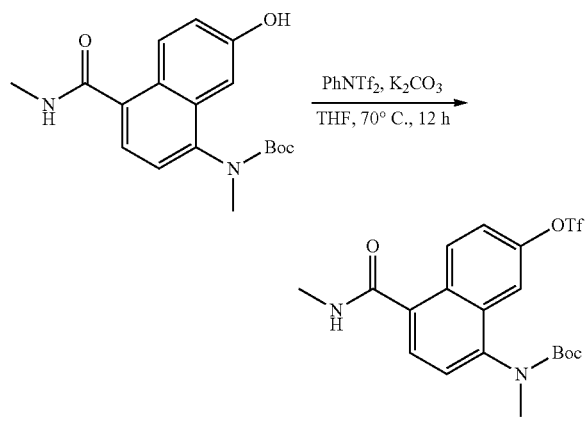

To a solution of 6-hydroxy-N-methyl-4-(methylamino)naphthalene-1-carboxamide (0.13 g, 564.57 µmol, 1 eq) in THF (3 mL) were added 1,1,1-trifluoro-N-phenyl-N-(trifluoromethylsulfonyl) methanesulfonamide (403.4 mg, 1.13 mmol, 2 eq) and $K_2CO_3$ (390 mg, 2.82 mmol, 5 eq) and the mixture was stirred at 70° C. for 12 hr. LCMS showed that the reaction was complete. The reaction was filtered, and concentrated in vacuo. The residue was purified by prep-TLC ($SiO_2$, DCM:MeOH=10:1) to afford the title compound [8-(Methylamino)-5-(methylcarbamoyl)-2-naphthyl]trifluoromethanesulfonate (0.1 g, 276 µmol, 48.89% yield) as a brown solid. LC-MS ($ES^+$, m/z): 363.2 [$(M+H)^+$]

Step 10-N-methyl-4-(methylamino)-6-[3-(prop-2-enoylamino)phenyl]naphthalene-1-carboxamide

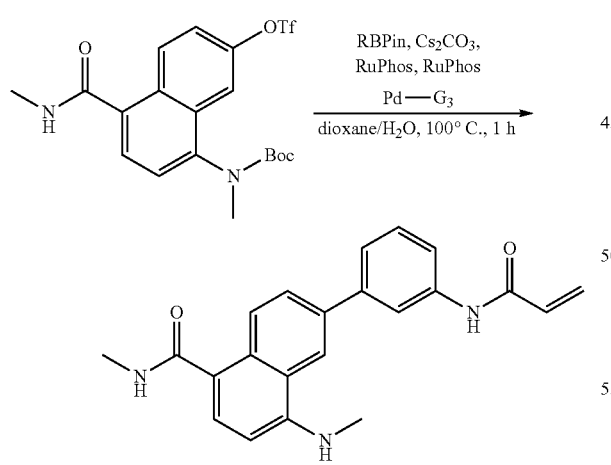

To a solution of [8-(methylamino)-5-(methylcarbamoyl)-2-naphthyl]trifluoro methane sulfonate (0.09 g, 248.4 µmol, 1 eq) and N-[3-(4,4,5,5-tetramethyl-1,3,2-dioxaborolan-2-yl)phenyl]prop-2-enamide (101.8 mg, 372.6 µmol, 1.5 eq) in dioxane (2 mL) and $H_2O$ (0.5 mL) were added $Cs_2CO_3$ (242.8 mg, 745.19 µmol, 3 eq), RuPhos (11.6 mg, 24.84 µmol, 0.1 eq) and RuPhos Pd G3 (2.1 mg, 2.48 µmol, 0.01 eq). Then the mixture was stirred at 100° C. for 1 h under $N_2$. LCMS showed that the reaction was complete. The reaction was diluted with 10 mL EtOAc and the mixture was poured into ~20 mL saturated EDTA. The mixture was stirred at 25° C. for 1 h and extracted with EtOAc (3×20 mL). The combined organic phase was washed with brine (3×40 mL), dried over anhydrous $Na_2SO_4$, filtered, and concentrated in vacuo. The residue was purified by prep-HPLC (FA condition) to afford the title compound N-methyl-4-(methylamino)-6-[3-(prop-2-enoylamino)phenyl]naphthalene-1-carboxamide (0.0115 g, 32 µmol, 12.88% yield, 100.0% purity) as a white solid. LC-MS ($ES^+$, m/z): 360.1 [$(M+H)^+$], 1H NMR (400 MHz, DMSO-d6)=10.28 (s, 1H), 8.56-8.51 (m, 1H), 8.40 (d, J=1.3 Hz, 1H), 8.12 (br d, J=4.6 Hz, 1H), 8.03 (s, 1H), 7.74 (br d, J=8.8 Hz, 2H), 7.57 (d, J=7.9 Hz, 1H), 7.54 (d, J=8.2 Hz, 1H), 7.50-7.43 (m, 1H), 6.93 (br d, J=4.6 Hz, 1H), 6.53-6.45 (m, 1H), 6.42 (d, J=8.2 Hz, 1H), 6.29 (dd, J=2.0, 17.0 Hz, 1H), 5.83-5.74 (m, 1H), 2.91 (d, J=4.6 Hz, 3H), 2.81 (d, J=4.4 Hz, 3H)

Route 8: General Scheme

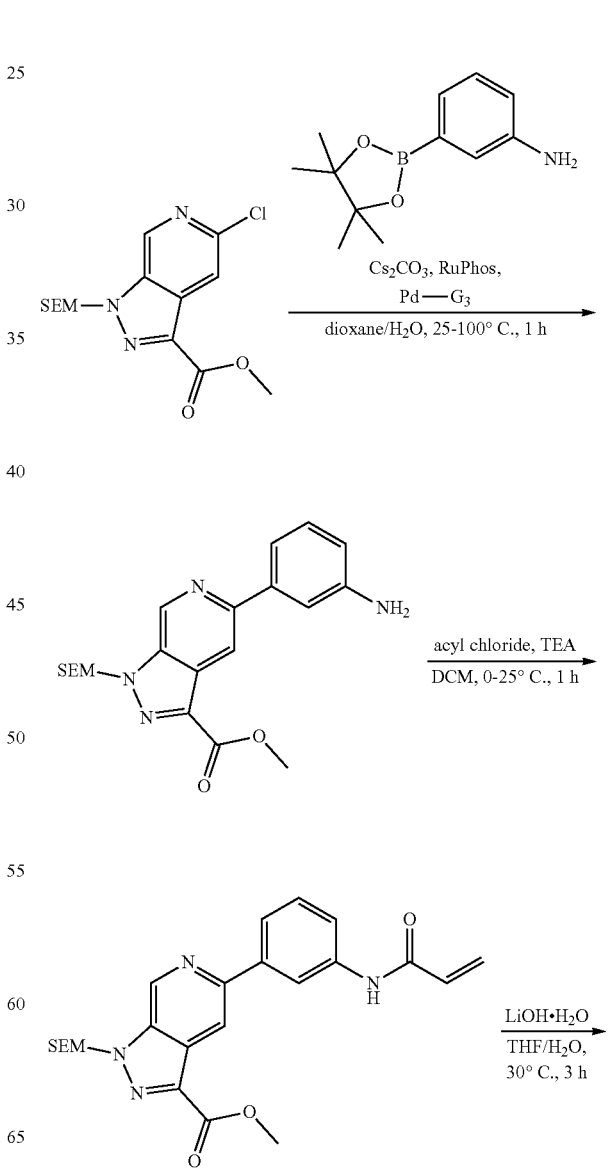

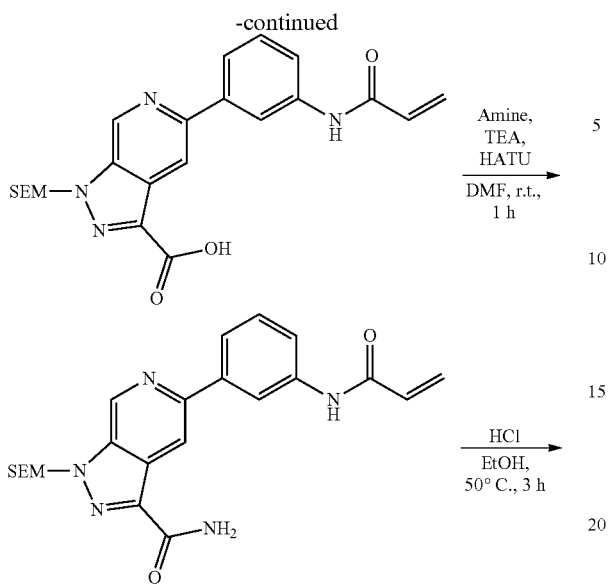

Step 1—Methyl 5-(3-aminophenyl)-1-(2-trimethylsilylethoxymethyl)pyrazolo[3,4-c]pyridine-3-carboxylate

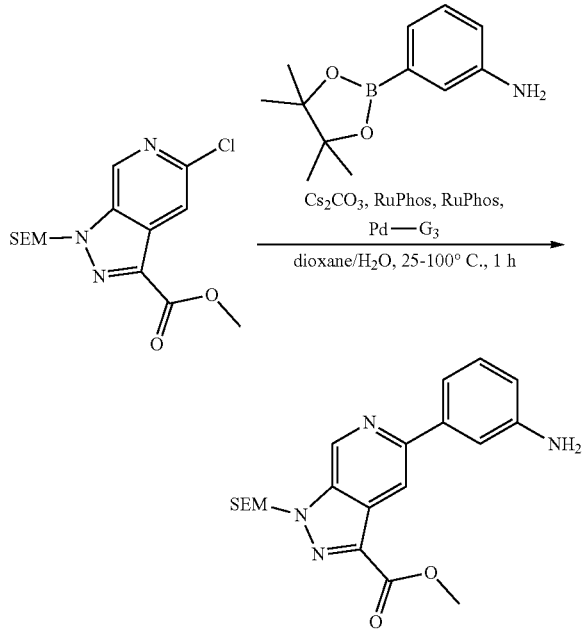

To a solution of methyl 5-chloro-1-(2-trimethylsilylethoxymethyl)pyrazolo[3,4-c]pyridine-3-carboxylate (0.8 g, 2.34 mmol, 1 eq) and 3-(4,4,5,5-tetramethyl-1,3,2-dioxaborolan-2-yl)aniline (564 mg, 2.57 mmol, 1.1 eq) in dioxane (8 mL) and H$_2$O (2 mL) were added Cs$_2$CO$_3$ (2.29 g, 7.02 mmol, 3 eq), RuPhos (109.2 mg, 234.01 µmol, 0.1 eq) and RuPhos Pd-G$_b$ (97.9 mg, 117.01 µmol, 0.05 eq) at 25° C. then stirred at 100° C. for 1 h under N$_2$. TLC (PE:EtOAc=1:1, SM Rf=0.54, TM Rf=0.28) showed that the reaction was complete. The reaction was diluted with 10 mL EtOAc. Then the mixture was poured into 50 mL saturated EDTA. The mixture was stirred at 25° C. for 1 h. The mixture was extracted with EtOAc (3×30 mL), washed with brine (3×30 mL), dried over by anhydrous Na$_2$SO$_4$, filtered, and concentrated in vacuo. The residue was purified by column chromatography (SiO$_2$, PE:EtOAc=10:1 to 4:1) to afford the title compound Methyl 5-(3-aminophenyl)-1-(2-trimethylsilylethoxymethyl)pyrazolo[3,4-c]pyridine-3-carboxylate (0.84 g, 2.11 mmol, 90.07% yield) as a yellow solid.

Step 2—Methyl 5-[3-(prop-2-enoylamino)phenyl]-1-(2-trimethylsilylethoxy methyl)pyrazolo[3,4-c]pyridine-3-carboxylate

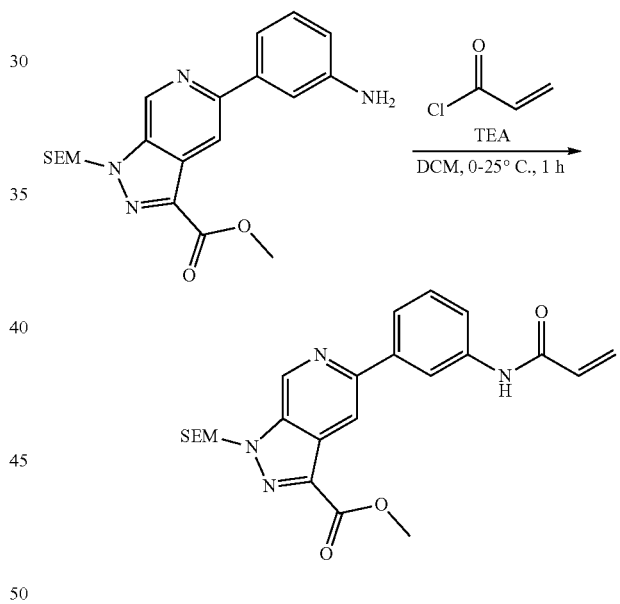

To a solution of prop-2-enoyl chloride (122.6 mg, 1.35 mmol, 110.48 µL, 2 eq) in DCM (3 mL) were added TEA (205.7 mg, 2.03 mmol, 282.89 µL, 3 eq) and methyl 5-(3-aminophenyl)-1-(2-trimethylsilylethoxymethyl)pyrazolo[3,4-c]pyridine-3-carboxylate (0.27 g, 677.49 µmol, 1 eq) at 0° C. Then the mixture was stirred at 25° C. for 1 hr. The reaction was diluted with 10 mL DCM and the mixture was poured into ~10 mL water. Then the mixture was extracted with DCM (3×10 mL), washed with brine (3×10 mL), dried over anhydrous Na$_2$SO$_4$, filtered, and concentrated in vacuo. The residue was purified by prep-TLC (SiO$_2$, PE:EtOAc=1:1) to afford the title compound Methyl 5-[3-(prop-2-enoylamino)phenyl]-1-(2-trimethylsilylethoxy methyl)pyrazolo[3,4-c]pyridine-3-carboxylate (0.21 g, 464.01 µmol, 68.49% yield) as a yellow oil. LC-MS (ES$^+$, m/z): 453.2 [(M+H)$^+$].

Step 3—5-[3-(prop-2-enoylamino)phenyl]-1-(2-trimethylsilylethoxymethyl) pyrazolo[3,4-c]pyridine-3-carboxylic acid

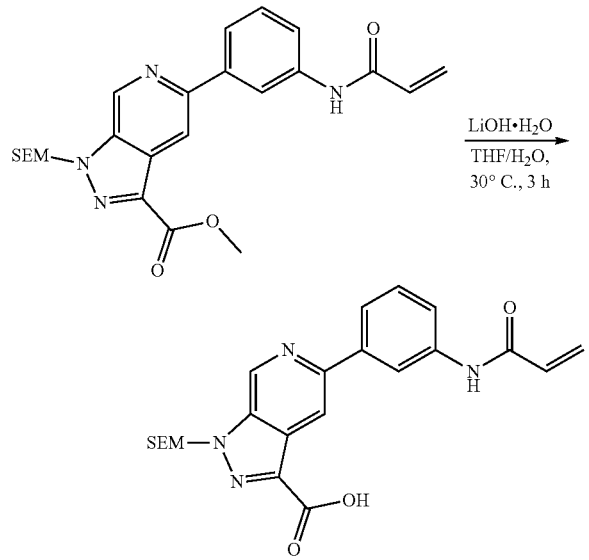

To a solution of methyl 5-[3-(prop-2-enoylamino)phenyl]-1-(2-trimethylsilylethoxymethyl) pyrazolo[3,4-c]pyridine-3-carboxylate (0.15 g, 331.44 µmol, 1 eq) in THF (4 mL) and H₂O (1 mL) was added LiOH·H₂O (139.1 mg, 3.31 mmol, 10 eq) and stirred at 30° C. for 3 hr. The reaction was poured into ~20 mL ice water then the aqueous phase was adjusted to pH=6 with saturated citric acid. The reaction mixture was extracted with EtOAc (3×30 mL). The combined organic phase was washed with brine (3×30 mL), dried over anhydrous Na₂SO₄, filtered, and concentrated in vacuo to afford the title compound 5-[3-(prop-2-enoyl amino)phenyl]-1-(2-trimethylsilylethoxymethyl)pyrazolo[3,4-c]pyridine-3-carboxylic acid (0.2 g, crude) as a yellow solid. LC-MS (ES⁺, m/z): 439.2 [(M+H)⁺].

Step 4—5-[3-(prop-2-enoylamino)phenyl]-1-(2-trimethylsilylethoxymethyl)pyrazolo[3,4-c]pyridine-3-carboxamide

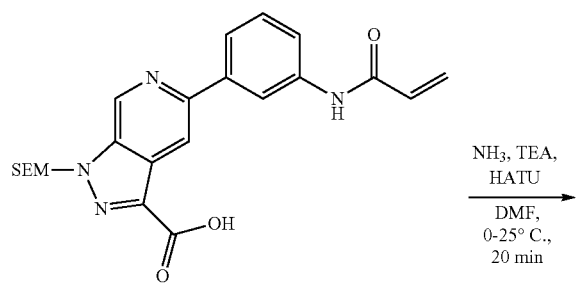

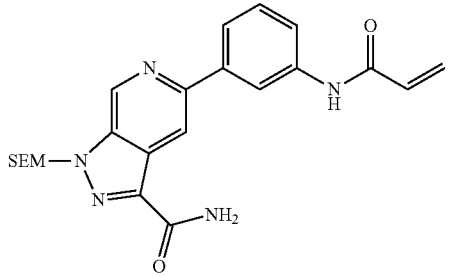

To a solution of 5-[3-(prop-2-enoylamino)phenyl]-1-(2-trimethylsilylethoxymethyl)pyrazolo[3,4-c]pyridine-3-carboxylic acid (0.18 g, 410.44 µmol, 1 eq) in DMF (12 mL) were added TEA (207.7 mg, 2.05 mmol, 285.64 µL, 5 eq) and HATU (234.1 mg, 615.66 µmol, 1.5 eq). Then, the mixture was stirred at 25° C. for 10 min. NH₃ (3 M in THF, 136.81 µL, 1 eq) was added to the solution at 0° C., then stirred at 0° C. for 10 min. The reaction was poured into ~10 mL water and extracted with EtOAc (3×10 mL), washed with brine (3×10 mL), dried over by anhydrous Na₂SO₄, filtered, and concentrated in vacuo. The residue was purified by prep-TLC (SiO₂, DCM:MeOH=15:1) to afford the title compound 5-[3-(prop-2-enoylamino)phenyl]-1-(2-trimethylsilylethoxymethyl)pyrazolo[3,4-c]pyridine-3-carboxamide (0.17 g, 388.51 µmol, 94.66% yield) as a yellow solid. LC-MS (ES⁺, m/z): 438.1 [(M+H)⁺].

Step 5—5-[3-(prop-2-enoylamino)phenyl]-1H-pyrazolo[3,4-c]pyridine-3-carboxamide

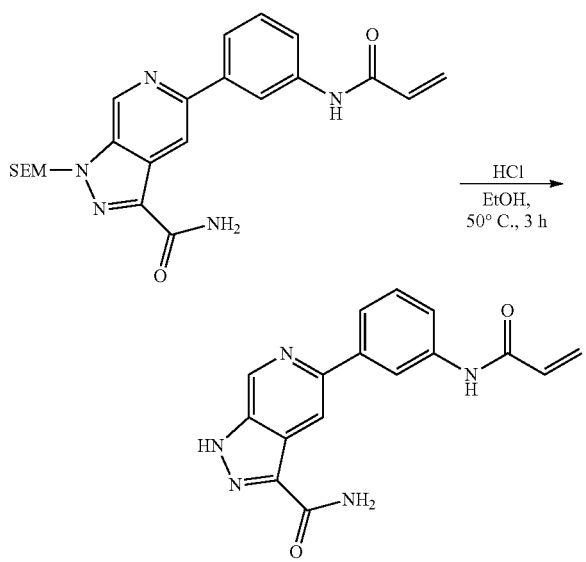

To a solution of 5-[3-(prop-2-enoylamino)phenyl]-1-(2-trimethylsilylethoxymethyl)pyrazolo[3,4-c]pyridine-3-carboxamide (0.18 g, 411.37 µmol, 1 eq) in EtOH (3.6 mL) was added concentrated HCl (1.84 g, 18.63 mmol, 1.8 mL, 37% purity, 45.29 eq) and the mixture was stirred at 50° C. for 3 hr. The reaction was concentrated under N₂. The residue was purified by prep-HPLC (FA condition) to afford the title compound 5-[3-(prop-2-enoylamino)phenyl]-1H-pyrazolo[3,4-c]pyridine-3-carboxamide (0.0185 g, 60.2 µmol, 14.63% yield, 100.0% purity) as a white solid. LC-MS (ES⁺, m/z): 308.0 [(M+H)⁺], 1H NMR (400 MHz, DMSO-d6): 14.14 (br s, 1H), 10.32 (s, 1H), 9.21 (d, J=1.1 Hz, 1H), 8.51 (d, J=1.1 Hz, 1H), 8.39 (s, 1H), 7.95 (s, 1H), 7.82 (br d, J=6.0 Hz, 2H), 7.56 (br s, 1H), 7.45 (t, J=7.9 Hz, 1H), 6.57-6.41 (m, 1H), 6.36-6.18 (m, 1H), 5.86-5.69 (m, 1H).

Route 9: General Scheme

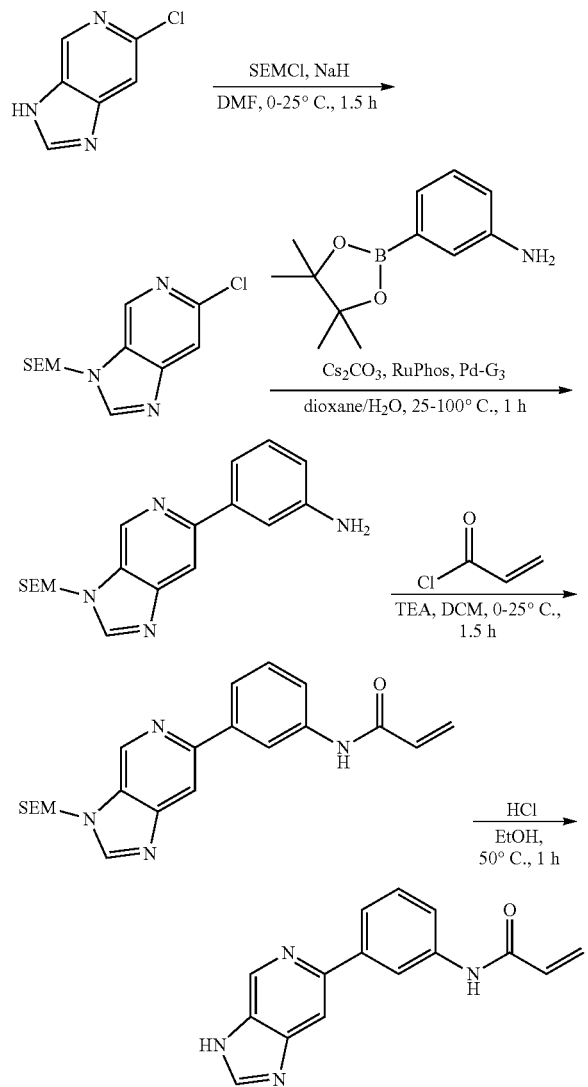

Step 1—2-[(6-chloroimidazo[4,5-c]pyridin-3-yl) methoxy]ethyl-trimethyl-silane

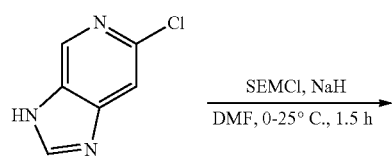

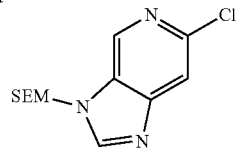

To a solution of 6-chloro-3H-imidazo[4,5-c]pyridine (0.13 g, 846.53 µmol, 1 eq) in DMF (2 mL) was added NaH (50.8 mg, 1.27 mmol, 60% purity, 1.5 eq) at 0° C. Then the mixture was stirred at 0° C. for 30 min. Then SEMCl (282.3 mg, 1.69 mmol, 299.65 µL, 2 eq) was added to the solution at 0° C., and stirred at 25° C. for 1 hr. TLC (DCM: MeOH=10:1, SM Rf=0.21, TM Rf=0.40) showed that the reaction was complete. The reaction was poured into ~20 mL water and extracted with EtOAc (3×10 mL). The combined organic phase was washed with brine (3×20 mL), dried over anhydrous Na₂SO₄, filtered, and concentrated in vacuo. The residue was purified by prep-TLC (SiO₂, DCM: MeOH=10:1) to afford the title compound 2-[(6-chloroimidazo[4,5-c]pyridin-3-yl) methoxy]ethyl-trimethyl-silane (0.18 g, 634.19 µmol, 74.92% yield) as a yellow oil.

Step 2—3-[3-(2-trimethylsilylethoxymethyl)imidazo [4,5-c]pyridin-6-yl]aniline

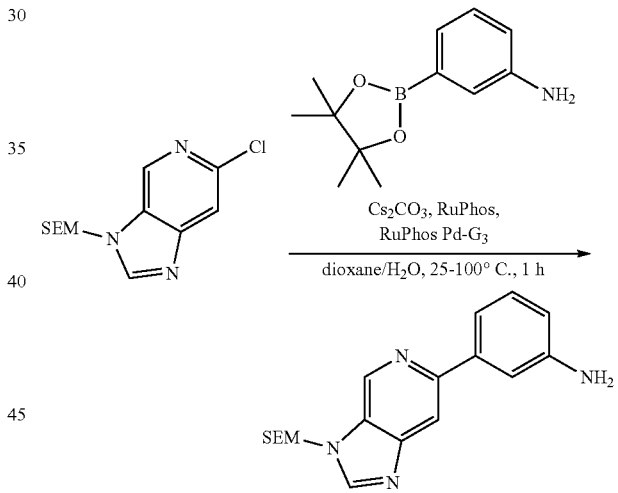

To a solution of 2-[(6-chloroimidazo[4,5-c]pyridin-3-yl) methoxy]ethyl-trimethyl-silane (0.18 g, 634.19 µmol, 1 eq) and 3-(4,4,5,5-tetramethyl-1,3,2-dioxaborolan-2-yl)aniline (166.7 mg, 761.02 µmol, 1.2 eq) in dioxane (4 mL) H₂O (1 mL) were added Cs₂CO₃ (619.9 mg, 1.9 mmol, 3 eq) and dicyclohexyl-[2-(2,6-diisopropoxyphenyl)phenyl]phosphane (29.6 mg, 63.42 µmol, 0.1 eq), [2-(2-aminophenyl) phenyl]-methylsulfonyloxy-palladium; dicyclohexyl-[2-(2, 6-diisopropoxyphenyl)phenyl]phosphane (26.5 mg, 31.71 µmol, 0.05 eq) at 25° C. The mixture was stirred at 100° C. for 1 hr under N₂. The reaction was diluted with ~10 mL EtOAc and poured into ~15 mL saturated EDTA. Then the mixture was stirred at 25° C. for 1 h and extracted with EtOAc (3×15 mL). The combined organic phase was washed with brine (3×15 mL), dried over anhydrous Na₂SO₄, filtered, and concentrated in vacuo. The residue was purified by prep-TLC (SiO₂, DCM:MeOH=15:1 to afford the title compound 3-[3-(2-trimethylsilylethoxymethyl)imidazo[4,5-c]pyridin-6-yl]aniline (0.2 g, 587.38 µmol, 92.62% yield) as a yellow oil. LC-MS (ES+, m/z): 341.1 [(M+H)+].

Step 3—N-[3-[3-(2-trimethylsilylethoxymethyl) imidazo[4,5-c]pyridin-6-yl]phenyl]prop-2-enamide

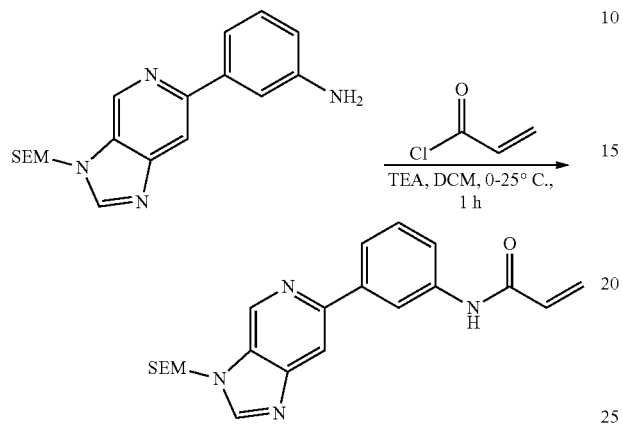

To a solution of 3-[3-(2-trimethylsilylethoxymethyl)imidazo[4,5-c]pyridin-6-yl]aniline (0.15 g, 440.54 µmol, 1 eq) in DCM (3 mL) was added TEA (133.7 mg, 1.32 mmol, 183.95 µL, 3 eq). Then, prop-2-enoyl chloride (79.7 mg, 881.07 µmol, 71.84 µL, 2 eq) in 0.5 mL DCM was added to the solution at 0° C. The mixture was stirred at 25° C. for 1 hr. The reaction was poured into ~10 mL water and extracted with DCM (3×10 mL). The combined organic phase was washed with brine (3×10 mL), dried over anhydrous Na2SO4, filtered, and concentrated in vacuo. The residue was purified by prep-TLC (SiO2, DCM:MeOH=15:1) to afford the title compound N-[3-[3-(2-trimethylsilylethoxymethyl) imidazo[4,5-c]pyridin-6-yl]phenyl]prop-2-enamide (0.13 g, 329.5 µmol, 74.79% yield) as a yellow oil. LC-MS (ES+, m/z): 395.2 [(M+H)+].

Step 4—N-[3-(3H-imidazo[4,5-c]pyridin-6-yl)phenyl]prop-2-enamide

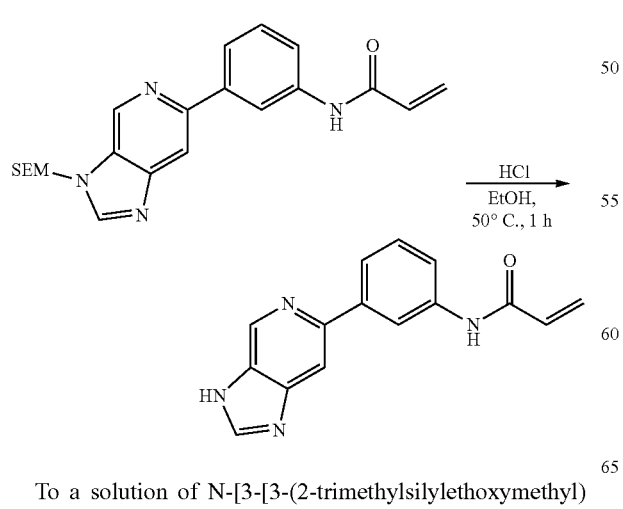

To a solution of N-[3-[3-(2-trimethylsilylethoxymethyl) imidazo[4,5-c]pyridin-6-yl]phenyl]prop-2-enamide (0.09 g, 228.11 µmol, 1 eq) in EtOH (1.2 mL) was added concentrated HCl (612 mg, 6.21 mmol, 0.6 mL, 37% purity, 27.23 eq) and the mixture was stirred at 50° C. for 1 hr. The reaction was concentrated under N2. The residue was purified by prep-HPLC (LA condition) to afford the title compound N-[3-(3H-imidazo[4,5-c]pyridin-6-yl)phenyl]prop-2-enamide (0.0209 g, 77.03 µmol, 33.77% yield, 97.4% purity) as a white solid. LC-MS (ES+, m/z): 265.0 [(M+H)+], 1H NMR (400 MHz, DMSO-d6) Shift=12.91 (br s, 1H), 10.27 (s, 1H), 9.01 (s, 1H), 8.51-8.33 (m, 2H), 8.13 (s, 1H), 8.04 (br s, 1H), 7.85-7.71 (m, 2H), 7.43 (t, J=7.8 Hz, 1H), 6.55-6.41 (m, 1H), 6.29 (dd, J=2.0, 17.1 Hz, 1H), 5.84-5.72 (m, 1H).

Route 10: General Scheme

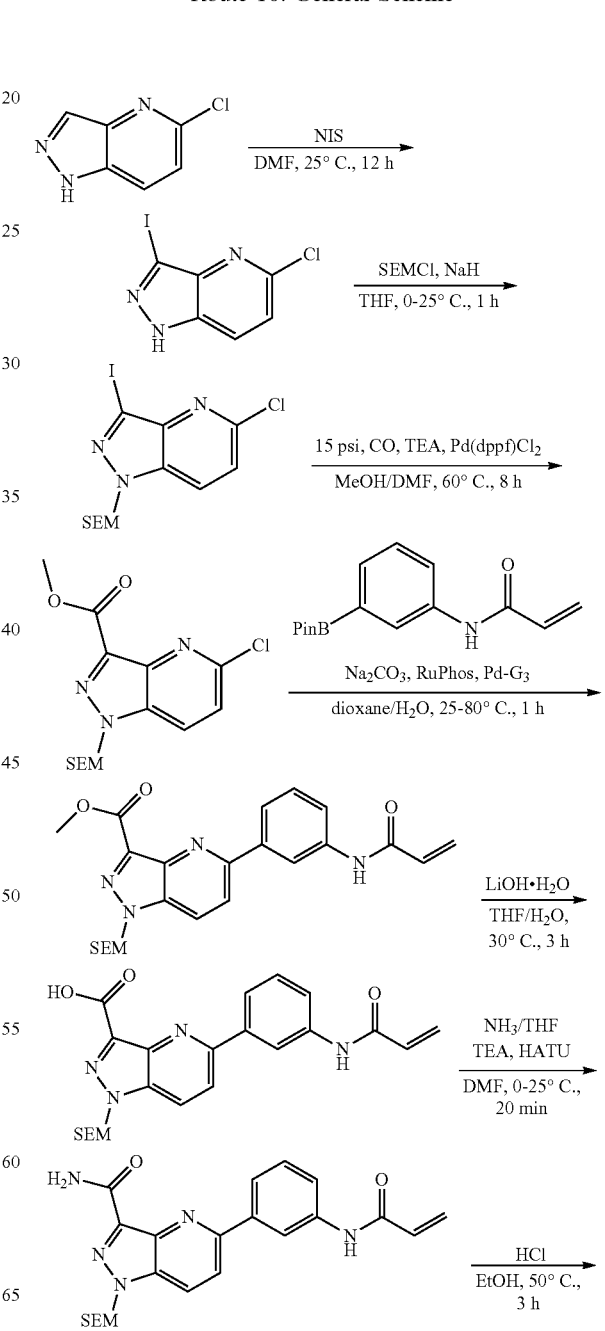

-continued

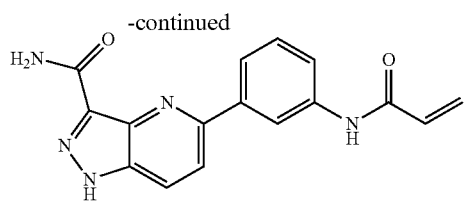

Step 1—5-chloro-3-iodo-1H-pyrazolo[4,3-b]pyridine

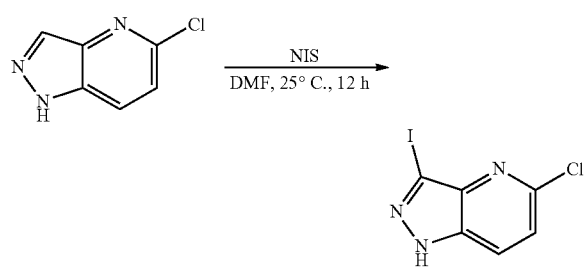

To a solution of 5-chloro-1H-pyrazolo[4,3-b]pyridine (1.5 g, 9.77 mmol, 1 eq) in DMF (15 mL) was added NIS (4.4 g, 19.54 mmol, 2 eq) and the mixture was stirred at 25° C. for 12 hr. TLC (PE:EtOAc=1:1, SM Rf=0.40, TM Rf=0.52) showed that the reaction was complete. The reaction was poured into ~50 mL water and extracted with EtOAc (3×50 mL). The combined organic phase was washed with brine (3×50 mL), dried over anhydrous $Na_2SO_4$, filtered, and concentrated in vacuo. The residue was purified by column chromatography ($SiO_2$, PE:EtOAc=10:1 to 4:1) to afford the title compound 5-chloro-3-iodo-1H-pyrazolo[4,3-b]pyridine (2.4 g, 8.59 mmol, 87.92% yield) as a white solid. 1H NMR (400 MHz, DMSO-d6) Shift=13.98 (s, 1H), 8.13 (d, J=8.8 Hz, 1H), 7.50 (d, J=8.8 Hz, 1H).

Step 2—2-[(5-chloro-3-iodo-pyrazolo[4,3-b]pyridin-1-yl)methoxy]ethyl-trimethyl-silane

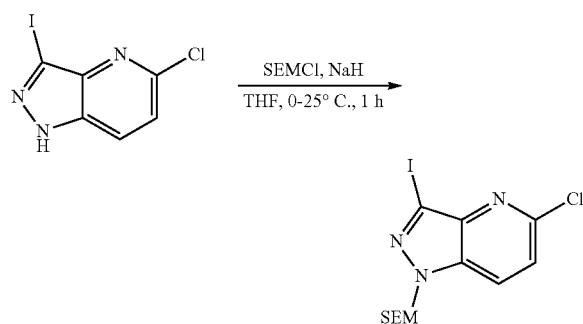

To a solution of 5-chloro-3-iodo-1H-pyrazolo[4,3-b]pyridine (2.1 g, 7.51 mmol, 1 eq) in THF (20 mL) was added NaH (450.9 mg, 11.27 mmol, 60% purity, 1.5 eq) at 0° C. The mixture was stirred at 0° C. for 0.5 h, SEMCl (1.5 g, 9.02 mmol, 1.60 mL, 1.2 eq) was added to the solution at 0° C. and stirred at 25° C. for 0.5 hr. The reaction was poured into ~25 mL water and extracted with EtOAc (3×20 mL). The combined organic phase was washed with brine (3×20 mL), dried over by anhydrous $Na_2SO_4$, filtered, and concentrated in vacuo. The residue was purified by column chromatography ($SiO_2$, PE:EtOAc=10:1 to 4:1) to afford the title compound 2-[(5-chloro-3-iodo-pyrazolo[4,3-b]pyridin-1-yl)methoxy]ethyl-trimethyl-silane (2.5 g, 6.1 mmol, 81.20% yield) as a white solid. LC-MS (ES+, m/z): 409.9 [(M+H)+].

Step 3—Methyl 5-chloro-1-(2-trimethylsilylethoxymethyl) pyrazolo[4,3-b]pyridine-3-carboxylate

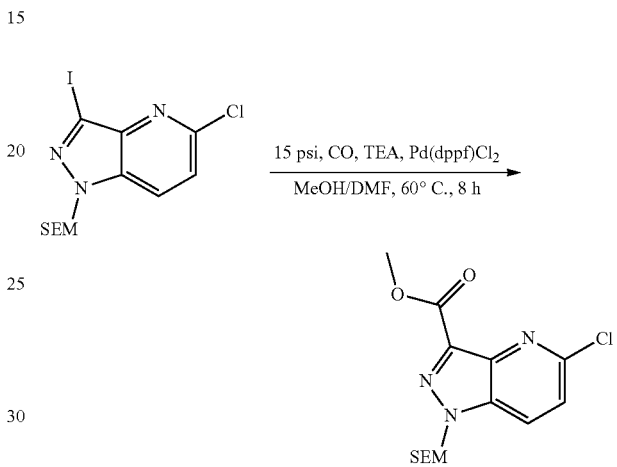

To a solution of 2-[(5-chloro-3-iodo-pyrazolo[4,3-b]pyridin-1-yl)methoxy]ethyl-trimethyl-silane (0.5 g, 1.22 mmol, 1 eq) in DMF (4 mL) and MeOH (1 mL) was added TEA (370.5 mg, 3.66 mmol, 509.56 μL, 3 eq) and Pd(dppf)Cl$_2$ (89.3 mg, 122.03 μmol, 0.1 eq). The mixture was stirred at 60° C. under 15 psi CO for 8 h. The reaction was diluted with 10 mL EtOAc and poured into 20 mL water and extracted with EtOAc (3×10 mL). The combined organic phase was washed with brine (3×20 mL), dried over by anhydrous $Na_2SO_4$, filtered, and concentrated in vacuo. The residue was purified by column chromatography ($SiO_2$, PE:EtOAc=10:1 to 4:1) to afford the title compound Methyl 5-chloro-1-(2-trimethyl silyl ethoxy methyl) pyrazolo[4,3-b]pyridine-3-carboxylate (0.28 g, 819.04 μmol, 67.12% yield) as a white solid. LC-MS (ES+, m/z): 342.1 [(M+H)+].

Step 4—Methyl 5-[3-(prop-2-enoylamino)phenyl]-1-(2-trimethylsilylethoxymethyl)pyrazolo[4,3-b]pyridine-3-carboxylate

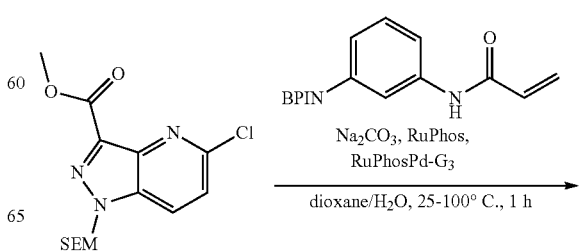

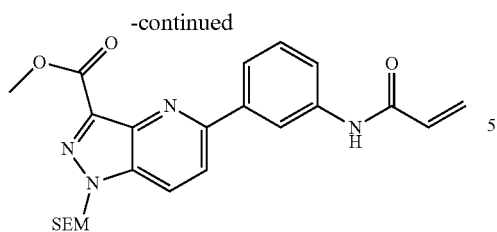

To a solution of methyl 5-chloro-1-(2-trimethylsilylethoxy methyl)pyrazolo[4,3-b]pyridine-3-carboxylate (0.25 g, 731.28 μmol, 1 eq) and N-[3-(4,4,5,5-tetramethyl-1,3,2-dioxaborolan-2-yl)phenyl]prop-2-enamide (199.7 mg, 731.28 μmol, 1 eq) in H₂O (1 mL) and dioxane (4 mL) was added Na₂CO₃ (232.5 mg, 2.19 mmol, 3 eq) and RuPhos (34.1 mg, 73.13 μmol, 0.1 eq) and RuPhos Pd G3 (30.6 mg, 36.56 μmol, 0.05 eq) at 25° C. The reaction was stirred at 100° C. for 1 hr under N₂. TLC (PE:EtOAc=1:1, SM Rf=0.44, TM Rf=0.17) showed that the reaction was complete. The reaction was diluted with 10 mL EtOAc and poured into ~15 mL saturated EDTA and stirred at 25° C. for 1 hr. Then the mixture was extracted with EtOAc (3×15 mL), washed with brine (3×15 mL), dried over anhydrous Na₂SO₄, filtered, and concentrated in vacuo. The residue was purified by column chromatography (SiO₂, PE:EtOAc=10:1 to 1/1) to afford the title compound Methyl 5-[3-(prop-2-enoyl amino)phenyl]-1-(2-trimethylsilylethoxymethyl)pyrazolo[4,3-b]pyridine-3-carboxylate (0.52 g, 1.15 mmol, 78.56% yield) as a yellow oil. LC-MS (ES⁺, m/z): 453.2 [(M+H)⁺].

Step 5—5-[3-(prop-2-enoylamino)phenyl]-1-(2-trimethylsilylethoxymethyl)pyrazolo[4,3-b]pyridine-3-carboxylic acid

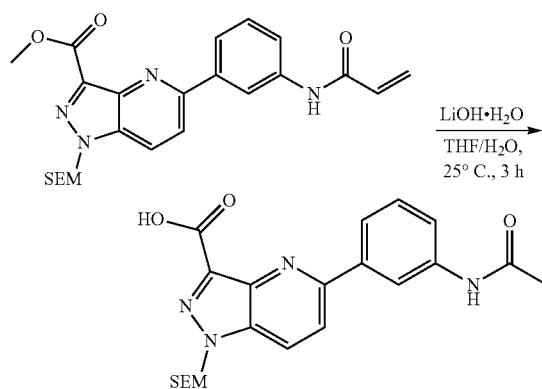

To a solution of methyl 5-[3-(prop-2-enoylamino)phenyl]-1-(2-trimethylsilyl ethoxymethyl) pyrazolo[4,3-b]pyridine-3-carboxylate (0.27 g, 596.58 μmol, 1 eq) in THF (4 mL) and H₂O (1 mL) was added LiOH·H₂O (250.4 mg, 5.97 mmol, 10 eq) and the mixture was stirred at 25° C. for 3 hr. The reaction was poured into ~20 mL ice water then adjusted to pH=6 with saturated citric acid. Then the mixture was extracted with EtOAc (3×30 mL). The combined organic phase was washed with brine (3×30 mL), dried over anhydrous Na₂SO₄, filtered, and concentrated in vacuo to afford the title compound 5-[3-(prop-2-enoyl amino)phenyl]-1-(2-trimethylsilylethoxymethyl)pyrazolo[4,3-b]pyridine-3-carboxylic acid (0.22 g, crude) as a yellow solid. LC-MS (ES⁺, m/z): 439.1 [(M+H)⁺].

Step 6—5-[3-(prop-2-enoylamino)phenyl]-1-(2-trimethylsilylethoxymethyl) pyrazolo[4,3-b]pyridine-3-carboxamide

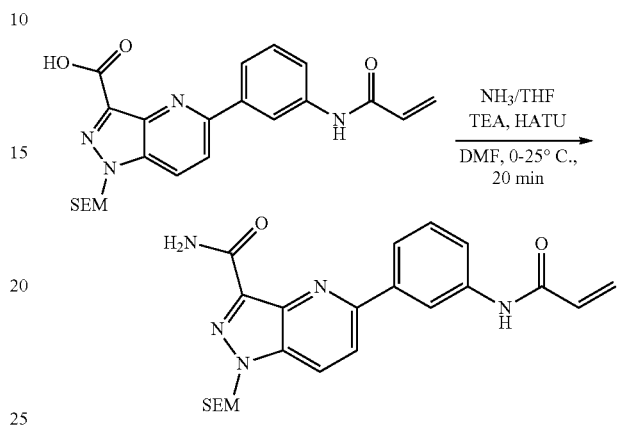

To a solution of 5-[3-(prop-2-enoylamino)phenyl]-1-(2-trimethylsilylethoxymethyl)pyrazolo[4,3-b]pyridine-3-carboxylic acid (0.16 g, 364.84 μmol, 1 eq) in DMF (8 mL) was added HATU (208.1 mg, 547.26 μmol, 1.5 eq) and TEA (184.6 mg, 1.82 mmol, 253.90 μL, 5 eq). Then stirred at 25° C. for 10 min. NH₃ (3 M in THF, 10 mL, 82.23 eq) was added to the solution at 0° C., then stirred at 0° C. for 10 min. LCMS showed that the reaction completed. The reaction was diluted with 10 mL EtOAc and poured into ~15 mL water. Then the mixture was extracted with EtOAc (3×15 mL), washed with brine (3×15 mL), dried over anhydrous Na₂SO₄, filtered, and concentrated in vacuo. The residue was purified by prep-TLC (SiO₂, DCM:MeOH=10:1) to afford the title compound 5-[3-(prop-2-enoylamino)phenyl]-1-(2-trimethylsilylethoxymethyl)pyrazolo[4,3-b]pyridine-3-carboxamide (0.12 g, 274.24 μmol, 75.17% yield) as a yellow oil. LC-MS (ES⁺, m/z): 438.2 [(M+H)⁺].

Step 7—5-[3-(prop-2-enoylamino)phenyl]-1H-pyrazolo[4,3-b]pyridine-3-carboxamide

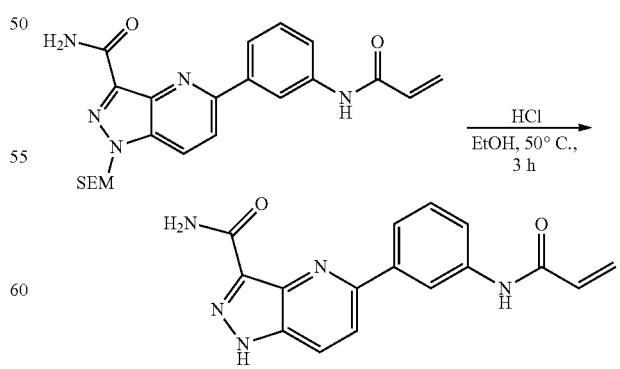

To a solution of 5-[3-(prop-2-enoylamino)phenyl]-1-(2-trimethylsilylethoxymethyl) pyrazolo[4,3-b]pyridine-3-carboxamide (0.1 g, 228.54 μmol, 1 eq) in EtOH (4 mL) was added concentrated HCl (1.02 g, 10.35 mmol, 1 mL, 37% purity, 45.29 eq) and stirred at 50° C. for 3 hr. The reaction was poured into ~10 mL saturated NaHCO₃ to adjust the pH to 7. Then the mixture was extracted with EtOAc (3×15 mL), washed with brine (3×20 mL), dried over anhydrous Na₂SO₄, filtered, and concentrated in vacuo. The residue was purified by prep-HPLC to afford the title compound 5-[3-(prop-2-enoylamino)phenyl]-1H-pyrazolo[4,3-b]pyridine-3-carboxamide (20.40 mg, 66.38 μmol, 29.05% yield, 100.0% purity) as a white solid. LC-MS (ES⁺, m/z): 308.0 [(M+H)⁺], 1H NMR (400 MHz, DMSO-d6) Shift=12.83 (br s, 1H), 10.36 (s, 1H), 8.44 (s, 1H), 8.26 (d, J=8.8 Hz, 2H), 7.99 (d, J=8.9 Hz, 1H), 7.95 (br s, 1H), 7.84 (dd, J=1.4, 8.0 Hz, 2H), 7.50 (t, J=7.8 Hz, 1H), 6.59-6.43 (m, 1H), 6.36-6.21 (m, 1H), 5.88-5.72 (m, 1H)

Route 10: General Scheme

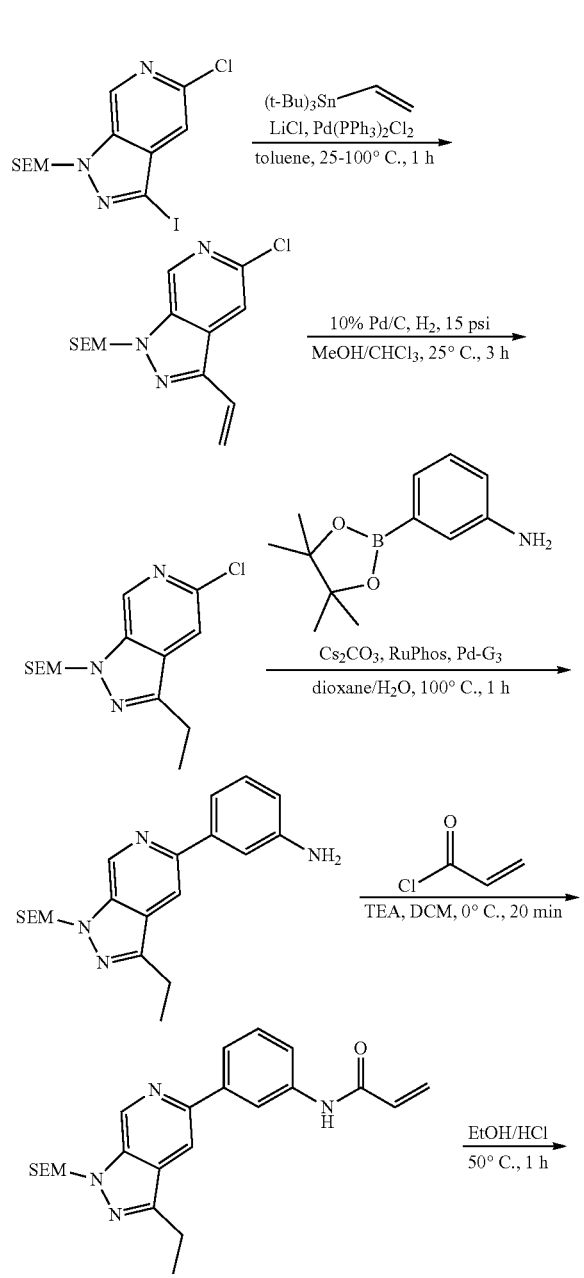

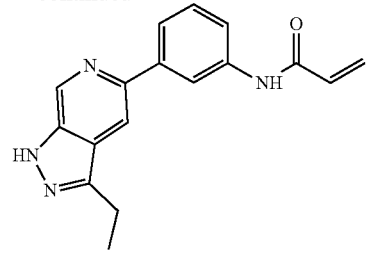

Step 1—2-[(5-chloro-3-vinyl-pyrazolo[3,4-c]pyridin-1-yl) methoxy]ethyl-trimethyl-silane

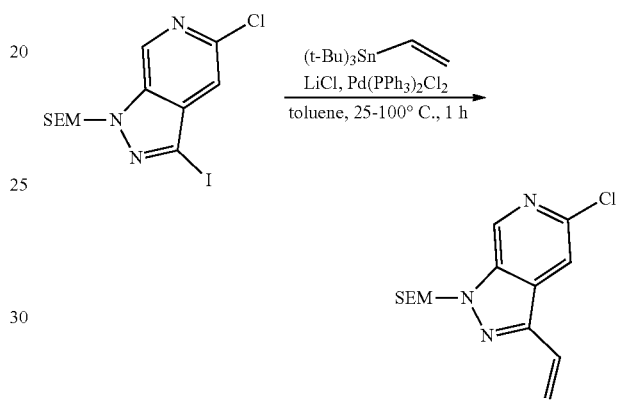

To a solution of 2-[(5-chloro-3-iodo-pyrazolo[3,4-c]pyridin-1-yl)methoxy]ethyl-trimethyl-silane (0.5 g, 1.22 mmol, 1 eq) and tributyl(vinyl)stannane (425.7 mg, 1.34 mmol, 390.51 μL, 1.1 eq) in toluene (5 mL) was added LiCl (134.5 mg, 3.17 mmol, 64.98 μL, 2.6 eq) and dichloropalladium;triphenylphosphane (85.7 mg, 122.03 μmol, 0.1 eq) at 25° C. under N₂. Then the mixture was stirred at 100° C. for 1 hr. The reaction was diluted with 10 mL EtOAc and poured into ~20 mL saturated EDTA. The mixture was stirred at 25° C. for 1 h. The aqueous layer was extracted with EtOAc (3×10 mL), and the combined organic layer was dried over by anhydrous Na₂SO₄, filtered, and concentrated in vacuo. The residue was purified by column chromatography (SiO₂, PE:EtOAc=10:1 to 4:1) to afford the title compound 2-[(5-chloro-3-vinyl-pyrazolo[3,4-c]pyridin-1-yl) methoxy]ethyl-trimethyl-silane (0.368 g, 1.19 mmol, 97.32% yield) as a yellow oil. LC-MS (ES⁺, m/z): 310.1 [(M+H)⁺].

Step 2—2-[(5-chloro-3-ethyl-pyrazolo[3,4-c]pyridin-1-yl)methoxy]ethyl-trimethyl-silane

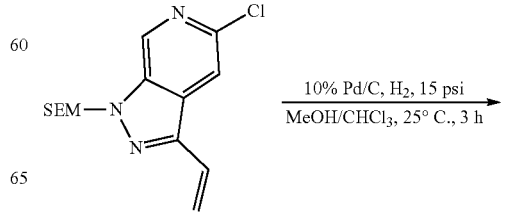

-continued

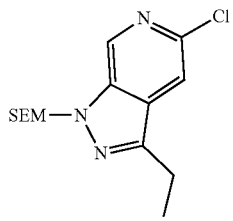

To a solution of 2-[(5-chloro-3-vinyl-pyrazolo[3,4-c]pyridin-1-yl)methoxy]ethyl-trimethyl-silane (0.2 g, 645.44 µmol, 1 eq) in MeOH (2 mL) and CHCl₃ (2 mL) was added Pd/C (200 mg, 187.93 µmol, 10% purity, 2.91e–1 eq) at 25° C. Then the mixture was stirred at 25° C. for 3 hr under H₂ 15 psi. The reaction was filtered and concentrated in vacuo. The residue was purified by prep-TLC (SiO₂, DCM: MeOH=4:1) to afford the title compound 2-[(5-chloro-3-ethyl-pyrazolo[3,4-c]pyridin-1-yl)methoxy]ethyl-trimethyl-silane (0.18 g, 577.14 µmol, 89.42% yield) as a yellow oil. LC-MS (ES⁺, m/z): 312.0 [(M+H)⁺].

Step 3—3-[3-ethyl-1-(2-trimethylsilylethoxymethyl)pyrazolo[3,4-c]pyridin-5-yl]aniline

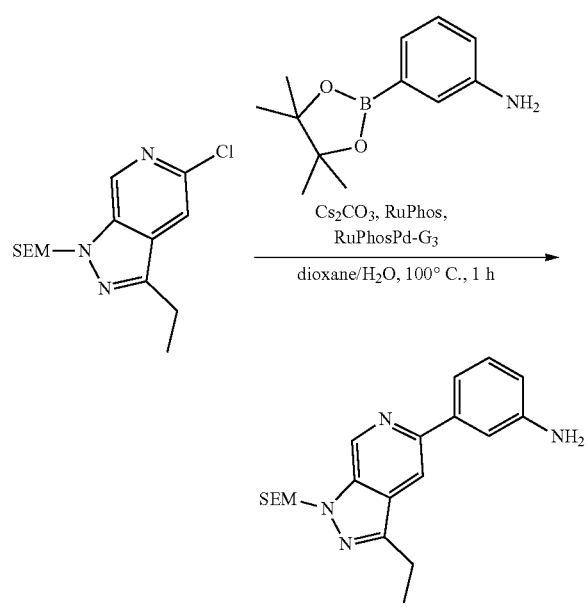

To the solution of 2-[(5-chloro-3-ethyl-pyrazolo[3,4-c]pyridin-1-yl) methoxy]ethyl-trimethyl-silane (0.21 g, 673.33 µmol, 1 eq) in the mixed solvent of dioxane (4 mL) and H₂O (1 mL) were successively added 3-(4,4,5,5-tetramethyl-1,3,2-dioxaborolan-2-yl)aniline (177 mg, 808 µmol, 1.2 eq), Cs₂CO₃ (658.2 mg, 2.02 mmol, 3 eq), RuPhos (31.4 mg, 67.33 µmol, 0.1 eq) and RuPhos Pd G₃ (28.2 mg, 33.67 µmol, 0.05 eq) then degassed with N₂ 3 times. The resulting reaction mixture was heated to 100° C. and stirred at 100° C. for 1 h under N₂. TLC (PE:EtOAc=1:1, SM Rf=0.46, TM Rf=0.31) showed that the reaction was complete. The reaction was poured into ~15 mL saturated EDTA and stirred at 25° C. for 1 h. The mixture was extracted with EtOAc (3×10 mL), washed with brine (3×20 mL), dried over anhydrous Na₂SO₄, filtered, and concentrated in vacuo. The residue was purified by prep-TLC (SiO₂, PE:EtOAc=1:1) to afford the title compound 3-[3-ethyl-1-(2-trimethylsilyl ethoxymethyl) pyrazolo[3,4-c]pyridin-5-yl]aniline (0.2 g, 542.67 µmol, 80.59% yield) as a brown oil.

Step 4—N-[3-[3-ethyl-1-(2-trimethylsilylethoxymethyl)pyrazolo[3,4-c]pyridin-5-yl]phenyl]prop-2-enamide

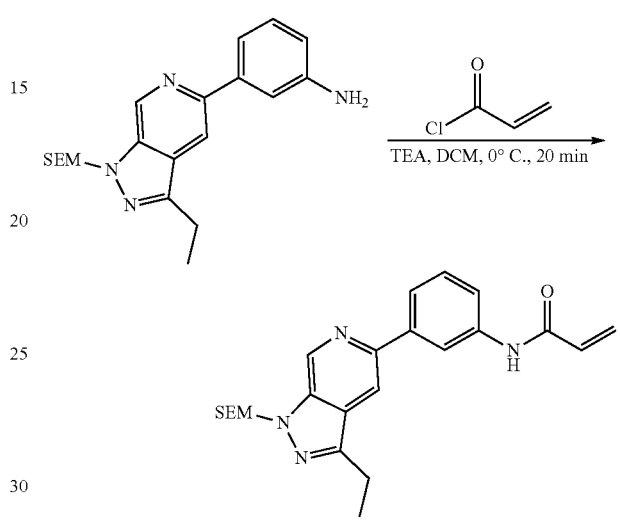

To a solution of 3-[3-ethyl-1-(2-trimethylsilyl ethoxymethyl)pyrazolo[3,4-c]pyridin-5-yl]aniline (0.2 g, 542.67 µmol, 1 eq) in DCM (4 mL) was added TEA (164.7 mg, 1.63 mmol, 226.60 µL, 3 eq), prop-2-enoyl chloride (98.2 mg, 1.09 mmol, 88.50 µL, 2 eq) was added to the solution at 0° C. Then stirred at 0° C. for 20 min. The reaction was poured into ~20 mL water then extracted with DCM (3×10 mL), washed with brine (3×10 mL), dried over anhydrous Na₂SO₄, filtered, and concentrated in vacuo. The residue was purified by prep-TLC (SiO₂, PE:EtOAc=1:1) to afford the title compound N-[3-[3-ethyl-1-(2-trimethylsilylethoxymethyl)pyrazolo[3,4-c]pyridin-5-yl]phenyl]prop-2-enamide (0.2 g, 473.27 µmol, 87.21% yield) as a yellow oil. LC-MS (ES⁺, m/z): 423.2 [(M+H)⁺].

Step 5—N-[3-(3-ethyl-1H-pyrazolo[3,4-c]pyridin-5-yl)phenyl]prop-2-enamide

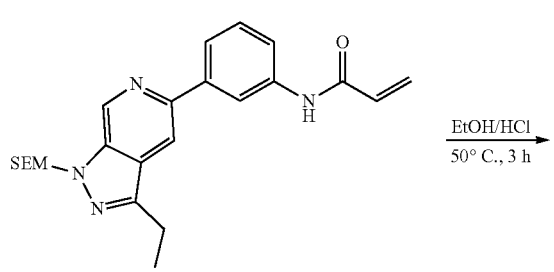

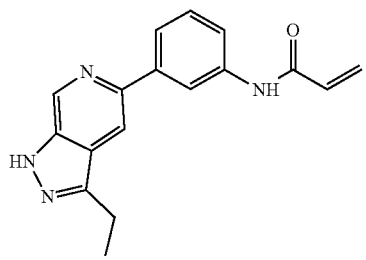

To a solution of N-[3-[3-ethyl-1-(2-trimethylsilylethoxymethyl)pyrazolo[3,4-c]pyridin-5-yl]phenyl]prop-2-enamide (0.16 g, 378.61 μmol, 1 eq) in EtOH (4 mL) was added concentrated HCl (2.04 g, 20.7 mmol, 2 mL, 37% purity, 54.68 eq) and the mixture was stirred at 50° C. for 3 hr. The reaction was poured into ~20 mL saturated NaHCO$_3$ to adjust the pH to 7. The mixture was extracted with EtOAc (3×10 mL), washed with brine (3×20 mL), dried over anhydrous Na$_2$SO$_4$, filtered, and concentrated in vacuo. The residue was purified by prep-HPLC to afford the title compound N-[3-(3-ethyl-1H-pyrazolo[3,4-c]pyridin-5-yl)phenyl]prop-2-enamide (0.0316 g, 108.1 μmol, 28.55% yield, 100.0% purity) as a white solid. LC-MS (ES$^+$, m/z): 293.1 [(M+H)$^+$], 1H NMR (400 MHz, DMSO-d6) Shift=10.25 (s, 1H), 9.04 (d, J=1.6 Hz, 1H), 8.40 (t, J=1.8 Hz, 1H), 8.23 (d, J=1.2 Hz, 1H), 7.87-7.80 (m, 1H), 7.77 (dd, J=1.2, 8.0 Hz, 1H), 7.42 (t, J=8.0 Hz, 1H), 6.57-6.40 (m, 1H), 6.29 (dd, J=2.0, 17.0 Hz, 1H), 5.88-5.64 (m, 1H), 3.32 (s, 11H), 3.03 (q, J=7.6 Hz, 2H), 1.36 (t, J=7.6 Hz, 3H).

Route 11: General Scheme

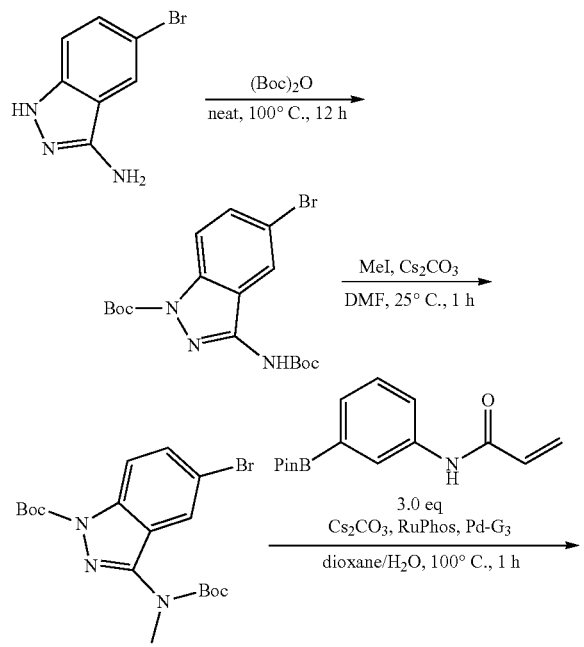

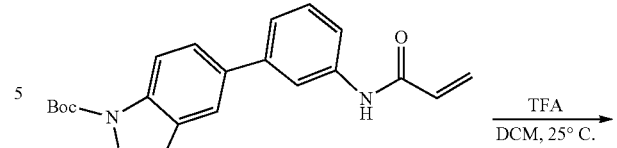

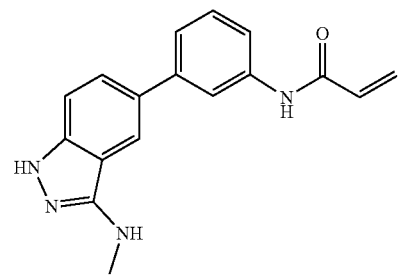

Step 1—5-tert-butyl 5-bromo-3-(tert-butoxycarbonylamino) indazole-1-carboxylate

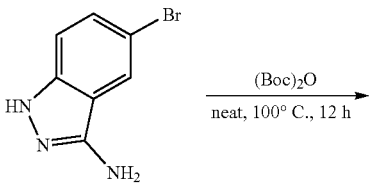

To a solution of 5-bromo-1H-indazol-3-amine (1 g, 4.72 mmol, 1 eq) in (Boc)$_2$O (9.5 g, 43.53 mmol, 10 mL, 9.23 eq) and the mixture was stirred at 100° C. for 12 hr. TLC (PE:EtOAc=1:1, SM Rf=0.27, TM Rf=0.76) showed that the reaction was complete. The reaction was concentrated in vacuo. The residue was purified by column chromatography (SiO$_2$, PE:EtOAc=10:1 to 4:1) to afford the title compound tert-butyl 5-bromo-3-(tert-butoxycarbonylamino) indazole-1-carboxylate (0.6 g, 1.46 mmol, 30.86% yield) as a colorless solid.

Step 2—Tert-butyl 5-bromo-3-[tert-butoxycarbonyl(methyl)amino]indazole-1-carboxylate

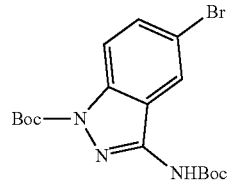

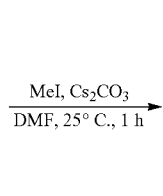

-continued

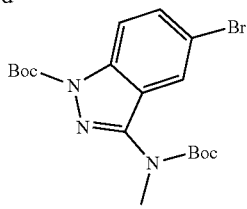

To a solution of tert-butyl 5-bromo-3-(tert-butoxycarbonylamino) indazole-1-carboxylate (0.4 g, 970.22 μmol, 1 eq) in DMF (4 mL) was added Cs$_2$CO$_3$ (632.2 mg, 1.94 mmol, 2 eq). Then, MeI (206.6 mg, 1.46 mmol, 90.60 μL, 1.5 eq) was added to the solution and stirred at 25° C. for 1 hr. TLC (PE:EtOAc=4:1, SM Rf=0.21, TM Rf=0.41) showed that the reaction was complete. The reaction was poured into 10 mL water and extracted with EtOAc (3×15 mL), dried over anhydrous Na$_2$SO$_4$, filtered, and concentrated in vacuo. The residue was purified by column chromatography (SiO$_2$, PE:EtOAc=10:1 to 4:1) to afford the title compound Tert-butyl 5-bromo-3-[tert-butoxycarbonyl(methyl)amino]indazole-1-carboxylate (0.338 g, 792.86 μmol, 81.72% yield) as a colorless solid.

Step 3—Tert-butyl 3-[tert-butoxycarbonyl(methyl)amino]-5-[3-(prop-2-enoylamino)phenyl]indazole-1-carboxylate

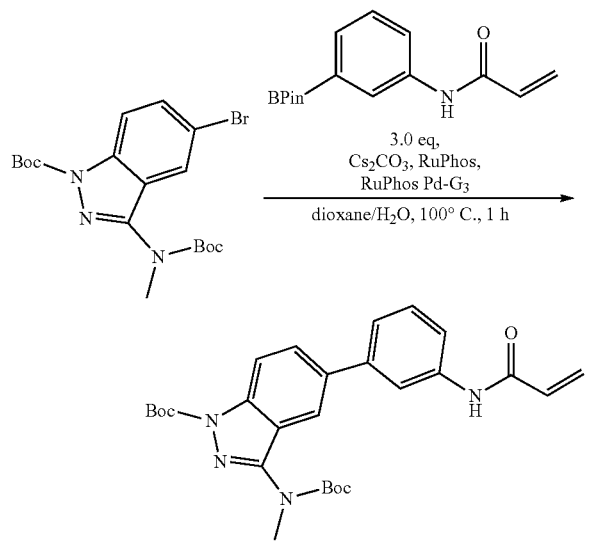

To a solution of tert-butyl 5-bromo-3-[tert-butoxycarbonyl(methyl)amino]indazole-1-carboxylate (0.2 g, 469.15 μmol, 1 eq) and N-[3-(4,4,5,5-tetramethyl-1,3,2-dioxaborolan-2-yl)phenyl]prop-2-enamide (384.4 mg, 1.41 mmol, 3 eq) in dioxane (6 mL) and H$_2$O (1.5 mL) were added Cs$_2$CO$_3$ (458.6 mg, 1.41 mmol, 3 eq), RuPhos (21.9 mg, 46.91 μmol, 0.1 eq) and RuPhos Pd G3 (19.6 mg, 23.46 μmol, 0.05 eq). Then stirred at 100° C. for 1 hr under N$_2$. LCMS showed that the reaction was complete. The reaction was poured into ~15 mL saturated EDTA and stirred at 25° C. for 1 h. The mixture was extracted with EtOAc (3×15 mL), washed with brine (3×30 mL), dried over anhydrous Na$_2$SO$_4$, filtered, and concentrated in vacuo. The residue was purified by prep-TLC (SiO$_2$, PE:EtOAc=1:1) to afford the title compound Tert-butyl 3-[tert-butoxycarbonyl(methyl)amino]-5-[3-(prop-2-enoylamino)phenyl]indazole-1-carboxylate (0.35 g, 355.28 μmol, 75.73% yield, 50% purity) as a yellow oil. LC-MS (ES$^+$, m/z): 493.3 [(M+H)$^+$].

Step 4—N-[3-[3-(methylamino)-1H-indazol-5-yl]phenyl]prop-2-enamide

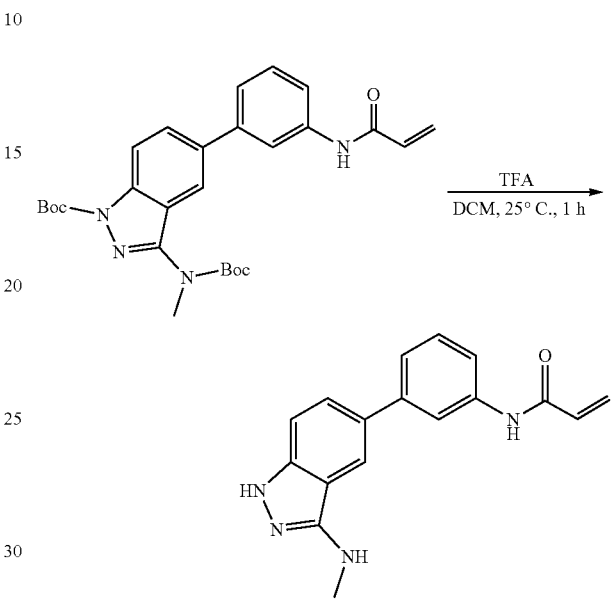

To a solution of tert-butyl 3-[tert-butoxycarbonyl(methyl)amino]-5-[3-(prop-2-enoylamino)phenyl]indazole-1-carboxylate (0.3 g, 609.06 μmol, 1 eq) in DCM (3 mL) was added TFA (1.54 g, 13.51 mmol, 1 mL, 22.18 eq) and stirred at 25° C. for 1 hr. The reaction was poured into ~10 mL ice water and the mixture was adjusted to pH=8 with saturated Na$_2$CO$_3$. The mixture was extracted with DCM (3×10 mL), washed with brine (3×20 mL), dried over anhydrous Na$_2$SO$_4$, filtered, and concentrated under reduced pressure. The residue was purified by prep-HPLC (FA condition) to afford the title compound N-[3-[3-(methylamino)-1H-indazol-5-yl]phenyl]prop-2-enamide (0.0096 g, 32.84 μmol, 5.39% yield, 100.0% purity) as a white solid. LC-MS (ES$^+$, m/z): 293.0 [(M+H)$^+$], $^1$H NMR (400 MHz, DMSO-d$_6$) δ=11.47 (br s, 1H), 10.22 (s, 1H), 8.03 (s, 1H), 7.95 (s, 1H), 7.56 (br d, J=7.6 Hz, 1H), 7.52 (br d, J=8.3 Hz, 1H), 7.45-7.37 (m, 1H), 7.36-7.27 (m, 2H), 6.52-6.43 (m, 1H), 6.33-6.25 (m, 1H), 6.06 (br d, J=4.8 Hz, 1H), 5.78 (br d, J=10.4 Hz, 1H), 2.88 (br d, J=4.8 Hz, 3H).

Route 12: General Scheme

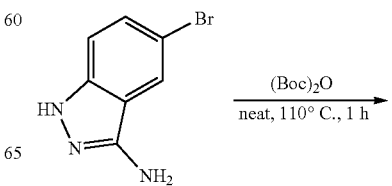

-continued

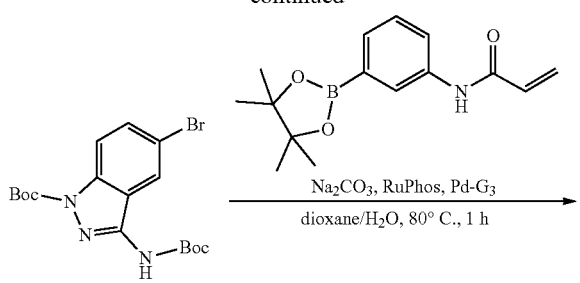

Step 2—tert-butyl 3-(tert-butoxycarbonylamino)-5-[3-(prop-2-enoylamino)phenyl]indazole-1-carboxylate

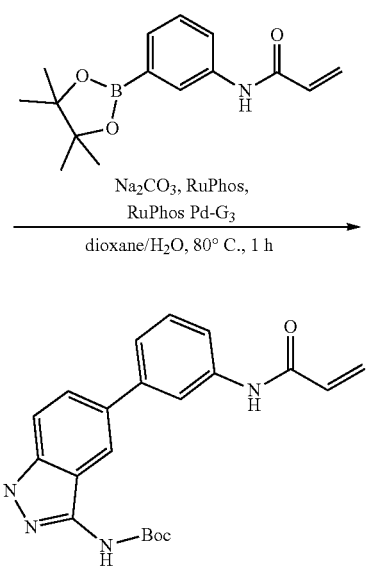

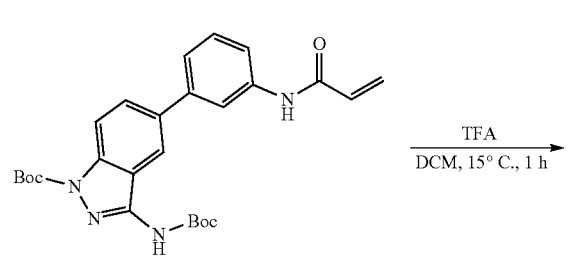

Step 1—tert-butyl 5-bromo-3-(tert-butoxycarbonylamino)indazole-1-carboxylate

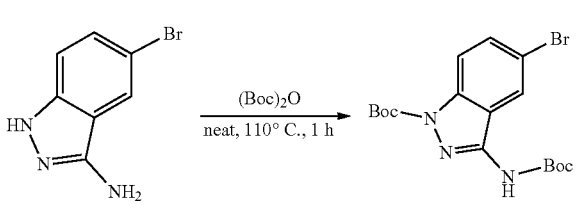 [SMILES: "(Boc)2O" ; Nc1n[nH]c2ccc(Br)cc12 ; "neat, 110° C., 1 h" ; CC(C)(C)OC(=O)Nc1nn(C(=O)OC(C)(C)C)c2ccc(Br)cc12]

The solution of 5-bromo-1H-indazol-3-amine (0.3 g, 1.41 mmol, 1 eq) in Boc$_2$O (1.9 g, 8.71 mmol, 2 mL, 6.15 eq) was heated to 110° C. and stirred at 110° C. for 1 hr. LCMS showed that the reaction was complete. The reaction mixture was concentrated in vacuo to give a residue. The residue was purified by column chromatography (SiO$_2$, PE:EtOAc=8/1 to 2/1) to afford the title compound tert-butyl 5-bromo-3-(tert-butoxy carbonylamino)indazole-1-carboxylate (0.21 g, 509.37 μmol, 36.00% yield) as a yellow oil. LC-MS (ES$^+$, m/z): 412.1 [(M+H)$^+$].

To a solution of N-[3-(4,4,5,5-tetramethyl-1,3,2-dioxaborolan-2-yl)phenyl]prop-2-en amide (0.15 g, 549.18 μmol, 1 eq) in dioxane (4 mL) and H$_2$O (1 mL) were added tert-butyl 5-bromo-3-(tert-butoxycarbonylamino)indazole-1-carboxylate (181.1 mg, 439.34 μmol, 0.8 eq), Na$_2$CO$_3$ (116.4 mg, 1.1 mmol, 2 eq), RuPhos (25.6 mg, 54.92 μmol, 0.1 eq) and [2-(2-aminophenyl)phenyl]-methylsulfonyloxy-palladium;dicyclohexyl-[2-(2,6-diisopropoxyphenyl)phenyl]phosphane (23 mg, 27.46 μmol, 0.05 eq). The reaction mixture was stirred at 80° C. for 1 hr under N$_2$. TLC (PE:EtOAc=1:1, SM Rf=0.56, Rf=0.32) showed that the reaction was complete. The reaction mixture was poured into saturated EDTA (50 mL) and EtOAc (50 mL) was added. The solution was stirred at 25° C. for 1 h and extracted with EtOAc (3×50 mL). The combined organic layers were washed with H$_2$O (2×50 mL) and brine (2×50 mL), dried over anhydrous Na$_2$SO$_4$, filtered, and concentrated in vacuo to give a residue. The residue was purified by prep-TLC (SiO$_2$, PE:EtOAc=1:1) to afford the title compound tert-butyl 3-(tert-butoxycarbonylamino)-5-[3-(prop-2-enoylamino)phenyl]indazole-1-carboxylate (0.15 g, 313.45 μmol, 57.08% yield) as a yellow oil.

Step 3—N-[3-(3-amino-1H-indazol-5-yl)phenyl]prop-2-enamide

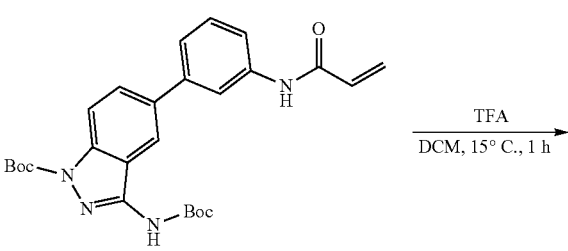

611

-continued

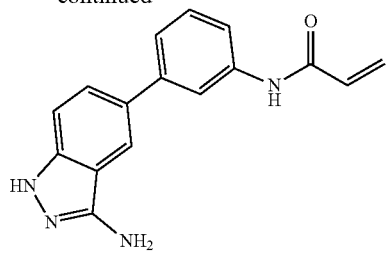

To a solution of tert-butyl 3-(tert-butoxycarbonylamino)-5-[3-(prop-2-enoylamino)phenyl]indazole-1-carboxylate (0.12 g, 250.76 μmol, 1 eq) in DCM (2 mL) was added TFA (770 mg, 6.75 mmol, 0.5 mL, 26.93 eq). The reaction mixture was stirred at 15° C. for 1 h. LCMS showed that the reaction was complete. The reaction mixture was poured into 50 mL H$_2$O and the pH was adjusted to 7 with saturated NaHCO$_3$. The mixture was extracted with EtOAc (3×50 mL). The combined organic layers were washed with H$_2$O (2×50 mL) and brine (2×50 mL), dried over anhydrous Na$_2$SO$_4$, filtered, and concentrated in vacuo to give a residue. The residue was purified by prep-HPLC (PA condition) to afford the title compound N-[3-(3-amino-1H-indazol-5-yl)phenyl]prop-2-enamide (16.3 mg, 58.57 μmol, 23.36% yield, 100.0% purity) as a white solid. LC-MS (ES$^+$, m/z): 279.1 [(M+H)$^+$] $^1$H NMR (400 MHz, DMSO-d$_6$) δ=11.49 (s, 1H), 10.21 (s, 1H), 7.96-8.04 (m, 2H), 7.58 (br d, J=7.70 Hz, 1H), 7.47-7.54 (m, 1H), 7.29-7.44 (m, 3H), 6.47 (dd, J=16.98, 10.00 Hz, 1H), 6.24-6.34 (m, 1H), 5.77 (dd, J=10.04, 1.96 Hz, 1H), 5.42 (br s, 2H).

Route 13: General Scheme

612

-continued

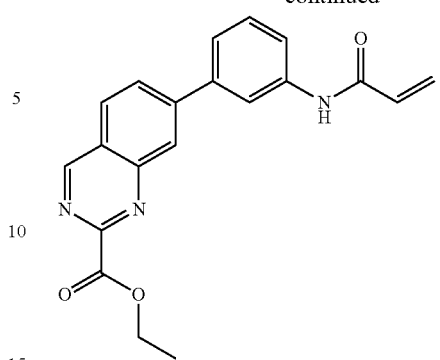

Step 1—ethyl 2-(5-bromo-2-formyl-anilino)-2-oxo-acetate

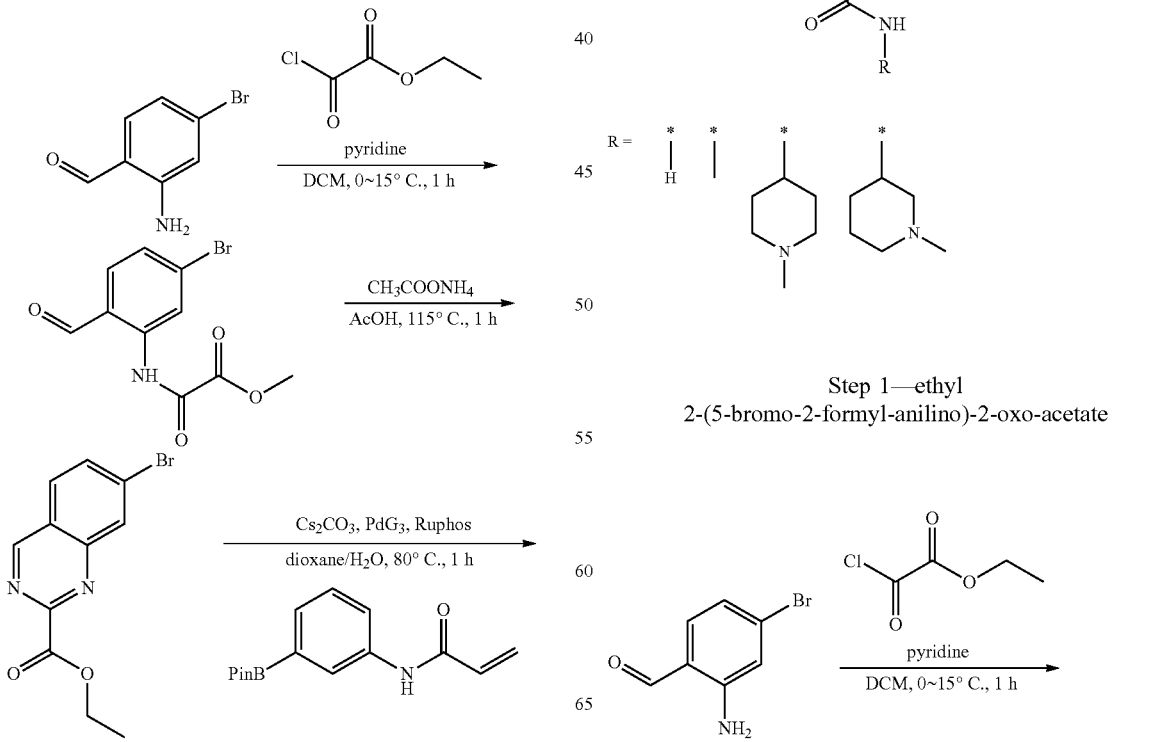

-continued

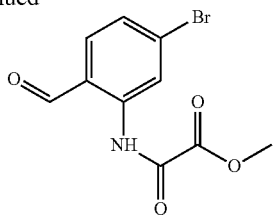

To a solution of 2-amino-4-bromo-benzaldehyde (2 g, 1 mmol, 1 eq) in DCM (20 mL) was added pyridine (2.37 g, 3 mmol, 2.42 mL, 3 eq) and ethyl 2-chloro-2-oxo-acetate (1.77 g, 13 mmol, 1.45 mL, 1.3 eq) at 0° C. The reaction mixture was stirred at 15° C. for 1 h. TLC (PE:EtOAc=4:1, SM Rf=0.41, TM Rf=0.11) showed that the reaction was complete. The reaction mixture was poured into 100 mL H$_2$O, extracted with DCM (3×100 mL). The combined organic layers were washed with H$_2$O (2×50 mL) and brine (2×50 mL), dried over anhydrous Na$_2$SO$_4$, filtered, and concentrated in vacuo to afford the title compound ethyl 2-(5-bromo-2-formyl-anilino)-2-oxo-acetate (3 g, crude) as a white solid, which was used for the next step directly without further purification.

Step 2—ethyl 7-bromoquinazoline-2-carboxylate

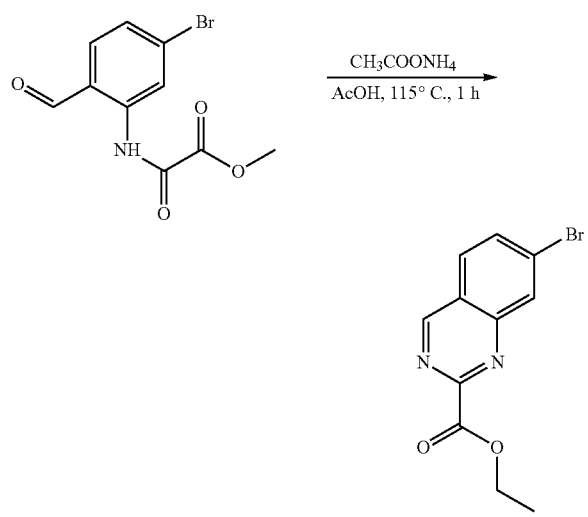

To a solution of ethyl 2-(5-bromo-2-formyl-anilino)-2-oxo-acetate (3 g, 1 mmol, 1 eq) in AcOH (90 mL) was added CH$_3$COONH$_4$ (7.71 g, 99.97 mmol, 10 eq). The reaction mixture was stirred at 115° C. for 1 h. TLC (PE:EtOAc=1:1, SM Rf=0.50, TM Rf=0.22) showed that the reaction was complete. The reaction mixture was poured into 100 mL H$_2$O. The mixture was adjusted to pH=7 with solid NaOH and extracted with DCM (3×100 mL). The combined organic layers were washed with H$_2$O (2×50 mL) and brine (2×50 mL), dried over anhydrous Na$_2$SO$_4$, filtered, and concentrated in vacuo to afford the title compound ethyl 7-bromoquinazoline-2-carboxylate (2.7 g, crude) as a white solid, which was used for the next step directly without further purification.

Step 3—ethyl 7-[3-(prop-2-enoylamino)phenyl]quinazoline-2-carboxylate

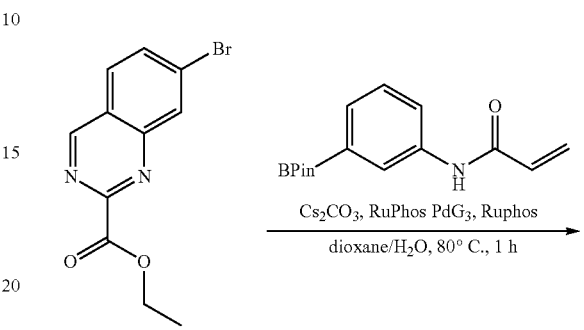

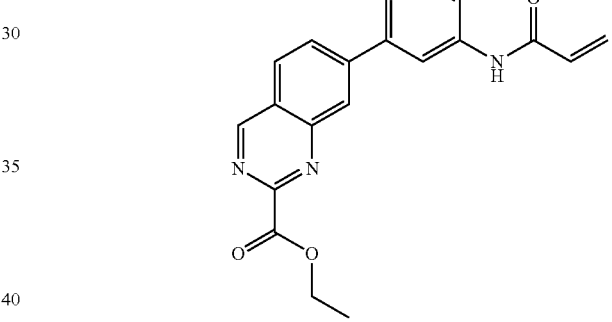

To a solution of N-[3-(4,4,5,5-tetramethyl-1,3,2-dioxaborolan-2-yl)phenyl]prop-2-en amide (0.68 g, 2.49 mmol, 1 eq) in dioxane (8 mL) and H$_2$O (2 mL) were added ethyl 7-bromoquinazoline-2-carboxylate (699.8 mg, 2.49 mmol, 1 eq), Cs$_2$CO$_3$ (1.62 g, 4.98 mmol, 2 eq), RuPhos (116.2 mg, 248.96 µmol, 0.1 eq) and [2-(2-aminophenyl)phenyl]-methylsulfonyloxy-palladium;dicyclohexyl-[2-(2,6-diisopropoxyphenyl)phenyl]phosphane (104.1 mg, 124.48 µmol, 0.05 eq). The reaction mixture was stirred at 80° C. for 1 hr under N$_2$. LCMS showed that the reaction was complete. The reaction mixture was poured into saturated EDTA (50 mL) and EtOAc (50 mL) was added. The solution was stirred at 25° C. for 1 h, extracted with EtOAc (3×100 mL). The combined organic layer was washed with H$_2$O (2×50 mL) and brine (2×50 mL), dried over anhydrous Na$_2$SO$_4$, filtered, and concentrated in vacuo to give a residue. The residue washed with EtOAc (5 mL) to afford the title compound ethyl 7-[3-(prop-2-enoylamino)phenyl]quinazoline-2-carboxylate (0.7 g, 2.02 mmol, 80.94% yield) as a white solid. LC-MS (ES$^+$, m/z): 348.1 [(M+H)$^+$].

Step 4—7-[3-(prop-2-enoylamino)phenyl]quinazoline-2-carboxylic acid

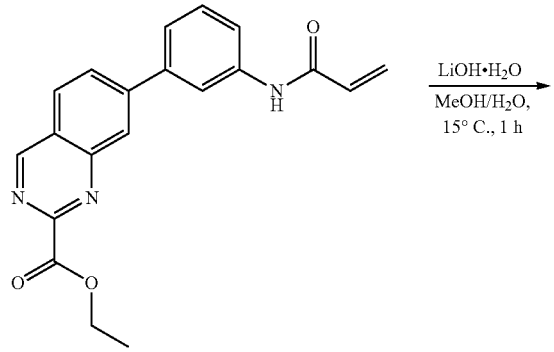

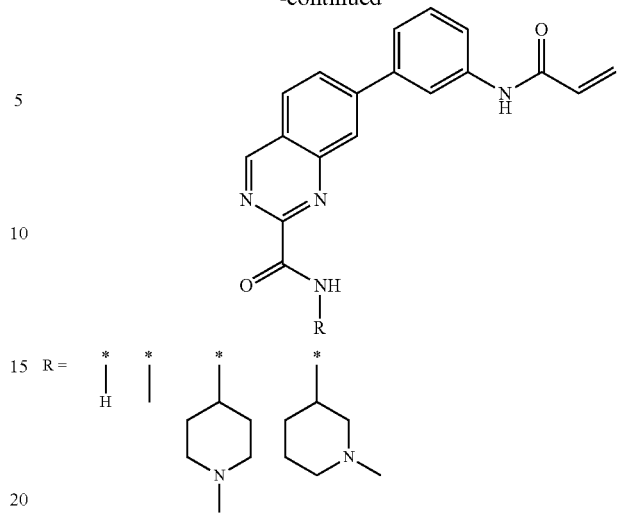

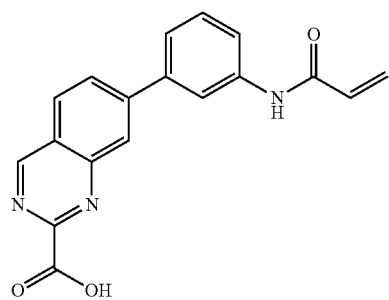

To a solution of ethyl 7-[3-(prop-2-enoylamino)phenyl]quinazoline-2-carboxylate (0.3 g, 863.64 μmol, 1 eq) in MeOH (8 mL) and H₂O (2 mL) was added LiOH·H₂O (108.7 mg, 2.59 mmol, 3 eq). The reaction mixture was stirred at 15° C. for 1 h. TLC (DCM:MeOH=10:1) showed that the reaction was complete. The reaction mixture was concentrated in vacuo to afford the title compound 7-[3-(prop-2-enoylamino)phenyl]quinazoline-2-carboxylic acid (0.35 g, crude) as a white solid which was used for the next step directly without purification.

Step 5—7-(3-acrylamidophenyl)-N—R-quinazoline-2-carboxamide

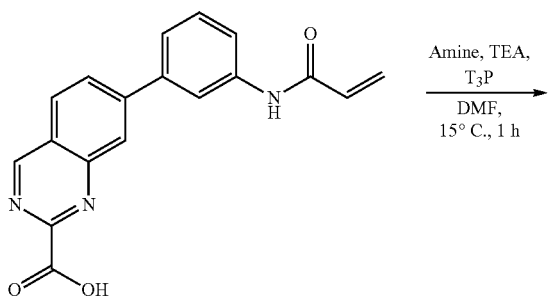

To a solution of 7-[3-(prop-2-enoylamino)phenyl]quinazoline-2-carboxylic acid (0.12 g, 375.81 μmol, 1 eq) in DMF (4 mL) were added acetic acid;ammonia (57.9 mg, 751.61 μmol, 2 eq) and TEA (190.1 mg, 1.88 mmol, 261.54 μL, 5 eq). Then, T₃P (358.7 mg, 563.71 μmol, 335.26 μL, 50% purity, 1.5 eq) was added. The reaction mixture was stirred at 15° C. for 1 h. LCMS showed that the reaction was complete. The reaction mixture was poured into 50 mL H₂O, extracted with EtOAc (3×50 mL). The combined organic layer was washed with H₂O (2×50 mL) and brine (2×50 mL), dried over anhydrous Na₂SO₄, filtered, and concentrated in vacuo to give a residue. The residue was purified by prep-HPLC (FA condition) to afford the title compound 7-[3-(prop-2-enoylamino)phenyl]quinazoline-2-carboxamide (10 mg, 30.75 μmol, 8.18% yield, 97.9% purity) as a white solid. 319.1 [(M+H)⁺], 1H NMR (400 MHz, DMSO-d6) δ=10.38 (s, 1H), 9.76 (s, 1H), 8.30-8.41 (m, 4H), 8.17 (dd, J=8.58, 1.68 Hz, 1H), 7.90 (br s, 1H), 7.71 (d, J=8.00 Hz, 1H), 7.64 (d, J=8.14 Hz, 1H), 7.54 (t, J=7.88 Hz, 1H), 6.49 (dd, J=16.96, 10.08 Hz, 1H), 6.31 (dd, J=17.00, 1.88 Hz, 1H), 5.79-5.83 (m, 1H).

Route 14: General Scheme

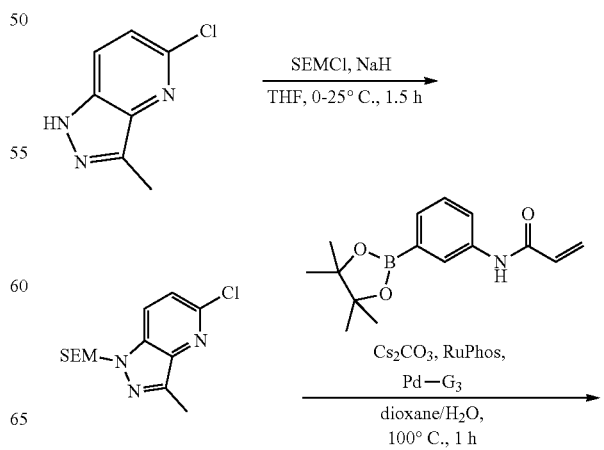

617

-continued

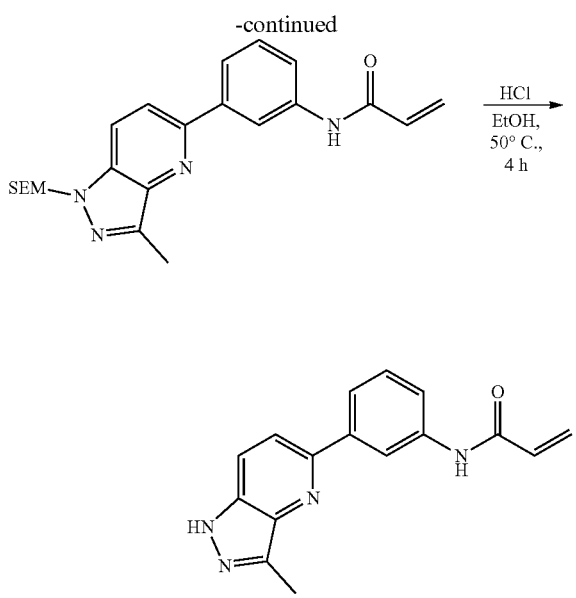

Step 1—2-[(5-chloro-3-methyl-pyrazolo[4,3-b]pyridin-1-yl) methoxy]ethyl-trimethyl-silane

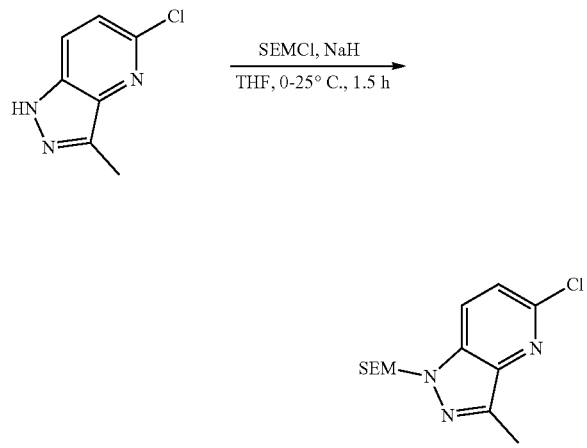 [SMILES: Cc1n[nH]c2ccc(Cl)nc12 ; Cc1nn(COCC[Si](C)(C)C)c2ccc(Cl)nc12]

To a solution of 5-chloro-3-methyl-1H-pyrazolo[4,3-b]pyridine (0.3 g, 1.79 mmol, 1 eq) in THF (3 mL), NaH (107.4 mg, 2.69 mmol, 60% purity, 1.5 eq) was added to the solution at 0° C. Then the mixture was stirred at 0° C. for 0.5 h. SEMCl (447.7 mg, 2.69 mmol, 475.21 µL, 1.5 eq) was added to the solution at 0° C. Then stirred at 25° C. for 1 h. TLC (PE:EtOAc=4:1, SM Rf=0.43, TM Rf=0.65) showed that the reaction was complete. The reaction mixture was poured into ~10 mL saturated NH₄Cl. The mixture was extracted with EtOAc (3×10 mL), washed with brine (3×15 mL), dried over anhydrous Na₂SO₄, filtered, and concentrated in vacuo. The residue was purified by column chromatography (SiO₂, PE:EtOAc=10:1 to 4:1) to afford the title compound 2-[(5-chloro-3-methyl-pyrazolo[4,3-b]pyridin-1-yl) methoxy]ethyl-trimethyl-silane (0.5 g, 1.68 mmol, 93.78% yield) as a colorless oil.

618

Step 2—N-[3-[3-methyl-1-(2-trimethylsilylethoxymethyl) pyrazolo[4,3-b]pyridin-5-yl]phenyl]prop-2-enamide

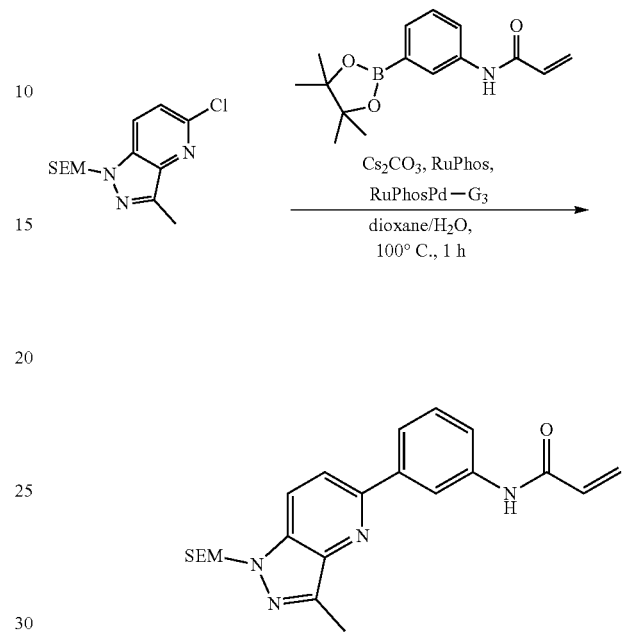

To a solution of 2-[(5-chloro-3-methyl-pyrazolo[4,3-b]pyridin-1-yl) methoxy]ethyl-trimethyl-silane (0.2 g, 671.47 µmol, 1 eq) and N-[3-(4,4,5,5-tetramethyl-1,3,2-dioxaborolan-2-yl)phenyl]prop-2-enamide (183.4 mg, 671.47 µmol, 1 eq) in dioxane (2 mL) and H₂O (0.5 mL) were added Cs₂CO₃ (656.3 mg, 2.01 mmol, 3 eq), RuPhos (31.3 mg, 67.15 µmol, 0.1 eq) and RuPhos Pd G3 (28.1 mg, 33.57 µmol, 0.05 eq). The mixture was stirred at 100° C. for 1 hr under N₂. The reaction was poured into ~15 mL saturated EDTA and stirred at 25° C. for 1 h. The mixture was extracted with EtOAc (3×10 mL), washed with brine (3×20 mL), dried over anhydrous Na₂SO₄, filtered, and concentrated in vacuo. The residue was purified by prep-TLC (SiO₂, PE:EtOAc=1:1) to afford the title compound N-[3-[3-methyl-1-(2-trimethyl silylethoxy methyl) pyrazolo[4,3-b]pyridin-5-yl]phenyl]prop-2-enamide (0.25 g, 611.89 µmol, 91.13% yield) as a yellow oil. LC-MS (ES⁺, m/z): 409.2 [(M+H)⁺].

Step 3—N-[3-(3-methyl-1H-pyrazolo[4,3-b]pyridin-5-yl)phenyl]prop-2-enamide

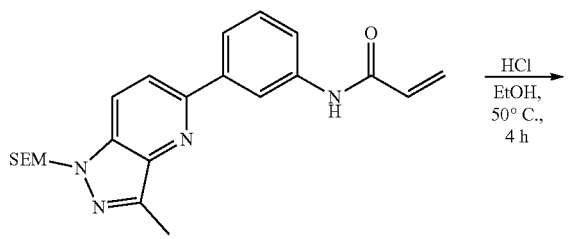

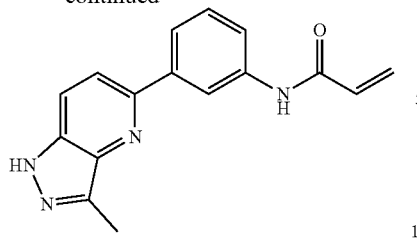

To a solution of N-[3-[3-methyl-1-(2-trimethylsilylethoxymethyl) pyrazolo[4,3-b]pyridin-5-yl]phenyl]prop-2-enamide (0.15 g, 367.14 μmol, 1 eq) in EtOH (2 mL) was added concentrated HCl (1.02 g, 10.35 mmol, 1 mL, 37% purity, 28.19 eq), and the mixture was stirred at 50° C. for 4 hr. The reaction was poured into ~10 mL ice water and saturated NaHCO$_3$ was added to adjust the pH to 7. The mixture was extracted with EtOAc (3×10 mL), washed with brine (3×30 mL), dried over anhydrous Na$_2$SO$_4$, filtered, and concentrated in vacuo. The residue was purified by prep-HPLC to afford the title compound N-[3-(3-methyl-1H-pyrazolo[4,3-b]pyridin-5-yl)phenyl]prop-2-enamide (0.0156 g, 56.05 μmol, 15.27% yield, 100% purity) as a white solid. LC-MS (ES$^+$, m/z): 279.0 [(M+H)$^+$], 1H NMR (400 MHz, DMSO-d6) Shift=12.94 (br s, 1H), 10.32 (s, 1H), 8.41-8.35 (m, 1H), 8.02 (d, J=8.8 Hz, 1H), 7.87 (d, J=8.9 Hz, 1H), 7.86-7.77 (m, 2H), 7.45 (t, J=7.9 Hz, 1H), 6.56-6.43 (m, 1H), 6.29 (dd, J=2.0, 17.0 Hz, 1H), 5.84-5.71 (m, 1H), 2.59 (s, 3H).

Route 15: General Scheme

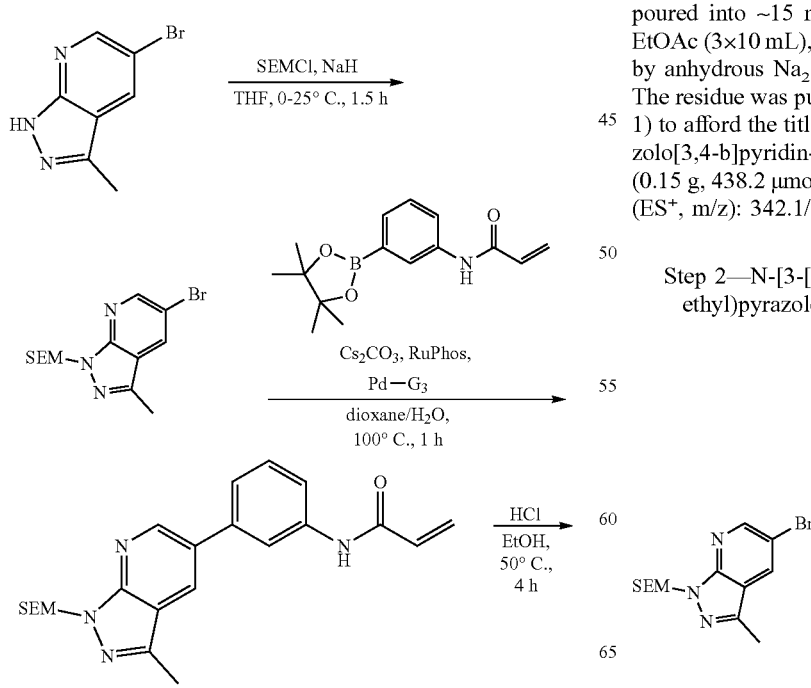

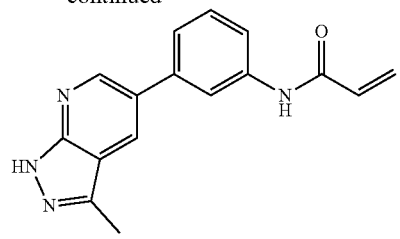

Step 1—2-[(5-bromo-3-methyl-pyrazolo[3,4-b]pyridin-1-yl) methoxy]ethyl-trimethyl-silane

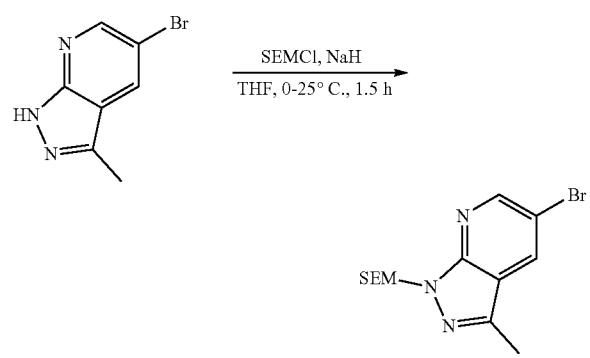

To a solution of 5-bromo-3-methyl-1H-pyrazolo[3,4-b]pyridine (0.3 g, 1.41 mmol, 1 eq) in THF (3 mL) was added NaH (84.9 mg, 2.12 mmol, 60% purity, 1.5 eq) at 0° C. under N$_2$. Then the mixture was stirred at 0° C. for 0.5 h. SEMCl (283.1 mg, 1.7 mmol, 300.48 μL, 1.2 eq) was added to the solution at 0° C. then stirred at 25° C. for 1 hr. LCMS showed that the reaction was complete. The reaction was poured into ~15 mL saturated NH$_4$Cl and extracted with EtOAc (3×10 mL), washed with brine (3×10 mL), dried over by anhydrous Na$_2$SO$_4$, filtered and concentrated in vacuo. The residue was purified by prep-TLC (SiO$_2$, PE:EtOAc=4:1) to afford the title compound 2-[(5-bromo-3-methyl-pyrazolo[3,4-b]pyridin-1-yl) methoxy]ethyl-trimethyl-silane (0.15 g, 438.2 μmol, 30.97% yield) as a white solid. LC-MS (ES$^+$, m/z): 342.1/344.1 [(M+H)$^+$].

Step 2—N-[3-[3-methyl-1-(2-trimethylsilylethoxymethyl)pyrazolo[3,4-b]pyridin-5-yl]phenyl]prop-2-enamide

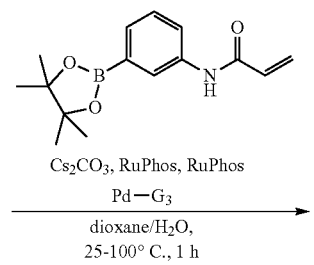

-continued

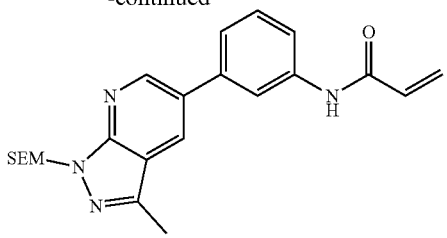

To a solution of 2-[(5-bromo-3-methyl-pyrazolo[3,4-b]pyridin-1-yl) methoxy]ethyl-trimethyl-silane (0.08 g, 233.71 μmol, 1 eq) and N-[3-(4,4,5,5-tetramethyl-1,3,2-dioxaborolan-2-yl)phenyl]prop-2-enamide (76.6 mg, 280.45 μmol, 1.2 eq) in dioxane (2 mL) and H₂O (0.5 mL) were added Cs₂CO₃ (228.4 mg, 701.13 μmol, 3 eq), RuPhos (10.9 mg, 23.37 μmol, 0.1 eq) and RuPhos Pd G3 (19.6 mg, 23.37 μmol, 0.1 eq) at 25° C. The mixture was stirred at 100° C. for 1 h under N₂. TLC (PE:EtOAc=1:1, SM Rf=0.49, TM Rf=0.01) showed that the reaction was complete. The reaction was poured into ~15 mL saturated EDTA and stirred at 25° C. for 1 h. The mixture was extracted with EtOAc (3×10 mL), washed with brine (3×20 mL), dried over anhydrous Na₂SO₄, filtered, and concentrated in vacuo. The residue was purified by prep-TLC (SiO₂, PE:EtOAc=1:1) to afford the title compound N-[3-[3-methyl-1-(2-trimethylsilylethoxymethyl) pyrazolo[3,4-b]pyridin-5-yl]phenyl]prop-2-enamide (0.08 g, 195.81 μmol, 83.78% yield) as a brown oil.

Step 3—N-[3-(3-methyl-1H-pyrazolo[3,4-b]pyridin-5-yl)phenyl]prop-2-enamide

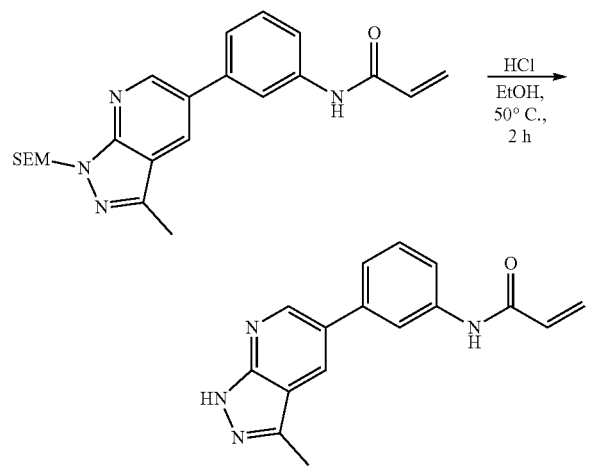

To a solution of N-[3-[3-methyl-1-(2-trimethylsilylethoxymethyl) pyrazolo[3,4-b]pyridin-5-yl]phenyl]prop-2-enamide (0.1 g, 244.76 μmol, 1 eq) in EtOH (4 mL) was added concentrated HCl (2.04 g, 20.7 mmol, 2 mL, 37% purity, 84.58 eq) and the mixture was stirred at 50° C. for 2 hr. The reaction was poured into 10 mL saturated NaHCO₃ to adjust the pH to 8. The mixture was extracted with EtOAc (3×15 mL), washed with brine (3×30 mL), dried over by anhydrous Na₂SO₄, filtered, and concentrated in vacuo. The residue was purified by prep-HPLC (neutral condition) to afford the title compound N-[3-(3-methyl-1H-pyrazolo[3,4-b]pyridin-5-yl)phenyl]prop-2-enamide (0.025 g, 88.12 μmol, 36.00% yield, 98.1% purity) as a white solid. LC-MS (ES⁺, m/z): 279.0 [(M+H)⁺], 1H NMR (400 MHz, DMSO-d6) Shift=13.29 (s, 1H), 10.28 (s, 1H), 8.75 (d, J=2.2 Hz, 1H), 8.40 (d, J=2.2 Hz, 1H), 8.03 (s, 1H), 7.69 (dd, J=2.6, 5.9 Hz, 1H), 7.49-7.42 (m, 2H), 6.57-6.36 (m, 1H), 6.35-6.19 (m, 1H), 5.93-5.65 (m, 1H), 2.55 (s, 3H).

Route 16: General Scheme

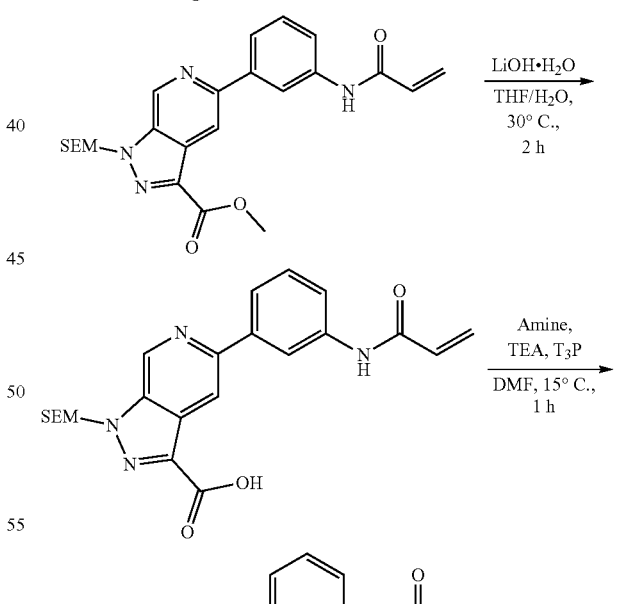

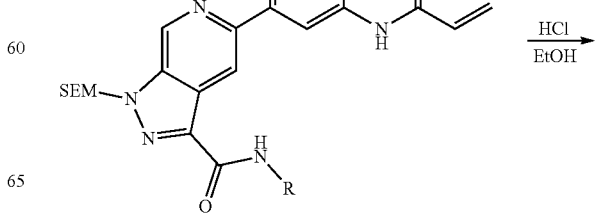

-continued

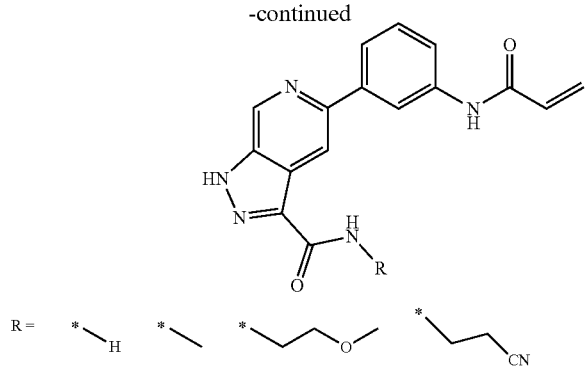

Step 1—Methyl 5-(3-aminophenyl)-1-((2-(trimethylsilyl)ethoxy)methyl)-1H-pyrazolo[3,4-c]pyridine-3-carboxylate

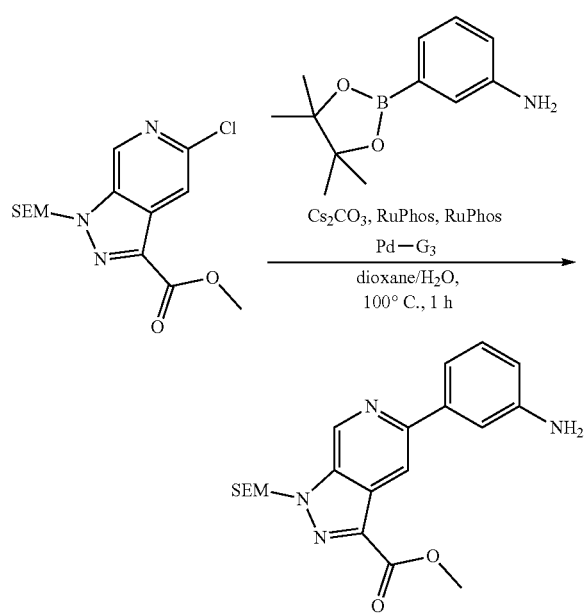

To a solution of methyl 5-chloro-1-(2-trimethylsilylethoxymethyl) pyrazolo[3,4-c]pyridine-3-carboxylate (0.9 g, 2.63 mmol, 1 eq) and 3-(4,4,5,5-tetramethyl-1,3,2-dioxaborolan-2-yl)aniline (634.5 mg, 2.9 mmol, 1.1 eq) in dioxane (8 mL) and H₂O (2 mL) were added RuPhos (122.9 mg, 263.26 µmol, 0.1 eq), Cs₂CO₃ (2.57 g, 7.9 mmol, 3 eq) and [2-(2-aminophenyl)phenyl]-methylsulfonyloxy-palladium;dicyclohexyl-[2-(2,6-diisopropoxyphenyl)phenyl] phosphane (110.1 mg, 131.63 µmol, 0.05 eq) at 25° C. under N₂. The reaction mixture was stirred at 100° C. for 1 h. The reaction mixture was poured into saturated EDTA (20 mL) and stirred for 20 min. The mixture was extracted with EtOAc (2×20 mL). The combined organic layer was washed with brine (2×20 mL), dried over anhydrous Na₂SO₄, filtered, and concentrated in vacuo to give a residue. The residue was purified by column chromatography (SiO₂, PE:EtOAc=10:1 to 1/1) to afford the title compound methyl 5-(3-aminophenyl)-1-((2-(trimethylsilyl)ethoxy)methyl)-1H-pyrazolo[3,4-c]pyridine-3-carboxylate (760 mg, 1.91 mmol, 72.44% yield) as a yellow oil.

Step 2—methyl 5-[3-(prop-2-enoylamino)phenyl]-1-(2-trimethylsilylethoxy methyl)pyrazolo[3,4-c]pyridine-3-carboxylate

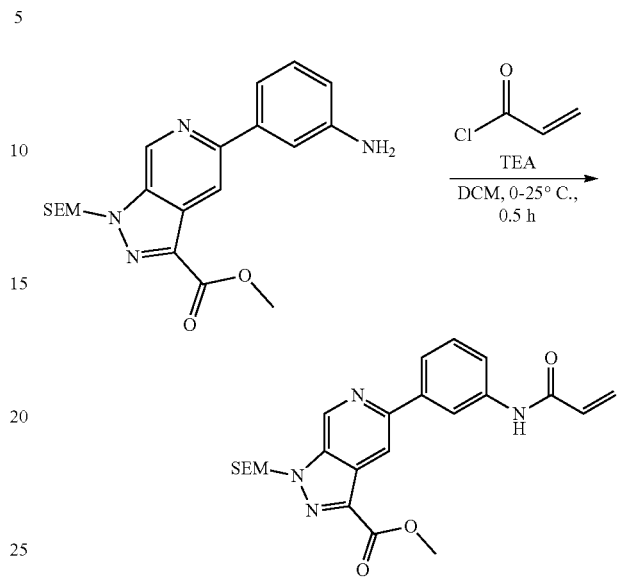

To a solution of methyl 5-(3-aminophenyl)-1-(2-trimethylsilyl ethoxymethyl)pyrazolo[3,4-c]pyridine-3-carboxylate (660 mg, 1.66 mmol, 1 eq) in DCM (7 mL) was added TEA (502.7 mg, 4.97 mmol, 691.52 µL, 3 eq) at 0° C. Then, prop-2-enoyl chloride (299.8 mg, 3.31 mmol, 270.07 µL, 2 eq) was added. The reaction mixture was stirred at 25° C. for 0.5 h. Upon completion of the reaction as indicated by LCMS and TLC. The reaction mixture was poured into water (20 mL) and extracted with DCM (2×30 mL). The combined organic layer was washed with brine (2×30 mL), dried over anhydrous Na₂SO₄, filtered, and concentrated in vacuo to afford a residue. The residue was purified by column chromatography (SiO₂, PE:EtOAc=10:1 to 1/1) to afford the title compound methyl 5-[3-(prop-2-enoylamino)phenyl]-1-(2-trimethylsilylethoxy methyl)pyrazolo[3,4-c]pyridine-3-carboxylate (760 mg, crude) as a yellow oil. TLC (PE:EtOAc=1:1, SM=0.45, TM=0.49), LC-MS (ES⁺, m/z): 453.1 [(M+H)⁺].

Step 3—5-[3-(prop-2-enoylamino)phenyl]-1-(2-trimethylsilylethoxymethyl)pyrazolo[3,4-c]pyridine-3-carboxylic acid

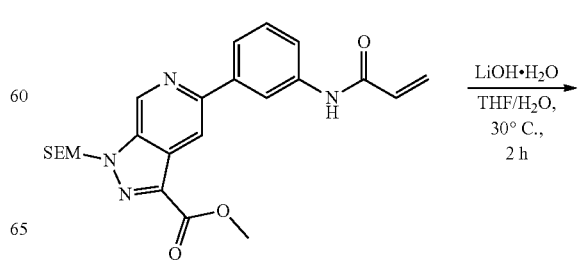

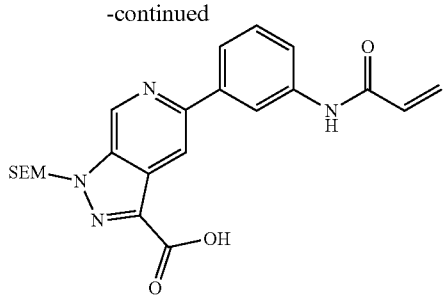

To a solution of methyl 5-[3-(prop-2-enoylamino)phenyl]-1-(2-trimethylsilyl ethoxymethyl) pyrazolo[3,4-c]pyridine-3-carboxylate (610 mg, 1.35 mmol, 1 eq) in THF (12 mL) and H₂O (3 mL) was added LiOH·H₂O (565.6 mg, 13.48 mmol, 10 eq). The resulting reaction mixture was stirred at 30° C. for 2 h. The reaction mixture was poured into water (20 mL), extracted with EtOAc (2×20 mL). The combined organic layer was washed with brine (2×20 mL), dried over anhydrous Na₂SO₄, filtered, and concentrated in vacuo to afford the title compound 5-[3-(prop-2-enoylamino)phenyl]-1-(2-trimethylsilylethoxymethyl)pyrazolo[3,4-c]pyridine-3-carboxylic acid (830 mg, crude) as a yellow solid.

Step 4—N-methyl-5-[3-(prop-2-enoylamino)phenyl]-1-(2-trimethylsilyl ethoxymethyl) pyrazolo[3,4-c]pyridine-3-carboxamide


To a solution of 5-[3-(prop-2-enoylamino)phenyl]-1-(2-trimethylsilyl ethoxymethyl) pyrazolo[3,4-c]pyridine-3-carboxylic acid (70 mg, 159.62 μmol, 1 eq) in DMF (2 mL) were added methanamine;hydrochloride (32.3 mg, 478.85 μmol, 3 eq) and TEA (80.8 mg, 798.08 μmol, 111.08 μL, 5 eq). Then, T₃P (152.4 mg, 239.42 μmol, 142.39 μL, 50% purity, 1.5 eq) was added. The reaction mixture was stirred at 15° C. for 1 h. TLC (DCM:MeOH=10:1, SM Rf=0.04, TM Rf=0.36) showed that the reaction was complete. The reaction mixture was poured into 10 mL H₂O, extracted with EtOAc (3×50 mL). The combined organic layers were washed with H₂O (2×50 mL) and brine (2×50 mL), dried over anhydrous Na₂SO₄, filtered, and concentrated in vacuo to give a residue. The residue was purified by prep-TLC (SiO₂, DCM:MeOH=10:1) to afford the title compound N-methyl-5-[3-(prop-2-enoylamino)phenyl]-1-(2-trimethylsilyl ethoxymethyl) pyrazolo[3,4-c]pyridine-3-carboxamide (60 mg, 132.86 μmol, 83.24% yield) as a yellow oil.

Step 5—5-[3-(prop-2-enoylamino)phenyl]-1H-pyrazolo[3,4-c]pyridine-3-carboxamide

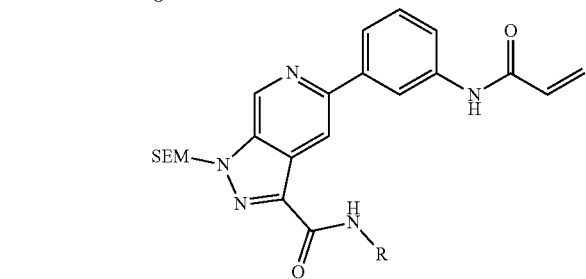

To a solution of 5-[3-(prop-2-enoylamino)phenyl]-1-(2-trimethylsilyl ethoxymethyl) pyrazolo[3,4-c]pyridine-3-carboxamide (50 mg, 114.27 μmol, 1 eq) in EtOH (1 mL) was added concentrated HCl (0.5 mL, 37% purity). The reaction mixture was heated to 50° C. and stirred at 50° C. for 2.5 h. LCMS showed that the reaction was complete. The reaction was concentrated under N₂ to give the residue. The residue was purified by prep-HPLC to afford the title compound 5-[3-(prop-2-enoylamino)phenyl]-1H-pyrazolo[3,4-c]pyridine-3-carboxamide (8.6 mg, 26.56 μmol, 23.24% yield, 94.9% purity) as a white solid. 308.0 [(M+H)⁺], 1H NMR (400 MHz, DMSO-d6), δ ppm 5.58 (1H, s), 5.68-5.84 (1H, m), 6.30 (1H, dd, J=16.8, 1.87 Hz), 6.47 (1H, dd, J=16.8, 10.14 Hz), 7.25 (1H, s), 7.45 (1H, t, J=8.0 Hz), 7.56 (1H, br s), 7.76-7.87 (2H, m), 7.94 (1H, br s), 8.05-8.26 (1H, m), 8.39 (1H, s), 8.45-8.58 (1H, m), 9.20 (1H, s), 10.31 (1H, s), 14.17 (1H, br s).

Route 17: General Scheme

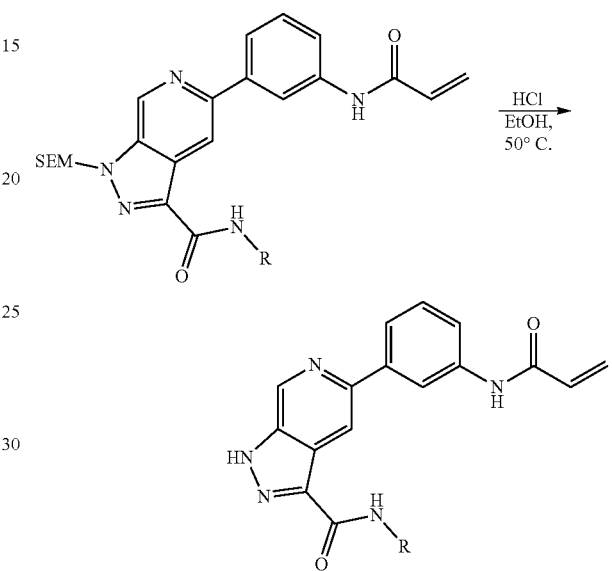

-continued

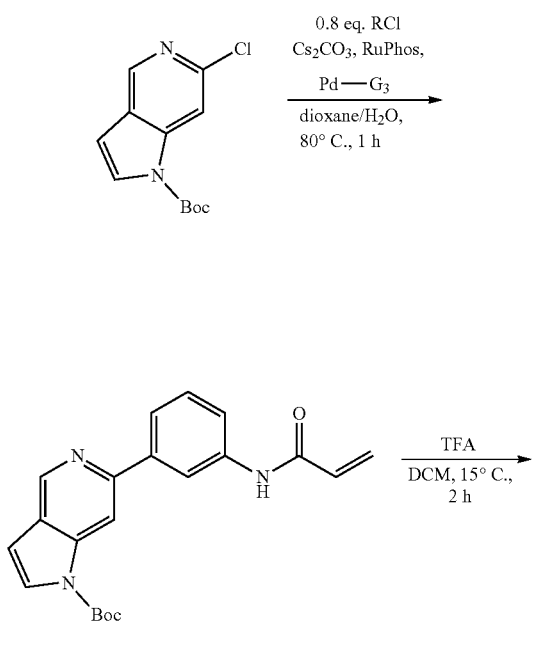

Step 1—tert-butyl 6-chloropyrrolo[3,2-c]pyridine-1-carboxylate

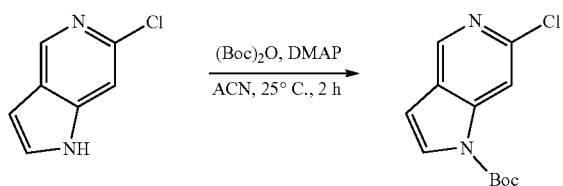 [SMILES: Clc1cc2[nH]ccc2cn1 ; CC(C)(C)OC(=O)n1ccc2cnc(Cl)cc21]

To a solution of 6-chloro-1H-pyrrolo[3,2-c]pyridine (0.2 g, 1.31 mmol, 1 eq) in ACN (6 mL) was added Boc$_2$O (343.3 mg, 1.57 mmol, 361.36 μL, 1.2 eq) and DMAP (192.2 mg, 1.57 mmol, 1.2 eq). The reaction mixture was stirred at 25° C. for 2 hr. TLC (PE:EtOAc=4:1, SM Rf=0.12, TM Rf=0.35) showed that the reaction was complete. The reaction mixture was concentrated in vacuo to give a residue. The residue was purified by prep-TLC (SiO$_2$, PE:EtOAc=4:1) to afford the title compound tert-butyl 6-chloropyrrolo[3,2-c]pyridine-1-carboxylate (0.24 g, 949.76 μmol, 72.46% yield) as a white solid.

Step 2—tert-butyl 6-[3-(prop-2-enoylamino)phenyl]pyrrolo[3,2-c]pyridine-1-carboxylate

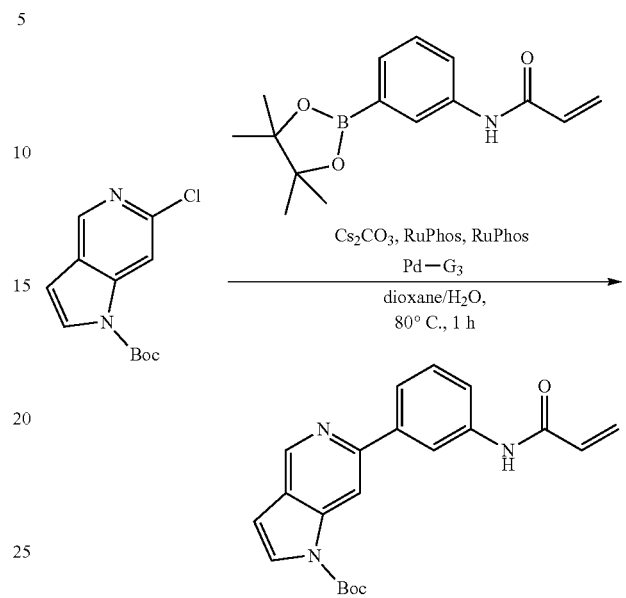

To a solution of N-[3-(4,4,5,5-tetramethyl-1,3,2-dioxaborolan-2-yl)phenyl]prop-2-en amide (0.15 g, 549.18 μmol, 1 eq) in dioxane (4 mL) and H$_2$O (1 mL) were successively added tert-butyl 6-chloropyrrolo[3,2-c]pyridine-1-carboxylate (111 mg, 439.34 μmol, 0.8 eq), Cs$_2$CO$_3$ (357.9 mg, 1.1 mmol, 2 eq), RuPhos (25.6 mg, 54.92 μmol, 0.1 eq) and [2-(2-aminophenyl)phenyl]-methylsulfonyloxy-palladium; dicyclohexyl-[2-(2,6-diisopropoxyphenyl)phenyl]phosphane (23 mg, 27.46 μmol, 0.05 eq). The reaction mixture was stirred at 80° C. for 1 hr under N$_2$. TLC (PE:EtOAc=1:1, SM Rf=0.56, TM Rf=0.26) showed that the reaction was complete. The reaction mixture poured into saturated EDTA (50 mL) and EtOAc (50 mL) was added. The solution was stirred at 25° C. for 1 h. The mixture was extracted with EtOAc (3×100 mL). The combined organic layer was washed with H$_2$O (2×50 mL) and brine (2×50 mL), dried over anhydrous Na$_2$SO$_4$, filtered, and concentrated in vacuo to give a residue. The residue was purified by prep-TLC (SiO$_2$, PE:EtOAc=1:1) to afford the title compound tert-butyl 6-[3-(prop-2-enoylamino)phenyl]pyrrolo[3,2-c]pyridine-1-carboxylate (0.15 g, 412.76 μmol, 75.16% yield) as a yellow oil.

Step 3—N-[3-(1H-pyrrolo[3,2-c]pyridin-6-yl)phenyl]prop-2-enamide

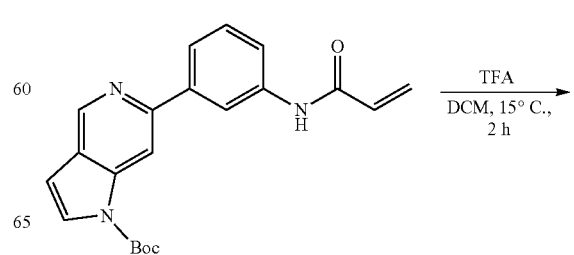

629

-continued

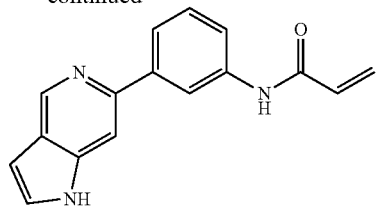

To a solution of tert-butyl 6-[3-(prop-2-enoylamino)phenyl]pyrrolo[3,2-c]pyridine-1-carboxylate (0.12 g, 330.21 µmol, 1 eq) in DCM (2 mL) was added TFA (3.08 g, 27.01 mmol, 2 mL, 81.80 eq). The mixture was stirred at 15° C. for 2 h. LCMS showed that the reaction was complete. The reaction mixture was poured into 50 mL $H_2O$ and adjusted to pH=7 with saturated $NaHCO_3$, extracted with EtOAc (2×50 mL). The combined organic layers were washed with $H_2O$ (2×50 mL) and brine (2×50 mL), dried over anhydrous $Na_2SO_4$, filtered, and concentrated in vacuo to give a residue. The residue was purified by prep-HPLC (FA condition) to afford the title compound N-[3-(1H-pyrrolo[3,2-c]pyridin-6-yl)phenyl]prop-2-enamide (9.6 mg, 36.46 µmol, 11.04% yield, 100% purity) as a white solid. LC-MS (ES+, m/z): 264.1 [(M+H)+] $^1$H NMR (400 MHz, DMSO-$d_6$) δ=12.22 (br s, 1H), 10.37 (s, 1H), 9.10 (s, 1H), 8.39 (s, 1H), 8.00 (s, 1H), 7.67-7.78 (m, 3H), 7.48-7.55 (m, 1H), 6.84 (br s, 1H), 6.49 (dd, 7=16.98, 10.00 Hz, 1H), 6.30 (dd, J=16.98, 1.96 Hz, 1H), 5.78-5.83 (m, 1H).

Route 18: General Scheme

630

-continued

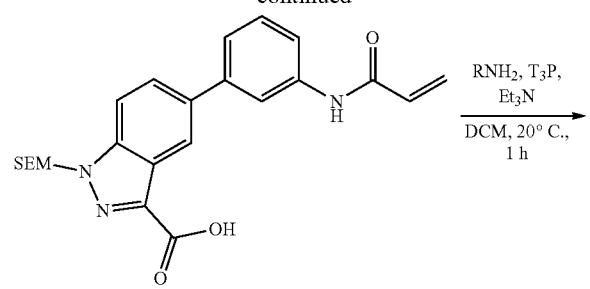

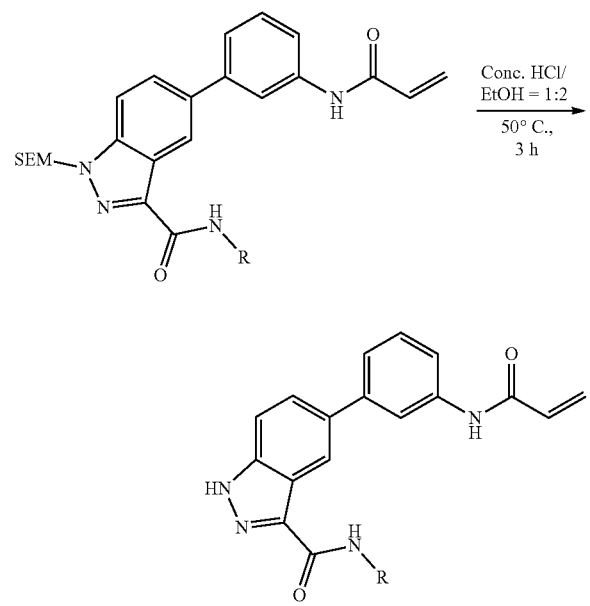

R = 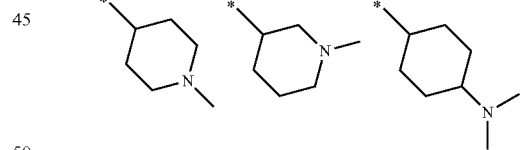

Step 1—5-bromo-1-(2-trimethylsilylethoxymethyl) indazole-3-carboxylate

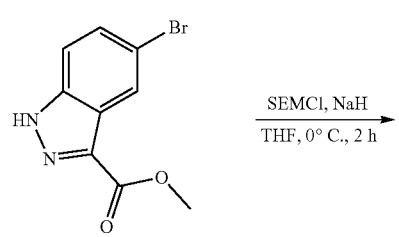

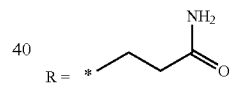

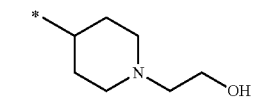

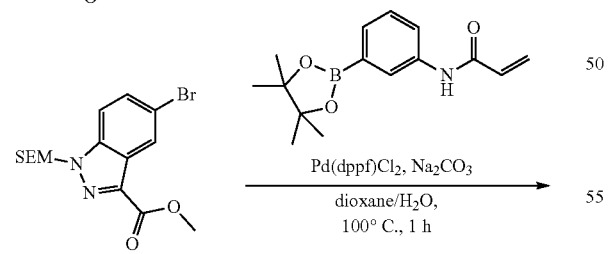

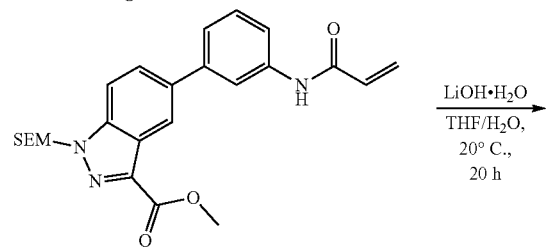

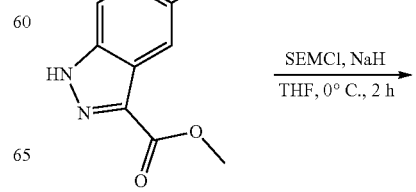

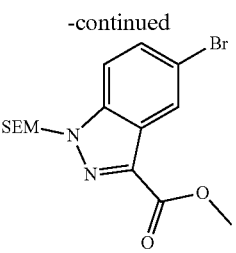

To a solution of methyl 5-bromo-1H-indazole-3-carboxylate (2 g, 7.84 mmol, 1 eq) and 2-(chloromethoxy)ethyl-trimethyl-silane (1.57 g, 9.41 mmol, 1.67 mL, 1.2 eq) in THF (30 mL) was added NaH (470.4 mg, 11.76 mmol, 60% purity, 1.5 eq) at 0° C. under N₂. The reaction mixture was stirred at 0° C. for 2 hours. The reaction was quenched by 20 mL saturated NH₄Cl, extracted with EtOAc (3×30 mL), and the combined organic layer was washed with brine (2×20 mL), dried over Na₂SO₄, filtered, and concentrated in vacuo to afford a residue. The residue was purified by column chromatography (SiO₂, PE:EtOAc=4:1 to 2:1) to afford the title compound methyl 5-bromo-1-(2-trimethylsilyl ethoxymethyl) indazole-3-carboxylate (2.1 g, 5.45 mmol, 69.50% yield) as a white solid. LC-MS (ES⁺, m/z): 385.0/386.9 [(M+H)⁺].

Step 2—methyl 5-[3-(prop-2-enoylamino)phenyl]-1-(2-trimethylsilylethoxymethyl) indazole-3-carboxylate

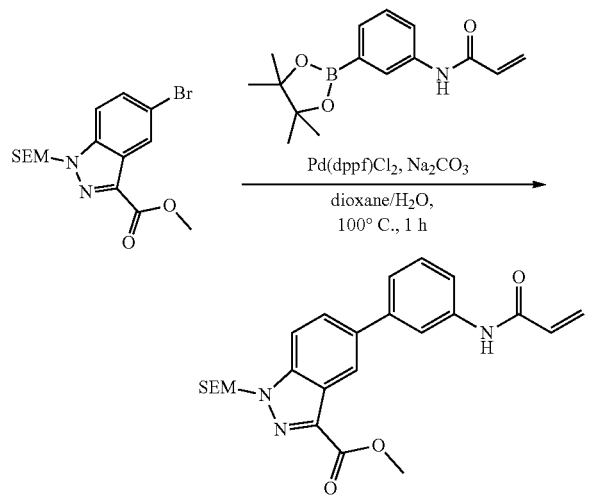

To a solution of N-[3-(4,4,5,5-tetramethyl-1,3,2-dioxaborolan-2-yl)phenyl]prop-2-enamide (354.4 mg, 1.3 mmol, 1 eq) and methyl 5-bromo-1-(2-trimethylsilylethoxymethyl) indazole-3-carboxylate (500 mg, 1.3 mmol, 1 eq) in dioxane (8 mL) and H₂O (2 mL) was added Na₂CO₃ (412.6 mg, 3.89 mmol, 3 eq) and Pd(dppf)Cl₂ (95 mg, 129.76 μmol, 0.1 eq) under N₂. The reaction mixture was stirred at 100° C. for 1 h. TLC showed that the reaction was complete. The reaction mixture was poured into saturated EDTA (40 mL) and 20 mL EtOAc was added. The solution was stirred for 1 h. After that the aqueous phase was extracted with EtOAc (3×20 mL). The combined organic layer was washed with brine (3×30 mL), dried anhydrous Na₂SO₄, filtered, and concentrated in vacuo to afford a residue. After column chromatography (SiO₂, PE:EtOAc=3:1 to 1:1) to afford the title compound methyl 5-[3-(prop-2-enoylamino)phenyl]-1-(2-trimethylsilylethoxymethyl)indazole-3-carboxylate (900 mg, 1.99 mmol) as a yellow solid. LC-MS (ES⁺, m/z): 452.0 [(M+H)⁺].

Step 3—5-[3-(prop-2-enoylamino)phenyl]-1-(2-trimethylsilylethoxymethyl)indazole-3-carboxylic acid To a solution of methyl 5-[3-(prop-2-enoylamino)phenyl]-1-(2-trimethylsilylethoxymethyl) indazole-3-carboxylate (450 mg, 996.48 μmol, 1 eq) in THF (8 mL) and H₂O (2 mL) was added LiOH·H₂O (418.2 mg, 9.96 mmol, 10 eq). The reaction mixture was stirred at 20° C. for 20 hours. LCMS showed that the reaction was complete. The reaction was poured into 40 mL water, adjusting the pH=6 with saturated critic acid. Then the aqueous phase was extracted with EtOAc (3×30 mL), and the combined organic layer was washed with brine (2×20 mL), dried over Na₂SO₄, filtered, and concentrated in vacuo to afford the title compound 5-[3-(prop-2-enoylamino)phenyl]-1-(2-trimethylsilylethoxymethyl)indazole-3-carboxylic acid (320 mg, crude) as a yellow gum. LC-MS (ES⁺, m/z): 438.0 [(M+H)⁺].

Step 4—N-[1-(2-hydroxyethyl)-4-piperidyl]-5-[3-(prop-2-enoylamino)phenyl]-1-(2-trimethylsilylethoxymethyl)indazole-3-carboxamide

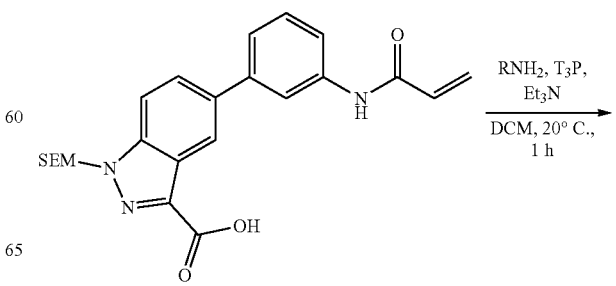

633

-continued

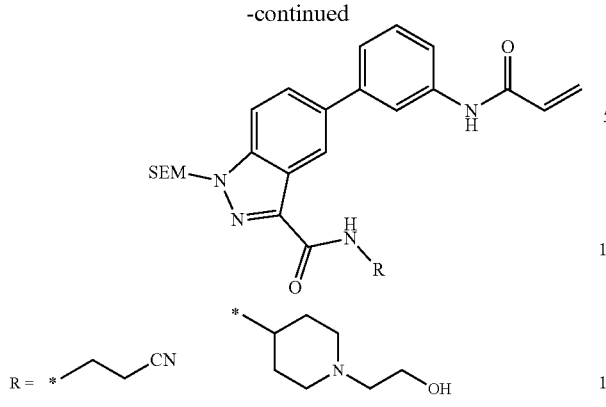

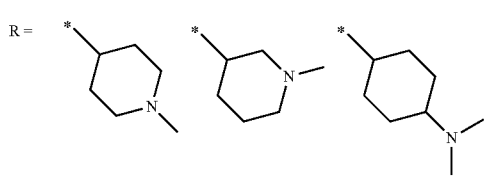

To a solution of 5-[3-(prop-2-enoylamino)phenyl]-1-(2-trimethylsilylethoxymethyl)indazole-3-carboxylic acid (100 mg, 228.54 µmol, 1 eq) and 3-aminopropanenitrile (24 mg, 342.81 µmol, 25.29 µL, 1.5 eq) in DCM (2 mL) was added Et₃N (115.6 mg, 1.14 mmol, 159.05 µL, 5 eq) T₃P (218.2 mg, 342.81 µmol, 203.88 µL, 50% purity, 1.5 eq) under N₂. The reaction mixture was stirred at 20° C. for 1 h. The reaction mixture was poured into 40 mL water, extracted with EtOAc (3×20 mL). The combined organic layer was washed with brine (3×30 mL), dried over anhydrous Na₂SO₄, filtered, and concentrated in vacuo to afford a residue. The residue was purified by prep-TLC (SiO₂, DCM:MeOH=10:1) to afford the title compound N-(2-cyanoethyl)-5-[3-(prop-2-enoylamino)phenyl]-1-(2-trimethylsilylethoxymethyl)indazole-3-carboxamide (70 mg, 142.96 µmol, 62.55% yield) as a yellow gum. LC-MS (ES⁺, m/z): 507.1 [(M+H)⁺].

Step 5—N-[1-(2-hydroxyethyl)-4-piperidyl]-5-[3-(prop-2-enoylamino)phenyl]-1H-indazole-3-carboxamide

634

-continued

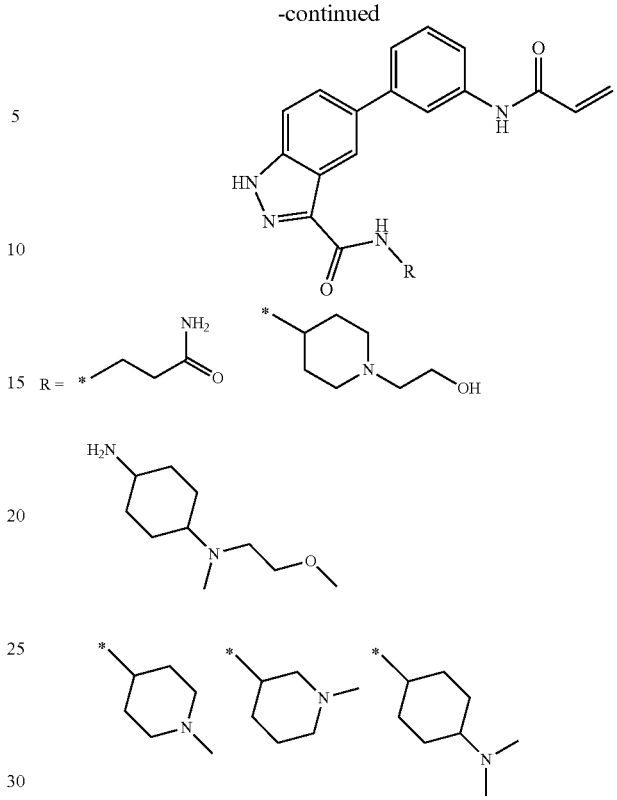

To a solution of N-[1-(2-hydroxyethyl)-4-piperidyl]-5-[3-(prop-2-enoyl amino)phenyl]-1-(2-trimethylsilylethoxymethyl)indazole-3-carboxamide (60 mg, 106.43 µmol, 1 eq) in EtOH (2 mL) was added concentrated HCl (1.02 g, 10.35 mmol, 1 mL, 37% purity, 97.26 eq) under N₂. The reaction mixture was stirred at 50° C. for 3 hours. The solvent was removed by blowing with N₂ to give the residue. The residue was purified by prep-HPLC (PA condition) to afford the title compound N-[1-(2-hydroxyethyl)-4-piperidyl]-5-[3-(prop-2-enoylamino)phenyl]-1H-indazole-3-carboxamide (6.8 mg, 15.14 µmol, 14.22% yield, 96.5% purity) as a white solid. 434.2. 1H NMR (400 MHz, DMSO-d6) δ=13.63 (br s, 1H), 10.27 (s, 1H), 8.41 (s, 1H), 8.22 (br d, J=8.0 Hz, 1H), 8.17 (s, 1H), 8.06 (s, 1H), 7.74-7.65 (m, 3H), 7.48-7.38 (m, 2H), 6.53-6.42 (m, 1H), 6.34-6.24 (m, 1H), 5.78 (br d, J=12.0 Hz, 1H), 3.84 (br s, 1H), 3.51 (br t, J=6.4 Hz, 2H), 2.92 (br d, J=11.6 Hz, 2H), 2.11 (br t, J=11.6 Hz, 2H), 1.77 (br s, 2H), 1.74-1.63 (m, 2H)

Step 3—N-[4-[2-methoxyethyl(methyl)amino]cyclohexyl]-5-[3-(prop-2-enoylamino)phenyl]-1H-indazole-3-carboxamide

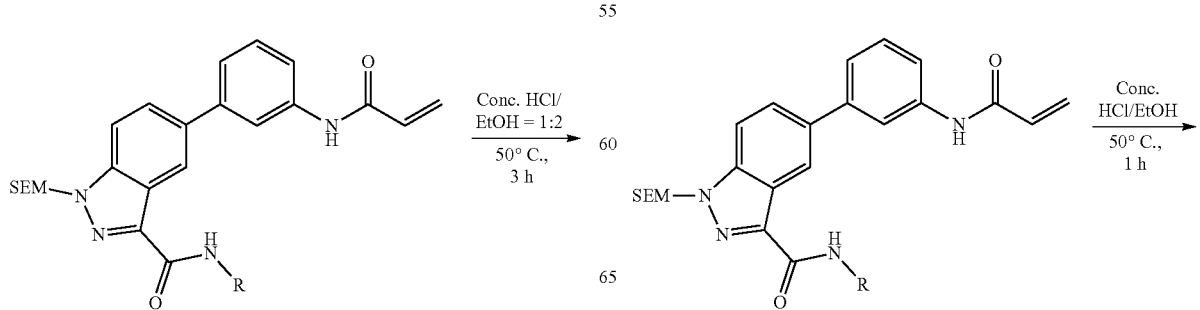

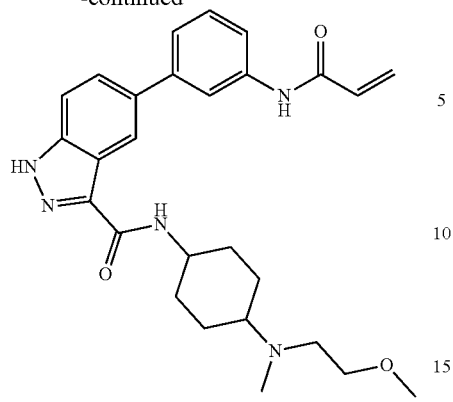

To a solution of N-[4-[2-methoxyethyl(methyl)amino]cyclohexyl]-5-[3-(prop-2-enoylamino)phenyl]-1-(2-trimethylsilylethoxymethyl)indazole-3-carboxamide (0.08 g, 132.05 μmol, 1 eq) in EtOH (0.3 mL) was added concentrated HCl (102 mg, 1.04 mmol, 0.1 mL, 37% purity, 7.84 eq). The reaction mixture was stirred at 50° C. for 1 hr. The reaction was concentrated under $N_2$ to give a residue. The residue was purified by prep-HPLC (FA condition) to afford the title compound N-[4-[2-methoxyethyl(methyl)amino]cyclohexyl]-5-[3-(prop-2-enoylamino)phenyl]-1H-indazole-3-carboxamide (0.0062 g, 13.04 μmol, 9.87% yield, 100% purity) as a pink solid. LC-MS (ES+, m/z): 476.3 [(M+H)+], 1H NMR (400 MHz, DMSO-d6) Shift=13.63 (br s, 1H), 10.27 (s, 1H), 8.40 (d, J=8.7 Hz, 1H), 8.18 (s, 1H), 8.12 (d, J=8.3 Hz, 1H), 8.05 (s, 1H), 7.88 (br d, J=7.6 Hz, 1H), 7.74-7.66 (m, 3H), 7.47-7.42 (m, 1H), 7.41-7.37 (m, 1H), 6.55-6.39 (m, 1H), 6.33-6.23 (m, 1H), 5.81-5.72 (m, 1H), 4.08 (br s, 1H), 3.87-3.73 (m, 1H), 3.42 (br d, J=2.4 Hz, 2H), 3.25 (s, 3H), 2.69-2.59 (m, 2H), 2.42 (br s, 1H), 2.27 (d, J=5.0 Hz, 3H), 1.91 (br d, J=12.0 Hz, 2H), 1.79 (br d, J=11.2 Hz, 1H), 1.72-1.64 (m, 1H), 1.62-1.50 (m, 2H), 1.50-1.41 (m, 1H), 1.40-1.28 (m, 1H).

Route 19: General Scheme

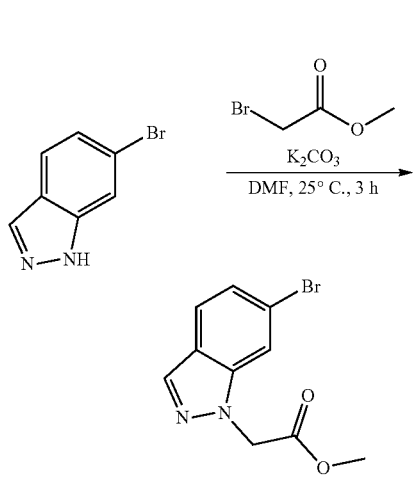

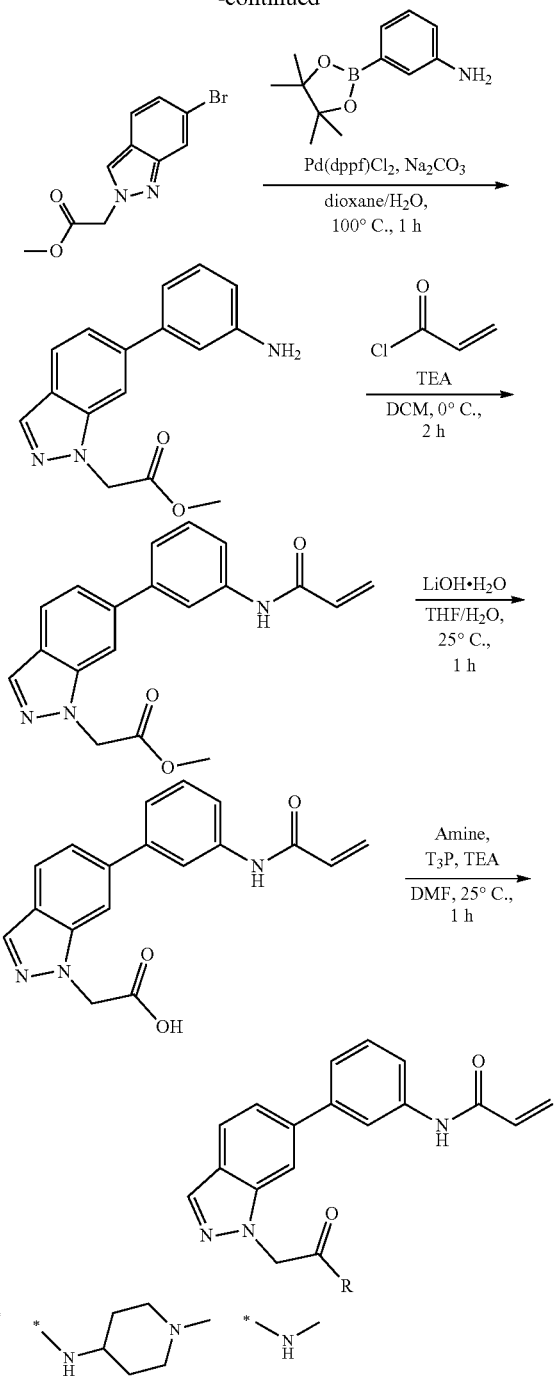

Step 1—methyl 2-(6-bromoindazol-1-yl)acetate; methyl 2-(6-bromoindazol-2-yl)acetate

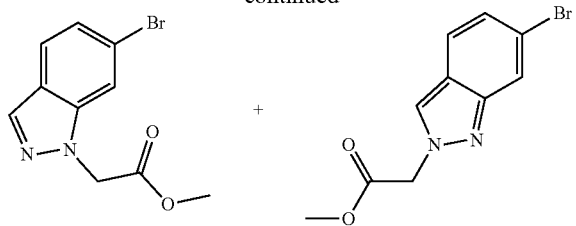

To a solution of methyl 2-bromoacetate (1.71 g, 11.17 mmol, 1.05 mL, 1.1 eq), 6-bromo-1H-indazole (2 g, 10.15 mmol, 1 eq) in DMF (20 mL) was added K₂CO₃ (2.81 g, 20.3 mmol, 2 eq) at 25° C. The reaction mixture was stirred at 25° C. for 3 h. The reaction mixture was poured into ice-water (60 mL) and the aqueous phase was extracted with EtOAc (3×30 mL). The combined organic phase was washed with brine (3×30 mL), dried over anhydrous Na₂SO₄, filtered, and concentrated in vacuo to afford a residue. The residue was purified by silica gel chromatography (SiO₂, PE:EtOAc=10:1, 3:1) to afford the title compound methyl 2-(6-bromoindazol-1-yl)acetate (2 g, 7.43 mmol, 73.22% yield) to afford the title compound methyl 2-(6-bromoindazol-2-yl)acetate (0.7 g, 2.6 mmol, 25.63% yield) as a light yellow solid. LCMS (ES⁺, m/z): 269.1, 271.0 [(M+H)⁺].

Step 4—methyl 2-[6-(3-aminophenyl)indazol-1-yl]acetate

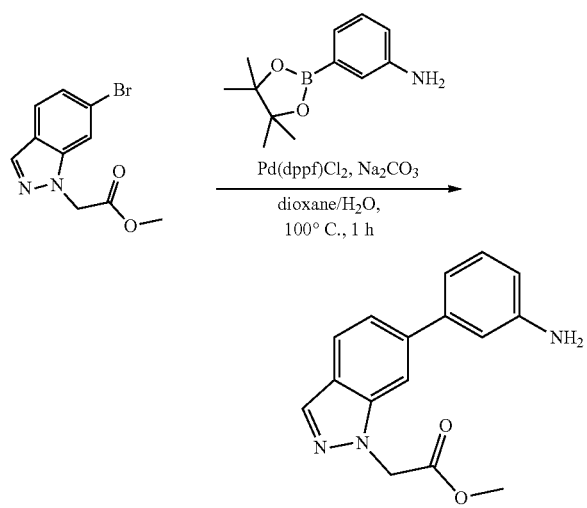

To a solution of 3-(4,4,5,5-tetramethyl-1,3,2-dioxaborolan-2-yl)aniline (800 mg, 3.65 mmol, 1 eq), methyl 2-(6-bromoindazol-1-yl)acetate (1.08 g, 4.02 mmol, 1.1 eq) in dioxane (8 mL) and H₂O (2 mL) was added Na₂CO₃ (774.1 mg, 7.3 mmol, 2 eq), Pd(dppf)Cl₂ (267.2 mg, 365.15 μmol, 0.1 eq) under N₂. The reaction mixture was stirred at 100° C. for 1 h. The reaction mixture was poured into saturated EDTA (50 mL) and stirred for 60 min. The aqueous phase was extracted with EtOAc (3×50 mL). The combined organic layer was washed with brine (3×50 mL), dried over anhydrous Na₂SO₄, filtered, and concentrated in vacuo to afford a residue. The residue was purified by silica gel chromatography (SiO₂, PE:EtOAc=10:1, 3:1) to afford the title compound (0.7 g, 2.49 mmol, 68.15% yield) as a yellow oil. LCMS (ES⁺, m/z): 282.2 [(M+H)⁺].

Step 4—methyl 2-[6-[3-(prop-2-enoylamino)phenyl]indazol-1-yl]acetate

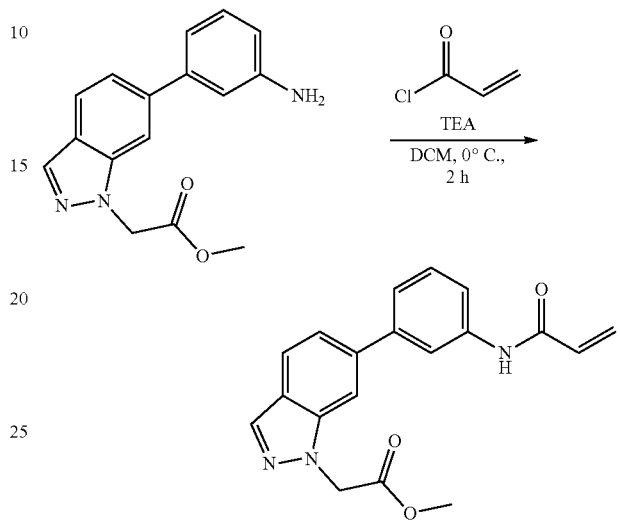

To a solution of methyl 2-[6-(3-aminophenyl)indazol-1-yl]acetate (200 mg, 710.96 μmol, 1 eq) in DCM (2 mL) were added TEA (143.9 mg, 1.42 mmol, 197.92 μL, 2 eq) and prop-2-enoyl chloride (77.2 mg, 853.15 μmol, 69.57 μL, 1.2 eq) at 0° C. The reaction mixture was stirred at 0° C. for 1 h. LCMS showed ~20% of the starting material remaining. Then, additional prop-2-enoyl chloride (32.2 mg, 355.48 μmol, 28.99 μL, 0.5 eq) was added and the mixture was stirred at 0° C. for further 1 h. LCMS showed that the reaction was complete. The reaction mixture was poured into H₂O (20 mL) and the aqueous phase was extracted with DCM (3×20 mL). The combined organic layer was washed with brine (3×20 mL), dried over anhydrous Na₂SO₄, filtered, and concentrated in vacuo to afford the title compound (220 mg, crude) as a brown solid. LCMS (ES⁺, m/z): 336.1 [(M+H)⁺].

Step 4—2-[6-[3-(prop-2-enoylamino)phenyl]indazol-1-yl]acetic acid

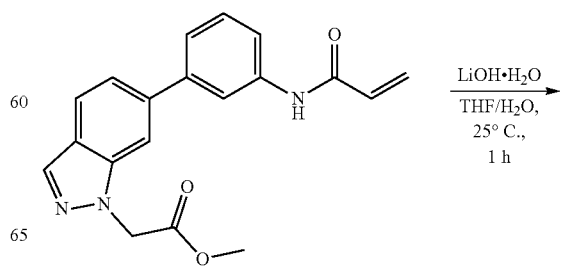

-continued

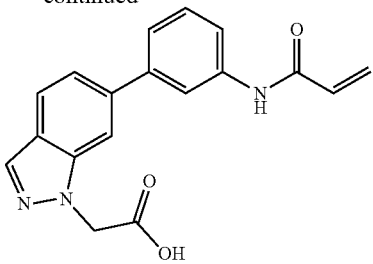

To a solution of methyl 2-[6-[3-(prop-2-enoylamino)phenyl]indazol-1-yl]acetate (150 mg, 447.29 μmol, 1 eq) in THF (5 mL) and H₂O (1.25 mL) was added LiOH·H₂O (37.5 mg, 894.57 μmol, 2 eq) at 25° C. The mixture was stirred at 25° C. for 1 h. TLC showed that the reaction was complete. The reaction mixture was poured into H₂O (20 mL) and the pH was adjusted to ~5 with 1N HCl. The aqueous phase was extracted with EtOAc (3×20 mL). The combined organic layer was washed with brine (3×20 mL), dried over anhydrous Na₂SO₄, filtered, and concentrated in vacuo to afford the title compound (150 mg, crude) as a white solid.

Step 5—N-[3-[1-[2-R-2-oxo-ethyl]indazol-6-yl]phenyl]prop-2-enamide

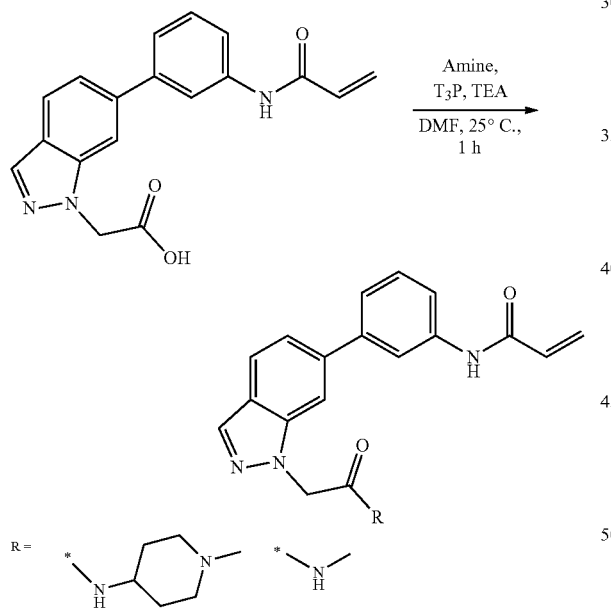

To a solution of 2-[6-[3-(prop-2-enoylamino)phenyl]indazol-1-yl]acetic acid (50 mg, 155.6 μmol, 1 eq), 1-methylpiperidin-4-amine (26.7 mg, 233.41 μmol, 1.5 eq) in DMF (2 mL) was added TEA (78.7 mg, 778.02 μmol, 108.29 μL, 5 eq) and T₃P (148.5 mg, 233.41 μmol, 138.81 μL, 50% purity, 1.5 eq) at 25° C. The reaction mixture was stirred at 25° C. for 1 h. The reaction mixture was poured into H₂O (20 mL) and the aqueous phase was extracted with EtOAc (3×20 mL). The combined organic layer was washed with brine (3×20 mL), dried with anhydrous Na₂SO₄, filtered, and concentrated in vacuo to afford a residue. The residue was purified by prep-HPLC to afford the title compound (17.2 mg, 39.47 μmol, 25.37% yield, 95.810% purity) as a white solid. 418.3. 1H NMR (400 MHz, DMSO-d6) δ=10.28 (s, 1H), 8.25 (d, J=8.0 Hz, 1H), 8.09 (s, 1H), 8.04 (s, 1H), 7.83 (s, 1H), 7.84 (d, J=8.4 Hz, 1H), 7.69 (d, J=6.4 Hz, 1H), 7.48-7.38 (m, 3H), 6.48 (dd, J=10.4 Hz, 17.2 Hz, 1H), 6.31 (dd, J=2.0 Hz, 16.8 Hz, 1H), 5.80 (dd, J=2.0 Hz, 10.0 Hz, 1H), 5.12 (s, 2H), 3.53-3.50 (m, 1H), 2.73 (br d, J=12.0 Hz, 2H), 2.18 (s, 3H), 2.01 (br s, 2H), 1.78-1.71 (m, 2H), 1.52-1.42 (m, 2H)

Route 20: General Scheme

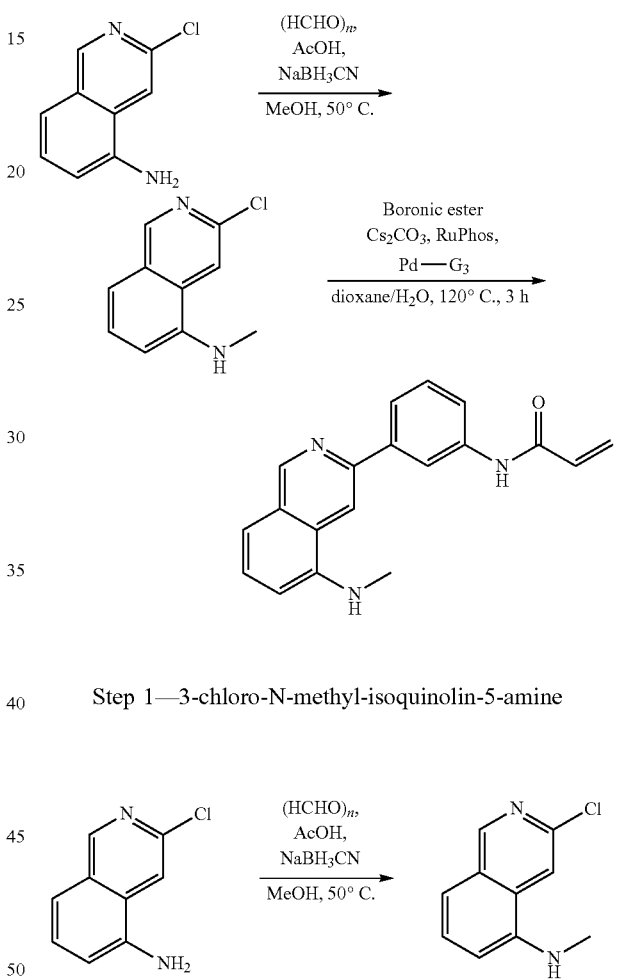

Step 1—3-chloro-N-methyl-isoquinolin-5-amine

To a solution of 3-chloroisoquinolin-5-amine (0.3 g, 1.68 mmol, 1 eq) in MeOH (5 mL) was added formaldehyde (151.3 mg, 5.04 mmol, 138.80 μL, 3 eq), AcOH (100.9 mg, 1.68 mmol, 96.06 μL, 1 eq) and NaBH₃CN (527.7 mg, 8.4 mmol, 5 eq). The reaction mixture was stirred at 50° C. for 1 hr under N₂. TLC (PE:EtOAc=3:1; SM=0.34, Rf=0.44) showed 25% of the starting material remained. The reaction mixture was poured into H₂O (20 mL), extracted with DCM (3×10 mL). The combined organic layer was washed with brine (2×20 mL), dried over anhydrous Na₂SO₄, filtered, and concentrated in vacuo to give a residue. The residue was purified by prep-TLC (SiO₂, PE:EtOAc=3:1) to afford the title compound 3-chloro-N-methyl-isoquinolin-5-amine (0.13 g, 674.82 μmol, 40.18% yield) as a yellow solid. LC-MS (ES⁺, m/z): 193.0 [(M+H)⁺]

Step 2—N-[3-[5-(methylamino)-3-isoquinolyl]phenyl]prop-2-enamide

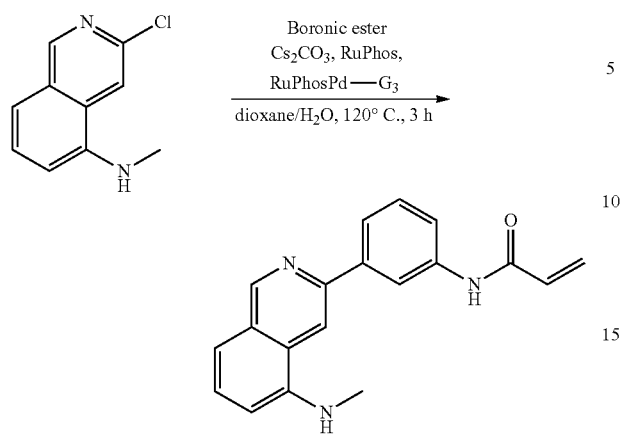

To a solution of N-[3-(4,4,5,5-tetramethyl-1,3,2-dioxaborolan-2-yl)phenyl]prop-2-enamide (119.1 mg, 436.04 μmol, 1.2 eq) in dioxane (2 mL) and H$_2$O (0.5 mL) were added 3-chloro-N-methyl-isoquinolin-5-amine (0.07 g, 363.36 μmol, 1 eq), Cs$_2$CO$_3$ (355.2 mg, 1.09 mmol, 3 eq) dicyclohexyl-[2-(2,6-diisopropoxyphenyl)phenyl]phosphane (17 mg, 36.34 μmol, 0.1 eq) and [2-(2-aminophenyl)phenyl]-methylsulfonyloxy-palladium;dicyclohexyl-[2-(2,6-diisopropoxyphenyl)phenyl]phosphane (30.4 mg, 36.34 μmol, 0.1 eq). The reaction mixture was stirred at 120° C. for 3 hr under N$_2$. LCMS showed ~40% of the starting material remained. The reaction mixture was poured into 20 mL saturated EDTA. Then 20 mL EtOAc was added. The solution was stirred at 20° C. for 1 hr. The aqueous phase was separated and extracted with EtOAc (2×20 mL). The combined organic layer was washed with 30 mL brine, dried over Na$_2$SO$_4$ and concentrated in vacuo to give a residue. The residue was purified by prep-HPLC (FA condition) to afford the title compound N-[3-[5-(methylamino)-3-isoquinolyl]phenyl]prop-2-enamide (0.0106 g, 34.94 μmol, 9.62% yield, 100.0% purity) as a yellow solid. 304.1. $^1$H NMR (400 MHz, DMSO-d$_6$) 5 ppm 10.297 (s, 1H) 9.208 (s, 1H) 8.560 (s, 1H) 8.498 (s, 1H) 7.922 (d, 7=8.0 Hz, 1H) 7.834 (br d, J=8.0 Hz, 1H) 7.465 (td, J=8.0, 6.11 Hz, 2H) 7.273 (d, J=8.0 Hz, 1H) 6.762-6.813 (m, 1H) 6.645 (d, J=7.6 Hz, 1H) 6.451-6.529 (m, 1H) 6.315 (d, J=2.0 Hz, 1H) 5.751-5.801 (m, 1H) 2.906 (d, J=4.8 Hz, 3H)

Route 21: General Scheme

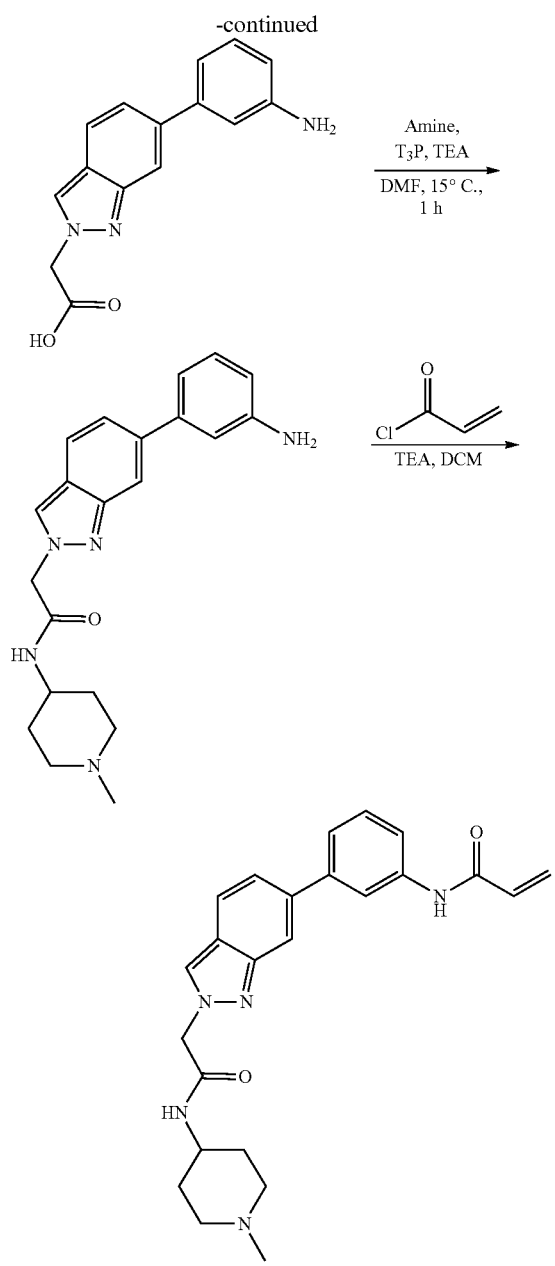

Step 1—2-[6-(3-aminophenyl)indazol-2-yl]acetic acid

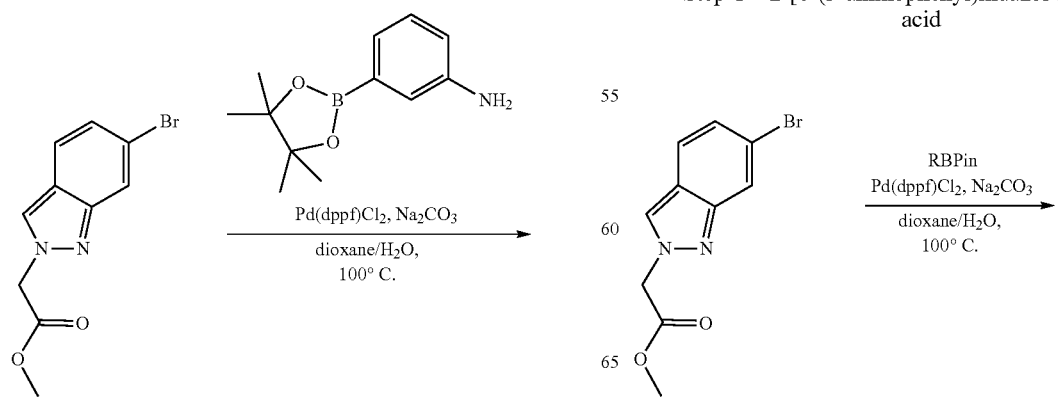

-continued

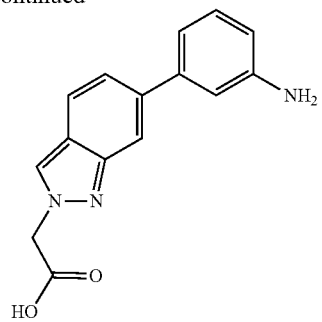

To a solution of methyl 2-(6-bromoindazol-2-yl)acetate (500.5 mg, 1.86 mmol, 1 eq) and 3-(4,4,5,5-tetramethyl-1,3,2-dioxaborolan-2-yl)aniline (489 mg, 2.23 mmol, 1.2 eq) in dioxane (4 mL) and $H_2O$ (1 mL) was added $Na_2CO_3$ (591.4 mg, 5.58 mmol, 3 eq) and Pd(dppf)Cl$_2$·CH$_2$Cl$_2$ (30.4 mg, 37.2 μmol, 0.02 eq). The reaction mixture was stirred at 100° C. for 0.5 hr under $N_2$. TLC showed 10% of the starting material remained. The reaction mixture was poured into 40 mL saturated EDTA then 20 mL EtOAc was added. The solution was stirred at 20° C. for 1 hr. The aqueous phase was separated and washed with EtOAc (3×20 mL). After that the aqueous phase was concentrated in vacuo to give a residue. The residue re-dissolved with (DCM:MeOH=10:1, 3×30 mL). Then removing the precipitate by filtration. The filtrate was concentrated in vacuo to afford the title compound 2-[6-(3-aminophenyl)indazol-2-yl]acetic acid (0.24 g, crude) as a yellow oil. LC-MS (ES$^+$, m/z): 268.4 [(M+H)$^+$].

Step 2—2-[6-(3-aminophenyl)indazol-2-yl]-N-(1-methyl-4-piperidyl)acetamide

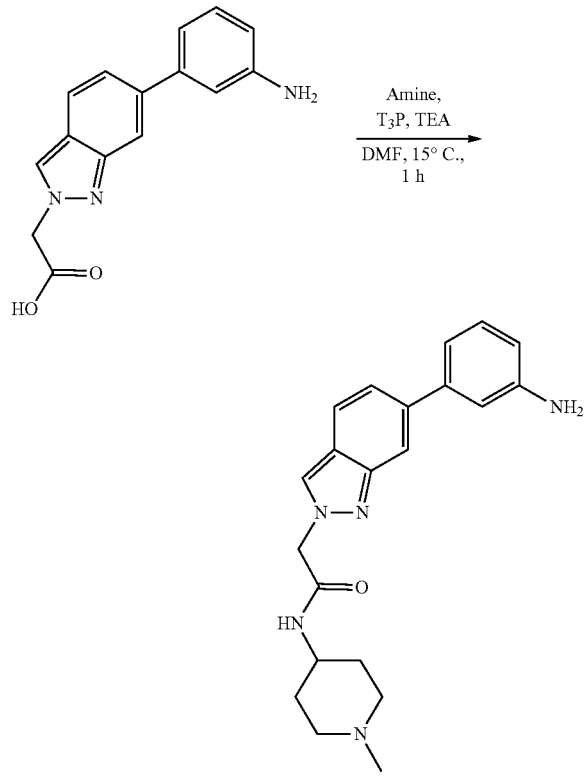

To a solution of 2-[6-(3-aminophenyl)indazol-2-yl]acetic acid (0.18 g, 673.45 μmol, 1 eq) in DMF (2 mL) were added 1-methylpiperidin-4-amine (153.8 mg, 1.35 mmol, 2 eq), TEA (204.4 mg, 2.02 mmol, 281.21 μL, 3 eq) and T$_3$P (857.1 mg, 1.35 mmol, 801.04 μL, 50% purity, 2 eq). The reaction mixture was stirred at 15° C. for 1 hr under $N_2$. TLC (DCM:MeOH=10:1; SM=0.0, Rf=0.12) showed that the reaction mixture was complete. The reaction mixture was poured into $H_2O$ (30 mL) and extracted with EtOAc (3×20 mL). The combined organic layer was washed with brine (2×20 mL), dried over anhydrous $Na_2SO_4$, filtered, and concentrated in vacuo to give a residue. The residue was purified by prep-TLC (SiO$_2$, 5% TEA, DCM:MeOH=10:1) to afford the title compound 2-[6-(3-aminophenyl)indazol-2-yl]-N-(1-methyl-4-piperidyl)acetamide (0.03 g, 82.54 μmol, 12.26% yield) as a light yellow solid. LC-MS (ES$^+$, m/z): 364.4 [(M+H)$^+$].

Step 3—N-[3-[2-[2-[(1-methyl-4-piperidyl)amino]-2-oxo-ethyl]indazol-6-yl]phenyl]prop-2-enamide

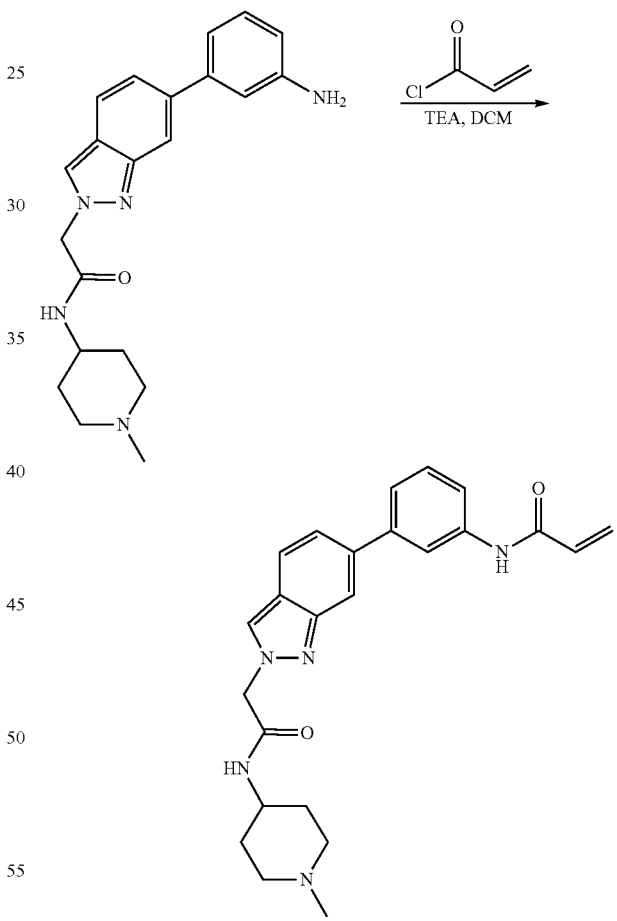

To a solution of 2-[6-(3-aminophenyl)indazol-2-yl]-N-(1-methyl-4-piperidyl) acetamide (0.025 g, 68.78 μmol, 1 eq) in DCM (2 mL) were added TEA (20.9 mg, 206.35 μmol, 28.72 μL, 3 eq) and prop-2-enoyl chloride (7.5 mg, 82.54 μmol, 6.73 μL, 1.2 eq) at 0° C. The reaction mixture was stirred at 15° C. for 0.5 hr under $N_2$. LCMS showed that the reaction was complete. The reaction mixture was poured into $H_2O$ (10 mL), extracted with DCM (3×10 mL). The combined organic layer was washed with brine (2×10 mL), dried over anhydrous Na₂SO₄, filtered, and concentrated in vacuo to give a residue. The residue was purified by prep-HPLC (FA condition) to afford the title compound N-[3-[2-[2-[(1-methyl-4-piperidyl)amino]-2-oxo-ethyl]indazol-6-yl]phenyl]prop-2-enamide (0.0077 g, 17.65 μmol, 25.66% yield, 95.7% purity) as a yellow solid. 1H NMR (400 MHz, DMSO-d6) δ ppm 10.26 (s, 1H) 8.37 (s, 1H) 8.32 (br d, J=7.6 Hz, 1H) 8.20 (s, 1H) 8.04 (s, 1H) 7.83 (d, J=8.8 Hz, 1H) 7.76 (s, 1H) 7.63-7.71 (m, 1H) 7.43 (d, J=5.2 Hz, 1H) 7.32 (dd, J=8.8, 1.32 Hz, 1H) 6.41-6.52 (m, 1H) 6.24-6.33 (m, 1H) 5.74-5.81 (m, 1H) 5.11 (s, 2H) 2.77 (br d, J=12.0 Hz, 2H) 2.21 (s, 3H) 2.07 (br t, J=10.8 Hz, 2H) 1.77 (br d, J=10.4 Hz, 2H) 1.40-1.54 (m, 2H).

Route 21: General Scheme

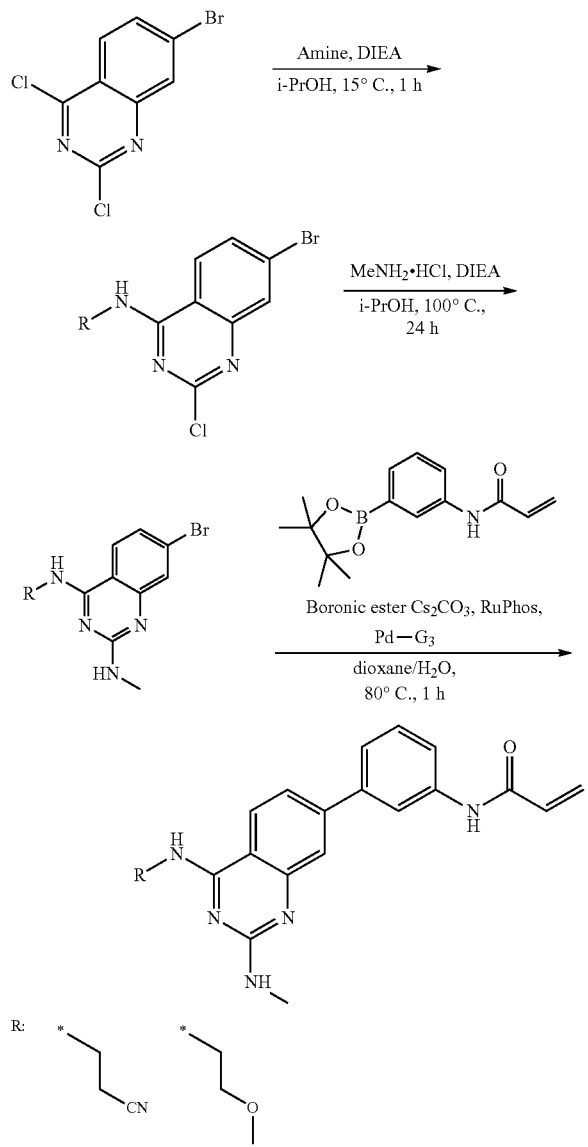

Step 1—7-bromo-2-chloro-N—R-quinazolin-4-amine

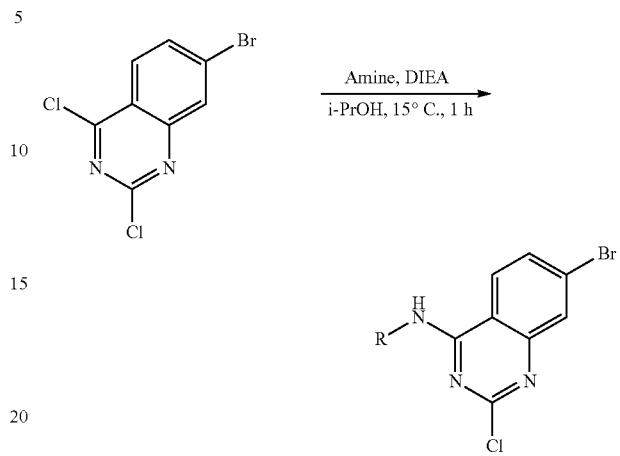

To a solution of 7-bromo-2,4-dichloro-quinazoline (0.3 g, 1.08 mmol, 1 eq) in i-PrOH (2 mL) was added 2-methoxyethanamine (81.1 mg, 1.08 mmol, 93.83 μL, 1 eq) and DIEA (279 mg, 2.16 mmol, 376.02 μL, 2 eq). The reaction mixture was stirred at 15° C. for 1 h. TLC (PE:EtOAc=1:1, SM Rf=0.53, TM Rf=0.05) showed that the reaction was complete. The reaction mixture was poured into 50 mL H₂O, extracted with EtOAc (3×50 mL). The combined organic layers were washed with H₂O (2×50 mL) and brine (2×50 mL)). Then dried over anhydrous Na₂SO₄, filtered, and concentrated in vacuo to afford the title compound 7-bromo-2-chloro-N-(2-methoxyethyl)quinazolin-4-amine (0.37 g, crude) as a white solid which was used for the next step directly without further purification.

Step 2—7-bromo-N4-R—N2-methylquinazoline-2,4-diamine

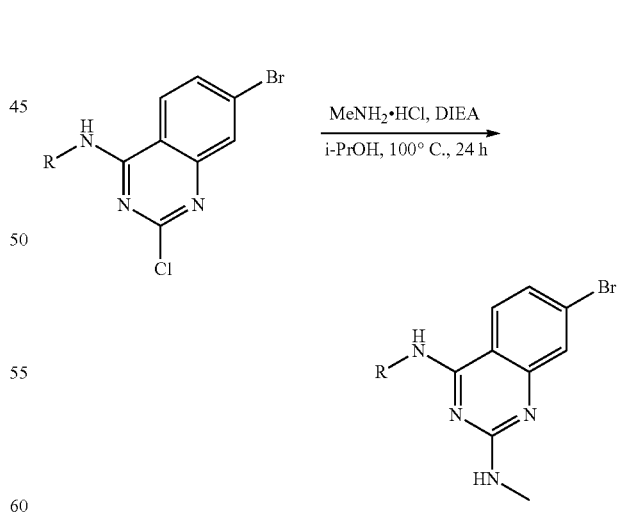

To a solution of 7-bromo-2-chloro-N-(2-methoxyethyl) quinazolin-4-amine (0.32 g, 1.01 mmol, 1 eq) in i-PrOH (3 mL) was added methanamine; hydrochloride (1.36 g, 20.22 mmol, 20 eq) and DIEA (2.61 g, 20.22 mmol, 3.52 mL, 20 eq). The reaction mixture was stirred at 100° C. for 24 h. LCMS showed 7% of the starting material remaining. The reaction mixture was poured into 50 mL H₂O, extracted with PE:EtOAc (3×50 mL), and the combined organic layers were washed with H₂O (2×50 mL) and brine (2×50 mL). Then dried over anhydrous Na₂SO₄, filtered, and concentrated in vacuo to afford the title compound 7-bromo-N4-(2-methoxyethyl)-N2-methyl-quinazoline-2,4-diamine (0.35 g, crude) as a yellow oil which was used for the next step directly without further purification.

Step 3—N-(3-(4-(R-lamino)-2-(methylamino)quinazolin-7-yl)phenyl)acrylamide

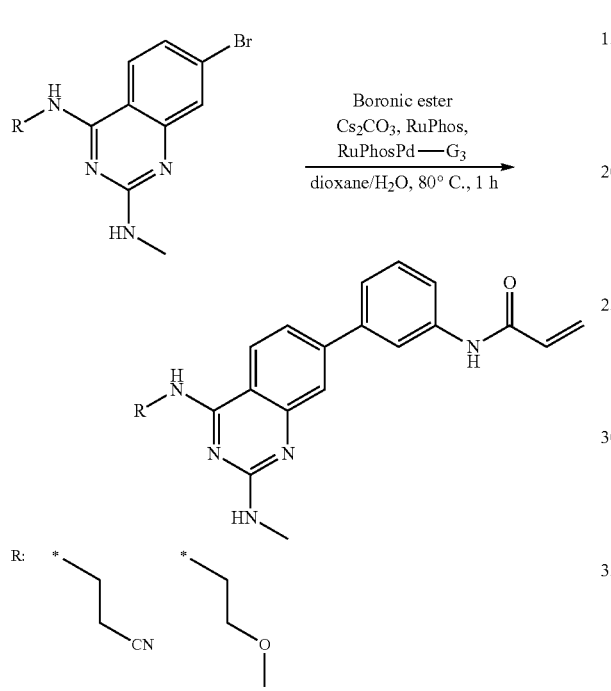

To a solution of N-[3-(4,4,5,5-tetramethyl-1,3,2-dioxaborolan-2-yl)phenyl]prop-2-enamide (80 mg, 292.9 μmol, 1 eq) in dioxane (2 mL) and H₂O (0.5 mL) was added 7-bromo-N4-(2-ethoxyethyl)-N2-methyl-quinazoline-2,4-diamine (72.9 mg, 234.32 μmol, 0.8 eq), Cs₂CO₃ (190.9 mg, 585.79 μmol, 2 eq), RuPhos (13.7 mg, 29.29 μmol, 0.1 eq) and [2-(2-aminophenyl)phenyl]-methylsulfonyloxy-palladium;dicyclohexyl-[2-(2,6-diisopropoxyphenyl)phenyl]phosphane (12.3 mg, 14.64 μmol, 0.05 eq). The reaction mixture was stirred at 80° C. for 1 hr under N₂. LCMS showed that the reaction was complete. The reaction mixture was poured into saturated EDTA (50 mL) and EtOAc (50 mL) was added. The solution was stirred at 25° C. for 1 h. The mixture was extracted with EtOAc (3×100 mL), and the combined organic layers were washed with H₂O (2×50 mL) and brine (2×50 mL). Then dried over anhydrous Na₂SO₄, filtered, and concentrated in vacuo to give a residue. The residue was purified by prep-HPLC to afford the title compound N-[3-[4-(2-methoxyethylamino)-2-(methylamino)quinazolin-7-yl]phenyl]prop-2-enamide (11 mg, 28.42 μmol, 9.70% yield, 97.5% purity) as a white solid. 378.1. 1H NMR (400 MHz, DMSO-d6) δ=10.28 (s, 1H), 8.05-8.19 (m, 4H), 7.67 (br d, J=7.08 Hz, 1H), 7.34-7.54 (m, 4H), 6.69 (s, 1H), 6.47 (dd, J=16.96, 10.08 Hz, 1H), 6.29 (dd, J=17.06, 1.90 Hz, 1H), 5.76-5.82 (m, 1H), 3.67 (br s, 2H), 3.53-3.63 (m, 2H), 3.28 (s, 3H), 2.86 (br d, 1=4.40 Hz, 3H).

Route 22: General Scheme

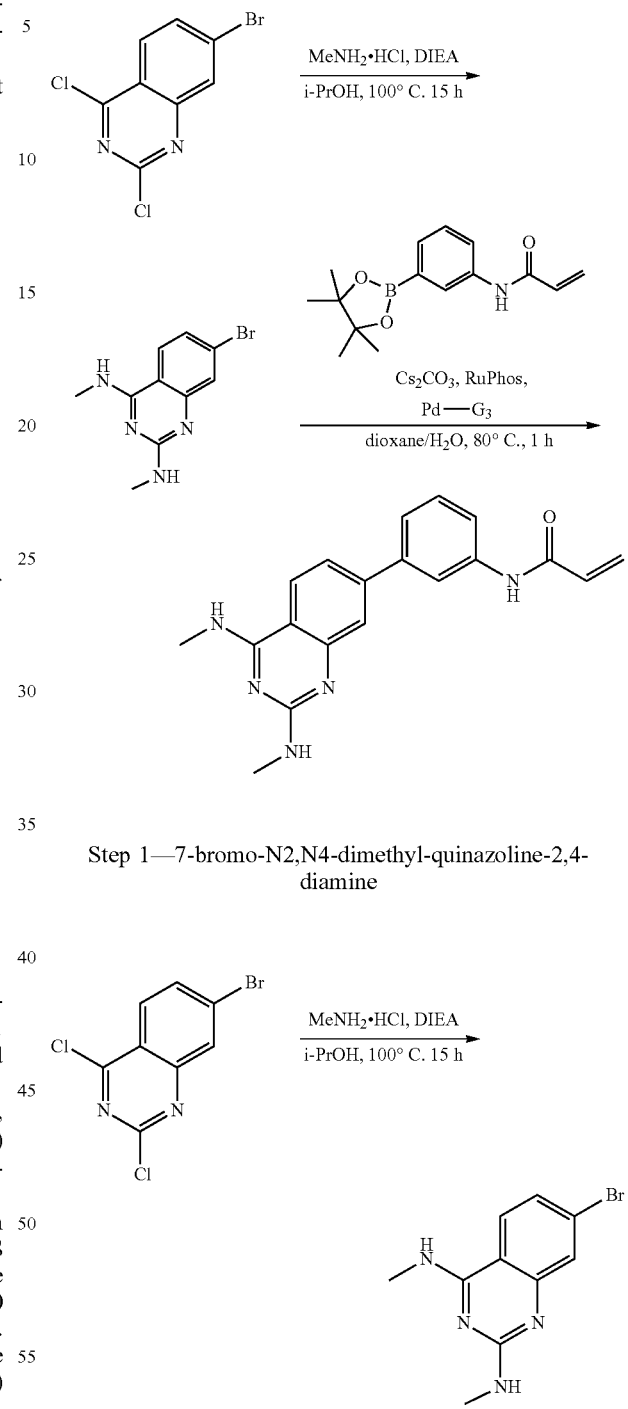

Step 1—7-bromo-N2,N4-dimethyl-quinazoline-2,4-diamine

To a solution of 7-bromo-2,4-dichloro-quinazoline (0.3 g, 1.08 mmol, 1 eq) in i-PrOH (3 mL) was added DIEA (1.4 g, 10.79 mmol, 1.88 mL, 10 eq). Then methanamine;hydrochloride (1.46 g, 21.59 mmol, 20 eq) was added and the reaction mixture was stirred at 100° C. for 15 h. LCMS showed that the reaction was complete. The reaction mixture was poured into 50 mL H₂O, extracted with EtOAc (3×50 mL), and the combined organic layer was washed with H₂O (2×50 mL) and brine (2×50 mL). Then dried over anhydrous Na$_2$SO$_4$, filtered, and concentrated in vacuo to afford the title compound 7-bromo-N2,N4-dimethyl-quinazoline-2,4-diamine (0.3 g, crude) as a yellow solid which was used for the next step without further purification. LC-MS (ES$^+$, m/z): 267.0 [(M+H)$^+$]

Step 2—N-[3-[2,4-bis(methylamino)quinazolin-7-yl]phenyl]prop-2-enamide

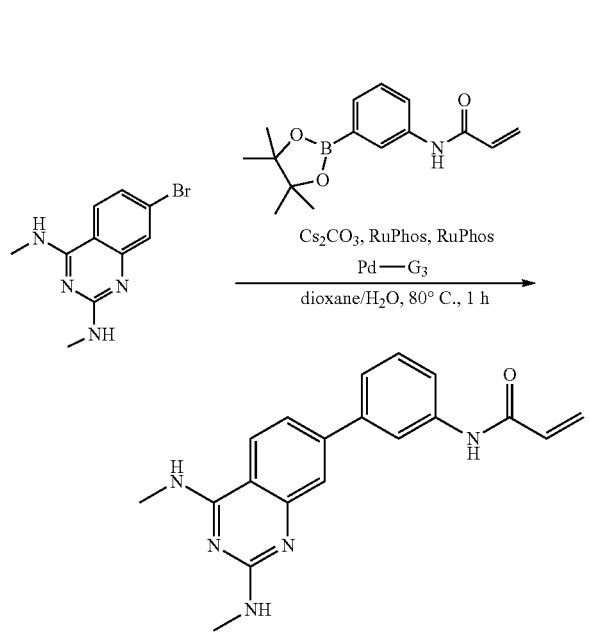

To a solution of N-[3-(4,4,5,5-tetramethyl-1,3,2-dioxaborolan-2-yl)phenyl]prop-2-enamide (80 mg, 292.9 µmol, 1 eq) in dioxane (2 mL) and H$_2$O (0.5 mL) was added 7-bromo-N2,N4-dimethyl-quinazoline-2,4-diamine (62.6 mg, 234.32 µmol, 0.8 eq), Cs$_2$CO$_3$ (190.9 mg, 585.79 µmol, 2 eq), RuPhos (13.7 mg, 29.29 µmol, 0.1 eq) and [2-(2-aminophenyl)phenyl]-methylsulfonyloxy-palladium;dicyclohexyl-[2-(2,6-diisopropoxyphenyl)phenyl]phosphane (12.3 mg, 14.64 µmol, 0.05 eq). The reaction mixture was stirred at 80° C. for 1 hr under N$_2$. LCMS showed that the reaction was complete. The reaction mixture was poured into saturated EDTA aqueous solution (50 mL) and EtOAc (50 mL) was added. The solution was stirred at 25° C. for 1 h, extracted with EtOAc (3×100 mL). The combined organic layers were washed with H$_2$O (2×50 mL) and brine (2×50 mL). Then dried over anhydrous Na$_2$SO$_4$, filtered, and concentrated in vacuo to give a residue. The residue was purified by prep-HPLC (PA condition) to afford the title compound N-[3-[2,4-bis(methylamino)quinazolin-7-yl]phenyl]prop-2-enamide (12.5 mg, 37.16 µmol, 12.69% yield, 99.1% purity) as a white solid. LC-MS (ES$^+$, m/z): 334.1 [(M+H)$^+$] $^1$H NMR (400 MHz, DMSO-d$_6$) δ=10.26 (s, 1H), 8.19 (s, 1H), 8.13 (br s, 1H), 8.02 (br d, J=8.44 Hz, 2H), 7.66 (br d, J=7.20 Hz, 1H), 7.40-7.53 (m, 3H), 7.33 (dd, J=8.44, 1.60 Hz, 1H), 6.46 (m, 2H), 6.29 (dd, J=16.94, 2.02 Hz, 1H), 5.77-5.81 (m, 1H), 2.97 (br s, 3H), 2.86 (br d, J=4.16 Hz, 3H).

Route 23: General Scheme

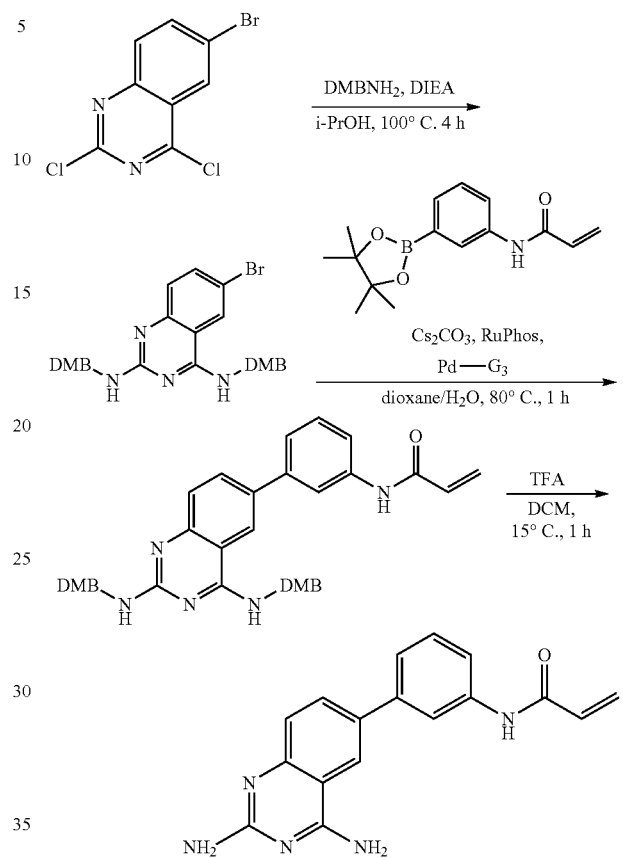

Step 1—6-bromo-N2,N4-bis[(2,4-dimethoxyphenyl)methyl]quinazoline-2,4-diamine

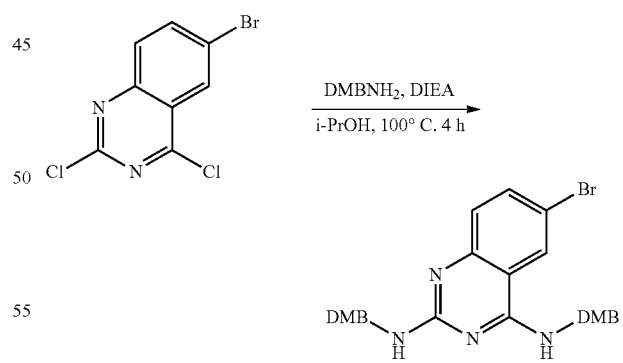

To a solution of 6-bromo-2,4-dichloro-quinazoline (0.3 g, 1.08 mmol, 1 eq) in i-PrOH (5 mL) was added DIEA (2.79 g, 21.6 mmol, 3.76 mL, 20 eq) and (2,4-dimethoxyphenyl)methanamine (3.61 g, 21.6 mmol, 3.25 mL, 20 eq). The reaction mixture was stirred at 100° C. for 4 h. LCMS showed that the reaction was complete. The reaction mixture was poured into 50 mL H$_2$O, extracted with EtOAc (3×50 mL), and the combined organic layers were washed with H$_2$O (2×50 mL) and brine (2×50 mL). Then dried over anhydrous Na₂SO₄, filtered, and concentrated in vacuo to give a residue. The residue was purified by column chromatography (SiO₂, PE:EtOAc=4:1 to 2/1) to afford the title compound 6-bromo-N2,N4-bis[(2,4-dimethoxyphenyl)methyl]quinazoline-2,4-diamine (0.55 g, 1.02 mmol, 94.41% yield) as a yellow solid. LC-MS (ES⁺, m/z): 539.2 [(M+H)⁺]

Step 2—N-[3-[2H-bis[(2H-dimethoxyphenyl)methylamino]quinazolin-6-yl]phenyl]prop-2-enamide

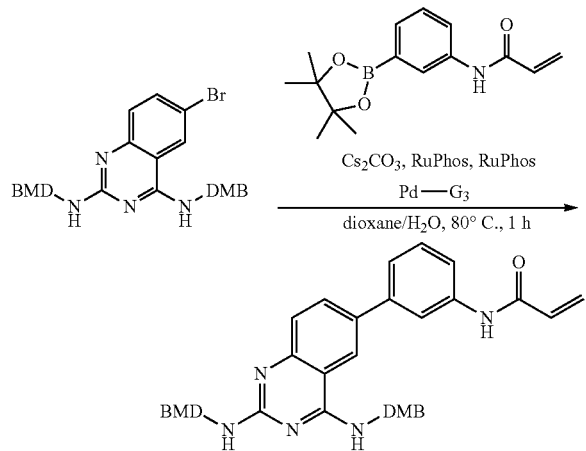

To a solution of N-[3-(4,4,5,5-tetramethyl-1,3,2-dioxaborolan-2-yl)phenyl]prop-2-enamide (0.15 g, 549.18 μmol, 1 eq) in dioxane (4 mL) and H₂O (1 mL) was added 6-bromo-N2,N4-bis[(2,4-dimethoxyphenyl)methyl]quinazoline-2,4-diamine (237 mg, 439.34 μmol, 0.8 eq), Cs₂CO₃ (357.9 mg, 1.1 mmol, 2 eq), RuPhos (25.6 mg, 54.92 μmol, 0.1 eq) and [2-(2-aminophenyl)phenyl]-methyl sulfonyloxy-palladium;dicyclohexyl-[2-(2,6-diisopropoxyphenyl)phenyl]phosphane (23 mg, 27.46 μmol, 0.05 eq). The reaction mixture was stirred at 80° C. for 1 hr under N₂. LCMS showed that the reaction was complete. The reaction mixture was poured into saturated EDTA (50 mL) and EtOAc (50 mL) was added. The solution was stirred at 25° C. for 1 h, extracted with EtOAc (3×100 mL), and the combined organic layer was washed with H₂O (2×50 mL) and brine (2×50 mL). Then dried over anhydrous Na₂SO₄, filtered, and concentrated in vacuo to give a residue. The residue was purified by prep-TLC (SiO₂, DCM:MeOH=10:1) to afford the title compound N-[3-[2,4-bis[(2,4-dimethoxyphenyl)methylamino]quinazolin-6-yl]phenyl]prop-2-enamide (0.2 g, 330.21 μmol, 60.13% yield) as a yellow solid. LC-MS (ES⁺, m/z): 606.3 (M+H)⁺]

Step 3—N-[3-(2,4-diaminoquinazolin-6-yl)phenyl]prop-2-enamide

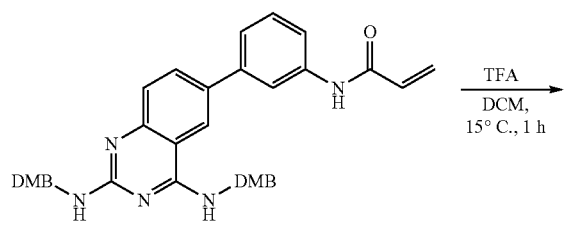

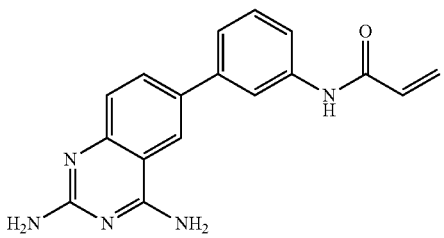

To a solution of N-[3-[2,4-bis[(2,4-dimethoxyphenyl)methylamino]quinazolin-6-yl]phenyl]prop-2-enamide (0.1 g, 165.1 μmol, 1 eq) in DCM (3 mL) was added TFA (1.54 g, 13.51 mmol, 1 mL, 81.80 eq). The reaction mixture was stirred at 15° C. for 1 h. LCMS showed that the reaction was complete. The reaction mixture was poured into 50 mL H₂O and adjusted to pH=7 with saturated NaHCO₃. The mixture was extracted with EtOAc (3×50 mL), and the combined organic layers were washed with H₂O (2×50 mL) and brine (2×50 mL). Then dried over anhydrous Na₂SO₄, filtered, and concentrated in vacuo to give a residue. The residue was purified by prep-HPLC (basic condition) to afford the title compound N-[3-(2,4-diaminoquinazolin-6-yl)phenyl]prop-2-enamide (10 mg, 31.8 μmol, 19.26% yield, 97.1% purity) as a white solid. LC-MS (ES⁺, m/z): 306.0 [(M+H)⁺]¹H NMR (400 MHz, DMSO-d₆) δ=10.22 (s, 1H), 8.28 (d, J=1.76 Hz, 1H), 7.96 (s, 1H), 7.74 (dd, J=8.70, 1.88 Hz, 1H), 7.64 (br d, J=7.28 Hz, 1H), 7.32-7.49 (m, 4H), 7.27 (d, J=8.60 Hz, 1H), 6.47 (dd, J=16.88, 10.00 Hz, 1H), 6.28 (dd, J=16.98, 1.98 Hz, 1H), 6.02 (s, 2H), 5.74-5.81 (m, 1H).

Route 23: General Scheme

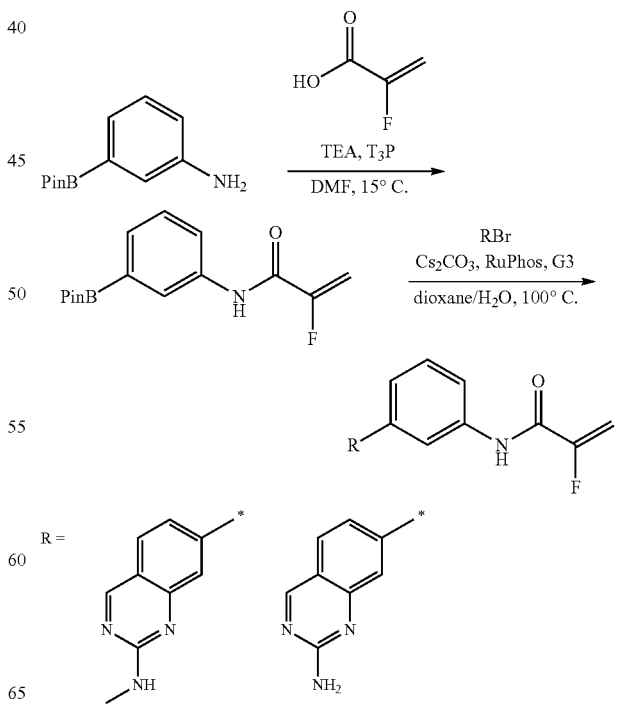

Step 1—2-fluoro-N-[3-(4,4,5,5-tetramethyl-1,3,2-dioxaborolan-2-yl)phenyl]prop-2-enamide

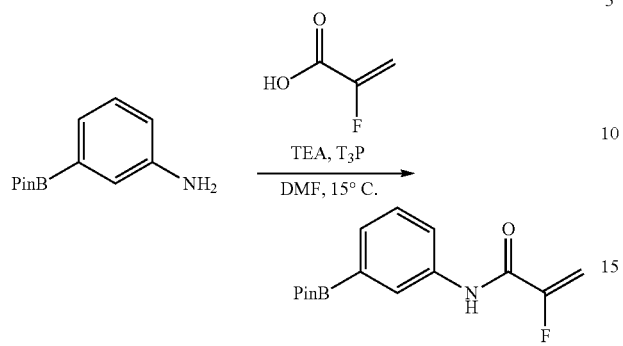

To a solution of 3-(4,4,5,5-tetramethyl-1,3,2-dioxaborolan-2-yl)aniline (0.5 g, 2.28 mmol, 1 eq) in DMF (2 mL) was added 2-fluoroprop-2-enoic acid (308.3 mg, 3.42 mmol, 1.5 eq), TEA (692.8 mg, 6.85 mmol, 952.96 μL, 3 eq) and $T_3P$ (1.09 g, 3.42 mmol, 1.02 mL, 1.5 eq). The reaction mixture was stirred at 15° C. for 1 hr under $N_2$. TLC (PE:EtOAc=3:1; SM=0.41, Rf=0.51) showed that the reaction was complete. The reaction mixture was poured into $H_2O$ (30 mL), extracted with EtOAc (3×30 mL). The combined organic layer was washed with brine (2×50 mL), dried over anhydrous $Na_2SO_4$, filtered, and concentrated in vacuo to give a residue. The residue was triturated with PE (20 mL) to afford the title compound 2-fluoro-N-[3-(4,4,5,5-tetramethyl-1,3,2-dioxaborolan-2-yl)phenyl]prop-2-enamide (0.5 g, 1.72 mmol, 75.26% yield) as a white solid. LC-MS (ES+, m/z): 292.1 [(M+H)+].

Step 2—N-[3-(2-aminoquinazolin-7-yl)phenyl]-2-fluoro-prop-2-enamide

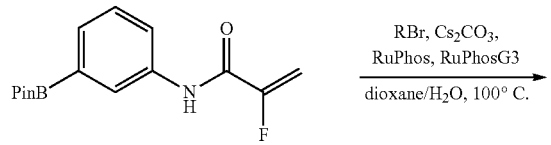

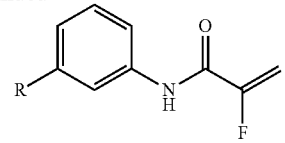

R =

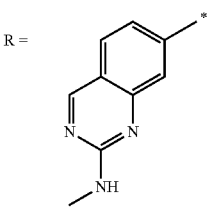 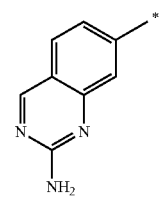

To a solution of 2-fluoro-N-[3-(4,4,5,5-tetramethyl-1,3,2-dioxaborolan-2-yl)phenyl]prop-2-enamide (0.06 g, 206.1 μmol, 1 eq) in dioxane (2 mL) and $H_2O$ (0.5 mL) was added 7-bromoquinazolin-2-amine (46.2 mg, 206.1 μmol, 1 eq), $Cs_2CO_3$ (201.5 mg, 618.3 μmol, 3 eq) dicyclohexyl-[2-(2,6-diisopropoxy phenyl)phenyl]phosphane (9.6 mg, 20.61 μmol, 0.1 eq) and [2-(2-aminophenyl)phenyl]-methylsulfonyloxy-palladium;dicyclohexyl-[2-(2,6-diisopropoxyphenyl)phenyl]phosphane (8.6 mg, 10.31 μmol, 0.05 eq). The reaction mixture was stirred at 100° C. for 1 hr under $N_2$. LCMS showed that the reaction was complete. The reaction was poured into 20 mL saturated EDTA and 20 mL EtOAc was added. The solution was stirred at 20° C. for 1 hr. Then the aqueous phase was separated, extracted with EtOAc (3×20 mL). The combined organic layer was washed with brine 30 mL, dried over $Na_2SO_4$, filtered, and concentrated in vacuo to give a residue. The residue was purified by prep-HPLC (neutral condition) to afford the title compound N-[3-(2-aminoquinazolin-7-yl)phenyl]-2-fluoro-prop-2-enamide (0.0177 g, 57.41 μmol, 27.86% yield, 100.0% purity) as a white solid. The residue was purified by prep-HPLC to afford the title compound 2-fluoro-N-[3-[2-(methylamino)quinazolin-7-yl]phenyl]prop-2-enamide (0.0155 g, 48.09 μmol, 23.33% yield, 100.0% purity) as a yellow solid. 323.1. $^1H$ NMR (400 MHz, DMSO-$d_6$) δ ppm 10.402 (br s, 1H) 9.119 (br s, 1H) 8.217 (s, 1H) 7.804-7.929 (m, 2H) 7.710 (br s, 1H) 7.602 (br d, J=7.70 Hz, 1H) 7.509 (q, J=7.8 Hz, 2H) 7.393 (br s, 1H) 5.822 (d, J=3.6 Hz, 1H) 5.477 (dd, J=15.6, 3.61 Hz, 1H) 2.925 (d, J=4.8 Hz, 3H).

TABLE 12 shows compounds synthesized using methods described in EXAMPLE 12 above.

TABLE 12

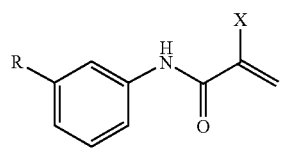

| Cpd. No. | Structure | IUPAC | LC-MS (ES+, m/z) |
|---|---|---|---|
| 445 | 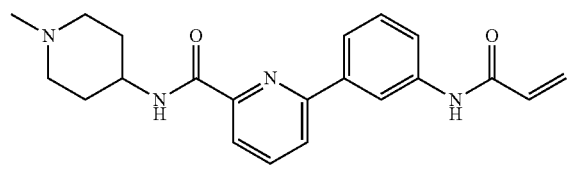 [SMILES: C=CC(=O)Nc1cccc(-c2cccc(C(=O)NC3CCN(C)CC3)n2)c1] | N-(1-methylpiperidin-4-yl)-6-[3-(prop-2-enamido)phenyl]pyridine-2-carboxamide | 365.2 |

TABLE 12-continued

| Cpd. No. | Structure | IUPAC | LC-MS (ES+, m/z) |
|---|---|---|---|
| 446 | 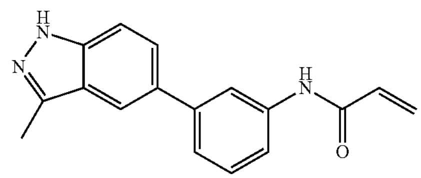 [SMILES: C=CC(=O)Nc1cccc(-c2ccc3[nH]nc(C)c3c2)c1] | N-[3-(3-methyl-1H-indazol-5-yl)phenyl]prop-2-enamide | 278.2 |
| 447 | 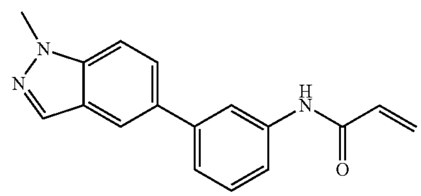 [SMILES: C=CC(=O)Nc1cccc(-c2ccc3c(cnn3C)c2)c1] | N-[3-(1-methyl-1H-indazol-5-yl)phenyl]prop-2-enamide | 278.2 |
| 448 | 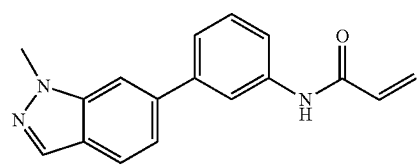 [SMILES: C=CC(=O)Nc1cccc(-c2ccc3cnn(C)c3c2)c1] | N-[3-(1-methyl-1H-indazol-6-yl)phenyl]prop-2-enamide | 278.1 |
| 449 | 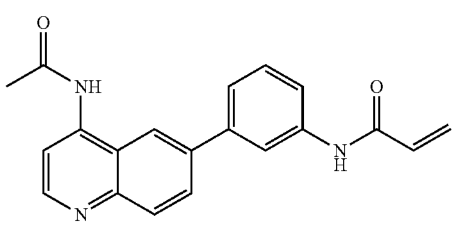 [SMILES: C=CC(=O)Nc1cccc(-c2ccc3nccc(NC(C)=O)c3c2)c1] | N-[3-(4-acetamidoquinolin-6-yl)phenyl]prop-2-enamide | 332.1 |
| 450 | 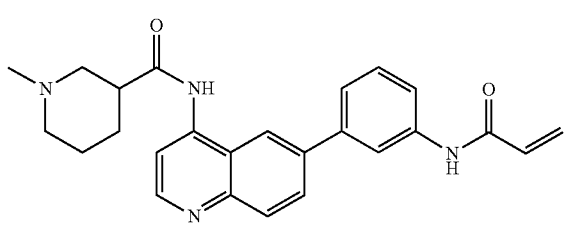 [SMILES: C=CC(=O)Nc1cccc(-c2ccc3nccc(NC(=O)C4CCCN(C)C4)c3c2)c1] | 1-methyl-N-{6-[3-(prop-2-enamido)phenyl]quinolin-4-yl}piperidine-3-carboxamide | 415.2 |
| 451 | 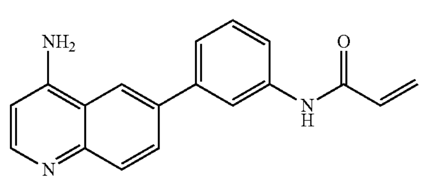 [SMILES: C=CC(=O)Nc1cccc(-c2ccc3nccc(N)c3c2)c1] | N-[3-(4-aminoquinolin-6-yl)phenyl]prop-2-enamide | 290.1 |

TABLE 12-continued

| Cpd. No. | Structure | IUPAC | LC-MS (ES+, m/z) |
|---|---|---|---|
| 452 | 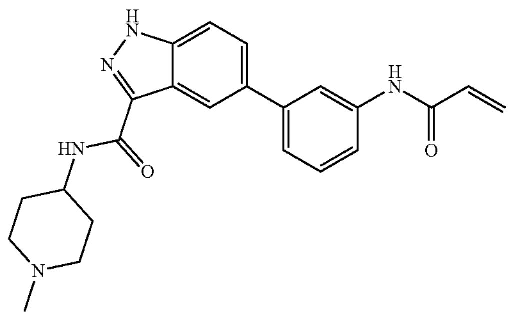 [SMILES: C=CC(=O)Nc1cccc(-c2ccc3[nH]nc(C(=O)NC4CCN(C)CC4)c3c2)c1] | N-(1-methylpiperidin-4-yl)-5-[3-(prop-2-enamido)phenyl]-1H-indazole-3-carboxamide | 404.2 |
| 453 | 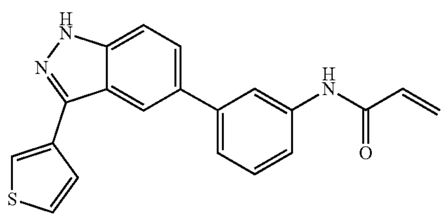 [SMILES: C=CC(=O)Nc1cccc(-c2ccc3[nH]nc(-c4ccsc4)c3c2)c1] | N-{3-[3-(thiophen-3-yl)-1H-indazol-5-yl]phenyl}prop-2-enamide | 346.1 |
| 454 | 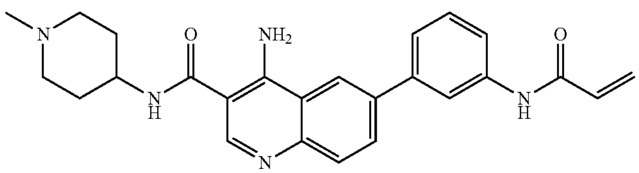 [SMILES: C=CC(=O)Nc1cccc(-c2ccc3ncc(C(=O)NC4CCN(C)CC4)c(N)c3c2)c1] | 4-amino-N-(1-methylpiperidin-4-yl)-6-[3-(prop-2-enamido)phenyl]quinoline-3-carboxamide | 430.2 |
| 455 | 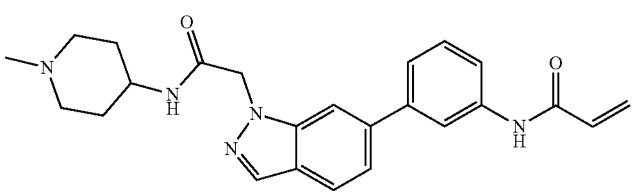 | N-[3-(1-{[(1-methylpiperidin-4-yl)carbamoyl]methyl}-1H-indazol-6-yl)phenyl]prop-2-enamide | 418.3 |
| 456 | 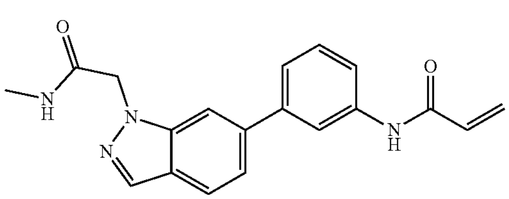 [SMILES: C=CC(=O)Nc1cccc(-c2ccc3cnn(CC(=O)NC)c3c2)c1] | N-(3-{1-[(methylcarbamoyl)methyl]-1H-indazol-6-yl}phenyl)prop-2-enamide | 335.1 |
| 457 | 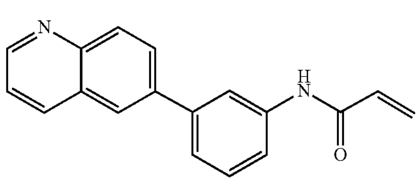 [SMILES: C=CC(=O)Nc1cccc(-c2ccc3ncccc3c2)c1] | N-[3-(quinolin-6-yl)phenyl]prop-2-enamide | 275.1 |

TABLE 12-continued

| Cpd. No. | Structure | IUPAC | LC-MS (ES+, m/z) |
|---|---|---|---|
| 458 | 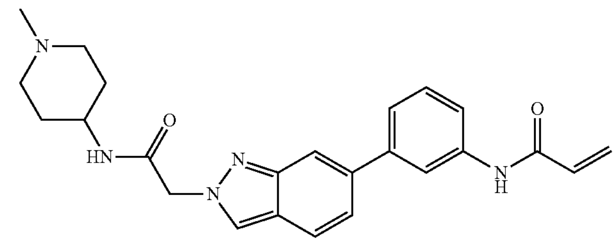 [SMILES: C=CC(=O)Nc1cccc(-c2ccc3cn(CC(=O)NC4CCN(C)CC4)nc3c2)c1] | N-[3-(2-{[(1-methylpiperidin-4-yl)carbamoyl]methyl}-2H-indazol-6-yl)phenyl]prop-2-enamide | 418.2 |
| 459 | 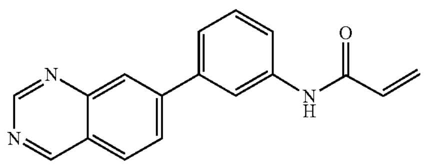 [SMILES: C=CC(=O)Nc1cccc(-c2ccc3cncnc3c2)c1] | N-[3-(quinazolin-7-yl)phenyl]prop-2-enamide | 276.1 |
| 460 | 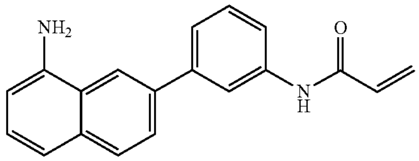 [SMILES: C=CC(=O)Nc1cccc(-c2ccc3cccc(N)c3c2)c1] | N-[3-(8-aminonaphthalen-2-yl)phenyl]prop-2-enamide | 289.1 |
| 461 | 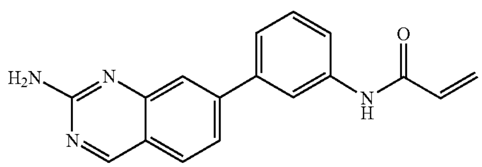 [SMILES: C=CC(=O)Nc1cccc(-c2ccc3cnc(N)nc3c2)c1] | N-[3-(2-aminoquinazolin-7-yl)phenyl]prop-2-enamide | 291.1 |
| 462 | 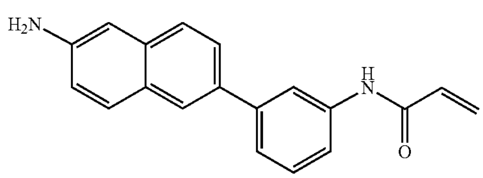 [SMILES: C=CC(=O)Nc1cccc(-c2ccc3cc(N)ccc3c2)c1] | N-[3-(6-aminonaphthalen-2-yl)phenyl]prop-2-enamide | 289.1 |
| 463 | 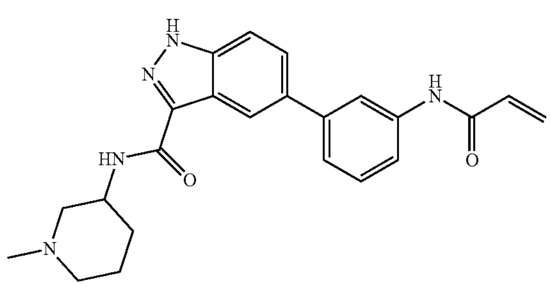 [SMILES: C=CC(=O)Nc1cccc(-c2ccc3[nH]nc(C(=O)NC4CCCN(C)C4)c3c2)c1] | N-(1-methylpiperidin-3-yl)-5-[3-(prop-2-enamido)phenyl]-1H-indazole-3-carboxamide | 404.2 |

TABLE 12-continued

| Cpd. No. | Structure | IUPAC | LC-MS (ES+, m/z) |
|---|---|---|---|
| 464 | 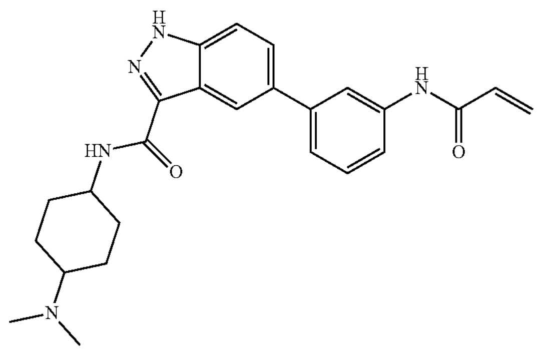 [SMILES: C=CC(=O)Nc1cccc(-c2ccc3[nH]nc(C(=O)NC4CCC(N(C)C)CC4)c3c2)c1] | N-[4-(dimethylamino)cyclohexyl]-5-[3-(prop-2-enamido)phenyl]-1H-indazole-3-carboxamide | 432.2 |
| 465 | 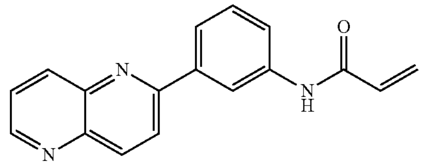 [SMILES: C=CC(=O)Nc1cccc(-c2ccc3ncccc3n2)c1] | N-[3-(1,5-naphthyridin-2-yl)phenyl]prop-2-enamide | 276.2 |
| 466 | 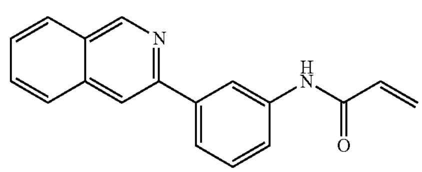 [SMILES: C=CC(=O)Nc1cccc(-c2cc3ccccc3cn2)c1] | N-[3-(isoquinolin-3-yl)phenyl]prop-2-enamide | 275.1 |
| 467 | 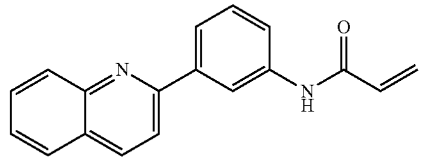 | N-[3-(quinolin-2-yl)phenyl]prop-2-enamide | 275.1 |
| 468 | 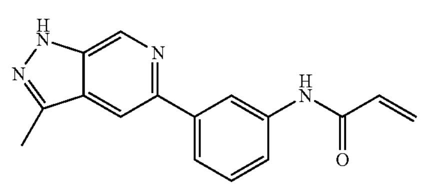 [SMILES: C=CC(=O)Nc1cccc(-c2cc3c(C)n[nH]c3cn2)c1] | N-(3-{3-methyl-1H-pyrazolo[3,4-c]pyridin-5-yl}phenyl)prop-2-enamide | 279.1 |
| 469 | 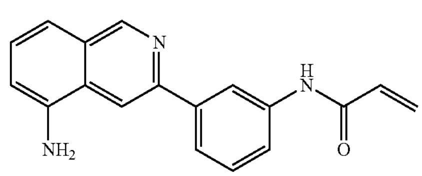 [SMILES: C=CC(=O)Nc1cccc(-c2cc3c(N)cccc3cn2)c1] | N-[3-(5-aminoisoquinolin-3-yl)phenyl]prop-2-enamide | 290.1 |

TABLE 12-continued

| Cpd. No. | Structure | IUPAC | LC-MS (ES+, m/z) |
|---|---|---|---|
| 470 | 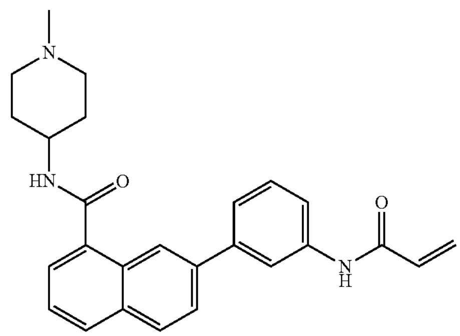 [SMILES: C=CC(=O)Nc1cccc(-c2ccc3cccc(C(=O)NC4CCN(C)CC4)c3c2)c1] | N-(1-methylpiperidin-4-yl)-7-[3-(prop-2-enamido)phenyl]naphthalene-1-carboxamide | 414.2 |
| 471 | 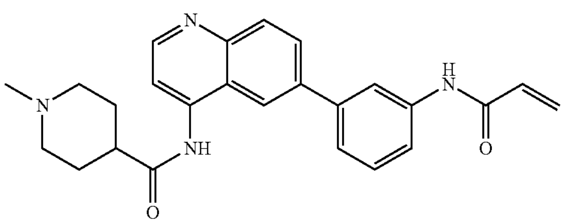 [SMILES: C=CC(=O)Nc1cccc(-c2ccc3nccc(NC(=O)C4CCN(C)CC4)c3c2)c1] | 1-methyl-N-{6-[3-(prop-2-enamido)phenyl]quinolin-4-yl}piperidine-4-carboxamide | 415.2 |
| 472 | 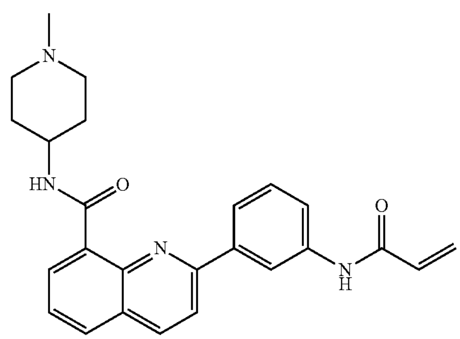 [SMILES: C=CC(=O)Nc1cccc(-c2ccc3cccc(C(=O)NC4CCN(C)CC4)c3n2)c1] | N-(1-methylpiperidin-4-yl)-2-[3-(prop-2-enamido)phenyl]quinoline-8-carboxamide | 415.2 |
| 473 | 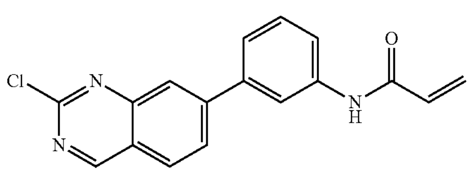 [SMILES: C=CC(=O)Nc1cccc(-c2ccc3cnc(Cl)nc3c2)c1] | N-[3-(2-chloroquinazolin-7-yl)phenyl]prop-2-enamide | 310.1 |
| 474 | 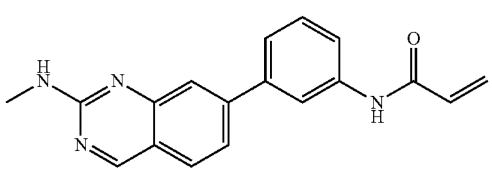 [SMILES: C=CC(=O)Nc1cccc(-c2ccc3cnc(NC)nc3c2)c1] | N-{3-[2-(methylamino)quinazolin-7-yl]phenyl}prop-2-enamide | 305.1 |

TABLE 12-continued

| Cpd. No. | Structure | IUPAC | LC-MS (ES+, m/z) |
|---|---|---|---|
| 475 | 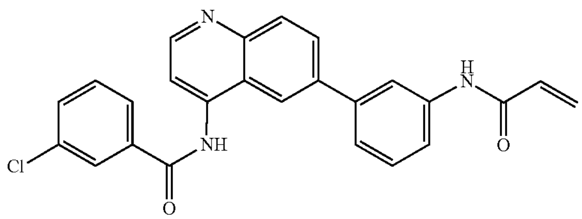 [SMILES: C=CC(=O)Nc1cccc(-c2ccc3nccc(NC(=O)c4cccc(Cl)c4)c3c2)c1] | 3-chloro-N-{6-[3-(prop-2-enamido)phenyl]quinolin-4-yl}benzamide | 428.1 |
| 476 | 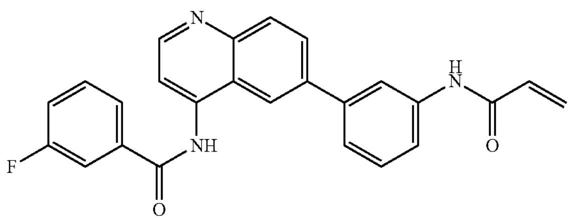 [SMILES: C=CC(=O)Nc1cccc(-c2ccc3nccc(NC(=O)c4cccc(F)c4)c3c2)c1] | 3-fluoro-N-{6-[3-(prop-2-enamido)phenyl]quinolin-4-yl}benzamide | 412.1 |
| 477 | 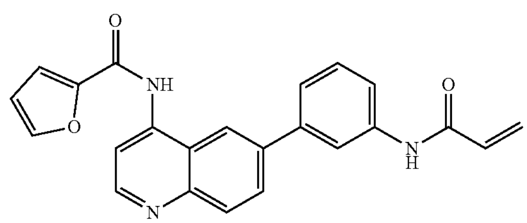 [SMILES: C=CC(=O)Nc1cccc(-c2ccc3nccc(NC(=O)c4ccco4)c3c2)c1] | N-{6-[3-(prop-2-enamido)phenyl]quinolin-4-yl}furan-2-carboxamide | 384.1 |
| 478 | 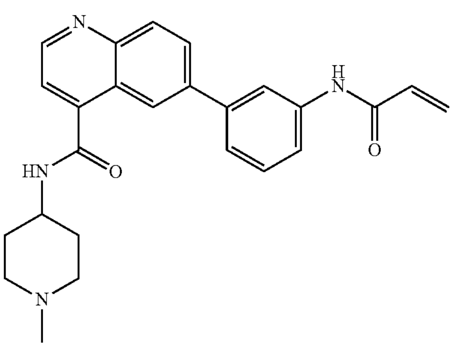 [SMILES: C=CC(=O)Nc1cccc(-c2ccc3nccc(C(=O)NC4CCN(C)CC4)c3c2)c1] | N-(1-methylpiperidin-4-yl)-6-[3-(prop-2-enamido)phenyl]quinoline-4-carboxamide | 415.2 |
| 479 | 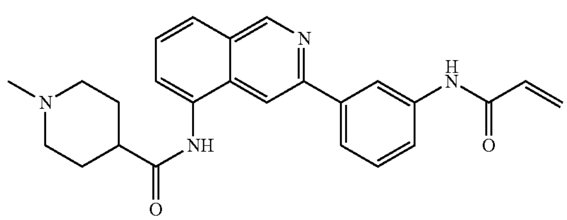 [SMILES: C=CC(=O)Nc1cccc(-c2cc3c(NC(=O)C4CCN(C)CC4)cccc3cn2)c1] | 1-methyl-N-{3-[3-(prop-2-enamido)phenyl]isoquinolin-5-yl}piperidine-4-carboxamide | 415.3 |
| 480 | 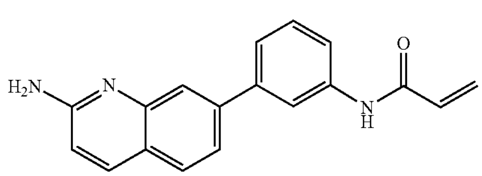 [SMILES: C=CC(=O)Nc1cccc(-c2ccc3ccc(N)nc3c2)c1] | N-[3-(2-aminoquinolin-7-yl)phenyl]prop-2-enamide | 290.1 |

TABLE 12-continued

| Cpd. No. | Structure | IUPAC | LC-MS (ES+, m/z) |
|---|---|---|---|
| 481 | 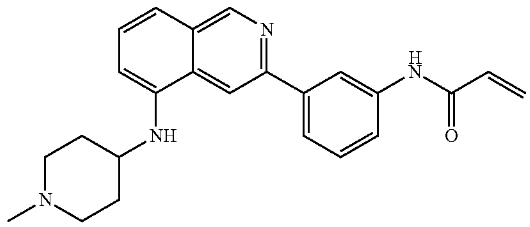 [SMILES: C=CC(=O)Nc1cccc(-c2cc3c(NC4CCN(C)CC4)cccc3cn2)c1] | N-(3-{5-[(1-methylpiperidin-4-yl)amino]isoquinolin-3-yl}phenyl)prop-2-enamide | 387.2 |
| 482 | 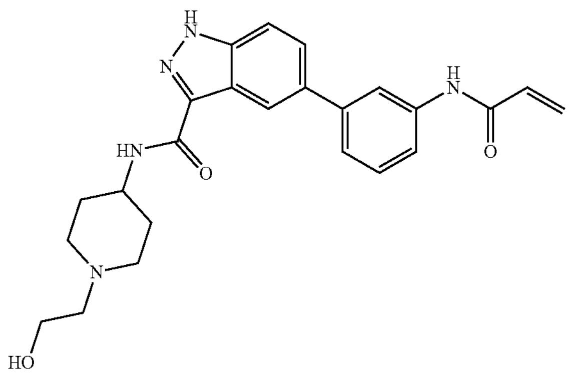 [SMILES: C=CC(=O)Nc1cccc(-c2ccc3[nH]nc(C(=O)NC4CCN(CCO)CC4)c3c2)c1] | N-[1-(2-hydroxyethyl)piperidin-4-yl]-5-[3-(prop-2-enamido)phenyl]-1H-indazole-3-carboxamide | 434.2 |
| 483 | 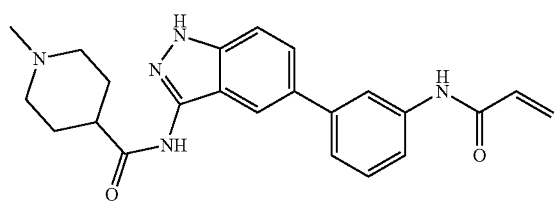 [SMILES: C=CC(=O)Nc1cccc(-c2ccc3[nH]nc(NC(=O)C4CCN(C)CC4)c3c2)c1] | 1-methyl-N-{5-[3-(prop-2-enamido)phenyl]-1H-indazol-3-yl}piperidine-4-carboxamide | 404.2 |
| 484 | 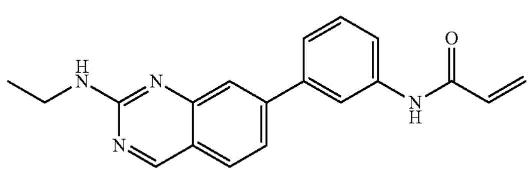 [SMILES: C=CC(=O)Nc1cccc(-c2ccc3cnc(NCC)nc3c2)c1] | N-{3-[2-(ethylamino)quinazolin-7-yl]phenyl}prop-2-enamide | 319.1 |
| 485 | 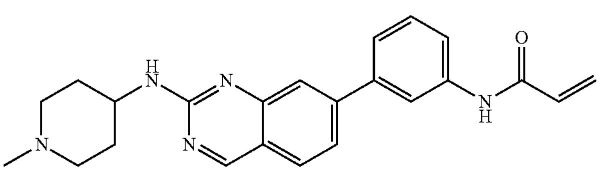 [SMILES: C=CC(=O)Nc1cccc(-c2ccc3cnc(NC4CCN(C)CC4)nc3c2)c1] | N-(3-{2-[(1-methylpiperidin-4-yl)amino]quinazolin-7-yl}phenyl)prop-2-enamide | 388.2 |
| 486 | 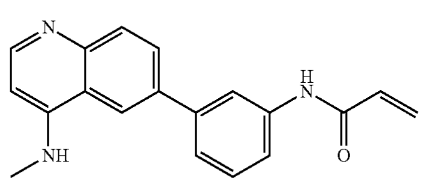 [SMILES: C=CC(=O)Nc1cccc(-c2ccc3nccc(NC)c3c2)c1] | N-{3-[4-(methylamino)quinolin-6-yl]phenyl}prop-2-enamide | 304.1 |

TABLE 12-continued

| Cpd. No. | Structure | IUPAC | LC-MS (ES+, m/z) |
|---|---|---|---|
| 487 | 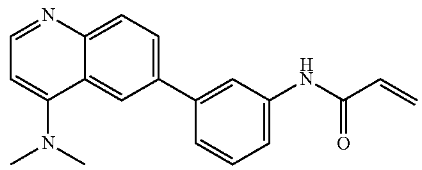 [SMILES: C=CC(=O)Nc1cccc(-c2ccc3nccc(N(C)C)c3c2)c1] | N-{3-[4-(dimethylamino)quinolin-6-yl]phenyl}prop-2-enamide | 318.2 |
| 488 | 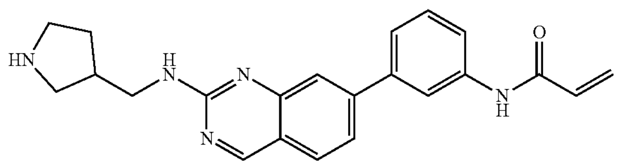 [SMILES: C=CC(=O)Nc1cccc(-c2ccc3cnc(NCC4CCNC4)nc3c2)c1] | N-[3-(2-{[(pyrrolidin-3-yl)methyl]amino}quinazolin-7-yl)phenyl]prop-2-enamide | 374.2 |
| 489 | 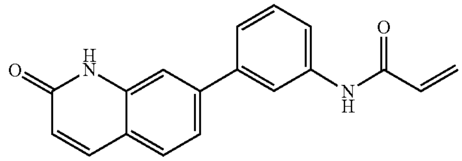 [SMILES: C=CC(=O)Nc1cccc(-c2ccc3ccc(=O)[nH]c3c2)c1] | N-[3-(2-oxo-1,2-dihydroquinolin-7-yl)phenyl]prop-2-enamide | 291.1 |
| 490 | 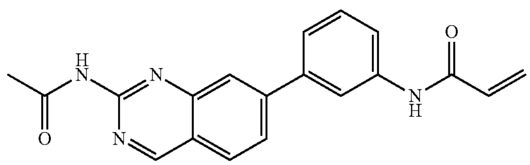 [SMILES: C=CC(=O)Nc1cccc(-c2ccc3cnc(NC(C)=O)nc3c2)c1] | N-[3-(2-acetamidoquinazolin-7-yl)phenyl]prop-2-enamide | 333.1 |
| 491 | 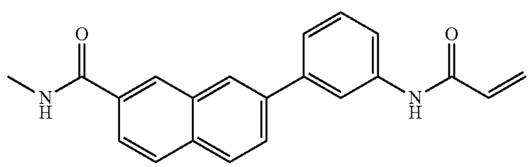 [SMILES: C=CC(=O)Nc1cccc(-c2ccc3ccc(C(=O)NC)cc3c2)c1] | N-methyl-7-[3-(prop-2-enamido)phenyl]naphthalene-2-carboxamide | 331.1 |
| 492 | 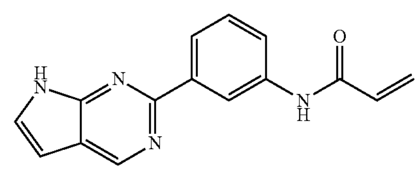 [SMILES: C=CC(=O)Nc1cccc(-c2ncc3cc[nH]c3n2)c1] | N-(3-{7H-pyrrolo[2,3-d]pyrimidin-2-yl}phenyl)prop-2-enamide | 265.1 |
| 493 | 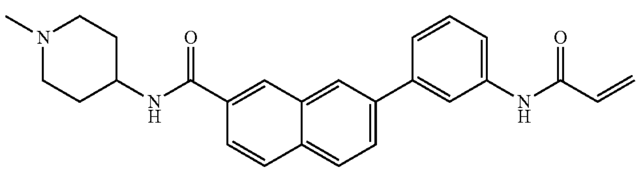 [SMILES: C=CC(=O)Nc1cccc(-c2ccc3ccc(C(=O)NC4CCN(C)CC4)cc3c2)c1] | N-(1-methylpiperidin-4-yl)-7-[3-(prop-2-enamido)phenyl]naphthalene-2-carboxamide | 414.2 |
| 494 | 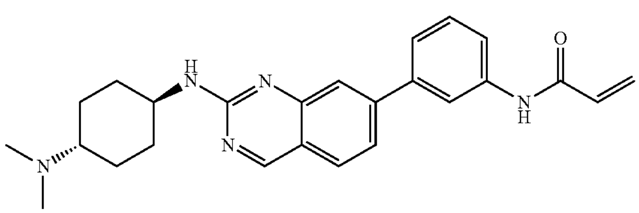 [SMILES: C=CC(=O)Nc1cccc(-c2ccc3cnc(N[C@H]4CC[C@H](N(C)C)CC4)nc3c2)c1] | N-[3-(2-{[(1r,4r)-4-(dimethylamino)cyclohexyl]amino}quinazolin-7-yl)phenyl]prop-2-enamide | 416.2 |

TABLE 12-continued

| Cpd. No. | Structure | IUPAC | LC-MS (ES+, m/z) |
|---|---|---|---|
| 495 | 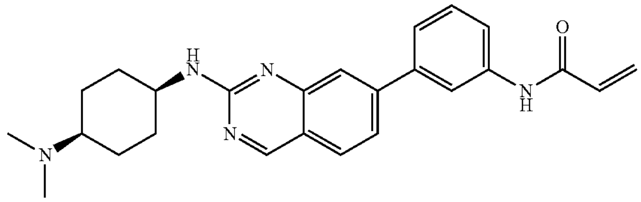 [SMILES: C=CC(=O)Nc1cccc(-c2ccc3cnc(N[C@H]4CC[C@@H](N(C)C)CC4)nc3c2)c1] | N-[3-(2-{[(1s,4s)-4-(dimethylamino)cyclohexyl]amino}quinazolin-7-yl)phenyl]prop-2-enamide | 416.3 |
| 496 | 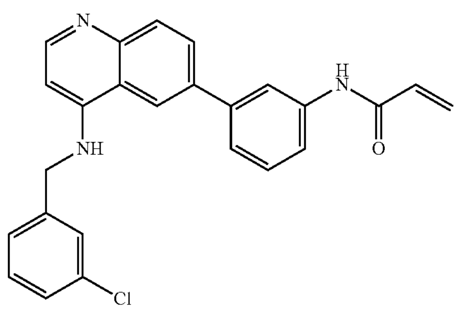 [SMILES: C=CC(=O)Nc1cccc(-c2ccc3nccc(NCc4cccc(Cl)c4)c3c2)c1] | N-[3-(4-{[(3-chlorophenyl)methyl]amino}quinolin-6-yl)phenyl]prop-2-enamide | 414.1 |
| 497 | 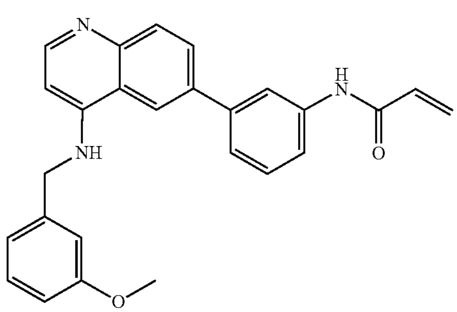 [SMILES: C=CC(=O)Nc1cccc(-c2ccc3nccc(NCc4cccc(OC)c4)c3c2)c1] | N-[3-(4-{[(3-methoxyphenyl)methyl]amino}quinolin-6-yl)phenyl]prop-2-enamide | 410.2 |
| 498 | 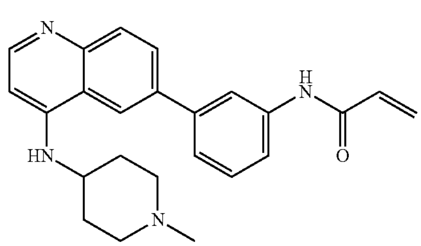 [SMILES: C=CC(=O)Nc1cccc(-c2ccc3nccc(NC4CCN(C)CC4)c3c2)c1] | N-(3-{4-[(1-methylpiperidin-4-yl)amino]quinolin-6-yl}phenyl)prop-2-enamide | 387.2 |

TABLE 12-continued

| Cpd. No. | Structure | IUPAC | LC-MS (ES+, m/z) |
|---|---|---|---|
| 499 | 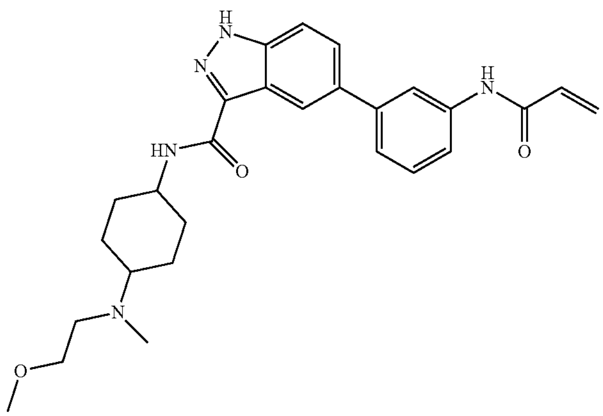 [SMILES: C=CC(=O)Nc1cccc(-c2ccc3[nH]nc(C(=O)NC4CCC(N(C)CCOC)CC4)c3c2)c1] | N-{4-[(2-methoxyethyl)(methyl)amino]cyclohexyl}-5-[3-(prop-2-enamido)phenyl]-1H-indazole-3-carboxamide | 476.3 |
| 500 | 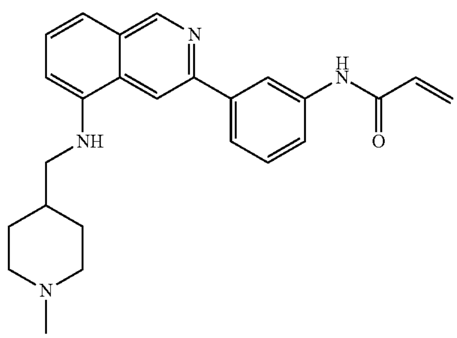 [SMILES: C=CC(=O)Nc1cccc(-c2cc3c(NCC4CCN(C)CC4)cccc3cn2)c1] | N-[3-(5-{[(1-methylpiperidin-4-yl)methyl]amino}isoquinolin-3-yl)phenyl]prop-2-enamide | 401.2 |
| 501 | 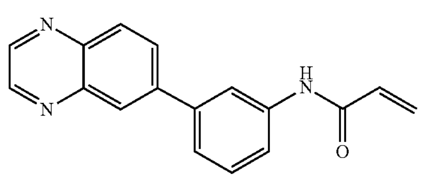 [SMILES: C=CC(=O)Nc1cccc(-c2ccc3nccnc3c2)c1] | N-[3-(quinoxalin-6-yl)phenyl]prop-2-enamide | 276.1 |
| 502 | 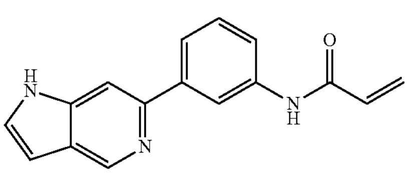 [SMILES: C=CC(=O)Nc1cccc(-c2cc3[nH]ccc3cn2)c1] | N-(3-{1H-pyrrolo[3,2-c]pyridin-6-yl}phenyl)prop-2-enamide | 264.1 |
| 503 | 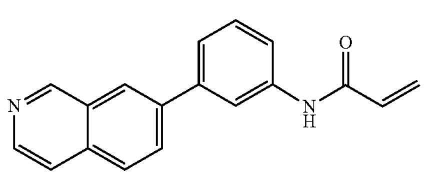 [SMILES: C=CC(=O)Nc1cccc(-c2ccc3ccncc3c2)c1] | N-[3-(isoquinolin-7-yl)phenyl]prop-2-enamide | 275.1 |

TABLE 12-continued

| Cpd. No. | Structure | IUPAC | LC-MS (ES+, m/z) |
|---|---|---|---|
| 504 | 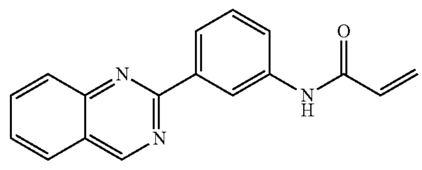 [SMILES: C=CC(=O)Nc1cccc(-c2ncc3ccccc3n2)c1] | N-[3-(quinazolin-2-yl)phenyl]prop-2-enamide | 276.1 |
| 505 | 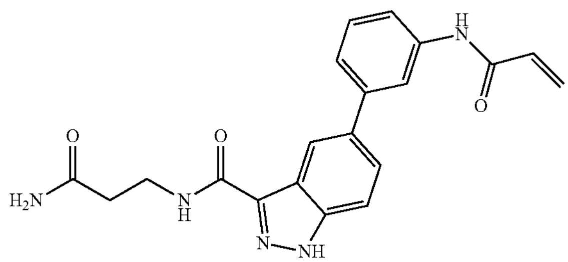 [SMILES: C=CC(=O)Nc1cccc(-c2ccc3[nH]nc(C(=O)NCCC(N)=O)c3c2)c1] | N-(3-{3-[(2-carbamoylethyl)carbamoyl]-1H-indazol-5-yl}phenyl)prop-2-enamide | 378.1 |
| 506 | 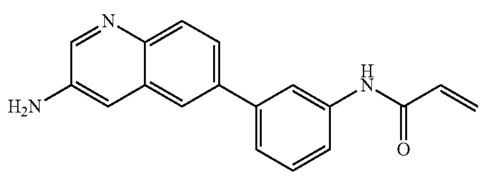 [SMILES: C=CC(=O)Nc1cccc(-c2ccc3ncc(N)cc3c2)c1] | N-[3-(3-aminoquinolin-6-yl)phenyl]prop-2-enamide | 290.1 |
| 507 | 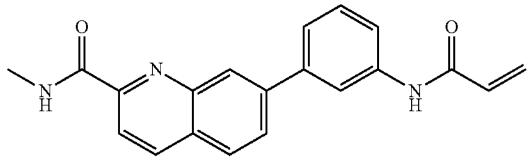 [SMILES: C=CC(=O)Nc1cccc(-c2ccc3ccc(C(=O)NC)nc3c2)c1] | N-methyl-7-[3-(prop-2-enamido)phenyl]quinoline-2-carboxamide | 332.1 |
| 508 | 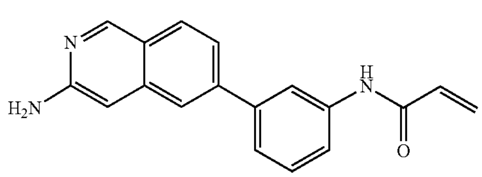 [SMILES: C=CC(=O)Nc1cccc(-c2ccc3cnc(N)cc3c2)c1] | N-[3-(3-aminoisoquinolin-6-yl)phenyl]prop-2-enamide | 290.2 |
| 509 | 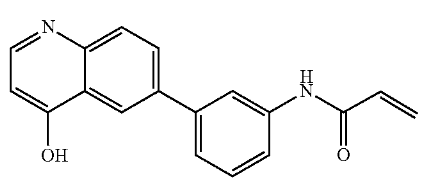 [SMILES: C=CC(=O)Nc1cccc(-c2ccc3nccc(O)c3c2)c1] | N-[3-(4-hydroxyquinolin-6-yl)phenyl]prop-2-enamide | 291.1 |
| 510 | 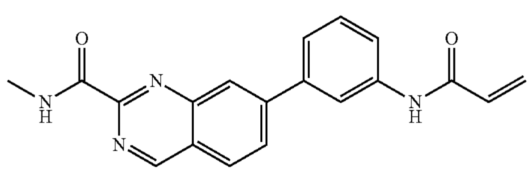 [SMILES: C=CC(=O)Nc1cccc(-c2ccc3cnc(C(=O)NC)nc3c2)c1] | N-methyl-7-[3-(prop-2-enamido)phenyl]quinazoline-2-carboxamide | 333.1 |

TABLE 12-continued

| Cpd. No. | Structure | IUPAC | LC-MS (ES+, m/z) |
|---|---|---|---|
| 511 | 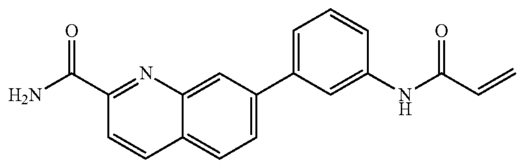 [SMILES: C=CC(=O)Nc1cccc(-c2ccc3ccc(C(N)=O)nc3c2)c1] | 7-[3-(prop-2-enamido)phenyl]quinoline-2-carboxamide | 318.1 |
| 512 | 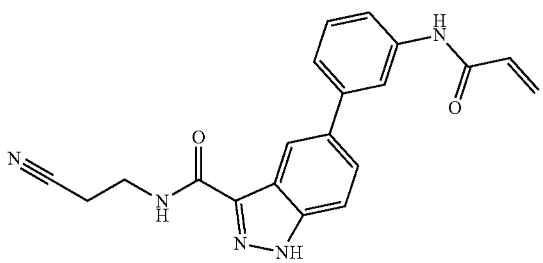 [SMILES: C=CC(=O)Nc1cccc(-c2ccc3[nH]nc(C(=O)NCCC#N)c3c2)c1] | N-(2-cyanoethyl)-5-[3-(prop-2-enamido)phenyl]-1H-indazole-3-carboxamide | 360.1 |
| 513 | 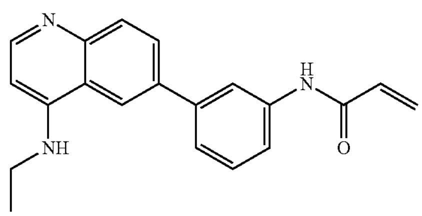 [SMILES: C=CC(=O)Nc1cccc(-c2ccc3nccc(NCC)c3c2)c1] | N-{3-[4-(ethylamino)quinolin-6-yl]phenyl}prop-2-enamide | 318.2 |
| 514 | 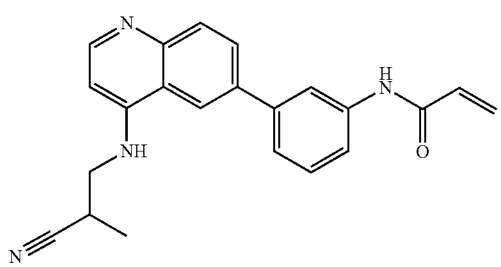 [SMILES: C=CC(=O)Nc1cccc(-c2ccc3nccc(NCC(C)C#N)c3c2)c1] | N-(3-{4-[(2-cyano-2-methylethyl)amino]quinolin-6-yl}phenyl)prop-2-enamide | 357.1 |
| 515 | 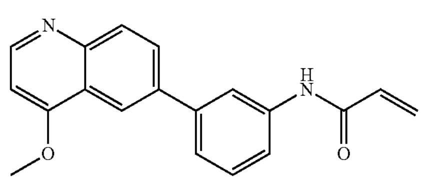 [SMILES: C=CC(=O)Nc1cccc(-c2ccc3nccc(OC)c3c2)c1] | N-[3-(4-methoxyquinolin-6-yl)phenyl]prop-2-enamide | 305.1 |
| 516 | 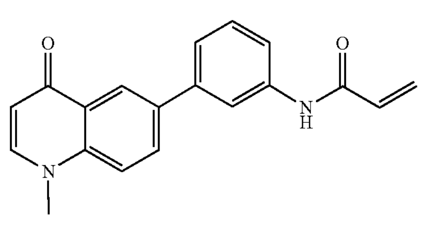 [SMILES: C=CC(=O)Nc1cccc(-c2ccc3c(c2)c(=O)ccn3C)c1] | N-[3-(1-methyl-4-oxo-1,4-dihydroquinolin-6-yl)phenyl]prop-2-enamide | 305.1 |

TABLE 12-continued

| Cpd. No. | Structure | IUPAC | LC-MS (ES+, m/z) |
|---|---|---|---|
| 517 | 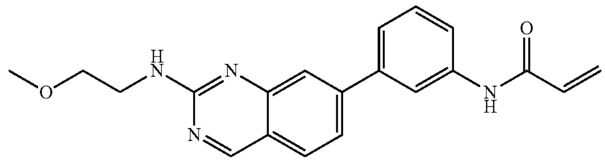 [SMILES: C=CC(=O)Nc1cccc(-c2ccc3cnc(NCCOC)nc3c2)c1] | N-(3-{2-[(2-methoxyethyl)amino]quinazolin-7-yl}phenyl)prop-2-enamide | 349.2 |
| 518 | 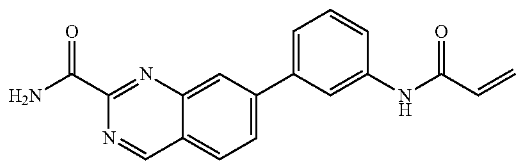 | 7-[3-(prop-2-enamido)phenyl]quinazoline-2-carboxamide | 319.1 |
| 519 | 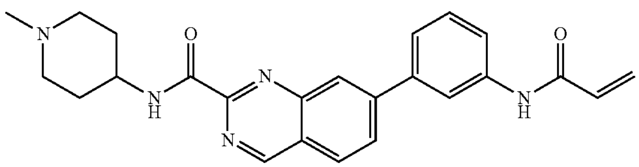 [SMILES: C=CC(=O)Nc1cccc(-c2ccc3cnc(C(=O)NC4CCN(C)CC4)nc3c2)c1] | N-(1-methylpiperidin-4-yl)-7-[3-(prop-2-enamido)phenyl]quinazoline-2-carboxamide | 416.2 |
| 520 | 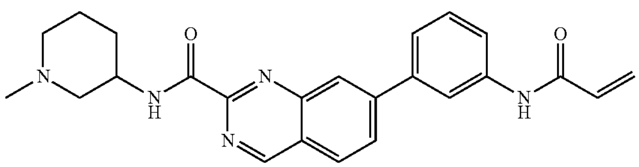 [SMILES: C=CC(=O)Nc1cccc(-c2ccc3cnc(C(=O)NC4CCCN(C)C4)nc3c2)c1] | N-(1-methylpiperidin-3-yl)-7-[3-(prop-2-enamido)phenyl]quinazoline-2-carboxamide | 416.1 |
| 521 | 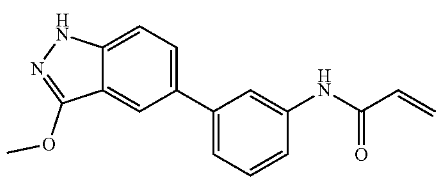 [SMILES: C=CC(=O)Nc1cccc(-c2ccc3[nH]nc(OC)c3c2)c1] | N-[3-(3-methoxy-1H-indazol-5-yl)phenyl]prop-2-enamide | 294.1 |
| 522 | 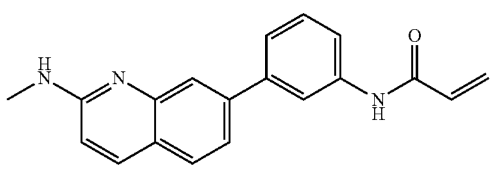 [SMILES: C=CC(=O)Nc1cccc(-c2ccc3ccc(NC)nc3c2)c1] | N-{3-[2-(methylamino)quinolin-7-yl]phenyl}prop-2-enamide | 304.2 |
| 523 | 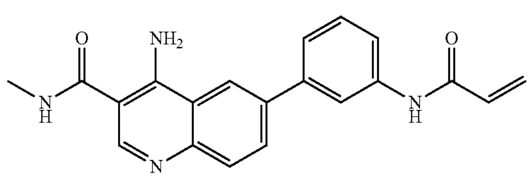 [SMILES: C=CC(=O)Nc1cccc(-c2ccc3ncc(C(=O)NC)c(N)c3c2)c1] | 4-amino-N-methyl-6-[3-(prop-2-enamido)phenyl]quinoline-3-carboxamide | 347.1 |
| 524 | 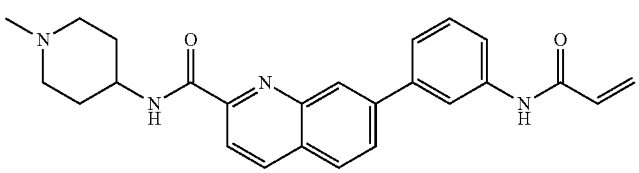 [SMILES: C=CC(=O)Nc1cccc(-c2ccc3ccc(C(=O)NC4CCN(C)CC4)nc3c2)c1] | N-(1-methylpiperidin-4-yl)-7-[3-(prop-2-enamido)phenyl]quinoline-2-carboxamide | 415.2 |

TABLE 12-continued

| Cpd. No. | Structure | IUPAC | LC-MS (ES+, m/z) |
|---|---|---|---|
| 525 | 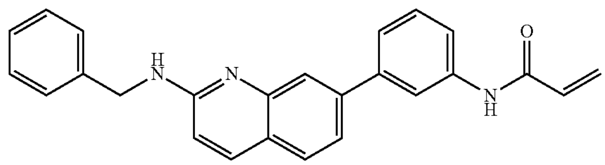 [SMILES: C=CC(=O)Nc1cccc(-c2ccc3ccc(NCc4ccccc4)nc3c2)c1] | N-{3-[2-(benzylamino)quinolin-7-yl]phenyl}prop-2-enamide | 380.1 |
| 526 | 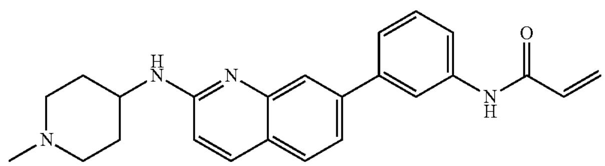 [SMILES: C=CC(=O)Nc1cccc(-c2ccc3ccc(NC4CCN(C)CC4)nc3c2)c1] | N-(3-{2-[(1-methylpiperidin-4-yl)amino]quinolin-7-yl}phenyl)prop-2-enamide | 387.2 |
| 527 | 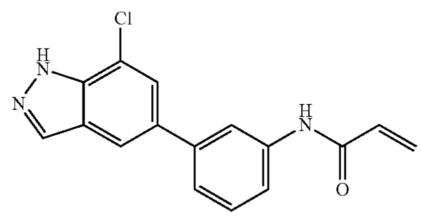 [SMILES: C=CC(=O)Nc1cccc(-c2cc(Cl)c3[nH]ncc3c2)c1] | N-[3-(7-chloro-1H-indazol-5-yl)phenyl]prop-2-enamide | 297.9 |
| 528 | 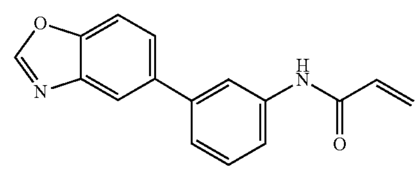 [SMILES: C=CC(=O)Nc1cccc(-c2ccc3ocnc3c2)c1] | N-[3-(1,3-benzoxazol-5-yl)phenyl]prop-2-enamide | 265 |
| 529 | 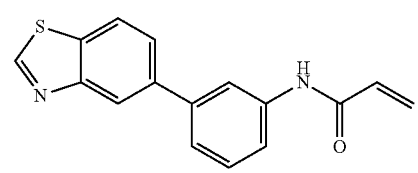 [SMILES: C=CC(=O)Nc1cccc(-c2ccc3scnc3c2)c1] | N-[3-(1,3-benzothiazol-5-yl)phenyl]prop-2-enamide | 280.9 |
| 530 | 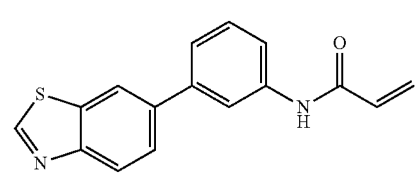 [SMILES: C=CC(=O)Nc1cccc(-c2ccc3ncsc3c2)c1] | N-[3-(1,3-benzothiazol-6-yl)phenyl]prop-2-enamide | 280.9 |
| 531 | 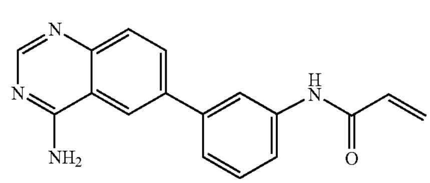 [SMILES: C=CC(=O)Nc1cccc(-c2ccc3ncnc(N)c3c2)c1] | N-[3-(4-aminoquinazolin-6-yl)phenyl]prop-2-enamide | 291 |

TABLE 12-continued

| Cpd. No. | Structure | IUPAC | LC-MS (ES+, m/z) |
|---|---|---|---|
| 532 | 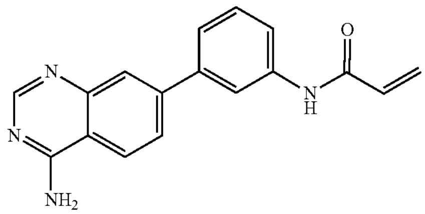 [SMILES: C=CC(=O)Nc1cccc(-c2ccc3c(N)ncnc3c2)c1] | N-[3-(4-aminoquinazolin-7-yl)phenyl]prop-2-enamide | 290.9 |
| 533 | 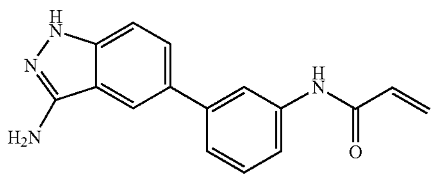 [SMILES: C=CC(=O)Nc1cccc(-c2ccc3[nH]nc(N)c3c2)c1] | N-[3-(3-amino-1H-indazol-5-yl)phenyl]prop-2-enamide | 279 |
| 534 | 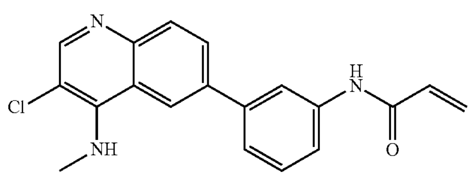 [SMILES: C=CC(=O)Nc1cccc(-c2ccc3ncc(Cl)c(NC)c3c2)c1] | N-{3-[3-chloro-4-(methylamino)quinolin-6-yl]phenyl}prop-2-enamide | 337.9 |
| 535 | 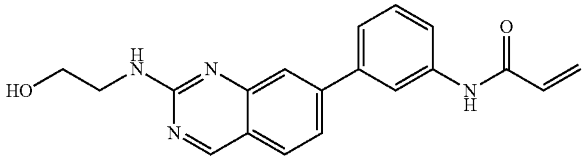 [SMILES: C=CC(=O)Nc1cccc(-c2ccc3cnc(NCCO)nc3c2)c1] | N-(3-{2-[(2-hydroxyethyl)amino]quinazolin-7-yl}phenyl)prop-2-enamide | 335.1 |
| 536 | 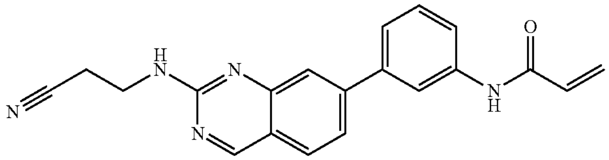 [SMILES: C=CC(=O)Nc1cccc(-c2ccc3cnc(NCCC#N)nc3c2)c1] | N-(3-{2-[(2-cyanoethyl)amino]quinazolin-7-yl}phenyl)prop-2-enamide | 344.1 |
| 537 | 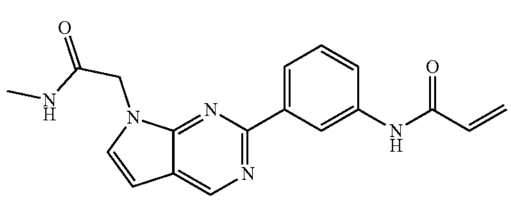 [SMILES: C=CC(=O)Nc1cccc(-c2ncc3ccn(CC(=O)NC)c3n2)c1] | N-(3-{7-[(methylcarbamoyl)methyl]-7H-pyrrolo[2,3-d]pyrimidin-2-yl}phenyl)prop-2-enamide | 336.1 |
| 538 | 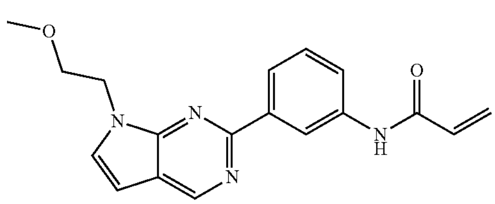 [SMILES: C=CC(=O)Nc1cccc(-c2ncc3ccn(CCOC)c3n2)c1] | N-{3-[7-(2-methoxyethyl)-7H-pyrrolo[2,3-d]pyrimidin-2-yl]phenyl}prop-2-enamide | 323.1 |

TABLE 12-continued
| Cpd. No. | Structure | IUPAC | LC-MS (ES+, m/z) |
|---|---|---|---|
| 539 | 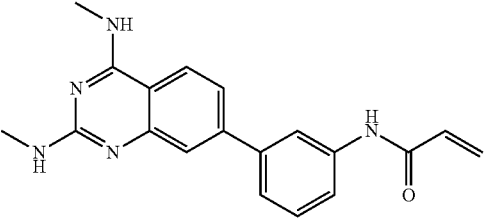 [SMILES: C=CC(=O)Nc1cccc(-c2ccc3c(NC)nc(NC)nc3c2)c1] | N-{3-[2,4-bis(methylamino)quinazolin-7-yl]phenyl}prop-2-enamide | 334.1 |
| 540 | 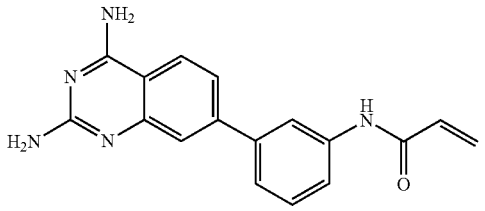 [SMILES: C=CC(=O)Nc1cccc(-c2ccc3c(N)nc(N)nc3c2)c1] | N-[3-(2,4-diaminoquinazolin-7-yl)phenyl]prop-2-enamide | 306.1 |
| 541 | 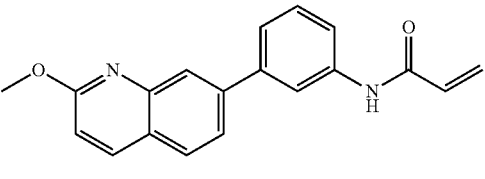 [SMILES: C=CC(=O)Nc1cccc(-c2ccc3ccc(OC)nc3c2)c1] | N-[3-(2-methoxyquinolin-7-yl)phenyl]prop-2-enamide | 305.1 |
| 542 | 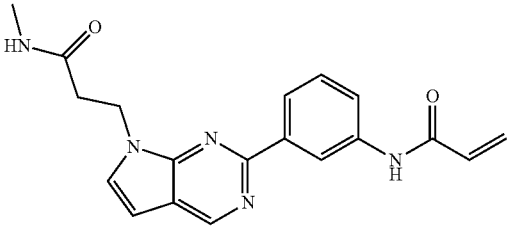 [SMILES: C=CC(=O)Nc1cccc(-c2ncc3ccn(CCC(=O)NC)c3n2)c1] | N-(3-{7-[2-(methylcarbamoyl)ethyl]-7H-pyrrolo[2,3-d]pyrimidin-2-yl}phenyl)prop-2-enamide | 350.1 |
| 543 | 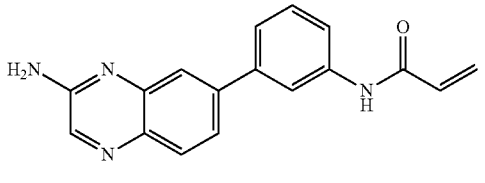 [SMILES: C=CC(=O)Nc1cccc(-c2ccc3ncc(N)nc3c2)c1] | N-[3-(3-aminoquinoxalin-6-yl)phenyl]prop-2-enamide | 291.1 |
| 544 | 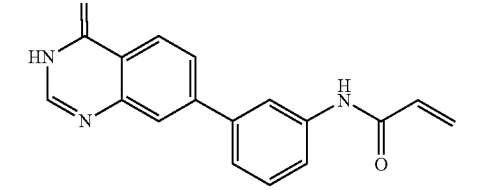 | N-[3-(4-oxo-3,4-dihydroquinazolin-7-yl)phenyl]prop-2-enamide | 292.1 |

TABLE 12-continued
| Cpd. No. | Structure | IUPAC | LC-MS (ES+, m/z) |
|---|---|---|---|
| 545 | 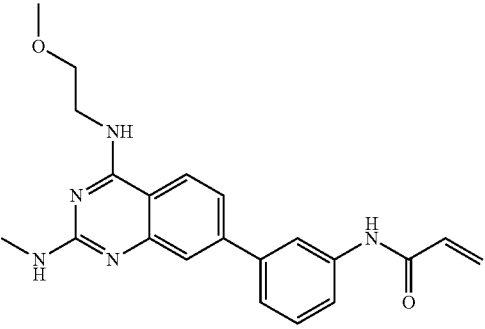 [SMILES: C=CC(=O)Nc1cccc(-c2ccc3c(NCCOC)nc(NC)nc3c2)c1] | N-(3-{4-[(2-methoxyethyl)amino]-2-(methylamino)quinazolin-7-yl}phenyl)prop-2-enamide | 378.1 |
| 546 | 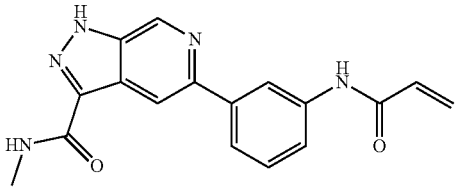 [SMILES: C=CC(=O)Nc1cccc(-c2cc3c(C(=O)NC)n[nH]c3cn2)c1] | N-methyl-5-[3-(prop-2-enamido)phenyl]-1H-pyrazolo[3,4-c]pyridine-3-carboxamide | 322.1 |
| 447 | 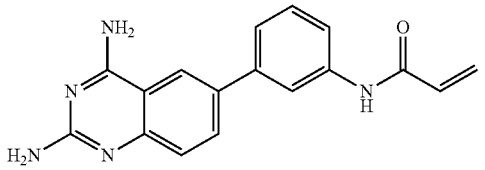 [SMILES: C=CC(=O)Nc1cccc(-c2ccc3nc(N)nc(N)c3c2)c1] | N-[3-(2,4-diaminoquinazolin-6-yl)phenyl]prop-2-enamide | 306 |
| 548 | 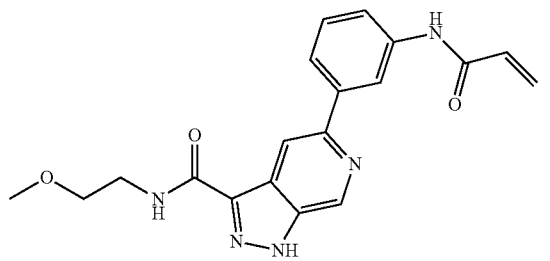 [SMILES: C=CC(=O)Nc1cccc(-c2cc3c(C(=O)NCCOC)n[nH]c3cn2)c1] | N-(2-methoxyethyl)-5-[3-(prop-2-enamido)phenyl]-1H-pyrazolo[3,4-c]pyridine-3-carboxamide | 366.1 |
| 549 | 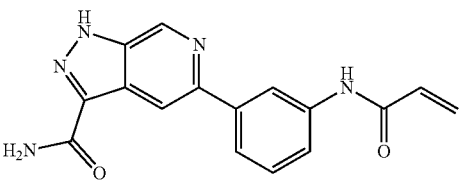 [SMILES: C=CC(=O)Nc1cccc(-c2cc3c(C(N)=O)n[nH]c3cn2)c1] | 5-[3-(prop-2-enamido)phenyl]-1H-pyrazolo[3,4-c]pyridine-3-carboxamide | 308 |

TABLE 12-continued

| Cpd. No. | Structure | IUPAC | LC-MS (ES+, m/z) |
|---|---|---|---|
| 550 | 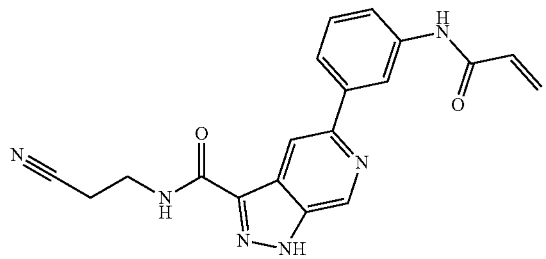 [SMILES: C=CC(=O)Nc1cccc(-c2cc3c(C(=O)NCCC#N)n[nH]c3cn2)c1] | N-(2-cyanoethyl)-5-[3-(prop-2-enamido)phenyl]-1H-pyrazolo[3,4-c]pyridine-3-carboxamide | 361 |
| 551 | 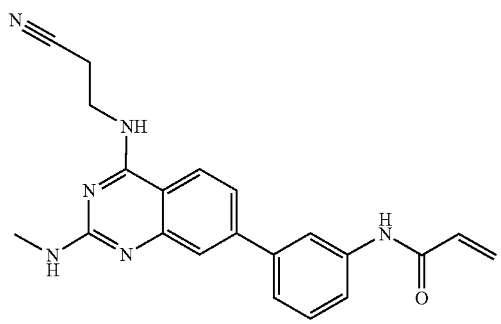 [SMILES: C=CC(=O)Nc1cccc(-c2ccc3c(NCCC#N)nc(NC)nc3c2)c1] | N-(3-{4-[(2-cyanoethyl)amino]-2-(methylamino)quinazolin-7-yl}phenyl)prop-2-enamide | 373.1 |
| 552 | 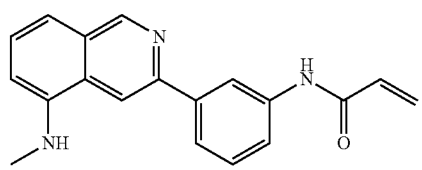 [SMILES: C=CC(=O)Nc1cccc(-c2cc3c(NC)cccc3cn2)c1] | N-{3-[5-(methylamino)isoquinolin-3-yl]phenyl}prop-2-enamide | 304.1 |
| 553 | 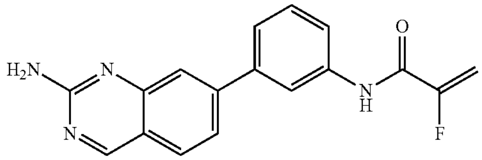 [SMILES: C=C(F)C(=O)Nc1cccc(-c2ccc3cnc(N)nc3c2)c1] | N-[3-(2-aminoquinazolin-7-yl)phenyl]-2-fluoroprop-2-enamide | 309.1 |
| 554 | 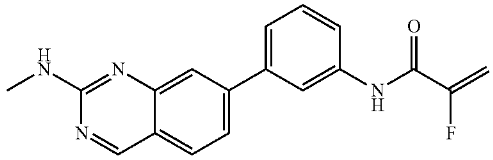 [SMILES: C=C(F)C(=O)Nc1cccc(-c2ccc3cnc(NC)nc3c2)c1] | 2-fluoro-N-{3-[2-(methylamino)quinazolin-7-yl]phenyl}prop-2-enamide | 323.1 |
| 555 | 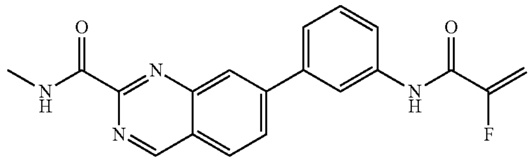 [SMILES: C=C(F)C(=O)Nc1cccc(-c2ccc3cnc(C(=O)NC)nc3c2)c1] | 7-[3-(2-fluoroprop-2-enamido)phenyl]-N-methylquinazoline-2-carboxamide | 351.1 |

TABLE 12-continued
| Cpd. No. | Structure | IUPAC | LC-MS (ES+, m/z) |
|---|---|---|---|
| 556 | 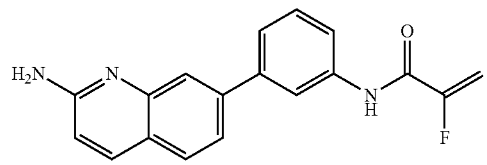 [SMILES: C=C(F)C(=O)Nc1cccc(-c2ccc3ccc(N)nc3c2)c1] | N-[3-(2-aminoquinolin-7-yl)phenyl]-2-fluoroprop-2-enamide | 308.1 |
| 557 | 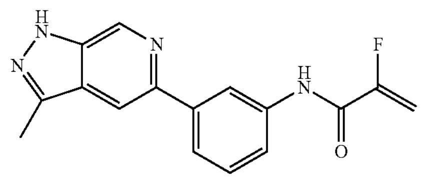 [SMILES: C=C(F)C(=O)Nc1cccc(-c2cc3c(C)n[nH]c3cn2)c1] | 2-fluoro-N-(3-{3-methyl-1H-pyrazolo[3,4-c]pyridin-5-yl}phenyl)prop-2-enamide | 297.1 |
| 558 | 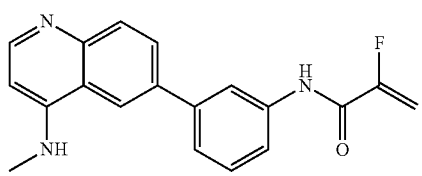 [SMILES: C=C(F)C(=O)Nc1cccc(-c2ccc3nccc(NC)c3c2)c1] | 2-fluoro-N-{3-[4-(methylamino)quinolin-6-yl]phenyl}prop-2-enamide | 322.1 |
| 559 | 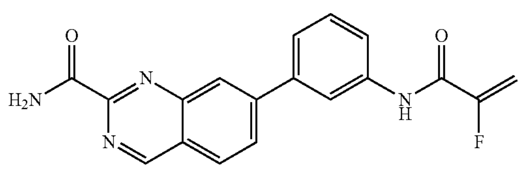 [SMILES: C=C(F)C(=O)Nc1cccc(-c2ccc3cnc(C(N)=O)nc3c2)c1] | 7-[3-(2-fluoroprop-2-enamido)phenyl]quinazoline-2-carboxamide | 337.1 |
Example 13: Method M
Route 1: General Scheme
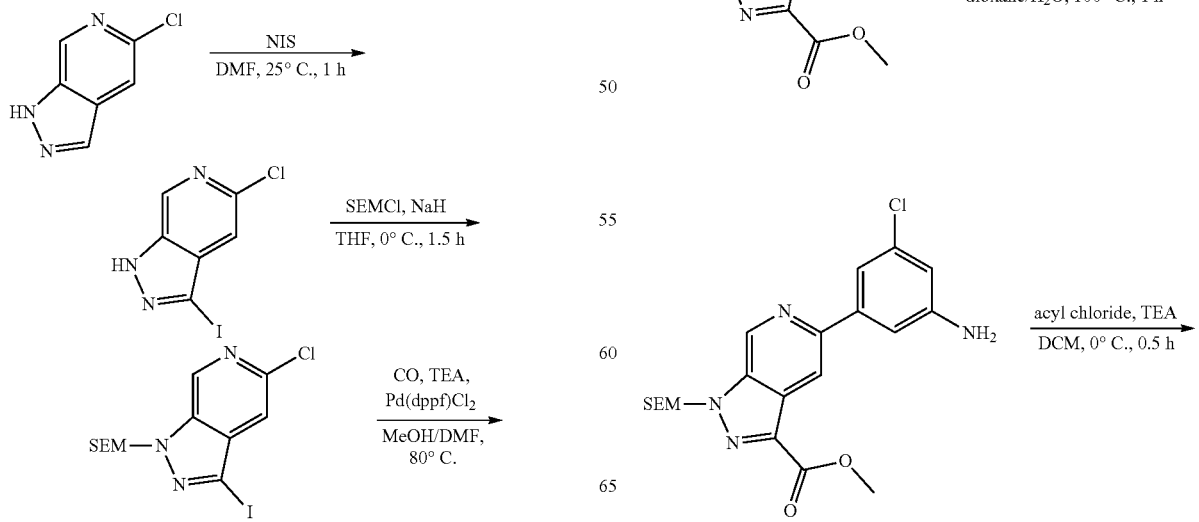

-continued

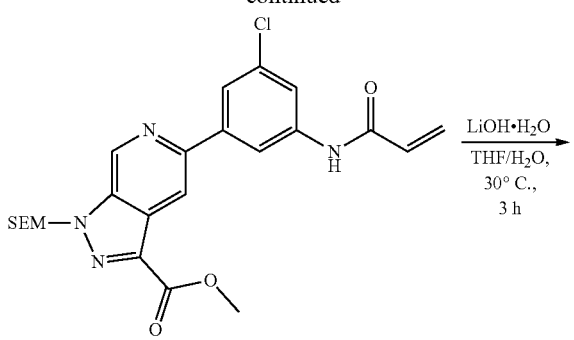

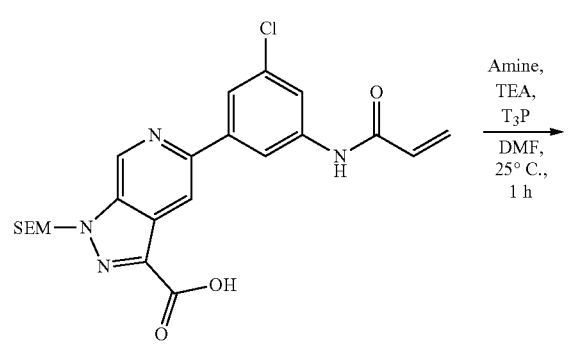

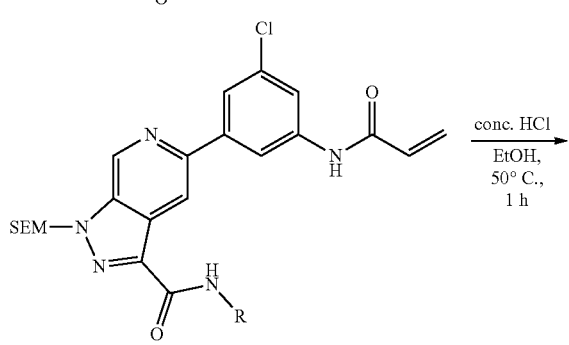

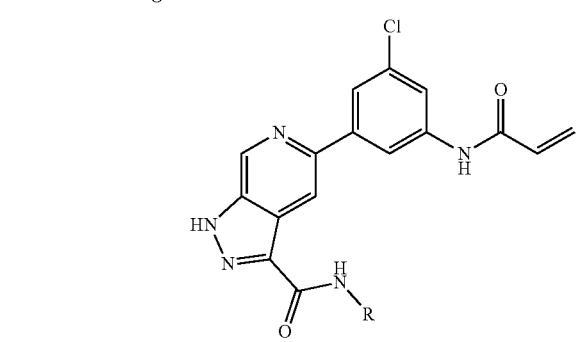

Step 1) Preparation of 5-chloro-3-iodo-1H-pyrazolo[3,4-c]pyridine

-continued

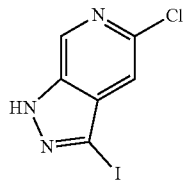

To a solution of 5-chloro-1H-pyrazolo[3,4-c]pyridine (1 g, 6.51 mmol, 1 eq) in DMF (10 mL) was added NIS (2.2 g, 9.77 mmol, 1.5 eq). The reaction mixture was stirred at 25° C. for 1 hr. The reaction mixture was poured into water (20 mL) and extracted with EtOAc (3×10 mL). The combined organic layer were washed with brine (3×30 mL), dried over anhydrous Na$_2$SO$_4$, filtered, and concentrated in vacuo. The residue was purified by column chromatography (SiO$_2$, PE:EtOAc=10:1 to 1/1) to afford the title compound (1.2 g, 65.9% yield) as a yellow solid.

Step 2) Preparation of 2-[(5-chloro-3-iodo-pyrazolo[3,4-c]pyridin-1-yl)methoxy]ethyl-trimethyl-silane

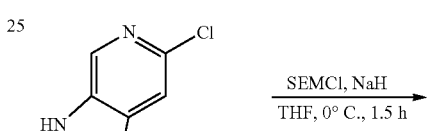

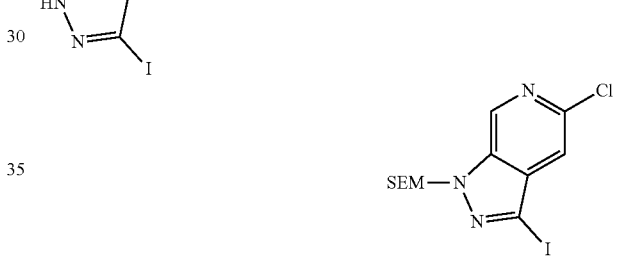

To a solution of 5-chloro-3-iodo-1H-pyrazolo[3,4-c]pyridine (1 g, 3.58 mmol, 1 eq) in THF (2 mL) was added NaH (214.7 mg, 5.37 mmol, 60% purity, 1.5 eq) at 0° C. The reaction mixture was stirred at 0° C. for 0.5 h. Then SEMCl (715.9 mg, 4.29 mmol, 759.96 µL, 1.2 eq) was added. The resulting reaction mixture was stirred at 0° C. for further 1 hr. The reaction mixture was poured into saturated NH$_4$Cl (100 mL) and extracted with EtOAc (3×50 mL). The combined organic layer were washed with brine (3×50 mL), dried over anhydrous Na$_2$SO$_4$, filtered, and concentrated in vacuo. The residue was purified by column chromatography (SiO$_2$, PE:EtOAc=10:1 to 4:1) to afford the title compound (1.3 g, 88.7% yield) as a yellow solid.

Step 3) Preparation of Methyl 5-chloro-1-(2-trimethylsilylethoxymethyl)pyrazolo[3,4-c]pyridine-3-carboxylate

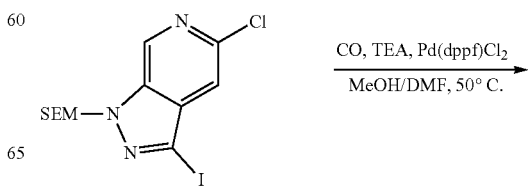

-continued

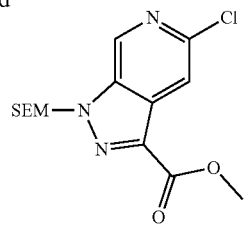

To a solution of 2-[(5-chloro-3-iodo-pyrazolo[3,4-c]pyridin-1-yl)methoxy]ethyl-trimethyl-silane (0.5 g, 1.22 mmol, 1 eq) in DMF (4 mL) and MeOH (1 mL) were added TEA (370.5 mg, 3.66 mmol, 509.56 μL, 3 eq) and Pd(dppf)Cl₂ (89.3 mg, 122.03 μmol, 0.1 eq). The reaction mixture was stirred at 50° C. for 8 hrs under CO at 15 psi. LCMS showed that the reaction was complete. The reaction mixture was poured into water (150 mL) and extracted with EtOAc (3×150 mL). The combined organic layer were washed with brine (3×150 mL), dried over anhydrous Na₂SO₄, filtered, and concentrated in vacuo. The residue was purified by column chromatography (SiO₂, PE:EtOAc=1/0 to 10:1) to afford the title compound (0.35 g, 83.9% yield) as a yellow solid.

Step 4) Preparation of Methyl 5-(3-amino-5-chloro-phenyl)-1-(2-trimethylsilylethoxymethyl) pyrazolo[3,4-c]pyridine-3-carboxylate

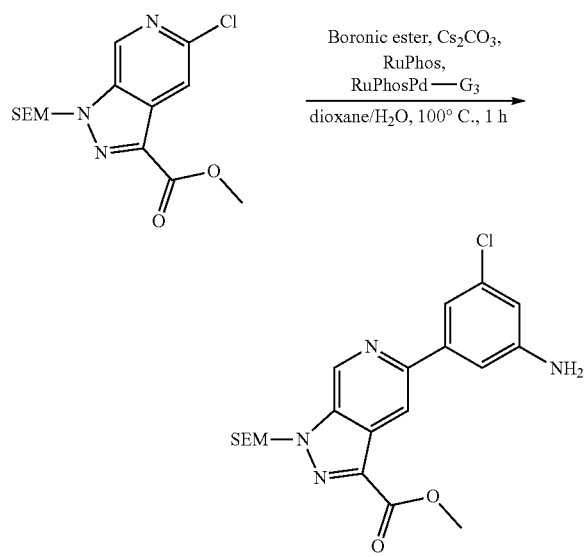

To a solution of methyl 5-chloro-1-(2-trimethylsilylethoxymethyl) pyrazolo[3,4-c]pyridine-3-carboxylate (0.2 g, 585.03 μmol, 1 eq) and 3-chloro-5-(4,4,5,5-tetramethyl-1,3,2-dioxaborolan-2-yl)aniline (178 mg, 702.03 μmol, 1.2 eq) in dioxane (4 mL) and H₂O (1 mL) were added dicyclohexyl-[2-(2,6-diisopropoxyphenyl)phenyl]phosphane (27.3 mg, 58.5 μmol, 0.1 eq), Cs₂CO₃ (571.8 mg, 1.76 mmol, 3 eq) and [2-(2-aminophenyl)phenyl]-methylsulfonyloxy-palladium;dicyclohexyl-[2-(2,6-diisopropoxyphenyl)phenyl]phosphane (24.5 mg, 29.25 μmol, 0.05 eq). The reaction mixture was stirred at 100° C. for 1 hr under N₂. The reaction mixture were poured into water (15 mL) and extracted with EtOAc (3×15 mL). The combined organic layer were washed with brine (3×15 mL), dried over anhydrous Na₂SO₄, filtered, and concentrated in vacuo. The residue was purified by prep-TLC (SiO₂, PE:EtOAc=1:1) to afford the title compound (0.11 g, 43.4% yield) as a yellow oil.

Step 5) Preparation of Methyl 5-(3-amino-5-chloro-phenyl)-1-(2-trimethylsilylethoxymethyl) pyrazolo[3,4-c]pyridine-3-carboxylate

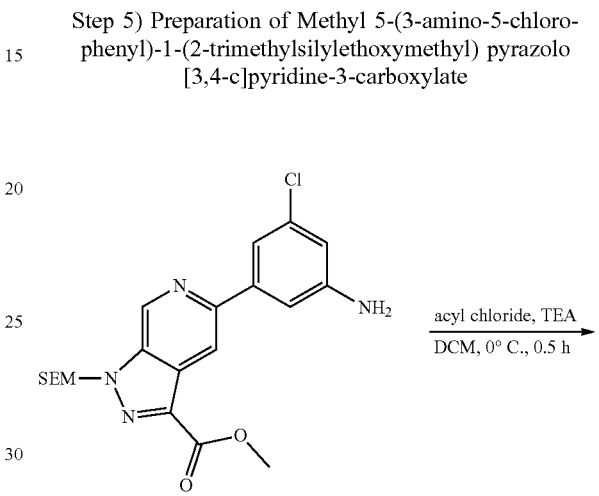

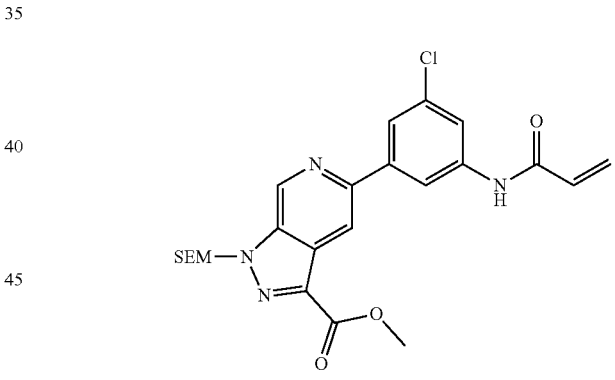

To a solution of methyl 5-(3-amino-5-chloro-phenyl)-1-(2-trimethylsilylethoxymethyl)pyrazolo[3,4-c]pyridine-3-carboxylate (0.9 g, 2.08 mmol, 1 eq) in DCM (18 mL) were added TEA (631 mg, 6.24 mmol, 867.96 μL, 3 eq) and prop-2-enoyl chloride (376.3 mg, 4.16 mmol, 338.98 μL, 2 eq) in DCM (0.5 mL) at 0° C. The resulting reaction mixture was stirred at 0° C. for 0.5 hr under N₂. The reaction mixture were poured into ice water (100 mL) and extracted with DCM (3×50 mL). The combined organic layer was washed with brine (3×50 mL), dried over anhydrous Na₂SO₄, filtered, and concentrated in vacuo. The residue was purified by column chromatography (SiO₂, PE:EtOAc=10:1 to 1/1) to afford the title compound (0.7 g, 69.2% yield) as a yellow solid.

Step 6) Preparation of 5-[3-chloro-5-(prop-2-enoy-lamino)phenyl]-1-(2-trimethylsilyl ethoxymethyl)pyrazolo[3,4-c]pyridine-3-carboxylic acid

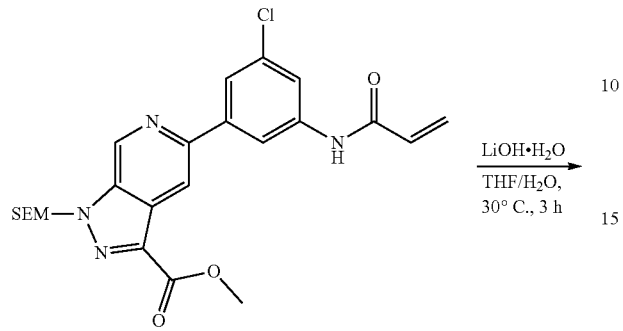

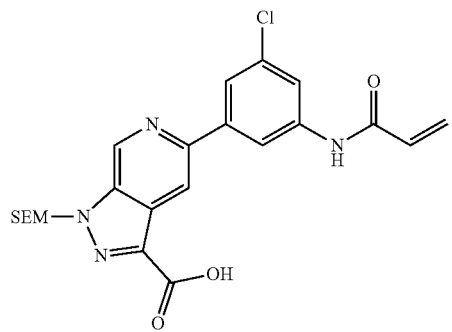

To a solution of methyl 5-[3-chloro-5-(prop-2-enoy-lamino)phenyl]-1-(2-trimethylsilyl ethoxymethyl)pyrazolo[3,4-c]pyridine-3-carboxylate (0.5 g, 1.03 mmol, 1 eq) in THF (12.5 mL) and H₂O (3.1 mL) was added LiOH·H₂O (430.8 mg, 10.27 mmol, 10 eq). The reaction mixture was stirred at 30° C. for 3 hrs. The reaction mixture were poured into ice water (20 mL), adjusted to pH=6 with saturated citric acid and extracted with EtOAc (3×30 mL). The combined organic layer were washed with brine (3×30 mL), dried over anhydrous Na₂SO₄, filtered, and concentrated in vacuo to afford the crude product (0.5 g) as a yellow solid.

Step 7) Preparation of 5-[3-chloro-5-(prop-2-enoy-lamino)phenyl]-N-(1-methyl-4-piperidyl)-1-(2-trim-ethylsilylethoxymethyl)pyrazolo[3,4-c]pyridine-3-carboxamide

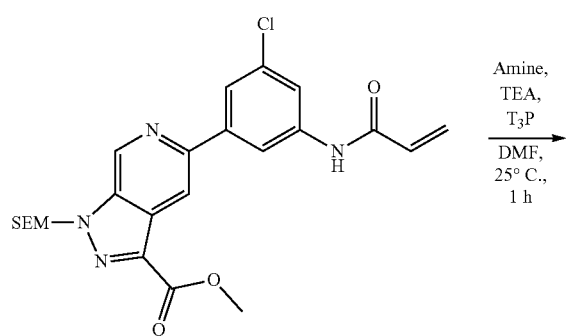

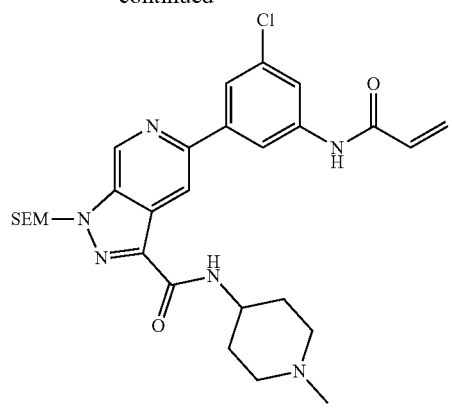

To a solution of 5-[3-chloro-5-(prop-2-enoylamino)phe-nyl]-1-(2-trimethylsilylethoxymethyl) pyrazolo[3,4-c]pyri-dine-3-carboxylic acid (0.13 g, 274.84 μmol, 1 eq) and 1-methylpiperidin-4-amine (47.1 mg, 412.27 μmol, 1.5 eq) in DMF (2 mL) were added TEA (83.4 mg, 824.53 μmol, 114.76 μL, 3 eq) and T₃P (262.4 mg, 412.27 μmol, 245.19 μL, 50% purity, 1.5 eq). The reaction mixture was stirred at 25° C. for 1 hr under N₂. The reaction mixture were poured into water (15 mL) and extracted with EtOAc (3×15 mL). The combined organic layer were washed with brine (3×15 mL), dried over anhydrous Na₂SO₄, filtered, and concentrated in vacuo. The residue was purified by prep-TLC (SiO₂, DCM:MeOH=8:1) to afford the title compound (0.11 g, 70.3% yield) as a white solid.

Step 8)

Preparation of 5-[3-chloro-5-(prop-2-enamido)phe-nyl]-N-(1-methylpiperidin-4-yl)-1H-pyrazolo[3,4-c]pyridine-3-carboxamide (Compound 565)

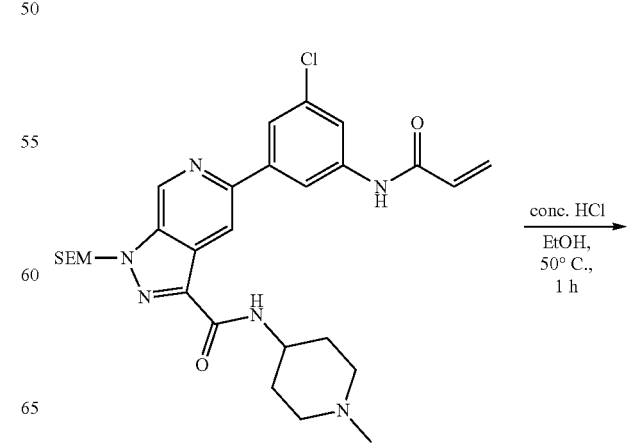

699
-continued

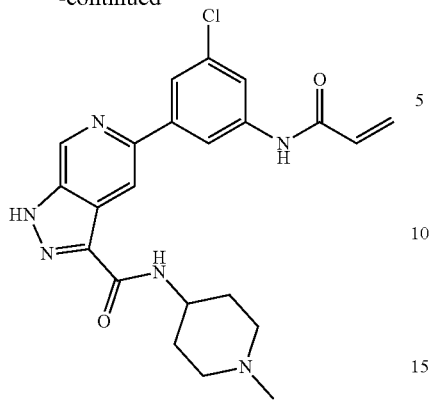

To a solution of 5-[3-chloro-5-(prop-2-enoylamino)phenyl]-N-(1-methyl-4-piperidyl)-1-(2-trimethylsilylethoxymethyl)pyrazolo[3,4-c]pyridine-3-carboxamide (0.05 g, 87.85 µmol, 1 eq) in EtOH (0.3 mL) was added concentrated HCl (8.7 mg, 87.85 µmol, 8.49 µL, 37% purity, 1 eq). The reaction mixture was stirred at 50° C. for 1 hr. The reaction mixture was concentrated in vacuo. The residue was purified by prep-HPLC to afford the title compound (23.8 mg, 29.7% yield) as a white solid. LC-MS (ES+, m/z): 439.1.

Route 2: General Scheme

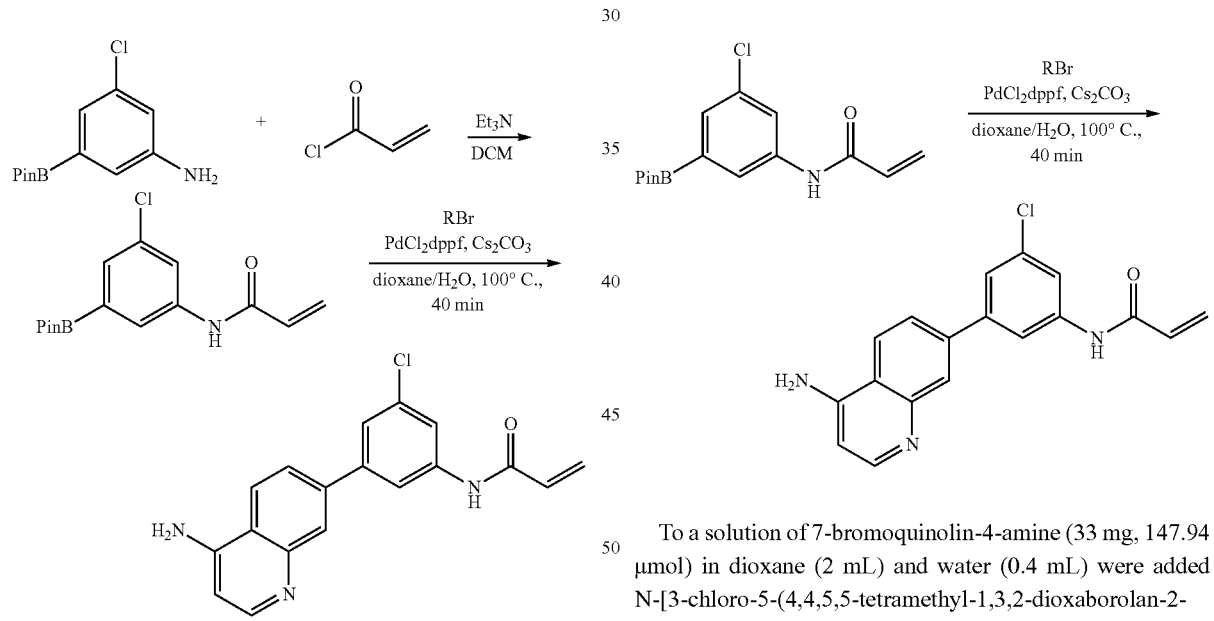

Step 1) Preparation of N-[3-chloro-5-(4,4,5,5-tetramethyl-1,3,2-dioxaborolan-2-yl)phenyl]prop-2-enamide

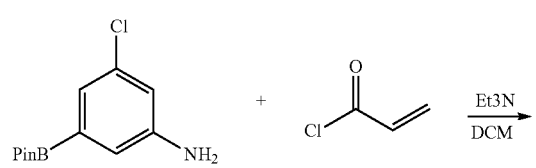

700
-continued

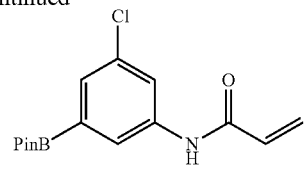

To a solution of 3-chloro-5-(4,4,5,5-tetramethyl-1,3,2-dioxaborolan-2-yl)aniline (300 mg, 1.18 mmol) and Et$_3$N (358.5 mg, 3.55 mmol) in DCM (10 mL) at 0° C. was added a solution of prop-2-enoyl chloride (128.5 mg, 1.42 mmol) in DCM (0.5 mL). The resulting solution was stirred at 0° C. for 2 h. The reaction mixture was diluted with water (30 mL) and extracted with DCM (3×20 mL). The combined organic phase was washed with brine (3×20 mL), dried over anhydrous sodium sulfate, filtered, and concentrated. The residue was purified by chromatography on silica gel eluting with 0-80% EtOAc/PE to afford the title compound (0.145 g, Yield 39%) as a white solid.

Step 2) (Compound 573) Preparation of N-[3-(4-aminoquinolin-7-yl)-5-chlorophenyl]prop-2-enamide To a solution of 7-bromoquinolin-4-amine (33 mg, 147.94 µmol) in dioxane (2 mL) and water (0.4 mL) were added N-[3-chloro-5-(4,4,5,5-tetramethyl-1,3,2-dioxaborolan-2-yl)phenyl]prop-2-enamide (50.1 mg, 162.73 µmol), Cs$_2$CO$_3$ (144.2 mg, 443.81 µmol) and PdCl$_2$dppf (12.1 mg, 14.79 µmol). The reaction was heated at 100° C. for 40 min in a microwave. The reaction mixture was passed through a celite pad, and 2 mL of EDTA was added. The resulting solution was stirred at r.t. for 30 minutes. The solution was washed with brine. The organic phases was dried over anhydrous sodium sulfate. The solvent was removed in vacuo. The residue was purified by reverse phase HPLC using a gradient of water 0.1% FA/acetonitrile 0.1% FA to afford the title compound (9 mg, Yield 18%). FC-MS: [M+H]$^+$323.9

Route 3: General Scheme

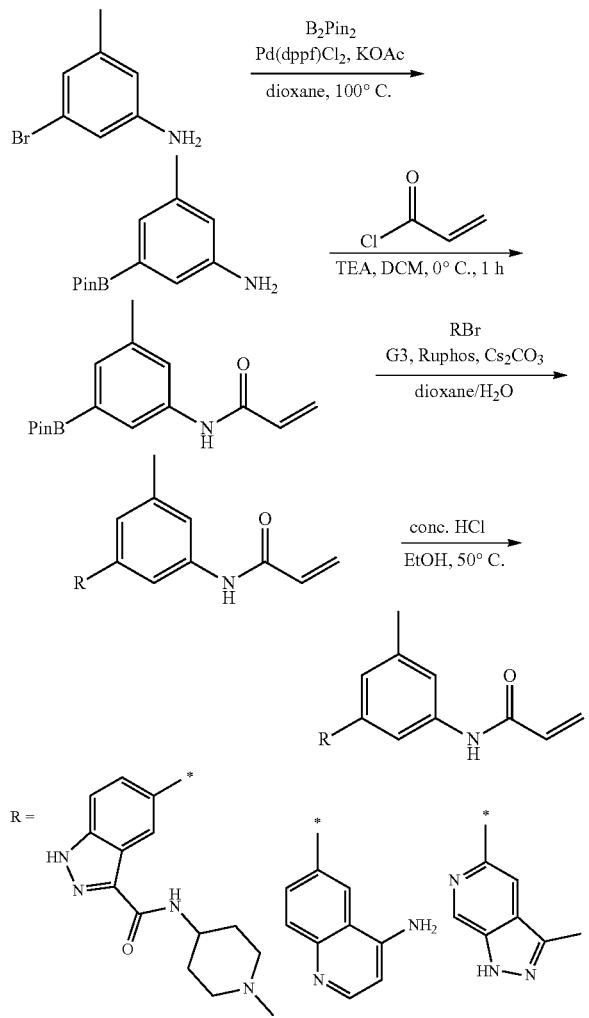

Step 1—3-methyl-5-(4,4,5,5-tetramethyl-1,3,2-dioxaborolan-2-yl)aniline

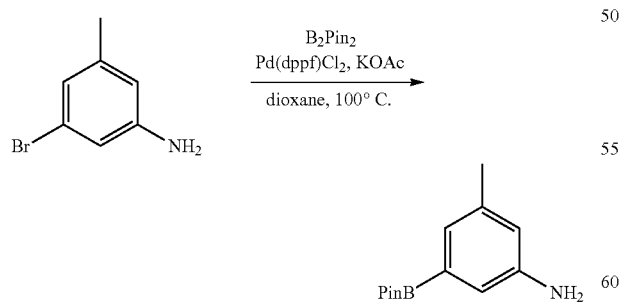

To a mixture of 3-bromo-5-methyl-aniline (2 g, 10.75 mmol, 1 eq) in dioxane (10 mL) was added KOAc (5.27 g, 53.75 mmol, 5 eq), Pin$_2$B$_2$ (4.09 g, 16.12 mmol, 1.5 eq) and Pd(dppf)Cl$_2$ (786.6 mg, 1.07 mmol, 0.1 eq) under N$_2$. Then the mixture was stirred at 100° C. for 1 h. LCMS showed ~60% of the starting material remaining. Then additional Pin$_2$B$_2$ (5.46 g, 21.5 mmol, 2 eq) was added and the mixture was stirred at 100° C. for further 2 h. The reaction mixture was poured into saturated EDTA (50 mL) and stirred for 60 min. The aqueous phase was extracted with EtOAc (3×30 mL). The combined organic layer was washed with brine (3×30 mL), dried over anhydrous Na$_2$SO$_4$, filtered, and concentrated in vacuo to afford a residue. The residue was purified by silica gel chromatography (SiO$_2$, PE:EtOAc=10:1, 3:1) to afford the title compound (3 g, 7.72 mmol, 71.83% yield, 60% purity) as a white solid. LCMS (ES$^+$, m/z): 234.1 [(M+H)$^+$]$^1$H NMR (400 MHz, DMSO-d$_6$) δ=6.74 (s, 1H), 6.66 (s, 1H), 6.48 (s, 1H), 4.93 (s, 2H), 2.15 (s, 3H), 1.26 (s, 12H).

Step 2—N-[3-methyl-5-(4,4,5,5-tetramethyl-1,3,2-dioxaborolan-2-yl)phenyl]prop-2-enamide

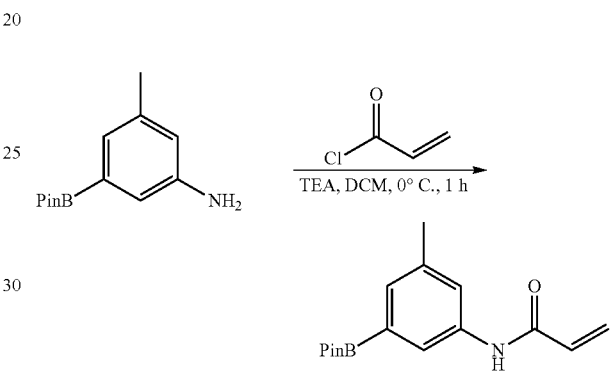

To a solution of 3-methyl-5-(4,4,5,5-tetramethyl-1,3,2-dioxaborolan-2-yl)aniline (2.3 g, 5.92 mmol, 6.20 μL, 1 eq) in DCM (20 mL) was added TEA (1.2 g, 11.84 mmol, 1.65 mL, 2 eq) and prop-2-enoyl chloride (803.7 mg, 8.88 mmol, 724.05 μL, 1.5 eq) at 0° C. The reaction mixture was stirred at 0° C. for 1 h. TLC showed that the reaction was complete. The reaction mixture was poured into H$_2$O (60 mL) and the aqueous phase was extracted with DCM (3×50 mL). The combined organic layer was washed with brine (3×50 mL), dried over anhydrous Na$_2$SO$_4$, filtered, and concentrated in vacuo to afford a residue. The residue was purified by silica gel chromatography (SiO$_2$, PE:EtOAc=10:1, 5:1) to afford the title compound (1.3 g, 4.53 mmol, 76.47% yield) as a white solid. 1H NMR (400 MHz, DMSO-d6) δ=10.05 (s, 1H), 7.77 (s, 1H), 7.67 (s, 1H), 7.20 (s, 1H), 6.41 (dd, J=10.0, 17.2 Hz, 1H), 6.24 (dd, J=2.0, 17.2 Hz, 1H), 5.77-5.71 (dd, J=2.0, 10.0 Hz, 1H), 2.29 (s, 3H), 1.28 (s, 12H).

Step 3—N-[3-(4-amino-6-quinolyl)-5-methyl-phenyl]prop-2-enamide

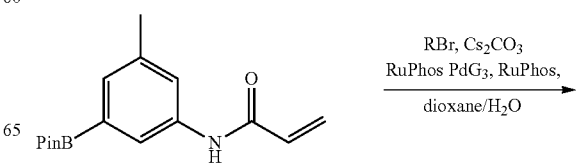

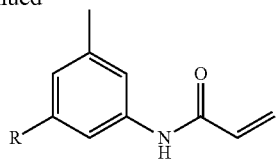

To a solution of N-[3-methyl-5-(4,4,5,5-tetramethyl-1,3,2-dioxaborolan-2-yl)phenyl]prop-2-enamide (100 mg, 348.24 µmol, 1.2 eq), 6-bromoquinolin-4-amine (64.7 mg, 290.2 µmol, 1 eq) in dioxane (3 mL), H₂O (0.75 mL) were added Cs₂CO₃ (283.7 mg, 870.59 µmol, 3 eq), [2-(2-aminophenyl)phenyl]-methylsulfonyloxy-palladium; dicyclohexyl-[2-(2,6-diisopropoxyphenyl)phenyl]phosphane (12.1 mg, 14.51 µmol, 0.05 eq), dicyclohexyl-[2-(2,6-diisopropoxyphenyl)phenyl]phosphane (13.5 mg, 29.02 µmol, 0.1 eq) under N₂. The reaction mixture was stirred at 80° C. for 1 h. The reaction mixture was poured into saturated EDTA (20 mL) and stirred for 60 min. The aqueous phase was extracted with EtOAc (3×15 mL). The combined organic layer was washed with brine (3×20 mL), dried over anhydrous Na₂SO₄, filtered, and concentrated in vacuo to afford a residue. The residue was purified by prep-HPLC to afford the title compound (10.1 mg, 33.29 µmol, 11.47% yield, 100% purity) as a white solid. 304.1. 1H NMR (400 MHz, DMSO-d6) δ=10.24 (s, 1H), 8.46 (s, 1H), 8.32 (d, J=5.6 Hz, 1H), 7.95-7.79 (m, 3H), 7.55 (s, 1H), 7.38 (s, 1H), 7.28 (s, 2H), 6.60 (d, J=5.6 Hz, 1H), 6.48 (dd, J=10.0, 16.8 Hz, 1H), 6.28 (dd, J=2.0, 17.2 Hz, 1H), 5.78 (dd, J=1.6, 10.0 Hz, 1H), 2.40 (s, 3H)

Step 4—N-[3-methyl-5-(3-methyl-1H-pyrazolo[3,4-c]pyridin-5-yl)phenyl]prop-2-enamide

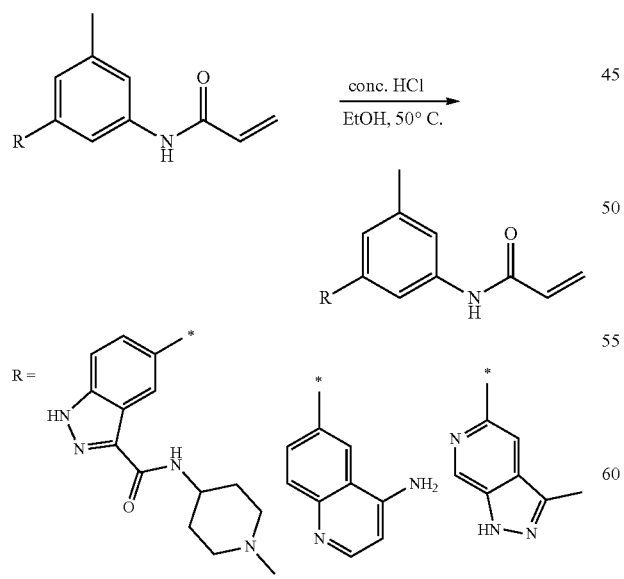

To a solution of N-[3-methyl-5-[3-methyl-1-(2-trimethylsilylethoxymethyl) pyrazolo[3,4-c]pyridin-5-yl]phenyl] prop-2-enamide (80 mg, 189.31 µmol, 1 eq) in EtOH (2 mL) was added concentrated HCl (1 mL). The reaction mixture was stirred at 50° C. for 1 h. The reaction mixture was poured into H₂O (10 mL) and adjusted to pH=7 with saturated Na₂CO₃. The aqueous phase was extracted with EtOAc (3×15 mL). The combined organic layer was washed with brine (3×20 mL), dried over anhydrous Na₂SO₄, filtered, and concentrated in vacuo to afford a residue. The residue was purified by prep-HPLC to afford the title compound (6.3 mg, 21.55 µmol, 11.38% yield, 100% purity) as a white solid. 293.1. 1H NMR (400 MHz, DMSO-d6) δ=13.20 (brs, 1H), 10.17 (s, 1H), 9.01 (s, 1H), 8.21 (d, J=4.4 Hz, 2H), 7.67 (s, 1H), 7.60 (s, 1H), 6.47 (dd, J=10.0, 17.2 Hz, 1H), 6.27 (dd, J=2.0, 16.8 Hz, 1H), 5.76 (dd, J=2.0, 10.10 Hz, 1H), 2.59 (s, 3H), 2.39 (s, 3H) PGP-1139 €3

Route 4: General Scheme

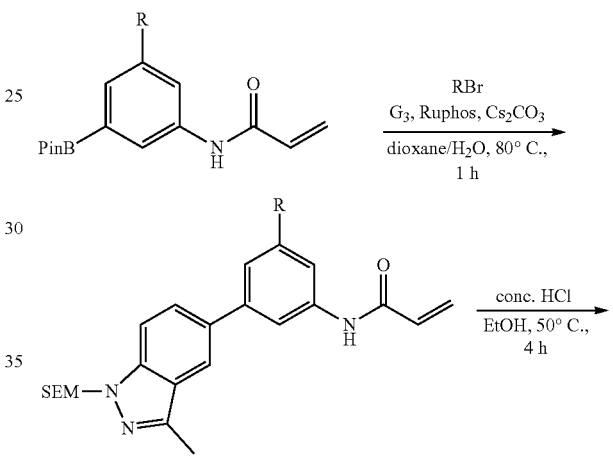

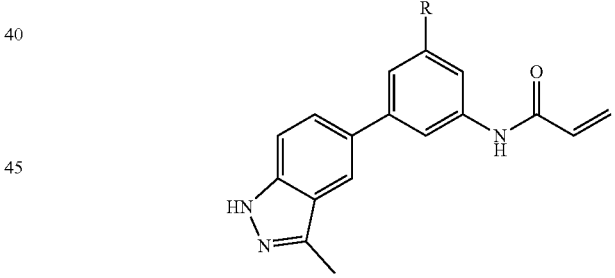

R: Me, Cl

Step 1—N-[3-methyl-5-[3-methyl-1-(2-trimethylsilylethoxymethyl)indazol-5-yl]phenyl]prop-2-enamide

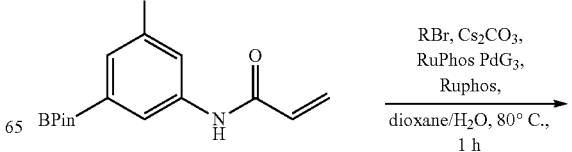

-continued

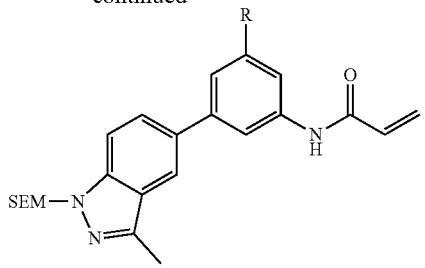

To a solution of N-[3-methyl-5-(4,4,5,5-tetramethyl-1,3,2-dioxaborolan-2-yl)phenyl]prop-2-enamide (126.2 mg, 439.47 μmol, 1 eq) and 2-[(5-bromo-3-methyl-indazol-1-yl)methoxy]ethyl-trimethyl-silane (0.15 g, 439.47 μmol, 1 eq) in dioxane (4 mL) and H$_2$O (1 mL) was added Na$_2$CO$_3$ (139.7 mg, 1.32 mmol, 3 eq) and Pd(dppf)Cl$_2$ (16.1 mg, 21.97 μmol, 0.05 eq). The reaction mixture was stirred at 80° C. for 1 h under N$_2$. The reaction mixture was poured into 15 mL saturated EDTA and stirred at 25° C. for 1 hr. The mixture was extracted with EtOAc (2×20 mL). The combined organic layer was washed with brine (3×20 mL), dried over anhydrous Na$_2$SO$_4$, filtered, and concentrated in vacuo to give the residue. The residue was purified by prep-TLC (SiO$_2$, PE:EtOAc=1:1) to afford the title compound N-[3-methyl-5-[3-methyl-1-(2-trimethylsilylethoxymethyl)indazol-5-yl]phenyl]prop-2-enamide (0.12 g, 170.78 μmol, 38.86% yield, 60% purity) as a colorless oil. LC-MS (ES$^+$, m/z): 422.3 [(M+H)$^+$].

Step 2—N-[3-methyl-5-(3-methyl-1H-indazol-5-yl)phenyl]prop-2-enamide

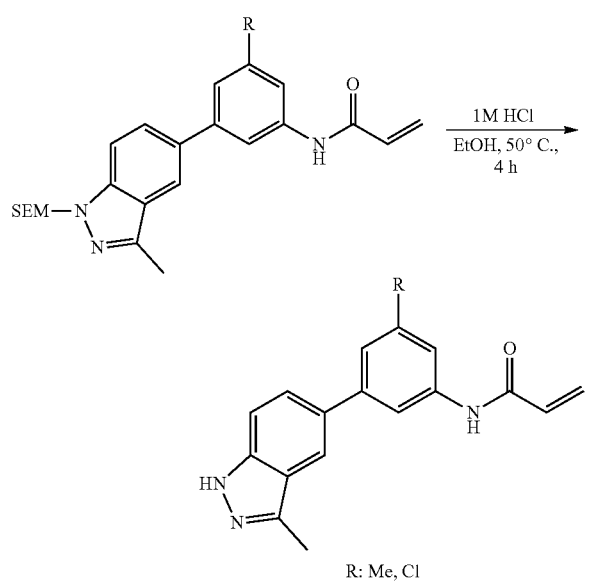

R: Me, Cl

To a solution of N-[3-methyl-5-[3-methyl-1-(2-trimethylsilylethoxymethyl)indazol-5-yl]phenyl]prop-2-enamide (0.04 g, 94.88 μmol, 1 eq) in EtOH (0.2 mL) was added aq.HCl (1 M aqueous solution, 800.00 μL, 8.43 eq). The reaction mixture was stirred at 50° C. for 4 hr. TLC showed that the reaction was complete. The reaction was concentrated under N$_2$ to give the residue. The residue was purified by prep-HPLC (FA condition) to afford the title compound N-[3-methyl-5-(3-methyl-1H-indazol-5-yl)phenyl]prop-2-enamide (0.0037 g, 12.26 μmol, 12.92% yield, 96.5% purity) as a white solid. LC-MS (ES$^+$, m/z): 292.1 [(M+H)$^+$]. $^1$H NMR (400 MHz, DMSO-d$_6$) δ=12.68 (br s, 1H), 10.15 (s, 1H), 7.90 (s, 1H), 7.80 (s, 1H), 7.62-7.57 (m, 1H), 7.55-7.51 (m, 1H), 7.49 (s, 1H), 7.25 (s, 1H), 6.46 (dd, 0.7=10.1, 17.0 Hz, 1H), 6.27 (dd, J=2.0, 17.0 Hz, 1H), 5.79-5.74 (m, 1H), 2.55-2.52 (m, 3H), 2.37 (s, 3H)

Route 4: General Scheme

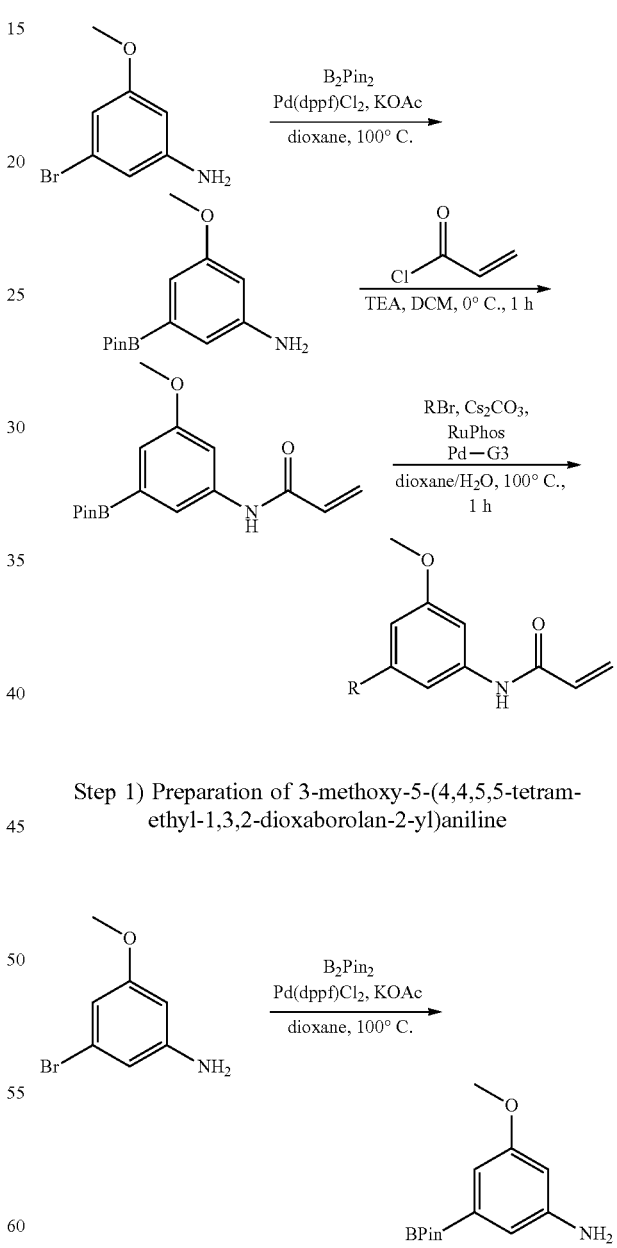

Step 1) Preparation of 3-methoxy-5-(4,4,5,5-tetramethyl-1,3,2-dioxaborolan-2-yl)aniline To a solution of 4,4,5,5-tetramethyl-2-(4,4,5,5-tetramethyl-1,3,2-dioxaborolan-2-yl)-1,3,2-dioxaborolane (3.77 g, 14.85 mmol, 1.5 eq) in dioxane (40 mL) were added KOAc (2.91 g, 29.7 mmol, 3 eq), Pd(dppf)Cl$_2$ (724.3 mg, 989.86 μmol, 0.1 eq) and 3-bromo-5-methoxy-aniline (2 g, 9.9 mmol, 1 eq). The mixture was stirred at 100° C. for 2 hrs. LC-MS showed that the reaction completed. The reaction mixture was filtered through celite. The filter cake was washed with EtOAc (2×20 mL) and the filtrate was concentrated in vacuo. The residue was purified by column chromatography (SiO$_2$, PE:EtOAc=1/0 to 4:1) to afford the title compound (1.8 g, 70.1% yield) as a white solid.

Step 2) Preparation of N-[3-methoxy-5-(4,4,5,5-tetramethyl-1,3,2-dioxaborolan-2-yl)phenyl]prop-2-enamide

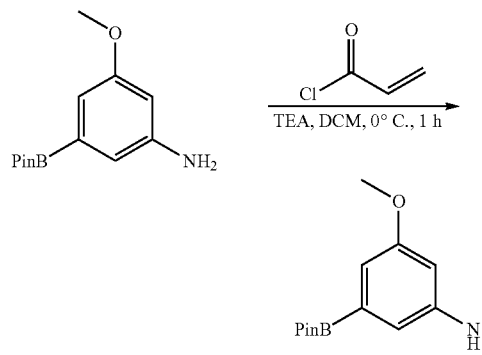

To a solution of 3-methoxy-5-(4,4,5,5-tetramethyl-1,3,2-dioxaborolan-2-yl)aniline (600 mg, 2.41 mmol, 1 eq) in DCM (5 mL) were added TEA (731.2 mg, 7.23 mmol, 1 mL, 3 eq) and prop-2-enoyl chloride (436 mg, 4.82 mmol, 392.78 μL, 2 eq) at 0° C. The mixture was stirred at 0° C. for 1 hr. LC-MS showed that the reaction was complete. The reaction mixture was poured into water (50 mL). The mixture was extracted with DCM (3×30 mL). The combined organic layer was washed with brine (30 mL), dried over anhydrous Na$_2$SO$_4$, filtered, and concentrated in vacuo. The residue was purified by column chromatography (SiO$_2$, PE:EtOAc=1/0 to 4:1) to afford the title compound (380 mg, 52.0% yield) as a yellow solid.

Step 3) (Compound 599) Preparation of N-{3-methoxy-5-[4-(methylamino)quinolin-6-yl]phenyl}prop-2-enamide

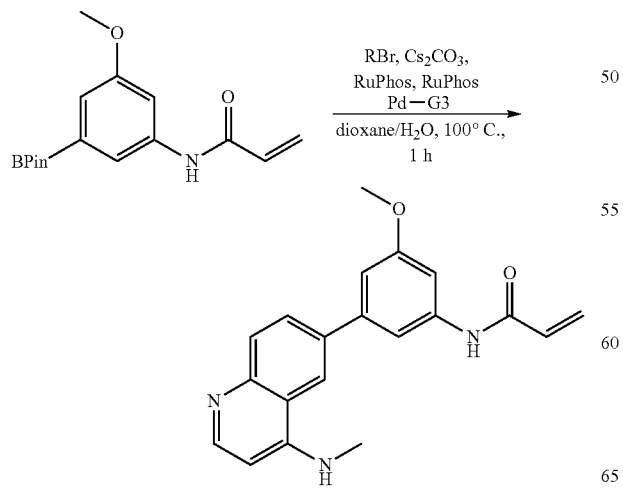

To a solution of N-[3-methoxy-5-(4,4,5,5-tetramethyl-1,3,2-dioxaborolan-2-yl)phenyl]prop-2-enamide (76.7 mg, 253.07 μmol, 1.2 ef) in dioxane (4 mL) and H$_2$O (1 mL) were added Cs$_2$CO$_3$ (206.1 mg, 632.67 μmol, 3 eq), RuPhos (19.7 mg, 42.18 μmol, 0.2 eq), [2-(2-aminophenyl)phenyl]methylsulfonyloxy-palladium;dicyclohexyl-[2-(2,6-diisopropoxyphenyl)phenyl]phosphane (17.6 mg, 21.09 μmol, 0.1 eq) and 6-bromo-N-methyl-quinolin-4-amine (50 mg, 210.89 μmol, 1 eq). The mixture was stirred at 100° C. for 1 hr under N$_2$. LC-MS showed that the reaction was complete. The reaction mixture was poured into saturated EDTA (50 mL) and stirred at 25° C. for 1 hr. The mixture was extracted with EtOAc (3×30 mL). The combined organic layer was washed with brine (30 mL), dried over anhydrous Na$_2$SO$_4$, filtered, and concentrated in vacuo. The residue was purified by prep-HPLC to afford the title compound (22.7 mg, 32.3% yield) as a white solid. LC-MS (ES+, m/z): 334.1.

Route 5: General Scheme

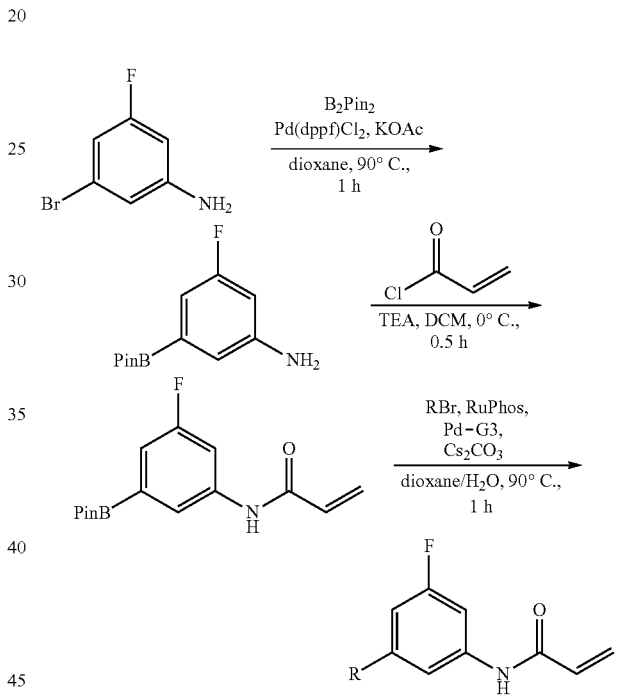

R = 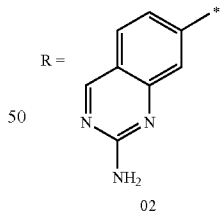

Step 1—3-fluoro-5-(4,4,5,5-tetramethyl-1,3,2-dioxaborolan-2-yl)aniline

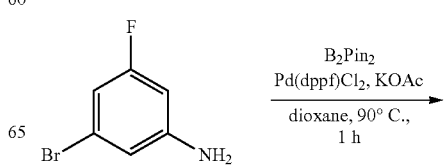

-continued

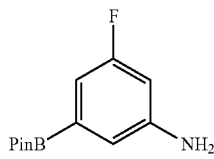

To a solution of 3-bromo-5-fluoro-aniline (1 g, 5.3 mmol, 1 eq) and 4,4,5,5-tetramethyl-2-(4,4,5,5-tetramethyl-1,3,2-dioxaborolan-2-yl)-1,3,2-dioxaborolane (2.67 g, 10.5 mmol, 2 eq) in dioxane (10 mL) was added KOAc (1.55 g, 15.8 mmol, 3 eq) and Pd(dppf)Cl$_2$ (385 mg, 526 µmol, 0.1 eq) at 25° C. The reaction mixture was stirred at 90° C. for 1 h. TLC showed that the reaction was complete. The reaction mixture was poured into 100 mL water, extracted with EtOAc (3×20 mL). The combined organic layer was washed with brine (3×50 mL), dried over anhydrous Na$_2$SO$_4$, filtered, and concentrated in vacuo to afford a residue. The residue was purified by prep-TLC (SiO$_2$, PE:EtOAc=3:1) to afford the title compound (2.3 g, crude) as a brown oil. LC-MS (ES+, m/z): 238.1 [(M+H)$^+$].

Step 2—N-[3-fluoro-5-(4,4,5,5-tetramethyl-1,3,2-dioxaborolan-2-yl)phenyl]prop-2-enamide

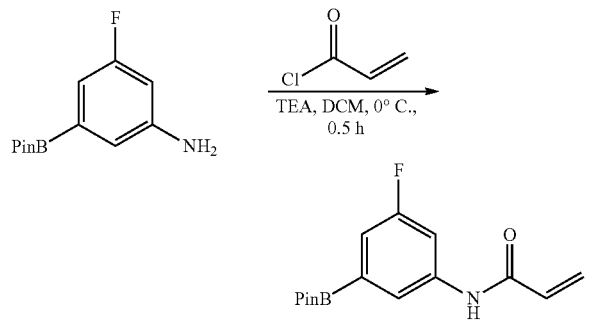

To a solution of 3-fluoro-5-(4,4,5,5-tetramethyl-1,3,2-dioxaborolan-2-yl)aniline (0.6 g, 1.2 mmol, 46% purity, 1 eq) in DCM (5 mL) was added TEA (589 mg, 5.8 mmol, 810 µL, 5 eq) and prop-2-enoyl chloride (116 mg, 1.3 mmol, 105 µL, 1.1 eq) at 0° C. The reaction mixture was stirred at 0° C. for 0.5 hour. The reaction mixture was concentrated in vacuo to give a residue. The residue was purified by prep-TLC (SiO$_2$, PE:EtOAc=1:1) to afford the title compound (0.34 g, 893 µmol, 76.7% yield, 76.5% purity) as a brown oil. LC-MS (ES+, m/z): 291.1 [(M+H)$^+$].

Step 3—N-[3-(2-aminoquinazolin-7-yl)-5-fluorophenyl]prop-2-enamide

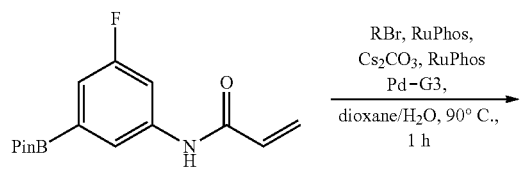

-continued

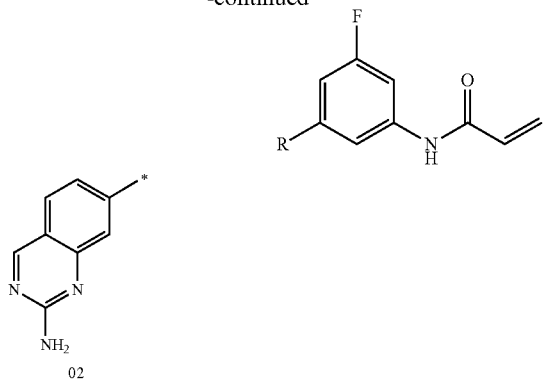

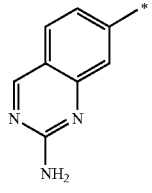

To a solution of N-[3-fluoro-5-(4,4,5,5-tetramethyl-1,3,2-dioxaborolan-2-yl)phenyl]prop-2-enamide (132 mg, 348 µmol, 76.5% purity, 1 eq), 7-bromoquinazolin-2-amine (86 mg, 382 µmol, 1.1 eq) in dioxane (4 mL) H$_2$O (1 mL) was added Cs$_2$CO$_3$ (340 mg, 1. mmol, 3 eq), [2-(2-aminophenyl)phenyl]-methylsulfonyloxy-palladium;dicyclohexyl-[2-(2,6-diisopropoxyphenyl)phenyl]phosphane (29.1 mg, 34.75 µmol, 0.1 eq) 2-(2-aminophenyl)phenyl]-methylsulfonyloxy-palladium; dicyclohexyl-[2-(2,6-isopropoxyphenyl)phenyl]phosphane (16 mg, 35 µmol, 0.1 eq) at 25° C. The reaction mixture was stirred at 90° C. for 1 hour. The reaction mixture was poured into saturated EDTA (60 mL) and stirred for 60 min. The aqueous phase was extracted with EtOAc (3×20 mL). The combined organic layer was washed with brine (3×50 mL), dried over anhydrous Na$_2$SO$_4$, filtered, and concentrated in vacuo to afford the title compound (0.08 g, crude) as a light yellow solid. LC-MS (ES+, m/z): 309.1 [(M+H)$^+$], 1H NMR (400 MHz, DMSO-d6) 5=10.51 (s, 1H), 9.15 (s, 1H), 8.18 (s, 1H), 7.90 (d, J=8.4 Hz, 1H), 7.80 (s, 1H), 7.67-7.75 (m, 1H), 7.62 (s, 1H), 7.49 (dd, J=8.4, 1.6 Hz, 1H), 7.36 (d, J=10.0 Hz, 1H), 6.93 (s, 2H), 6.41-6.49 (m, 1H), 6.34 (d, J=2.0 Hz, 1H), 6.30 (d, J=2.0 Hz, 1H), 6.23-6.37 (m, 1H), 5.81-5.86 (m, 1H), 2.52-2.58 (m, 1H).

Step 1—3-fluoro-5-(4,4,5,5-tetramethyl-1,3,2-dioxaborolan-2-yl)aniline

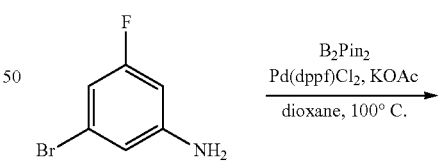

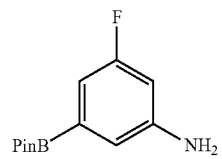

A solution of 3-bromo-5-fluoro-aniline (1.5 g, 7.89 mmol, 1 eq) in dioxane (40 mL) was added 4,4,5,5-tetramethyl-2-(4,4,5,5-tetramethyl-1,3,2-dioxaborolan-2-yl)-1,3,2-dioxaborolane (4.01 g, 15.8 mmol, 2 eq), KOAc (2.32 g, 23.7 mmol, 3 eq), and Pd(dppf)Cl$_2$ (577 mg, 789 µmol, 0.1 eq). Then degassed and purged with N$_2$ 3 times. The resulting reaction mixture was stirred at 100° C. for 2 hours under N$_2$ atmosphere. The reaction mixture was filtered to remove the insoluble substance and the filtrate was concentrated in vacuo to give a residue. The residue was purified by column chromatography (SiO₂, PE:EtOAc=5/1 to 0/1) to afford the title compound (1.5 g, 6.33 mmol, 80.15% yield) as a light yellow solid. LC-MS (ES+, m/z): 238.2 [(M+H)⁺].

Step 2—N-(3-fluoro-5-(4,4,5,5-tetramethyl-1,3,2-dioxaborolan-2-yl)phenyl) acrylamide

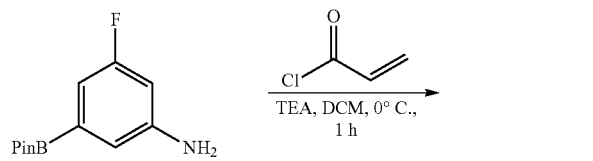

To a solution of 3-fluoro-5-(4,4,5,5-tetramethyl-1,3,2-dioxaborolan-2-yl)aniline (400 mg, 1.69 mmol, 1 eq) in DCM (10 mL) was added TEA (512 mg, 5.06 mmol, 704 μL, 3 eq) and prop-2-enoyl chloride (167 mg, 1.86 mmol, 151 μL, 1.1 eq). The reaction mixture was stirred at 0° C. for 1 hour. The reaction mixture was concentrated in vacuo to give a residue. The residue was purified by column chromatography (SiO₂, PE:EtOAc=20/1 to 10/1) to afford the title compound (400 mg, 1.37 mmol, 81.44% yield) as a white solid.

Step 3—N-(3-fluoro-5-(2-(methylamino)quinazolin-7-yl)phenyl)acrylamide

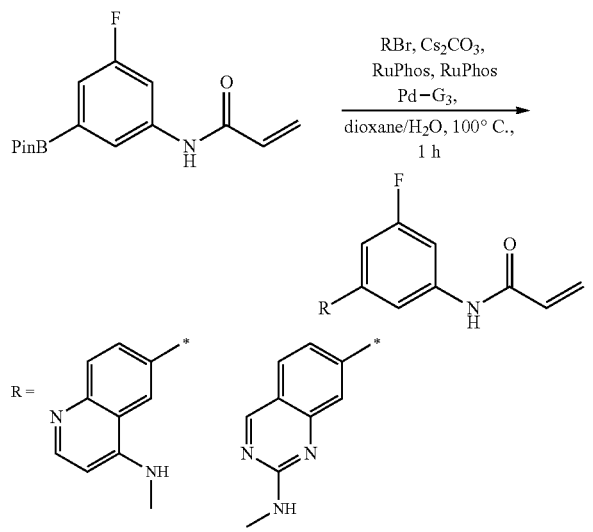

To a solution of N-[3-fluoro-5-(4,4,5,5-tetramethyl-1,3,2-dioxaborolan-2-yl)phenyl]prop-2-enamide (58.6 mg, 201 μmol, 1.2 eq) in dioxane (4 mL) and H₂O (1 mL) was 7-bromo-N-methyl-quinazolin-2-amine (40 mg, 168 μmol, 1 eq), Cs₂CO₃ (164.2 mg, 504.02 μmol, 3 eq), RuPhos (15.6 mg, 33.6 μmol, 0.2 eq) and [2-(2-aminophenyl)phenyl]-methylsulfonyloxy-palladium;dicyclohexyl-[2-(2,6-diisopropoxyphenyl)phenyl]phosphane (14 mg, 16.8 μmol, 0.1 eq). The reaction mixture was degassed and purged with N₂ 3 times. Then stirred at 100° C. for 1 hour under N₂ atmosphere. The reaction mixture was poured into saturated EDTA (30 mL) and stirred for 1 hour, extracted with EtOAc (3×20 mL). The combined organic layers were washed with brine (3×20 mL), dried over anhydrous Na₂SO₄, filtered, and concentrated in vacuo to give a residue. The residue was purified by prep-HPLC to afford the title compound (14.6 mg, 44.89 μmol, 26.72% yield, 99.1% purity) as a white solid. 323.1. 1H NMR (400 MHz, DMSO-d6) δ=10.46 (s, 1H), 9.12 (br s, 1H), 7.83-7.94 (m, 2H), 7.65-7.77 (m, 2H), 7.47-7.56 (m, 1H), 7.40 (br d, J=9.6 Hz, 2H), 6.39-6.52 (m, 1H), 6.25-6.37 (m, 1H), 5.77-5.91 (m, 1H), 2.92 (d, J=4.8 Hz, 3H).

Route 5

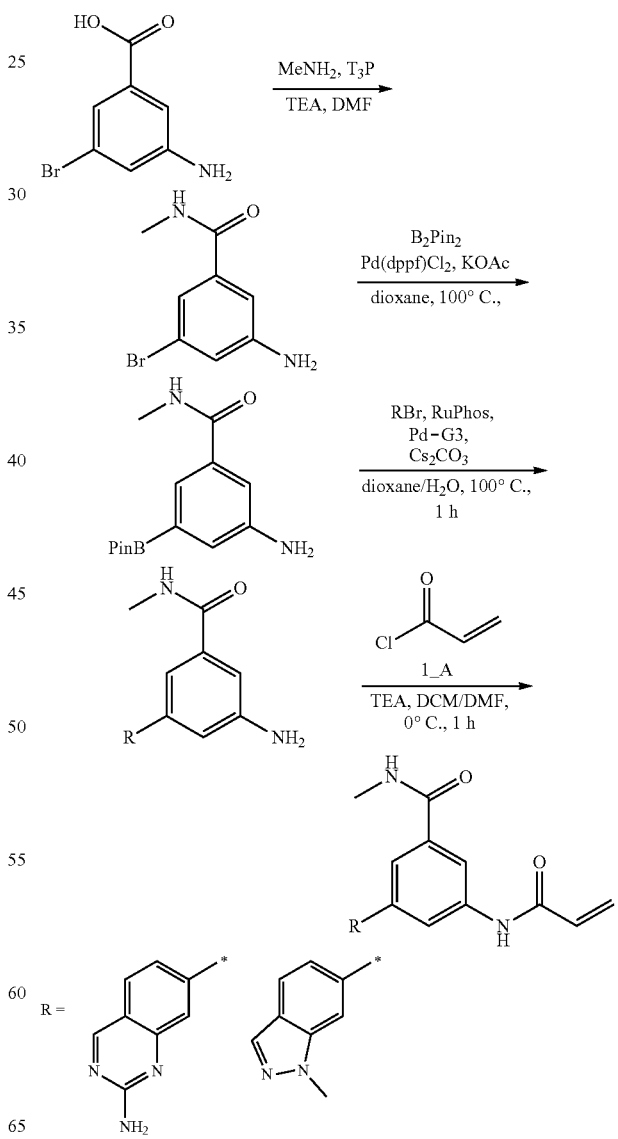

Step 1—3-amino-5-bromo-N-methyl-benzamide

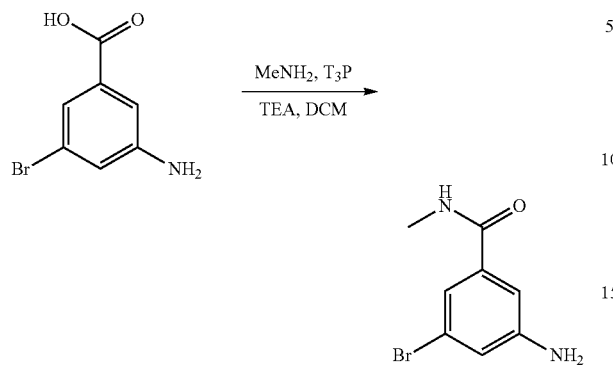

To a solution of 3-amino-5-bromo-benzoic acid (2 g, 9.26 mmol, 1 eq) in DCM (40 mL) was added TEA (7.49 g, 74. mmol, 10.3 mL, 8 eq) and MeNH$_2$ (3.13 g, 46.2 mmol, 5 eq, HCl). Then T$_3$P (8.84 g, 13.8 mmol, 8.26 mL, 50% purity, 1.5 eq) was added at 0° C. The resulting reaction mixture was stirred at 20° C. for 2 hours. The reaction mixture poured into water 100 mL at 0° C. Then adjusting pH=8 with solid Na$_2$CO$_3$, extracted with DCM (3×150 mL). The combined organic layers were washed with brine (100 mL), dried over anhydrous Na$_2$SO$_4$, filtered, and concentrated in vacuo to afford the title compound (2. g, crude) as a light yellow solid. LC-MS (ES+, m/z): 229.1 [(M+H)$^+$].

Step 2—3-amino-N-methyl-5-(4,4,5,5-tetramethyl-1,3,2-dioxaborolan-2-yl)benzamide

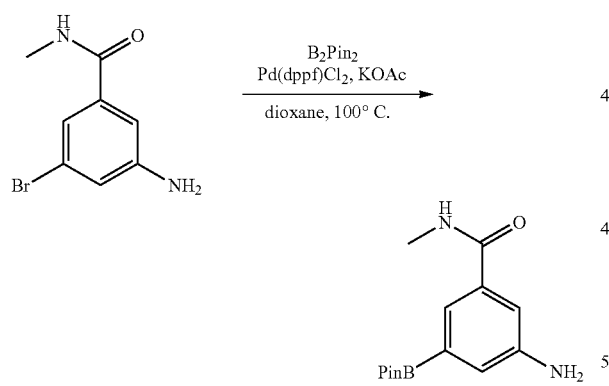

A solution of 3-amino-5-bromo-N-methyl-benzamide (1 g, 3.49 mmol, 80% purity, 1 eq) in dioxane (40 mL) was added 4,4,5,5-tetramethyl-2-(4,4,5,5-tetramethyl-1,3,2-dioxaborolan-2-yl)-1,3,2-dioxaborolane (1.77 g, 6.98 mmol, 2 eq), KOAc (1.03 g, 10.5 mmol, 3 eq) and Pd(dppf)Cl$_2$ (255 mg, 349 µmol, 0.1 eq). The reaction mixture was degassed and purged with N$_2$ 3 times, and the reaction mixture was stirred at 100° C. for 2 hours under N$_2$ atmosphere. The reaction mixture was filtered through Celite and the filter cake was washed with 50 mL EtOAc. The combined filtrates were concentrated to give a residue. The residue was purified by column chromatography (SiO$_2$, PE:EtOAc=5/1 to 0/1) to afford the title product (900 mg, 2.93 mmol, 83.9% yield, 90% purity) as a light yellow solid. LC-MS (ES+, m/z): 277.2 [(M+H)$^+$].

Step 3—3-amino-5-X—N-methylbenzamide

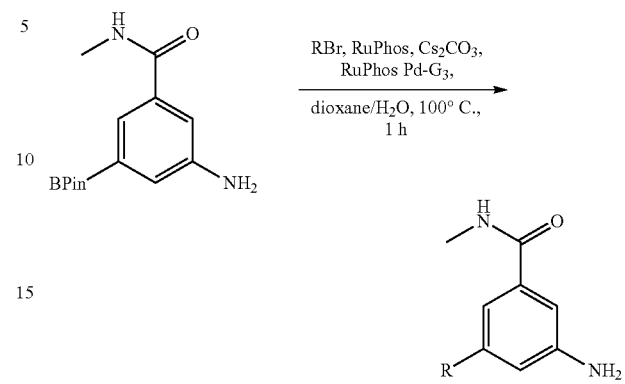

A solution of 3-amino-N-methyl-5-(4,4,5,5-tetramethyl-1,3,2-dioxaborolan-2-yl)benzamide (148 mg, 535 µmol, 1.2 eq) in dioxane (4 mL) and H$_2$O (1 mL) was added 7-bromoquinazolin-2-amine (100 mg, 446 µmol, 1 eq), RuPhos (41 mg, 89 µmol, 0.2 eq), Cs$_2$CO$_3$ (436 mg, 1.34 mmol, 3 eq) and [2-(2-aminophenyl)phenyl]-methylsulfonyloxy-palladium;dicyclohexyl-[2-(2,6-diisopropoxyphenyl)phenyl]phosphane (37 mg, 44 µmol, 0.1 eq). The reaction mixture was degassed and purged with N$_2$ 3 times. The reaction mixture was stirred at 100° C. for 1 hour under N$_2$ atmosphere. The reaction mixture was poured into saturated EDTA (30 mL) and stirred for 1 hour, extracted with EtOAc (3×20 mL). The combined organic layers were washed with brine (3×20 mL), dried over anhydrous Na$_2$SO$_4$, filtered, and concentrated in vacuo to give a residue. The residue was washed with EtOAc (2 mL) to afford the title compound (50 mg, crude) as a light yellow solid. LC-MS (ES+, m/z): 294.2 [(M+H)$^+$]

Step 4—3-acrylamido-5-X—N-methylbenzamide

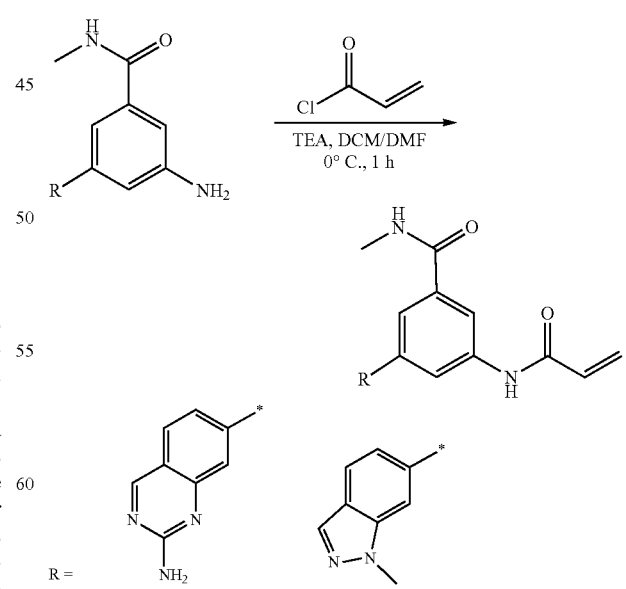

Procedure for R=O3: To a solution of 3-amino-5-(2-aminoquinazolin-7-yl)-N-methyl-benzamide (40 mg, 136

μmol, 1 eq) in DCM (4 mL) and DMF (1 mL) was added TEA (41 mg, 409 μmol, 56 μL, 3 eq) and prop-2-enoyl chloride (14 mg, 163 μmol, 13 μL, 1.2 eq) at 0° C. The reaction mixture was stirred at 0° C. for 1 hour. The reaction mixture was poured into 50 mL water then adjusting the pH=8 with saturated Na$_2$CO$_3$. The mixture was extracted with DCM (3×15 mL). The combined organic layers were washed with brine (10 mL), dried over anhydrous Na$_2$SO$_4$, filtered, and concentrated in vacuo to give a residue. The residue was purified by prep-HPLC to afford the title compound (3 mg, 8.35 μmol, 6.12% yield, 96.7% purity) as a white solid. 6.12% yield, LC-MS (ES+, m/z): 348.2 [(M+H)+]$^1$H NMR (400 MHz, DMSO-d6) δ=10.45 (s, 1H), 9.15 (s, 1H), 8.66 (br d, J=4.4 Hz, 1H), 8.32 (s, 1H), 8.15 (s, 1H), 7.88-7.99 (m, 2H), 7.72 (s, 1H), 7.55 (br d, J=8.4 Hz, 1H), 6.91 (s, 2H), 6.40-6.53 (m, 1H), 6.26-6.37 (m, 1H), 5.81 (br d, J=10.8 Hz, 1H), 2.82 (br d, J=4.0 Hz, 3H). 23.2% yield, LC-MS (ES+, m/z): 335.1 [(M+H)$^+$], 1H NMR (400 MHz, DMSO-d6) 5=10.43 (s, 1H), 8.59 (br d, J=4.4 Hz, 1H), 8.24 (s, 1H), 8.12 (s, 1H), 8.09 (s, 1H), 7.91 (d, J=4.4 Hz, 2H), 7.88 (d, J=8.4 Hz, 1H), 7.47 (dd, J=8.4, 1.2 Hz, 1H), 6.42-6.54 (m, 1H), 6.26-6.35 (m, 1H), 5.77-5.86 (m, 1H), 4.12 (s, 3H), 2.83 (d, J=4.4 Hz, 3H).

Route 6: General Scheme

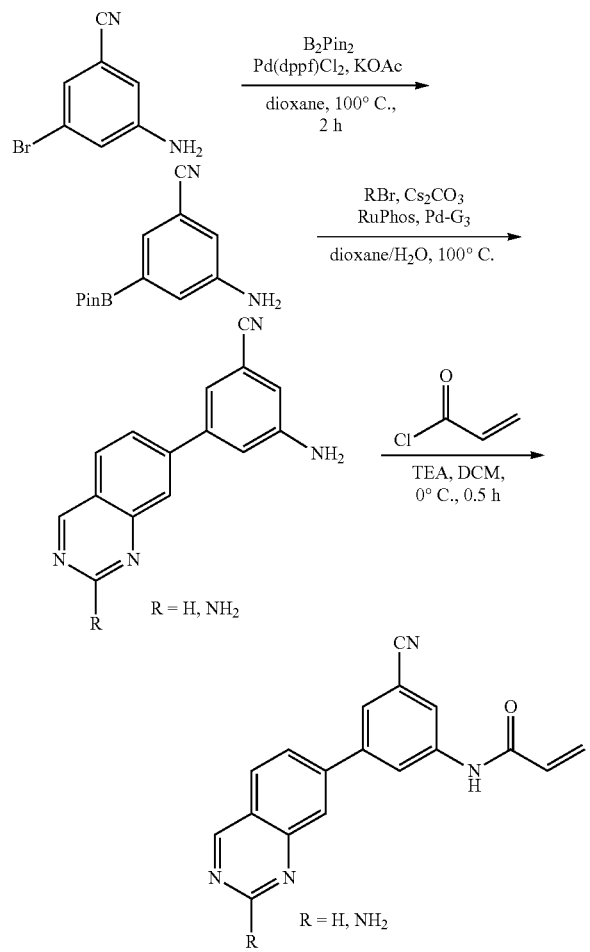

Step 1—3-amino-5-(4,4,5,5-tetramethyl-1,3,2-dioxaborolan-2-yl)benzonitrile

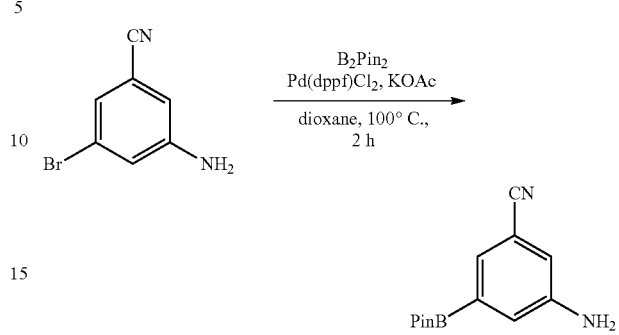

To a solution of 3-amino-5-bromo-benzonitrile (2 g, 10.1 mmol, 1 eq) in dioxane (40 mL) was added 4,4,5,5-tetramethyl-2-(4,4,5,5-tetramethyl-1,3,2-dioxaborolan-2-yl)-1,3,2-dioxaborolane (5.16 g, 20.3 mmol, 2 eq), KOAc (2.99 g, 30.4 mmol, 3 eq) and Pd(dppf)Cl$_2$ (742 mg, 1.02 mmol, 0.1 eq). The reaction mixture was degassed and purged with N$_2$ 3 times. The resulting reaction mixture was stirred at 100° C. for 2 hours under N$_2$ atmosphere. The reaction mixture was filtered, and concentrated in vacuo to give a residue. The residue was purified by column chromatography (SiO$_2$, PE:EtOAc=5/1 to 0/1) to afford the title compound (1.3 g, 5.33 mmol, 52.47% yield) as a light yellow solid.

Step 2—3-amino-5-(2-X-quinazolin-7-yl)benzonitrile

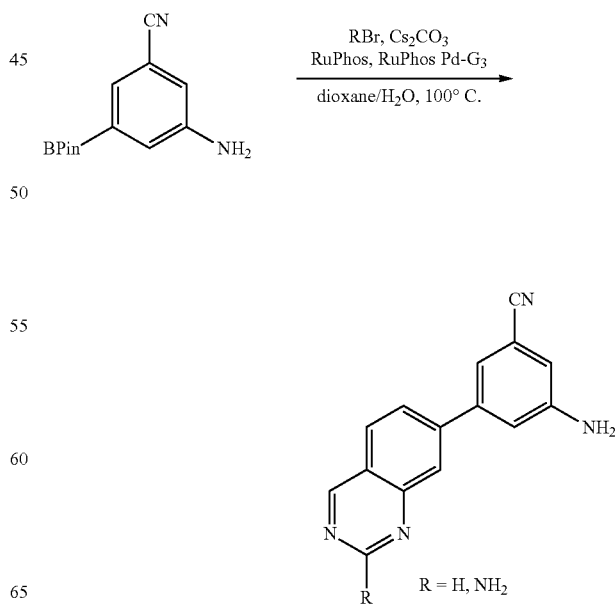

Procedure for R=10: To a solution of 3-amino-5-(4,4,5,5-tetramethyl-1,3,2-dioxaborolan-2-yl)benzonitrile (168 mg, 688 µmol, 1.2 eq) in dioxane (4 mL) and H₂O (1 mL) was added 7-bromoquinazoline (120 mg, 574 µmol, 1 eq), Cs₂CO₃ (561 mg, 1.72 mmol, 3 eq), [2-(2-aminophenyl)phenyl]-methylsulfonyloxy-palladium;dicyclohexyl-[2-(2,6-diisopropoxyphenyl)phenyl]phosphane (48 mg, 57 µmol, 0.1 eq) and RuPhos (53 mg, 114 µmol, 0.2 eq). The reaction mixture was degassed and purged with N₂ 3 times. Then stirred at 100° C. for 1 hour under N₂ atmosphere. The reaction mixture poured into saturated EDTA (30 mL) and EtOAc (20 mL) was added. The solution was stirred for 1 hour. The insoluble substance was removed by filtration. The filtrate was concentrated in vacuo to give a residue. The residue was purified by prep-HPLC to afford the title compound (40 mg, 154 µmol, 26.8% yield, 95% purity) as a white solid. LC-MS (ES+, m/z): 247.1 [(M+H)⁺].

Step 3—N-(3-cyano-5-(quinazolin-7-yl)phenyl)acrylamide

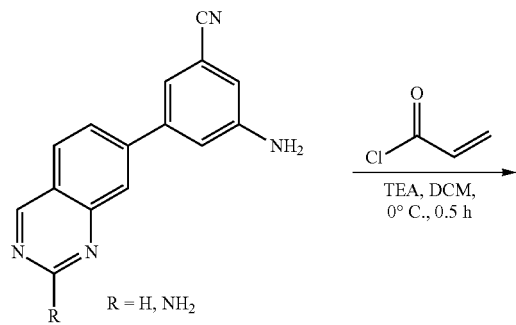

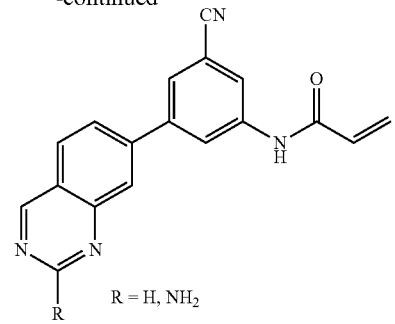

To a solution of 3-amino-5-quinazolin-7-yl-benzonitrile (30 mg, 121 µmol, 1 eq) in DCM (5 mL) was added TEA (61 mg, 609 µmol, 84 µL, 5 eq) and the solution of prop-2-enoyl chloride (22 mg, 243 µmol, 19 µL, 2 eq) in DCM (1 mL) was added dropwise at 0° C. The resulting reaction mixture was stirred at 0° C. for 0.5 hour. The reaction mixture was poured into ice water (10 mL) at 0° C. The mixture was extracted with DCM (3×15 mL). The combined organic layers were washed with brine (10 mL), dried over anhydrous Na₂SO₄, filtered, and concentrated in vacuo to give a residue. The residue was purified by prep-HPLC to afford the title compound ((6.3 mg, 18.9 µmol, 15.52% yield, 90.1% purity) as a white solid. LC-MS (ES+, m/z): 301.1 [(M+H)⁺], 1H NMR (400 MHz, DMSO-d6) δ=10.42 (br s, 1H), 9.65 (s, 1H), 9.35 (s, 1H), 8.39 (s, 1H), 8.30 (s, 1H), 8.31 (d, J=7.6 Hz, 1H), 8.21 (s, 1H), 8.10 (d, J=8.4 Hz, 1H), 8.06 (s, 1H), 6.41-6.51 (m, 1H), 6.31-6.40 (m, 1H), 5.85 (dd, J=10.0, 1.6 Hz, 1H).

TABLE 13 shows compounds synthesized using methods described in EXAMPLE 13 above.

TABLE 13

| Cpd. No. | Structure | IUPAC | LC-MS (ES+, m/z) |
|---|---|---|---|
| 560 | 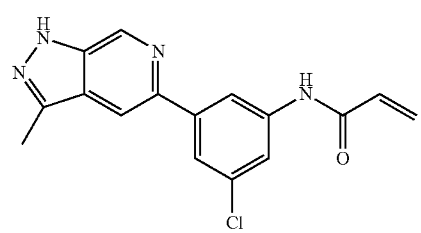 [SMILES: C=CC(=O)Nc1cc(Cl)cc(-c2cc3c(C)n[nH]c3cn2)c1] | N-(3-chloro-5-{3-methyl-1H-pyrazolo[3,4-c]pyridin-5-yl}phenyl)prop-2-enamide | 313.1 |
| 561 | 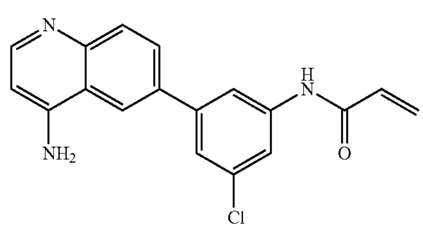 [SMILES: C=CC(=O)Nc1cc(Cl)cc(-c2ccc3nccc(N)c3c2)c1] | N-[3-(4-aminoquinolin-6-yl)-5-chlorophenyl]prop-2-enamide | 324 |

TABLE 13-continued

| Cpd. No. | Structure | IUPAC | LC-MS (ES+, m/z) |
|---|---|---|---|
| 562 | 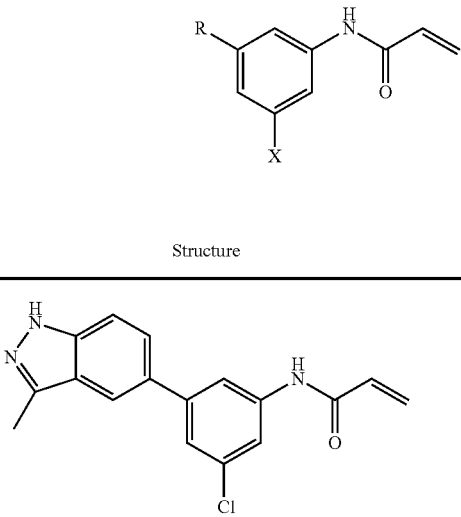 | N-[3-chloro-5-(3-methyl-1H-indazol-5-yl)phenyl]prop-2-enamide | 312.1 |
| 563 | 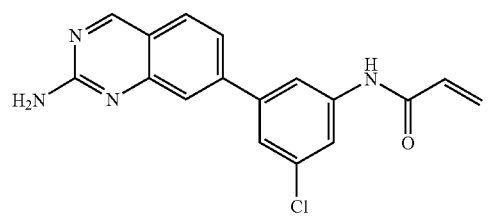 [SMILES: C=CC(=O)Nc1cc(Cl)cc(-c2ccc3cnc(N)nc3c2)c1] | N-[3-(2-aminoquinazolin-7-yl)-5-chlorophenyl]prop-2-enamide | 325.1 |
| 564 | 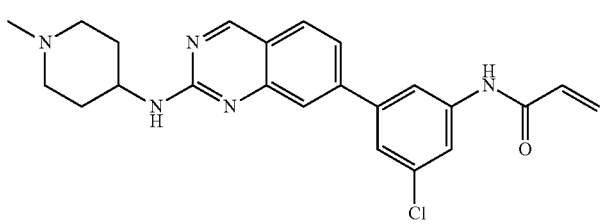 [SMILES: C=CC(=O)Nc1cc(Cl)cc(-c2ccc3cnc(NC4CCN(C)CC4)nc3c2)c1] | N-(3-chloro-5-{2-[(1-methylpiperidin-4-yl)amino]quinazolin-7-yl}phenyl)prop-2-enamide | 422.2 |
| 565 | 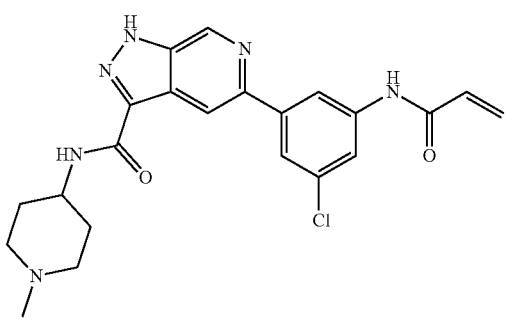 [SMILES: C=CC(=O)Nc1cc(Cl)cc(-c2cc3c(C(=O)NC4CCN(C)CC4)n[nH]c3cn2)c1] | 5-[3-chloro-5-(prop-2-enamido)phenyl]-N-(1-methylpiperidin-4-yl)-1H-pyrazolo[3,4-c]pyridine-3-carboxamide | 439.1 |
| 566 | 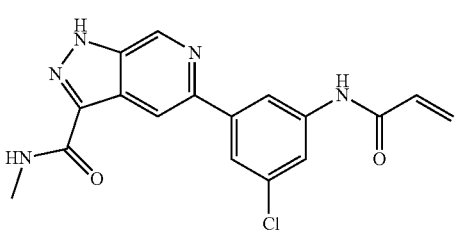 [SMILES: C=CC(=O)Nc1cc(Cl)cc(-c2cc3c(C(=O)NC)n[nH]c3cn2)c1] | 5-[3-chloro-5-(prop-2-enamido)phenyl]-N-methyl-1H-pyrazolo[3,4-c]pyridine-3-carboxamide | 356.1 |

TABLE 13-continued

| Cpd. No. | Structure | IUPAC | LC-MS (ES+, m/z) |
|---|---|---|---|
| 567 | 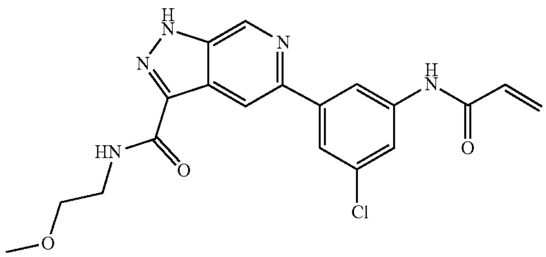 [SMILES: C=CC(=O)Nc1cc(Cl)cc(-c2cc3c(C(=O)NCCOC)n[nH]c3cn2)c1] | 5-[3-chloro-5-(prop-2-enamido)phenyl]-N-(2-methoxyethyl)-1H-pyrazolo[3,4-c]pyridine-3-carboxamide | 400.1 |
| 568 | 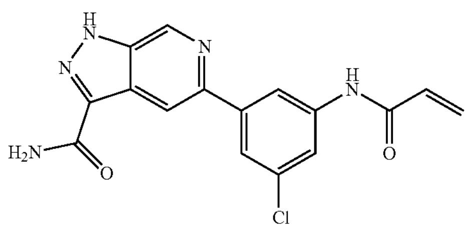 [SMILES: C=CC(=O)Nc1cc(Cl)cc(-c2cc3c(C(N)=O)n[nH]c3cn2)c1] | 5-[3-chloro-5-(prop-2-enamido)phenyl]-1H-pyrazolo[3,4-c]pyridine-3-carboxamide | 342.1 |
| 569 | 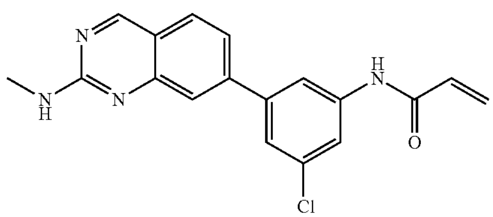 [SMILES: C=CC(=O)Nc1cc(Cl)cc(-c2ccc3cnc(NC)nc3c2)c1] | N-{3-chloro-5-[2-(methylamino)quinazolin-7-yl]phenyl}prop-2-enamide | 339 |
| 570 | 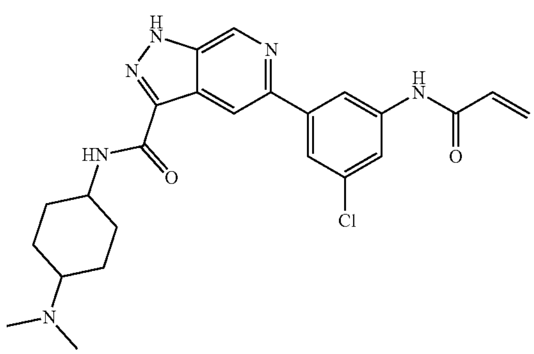 [SMILES: C=CC(=O)Nc1cc(Cl)cc(-c2cc3c(C(=O)NC4CCC(N(C)C)CC4)n[nH]c3cn2)c1] | 5-[3-chloro-5-(prop-2-enamido)phenyl]-N-[4-(dimethylamino)cyclohexyl]-1H-pyrazolo[3,4-c]pyridine-3-carboxamide | 467.2 |
| 571 | 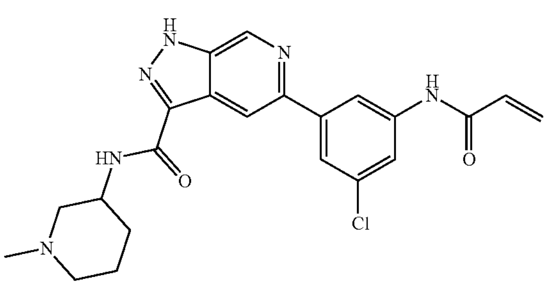 | 5-[3-chloro-5-(prop-2-enamido)phenyl]-N-(1-methylpiperidin-3-yl)-1H-pyrazolo[3,4-c]pyridine-3-carboxamide | 439.1 |

TABLE 13-continued

| Cpd. No. | Structure | IUPAC | LC-MS (ES+, m/z) |
|---|---|---|---|
| 572 | 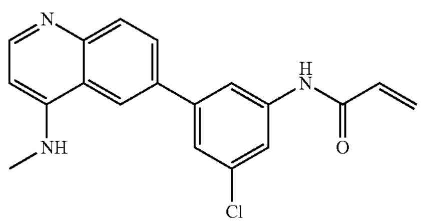 [SMILES: C=CC(=O)Nc1cc(Cl)cc(-c2ccc3nccc(NC)c3c2)c1] | N-{3-chloro-5-[4-(methylamino)quinolin-6-yl]phenyl}prop-2-enamide | 338 |
| 573 | 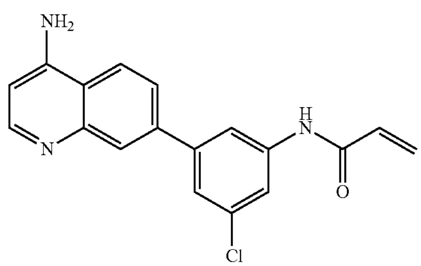 [SMILES: C=CC(=O)Nc1cc(Cl)cc(-c2ccc3c(N)ccnc3c2)c1] | N-[3-(4-aminoquinolin-7-yl)-5-chlorophenyl]prop-2-enamide | 323.9 |
| 574 | 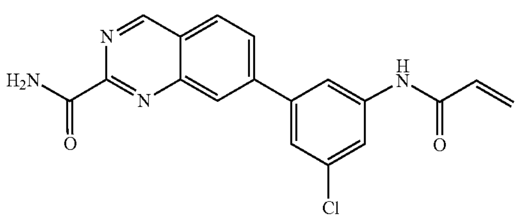 [SMILES: C=CC(=O)Nc1cc(Cl)cc(-c2ccc3cnc(C(N)=O)nc3c2)c1] | 7-[3-chloro-5-(prop-2-enamido)phenyl]quinazoline-2-carboxamide | 352.9 |
| 575 | 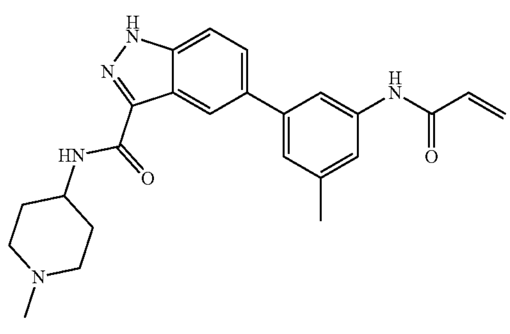 [SMILES: C=CC(=O)Nc1cc(C)cc(-c2ccc3[nH]nc(C(=O)NC4CCN(C)CC4)c3c2)c1] | 5-[3-methyl-5-(prop-2-enamido)phenyl]-N-(1-methylpiperidin-4-yl)-1H-indazole-3-carboxamide | 418.2 |
| 576 | 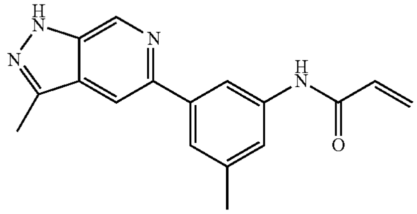 [SMILES: C=CC(=O)Nc1cc(C)cc(-c2cc3c(C)n[nH]c3cn2)c1] | N-(3-methyl-5-{3-methyl-1H-pyrazolo[3,4-c]pyridin-5-yl}phenyl)prop-2-enamide | 293.1 |

TABLE 13-continued

| Cpd. No. | Structure | IUPAC | LC-MS (ES+, m/z) |
|---|---|---|---|
| 577 | 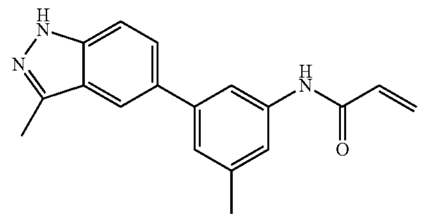 [SMILES: C=CC(=O)Nc1cc(C)cc(-c2ccc3[nH]nc(C)c3c2)c1] | N-[3-methyl-5-(3-methyl-1H-indazol-5-yl)phenyl]prop-2-enamide | 292.1 |
| 578 | 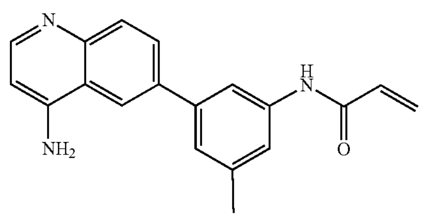 [SMILES: C=CC(=O)Nc1cc(C)cc(-c2ccc3nccc(N)c3c2)c1] | N-[3-(4-aminoquinolin-6-yl)-5-methylphenyl]prop-2-enamide | 304.1 |
| 579 | 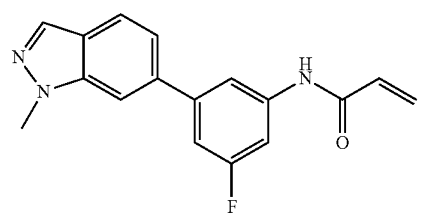 [SMILES: C=CC(=O)Nc1cc(F)cc(-c2ccc3cnn(C)c3c2)c1] | N-[3-fluoro-5-(1-methyl-1H-indazol-6-yl)phenyl]prop-2-enamide | 296.1 |
| 580 | 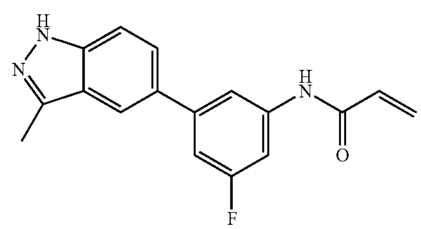 [SMILES: C=CC(=O)Nc1cc(F)cc(-c2ccc3[nH]nc(C)c3c2)c1] | N-[3-fluoro-5-(3-methyl-1H-indazol-5-yl)phenyl]prop-2-enamide | 296.1 |
| 581 | 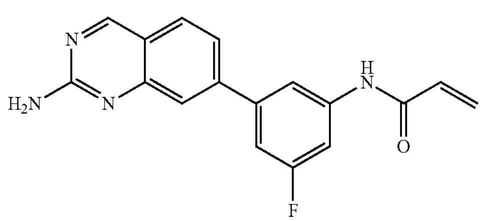 [SMILES: C=CC(=O)Nc1cc(F)cc(-c2ccc3cnc(N)nc3c2)c1] | N-[3-(2-aminoquinazolin-7-yl)-5-fluorophenyl]prop-2-enamide | 309.1 |
| 582 | 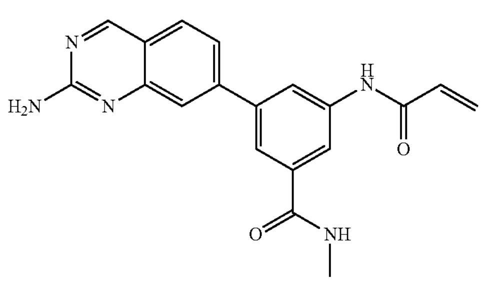 [SMILES: C=CC(=O)Nc1cc(C(=O)NC)cc(-c2ccc3cnc(N)nc3c2)c1] | 3-(2-aminoquinazolin-7-yl)-N-methyl-5-(prop-2-enamido)benzamide | 348.2 |

TABLE 13-continued

| Cpd. No. | Structure | IUPAC | LC-MS (ES+, m/z) |
|---|---|---|---|
| 583 | 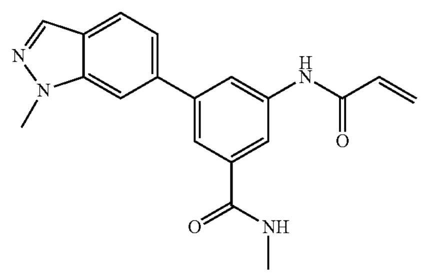 [SMILES: C=CC(=O)Nc1cc(C(=O)NC)cc(-c2ccc3cnn(C)c3c2)c1] | N-methyl-3-(1-methyl-1H-indazol-6-yl)-5-(prop-2-enamido)benzamide | 335.1 |
| 584 | 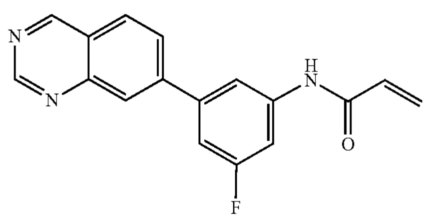 [SMILES: C=CC(=O)Nc1cc(F)cc(-c2ccc3cncnc3c2)c1] | N-[3-fluoro-5-(quinazolin-7-yl)phenyl]prop-2-enamide | 294.1 |
| 585 | 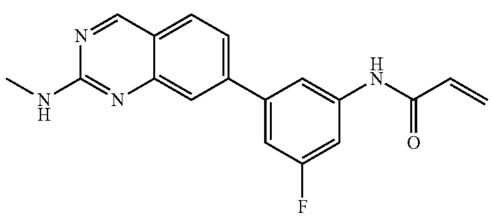 | N-{3-fluoro-5-[2-(methylamino)quinazolin-7-yl]phenyl}prop-2-enamide | 323.1 |
| 586 | 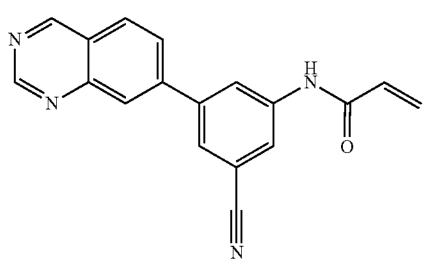 [SMILES: C=CC(=O)Nc1cc(C#N)cc(-c2ccc3cncnc3c2)c1] | N-[3-cyano-5-(quinazolin-7-yl)phenyl]prop-2-enamide | 301.1 |
| 587 | 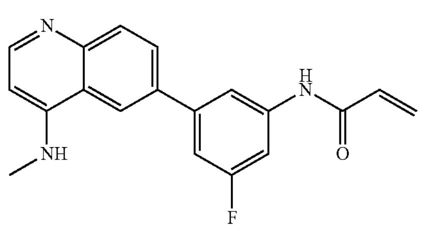 [SMILES: C=CC(=O)Nc1cc(F)cc(-c2ccc3nccc(NC)c3c2)c1] | N-{3-fluoro-5-[4-(methylamino)quinolin-6-yl]phenyl}prop-2-enamide | 322.1 |

TABLE 13-continued

| Cpd. No. | Structure | IUPAC | LC-MS (ES+, m/z) |
|---|---|---|---|
| 588 | 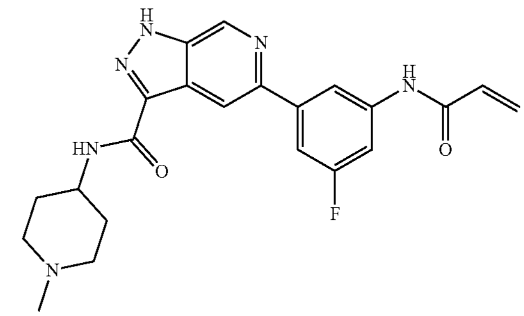 | 5-[3-fluoro-5-(prop-2-enamido)phenyl]-N-(1-methylpiperidin-4-yl)-1H-pyrazolo[3,4-c]pyridine-3-carboxamide | 423.1 |
| 589 | 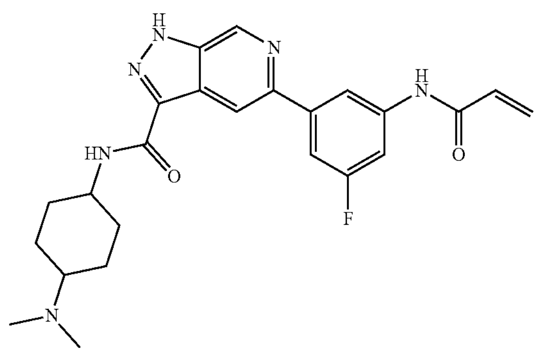 | N-[4-(dimethylamino)cyclohexyl]-5-[3-fluoro-5-(prop-2-enamido)phenyl]-1H-pyrazolo[3,4-c]pyridine-3-carboxamide | 451.2 |
| 590 | 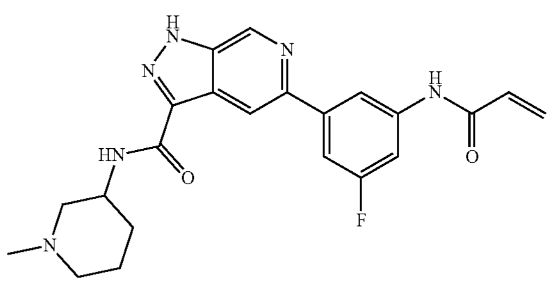 [SMILES: C=CC(=O)Nc1cc(F)cc(-c2cc3c(C(=O)NC4CCCN(C)C4)n[nH]c3cn2)c1] | 5-[3-fluoro-5-(prop-2-enamido)phenyl]-N-(1-methylpiperidin-3-yl)-1H-pyrazolo[3,4-c]pyridine-3-carboxamide | 423.2 |
| 591 | 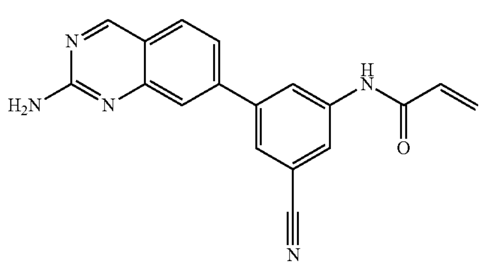 [SMILES: C=CC(=O)Nc1cc(C#N)cc(-c2ccc3cnc(N)nc3c2)c1] | N-[3-(2-aminoquinazolin-7-yl)-5-cyanophenyl]prop-2-enamide | 316.1 |
| 592 | 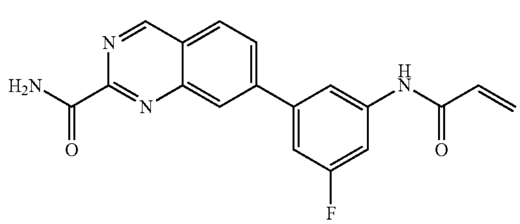 | 7-[3-fluoro-5-(prop-2-enamido)phenyl]quinazoline-2-carboxamide | 337 |

US 11,926,632 B2
731                                                                732
TABLE 13-continued
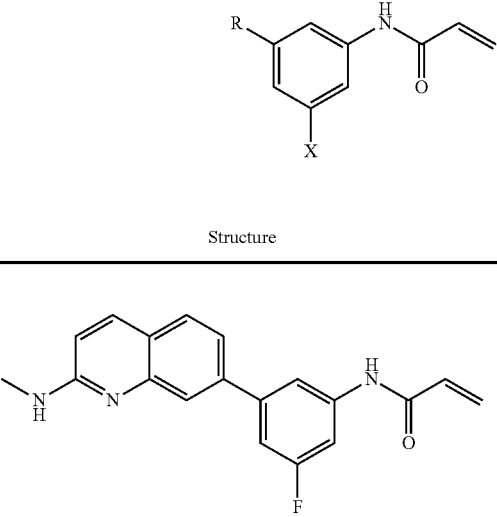
| Cpd. No. | Structure | IUPAC | LC-MS (ES+, m/z) |
| --- | --- | --- | --- |
| 593 | 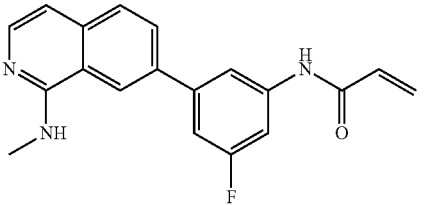 [SMILES: C=CC(=O)Nc1cc(F)cc(-c2ccc3ccnc(NC)c3c2)c1] | N-{3-fluoro-5-[2-(methylamino)quinolin-7-yl]phenyl}prop-2-enamide | 322 |
| 594 | 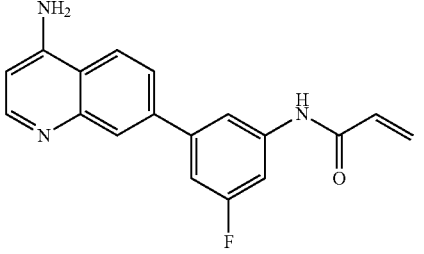 [SMILES: C=CC(=O)Nc1cc(F)cc(-c2ccc3c(N)ccnc3c2)c1] | N-{3-fluoro-5-[1-(methylamino)isoquinolin-7-yl]phenyl}prop-2-enamide | 322 |
| 595 | 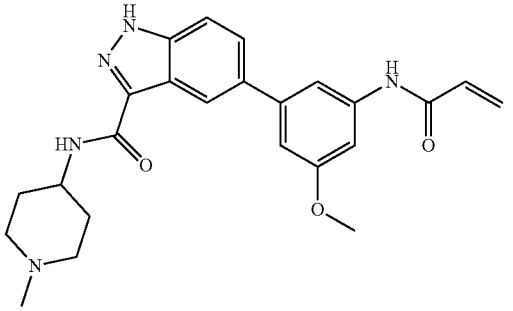 [SMILES: C=CC(=O)Nc1cc(OC)cc(-c2ccc3[nH]nc(C(=O)NC4CCN(C)CC4)c3c2)c1] | N-[3-(4-aminoquinolin-7-yl)-5-fluorophenyl]prop-2-enamide | 308 |
| 596 | 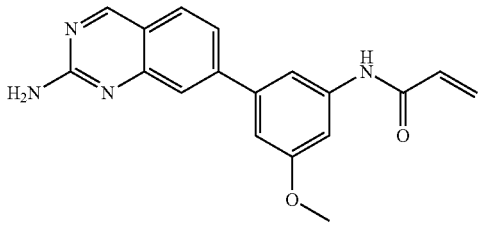 | 5-[3-methoxy-5-(prop-2-enamido)phenyl]-N-(1-methylpiperidin-4-yl)-1H-indazole-3-carboxamide | 434.2 |
| 597 | 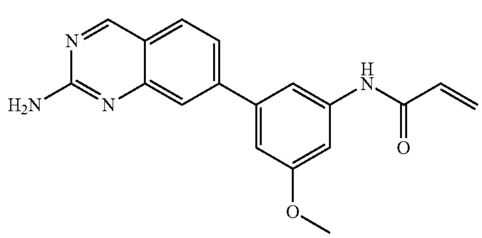 [SMILES: C=CC(=O)Nc1cc(OC)cc(-c2ccc3cnc(N)nc3c2)c1] | N-[3-(2-aminoquinazolin-7-yl)-5-methoxyphenyl]prop-2-enamide | 321.2 |

TABLE 13-continued

| Cpd. No. | Structure | IUPAC | LC-MS (ES+, m/z) |
|---|---|---|---|
| 598 | 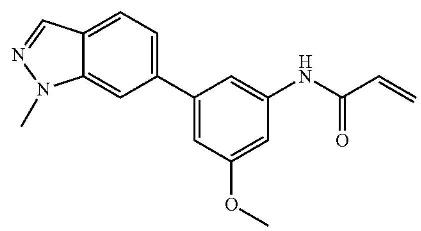 [SMILES: C=CC(=O)Nc1cc(OC)cc(-c2ccc3cnn(C)c3c2)c1] | N-[3-methoxy-5-(1-methyl-1H-indazol-6-yl)phenyl]prop-2-enamide | 308.1 |
| 599 | 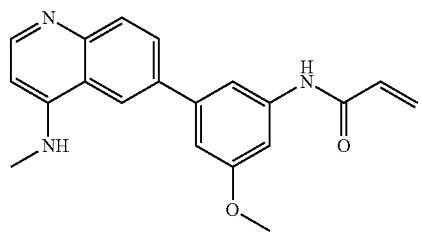 [SMILES: C=CC(=O)Nc1cc(OC)cc(-c2ccc3nccc(NC)c3c2)c1] | N-{3-methoxy-5-[4-(methylamino)quinolin-6-yl]phenyl}prop-2-enamide | 334.1 |
| 600 | 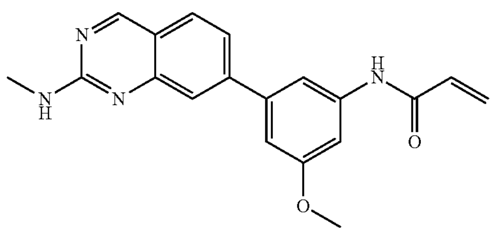 [SMILES: C=CC(=O)Nc1cc(OC)cc(-c2ccc3cnc(NC)nc3c2)c1] | N-{3-methoxy-5-[2-(methylamino)quinazolin-7-yl]phenyl}prop-2-enamide | 335.1 |
| 601 | 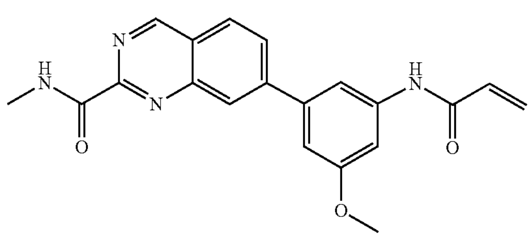 [SMILES: C=CC(=O)Nc1cc(OC)cc(-c2ccc3cnc(C(=O)NC)nc3c2)c1] | 7-[3-methoxy-5-(prop-2-enamido)phenyl]-N-methylquinazoline-2-carboxamide | 363.1 |
| 602 | 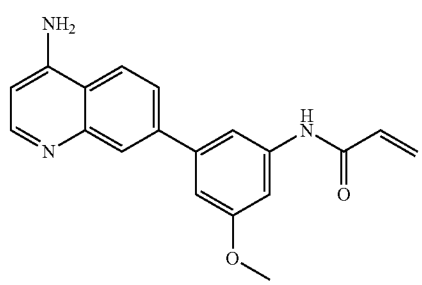 [SMILES: C=CC(=O)Nc1cc(OC)cc(-c2ccc3c(N)ccnc3c2)c1] | N-[3-(4-aminoquinolin-7-yl)-5-methoxyphenyl]prop-2-enamide | 319.9 |

TABLE 13-continued

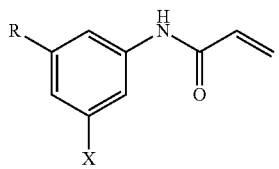

| Cpd. No. | Structure | IUPAC | LC-MS (ES+, m/z) |
|---|---|---|---|
| 603 | 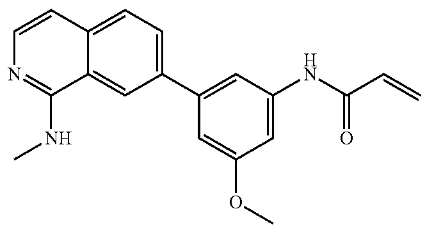 [SMILES: C=CC(=O)Nc1cc(OC)cc(-c2ccc3ccnc(NC)c3c2)c1] | N-{3-methoxy-5-[1-(methylamino)isoquinolin-7-yl]phenyl}prop-2-enamide | 333.9 |

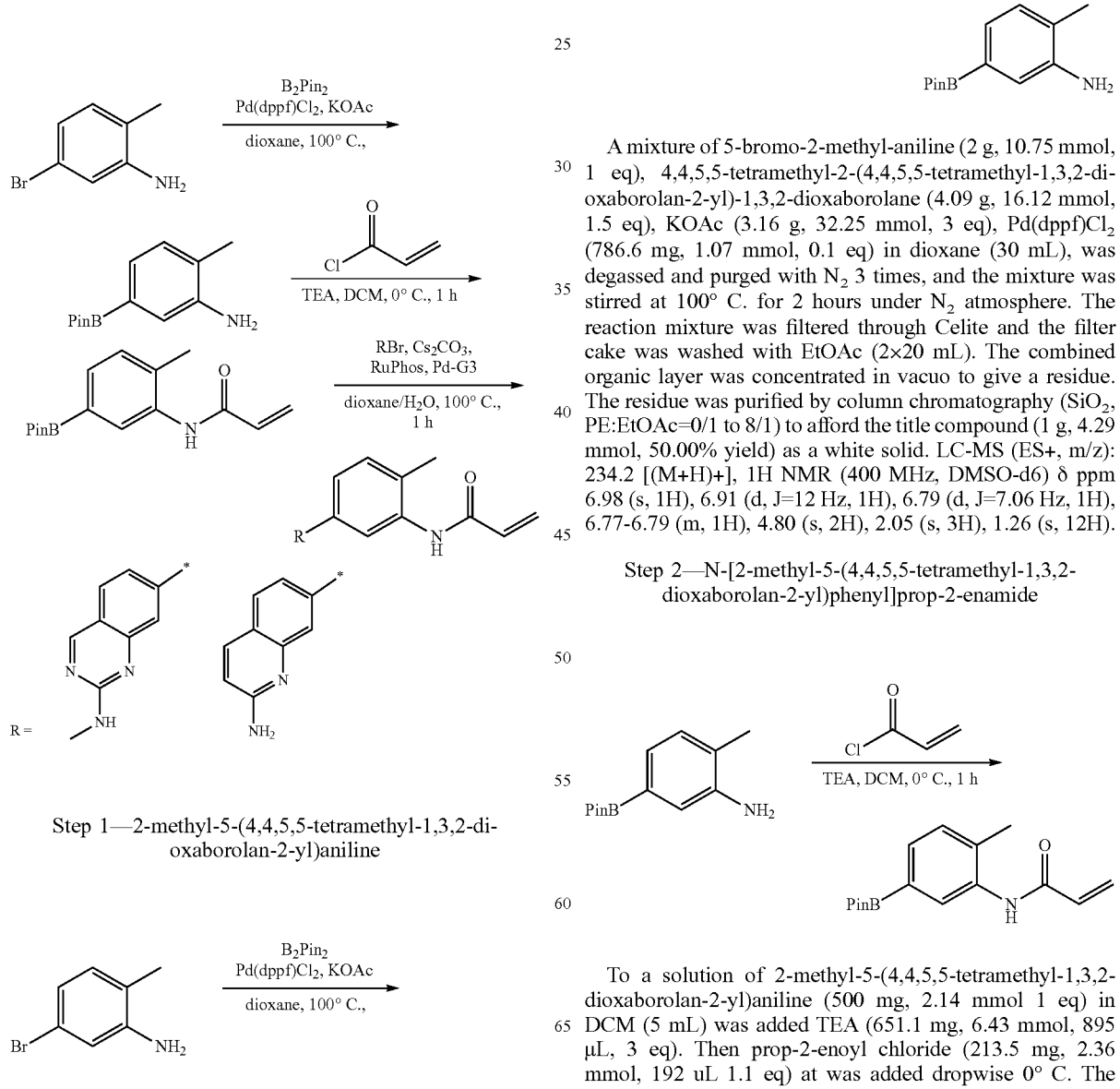

Example 14: Method N

Step 1—2-methyl-5-(4,4,5,5-tetramethyl-1,3,2-dioxaborolan-2-yl)aniline

A mixture of 5-bromo-2-methyl-aniline (2 g, 10.75 mmol, 1 eq), 4,4,5,5-tetramethyl-2-(4,4,5,5-tetramethyl-1,3,2-dioxaborolan-2-yl)-1,3,2-dioxaborolane (4.09 g, 16.12 mmol, 1.5 eq), KOAc (3.16 g, 32.25 mmol, 3 eq), Pd(dppf)Cl$_2$ (786.6 mg, 1.07 mmol, 0.1 eq) in dioxane (30 mL), was degassed and purged with N$_2$ 3 times, and the mixture was stirred at 100° C. for 2 hours under N$_2$ atmosphere. The reaction mixture was filtered through Celite and the filter cake was washed with EtOAc (2×20 mL). The combined organic layer was concentrated in vacuo to give a residue. The residue was purified by column chromatography (SiO$_2$, PE:EtOAc=0/1 to 8/1) to afford the title compound (1 g, 4.29 mmol, 50.00% yield) as a white solid. LC-MS (ES+, m/z): 234.2 [(M+H)+], 1H NMR (400 MHz, DMSO-d6) δ ppm 6.98 (s, 1H), 6.91 (d, J=12 Hz, 1H), 6.79 (d, J=7.06 Hz, 1H), 6.77-6.79 (m, 1H), 4.80 (s, 2H), 2.05 (s, 3H), 1.26 (s, 12H).

Step 2—N-[2-methyl-5-(4,4,5,5-tetramethyl-1,3,2-dioxaborolan-2-yl)phenyl]prop-2-enamide To a solution of 2-methyl-5-(4,4,5,5-tetramethyl-1,3,2-dioxaborolan-2-yl)aniline (500 mg, 2.14 mmol 1 eq) in DCM (5 mL) was added TEA (651.1 mg, 6.43 mmol, 895 μL, 3 eq). Then prop-2-enoyl chloride (213.5 mg, 2.36 mmol, 192 uL 1.1 eq) at was added dropwise 0° C. The mixture was stirred at 0° C. for 1 h. The reaction mixture was poured into water (50 mL). The mixture was extracted with EtOAc (3×30 mL). The combined organic layers were washed with brine (1×30 mL), dried over anhydrous Na₂SO₄, filtered, and concentrated in vacuo to give a residue. The residue was purified by column chromatography (SiO₂, PE:EtOAc=1/0 to 8/1) to afford the title compound (380 mg, 1.32 mmol, 61.70% yield) as a light yellow solid. LC-MS (ES⁺, m/z): 288.2 [(M+H)⁺]

Step 3—N-[2-[6-methyl-2-(2-pyridyl)pyrimidin-4-yl]sulfanylethyl]furan-2-carboxamide

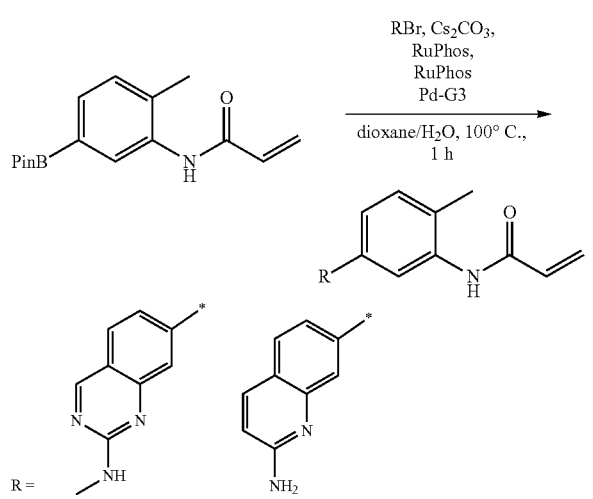

To a solution of N-[2-methyl-5-(4,4,5,5-tetramethyl-1,3,2-dioxaborolan-2-yl)phenyl]prop-2-enamide (66.3 mg, 231.01 μmol, 1.1 eq) in dioxane (4 mL) and H₂O (1 mL) was successively added Cs₂CO₃ (205.3 mg, 630. μmol, 3 eq), 7-bromo-N-methyl-quinazolin-2-amine (50 mg, 210. μmol, 1 eq), [2-(2-aminophenyl)phenyl]-methylsulfonyloxy-palladium;dicyclohexyl-[2-(2,6-diisopropoxyphenyl)phenyl]phosphane (17.6 mg, 21 μmol, 0.1 eq), RuPhos (19.6 mg, 42 μmol, 0.2 eq). The resulting reaction mixture was stirred at 100° C. for 1 hr under N₂. LC-MS showed that the reaction was complete. The reaction mixture was poured into saturated EDTA (50 mL). The mixture was stirred at 25° C. for 1 h. The mixture was extracted with EtOAc (3×30 mL). The combined organic layers were washed with brine (1×30 mL), dried over anhydrous Na₂SO₄, filtered, and concentrated in vacuo to give a residue. The residue was purified by prep-HPLC to afford the title compound (12.7 mg, 39.89 μmol, 18.99% yield, 100% purity) as a yellow solid. 319.1. 1H NMR (400 MHz, DMSO-d6) δ=9.59 (brs, 1H), 9.00-9.22 (m, 1H), 8.01 (br s, 1H), 7.86 (br d, J=7.6 Hz, 1H), 7.62-7.70 (m, 1H), 7.53 (br dd, J=20.0, 7.6 Hz, 2H), 7.27-7.40 (m, 2H), 6.49-6.73 (m, 1H), 6.29 (br d, J=17.2 Hz, 1H), 6.21-6.25 (m, 1H), 2.91 (br d, J=2.8 Hz, 3H), 2.22-2.32 (m, 3H).

Route 2: General Scheme

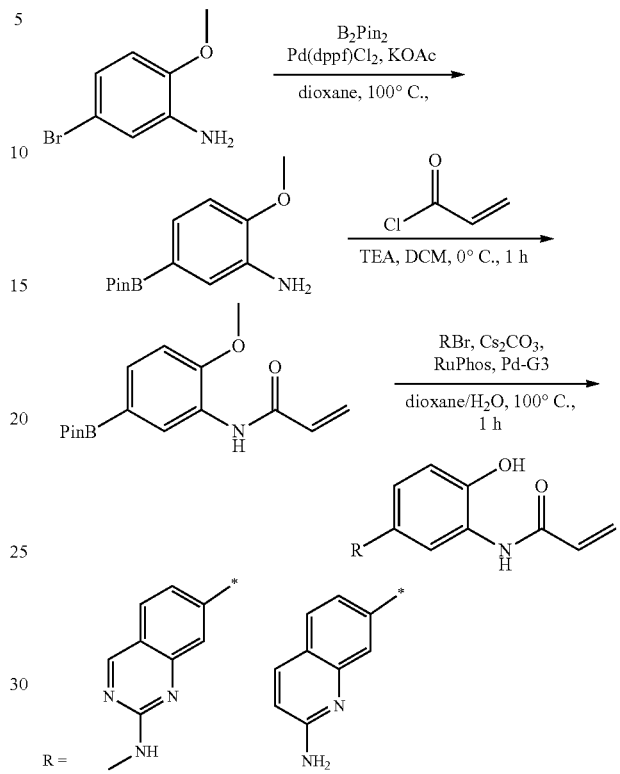

Step 1—2-methoxy-5-(4,4,5,5-tetramethyl-1,3,2-dioxaborolan-2-yl)aniline

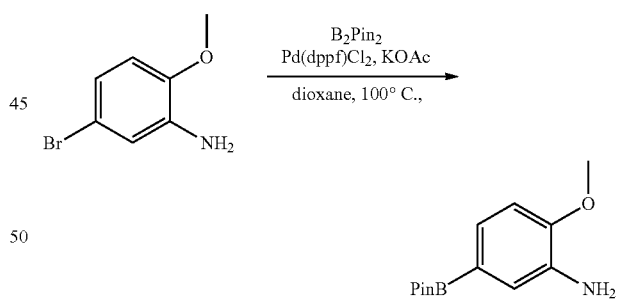

A mixture of 5-bromo-2-methoxy-aniline (2 g, 9.9 mmol, 1 eq), 4,4,5,5-tetramethyl-2-(4,4,5,5-tetramethyl-1,3,2-dioxaborolan-2-yl)-1,3,2-dioxaborolane (3.77 g, 14.85 mmol, 1.5 eq), KOAc (2.91 g, 29.7 mmol, 3 eq), Pd(dppf)Cl₂ (724.3 mg, 989.86 μmol, 0.1 eq) in dioxane (30 mL), was degassed and purged with N₂ 3 times, and the mixture was stirred at 100° C. for 2 hr under N₂ atmosphere. The reaction mixture was filtered through Celite and the filter cake was washed with EtOAc (2×20 mL). The combined filtrates were concentrated in vacuo to give a residue. The residue was purified by column chromatography (SiO₂, PE:EtOAc=0/1 to 8/1) to afford the title compound (2 g, 7.23 mmol, 90.00% yield, 90% purity) as a white solid. 1H NMR (400 MHz, DMSO-d<sub>6</sub>) δ=7.00 (d, J=1.6 Hz, 1H), 6.88-6.93 (m, 1H), 6.77 (d, 7=8.0 Hz, 1H), 4.66 (s, 2H), 3.77 (s, 3H), 1.25 (s, 12H).

Step 2—N-[2-methoxy-5-(4,4,5,5-tetramethyl-1,3,2-dioxaborolan-2-yl)phenyl]prop-2-enamide

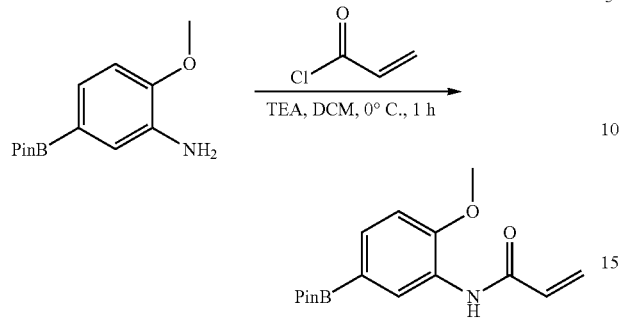

To a solution of 2-methoxy-5-(4,4,5,5-tetramethyl-1,3,2-dioxaborolan-2-yl)aniline (500 mg, 2.01 mmol, 1 eq) in DCM (3 mL) was added TEA (609.3 mg, 6.02 mmol, 838 µL, 3 eq) and prop-2-enoyl chloride (199.8 mg, 2.21 mmol, 180 µL, 1.1 eq) at 0° C. The mixture was stirred at 0° C. for 1 hr. TLC indicated the reaction was complete. The reaction mixture was poured into cold water (50 mL). The mixture was extracted with DCM (3×30 mL). The combined organic layers were washed with brine (1×30 mL), dried over anhydrous Na<sub>2</sub>SO<sub>4</sub>, filtered, and concentrated in vacuo to give a residue. The residue was purified by column chromatography (SiO<sub>2</sub>, PE:EtOAc=1/0 to 8/1) to afford the title compound (350 mg, 1.15 mmol, 57.52% yield) as a white solid.

Step 3—N-[5-(2-amino-7-quinolyl)-2-methoxy-phenyl]prop-2-enamide

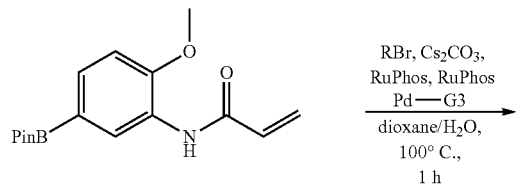

To a solution of N-[2-methoxy-5-(4,4,5,5-tetramethyl-1,3,2-dioxaborolan-2-yl)phenyl]prop-2-enamide (81.5 mg, 268.98 µmol, 1.2 eq) in dioxane (4 mL) and H<sub>2</sub>O (1 mL) was successively added Cs<sub>2</sub>CO<sub>3</sub> (219.1 mg, 672.44 µmol, 3 eq), RuPhos (20.9 mg, 44.83 µmol, 0.2 eq), [2-(2-aminophenyl)phenyl]-methylsulfonyloxy-palladium;dicyclohexyl-[2-(2,6-diisopropoxyphenyl)phenyl]phosphane (18.8 mg, 22.41 µmol, 0.1 eq) and 7-bromoquinolin-2-amine (50 mg, 224.15 µmol, 1 eq). The mixture was stirred at 100° C. for 1 hr under N<sub>2</sub> atmosphere. LC-MS showed that the reaction was complete. The reaction mixture was poured into saturated EDTA (50 mL). The mixture was stirred at 25° C. for 1 hr. The mixture was extracted with EtOAc (3×30 mL). The combined organic layers were washed with brine (1×30 mL), dried over anhydrous Na<sub>2</sub>SO<sub>4</sub>, filtered, and concentrated in vacuo to give a residue. The residue was purified by prep-HPLC to afford the title compound (7.7 mg, 23.27 µmol, 10.38% yield, 96.5% purity) as a white solid. 1H NMR (400 MHz, DMSO-d6) 5=9.50 (s, 1H), 8.51 (br d, J=1.2 Hz, 1H), 7.89 (d, J=8.8 Hz, 1H), 7.68 (d, J=8.4 Hz, 1H), 7.61 (d, J=1.2 Hz, 1H), 7.49 (dd, J=8.4, 2.4 Hz, 1H), 7.39 (dd, J=8.0, 1.6 Hz, 1H), 7.17 (d, J=8.8 Hz, 1H), 6.70-6.80 (m, 2H), 6.43 (s, 2H), 6.27 (dd, J=16.0 Hz, 1H), 5.59-5.86 (m, 1H), 3.91 (s, 3H).

TABLE 14 shows compounds prepared using the methods described in EXAMPLE 14 above.

TABLE 14

| Cpd. No. | Structure | IUPAC | LC-MS (ES+, m/z) |
|---|---|---|---|
| 604 | 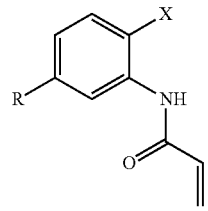 | N-[2-methoxy-5-(1-methyl-1H-indazol-6-yl)phenyl]prop-2-enamide | 308.1 |

TABLE 14-continued

| Cpd. No. | Structure | IUPAC | LC-MS (ES+, m/z) |
|---|---|---|---|
| 605 | 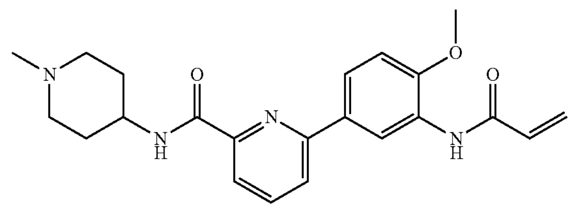 [SMILES: C=CC(=O)Nc1cc(-c2cccc(C(=O)NC3CCN(C)CC3)n2)ccc1OC] | 6-[4-methoxy-3-(prop-2-enamido)phenyl]-N-(1-methylpiperidin-4-yl)pyridine-2-carboxamide | 395.2 |
| 606 | 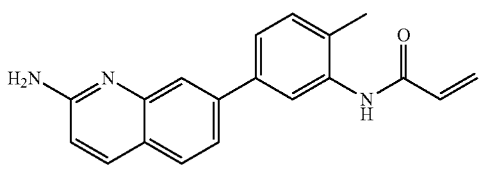 [SMILES: C=CC(=O)Nc1cc(-c2ccc3ccc(N)nc3c2)ccc1C] | N-[5-(2-aminoquinolin-7-yl)-2-methylphenyl]prop-2-enamide | 304.1 |
| 607 | 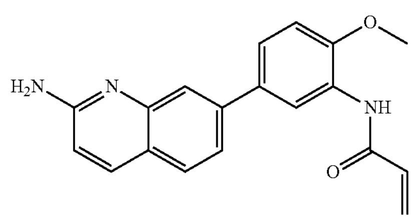 [SMILES: C=CC(=O)Nc1cc(-c2ccc3ccc(N)nc3c2)ccc1OC] | N-[5-(2-aminoquinolin-7-yl)-2-methoxyphenyl]prop-2-enamide | 320.1 |
| 608 | 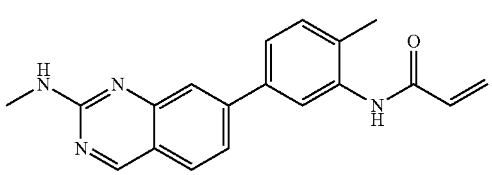 [SMILES: C=CC(=O)Nc1cc(-c2ccc3cnc(NC)nc3c2)ccc1C] | N-{2-methyl-5-[2-(methylamino)quinazolin-7-yl]phenyl}prop-2-enamide | 319.1 |
| 609 | 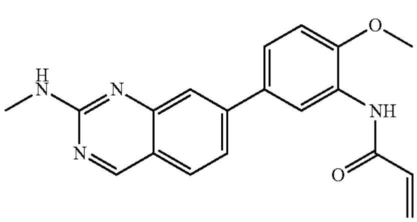 | N-{2-methoxy-5-[2-(methylamino)quinazolin-7-yl]phenyl}prop-2-enamide | 335.1 |
| 610 | 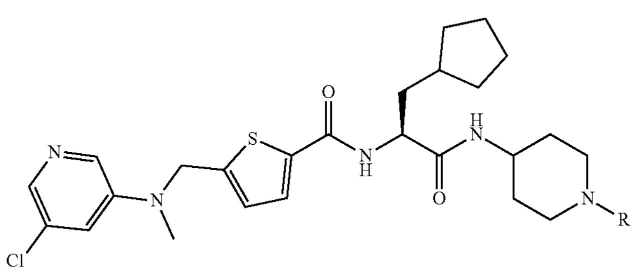 | N-{2-methoxy-5-[4-(methylamino)quinolin-6-yl]phenyl}prop-2-enamide | 334 |

TABLE 14-continued
| Cpd. No. | Structure | IUPAC | LC-MS (ES+, m/z) |
|---|---|---|---|
| 611 | 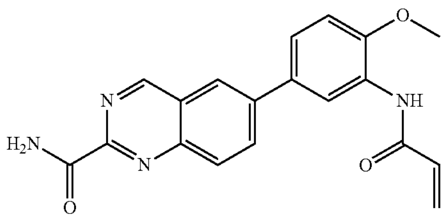 [SMILES: C=CC(=O)Nc1cc(-c2ccc3nc(C(N)=O)ncc3c2)ccc1OC] | 6-[4-methoxy-3-(prop-2-enamido)phenyl]quinazoline-2-carboxamide | 349 |
| 612 | 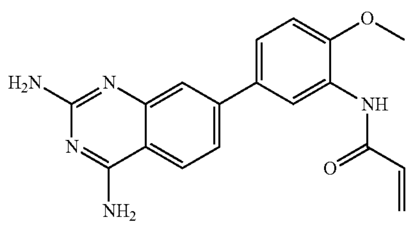 [SMILES: C=CC(=O)Nc1cc(-c2ccc3c(N)nc(N)nc3c2)ccc1OC] | N-[5-(2,4-diaminoquinazolin-7-yl)-2-methoxyphenyl]prop-2-enamide | 336 |
| 613 | 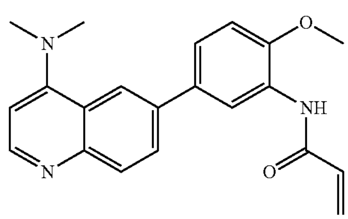 [SMILES: C=CC(=O)Nc1cc(-c2ccc3nccc(N(C)C)c3c2)ccc1OC] | N-{5-[4-(dimethylamino)quinolin-6-yl]-2-methoxyphenyl}prop-2-enamide | 348 |
Example 15: Method O
Route 1: General Scheme
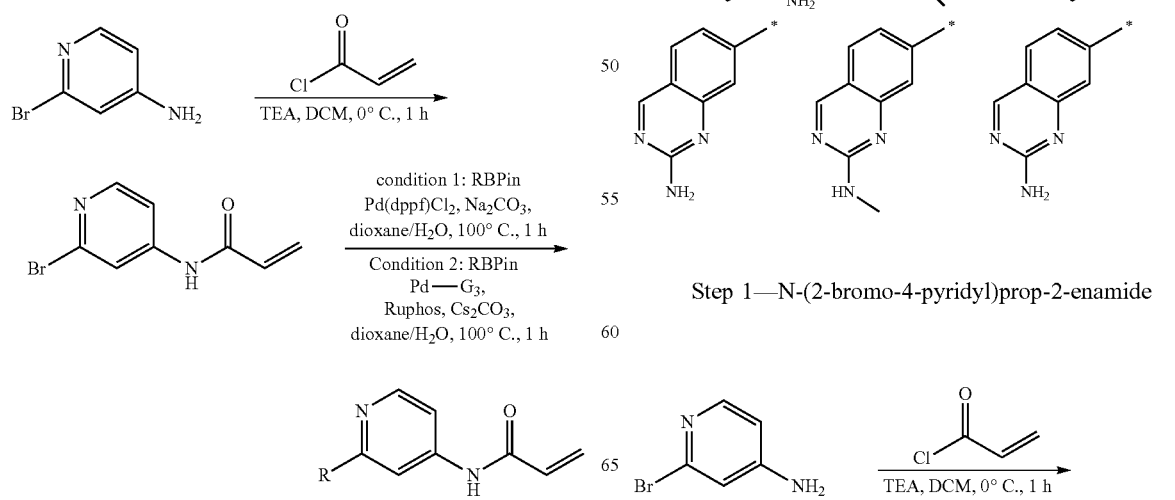
Step 1—N-(2-bromo-4-pyridyl)prop-2-enamide

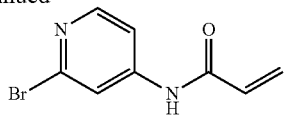

To a solution of 2-bromopyridin-4-amine (0.9 g, 5.2 mmol, 1 eq) in DCM (10 mL) was added TEA (2.63 g, 26.01 mmol, 3.62 mL, 5 eq) and prop-2-enoyl chloride (565 mg, 6.24 mmol, 509.00 µL, 1.2 eq). The reaction mixture was stirred at 0° C. for 1 h under N₂. LCMS showed that the reaction was complete. The reaction mixture was poured into 100 mL H₂O. The mixture was extracted with DCM (3×50 mL). The combined organic layers were washed with H₂O (2×50 mL) and brine (2×50 mL), dried over anhydrous Na₂SO₄, filtered, and concentrated in vacuo to give a residue. The residue was purified by column chromatography (SiO₂, PE:EtOAc=10:1 to 4:1) to afford the title compound N-(2-bromo-4-pyridyl)prop-2-enamide (0.88 g, 2.33 mmol, 44.70% yield, 60% purity) as a white solid. LC-MS (ES⁺, m/z): 227.2 [(M+H)⁺]

Step 2—N-(2-R-pyridin-4-yl)acrylamide

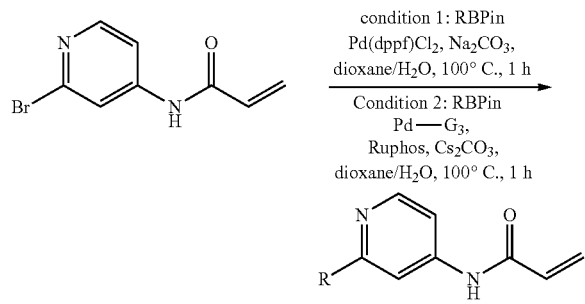

To a solution of N-(2-bromo-4-pyridyl)prop-2-enamide (0.2 g, 880.83 µmol, 1 eq) and 6-(4,4,5,5-tetramethyl-1,3,2-dioxaborolan-2-yl)quinolin-4-amine (594.9 mg, 2.2 mmol, 2.5 eq) in dioxane (4 mL) and H₂O (1 mL) was added Na₂CO₃ (280.1 mg, 2.64 mmol, 3 eq) and Pd(dppf)Cl₂ (64.5 mg, 88.08 µmol, 0.1 eq). The reaction was heated to 100° C. under N₂ and stirred for 1 h. LCMS showed that the reaction was complete. The reaction mixture was poured into saturated EDTA (50 mL) and stirred for 60 min. The mixture was extracted with EtOAc (3×30 mL), and the combined organic layers were washed with H₂O (2×30 mL) and brine (2×30 mL), dried over anhydrous Na₂SO₄, filtered, and concentrated in vacuo to give a residue. The residue was purified by prep-HPLC (PA condition) to afford the title compound N-[2-(4-amino-6-quinolyl)-4-pyridyl]prop-2-enamide (14.4 mg, 48.36 µmol, 5.49% yield, 97.5% purity) as a white solid. 291.1. 1H NMR (400 MHz, DMSO-d6) δ=10.75 fs, 1H), 8.82 (d, j 1.63 Hz, 1H), 8.60 (d, J=5.50 Hz, 1H), 8.33 (d, J=5.45 Hz, 1H), 8.31 (s, 1H), 8.21-8.28 (m, 2H), 7.87 (d, J=8.88 Hz, 1H), 7.66 (dd, J=5.50, 1.75 Hz, 1H), 7.35 (s, 2H), 6.61 (d, J=5.38 Hz, 1H), 6.52 (dd, J=16.95, 10.07 Hz, 1H), 6.36 (dd, J=17.01, 1.88 Hz, 1H), 5.84-5.92 (m, 1H).

To a solution of N-(2-bromo-4-pyridyl)prop-2-enamide (50 mg, 220.21 µmol, 1 eq), 7-(4,4,5,5-tetramethyl-1,3,2-dioxaborolan-2-yl)quinazolin-2-amine (119.4 mg, 440.42 µmol, 2 eq) in dioxane (3 mL), H₂O (0.75 mL) was added Cs₂CO₃ (215.2 mg, 660.63 µmol, 3 eq), [2-(2-aminophenyl)phenyl]-methylsulfonyloxy-palladium; dicyclohexyl-[2-(2,6-diisopropoxyphenyl)phenyl]phosphane (9.2 mg, 11.01 µmol, 0.05 eq) and dicyclohexyl-[2-(2,6-diisopropoxyphenyl)phenyl]phosphane (10.3 mg, 22.02 µmol, 0.1 eq) at 25° C. The reaction mixture was stirred at 100° C. for 1 h. The reaction mixture was poured into saturated EDTA (20 mL) and stirred for 60 min. The aqueous phase was extracted with EtOAc (3×20 mL). The combined organic phase was washed with brine (3×20 mL), dried over anhydrous Na₂SO₄, filtered, and concentrated in vacuo to afford a residue. The residue was purified by prep-TLC. Then further purified by prep-HPLC to afford the title compound N-[2-(2-aminoquinazolin-7-yl)-4-pyridyl]prop-2-enamide (6.3 mg, 21.63 µmol, 9.82% yield, 100% purity) as a white solid. 292.1. 1H NMR (400 MHz, DMSO-d6) δ=10.65 (s, 1H), 9.15 (s, 1H), 8.61 (d, J=5.6 Hz, 1H), 8.30 (d, J=1.2 Hz, 1H), 7.96 (s, 1H), 7.92 (d, J=4.8 Hz, 1H), 7.82 (dd, J=1.6, 8.4 Hz, 1H), 7.67 (dd, J=1.6, 5.2 Hz, 1H), 6.91 (s, 2H), 6.48 (dd, J=10.0, 16.8 Hz, 1H), 6.36 (dd, J=2.0, 17.2 Hz, 1H), 5.91 (dd, J=1.6, 9.6 Hz, 1H)

Route 2: General Scheme

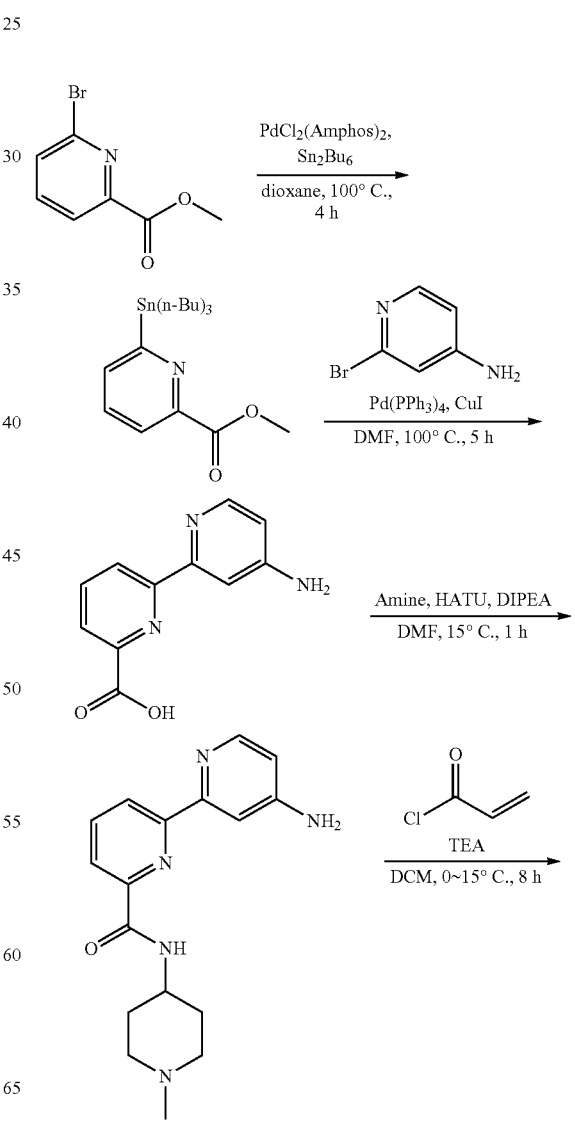

747
-continued

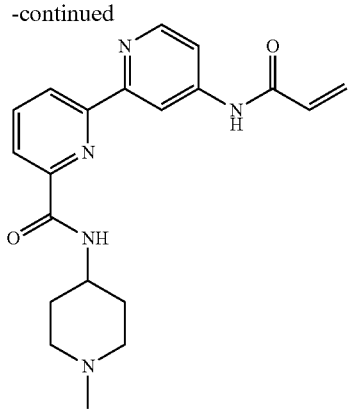

Step 1—methyl 6-tributylstannylpyridine-2-carboxylate

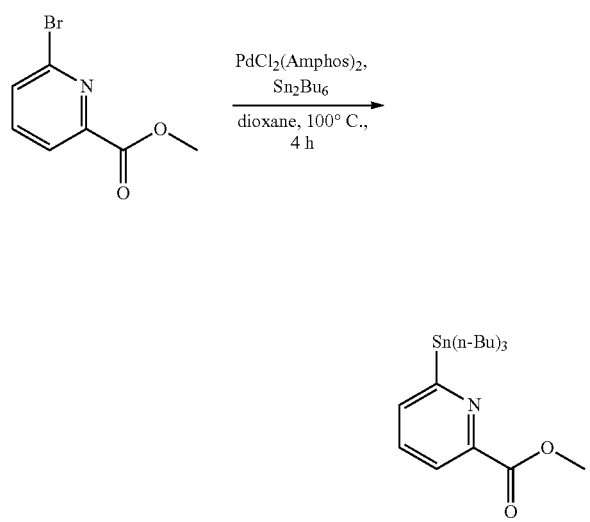

To a solution of methyl 6-bromopyridine-2-carboxylate (1 g, 4.63 mmol, 1 eq) in dioxane (20 mL) was added 4-ditert-butylphosphanyl-N,N-dimethyl-aniline;dichloropalladium (262.2 mg, 370.32 μmol, 262.21 μL, 0.08 eq) and tributyl(tributylstannyl)stannane (5.37 g, 9.26 mmol, 4.63 mL, 2 eq). The reaction mixture was stirred at 100° C. for 4 h under N$_2$. LCMS showed that the reaction was complete. The reaction mixture was poured into H$_2$O (50 mL). The mixture was extracted with EtOAc (2×30 mL), and the combined organic layers were washed with H$_2$O (2×30 mL) and brine (2×30 mL). Then dried over anhydrous Na$_2$SO$_4$, filtered, and concentrated in vacuo to afford the title compound methyl 6-tributylstannylpyridine-2-carboxylate (6 g, crude) as an black brown oil which was used for the next step directly without further purification. LC-MS (ES$^+$, m/z): 428.1 [(M+H)$^+$]

748

Step 2—6-(4-amino-2-pyridyl)pyridine-2-carboxylic acid

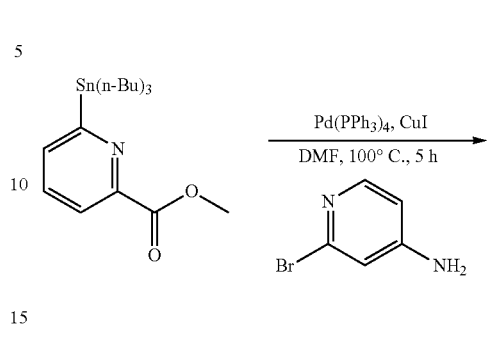

To a solution of 2-bromopyridin-4-amine (0.5 g, 2.89 mmol, 1 eq) and methyl 6-tributyl stannylpyridine-2-carboxylate (4.93 g, 11.56 mmol, 4 eq) in DMF (5 mL) was added Pd(PPh$_3$)$_4$ (334 mg, 289 μmol, 0.1 eq) and CuI (55 mg, 289 μmol, 0.1 eq). The reaction mixture was heated to 100° C. under N$_2$ and stirred at 100° C. for 5 h. LCMS showed that the reaction was complete. The reaction mixture was poured into saturated EDTA (60 mL) and stirred for 60 min, extracted with EtOAc (3×40 mL), and the combined organic layer was washed with H$_2$O (2×40 mL) and brine (2×50 mL). Then dried over anhydrous Na$_2$SO$_4$, filtered, and concentrated in vacuo to give a residue. The residue was purified by prep-HPLC to afford the title compound 6-(4-amino-2-pyridyl)pyridine-2-carboxylic acid (100 mg, 464.67 μmol, 16.08% yield) as a white solid. LC-MS (ES$^+$, m/z): 216.0 [(M+H)$^+$]

Step 3—6-(4-amino-2-pyridyl)-N-(1-methyl-4-piperidyl)pyridine-2-carboxamide

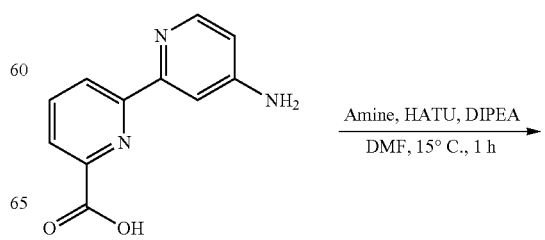

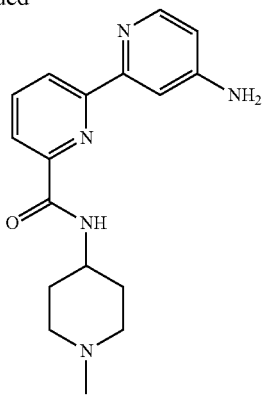

To a solution of 6-(4-amino-2-pyridyl)pyridine-2-carboxylic acid (80 mg, 371.73 μmol, 1 eq) in DMF (3 mL) was added DIPEA (240.2 mg, 1.86 mmol, 323.75 μL, 5 eq) and 1-methylpiperidin-4-amine (50.9 mg, 446.08 μmol, 1.2 eq). Then HATU (212 mg, 557.6 μmol, 1.5 eq) was added. The resulting reaction mixture was stirred at 15° C. for 1 h. LCMS showed that the reaction was complete. The reaction mixture was poured into H₂O (20 mL). The mixture was extracted with EtOAc (3×20 mL), and the combined organic layers were washed with H₂O (2×20 mL) and brine (2×50 mL). Then dried over anhydrous Na₂SO₄, filtered, and concentrated in vacuo to afford the title compound 6-(4-amino-2-pyridyl)-N-(1-methyl-4-piperidyl)pyridine-2-carboxamide (60 mg, crude) as a yellow oil which was used for the next step directly without further purification. LC-MS (ES⁺, m/z): 312.1 [(M+H)⁺]

Step 4—Compound N-(1-methyl-4-piperidyl)-6-[4-(prop-2-enoylamino)-2-pyridyl]pyridine-2-carboxamide

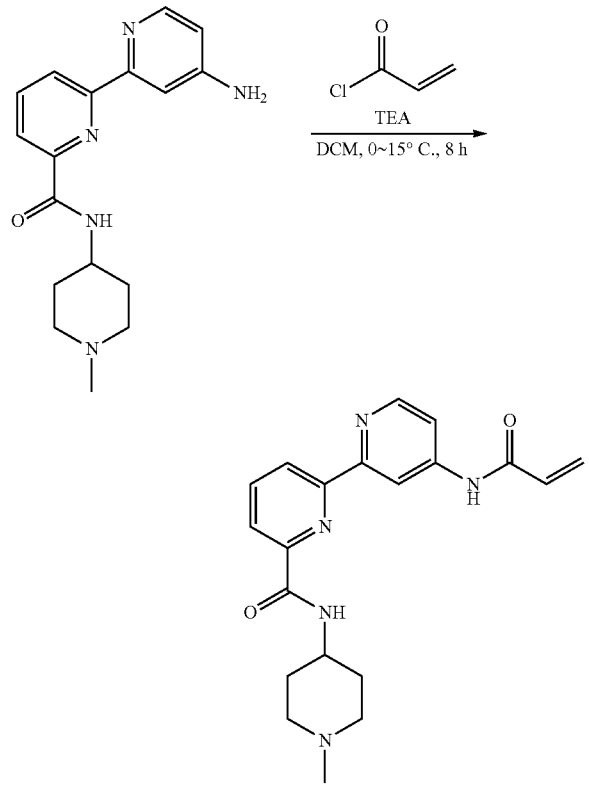

To a solution of 6-(4-amino-2-pyridyl)-N-(1-methyl-4-piperidyl)pyridine-2-carboxamide (50 mg, 160.58 μmol, 1 eq) in DCM (2 mL) was added TEA (81.2 mg, 802.88 μmol, 111.75 μL, 5 eq) and prop-2-enoyl chloride (72.7 mg, 802.88 μmol, 65.47 μL, 5 eq) at 0° C. The reaction mixture was stirred at 15° C. for 8 h under N₂. LCMS showed that the reaction was complete. The reaction mixture was poured into H₂O (20 mL). The mixture was extracted with DCM (3×15 mL), and the combined organic layers were washed with H₂O (2×15 mL) and brine (2×15 mL). Then dried over anhydrous Na₂SO₄, filtered, and concentrated in vacuo to give a residue. The residue was purified by prep-HPLC (basic condition) to afford the title compound N-(1-methyl-4-piperidyl)-6-[4-(prop-2-enoylamino)-2-pyridyl]pyridine-2-carboxamide (7.1 mg, 19.43 μmol, 12.10% yield, 100.0% purity) as a white solid. LC-MS (ES⁺, m/z): 366.1 [(M+H)⁺] ¹H NMR (400 MHz, DMSO-d6) δ=10.69 (br s, 1H), 8.69 (s, 1H), 8.60 (d, J=5.38 Hz, 1H), 8.52 (dd, J=7.76, 1.00 Hz, 1H), 8.36 (br d, J=8.38 Hz, 1H), 8.01-8.18 (m, 2H), 7.83 (br d, J=3.88 Hz, 1H), 6.52 (dd, J=17.00, 10.14 Hz, 1H), 6.36 (dd, J=17.00, 1.76 Hz, 1H), 5.85-5.91 (m, 1H), 3.78-3.89 (m, 1H), 2.68-2.81 (m, 2H), 2.20 (s, 3H), 1.96-2.14 (m, 2H), 1.83-1.92 (m, 2H), 1.61-1.76 (m, 2H).

Route 3: General Scheme

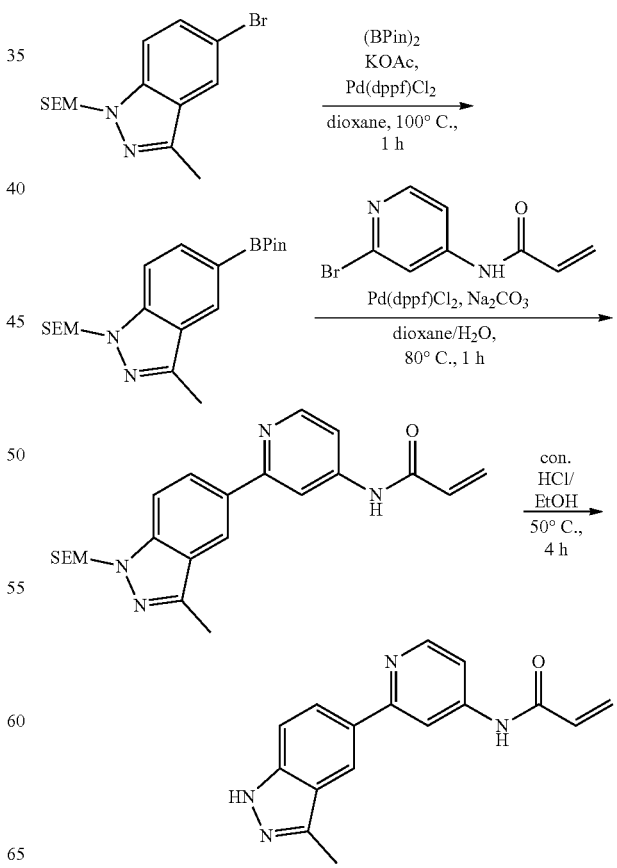

Step 1—Trimethyl-[2-[[3-methyl-5-(4,4,5,5-tetramethyl-1,3,2-dioxaborolan-2-yl)indazol-1-yl]methoxy]ethyl]silane

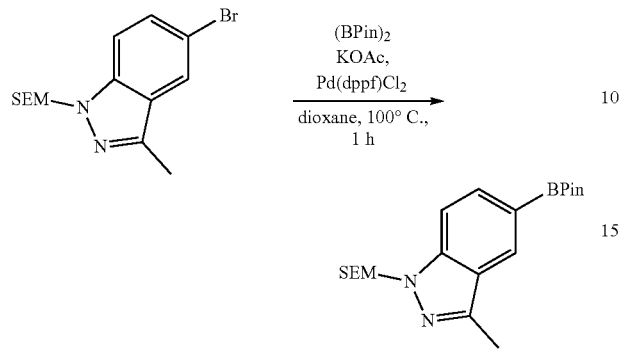

To a solution of 2-[(5-bromo-3-methyl-indazol-1-yl)methoxy]ethyl-trimethyl-silane (0.25 g, 732.45 μmol, 1 eq) and 4,4,5,5-tetramethyl-2-(4,4,5,5-tetramethyl-1,3,2-dioxaborolan-2-yl)-1,3,2-dioxaborolane (241.8 mg, 952.19 μmol, 1.3 eq) in dioxane (2 mL) was added KOAc (215.7 mg, 2.2 mmol, 3 eq) and Pd(dppf)Cl$_2$ (53.6 mg, 73.25 μmol, 0.1 eq). The reaction mixture was stirred at 100° C. for 1 hr under N$_2$. TLC (PE:EtOAc=4:1, SM Rf=0.38, TM Rf=0.49) showed that the reaction was complete. The reaction mixture was filtered and the filtrate was concentrated in vacuo to give a residue. The residue was purified by prep-TLC (SiO$_2$, PE:EtOAc=4:1) to afford the title compound Trimethyl-[2-[[3-methyl-5-(4,4,5,5-tetramethyl-1,3,2-dioxaborolan-2-yl)indazol-1-yl]methoxy]ethyl]silane (0.25 g, 643.69 μmol, 87.88% yield) as a colorless oil.

Step 2—N-[2-[3-methyl-1-(2-trimethylsilylethoxymethyl)indazol-5-yl]-4-pyridyl]prop-2-enamide

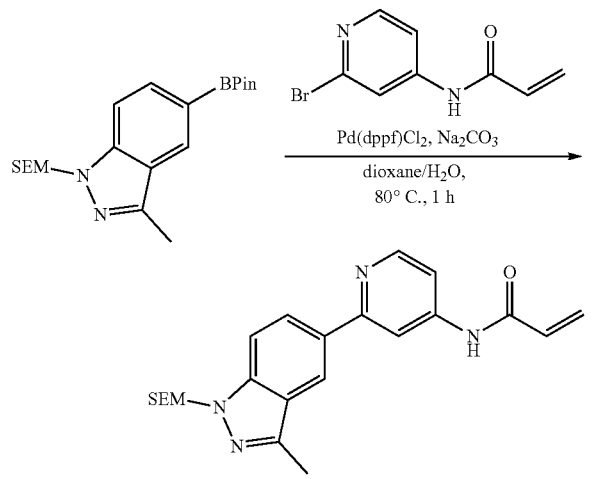

To a solution of trimethyl-[2-[[3-methyl-5-(4,4,5,5-tetramethyl-1,3,2-dioxaborolan-2-yl)indazol-1-yl]methoxy]ethyl]silane (0.27 g, 695.19 μmol, 1 eq) and N-(2-bromo-4-pyridyl)prop-2-enamide (157.9 mg, 695.19 μmol, 1 eq) in dioxane (4 mL) and H$_2$O (1 mL) was added Na$_2$CO$_3$ (221.1 mg, 2.09 mmol, 3 eq) and Pd(dppf)Cl$_2$ (50.9 mg, 69.52 μmol, 0.1 eq). The reaction mixture was stirred at 80° C. for 1 hr under N$_2$. LCMS showed that the starting material was converted to the desired product. The reaction mixture was poured into ~15 mL saturated EDTA and stirred at 25° C. for 1 hr. The mixture was extracted with EtOAc (3×15 mL). The combined organic layer was washed with brine (3×15 mL), dried over anhydrous Na$_2$SO$_4$, filtered, and concentrated in vacuo to give a residue. The residue was purified by prep-TLC (SiO$_2$, PE:EtOAc=1:1) to afford the title compound N-[2-[3-methyl-1-(2-trimethylsilylethoxymethyl)indazol-5-yl]-4-pyridyl]prop-2-enamide (0.11 g, 269.23 μmol, 38.73% yield) as a brown oil. LC-MS (ES+, m/z) 409.1 [(M+H)$^+$]

Step 3—N-[2-(3-methyl-1H-indazol-5-yl)-4-pyridyl]prop-2-enamide

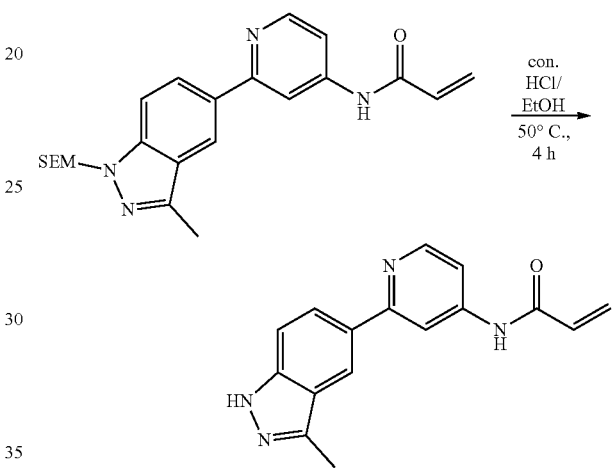

To a solution of N-[2-[3-methyl-1-(2-trimethylsilylethoxymethyl)indazol-5-yl]-4-pyridyl]prop-2-enamide (0.09 g, 220.28 μmol, 1 eq) in EtOH (3 mL) was added concentrated HCl (1.02 g, 10.35 mmol, 1 mL, 37% purity, 46.99 eq). The reaction mixture was stirred at 50° C. for 1 hr. The reaction mixture was concentrated under N$_2$ to give a residue. The residue was purified by prep-HPLC to afford the title compound N-[2-(3-methyl-1H-indazol-5-yl)-4-pyridyl]prop-2-enamide (0.0057 g, 20.48 μmol, 9.30% yield, 100% purity) as a white solid. LC-MS (ES+, m/z) 249.1 [(M+H)$^+$], $^1$H NMR (400 MHz, DMSO-d$_6$) J=12.79 (br s, 1H), 10.66 (br s, 1H), 8.54 (d, J=5.6 Hz, 1H), 8.30 (s, 1H), 8.22 (d, J=1.5 Hz, 1H), 8.13 (s, 1H), 7.99 (dd, J=1.3, 8.8 Hz, 1H), 7.62 (br d, J=3.9 Hz, 1H), 7.57 (d, J=8.7 Hz, 1H), 6.53-6.44 (m, 1H), 6.34 (d, J=1.8 Hz, 1H), 6.38 (d, J=1.8 Hz, 1H), 5.91-5.86 (m, 1H), 2.57-2.54 (m, 3H).

Route 4: General Scheme

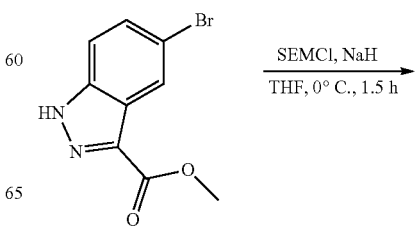

753

-continued

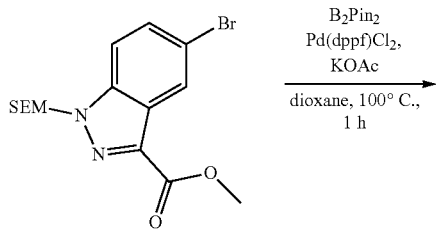

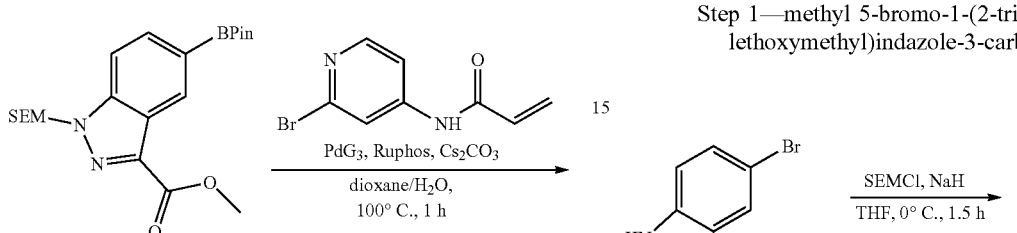

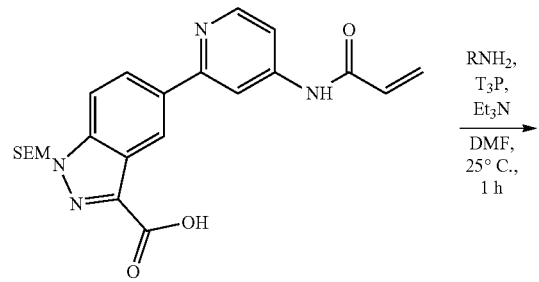

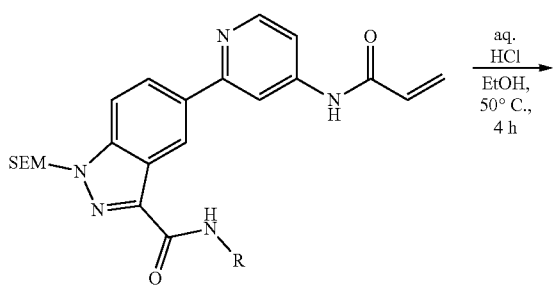

754

-continued

R = 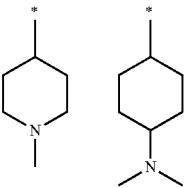

Step 1—methyl 5-bromo-1-(2-trimethylsilylethoxymethyl)indazole-3-carboxylate

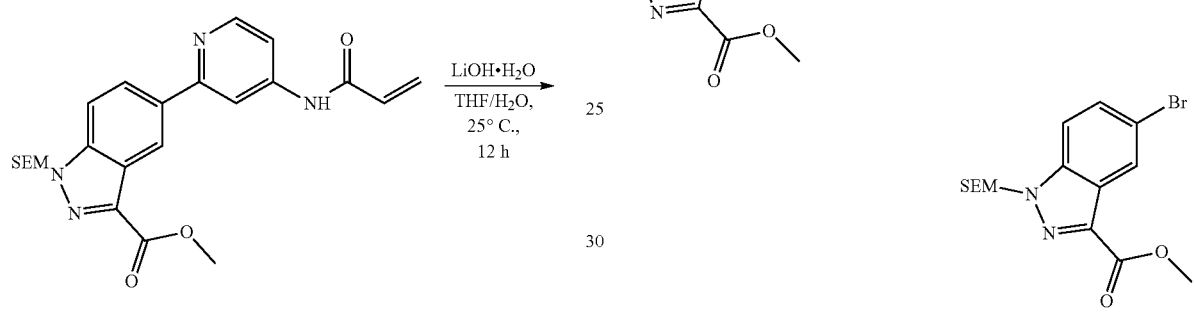

To a solution of methyl 5-bromo-1H-indazole-3-carboxylate (1 g, 3.92 mmol, 1 eq) in THF (10 mL) was added NaH (235.2 mg, 5.88 mmol, 60% purity, 1.5 eq) at 0° C. The reaction mixture was stirred at 0° C. for 0.5 h. Then SEMCl (784.4 mg, 4.7 mmol, 832.65 µL, 1.2 eq) was added and the resulting reaction mixture was stirred at 0° C. for further 1 h. The reaction mixture was poured into saturated NH$_4$Cl (30 mL) and stirred for 15 min. The aqueous phase was extracted with EtOAc (3×30 mL). The combined organic layer was washed with brine (3×30 mL), dried over anhydrous Na$_2$SO$_4$, filtered, and concentrated in vacuo to give a residue. The residue was purified by silica gel chromatography (SiO$_2$, PE:EtOAc=10:1, 3:1) to afford the title compound methyl 5-bromo-1-(2-trimethylsilylethoxymethyl)indazole-3-carboxylate (1. g, 2.6 mmol, 66.20% yield) as a colorless oil. LC-MS (ES+, m/z) 385.1, 387.0 [(M+H)$^+$]

Step 2—methyl 5-(4,4,5,5-tetramethyl-1,3,2-dioxaborolan-2-yl)-1-(2-trimethylsilylethoxymethyl) indazole-3-carboxylate

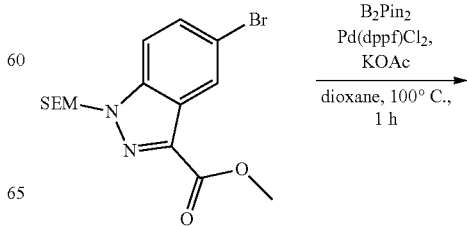

-continued

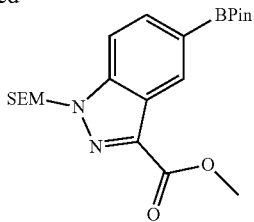

To a solution of methyl 5-bromo-1-(2-trimethylsilylethoxymethyl)indazole-3-carboxylate (900 mg, 2.34 mmol, 1 eq) in dioxane (10 mL) was added Pin$_2$B$_2$ (889.7 mg, 3.5 mmol, 1.5 eq), KOAc (1.15 g, 11.68 mmol, 5 eq) and Pd(dppf)Cl$_2$ (85.5 mg, 116.78 μmol, 0.05 eq) under N$_2$. The reaction mixture was stirred at 100° C. for 1 h. The reaction mixture was poured into saturated EDTA (50 mL) and stirred for 60 min. The mixture was extracted with EtOAc (3×50 mL). The combined organic layer was washed with brine (3×50 mL), dried over anhydrous Na$_2$SO$_4$, filtered, and concentrated in vacuo to afford a residue. The residue was purified by silica gel chromatography (SiO$_2$, PE:EtOAc=10:1, 3:1) to afford the title compound methyl 5-(4,4,5,5-tetramethyl-1,3,2-dioxaborolan-2-yl)-1-(2-trimethylsilyl ethoxy methyl)indazole-3-carboxylate (1 g, 2.31 mmol, 99.02% yield) as a white solid, LC-MS (ES+, m/z) 433.1 [(M+H)$^+$]

Step 3—methyl 5-[4-(prop-2-enoylamino)-2-pyridyl]-1-(2-trimethylsilylethoxymethyl) indazole-3-carboxylate

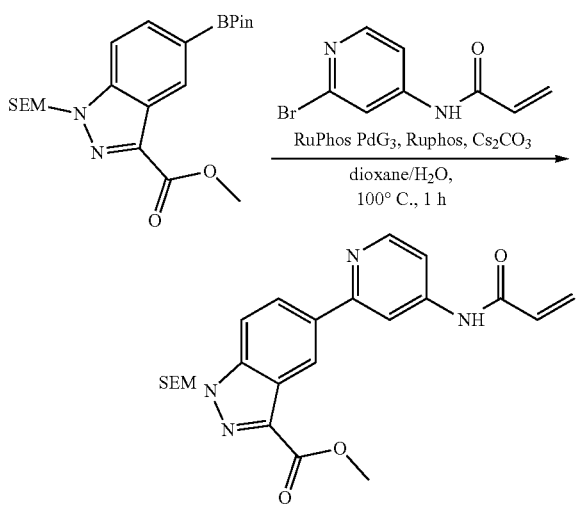

To a solution of N-(2-bromo-4-pyridyl)prop-2-enamide (250 mg, 1.1 mmol, 1 eq), methyl, 5-(4,4,5,5-tetramethyl-1,3,2-dioxaborolan-2-yl)-1-(2-trimethylsilylethoxymethyl) indazole-3-carboxylate (476.1 mg, 1.1 mmol, 1 eq) in dioxane (10 mL), H$_2$O (2.5 mL) was added Cs$_2$CO$_3$ (1.08 g, 3.3 mmol, 3 eq), [2-(2-aminophenyl)phenyl]-methylsulfonyloxy-palladium;dicyclohexyl-[2-(2,6-diisopropoxyphenyl)phenyl]phosphane (46 mg, 55 μmol, 0.05 eq) and dicyclohexyl-[2-(2,6-diisopropoxyphenyl)phenyl]phosphane (51.4 mg, 11 μmol, 0.1 eq). The reaction mixture was stirred at 100° C. for 1 h. The reaction mixture was poured into saturated EDTA (60 mL) and stirred for 60 min. The aqueous phase was extracted with EtOAc (3×20 mL). The combined organic phase was washed with brine (3×20 mL), dried over anhydrous Na$_2$SO$_4$, filtered, and concentrated in vacuo to give a residue. The residue was purified by silica gel chromatography (SiO$_2$, PE:EtOAc=10:1, 1/1) to afford the title compound methyl 5-[4-(prop-2-enoylamino)-2-pyridyl]-1-(2-trimethylsilylethoxy methyl)indazole-3-carboxylate (300 mg, 464.01 μmol, 42.18% yield, 70% purity) as a white solid. LC-MS (ES+, m/z) 453.1 [(M+H)$^+$]

Step 4—5-[4-(prop-2-enoylamino)-2-pyridyl]-1-(2-trimethylsilylethoxymethyl) indazole-3-carboxylic acid

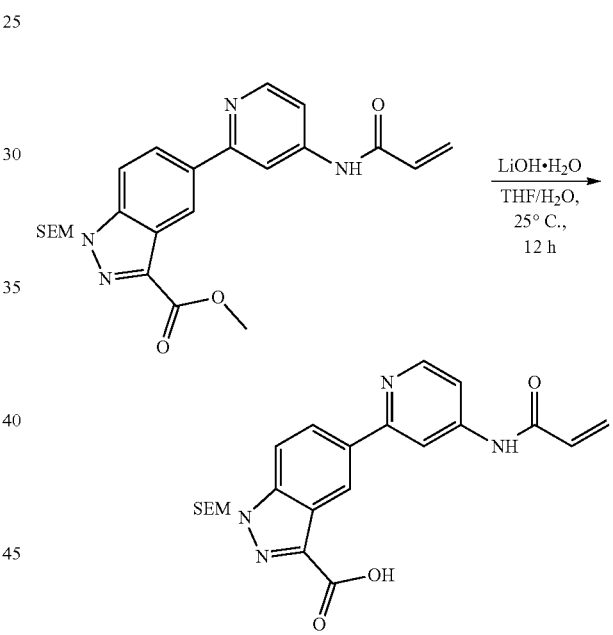

To a solution of methyl 5-[4-(prop-2-enoylamino)-2-pyridyl]-1-(2-trimethylsilylethoxymethyl) indazole-3-carboxylate (260 mg, 574.49 μmol, 1 eq) in THF (10 mL) and H$_2$O (2.5 mL) was added LiOH·H$_2$O (241.1 mg, 5.74 mmol, 10 eq) at 25° C. The reaction mixture was stirred at 25° C. for 12 h. The reaction mixture was poured into ice-water (10 mL) and adjusting the pH to 5 with concentrated HCl. The aqueous phase was extracted with EtOAc (3×15 mL). The combined organic layer was washed with brine (3×15 mL), dried over anhydrous Na$_2$SO$_4$, filtered, and concentrated in vacuo to afford the title compound 5-[4-(prop-2-enoylamino)-2-pyridyl]-1-(2-trimethylsilylethoxy methyl)indazole-3-carboxylic acid (240 mg, crude) as a white solid. LC-MS (ES+, m/z) 439.2 [(M+H)$^+$]

Step 5—N-[4-(dimethylamino)cyclohexyl]-5-[4-(prop-2-enoylamino)-2-pyridyl]-1-(2-trimethylsilylethoxymethyl)indazole-3

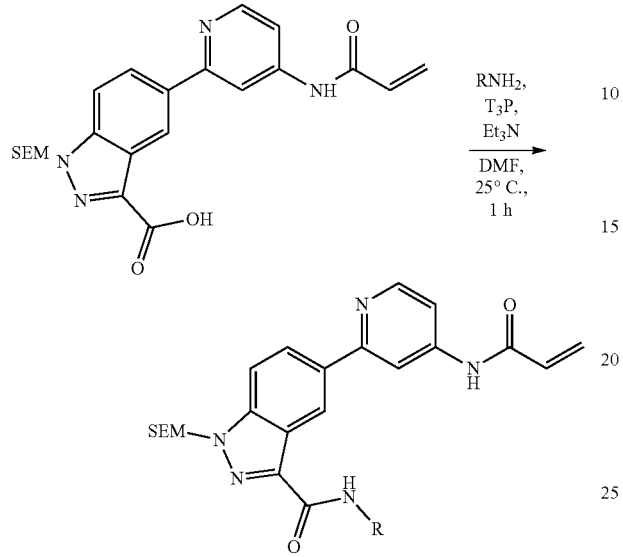

To a solution of 5-[4-(prop-2-enoylamino)-2-pyridyl]-1-(2-trimethylsilylethoxymethyl) indazole-3-carboxylic acid (120 mg, 273.63 µmol, 1 eq), $N_4,N_4$-dimethyl cyclohexane-1,4-diamine (77.8 mg, 547.26 µmol, 2 eq) in DMF (3 mL) was added $Et_3N$ (55.4 mg, 547.26 µmol, 76.17 µL, 2 eq) and $T_3P$ (261.2 mg, 410.44 µmol, 244.10 µL, 50% purity, 1.5 eq) at 25° C. The reaction mixture was stirred at 25° C. for 1 h. The reaction mixture was poured into $H_2O$ (15 mL) and the aqueous phase was extracted with EtOAc (3×15 mL). The combined organic layer was washed with brine (3×15 mL), dried over anhydrous $Na_2SO_4$, filtered, and concentrated in vacuo to afford the title compound N-[4-(dimethylamino)cyclohexyl]-5-[4-(prop-2-enoylamino)-2-pyridyl]-1-(2-trimethylsilylethoxymethyl)indazole-3-carboxamide (120 mg, crude) as a yellow solid. LC-MS (ES+, m/z) 563.3 [(M+H)$^+$]

Step 6—N-[4-(dimethylamino)cyclohexyl]-5-[4-(prop-2-enoylamino)-2-pyridyl]-1H-indazole-3-carboxamide

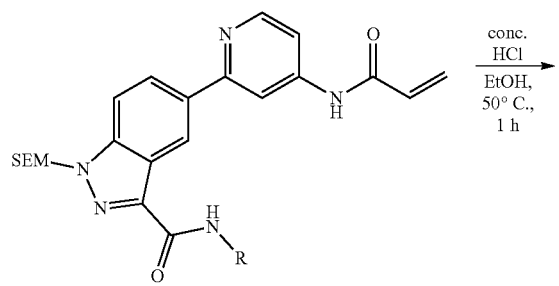

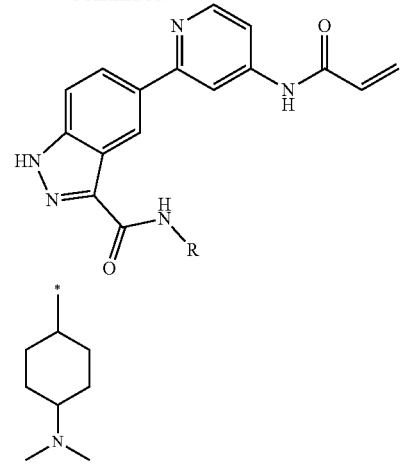

To a solution of N-[4-(dimethylamino)cyclohexyl]-5-[4-(prop-2-enoylamino)-2-pyridyl]-1-(2-trimethylsilylethoxymethyl)indazole-3-carboxamide (40 mg, 71.08 µmol, 1 eq) in EtOH (1 mL) was added concentrated HCl (0.5 mL) and the reaction mixture was stirred at 50° C. for 1 h. The solvent was removed by blowing with $N_2$ to give a residue. The residue was purified by prep-HPLC to afford the title compound N-[4-(dimethylamino)cyclohexyl]-5-[4-(prop-2-enoylamino)-2-pyridyl]-1H-indazole-3-carboxamide (3.5 mg, 7.46 µmol, 10.50% yield, 100% purity, HCl salt) as a white solid. 433.2. 1H NMR (400 MHz, DMSO-d6) δ=14.08 (s, 1H), 11.95 (s, 1H), 10.55 (s, 1H), 10.41 (s, 1H), 8.79-8.73 (m, 1H), 8.68 (d, J=6.8 Hz, 1H), 8.52 (s, 1H), 8.49-8.42 (m, 0.5H), 8.22 (br d, J=6.8 Hz, 0.7H), 8.12 (br s, 1H), 8.04-7.95 (m, 1H), 7.94-7.83 (m, 1H), 6.68 (dd, J=4.8 Hz, 10.0 Hz, 1H), 6.50 (d, J=16.4 Hz 1H), 5.99 (br d, J=10.8 Hz, 1H), 4.22 (m, 1H), 3.96-3.84 (m, 1H), 3.21-3.21 (m, 1H), 2.75-2.70 (m, 6H), 2.16-1.94 (m, 3H), 1.92-1.80 (m, 3H), 1.70 (br d, J=12.2 Hz, 1H), 1.63-1.55 (m, 1H); 1H NMR (400 MHz, DMSO-d6) δ=8.72 (s, 1H), 8.63 (d, J=6.4 Hz, 1H), 8.42 (s, 1H), 7.99 (dd, J=1.6, 6.4 Hz, 1H), 7.97-7.92 (m, 1H), 7.90-7.83 (m, 1H), 6.58 (dd, J=5.6 Hz, 16.8 Hz, 1H), 6.48 (dd, J=1.6, 16.8 Hz, 1H), 6.00 (dd, J=1.6 Hz, 16.8 Hz, 1H), 4.19 (br t, J=3.2 Hz, 1H), 3.93-3.82 (m, 1H), 3.23-3.09 (m, 1H), 2.75-2.70 (m, 6H), 2.09-1.90 (m, 3H), 1.89-1.77 (m, 3H), 1.71-1.70 (m, 1H), 1.60-1.50 (m, 1H)

Route 6: Genera Scheme

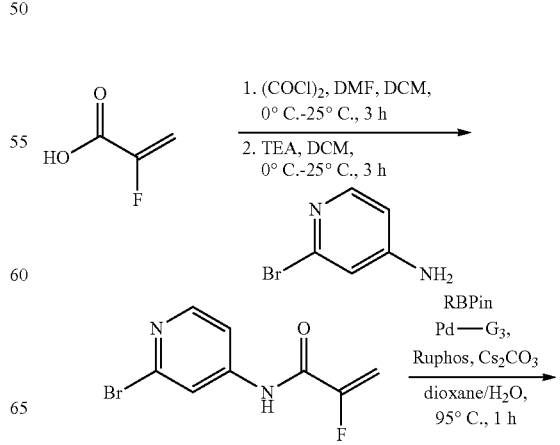

759

-continued

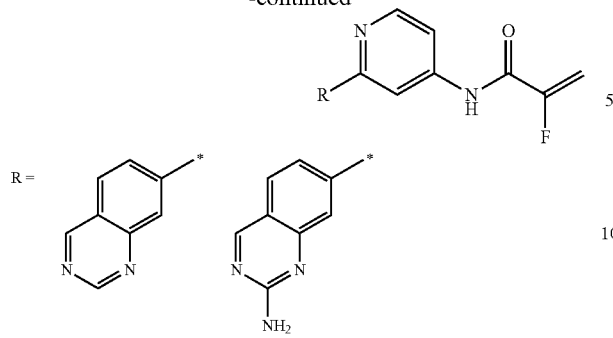

R =

Step 1—N-(2-bromo-4-pyridyl)-2-fluoro-prop-2-enamide

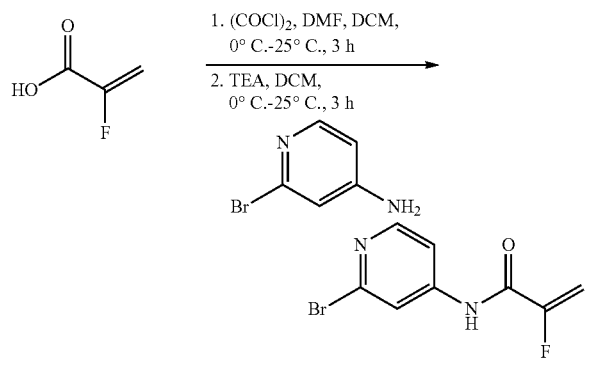

To a solution of 2-fluoroprop-2-enoic acid (500 mg, 5.55 mmol, 1 eq) in DCM (10 mL) was added DMF (40.6 mg, 555 μmol, 42.72 μL, 0.1 eq) and (COCl)$_2$ (704.7 mg, 5.55 mmol, 486.02 μL, 1 eq) at 0° C. The reaction mixture was stirred at 25° C. for 3 h. Then 2-bromopyridin-4-amine (960.2 mg, 5.55 mmol, 1 eq), Et$_3$N (1.68 g, 16.65 mmol, 2.32 mL, 3 eq) was added at 0° C. and the reaction mixture was stirred at 25° C. for further 3 h. LCMS showed ~45% of the starting material remained. The reaction mixture was poured into ice-water (25 mL) and the aqueous phase was extracted with EtOAc (3×20 mL). The combined organic phase was washed with brine (3×25 mL), dried over anhydrous Na$_2$SO$_4$, filtered, and concentrated in vacuo to afford a residue. The residue was purified by silica gel chromatography (SiO$_2$, PE:EtOAc=4:1, 4:1) to afford the title compound N-(2-bromo-4-pyridyl)-2-fluoro-prop-2-enamide (0.22 g, 897.78 μmol, 16.18% yield) as a white solid. LC-MS (ES+, m/z) 245.0, 246.9 [(M+H)$^+$]

Step 2—2-fluoro-N-(2-quinazolin-7-yl-4-pyridyl)prop-2-enamide

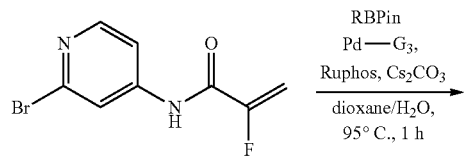

760

-continued

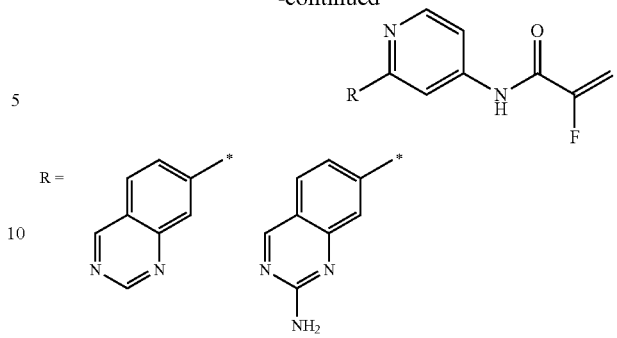

R =

To a solution of N-(2-bromo-4-pyridyl)-2-fluoro-prop-2-enamide (40 mg, 163.23 μmol, 1 eq), 7-(4,4,5,5-tetramethyl-1,3,2-dioxaborolan-2-yl)quinazoline (50.2 mg, 195.88 μmol, 1.2 eq) in dioxane (2 mL) and H$_2$O (0.25) was added Cs$_2$CO$_3$ (159.6 mg, 489.7 μmol, 3 eq), [2-(2-aminophenyl)phenyl]-methylsulfonyloxy-palladium;dicyclohexyl-[2-(2,6-diisopropoxyphenyl)phenyl]phosphane (6.9 mg, 8.16 μmol, 0.05 eq) and dicyclohexyl-[2-(2,6-diisopropoxyphenyl)phenyl]phosphane (7.6 mg, 16.32 μmol, 0.1 eq) under N$_2$. The reaction mixture was stirred at 95° C. for 1 h. The reaction mixture was poured into saturated EDTA (20 mL) and stirred for 60 min. The aqueous phase was extracted with EtOAc (3×20 mL). The combined organic phase was washed with brine (3×20 mL), dried with anhydrous Na$_2$SO$_4$, filtered, and concentrated in vacuo to afford a residue. The residue was purified by prep-HPLC to afford the title compound 2-fluoro-N-(2-quinazolin-7-yl-4-pyridyl)prop-2-enamide (18.6 mg, 63.07 μmol, 38.64% yield, 99.795% purity) as a white solid. 295.1. 1H NMR (400 MHz, DMSO-d6) δ=9.67 (s, 1H), 9.36 (s, 1H), 8.71 (d, J=5.6 Hz, 1H), 8.54 (s, 2H), 8.43 (dd, J=1.6, 8.4 Hz, 1H), 8.31 (d, J=8.4 Hz, 1H), 7.89 (dd, J=2.0, 5.6 Hz, 1H), 5.93-5.74 (m, 1H), 5.57 (dd, J=4.0, 15.6 Hz, 1H)

Step 1—(E)-N-(2-bromo-4-pyridyl)but-2-enamide

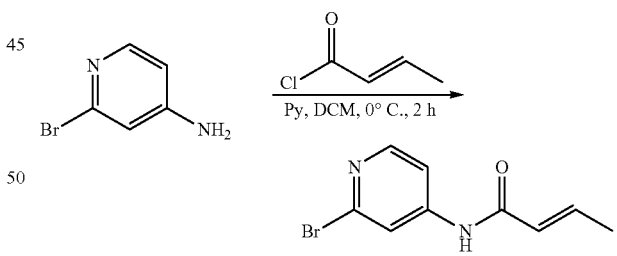

To a solution of 2-bromopyridin-4-amine (1 g, 5.78 mmol, 1 eq) in DCM (10 mL) was added Py (914.4 mg, 11.56 mmol, 933.06 μL, 2 eq), (E)-but-2-enoyl chloride (1.21 g, 11.56 mmol, 1.11 mL, 2 eq) at 0° C. and the reaction mixture was stirred at 0° C. for 2 h. HPLC showed that the reaction was complete. The reaction mixture was poured into H$_2$O (60 mL) and the aqueous phase was extracted with DCM (3×30 mL). The combined organic phase was washed with brine (3×30 mL), dried over anhydrous Na$_2$SO$_4$, filtered, and concentrated in vacuo to give a residue. The residue was purified by silica gel chromatography (SiO$_2$, PE:EtOAc=5/1, 4:1 to afford the title compound (E)-N-(2-bromo-4-pyridyl)but-2-enamide (0.8 g, 3.32 mmol, 57.41% yield) as a white solid. 1H NMR (400 MHz, DMSO-d6) δ=10.51 (br s, 1H), 8.22 (d, J=5.6 Hz, 1H), 7.96 (d, J=2.0 Hz, 1H), 7.51 (dd, J=1.6, 5.6 Hz, 1H), 6.92-6.87 (m, 1H), 6.10 (br dd, J=1.6, 15.2 Hz, 1H), 1.89 (dd, J=1.6, 6.8 Hz, 3H)

Step 2—(E)-N-(2-quinazolin-7-yl-4-pyridyl)but-2-enamide

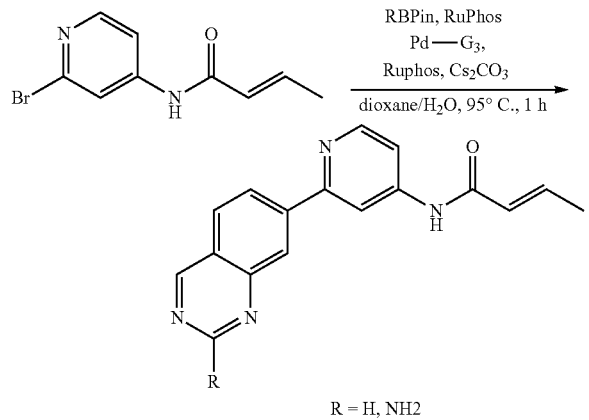

R = H, NH2

To a solution of (E)-N-(2-bromo-4-pyridyl)but-2-enamide (40 mg, 165.92 µmol, 1 eq), 7-(4,4,5,5-tetramethyl-1,3,2-dioxaborolan-2-yl)quinazoline (63.7 mg, 248.88 µmol, 1.5 eq), in dioxane (2 mL) and H₂O (0.5 mL) was added Cs₂CO₃ (162.2 mg, 497.75 µmol, 3 eq), [2-(2-aminophenyl)phenyl]-methylsulfonyloxy-palladium; dicyclohexyl-[2-(2,6-diisopropoxyphenyl)phenyl]phosphane (7 mg, 8.3 µmol, 0.05 eq) and dicyclohexyl-[2-(2,6-diisopropoxy phenyl)phenyl] phosphane (7.7 mg, 16.59 µmol, 0.1 eq) under N₂. The mixture was stirred at 95° C. for 1 h. The reaction mixture was poured into saturated EDTA (30 mL) and stirred for 60 min. The aqueous phase was extracted with EtOAc (3×15 mL). The combined organic layer was washed with brine (3×15 mL), dried over anhydrous Na₂SO₄, filtered, and concentrated in vacuo to give a residue. The residue was purified by prep-HPLC to afford the title compound (E)-N-(2-quinazolin-7-yl-4-pyridyl) but-2-enamide (10.9 mg, 37.5 µmol, 22.60% yield, 99.876% purity) as a white solid. 291.1. 1H NMR (400 MHz, DMSO-d6) δ=10.51 (s, 1H), 9.67 (s, 1H), 9.36 (s, 1H), 8.64 (d, J=5.6 Hz, 1H), 8.51 (s, 1H), 8.44-8.38 (m, 2H), 8.29 (d, J=8.4 Hz, 1H), 7.69 (dd, J=2.0, 5.6 Hz, 1H), 6.96-6.90 (m, 1H).

Step 1—N-(2-bromo-4-pyridyl)-2-methyl-prop-2-enamide

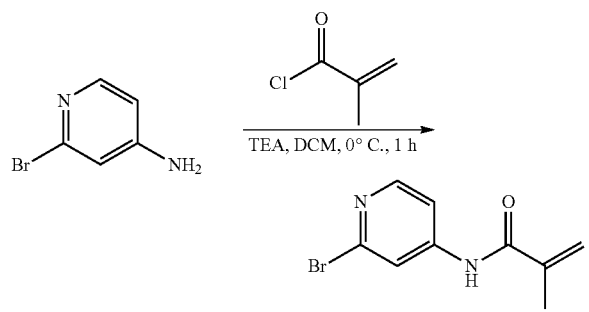

To a solution of 2-bromopyridin-4-amine (2 g, 11.56 mmol, 1 eq) in DCM (20 mL) was added TEA (3.51 g, 34.68 mmol, 4.83 mL, 3 eq), 2-methylprop-2-enoyl chloride (2.42 g, 23.12 mmol, 2.26 mL, 2 eq) at 0° C. and the reaction mixture was stirred at 0° C. for 1 h. The reaction mixture was poured into ice-water (60 mL) and the aqueous phase was extracted with DCM (3×20 mL). The combined organic layer was washed with brine (3×25 mL), dried over anhydrous Na₂SO₄, filtered, and concentrated in vacuo to give a residue. The residue was purified by silica gel chromatography (SiO₂, PE/EtOAc=4:1, 4:1) to afford the title compound N-(2-bromo-4-pyridyl)-2-methyl-prop-2-enamide (2. g, 8.3 mmol, 71.76% yield) as a white solid. LC-MS (ES+, m/z) 240.9, 242.9 [(M+H)⁺] 1H NMR (400 MHz, DMSO-d6) δ=10.31 (s, 1H), 8.24 (d, J=6.0 Hz, 1H), 7.99 (d, J=1.6 Hz, 1H), 7.69 (dd, J=2.0, 5.6 Hz, 1H), 5.88 (s, 1H), 5.66 (d, J=1.2 Hz, 1H), 1.94 (s, 3H)

Step 2—2-methyl-N-(2-quinazolin-7-yl-4-pyridyl)prop-2-enamide

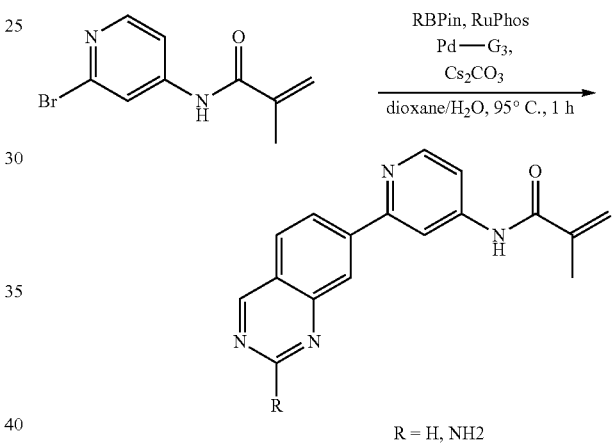

R = H, NH2

To a solution of N-(2-bromo-4-pyridyl)-2-methyl-prop-2-enamide (50 mg, 207.4 µmol, 1 eq), 7-(4,4,5,5-tetramethyl-1,3,2-dioxaborolan-2-yl)quinazoline (53.1 mg, 207.4 µmol, 1 eq) in dioxane (2 mL), H₂O (0.25) was added Cs₂CO₃ (202.7 mg, 622.19 µmol, 3 eq), [2-(2-aminophenyl)phenyl]-methylsulfonyloxy-palladium; dicyclohexyl-[2-(2,6-diisopropoxyphenyl)phenyl]phosphane (8.7 mg, 10.37 µmol, 0.05 eq) and dicyclohexyl-[2-(2,6-diisopropoxy phenyl)phenyl]phosphane (9.7 mg, 20.74 µmol, 0.1 eq). The reaction mixture was stirred at 95° C. for 1 h. The reaction mixture was poured into saturated EDTA (20 mL) and stirred for 60 min. The aqueous phase was extracted with EtOAc (3×15 mL). The combined organic layer was washed with brine (3×20 mL), dried over anhydrous Na₂SO₄, filtered, and concentrated in vacuo to give a residue. The residue was purified by prep-HPLC to afford the title compound 2-methyl-N-(2-quinazolin-7-yl-4-pyridyl)prop-2-enamide (12.6 mg, 43.4 µmol, 20.93% yield, 100.0% purity) as a white solid. 291.1. 1H NMR (400 MHz, DMSO-d6) δ=10.40 (br, s, 1H), 9.67 (s, 1H), 9.36 (s, 1H), 8.66 (d, J=5.6 Hz, 1H), 8.53 (s, 1H), 8.50 (d, J=1.6 Hz, 1H), 8.42 (dd, J=1.6, 8.8 Hz, 1H), 8.30 (d, J=8.8 Hz, 1H), 7.85 (dd, J=2.0, 5.6 Hz, 1H), 5.95 (s, 1H), 5.68 (d, J=1.2 Hz, 1H), 2.00 (s, 3H)

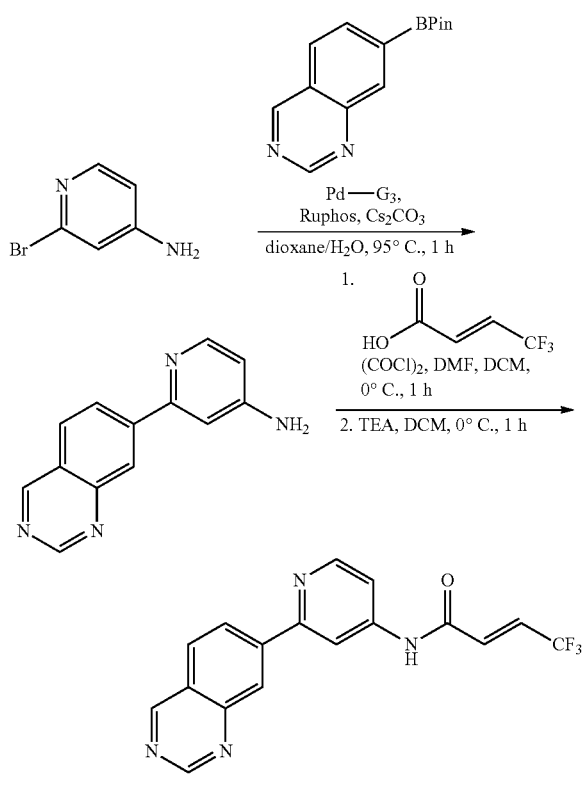

Route 9

Step 1—2-quinazolin-7-ylpyridin-4-amine

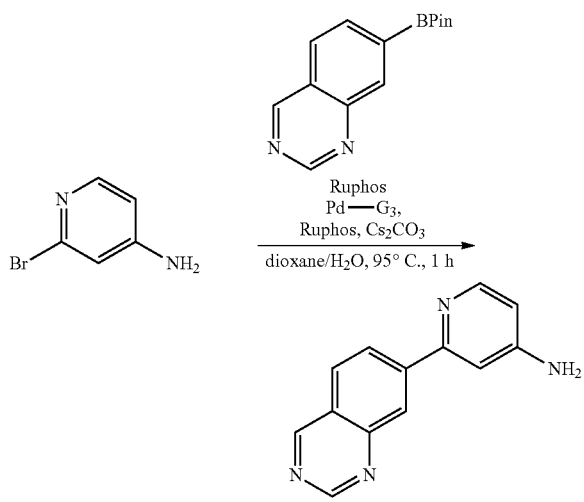

To a solution of 2-bromopyridin-4-amine (100 mg, 578 µmol, 1 eq), 7-(4,4,5,5-tetramethyl-1,3,2-dioxaborolan-2-yl)quinazoline (162.8 mg, 635.8 µmol, 1.1 eq) in dioxane (4 mL), H₂O (1 mL) was added Cs₂CO₃ (565 mg, 1.73 mmol, 3.0 eq), [2-(2-aminophenyl)phenyl]-methylsulfonyloxy-palladium; dicyclohexyl-[2-(2,6-diisopropoxyphenyl)phenyl]phosphane (24.2 mg, 28.9 µmol, 0.05 eq) and dicyclohexyl-[2-(2,6-diisopropoxyphenyl)phenyl]phosphane (27 mg, 57.8 µmol, 0.1 eq) under N₂. The reaction mixture was stirred at 95° C. for 1 h. LCMS showed ~10% of the starting material remained. The reaction mixture was poured into saturated EDTA (20 mL) and stirred for 1 h. The aqueous phase was extracted with EtOAc (3×20 mL). The combined organic layer was washed with brine (3×20 mL), dried over anhydrous Na₂SO₄, filtered, and concentrated in vacuo to give a residue. The residue was washed with DCM (3×5 mL) to afford the title compound 2-quinazolin-7-ylpyridin-4-amine (80 mg, crude) as a light yellow solid. LC-MS (ES+, m/z) 223.2 [(M+H)⁺]

Step 2—(E)-4,4,4-trifluoro-N-(2-quinazolin-7-yl-4-pyridyl)but-2-enamide

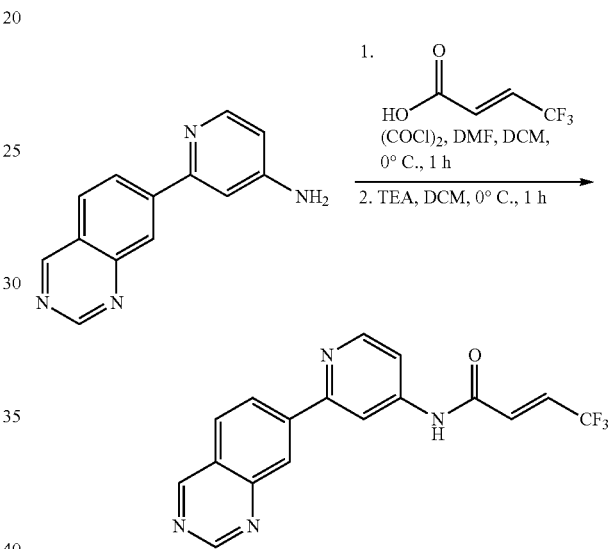

To a solution of (E)-4,4,4-trifluorobut-2-enoic acid (50 mg, 356.99 µmol, 1 eq) in DCM (1 mL) was added DMF (2.6 mg, 35.7 µmol, 2.75 µL, 0.1 eq) and (COCl)₂ (49.8 mg, 392.69 µmol, 34.37 µL, 1.1 eq) at 0° C. and the reaction mixture was stirred at 0° C. for 1 h. Then 2-quinazolin-7-ylpyridin-4-amine (20 mg, 89.99 µmol, 2.52e−1 eq), TEA (108.4 mg, 1.07 mmol, 149.07 µL, 3 eq) was added at 0° C. and the reaction mixture was stirred at 0° C. for further 1 h. LCMS and HPLC showed that the reaction was complete. The reaction mixture was poured into ice-water (25 mL) and the aqueous phase was extracted with DCM (3×20 mL). The combined organic layer was washed with brine (3×25 mL), dried over anhydrous Na₂SO₄, filtered, and concentrated in vacuo to give a residue. The residue was purified by prep-HPLC to afford the title compound (E)-4,4,4-trifluoro-N-(2-quinazolin-7-yl-4-pyridyl)but-2-enamide (2.7 mg, 7.6 µmol, 2.13% yield, 96.967% purity) as a pink solid. 345.1. ¹H NMR (400 MHz, DMSO-d₆) δ=9.68 (s, 1H), 9.37 (s, 1H), 8.72 (br d, J=5.2 Hz, 1H), 8.53 (s, 1H), 8.48-8.37 (m, 2H), 8.31 (br d, J=8.0 Hz, 1H), 7.71 (br d, J=4.8 Hz, 1H), 7.12-6.97 (m, 2H)

Step 3—tert-butyl N-[7-(4-amino-2-pyridyl) quinazolin-2-yl]carbamate

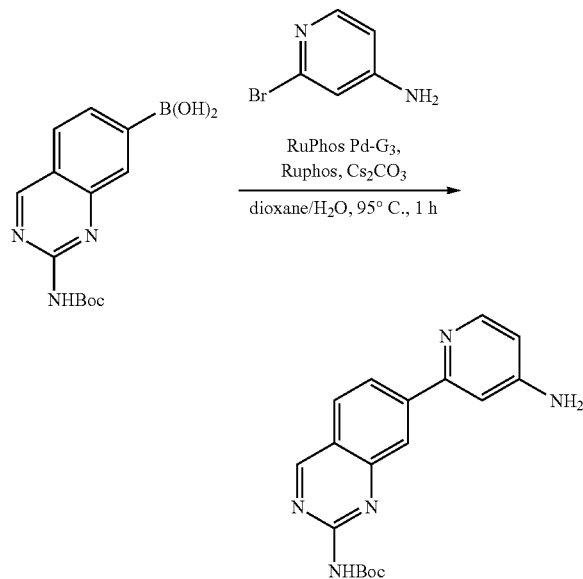

To a mixture of 2-bromopyridin-4-amine (650 mg, 3.76 mmol, 1 eq), [2-(tert-butoxy carbonylamino)quinazolin-7-yl]boronic acid (2.72 g, 9.39 mmol, 2.5 eq) in dioxane (10 mL), H₂O (2.5 mL) was added Cs₂CO₃ (3.67 g, 11.27 mmol, 3 eq), [2-(2-aminophenyl)phenyl]-methylsulfonyloxy-palladium;dicyclohexyl-[2-(2,6-diisopropoxyphenyl)phenyl]phosphane (157.1 mg, 187.85 μmol, 0.05 eq), dicyclohexyl-[2-(2,6-diisopropoxyphenyl)phenyl]phosphane (175.3 mg, 375.7 μmol, 0.1 eq) under N₂. The mixture was stirred at 95° C. for 1 h. TLC showed no starting material remained. The residue was poured into saturated EDTA (100 mL) and stirred for 60 min. The aqueous phase was extracted with EtOAc (3×60 mL). The combined organic phase was washed with brine (3×80 mL), dried with anhydrous Na₂SO₄, filtered, and concentrated in vacuo. The residue was purified by silica gel chromatography (SiO₂, DCM/MeOH=50:1, 20:1) to afford the title compound tert-butyl N-[7-(4-amino-2-pyridyl) quinazolin-2-yl]carbamate (0.7 g, 2.07 mmol, 55.23% yield) as black brown solid. LC-MS (ES⁺, m/z): 338.2 [(M+H)⁺]

Step 4—tert-butyl N-[7-[4-[[(E)-4,4,4-trifluorobut-2-enoyl]amino]-2-pyridyl]quinazolin-2-yl]carbamate

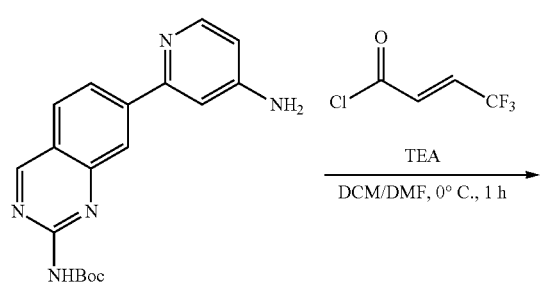

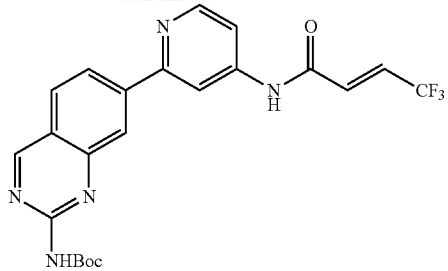

To a mixture of (E)-4,4,4-trifluorobut-2-enoyl chloride (469.8 mg, 2.96 mmol, 5 eq) in DCM (5 mL), DMF (1 mL) was added tert-butyl N-[7-(4-amino-2-pyridyl) quinazolin-2-yl]carbamate (200 mg, 592.81 μmol, 1 eq), Et₃N (180 mg, 1.78 mmol, 247.54 μL, 3 eq) at 0° C. and the mixture was stirred at 0° C. for 1 h. TLC showed no starting material remained. The residue was poured into ice-water (20 mL) and the aqueous phase was extracted with DCM (3×15 mL). The combined organic phase was washed with brine (3×15 mL), dried with anhydrous Na₂SO₄, filtered, and concentrated in vacuo. The residue was purified by prep-TLC to afford the title compound tert-butyl N-[7-[4-[[(E)-4,4,4-trifluorobut-2-enoyl]amino]-2-pyridyl]quinazolin-2-yl]carbamate (90 mg, 195.9 μmol, 33.05% yield) as a yellow solid. LC-MS (ES⁺, m/z): 460.2 [(M+H)⁺]

Step 5—(E)-N-[2-(2-aminoquinazolin-7-yl)-4-pyridyl]-4,4,4-trifluoro-but-2-enamide

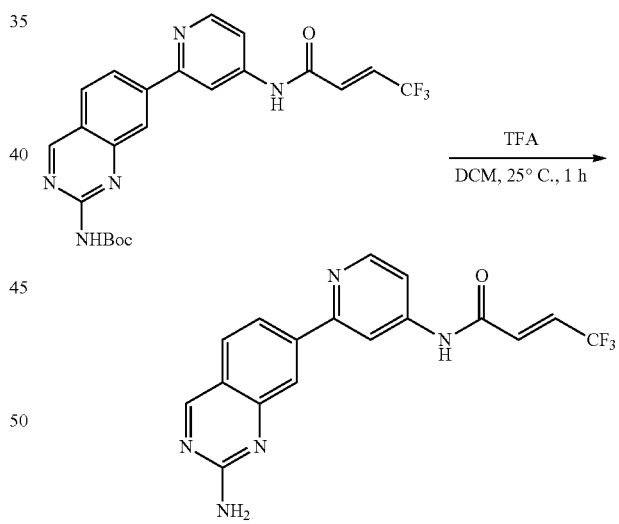

To a mixture of tert-butyl N-[7-[4-[[(E)-4,4,4-trifluorobut-2-enoyl]amino]-2-pyridyl]quinazolin-2-yl]carbamate (80 mg, 174.13 μmol, 1 eq) in DCM (4 mL) was added TFA (1 mL) at 25° C. and the mixture was stirred at 25° C. for 1 h. HPLC showed no starting material remained. The reaction mixture was poured into saturated Na₂CO₃ (20 mL) and the aqueous phase was extracted with DCM (3×15 mL). The combined organic phase was washed with brine (3×15 mL), dried with anhydrous Na₂SO₄, filtered, and concentrated in vacuo. The residue was purified by prep-HPLC to afford the title compound (E)-N-[2-(2-aminoquinazolin-7-yl)-4-pyridyl]-4,4,4-trifluoro-but-2-enamide (10 mg, 27.53

µmol, 15.81% yield, 98.923% purity) as a white solid. LC-MS (ES+, m/z): 360.1 [(M+H)+] 1H NMR (400 MHz, DMSO-d6) δ=11.03 (s, 1H), 9.16 (s, 1H), 8.66 (d, J=5.6 Hz, 1H), 8.28 (d, J=1.6 Hz, 1H), 7.96 (s, 1H), 7.93 (d, J=8.4 Hz, 1H), 7.83 (dd, J=1.6, 8.4 Hz, 1H), 7.64 (dd, J=2.0, 5.6 Hz, 1H), 7.08-6.96 (m, 2H), 6.91 (s, 2H)

Route 7: General Scheme

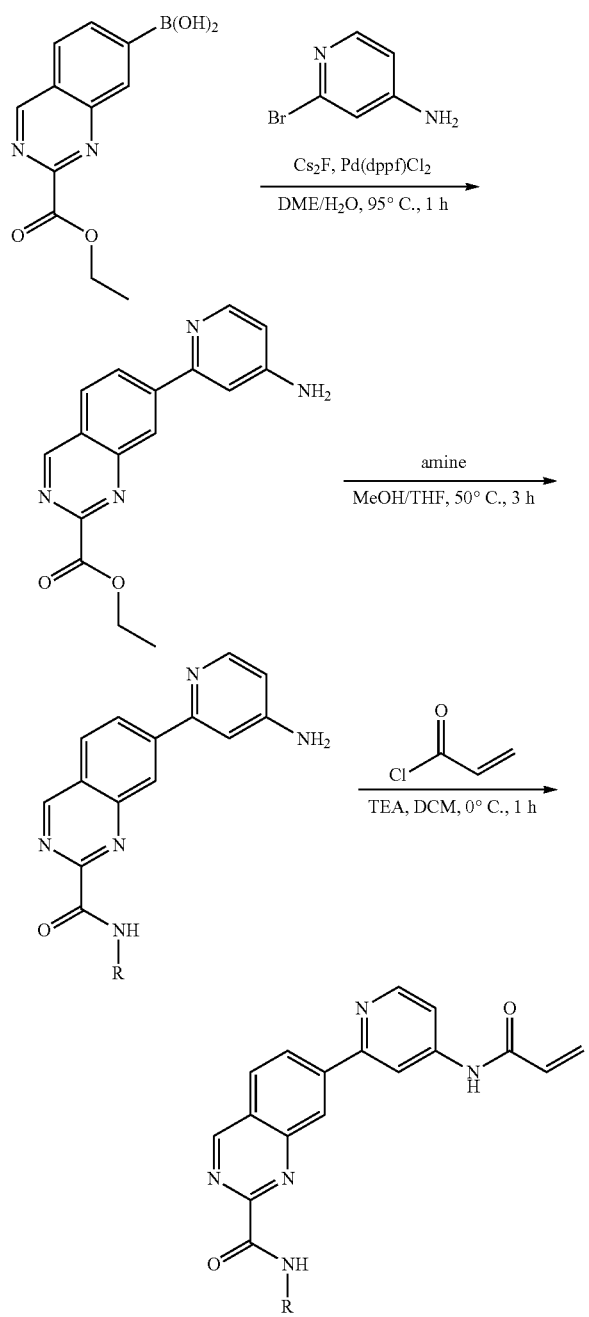

Step 1—ethyl 7-(4-amino-2-pyridyl)quinazoline-2-carboxylate

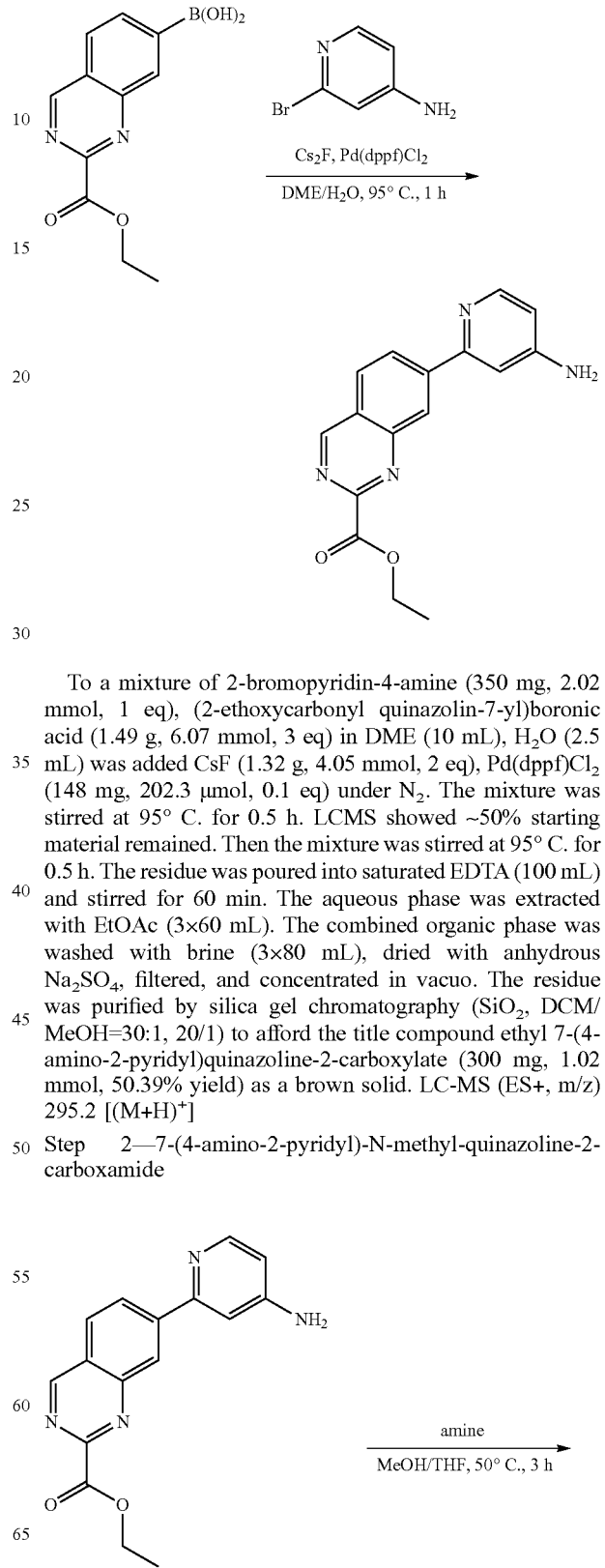

To a mixture of 2-bromopyridin-4-amine (350 mg, 2.02 mmol, 1 eq), (2-ethoxycarbonyl quinazolin-7-yl)boronic acid (1.49 g, 6.07 mmol, 3 eq) in DME (10 mL), H₂O (2.5 mL) was added CsF (1.32 g, 4.05 mmol, 2 eq), Pd(dppf)Cl₂ (148 mg, 202.3 µmol, 0.1 eq) under N₂. The mixture was stirred at 95° C. for 0.5 h. LCMS showed ~50% starting material remained. Then the mixture was stirred at 95° C. for 0.5 h. The residue was poured into saturated EDTA (100 mL) and stirred for 60 min. The aqueous phase was extracted with EtOAc (3×60 mL). The combined organic phase was washed with brine (3×80 mL), dried with anhydrous Na₂SO₄, filtered, and concentrated in vacuo. The residue was purified by silica gel chromatography (SiO₂, DCM/MeOH=30:1, 20/1) to afford the title compound ethyl 7-(4-amino-2-pyridyl)quinazoline-2-carboxylate (300 mg, 1.02 mmol, 50.39% yield) as a brown solid. LC-MS (ES+, m/z) 295.2 [(M+H)+]

Step 2—7-(4-amino-2-pyridyl)-N-methyl-quinazoline-2-carboxamide

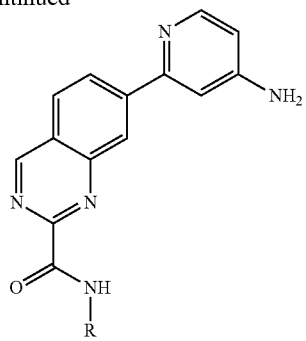

To a mixture of ethyl 7-(4-amino-2-pyridyl)quinazoline-2-carboxylate (100 mg, 339.78 μmol, 1 eq) in MeOH (3 mL) was added MeNH$_2$ (2 M in THF, 33.98 mL, 200 eq) in THF (3 mL). The mixture was stirred at 50° C. for 3 h. LCMS showed no starting material remained. The reaction mixture was concentrated in vacuo to afford the title compound 7-(4-amino-2-pyridyl)-N-methyl-quinazoline-2-carboxamide (100 mg, crude) as black brown solid. LC-MS (ES+, m/z) 280.2 [(M+H)$^+$].

Step 3—methyl-7-[4-(prop-2-enoylamino)-2-pyridyl]quinazoline-2-carboxamide

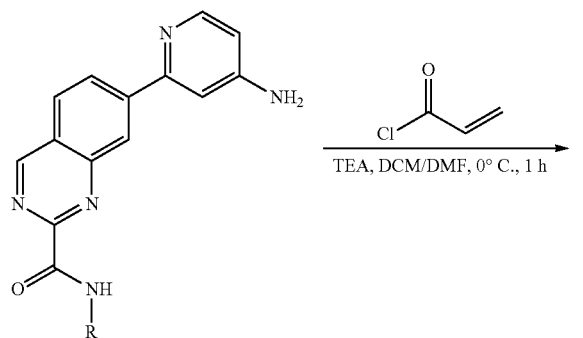

R = H, Me

R = 

To a mixture of prop-2-enoyl chloride (51.9 mg, 572.87 μmol, 46.71 μL, 2 eq) in DCM (3 mL), DMF (0.6 mL) was added 7-(4-amino-2-pyridyl)-N-methyl-quinazoline-2-carboxamide (80 mg, 286.43 μmol, 1 eq), Et$_3$N (87 mg, 859.3 μmol, 119.61 μL, 3 eq) at 0° C. and the mixture was stirred at 0° C. for 1 h. LCMS and showed no starting material remained. The residue was poured into ice-water (20 mL) and the aqueous phase was extracted with DCM (3×20 mL). The combined organic phase was washed with brine (3×15 mL), dried with anhydrous Na$_2$SO$_4$, filtered, and concentrated in vacuo. The residue was purified by prep-HPLC to afford the title compound N-methyl-7-[4-(prop-2-enoylamino)-2-pyridyl]quinazoline-2-carboxamide (8.6 mg, 24.44 μmol, 8.53% yield, 94.722% purity) as a white solid. 334.0. 1H NMR (400 MHz, DMSO-d6) δ=10.75 (s, 1H), 9.79 (s, 1H), 9.09 (br d, J=4.8 Hz, 1H), 8.68 (d, J=5.6 Hz, 1H), 8.64 (s, 1H), 8.56 (d, J=1.6 Hz, 1H), 8.51 (dd, J=1.6, 8.8 Hz, 1H), 8.38 (d, J=8.8 Hz, 1H), 7.64 (dd, J=2.0, 5.2 Hz, 1H), 6.50 (dd, J=10.4, 17.2 Hz, 1H), 6.38 (dd, J=1.6, 16.8 Hz, 1H), 5.91 (dd, J=1.6, 10.0 Hz, 1H), 2.90 (d, J=4.8 Hz, 3H)

N-[2-[4-(methylamino)-6-quinolyl]-4-pyridyl]prop-2-enamide

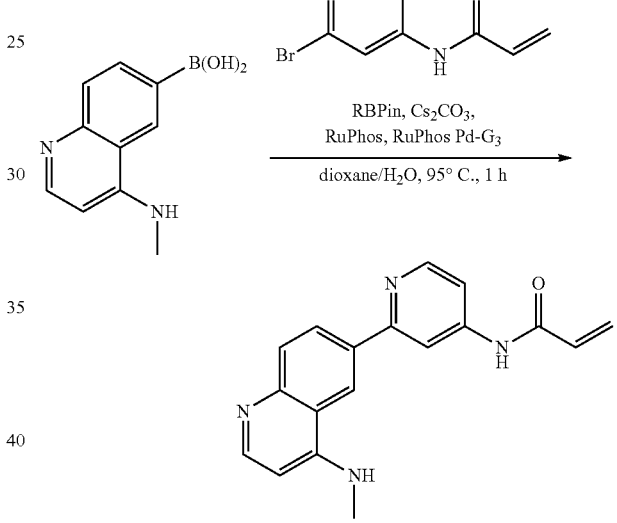

To a mixture of N-(2-bromo-4-pyridyl)prop-2-enamide (80 mg, 352.33 μmol, 1 eq), [4-(methylamino)-6-quinolyl]boronic acid (474.5 mg, 704.67 μmol, 30% purity, 2 eq) in dioxane (3 mL), H$_2$O (0.75 mL) was added Cs$_2$CO$_3$ (344.4 mg, 1.06 mmol, 3 eq), [2-(2-aminophenyl)phenyl]-methyl-sulfonyloxy-palladium;dicyclohexyl-[2-(2,6-diisopropoxyphenyl)phenyl]phosphane (14.7 mg, 17.62 μmol, 0.05 eq), dicyclohexyl-[2-(2,6-diisopropoxyphenyl)phenyl]phosphane (16.4 mg, 35.23 μmol, 0.1 eq) under N$_2$. The mixture was stirred at 95° C. for 1 h. The residue was poured into saturated EDTA (20 mL) and stirred for 60 min. The aqueous phase was extracted with EtOAc (3×15 mL). The combined organic phase was washed with brine (3×20 mL), dried with anhydrous Na$_2$SO$_4$, filtered, and concentrated in vacuo. The residue was purified by prep-HPLC to afford the title compound N-[2-[4-(methylamino)-6-quinolyl]-4-pyridyl]prop-2-enamide (20.8 mg, 53.9 μmol, 15.30% yield, 90.791% purity, FA) as a white solid. 305.0. 1H NMR (400 MHz, DMSO-d6) δ=10.67 (s, 1H), 8.79 (d, J=1.6 Hz, 1H), 8.60 (d, J=5.6 Hz, 1H), 8.44 (d, J=5.6 Hz, 1H), 8.28 (d, J=1.6 Hz, 1H), 8.19 (dd, J=2.0, 9.2 Hz, 1H), 7.88 (d, J=8.8 Hz, 1H), 7.73 (br d, J=4.4 Hz, 1H), 7.63 (dd, J=1.6, 5.6 Hz, 1H), 6.50

(dd, J=10.0, 16.8 Hz, 1H), 6.45 (d, J=5.6 Hz, 1H), 6.41 (dd, J=2.0, 17.2 Hz, 1H, 1H), 5.91 (dd, J=1.6, 9.6 Hz, 1H), 2.93 (d, J=4.4 Hz, 3H)

N-[2-[2-(methylamino)-7-quinolyl]-4-pyridyl]prop-2-enamide

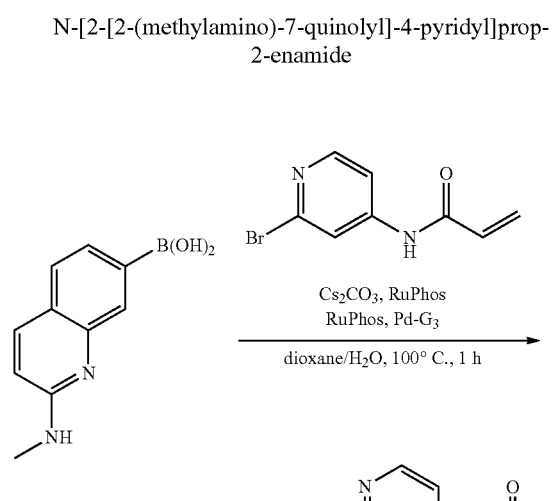

A mixture of N-(2-bromo-4-pyridyl)prop-2-enamide (100 mg, 440.42 μmol, 1 eq), N-methyl-7-(4,4,5,5-tetramethyl-1,3,2-dioxaborolan-2-yl)quinolin-2-amine (187.7 mg, 660.63 μmol, 1.5 eq), $Cs_2CO_3$ (287 mg, 880.83 μmol, 2 eq), RuPhos (20.6 mg, 44.04 μmol, 0.1 eq) and [2-(2-aminophenyl)phenyl]-methylsulfonyloxy-palladium;dicyclohexyl-[2-(2,6-diisopropoxyphenyl)phenyl]phosphane (18.4 mg, 22.02 μmol, 0.05 eq) in dioxane (21 mL) and $H_2O$ (0.5 mL). The mixture was stirred at 100° C. for 1 hr under $N_2$. LCMS (ET21787-677-P1A) showed that the reaction was complete. The reaction mixture was added to saturated EDTA and the mixture was stirred at 25° C. for 1 h. Then the mixture was extracted with EtOAc (3×30 mL). The organic phase was separated, washed with $H_2O$ (2×30 mL) and brine (2×30 mL), dried over anhydrous $Na_2SO_4$, filtered, and concentrated in vacuo to give a residue. The residue was purified by prep-HPLC to afford the title compound N-[2-[2-(methylamino)-7-quinolyl]-4-pyridyl]prop-2-enamide (17.5 mg, 57.5 μmol, 13.06% yield, 100% purity) as a light yellow solid. 305.1. $^1$H NMR (400 MHz, DMSO-$d_6$) δ=10.59 (s, 1H), 8.57 (d, J=5.4 Hz, 1H), 8.36 (d, J=1.5 Hz, 1H), 8.10 (d, J=0.9 Hz, 1H), 7.87 (d, J=8.9 Hz, 1H), 7.82 (d, J=8.3 Hz, 1H), 7.72 (d, J=8.4 Hz, 1H), 7.59 (d, J=5.5 Hz, 1H), 6.78 (d, J=8.9 Hz, 1H), 6.55-6.41 (m, 1H), 6.40-6.30 (m, 1H), 5.90-5.89 (m, 1H), 5.87 (m, 1H), 2.93 (d, J=4.60 Hz, 3H).

Route 10

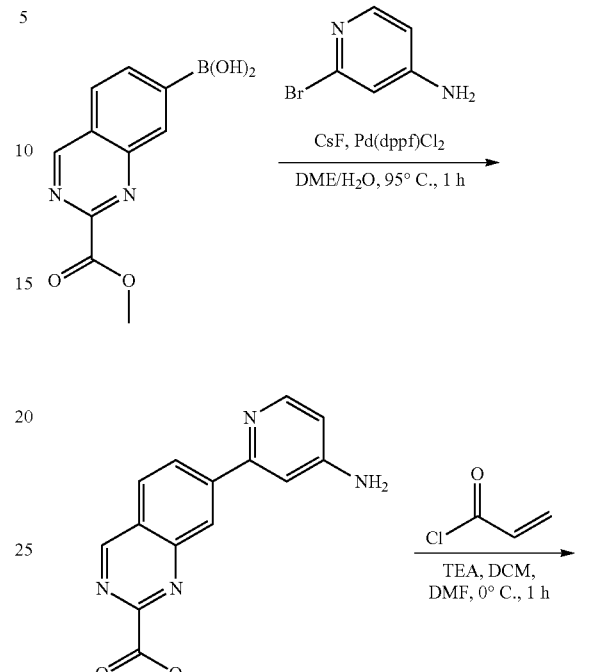

Step 4—methyl 7-(4-amino-2-pyridyl)quinazoline-2-carboxylate

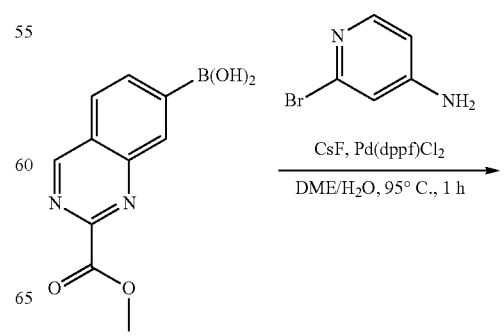

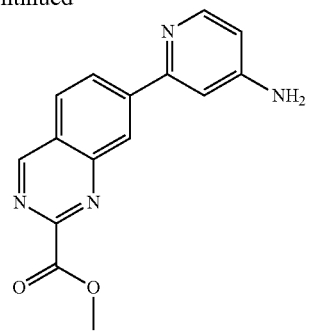

To a mixture of 2-bromopyridin-4-amine (350 mg, 2.02 mmol, 1 eq), (2-methoxycarbonyl quinazolin-7-yl)boronic acid (1.41 g, 6.07 mmol, 3 eq) in DME (10 mL), H₂O (2.5 mL) was added CsF (1.32 g, 4.05 mmol, 2 eq), Pd(dppf)Cl₂ (148 mg, 202.3 µmol, 0.1 eq). The mixture was stirred at 95° C. for 1 h. The reaction mixture was poured into saturated EDTA (20 mL) and stirred for 60 min. The aqueous phase was extracted with EtOAc (3×15 mL). The combined organic phase was washed with brine (3×20 mL), dried with anhydrous Na₂SO₄, filtered, and concentrated in vacuo. The residue was purified by silica gel chromatography (SiO₂, DCM/MeOH=50/1, 10:1) to afford the title compound methyl 7-(4-amino-2-pyridyl)quinazoline-2-carboxylate (300 mg, 1.07 mmol, 52.91% yield) as a white solid. LC-MS (ES+, m/z) 281.1 [(M+H)⁺].

Step 5—methyl 7-[4-(prop-2-enoylamino)-2-pyridyl]quinazoline-2-carboxylate

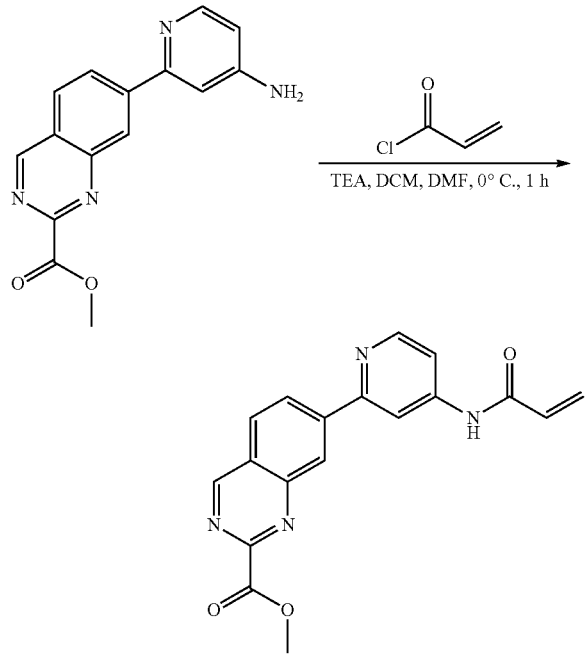

To a mixture of methyl 7-(4-amino-2-pyridyl)quinazoline-2-carboxylate (0.1 g, 356.78 µmol, 1 eq) in DCM (6 mL), DMF (3 mL) was added TEA (108.3 mg, 1.07 mmol, 148.98 µL, 3 eq), prop-2-enoyl chloride (96.9 mg, 1.07 mmol, 87.28 µL, 3 eq) at 0° C. The mixture was stirred at 0° C. for 1 h. The residue was poured into H₂O (20 mL) and the aqueous phase was extracted with DCM (3×20 mL). The combined organic phase was washed with brine (3×20 mL), dried with anhydrous Na₂SO₄, filtered, and concentrated in vacuo. methyl 7-[4-(prop-2-enoylamino)-2-pyridyl]quinazoline-2-carboxylate (60 mg, crude) was obtained, 40 mg of the residue was purified by prep-HPLC to afford the title compound methyl 7-[4-(prop-2-enoylamino)-2-pyridyl]quinazoline-2-carboxylate (5.2 mg, 15.13 µmol, 12.65% yield, 97.304% purity) as a white solid. 335.1. 1H NMR (400 MHz, DMSO-d6) δ=10.72 (s, 1H), 9.82 (s, 1H), 8.68 (d, J=5.6 Hz, 1H), 8.64 (s, 1H), 8.53 (dd, J=1.6, 8.6 Hz, 1H), 8.49 (s, 1H), 8.41 (d, J=8.6 Hz, 1H), 7.70 (dd, J=1.6, 5.6 Hz, 1H), 6.50 (dd, J=10.0, 17.2 Hz, 1H), 6.40 (dd, J=2.0, 16.8 Hz, 1H), 5.93-5.87 (dd, J=2.0, 10.0 Hz, 1H), 3.99 (s, 3H).

Step 6—7-[4-(prop-2-enoylamino)-2-pyridyl]quinazoline-2-carboxylic acid

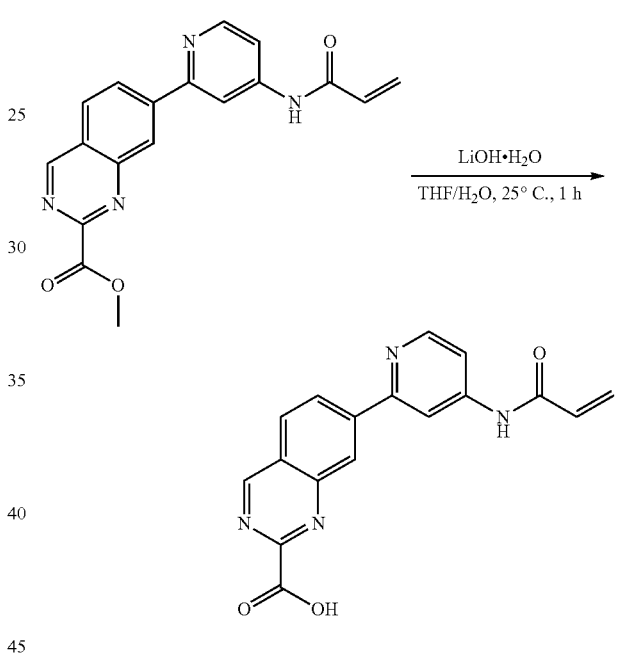

To a mixture of methyl 7-[4-(prop-2-enoylamino)-2-pyridyl]quinazoline-2-carboxy late (100 mg, 299.11 µmol, 1 eq) in THF (10 mL), H₂O (2.5 mL) was added LiOH·H₂O (25.1 mg, 598.21 µmol, 2 eq). The mixture was stirred at 25° C. for 1 h. The reaction mixture was poured into H₂O (20 mL) and the aqueous phase was adjusted to pH=2 with saturated citric acid (2 mL), but the product can not be extracted. Then the solution was adjusted to pH=7 with saturated Na₂CO₃ (2 mL), and the solution was lyophilized. 7-[4-(prop-2-enoylamino)-2-pyridyl]quinazoline-2-carboxylic acid (1.4 g, crude) was obtained as a white solid. The residue was purified by prep-HPLC to afford the title compound 7-[4-(prop-2-enoylamino)-2-pyridyl]quinazoline-2-carboxylic acid (4.4 mg, 13.58 µmol, 3.11e-1% yield, 98.893% purity) as a white solid. 321.1. ¹H NMR (400 MHz, DMSO-d₆) δ=11.06 (s, 1H), 9.72 (br s, 1H), 8.67 (br d, J=5.6 Hz, 2H), 8.57 (s, 2H), 8.50-8.46 (m, 1H), 8.40-8.30 (m, 1H), 7.82 (br d, J=5.2 Hz, 1H), 6.57 (dd, J=10.0, 16.8 Hz, 1H), 6.39 (dd, J=1.6, 17.2 Hz, 1H), 5.90 (dd, J=1.6, 10.0 Hz, 1H).

TABLE 15 shows compounds synthesized using methods described in EXAMPLE 15.

TABLE 15

| Cpd. No. | Structure | IUPAC | LC-MS (ES+, m/z) |
|---|---|---|---|
| 614 | 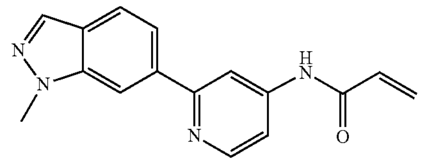 [SMILES: C=CC(=O)Nc1ccnc(-c2ccc3cnn(C)c3c2)c1] | N-[2-(1-methyl-1H-indazol-6-yl)pyridin-4-yl]prop-2-enamide | 279.1 |
| 615 | 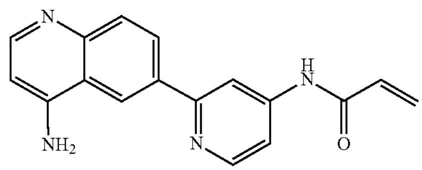 [SMILES: C=CC(=O)Nc1ccnc(-c2ccc3nccc(N)c3c2)c1] | N-[2-(4-aminoquinolin-6-yl)pyridin-4-yl]prop-2-enamide | 291.1 |
| 616 | 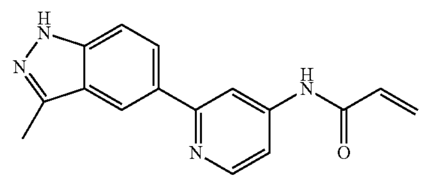 [SMILES: C=CC(=O)Nc1ccnc(-c2ccc3[nH]nc(C)c3c2)c1] | N-[2-(3-methyl-1H-indazol-5-yl)pyridin-4-yl]prop-2-enamide | 279.1 |
| 617 | 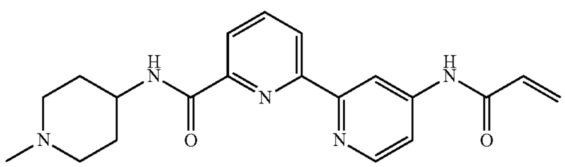 [SMILES: C=CC(=O)Nc1ccnc(-c2cccc(C(=O)NC3CCN(C)CC3)n2)c1] | N-(1-methylpiperidin-4-yl)-4'-(prop-2-enamido)-[2,2'-bipyridine]-6-carboxamide | 366.1 |
| 618 | 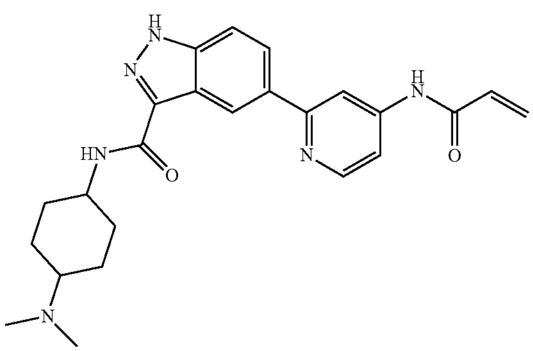 [SMILES: C=CC(=O)Nc1ccnc(-c2ccc3[nH]nc(C(=O)NC4CCC(N(C)C)CC4)c3c2)c1] | N-[4-(dimethylamino)cyclohexyl]-5-[4-(prop-2-enamido)pyridin-2-yl]-1H-indazole-3-carboxamide | 433.2 |
| 619 | 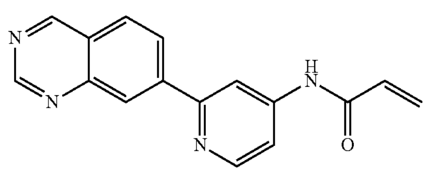 [SMILES: C=CC(=O)Nc1ccnc(-c2ccc3cncnc3c2)c1] | N-[2-(quinazolin-7-yl)pyridin-4-yl]prop-2-enamide | 277.1 |
| 620 | 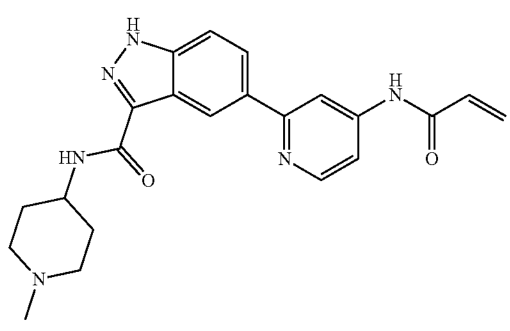 | N-(1-methylpiperidin-4-yl)-5-[4-(prop-2-enamido)pyridin-2-yl]-1H-indazole-3-carboxamide | 405.2 |

TABLE 15-continued

| Cpd. No. | Structure | IUPAC | LC-MS (ES+, m/z) |
|---|---|---|---|
| 621 | 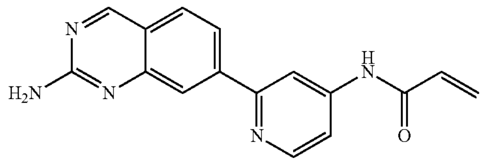 [SMILES: C=CC(=O)Nc1ccnc(-c2ccc3cnc(N)nc3c2)c1] | N-[2-(2-aminoquinazolin-7-yl)pyridin-4-yl]prop-2-enamide | 292.1 |
| 622 | 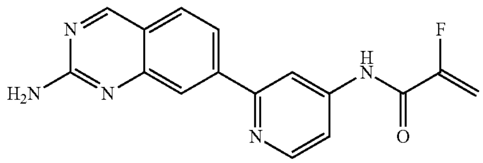 [SMILES: C=C(F)C(=O)Nc1ccnc(-c2ccc3cnc(N)nc3c2)c1] | N-[2-(2-aminoquinazolin-7-yl)pyridin-4-yl]-2-fluoroprop-2-enamide | 310.1 |
| 623 | 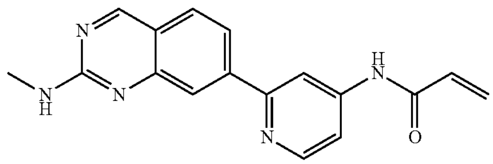 [SMILES: C=CC(=O)Nc1ccnc(-c2ccc3cnc(NC)nc3c2)c1] | N-{2-[2-(methylamino)quinazolin-7-yl]pyridin-4-yl}prop-2-enamide | 306.1 |
| 624 | 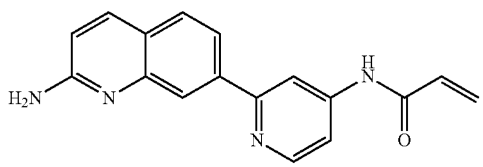 [SMILES: C=CC(=O)Nc1ccnc(-c2ccc3ccc(N)nc3c2)c1] | N-[2-(2-aminoquinolin-7-yl)pyridin-4-yl]prop-2-enamide | 291.1 |
| 625 | 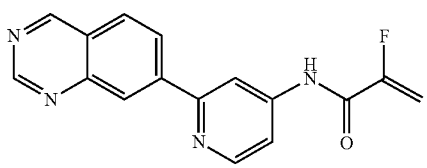 [SMILES: C=C(F)C(=O)Nc1ccnc(-c2ccc3cncnc3c2)c1] | 2-fluoro-N-[2-(quinazolin-7-yl)pyridin-4-yl]prop-2-enamide | 295.1 |
| 626 | 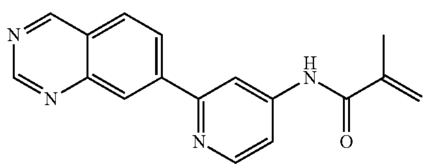 | 2-methyl-N-[2-(quinazolin-7-yl)pyridin-4-yl]prop-2-enamide | 291.1 |
| 627 | 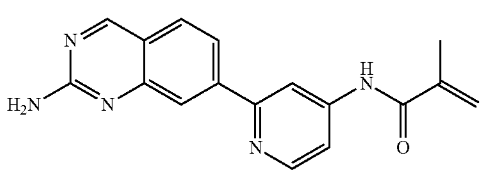 [SMILES: C=C(C)C(=O)Nc1ccnc(-c2ccc3cnc(N)nc3c2)c1] | N-[2-(2-aminoquinazolin-7-yl)pyridin-4-yl]-2-methylprop-2-enamide | 306.1 |
| 628 | 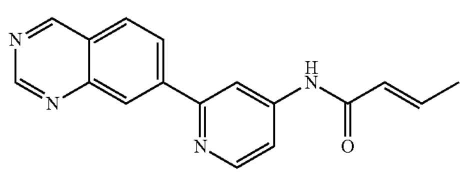 [SMILES: C/C=C/C(=O)Nc1ccnc(-c2ccc3cncnc3c2)c1] | (2E)-N-2-(quinazolin-7-yl)pyridin-4-yl]but-2-enamide | 291.1 |
| 629 | 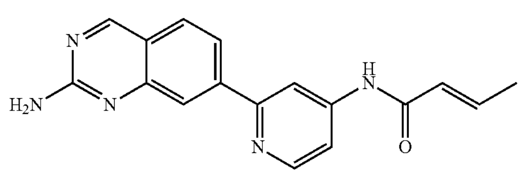 [SMILES: C/C=C/C(=O)Nc1ccnc(-c2ccc3cnc(N)nc3c2)c1] | (2E)-N-[2-(2-aminoquinazolin-7-yl)pyridin-4-yl]but-2-enamide | 306.2 |

| Cpd. No. | Structure | IUPAC | LC-MS (ES+, m/z) |
|---|---|---|---|
| 630 | 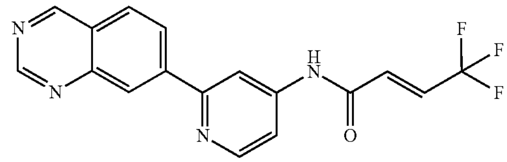 [SMILES: O=C(/C=C/C(F)(F)F)Nc1ccnc(-c2ccc3cncnc3c2)c1] | (2E)-4,4,4-trifluoro-N-[2-(quinazolin-7-yl)pyridin-4-yl]but-2-enamide | 345.1 |
| 631 | 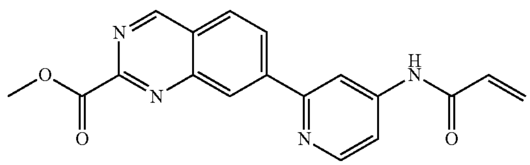 [SMILES: C=CC(=O)Nc1ccnc(-c2ccc3cnc(C(=O)OC)nc3c2)c1] | methyl 7-[4-(prop-2-enamido)pyridin-2-yl]quinazoline-2-carboxylate | 335 |
| 632 | 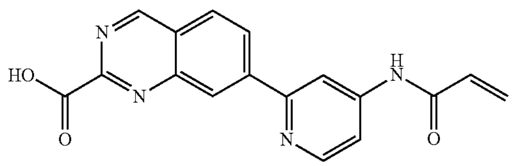 [SMILES: C=CC(=O)Nc1ccnc(-c2ccc3cnc(C(=O)O)nc3c2)c1] | 7-[4-(prop-2-enamido)pyridin-2-yl]quinazoline-2-carboxylic acid | 321.1 |
| 633 | 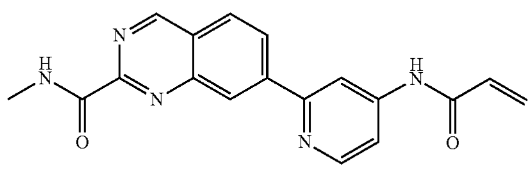 [SMILES: C=CC(=O)Nc1ccnc(-c2ccc3cnc(C(=O)NC)nc3c2)c1] | N-methyl-7-[4-(prop-2-enamido)pyridin-2-yl]quinazoline-2-carboxamide | 334 |
| 634 | 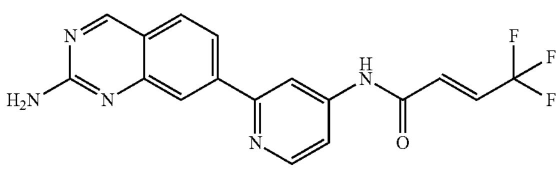 [SMILES: Nc1ncc2ccc(-c3cc(NC(=O)/C=C/C(F)(F)F)ccn3)cc2n1] | (2E)-N-[2-(2-aminoquinazolin-7-yl)pyridin-4-yl]-4,4,4-trifluorobut-2-enamide | 360.1 |
| 635 | 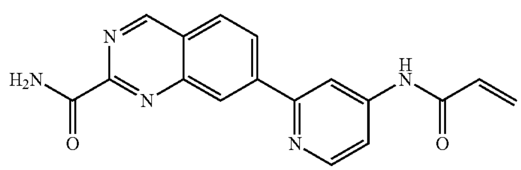 [SMILES: C=CC(=O)Nc1ccnc(-c2ccc3cnc(C(N)=O)nc3c2)c1] | 7-[4-(prop-2-enamido)pyridin-2-yl]quinazoline-2-carboxamide | 320 |
| 636 | 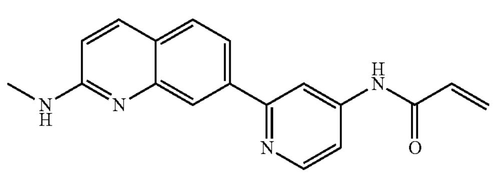 [SMILES: C=CC(=O)Nc1ccnc(-c2ccc3ccc(NC)nc3c2)c1] | N-{2-[2-(methylamino)quinolin-7-yl]pyridin-4-yl}prop-2-enamide | 305.1 |
| 637 | 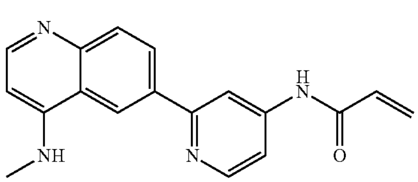 [SMILES: C=CC(=O)Nc1ccnc(-c2ccc3nccc(NC)c3c2)c1] | N-{2-[4-(methylamino)quinolin-6-yl]pyridin-4-yl}prop-2-enamide | 305 |

TABLE 15-continued

| Cpd. No. | Structure | IUPAC | LC-MS (ES+, m/z) |
|---|---|---|---|
| 638 | 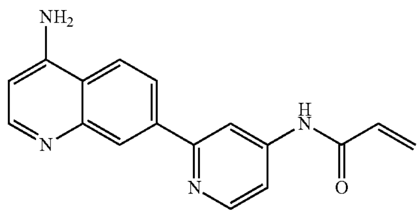 [SMILES: C=CC(=O)Nc1ccnc(-c2ccc3c(N)ccnc3c2)c1] | N-[2-(4-aminoquinolin-7-yl)pyridin-4-yl]prop-2-enamide | 290.9 |
| 639 | 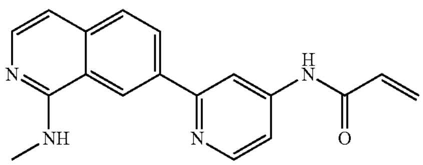 [SMILES: C=CC(=O)Nc1ccnc(-c2ccc3ccnc(NC)c3c2)c1] | N-{2-[1-(methylamino)isoquinolin-7-yl]pyridin-4-yl}prop-2-enamide | 305 |
| 640 | 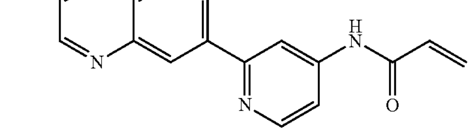 | N-[2-(3-chloroquinolin-7-yl)pyridin-4-yl]prop-2-enamide | 309.9 |
| 641 | 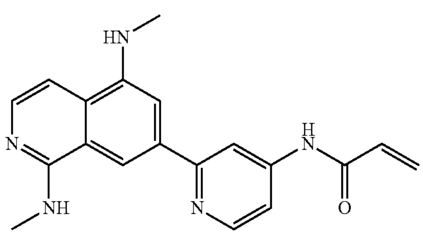 [SMILES: C=CC(=O)Nc1ccnc(-c2cc(NC)c3ccnc(NC)c3c2)c1] | N-{2-[1,5-bis(methylamino)isoquinolin-7-yl]pyridin-4-yl}prop-2-enamide | 334.2 |

Example 16: Synthesis of Intermediates

Route 1

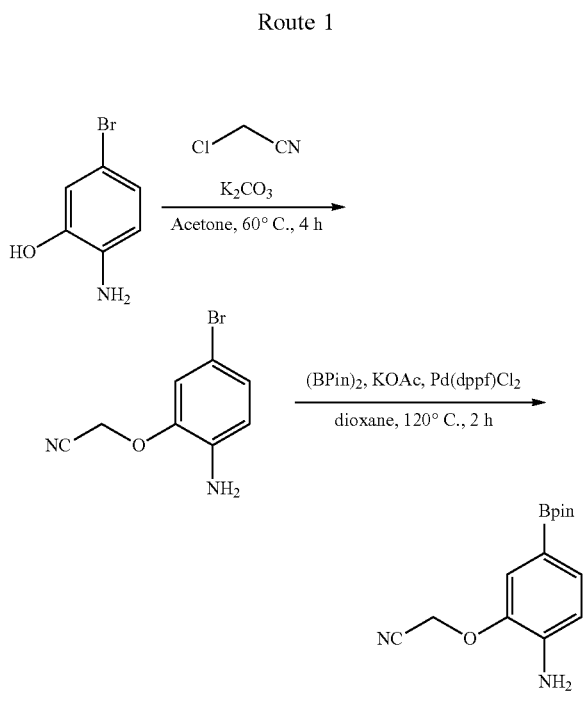

2-(2-amino-5-bromo-phenoxy)acetonitrile

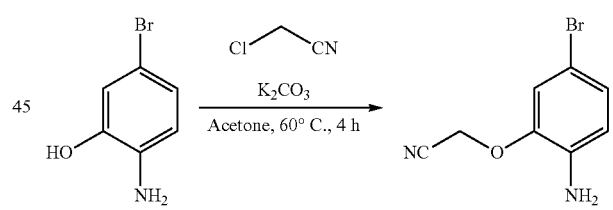

To a mixture of 2-amino-5-bromo-phenol (1 g, 5.32 mmol, 1 eq) in acetone (10 mL) was added $K_2CO_3$ (1.1 g, 7.98 mmol, 1.5 eq). Then 2-chloroacetonitrile (481.8 mg, 6.38 mmol, 404.91 μL, 1.2 eq) was added to the mixture. The mixture was heated to 60° C. and stirred at 60° C. for 4 h. The reaction mixture was poured into ice-water (100 mL). The aqueous phase was extracted with EtOAc (3×50 mL). The combined organic phase was washed with brine (3×50 mL), dried with anhydrous $Na_2SO_4$, filtered, and concentrated in vacuo. The residue was purified by silica gel chromatography (PE:EtOAc=1/0, 1/1) to afford the title compound (1 g, 4.4 mmol, 82.81% yield) as a brown solid.

783

2-[2-amino-5-(4,4,5,5-tetramethyl-1,3,2-dioxaborolan-2-yl)phenoxy]acetonitrile

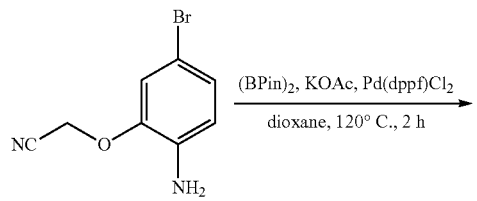

To a mixture of (BPin)$_2$ (503.3 mg, 1.98 mmol, 1.5 eq) and 2-(2-amino-5-bromo-phenoxy) acetonitrile (300 mg, 1.32 mmol, 1 eq) in dioxane (5 mL) was added POTASSIUM ACETATE (389 mg, 3.96 mmol, 3 eq) and Pd(dppf)Cl$_2$ (48.3 mg, 66.06 μmol, 0.05 eq) under N$_2$. The mixture was heated to 120° C. and stirred for 2 hours. TLC and LCMS (ET16123-1094-P1A) showed that the reaction was complete. The reaction was filtered, and concentrated in vacuo. The crude was the desired product. The crude was purified by prep-TLC (SiO$_2$, PE:EtOAc=3:1) to afford the title compound 2-[2-amino-5-(4,4,5,5-tetramethyl-1,3,2-dioxaborolan-2-yl)phenoxy]acetonitrile (200 mg, 729.6 μmol, 55.22% yield) as a white solid Route 2

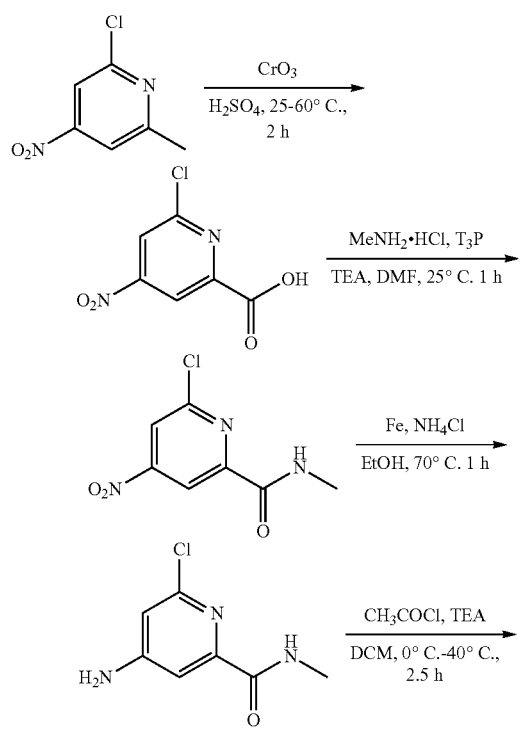

784

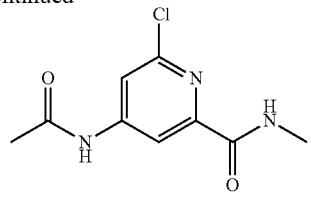

6-chloro-4-nitro-pyridine-2-carboxylic acid

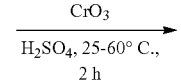

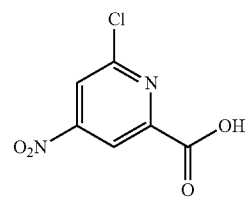

To a mixture of 2-chloro-6-methyl-4-nitro-pyridine (4 g, 23.18 mmol, 1 eq) in H$_2$SO$_4$ (40 mL) was added CrO$_3$ (9.27 g, 92.72 mmol, 3.43 mL, 4 eq) at 25° C. Then the mixture was stirred at 25° C. for 1 h. Then heated to 60° C. for 1 h. TLC showed no starting material remained. The reaction mixture was poured into ice-water (50 mL) and a lot of solid came out, filtered. Then the aqueous phase was extracted with EtOAc (3×50 mL). The combined organic phase was washed with brine (3×50 mL), dried with anhydrous Na$_2$SO$_4$, filtered, and concentrated in vacuo to afford the title compound 6-chloro-4-nitro-pyridine-2-carboxylic acid (4 g, crude) as a white solid.

6-chloro-N-methyl-4-nitro-pyridine-2-carboxamide

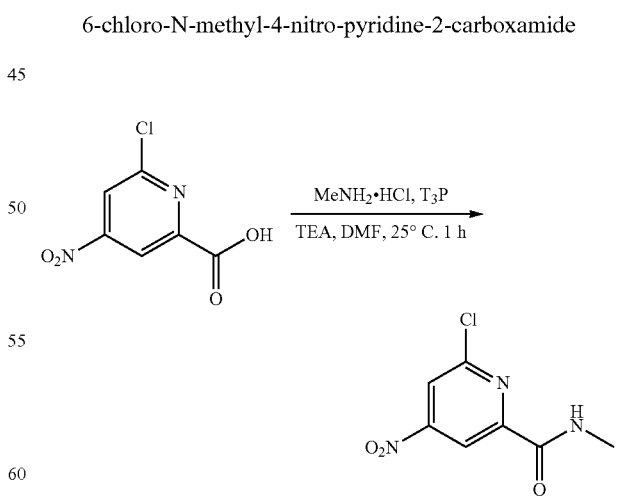

To a mixture of 6-chloro-4-nitro-pyridine-2-carboxylic acid (1 g, 4.94 mmol, 1 eq) in DMF (10 mL) was added MeNH$_2$·HCl (1 g, 14.81 mmol, 3 eq, HCl), TEA (2.5 g, 24.69 mmol, 3.44 mL, 5 eq) at 25° C. Then T$_3$P (2.36 g, 7.41 mmol, 2.20 mL, 1.5 eq) was added and the mixture was stirred at 25° C. for 1 h. The reaction mixture was poured into ice-water (30 mL) and the aqueous phase was extracted with EtOAc (3×30 mL). The combined organic phase was washed with brine (3×20 mL), dried with anhydrous Na₂SO₄, filtered, and concentrated in vacuo to afford the title compound (650 mg, crude) as a yellow solid.

4-amino-6-chloro-N-methyl-pyridine-2-carboxamide

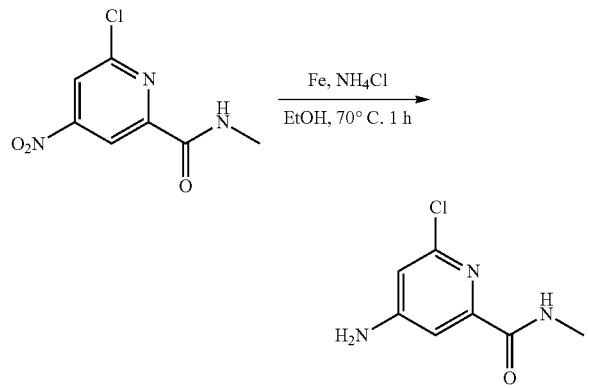

To a mixture of 6-chloro-N-methyl-4-nitro-pyridine-2-carboxamide (550 mg, 2.55 mmol, 1 eq) in EtOH (10 mL) was added saturated NH₄Cl (2 mL) at 25° C. Then the mixture was heated to 70° C. Le (1.42 g, 25.51 mmol, 10 eq) was added and the mixture was stirred at 70° C. for 1 h. The residue was poured into H₂O (15 mL) and EtOAc (15 mL) was added. The mixture was filtered with diamate. The aqueous phase was extracted with EtOAc (3×15 mL). The combined organic phase was washed with brine (3×15 mL), dried with anhydrous Na₂SO₄, filtered, and concentrated in vacuo to afford the title compound 4-amino-6-chloro-N-methyl-pyridine-2-carboxamide (450 mg, crude) as a yellow solid.

4-acetamido-6-chloro-N-methyl-pyridine-2-carboxamide

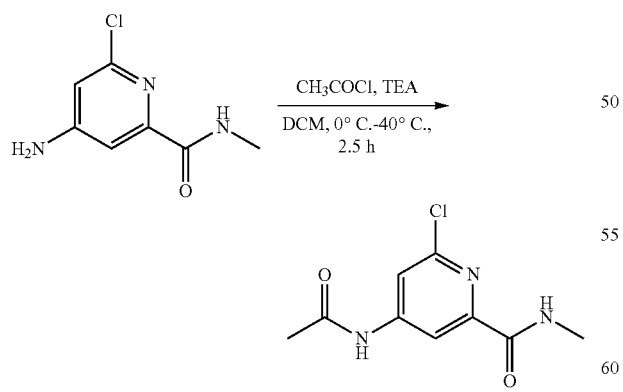

To a mixture of 4-amino-6-chloro-N-methyl-pyridine-2-carboxamide (250 mg, 1.35 mmol, 1 eq) in DCM (6 mL) was added TEA (408.9 mg, 4.04 mmol, 562.42 μL, 3 eq), AcCl (422.9 mg, 5.39 mmol, 384.47 μL, 4 eq) at 0° C. The mixture was stirred at 25° C. for 2 h. TLC showed two spot was detected. Then the mixture was stirred at 40° C. for 0.5 h. The reaction mixture was poured into H₂O (15 mL) and the aqueous phase was extracted with EtOAc (3×20 mL). Some solid come out and filtered. The combined organic phase was washed with brine (3×15 mL), dried with anhydrous Na₂SO₄, filtered, and concentrated in vacuo to afford the title compound 4-acetamido-6-chloro-N-methyl-pyridine-2-carboxamide (200 mg, crude) as a white solid.

Route 3

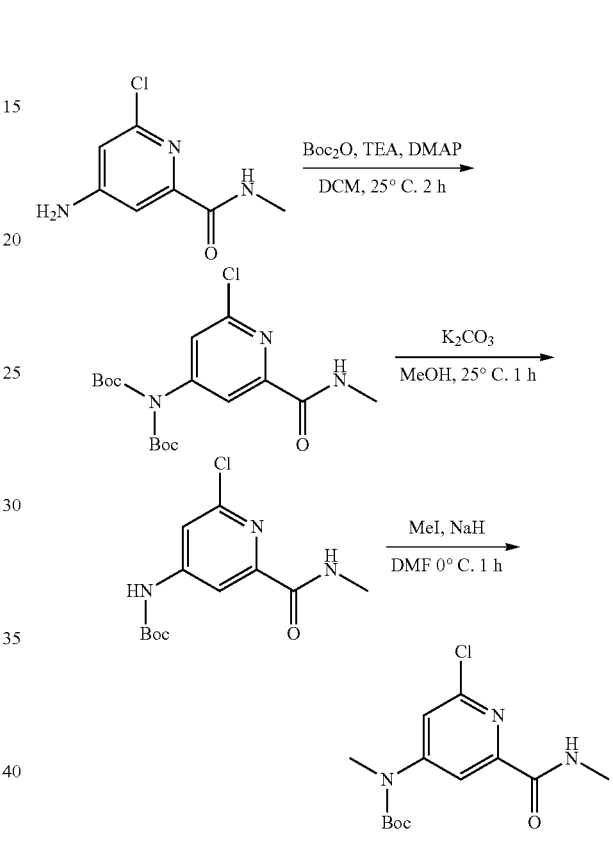

tert-butyl N-tert-butoxycarbonyl-N-[2-chloro-6-(methylcarbamoyl)-4-pyridyl]carbamate

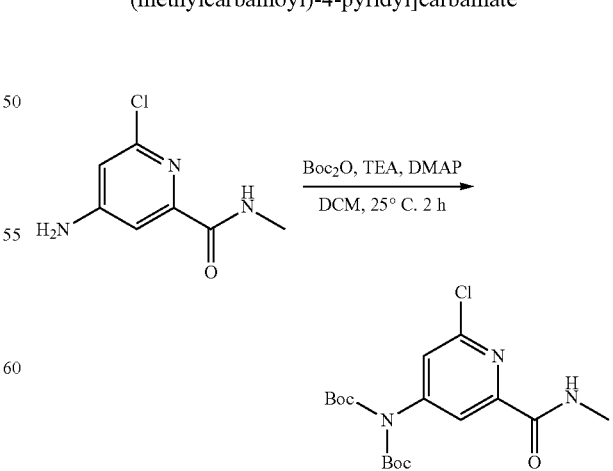

To a mixture of 4-amino-6-chloro-N-methyl-pyridine-2-carboxamide (500 mg, 2.69 mmol, 1 eq) in DCM (6 mL) was added TEA (817.8 mg, 8.08 mmol, 1.12 mL, 3 eq), Boc₂O (1.76 g, 8.08 mmol, 1.86 mL, 3 eq), DMAP (32.9 mg, 269.38 μmol, 0.1 eq) at 25° C. The mixture was stirred at 25° C. for 2 h. The reaction mixture was poured into H2O (15 mL) and the aqueous phase was extracted with DCM (3×15 mL). The combined organic phase was washed with brine (3×15 mL), dried with anhydrous Na₂SO₄, filtered, and concentrated in vacuo. The residue was purified by silica gel chromatography (PE:EtOAc=1/0, 4:1) to afford the title compound (600 mg, 1.48 mmol, 54.84% yield, 95% purity) as a white solid.

tert-butyl N-[2-chloro-6-(methylcarbamoyl)-4-pyridyl]carbamate

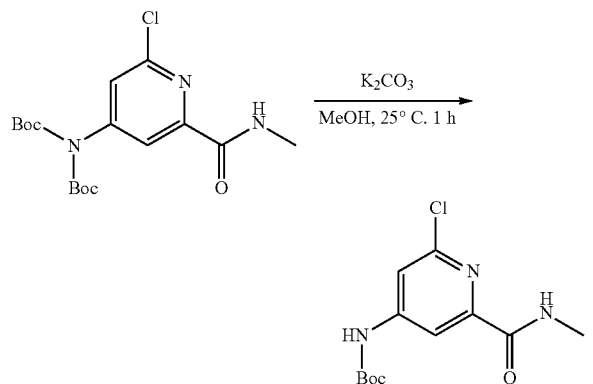

To a mixture of tert-butyl N-tert-butoxycarbonyl-N-[2-chloro-6-(methylcarbamoyl)-4-pyridyl]carbamate (550 mg, 1.43 mmol, 1 eq) in MeOH (10 mL) was added K₂CO₃ (788 mg, 5.7 mmol, 4 eq) at 25° C. The mixture was stirred at 25° C. for 1 h. The residue was filtered, and concentrated in vacuo to afford the title compound tert-butyl N-[2-chloro-6-(methylcarbamoyl)-4-pyridyl]carbamate (350 mg, crude) as a white solid.

tert-butyl N-[2-chloro-6-(methylcarbamoyl)-4-pyridyl]-N-methyl-carbamate

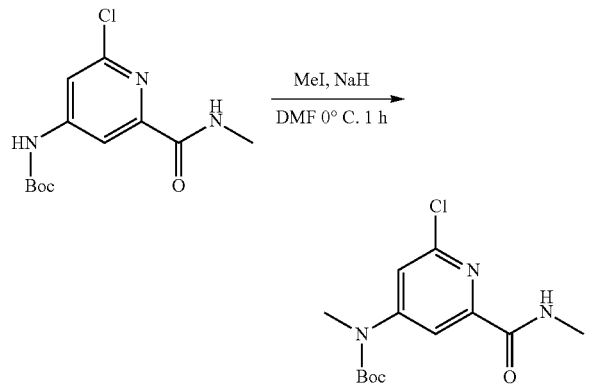

To a mixture of tert-butyl N-[2-chloro-6-(methylcarbamoyl)-4-pyridyl]carbamate (180 mg, 629.97 μmol, 1 eq) in DMF (2 mL) was added NaH (30.2 mg, 755.97 μmol, 60% purity, 1.2 eq) at 0° C. The mixture was stirred at 0° C. for 0.5 h. MeI (89.4 mg, 629.97 μmol, 39.22 μL, 1 eq) was added and the mixture was stirred at 0° C. for 0.5 h. The reaction mixture was poured into saturated NH₄Cl (10 mL) and the aqueous phase was extracted with EtOAc (3×10 mL). The combined organic phase was washed with brine (3×10 mL), dried with anhydrous Na₂SO₄, filtered, and concentrated in vacuo. The residue was purified by prep-TLC to afford the title compound tert-butyl N-[2-chloro-6-(methylcarbamoyl)-4-pyridyl]-N-methyl-carbamate (120 mg, 240.2 μmol, 38.13% yield, 60% purity) as a white solid.

Route 4

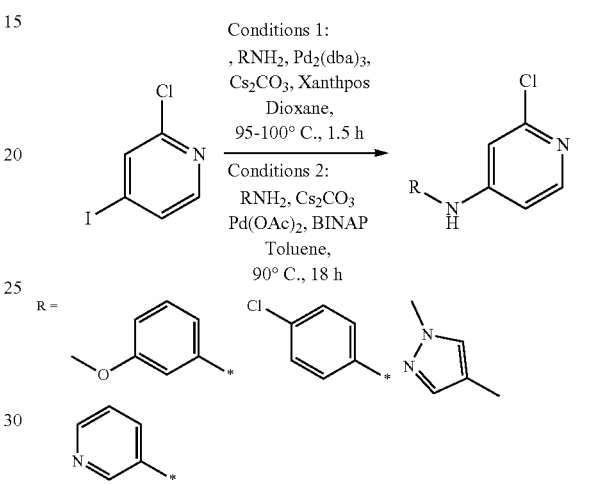

2-chloro-N-(1-methylpyrazol-4-yl)pyridin-4-amine

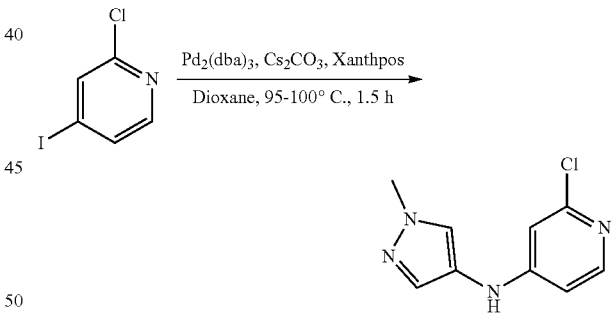

To a solution of 1-methylpyrazol-4-amine (365 mg, 3.76 mmol, 3 eq), 2-chloro-4-iodo-pyridine (300 mg, 1.25 mmol, 1 eq) in dioxane (10 mL) was added Cs₂CO₃ (816.5 mg, 2.51 mmol, 2 eq). Then Pd₂(dba)₃ (57.4 mg, 62.65 μmol, 0.05 eq) and (5-diphenyl phosphanyl-9,9-dimethyl-xanthen-4-yl)-diphenyl-phosphane (72.5 mg, 125.29 μmol, 0.1 eq) was added to the reaction. The reaction was stirred at 95-100° C. for 1.5 h under N2 atmosphere. The reaction was poured into ice-water (10 mL) and extracted with EtOAc (3×10 mL). The combined organic layer was washed with water (3×10 mL) and brine (3×10 mL), dried over Na₂SO₄, filtered, and concentrated. The crude was purified by silica gel chromatography (EtOAc) and purified by prep-TLC (SiO₂, DCM/MeOH=18/1, Rf=0.5) to afford the title compound (150 mg, 575.13 μmol, 85.71% yield, 80% purity) as black oil.

2-chloro-N-(3-methoxyphenyl)pyridin-4-amine

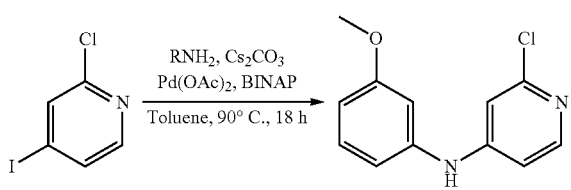 [SMILES: Clc1cc(I)ccn1 ; COc1cccc(Nc2ccnc(Cl)c2)c1]

To a mixture of 2-chloro-4-iodo-pyridine (300 mg, 1.25 mmol, 1 eq), 3-methoxyaniline (185.2 mg, 1.5 mmol, 168.33 μL, 1.2 eq) in Tol. (7 mL) was added $Cs_2CO_3$ (816.5 mg, 2.51 mmol, 2 eq), BINAP (156 mg, 250.58 μmol, 0.2 eq), $Pd(OAc)_2$ (28.1 mg, 125.29 μmol, 0.1 eq) at 25° C. The mixture was stirred at 90° C. for 10 h. LCMS showed no starting material remained. The reaction mixture was poured into $H_2O$ (15 mL) and the aqueous phase was extracted with EtOAc (3×20 mL). The combined organic phase was washed with brine (3×15 mL), dried with anhydrous $Na_2SO_4$, filtered, and concentrated in vacuo. The residue was purified by silica gel chromatography (PE:EtOAc=1:0, 4:1) to afford the title compound 2-chloro-N-(3-methoxyphenyl)pyridin-4-amine (260 mg, 997.1 μmol, 79.58% yield, 90% purity) as a yellow oil.

Route 5

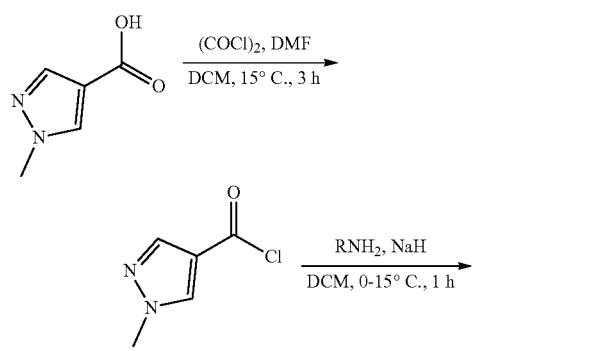

1-methylpyrazole-4-carbonyl chloride

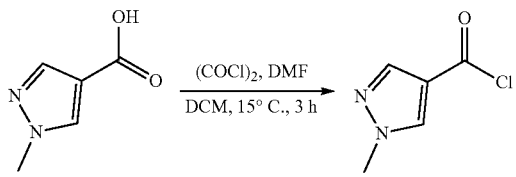

To a solution of 1-methylpyrazole-4-carboxylic acid (300 mg, 2.38 mmol, 1 eq) in DCM (6 mL) was added $(COCl)_2$ (603.9 mg, 4.76 mmol, 416.46 μL, 2 eq). Then DMF (17.4 mg, 237.88 μmol, 18.30 μL, 0.1 eq) was added to the reaction and the reaction was stirred at 15° C. for 3 h. The reaction mixture was concentrated to afford the title compound 1-methylpyrazole-4-carbonyl chloride (340 mg, crude) as a yellow oil, which was used directly.

N-(2-bromo-4-pyridyl)-1-methyl-pyrazole-4-carboxamide

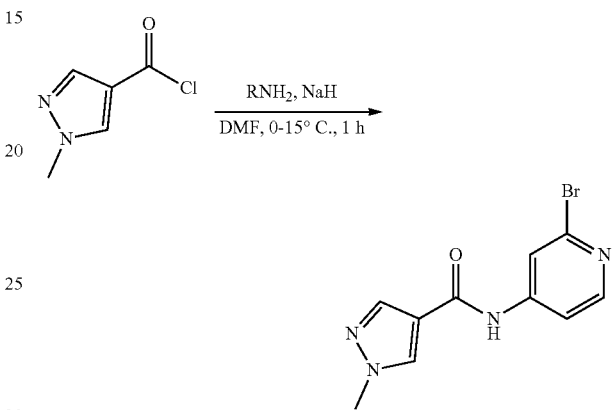

To a solution of 2-bromopyridin-4-amine (300 mg, 1.73 mmol, 1 eq) in DMF (2.5 mL) was added NaH (180 mg, 4.5 mmol, 60% purity, 2.60 eq) at 0° C. Then the reaction mixture was stirred at 0° C. for 30 min. Then 1-methylpyrazole-4-carbonyl chloride (340 mg, 2.35 mmol, 1.36 eq) in 1.5 mL DMF was added to the reaction and the reaction was stirred at 15° C. for 30 min. The reaction was poured into ice-water (10 mL) and extracted with EtOAc (3×10 mL). The combined organic layer was washed with water (3×10 mL) and brine (3×10 mL), dried over $Na_2SO_4$, filtered, and concentrated to afford the title compound (500 mg, crude) as a light yellow solid used directly.

N-(6-bromopyrimidin-4-yl)acetamide

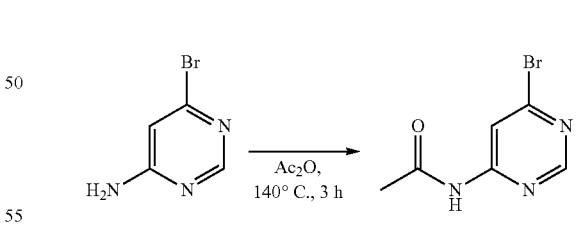

A solution of 6-bromopyrimidin-4-amine (200 mg, 1.15 mmol, 1 eq) in $Ac_2O$ (1 mL) was stirred at 140° C. for 3 h. TLC showed that the reaction was complete. After cooled to 20° C. The reaction mixture was treated with Saturated $NaHCO_3$ (50 mL, keep PH to 8-9) and stirred at 20° C. for 20 min. The reaction mixture was extracted with DCM (3×30 mL). The combined organic layer was washed with brine (3×20 mL), dried over $Na_2SO_4$, filtered, and concentrated to afford the title compound N-(6-bromopyrimidin-4-yl)acetamide (210 mg, crude) as a light yellow solid without further purification.

791

3-amino-6-chloro-N-(1-methyl-4-piperidyl)pyridine-2-carboxamide

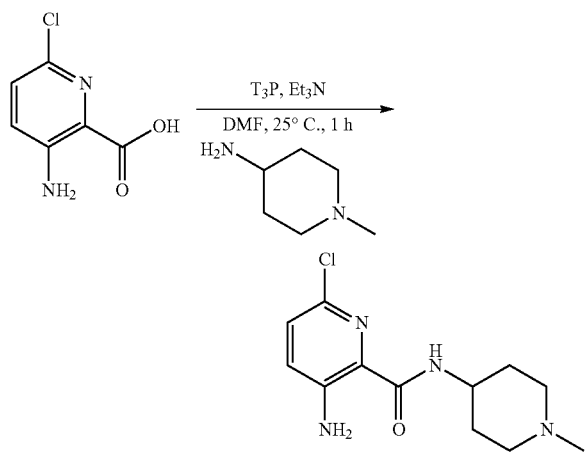

To a mixture of 3-amino-6-chloro-pyridine-2-carboxylic acid (200 mg, 1.16 mmol, 1 eq) in DMF (6 mL) was added 1-methylpiperidin-4-amine RNH$_2$ (264.7 mg, 2.32 mmol, 265.41 μL, 2 eq), Et$_3$N (586.4 mg, 5.79 mmol, 806.57 μL, 5 eq), T$_3$P (1.11 g, 1.74 mmol, 1.03 mL, 50% purity, 1.5 eq) at 25° C. The mixture was stirred at 25° C. for 1 h. The reaction mixture was poured into H$_2$O (20 mL) and the aqueous phase was extracted with EtOAc (3×15 mL). The combined organic phase was washed with brine (3×15 mL), dried with anhydrous Na$_2$SO$_4$, filtered, and concentrated in vacuo to afford the title compound (260 mg, crude) as a brown oil. ET8911-1347

Route 6

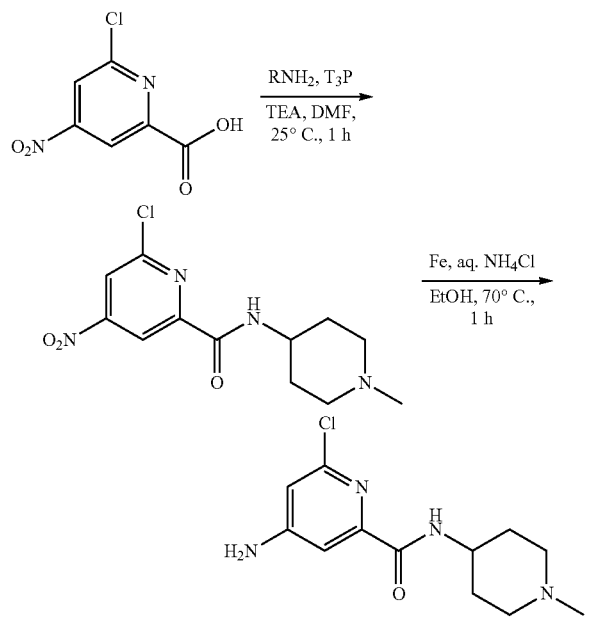

792

6-chloro-4-nitro-pyridine-2-carboxylic acid

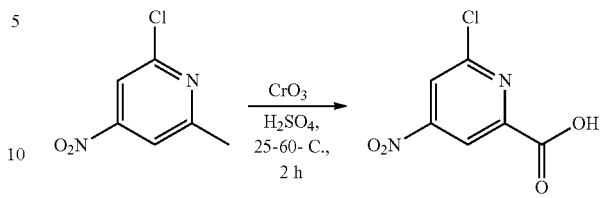

To a solution of 2-chloro-6-methyl-4-nitro-pyridine (3 g, 17.38 mmol, 1 eq) in H$_2$SO$_4$ (30 mL) was added CrO$_3$ (6.95 g, 69.54 mmol, 2.58 mL, 4 eq). The mixture was stirred at 25° C. for 1 h, stirred at 60° C. for 1 h. LCMS showed that the reaction was complete. The residue was poured into ice-water (200 mL) and a lot of solid came out, filtered. Then the aqueous phase was extracted with EtOAc (3×100 mL). The combined organic phase was washed with brine (3×100 mL), dried with anhydrous Na$_2$SO$_4$, filtered, and concentrated in vacuo. The crude was used directly to afford the title compound 6-chloro-4-nitro-pyridine-2-carboxylic acid (4 g, crude) as a gray solid.

6-chloro-N-(1-methyl-4-piperidyl)-4-nitro-pyridine-2-carboxamide

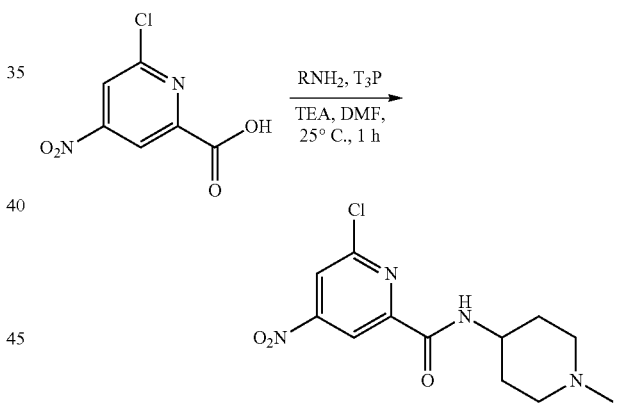

To a solution of 6-chloro-4-nitro-pyridine-2-carboxylic acid (1 g, 4.94 mmol, 1 eq) in DMF (10 mL) was added TEA (2.5 g, 24.69 mmol, 3.44 mL, 5 eq) and 1-methylpiperidin-4-amine (845.6 mg, 7.41 mmol, 1.5 eq). Then T$_3$P (4.71 g, 7.41 mmol, 4.40 mL, 50% purity, 1.5 eq) was added to the reaction and the reaction was stirred at 25° C. for 1 h. LCMS showed that the reaction was complete. The reaction mixture was diluted with H$_2$O (200 mL). The mixture was extracted with EtOAc (3×100 mL), and the combined organic layers were washed with H$_2$O (2×50 mL) and brine (2×50 mL), dried over anhydrous Na$_2$SO$_4$, filtered, and concentrated in vacuo to give a residue to afford the title compound 6-chloro-N-(1-methyl-4-piperidyl)-4-nitro-pyridine-2-carboxamide (1.5 g, crude) as a yellow solid, which was used directly.

4-amino-6-chloro-N-(1-methyl-4-piperidyl)pyridine-2-carboxamide

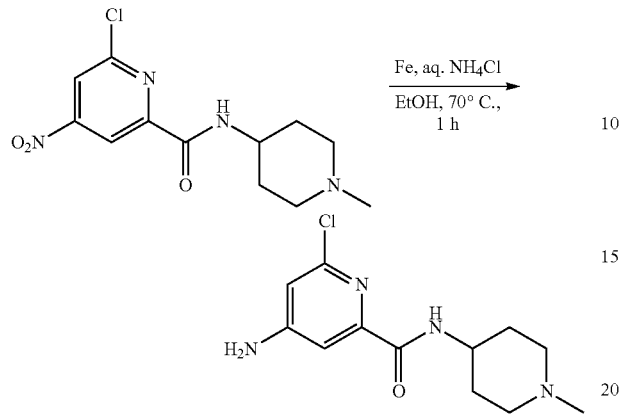

To a mixture of 6-chloro-N-(1-methyl-4-piperidyl)-4-nitro-pyridine-2-carboxamide (1.3 g, 4.35 mmol, 1 eq) in EtOH (10 mL) was added saturated NH$_4$Cl (4.35 mmol, 2.5 mL, 1 eq) and the reaction mixture was heated to 70° C. Then Fe (729.1 mg, 13.06 mmol, 3 eq) was added and the mixture was stirred for 1 hr. TLC showed that the reaction was complete. The reaction mixture was diluted with H$_2$O (100 mL). The mixture was extracted with EtOAc (2×100 mL), and the combined organic layers were washed with H$_2$O (2×100 mL) and brine (2×50 mL), dried over anhydrous Na$_2$SO$_4$, filtered, and concentrated in vacuo to give a residue to afford the title compound 4-amino-6-chloro-N-(1-methyl-4-piperidyl)pyridine-2-carboxamide (1.1 g, crude) as a yellow solid which was used directly without further purification.

4-acetamido-6-chloro-N-(1-methylpiperidin-4-yl)picolinamide

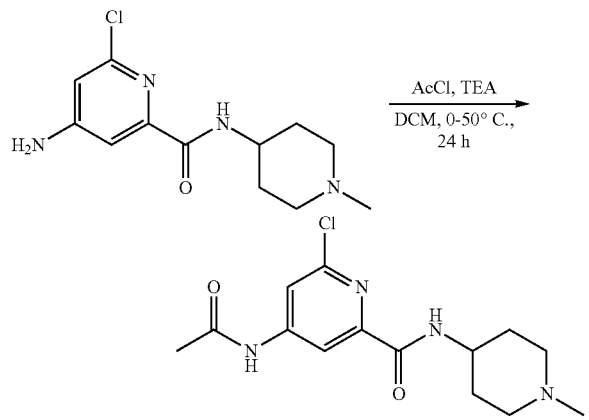

To a mixture of 4-amino-6-chloro-N-(1-methyl-4-piperidyl)pyridine-2-carboxamide (0.2 g, 744.21 µmol, 1 eq) in DCM (4 mL) was added TEA (225.9 mg, 2.23 mmol, 310.76 µL, 3 eq) and acetyl chloride (584.2 mg, 7.44 mmol, 531.08 µL, 10 eq) at 0° C. The reaction was stirred at 50° C. for 24 hr. LCMS showed that the reaction was complete. The reaction mixture was adjusted with saturated Na$_2$CO$_3$ to pH=8. The mixture was extracted with EtOAc (2×100 mL), and the combined organic layers were washed with H$_2$O (2×100 mL) and brine (2×50 mL), dried over anhydrous Na$_2$SO$_4$, filtered, and concentrated in vacuo to give a residue. The residue was purified by prep-TLC (SiO$_2$, DCM:MeOH=10:1) to afford the title compound 4-acetamido-6-chloro-N-(1-methylpiperidin-4-yl)picolinamide (0.16 g, 514.84 µmol, 69.18% yield) as a yellow solid.

1-methylpiperidine-4-carbonyl chloride

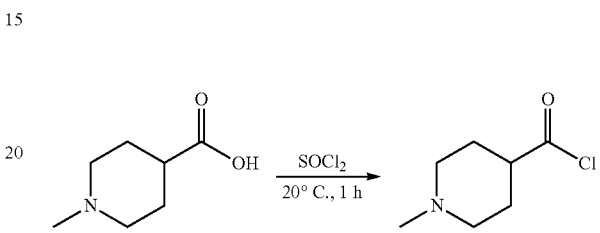

To a mixture of 1-methylpiperidine-4-carboxylic acid (1 g, 5.57 mmol, 825.32 µL, 1 eq, HCl) in SOCl$_2$ (4.41 g, 37.08 mmol, 2.69 mL, 6.66 eq) and the mixture was stirred until the solid was dissolved and stirred for another 60 min at 20° C. The reaction was concentrated directly to give crude product to afford the title compound (1 g, crude, HCl) as an off-white solid.

N-(2-bromo-4-pyridyl)-1-methyl-piperidine-4-carboxamide

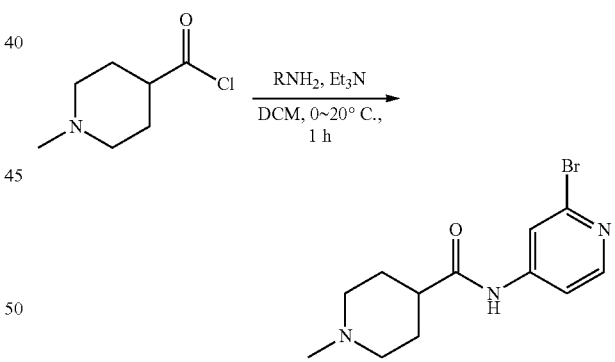

To a mixture of 2-bromopyridin-4-amine (300 mg, 1.73 mmol, 1 eq) in DCM (10 mL) was added Et$_3$N (875.3 mg, 8.65 mmol, 1.20 mL, 5 eq), 1-methylpiperidine-4-carbonyl chloride (685.4 mg, 3.46 mmol, 2 eq, HCl) in one portion at 0° C. under N$_2$. The mixture was stirred at 20° C. for 60 min. TLC showed ~30% starting material remained. The reaction mixture was diluted with 30 mL water, extracted with EtOAc (3×30 mL), and the combined organic layer was washed with brine (2×25 mL), dried over Na$_2$SO$_4$, filtered, and concentrated in vacuo. The residue was by prep-TLC (SiO$_2$, DCM:MeOH=10:1) to afford the title compound N-(2-bromo-4-pyridyl)-1-methyl-piperidine-4-carboxamide (320 mg, 1.07 mmol, 62.03% yield) as a colorless gum.

N-(2-bromo-4-pyridyl)-3-methoxy-benzamide

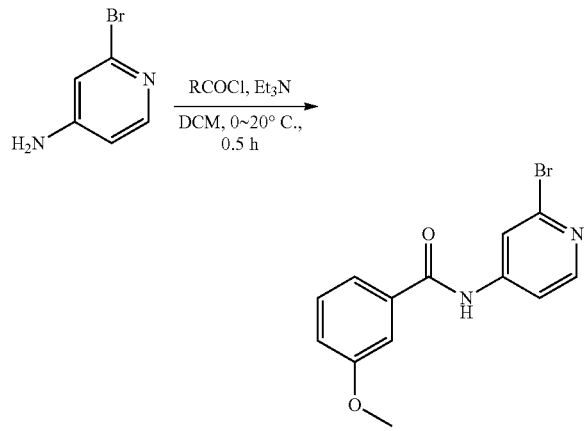

To a mixture of 2-bromopyridin-4-amine (300 mg, 1.73 mmol, 1 eq) in DCM (10 mL) was added Et₃N (526.4 mg, 5.2 mmol, 724.06 µL, 3 eq), 3-methoxybenzoyl chloride (443.7 mg, 2.6 mmol, 354.97 µL, 1.5 eq) in one portion at 0° C. under N₂. The mixture was stirred at 20° C. for 30 min. TLC showed the starting material was consumed. The reaction was diluted with 30 mL water, extracted with EtOAc (3×30 mL), and the combined organic layer was washed with brine (2×30 mL), dried over Na₂SO₄, filtered, and concentrated in vacuo. The residue was purified by prep-TLC (SiO₂, DCM:MeOH=20:1) to afford the title N-(2-bromo-4-pyridyl)-3-methoxy-benzamide compound (350 mg, 1.14 mmol, 65.72% yield) as a colorless gum.

1-methylpiperidine-4-carbonyl chloride

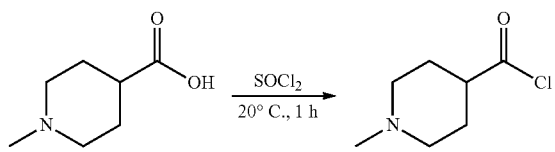

To a mixture of 1-methylpiperidine-4-carboxylic acid (1 g, 5.57 mmol, 1 eq, HCl) in SOCl₂ (3.27 g, 27.48 mmol, 1.99 mL, 4.94 eq) and the mixture was stirred until the solid was dissolved and stirred for another 60 min at 20° C. The reaction was concentrated directly to give crude to afford the title compound 1-methylpiperidine-4-carbonyl chloride (1 g, crude, HCl) as an off-white solid

6-bromo-N-methyl-4-[(l-methylpiperidine-4-carbonyl)amino]pyridine-2-carboxamide

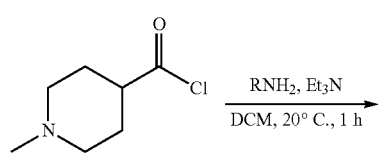

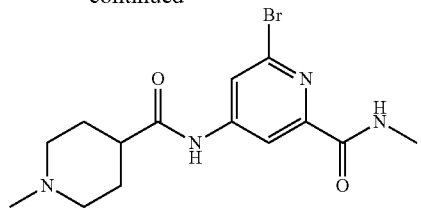

To a mixture of 4-amino-6-bromo-N-methyl-pyridine-2-carboxamide (200 mg, 869.33 µmol, 1 eq) in DCM (5 mL) was added Et₃N (263.9 mg, 2.61 mmol, 363.00 µL, 3 eq), 1-methylpiperidine-4-carbonyl chloride (281 mg, 1.74 mmol, 2 eq). The mixture was stirred at 20° C. for 1 hour. TLC showed that the reaction was complete. The reaction was diluted with 20 mL water, extracted with EtOAc (3×20 mL), and the combined organic layer was washed with water (2×20 mL) and brine (2×20 mL), dried over Na₂SO₄, filtered, and concentrated in vacuo. The residue was purified by prep-TLC (SiO₂, DCM:MeOH=5:1) to afford the title compound 6-bromo-N-methyl-4-[(l-methylpiperidine-4-carbonyl)amino]pyridine-2-carboxamide (150 mg, 422.26 µmol, 48.57% yield) as a yellow solid.

N-(2-chloropyrimidin-4-yl)acetamide

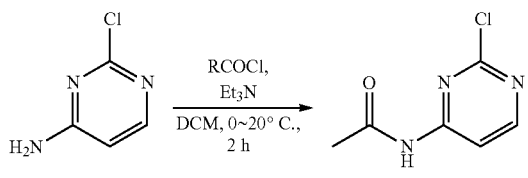

To a mixture of 2-chloropyrimidin-4-amine (200 mg, 1.54 mmol, 1 eq) in DCM (4 mL) was added Et₃N (468.7 mg, 4.63 mmol, 644.65 µL, 3 eq), acetyl chloride (1.21 g, 15.44 mmol, 1.10 mL, 10 eq) in one portion at 0° C. under N₂. The mixture was stirred at 20° C. for 2 hours. The reaction was diluted with 20 mL water, extracted with EtOAc (3×30 mL), and the combined organic layer was washed with brine (2×20 mL), dried over Na₂SO₄, filtered, and concentrated in vacuo. The residue was purified by prep-TLC (SiO₂, PE:EtOAc=1:1) to afford the title compound N-(2-chloropyrimidin-4-yl)acetamide (130 mg, 757.65 µmol, 49.08% yield) as an off-white solid.

N-(2-bromo-4-pyridyl)-3-methoxy-propanamide

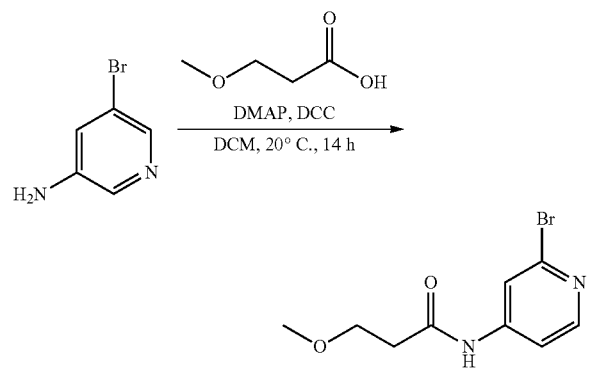

To a mixture of 3-methoxypropanoic acid (601.7 mg, 5.78 mmol, 542.09 µL, 5 eq) in DCM (5 mL) was added DMAP (42.4 mg, 346.8 µmol, 0.3 eq), DCC (477 mg, 2.31 mmol, 467.67 µL, 2 eq) and 2-bromopyridin-4-amine (200 mg, 1.16 mmol, 1 eq) was added to the reaction and stirred for 14 hours at 20° C. The reaction was diluted with 20 mL water, extracted with EtOAc (2×20 mL), and the combined organic layer was washed with brine (2×20 mL), dried over Na₂SO₄, filtered, and concentrated in vacuo to afford the title compound N-(2-bromo-4-pyridyl)-3-methoxy-propanamide (220 mg, crude) as an off-white solid.

4-bromo-2-((difluoromethoxy)aniline

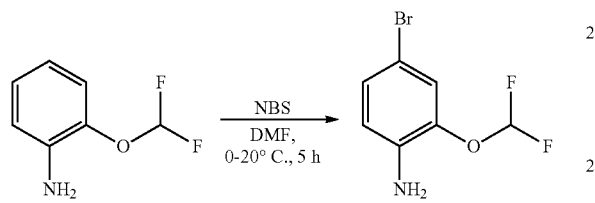

To a mixture of 1-bromopyrrolidine-2,5-dione (134.2 mg, 754.09 µmol, 1.2 eq) in DMF (1 mL) was added 2-(difluoromethoxy)aniline (100 mg, 628.4 µmol, 1 eq) at 0° C. The mixture was stirred at 0° C. for 2 h. Then the mixture was stirred for 3 h at 20° C. TLC and LCMS (ET16123-1101-P1A) showed that the reaction was complete. The residue was poured into ice-water (50 mL). The aqueous phase was extracted with EtOAc (3×20 mL). The combined organic phase was washed with brine (3×20 mL), dried with anhydrous Na₂SO₄, filtered, and concentrated in vacuo. The residue was purified by prep-TLC (SiO₂, PE:EtOAc=3:1) to afford the title compound 4-bromo-2-(difluoromethoxy)aniline (80 mg, 336.09 µmol, 53.48% yield) as a brown oil.

N-(2-bromo-4-pyridyl)propanamide

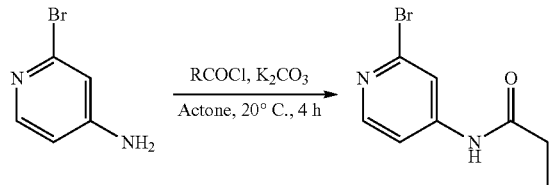

To a mixture of 2-bromopyridin-4-amine (100 mg, 578 µmol, 1 eq) in acetone (2 mL) was added K₂CO₃ (239.7 mg, 1.73 mmol, 3 eq). Then propanoyl chloride (80.2 mg, 867 µmol, 80.22 µL, 1.5 eq) was added to the mixture. The mixture was stirred at 20° C. for 4 h. LCMS (ET16123-1129-P1A) and HPLC (ET16123-1129-P1A) showed that the reaction was not completed. The residue was poured into ice-water (100 mL). The aqueous phase was extracted with EtOAc (3×50 mL). The combined organic phase was washed with brine (3×50 mL), dried with anhydrous Na₂SO₄, filtered, and concentrated in vacuo to afford the title compound N-(2-bromo-4-pyridyl)propanamide (150 mg, crude) as white oil, which was used directly without further purification.

N-(2-bromo-4-pyridyl)benzamide

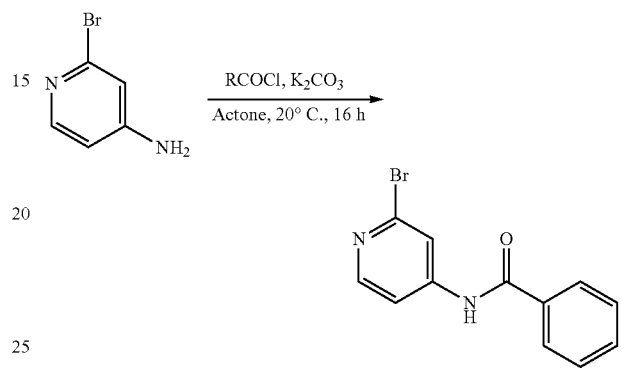

To a stirred solution of 2-bromopyridin-4-amine (100 mg, 578 µmol, 1 eq) in acetone (1 mL) was added K₂CO₃ (239.7 mg, 1.73 mmol, 3 eq). Benzoyl chloride (121.9 mg, 867 µmol, 100.72 µL, 1.5 eq) in acetone (1 mL) was added into the solution. Then the reaction was stirred at 20° C. for 16 hr. TLC (PE:EtOAc=1:1, Rf=0.55) and LCMS showed that the reaction was not completed. The mixture was diluted with DCM (5 mL) and filtrated. The filtrate was concentrate in vacuo. The crude product was purified by prep-TLC (PE:EtOAc=1:1) to afford the title compound N-(2-bromo-4-pyridyl)benzamide (62 mg, 223.73 µmol, 38.71% yield) as a yellow solid N-(2-bromo-4-pyridyl)methanesulfonamide

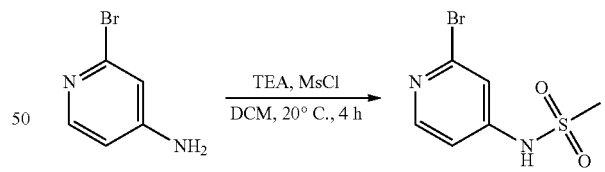

To a mixture of 2-bromopyridin-4-amine (200 mg, 1.16 mmol, 1 eq) in DCM (3 mL) was added TEA (584.9 mg, 5.78 mmol, 804.51 µL, 5 eq). Then methanesulfonyl chloride (132.4 mg, 1.16 mmol, 89.47 µL, 1 eq) was added to the mixture. The mixture was stirred at 20° C. for 4 h. LCMS (ET16123-1141-P1W) showed that the reaction was complete. The residue was poured into ice-water (100 mL). The aqueous phase was extracted with EtOAc (3×50 mL). The combined organic phase was washed with brine (3×50 mL), dried with anhydrous Na₂SO₄, filtered, and concentrated in vacuo to afford the title compound N-(2-bromo-4-pyridyl)methanesulfonamide (300 mg, crude) as white oil, which was used directly without further purification.

General Procedure for 4-bromo-2-methylsulfonyl-aniline

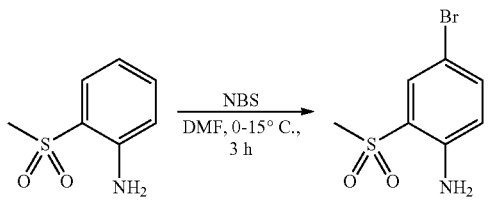

To a solution of 2-methylsulfonylaniline (100 mg, 584.06 µmol, 1 eq) in DMF (2 mL) was added NBS (114.3 mg, 642.11 µmol, 1.10 eq) (in 1 mL DMF) at 0° C. under N₂ atmosphere. Then the reaction was stirred at 15° C. for 3 h. The reaction was quenched with Saturated NH₄Cl (10 mL) at 0° C. and the reaction mixture was extracted with EtOAc (3×10 mL). The combined organic layer was washed with water (3×10 mL) and brine (3×10 mL), dried over Na₂SO₄, filtered, and concentrated. The crude was purified by prep-TLC (SiO₂, PE:EtOAc=3:1) to afford the title compound 4-bromo-2-methylsulfonylaniline (120 mg, 479.78 µmol, 82.15% yield) as a light yellow solid.

3-amino-6-chloro-N-((1-methylpiperidin-4-yl)methyl)picolinamide

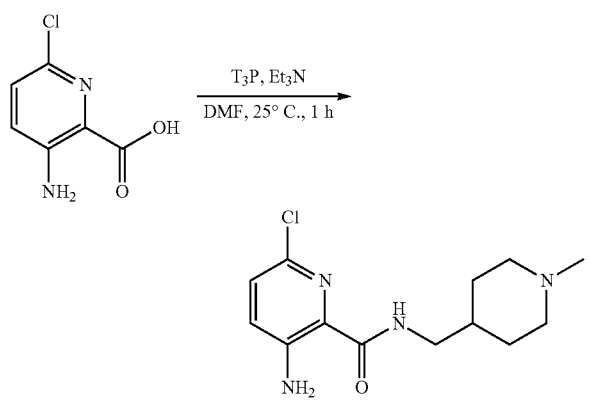

To a mixture of 3-amino-6-chloropicolinic acid (200 mg, 1.16 mmol, 1 eq) in DMF (5 mL) was added T₃P (1.11 g, 1.74 mmol, 1.03 mL, 50% purity, 1.5 eq), Et₃N (351.8 mg, 3.48 mmol, 483.9 µL, 3 eq), (1-methyl-4-piperidyl)methanamine (297.2 mg, 2.32 mmol, 2 eq) in one portion. The mixture was stirred at 25° C. for 1 hour. The reaction was diluted with 20 mL water, extracted with EtOAc (2×20 mL), and the combined organic layer was washed with brine (2×20 mL), dried over Na₂SO₄, filtered, and concentrated in vacuo to afford the title compound 3-amino-6-chloro-N-((1-methylpiperidin-4-yl)methyl)picolinamide (240 mg, crude) as a yellow gum. LC-MS (ES⁺, m/z): 283.1 [(M+H)⁺]

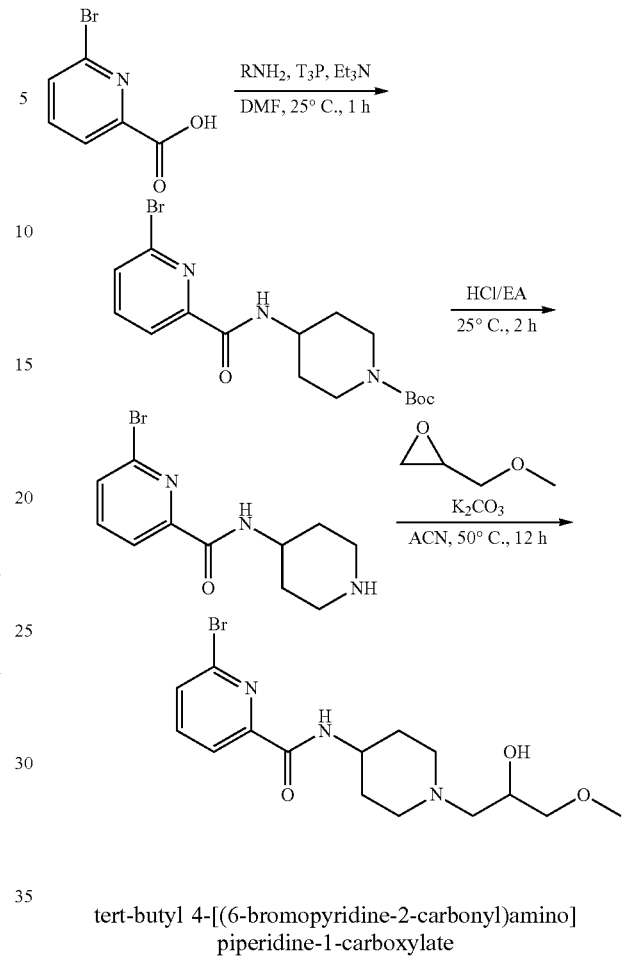

tert-butyl 4-[(6-bromopyridine-2-carbonyl)amino]piperidine-1-carboxylate

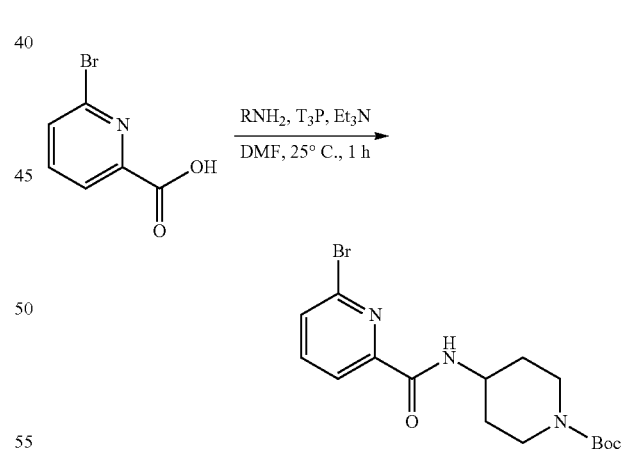

To a mixture of 6-bromopyridine-2-carboxylic acid (1 g, 4.95 mmol, 1 eq) in DMF (15 mL) was added T₃P (4.73 g, 7.43 mmol, 4.42 mL, 50% purity, 1.5 eq), Et₃N (1.5 g, 14.85 mmol, 2.1 mL, 3 eq) and tert-butyl 4-aminopiperidine-1-carboxylate (1.49 g, 7.43 mmol, 1.5 eq). The reaction mixture was stirred at 25° C. for 1 hour. The reaction was diluted with 30 mL water, extracted with EtOAc (2×30 mL), and the combined organic layer was washed with brine (2×30 mL), dried over Na₂SO₄, filtered, and concentrated in vacuo to afford the title compound tert-butyl 4-[(6-bromopyridine-2-carbonyl)amino]piperidine-1-carboxylate (1.8 g, crude) as a yellow oil.

6-bromo-N-(4-piperidyl)pyridine-2-carboxamide

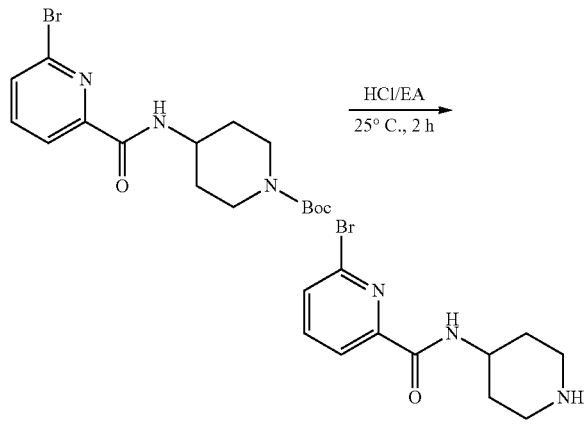

To a solution of compound tert-butyl 4-[(6-bromopyridine-2-carbonyl)amino]piperidine-1-carboxylate (1.8 g, 4.68 mmol, 1 eq) was added HCl/EtOAc (4 M, 30 mL, 25.62 eq) in one portion. The mixture was stirred at 25° C. for 2 hours. The reaction mixture was concentrated directly in vacuo to give crude to afford the title compound 6-bromo-N-(4-piperidyl)pyridine-2-carboxamide (1.2 g, crude) as an off-white solid.

6-bromo-N-[1-(2-hydroxy-3-methoxy-propyl)-4-piperidyl]pyridine-2-carboxamide

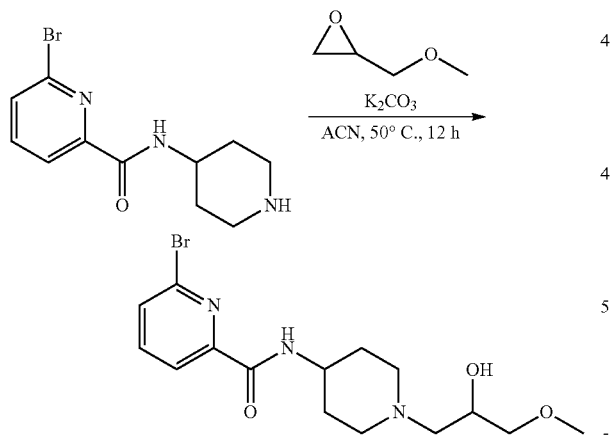

To a mixture of 6-bromo-N-(4-piperidyl)pyridine-2-carboxamide (200 mg, 703.85 µmol, 1 eq) in ACN (6 mL) was added K₂CO₃ (291.8 mg, 2.11 mmol, 3 eq), 2-(methoxymethyl)oxirane (310.1 mg, 3.52 mmol, 313.2 µL, 5 eq) in one portion. The mixture was stirred at 50° C. for 12 hours. The reaction was diluted with 20 mL water, extracted with EtOAc (2×20 mL), and the combined organic layer was washed with brine (2×20 mL), dried over Na₂SO₄, filtered, and concentrated in vacuo. The residue was purified by prep-TLC (SiO₂, DCM:MeOH=20:1) to afford the title compound 6-bromo-N-[1-(2-hydroxy-3-methoxy-propyl)-4-piperidyl]pyridine-2-carboxamide (180 mg, 483.54 µmol, 68.7% yield) as a colorless oil. LC-MS (ES⁺, m/z): 372.1 [(M+H)⁺]

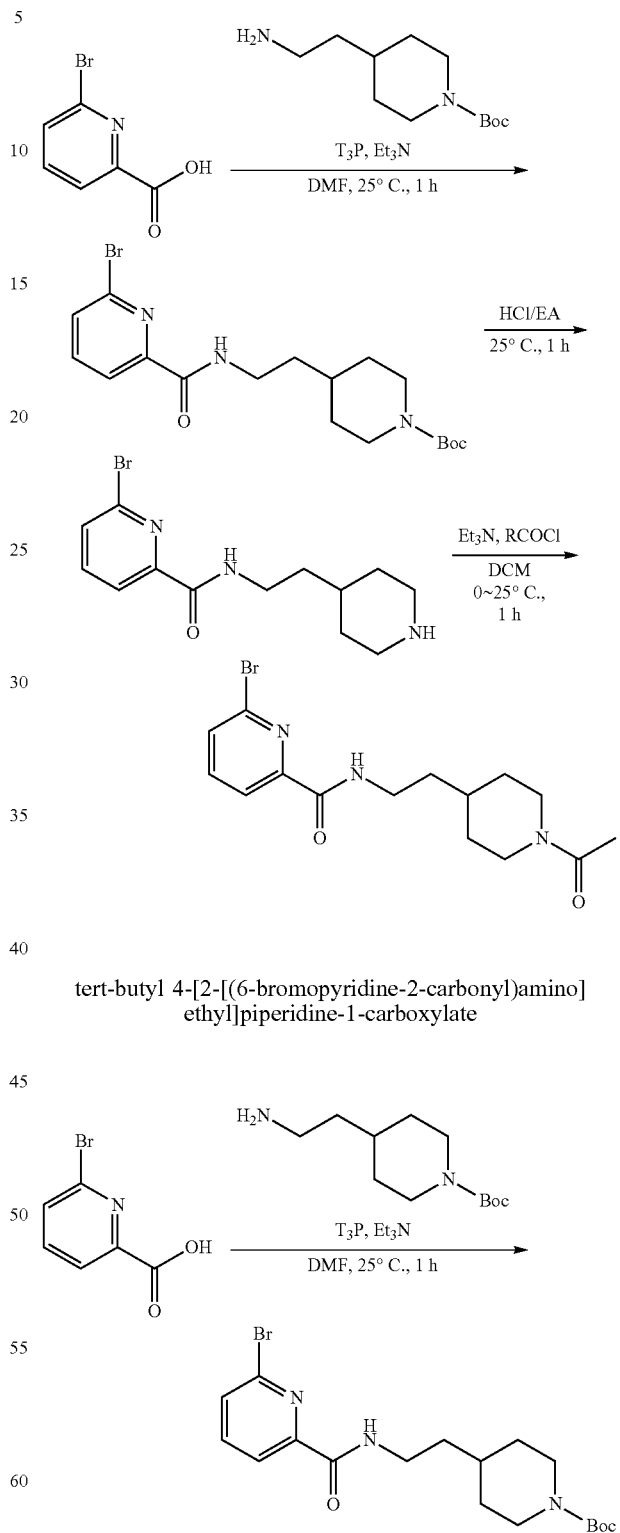

tert-butyl 4-[2-[(6-bromopyridine-2-carbonyl)amino]ethyl]piperidine-1-carboxylate To a solution of compound 6-bromopyridine-2-carboxylic acid (1 g, 4.95 mmol, 1 eq) in DMF (15 mL), Et₃N (1.5 g, 14.85 mmol, 2.1 mL, 3 eq) and T₃P (4.72 g, 7.43 mmol, 4.42 mL, 50% purity, 1.5 eq) and tert-butyl 4-(2-aminoethyl)

piperidine-1-carboxylate (1.36 g, 5.94 mmol, 1.2 eq) was added dropwise. Then the mixture was stirred at 25° C. for 1 h. TLC (DCM:MeOH=10:1) indicated starting material was consumed completely and one new spot formed. The reaction was clean according to TLC. The reaction mixture was quenched by adding H₂O (100 mL), and extracted with EtOAc 120 mL (3×40 mL). The combined organic layers were washed with brine 60 mL, dried over Na₂SO₄, filtered, and concentrated in vacuo to give a residue. The residue was purified by column chromatography (SiO₂, PE:EtOAc=10:1 to 0/1) to afford the title compound tert-butyl 4-[2-[(6-bromopyridine-2-carbonyl)amino]ethyl]piperidine-1-carboxylate (1.7 g, 4.12 mmol, 83.3% yield) as a colorless oil.

6-bromo-N-[2-(4-piperidyl)ethyl]pyridine-2-carboxamide

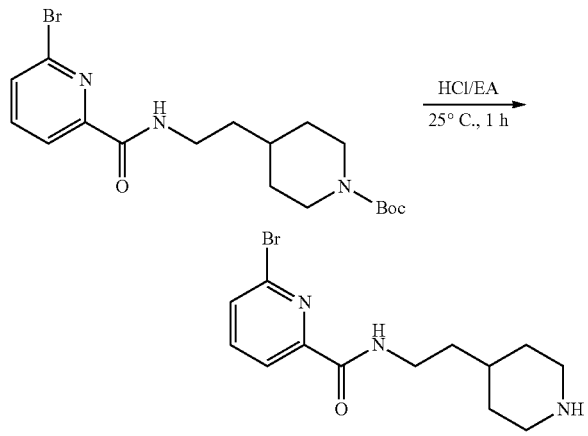

To a solution of compound tert-butyl 4-[2-[(6-bromopyridine-2-carbonyl)amino]ethyl]piperidine-1-carboxylate (1.7 g, 4.12 mmol, 1 eq) in HCl/EtOAc (4 M, 30 mL, 29.10 eq). The mixture was stirred at 25° C. for 1 h. LC-MS showed starting material was consumed completely and one main peak with desired mass was detected. The reaction mixture was concentrated in vacuo to give a residue to afford the title compound 6-bromo-N-[2-(4-piperidyl)ethyl]pyridine-2-carboxamide (1.3 g, crude, HCl) as a white solid. LC-MS (ES⁺, m/z): 12.1 [(M+H)⁺].

N-[2-(1-acetyl-4-piperidyl)ethyl]-6-bromo-pyridine-2-carboxamide

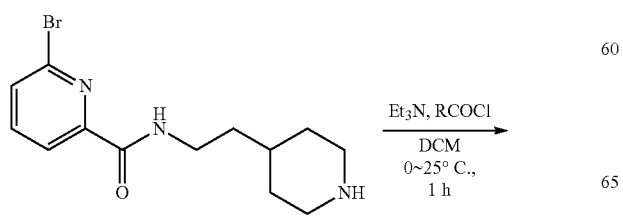

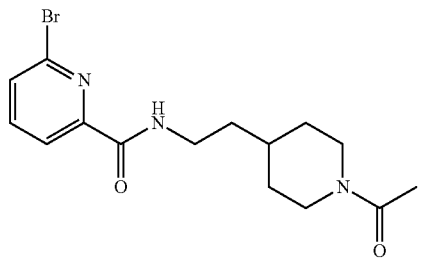

To a mixture of 6-bromo-N-[2-(4-piperidyl)ethyl]pyridine-2-carboxamide (250 mg, 800.76 μmol, 1 eq) in DCM (5 mL) was added TEA (243.1 mg, 2.4 mmol, 334.4 μL, 3 eq) acetyl chloride (125.7 mg, 1.6 mmol, 114.3 μL, 2 eq) at 0° C. under N₂. The reaction was stirred at 25° C. for 1 hour. The reaction was diluted with 30 mL water, extracted with EtOAc (2×30 mL), and the combined organic layer was washed with brine (2×30 mL), dried over Na₂SO₄, filtered, and concentrated in vacuo to afford the title compound N-[2-(1-acetyl-4-piperidyl)ethyl]-6-bromo-pyridine-2-carboxamide (260 mg, crude) as a brown oil.

805 tert-butyl (3R,4R)-4-[(6-bromopyridine-2-carbonyl)amino]-3-fluoro-piperidine-1-carboxylate

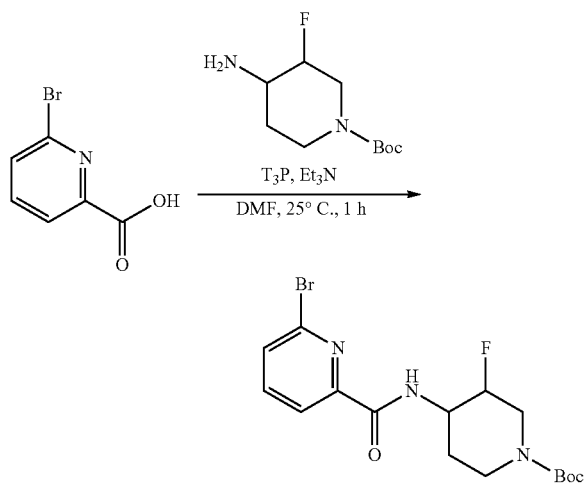

To a mixture of 6-bromopyridine-2-carboxylic acid (250 mg, 1.24 mmol, 1 eq) in DMF (5 mL) was added T₃P (1.18 g, 1.86 mmol, 1.11 mL, 50% purity, 1.5 eq), Et₃N (376.4 mg, 3.72 mmol, 517.8 µL, 3 eq), tert-butyl (3R,4R)-4-amino-3-fluoro-piperidine-1-carboxylate (297.7 mg, 1.36 mmol, 1.1 eq) in one portion. The reaction was stirred at 25° C. for 1 hour. The reaction was diluted with water (20 mL), extracted with EtOAc (2×200 mL), and the combined organic layer was washed with brine (2×20 mL), dried over Na₂SO₄, filtered, and concentrated in vacuo to afford the title compound tert-butyl (3R,4R)-4-[(6-bromopyridine-2-carbonyl)amino]-3-fluoro-piperidine-1-carboxylate (500 mg, crude) as an off-white solid.

6-bromo-N-(3-fluoropiperidin-4-yl)picolinamide

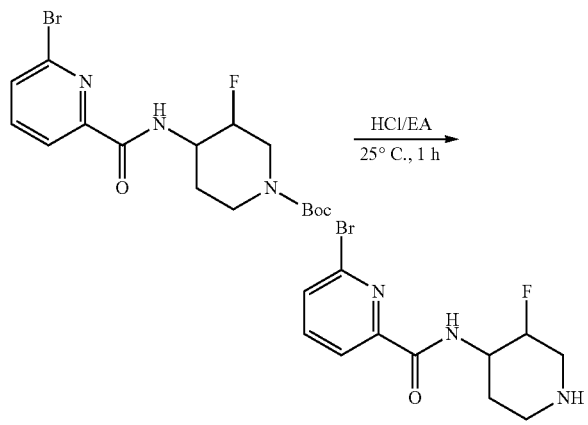

The solution of compound tert-butyl (3R,4R)-4-[(6-bromopyridine-2-carbonyl)amino]-3-fluoro-piperidine-1-carboxylate (250 mg, 621.49 µmol, 1 eq) was added HCl/EtOAc (4 M, 10 mL, 64.36 eq) in one portion. The reaction mixture was stirred at 25° C. for 1 hour. The reaction was concentrated to give crude to afford the title compound

806

6-bromo-N-(3-fluoropiperidin-4-yl)picolinamide (150 mg, crude) as an off-white solid. LC-MS (ES⁺, m/z): 302.0 [(M+H)⁺].

6-bromo-N-[(3R,4R)-3-fluoro-1-methyl-4-piperidyl]pyridine-2-carboxamide

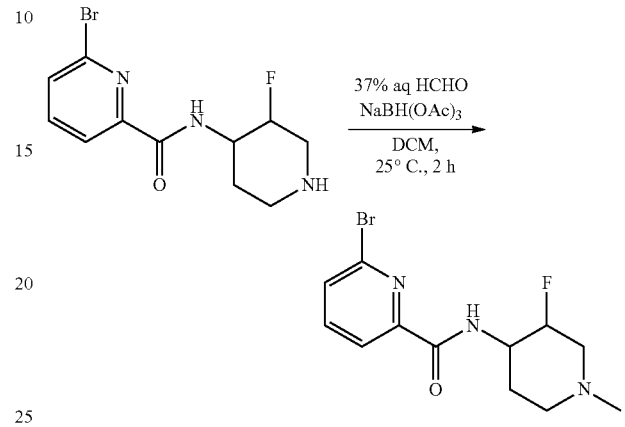

To a mixture of 6-bromo-N-[(3R,4R)-3-fluoro-4-piperidyl]pyridine-2-carboxamide (150 mg, 496.46 µmol, 1 eq) and HCHO (80.6 mg, 992.91 µmol, 73.9 µL, 2 eq) in DCM (3 mL) was added NaBH(OAc)₃ (210.4 mg, 992.91 µmol, 2 eq) in one portion. The mixture was stirred at 25° C. for 2 hours. The reaction was diluted with water (20 mL), extracted with EtOAc (2×20 mL), and the combined organic layer was washed with brine (2×20 mL), dried over Na₂SO₄, filtered, and concentrated in vacuo to afford the title compound (130 mg, crude) as a yellow oil. LC-MS (ES⁺, m/z): 316.0 [(M+H)⁺]

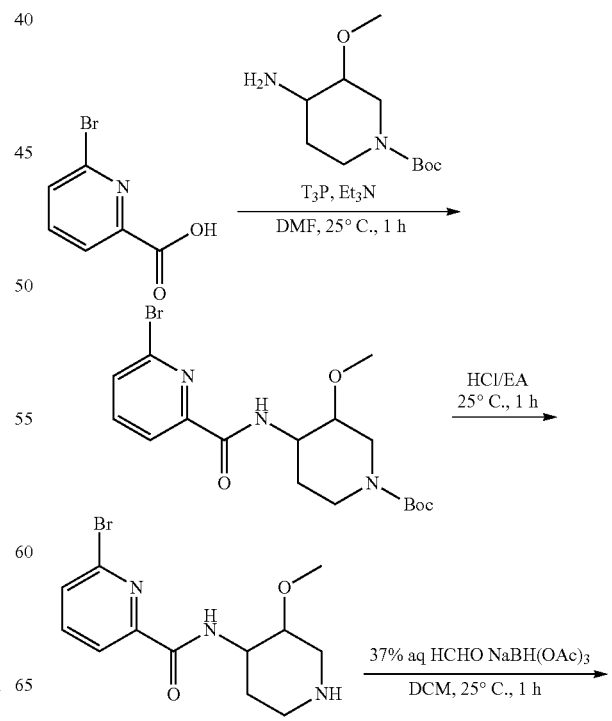

-continued

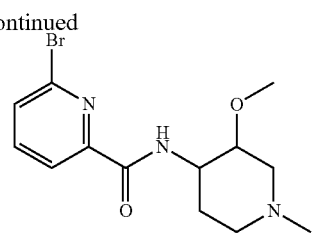

tert-butyl 4-[(6-bromopyridine-2-carbonyl)amino]-3-methoxy-piperidine-1-carboxylate

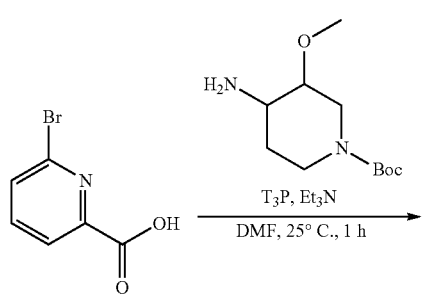

To a solution of 6-bromopyridine-2-carboxylic acid (0.35 g, 1.73 mmol, 1 eq) in DMF (4 mL) was added TEA (876.6 mg, 8.66 mmol, 1.21 mL, 5 eq) and tert-butyl 4-amino-3-methoxy-piperidine-1-carboxylate (518.7 mg, 2.25 mmol, 1.3 eq). Then T$_3$P (1.65 g, 2.6 mmol, 1.55 mL, 50% purity, 1.5 eq) was added to the reaction and the reaction was stirred at 25° C. for 1 h. TLC showed that the reaction was complete. The reaction mixture was diluted with H$_2$O (50 mL). The mixture was extracted with EtOAc (2×50 mL), and the combined organic layers were washed with H$_2$O (2×50 mL) and brine (2×50 mL), dried over anhydrous Na$_2$SO$_4$, filtered, and concentrated in vacuo to give a residue. The residue was purified by column chromatography (SiO$_2$, PE:EtOAc=10:1 to 6:1) to afford the title compound tert-butyl 4-[(6-bromopyridine-2-carbonyl)amino]-3-methoxy-piperidine-1-carboxylate (0.65 g, 1.57 mmol, 90.6% yield) as a yellow oil.

6-bromo-N-(3-methoxy-4-piperidyl)pyridine-2-carboxamide

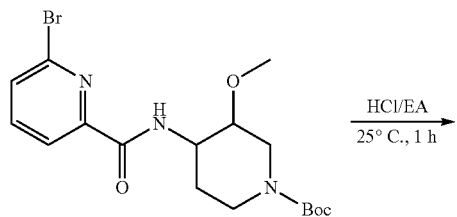

-continued

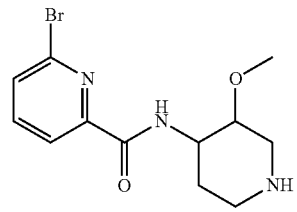

To a solution of tert-butyl 4-[(6-bromopyridine-2-carbonyl)amino]-3-methoxy-piperidine-1-carboxylate (0.3 g, 724.12 μmol, 1 eq) in HCl/EtOAc (4 M, 3 mL, 16.57 eq). The mixture was stirred at 25° C. for 1 h. LCMS showed that the reaction was complete. The reaction mixture was filtered, and concentrated in vacuo to give a residue. The crude product used was directly without further purification to afford the title compound 6-bromo-N-(3-methoxy-4-piperidyl)pyridine-2-carboxamide (0.22 g, crude, HCl) as a white solid. LC-MS (ES$^+$, m/z): 314.0 [(M+H)$^+$]

6-bromo-N-(3-methoxy-1-methyl-4-piperidyl)pyridine-2-carboxamide

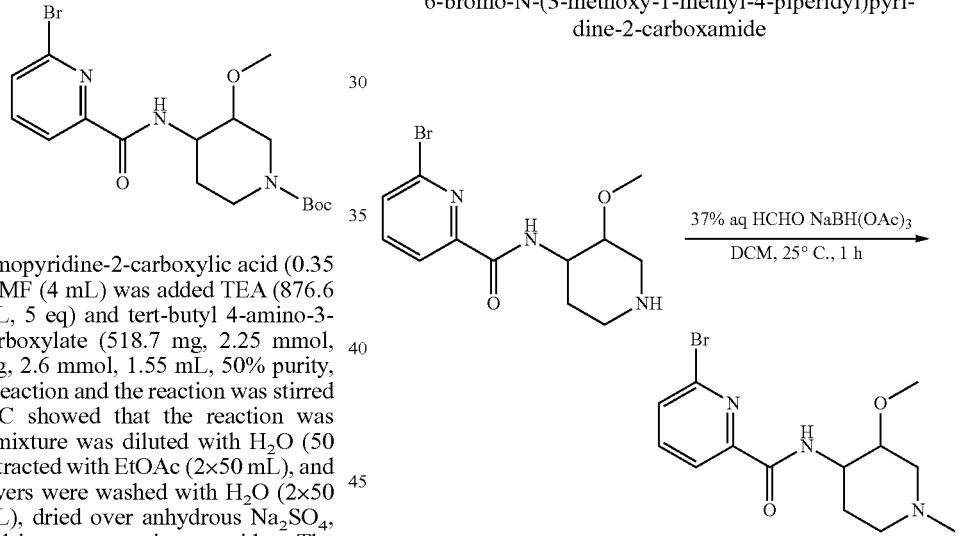

To a solution of 6-bromo-N-(3-methoxy-4-piperidyl)pyridine-2-carboxamide (0.15 g, 477.44 μmol, 1 eq) in DCM (3 mL) was added formaldehyde (77.5 mg, 954.87 μmol, 71.1 μL, 2 eq) and NaBH(OAc)$_3$ (202.4 mg, 954.87 μmol, 2 eq). The mixture was stirred at 25° C. for 1 hr. LCMS showed that the reaction was complete. The reaction mixture was quenched with saturated Na$_2$CO$_3$ (100 mL), extracted with EtOAc (2×50 mL). Then washed with brine (2×50 mL), dried with anhydrous Na$_2$SO$_4$, filtered, and concentrated in vacuo to give a residue. The residue was purified by prep-TLC (SiO$_2$, DCM:MeOH=8:1) to afford the title compound 6-bromo-N-(3-methoxy-1-methyl-4-piperidyl)pyridine-2-carboxamide (0.11 g, 335.16 μmol, 70.2% yield) as a yellow oil. LC-MS (ES$^+$, m/z): 328.0 [(M+H)$^+$]

General Procedure for Preparation of Compound 6-bromo-N-(1-methyl-4-piperidyl)pyridine-2-carboxamide

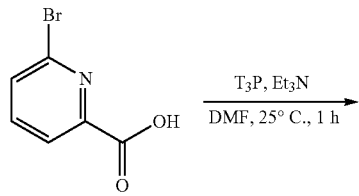

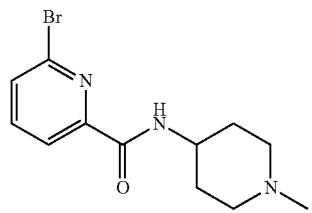

To a solution of 6-bromopyridine-2-carboxylic acid (0.85 g, 4.21 mmol, 1 eq) in DMF (10 mL) was added TEA (2.13 g, 21.04 mmol, 2.93 mL, 5 eq) and 1-methylpiperidin-4-amine (720.7 mg, 6.31 mmol, 1.5 eq). Then $T_3P$ (4.02 g, 6.31 mmol, 3.75 mL, 50% purity, 1.5 eq) was added to the reaction and the reaction was stirred at 25° C. for 1 h. TLC showed that the reaction was complete. The reaction mixture was diluted with $H_2O$ (100 mL). The mixture was extracted with EtOAc (3×100 mL), and the combined organic layers were washed with $H_2O$ (2×100 mL) and brine (2×100 mL), dried over anhydrous $Na_2SO_4$, filtered, and concentrated in vacuo to give a residue which was used directly without further purification to afford the title compound 6-bromo-N-(1-methyl-4-piperidyl)pyridine-2-carboxamide (1.5 g, crude) as a yellow oil.

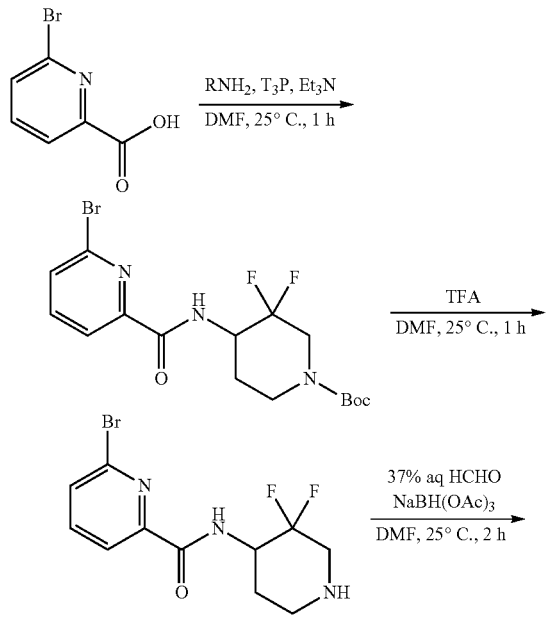

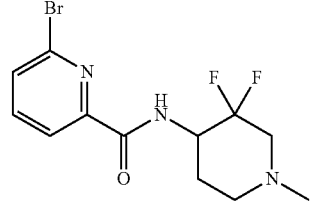

tert-butyl 4-[(6-bromopyridine-2-carbonyl)amino]-3,3-difluoro-piperidine-1-carboxylate

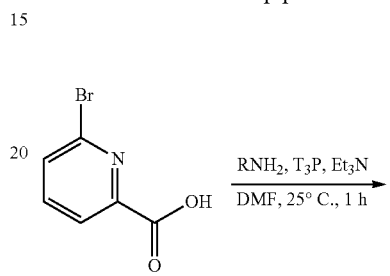

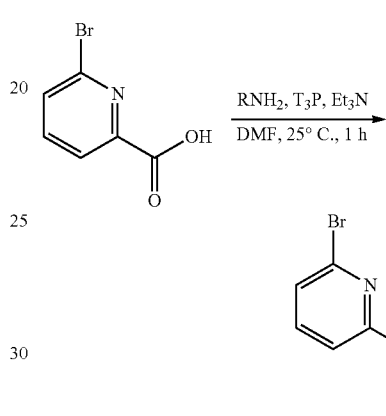

To a solution of compound 6-bromopyridine-2-carboxylic acid (800 mg, 3.96 mmol, 1 eq) in DMF (10 mL) was added drop-wise tert-Butyl 4-amino-3,3-difluoropiperidine-1-carboxylate (1.12 g, 4.75 mmol, 1.2 eq) and $Et_3N$ (1.2 g, 11.88 mmol, 1.65 mL, 3 eq) and $T_3P$ (3.78 g, 5.94 mmol, 3.53 mL, 50% purity, 1.5 eq). The reaction mixture was stirred at 25° C. for 1 hr. TLC showed that the reaction was complete. The reaction mixture was quenched by adding $H_2O$ (60 mL), and extracted with EtOAc (3×40 mL). The combined organic layer was washed with brine (2×30 mL×2), dried over $Na_2SO_4$, filtered, and concentrated to afford the title compound tert-butyl 4-[(6-bromopyridine-2-carbonyl)amino]-3,3-difluoro-piperidine-1-carboxylate (1.5 g, crude) as a yellow oil.

General Procedure for 6-bromo-N-(3,3-difluoro-4-piperidyl)pyridine-2-carboxamide

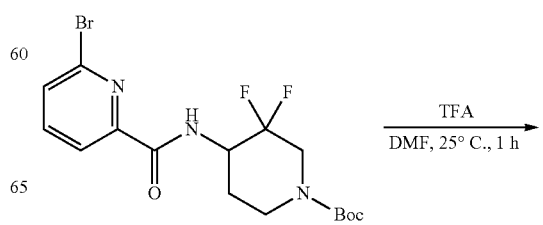

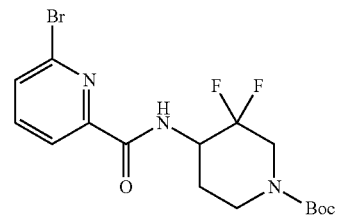

811
-continued

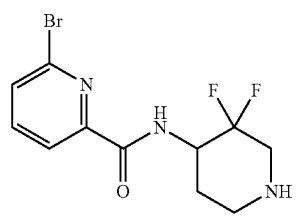

A mixture of tert-butyl 4-[(6-bromopyridine-2-carbonyl)amino]-3,3-difluoro-piperidine-1-carboxylate (1.2 g, 2.86 mmol, 1 eq) in DCM (12 mL) and TFA (4.62 g, 40.52 mmol, 3 mL, 14.19 eq) was added drop-wise. The mixture was stirred at 25° C. for 1 hr. TLC (PE:ethyl aectate=1:1) indicated Reactant 1 was consumed completely and one new spot formed. The reaction mixture was quenched by adding H₂O 50 mL at 0° C., and extracted with DCM (3×40 mL). The combined organic layers were washed with brine 60 mL, dried over Na₂SO₄, filtered, and concentrated in vacuo to give a residue. The residue was purified by column chromatography (SiO₂, PE:EtOAc=1/0 to 0/1) to afford the title compound 6-bromo-N-(3,3-difluoro-4-piperidyl)pyridine-2-carboxamide (800 mg, 2.5 mmol, 87.52% yield) as a yellow solid 6-bromo-N-(3,3-difluoro-1-methyl-4-piperidyl)pyridine-2-carboxamide

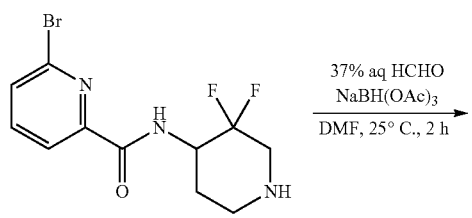

To a solution of compound 6-bromo-N-(3,3-difluoro-4-piperidyl)pyridine-2-carboxamide (100 mg, 312.37 µmol, 1 eq) in DCM (3 mL) was added drop-wise formaldehyde (50.7 mg, 624.74 µmol, 46.51 µL, 2 eq) and NaBH(OAc)₃ (99.3 mg, 468.56 µmol, 1.5 eq). Then the mixture was stirred at 25° C. for 2 h. LCMS showed that the reaction was complete. The reaction mixture was quenched by adding H₂O (30 mL), and extracted with DCM (5×20 mL). The combined organic layer was washed with brine (60 mL), dried over Na₂SO₄, filtered, and concentrated to give a residue which was purified by prep-TLC (PE:EtOAc=1:2) to afford the title compound 6-bromo-N-(3,3-difluoro-1-methyl-4-piperidyl)pyridine-2-carboxamide (80 mg, 239.41 µmol, 76.6% yield) as a colorless oil. LC-MS (ES⁺, m/z): 334.0 [(M+H)⁺]

812
2-chloro-N-((3R,4S)-3-fluoro-1-methylpiperidin-4-yl)pyrimidine-4-carboxamide

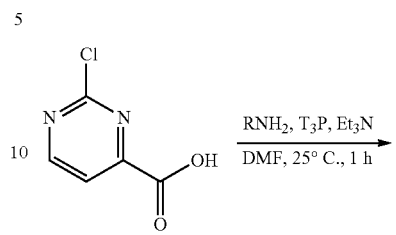

To a solution of compound 2-chloropyrimidine-4-carboxylic acid (150 mg, 946.12 µmol, 1 eq) in DMF (3 mL) was added dropwise (3R,4S)-3-fluoro-1-methyl-piperidin-4-amine (239.3 mg, 1.42 mmol, 1.5 eq, HCl) and Et₃N (287.2 mg, 2.84 mmol, 395.07 µL, 3 eq) and T₃P (903.1 mg, 1.42 mmol, 844.03 µL, 50% purity, 1.5 eq). The reaction mixture was stirred at 25° C. for 1 hr. LCMS showed that the reaction was complete. The reaction mixture was quenched by adding H₂O (40 mL), and extracted with EtOAc (6×15 mL). The combined organic layer was washed with brine (3×20 mL), dried over Na₂SO₄, filtered, and concentrated to afford the title compound 2-chloro-N-((3R,4S)-3-fluoro-1-methylpiperidin-4-yl)pyrimidine-4-carboxamide (130 mg, crude) as a yellow solid. LC-MS (ES⁺, m/z): 273.1 [(M+H)⁺]

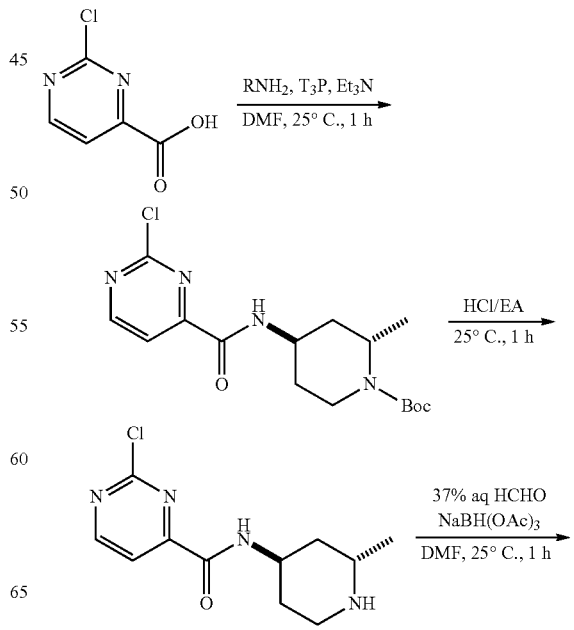

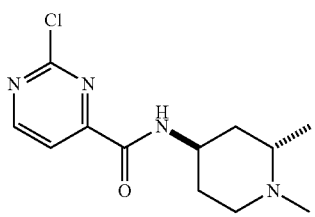

tert-butyl (2S,4R)-4-[(2-chloropyrimidine-4-carbonyl)amino]-2-methyl-piperidine-1-carboxylate

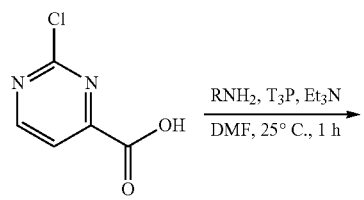

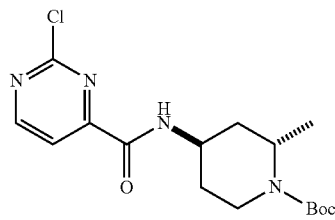

To a solution of compound 2-chloropyrimidine-4-carboxylic acid (250 mg, 1.58 mmol, 1 eq) in DMF (4 mL) was added dropwise tert-butyl 4-amino-2-methyl-piperidine-1-carboxylate (506.9 mg, 2.37 mmol, 1.5 eq) and Et$_3$N (478.7 mg, 4.73 mmol, 658.44 µL, 3 eq) and T$_3$P (1.51 g, 2.37 mmol, 1.41 mL, 50% purity, 1.5 eq). The reaction mixture was stirred at 25° C. for 1 hr. TLC showed that the reaction was complete. The reaction mixture was quenched by adding H$_2$O (40 mL), and extracted with EtOAc (3×20 mL). The combined organic layer was washed with brine (2×20 mL), dried over Na$_2$SO$_4$, filtered, and concentrated to give a residue. The residue was purified by prep-TLC (SiO$_2$, PE:EtOAc=2:1) to afford the title compound tert-butyl (2S,4R)-4-[(2-chloropyrimidine-4-carbonyl)amino]-2-methyl-piperidine-1-carboxylate (500 mg, 1.41 mmol, 89.4% yield) as a colourless oil.

2-chloro-N-[(2S,4R)-2-methyl-4-piperidyl]pyrimidine-4-carboxamide

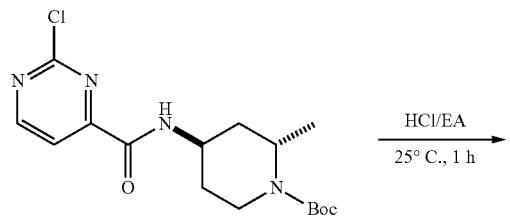

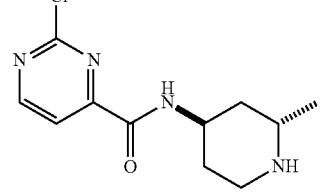

To a solution of compound tert-butyl (2S,4R)-4-[(2-chloropyrimidine-4-carbonyl)amino]-2-methyl-piperidine-1-carboxylate (450 mg, 1.27 mmol, 1 eq) in HCl/EtOAc (4 M, 20 mL, 63.08 eq). Then the mixture was stirred at 25° C. for 1 h. LCMS showed that the reaction was complete. The reaction mixture was concentrated to afford the title compound 2-chloro-N-[(2S,4R)-2-methyl-4-piperidyl]pyrimidine-4-carboxamide (350 mg, crude, HCl) as a white solid. LC-MS (ES$^+$, m/z): 255.1 [(M+H)$^+$]

2-chloro-N-[(2S,4R)-1,2-dimethyl-4-piperidyl]pyrimidine-4-carboxamide

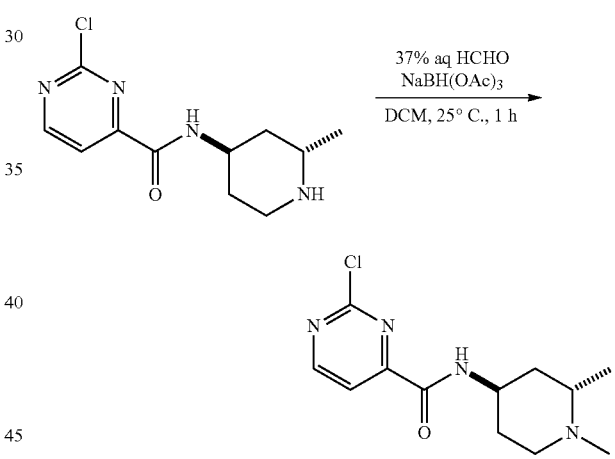

To a solution of compound 2-chloro-N-[(2S,4R)-2-methyl-4-piperidyl]pyrimidine-4-carboxamide (200 mg, 686.87 µmol, 1 eq, HCl) and formaldehyde (111.5 mg, 1.37 mmol, 102.28 µL, 2 eq) in DCM (3 mL) was added NaBH(OAc)$_3$ (218.4 mg, 1.03 mmol, 1.5 eq) in one portion under N$_2$. Then the mixture was stirred at 25° C. for 1 h. TLC showed that the reaction was complete. The reaction mixture was quenched by adding saturated Na$_2$CO$_3$ (30 mL) at 0° C., and extracted with EtOAc (3×20 mL). The combined organic layer was washed with brine (2×20 mL), dried over Na$_2$SO$_4$, filtered, and concentrated to give a residue which was purified by prep-TLC (DCM:MeOH=10:1) to afford the title compound 2-chloro-N-[(2S,4R)-1,2-dimethyl-4-piperidyl]pyrimidine-4-carboxamide (160 mg, 595.37 µmol, 86.7% yield) as a yellow oil. LC-MS (ES$^+$, m/z): 269.1 [(M+H)$^+$]

815 tert-butyl N-[4-(2-oxa-6-azaspiro[3.3]heptan-6-yl) cyclohexyl]carbamate

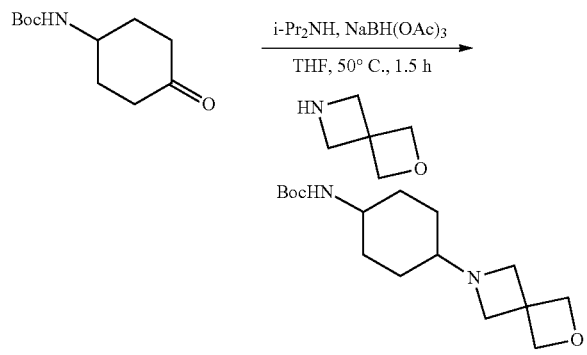

To a solution of tert-butyl N-(4-oxocyclohexyl)carbamate (0.4 g, 1.88 mmol, 400 μL, 1 eq) and 2-oxa-6-azaspiro[3.3] heptane;oxalic acid (1.06 g, 5.63 mmol, 3 eq) in THF (5 mL) was added i-Pr$_2$NH (1.9 g, 18.76 mmol, 2.65 mL, 10 eq). Then the mixture was stirred at 50° C. for 0.5 h. Then NaBH(OAc)$_3$ (1.19 g, 5.63 mmol, 3 eq) was added and the reaction was heated to 50° C. under N$_2$ and stirred for 1 h. TLC showed that the reaction was complete. The reaction mixture was diluted with saturated Na$_2$CO$_3$ to adjust to pH=8. The mixture was extracted with EtOAc (2×50 mL), and the combined organic layers were washed with H$_2$O (2×50 mL) and brine (2×50 mL), dried over anhydrous Na$_2$SO$_4$, filtered, and concentrated in vacuo to give a residue. N/A (used the crude product directly) to afford the title compound tert-butyl N-[4-(2-oxa-6-azaspiro[3.3]heptan-6-yl)cyclohexyl]carbamate (0.6 g, crude) as a white oil.

4-(2-oxa-6-azaspiro[3.3]heptan-6-yl)cyclohexanamine

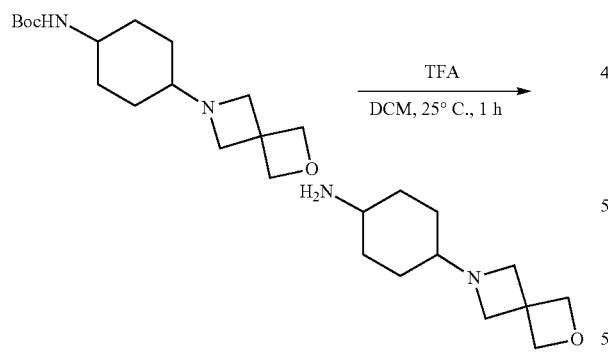

To a solution of tert-butyl N-[4-(2-oxa-6-azaspiro[3.3] heptan-6-yl)cyclohexyl]carbamate (0.5 g, 1.69 mmol, 1 eq) in DCM (2 mL) was added TFA (770 mg, 6.75 mmol, 0.5 mL, 4 eq). The mixture was stirred at 25° C. for 1 hr. TLC showed that the reaction was complete. The reaction mixture was diluted with saturated Na$_2$CO$_3$ to adjust to pH=8. The mixture was extracted with EtOAc (2×50 mL), and the combined organic layers were washed with H$_2$O (2×50 mL) and brine (2×50 mL), dried over anhydrous Na$_2$SO$_4$, filtered, and concentrated in vacuo to give a residue. N/A (used the crude product directly) to afford the title compound 4-(2-oxa-6-azaspiro[3.3]heptan-6-yl)cyclohexanamine (0.7 g, crude) as a white oil.

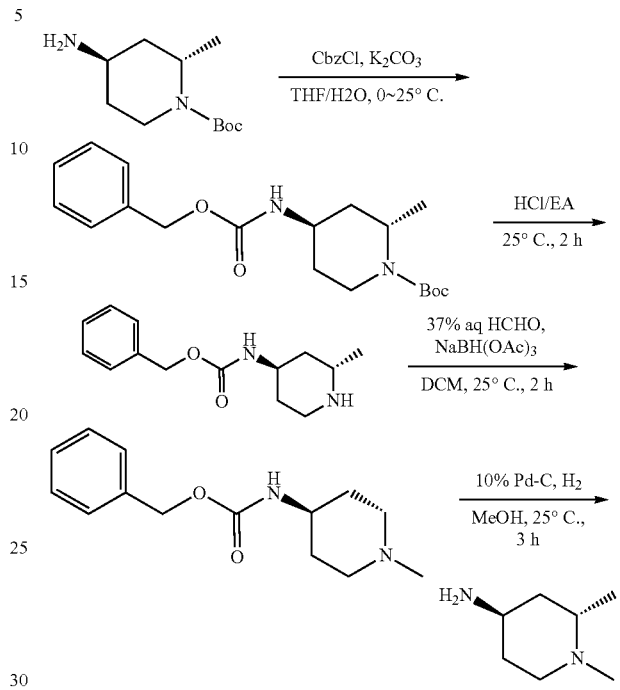

tert-butyl (2S,4R)-4-(benzyloxycarbonylamino)-2-methyl-piperidine-1-carboxylate

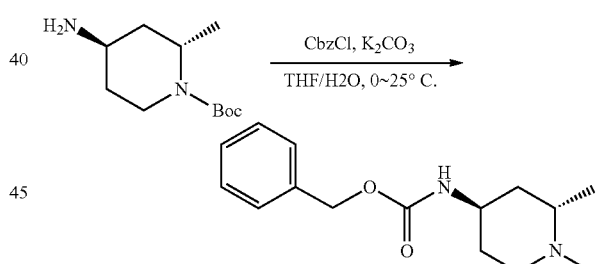

To a mixture of tert-butyl (2S,4R)-4-amino-2-methyl-piperidine-1-carboxylate (400 mg, 1.87 mmol, 1 eq) and K$_2$CO$_3$ (386.9 mg, 2.8 mmol, 1.5 eq) in THF (7 mL) H$_2$O (2 mL) was added benzyl carbonochloridate (350.3 mg, 2.05 mmol, 291.88 μL, 1.1 eq) in one portion at 0° C. under N$_2$. The mixture was stirred at 25° C. for 1 hour. The reaction was diluted with 20 mL water, extracted with EtOAc (2×20 mL), and the combined organic layer was washed with brine (2×20 mL), dried over Na$_2$SO$_4$, filtered, and concentrated in vacuo. The residue was purified by prep-TLC (SiO$_2$, PE:EtOAc=1:1) to afford the title compound tert-butyl (2S,4R)-4-(benzyloxycarbonylamino)-2-methyl-piperidine-1-carboxylate (440 mg, 1.26 mmol, 67.66% yield) as a colourless oil. no spectra data for this compound, just by TLC.

817
benzyl N-[(2S,4R)-2-methyl-4-piperidyl]carbamate

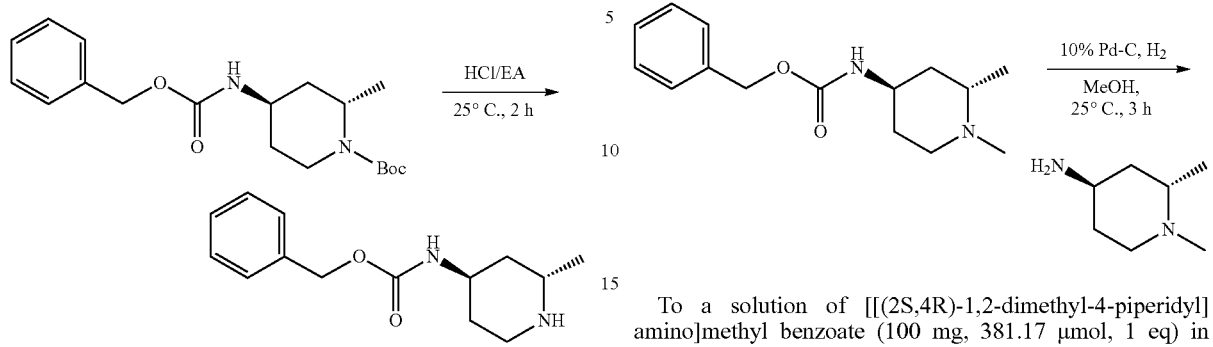

The solution of tert-butyl (2S,4R)-4-(benzyloxycarbonylamino)-2-methyl-piperidine-1-carboxylate (200 mg, 573.99 μmol, 1 eq) in HCl/EtOAc (4 M, 4 mL, 27.87 eq) was stirred at 25° C. for 2 hour. TLC showed that the reaction was complete. The reaction was diluted with 20 mL EtOAc, concentrated directly to give crude to afford the title compound benzyl N-[(2S,4R)-2-methyl-4-piperidyl]carbamate (200 mg, crude, HCl) as an off-white solid, no spectra data for this compound, just by TLC (SiO$_2$, I$_2$, PE:EtOAc=1:1, Rf SM=0.63, Rf TM=0.00)

benzyl N-[(2S,4R)-1,2-dimethyl-4-piperidyl]carbamate

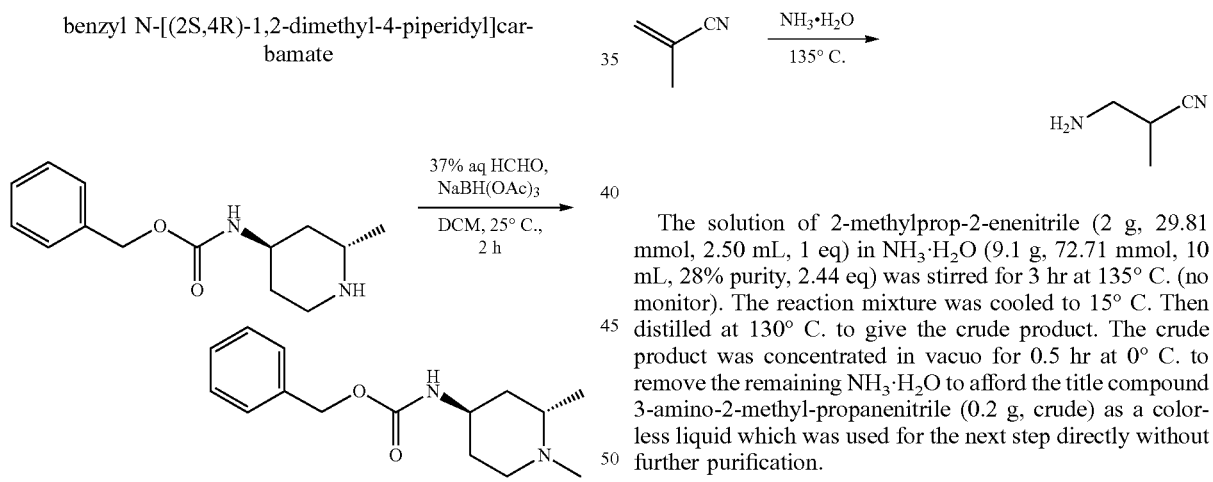

To a mixture of benzyl N-[(2S,4R)-2-methyl-4-piperidyl]carbamate (200 mg, 805.41 μmol, 1 eq) in DCM (4 mL) was added HCHO (196.1 mg, 2.42 mmol, 179.89 μL, 3 eq) NaBH(OAc)$_3$ (512.1 mg, 2.42 mmol, 3 eq). The mixture was stirred at 25° C. for 2 hour. The reaction was diluted with 20 mL water, adjust to pH=9 with saturated aq. Na$_2$CO$_3$, extracted with EtOAc (2×20 mL), and the combined organic layer was washed with brine (2×20 mL), dried over Na$_2$SO$_4$, filtered, and concentrated in vacuo to afford the title compound benzyl N-[(2S,4R)-1,2-dimethyl-4-piperidyl]carbamate (100 mg, 381.18 μmol, 47.33% yield) as a colourless oil. LC-MS (ES$^+$, m/z): 263.2 [(M+H)$^+$]

818
(2S,4R)-1,2-dimethylpiperidin-4-amine

To a solution of [[(2S,4R)-1,2-dimethyl-4-piperidyl]amino]methyl benzoate (100 mg, 381.17 μmol, 1 eq) in MeOH (3 mL) was added 10% Pd—C (138.9 mg, 114.35 μmol, 10% purity, 0.3 eq). The suspension was degassed in vacuo and purged with H$_2$ several times. The mixture was stirred under H$_2$ (768.40 ug, 381.17 μmol, 1 eq) (15 psi) at 25° C. for 3 hours. The reaction mixture was diluted with 10 mL MeOH, heated to 50° C. and filtered to give filtrate. The filtrate was concentrated to give crude to afford the title compound (2S,4R)-1,2-dimethylpiperidin-4-amine (30 mg, crude) as a colourless gum. no spectra data for this compound, just by TLC (SiO$_2$, I$_2$, DCM:MeOH=10:1, Rf SM=0.58, Rf TM 3-amino-2-methyl-propanenitrile The solution of 2-methylprop-2-enenitrile (2 g, 29.81 mmol, 2.50 mL, 1 eq) in NH$_3$·H$_2$O (9.1 g, 72.71 mmol, 10 mL, 28% purity, 2.44 eq) was stirred for 3 hr at 135° C. (no monitor). The reaction mixture was cooled to 15° C. Then distilled at 130° C. to give the crude product. The crude product was concentrated in vacuo for 0.5 hr at 0° C. to remove the remaining NH$_3$·H$_2$O to afford the title compound 3-amino-2-methyl-propanenitrile (0.2 g, crude) as a colorless liquid which was used for the next step directly without further purification.

tert-butyl N-[1-(2-hydroxyethyl)-4-piperidyl]carbamate

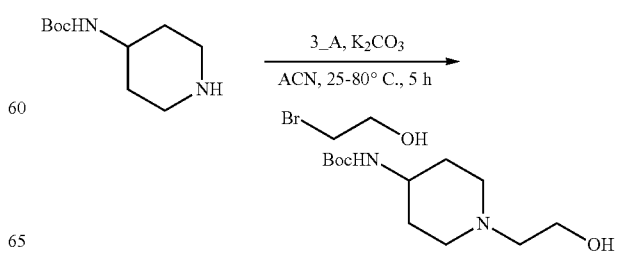

To a solution of tert-butyl N-(4-piperidyl)carbamate (5 g, 24.97 mmol, 1 eq) in ACN (100 mL) was added K₂CO₃ (27.6 g, 199.72 mmol, 8 eq) and 2-bromoethanol (9.36 g, 74.9 mmol, 5.32 mL, 3 eq) at 25° C. under N₂. The reaction mixture was stirred at 80° C. for 5 h. TLC showed that the reaction was complete. The reaction mixture was filtered, and the filtrated cake was washed with DCM (3×30 mL). The combined filtrate was concentrated to afford the title compound tert-butyl N-[1-(2-hydroxyethyl)-4-piperidyl] carbamate (9 g, crude) as a yellow oil. LC-MS (ES⁺, m/z): 245.3 [(M+H)⁺].

2-(4-amino-1-piperidyl)ethanol

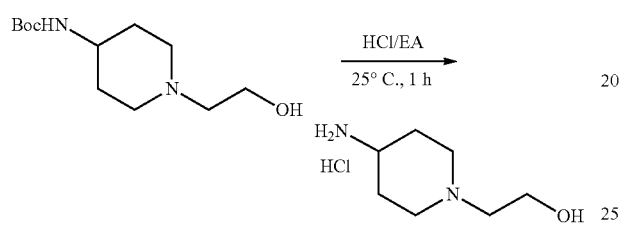

The solution of tert-butyl N-[1-(2-hydroxyethyl)-4-piperidyl]carbamate (4.5 g, 18.42 mmol, 1 eq) in 4N HCl/EtOAc (18.42 mmol, 45 mL, 4% purity, 1 eq) and the mixture was stirred at 25° C. for 1 h. LCMS showed that the reaction was complete. The reaction mixture was concentrated in vacuo to afford the title compound 2-(4-amino-1-piperidyl)ethanol (5 g, crude, 2HCl) as a yellow solid. LC-MS (ES⁺, m/z): 217.2 [(M+H)⁺].

3-amino-6-chloro-N-[1-(2-hydroxyethyl)-4-piperidyl]pyridine-2-carboxamide

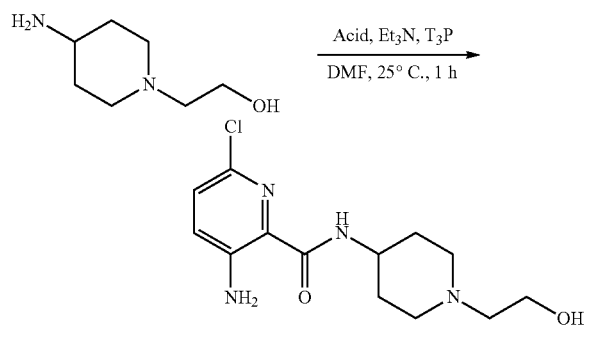

To a solution of 3-amino-6-chloro-pyridine-2-carboxylic acid (1 g, 5.79 mmol, 1 eq) and 2-(4-amino-1-piperidyl)ethanol (3.15 g, 14.49 mmol, 2.5 eq, 2HCl) in DMF (10 mL) was added T₃P (5.53 g, 8.69 mmol, 5.17 mL, 50% purity, 1.5 eq) and Et₃N (2.93 g, 28.97 mmol, 4.03 mL, 5 eq). The resulting reaction mixture was stirred at 25° C. for 1 h. TLC showed that the reaction was complete. The reaction mixture was poured into water (30 mL), extracted with EtOAc (2×30 mL). The combined organic layer was washed with brine (2×30 mL), dried over anhydrous Na₂SO₄, filtered, and concentrated in vacuo to afford the title compound 3-amino-6-chloro-N-[1-(2-hydroxyethyl)-4-piperidyl]pyridine-2-carboxamide (4 g, crude) as a white solid.
LC-MS (ES⁺, m/z): 299.2 [(M+H)⁺].

7-bromo-N-methyl-quinoline-2-carboxamide

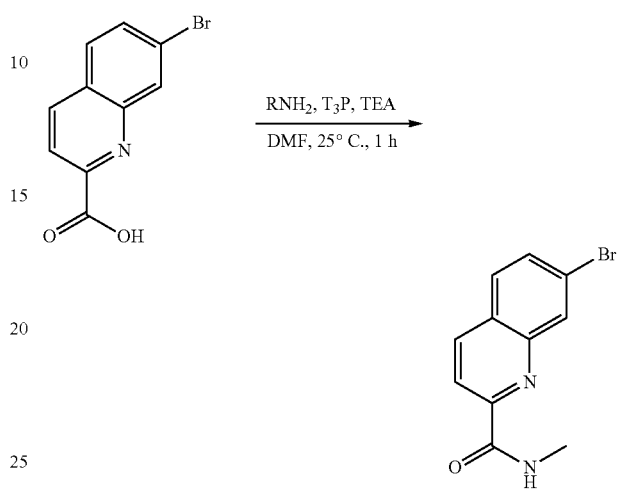

To a solution of 7-bromoquinoline-2-carboxylic acid (200 mg, 793.45 μmol, 1 eq), MeNH₂ (80.4 mg, 1.19 mmol, 1.5 eq, HCl) in DMF (2 mL) was added TEA (401.5 mg, 3.97 mmol, 552.19 μL, 5 eq) and T₃P (757.38 mg, 1.19 mmol, 707.83 μL, 50% purity, 1.5 eq) at 25° C. The reaction mixture was stirred at 25° C. for 1 h. The reaction mixture was poured into H₂O (15 mL) and the aqueous phase was extracted with EtOAc (3×15 mL). The combined organic layer was washed with brine (3×15 mL), dried with anhydrous Na₂SO₄, filtered, and concentrated in vacuo to afford the title compound 7-bromo-N-methyl-quinoline-2-carboxamide (200 mg, crude) as a yellow solid. LCMS (ES⁺, m/z): 265.0, 267.0 [(M+H)⁺]

6-bromo-1-methyl-quinolin-4-one (SM 55A)

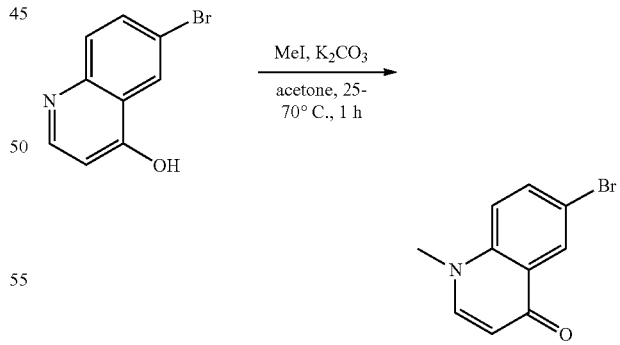

To a solution of 6-bromoquinolin-4-ol (200 mg, 892.64 μmol, 384.62 μL, 1 eq) in acetone (5 mL) was added K₂CO₃ (370.1 mg, 2.68 mmol, 3 eq) and MeI (253.4 mg, 1.79 mmol, 111.14 μL, 2 eq) at 25° C. The reaction mixture was stirred at 70° C. for 1 h. The reaction mixture was concentrated in vacuo to give the residue. The residue was purified by prep-TLC to afford the title compound 6-bromo-1-methyl-quinolin-4-one (150 mg, 630.04 μmol, 70.58% yield) as a white solid and confirmed by 1H NMR, C NMR, HSQC. 1H NMR (400 MHz, DMSO-d6) δ=8.24 (d, J=2.4 Hz, 1H), 8.00 (d, J=7.6 Hz, 1H), 7.90 (dd, J=2.4, 9.2 Hz, 1H), 7.66 (d, J=9.2 Hz, 1H), 6.09 (d, J=7.6 Hz, 1H), 3.81 (s, 3H), 6-bromo-4-methoxy-quinoline

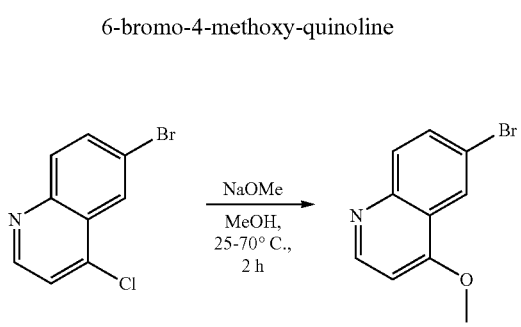

To a solution of 6-bromo-4-chloro-quinoline (200 mg, 824.74 μmol, 384.62 μL, 1 eq) in MeOH (6 mL) was added NaOMe (445.6 mg, 8.25 mmol, 10 eq) at 25° C. The reaction mixture was stirred at 70° C. for 2 h. The reaction mixture was concentrated in vacuo to give the residue. The residue was poured into H$_2$O (6 mL) and the aqueous phase was extracted with EtOAc (3×10 mL). The combined organic layer was washed with brine (3×10 mL), dried over anhydrous Na$_2$SO$_4$, filtered, and concentrated in vacuo to afford the title compound 6-bromo-4-methoxy-quinoline (180 mg, crude) as a white solid, confirmed by 1H NMR. TLC (PE:EtOAc=0:1, SM=0.86, TM=0.20) 1H NMR (400 MHz, DMSO-d6) δ=8.78 (d, J=5.6 Hz, 1H), 8.25 (d, J=2.0 Hz, 1H), 7.93-7.83 (m, 2H), 7.09 (d, J=5.6 Hz, 1H), 4.05 (s, 3H)

7-bromo-2-methoxy-quinoline

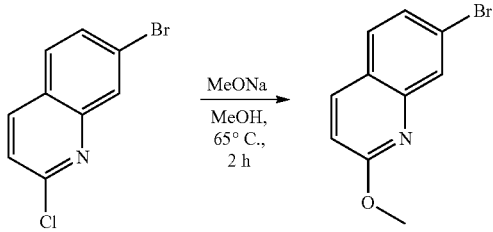

To a solution of 7-bromo-2-chloro-quinoline (1 g, 4.12 mmol, 1 eq) in MeOH (10 mL) was added NaOMe (2.23 g, 41.24 mmol, 10 eq). The reaction mixture was heated to 65° C. and stirred at 65° C. for 2 h. The reaction mixture was concentrated in vacuo to give the residue. The residue was poured into H$_2$O (20 mL) and the aqueous phase was extracted with EtOAc (3×10 mL). The combined organic layer was washed with brine (3×10 mL), dried over anhydrous Na$_2$SO$_4$, filtered, and concentrated in vacuo to afford the title compound 7-bromo-2-methoxy-quinoline (0.9 g, crude) as a white solid, confirmed by 1H NMR. TLC (PE:EtOAc=1:0, SM=0.20, TM=0.30) 1H NMR (400 MHz, DMSO-d6) δ=8.27 (d, J=8.8 Hz, 1H), 7.96 (d, J=2.0 Hz, 1H), 7.86 (d, J=8.8 Hz, 1H), 7.59 (dd, J=2.0, 8.4 Hz, 1H), 7.07 (d, J=8.8 Hz, 1H), 3.98 (s, 3H)

Step 1 6-bromo-N-phenyl-quinolin-4-amine

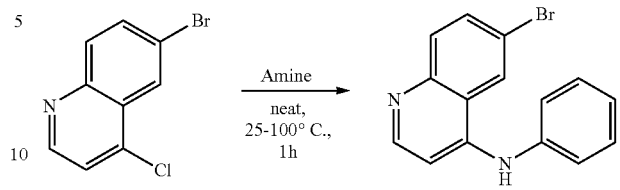

6-bromo-4-chloro-quinoline (0.3 g, 1.24 mmol, 1 eq) was dissolved in aniline (3.06 g, 32.86 mmol, 3 mL, 26.56 eq) in a 10 mL single-necked round bottom flask at 25° C. The mixture was stirred reflux at 100° C. for 1 h. The reaction was diluted with 10 mL EtOAc and poured into 20 mL water and extracted with EtOAc (3×15 mL), washed with brine (3×15 mL), dried over anhydrous Na$_2$SO$_4$, filtered, and concentrated in vacuo. The residue was purified by column chromatography (SiO$_2$, PE:EtOAc=10:1 to 1/1) to afford the title compound 6-bromo-N-phenyl-quinolin-4-amine (0.3 g, 1 mmol, 81.06% yield) as a brown solid. LC-MS (ES$^+$, m/z): 298.9/300.8 [(M+H)$^+$].

7-bromo-N-phenyl-quinazolin-2-amine

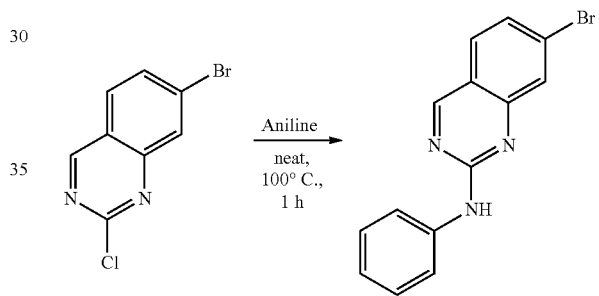

To a solution of 7-bromo-2-chloro-quinazoline (0.3 g, 1.23 mmol, 1 eq) in aniline (3.06 g, 32.86 mmol, 3 mL, 26.67 eq) was stirred at 100° C. for 1 hr. TLC (PE:EtOAc=1:1, SM Rf=0.58, TM Rf=0.51) showed that the reaction was complete. The reaction was diluted with ~10 mL EtOAc and poured into 20 mL water and extracted with EtOAc (3×20 mL), washed with brine (3×20 mL), dried over anhydrous Na$_2$SO$_4$, filtered, and concentrated in vacuo. The residue was washed with PE (3×15 mL) to afford the title compound 7-bromo-N-phenyl-quinazolin-2-amine (0.25 g, crude) as a yellow solid. LC-MS (ES$^+$, m/z): 300.1/302.1 [(M+H)$^+$]

Route 3f

Step 1 7-bromo-N-methyl-isoquinolin-1-amine

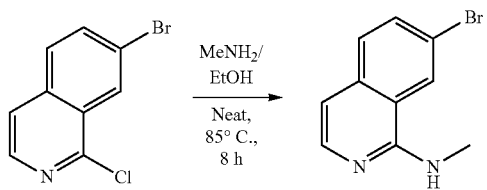

To a solution of 7-bromo-1-chloro-isoquinoline (0.3 g, 1.24 mmol, 1 eq) in MeNH$_2$ (116.4 mg, 1.24 mmol, 2 mL, 33% purity in EtOH, 1 eq) and the mixture was stirred at 85° C. for 8 hr. TLC (PE:EtOAc=4:1, SM Rf=0.53, TM Rf=0.25) showed that the reaction was complete. The reaction was concentrate in vacuo. The residue was purified by column chromatography (SiO$_2$, PE:EtOAc=10:1 to 4:1) to afford the title compound 7-bromo-N-methyl-isoquinolin-1-amine (0.24 g, 1.01 mmol, 81.82% yield) as a yellow solid.

7-Bromo-2-methoxy-quinazoline

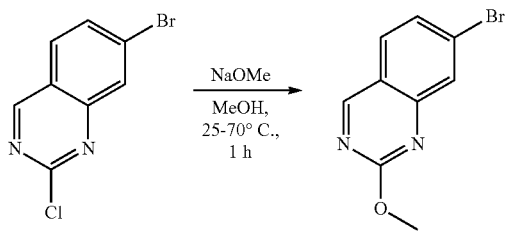

To a solution of 7-bromo-2-chloro-quinazoline (0.3 g, 1.23 mmol, 1 eq) in MeOH (3 mL) was added NaOMe (0.15 g, 2.78 mmol, 2.25 eq) at 25° C. Then stirred at 70° C. for 1 hr. TLC (PE:EtOAc=3:1, SM Rf=0.51, TM Rf=0.45) showed that the reaction was complete. The reaction was poured into ~20 mL water. The mixture was extracted with EtOAc (3×10 mL), washed with brine (3×10 mL), dried over by anhydrous Na$_2$SO$_4$, filtered, and concentrated in vacuo to afford the title compound 7-Bromo-2-methoxy-quinazoline (0.23 g, crude) as a yellow solid.

7-bromo-N,N-dimethyl-isoquinolin-1-amine

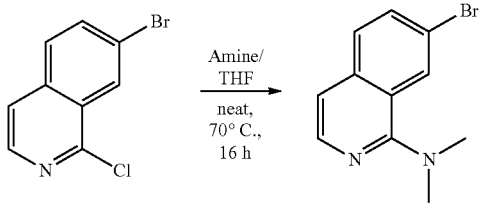

To a solution of 7-bromo-1-chloro-isoquinoline (0.3 g, 1.24 mmol, 1 eq) in N-methyl methan amine (2 M in THF, 6 mL, 9.70 eq) and the mixture was stirred at 70° C. for 8 hr. LCMS showed some starting material remained. Then stirred at 70° C. for further 8 h, LCMS showed that the reaction was complete. The reaction was concentrated in vacuo. The residue was purified by prep-TLC (SiO$_2$, PE:EtOAc=4:1) to afford the title compound 7-bromo-N,N-dimethyl-isoquinolin-1-amine (0.27 g, 1.08 mmol, 86.91% yield) as a yellow oil. LC-MS (ES$^+$, m/z): 251.1/253.1 [(M+H)$^+$].

6-bromo-4-(4-methylpiperazin-1-yl)quinoline

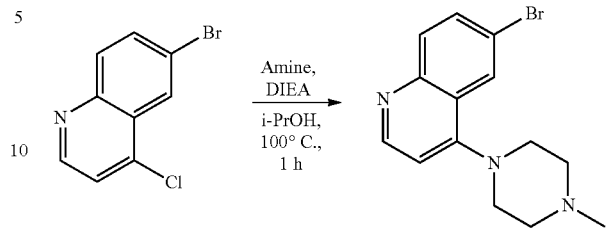

A solution of 6-bromo-4-chloro-quinoline (1 g, 4.12 mmol, 1 eq) in i-PrOH (10 mL) was added DIPEA (2.66 g, 20.62 mmol, 3.59 mL, 5 eq) and 1-methylpiperazine (2.48 g, 24.74 mmol, 2.74 mL, 6 eq). Then the mixture was stirred at 100° C. for 1 h. The reaction was poured into ~50 mL water and extracted with EtOAc (3×50 mL), washed with brine (3×100 mL), dried over anhydrous Na$_2$SO$_4$, filtered, and concentrated in vacuo. The residue was purified by column chromatography (SiO$_2$, PE:EtOAc=30:1 to 10:1) to afford the title compound 6-bromo-4-(4-methylpiperazin-1-yl)quinoline (1 g, 3.27 mmol, 79.20% yield) as a yellow solid. LC-MS (ES$^+$, m/z): 305.9/307.8 [(M+H)$^+$].

4-(6-bromo-4-quinolyl)morpholine

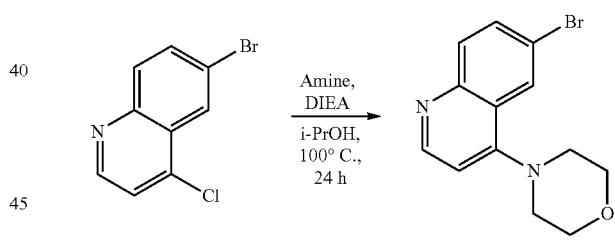

To a solution of 6-bromo-4-chloro-quinoline (1 g, 4.12 mmol, 1 eq) in i-PrOH (10 mL) was added DIPEA (1.6 g, 12.37 mmol, 2.15 mL, 3 eq) and morpholine (1.8 g, 20.62 mmol, 1.81 mL, 5 eq) and the mixture was stirred at 100° C. for 12 h in a 100 mL of sealed tube. LCMS showed some starting material remained. Then stirred at 100° C. for further 12 hr. The reaction was poured into ~50 mL water and extracted with EtOAc (3×50 mL), washed with brine (3×100 mL), dried over anhydrous Na$_2$SO$_4$, filtered, and concentrated in vacuo. The residue was purified by column chromatography (SiO$_2$, PE:EtOAc=30:1 to 10:1) to afford the title compound 4-(6-bromo-4-quinolyl)morpholine (1 g, 3.41 mmol, 82.72% yield) as a yellow solid. LC-MS (ES$^+$, m/z): 292.8/294.8 [(M+H)$^+$].

825

7-bromo-2-(4-methylpiperazin-1-yl)quinoline

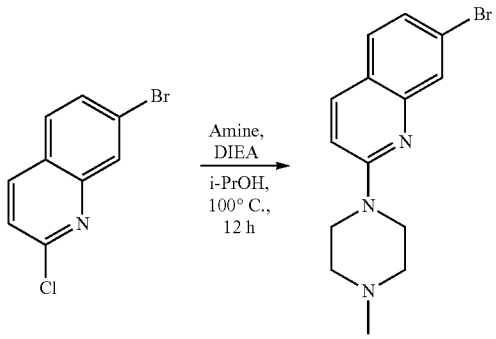 [SMILES: Clc1ccc2ccc(Br)cc2n1 ; "Amine,DIEA" ; CN1CCN(c2ccc3ccc(Br)cc3n2)CC1]

To a solution of 7-bromo-2-chloro-quinoline (0.3 g, 1.24 mmol, 1 eq) in i-PrOH (6 mL) was added 1-methylpiperazine (619.6 mg, 6.19 mmol, 686.11 μL, 5 eq) and DIPEA (799.4 mg, 6.19 mmol, 1.08 mL, 5 eq) and the mixture was stirred at 100° C. for 12 hr. The reaction was poured into ~20 mL water and extracted with EtOAc (3×15 mL), washed with brine (3×30 mL), dried over anhydrous $Na_2SO_4$, filtered, and concentrated in vacuo. The residue was purified by column chromatography ($SiO_2$, DCM/MeOH=20/1 to 10:1) to afford the title compound 7-bromo-2-(4-methylpiperazin-1-yl)quinoline (0.27 g, 881.78 μmol, 71.28% yield) as a yellow solid. LC-MS ($ES^+$, m/z): 306.2/308.2 [(M+H)$^+$].

7-bromo-2-chloro-N-methyl-quinazolin-4-amine

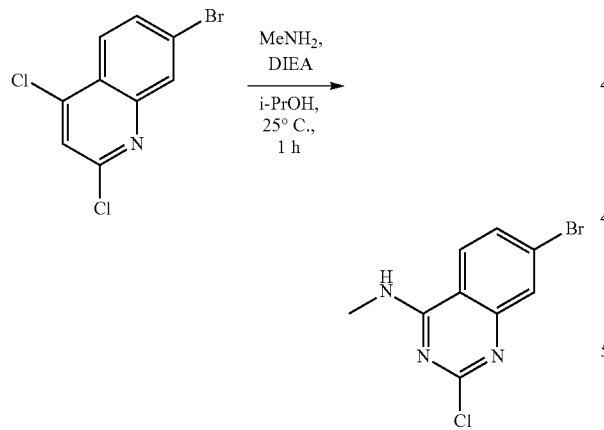

To a solution of 7-bromo-2,4-dichloro-quinazoline (0.4 g, 1.44 mmol, 1 eq) in i-PrOH (4 mL) was added DIEA (372 mg, 2.88 mmol, 501.36 μL, 2 eq) and methanamine; hydrochloride (97.2 mg, 1.44 mmol, 1 eq). Then the mixture was stirred at 25° C. for 1 h. LCMS showed that the reaction was complete. The reaction mixture was poured into water (100 mL) and extracted with EtOAc (3×30 mL), washed with $H_2O$ (2×30 mL) and brine (2×30 mL), dried over anhydrous $Na_2SO_4$, filtered, and concentrated in vacuo to give a residue. The residue was purified by column chromatography ($SiO_2$, PE:EtOAc=10:1 to 1:1) to afford the title compound 7-bromo-2-chloro-N-methyl-quinazolin-4-amine (0.33 g, 1.21 mmol, 84.14 yield) as a light yellow solid.

826

7-bromo-N2-[(2,4-dimethoxyphenyl)methyl]-N4-methyl-quinazoline-2,4-diamine

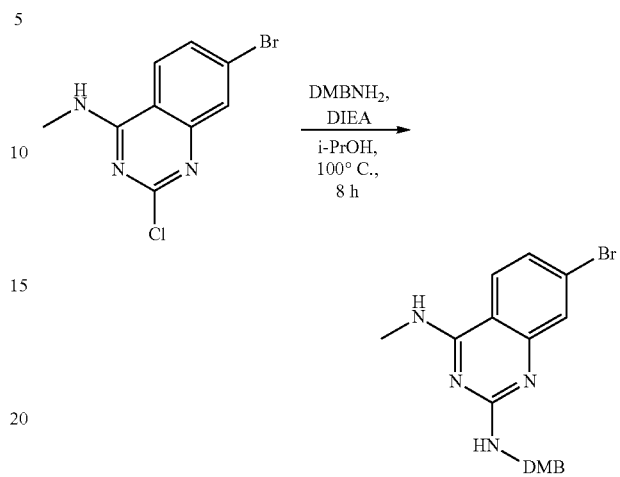

To a solution of 7-bromo-2-chloro-N-methyl-quinazolin-4-amine (0.15 g, 550.4 μmol, 1 eq) in i-PrOH (3 mL) was added DIEA (355.7 mg, 2.75 mmol, 479.35 μL, 5 eq) and (2,4-dimethoxyphenyl)methanamine (460.2 mg, 2.75 mmol, 414.55 μL, 5 eq). Then the mixture was stirred at 100° C. for 8 hr. The reaction was poured into 10 mL water and extracted with EtOAc (3×10 mL), washed with brine (3×20 mL), dried over anhydrous $Na_2SO_4$, filtered, and concentrated in vacuo. The residue was purified by prep-TLC ($SiO_2$, PE:EtOAc=1:1) to afford the title compound 7-bromo-N2-[(2,4-dimethoxyphenyl)methyl]-N4-methyl-quinazoline-2,4-diamine (0.2 g, 495.94 μmol, 90.11% yield) as a yellow solid. LC-MS ($ES^+$, m/z): 403.2/405.2 [(M+H)$^+$].

7-Bromo-2-chloro-N-(2-methoxyethyl)quinazolin-4-amine

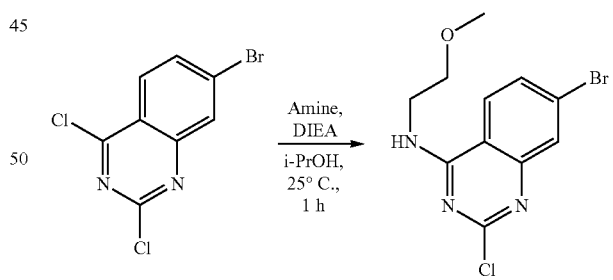

To a solution of 7-bromo-2,4-dichloro-quinazoline (0.4 g, 1.44 mmol, 1 eq) in i-PrOH (4 mL) was added DIEA (372 mg, 2.88 mmol, 501.36 μL, 2 eq) and 2-methoxyethanamine (108.1 mg, 1.44 mmol, 125.11 μL, 1 eq). Then the mixture was stirred at 25° C. for 1 h. The reaction mixture was poured into water (100 mL) and extracted with EtOAc (3×30 mL), washed with $H_2O$ (2×30 mL) and brine (2×30 mL), dried over anhydrous $Na_2SO_4$, filtered, and concentrated in vacuo to give a residue. The residue was purified by column chromatography ($SiO_2$, PE:EtOAc=10:1 to 1:1) to afford the title compound 7-Bromo-2-chloro-N-(2-methoxyethyl) quinazolin-4-amine (0.38 g, 1.2 mmol, 83.40% yield) as alight yellow solid. LC-MS (ES+, m/z): 316.0/318.0 [(M+H)+].

7-bromo-N2-[(2,4-dimethoxyphenyl)methyl]-N4-(2-methoxyethyl) quinazoline-2,4-diamine

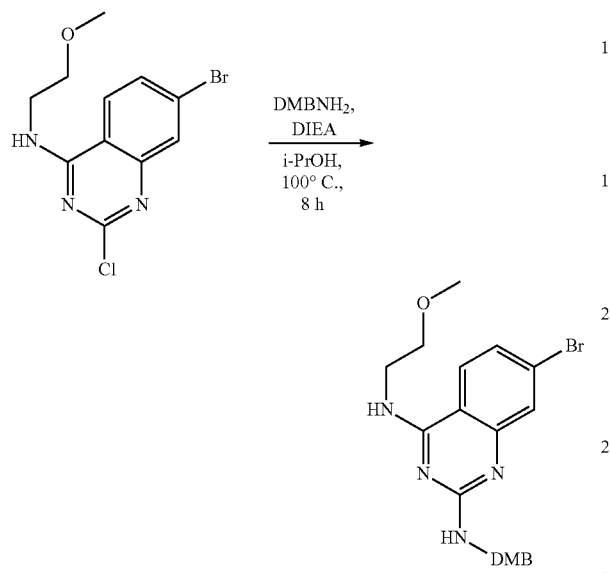

To a solution of 7-bromo-2-chloro-N-(2-methoxyethyl) quinazolin-4-amine (0.18 g, 568.57 μmol, 1 eq) in i-PrOH (3 mL) was added DIEA (367.4 mg, 2.84 mmol, 495.18 μL, 5 eq) and (2,4-dimethoxyphenyl)methanamine (475.3 mg, 2.84 mmol, 428.24 μL, 5 eq). Then stirred at 100° C. for 8 hr. The reaction was poured into 10 mL water and extracted with EtOAc (3×10 mL), washed with brine (3×20 mL), dried over anhydrous Na2SO4, filtered, and concentrated in vacuo. The residue was purified by prep-TLC (SiO2, PE:EtOAc=1:1) to afford the title compound 7-bromo-N2-[(2,4-dimethoxyphenyl)methyl]-N4-(2-methoxyethyl) quinazoline-2,4-diamine (0.2 g, 447.1 μmol, 78.64% yield) as a yellow solid. LC-MS (ES+, m/z): 447.2/449.2 [(M+H)+].

2-[(7-bromoquinazolin-2-yl)amino]ethanol

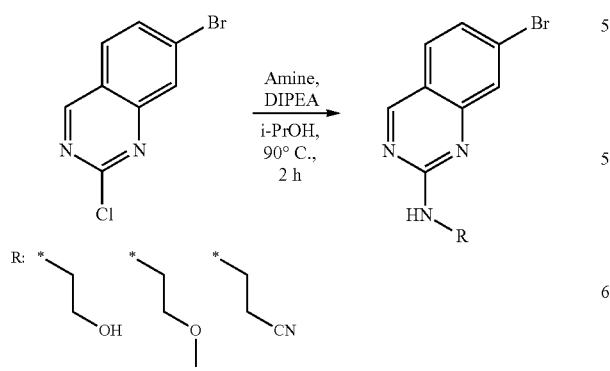

To the solution of 7-bromo-2-chloro-quinazoline (260 mg, 1.07 mmol, 1 eq) in i-PrOH (5 mL) was added 2-aminoethanol (326.1 mg, 5.34 mmol, 5 eq), DIPEA (690 mg, 5.34 mmol, 5 eq). The reaction mixture was stirred at 90° C. for 2 hours. The reaction mixture was poured into water (80 mL) and extracted with EtOAc (3×30 mL). The combined organic layer was washed with H2O (2×30 mL) and brine (2×30 mL), dried over anhydrous Na2SO4, filtered, and concentrated in vacuo to afford the title compound (200 mg, crude) which was used for the next step directly without further purification.

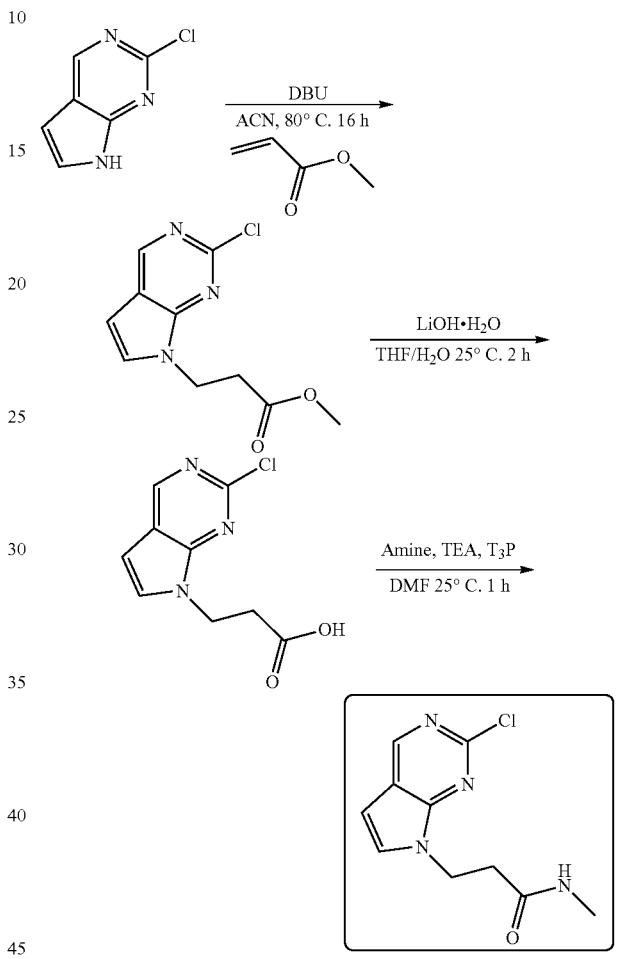

2-(2-chloropyrrolo[2,3-d]pyrimidin-7-yl)-N-methyl-acetamide

To a solution of 2-chloro-7H-pyrrolo[2,3-d]pyrimidine (220 mg, 1.43 mmol, 1 eq) in DMF (5 mL) was added NaH (114.6 mg, 2.87 mmol, 60% purity, 2 eq). The reaction mixture was stirred at 0° C. for 30 min. Then 2-bromo-N-methyl-acetamide (653.2 mg, 4.3 mmol, 3 eq) was added at 0° C. The resulting reaction mixture was stirred at 0° C. for 1 hour. The reaction mixture was poured into saturated NH₄Cl (80 mL) and extracted with EtOAc (3×30 mL). The combined organic layers were washed with brine (3×20 mL), dried over Na₂SO₄, filtered, and concentrated in vacuo to give a residue. The residue was purified by prep-TLC (SiO₂, DCM:MeOH=30:1) to afford the title compound 2-(2-chloropyrrolo[2,3-d]pyrimidin-7-yl)-N-methyl-acetamide (250 mg, 1.11 mmol, 77.68% yield) as a white solid.

Route 1c: methyl 3-(2-chloropyrrolo[2,3-d]pyrimidin-7-yl)propanoate

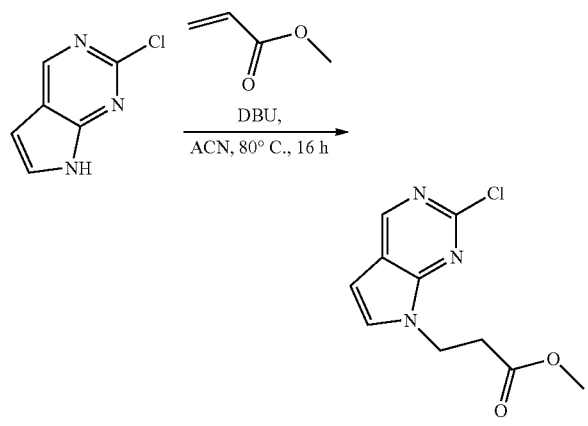

To a solution of 2-chloro-7H-pyrrolo[2,3-d]pyrimidine (800 mg, 5.21 mmol, 1 eq) in ACN (6 mL) was added DBU (396.5 mg, 2.6 mmol, 0.5 eq) and methyl prop-2-enoate (538.2 mg, 6.25 mmol, 1.2 eq) at 25° C. The reaction mixture was stirred at 80° C. for 16 hours. The reaction mixture was poured into water (80 mL) and extracted with EtOAc (3×30 mL). The combined organic layer was washed with H₂O (2×30 mL) and brine (2×30 mL), dried over anhydrous Na₂SO₄, filtered, and concentrated in vacuo to give a residue. The residue was purified by column chromatography (SiO₂, PE:EtOAc=20:1 to 1/1) to afford the title compound methyl 3-(2-chloropyrrolo[2,3-d]pyrimidin-7-yl)propanoate (1 g, 4.17 mmol, 80.10% yield) as a white solid. LC-MS (ES⁺, m/z): 240.1 [(M+H)⁺]

3-(2-chloropyrrolo[2,3-d]pyrimidin-7-yl)propanoic acid

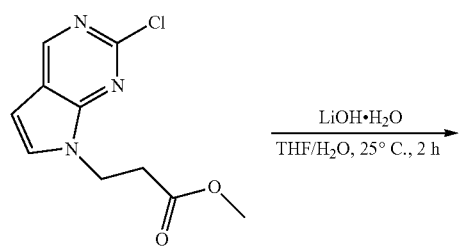

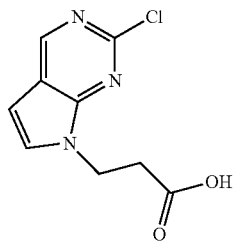

To a solution of methyl 3-(2-chloropyrrolo[2,3-d]pyrimidin-7-yl)propanoate (500 mg, 2.09 mmol, 1 eq) in THF (8 mL) and H₂O (2 mL) was added LiOH·H₂O (262.7 mg, 6.26 mmol, 3 eq). The mixture was stirred at 25° C. for 2 hours. TLC (MeOH:DCM=10:1, SM/Rf=0.7, TM/Rf=0.2) showed that the reaction was complete. The reaction mixture was poured into ice water (80 mL). Then adjusting the pH=5~6 with saturated citric acid. The solution was extracted with EtOAc (3×30 mL), washed with H₂O (2×30 mL) and brine (2×30 mL), dried over anhydrous Na₂SO₄, filtered, and concentrated in vacuo to afford the title compound (400 mg, crude) as a white solid, which was used directly.

3-(2-chloropyrrolo[2,3-d]pyrimidin-7-yl)-N-methyl-propanamide

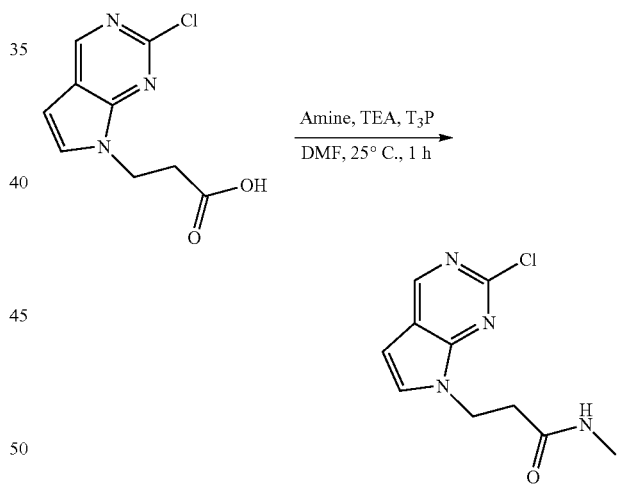

To the solution of 3-(2-chloropyrrolo[2,3-d]pyrimidin-7-yl)propanoic acid (350 mg, 1.55 mmol, 1 eq) in DMF (5 mL) was successively added methanamine (523.7 mg, 7.76 mmol, 5 eq, HCl), T₃P (1.48 g, 2.33 mmol, 50% purity, 1.5 eq) and TEA (470.9 mg, 4.65 mmol, 3 eq). The resulting reaction mixture was stirred at 25° C. for 1 hour. The reaction mixture was poured into water (80 mL) and extracted with EtOAc (3×30 mL), washed with H₂O (2×30 mL) and brine (2×30 mL), dried over anhydrous Na₂SO₄, filtered, and concentrated in vacuo to afford the title compound (300 mg, crude) as a light yellow solid. LC-MS (ES⁺, m/z): 239.1 [(M+H)⁺]

831

7-bromoquinoxalin-2-amine

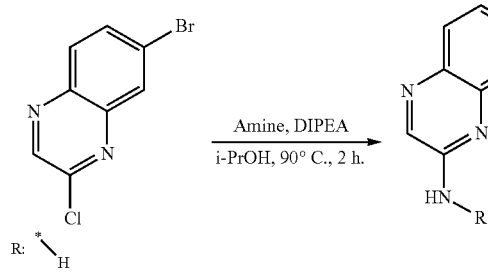

To the solution of 7-bromo-2-chloro-quinoxaline (500 mg, 2.05 mmol, 1 eq) in i-PrOH (10 mL) was added $NH_3·H_2O$ (2.4 g, 20.53 mmol, 2.64 mL, 30% purity, 10 eq) and DIPEA (2.65 g, 20.53 mmol, 10 eq). The reaction mixture was stirred at 90° C. for 2 hours. The reaction mixture was poured into water (80 mL) and extracted with EtOAc (3×30 mL). The combined organic layer was washed with $H_2O$ (2×30 mL) and brine (2×30 mL), dried over anhydrous $Na_2SO_4$, filtered, and concentrated in vacuo to give a residue. The residue was purified by column chromatography ($SiO_2$, PE:EtOAc=5:1 to 1:1) to afford the title compound (110 mg, 490.95 μmol, 23.91% yield) as a white solid. LC-MS ($ES^+$, m/z): 223.9 $[(M+H)^+]$ 7-bromo-N2,N4-dimethyl-quinazoline-2,4-diamine

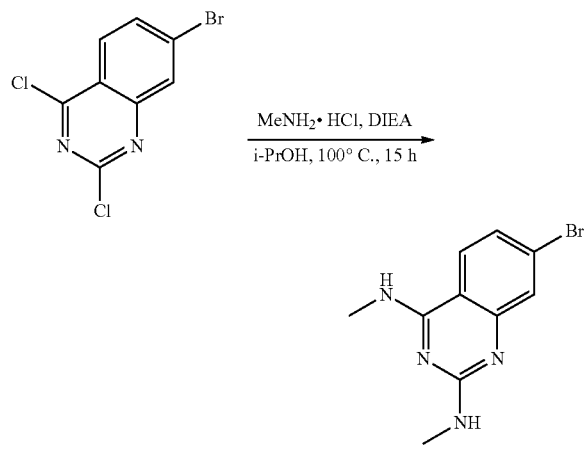

To a solution of 7-bromo-2,4-dichloro-quinazoline (0.3 g, 1.08 mmol, 1 eq) in i-PrOH (3 mL) was added DIEA (1.4 g, 10.79 mmol, 1.88 mL, 10 eq). Then methanamine;hydrochloride (1.46 g, 21.59 mmol, 20 eq) was added and the reaction mixture was stirred at 100° C. for 15 h. LCMS showed that the reaction was complete. The reaction mixture was poured into 50 mL $H_2O$, extracted with EtOAc (3×50 mL), and the combined organic layer was washed with $H_2O$ (2×50 mL) and brine (2×50 mL). Then dried over anhydrous $Na_2SO_4$, filtered, and concentrated in vacuo to afford the title compound 7-bromo-N2,N4-dimethyl-quinazoline-2,4-diamine (0.3 g, crude) as a yellow solid which was used for the next step without further purification. LC-MS ($ES^+$, m/z): 267.0 $[(M+H)^+]$

832

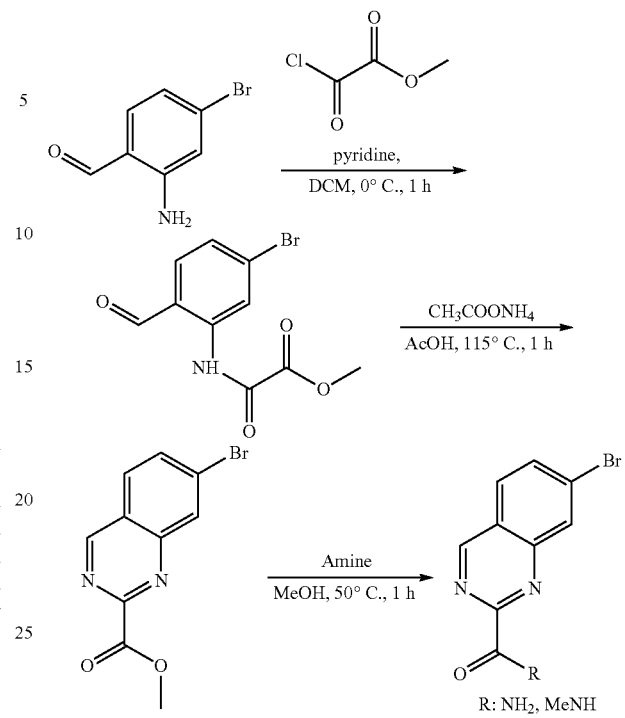

Methyl 2-(5-bromo-2-formyl-anilino)-2-oxo-acetate

To a solution of 2-amino-4-bromo-benzaldehyde (8 g, 39.99 mmol, 1 eq) in DCM (120 mL) was added pyridine (9.49 g, 119.98 mmol, 9.68 mL, 3 eq) and methyl 2-chloro-2-oxo-acetate (6.37 g, 51.99 mmol, 4.79 mL, 1.3 eq) at 0° C. Then the mixture was stirred at 0° C. for 1 hr. The reaction was poured into water (300 mL) and extracted with DCM (3×150 mL), washed with brine (3×150 mL), dried over anhydrous $Na_2SO_4$, filtered, and concentrated in vacuo to afford the title compound Methyl 2-(5-bromo-2-formyl-anilino)-2-oxo-acetate (12.8 g, crude) as a yellow solid. LC-MS ($ES^+$, m/z): 285.9/288.0 $[(M+H)^+]$. $^1H$ NMR (400 MHz, DMSO-de) δ=12.27 (s, 1H), 10.00 (s, 1H), 8.68 (d, J=1.6 Hz, 1H), 7.95 (d, J=8.2 Hz, 1H), 7.67 (dd, J=1.8, 8.3 Hz, 1H), 3.90 (s, 3H).

833

Methyl 7-bromoquinazoline-2-carboxylate

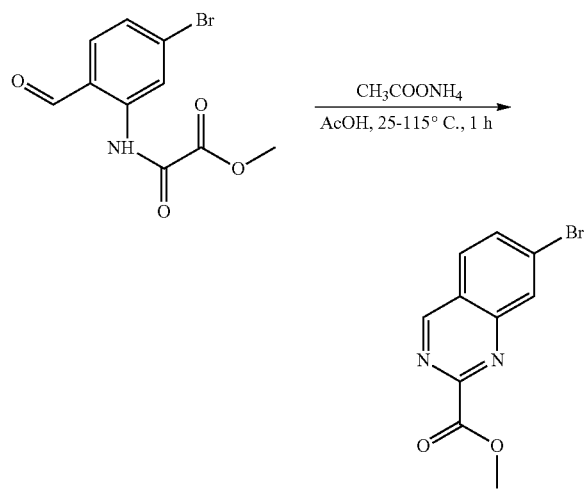

To a mixture of methyl 2-(5-bromo-2-formyl-anilino)-2-oxo-acetate (10.6 g, 37.05 mmol, 1 eq) in AcOH (106 mL) was added CH$_3$COONH$_4$ (28.56 g, 370.53 mmol, 10 eq) at 25° C. and the reaction mixture was stirred at 115° C. for 1 h. The reaction was poured into 20 mL water and added NaOH solid until pH=8. The mixture was extracted with EtOAc (3×200 mL), washed with brine (3×200 mL), dried over anhydrous Na$_2$SO$_4$, filtered, and concentrated in vacuo to afford the title compound Methyl 7-bromoquinazoline-2-carboxylate (6.9 g, crude) as a yellow solid. LC-MS (ES$^+$, m/z): 267.0/269.0 [(M+H)$^+$]. $^1$H NMR (400 MHz, DMSO-d$_6$) δ=9.80 (s, 1H), 8.46 (s, 1H), 8.25 (d, J=8.8 Hz, 1H), 8.10-8.04 (m, 1H), 3.97 (s, 3H)

7-bromoquinazoline-2-carboxamide

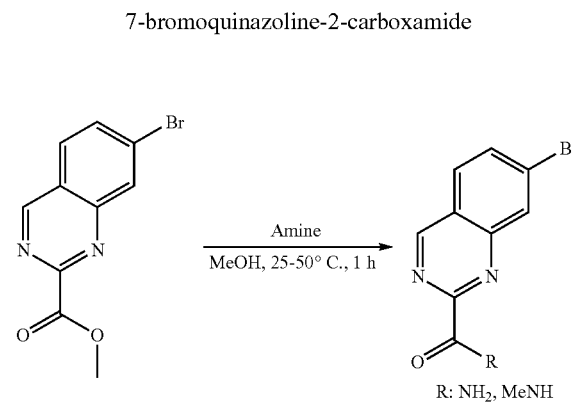

R: NH$_2$, MeNH

To a solution of methyl 7-bromoquinazoline-2-carboxylate (3 g, 11.23 mmol, 1 eq) in MeOH (30 mL) was added NH$_3$·H$_2$O (6.83 g, 54.53 mmol, 7.5 mL, 28% purity, 4.85 eq) at 25° C. Then stirred at 50° C. for 1 hr. The reaction was concentrated in vacuo. Then the residue was washed with EtOAc (3×20 mL) to afford the title compound 7-bromo-quinazoline-2-carboxamide (3.1 g, crude) as a yellow solid. LC-MS (ES$^+$, m/z): 251.9/253.9 [(M+H)$^+$], 1H NMR (400 MHz, DMSO-d6) Shift=9.76 (s, 1H), 8.37 (s, 1H), 8.35-8.31 (m, 1H), 8.34 (br s, 1H), 8.23 (d, J=8.6 Hz, 1H), 8.03 (dd, J=1.8, 8.6 Hz, 1H), 7.93 (br s, 1H)

To a solution of methyl 7-bromoquinazoline-2-carboxylate (3.1 g, 11.61 mmol, 1 eq) in MeOH (36 mL) was added methanamine (6.6 g, 70.13 mmol, 9 mL, 33% purity in EtOH, 6.04 eq) at 25° C. Then stirred at 50° C. for 1 hr. The reaction was concentrated in vacuo, and washed with PE (3×50 mL) to afford the title compound 7-bromo-N-methyl-quinazoline-2-carboxamide (2.5 g, crude) as a yellow solid. LC-MS (ES$^+$, m/z): 266.0/268.0 [(M+H)$^+$], 1H NMR (400 MHz, DMSO-d6) Shift=9.77 (s, 1H), 9.04 (br d, J=3.9 Hz, 1H), 8.38 (s, 1H), 8.23 (d, J=8.6 Hz, 1H), 8.04 (dd, J=1.8, 8.7 Hz, 1H), 2.87 (d, J=4.8 Hz, 3H).

3-iodo-6-methyl-1H-indazole

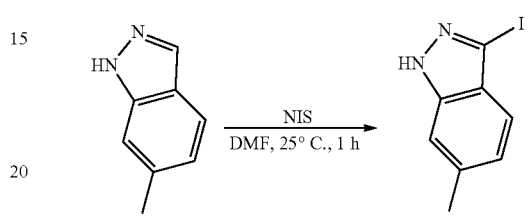

To a solution of 6-methyl-1H-indazole (0.5 g, 3.78 mmol, 1 eq) in DMF (5 mL) was added NIS (1.28 g, 5.67 mmol, 1.5 ef) and the mixture was stirred at 25° C. for 1 hr. TLC (PE:EtOAc=4:1, SM Rf=0.40, TM Rf=0.58) showed that the reaction was complete. The reaction was poured into ~10 mL water and extracted with EtOAc (3×10 mL), washed with brine (3×10 mL), dried over anhydrous Na$_2$SO$_4$, filtered, and concentrated in vacuo. The residue was purified by column chromatography (SiO$_2$, PE:EtOAc=10:1 to 1/1) to afford the title compound 3-iodo-6-methyl-1H-indazole (0.9 g, 3.49 mmol, 92.19% yield) as a white solid.

(2-aminoquinazolin-7-yl)boronic acid

To a mixture of 7-bromoquinazolin-2-amine (500 mg, 2.23 mmol, 1 eq) in dioxane (5 mL) was added Pin$_2$B$_2$ (736.7 mg, 2.9 mmol, 1.3 eq), KOAc (1.1 g, 11.16 mmol, 5 eq), Pd(dppf)Cl$_2$ (81.6 mg, 111.58 μmol, 0.05 eq) under N$_2$. The mixture was stirred at 100° C. for 1 h. The reaction mixture was concentrated in vacuo. The residue was dissolved in DCM (20 mL), filtered and the liquid was desired. The liquid was washed with PE (3×10 mL) to afford the title compound (2-aminoquinazolin-7-yl)boronic acid (500 mg, crude) as black brown solid. LC-MS (ES+, m/z) 190.0 [(M+H)$^+$]

835

7-bromo-N-methyl-quinolin-2-amine

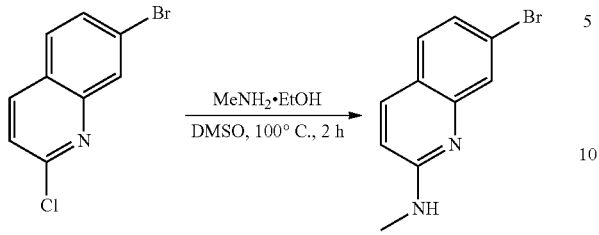

836

-continued

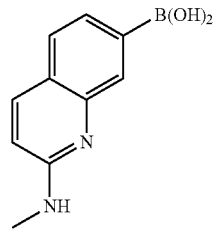

To a mixture of 7-bromo-2-chloro-quinoline (1 g, 4.12 mmol, 1 eq) in DMSO (5 mL) was added MeNH$_2$ (6.4 g, 61.86 mmol, 30% purity in EtOH, 15 eq). The mixture was stirred at 100° C. for 2 h. The reaction mixture was poured into H$_2$O (20 mL) and the aqueous phase was filtered. The solid was collected. Then the solid was dissolved in PE:E-tOAc=10:1 (20 mL) and stirred at 25° C. for 0.5 h. Then filtered. The solid was collected to afford the title compound 7-bromo-N-methyl-quinolin-2-amine (800 mg, crude) as a white solid. LC-MS (ES+, m/z) 236.9, 238.9 [(M+H)$^+$]

(2-(methylamino)quinolin-7-yl)boronic acid

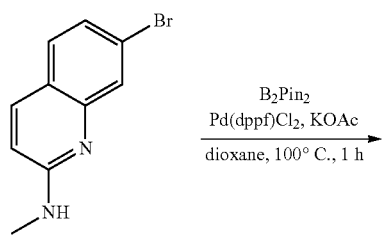

A mixture of 7-bromo-N-methyl-quinolin-2-amine (400 mg, 1.69 mmol, 1 eq), 4,4,5,5-tetramethyl-2-(4,4,5,5-tetramethyl-1,3,2-dioxaborolan-2-yl)-1,3,2-dioxaborolane (514.1 mg, 2.02 mmol, 1.2 eq), KOAc (331.2 mg, 3.37 mmol, 2 eq), Pd(dppf)Cl$_2$ (123.4 mg, 168.71 µmol, 0.1 eq) in dioxane (8 mL). The mixture was stirred at 100° C. for 2 hours. The reaction mixture was filtered, and concentrated in vacuo to give a residue and washed with DCM (3×10 mL) to afford the title compound (2-(methylamino)quinolin-7-yl)boronic acid (600 mg, crude) as black brown oil. LC-MS (ES+, m/z) 202.9 [(M+H)$^+$]

Example 17: Additional Compounds of the Disclosure

Compounds that bind to mutant p53 and restore DNA binding activity of the mutant p53 include compounds of TABLE 16.

TABLE 16

| Cpd No. | Structure | IUPAC | MW (g/mol) |
|---|---|---|---|
| 642 | 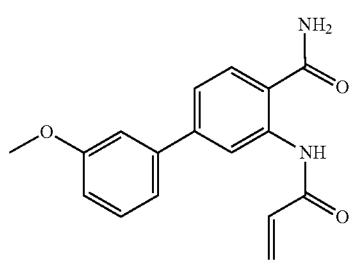 [SMILES: C=CC(=O)Nc1cc(-c2cccc(OC)c2)ccc1C(N)=O] | 3'-methoxy-3-(prop-2-enamido)-[1,1'-biphenyl]-4-carboxamide | 296.3 |
| 643 | 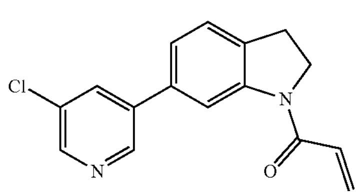 [SMILES: C=CC(=O)N1CCc2ccc(-c3cncc(Cl)c3)cc21] | 1-[6-(5-chloropyridin-3-yl)-2,3-dihydro-1H-indol-1-yl]prop-2-en-1-one | 284.7 |

TABLE 16-continued

| Cpd No. | Structure | IUPAC | MW (g/mol) |
|---|---|---|---|
| 644 | 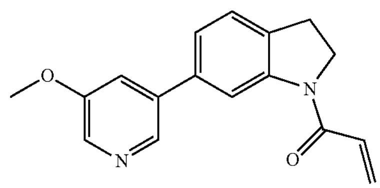 [SMILES: C=CC(=O)N1CCc2ccc(-c3cncc(OC)c3)cc21] | 1-[6-(5-methoxypyridin-3-yl)-2,3-dihydro-1H-indol-1-yl]prop-2-en-1-one | 280.3 |
| 645 | 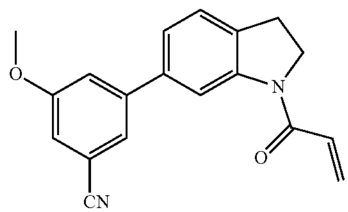 [SMILES: C=CC(=O)N1CCc2ccc(-c3cc(C#N)cc(OC)c3)cc21] | 3-methoxy-5-[1-(prop-2-enoyl)-2,3-dihydro-1H-indol-6-yl]benzonitrile | 304.3 |
| 646 | 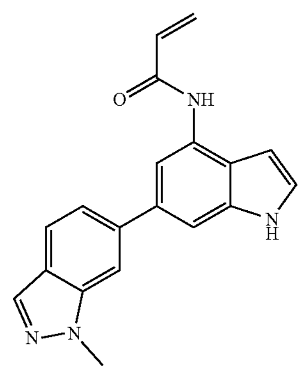 [SMILES: C=CC(=O)Nc1cc(-c2ccc3cnn(C)c3c2)cc2[nH]ccc12] | N-[6-(1-methyl-1H-indazol-6-yl)-1H-indol-4-yl]prop-2-enamide | 316.4 |
| 647 | 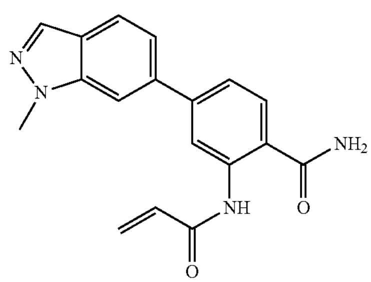 [SMILES: C=CC(=O)Nc1cc(-c2ccc3cnn(C)c3c2)ccc1C(N)=O] | 4-(1-methyl-1H-indazol-6-yl)-2-(prop-2-enamido)benzamide | 320.4 |
| 648 | 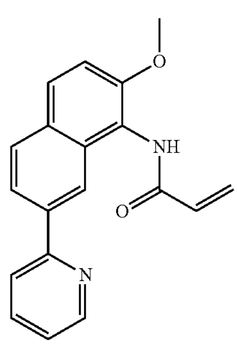 [SMILES: C=CC(=O)Nc1c(OC)ccc2ccc(-c3ccccn3)cc12] | N-[2-methoxy-7-(pyridin-2-yl)naphthalen-1-yl]prop-2-enamide | 304.3 |

TABLE 16-continued

| Cpd No. | Structure | IUPAC | MW (g/mol) |
|---|---|---|---|
| 649 | 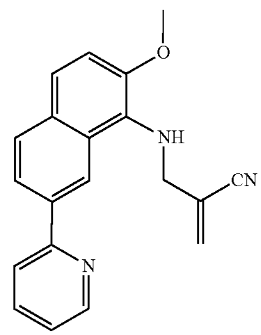 [SMILES: C=C(C#N)CNc1c(OC)ccc2ccc(-c3ccccn3)cc12] | 2-({[2-methoxy-7-(pyridin-2-yl)naphthalen-1-yl]amino}methyl)prop-2-enenitrile | 315.4 |
| 650 | 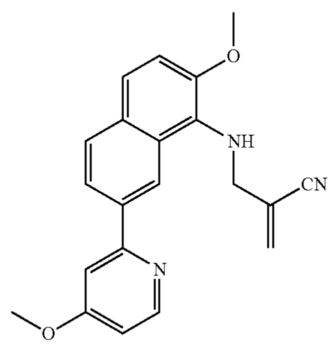 [SMILES: C=C(C#N)CNc1c(OC)ccc2ccc(-c3cc(OC)ccn3)cc12] | 2-({[2-methoxy-7-(4-methoxypyridin-2-yl)naphthalen-1-yl]amino}methyl)prop-2-enenitrile | 345.4 |
| 651 | 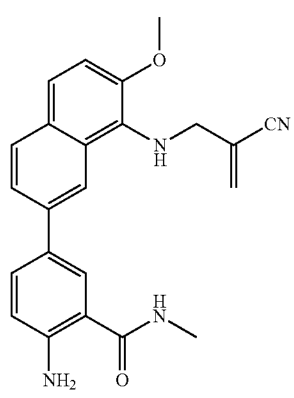 [SMILES: C=C(C#N)CNc1c(OC)ccc2ccc(-c3ccc(N)c(C(=O)NC)c3)cc12] | 2-amino-5-{8-[(2-cyano-2-methylideneethyl)amino]-7-methoxynaphthalen-2-yl}-N-methylbenzamide | 386.5 |
| 652 | 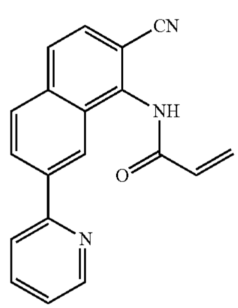 [SMILES: C=CC(=O)Nc1c(C#N)ccc2ccc(-c3ccccn3)cc12] | N-[2-cyano-7-(pyridin-2-yl)naphthalen-1-yl]prop-2-enamide | 299.3 |

TABLE 16-continued

| Cpd No. | Structure | IUPAC | MW (g/mol) |
|---|---|---|---|
| 653 | 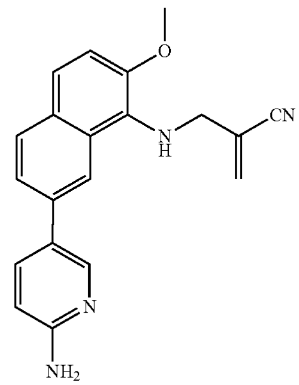 [SMILES: C=C(C#N)CNc1c(OC)ccc2ccc(-c3ccc(N)nc3)cc12] | 2-({[7-(6-aminopyridin-3-yl)-2-methoxynaphthalen-1-yl]amino}methyl)prop-2-enenitrile | 330.4 |
| 654 | 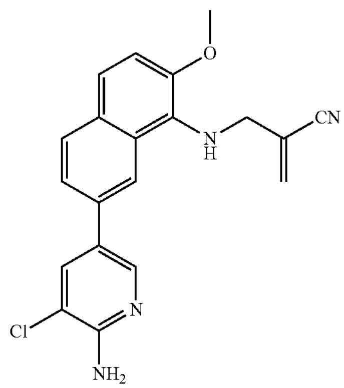 [SMILES: C=C(C#N)CNc1c(OC)ccc2ccc(-c3cnc(N)c(Cl)c3)cc12] | 2-({[7-(6-amino-5-chloropyridin-3-yl)-2-methoxynaphthalen-1-yl]amino}methyl)prop-2-enenitrile | 364.8 |
| 655 | 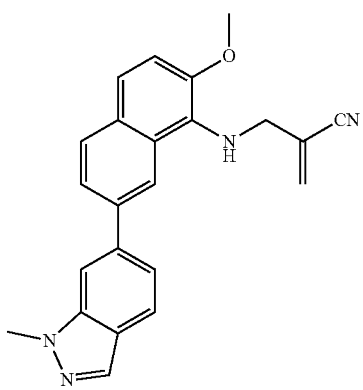 [SMILES: C=C(C#N)CNc1c(OC)ccc2ccc(-c3ccc4cnn(C)c4c3)cc12] | 2-({[2-methoxy-7-(1-methyl-1H-indazol-6-yl)naphthalen-1-yl]amino}methyl)prop-2-enenitrile | 368.4 |
| 656 | 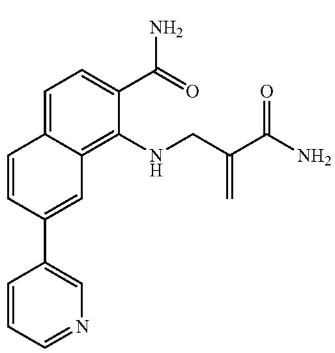 [SMILES: C=C(CNc1c(C(N)=O)ccc2ccc(-c3cccnc3)cc12)C(N)=O] | 1-[(2-carbamoyl-2-methylideneethyl)amino]-7-(pyridin-3-yl)naphthalene-2-carboxamide | 346.4 |

TABLE 16-continued

| Cpd No. | Structure | IUPAC | MW (g/mol) |
|---|---|---|---|
| 657 | 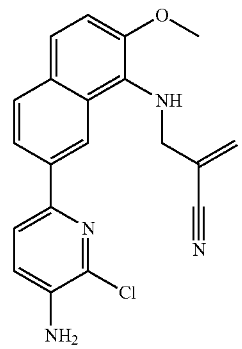 [SMILES: C=C(C#N)CNc1c(OC)ccc2ccc(-c3ccc(N)c(Cl)n3)cc12] | 2-({[7-(5-amino-6-chloropyridin-2-yl)-2-methoxynaphthalen-1-yl]amino}methyl)prop-2-enenitrile | 364.8 |
| 658 | 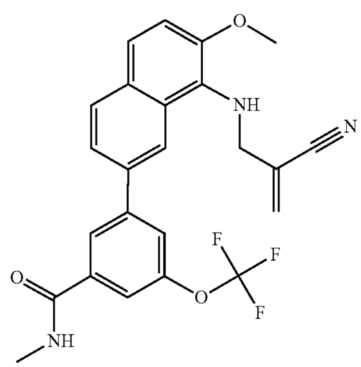 [SMILES: C=C(C#N)CNc1c(OC)ccc2ccc(-c3cc(OC(F)(F)F)cc(C(=O)NC)c3)cc12] | 3-{8-[(2-cyano-2-methylideneethyl)amino]-7-methoxynaphthalen-2-yl}-N-methyl-5-(trifluoromethoxy)benzamide | 455.4 |
| 659 | 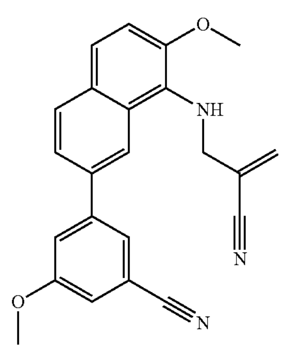 [SMILES: C=C(C#N)CNc1c(OC)ccc2ccc(-c3cc(C#N)cc(OC)c3)cc12] | 3-{8-[(2-cyano-2-methylideneethyl)amino]-7-methoxynaphthalen-2-yl}-5-methoxybenzonitrile | 369.4 |
| 660 | 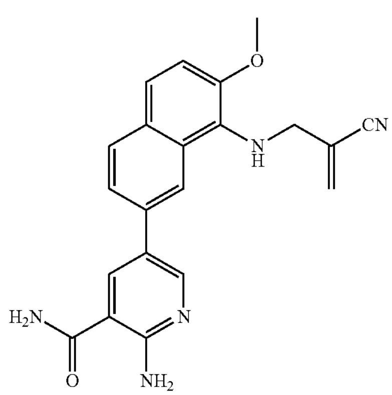 [SMILES: C=C(C#N)CNc1c(OC)ccc2ccc(-c3cnc(N)c(C(N)=O)c3)cc12] | 2-amino-5-{8-[(2-cyano-2-methylideneethyl)amino]-7-methoxynaphthalen-2-yl}pyridine-3-carboxamide | 373.4 |

TABLE 16-continued

| Cpd No. | Structure | IUPAC | MW (g/mol) |
|---|---|---|---|
| 661 | 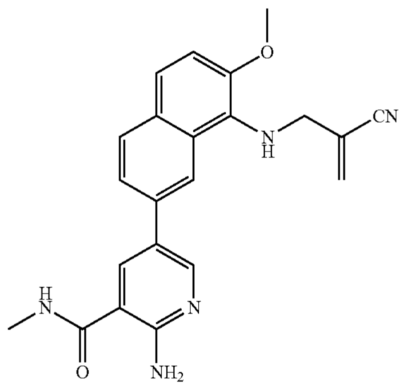 [SMILES: C=C(C#N)CNc1c(OC)ccc2ccc(-c3cnc(N)c(C(=O)NC)c3)cc12] | 2-amino-5-{8-[(2-cyano-2-methylideneethyl)amino]-7-methoxynaphthalen-2-yl}-N-methylpyridine-3-carboxamide | 387.4 |
| 662 | 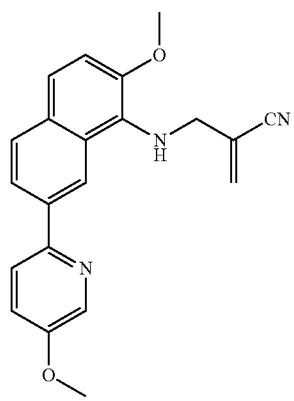 [SMILES: C=C(C#N)CNc1c(OC)ccc2ccc(-c3ccc(OC)cn3)cc12] | 2-({[2-methoxy-7-(5-methoxypyridin-2-yl)naphthalen-1-yl]amino}methyl)prop-2-enenitrile | 345.4 |
| 663 | 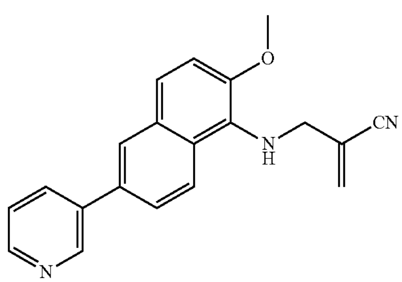 [SMILES: C=C(C#N)CNc1c(OC)ccc2cc(-c3cccnc3)ccc12] | 2-({[2-methoxy-6-(pyridin-3-yl)naphthalen-1-yl]amino}methyl)prop-2-enenitrile | 315.4 |
| 664 | 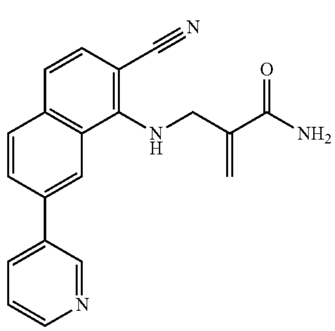 [SMILES: C=C(CNc1c(C#N)ccc2ccc(-c3cccnc3)cc12)C(N)=O] | 2-({[2-cyano-7-(pyridin-3-yl)naphthalen-1-yl]amino}methyl)prop-2-enamide | 328.4 |

TABLE 16-continued

| Cpd No. | Structure | IUPAC | MW (g/mol) |
|---|---|---|---|
| 665 | 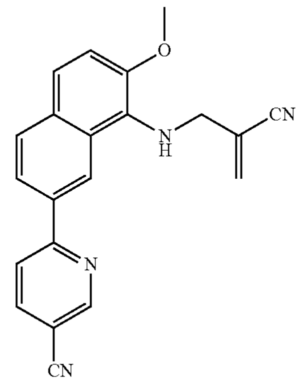 [SMILES: C=C(C#N)CNc1c(OC)ccc2ccc(-c3ccc(C#N)cn3)cc12] | 6-{8-[(2-cyano-2-methylideneethyl)amino]-7-methoxynaphthalen-2-yl}pyridine-3-carbonitrile | 340.4 |
| 666 | 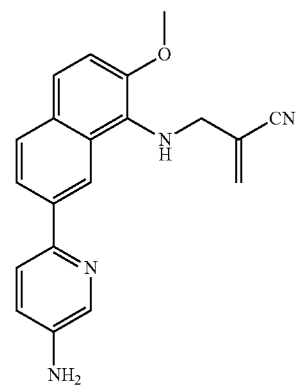 [SMILES: C=C(C#N)CNc1c(OC)ccc2ccc(-c3ccc(N)cn3)cc12] | 2-({[7-(5-aminopyridin-2-yl)-2-methoxynaphthalen-1-yl]amino}methyl)prop-2-enenitrile | 330.4 |
| 667 | 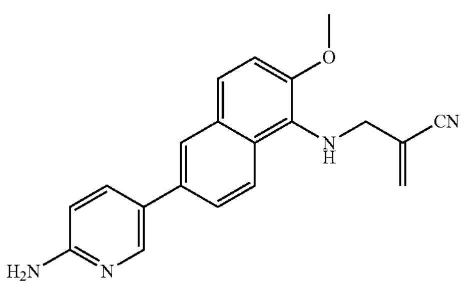 [SMILES: C=C(C#N)CNc1c(OC)ccc2cc(-c3ccc(N)nc3)ccc12] | 2-({[6-(6-aminopyridin-3-yl)-2-methoxynaphthalen-1-yl]amino}methyl)prop-2-enenitrile | 330.4 |
| 668 | 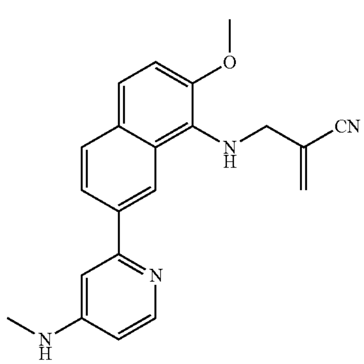 [SMILES: C=C(C#N)CNc1c(OC)ccc2ccc(-c3cc(NC)ccn3)cc12] | 2-[({2-methoxy-7-[4-(methylamino)pyridin-2-yl]naphthalen-1-yl}amino)methyl]prop-2-enenitrile | 344.4 |

TABLE 16-continued

| Cpd No. | Structure | IUPAC | MW (g/mol) |
| --- | --- | --- | --- |
| 669 | 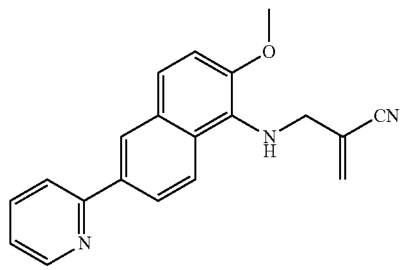 [SMILES: C=C(C#N)CNc1c(OC)ccc2cc(-c3ccccn3)ccc12] | 2-({[2-methoxy-6-(pyridin-2-yl)naphthalen-1-yl]amino}methyl)prop-2-enenitrile | 315.4 |
| 670 | 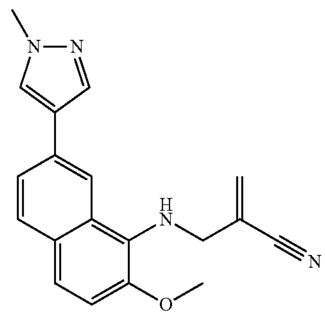 [SMILES: C=C(C#N)CNc1c(OC)ccc2ccc(-c3cnn(C)c3)cc12] | 2-({[2-methoxy-7-(1-methyl-1H-pyrazol-4-yl)naphthalen-1-yl]amino}methyl)prop-2-enenitrile | 318.4 |
| 671 | 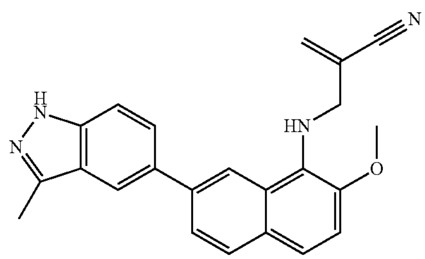 [SMILES: C=C(C#N)CNc1c(OC)ccc2ccc(-c3ccc4[nH]nc(C)c4c3)cc12] | 2-({[2-methoxy-7-(3-methyl-1H-indazol-5-yl)naphthalen-1-yl]amino}methyl)prop-2-enenitrile | 368.4 |
| 672 | 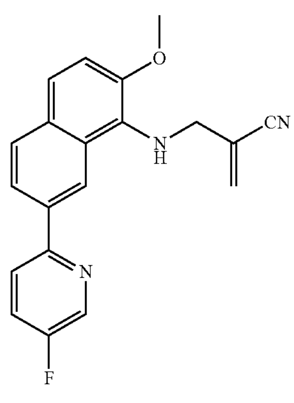 [SMILES: C=C(C#N)CNc1c(OC)ccc2ccc(-c3ccc(F)cn3)cc12] | 2-({[7-(5-fluoropyridin-2-yl)-2-methoxynaphthalen-1-yl]amino}methyl)prop-2-enenitrile | 333.4 |
| 673 | 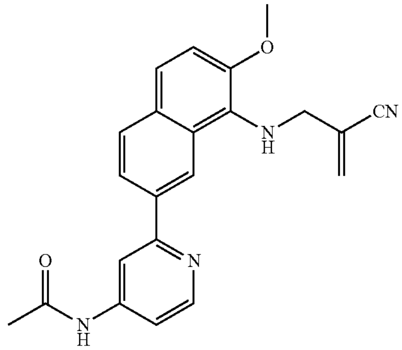 [SMILES: C=C(C#N)CNc1c(OC)ccc2ccc(-c3cc(NC(C)=O)ccn3)cc12] | N-(2-{8-[(2-cyano-2-methylideneethyl)amino]-7-methoxynaphthalen-2-yl}pyridin-4-yl)acetamide | 372.4 |

TABLE 16-continued

| Cpd No. | Structure | IUPAC | MW (g/mol) |
|---|---|---|---|
| 674 | 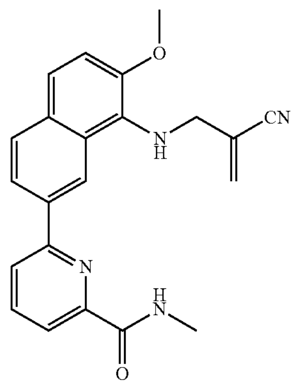 [SMILES: C=C(C#N)CNc1c(OC)ccc2ccc(-c3cccc(C(=O)NC)n3)cc12] | 6-{8-[(2-cyano-2-methylideneethyl)amino]-7-methoxynaphthalen-2-yl}-N-methylpyridine-2-carboxamide | 372.4 |
| 675 | 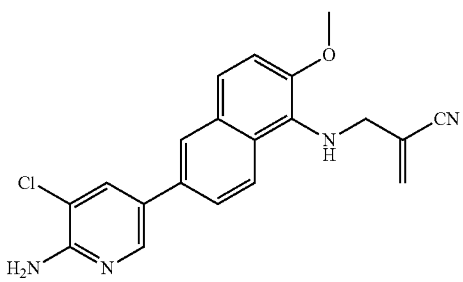 [SMILES: C=C(C#N)CNc1c(OC)ccc2cc(-c3cnc(N)c(Cl)c3)ccc12] | 2-({[6-(6-amino-5-chloropyridin-3-yl)-2-methoxynaphthalen-1-yl]amino}methyl)prop-2-enenitrile | 364.8 |
| 676 | 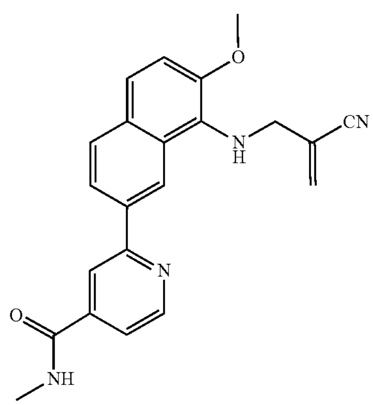 [SMILES: C=C(C#N)CNc1c(OC)ccc2ccc(-c3cc(C(=O)NC)ccn3)cc12] | 2-{8-[(2-cyano-2-methylideneethyl)amino]-7-methoxynaphthalen-2-yl}-N-methylpyridine-4-carboxamide | 372.4 |
| 677 | 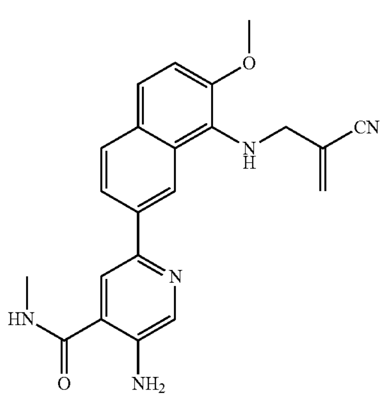 [SMILES: C=C(C#N)CNc1c(OC)ccc2ccc(-c3cc(C(=O)NC)c(N)cn3)cc12] | 5-amino-2-{8-[(2-cyano-2-methylideneethyl)amino]-7-methoxynaphthalen-2-yl}-N-methylpyridine-4-carboxamide | 387.4 |

TABLE 16-continued

| Cpd No. | Structure | IUPAC | MW (g/mol) |
|---|---|---|---|
| 678 | 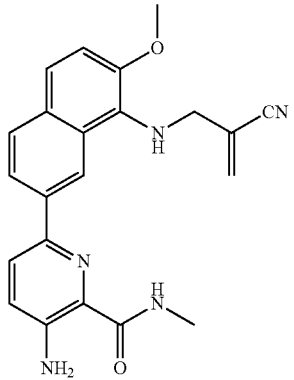 | 3-amino-6-{8-[(2-cyano-2-methylideneethyl)amino]-7-methoxynaphthalen-2-yl}-N-methylpyridine-2-carboxamide | 387.4 |
| 679 | 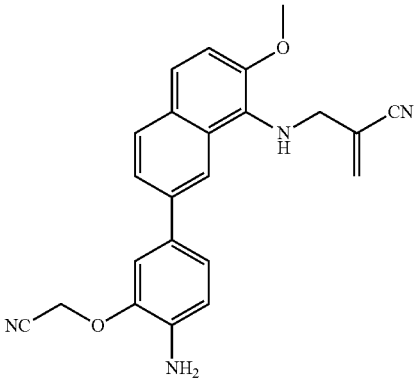 [SMILES: C=C(C#N)CNc1c(OC)ccc2ccc(-c3ccc(N)c(OCC#N)c3)cc12] | 2-[({7-[4-amino-3-(cyanomethoxy)phenyl]-2-methoxynaphthalen-1-yl}amino)methyl]prop-2-enenitrile | 384.4 |
| 680 | 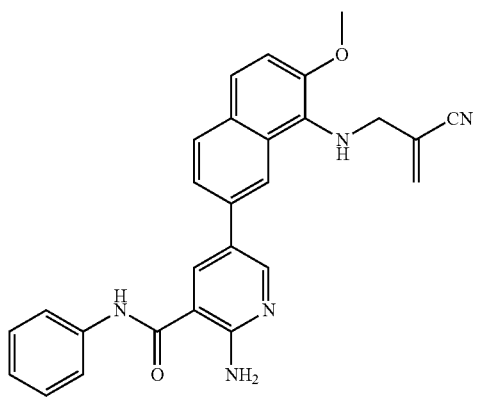 [SMILES: C=C(C#N)CNc1c(OC)ccc2ccc(-c3cnc(N)c(C(=O)Nc4ccccc4)c3)cc12] | 2-amino-5-{8-[(2-cyano-2-methylideneethyl)amino]-7-methoxynaphthalen-2-yl}-N-phenylpyridine-3-carboxamide | 449.5 |
| 681 | 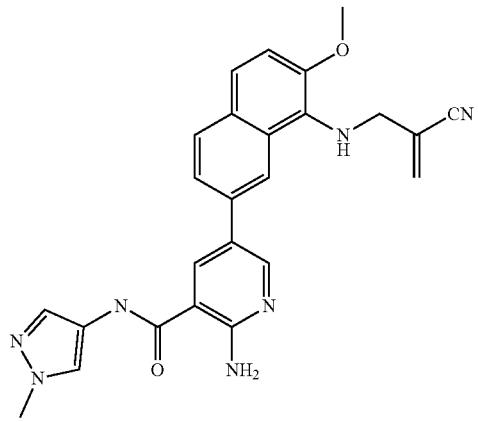 | 2-amino-5-{8-[(2-cyano-2-methylideneethyl)amino]-7-methoxynaphthalen-2-yl}-N-(1-methyl-1H-pyrazol-4-yl)pyridine-3-carboxamide | 453.5 |

TABLE 16-continued

| Cpd No. | Structure | IUPAC | MW (g/mol) |
|---|---|---|---|
| 682 | 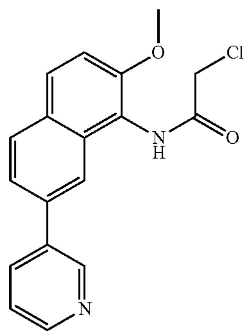 [SMILES: COc1ccc2ccc(-c3cccnc3)cc2c1NC(=O)CCl] | 2-chloro-N-[2-methoxy-7-(pyridin-3-yl)naphthalen-1-yl]acetamide | 326.8 |
| 683 | 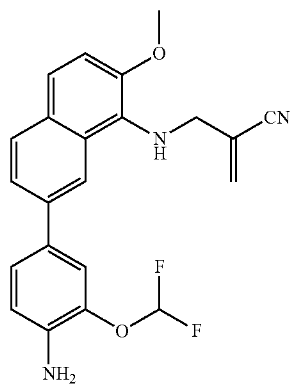 [SMILES: C=C(C#N)CNc1c(OC)ccc2ccc(-c3ccc(N)c(OC(F)F)c3)cc12] | 2-[({7-[4-amino-3-(difluoromethoxy)phenyl]-2-methoxynaphthalen-1-yl}amino)methyl]prop-2-enenitrile | 395.4 |
| 684 | 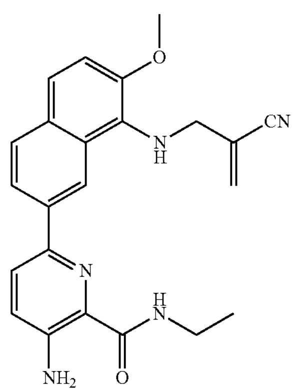 [SMILES: C=C(C#N)CNc1c(OC)ccc2ccc(-c3ccc(N)c(C(=O)NCC)n3)cc12] | 3-amino-6-{8-[(2-cyano-2-methylideneethyl)amino]-7-methoxynaphthalen-2-yl}-N-ethylpyridine-2-carboxamide | 401.5 |
| 685 | 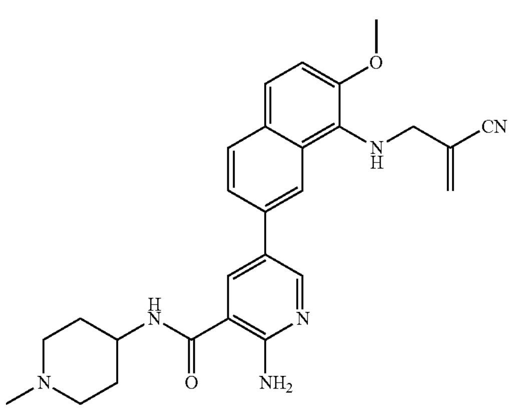 [SMILES: C=C(C#N)CNc1c(OC)ccc2ccc(-c3cnc(N)c(C(=O)NC4CCN(C)CC4)c3)cc12] | 2-amino-5-{8-[(2-cyano-2-methylideneethyl)amino]-7-methoxynaphthalen-2-yl}-N-(1-methylpiperidin-4-yl)pyridine-3-carboxamide | 470.6 |

TABLE 16-continued

| Cpd No. | Structure | IUPAC | MW (g/mol) |
|---|---|---|---|
| 686 | 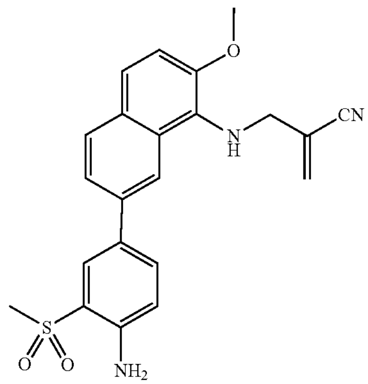 [SMILES: C=C(C#N)CNc1c(OC)ccc2ccc(-c3ccc(N)c(S(C)(=O)=O)c3)cc12] | 2-({[7-(4-amino-3-methanesulfonylphenyl)-2-methoxynaphthalen-1-yl]amino}methyl)prop-2-enenitrile | 407.5 |
| 687 | 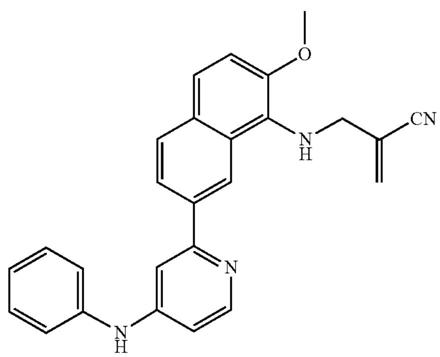 [SMILES: C=C(C#N)CNc1c(OC)ccc2ccc(-c3cc(Nc4ccccc4)ccn3)cc12] | 2-[({2-methoxy-7-[4-(phenylamino)pyridin-2-yl]naphthalen-1-yl}amino)methyl]prop-2-enenitrile | 406.5 |
| 688 | 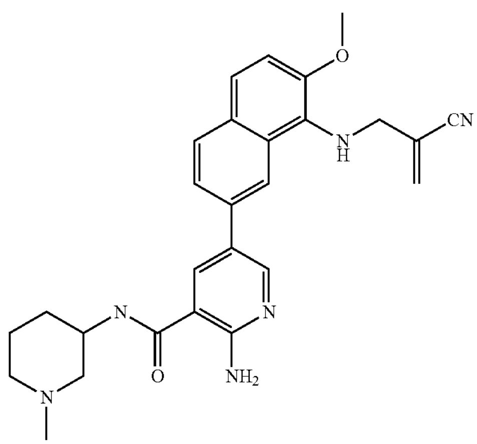 | 2-amino-5-{8-[(2-cyano-2-methylideneethyl)amino]-7-methoxynaphthalen-2-yl}-N-(1-methylpiperidin-3-yl)pyridine-3-carboxamide | 470.6 |
| 689 | 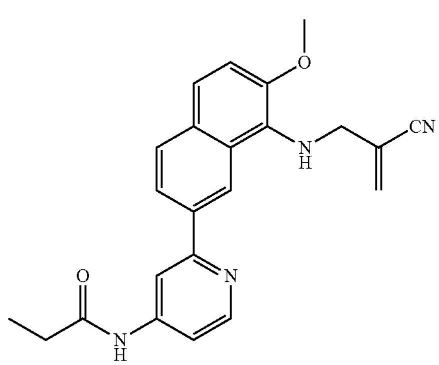 [SMILES: C=C(C#N)CNc1c(OC)ccc2ccc(-c3cc(NC(=O)CC)ccn3)cc12] | N-(2-{8-[(2-cyano-2-methylideneethyl)amino]-7-methoxynaphthalen-2-yl}pyridin-4-yl)propanamide | 386.5 |

TABLE 16-continued

| Cpd No. | Structure | IUPAC | MW (g/mol) |
|---|---|---|---|
| 690 | 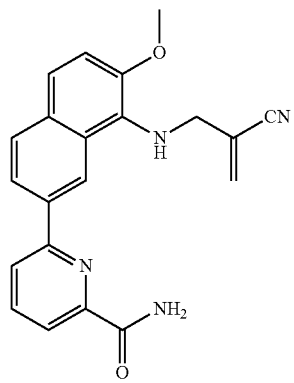 [SMILES: C=C(C#N)CNc1c(OC)ccc2ccc(-c3cccc(C(N)=O)n3)cc12] | 6-{8-[(2-cyano-2-methylideneethyl)amino]-7-methoxynaphthalen-2-yl}pyridine-2-carboxamide | 358.4 |
| 691 | 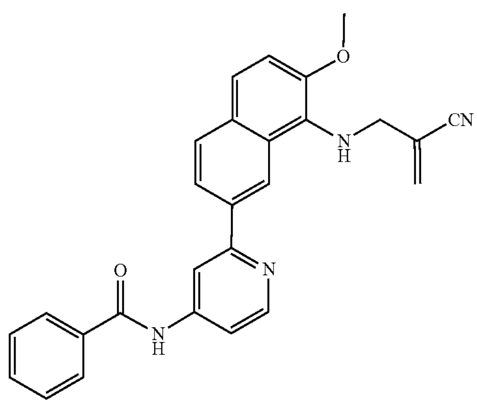 [SMILES: C=C(C#N)CNc1c(OC)ccc2ccc(-c3cc(NC(=O)c4ccccc4)ccn3)cc12] | N-(2-{8-[(2-cyano-2-methylideneethyl)amino]-7-methoxynaphthalen-2-yl}pyridin-4-yl)benzamide | 434.5 |
| 692 | 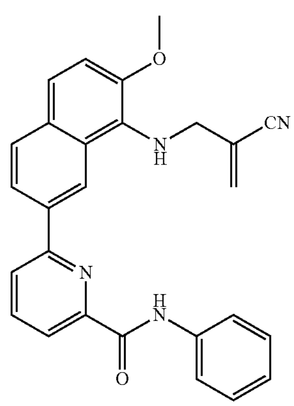 [SMILES: C=C(C#N)CNc1c(OC)ccc2ccc(-c3cccc(C(=O)Nc4ccccc4)n3)cc12] | 6-{8-[(2-cyano-2-methylideneethyl)amino]-7-methoxynaphthalen-2-yl}-N-phenylpyridine-2-carboxamide | 434.5 |
| 693 | 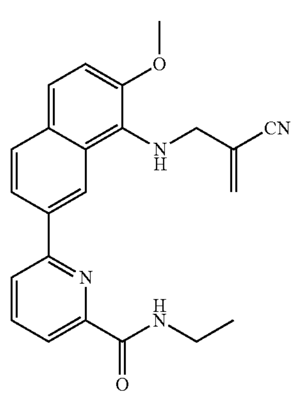 [SMILES: C=C(C#N)CNc1c(OC)ccc2ccc(-c3cccc(C(=O)NCC)n3)cc12] | 6-{8-[(2-cyano-2-methylideneethyl)amino]-7-methoxynaphthalen-2-yl}-N-ethylpyridine-2-carboxamide | 386.5 |

TABLE 16-continued

| Cpd No. | Structure | IUPAC | MW (g/mol) |
|---|---|---|---|
| 694 | 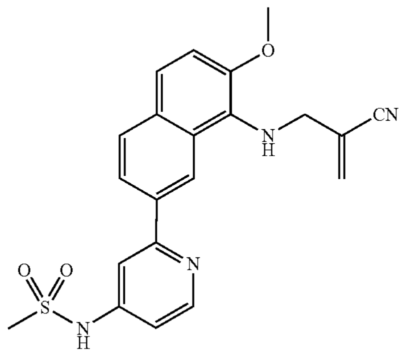 [SMILES: C=C(C#N)CNc1c(OC)ccc2ccc(-c3cc(NS(C)(=O)=O)ccn3)cc12] | N-(2-{8-[(2-cyano-2-methylideneethyl)amino]-7-methoxynaphthalen-2-yl}pyridin-4-yl)methanesulfonamide | 408.5 |
| 695 | 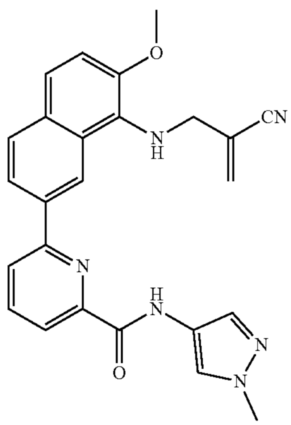 [SMILES: C=C(C#N)CNc1c(OC)ccc2ccc(-c3cccc(C(=O)Nc4cnn(C)c4)n3)cc12] | 6-{8-[(2-cyano-2-methylideneethyl)amino]-7-methoxynaphthalen-2-yl}-N-(1-methyl-1H-pyrazol-4-yl)pyridine-2-carboxamide | 438.5 |
| 696 | 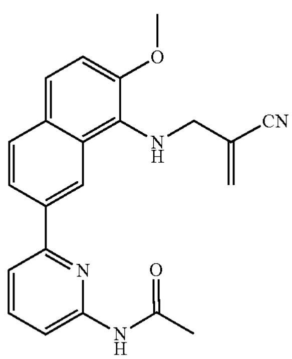 [SMILES: C=C(C#N)CNc1c(OC)ccc2ccc(-c3cccc(NC(C)=O)n3)cc12] | N-(6-{8-[(2-cyano-2-methylideneethyl)amino]-7-methoxynaphthalen-2-yl}pyridin-2-yl)acetamide | 372.4 |
| 697 | 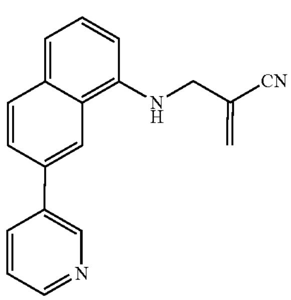 [SMILES: C=C(C#N)CNc1cccc2ccc(-c3cccnc3)cc12] | 2-({[7-(pyridin-3-yl)naphthalen-1-yl]amino}methyl)prop-2-enenitrile | 285.4 |

TABLE 16-continued

| Cpd No. | Structure | IUPAC | MW (g/mol) |
|---|---|---|---|
| 698 | 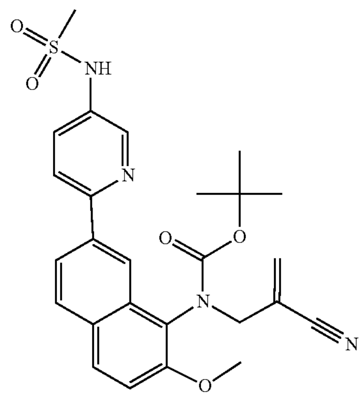 [SMILES: C=C(C#N)CN(C(=O)OC(C)(C)C)c1c(OC)ccc2ccc(-c3ccc(NS(C)(=O)=O)cn3)cc12] | tert-butyl N-(2-cyano-2-methylideneethyl)-N-[7-[5-methanesulfonamidopyridin-2-yl)-2-methoxynaphthalen-1-yl]carbamate | 508.6 |
| 699 | 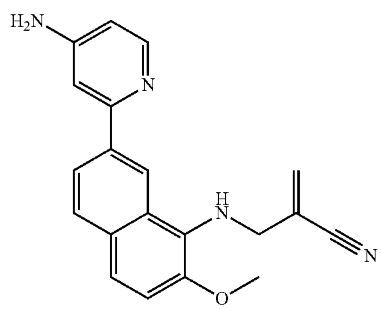 [SMILES: C=C(C#N)CNc1c(OC)ccc2ccc(-c3cc(N)ccn3)cc12] | 2-({[7-(4-aminopyridin-2-yl)-2-methoxynaphthalen-1-yl]amino}methyl)prop-2-enenitrile | 330.4 |
| 700 | 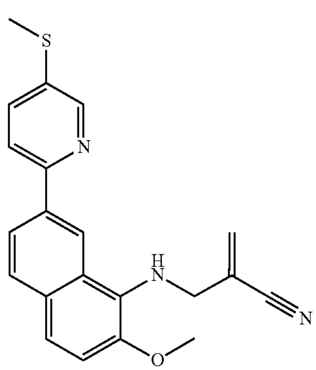 [SMILES: C=C(C#N)CNc1c(OC)ccc2ccc(-c3ccc(SC)cn3)cc12] | 2-[({2-methoxy-7-[5-(methylsulfanyl)pyridin-2-yl]naphthalen-1-yl}amino)methyl]prop-2-enenitrile | 361.5 |
| 701 | 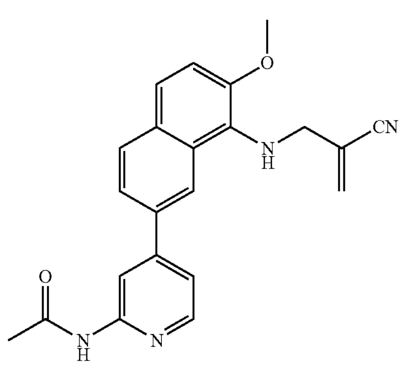 [SMILES: C=C(C#N)CNc1c(OC)ccc2ccc(-c3ccnc(NC(C)=O)c3)cc12] | N-(4-{8-[(2-cyano-2-methylideneethyl)amino]-7-methoxynaphthalen-2-yl}pyridin-2-yl)acetamide | 372.4 |

TABLE 16-continued

| Cpd No. | Structure | IUPAC | MW (g/mol) |
|---|---|---|---|
| 702 | 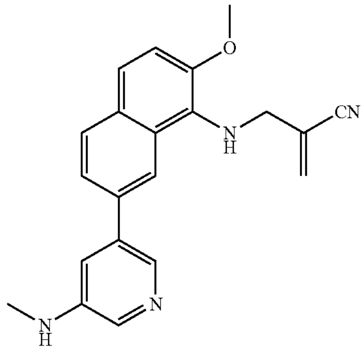 [SMILES: C=C(C#N)CNc1c(OC)ccc2ccc(-c3cncc(NC)c3)cc12] | 2-[({2-methoxy-7-[5-(methylamino)pyridin-3-yl]naphthalen-1-yl}amino)methyl]prop-2-enenitrile | 344.4 |
| 703 | 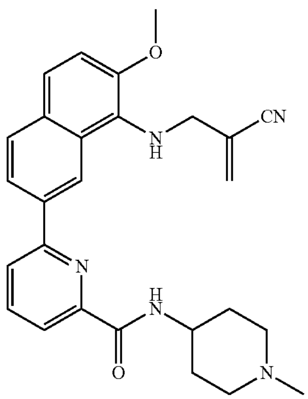 [SMILES: C=C(C#N)CNc1c(OC)ccc2ccc(-c3cccc(C(=O)NC4CCN(C)CC4)n3)cc12] | 6-{8-[(2-cyano-2-methylideneethyl)amino]-7-methoxynaphthalen-2-yl}-N-(1-methylpiperidin-4-yl)pyridine-2-carboxamide | 455.6 |
| 704 | 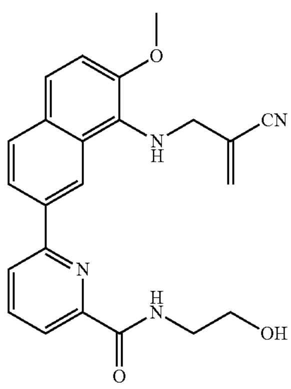 [SMILES: C=C(C#N)CNc1c(OC)ccc2ccc(-c3cccc(C(=O)NCCO)n3)cc12] | 6-{8-[(2-cyano-2-methylideneethyl)amino]-7-methoxynaphthalen-2-yl}-N-(2-hydroxyethyl)pyridine-2-carboxamide | 402.5 |
| 705 | 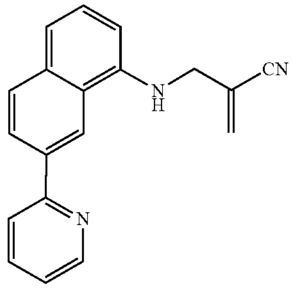 [SMILES: C=C(C#N)CNc1cccc2ccc(-c3ccccn3)cc12] | 2-({[7-(pyridin-2-yl)naphthalen-1-yl]amino}methyl)prop-2-enenitrile | 285.4 |

TABLE 16-continued

| Cpd No. | Structure | IUPAC | MW (g/mol) |
|---|---|---|---|
| 706 | 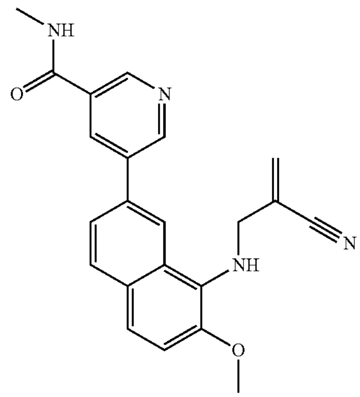 [SMILES: C=C(C#N)CNc1c(OC)ccc2ccc(-c3cncc(C(=O)NC)c3)cc12] | 5-{8-[(2-cyano-2-methylideneethyl)amino]-7-methoxynaphthalen-2-yl}-N-methylpyridine-3-carboxamide | 372.4 |
| 707 | 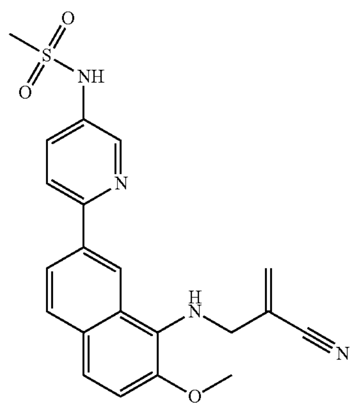 [SMILES: C=C(C#N)CNc1c(OC)ccc2ccc(-c3ccc(NS(C)(=O)=O)cn3)cc12] | N-(6-{8-[(2-cyano-2-methylideneethyl)amino]-7-methoxynaphthalen-2-yl}pyridin-3-yl)methanesulfonamide | 408.5 |
| 708 | 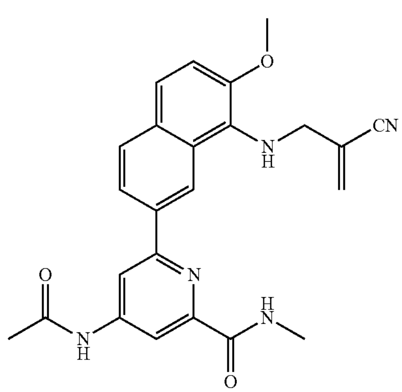 [SMILES: C=C(C#N)CNc1c(OC)ccc2ccc(-c3cc(NC(C)=O)cc(C(=O)NC)n3)cc12] | 6-{8-[(2-cyano-2-methylideneethyl)amino]-7-methoxynaphthalen-2-yl}-4-acetamido-N-methylpyridine-2-carboxamide | 429.5 |
| 709 | 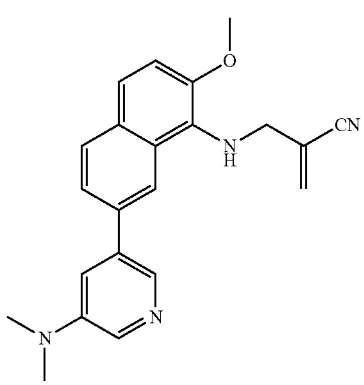 [SMILES: C=C(C#N)CNc1c(OC)ccc2ccc(-c3cncc(N(C)C)c3)cc12] | 2-[({7-[5-(dimethylamino)pyridin-3-yl]-2-methoxynaphthalen-1-yl}amino)methyl]prop-2-enenitrile | 358.4 |

TABLE 16-continued

| Cpd No. | Structure | IUPAC | MW (g/mol) |
|---|---|---|---|
| 710 | 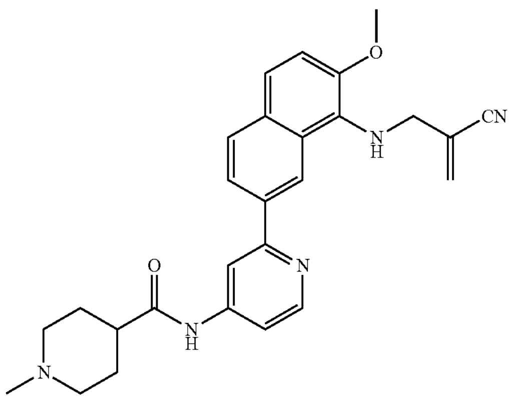 [SMILES: C=C(C#N)CNc1c(OC)ccc2ccc(-c3cc(NC(=O)C4CCN(C)CC4)ccn3)cc12] | N-(2-{8-[(2-cyano-2-methylideneethyl)amino]-7-methoxynaphthalen-2-yl}pyridin-4-yl)-1-methylpiperidine-4-carboxamide | 455.6 |
| 711 | 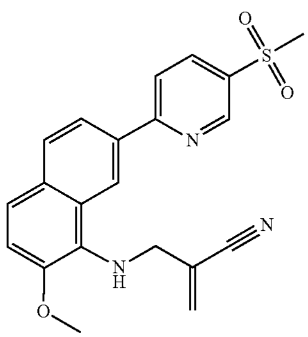 [SMILES: C=C(C#N)CNc1c(OC)ccc2ccc(-c3ccc(S(C)(=O)=O)cn3)cc12] | 2-({[7-(5-methanesulfonylpyridin-2-yl)-2-methoxynaphthalen-1-yl]amino}methyl)prop-2-enenitrile | 393.5 |
| 712 | 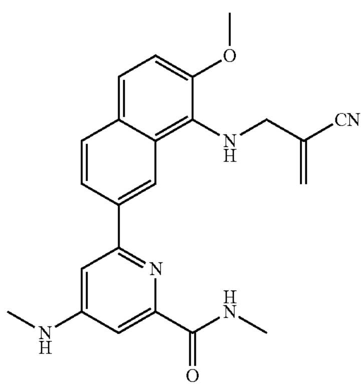 [SMILES: C=C(C#N)CNc1c(OC)ccc2ccc(-c3cc(NC)cc(C(=O)NC)n3)cc12] | 6-{8-[(2-cyano-2-methylideneethyl)amino]-7-methoxynaphthalen-2-yl}-N-methyl-4-(methylamino)pyridine-2-carboxamide | 401.5 |
| 713 | 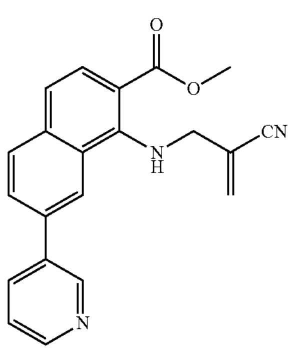 [SMILES: C=C(C#N)CNc1c(C(=O)OC)ccc2ccc(-c3cccnc3)cc12] | methyl 1-[(2-cyano-2-methylideneethyl)amino]-7-(pyridin-3-yl)naphthalene-2-carboxylate | 343.4 |

TABLE 16-continued

| Cpd No. | Structure | IUPAC | MW (g/mol) |
|---|---|---|---|
| 714 | 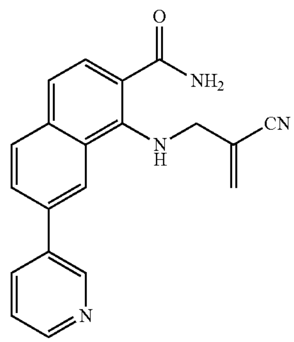 [SMILES: C=C(C#N)CNc1c(C(N)=O)ccc2ccc(-c3cccnc3)cc12] | 1-[(2-cyano-2-methylideneethyl)amino]-7-(pyridin-3-yl)naphthalene-2-carboxamide | 328.4 |
| 715 | 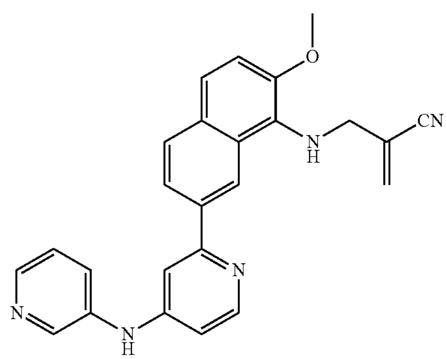 [SMILES: C=C(C#N)CNc1c(OC)ccc2ccc(-c3cc(Nc4cccnc4)ccn3)cc12] | 2-{[(2-methoxy-7-{4-[(pyridin-3-yl)amino]pyridin-2-yl}naphthalen-1-yl)amino]methyl}prop-2-enenitrile | 407.5 |
| 716 | 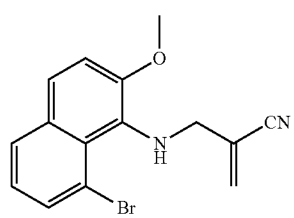 [SMILES: C=C(C#N)CNc1c(OC)ccc2cccc(Br)c12] | 2-{[(8-bromo-2-methoxynaphthalen-1-yl)amino]methyl}prop-2-enenitrile | 317.2 |
| 717 | 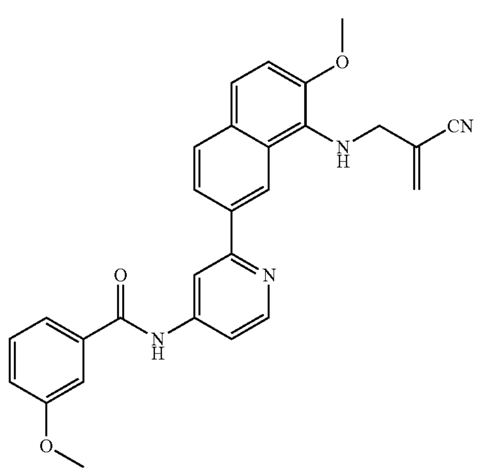 [SMILES: C=C(C#N)CNc1c(OC)ccc2ccc(-c3cc(NC(=O)c4cccc(OC)c4)ccn3)cc12] | N-(2-{8-[(2-cyano-2-methylideneethyl)amino]-7-methoxynaphthalen-2-yl}pyridin-4-yl)-3-methoxybenzamide | 464.5 |

TABLE 16-continued

| Cpd No. | Structure | IUPAC | MW (g/mol) |
|---|---|---|---|
| 718 | 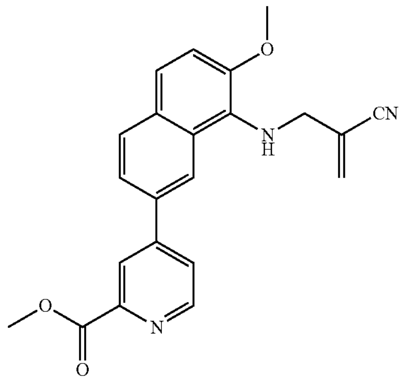 [SMILES: C=C(C#N)CNc1c(OC)ccc2ccc(-c3ccnc(C(=O)OC)c3)cc12] | methyl 4-{8-[(2-cyano-2-methylideneethyl)amino]-7-methoxynaphthalen-2-yl}pyridine-2-carboxylate | 373.4 |
| 719 | 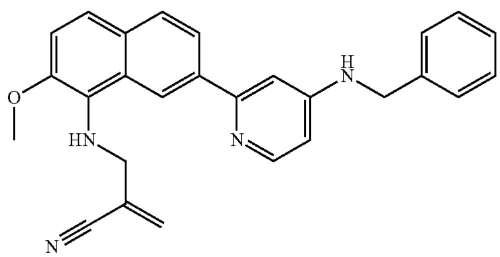 [SMILES: C=C(C#N)CNc1c(OC)ccc2ccc(-c3cc(NCc4ccccc4)ccn3)cc12] | 2-[({7-[4-(benzylamino)pyridin-2-yl]-2-methoxynaphthalen-1-yl}amino)methyl]prop-2-enenitrile | 420.5 |
| 720 | 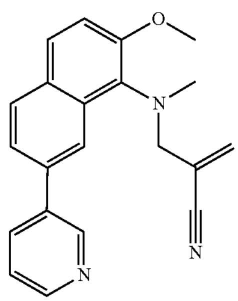 [SMILES: C=C(C#N)CN(C)c1c(OC)ccc2ccc(-c3cccnc3)cc12] | 2-({[2-methoxy-7-(pyridin-3-yl)naphthalen-1-yl](methyl)amino}methyl)prop-2-enenitrile | 329.4 |
| 721 | 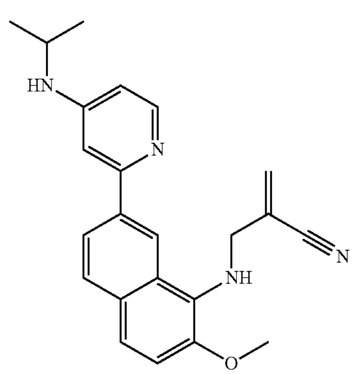 [SMILES: C=C(C#N)CNc1c(OC)ccc2ccc(-c3cc(NC(C)C)ccn3)cc12] | 2-{[(2-methoxy-7-{4-[(propan-2-yl)amino]pyridin-2-yl}naphthalen-1-yl)amino]methyl}prop-2-enenitrile | 372.5 |

TABLE 16-continued

| Cpd No. | Structure | IUPAC | MW (g/mol) |
|---|---|---|---|
| 722 | 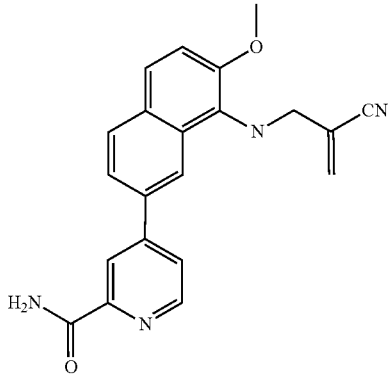 | 4-{8-[(2-cyano-2-methylideneethyl)amino]-7-methoxynaphthalen-2-yl}pyridine-2-carboxamide | 358.4 |
| 723 | 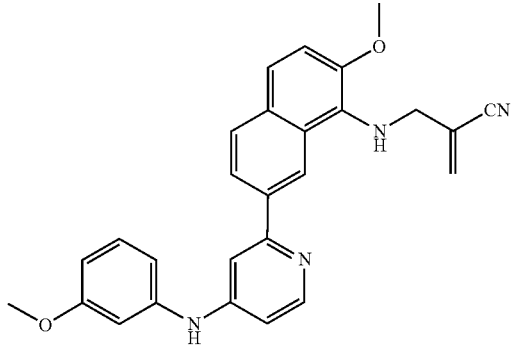 [SMILES: C=C(C#N)CNc1c(OC)ccc2ccc(-c3cc(Nc4cccc(OC)c4)ccn3)cc12] | 2-{[(2-methoxy-7-{4-[(3-methoxyphenyl)amino]pyridin-2-yl}naphthalen-1-yl)amino]methyl}prop-2-enenitrile | 436.5 |
| 724 | 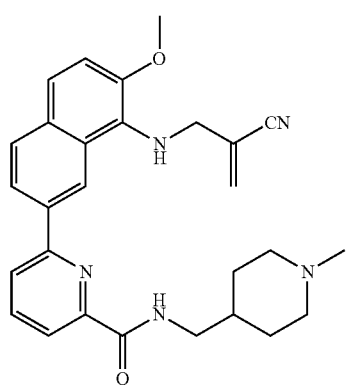 [SMILES: C=C(C#N)CNc1c(OC)ccc2ccc(-c3cccc(C(=O)NCC4CCN(C)CC4)n3)cc12] | 6-{8-[(2-cyano-2-methylideneethyl)amino]-7-methoxynaphthalen-2-yl}-N-[(1-methylpiperidin-4-yl)methyl]pyridine-2-carboxamide | 469.6 |
| 725 | 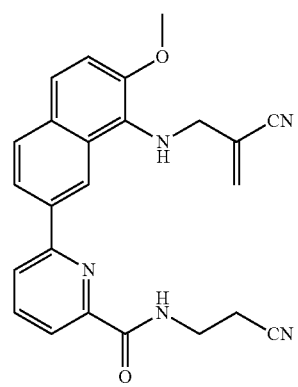 [SMILES: C=C(C#N)CNc1c(OC)ccc2ccc(-c3cccc(C(=O)NCCC#N)n3)cc12] | 6-{8-[(2-cyano-2-methylideneethyl)amino]-7-methoxynaphthalen-2-yl}-N-(2-cyanoethyl)pyridine-2-carboxamide | 411.5 |

TABLE 16-continued

| Cpd No. | Structure | IUPAC | MW (g/mol) |
|---|---|---|---|
| 726 | 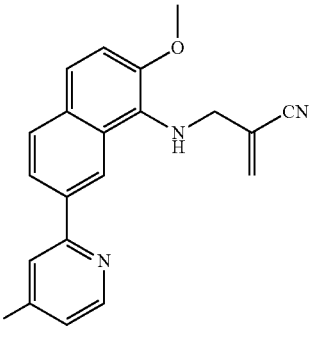 | 2-{[(7-{4-[(4-chlorophenyl)amino]pyridin-2-yl}-2-methoxynaphthalen-1-yl)amino]methyl}prop-2-enenitrile | 440.9 |
| 727 | 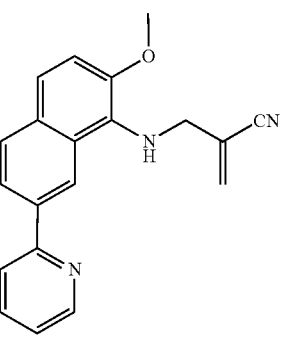 | N-(2-{8-[(2-cyano-2-methylideneethyl)amino]-7-methoxynaphthalen-2-yl}pyridin-4-yl)-1-methyl-1H-pyrazole-4-carboxamide | 438.5 |
| 728 | 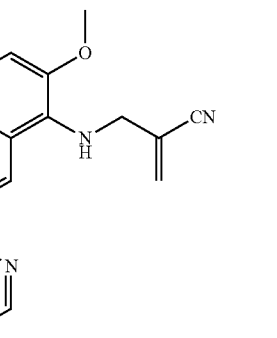 | 2-({[7-(4-hydroxypyridin-2-yl)-2-methoxynaphthalen-1-yl]amino}methyl)prop-2-enenitrile | 331.4 |
| 729 | 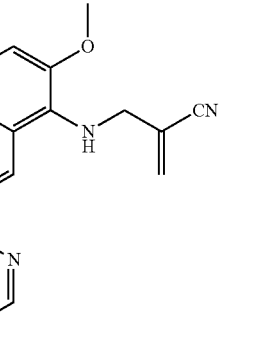 | 2-({[7-(6-aminopyrimidin-4-yl)-2-methoxynaphthalen-1-yl]amino}methyl)prop-2-enenitrile | 331.4 |

TABLE 16-continued

| Cpd No. | Structure | IUPAC | MW (g/mol) |
|---|---|---|---|
| 730 | 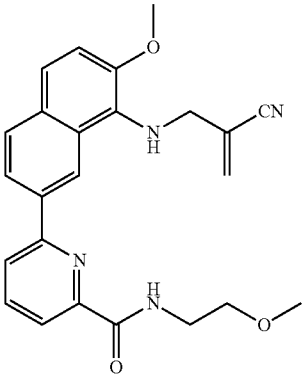 [SMILES: C=C(C#N)CNc1c(OC)ccc2ccc(-c3cccc(C(=O)NCCOC)n3)cc12] | 6-{8-[(2-cyano-2-methylideneethyl)amino]-7-methoxynaphthalen-2-yl}-N-(2-methoxyethyl)pyridine-2-carboxamide | 416.5 |
| 731 | 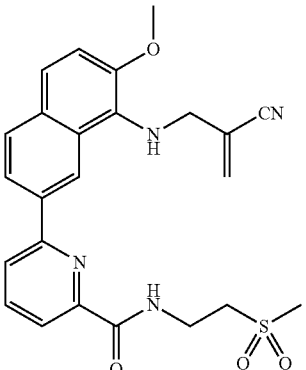 | 6-{8-[(2-cyano-2-methylideneethyl)amino]-7-methoxynaphthalen-2-yl}-N-(2-methanesulfonylethyl)pyridine-2-carboxamide | 464.5 |
| 732 | 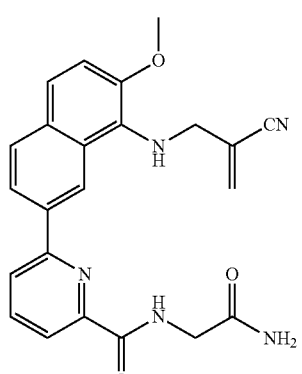 | 2-[(6-{8-[(2-cyano-2-methylideneethyl)amino]-7-methoxynaphthalen-2-yl}pyridin-2-yl)formamido]acetamide | 415.5 |
| 733 | 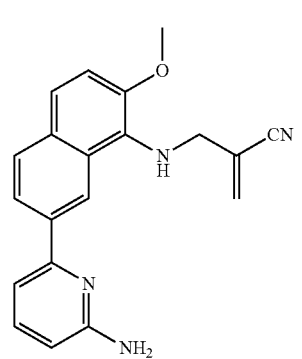 [SMILES: C=C(C#N)CNc1c(OC)ccc2ccc(-c3cccc(N)n3)cc12] | 2-({[7-(6-aminopyridin-2-yl)-2-methoxynaphthalen-1-yl]amino}methyl)prop-2-enenitrile | 330.4 |

TABLE 16-continued

| Cpd No. | Structure | IUPAC | MW (g/mol) |
|---|---|---|---|
| 734 | 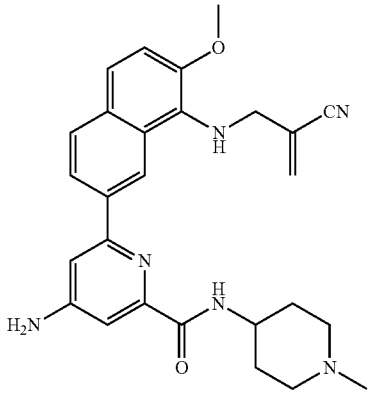 [SMILES: C=C(C#N)CNc1c(OC)ccc2ccc(-c3cc(N)cc(C(=O)NC4CCN(C)CC4)n3)cc12] | 4-amino-6-{8-[(2-cyano-2-methylideneethyl)amino]-7-methoxynaphthalen-2-yl}-N-(1-methylpiperidin-4-yl)pyridine-2-carboxamide | 470.6 |
| 735 | 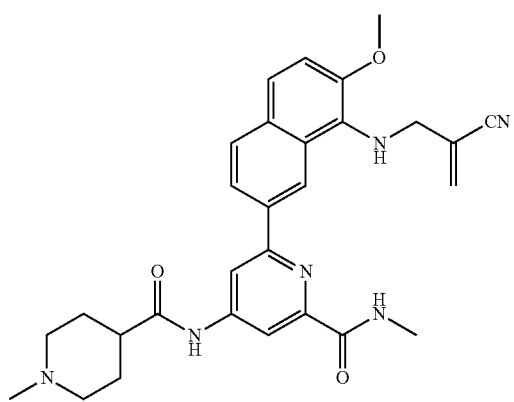 [SMILES: C=C(C#N)CNc1c(OC)ccc2ccc(-c3cc(NC(=O)C4CCN(C)CC4)cc(C(=O)NC)n3)cc12] | 6-{8-[(2-cyano-2-methylideneethyl)amino]-7-methoxynaphthalen-2-yl}-N-methyl-4-(1-methylpiperidine-4-amido)pyridine-2-carboxamide | 512.6 |
| 736 | 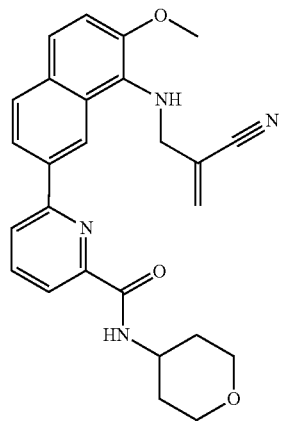 [SMILES: C=C(C#N)CNc1c(OC)ccc2ccc(-c3cccc(C(=O)NC4CCOCC4)n3)cc12] | 6-{8-[(2-cyano-2-methylideneethyl)amino]-7-methoxynaphthalen-2-yl}-N-(oxan-4-yl)pyridine-2-carboxamide | 442.5 |
| 737 | 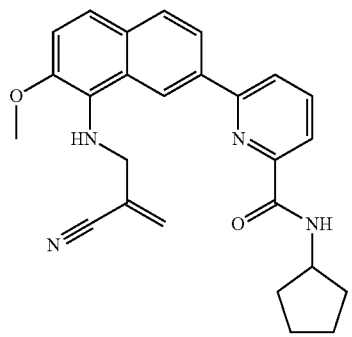 [SMILES: C=C(C#N)CNc1c(OC)ccc2ccc(-c3cccc(C(=O)NC4CCCC4)n3)cc12] | 6-{8-[(2-cyano-2-methylideneethyl)amino]-7-methoxynaphthalen-2-yl}-N-cyclopentylpyridine-2-carboxamide | 426.5 |

TABLE 16-continued

| Cpd No. | Structure | IUPAC | MW (g/mol) |
|---|---|---|---|
| 738 | 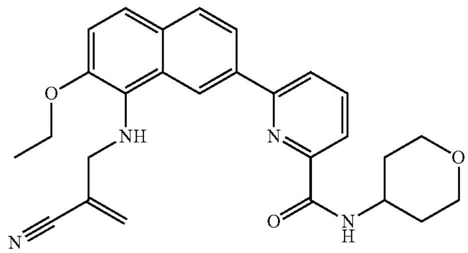 [SMILES: C=C(C#N)CNc1c(OCC)ccc2ccc(-c3cccc(C(=O)NC4CCOCC4)n3)cc12] | 6-{8-[(2-cyano-2-methylideneethyl)amino]-7-ethoxynaphthalen-2-yl}-N-(oxan-4-yl)pyridine-2-carboxamide | 456.5 |
| 739 | 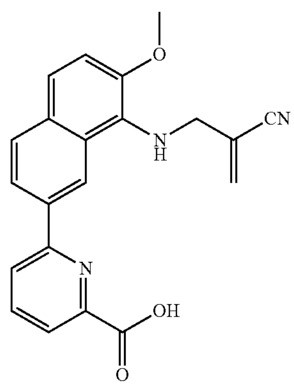 [SMILES: C=C(C#N)CNc1c(OC)ccc2ccc(-c3cccc(C(=O)O)n3)cc12] | 6-{8-[(2-cyano-2-methylideneethyl)amino]-7-methoxynaphthalen-2-yl}pyridine-2-carboxylic acid | 359.4 |
| 740 | 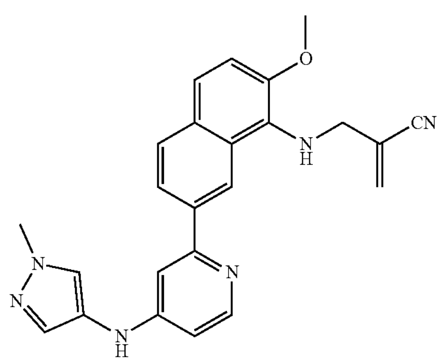 [SMILES: C=C(C#N)CNc1c(OC)ccc2ccc(-c3cc(Nc4cnn(C)c4)ccn3)cc12] | 2-{[(2-methoxy-7-{4-[(1-methyl-1H-pyrazol-4-yl)amino]pyridin-2-yl}naphthalen-1-yl)amino]methyl}prop-2-enenitrile | 410.5 |
| 741 | 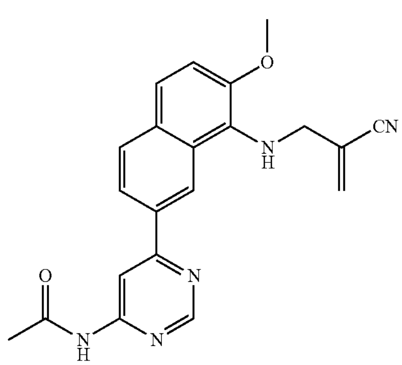 [SMILES: C=C(C#N)CNc1c(OC)ccc2ccc(-c3cc(NC(C)=O)ncn3)cc12] | N-(6-{8-[(2-cyano-2-methylideneethyl)amino]-7-methoxynaphthalen-2-yl}pyrimidin-4-yl)acetamide | 373.4 |

TABLE 16-continued

| Cpd No. | Structure | IUPAC | MW (g/mol) |
|---|---|---|---|
| 742 | 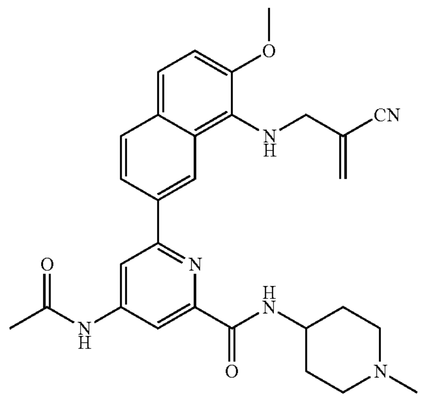 [SMILES: C=C(C#N)CNc1c(OC)ccc2ccc(-c3cc(NC(C)=O)cc(C(=O)NC4CCN(C)CC4)n3)cc12] | 6-{8-[(2-cyano-2-methylideneethyl)amino]-7-methoxynaphthalen-2-yl}-4-acetamido-N-(1-methylpiperidin-4-yl)pyridine-2-carboxamide | 512.6 |
| 743 | 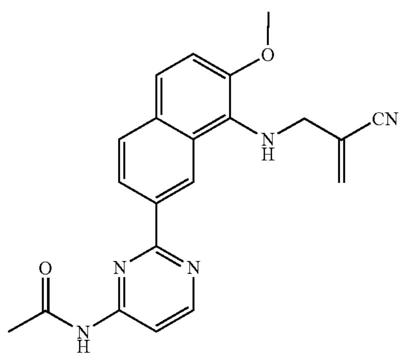 [SMILES: C=C(C#N)CNc1c(OC)ccc2ccc(-c3nccc(NC(C)=O)n3)cc12] | N-(2-{8-[(2-cyano-2-methylideneethyl)amino]-7-methoxynaphthalen-2-yl}pyrimidin-4-yl)acetamide | 373.4 |
| 744 | 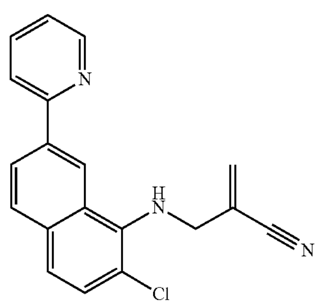 [SMILES: C=C(C#N)CNc1c(Cl)ccc2ccc(-c3ccccn3)cc12] | 2-({[2-chloro-7-(pyridin-2-yl)naphthalen-1-yl]amino}methyl)prop-2-enenitrile | 319.8 |
| 745 | 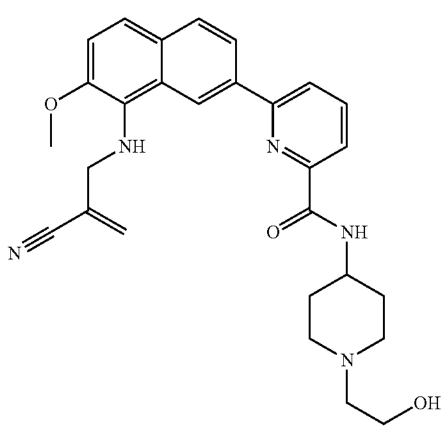 [SMILES: C=C(C#N)CNc1c(OC)ccc2ccc(-c3cccc(C(=O)NC4CCN(CCO)CC4)n3)cc12] | 6-{8-[(2-cyano-2-methylideneethyl)amino]-7-methoxynaphthalen-2-yl}-N-[1-(2-hydroxyethyl)piperidin-4-yl]pyridine-2-carboxamide | 485.6 |

TABLE 16-continued

| Cpd No. | Structure | IUPAC | MW (g/mol) |
|---|---|---|---|
| 746 | 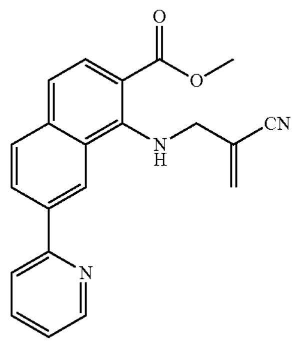 [SMILES: C=C(C#N)CNc1c(C(=O)OC)ccc2ccc(-c3ccccn3)cc12] | methyl 1-[(2-cyano-2-methylideneethyl)amino]-7-(pyridin-2-yl)naphthalene-2-carboxylate | 343.4 |
| 747 | 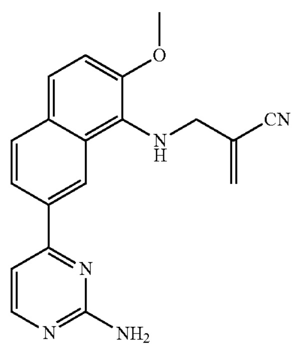 [SMILES: C=C(C#N)CNc1c(OC)ccc2ccc(-c3ccnc(N)n3)cc12] | 2-({[7-(2-aminopyrimidin-4-yl)-2-methoxynaphthalen-1-yl]amino}methyl)prop-2-enenitrile | 331.4 |
| 748 | 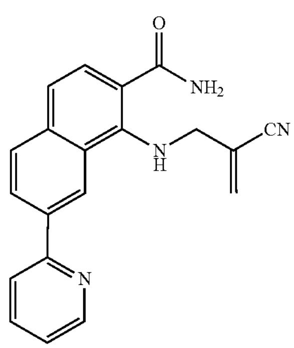 [SMILES: C=C(C#N)CNc1c(C(N)=O)ccc2ccc(-c3ccccn3)cc12] | 1-[(2-cyano-2-methylideneethyl)amino]-7-(pyridin-2-yl)naphthalene-2-carboxamide | 328.4 |
| 749 | 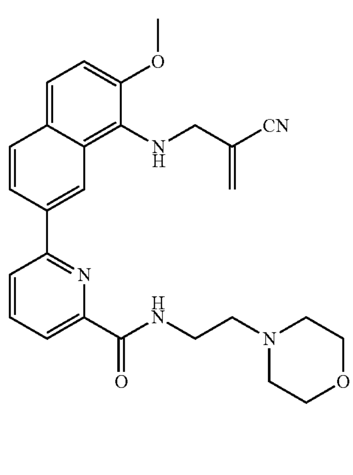 [SMILES: C=C(C#N)CNc1c(OC)ccc2ccc(-c3cccc(C(=O)NCCN4CCOCC4)n3)cc12] | 6-{8-[(2-cyano-2-methylideneethyl)amino]-7-methoxynaphthalen-2-yl}-N-[2-(morpholin-4-yl)ethyl]pyridine-2-carboxamide | 471.6 |

TABLE 16-continued

| Cpd No. | Structure | IUPAC | MW (g/mol) |
|---|---|---|---|
| 750 | 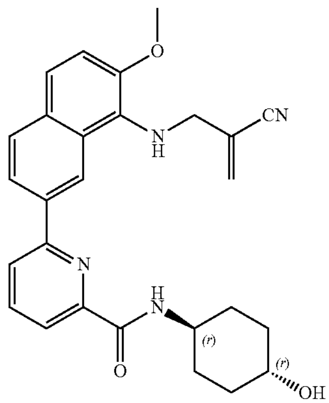 [SMILES: C=C(C#N)CNc1c(OC)ccc2ccc(-c3cccc(C(=O)N[C@H]4CC[C@H](O)CC4)n3)cc12] | 6-{8-[(2-cyano-2-methylideneethyl)amino]-7-methoxynaphthalen-2-yl}-N-[(1r,4r)-4-hydroxycyclohexyl]pyridine-2-carboxamide | 456.5 |
| 751 | 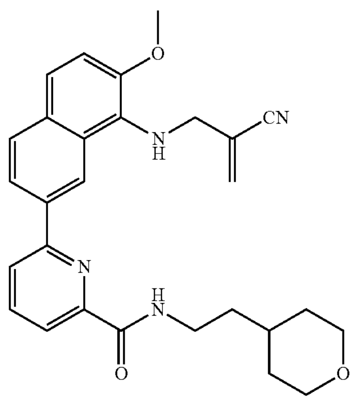 [SMILES: C=C(C#N)CNc1c(OC)ccc2ccc(-c3cccc(C(=O)NCCC4CCOCC4)n3)cc12] | 6-{8-[(2-cyano-2-methylideneethyl)amino]-7-methoxynaphthalen-2-yl}-N-[2-(oxan-4-yl)ethyl]pyridine-2-carboxamide | 470.6 |
| 752 | 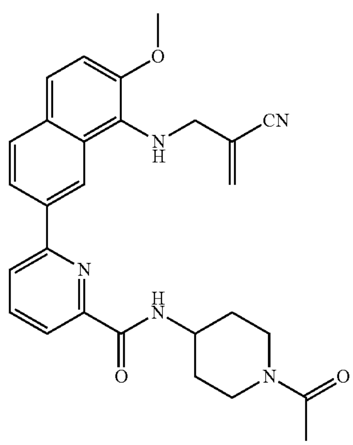 [SMILES: C=C(C#N)CNc1c(OC)ccc2ccc(-c3cccc(C(=O)NC4CCN(C(C)=O)CC4)n3)cc12] | N-(1-acetylpiperidin-4-yl)-6-{8-[(2-cyano-2-methylideneethyl)amino]-7-methoxynaphthalen-2-yl}pyridine-2-carboxamide | 483.6 |
| 753 | 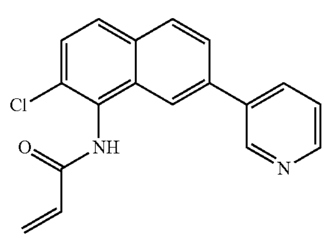 [SMILES: C=CC(=O)Nc1c(Cl)ccc2ccc(-c3cccnc3)cc12] | N-[2-chloro-7-(pyridin-3-yl)naphthalen-1-yl]prop-2-enamide | 308.8 |

TABLE 16-continued

| Cpd No. | Structure | IUPAC | MW (g/mol) |
|---|---|---|---|
| 754 | 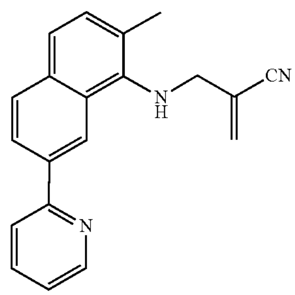 [SMILES: C=C(C#N)CNc1c(C)ccc2ccc(-c3ccccn3)cc12] | 2-({[2-methyl-7-(pyridin-2-yl)naphthalen-1-yl]amino}methyl)prop-2-enenitrile | 299.4 |
| 755 | 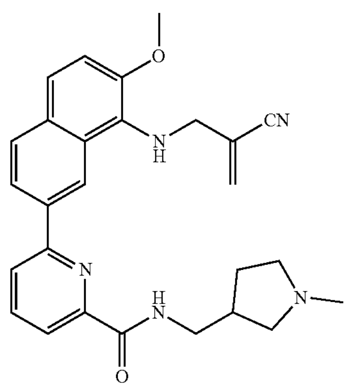 [SMILES: C=C(C#N)CNc1c(OC)ccc2ccc(-c3cccc(C(=O)NCC4CCN(C)C4)n3)cc12] | 6-{8-[(2-cyano-2-methylideneethyl)amino]-7-methoxynaphthalen-2-yl}-N-[(1-methylpyrrolidin-3-yl)methyl]pyridine-2-carboxamide | 455.6 |
| 756 | 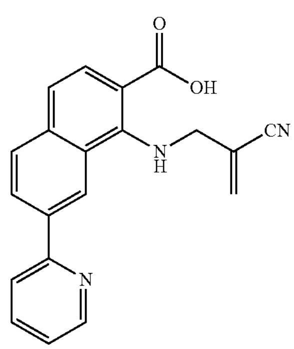 [SMILES: C=C(C#N)CNc1c(C(=O)O)ccc2ccc(-c3ccccn3)cc12] | 1-[(2-cyano-2-methylideneethyl)amino]-7-(pyridin-2-yl)naphthalene-2-carboxylic acid | 329.4 |
| 757 | 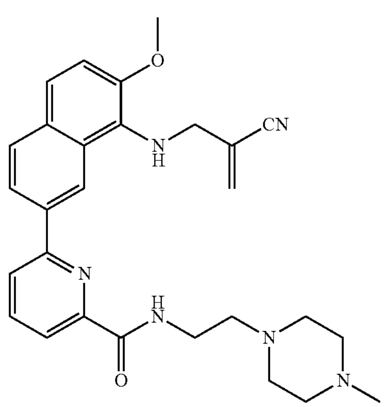 [SMILES: C=C(C#N)CNc1c(OC)ccc2ccc(-c3cccc(C(=O)NCCN4CCN(C)CC4)n3)cc12] | 6-{8-[(2-cyano-2-methylideneethyl)amino]-7-methoxynaphthalen-2-yl}-N-[2-(4-methylpiperazin-1-yl)ethyl]pyridine-2-carboxamide | 484.6 |

TABLE 16-continued

| Cpd No. | Structure | IUPAC | MW (g/mol) |
|---|---|---|---|
| 758 | 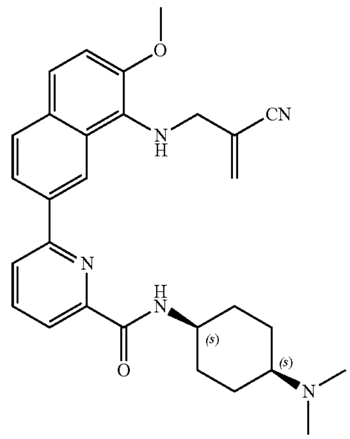 [SMILES: C=C(C#N)CNc1c(OC)ccc2ccc(-c3cccc(C(=O)N[C@H]4CC[C@@H](N(C)C)CC4)n3)cc12] | 6-{8-[(2-cyano-2-methylideneethyl)amino]-7-methoxynaphthalen-2-yl}-N-[(1s,4s)-4-(dimethylamino)cyclohexyl]pyridine-2-carboxamide | 483.6 |
| 759 | 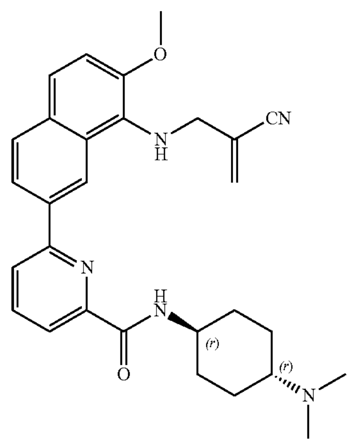 [SMILES: C=C(C#N)CNc1c(OC)ccc2ccc(-c3cccc(C(=O)N[C@H]4CC[C@H](N(C)C)CC4)n3)cc12] | 6-{8-[(2-cyano-2-methylideneethyl)amino]-7-methoxynaphthalen-2-yl}-N-[(1r,4r)-4-(dimethylamino)cyclohexyl]pyridine-2-carboxamide | 483.6 |
| 760 | 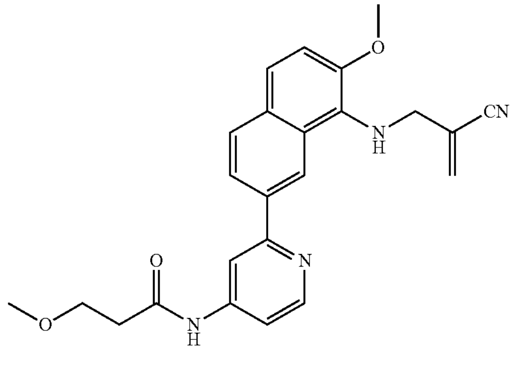 [SMILES: C=C(C#N)CNc1c(OC)ccc2ccc(-c3cc(NC(=O)CCOC)ccn3)cc12] | N-(2-{8-[(2-cyano-2-methylideneethyl)amino]-7-methoxynaphthalen-2-yl}pyridin-4-yl)-3-methoxypropanamide | 416.5 |

TABLE 16-continued

| Cpd No. | Structure | IUPAC | MW (g/mol) |
|---|---|---|---|
| 761 | 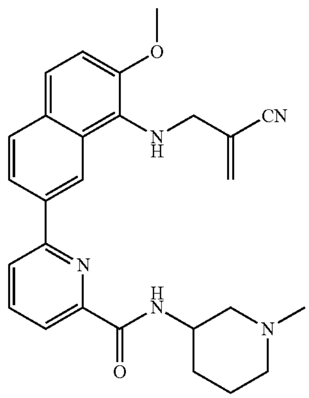 [SMILES: C=C(C#N)CNc1c(OC)ccc2ccc(-c3cccc(C(=O)NC4CCCN(C)C4)n3)cc12] | 6-{8-[(2-cyano-2-methylideneethyl)amino]-7-methoxynaphthalen-2-yl}-N-(1-methylpiperidin-3-yl)pyridine-2-carboxamide | 455.6 |
| 762 | 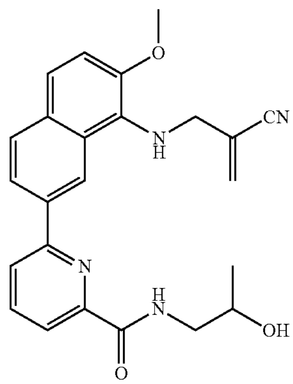 [SMILES: C=C(C#N)CNc1c(OC)ccc2ccc(-c3cccc(C(=O)NCC(C)O)n3)cc12] | 6-{8-[(2-cyano-2-methylideneethyl)amino]-7-methoxynaphthalen-2-yl}-N-(2-hydroxypropyl)pyridine-2-carboxamide | 416.5 |
| 763 | 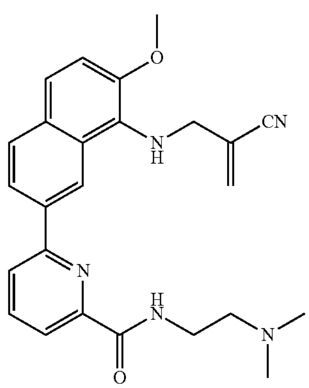 [SMILES: C=C(C#N)CNc1c(OC)ccc2ccc(-c3cccc(C(=O)NCCN(C)C)n3)cc12] | 6-{8-[(2-cyano-2-methylideneethyl)amino]-7-methoxynaphthalen-2-yl}-N-[2-(dimethylamino)ethyl]pyridine-2-carboxamide | 429.5 |
| 764 | 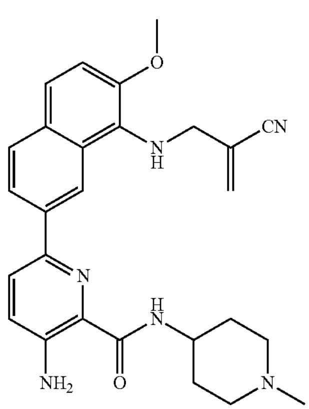 [SMILES: C=C(C#N)CNc1c(OC)ccc2ccc(-c3ccc(N)c(C(=O)NC4CCN(C)CC4)n3)cc12] | 3-amino-6-{8-[(2-cyano-2-methylideneethyl)amino]-7-methoxynaphthalen-2-yl}-N-(1-methylpiperidin-4-yl)pyridine-2-carboxamide | 470.6 |

TABLE 16-continued

| Cpd No. | Structure | IUPAC | MW (g/mol) |
|---|---|---|---|
| 765 | 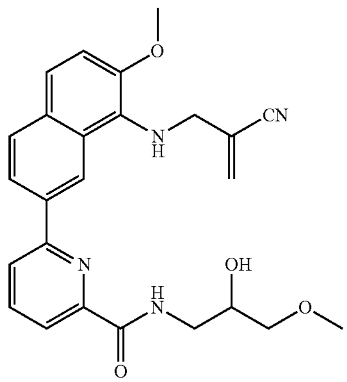 [SMILES: C=C(C#N)CNc1c(OC)ccc2ccc(-c3cccc(C(=O)NCC(O)COC)n3)cc12] | 6-{8-[(2-cyano-2-methylideneethyl)amino]-7-methoxynaphthalen-2-yl}-N-(2-hydroxy-3-methoxypropyl)pyridine-2-carboxamide | 446.5 |
| 766 | 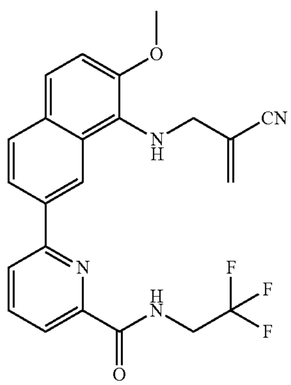 [SMILES: C=C(C#N)CNc1c(OC)ccc2ccc(-c3cccc(C(=O)NCC(F)(F)F)n3)cc12] | 6-{8-[(2-cyano-2-methylideneethyl)amino]-7-methoxynaphthalen-2-yl}-N-(2,2,2-trifluoroethyl)pyridine-2-carboxamide | 440.4 |
| 767 | 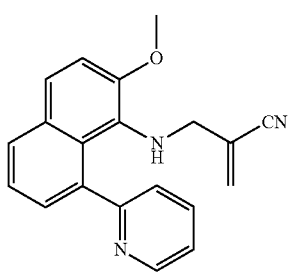 [SMILES: C=C(C#N)CNc1c(OC)ccc2cccc(-c3ccccn3)c12] | 2-({[2-methoxy-8-(pyridin-2-yl)naphthalen-1-yl]amino}methyl)prop-2-enenitrile | 315.4 |
| 768 | 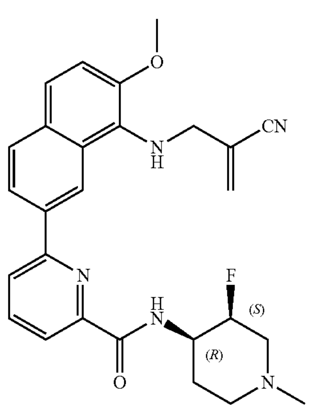 | 6-{8-[(2-cyano-2-methylideneethyl)amino]-7-methoxynaphthalen-2-yl}-N-[(3S,4R)-3-fluoro-1-methylpiperidin-4-yl]pyridine-2-carboxamide | 473.6 |

TABLE 16-continued

| Cpd No. | Structure | IUPAC | MW (g/mol) |
|---|---|---|---|
| 769 | 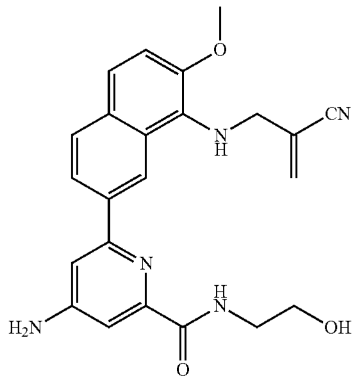 [SMILES: C=C(C#N)CNc1c(OC)ccc2ccc(-c3cc(N)cc(C(=O)NCCO)n3)cc12] | 4-amino-6-{8-[(2-cyano-2-methylideneethyl)amino]-7-methoxynaphthalen-2-yl}-N-(2-hydroxyethyl)pyridine-2-carboxamide | 417.5 |
| 770 | 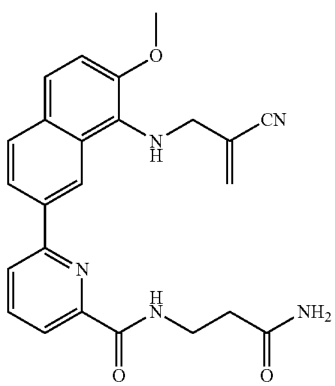 [SMILES: C=C(C#N)CNc1c(OC)ccc2ccc(-c3cccc(C(=O)NCCC(N)=O)n3)cc12] | 3-[(6-{8-[(2-cyano-2-methylideneethyl)amino]-7-methoxynaphthalen-2-yl}pyridin-2-yl)formamido]propanamide | 429.5 |
| 771 | 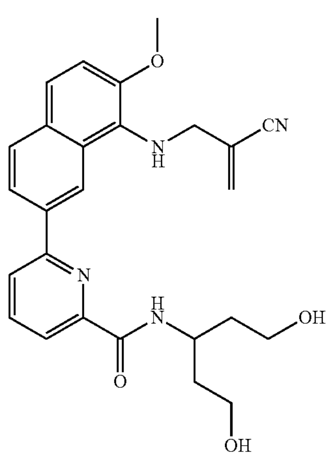 [SMILES: C=C(C#N)CNc1c(OC)ccc2ccc(-c3cccc(C(=O)NC(CCO)CCO)n3)cc12] | 6-{8-[(2-cyano-2-methylideneethyl)amino]-7-methoxynaphthalen-2-yl}-N-(1,5-dihydroxypentan-3-yl)pyridine-2-carboxamide | 460.5 |

TABLE 16-continued

| Cpd No. | Structure | IUPAC | MW (g/mol) |
|---|---|---|---|
| 772 | 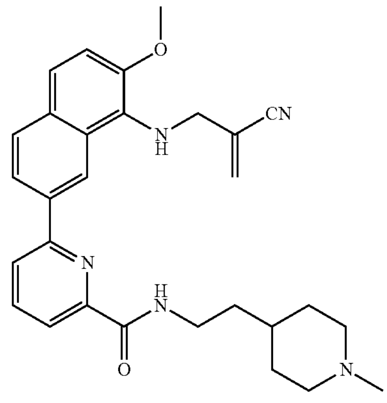 [SMILES: C=C(C#N)CNc1c(OC)ccc2ccc(-c3cccc(C(=O)NCCC4CCN(C)CC4)n3)cc12] | 6-{8-[(2-cyano-2-methylideneethyl)amino]-7-methoxynaphthalen-2-yl}-N-[2-(1-methylpiperidin-4-yl)ethyl]pyridine-2-carboxamide | 483.6 |
| 773 | 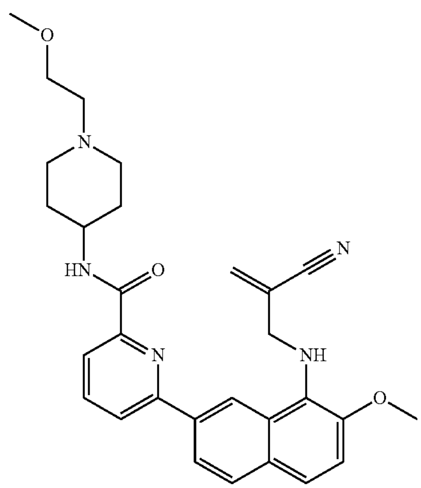 | 6-{8-[(2-cyano-2-methylideneethyl)amino]-7-methoxynaphthalen-2-yl}-N-[1-(2-methoxyethyl)piperidin-4-yl]pyridine-2-carboxamide | 499.6 |
| 774 | 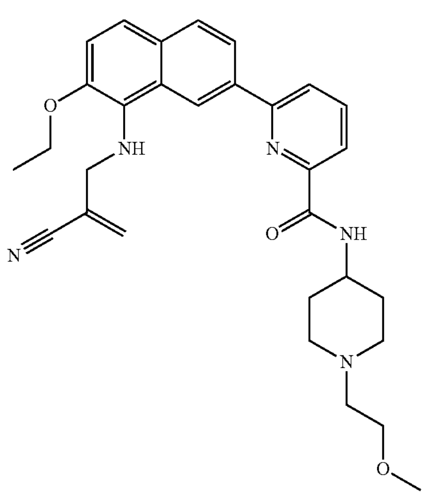 [SMILES: C=C(C#N)CNc1c(OCC)ccc2ccc(-c3cccc(C(=O)NC4CCN(CCOC)CC4)n3)cc12] | 6-{8-[(2-cyano-2-methylideneethyl)amino]-7-ethoxynaphthalen-2-yl}-N-[1-(2-methoxyethyl)piperidin-4-yl]pyridine-2-carboxamide | 513.6 |

TABLE 16-continued

| Cpd No. | Structure | IUPAC | MW (g/mol) |
|---|---|---|---|
| 775 | 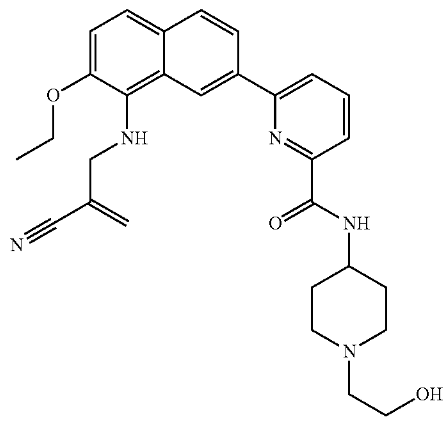 [SMILES: C=C(C#N)CNc1c(OCC)ccc2ccc(-c3cccc(C(=O)NC4CCN(CCO)CC4)n3)cc12] | 6-{8-[(2-cyano-2-methylideneethyl)amino]-7-ethoxynaphthalen-2-yl}-N-[1-(2-hydroxyethyl)piperidin-4-yl]pyridine-2-carboxamide | 499.6 |
| 776 | 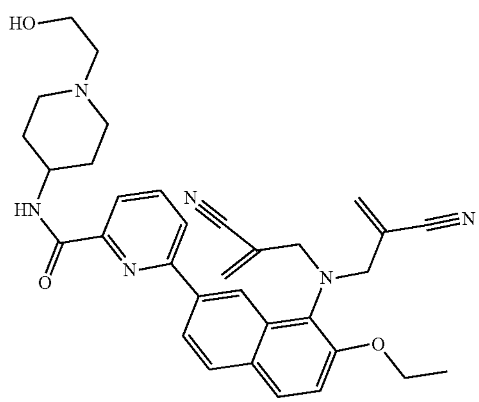 [SMILES: C=C(C#N)CN(CC(=C)C#N)c1c(OCC)ccc2ccc(-c3cccc(C(=O)NC4CCN(CCO)CC4)n3)cc12] | 6-{8-[bis(2-cyano-2-methylideneethyl)amino]-7-ethoxynaphthalen-2-yl}-N-[1-(2-hydroxyethyl)piperidin-4-yl]pyridine-2-carboxamide | 564.7 |
| 777 | 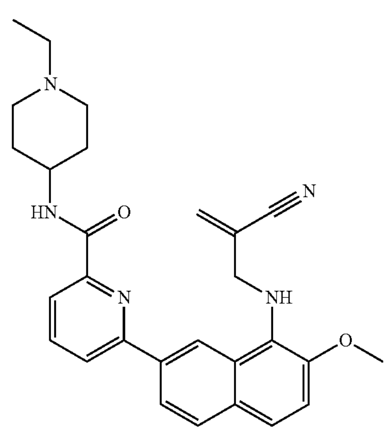 [SMILES: C=C(C#N)CNc1c(OC)ccc2ccc(-c3cccc(C(=O)NC4CCN(CC)CC4)n3)cc12] | 6-{8-[(2-cyano-2-methylideneethyl)amino]-7-methoxynaphthalen-2-yl}-N-(1-ethylpiperidin-4-yl)pyridine-2-carboxamide | 469.6 |

TABLE 16-continued

| Cpd No. | Structure | IUPAC | MW (g/mol) |
|---|---|---|---|
| 778 | 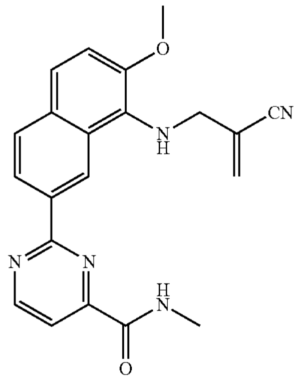 [SMILES: C=C(C#N)CNc1c(OC)ccc2ccc(-c3nccc(C(=O)NC)n3)cc12] | 2-{8-[(2-cyano-2-methylideneethyl)amino]-7-methoxynaphthalen-2-yl}-N-methylpyrimidine-4-carboxamide | 373.4 |
| 779 | 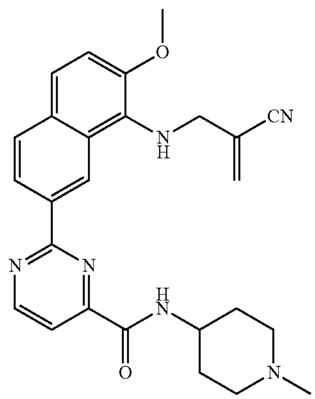 [SMILES: C=C(C#N)CNc1c(OC)ccc2ccc(-c3nccc(C(=O)NC4CCN(C)CC4)n3)cc12] | 2-{8-[(2-cyano-2-methylideneethyl)amino]-7-methoxynaphthalen-2-yl}-N-(1-methylpiperidin-4-yl)pyrimidine-4-carboxamide | 456.6 |
| 780 | 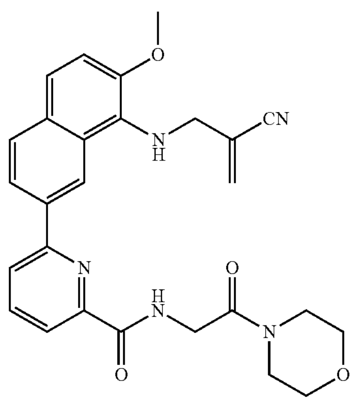 [SMILES: C=C(C#N)CNc1c(OC)ccc2ccc(-c3cccc(C(=O)NCC(=O)N4CCOCC4)n3)cc12] | 6-{8-[(2-cyano-2-methylideneethyl)amino]-7-methoxynaphthalen-2-yl}-N-[2-(morpholin-4-yl)-2-oxoethyl]pyridine-2-carboxamide | 485.5 |
| 781 | 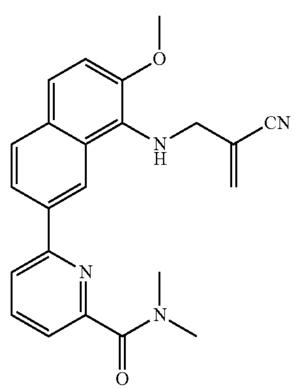 [SMILES: C=C(C#N)CNc1c(OC)ccc2ccc(-c3cccc(C(=O)N(C)C)n3)cc12] | 6-{8-[(2-cyano-2-methylideneethyl)amino]-7-methoxynaphthalen-2-yl}-N,N-dimethylpyridine-2-carboxamide | 386.5 |

TABLE 16-continued

| Cpd No. | Structure | IUPAC | MW (g/mol) |
|---|---|---|---|
| 782 | 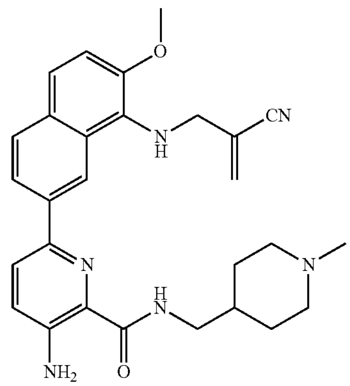 [SMILES: C=C(C#N)CNc1c(OC)ccc2ccc(-c3ccc(N)c(C(=O)NCC4CCN(C)CC4)n3)cc12] | 3-amino-6-{8-[(2-cyano-2-methylideneethyl)amino]-7-methoxynaphthalen-2-yl}-N-[(1-methylpiperidin-4-yl)methyl]pyridine-2-carboxamide | 484.6 |
| 783 | 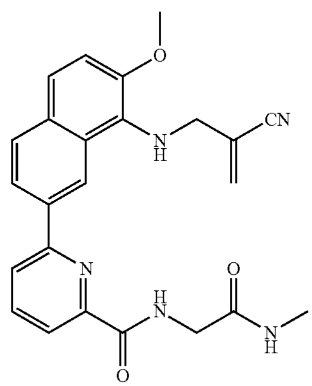 [SMILES: C=C(C#N)CNc1c(OC)ccc2ccc(-c3cccc(C(=O)NCC(=O)NC)n3)cc12] | 2-[(6-{8-[(2-cyano-2-methylideneethyl)amino]-7-methoxynaphthalen-2-yl}pyridin-2-yl)formamido]-N-methylacetamide | 429.5 |
| 784 | 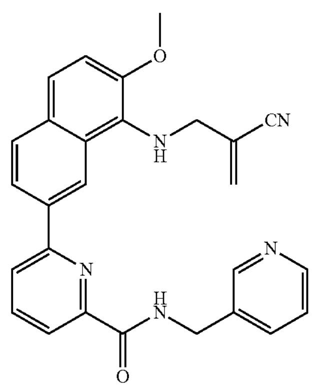 [SMILES: C=C(C#N)CNc1c(OC)ccc2ccc(-c3cccc(C(=O)NCc4cccnc4)n3)cc12] | 6-{8-[(2-cyano-2-methylideneethyl)amino]-7-methoxynaphthalen-2-yl}-N-[(pyridin-3-yl)methyl]pyridine-2-carboxamide | 449.5 |
| 785 | 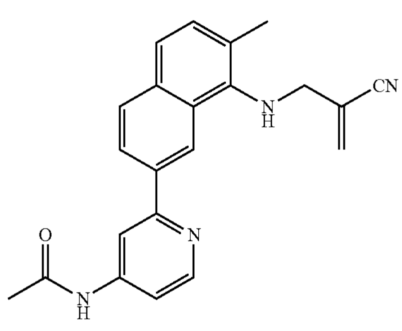 [SMILES: C=C(C#N)CNc1c(C)ccc2ccc(-c3cc(NC(C)=O)ccn3)cc12] | N-(2-{8-[(2-cyano-2-methylideneethyl)amino]-7-methylnaphthalen-2-yl}pyridin-4-yl)acetamide | 356.4 |

TABLE 16-continued

| Cpd No. | Structure | IUPAC | MW (g/mol) |
|---|---|---|---|
| 786 | 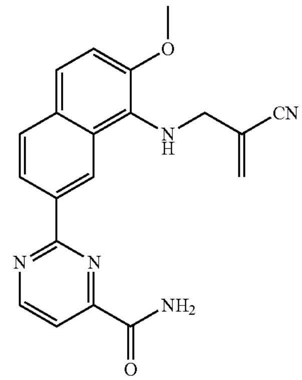 [SMILES: C=C(C#N)CNc1c(OC)ccc2ccc(-c3nccc(C(N)=O)n3)cc12] | 2-{8-[(2-cyano-2-methylideneethyl)amino]-7-methoxynaphthalen-2-yl}pyrimidine-4-carboxamide | 359.4 |
| 787 | 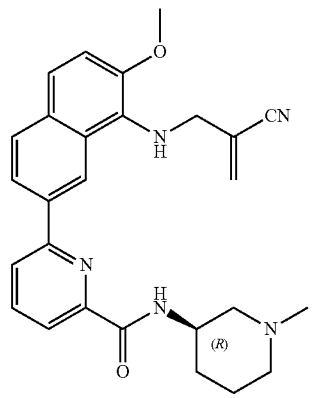 | 6-{8-[(2-cyano-2-methylideneethyl)amino]-7-methoxynaphthalen-2-yl}-N-[(3R)-1-methylpiperidin-3-yl]pyridine-2-carboxamide | 455.6 |
| 788 | 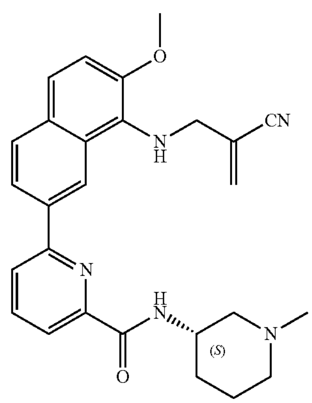 | 6-{8-[(2-cyano-2-methylideneethyl)amino]-7-methoxynaphthalen-2-yl}-N-[(3S)-1-methylpiperidin-3-yl]pyridine-2-carboxamide | 455.6 |
| 789 | 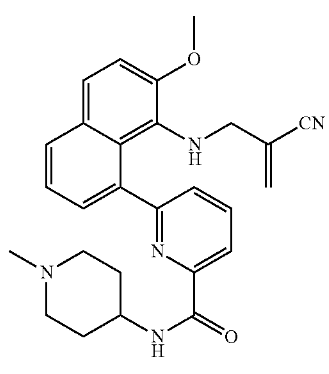 [SMILES: C=C(C#N)CNc1c(OC)ccc2cccc(-c3cccc(C(=O)NC4CCN(C)CC4)n3)c12] | 6-{8-[(2-cyano-2-methylideneethyl)amino]-7-methoxynaphthalen-1-yl}-N-(1-methylpiperidin-4-yl)pyridine-2-carboxamide | 455.6 |

TABLE 16-continued

| Cpd No. | Structure | IUPAC | MW (g/mol) |
|---|---|---|---|
| 790 | 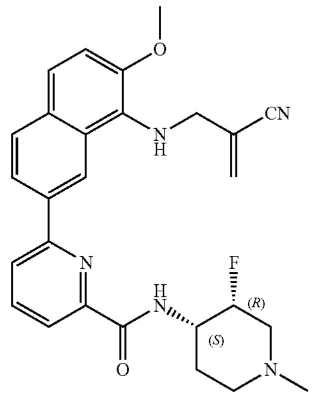 | 6-{8-[(2-cyano-2-methylideneethyl)amino]-7-methoxynaphthalen-2-yl}-N-[(3R,4S)-3-fluoro-1-methylpiperidin-4-yl]pyridine-2-carboxamide | 473.6 |
| 791 | 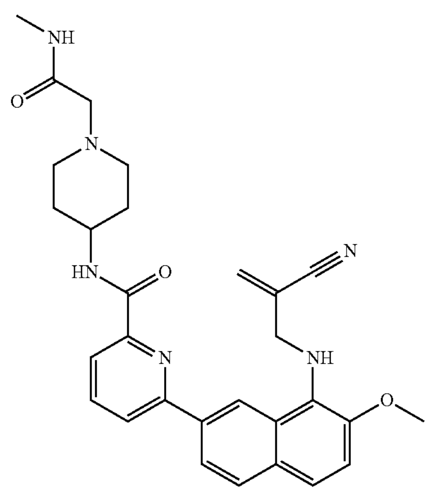 | 6-{8-[(2-cyano-2-methylideneethyl)amino]-7-methoxynaphthalen-2-yl}-N-{1-[(methylcarbamoyl)methyl]piperidin-4-yl}pyridine-2-carboxamide | 512.6 |
| 792 | 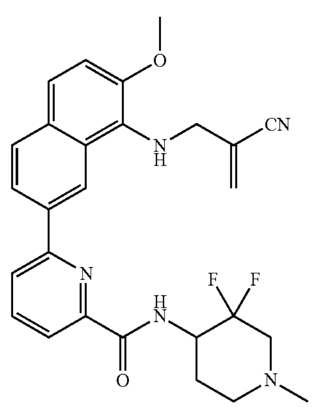 [SMILES: C=C(C#N)CNc1c(OC)ccc2ccc(-c3cccc(C(=O)NC4CCN(C)CC4(F)F)n3)cc12] | 6-{8-[(2-cyano-2-methylideneethyl)amino]-7-methoxynaphthalen-2-yl}-N-(3,3-difluoro-1-methylpiperidin-4-yl)pyridine-2-carboxamide | 491.5 |

TABLE 16-continued

| Cpd No. | Structure | IUPAC | MW (g/mol) |
|---|---|---|---|
| 793 | 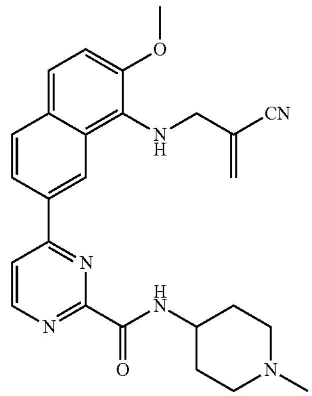 [SMILES: C=C(C#N)CNc1c(OC)ccc2ccc(-c3ccnc(C(=O)NC4CCN(C)CC4)n3)cc12] | 4-{8-[(2-cyano-2-methylideneethyl)amino]-7-methoxynaphthalen-2-yl}-N-(1-methylpiperidin-4-yl)pyrimidine-2-carboxamide | 456.6 |
| 794 | 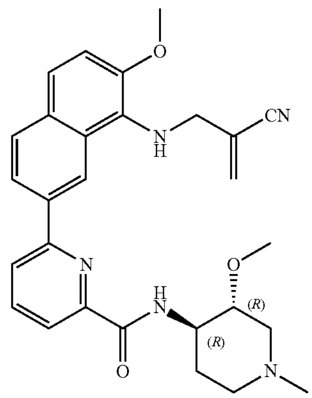 | 6-{8-[(2-cyano-2-methylideneethyl)amino]-7-methoxynaphthalen-2-yl}-N-[(3R,4R)-3-methoxy-1-methylpiperidin-4-yl]pyridine-2-carboxamide | 485.6 |
| 795 | 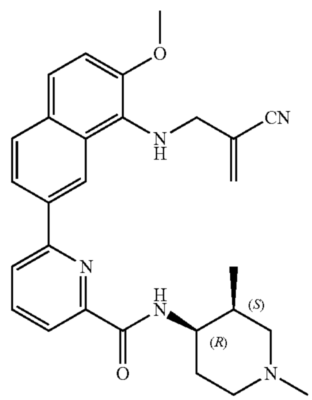 | 6-{8-[(2-cyano-2-methylideneethyl)amino]-7-methoxynaphthalen-2-yl}-N-[(3S,4R)-1,3-dimethylpiperidin-4-yl]pyridine-2-carboxamide | 469.6 |
| 796 | 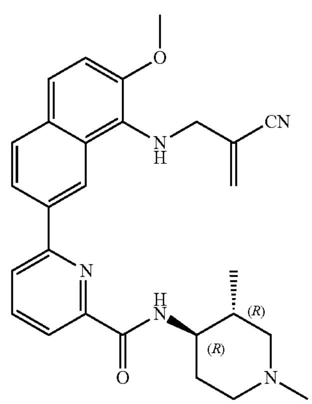 | 6-{8-[(2-cyano-2-methylideneethyl)amino]-7-methoxynaphthalen-2-yl}-N-[(3R,4R)-1,3-dimethylpiperidin-4-yl]pyridine-2-carboxamide | 469.6 |

TABLE 16-continued

| Cpd No. | Structure | IUPAC | MW (g/mol) |
|---|---|---|---|
| 797 | 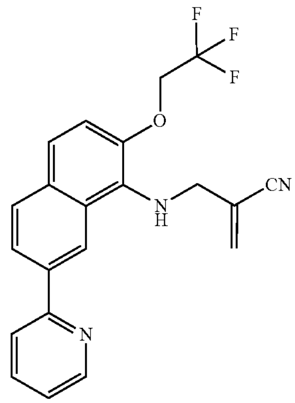 [SMILES: C=C(C#N)CNc1c(OCC(F)(F)F)ccc2ccc(-c3ccccn3)cc12] | 2-({[7-(pyridin-2-yl)-2-(2,2,2-trifluoroethoxy)naphthalen-1-yl]amino}methyl)prop-2-enenitrile | 383.4 |
| 798 | 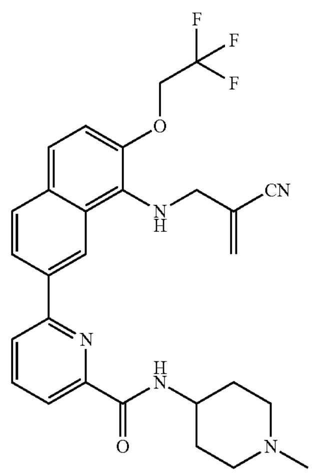 [SMILES: C=C(C#N)CNc1c(OCC(F)(F)F)ccc2ccc(-c3cccc(C(=O)NC4CCN(C)CC4)n3)cc12] | 6-{8-[(2-cyano-2-methylideneethyl)amino]-7-(2,2,2-trifluoroethoxy)naphthalen-2-yl}-N-(1-methylpiperidin-4-yl)pyridine-2-carboxamide | 523.6 |
| 799 | 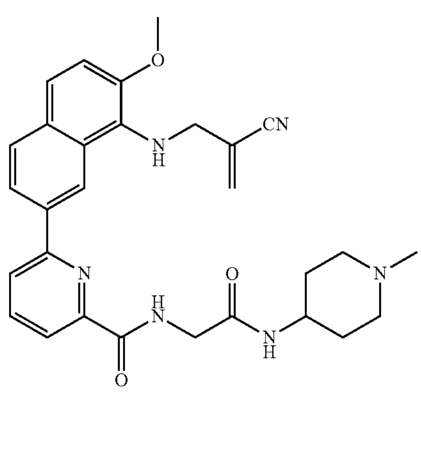 [SMILES: C=C(C#N)CNc1c(OC)ccc2ccc(-c3cccc(C(=O)NCC(=O)NC4CCN(C)CC4)n3)cc12] | 2-[(6-{8-[(2-cyano-2-methylideneethyl)amino]-7-methoxynaphthalen-2-yl}pyridin-2-yl)formamido]-N-(1-methylpiperidin-4-yl)acetamide | 512.6 |

TABLE 16-continued

| Cpd No. | Structure | IUPAC | MW (g/mol) |
|---|---|---|---|
| 800 | 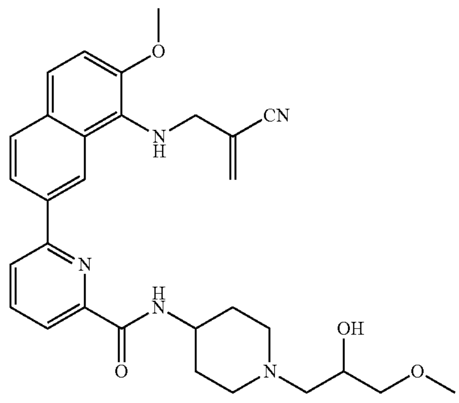 [SMILES: C=C(C#N)CNc1c(OC)ccc2ccc(-c3cccc(C(=O)NC4CCN(CC(O)COC)CC4)n3)cc12] | 6-{8-[(2-cyano-2-methylideneethyl)amino]-7-methoxynaphthalen-2-yl}-N-[1-(2-hydroxy-3-methoxypropyl)piperidin-4-yl]pyridine-2-carboxamide | 529.6 |
| 801 | 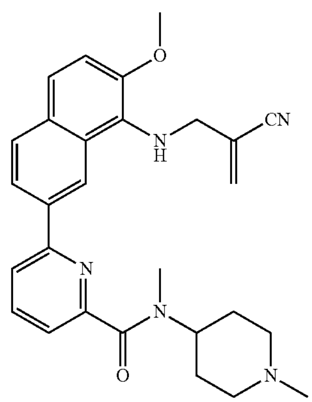 [SMILES: C=C(C#N)CNc1c(OC)ccc2ccc(-c3cccc(C(=O)N(C)C4CCN(C)CC4)n3)cc12] | 6-{8-[(2-cyano-2-methylideneethyl)amino]-7-methoxynaphthalen-2-yl}-N-methyl-N-(1-methylpiperidin-4-yl)pyridine-2-carboxamide | 469.6 |
| 802 | 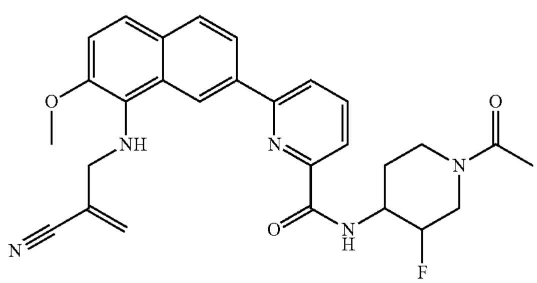 [SMILES: C=C(C#N)CNc1c(OC)ccc2ccc(-c3cccc(C(=O)NC4CCN(C(C)=O)CC4F)n3)cc12] | N-(1-acetyl-3-fluoropiperidin-4-yl)-6-{8-[(2-cyano-2-methylideneethyl)amino]-7-methoxynaphthalen-2-yl}pyridine-2-carboxamide | 501.6 |
| 803 | 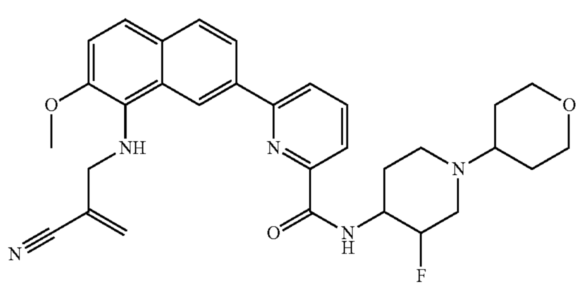 [SMILES: C=C(C#N)CNc1c(OC)ccc2ccc(-c3cccc(C(=O)NC4CCN(C5CCOCC5)CC4F)n3)cc12] | 6-{8-[(2-cyano-2-methylideneethyl)amino]-7-methoxynaphthalen-2-yl}-N-[3-fluoro-1-(oxan-4-yl)piperidin-4-yl]pyridine-2-carboxamide | 543.6 |

TABLE 16-continued

| Cpd No. | Structure | IUPAC | MW (g/mol) |
|---|---|---|---|
| 804 | 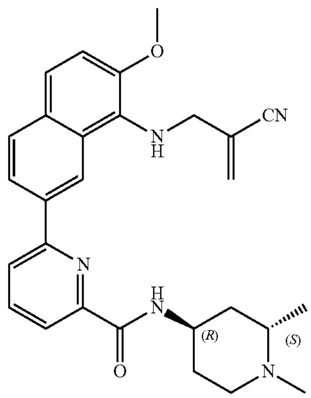 | 6-{8-[(2-cyano-2-methylideneethyl)amino]-7-methoxynaphthalen-2-yl}-N-[(2S,4R)-1,2-dimethylpiperidin-4-yl]pyridine-2-carboxamide | 469.6 |
| 805 | 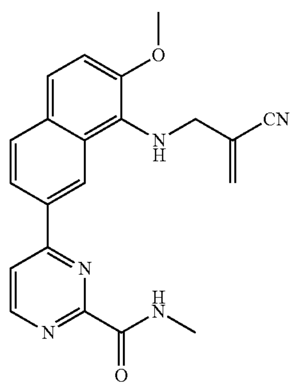 | 4-{8-[(2-cyano-2-methylideneethyl)amino]-7-methoxynaphthalen-2-yl}-N-methylpyrimidine-2-carboxamide | 373.4 |
| 806 | 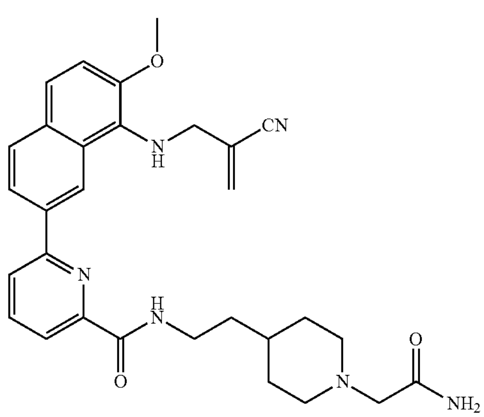 [SMILES: C=C(C#N)CNc1c(OC)ccc2ccc(-c3cccc(C(=O)NCCC4CCN(CC(N)=O)CC4)n3)cc12] | N-{2-[1-(carbamoylmethyl)piperidin-4-yl]ethyl}-6-{8-[(2-cyano-2-methylideneethyl)amino]-7-methoxynaphthalen-2-yl}pyridine-2-carboxamide | 526.6 |

TABLE 16-continued
| Cpd No. | Structure | IUPAC | MW (g/mol) |
|---|---|---|---|
| 807 | 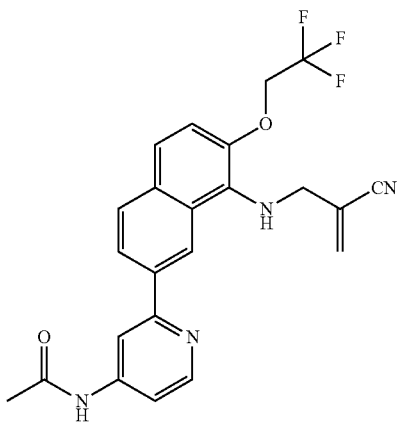 [SMILES: C=C(C#N)CNc1c(OCC(F)(F)F)ccc2ccc(-c3cc(NC(C)=O)ccn3)cc12] | N-(2-{8-[(2-cyano-2-methylideneethyl)amino]-7-(2,2,2-trifluoroethoxy)naphthalen-2-yl}pyridin-4-yl)acetamide | 440.4 |
| 808 | 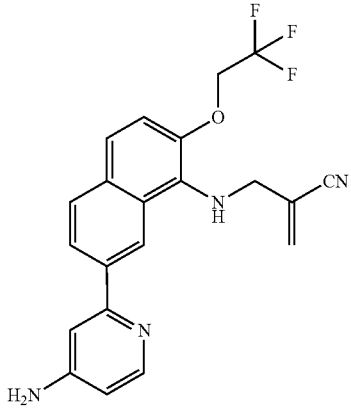 [SMILES: C=C(C#N)CNc1c(OCC(F)(F)F)ccc2ccc(-c3cc(N)ccn3)cc12] | 2-({[7-(4-aminopyridin-2-yl)-2-(2,2,2-trifluoroethoxy)naphthalen-1-yl]amino}methyl)prop-2-enenitrile | 398.4 |
| 809 | 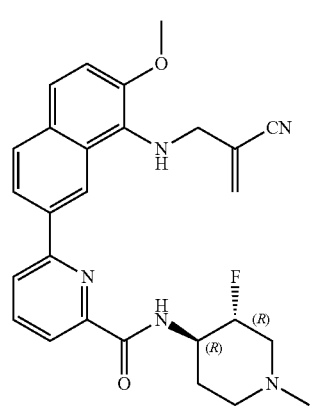 | 6-{8-[(2-cyano-2-methylideneethyl)amino]-7-methoxynaphthalen-2-yl}-N-[(3R,4R)-3-fluoro-1-methylpiperidin-4-yl]pyridine-2-carboxamide | 473.6 |

TABLE 16-continued

| Cpd No. | Structure | IUPAC | MW (g/mol) |
|---|---|---|---|
| 810 | 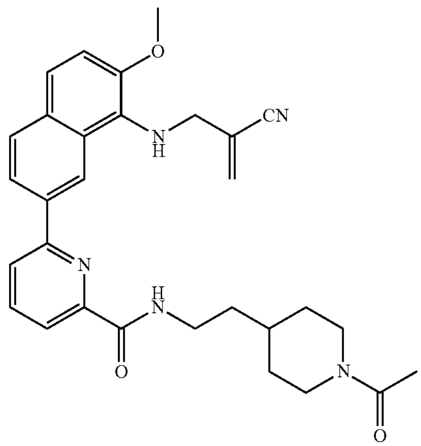 [SMILES: C=C(C#N)CNc1c(OC)ccc2ccc(-c3cccc(C(=O)NCCC4CCN(C(C)=O)CC4)n3)cc12] | N-[2-(1-acetylpiperidin-4-yl)ethyl]-6-{8-[(2-cyano-2-methylideneethyl)amino]-7-methoxynaphthalen-2-yl}pyridine-2-carboxamide | 511.6 |
| 811 | 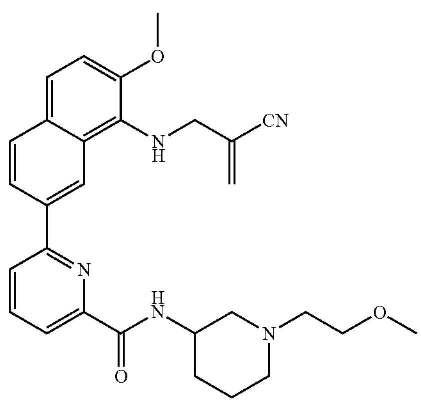 [SMILES: C=C(C#N)CNc1c(OC)ccc2ccc(-c3cccc(C(=O)NC4CCCN(CCOC)C4)n3)cc12] | 6-{8-[(2-cyano-2-methylideneethyl)amino]-7-methoxynaphthalen-2-yl}-N-[1-(2-methoxyethyl)piperidin-3-yl]pyridine-2-carboxamide | 499.6 |
| 812 | 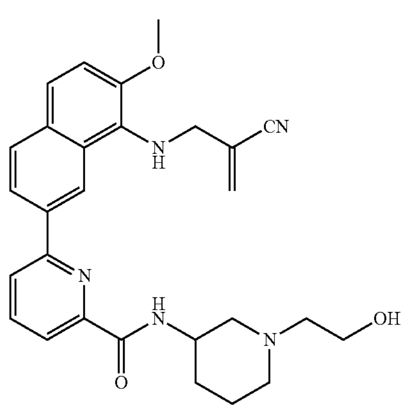 [SMILES: C=C(C#N)CNc1c(OC)ccc2ccc(-c3cccc(C(=O)NC4CCCN(CCO)C4)n3)cc12] | 6-{8-[(2-cyano-2-methylideneethyl)amino]-7-methoxynaphthalen-2-yl}-N-[1-(2-hydroxyethyl)piperidin-3-yl]pyridine-2-carboxamide | 485.6 |

TABLE 16-continued

| Cpd No. | Structure | IUPAC | MW (g/mol) |
|---|---|---|---|
| 813 | 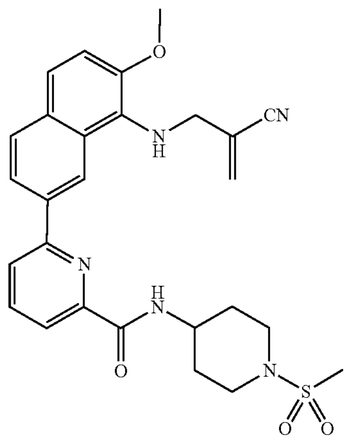 [SMILES: C=C(C#N)CNc1c(OC)ccc2ccc(-c3cccc(C(=O)NC4CCN(S(C)(=O)=O)CC4)n3)cc12] | 6-{8-[(2-cyano-2-methylideneethyl)amino]-7-methoxynaphthalen-2-yl}-N-(1-methanesulfonylpiperidin-4-yl)pyridine-2-carboxamide | 519.6 |
| 814 | 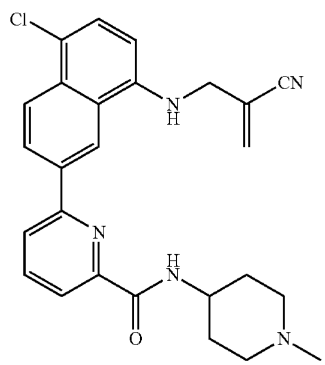 [SMILES: C=C(C#N)CNc1ccc(Cl)c2ccc(-c3cccc(C(=O)NC4CCN(C)CC4)n3)cc12] | 6-{5-chloro-8-[(2-cyano-2-methylideneethyl)amino]naphthalen-2-yl}-N-(1-methylpiperidin-4-yl)pyridine-2-carboxamide | 460.0 |
| 815 | 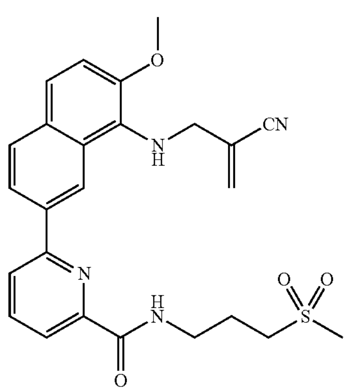 [SMILES: C=C(C#N)CNc1c(OC)ccc2ccc(-c3cccc(C(=O)NCCCS(C)(=O)=O)n3)cc12] | 6-{8-[(2-cyano-2-methylideneethyl)amino]-7-methoxynaphthalen-2-yl}-N-(3-methanesulfonylpropyl)pyridine-2-carboxamide | 478.6 |
| 816 | 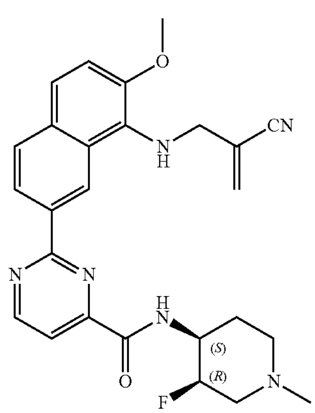 | 2-{8-[(2-cyano-2-methylideneethyl)amino]-7-methoxynaphthalen-2-yl}-N-[(3R,4S)-3-fluoro-1-methylpiperidin-4-yl]pyrimidine-4-carboxamide | 474.5 |

TABLE 16-continued

| Cpd No. | Structure | IUPAC | MW (g/mol) |
|---|---|---|---|
| 817 | 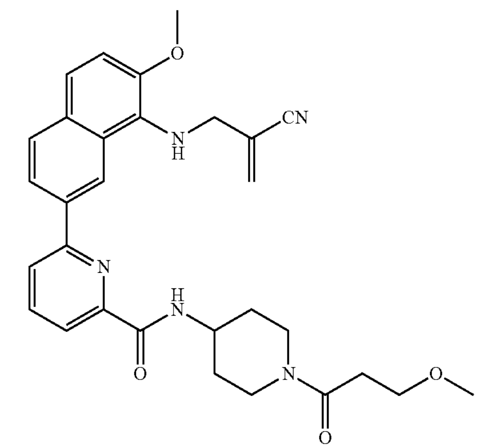 [SMILES: C=C(C#N)CNc1c(OC)ccc2ccc(-c3cccc(C(=O)NC4CCN(C(=O)CCOC)CC4)n3)cc12] | 6-{8-[(2-cyano-2-methylideneethyl)amino]-7-methoxynaphthalen-2-yl}-N-[1-(3-methoxypropanoyl)piperidin-4-yl]pyridine-2-carboxamide | 527.6 |
| 818 | 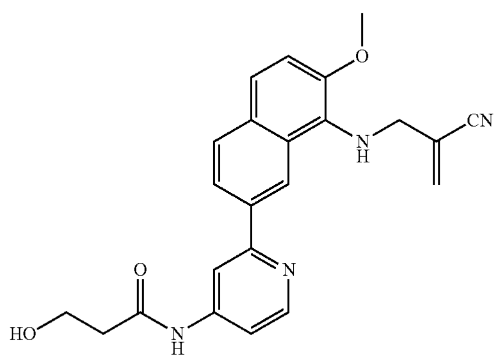 [SMILES: C=C(C#N)CNc1c(OC)ccc2ccc(-c3cc(NC(=O)CCO)ccn3)cc12] | N-(2-{8-[(2-cyano-2-methylideneethyl)amino]-7-methoxynaphthalen-2-yl}pyridin-4-yl)-3-hydroxypropanamide | 402.5 |
| 819 | 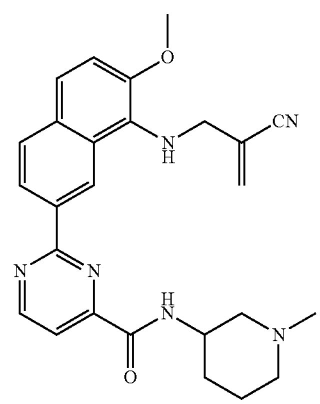 [SMILES: C=C(C#N)CNc1c(OC)ccc2ccc(-c3nccc(C(=O)NC4CCCN(C)C4)n3)cc12] | 2-{8-[(2-cyano-2-methylideneethyl)amino]-7-methoxynaphthalen-2-yl}-N-(1-methylpiperidin-3-yl)pyrimidine-4-carboxamide | 456.6 |
| 820 | 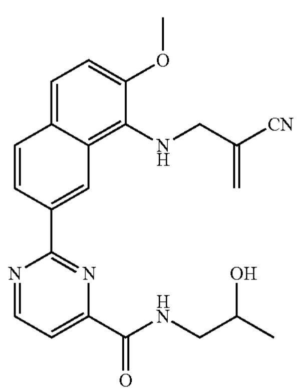 [SMILES: C=C(C#N)CNc1c(OC)ccc2ccc(-c3nccc(C(=O)NCC(C)O)n3)cc12] | 2-{8-[(2-cyano-2-methylideneethyl)amino]-7-methoxynaphthalen-2-yl}-N-(2-hydroxypropyl)pyrimidine-4-carboxamide | 417.5 |

TABLE 16-continued
| Cpd No. | Structure | IUPAC | MW (g/mol) |
|---|---|---|---|
| 821 | 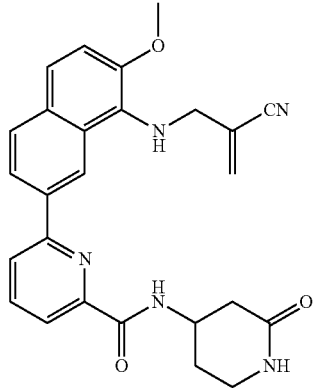 [SMILES: C=C(C#N)CNc1c(OC)ccc2ccc(-c3cccc(C(=O)NC4CCNC(=O)C4)n3)cc12] | 6-{8-[(2-cyano-2-methylideneethyl)amino]-7-methoxynaphthalen-2-yl}-N-(2-oxopiperidin-4-yl)pyridine-2-carboxamide | 455.5 |
| 822 | 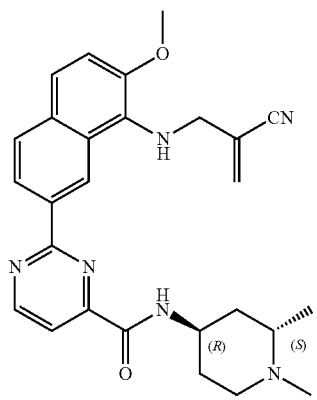 | 2-{8-[(2-cyano-2-methylideneethyl)amino]-7-methoxynaphthalen-2-yl}-N-[(2S,4R)-1,2-dimethylpiperidin-4-yl]pyrimidine-4-carboxamide | 470.6 |
| 823 | 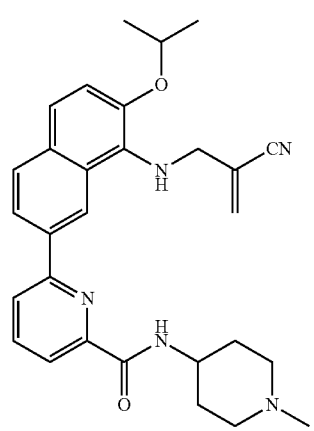 [SMILES: C=C(C#N)CNc1c(OC(C)C)ccc2ccc(-c3cccc(C(=O)NC4CCN(C)CC4)n3)cc12] | 6-{8-[(2-cyano-2-methylideneethyl)amino]-7-(propan-2-yloxy)naphthalen-2-yl}-N-(1-methylpiperidin-4-yl)pyridine-2-carboxamide | 483.6 |

TABLE 16-continued

| Cpd No. | Structure | IUPAC | MW (g/mol) |
|---|---|---|---|
| 824 | 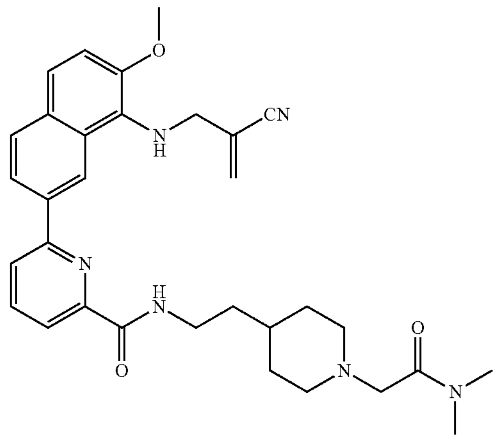 [SMILES: C=C(C#N)CNc1c(OC)ccc2ccc(-c3cccc(C(=O)NCCC4CCN(CC(=O)N(C)C)CC4)n3)cc12] | 6-{8-[(2-cyano-2-methylideneethyl)amino]-7-methoxynaphthalen-2-yl}-N-(2-{1-[(dimethylcarbamoyl)methyl]piperidin-4-yl}ethyl)pyridine-2-carboxamide | 554.7 |
| 825 | 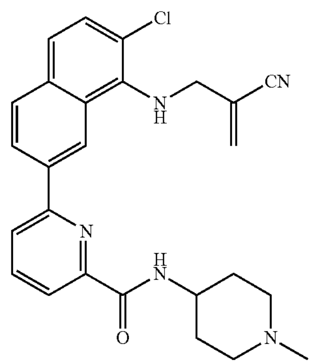 [SMILES: C=C(C#N)CNc1c(Cl)ccc2ccc(-c3cccc(C(=O)NC4CCN(C)CC4)n3)cc12] | 6-{7-chloro-8-[(2-cyano-2-methylideneethyl)amino]naphthalen-2-yl}-N-(1-methylpiperidin-4-yl)pyridine-2-carboxamide | 460.0 |
| 826 | 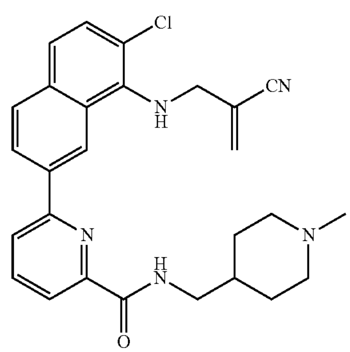 [SMILES: C=C(C#N)CNc1c(Cl)ccc2ccc(-c3cccc(C(=O)NCC4CCN(C)CC4)n3)cc12] | 6-{7-chloro-8-[(2-cyano-2-methylideneethyl)amino]naphthalen-2-yl}-N-[(1-methylpiperidin-4-yl)methyl]pyridine-2-carboxamide | 474.0 |
| 827 | 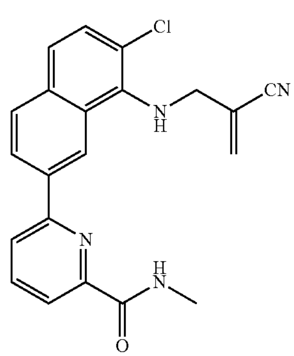 [SMILES: C=C(C#N)CNc1c(Cl)ccc2ccc(-c3cccc(C(=O)NC)n3)cc12] | 6-{7-chloro-8-[(2-cyano-2-methylideneethyl)amino]naphthalen-2-yl}-N-methylpyridine-2-carboxamide | 376.8 |

TABLE 16-continued

| Cpd No. | Structure | IUPAC | MW (g/mol) |
|---|---|---|---|
| 828 | 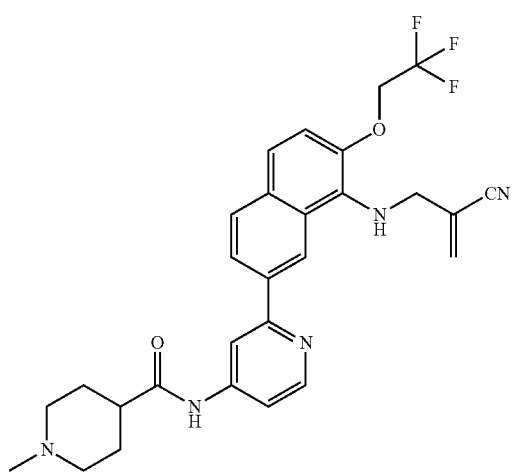 [SMILES: C=C(C#N)CNc1c(OCC(F)(F)F)ccc2ccc(-c3cc(NC(=O)C4CCN(C)CC4)ccn3)cc12] | N-(2-{8-[(2-cyano-2-methylideneethyl)amino]-7-(2,2,2-trifluoroethoxy)naphthalen-2-yl}pyridin-4-yl)-1-methylpiperidine-4-carboxamide | 523.6 |
| 829 | 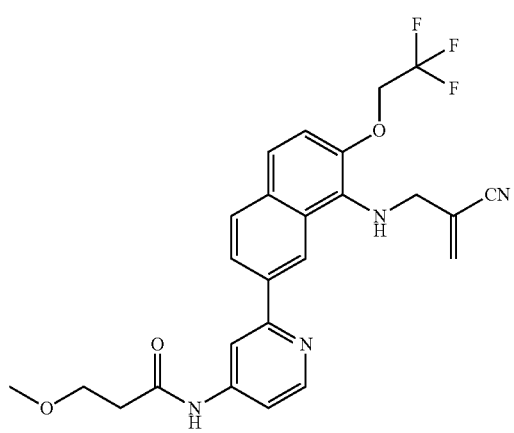 [SMILES: C=C(C#N)CNc1c(OCC(F)(F)F)ccc2ccc(-c3cc(NC(=O)CCOC)ccn3)cc12] | N-(2-{8-[(2-cyano-2-methylideneethyl)amino]-7-(2,2,2-trifluoroethoxy)naphthalen-2-yl}pyridin-4-yl)-3-methoxypropanamide | 484.5 |
| 830 | 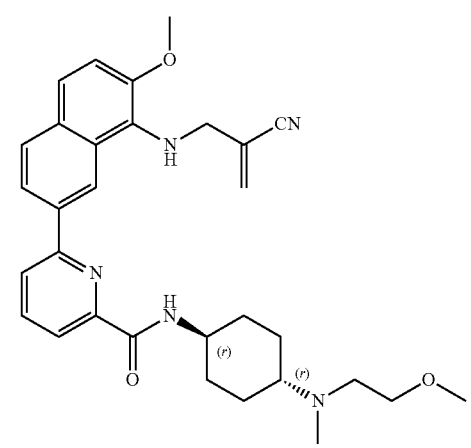 [SMILES: C=C(C#N)CNc1c(OC)ccc2ccc(-c3cccc(C(=O)N[C@H]4CC[C@H](N(C)CCOC)CC4)n3)cc12] | 6-{8-[(2-cyano-2-methylideneethyl)amino]-7-methoxynaphthalen-2-yl}-N-[(1r,4r)-4-[(2-methoxyethyl)(methyl)amino]cyclohexyl]pyridine-2-carboxamide | 527.7 |

TABLE 16-continued

| Cpd No. | Structure | IUPAC | MW (g/mol) |
|---|---|---|---|
| 831 | 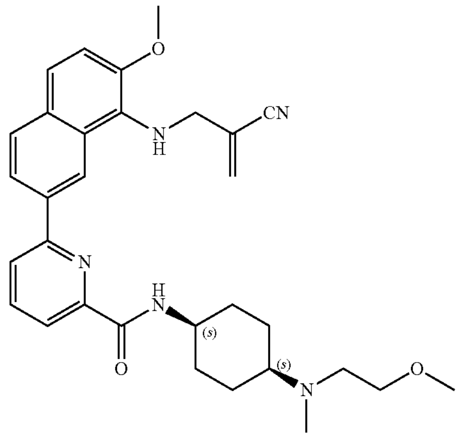 [SMILES: C=C(C#N)CNc1c(OC)ccc2ccc(-c3cccc(C(=O)N[C@H]4CC[C@@H](N(C)CCOC)CC4)n3)cc12] | 6-{8-[(2-cyano-2-methylideneethyl)amino]-7-methoxynaphthalen-2-yl}-N-[(1s,4s)-4-[(2-methoxyethyl)(methyl)amino]cyclohexyl]pyridine-2-carboxamide | 527.7 |
| 832 | 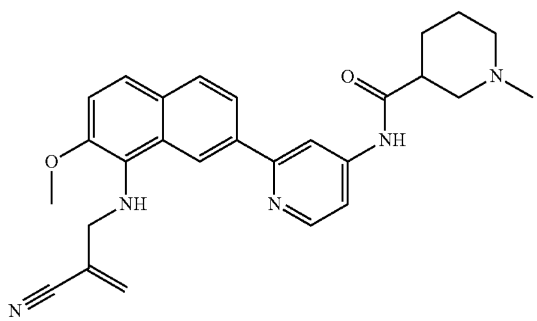 [SMILES: C=C(C#N)CNc1c(OC)ccc2ccc(-c3cc(NC(=O)C4CCCN(C)C4)ccn3)cc12] | N-(2-{8-[(2-cyano-2-methylideneethyl)amino]-7-methoxynaphthalen-2-yl}pyridin-4-yl)-1-methylpiperidine-3-carboxamide | 455.6 |
| 833 | 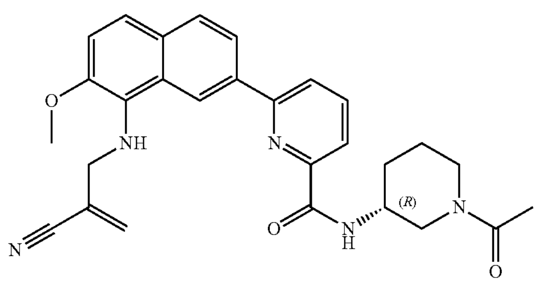 | N-[(3R)-1-acetylpiperidin-3-yl]-6-{8-[(2-cyano-2-methylideneethyl)amino]-7-methoxynaphthalen-2-yl}pyridine-2-carboxamide | 483.6 |
| 834 | 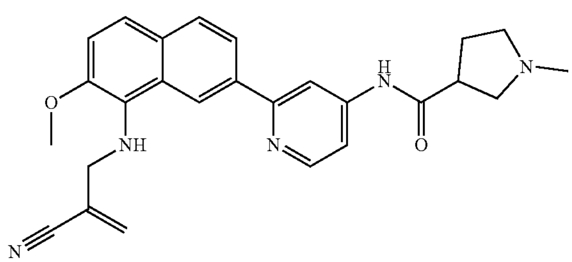 [SMILES: C=C(C#N)CNc1c(OC)ccc2ccc(-c3cc(NC(=O)C4CCN(C)C4)ccn3)cc12] | N-(2-{8-[(2-cyano-2-methylideneethyl)amino]-7-methoxynaphthalen-2-yl}pyridin-4-yl)-1-methylpyrrolidine-3-carboxamide | 441.5 |
| 835 | 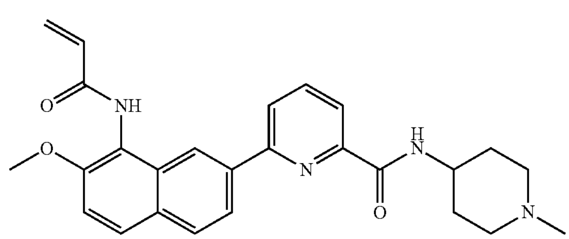 | 6-[7-methoxy-8-(prop-2-enamido)naphthalen-2-yl]-N-(1-methylpiperidin-4-yl)pyridine-2-carboxamide | 444.5 |

TABLE 16-continued

| Cpd No. | Structure | IUPAC | MW (g/mol) |
|---|---|---|---|
| 836 | 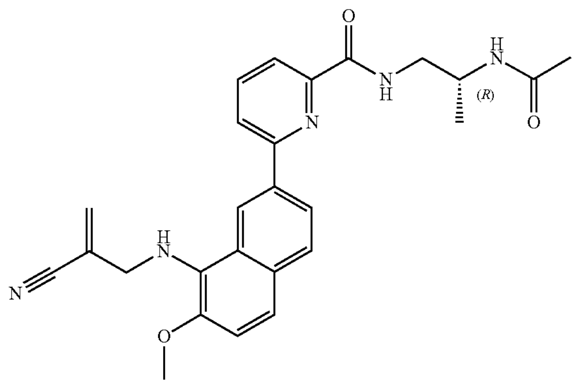 | N-[(2R)-1-[(6-{8-[(2-cyano-2-methylideneethyl)amino]-7-methoxynaphthalen-2-yl}pyridin-2-yl)formamido]propan-2-yl]acetamide | 457.5 |
| 837 | 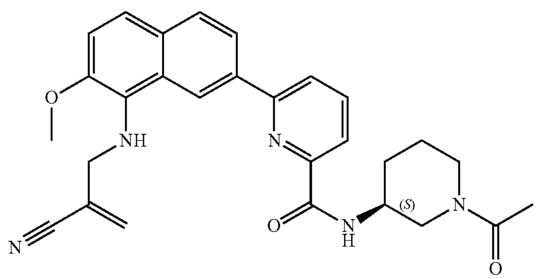 | N-[(3S)-1-acetylpiperidin-3-yl]-6-{8-[(2-cyano-2-methylideneethyl)amino]-7-methoxynaphthalen-2-yl}pyridine-2-carboxamide | 483.6 |
| 838 | 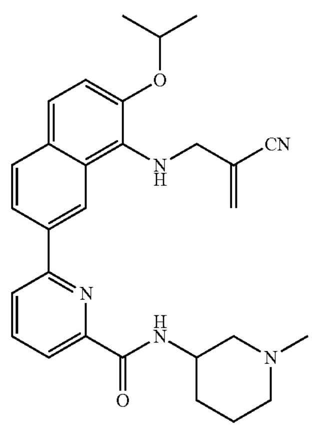 [SMILES: C=C(C#N)CNc1c(OC(C)C)ccc2ccc(-c3cccc(C(=O)NC4CCCN(C)C4)n3)cc12] | 6-{8-[(2-cyano-2-methylideneethyl)amino]-7-(propan-2-yloxy)naphthalen-2-yl}-N-(1-methylpiperidin-3-yl)pyridine-2-carboxamide | 483.6 |
| 839 | 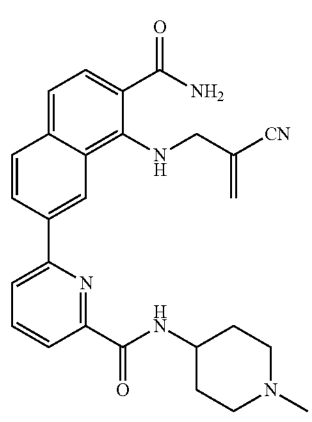 [SMILES: C=C(C#N)CNc1c(C(N)=O)ccc2ccc(-c3cccc(C(=O)NC4CCN(C)CC4)n3)cc12] | 6-{7-carbamoyl-8-[(2-cyano-2-methylideneethyl)amino]naphthalen-2-yl}-N-(1-methylpiperidin-4-yl)pyridine-2-carboxamide | 468.6 |

TABLE 16-continued

| Cpd No. | Structure | IUPAC | MW (g/mol) |
|---|---|---|---|
| 840 | 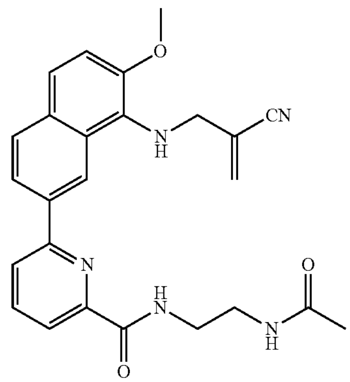 [SMILES: C=C(C#N)CNc1c(OC)ccc2ccc(-c3cccc(C(=O)NCCNC(C)=O)n3)cc12] | N-{2-[(6-{8-[(2-cyano-2-methylideneethyl)amino]-7-methoxynaphthalen-2-yl}pyridin-2-yl)formamido]ethyl}acetamide | 443.5 |
| 841 | 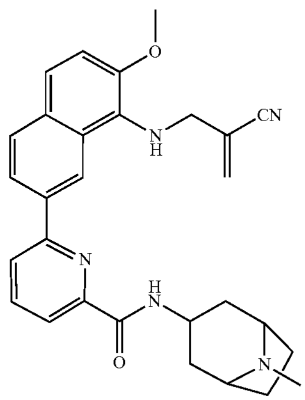 | 6-{8-[(2-cyano-2-methylideneethyl)amino]-7-methoxynaphthalen-2-yl}-N-{8-methyl-8-azabicyclo[3.2.1]octan-3-yl}pyridine-2-carboxamide | 481.6 |
| 842 | 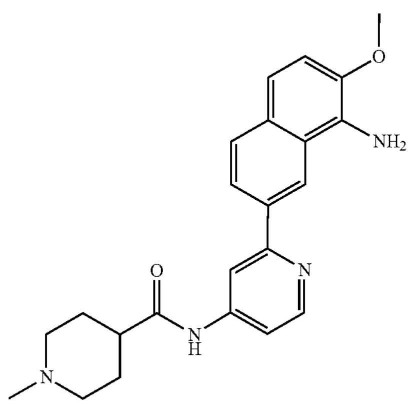 [SMILES: COc1ccc2ccc(-c3cc(NC(=O)C4CCN(C)CC4)ccn3)cc2c1N] | N-[2-(8-amino-7-methoxynaphthalen-2-yl)pyridin-4-yl]-1-methylpiperidine-4-carboxamide | 390.5 |
| 843 | 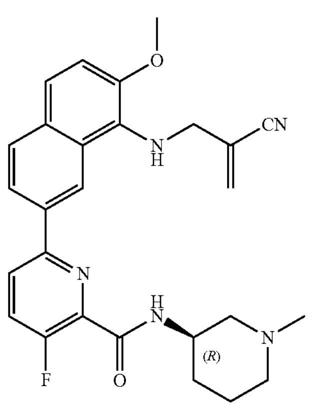 | 6-{8-[(2-cyano-2-methylideneethyl)amino]-7-methoxynaphthalen-2-yl}-3-fluoro-N-[(3R)-1-methylpiperidin-3-yl]pyridine-2-carboxamide | 473.6 |

TABLE 16-continued

| Cpd No. | Structure | IUPAC | MW (g/mol) |
|---|---|---|---|
| 844 | 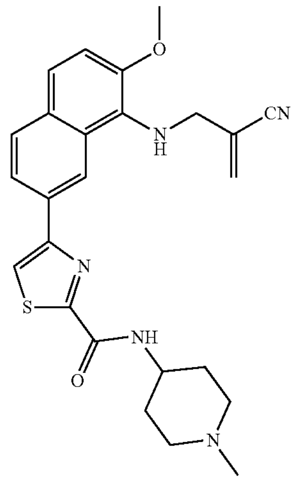 [SMILES: C=C(C#N)CNc1c(OC)ccc2ccc(-c3csc(C(=O)NC4CCN(C)CC4)n3)cc12] | 4-{8-[(2-cyano-2-methylideneethyl)amino]-7-methoxynaphthalen-2-yl}-N-(1-methylpiperidin-4-yl)-1,3-thiazole-2-carboxamide | 461.6 |
| 845 | 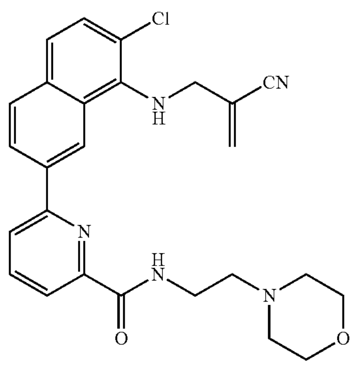 [SMILES: C=C(C#N)CNc1c(Cl)ccc2ccc(-c3cccc(C(=O)NCCN4CCOCC4)n3)cc12] | 6-{7-chloro-8-[(2-cyano-2-methylideneethyl)amino]naphthalen-2-yl}-N-[2-(morpholin-4-yl)ethyl]pyridine-2-carboxamide | 476.0 |
| 846 | 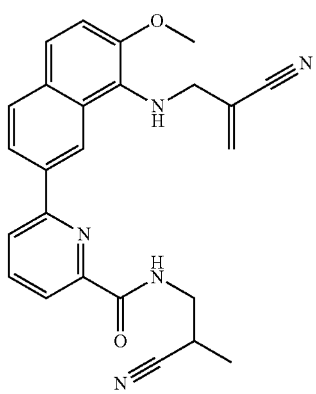 [SMILES: C=C(C#N)CNc1c(OC)ccc2ccc(-c3cccc(C(=O)NCC(C)C#N)n3)cc12] | N-(2-cyano-2-methylethyl)-6-{8-[(2-cyano-2-methylideneethyl)amino]-7-methoxynaphthalen-2-yl}pyridine-2-carboxamide | 425.5 |
| 847 | 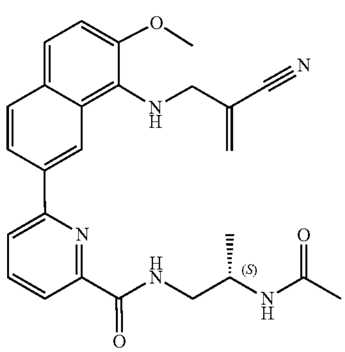 | N-[(2S)-1-[(6-{8-[(2-cyano-2-methylideneethyl)amino]-7-methoxynaphthalen-2-yl}pyridin-2-yl)formamido]propan-2-yl]acetamide | 457.5 |

TABLE 16-continued

| Cpd No. | Structure | IUPAC | MW (g/mol) |
|---|---|---|---|
| 848 | 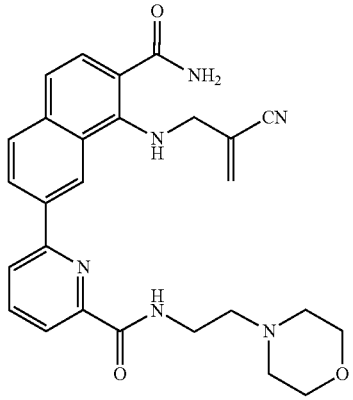 [SMILES: C=C(C#N)CNc1c(C(N)=O)ccc2ccc(-c3cccc(C(=O)NCCN4CCOCC4)n3)cc12] | 6-{7-carbamoyl-8-[(2-cyano-2-methylideneethyl)amino]naphthalen-2-yl}-N-[2-(morpholin-4-yl)ethyl]pyridine-2-carboxamide | 484.6 |
| 849 | 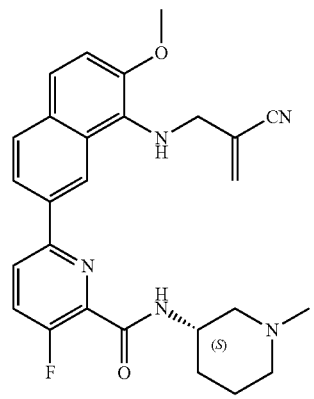 | 6-{8-[(2-cyano-2-methylideneethyl)amino]-7-methoxynaphthalen-2-yl}-3-fluoro-N-[(3S)-1-methylpiperidin-3-yl]pyridine-2-carboxamide | 473.6 |
| 850 | 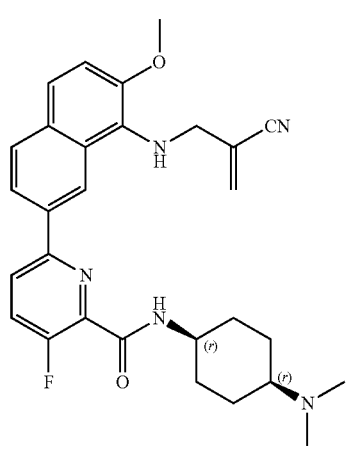 [SMILES: C=C(C#N)CNc1c(OC)ccc2ccc(-c3ccc(F)c(C(=O)N[C@H]4CC[C@@H](N(C)C)CC4)n3)cc12] | 6-{8-[(2-cyano-2-methylideneethyl)amino]-7-methoxynaphthalen-2-yl}-3-fluoro-N-[(1r,4r)-4-(dimethylamino)cyclohexyl]pyridine-2-carboxamide | 501.6 |

TABLE 16-continued

| Cpd No. | Structure | IUPAC | MW (g/mol) |
|---|---|---|---|
| 851 | 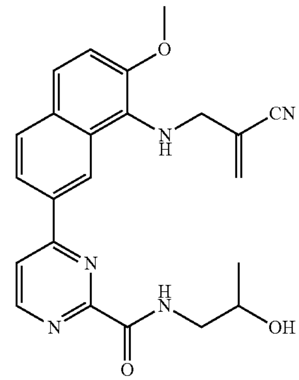 [SMILES: C=C(C#N)CNc1c(OC)ccc2ccc(-c3ccnc(C(=O)NCC(C)O)n3)cc12] | 4-{8-[(2-cyano-2-methylideneethyl)amino]-7-methoxynaphthalen-2-yl}-N-(2-hydroxypropyl)pyrimidine-2-carboxamide | 417.5 |
| 852 | 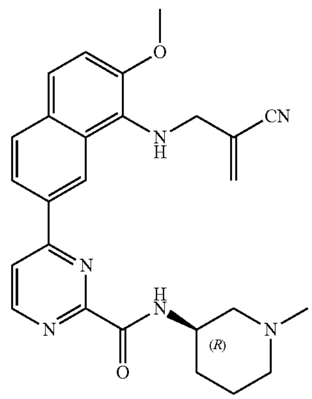 | 4-{8-[(2-cyano-2-methylideneethyl)amino]-7-methoxynaphthalen-2-yl}-N-[(3R)-1-methylpiperidin-3-yl]pyrimidine-2-carboxamide | 456.6 |
| 853 | 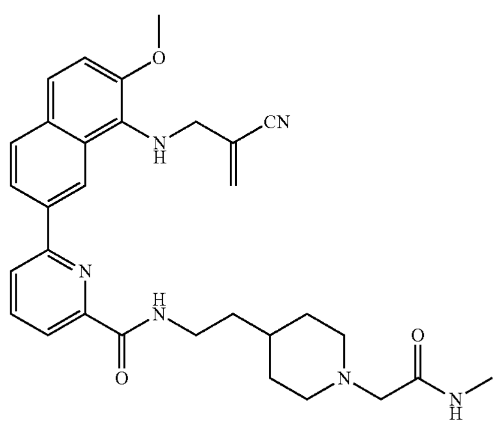 [SMILES: C=C(C#N)CNc1c(OC)ccc2ccc(-c3cccc(C(=O)NCCC4CCN(CC(=O)NC)CC4)n3)cc12] | 6-{8-[(2-cyano-2-methylideneethyl)amino]-7-methoxynaphthalen-2-yl}-N-(2-{1-[(methylcarbamoyl)methyl]piperidin-4-yl}ethyl)pyridine-2-carboxamide | 540.7 |
| 854 | 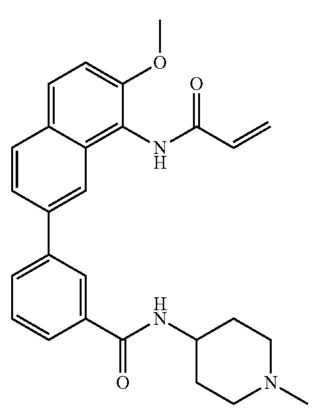 [SMILES: C=CC(=O)Nc1c(OC)ccc2ccc(-c3cccc(C(=O)NC4CCN(C)CC4)c3)cc12] | 3-[7-methoxy-8-(prop-2-enamido)naphthalen-2-yl]-N-(1-methylpiperidin-4-yl)benzamide | 443.5 |

TABLE 16-continued

| Cpd No. | Structure | IUPAC | MW (g/mol) |
|---|---|---|---|
| 855 | 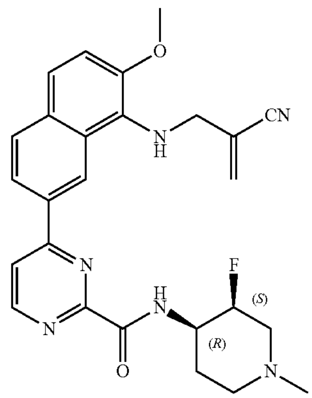 | 4-{8-[(2-cyano-2-methylideneethyl)amino]-7-methoxynaphthalen-2-yl}-N-[(3S,4R)-3-fluoro-1-methylpiperidin-4-yl]pyrimidine-2-carboxamide | 474.5 |
| 856 | 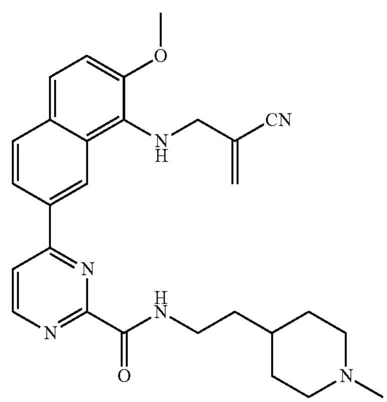 [SMILES: C=C(C#N)CNc1c(OC)ccc2ccc(-c3ccnc(C(=O)NCCC4CCN(C)CC4)n3)cc12] | 4-{8-[(2-cyano-2-methylideneethyl)amino]-7-methoxynaphthalen-2-yl}-N-[2-(1-methylpiperidin-4-yl)ethyl]pyrimidine-2-carboxamide | 484.6 |
| 857 | 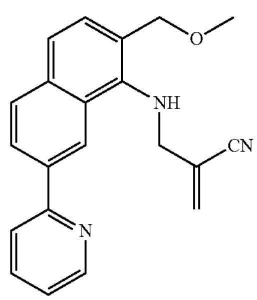 [SMILES: C=C(C#N)CNc1c(COC)ccc2ccc(-c3ccccn3)cc12] | 2-({[2-(methoxymethyl)-7-(pyridin-2-yl)naphthalen-1-yl]amino}methyl)prop-2-enenitrile | 329.4 |
| 858 | 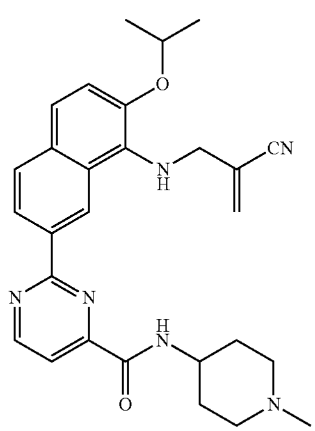 [SMILES: C=C(C#N)CNc1c(OC(C)C)ccc2ccc(-c3nccc(C(=O)NC4CCN(C)CC4)n3)cc12] | 2-{8-[(2-cyano-2-methylideneethyl)amino]-7-(propan-2-yloxy)naphthalen-2-yl}-N-(1-methylpiperidin-4-yl)pyrimidine-4-carboxamide | 484.6 |

TABLE 16-continued

| Cpd No. | Structure | IUPAC | MW (g/mol) |
|---|---|---|---|
| 859 | 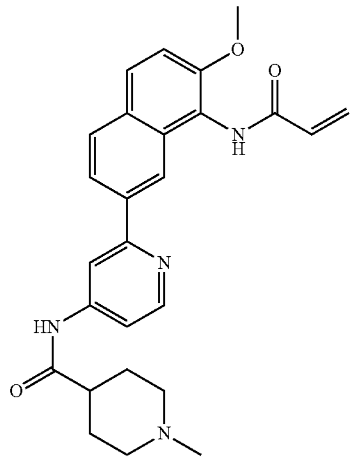 [SMILES: C=CC(=O)Nc1c(OC)ccc2ccc(-c3cc(NC(=O)C4CCN(C)CC4)ccn3)cc12] | N-{2-[7-methoxy-8-(prop-2-enamido)naphthalen-2-yl]pyridin-4-yl}-1-methylpiperidine-4-carboxamide | 444.5 |
| 860 | 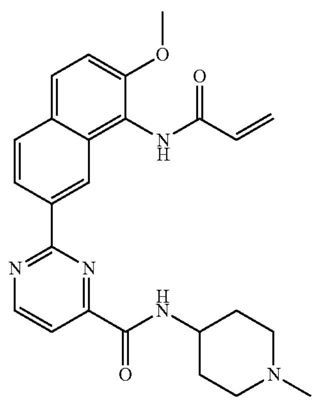 [SMILES: C=CC(=O)Nc1c(OC)ccc2ccc(-c3nccc(C(=O)NC4CCN(C)CC4)n3)cc12] | 2-[7-methoxy-8-(prop-2-enamido)naphthalen-2-yl]-N-(1-methylpiperidin-4-yl)pyrimidine-4-carboxamide | 445.5 |
| 861 | 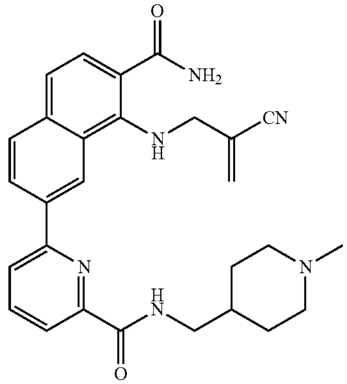 [SMILES: C=C(C#N)CNc1c(C(N)=O)ccc2ccc(-c3cccc(C(=O)NCC4CCN(C)CC4)n3)cc12] | 6-{7-carbamoyl-8-[(2-cyano-2-methylideneethyl)amino]naphthalen-2-yl}-N-[(1-methylpiperidin-4-yl)methyl]pyridine-2-carboxamide | 482.6 |

TABLE 16-continued

| Cpd No. | Structure | IUPAC | MW (g/mol) |
|---|---|---|---|
| 862 | 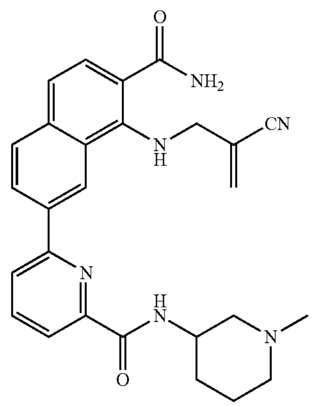 [SMILES: C=C(C#N)CNc1c(C(N)=O)ccc2ccc(-c3cccc(C(=O)NC4CCCN(C)C4)n3)cc12] | 6-{7-carbamoyl-8-[(2-cyano-2-methylideneethyl)amino]naphthalen-2-yl}-N-(1-methylpiperidin-3-yl)pyridine-2-carboxamide | 468.6 |
| 863 | 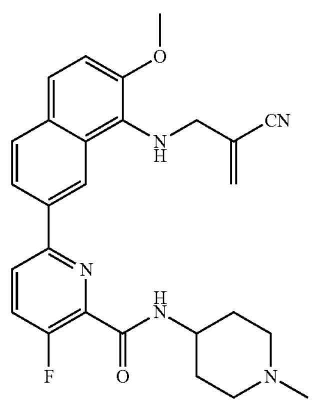 [SMILES: C=C(C#N)CNc1c(OC)ccc2ccc(-c3ccc(F)c(C(=O)NC4CCN(C)CC4)n3)cc12] | 6-{8-[(2-cyano-2-methylideneethyl)amino]-7-methoxynaphthalen-2-yl}-3-fluoro-N-(1-methylpiperidin-4-yl)pyridine-2-carboxamide | 473.6 |
| 864 | 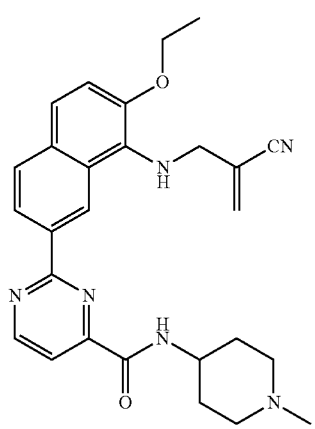 [SMILES: C=C(C#N)CNc1c(OCC)ccc2ccc(-c3nccc(C(=O)NC4CCN(C)CC4)n3)cc12] | 2-{8-[(2-cyano-2-methylideneethyl)amino]-7-ethoxynaphthalen-2-yl}-N-(1-methylpiperidin-4-yl)pyrimidine-4-carboxamide | 470.6 |

TABLE 16-continued

| Cpd No. | Structure | IUPAC | MW (g/mol) |
|---|---|---|---|
| 865 | 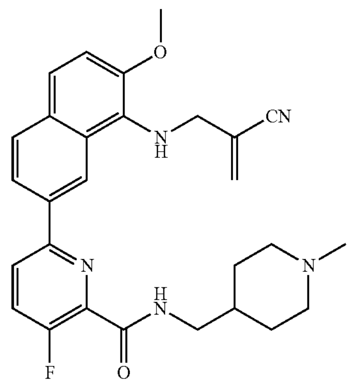 [SMILES: C=C(C#N)CNc1c(OC)ccc2ccc(-c3ccc(F)c(C(=O)NCC4CCN(C)CC4)n3)cc12] | 6-{8-[(2-cyano-2-methylideneethyl)amino]-7-methoxynaphthalen-2-yl}-3-fluoro-N-[(1-methylpiperidin-4-yl)methyl]pyridine-2-carboxamide | 487.6 |
| 866 | 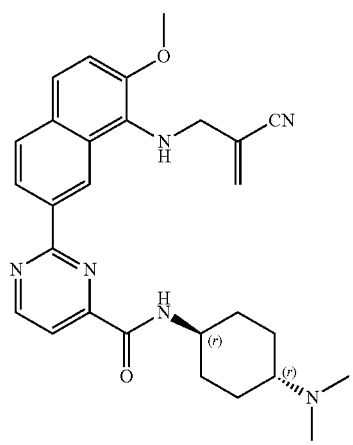 [SMILES: C=C(C#N)CNc1c(OC)ccc2ccc(-c3nccc(C(=O)N[C@H]4CC[C@H](N(C)C)CC4)n3)cc12] | 2-{8-[(2-cyano-2-methylideneethyl)amino]-7-methoxynaphthalen-2-yl}-N-[(1r,4r)-4-(dimethylamino)cyclohexyl]pyrimidine-4-carboxamide | 484.6 |
| 867 | 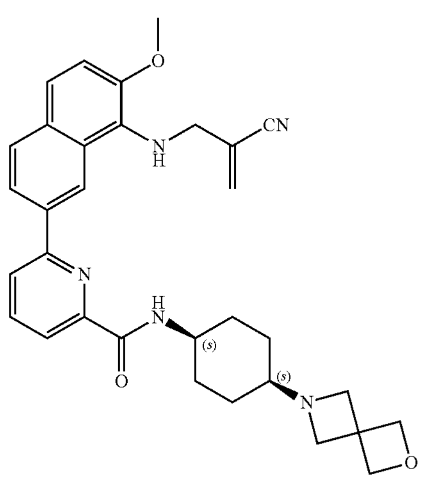 [SMILES: C=C(C#N)CNc1c(OC)ccc2ccc(-c3cccc(C(=O)N[C@H]4CC[C@@H](N5CC6(COC6)C5)CC4)n3)cc12] | 6-{8-[(2-cyano-2-methylideneethyl)amino]-7-methoxynaphthalen-2-yl}-N-[(1s,4s)-4-{2-oxa-6-azaspiro[3.3]heptan-6-yl}cyclohexyl]pyridine-2-carboxamide | 537.7 |

TABLE 16-continued

| Cpd No. | Structure | IUPAC | MW (g/mol) |
|---|---|---|---|
| 868 | 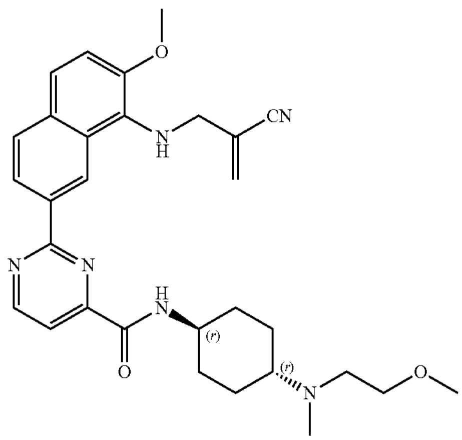 [SMILES: C=C(C#N)CNc1c(OC)ccc2ccc(-c3nccc(C(=O)N[C@H]4CC[C@H](N(C)CCOC)CC4)n3)cc12] | 2-{8-[(2-cyano-2-methylideneethyl)amino]-7-methoxynaphthalen-2-yl}-N-[(1r,4r)-4-[(2-methoxyethyl)(methyl)amino]cyclohexyl]pyrimidine-4-carboxamide | 528.7 |
| 869 | 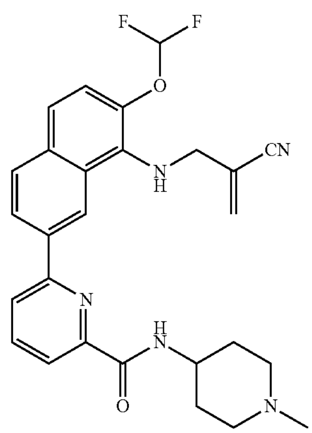 [SMILES: C=C(C#N)CNc1c(OC(F)F)ccc2ccc(-c3cccc(C(=O)NC4CCN(C)CC4)n3)cc12] | 6-{8-[(2-cyano-2-methylideneethyl)amino]-7-(difluoromethoxy)naphthalen-2-yl}-N-(1-methylpiperidin-4-yl)pyridine-2-carboxamide | 491.5 |
| 870 | 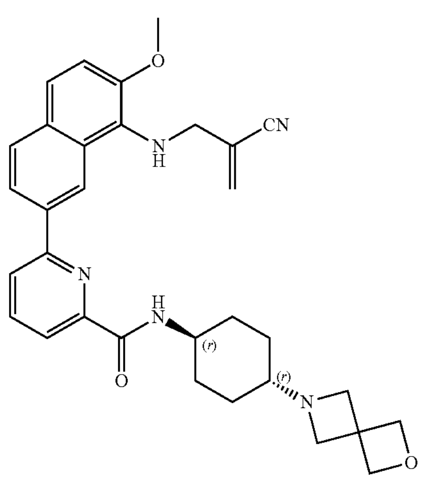 [SMILES: C=C(C#N)CNc1c(OC)ccc2ccc(-c3cccc(C(=O)N[C@H]4CC[C@H](N5CC6(COC6)C5)CC4)n3)cc12] | 6-{8-[(2-cyano-2-methylideneethyl)amino]-7-methoxynaphthalen-2-yl}-N-[(1r,4θ-4-{2-oxa-6-azaspiro[3.3]heptan-6-yl}cyclohexyl]pyridine-2-carboxamide | 537.7 |

TABLE 16-continued

| Cpd No. | Structure | IUPAC | MW (g/mol) |
|---|---|---|---|
| 871 | 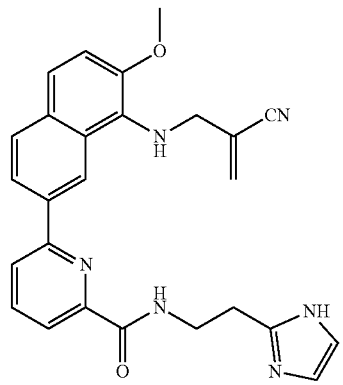 [SMILES: C=C(C#N)CNc1c(OC)ccc2ccc(-c3cccc(C(=O)NCCc4ncc[nH]4)n3)cc12] | 6-{8-[(2-cyano-2-methylideneethyl)amino]-7-methoxynaphthalen-2-yl}-N-[2-(1H-imidazol-2-yl)ethyl]pyridine-2-carboxamide | 452.5 |
| 872 | 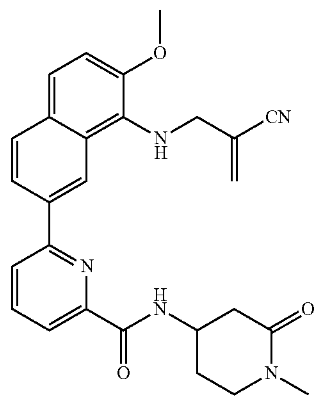 [SMILES: C=C(C#N)CNc1c(OC)ccc2ccc(-c3cccc(C(=O)NC4CCN(C)C(=O)C4)n3)cc12] | 6-{8-[(2-cyano-2-methylideneethyl)amino]-7-methoxynaphthalen-2-yl}-N-(1-methyl-2-oxopiperidin-4-yl)pyridine-2-carboxamide | 469.5 |
| 873 | 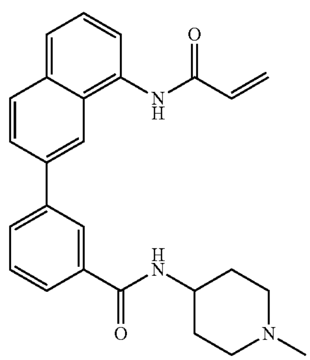 [SMILES: C=CC(=O)Nc1cccc2ccc(-c3cccc(C(=O)NC4CCN(C)CC4)c3)cc12] | N-(1-methylpiperidin-4-yl)-3-[8-(prop-2-enamido)naphthalen-2-yl]benzamide | 413.5 |
| 874 | 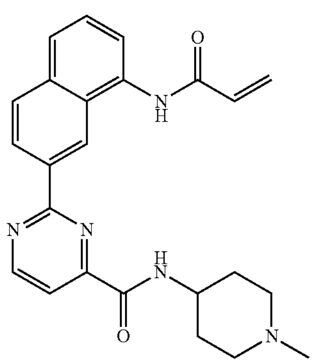 [SMILES: C=CC(=O)Nc1cccc2ccc(-c3nccc(C(=O)NC4CCN(C)CC4)n3)cc12] | N-(1-methylpiperidin-4-yl)-2-[8-(prop-2-enamido)naphthalen-2-yl]pyrimidine-4-carboxamide | 415.5 |

TABLE 16-continued

| Cpd No. | Structure | IUPAC | MW (g/mol) |
|---|---|---|---|
| 875 | 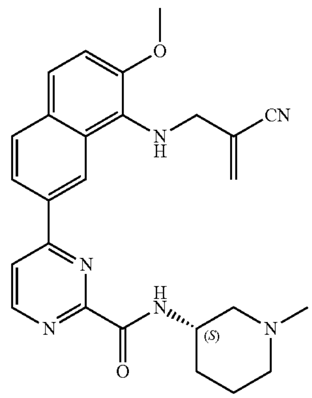 | 4-{8-[(2-cyano-2-methylideneethyl)amino]-7-methoxynaphthalen-2-yl}-N-[(3S)-1-methylpiperidin-3-yl]pyrimidine-2-carboxamide | 456.6 |
| 876 | 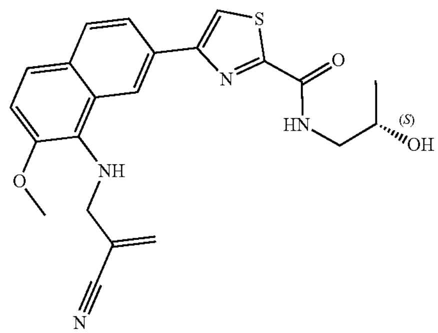 | 4-{8-[(2-cyano-2-methylideneethyl)amino]-7-methoxynaphthalen-2-yl}-N-[(2S)-2-hydroxypropyl]-1,3-thiazole-2-carboxamide | 422.5 |
| 877 | 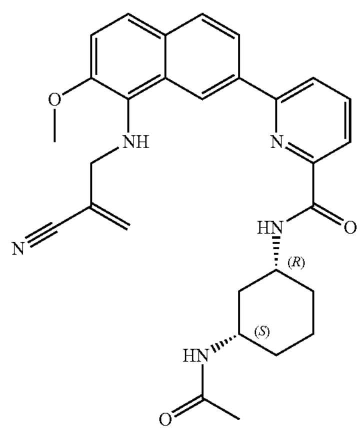 | 6-{8-[(2-cyano-2-methylideneethyl)amino]-7-methoxynaphthalen-2-yl}-N-[(1R,3S)-3-acetamidocyclohexyl]pyridine-2-carboxamide | 497.6 |
| 878 | 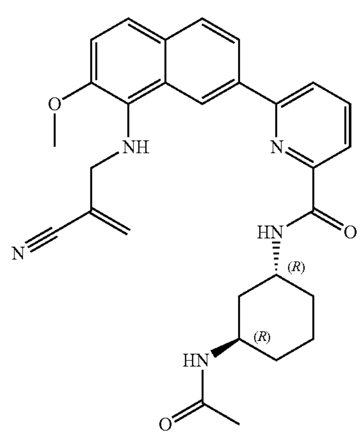 | 6-{8-[(2-cyano-2-methylideneethyl)amino]-7-methoxynaphthalen-2-yl}-N-[(1R,3R)-3-acetamidocyclohexyl]pyridine-2-carboxamide | 497.6 |

TABLE 16-continued

| Cpd No. | Structure | IUPAC | MW (g/mol) |
|---|---|---|---|
| 879 | 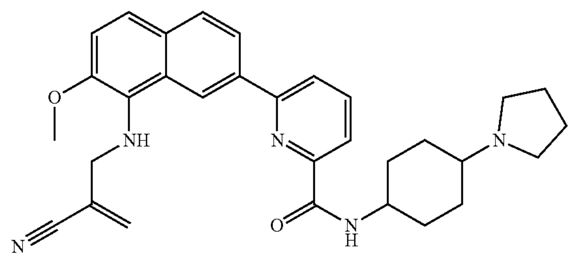 [SMILES: C=C(C#N)CNc1c(OC)ccc2ccc(-c3cccc(C(=O)NC4CCC(N5CCCC5)CC4)n3)cc12] | 6-{8-[(2-cyano-2-methylideneethyl)amino]-7-methoxynaphthalen-2-yl}-N-[4-(pyrrolidin-1-yl)cyclohexyl]pyridine-2-carboxamide | 509.7 |
| 880 | 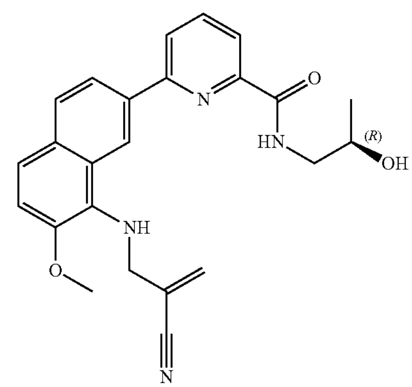 | 6-{8-[(2-cyano-2-methylideneethyl)amino]-7-methoxynaphthalen-2-yl}-N-[(2R)-2-hydroxypropyl]pyridine-2-carboxamide | 416.5 |
| 881 | 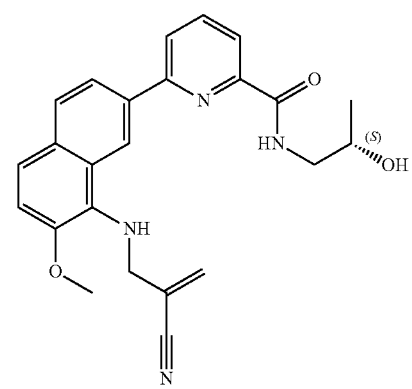 | 6-{8-[(2-cyano-2-methylideneethyl)amino]-7-methoxynaphthalen-2-yl}-N-[(2S)-2-hydroxypropyl]pyridine-2-carboxamide | 416.5 |
| 882 | 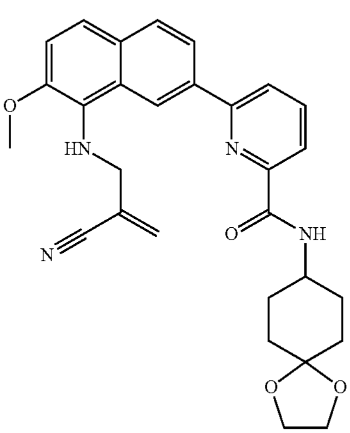 [SMILES: C=C(C#N)CNc1c(OC)ccc2ccc(-c3cccc(C(=O)NC4CCC5(CC4)OCCO5)n3)cc12] | 6-{8-[(2-cyano-2-methylideneethyl)amino]-7-methoxynaphthalen-2-yl}-N-{1,4-dioxaspiro[4.5]decan-8-yl}pyridine-2-carboxamide | 498.6 |

TABLE 16-continued

| Cpd No. | Structure | IUPAC | MW (g/mol) |
|---|---|---|---|
| 883 | 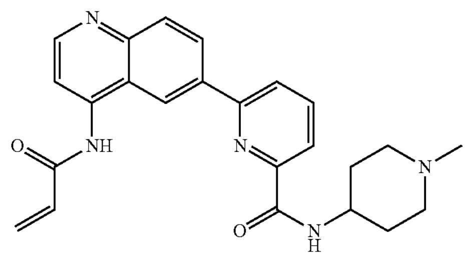 [SMILES: C=CC(=O)Nc1ccnc2ccc(-c3cccc(C(=O)NC4CCN(C)CC4)n3)cc12] | N-(1-methylpiperidin-4-yl)-6-[4-(prop-2-enamido)quinolin-6-yl]pyridine-2-carboxamide | 415.5 |
| 884 | 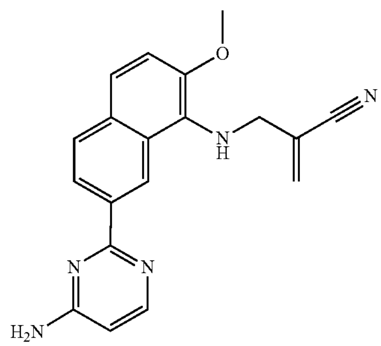 [SMILES: C=C(C#N)CNc1c(OC)ccc2ccc(-c3nccc(N)n3)cc12] | 2-({[7-(4-aminopyrimidin-2-yl)-2-methoxynaphthalen-1-yl]amino}methyl)prop-2-enenitrile | 331.4 |
| 885 | 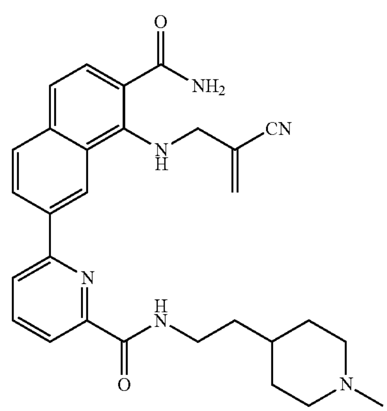 [SMILES: C=C(C#N)CNc1c(C(N)=O)ccc2ccc(-c3cccc(C(=O)NCCC4CCN(C)CC4)n3)cc12] | 6-{7-carbamoyl-8-[(2-cyano-2-methylideneethyl)amino]naphthalen-2-yl}-N-[2-(1-methylpiperidin-4-yl)ethyl]pyridine-2-carboxamide | 496.6 |
| 886 | 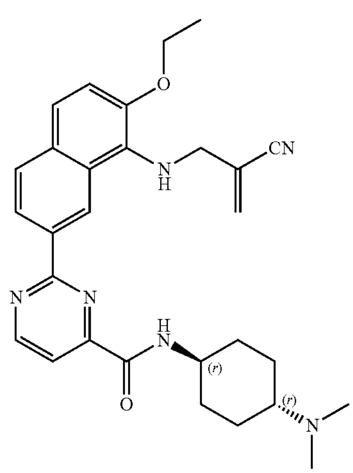 [SMILES: C=C(C#N)CNc1c(OCC)ccc2ccc(-c3nccc(C(=O)N[C@H]4CC[C@H](N(C)C)CC4)n3)cc12] | 2-{8-[(2-cyano-2-methylideneethyl)amino]-7-ethoxynaphthalen-2-yl}-N-[(1r,4r)-4-(dimethylamino)cyclohexyl]pyrimidine-4-carboxamide | 498.6 |

TABLE 16-continued

| Cpd No. | Structure | IUPAC | MW (g/mol) |
|---|---|---|---|
| 887 | 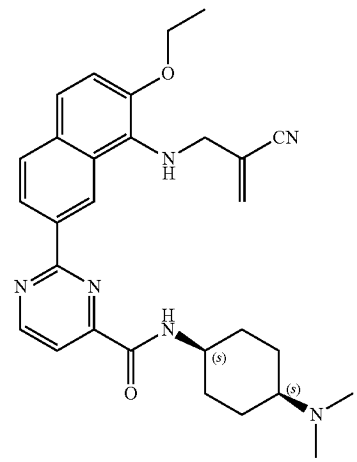 [SMILES: C=C(C#N)CNc1c(OCC)ccc2ccc(-c3nccc(C(=O)N[C@H]4CC[C@@H](N(C)C)CC4)n3)cc12] | 2-{8-[(2-cyano-2-methylideneethyl)amino]-7-ethoxynaphthalen-2-yl}-N-[(1s,4s)-4-(dimethylamino)cyclohexyl]pyrimidine-4-carboxamide | 498.6 |
| 888 | 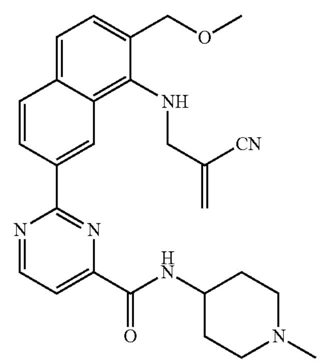 [SMILES: C=C(C#N)CNc1c(COC)ccc2ccc(-c3nccc(C(=O)NC4CCN(C)CC4)n3)cc12] | 2-{8-[(2-cyano-2-methylideneethyl)amino]-7-(methoxymethyl)naphthalen-2-yl}-N-(1-methylpiperidin-4-yl)pyrimidine-4-carboxamide | 470.6 |
| 889 | 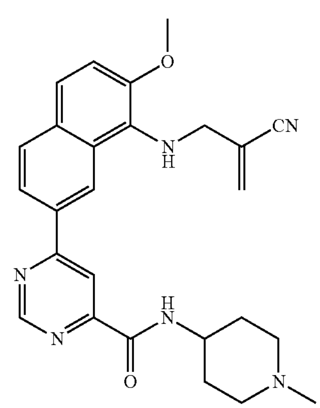 [SMILES: C=C(C#N)CNc1c(OC)ccc2ccc(-c3cc(C(=O)NC4CCN(C)CC4)ncn3)cc12] | 6-{8-[(2-cyano-2-methylideneethyl)amino]-7-methoxynaphthalen-2-yl}-N-(1-methylpiperidin-4-yl)pyrimidine-4-carboxamide | 456.6 |

TABLE 16-continued

| Cpd No. | Structure | IUPAC | MW (g/mol) |
|---|---|---|---|
| 890 | 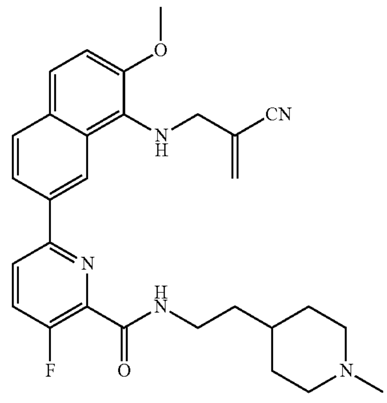 [SMILES: C=C(C#N)CNc1c(OC)ccc2ccc(-c3ccc(F)c(C(=O)NCCC4CCN(C)CC4)n3)cc12] | 6-{8-[(2-cyano-2-methylideneethyl)amino]-7-methoxynaphthalen-2-yl}-3-fluoro-N-[2-(1-methylpiperidin-4-yl)ethyl]pyridine-2-carboxamide | 501.6 |
| 891 | 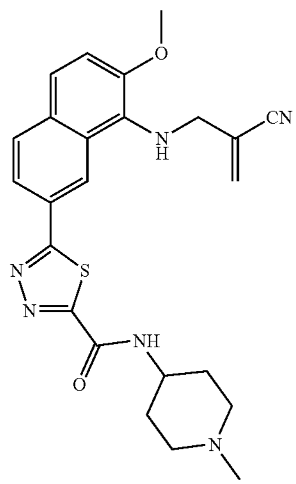 | 5-{8-[(2-cyano-2-methylideneethyl)amino]-7-methoxynaphthalen-2-yl}-N-(1-methylpiperidin-4-yl)-1,3,4-thiadiazole-2-carboxamide | 462.6 |
| 892 | 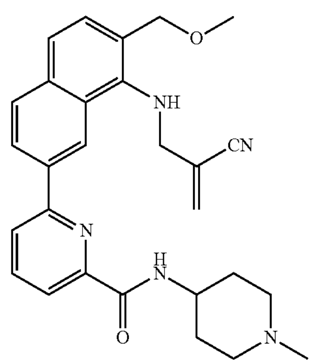 [SMILES: C=C(C#N)CNc1c(COC)ccc2ccc(-c3cccc(C(=O)NC4CCN(C)CC4)n3)cc12] | 6-{8-[(2-cyano-2-methylideneethyl)amino]-7-(methoxymethyl)naphthalen-2-yl}-N-(1-methylpiperidin-4-yl)pyridine-2-carboxamide | 469.6 |
| 893 | 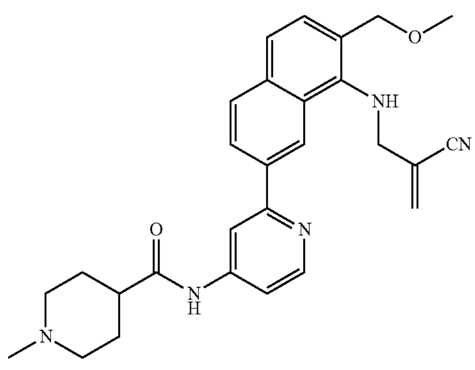 [SMILES: C=C(C#N)CNc1c(COC)ccc2ccc(-c3cc(NC(=O)C4CCN(C)CC4)ccn3)cc12] | N-(2-{8-[(2-cyano-2-methylideneethyl)amino]-7-(methoxymethyl)naphthalen-2-yl}pyridin-4-yl)-1-methylpiperidine-4-carboxamide | 469.6 |

TABLE 16-continued

| Cpd No. | Structure | IUPAC | MW (g/mol) |
|---|---|---|---|
| 894 | 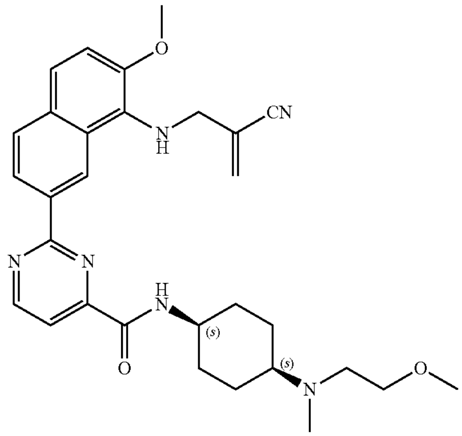 [SMILES: C=C(C#N)CNc1c(OC)ccc2ccc(-c3nccc(C(=O)N[C@H]4CC[C@@H](N(C)CCOC)CC4)n3)cc12] | 2-{8-[(2-cyano-2-methylideneethyl)amino]-7-methoxynaphthalen-2-yl}-N-[(1s,4s)-4-[(2-methoxyethyl)(methyl)amino]cyclohexyl]pyrimidine-4-carboxamide | 528.7 |
| 895 | 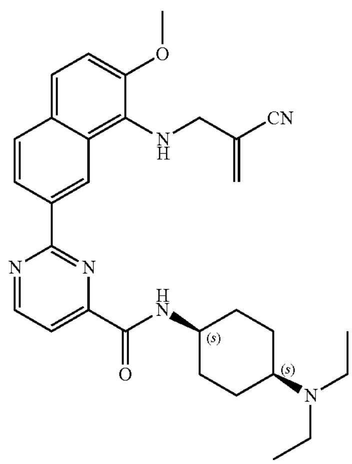 [SMILES: C=C(C#N)CNc1c(OC)ccc2ccc(-c3nccc(C(=O)N[C@H]4CC[C@@H](N(CC)CC)CC4)n3)cc12] | 2-{8-[(2-cyano-2-methylideneethyl)amino]-7-methoxynaphthalen-2-yl}-N-[(1s,4s)-4-(diethylamino)cyclohexyl]pyrimidine-4-carboxamide | 512.7 |
| 896 | 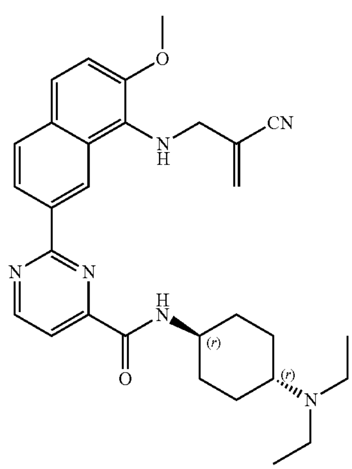 [SMILES: C=C(C#N)CNc1c(OC)ccc2ccc(-c3nccc(C(=O)N[C@H]4CC[C@H](N(CC)CC)CC4)n3)cc12] | 2-{8-[(2-cyano-2-methylideneethyl)amino]-7-methoxynaphthalen-2-yl}-N-[(1r,4r)-4-(diethylamino)cyclohexyl]pyrimidine-4-carboxamide | 512.7 |

TABLE 16-continued

| Cpd No. | Structure | IUPAC | MW (g/mol) |
|---|---|---|---|
| 897 | 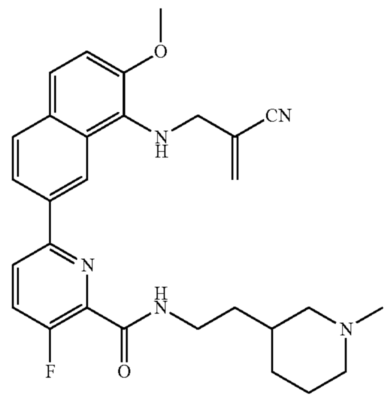 [SMILES: C=C(C#N)CNc1c(OC)ccc2ccc(-c3ccc(F)c(C(=O)NCCC4CCCN(C)C4)n3)cc12] | 6-{8-[(2-cyano-2-methylideneethyl)amino]-7-methoxynaphthalen-2-yl}-3-fluoro-N-[2-(1-methylpiperidin-3-yl)ethyl]pyridine-2-carboxamide | 501.6 |
| 898 | 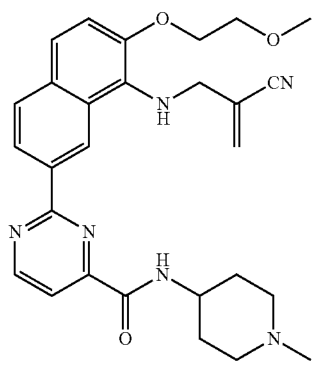 [SMILES: C=C(C#N)CNc1c(OCCOC)ccc2ccc(-c3nccc(C(=O)NC4CCN(C)CC4)n3)cc12] | 2-{8-[(2-cyano-2-methylideneethyl)amino]-7-(2-methoxyethoxy)naphthalen-2-yl}-N-(1-methylpiperidin-4-yl)pyrimidine-4-carboxamide | 500.6 |
| 899 | 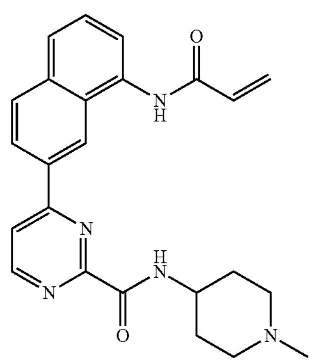 [SMILES: C=CC(=O)Nc1cccc2ccc(-c3ccnc(C(=O)NC4CCN(C)CC4)n3)cc12] | N-(1-methylpiperidin-4-yl)-4-[8-(prop-2-enamido)naphthalen-2-yl]pyrimidine-2-carboxamide | 415.5 |
| 900 | 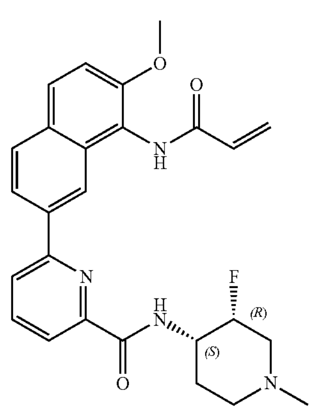 | N-[(3R,4S)-3-fluoro-1-methylpiperidin-4-yl]-6-[7-methoxy-8-(prop-2-enamido)naphthalen-2-yl]pyridine-2-carboxamide | 462.5 |

TABLE 16-continued

| Cpd No. | Structure | IUPAC | MW (g/mol) |
|---|---|---|---|
| 901 | 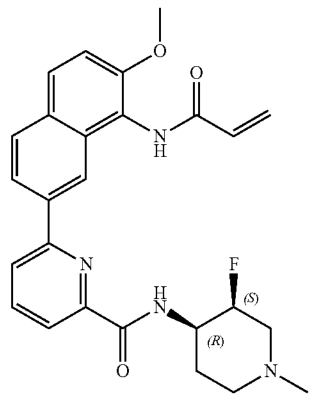 | N-[(3S,4R)-3-fluoro-1-methylpiperidin-4-yl]-6-[7-methoxy-8-(prop-2-enamido)naphthalen-2-yl]pyridine-2-carboxamide | 462.5 |
| 902 | 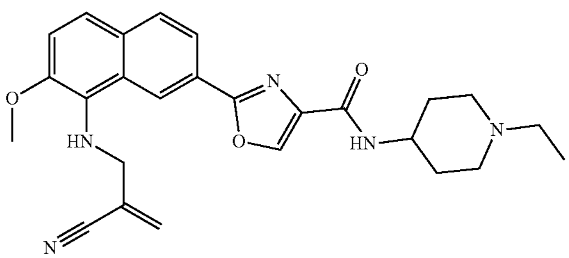 [SMILES: C=C(C#N)CNc1c(OC)ccc2ccc(-c3nc(C(=O)NC4CCN(CC)CC4)co3)cc12] | 2-{8-[(2-cyano-2-methylideneethyl)amino]-7-methoxynaphthalen-2-yl}-N-(1-ethylpiperidin-4-yl)-1,3-oxazole-4-carboxamide | 459.6 |
| 903 | 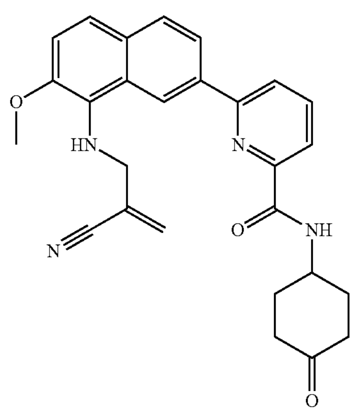 [SMILES: C=C(C#N)CNc1c(OC)ccc2ccc(-c3cccc(C(=O)NC4CCC(=O)CC4)n3)cc12] | 6-{8-[(-cyano-2-methylideneethyl)amino]-7-methoxynaphthalen-2-yl}-N-(4-oxocyclohexyl)pyridine-2-carboxamide | 454.5 |
| 904 | 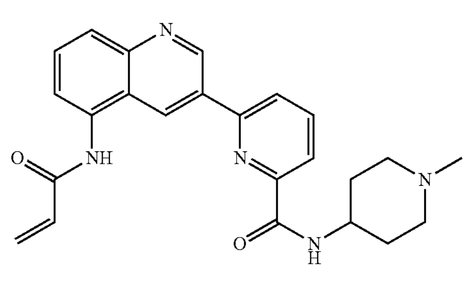 [SMILES: C=CC(=O)Nc1cccc2ncc(-c3cccc(C(=O)NC4CCN(C)CC4)n3)cc12] | N-(1-methylpiperidin-4-yl)-6-[5-(prop-2-enamido)quinolin-3-yl]pyridine-2-carboxamide | 415.5 |

TABLE 16-continued

| Cpd No. | Structure | IUPAC | MW (g/mol) |
|---|---|---|---|
| 905 | 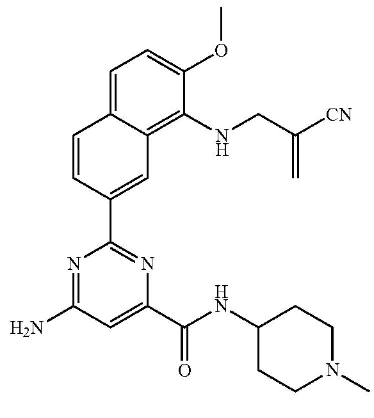 [SMILES: C=C(C#N)CNc1c(OC)ccc2ccc(-c3nc(N)cc(C(=O)NC4CCN(C)CC4)n3)cc12] | 6-amino-2-{8-[(2-cyano-2-methylideneethyl)amino]-7-methoxynaphthalen-2-yl}-N-(1-methylpiperidin-4-yl)pyrimidine-4-carboxamide | 471.6 |
| 906 | 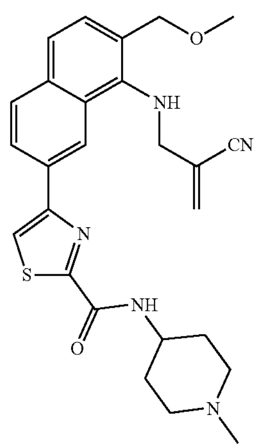 [SMILES: C=C(C#N)CNc1c(COC)ccc2ccc(-c3csc(C(=O)NC4CCN(C)CC4)n3)cc12] | 4-{8-[(2-cyano-2-methylideneethyl)amino]-7-(methoxymethyl)naphthalen-2-yl}-N-(1-methylpiperidin-4-yl)-1,3-thiazole-2-carboxamide | 475.6 |
| 907 | 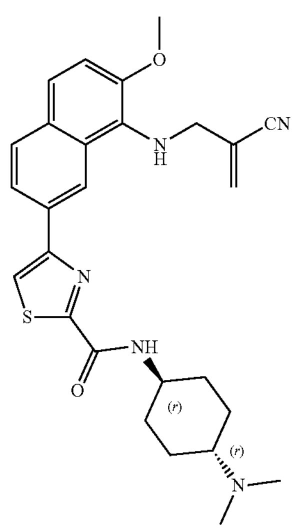 [SMILES: C=C(C#N)CNc1c(OC)ccc2ccc(-c3csc(C(=O)N[C@H]4CC[C@H](N(C)C)CC4)n3)cc12] | 4-{8-[(2-cyano-2-methylideneethyl)amino]-7-methoxynaphthalen-2-yl}-N-[(1r,4r)-4-(dimethylamino)cyclohexyl]-1,3-thiazole-2-carboxamide | 489.6 |

TABLE 16-continued

| Cpd No. | Structure | IUPAC | MW (g/mol) |
|---|---|---|---|
| 908 | 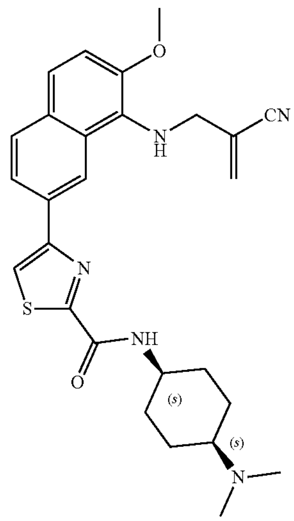 [SMILES: C=C(C#N)CNc1c(OC)ccc2ccc(-c3csc(C(=O)N[C@H]4CC[C@@H](N(C)C)CC4)n3)cc12] | 4-{8-[(2-cyano-2-methylideneethyl)amino]-7-methoxynaphthalen-2-yl}-N-[(1s,4s)-4-(dimethylamino)cyclohexyl]-1,3-thiazole-2-carboxamide | 489.6 |
| 909 | 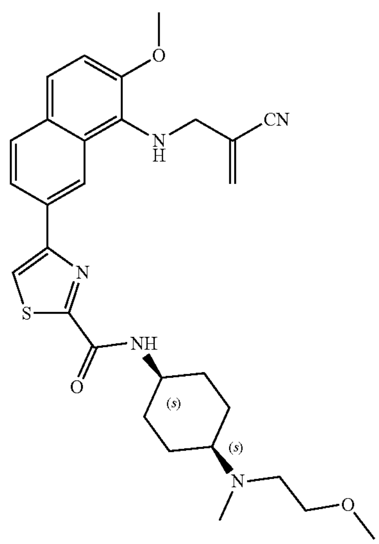 [SMILES: C=C(C#N)CNc1c(OC)ccc2ccc(-c3csc(C(=O)N[C@H]4CC[C@@H](N(C)CCOC)CC4)n3)cc12] | 4-{8-[(2-cyano-2-methylideneethyl)amino]-7-methoxynaphthalen-2-yl}-N-[(1s,4s)-4-[(2-methoxyethyl)(methyl)amino]cyclohexyl]-1,3-thiazole-2-carboxamide | 533.7 |
| 910 | 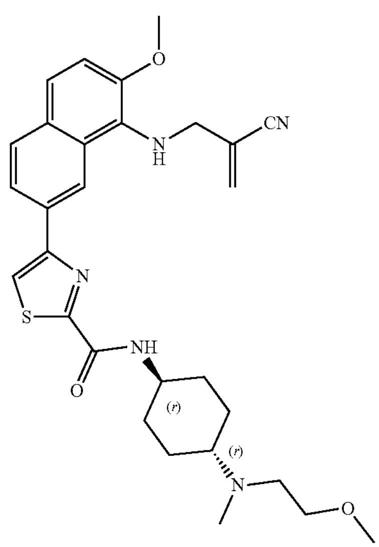 [SMILES: C=C(C#N)CNc1c(OC)ccc2ccc(-c3csc(C(=O)N[C@H]4CC[C@H](N(C)CCOC)CC4)n3)cc12] | 4-{8-[(2-cyano-2-methylideneethyl)amino]-7-methoxynaphthalen-2-yl}-N-[(1r,4r)-4-[(2-methoxyethyl)(methyl)amino]cyclohexyl]-1,3-thiazole-2-carboxamide | 533.7 |

TABLE 16-continued

| Cpd No. | Structure | IUPAC | MW (g/mol) |
|---|---|---|---|
| 911 | 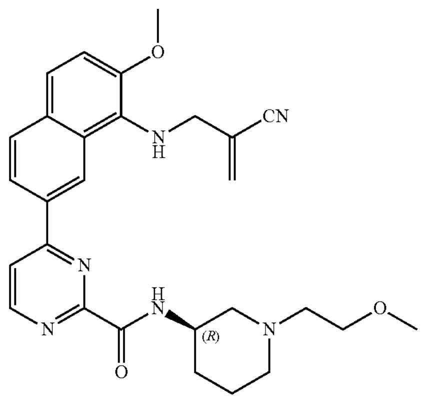 | 4-{8-[(2-cyano-2-methylideneethyl)amino]-7-methoxynaphthalen-2-yl}-N-[(3R)-1-(2-methoxyethyl)piperidin-3-yl]pyrimidine-2-carboxamide | 500.6 |
| 912 | 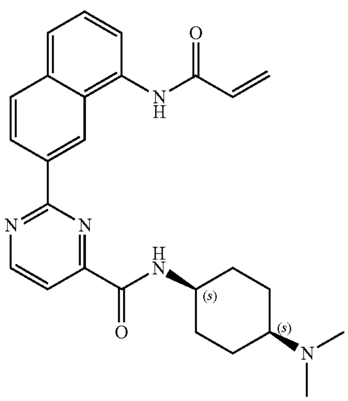 [SMILES: C=CC(=O)Nc1cccc2ccc(-c3nccc(C(=O)N[C@H]4CC[C@@H](N(C)C)CC4)n3)cc12] | 2-[8-(prop-2-enamido)naphthalen-2-yl]-N-[(1s,4s)-4-(dimethylamino)cyclohexyl]pyrimidine-4-carboxamide | 443.6 |
| 913 | 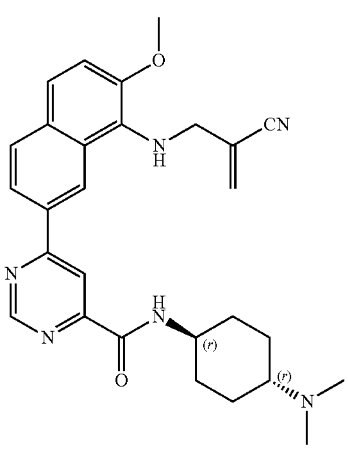 [SMILES: C=C(C#N)CNc1c(OC)ccc2ccc(-c3cc(C(=O)N[C@H]4CC[C@H](N(C)C)CC4)ncn3)cc12] | 6-{8-[(2-cyano-2-methylideneethyl)amino]-7-methoxynaphthalen-2-yl}-N-[(1r,4r)-4-(dimethylamino)cyclohexyl]pyrimidine-4-carboxamide | 484.6 |

TABLE 16-continued

| Cpd No. | Structure | IUPAC | MW (g/mol) |
|---|---|---|---|
| 914 | 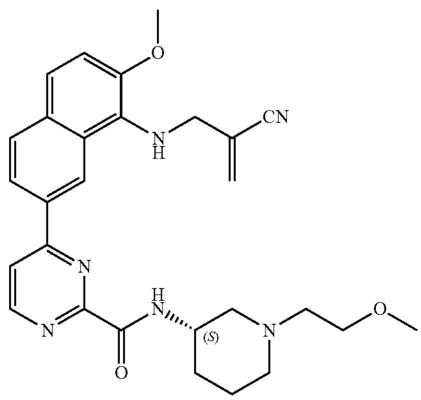 | 4-{8-[(2-cyano-2-methylideneethyl)amino]-7-methoxynaphthalen-2-yl}-N-[(3S)-1-(2-methoxyethyl)piperidin-3-yl]pyrimidine-2-carboxamide | 500.6 |
| 915 | 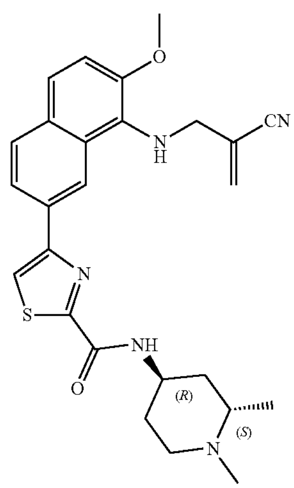 | 4-{8-[(2-cyano-2-methylideneethyl)amino]-7-methoxynaphthalen-2-yl}-N-[(2S,4R)-1,2-dimethylpiperidin-4-yl]-1,3-thiazole-2-carboxamide | 475.6 |
| 916 | 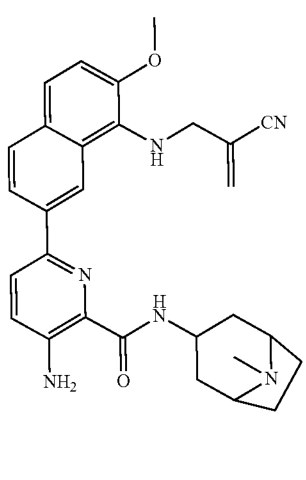 [SMILES: C=C(C#N)CNc1c(OC)ccc2ccc(-c3ccc(N)c(C(=O)NC4CC5CCC(C4)N5C)n3)cc12] | 3-amino-6-{8-[(2-cyano-2-methylideneethyl)amino]-7-methoxynaphthalen-2-yl}-N-{8-methyl-8-azabicyclo[3.2.1]octan-3-yl}pyridine-2-carboxamide | 496.6 |

TABLE 16-continued

| Cpd No. | Structure | IUPAC | MW (g/mol) |
| --- | --- | --- | --- |
| 917 | 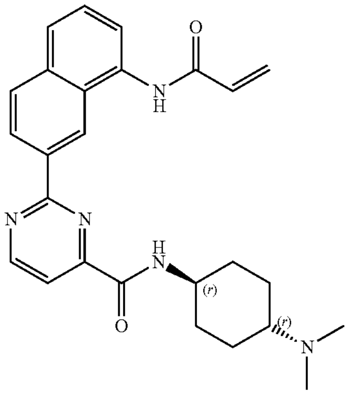 | 2-[8-(prop-2-enamido)naphthalen-2-yl]-N-[(1r,4r)-4-(dimethylamino)cyclohexyl]pyrimidine-4-carboxamide | 443.6 |
| 918 | 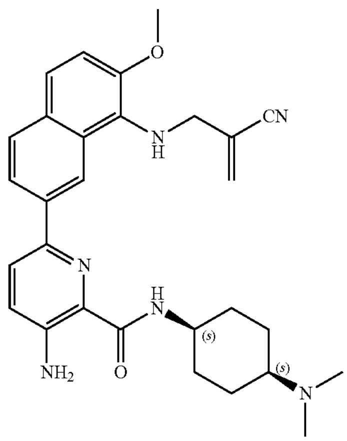 [SMILES: C=C(C#N)CNc1c(OC)ccc2ccc(-c3ccc(N)c(C(=O)N[C@H]4CC[C@@H](N(C)C)CC4)n3)cc12] | 3-amino-6-{8-[(2-cyano-2-methylideneethyl)amino]-7-methoxynaphthalen-2-yl}-N-[(1s,4s)-4-(dimethylamino)cyclohexyl]pyridine-2-carboxamide | 498.6 |
| 919 | 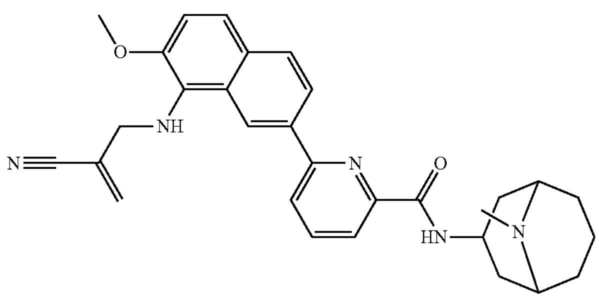 [SMILES: C=C(C#N)CNc1c(OC)ccc2ccc(-c3cccc(C(=O)NC4CC5CCCC(C4)N5C)n3)cc12] | 6-{8-[(2-cyano-2-methylideneethyl)amino]-7-methoxynaphthalen-2-yl}-N-{9-methyl-9-azabicyclo[3.3.1]nonan-3-yl}pyridine-2-carboxamide | 495.6 |
| 920 | 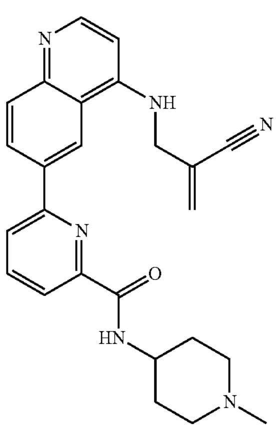 [SMILES: C=C(C#N)CNc1ccnc2ccc(-c3cccc(C(=O)NC4CCN(C)CC4)n3)cc12] | 6-{4-[(2-cyano-2-methylideneethyl)amino]quinolin-6-yl}-N-(1-methylpiperidin-4-yl)pyridine-2-carboxamide | 426.5 |

TABLE 16-continued

| Cpd No. | Structure | IUPAC | MW (g/mol) |
|---|---|---|---|
| 921 | 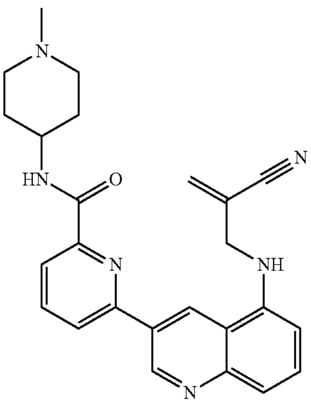 [SMILES: C=C(C#N)CNc1cccc2ncc(-c3cccc(C(=O)NC4CCN(C)CC4)n3)cc12] | 6-{5-[(2-cyano-2-methylideneethyl)amino]quinolin-3-yl}-N-(1-methylpiperidin-4-yl)pyridine-2-carboxamide | 426.5 |
| 922 | 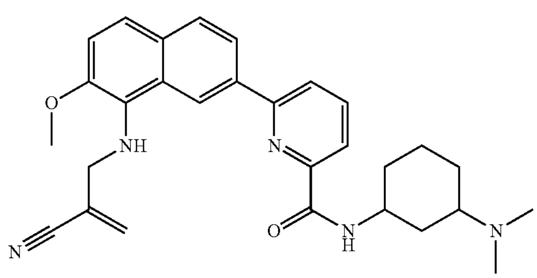 [SMILES: C=C(C#N)CNc1c(OC)ccc2ccc(-c3cccc(C(=O)NC4CCCC(N(C)C)C4)n3)cc12] | 6-{8-[(2-cyano-2-methylideneethyl)amino]-7-methoxynaphthalen-2-yl}-N-[3-(dimethylamino)cyclohexyl]pyridine-2-carboxamide | 483.6 |
| 923 | 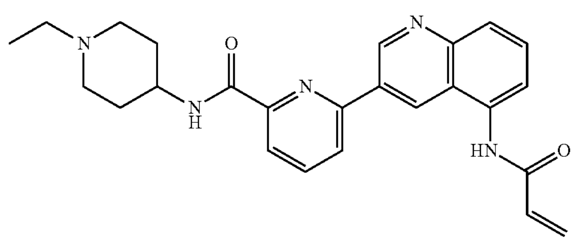 [SMILES: C=CC(=O)Nc1cccc2ncc(-c3cccc(C(=O)NC4CCN(CC)CC4)n3)cc12] | N-(1-ethylpiperidin-4-yl)-6-[5-(prop-2-enamido)quinolin-3-yl]pyridine-2-carboxamide | 429.5 |
| 924 | 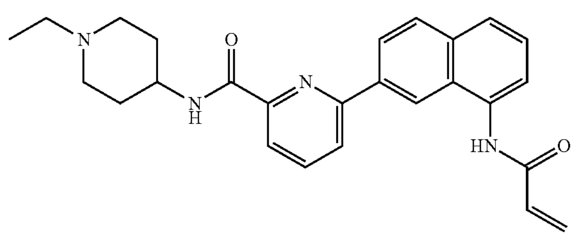 [SMILES: C=CC(=O)Nc1cccc2ccc(-c3cccc(C(=O)NC4CCN(CC)CC4)n3)cc12] | N-(1-ethylpiperidin-4-yl)-6-[8-(prop-2-enamido)naphthalen-2-yl]pyridine-2-carboxamide | 428.5 |
| 925 | 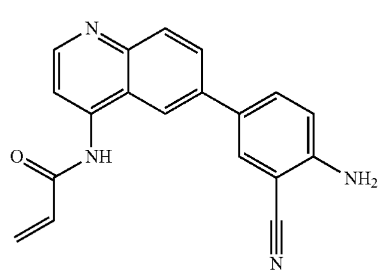 [SMILES: C=CC(=O)Nc1ccnc2ccc(-c3ccc(N)c(C#N)c3)cc12] | N-[6-(4-amino-3-cyanophenyl)quinolin-4-yl]prop-2-enamide | 314.3 |

TABLE 16-continued

| Cpd No. | Structure | IUPAC | MW (g/mol) |
|---|---|---|---|
| 926 | 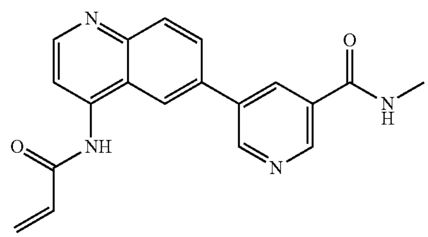 [SMILES: C=CC(=O)Nc1ccnc2ccc(-c3cncc(C(=O)NC)c3)cc12] | N-methyl-5-[4-(prop-2-enamido)quinolin-6-yl]pyridine-3-carboxamide | 332.4 |
| 927 | 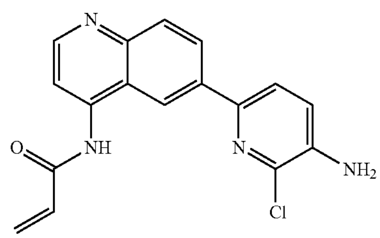 [SMILES: C=CC(=O)Nc1ccnc2ccc(-c3ccc(N)c(Cl)n3)cc12] | N-[6-(5-amino-6-chloropyridin-2-yl)quinolin-4-yl]prop-2-enamide | 324.8 |
| 928 | 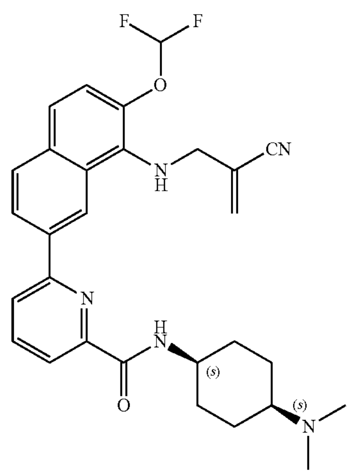 | 6-{8-[(2-cyano-2-methylideneethyl)amino]-7-(difluoromethoxy)naphthalen-2-yl}-N-[(1s,4s)-4-(dimethylamino)cyclohexyl]pyridine-2-carboxamide | 519.6 |
| 929 | 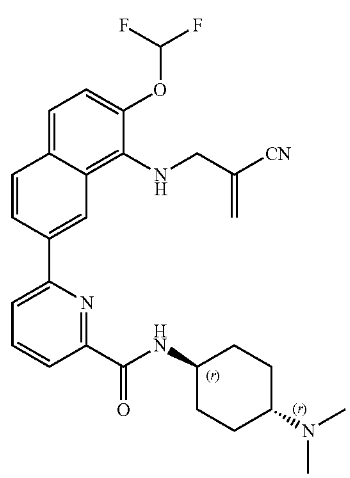 | 6-{8-[(2-cyano-2-methylideneethyl)amino]-7-(difluoromethoxy)naphthalen-2-yl}-N-[(1r,4r)-4-(dimethylamino)cyclohexyl]pyridine-2-carboxamide | 519.6 |

TABLE 16-continued

| Cpd No. | Structure | IUPAC | MW (g/mol) |
|---|---|---|---|
| 930 | 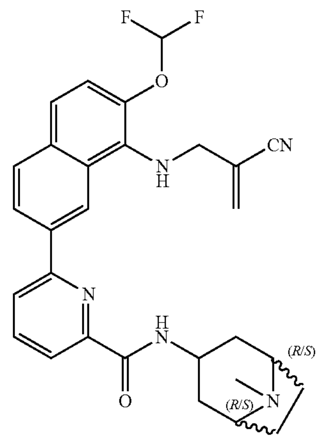 [SMILES: C=C(C#N)CNc1c(OC(F)F)ccc2ccc(-c3cccc(C(=O)NC4CC5CCC(C4)N5C)n3)cc12] | 6-{8-[(2-cyano-2-methylideneethyl)amino]-7-(difluoromethoxy)naphthalen-2-yl}-N-{8-methyl-8-azabicyclo[3.2.1]octan-3-yl}pyridine-2-carboxamide | 517.6 |
| 931 | 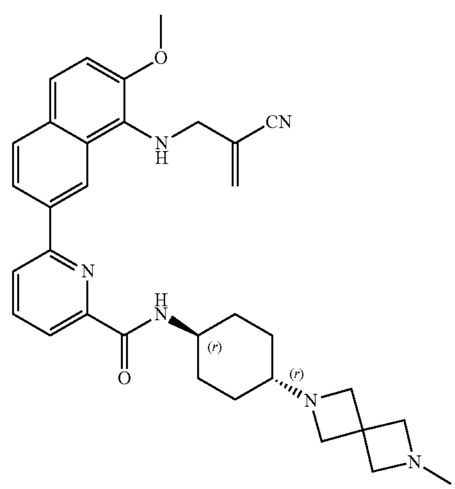 | 6-{8-[(2-cyano-2-methylideneethyl)amino]-7-methoxynaphthalen-2-yl}-N-[(1r,4r)-4-{6-methyl-2,6-diazaspiro[3.3]heptan-2-yl}cyclohexyl]pyridine-2-carboxamide | 550.7 |
| 932 | 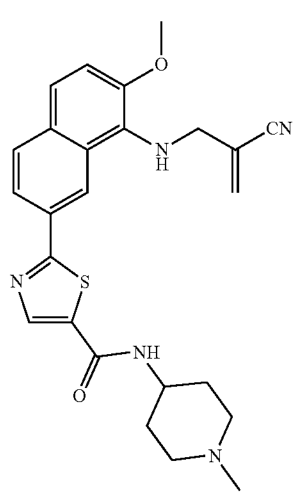 [SMILES: C=C(C#N)CNc1c(OC)ccc2ccc(-c3ncc(C(=O)NC4CCN(C)CC4)s3)cc12] | 2-{8-[(2-cyano-2-methylideneethyl)amino]-7-methoxynaphthalen-2-yl}-N-(1-methylpiperidin-4-yl)-1,3-thiazole-5-carboxamide | 461.6 |

TABLE 16-continued

| Cpd No. | Structure | IUPAC | MW (g/mol) |
|---|---|---|---|
| 933 | 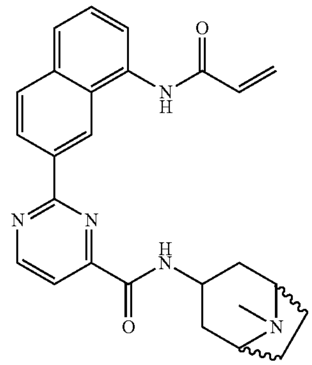 [SMILES: C=CC(=O)Nc1cccc2ccc(-c3nccc(C(=O)NC4CC5CCC(C4)N5C)n3)cc12] | N-{8-methyl-8-azabicyclo[3.2.1]octan-3-yl}-2-[8-(prop-2-enamido)naphthalen-2-yl]pyrimidine-4-carboxamide | 441.5 |
| 934 | 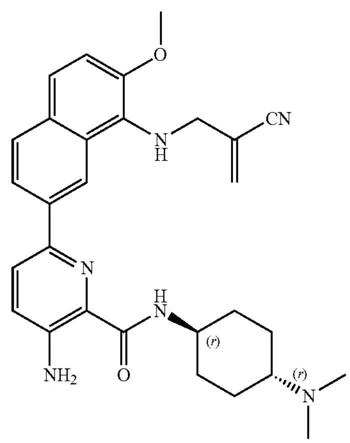 | 3-amino-6-{8-[(2-cyano-2-methylideneethyl)amino]-7-methoxynaphthalen-2-yl}-N-[(1r,4r)-4-(dimethylamino)cyclohexyl]pyridine-2-carboxamide | 498.6 |
| 935 | 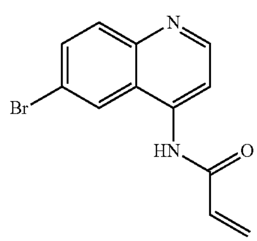 [SMILES: C=CC(=O)Nc1ccnc2ccc(Br)cc12] | N-(6-bromoquinolin-4-yl)prop-2-enamide | 277.1 |
| 936 | 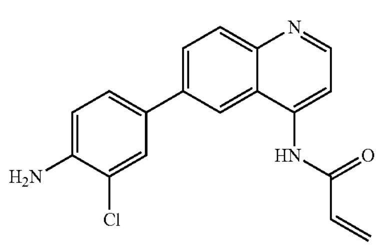 [SMILES: C=CC(=O)Nc1ccnc2ccc(-c3ccc(N)c(Cl)c3)cc12] | N-[6-(4-amino-3-chlorophenyl)quinolin-4-yl]prop-2-enamide | 323.8 |

TABLE 16-continued

| Cpd No. | Structure | IUPAC | MW (g/mol) |
|---|---|---|---|
| 937 | 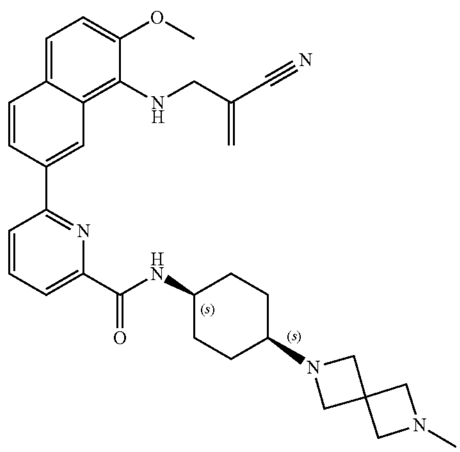 [SMILES: C=C(C#N)CNc1c(OC)ccc2ccc(-c3cccc(C(=O)N[C@H]4CC[C@@H](N5CC6(CN(C)C6)C5)CC4)n3)cc12] | 6-{8-[(2-cyano-2-methylideneethyl)amino]-7-methoxynaphthalen-2-yl}-N-[(1s,4s)-4-{6-methyl-2,6-diazaspiro[3.3]heptan-2-yl}cyclohexyl]pyridine-2-carboxamide | 550.7 |
| 938 | 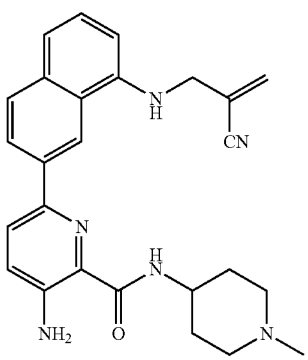 [SMILES: C=C(C#N)CNc1cccc2ccc(-c3ccc(N)c(C(=O)NC4CCN(C)CC4)n3)cc12] | 3-amino-6-{8-[(2-cyano-2-methylideneethyl)amino]naphthalen-2-yl}-N-(1-methylpiperidin-4-yl)pyridine-2-carboxamide | 440.6 |
| 939 | 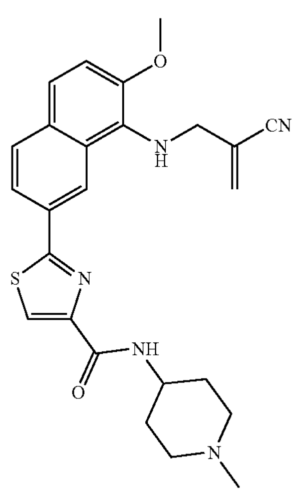 [SMILES: C=C(C#N)CNc1c(OC)ccc2ccc(-c3nc(C(=O)NC4CCN(C)CC4)cs3)cc12] | 2-{8-[(2-cyano-2-methylideneethyl)amino]-7-methoxynaphthalen-2-yl}-N-(1-methylpiperidin-4-yl)-1,3-thiazole-4-carboxamide | 461.6 |

TABLE 16-continued

| Cpd No. | Structure | IUPAC | MW (g/mol) |
|---|---|---|---|
| 940 | 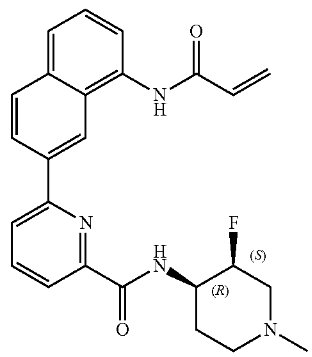 | N-[(3S,4R)-3-fluoro-1-methylpiperidin-4-yl]-6-[8-(prop-2-enamido)naphthalen-2-yl]pyridine-2-carboxamide | 432.5 |
| 941 | 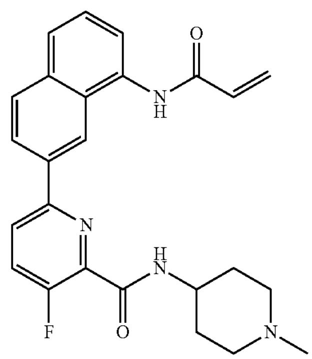 [SMILES: C=CC(=O)Nc1cccc2ccc(-c3ccc(F)c(C(=O)NC4CCN(C)CC4)n3)cc12] | 3-fluoro-N-(1-methylpiperidin-4-yl)-6-[8-(prop-2-enamido)naphthalen-2-yl]pyridine-2-carboxamide | 432.5 |
| 942 | 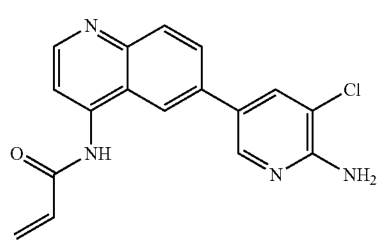 [SMILES: C=CC(=O)Nc1ccnc2ccc(-c3cnc(N)c(Cl)c3)cc12] | N-[6-(6-amino-5-chloropyridin-3-yl)quinolin-4-yl]prop-2-enamide | 324.8 |
| 943 | 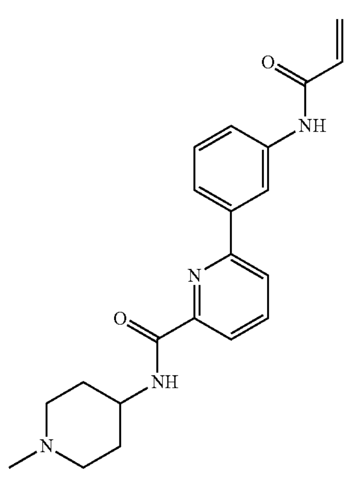 [SMILES: C=CC(=O)Nc1cccc(-c2cccc(C(=O)NC3CCN(C)CC3)n2)c1] | N-(1-methylpiperidin-4-yl)-6-[3-(prop-2-enamido)phenyl]pyridine-2-carboxamide | 364.4 |

TABLE 16-continued

| Cpd No. | Structure | IUPAC | MW (g/mol) |
|---|---|---|---|
| 944 | 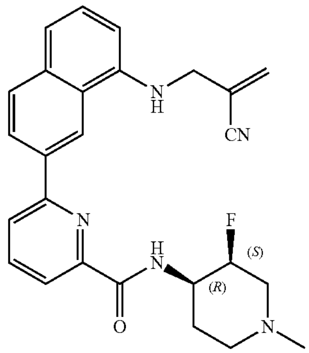 | 6-{8-[(2-cyano-2-methylideneethyl)amino]naphthalen-2-yl}-N-[(3S,4R)-3-fluoro-1-methylpiperidin-4-yl]pyridine-2-carboxamide | 443.5 |
| 945 | 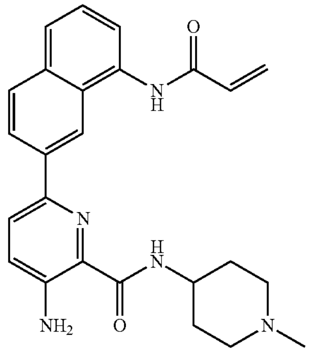 [SMILES: C=CC(=O)Nc1cccc2ccc(-c3ccc(N)c(C(=O)NC4CCN(C)CC4)n3)cc12] | 3-amino-N-(1-methylpiperidin-4-yl)-6-[8-(prop-2-enamido)naphthalen-2-yl]pyridine-2-carboxamide | 429.5 |
| 946 | 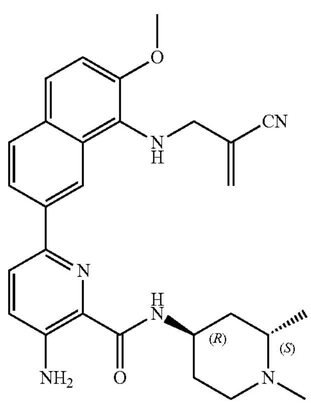 | 3-amino-6-{8-[(2-cyano-2-methylideneethyl)amino]-7-methoxynaphthalen-2-yl}-N-[(2S,4R)-1,2-dimethylpiperidin-4-yl]pyridine-2-carboxamide | 484.6 |
| 947 | 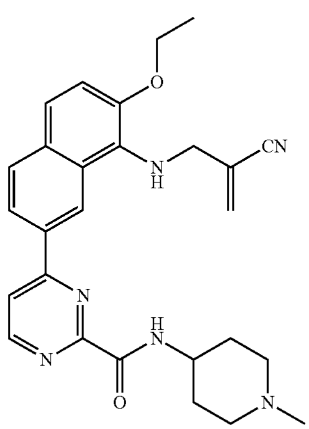 [SMILES: C=C(C#N)CNc1c(OCC)ccc2ccc(-c3ccnc(C(=O)NC4CCN(C)CC4)n3)cc12] | 4-{8-[(2-cyano-2-methylideneethyl)amino]-7-ethoxynaphthalen-2-yl}-N-(1-methylpiperidin-4-yl)pyrimidine-2-carboxamide | 470.6 |

TABLE 16-continued

| Cpd No. | Structure | IUPAC | MW (g/mol) |
|---|---|---|---|
| 948 | 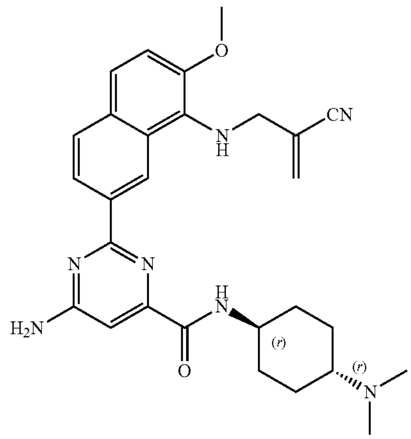 | 6-amino-2-{8-[(2-cyano-2-methylideneethyl)amino]-7-methoxynaphthalen-2-yl}-N-[(1r,4r)-4-(dimethylamino)cyclohexyl]pyrimidine-4-carboxamide | 499.6 |
| 949 | 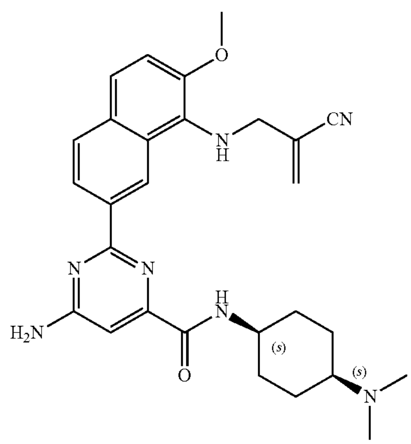 | 6-amino-2-{8-[(2-cyano-2-methylideneethyl)amino]-7-methoxynaphthalen-2-yl}-N-[(1s,4s)-4-(dimethylamino)cyclohexyl]pyrimidine-4-carboxamide | 499.6 |
| 950 | 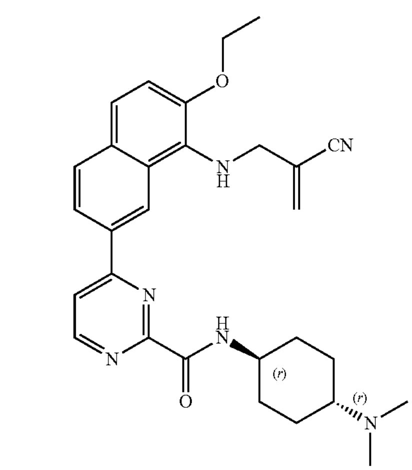 | 4-{8-[(2-cyano-2-methylideneethyl)amino]-7-ethoxynaphthalen-2-yl}-N-[(1r,4r)-4-(dimethylamino)cyclohexyl]pyrimidine-2-carboxamide | 498.6 |

TABLE 16-continued

| Cpd No. | Structure | IUPAC | MW (g/mol) |
|---|---|---|---|
| 951 | 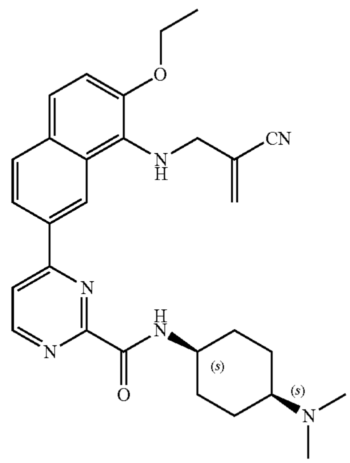 | 4-{8-[(2-cyano-2-methylideneethyl)amino]-7-ethoxynaphthalen-2-yl}-N-[(1s,4s)-4-(dimethylamino)cyclohexyl]pyrimidine-2-carboxamide | 498.6 |
| 952 | 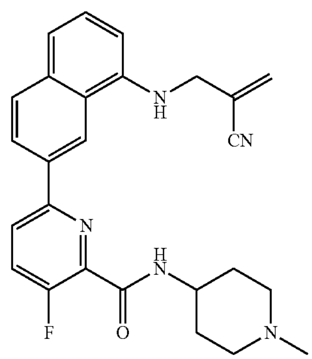 [SMILES: C=C(C#N)CNc1cccc2ccc(-c3ccc(F)c(C(=O)NC4CCN(C)CC4)n3)cc12] | 6-{8-[(2-cyano-2-methylideneethyl)amino]naphthalen-2-yl}-3-fluoro-N-(1-methylpiperidin-4-yl)pyridine-2-carboxamide | 443.5 |
| 953 | 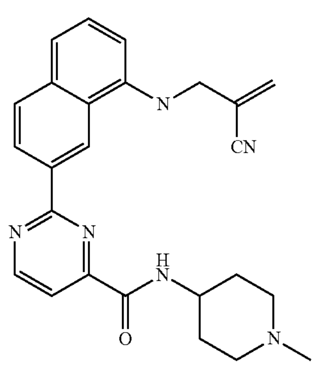 | 2-{8-[(2-cyano-2-methylideneethyl)amino]naphthalen-2-yl}-N-(1-methylpiperidin-4-yl)pyrimidine-4-carboxamide | 426.5 |

TABLE 16-continued

| Cpd No. | Structure | IUPAC | MW (g/mol) |
|---|---|---|---|
| 954 | 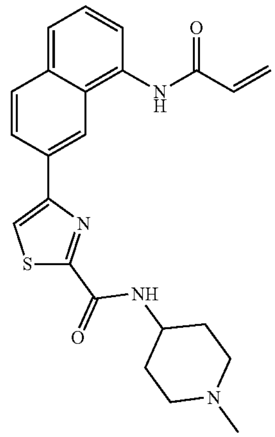 [SMILES: C=CC(=O)Nc1cccc2ccc(-c3csc(C(=O)NC4CCN(C)CC4)n3)cc12] | N-(1-methylpiperidin-4-yl)-4-[8-(prop-2-enamido)naphthalen-2-yl]-1,3-thiazole-2-carboxamide | 420.5 |
| 955 | 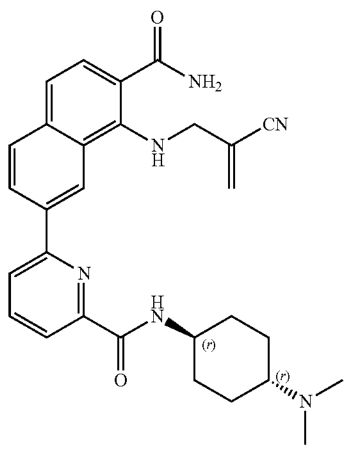 [SMILES: C=C(C#N)CNc1c(C(N)=O)ccc2ccc(-c3cccc(C(=O)N[C@H]4CC[C@H](N(C)C)CC4)n3)cc12] | 6-{7-carbamoyl-8-[(2-cyano-2-methylideneethyl)amino]naphthalen-2-yl}-N-(1r,4r)-4-(dimethylamino)cyclohexyl]pyridine-2-carboxamide | 496.6 |
| 956 | 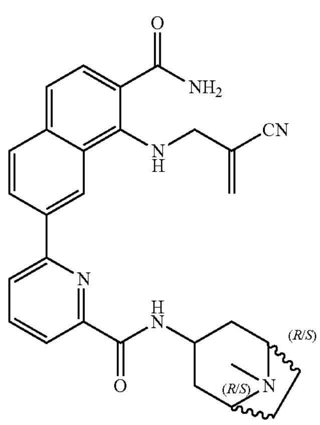 [SMILES: C=C(C#N)CNc1c(C(N)=O)ccc2ccc(-c3cccc(C(=O)NC4CC5CCC(C4)N5C)n3)cc12] | 6-{7-carbamoyl-8-[(2-cyano-2-methylideneethyl)amino]naphthalen-2-yl}-N-{8-methyl-8-azabicyclo[3.2.1]octan-3-yl}pyridine-2-carboxamide | 494.6 |

TABLE 16-continued

| Cpd No. | Structure | IUPAC | MW (g/mol) |
|---|---|---|---|
| 957 | 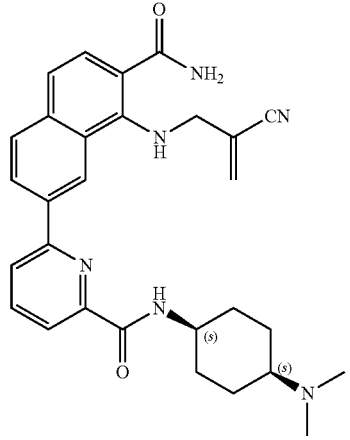 [SMILES: C=C(C#N)CNc1c(C(N)=O)ccc2ccc(-c3cccc(C(=O)N[C@H]4CC[C@@H](N(C)C)CC4)n3)cc12] | 6-{7-carbamoyl-8-[(2-cyano-2-methylideneethyl)amino]naphthalen-2-yl}-N-[(1s,4s)-4-(dimethylamino)cyclohexyl]pyridine-2-carboxamide | 496.6 |
| 958 | 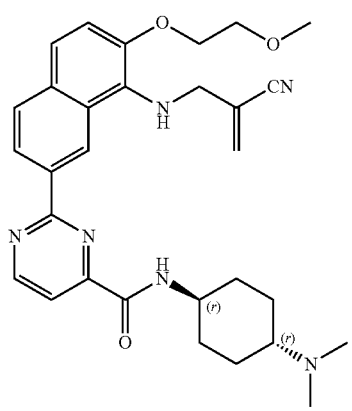 [SMILES: C=C(C#N)CNc1c(OCCOC)ccc2ccc(-c3nccc(C(=O)N[C@H]4CC[C@H](N(C)C)CC4)n3)cc12] | 2-{8-[(2-cyano-2-methylideneethyl)amino]-7-(2-methoxyethoxy)naphthalen-2-yl}-N-[(1r,4r)-4-(dimethylamino)cyclohexyl]pyrimidine-4-carboxamide | 528.7 |
| 959 | 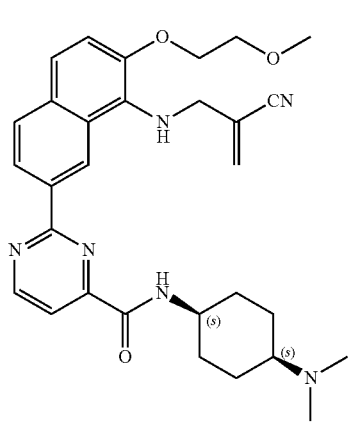 [SMILES: C=C(C#N)CNc1c(OCCOC)ccc2ccc(-c3nccc(C(=O)N[C@H]4CC[C@@H](N(C)C)CC4)n3)cc12] | 2-{8-[(2-cyano-2-methylideneethyl)amino]-7-(2-methoxyethoxy)naphthalen-2-yl}-N-[(1s,4s)-4-(dimethylamino)cyclohexyl]pyrimidine-4-carboxamide | 528.7 |

TABLE 16-continued

| Cpd No. | Structure | IUPAC | MW (g/mol) |
|---|---|---|---|
| 960 | 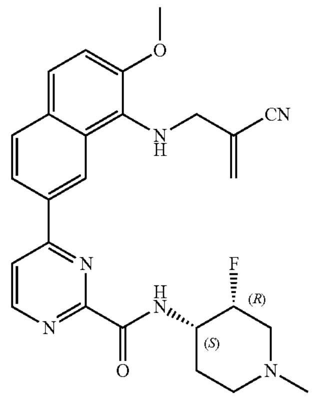 | 4-{8-[(2-cyano-2-methylideneethyl)amino]-7-methoxynaphthalen-2-yl}-N-[(3R,4S)-3-fluoro-1-methylpiperidin-4-yl]pyrimidine-2-carboxamide | 474.5 |
| 961 | 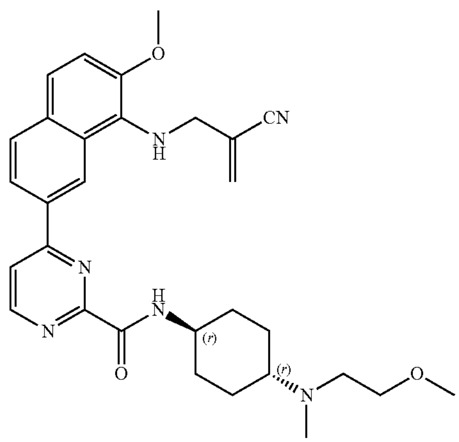 [SMILES: C=C(C#N)CNc1c(OC)ccc2ccc(-c3ccnc(C(=O)N[C@H]4CC[C@H](N(C)CCOC)CC4)n3)cc12] | 4-{8-[(2-cyano-2-methylideneethyl)amino]-7-methoxynaphthalen-2-yl}-N-[(1r,4r)-4-[(2-methoxyethyl)(methyl)amino]cyclohexyl]pyrimidine-2-carboxamide | 528.7 |
| 962 | 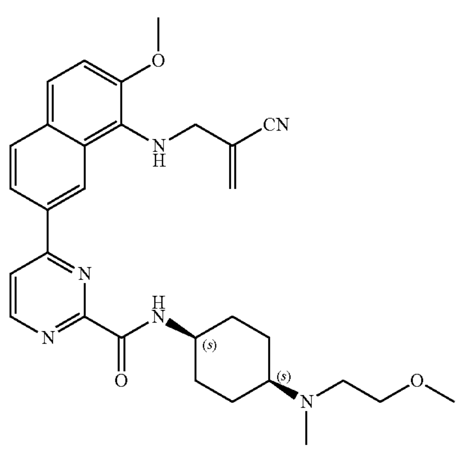 [SMILES: C=C(C#N)CNc1c(OC)ccc2ccc(-c3ccnc(C(=O)N[C@H]4CC[C@@H](N(C)CCOC)CC4)n3)cc12] | 4-{8-[(2-cyano-2-methylideneethyl)amino]-7-methoxynaphthalen-2-yl}-N-[(1s,4s)-4-[(2-methoxyethyl)(methyl)amino]cyclohexyl]pyrimidine-2-carboxamide | 528.7 |

TABLE 16-continued

| Cpd No. | Structure | IUPAC | MW (g/mol) |
|---|---|---|---|
| 963 | 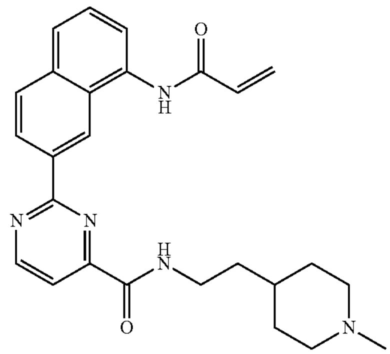 [SMILES: C=CC(=O)Nc1cccc2ccc(-c3nccc(C(=O)NCCC4CCN(C)CC4)n3)cc12] | N-[2-(1-methylpiperidin-4-yl)ethyl]-2-[8-(prop-2-enamido)naphthalen-2-yl]pyrimidine-4-carboxamide | 443.6 |
| 964 | 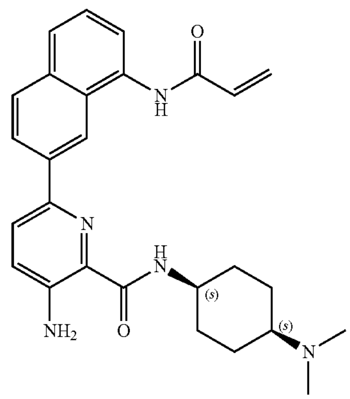 [SMILES: C=CC(=O)Nc1cccc2ccc(-c3ccc(N)c(C(=O)N[C@H]4CC[C@@H](N(C)C)CC4)n3)cc12] | 3-amino-6-[8-(prop-2-enamido)naphthalen-2-yl]-N-[(1s,4s)-4-(dimethylamino)cyclohexyl]pyridine-2-carboxamide | 457.6 |
| 965 | 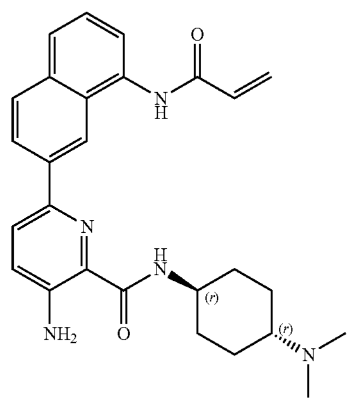 [SMILES: C=CC(=O)Nc1cccc2ccc(-c3ccc(N)c(C(=O)N[C@H]4CC[C@H](N(C)C)CC4)n3)cc12] | 3-amino-6-[8-(prop-2-enamido)naphthalen-2-yl]-N-[(1r,4r)-4-(dimethylamino)cyclohexyl]pyridine-2-carboxamide | 457.6 |
| 966 | 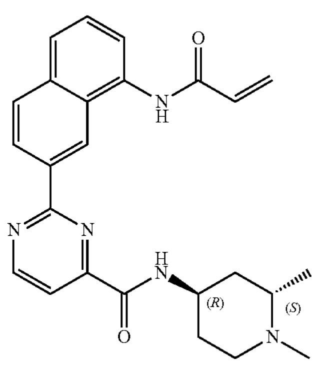 | N-[(2S,4R)-1,2-dimethylpiperidin-4-yl]-2-[8-(prop-2-enamido)naphthalen-2-yl]pyrimidine-4-carboxamide | 429.5 |

TABLE 16-continued

| Cpd No. | Structure | IUPAC | MW (g/mol) |
| --- | --- | --- | --- |
| 967 | 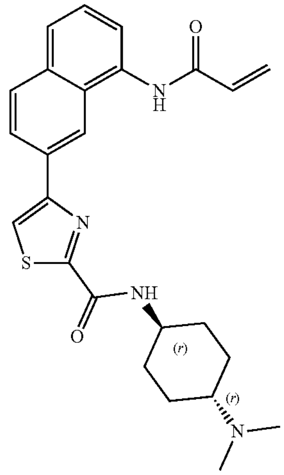 [SMILES: C=CC(=O)Nc1cccc2ccc(-c3csc(C(=O)N[C@H]4CC[C@H](N(C)C)CC4)n3)cc12] | 4-[8-(prop-2-enamido)naphthalen-2-yl]-N-[(1r,4r)-4-(dimethylamino)cyclohexyl]-1,3-thiazole-2-carboxamide | 448.6 |
| 968 | 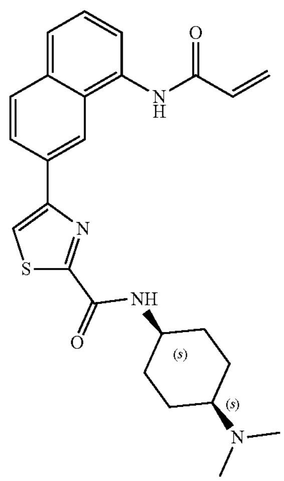 [SMILES: C=CC(=O)Nc1cccc2ccc(-c3csc(C(=O)N[C@H]4CC[C@@H](N(C)C)CC4)n3)cc12] | 4-[8-(prop-2-enamido)naphthalen-2-yl]-N-[(1s,4s)-4-(dimethylamino)cyclohexyl]-1,3-thiazole-2-carboxamide | 448.6 |
| 969 | 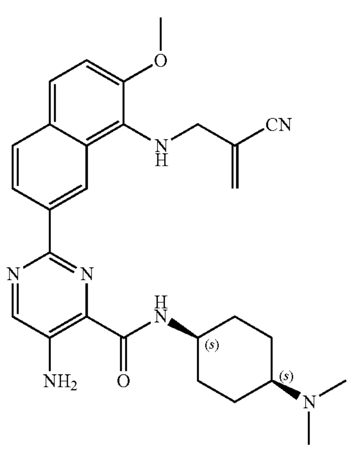 [SMILES: C=C(C#N)CNc1c(OC)ccc2ccc(-c3ncc(N)c(C(=O)N[C@H]4CC[C@@H](N(C)C)CC4)n3)cc12] | 5-amino-2-{8-[(2-cyano-2-methylideneethyl)amino]-7-methoxynaphthalen-2-yl}-N-[(1s,4s)-4-(dimethylamino)cyclohexyl]pyrimidine-4-carboxamide | 499.6 |

TABLE 16-continued

| Cpd No. | Structure | IUPAC | MW (g/mol) |
|---|---|---|---|
| 970 | 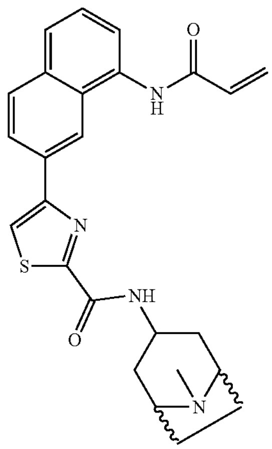 [SMILES: C=CC(=O)Nc1cccc2ccc(-c3csc(C(=O)NC4CC5CCC(C4)N5C)n3)cc12] | N-{8-methyl-8-azabicyclo[3.2.1]octan-3-yl}-4-[8-(prop-2-enamido)naphthalen-2-yl]-1,3-thiazole-2-carboxamide | 446.6 |
| 971 | 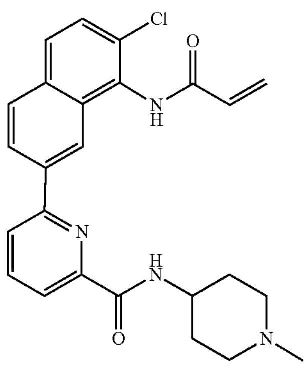 [SMILES: C=CC(=O)Nc1c(Cl)ccc2ccc(-c3cccc(C(=O)NC4CCN(C)CC4)n3)cc12] | 6-[7-chloro-8-(prop-2-enamido)naphthalen-2-yl]-N-(1-methylpiperidin-4-yl)pyridine-2-carboxamide | 449.0 |
| 972 | 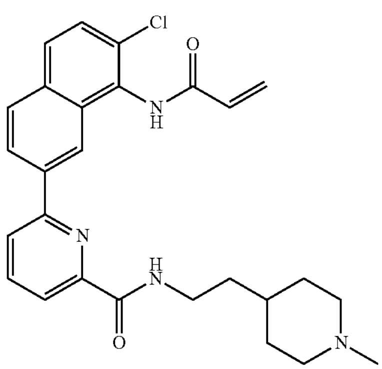 [SMILES: C=CC(=O)Nc1c(Cl)ccc2ccc(-c3cccc(C(=O)NCCC4CCN(C)CC4)n3)cc12] | 6-[7-chloro-8-(prop-2-enamido)naphthalen-2-yl]-N-[2-(1-methylpiperidin-4-yl)ethyl]pyridine-2-carboxamide | 477.0 |
| 973 | 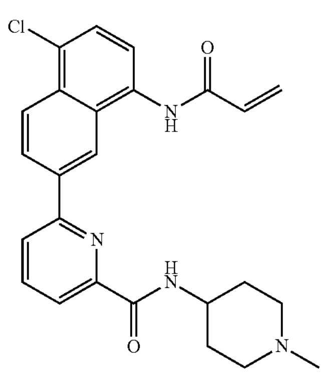 [SMILES: C=CC(=O)Nc1ccc(Cl)c2ccc(-c3cccc(C(=O)NC4CCN(C)CC4)n3)cc12] | 6-[5-chloro-8-(prop-2-enamido)naphthalen-2-yl]-N-(1-methylpiperidin-4-yl)pyridine-2-carboxamide | 449.0 |

TABLE 16-continued

| Cpd No. | Structure | IUPAC | MW (g/mol) |
|---|---|---|---|
| 974 | 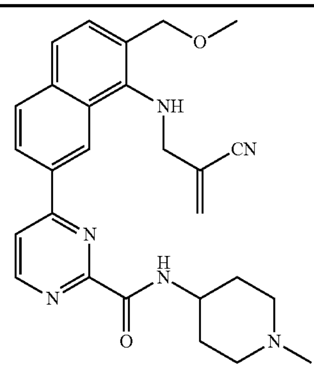 | 4-{8-[(2-cyano-2-methylideneethyl)amino]-7-(methoxymethyl)naphthalen-2-yl}-N-(1-methylpiperidin-4-yl)pyrimidine-2-carboxamide | 470.6 |
| 975 | 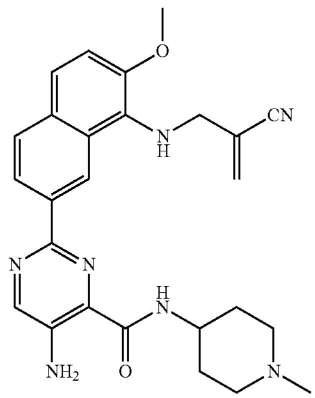 [SMILES: C=C(C#N)CNc1c(OC)ccc2ccc(-c3ncc(N)c(C(=O)NC4CCN(C)CC4)n3)cc12] | 5-amino-2-{8-[(2-cyano-2-methylideneethyl)amino]-7-methoxynaphthalen-2-yl}-N-(1-methylpiperidin-4-yl)pyrimidine-4-carboxamide | 471.6 |
| 976 | 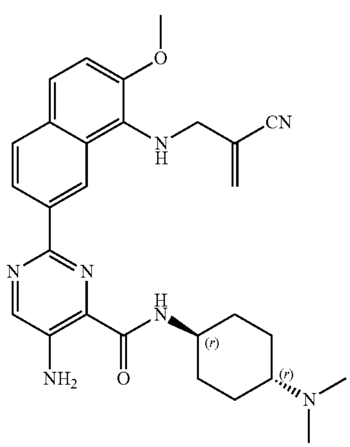 [SMILES: C=C(C#N)CNc1c(OC)ccc2ccc(-c3ncc(N)c(C(=O)N[C@H]4CC[C@H](N(C)C)CC4)n3)cc12] | 5-amino-2-{8-[(2-cyano-2-methylideneethyl)amino]-7-methoxynaphthalen-2-yl}-N-[(1r,4r)-4-(dimethylamino)cyclohexyl]pyrimidine-4-carboxamide | 499.6 |
| 977 | 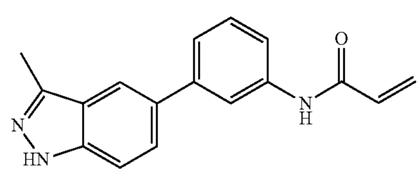 [SMILES: C=CC(=O)Nc1cccc(-c2ccc3[nH]nc(C)c3c2)c1] | N-[3-(3-methyl-1H-indazol-5-yl)phenyl]prop-2-enamide | 277.3 |
| 978 | 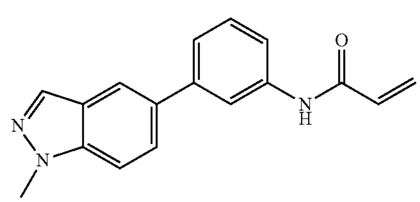 [SMILES: C=CC(=O)Nc1cccc(-c2ccc3c(cnn3C)c2)c1] | N-[3-(1-methyl-1H-indazol-5-yl)phenyl]prop-2-enamide | 277.3 |

TABLE 16-continued

| Cpd No. | Structure | IUPAC | MW (g/mol) |
|---|---|---|---|
| 979 | 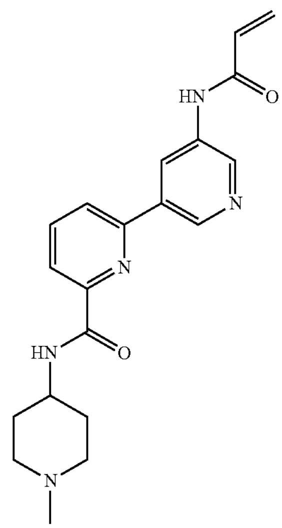 [SMILES: C=CC(=O)Nc1cncc(-c2cccc(C(=O)NC3CCN(C)CC3)n2)c1] | N-(1-methylpiperidin-4-yl)-5'-(prop-2-enamido)-[2,3'-bipyridine]-6-carboxamide | 365.4 |
| 980 | 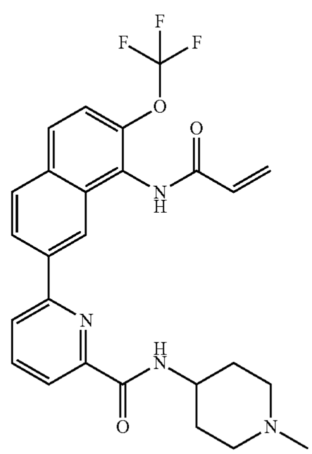 [SMILES: C=CC(=O)Nc1c(OC(F)(F)F)ccc2ccc(-c3cccc(C(=O)NC4CCN(C)CC4)n3)cc12] | N-(1-methylpiperidin-4-yl)-6-[8-(prop-2-enamido)-7-(trifluoromethoxy)naphthalen-2-yl]pyridine-2-carboxamide | 498.5 |
| 981 | 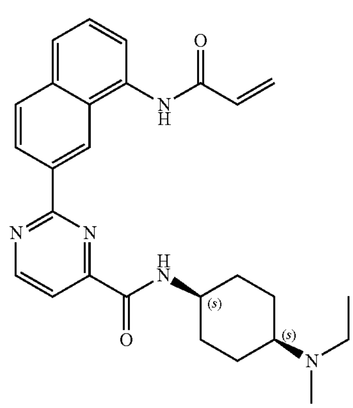 [SMILES: C=CC(=O)Nc1cccc2ccc(-c3nccc(C(=O)N[C@H]4CC[C@@H](N(C)CC)CC4)n3)cc12] | 2-[8-(prop-2-enamido)naphthalen-2-yl]-N-[(1s,4s)-4-[ethyl(methyl)amino]cyclohexyl]pyrimidine-4-carboxamide | 457.6 |

TABLE 16-continued

| Cpd No. | Structure | IUPAC | MW (g/mol) |
|---|---|---|---|
| 982 | 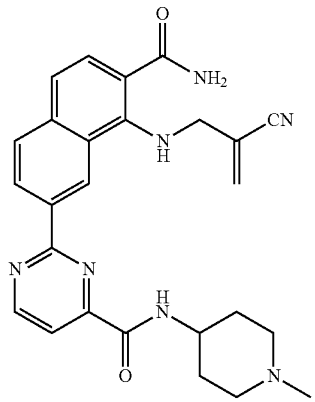 [SMILES: C=C(C#N)CNc1c(C(N)=O)ccc2ccc(-c3nccc(C(=O)NC4CCN(C)CC4)n3)cc12] | 2-{7-carbamoyl-8-[(2-cyano-2-methylideneethyl)amino]naphthalen-2-yl}-N-(1-methylpiperidin-4-yl)pyrimidine-4-carboxamide | 469.5 |
| 983 | 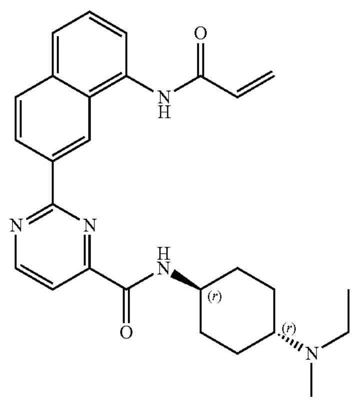 [SMILES: C=CC(=O)Nc1cccc2ccc(-c3nccc(C(=O)N[C@H]4CC[C@H](N(C)CC)CC4)n3)cc12] | 2-[8-(prop-2-enamido)naphthalen-2-yl]-N-[(1r,4r)-4-[ethyl(methyl)amino]cyclohexyl]pyrimidine-4-carboxamide | 457.6 |
| 984 | 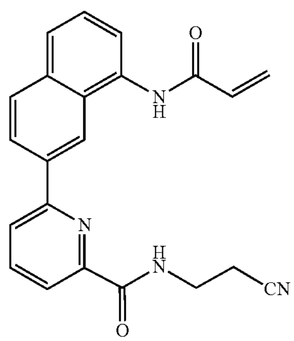 [SMILES: C=CC(=O)Nc1cccc2ccc(-c3cccc(C(=O)NCCC#N)n3)cc12] | N-(2-cyanoethyl)-6-[8-(prop-2-enamido)naphthalen-2-yl]pyridine-2-carboxamide | 370.4 |
| 985 | 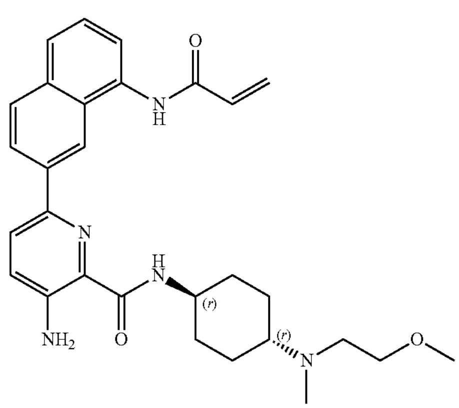 [SMILES: C=CC(=O)Nc1cccc2ccc(-c3ccc(N)c(C(=O)N[C@H]4CC[C@H](N(C)CCOC)CC4)n3)cc12] | 3-amino-6-[8-(prop-2-enamido)naphthalen-2-yl]-N-[(1r,4r)-4-[(2-methoxyethyl)(methyl)amino]cyclohexyl]pyridine-2-carboxamide | 501.6 |

TABLE 16-continued

| Cpd No. | Structure | IUPAC | MW (g/mol) |
|---|---|---|---|
| 986 | 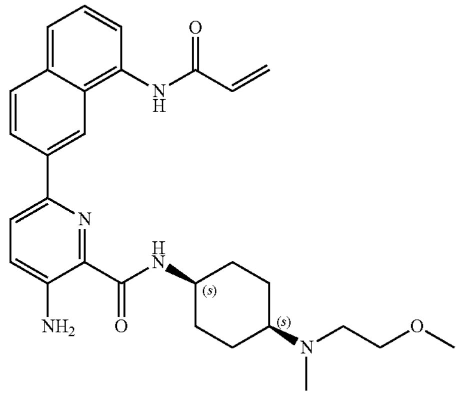 [SMILES: C=CC(=O)Nc1cccc2ccc(-c3ccc(N)c(C(=O)N[C@H]4CC[C@@H](N(C)CCOC)CC4)n3)cc12] | 3-amino-6-[8-(prop-2-enamido)naphthalen-2-yl]-N-[(1s,4s)-4-[(2-methoxyethyl)(methyl)amino]cyclohexyl]pyridine-2-carboxamide | 501.6 |
| 987 | 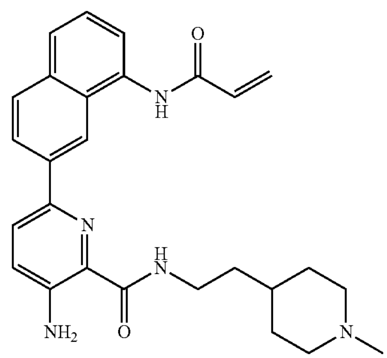 [SMILES: C=CC(=O)Nc1cccc2ccc(-c3ccc(N)c(C(=O)NCCC4CCN(C)CC4)n3)cc12] | 3-amino-N-[2-(1-methylpiperidin-4-yl)ethyl]-6-[8-(prop-2-enamido)naphthalen-2-yl]pyridine-2-carboxamide | 457.6 |
| 988 | 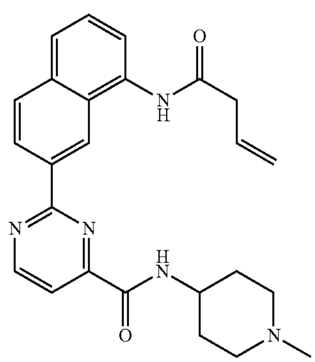 [SMILES: C=CCC(=O)Nc1cccc2ccc(-c3nccc(C(=O)NC4CCN(C)CC4)n3)cc12] | 2-[8-(but-3-enamido)naphthalen-2-yl]-N-(1-methylpiperidin-4-yl)pyrimidine-4-carboxamide | 429.5 |
| 989 | 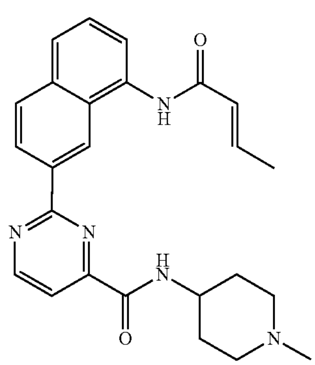 [SMILES: C/C=C/C(=O)Nc1cccc2ccc(-c3nccc(C(=O)NC4CCN(C)CC4)n3)cc12] | 2-{8-[(2E)-but-2-enamido]naphthalen-2-yl}-N-(1-methylpiperidin-4-yl)pyrimidine-4-carboxamide | 429.5 |

TABLE 16-continued

| Cpd No. | Structure | IUPAC | MW (g/mol) |
|---|---|---|---|
| 990 | 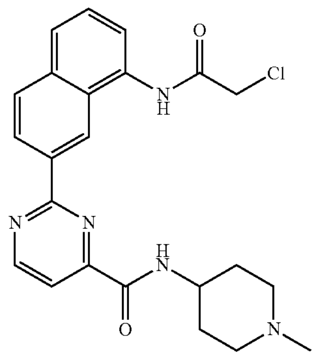 [SMILES: CN1CCC(NC(=O)c2ccnc(-c3ccc4cccc(NC(=O)CCl)c4c3)n2)CC1] | 2-[8-(2-chloroacetamido)naphthalen-2-yl]-N-(1-methylpiperidin-4-yl)pyrimidine-4-carboxamide | 437.9 |
| 991 | 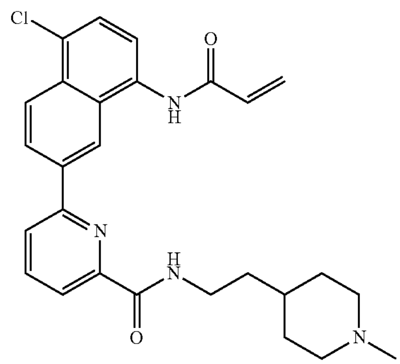 [SMILES: C=CC(=O)Nc1ccc(Cl)c2ccc(-c3cccc(C(=O)NCCC4CCN(C)CC4)n3)cc12] | 6-[5-chloro-8-(prop-2-enamido)naphthalen-2-yl]-N-[2-(1-methylpiperidin-4-yl)ethyl]pyridine-2-carboxamide | 477.0 |
| 992 | 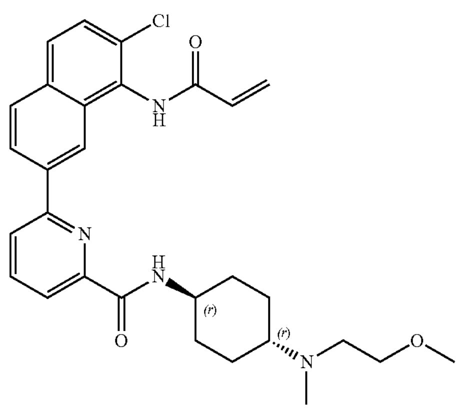 [SMILES: C=CC(=O)Nc1c(Cl)ccc2ccc(-c3cccc(C(=O)N[C@H]4CC[C@H](N(C)CCOC)CC4)n3)cc12] | 6-[7-chloro-8-(prop-2-enamido)naphthalen-2-yl]-N-[(1r,4r)-4-[(2-methoxyethyl)(methyl)amino]cyclohexyl]pyridine-2-carboxamide | 521.1 |
| 993 | 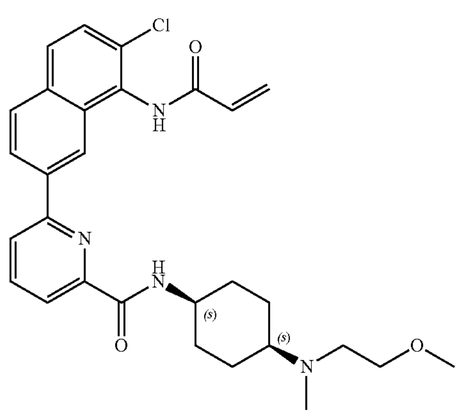 [SMILES: C=CC(=O)Nc1c(Cl)ccc2ccc(-c3cccc(C(=O)N[C@H]4CC[C@@H](N(C)CCOC)CC4)n3)cc12] | 6-[7-chloro-8-(prop-2-enamido)naphthalen-2-yl]-N-[(1s,4s)-4-[(2-methoxyethyl)(methyl)amino]cyclohexyl]pyridine-2-carboxamide | 521.1 |

TABLE 16-continued

| Cpd No. | Structure | IUPAC | MW (g/mol) |
|---|---|---|---|
| 994 | 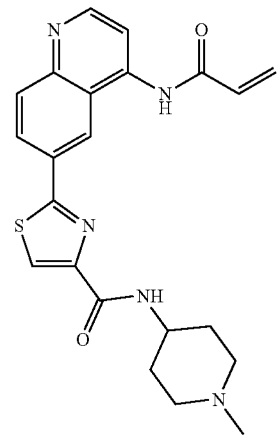 [SMILES: C=CC(=O)Nc1ccnc2ccc(-c3nc(C(=O)NC4CCN(C)CC4)cs3)cc12] | N-(1-methylpiperidin-4-yl)-2-[4-(prop-2-enamido)quinolin-6-yl]-1,3-thiazole-4-carboxamide | 421.5 |
| 995 | 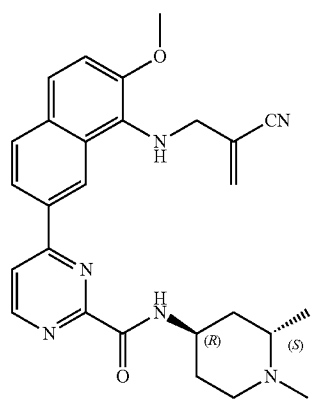 | 4-{8-[(2-cyano-2-methylideneethyl)amino]-7-methoxynaphthalen-2-yl}-N-[(2S,4R)-1,2-dimethylpiperidin-4-yl]pyrimidine-2-carboxamide | 470.6 |
| 996 | 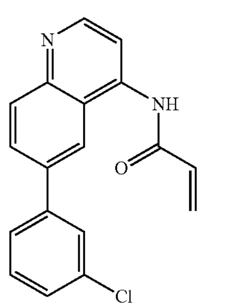 [SMILES: C=CC(=O)Nc1ccnc2ccc(-c3cccc(Cl)c3)cc12] | N-[6-(3-chlorophenyl)quinolin-4-yl]prop-2-enamide | 308.8 |

TABLE 16-continued

| Cpd No. | Structure | IUPAC | MW (g/mol) |
|---|---|---|---|
| 997 | 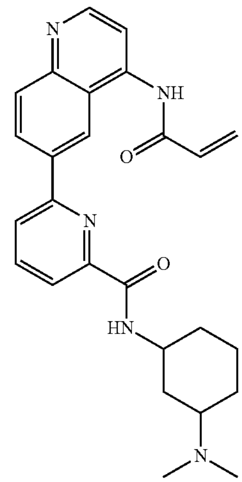 [SMILES: C=CC(=O)Nc1ccnc2ccc(-c3cccc(C(=O)NC4CCCC(N(C)C)C4)n3)cc12] | N-[3-(dimethylamino)cyclohexyl]-6-[4-(prop-2-enamido)quinolin-6-yl]pyridine-2-carboxamide | 443.6 |
| 998 | 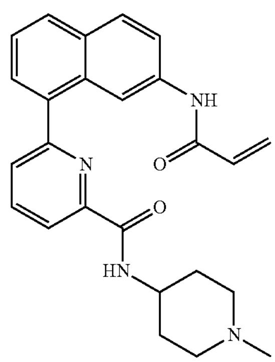 [SMILES: C=CC(=O)Nc1ccc2cccc(-c3cccc(C(=O)NC4CCN(C)CC4)n3)c2c1] | N-(1-methylpiperidin-4-yl)-6-[7-(prop-2-enamido)naphthalen-1-yl]pyridine-2-carboxamide | 414.5 |
| 999 | 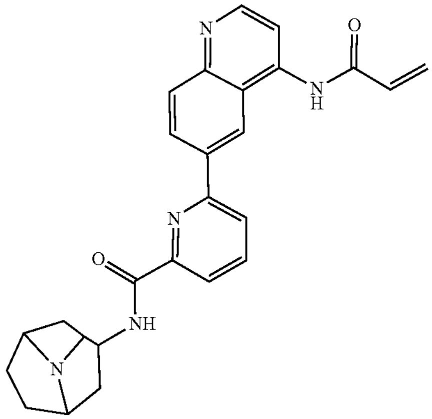 [SMILES: C=CC(=O)Nc1ccnc2ccc(-c3cccc(C(=O)NC4CC5CCC6CC4N56)n3)cc12] | N-{8-methyl-8-azabicyclo[3.2.1]octan-3-yl}-6-[4-(prop-2-enamido)quinolin-6-yl]pyridine-2-carboxamide | 441.5 |

TABLE 16-continued

| Cpd No. | Structure | IUPAC | MW (g/mol) |
|---|---|---|---|
| 1000 | 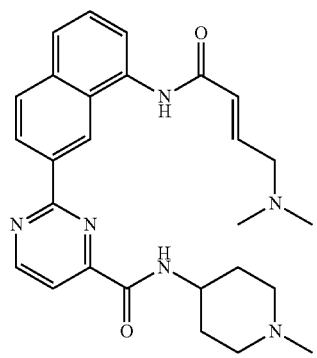 [SMILES: CN(C)C/C=C/C(=O)Nc1cccc2ccc(-c3nccc(C(=O)NC4CCN(C)CC4)n3)cc12] | 2-{8-[(2E)-4-(dimethylamino)but-2-enamido]naphthalen-2-yl}-N-(1-methylpiperidin-4-yl)pyrimidine-4-carboxamide | 472.6 |
| 1001 | 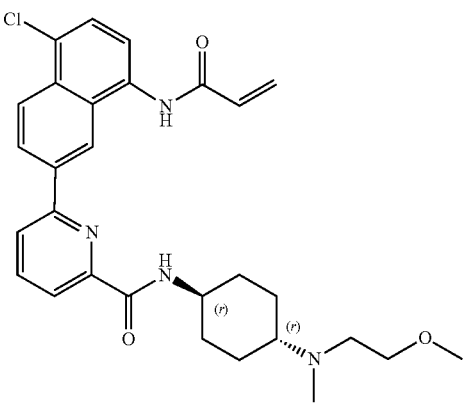 [SMILES: C=CC(=O)Nc1ccc(Cl)c2ccc(-c3cccc(C(=O)N[C@H]4CC[C@H](N(C)CCOC)CC4)n3)cc12] | 6-[5-chloro-8-(prop-2-enamido)naphthalen-2-yl]-N-[(1r,4r)-4-[(2-methoxyethyl)(methyl)amino]cyclohexyl]pyridine-2-carboxamide | 521.1 |
| 1002 | 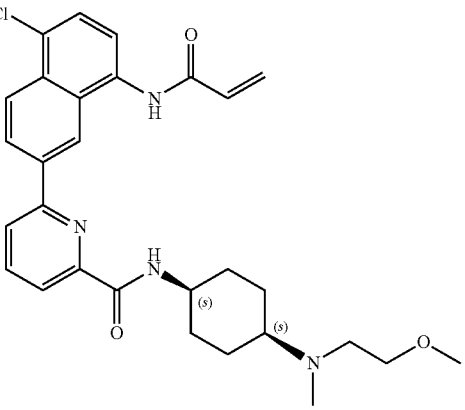 | 6-[5-chloro-8-(prop-2-enamido)naphthalen-2-yl]-N-[(1s,4s)-4-[(2-methoxyethyl)(methyl)amino]cyclohexyl]pyridine-2-carboxamide | 521.1 |
| 1003 | 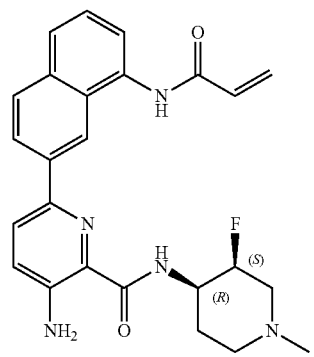 | 3-amino-N-[(3S,4R)-3-fluoro-1-methylpiperidin-4-yl]-6-[8-(prop-2-enamido)naphthalen-2-yl]pyridine-2-carboxamide | 447.5 |

TABLE 16-continued

| Cpd No. | Structure | IUPAC | MW (g/mol) |
|---|---|---|---|
| 1004 | 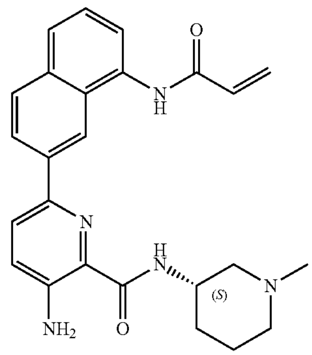 | 3-amino-N-[(3S)-1-methylpiperidin-3-yl]-6-[8-(prop-2-enamido)naphthalen-2-yl]pyridine-2-carboxamide | 429.5 |
| 1005 | 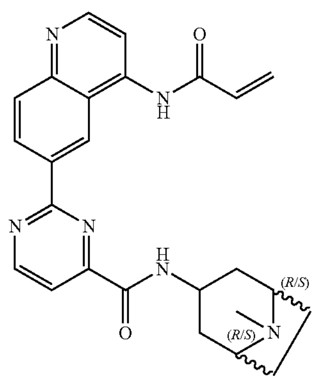 [SMILES: C=CC(=O)Nc1ccnc2ccc(-c3nccc(C(=O)NC4CC5CCC(C4)N5C)n3)cc12] | N-{8-methyl-8-azabicyclo[3.2.1]octan-3-yl}-2-[4-(prop-2-enamido)quinolin-6-yl]pyrimidine-4-carboxamide | 442.5 |
| 1006 | 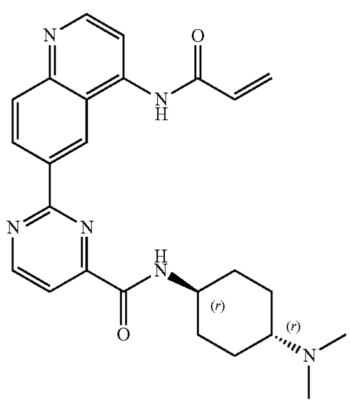 [SMILES: C=CC(=O)Nc1ccnc2ccc(-c3nccc(C(=O)N[C@H]4CC[C@H](N(C)C)CC4)n3)cc12] | 2-[4-(prop-2-enamido)quinolin-6-yl]-N-[(1r,4r)-4-(dimethylamino)cyclohexyl]pyrimidine-4-carboxamide | 444.5 |
| 1007 | 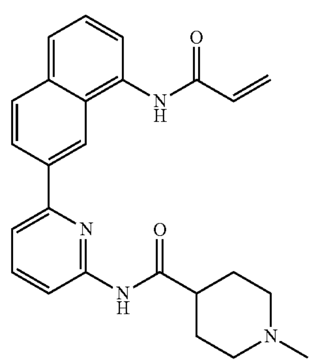 [SMILES: C=CC(=O)Nc1cccc2ccc(-c3cccc(NC(=O)C4CCN(C)CC4)n3)cc12] | 1-methyl-N-{6-[8-(prop-2-enamido)naphthalen-2-yl]pyridin-2-yl}piperidine-4-carboxamide | 414.5 |

TABLE 16-continued

| Cpd No. | Structure | IUPAC | MW (g/mol) |
|---|---|---|---|
| 1008 | 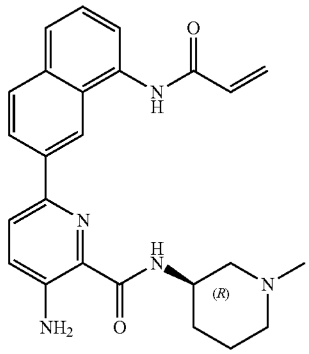 | 3-amino-N-[(3R)-1-methylpiperidin-3-yl]-6-[8-(prop-2-enamido)naphthalen-2-yl]pyridine-2-carboxamide | 429.5 |
| 1009 | 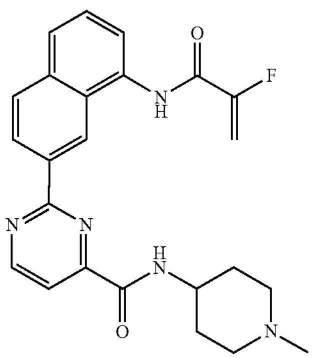 [SMILES: C=C(F)C(=O)Nc1cccc2ccc(-c3nccc(C(=O)NC4CCN(C)CC4)n3)cc12] | 2-[8-(2-fluoroprop-2-enamido)naphthalen-2-yl]-N-(1-methylpiperidin-4-yl)pyrimidine-4-carboxamide | 433.5 |
| 1010 | 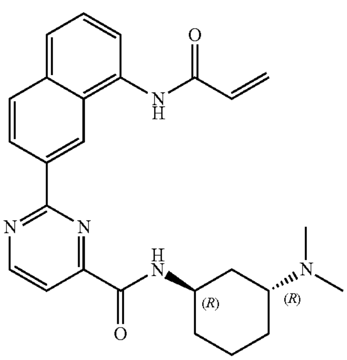 | N-[(1R,3R)-3-(dimethylamino)cyclohexyl]-2-[8-(prop-2-enamido)naphthalen-2-yl]pyrimidine-4-carboxamide | 443.6 |
| 1011 | 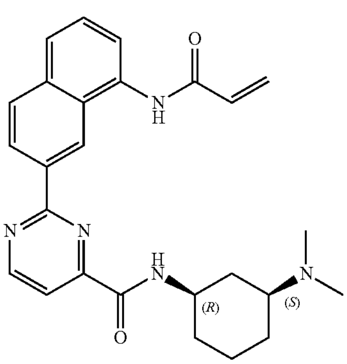 | N-[(1R,3S)-3-(dimethylamino)cyclohexyl]-2-[8-(prop-2-enamido)naphthalen-2-yl]pyrimidine-4-carboxamide | 443.6 |

TABLE 16-continued
| Cpd No. | Structure | IUPAC | MW (g/mol) |
|---|---|---|---|
| 1012 | 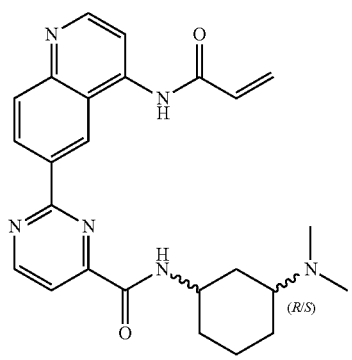 [SMILES: C=CC(=O)Nc1ccnc2ccc(-c3nccc(C(=O)NC4CCCC(N(C)C)C4)n3)cc12] | N-[3-(dimethylamino)cyclohexyl]-2-[4-(prop-2-enamido)quinolin-6-yl]pyrimidine-4-carboxamide | 444.5 |
| 1013 | 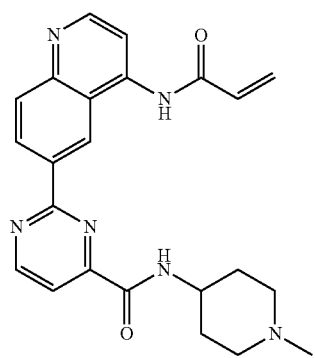 [SMILES: C=CC(=O)Nc1ccnc2ccc(-c3nccc(C(=O)NC4CCN(C)CC4)n3)cc12] | N-(1-methylpiperidin-4-yl)-2-[4-(prop-2-enamido)quinolin-6-yl]pyrimidine-4-carboxamide | 416.5 |
| 1014 | 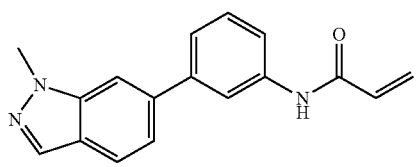 [SMILES: C=CC(=O)Nc1cccc(-c2ccc3cnn(C)c3c2)c1] | N-[3-(1-methyl-1H-indazol-6-yl)phenyl]prop-2-enamide | 277.3 |
| 1015 | 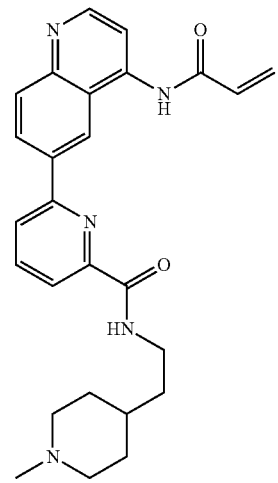 [SMILES: C=CC(=O)Nc1ccnc2ccc(-c3cccc(C(=O)NCCC4CCN(C)CC4)n3)cc12] | N-[2-(1-methylpiperidin-4-yl)ethyl]-6-[4-(prop-2-enamido)quinolin-6-yl]pyridine-2-carboxamide | 443.6 |

TABLE 16-continued

| Cpd No. | Structure | IUPAC | MW (g/mol) |
|---|---|---|---|
| 1016 | 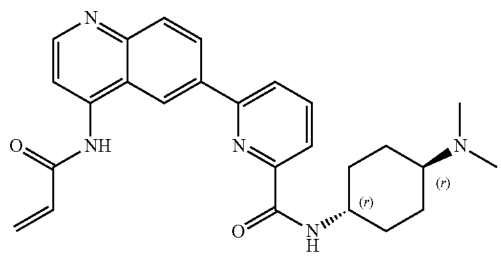 [SMILES: C=CC(=O)Nc1ccnc2ccc(-c3cccc(C(=O)N[C@H]4CC[C@H](N(C)C)CC4)n3)cc12] | 6-[4-(prop-2-enamido)quinolin-6-yl]-N-[(1r,4r)-4-(dimethylamino)cyclohexyl]pyridine-2-carboxamide | 443.6 |
| 1017 | 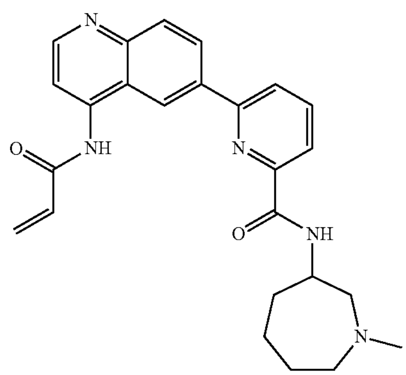 [SMILES: C=CC(=O)Nc1ccnc2ccc(-c3cccc(C(=O)NC4CCCCN(C)C4)n3)cc12] | N-(1-methylazepan-3-yl)-6-[4-(prop-2-enamido)quinolin-6-yl]pyridine-2-carboxamide | 429.5 |
| 1018 | 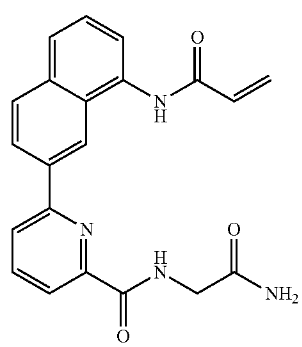 [SMILES: C=CC(=O)Nc1cccc2ccc(-c3cccc(C(=O)NCC(N)=O)n3)cc12] | N-(7-{6-[(carbamoylmethyl)carbamoyl]pyridin-2-yl}naphthalen-1-yl)prop-2-enamide | 374.4 |
| 1019 | 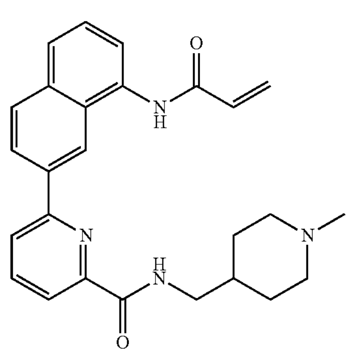 [SMILES: C=CC(=O)Nc1cccc2ccc(-c3cccc(C(=O)NCC4CCN(C)CC4)n3)cc12] | N-[(1-methylpiperidin-4-yl)methyl]-6-[8-(prop-2-enamido)naphthalen-2-yl]pyridine-2-carboxamide | 428.5 |

TABLE 16-continued

| Cpd No. | Structure | IUPAC | MW (g/mol) |
|---|---|---|---|
| 1020 | 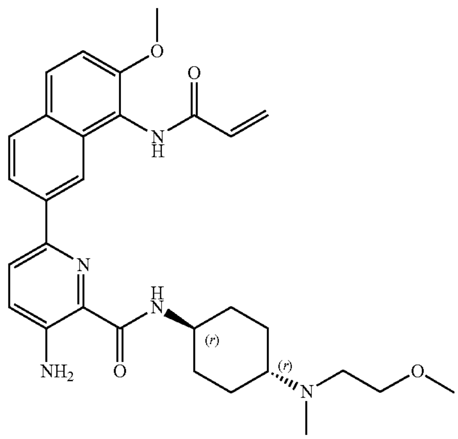 | 3-amino-6-[7-methoxy-8-(prop-2-enamido)naphthalen-2-yl]-N-[(1r,4r)-4-[(2-methoxyethyl)(methyl)amino]cyclohexyl]pyridine-2-carboxamide | 531.7 |
| 1021 | 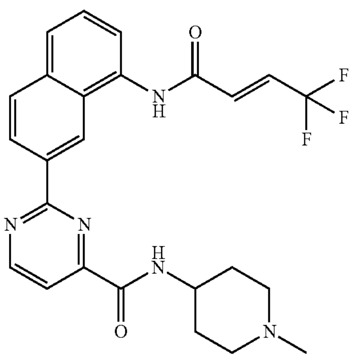 [SMILES: CN1CCC(NC(=O)c2ccnc(-c3ccc4cccc(NC(=O)/C=C/C(F)(F)F)c4c3)n2)CC1] | N-(1-methylpiperidin-4-yl)-2-{8-[(2E)-4,4,4-trifluorobut-2-enamido]naphthalen-2-yl}pyrimidine-4-carboxamide | 483.5 |
| 1022 | 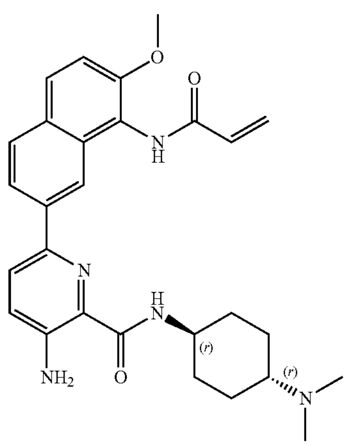 [SMILES: C=CC(=O)Nc1c(OC)ccc2ccc(-c3ccc(N)c(C(=O)N[C@H]4CC[C@H](N(C)C)CC4)n3)cc12] | 3-amino-6-[7-methoxy-8-(prop-2-enamido)naphthalen-2-yl]-N-[(1r,4r)-4-(dimethylamino)cyclohexyl]pyridine-2-carboxamide | 487.6 |
| 1023 | 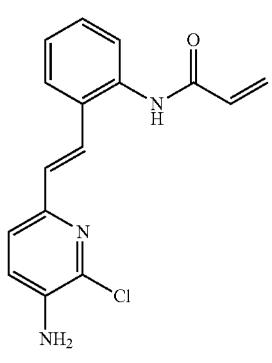 [SMILES: C=CC(=O)Nc1ccccc1/C=C/c1ccc(N)c(Cl)n1] | N-{2-[(1E)-2-(5-amino-6-chloropyridin-2-yl)ethenyl]phenyl}prop-2-enamide | 299.8 |

TABLE 16-continued

| Cpd No. | Structure | IUPAC | MW (g/mol) |
|---|---|---|---|
| 1024 | 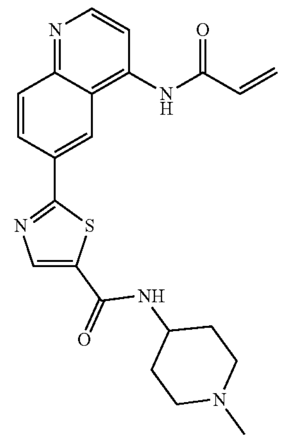 [SMILES: C=CC(=O)Nc1ccnc2ccc(-c3ncc(C(=O)NC4CCN(C)CC4)s3)cc12] | N-(1-methylpiperidin-4-yl)-2-[4-(prop-2-enamido)quinolin-6-yl]-1,3-thiazole-5-carboxamide | 421.5 |
| 1025 | 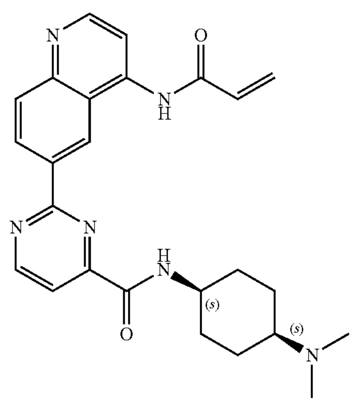 [SMILES: C=CC(=O)Nc1ccnc2ccc(-c3nccc(C(=O)N[C@H]4CC[C@@H](N(C)C)CC4)n3)cc12] | 2-[4-(prop-2-enamido)quinolin-6-yl]-N-[(1s,4s)-4-(dimethylamino)cyclohexyl]pyrimidine-4-carboxamide | 444.5 |
| 1026 | 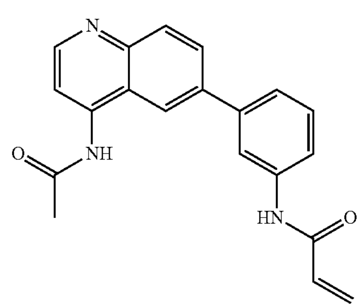 [SMILES: C=CC(=O)Nc1cccc(-c2ccc3nccc(NC(C)=O)c3c2)c1] | N-[3-(4-acetamidoquinolin-6-yl)phenyl]prop-2-enamide | 331.4 |
| 1027 | 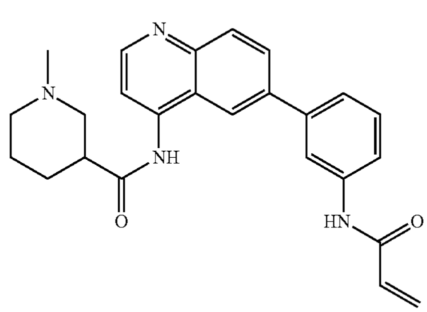 [SMILES: C=CC(=O)Nc1cccc(-c2ccc3nccc(NC(=O)C4CCCN(C)C4)c3c2)c1] | 1-methyl-N-{6-[3-(prop-2-enamido)phenyl]quinolin-4-yl}piperidine-3-carboxamide | 414.5 |

TABLE 16-continued

| Cpd No. | Structure | IUPAC | MW (g/mol) |
|---|---|---|---|
| 1028 | 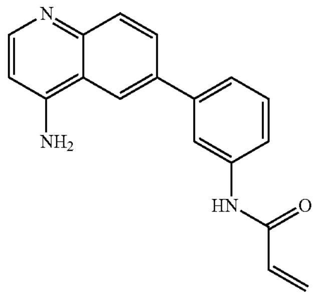 [SMILES: C=CC(=O)Nc1cccc(-c2ccc3nccc(N)c3c2)c1] | N-[3-(4-aminoquinolin-6-yl)phenyl]prop-2-enamide | 289.3 |
| 1029 | 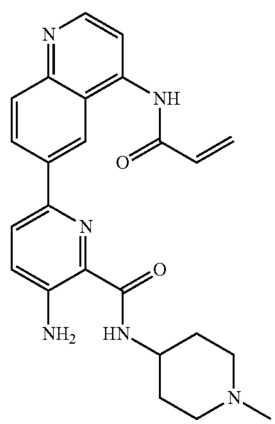 [SMILES: C=CC(=O)Nc1ccnc2ccc(-c3ccc(N)c(C(=O)NC4CCN(C)CC4)n3)cc12] | 3-amino-N-(1-methylpiperidin-4-yl)-6-[4-(prop-2-enamido)quinolin-6-yl]pyridine-2-carboxamide | 430.5 |
| 1030 | 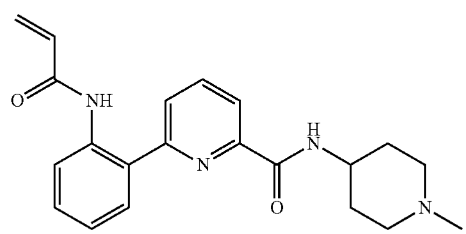 [SMILES: C=CC(=O)Nc1ccccc1-c1cccc(C(=O)NC2CCN(C)CC2)n1] | N-(1-methylpiperidin-4-yl)-6-[2-(prop-2-enamido)phenyl]pyridine-2-carboxamide | 364.4 |
| 1031 | 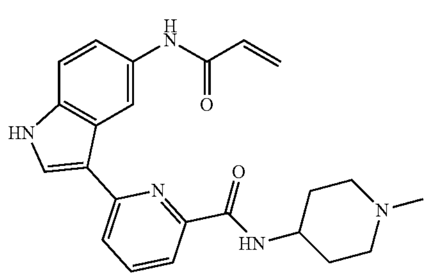 [SMILES: C=CC(=O)Nc1ccc2[nH]cc(-c3cccc(C(=O)NC4CCN(C)CC4)n3)c2c1] | N-(1-methylpiperidin-4-yl)-6-[5-(prop-2-enamido)-1H-indol-3-yl]pyridine-2-carboxamide | 403.5 |
| 1032 | 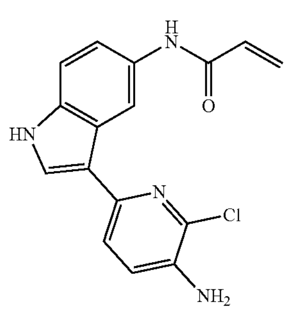 [SMILES: C=CC(=O)Nc1ccc2[nH]cc(-c3ccc(N)c(Cl)n3)c2c1] | N-[3-(5-amino-6-chloropyridin-2-yl)-1H-indol-5-yl]prop-2-enamide | 312.8 |

TABLE 16-continued

| Cpd No. | Structure | IUPAC | MW (g/mol) |
|---|---|---|---|
| 1033 | 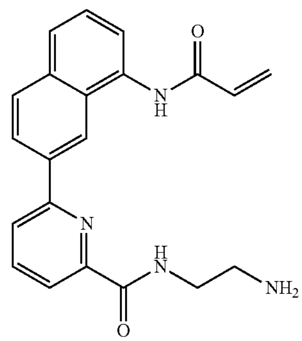 [SMILES: C=CC(=O)Nc1cccc2ccc(-c3cccc(C(=O)NCCN)n3)cc12] | N-(2-aminoethyl)-6-[8-(prop-2-enamido)naphthalen-2-yl]pyridine-2-carboxamide | 360.4 |
| 1034 | 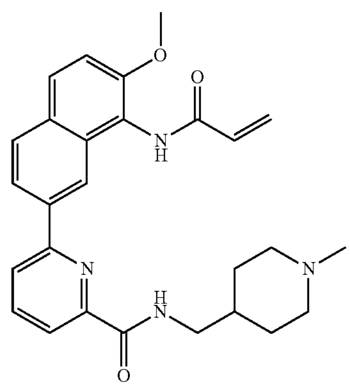 [SMILES: C=CC(=O)Nc1c(OC)ccc2ccc(-c3cccc(C(=O)NCC4CCN(C)CC4)n3)cc12] | 6-[7-methoxy-8-(prop-2-enamido)naphthalen-2-yl]-N-[(1-methylpiperidin-4-yl)methyl]pyridine-2-carboxamide | 458.6 |
| 1035 | 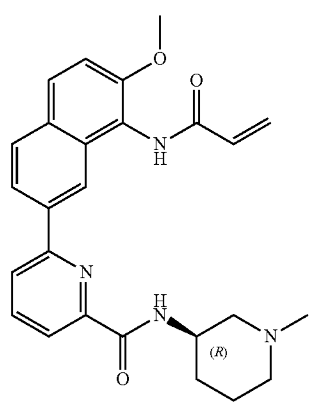 | 6-[7-methoxy-8-(prop-2-enamido)naphthalen-2-yl]-N-[(3R)-1-methylpiperidin-3-yl]pyridine-2-carboxamide | 444.5 |
| 1036 | 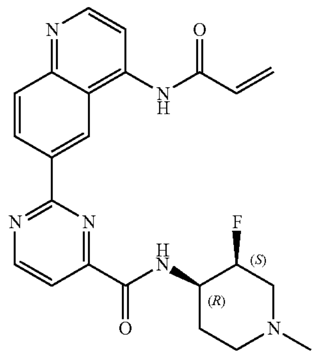 | N-[(3S,4R)-3-fluoro-1-methylpiperidin-4-yl]-2-[4-(prop-2-enamido)quinolin-6-yl]pyrimidine-4-carboxamide | 434.5 |

TABLE 16-continued

| Cpd No. | Structure | IUPAC | MW (g/mol) |
| --- | --- | --- | --- |
| 1037 | 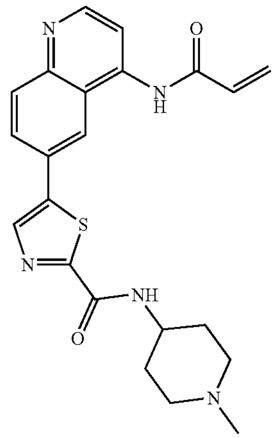 [SMILES: C=CC(=O)Nc1ccnc2ccc(-c3cnc(C(=O)NC4CCN(C)CC4)s3)cc12] | N-(1-methylpiperidin-4-yl)-5-[4-(prop-2-enamido)quinolin-6-yl]-1,3-thiazole-2-carboxamide | 421.5 |
| 1038 | 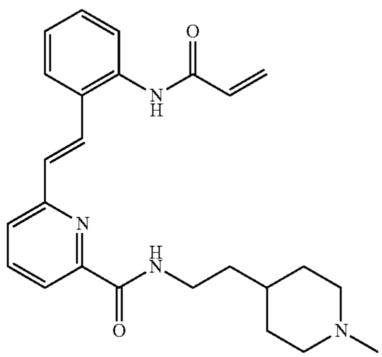 [SMILES: C=CC(=O)Nc1ccccc1/C=C/c1cccc(C(=O)NCCC2CCN(C)CC2)n1] | N-[2-(1-methylpiperidin-4-yl)ethyl]-6-[(1E)-2-[2-(prop-2-enamido)phenyl]ethenyl]pyridine-2-carboxamide | 418.5 |
| 1039 | 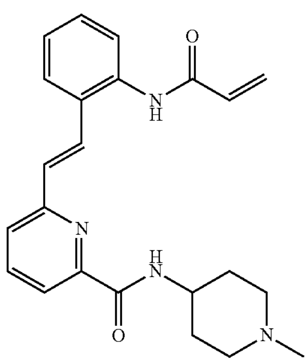 [SMILES: C=CC(=O)Nc1ccccc1/C=C/c1cccc(C(=O)NC2CCN(C)CC2)n1] | N-(1-methylpiperidin-4-yl)-6-[(1E)-2-[2-(prop-2-enamido)phenyl]ethenyl]pyridine-2-carboxamide | 390.5 |
| 1040 | 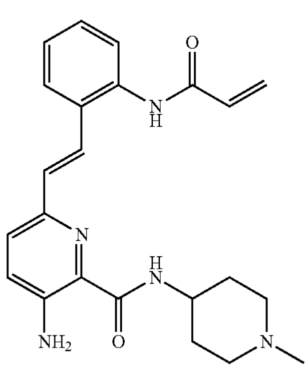 [SMILES: C=CC(=O)Nc1ccccc1/C=C/c1ccc(N)c(C(=O)NC2CCN(C)CC2)n1] | 3-amino-N-(1-methylpiperidin-4-yl)-6-[(1E)-2-[2-(prop-2-enamido)phenyl]ethenyl]pyridine-2-carboxamide | 405.5 |

TABLE 16-continued

| Cpd No. | Structure | IUPAC | MW (g/mol) |
|---|---|---|---|
| 1041 | 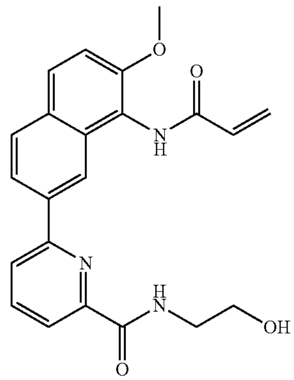 [SMILES: C=CC(=O)Nc1c(OC)ccc2ccc(-c3cccc(C(=O)NCCO)n3)cc12] | N-(2-hydroxyethyl)-6-[7-methoxy-8-(prop-2-enamido)naphthalen-2-yl]pyridine-2-carboxamide | 391.4 |
| 1042 | 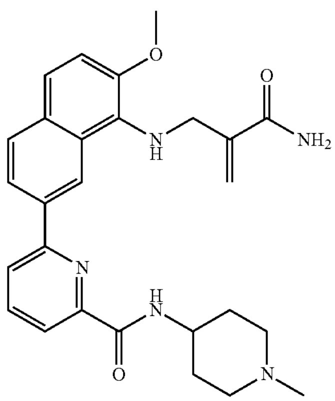 [SMILES: C=C(CNc1c(OC)ccc2ccc(-c3cccc(C(=O)NC4CCN(C)CC4)n3)cc12)C(N)=O] | 6-{8-[(2-carbamoyl-2-methylideneethyl)amino]-7-methoxynaphthalen-2-yl}-N-(1-methylpiperidin-4-yl)pyridine-2-carboxamide | 473.6 |
| 1043 | 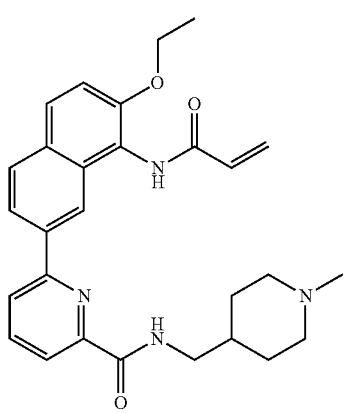 [SMILES: C=CC(=O)Nc1c(OCC)ccc2ccc(-c3cccc(C(=O)NCC4CCN(C)CC4)n3)cc12] | 6-[7-ethoxy-8-(prop-2-enamido)naphthalen-2-yl]-N-[(1-methylpiperidin-4-yl)methyl]pyridine-2-carboxamide | 472.6 |

TABLE 16-continued

| Cpd No. | Structure | IUPAC | MW (g/mol) |
|---|---|---|---|
| 1044 | 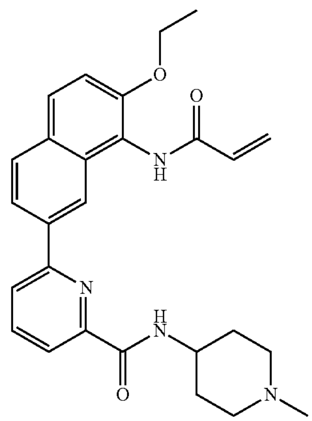 [SMILES: C=CC(=O)Nc1c(OCC)ccc2ccc(-c3cccc(C(=O)NC4CCN(C)CC4)n3)cc12] | 6-[7-ethoxy-8-(prop-2-enamido)naphthalen-2-yl]-N-(1-methylpiperidin-4-yl)pyridine-2-carboxamide | 458.6 |
| 1045 | 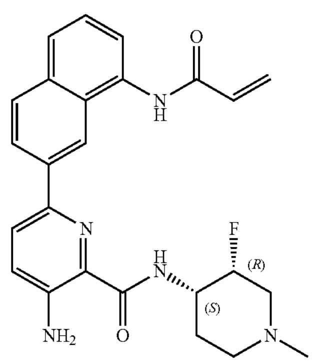 | 3-amino-N-[(3R,4S)-3-fluoro-1-methylpiperidin-4-yl]-6-[8-(prop-2-enamido)naphthalen-2-yl]pyridine-2-carboxamide | 447.5 |
| 1046 | 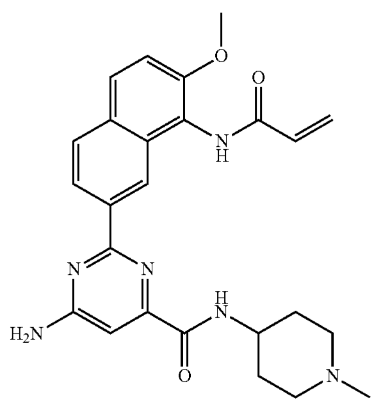 [SMILES: C=CC(=O)Nc1c(OC)ccc2ccc(-c3nc(N)cc(C(=O)NC4CCN(C)CC4)n3)cc12] | 6-amino-2-[7-methoxy-8-(prop-2-enamido)naphthalen-2-yl]-N-(1-methylpiperidin-4-yl)pyrimidine-4-carboxamide | 460.5 |
| 1047 | 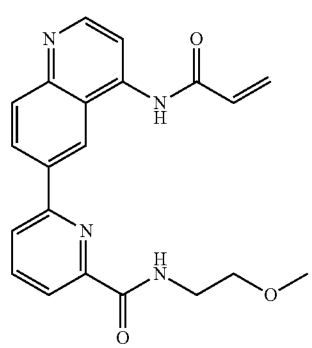 [SMILES: C=CC(=O)Nc1ccnc2ccc(-c3cccc(C(=O)NCCOC)n3)cc12] | N-(2-methoxyethyl)-6-[4-(prop-2-enamido)quinolin-6-yl]pyridine-2-carboxamide | 376.4 |

TABLE 16-continued

| Cpd No. | Structure | IUPAC | MW (g/mol) |
|---|---|---|---|
| 1048 | 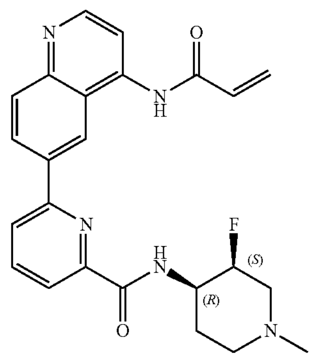 | N-[(3S,4R)-3-fluoro-1-methylpiperidin-4-yl]-6-[4-(prop-2-enamido)quinolin-6-yl]pyridine-2-carboxamide | 433.5 |
| 1049 | 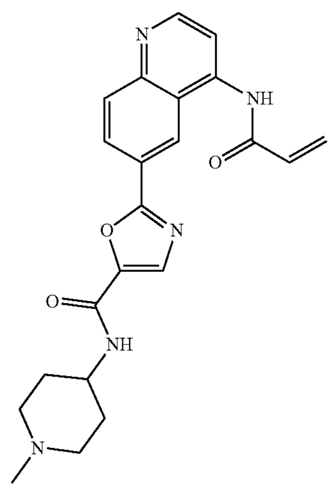 [SMILES: C=CC(=O)Nc1ccnc2ccc(-c3ncc(C(=O)NC4CCN(C)CC4)o3)cc12] | N-(1-methylpiperidin-4-yl)-2-[4-(prop-2-enamido)quinolin-6-yl]-1,3-oxazole-5-carboxamide | 405.5 |
| 1050 | 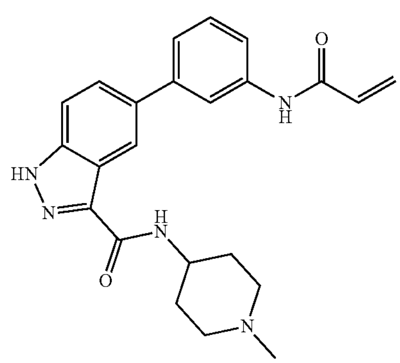 [SMILES: C=CC(=O)Nc1cccc(-c2ccc3[nH]nc(C(=O)NC4CCN(C)CC4)c3c2)c1] | N-(1-methylpiperidin-4-yl)-5-[3-(prop-2-enamido)phenyl]-1H-indazole-3-carboxamide | 403.5 |
| 1051 | 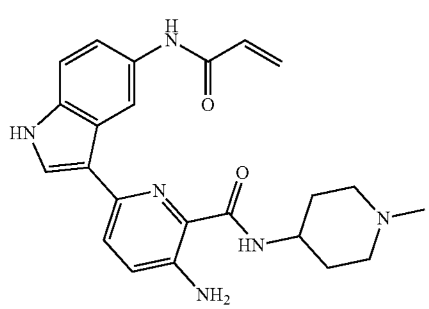 [SMILES: C=CC(=O)Nc1ccc2[nH]cc(-c3ccc(N)c(C(=O)NC4CCN(C)CC4)n3)c2c1] | 3-amino-N-(1-methylpiperidin-4-yl)-6-[5-(prop-2-enamido)-1H-indol-3-yl]pyridine-2-carboxamide | 418.5 |

TABLE 16-continued

| Cpd No. | Structure | IUPAC | MW (g/mol) |
|---|---|---|---|
| 1052 | 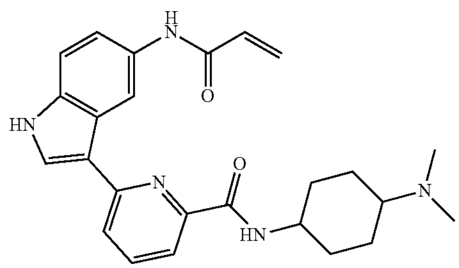 [SMILES: C=CC(=O)Nc1ccc2[nH]cc(-c3cccc(C(=O)NC4CCC(N(C)C)CC4)n3)c2c1] | N-[4-(dimethylamino)cyclohexyl]-6-[5-(prop-2-enamido)-1H-indol-3-yl]pyridine-2-carboxamide | 431.5 |
| 1053 | 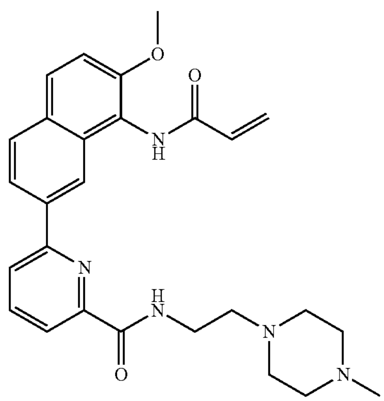 [SMILES: C=CC(=O)Nc1c(OC)ccc2ccc(-c3cccc(C(=O)NCCN4CCN(C)CC4)n3)cc12] | 6-[7-methoxy-8-(prop-2-enamido)naphthalen-2-yl]-N-[2-(4-methylpiperazin-1-yl)ethyl]pyridine-2-carboxamide | 473.6 |
| 1054 | 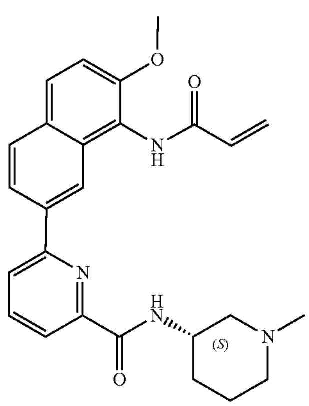 | 6-[7-methoxy-8-(prop-2-enamido)naphthalen-2-yl]-N-[(3S)-1-methylpiperidin-3-yl]pyridine-2-carboxamide | 444.5 |
| 1055 | 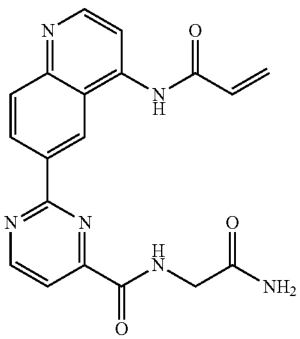 [SMILES: C=CC(=O)Nc1ccnc2ccc(-c3nccc(C(=O)NCC(N)=O)n3)cc12] | N-(6-{4-[(carbamoylmethyl)carbamoyl]pyrimidin-2-yl}quinolin-4-yl)prop-2-enamide | 376.4 |

TABLE 16-continued

| Cpd No. | Structure | IUPAC | MW (g/mol) |
|---|---|---|---|
| 1056 | 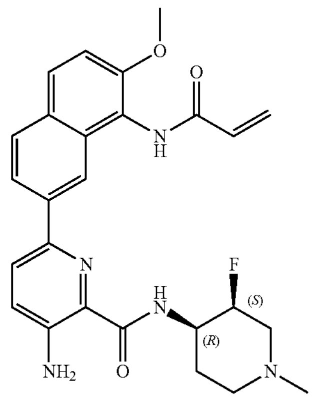 | 3-amino-N-[(3S,4R)-3-fluoro-1-methylpiperidin-4-yl]-6-[7-methoxy-8-(prop-2-enamido)naphthalen-2-yl]pyridine-2-carboxamide | 477.5 |
| 1057 | 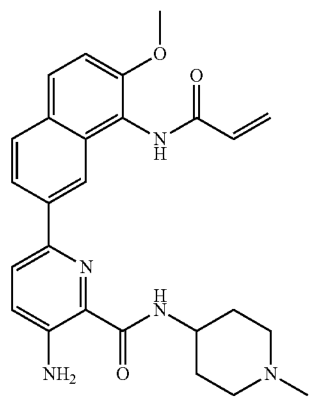 [SMILES: C=CC(=O)Nc1c(OC)ccc2ccc(-c3ccc(N)c(C(=O)NC4CCN(C)CC4)n3)cc12] | 3-amino-6-[7-methoxy-8-(prop-2-enamido)naphthalen-2-yl]-N-(1-rnethylpiperidin-4-yl)pyridine-2-carboxamide | 459.6 |
| 1058 | 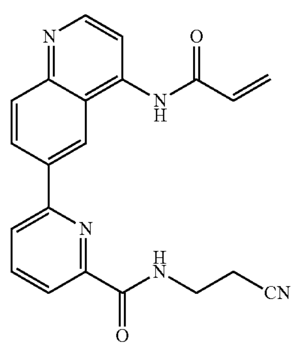 [SMILES: C=CC(=O)Nc1ccnc2ccc(-c3cccc(C(=O)NCCC#N)n3)cc12] | N-(2-cyanoethyl)-6-[4-(prop-2-enamido)quinolin-6-yl]pyridine-2-carboxamide | 371.4 |
| 1059 | 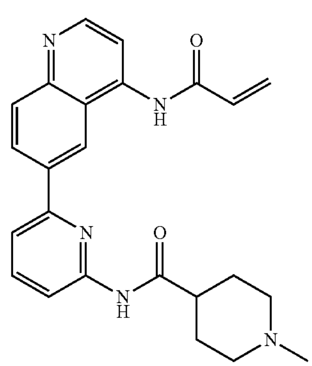 [SMILES: C=CC(=O)Nc1ccnc2ccc(-c3cccc(NC(=O)C4CCN(C)CC4)n3)cc12] | 1-methyl-N-{6-[4-(prop-2-enamido)quinolin-6-yl]pyridin-2-yl}piperidine-4-carboxamide | 415.5 |

TABLE 16-continued

| Cpd No. | Structure | IUPAC | MW (g/mol) |
|---|---|---|---|
| 1060 | 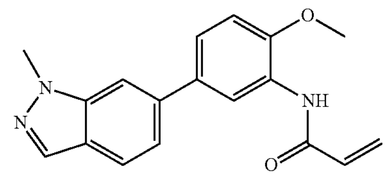 [SMILES: C=CC(=O)Nc1cc(-c2ccc3cnn(C)c3c2)ccc1OC] | N-[2-methoxy-5-(1-methyl-1H-indazol-6-yl)phenyl]prop-2-enamide | 307.4 |
| 1061 | 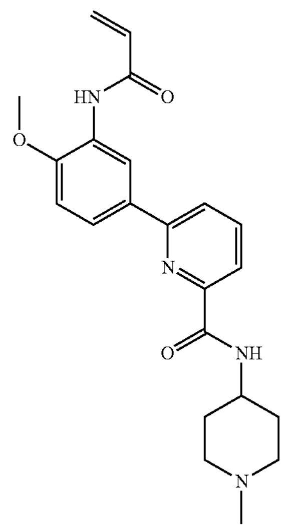 [SMILES: C=CC(=O)Nc1cc(-c2cccc(C(=O)NC3CCN(C)CC3)n2)ccc1OC] | 6-[4-methoxy-3-(prop-2-enamido)phenyl]-N-(1-methylpiperidin-4-yl)pyridine-2-carboxamide | 394.5 |
| 1062 | 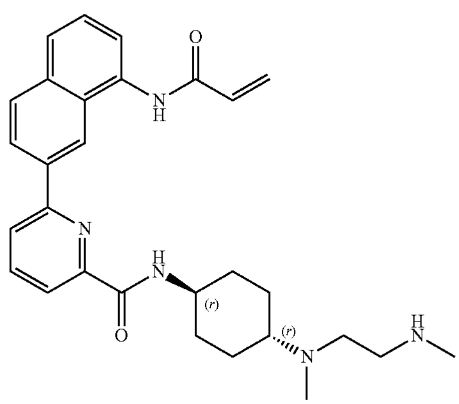 [SMILES: C=CC(=O)Nc1cccc2ccc(-c3cccc(C(=O)N[C@H]4CC[C@H](N(C)CCNC)CC4)n3)cc12] | 6-[8-(prop-2-enamido)naphthalen-2-yl]-N-[(1r,4r)-4-{methyl[2-(methylamino)ethyl]amino}cyclohexyl]pyridine-2-carboxamide | 485.6 |
| 1063 | 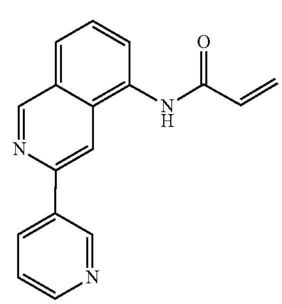 [SMILES: C=CC(=O)Nc1cccc2cnc(-c3cccnc3)cc12] | N-[3-(pyridin-3-yl)isoquinolin-5-yl]prop-2-enamide | 275.3 |

TABLE 16-continued

| Cpd No. | Structure | IUPAC | MW (g/mol) |
|---|---|---|---|
| 1064 | 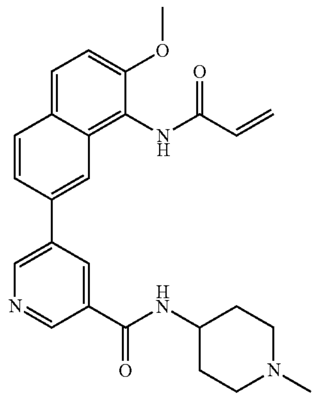 [SMILES: C=CC(=O)Nc1c(OC)ccc2ccc(-c3cncc(C(=O)NC4CCN(C)CC4)c3)cc12] | 5-[7-methoxy-8-(prop-2-enamido)naphthalen-2-yl]-N-(1-methylpiperidin-4-yl)pyridine-3-carboxamide | 444.5 |
| 1065 | 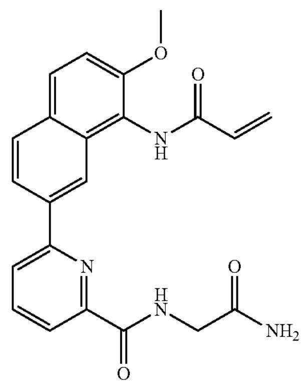 [SMILES: C=CC(=O)Nc1c(OC)ccc2ccc(-c3cccc(C(=O)NCC(N)=O)n3)cc12] | N-(7-{6-[(carbamoylmethyl)carbamoyl]pyridin-2-yl}-2-methoxynaphthalen-1-yl)prop-2-enamide | 404.4 |
| 1066 | 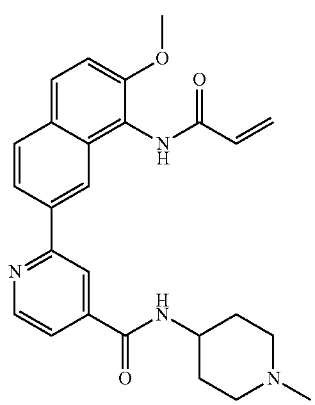 [SMILES: C=CC(=O)Nc1c(OC)ccc2ccc(-c3cc(C(=O)NC4CCN(C)CC4)ccn3)cc12] | 2-[7-methoxy-8-(prop-2-enamido)naphthalen-2-yl]-N-(1-methylpiperidin-4-yl)pyridine-4-carboxamide | 444.5 |
| 1067 | 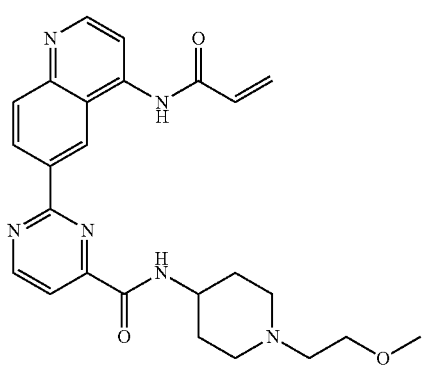 [SMILES: C=CC(=O)Nc1ccnc2ccc(-c3nccc(C(=O)NC4CCN(CCOC)CC4)n3)cc12] | N-[1-(2-methoxyethyl)piperidin-4-yl]-2-[4-(prop-2-enamido)quinolin-6-yl]pyrimidine-4-carboxamide | 460.5 |

| Cpd No. | Structure | IUPAC | MW (g/mol) |
|---|---|---|---|
| 1068 | 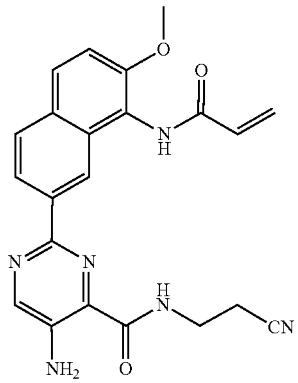 [SMILES: C=CC(=O)Nc1c(OC)ccc2ccc(-c3ncc(N)c(C(=O)NCCC#N)n3)cc12] | 5-amino-N-(2-cyanoethyl)-2-[7-methoxy-8-(prop-2-enamido)naphthalen-2-yl]pyrimidine-4-carboxamide | 416.4 |
| 1069 | 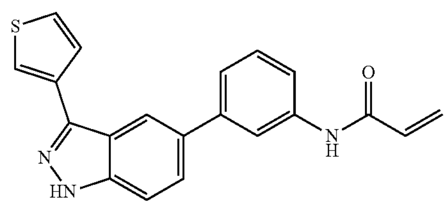 [SMILES: C=CC(=O)Nc1cccc(-c2ccc3[nH]nc(-c4ccsc4)c3c2)c1] | N-{3-[3-(thiophen-3-yl)-1H-indazol-5-yl]phenyl}prop-2-enamide | 345.4 |
| 1070 | 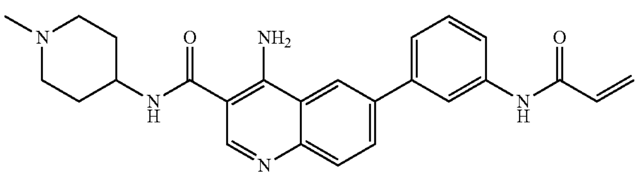 [SMILES: C=CC(=O)Nc1cccc(-c2ccc3ncc(C(=O)NC4CCN(C)CC4)c(N)c3c2)c1] | 4-amino-N-(1-methylpiperidin-4-yl)-6-[3-(prop-2-enamido)phenyl]quinoline-3-carboxamide | 429.5 |
| 1071 | 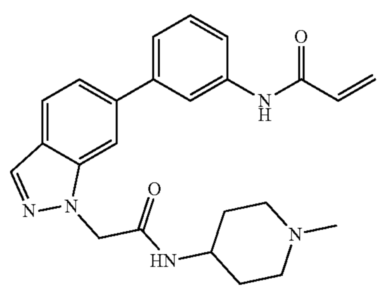 [SMILES: C=CC(=O)Nc1cccc(-c2ccc3cnn(CC(=O)NC4CCN(C)CC4)c3c2)c1] | N-[3-(1-{[(1-methylpiperidin-4-yl)carbamoyl]methyl}-1H-indazol-6-yl)phenyl]prop-2-enamide | 417.5 |
| 1072 | 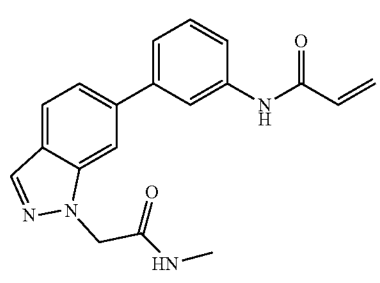 [SMILES: C=CC(=O)Nc1cccc(-c2ccc3cnn(CC(=O)NC)c3c2)c1] | N-(3-{1-[(methylcarbamoyl)methyl]-1H-indazol-6-yl}phenyl)prop-2-enamide | 334.4 |
| 1073 | 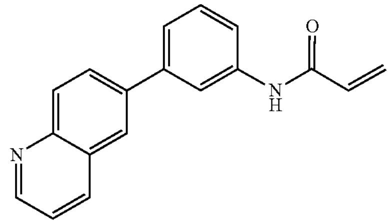 [SMILES: C=CC(=O)Nc1cccc(-c2ccc3ncccc3c2)c1] | N-[3-(quinolin-6-yl)phenyl]prop-2-enamide | 274.3 |

TABLE 16-continued

| Cpd No. | Structure | IUPAC | MW (g/mol) |
|---|---|---|---|
| 1074 | 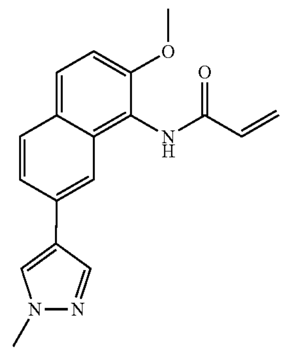 [SMILES: C=CC(=O)Nc1c(OC)ccc2ccc(-c3cnn(C)c3)cc12] | N-[2-methoxy-7-(1-methyl-1H-pyrazol-4-yl)naphthalen-1-yl]prop-2-enamide | 307.4 |
| 1075 | 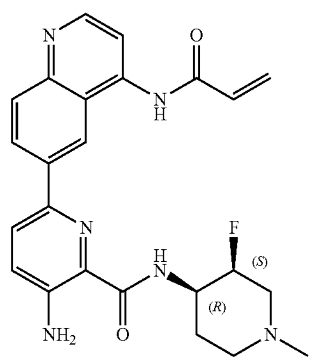 | 3-amino-N-[(3S,4R)-3-fluoro-1-methylpiperidin-4-yl]-6-[4-(prop-2-enamido)quinolin-6-yl]pyridine-2-carboxamide | 448.5 |
| 1076 | 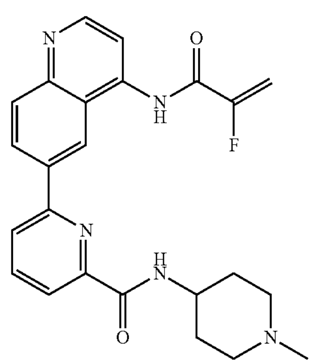 [SMILES: C=C(F)C(=O)Nc1ccnc2ccc(-c3cccc(C(=O)NC4CCN(C)CC4)n3)cc12] | 6-[4-(2-fluoroprop-2-enamido)quinolin-6-yl]-N-(1-methylpiperidin-4-yl)pyridine-2-carboxamide | 433.5 |
| 1077 | 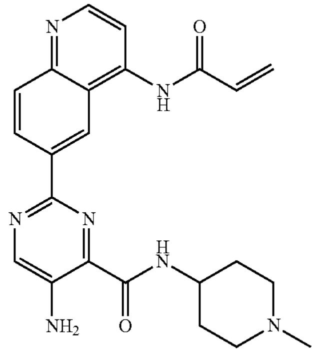 [SMILES: C=CC(=O)Nc1ccnc2ccc(-c3ncc(N)c(C(=O)NC4CCN(C)CC4)n3)cc12] | 5-amino-N-(1-methylpiperidin-4-yl)-2-[4-(prop-2-enamido)quinolin-6-yl]pyrimidine-4-carboxamide | 431.5 |

TABLE 16-continued

| Cpd No. | Structure | IUPAC | MW (g/mol) |
|---|---|---|---|
| 1078 | 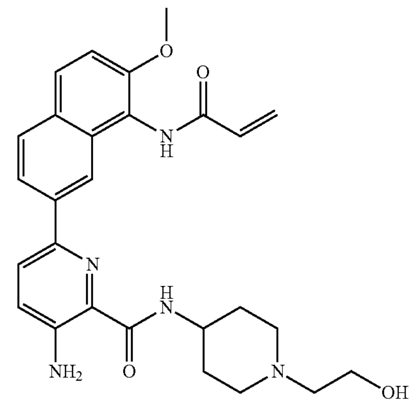 [SMILES: C=CC(=O)Nc1c(OC)ccc2ccc(-c3ccc(N)c(C(=O)NC4CCN(CCO)CC4)n3)cc12] | 3-amino-N-[1-(2-hydroxyethyl)piperidin-4-yl]-6-[7-methoxy-8-(prop-2-enamido)naphthalen-2-yl]pyridine-2-carboxamide | 489.6 |
| 1079 | 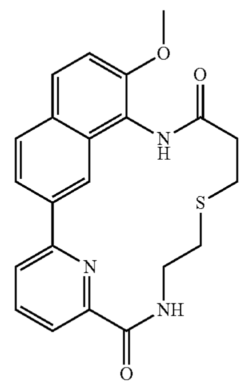 [SMILES: COc1ccc2ccc3cc2c1NC(=O)CCSCCNC(=O)c1cccc-3n1] | 17-methoxy-11-thia-8,15,25-triazatetracyclo[14.6.2.1$^{2,6}$.0$^{20,24}$]pentacosa-1(23),2,4,6(25),16(24),17,19,21-octaene-7,14-dione | 407.5 |
| 1080 | 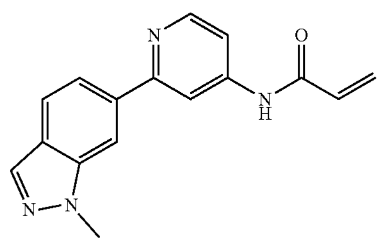 [SMILES: C=CC(=O)Nc1ccnc(-c2ccc3cnn(C)c3c2)c1] | N-[2-(1-methyl-1H-indazol-6-yl)pyridin-4-yl]prop-2-enamide | 278.3 |
| 1081 | 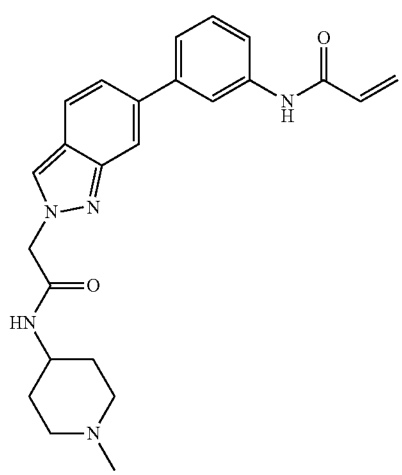 [SMILES: C=CC(=O)Nc1cccc(-c2ccc3cn(CC(=O)NC4CCN(C)CC4)nc3c2)c1] | N-[3-(2-{[(1-methylpiperidin-4-yl)carbamoyl]methyl}-2H-indazol-6-yl)phenyl]prop-2-enamide | 417.5 |

TABLE 16-continued

| Cpd No. | Structure | IUPAC | MW (g/mol) |
|---|---|---|---|
| 1082 | 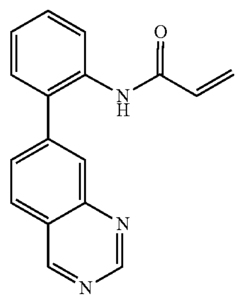 [SMILES: C=CC(=O)Nc1ccccc1-c1ccc2cncnc2c1] | N-[2-(quinazolin-7-yl)phenyl]prop-2-enamide | 275.3 |
| 1083 | 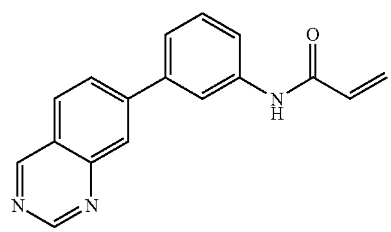 | N-[3-(quinazolin-7-yl)phenyl]prop-2-enamide | 275.3 |
| 1084 | 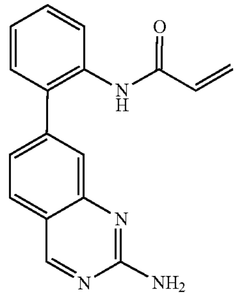 [SMILES: C=CC(=O)Nc1ccccc1-c1ccc2cnc(N)nc2c1] | N-[2-(2-aminoquinazolin-7-yl)phenyl]prop-2-enamide | 290.3 |
| 1085 | 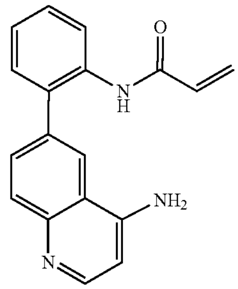 [SMILES: C=CC(=O)Nc1ccccc1-c1ccc2nccc(N)c2c1] | N-[2-(4-aminoquinolin-6-yl)phenyl]prop-2-enamide | 289.3 |
| 1086 | 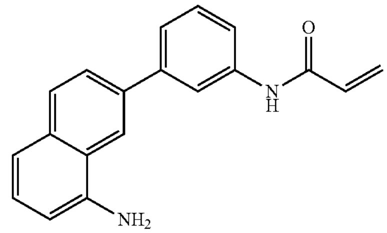 | N-[3-(8-aminonaphthalen-2-yl)phenyl]prop-2-enamide | 288.4 |

TABLE 16-continued
| Cpd No. | Structure | IUPAC | MW (g/mol) |
|---|---|---|---|
| 1087 | 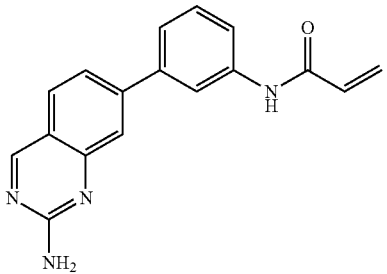 [SMILES: C=CC(=O)Nc1cccc(-c2ccc3cnc(N)nc3c2)c1] | N-[3-(2-aminoquinazolin-7-yl)phenyl]prop-2-enamide | 290.3 |
| 1088 | 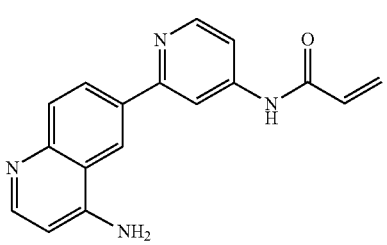 [SMILES: C=CC(=O)Nc1ccnc(-c2ccc3nccc(N)c3c2)c1] | N-[2-(4-aminoquinolin-6-yl)pyridin-4-yl]prop-2-enamide | 290.3 |
| 1089 | 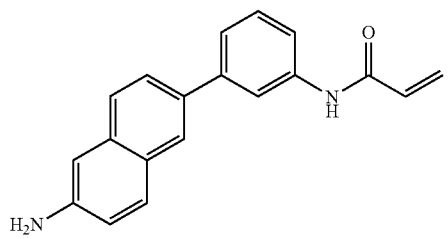 [SMILES: C=CC(=O)Nc1cccc(-c2ccc3cc(N)ccc3c2)c1] | N-[3-(6-aminonaphthalen-2-yl)phenyl]prop-2-enamide | 288.4 |
| 1090 | 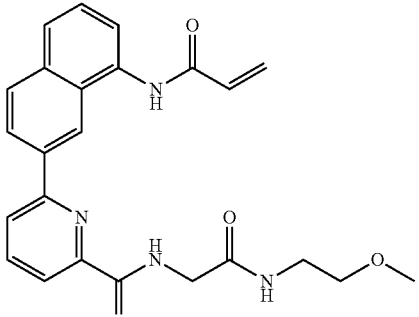 | N-{7-[6-({[(2-methoxyethyl)carbamoyl]methyl}carbamoyl)pyridin-2-yl]naphthalen-1-yl}prop-2-enamide | 432.5 |
| 1091 | 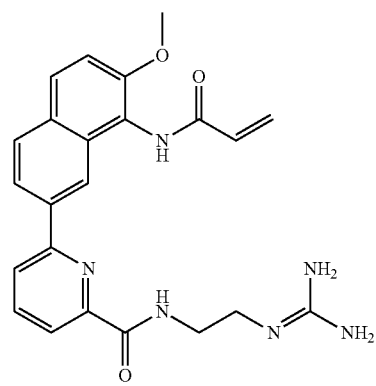 [SMILES: C=CC(=O)Nc1c(OC)ccc2ccc(-c3cccc(C(=O)NCCN=C(N)N)n3)cc12] | N-{2-[(diaminomethylidene)amino]ethyl}-6-[7-methoxy-8-(prop-2-enamido)naphthalen-2-yl]pyridine-2-carboxamide | 432.5 |

TABLE 16-continued

| Cpd No. | Structure | IUPAC | MW (g/mol) |
|---|---|---|---|
| 1092 | 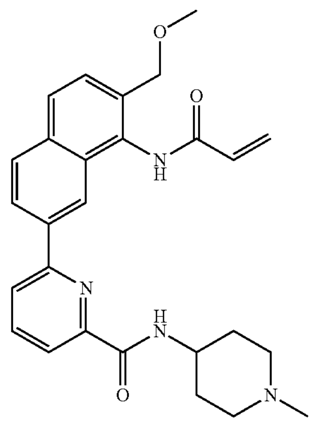 [SMILES: C=CC(=O)Nc1c(COC)ccc2ccc(-c3cccc(C(=O)NC4CCN(C)CC4)n3)cc12] | 6-[7-(methoxymethyl)-8-(prop-2-enamido)naphthalen-2-yl]-N-(1-methylpiperidin-4-yl)pyridine-2-carboxamide | 458.6 |
| 1093 | 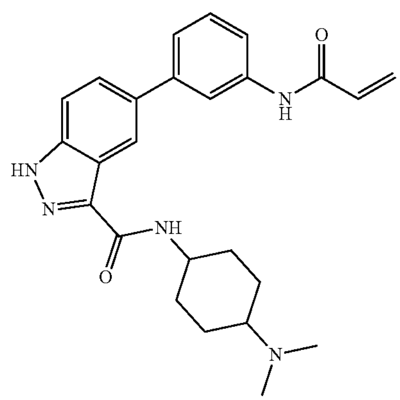 [SMILES: C=CC(=O)Nc1cccc(-c2ccc3[nH]nc(C(=O)NC4CCC(N(C)C)CC4)c3c2)c1] | N-[4-(dimethylamino)cyclohexyl]-5-[3-(prop-2-enamido)phenyl]-1H-indazole-3-carboxamide | 431.5 |
| 1094 | 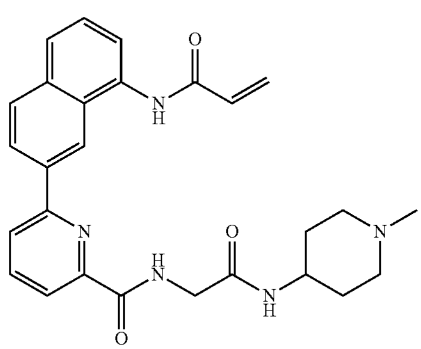 [SMILES: C=CC(=O)Nc1cccc2ccc(-c3cccc(C(=O)NCC(=O)NC4CCN(C)CC4)n3)cc12] | N-{7-[6-({[(1-methylpiperidin-4-yl)carbamoyl]methyl}carbamoyl)pyridin-2-yl]naphthalen-1-yl}prop-2-enamide | 471.6 |
| 1095 | 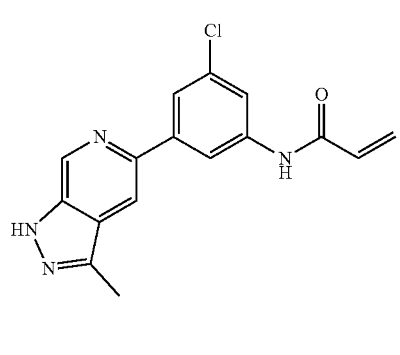 [SMILES: C=CC(=O)Nc1cc(Cl)cc(-c2cc3c(C)n[nH]c3cn2)c1] | N-(3-chloro-5-{3-methyl-1H-pyrazolo[3,4-c]pyridin-5-yl}phenyl)prop-2-enamide | 312.8 |

TABLE 16-continued

| Cpd No. | Structure | IUPAC | MW (g/mol) |
|---|---|---|---|
| 1096 | 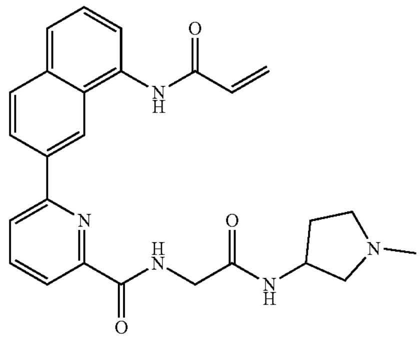 [SMILES: C=CC(=O)Nc1cccc2ccc(-c3cccc(C(=O)NCC(=O)NC4CCN(C)C4)n3)cc12] | N-{7-[6-({[(1-methylpyrrolidin-3-yl)carbamoyl]methyl}carbamoyl)pyridin-2-yl]naphthalen-1-yl}prop-2-enamide | 457.5 |
| 1097 | 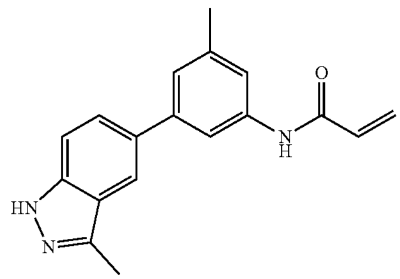 [SMILES: C=CC(=O)Nc1cc(C)cc(-c2ccc3[nH]nc(C)c3c2)c1] | N-[3-methyl-5-(3-methyl-1H-indazol-5-yl)phenyl]prop-2-enamide | 291.4 |
| 1098 | 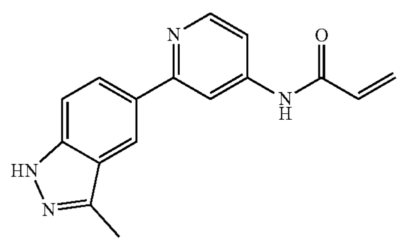 [SMILES: C=CC(=O)Nc1ccnc(-c2ccc3[nH]nc(C)c3c2)c1] | N--[2-[3-methyl-1H-indazol-5-yl)pyridin-4-yl]prop-2-enamide | 278.3 |
| 1099 | 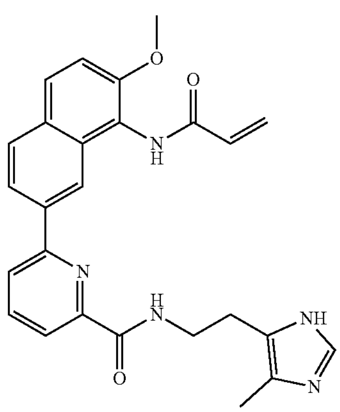 [SMILES: C=CC(=O)Nc1c(OC)ccc2ccc(-c3cccc(C(=O)NCCc4[nH]cnc4C)n3)cc12] | 6-[7-methoxy-8-(prop-2-enamido)naphthalen-2-yl]-N-[2-(4-methyl-1H-imidazol-5-yl)ethyl]pyridine-2-carboxamide | 455.5 |
| 1100 | 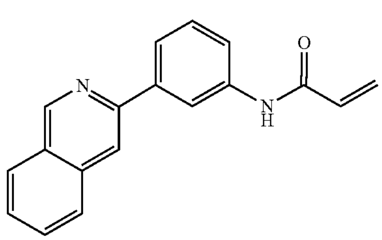 [SMILES: C=CC(=O)Nc1cccc(-c2cc3ccccc3cn2)c1] | N-[3-(isoquinolin-3-yl)phenyl]prop-2-enamide | 274.3 |

TABLE 16-continued

| Cpd No. | Structure | IUPAC | MW (g/mol) |
|---|---|---|---|
| 1101 | 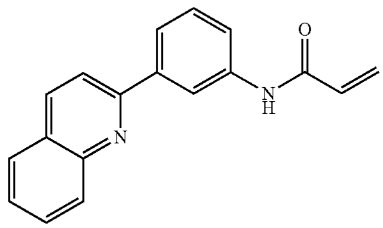 [SMILES: C=CC(=O)Nc1cccc(-c2ccc3ccccc3n2)c1] | N-[3-(quinolin-2-yl)phenyl]prop-2-enamide | 274.3 |
| 1102 | 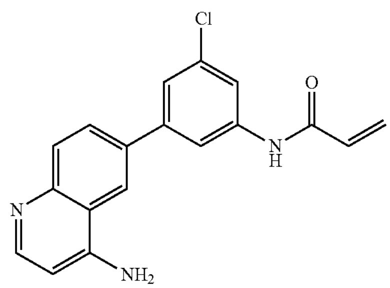 [SMILES: C=CC(=O)Nc1cc(Cl)cc(-c2ccc3nccc(N)c3c2)c1] | N-[3-(4-aminoquinolin-6-yl)-5-chlorophenyl]prop-2-enamide | 323.8 |
| 1103 | 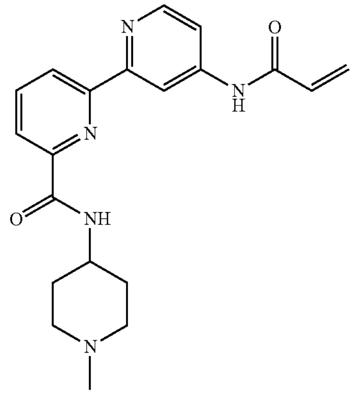 [SMILES: C=CC(=O)Nc1ccnc(-c2cccc(C(=O)NC3CCN(C)CC3)n2)c1] | N-(1-methylpiperidin-4-yl)-4'-(prop-2-enamido)-[2,2'-bipyridine]-6-carboxamide | 365.4 |
| 1104 | 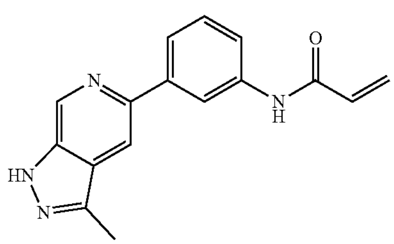 | N-(3-{3-methyl-1H-pyrazolo[3,4-c]pyridin-5-yl}phenyl)prop-2-enamide | 278.3 |
| 1105 | 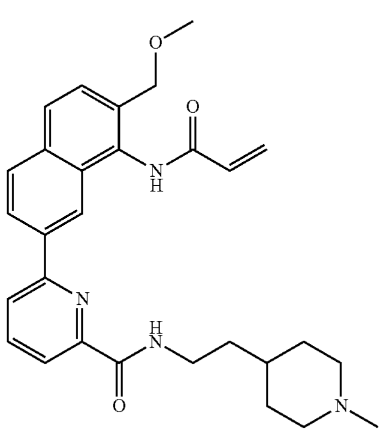 [SMILES: C=CC(=O)Nc1c(COC)ccc2ccc(-c3cccc(C(=O)NCCC4CCN(C)CC4)n3)cc12] | 6-[7-(methoxymethyl)-8-(prop-2-enamido)naphthalen-2-yl]-N-[2-(1-methylpiperidin-4-yl)ethyl]pyridine-2-carboxamide | 486.6 |

TABLE 16-continued

| Cpd No. | Structure | IUPAC | MW (g/mol) |
|---|---|---|---|
| 1106 | 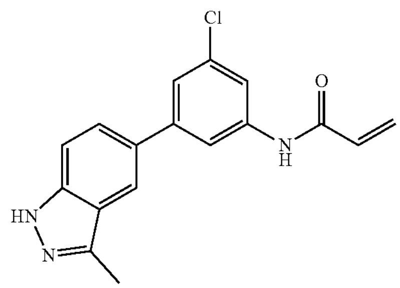 [SMILES: C=CC(=O)Nc1cc(Cl)cc(-c2ccc3[nH]nc(C)c3c2)c1] | N-[3-chloro-5-(3-methyl-1H-indazol-5-yl)phenyl]prop-2-enamide | 311.8 |
| 1107 | 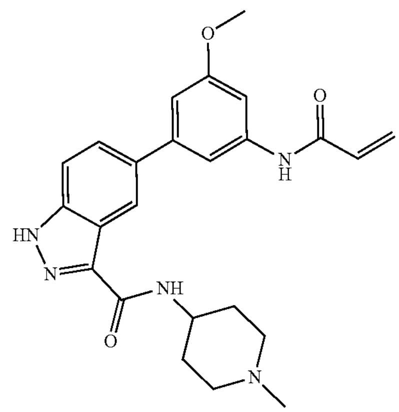 | 5-[3-methoxy-5-(prop-2-enamido)phenyl]-N-(1-methylpiperidin-4-yl)-1H-indazole-3-carboxamide | 433.5 |
| 1108 | 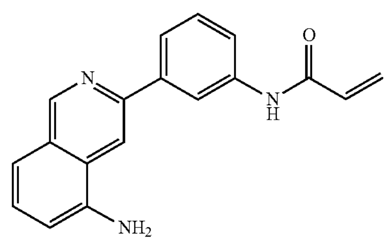 [SMILES: C=CC(=O)Nc1cccc(-c2cc3c(N)cccc3cn2)c1] | N-[3-(5-aminoisoquinolin-3-yl)phenyl]prop-2-enamide | 289.3 |
| 1109 | 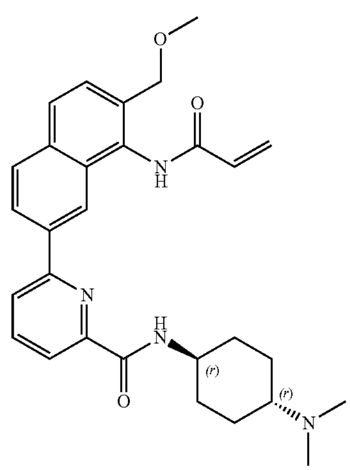 [SMILES: C=CC(=O)Nc1c(COC)ccc2ccc(-c3cccc(C(=O)N[C@H]4CC[C@H](N(C)C)CC4)n3)cc12] | 6-[7-(methoxymethyl)-8-(prop-2-enamido)naphthalen-2-yl]-N-[(1r,4r)-4-(dimethylamino)cyclohexyl]pyridine-2-carboxamide | 486.6 |

TABLE 16-continued

| Cpd No. | Structure | IUPAC | MW (g/mol) |
|---|---|---|---|
| 1110 | 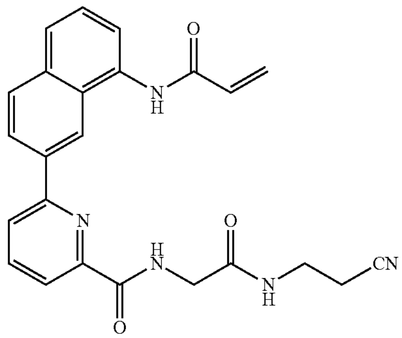 | N-{7-[6-({[(2-cyanoethyl)carbamoyl]methyl}carbamoyl)pyridin-2-yl]naphthalen-1-yl}prop-2-enamide | 427.5 |
| 1111 | 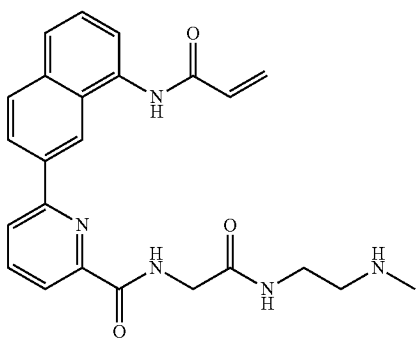 [SMILES: C=CC(=O)Nc1cccc2ccc(-c3cccc(C(=O)NCC(=O)NCCNC)n3)cc12] | N-(7-{6-[({[2-(methylamino)ethyl]carbamoyl}methyl)carbamoyl]pyridin-2-yl}naphthalen-1-yl)prop-2-enamide | 431.5 |
| 1112 | 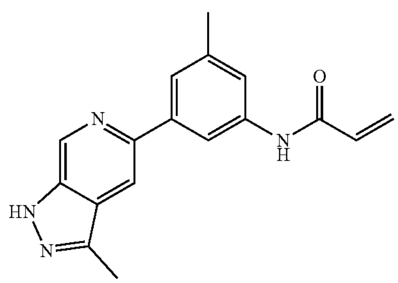 [SMILES: C=CC(=O)Nc1cc(C)cc(-c2cc3c(C)n[nH]c3cn2)c1] | N-(3-methyl-5-{3-methyl-1H-pyrazolo[3,4-c]pyridin-5-yl}phenyl)prop-2-enamide | 292.3 |
| 1113 | 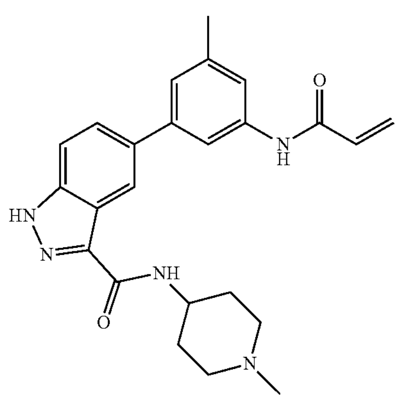 [SMILES: C=CC(=O)Nc1cc(C)cc(-c2ccc3[nH]nc(C(=O)NC4CCN(C)CC4)c3c2)c1] | 5-[3-methyl-5-(prop-2-enamido)phenyl]-N-(1-methylpiperidin-4-yl)-1H-indazole-3-carboxamide | 417.5 |

TABLE 16-continued

| Cpd No. | Structure | IUPAC | MW (g/mol) |
|---|---|---|---|
| 1114 | 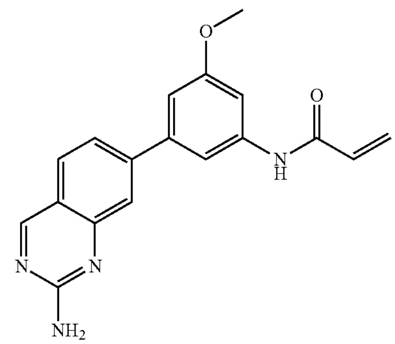 [SMILES: C=CC(=O)Nc1cc(OC)cc(-c2ccc3cnc(N)nc3c2)c1] | N-[3-(2-aminoquinazolin-7-yl)-5-methoxyphenyl]prop-2-enamide | 320.4 |
| 1115 | 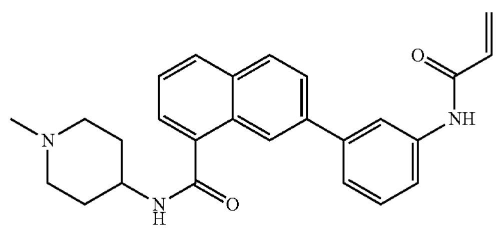 [SMILES: C=CC(=O)Nc1cccc(-c2ccc3cccc(C(=O)NC4CCN(C)CC4)c3c2)c1] | N-(1-methylpiperidin-4-yl)-7-[3-(prop-2-enamido)phenyl]naphthalene-1-carboxamide | 413.5 |
| 1116 | 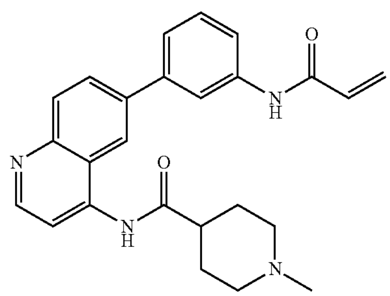 [SMILES: C=CC(=O)Nc1cccc(-c2ccc3nccc(NC(=O)C4CCN(C)CC4)c3c2)c1] | 1-methyl-N-{6-[3-(prop-2-enamido)phenyl]quinolin-4-yl}piperidine-4-carboxamide | 414.5 |
| 1117 | 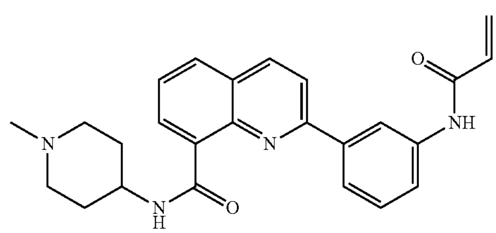 [SMILES: C=CC(=O)Nc1cccc(-c2ccc3cccc(C(=O)NC4CCN(C)CC4)c3n2)c1] | N-(1-methylpiperidin-4-yl)-2-[3-(prop-2-enamido)phenyl]quinoline-8-carboxamide | 414.5 |
| 1118 | 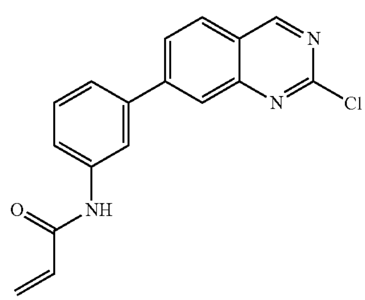 [SMILES: C=CC(=O)Nc1cccc(-c2ccc3cnc(Cl)nc3c2)c1] | N-[3-(2-chloroquinazolin-7-yl)phenyl]prop-2-enamide | 309.8 |
| 1119 | 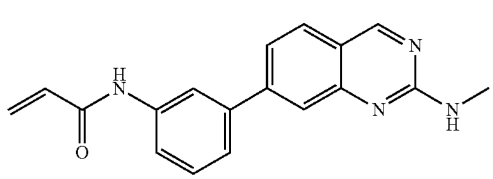 [SMILES: C=CC(=O)Nc1cccc(-c2ccc3cnc(NC)nc3c2)c1] | N-{3-[2-(methylamino)quinazolin-7-yl]phenyl}prop-2-enamide | 304.4 |

TABLE 16-continued

| Cpd No. | Structure | IUPAC | MW (g/mol) |
| --- | --- | --- | --- |
| 1120 | 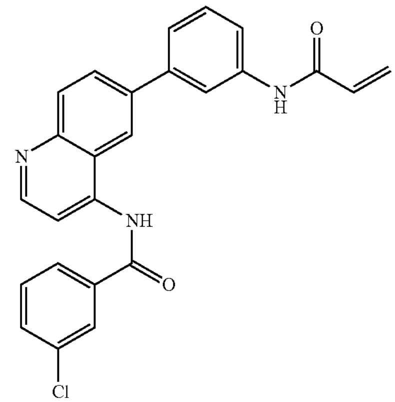 [SMILES: C=CC(=O)Nc1cccc(-c2ccc3nccc(NC(=O)c4cccc(Cl)c4)c3c2)c1] | 3-chloro-N-{6-[3-(prop-2-enamido)phenyl]quinolin-4-yl}benzamide | 427.9 |
| 1121 | 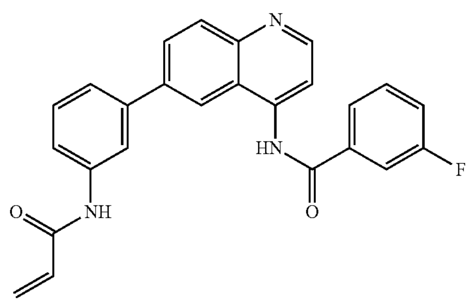 [SMILES: C=CC(=O)Nc1cccc(-c2ccc3nccc(NC(=O)c4cccc(F)c4)c3c2)c1] | 3-fluoro-N-{6-[3-(prop-2-enamido)phenyl]quinolin-4-yl}benzamide | 411.4 |
| 1122 | 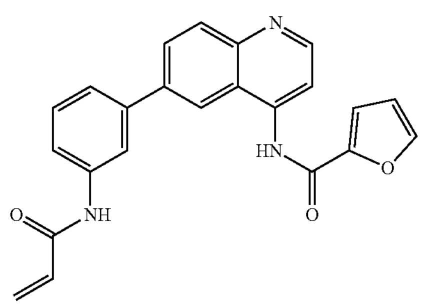 [SMILES: C=CC(=O)Nc1cccc(-c2ccc3nccc(NC(=O)c4ccco4)c3c2)c1] | N-{6-[3-(prop-2-enamido)phenyl]quinolin-4-yl}furan-2-carboxamide | 383.4 |
| 1123 | 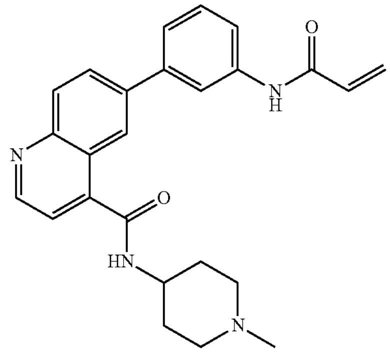 [SMILES: C=CC(=O)Nc1cccc(-c2ccc3nccc(C(=O)NC4CCN(C)CC4)c3c2)c1] | N-(1-methylpiperidin-4-yl)-6-[3-(prop-2-enamido)phenyl]quinoline-4-carboxamide | 414.5 |

TABLE 16-continued

| Cpd No. | Structure | IUPAC | MW (g/mol) |
|---|---|---|---|
| 1124 | 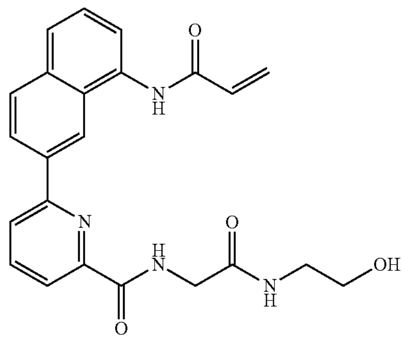 [SMILES: C=CC(=O)Nc1cccc2ccc(-c3cccc(C(=O)NCC(=O)NCCO)n3)cc12] | N-{7-[6-({[(2-hydroxyethyl)carbamoyl]methyl}carbamoyl)pyridin-2-yl]naphthalen-1-yl}prop-2-enamide | 418.5 |
| 1125 | 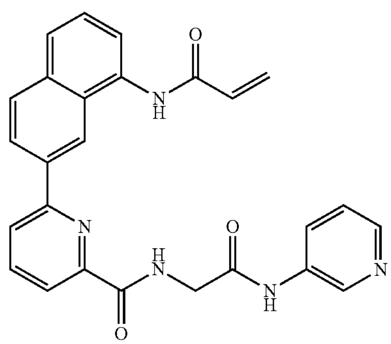 [SMILES: C=CC(=O)Nc1cccc2ccc(-c3cccc(C(=O)NCC(=O)Nc4cccnc4)n3)cc12] | N-{7-[6-({[(pyridin-3-yl)carbamoyl]methyl}carbamoyl)pyridin-2-yl]naphthalen-1-yl}prop-2-enamide | 451.5 |
| 1126 | 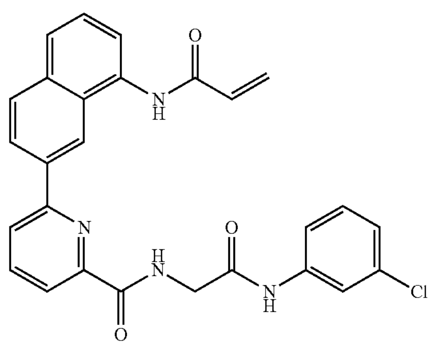 [SMILES: C=CC(=O)Nc1cccc2ccc(-c3cccc(C(=O)NCC(=O)Nc4cccc(Cl)c4)n3)cc12] | N-{7-[6-({[(3-chlorophenyl)carbamoyl]methyl}carbamoyl)pyridin-2-yl]naphthalen-1-yl}prop-2-enamide | 484.9 |
| 1127 | 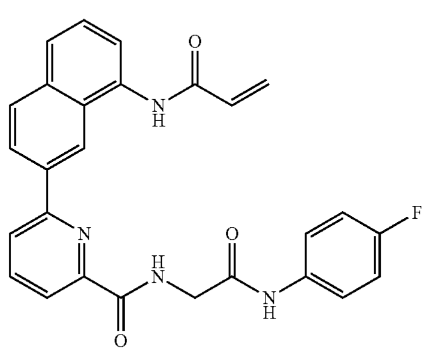 [SMILES: C=CC(=O)Nc1cccc2ccc(-c3cccc(C(=O)NCC(=O)Nc4ccc(F)cc4)n3)cc12] | N-{7-[6-({[(4-fluorophenyl)carbamoyl]methyl}carbamoyl)pyridin-2-yl]naphthalen-1-yl}prop-2-enamide | 468.5 |

TABLE 16-continued

| Cpd No. | Structure | IUPAC | MW (g/mol) |
|---|---|---|---|
| 1128 | 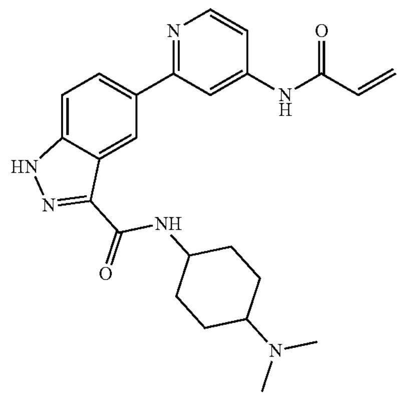 [SMILES: C=CC(=O)Nc1ccnc(-c2ccc3[nH]nc(C(=O)NC4CCC(N(C)C)CC4)c3c2)c1] | N-[4-(dimethylamino)cyclohexyl]-5-[4-(prop-2-enamido)pyridin-2-yl]-1H-indazole-3-carboxamide | 432.5 |
| 1129 | 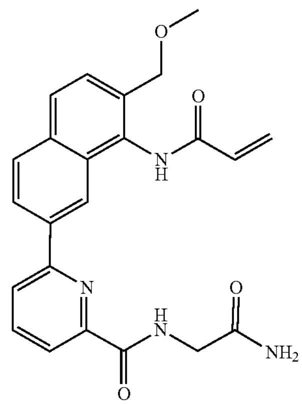 [SMILES: C=CC(=O)Nc1c(COC)ccc2ccc(-c3cccc(C(=O)NCC(N)=O)n3)cc12] | N-(7-{6-[(carbamoylmethyl)carbamoyl]pyridin-2-yl}-2-(methoxymethyl)naphthalen-1-yl)prop-2-enamide | 418.5 |
| 1130 | 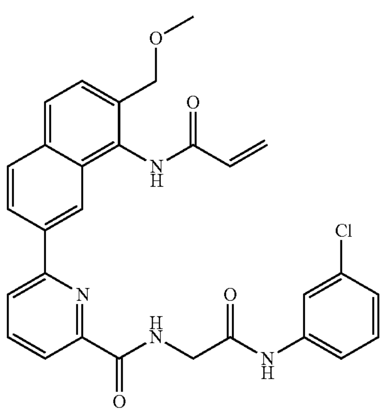 [SMILES: C=CC(=O)Nc1c(COC)ccc2ccc(-c3cccc(C(=O)NCC(=O)Nc4cccc(Cl)c4)n3)cc12] | N-{7-[6-({[(3-chlorophenyl)carbamoyl]methyl}carbamoyl)pyridin-2-yl]-2-(methoxymethyl)naphthalen-1-yl}prop-2-enamide | 529.0 |
| 1131 | 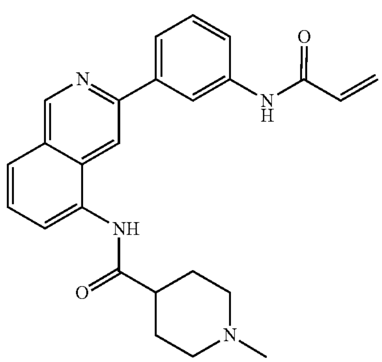 [SMILES: C=CC(=O)Nc1cccc(-c2cc3c(NC(=O)C4CCN(C)CC4)cccc3cn2)c1] | 1-methyl-N-{3-[3-(prop-2-enamido)phenyl]isoquinolin-5-yl}piperidine-4-carboxamide | 414.5 |

TABLE 16-continued

| Cpd No. | Structure | IUPAC | MW (g/mol) |
|---|---|---|---|
| 1132 | 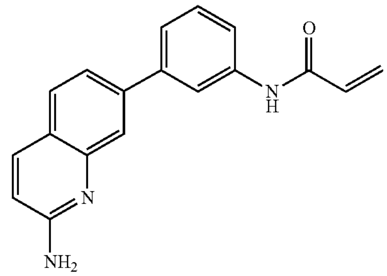 [SMILES: C=CC(=O)Nc1cccc(-c2ccc3ccc(N)nc3c2)c1] | N-[3-(2-aminoquinolin-7-yl)phenyl]prop-2-enamide | 289.3 |
| 1133 | 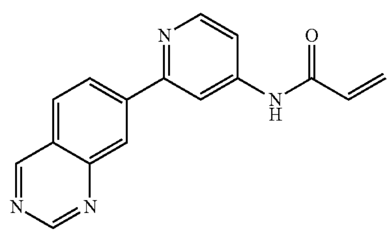 [SMILES: C=CC(=O)Nc1ccnc(-c2ccc3cncnc3c2)c1] | N-[2-(quinazolin-7-yl)pyridin-4-yl]prop-2-enamide | 276.3 |
| 1134 | 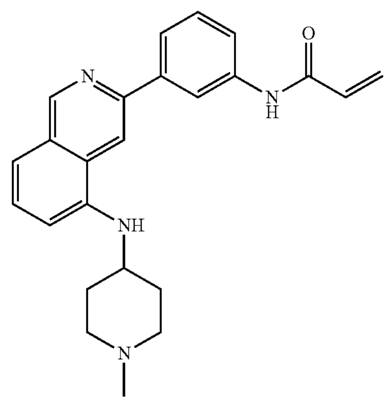 [SMILES: C=CC(=O)Nc1cccc(-c2cc3c(NC4CCN(C)CC4)cccc3cn2)c1] | N-(3-{5-[(1-methylpiperidin-4-yl)amino]isoquinolin-3-yl}phenyl)prop-2-enamide | 386.5 |
| 1135 | 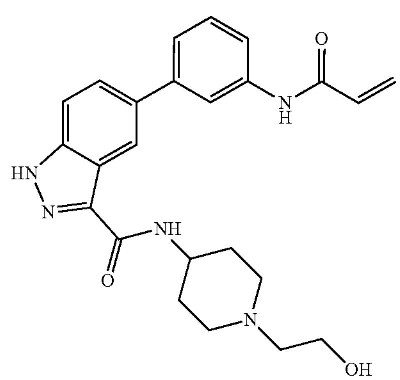 [SMILES: C=CC(=O)Nc1cccc(-c2ccc3[nH]nc(C(=O)NC4CCN(CCO)CC4)c3c2)c1] | N-[1-(2-hydroxyethyl)piperidin-4-yl]-5-[3-(prop-2-enamido)phenyl]-1H-indazole-3-carboxamide | 433.5 |

TABLE 16-continued

| Cpd No. | Structure | IUPAC | MW (g/mol) |
|---|---|---|---|
| 1136 | 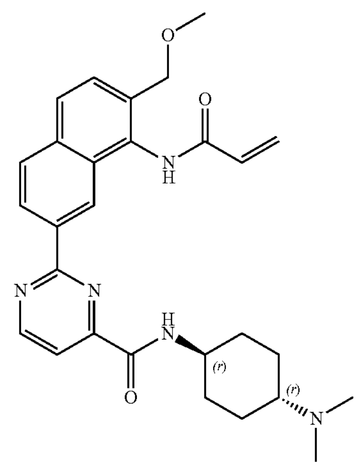 [SMILES: C=CC(=O)Nc1c(COC)ccc2ccc(-c3nccc(C(=O)N[C@H]4CC[C@H](N(C)C)CC4)n3)cc12] | 2-[7-(methoxymethyl)-8-(prop-2-enamido)naphthalen-2-yl]-N-[(1r,4r)-4-(dimethylamino)cyclohexyl]pyrimidine-4-carboxamide | 487.6 |
| 1137 | 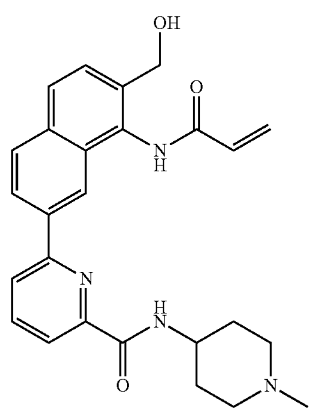 [SMILES: C=CC(=O)Nc1c(CO)ccc2ccc(-c3cccc(C(=O)NC4CCN(C)CC4)n3)cc12] | 6-[7-(hydroxymethyl)-8-(prop-2-enamido)naphthalen-2-yl]-N-(1-methylpiperidin-4-yl)pyridine-2-carboxamide | 444.5 |
| 1138 | 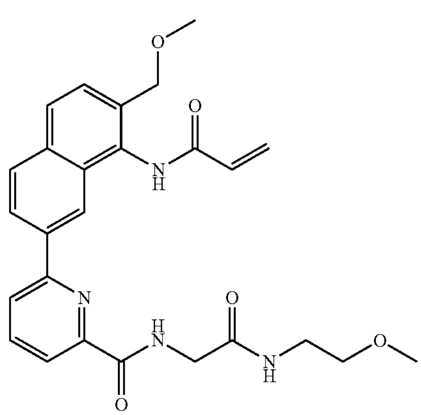 [SMILES: C=CC(=O)Nc1c(COC)ccc2ccc(-c3cccc(C(=O)NCC(=O)NCCOC)n3)cc12] | N-{7-[6-({[(2-methoxyethyl)carbamoyl]methyl}carbamoyl)pyridin-2-yl]-2-(methoxymethyl)naphthalen-1-yl}prop-2-enamide | 476.5 |

TABLE 16-continued

| Cpd No. | Structure | IUPAC | MW (g/mol) |
|---|---|---|---|
| 1139 | 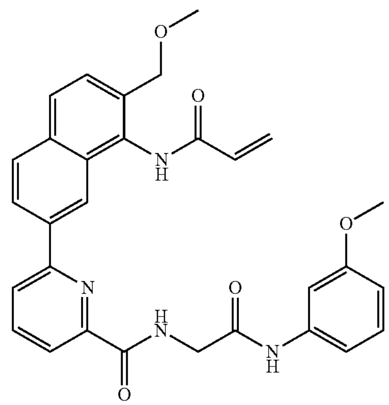 [SMILES: C=CC(=O)Nc1c(COC)ccc2ccc(-c3cccc(C(=O)NCC(=O)Nc4cccc(OC)c4)n3)cc12] | N-[2-(methoxymethyl)-7-[6-({[(3-methoxyphenyl)carbamoyl]methyl}carbamoyl)pyridin-2-yl]naphthalen-1-yl]prop-2-enamide | 524.6 |
| 1140 | 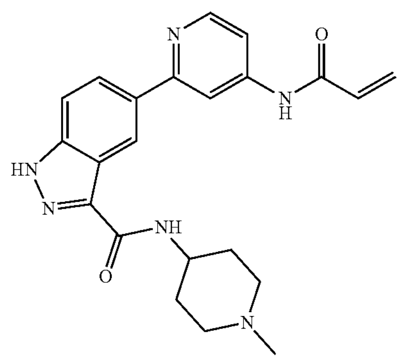 [SMILES: C=CC(=O)Nc1ccnc(-c2ccc3[nH]nc(C(=O)NC4CCN(C)CC4)c3c2)c1] | N-(1-methylpiperidin-4-yl)-5-[4-(prop-2-enamido)pyridin-2-yl]-1H-indazole-3-carboxamide | 404.5 |
| 1141 | 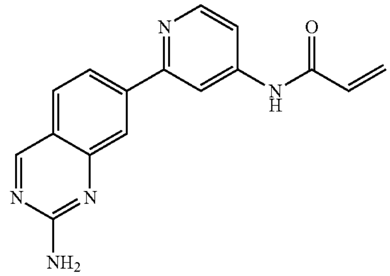 | N-[2-(2-aminoquinazolin-7-yl)pyridin-4-yl]prop-2-enamide | 291.3 |
| 1142 | 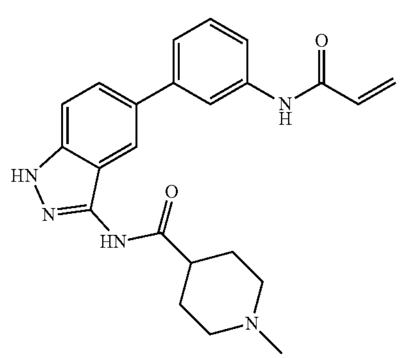 [SMILES: C=CC(=O)Nc1cccc(-c2ccc3[nH]nc(NC(=O)C4CCN(C)CC4)c3c2)c1] | 1-methyl-N-{5-[3-(prop-2-enamido)phenyl]-1H-indazol-3-yl}piperidine-4-carboxamide | 403.5 |

TABLE 16-continued
| Cpd No. | Structure | IUPAC | MW (g/mol) |
|---|---|---|---|
| 1143 | 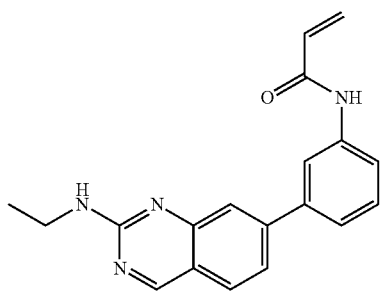 [SMILES: C=CC(=O)Nc1cccc(-c2ccc3cnc(NCC)nc3c2)c1] | N-{3-[2-(ethylamino)quinazolin-7-yl]phenyl}prop-2-enamide | 318.4 |
| 1144 | 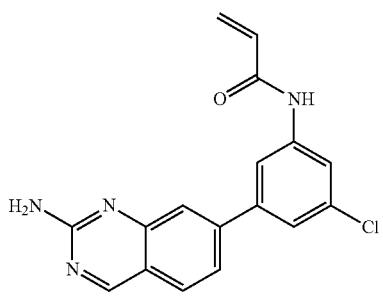 [SMILES: C=CC(=O)Nc1cc(Cl)cc(-c2ccc3cnc(N)nc3c2)c1] | N-[3-(2-aminoquinazolin-7-yl)-5-chlorophenyl]prop-2-enamide | 324.8 |
| 1145 | 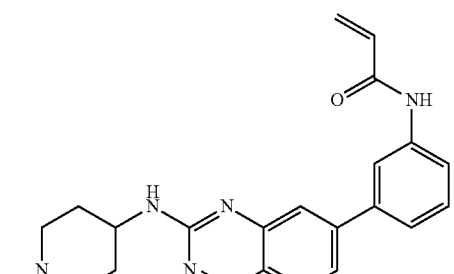 | N-(3-{2-[(1-methylpiperidin-4-yl)amino]quinazolin-7-yl}phenyl)prop-2-enamide | 387.5 |
| 1146 | 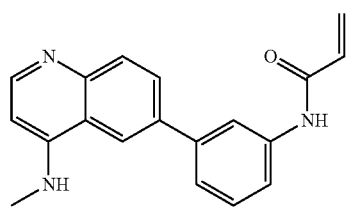 [SMILES: C=CC(=O)Nc1cccc(-c2ccc3nccc(NC)c3c2)c1] | N-{3-[4-(methylamino)quinolin-6-yl]phenyl}prop-2-enamide | 303.4 |
| 1147 | 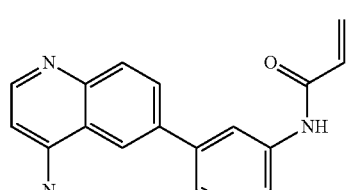 | N-{3-[4-(dimethylamino)quinolin-6-yl]phenyl}prop-2-enamide | 317.4 |

TABLE 16-continued

| Cpd No. | Structure | IUPAC | MW (g/mol) |
|---|---|---|---|
| 1148 | 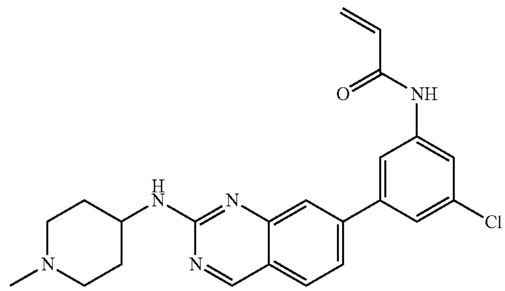 [SMILES: C=CC(=O)Nc1cc(Cl)cc(-c2ccc3cnc(NC4CCN(C)CC4)nc3c2)c1] | N-(3-chloro-5-{2-[(1-methylpiperidin-4-yl)amino]quinazolin-7-yl}phenyl)prop-2-enamide | 421.9 |
| 1149 | 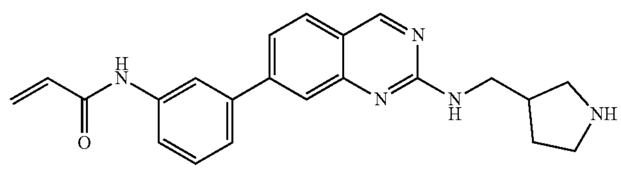 [SMILES: C=CC(=O)Nc1cccc(-c2ccc3cnc(NCC4CCNC4)nc3c2)c1] | N-[3-(2-{[(pyrrolidin-3-yl)methyl]amino}quinazolin-7-yl)phenyl]prop-2-enamide | 373.5 |
| 1150 | 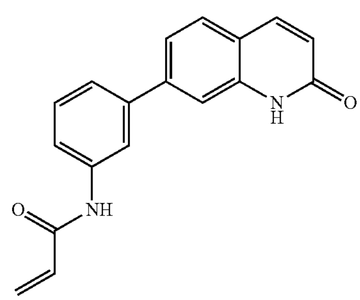 [SMILES: C=CC(=O)Nc1cccc(-c2ccc3ccc(=O)[nH]c3c2)c1] | N-[3-(2-oxo-1,2-dihydroquinolin-7-yl)phenyl]prop-2-enamide | 290.3 |
| 1151 | 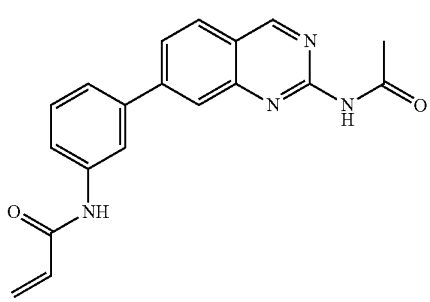 [SMILES: C=CC(=O)Nc1cccc(-c2ccc3cnc(NC(C)=O)nc3c2)c1] | N-[3-(2-acetamidoquinazolin-7-yl)phenyl]prop-2-enamide | 332.4 |
| 1152 | 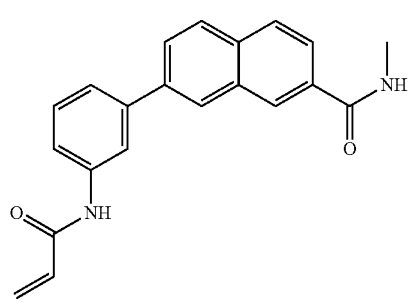 [SMILES: C=CC(=O)Nc1cccc(-c2ccc3ccc(C(=O)NC)cc3c2)c1] | N-methyl-7-[3-(prop-2-enamido)phenyl]naphthalene-2-carboxamide | 330.4 |

TABLE 16-continued

| Cpd No. | Structure | IUPAC | MW (g/mol) |
|---|---|---|---|
| 1153 | 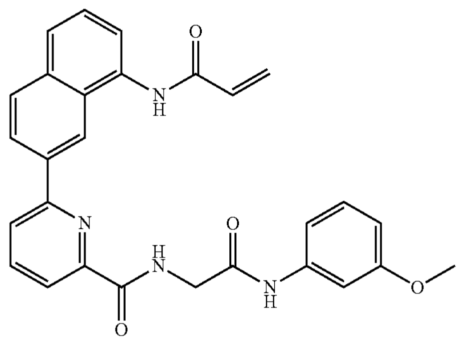 [SMILES: C=CC(=O)Nc1cccc2ccc(-c3cccc(C(=O)NCC(=O)Nc4cccc(OC)c4)n3)cc12] | N-{7-[6-({[(3-methoxyphenyl)carbamoyl]methyl}carbamoyl)pyridin-2-yl]naphthalen-1-yl}prop-2-enamide | 480.5 |
| 1154 | 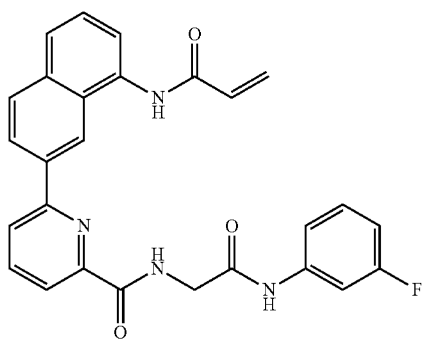 [SMILES: C=CC(=O)Nc1cccc2ccc(-c3cccc(C(=O)NCC(=O)Nc4cccc(F)c4)n3)cc12] | N-{7-[6-({[(3-fluorophenyl)carbamoyl]methyl}carbamoyl)pyridin-2-yl]naphthalen-1-yl}prop-2-enamide | 468.5 |
| 1155 | 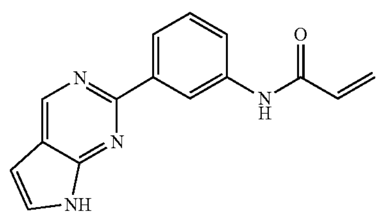 [SMILES: C=CC(=O)Nc1cccc(-c2ncc3cc[nH]c3n2)c1] | N-(3-{7H-pyrrolo[2,3-d]pyrimidin-2-yl}phenyl)prop-2-enamide | 264.3 |
| 1156 | 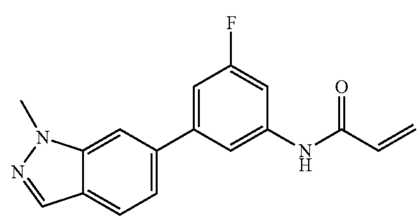 [SMILES: C=CC(=O)Nc1cc(F)cc(-c2ccc3cnn(C)c3c2)c1] | N-[3-fluoro-5-(1-methyl-1H-indazol-6-yl)phenyl]prop-2-enamide | 295.3 |
| 1157 | 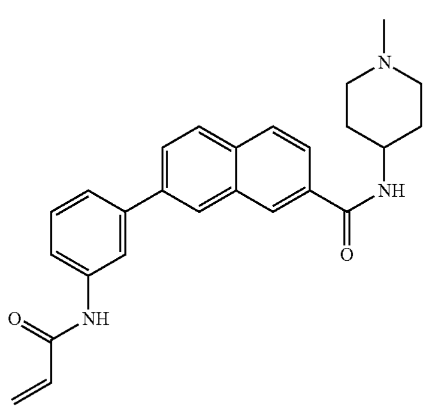 [SMILES: C=CC(=O)Nc1cccc(-c2ccc3ccc(C(=O)NC4CCN(C)CC4)cc3c2)c1] | N-(1-methylpiperidin-4-yl)-7-[3-(prop-2-enamido)phenyl]naphthalene-2-carboxamide | 413.5 |

TABLE 16-continued

| Cpd No. | Structure | IUPAC | MW (g/mol) |
|---|---|---|---|
| 1158 | 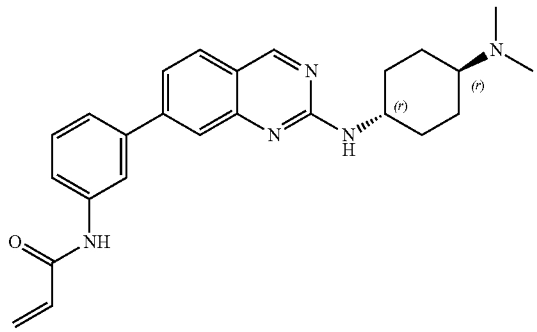 [SMILES: C=CC(=O)Nc1cccc(-c2ccc3cnc(N[C@H]4CC[C@H](N(C)C)CC4)nc3c2)c1] | N-[3-(2-{[(1r,4r)-4-(dimethylamino)cyclohexyl]amino}quinazolin-7-yl)phenyl]prop-2-enamide | 415.5 |
| 1159 | 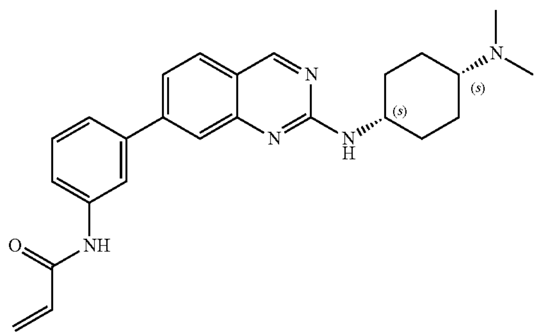 [SMILES: C=CC(=O)Nc1cccc(-c2ccc3cnc(N[C@H]4CC[C@@H](N(C)C)CC4)nc3c2)c1] | N-[3-(2-{[(1s,4s)-4-(dimethylamino)cyclohexyl]amino}quinazolin-7-yl)phenyl]prop-2-enamide | 415.5 |
| 1160 | 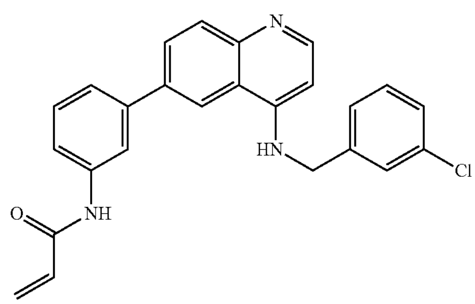 [SMILES: C=CC(=O)Nc1cccc(-c2ccc3nccc(NCc4cccc(Cl)c4)c3c2)c1] | N-[3-(4-{[(3-chlorophenyl)methyl]amino}quinolin-6-yl)phenyl]prop-2-enamide | 413.9 |
| 1161 | 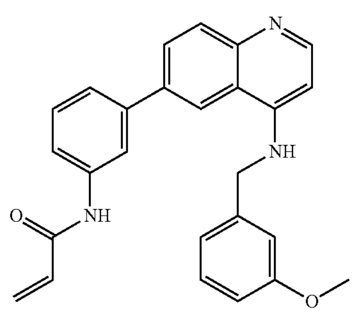 [SMILES: C=CC(=O)Nc1cccc(-c2ccc3nccc(NCc4cccc(OC)c4)c3c2)c1] | N-[3-(4-{[(3-methoxyphenyl)methyl]amino}quinolin-6-yl)phenyl]prop-2-enamide | 409.5 |
| 1162 | 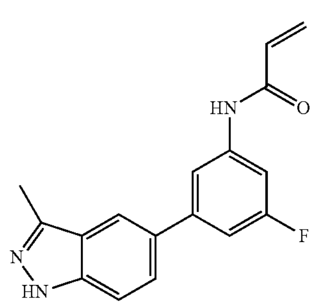 [SMILES: C=CC(=O)Nc1cc(F)cc(-c2ccc3[nH]nc(C)c3c2)c1] | N-[3-fluoro-5-(3-methyl-1H-indazol-5-yl)phenyl]prop-2-enamide | 295.3 |

TABLE 16-continued

| Cpd No. | Structure | IUPAC | MW (g/mol) |
|---|---|---|---|
| 1163 | 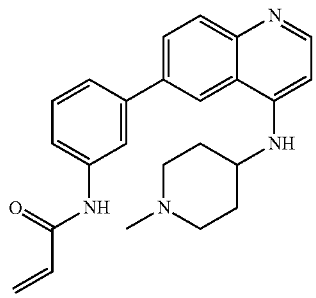 [SMILES: C=CC(=O)Nc1cccc(-c2ccc3nccc(NC4CCN(C)CC4)c3c2)c1] | N-(3-{4-[(1-methylpiperidin-4-yl)amino]quinolin-6-yl}phenyl)prop-2-enamide | 386.5 |
| 1164 | 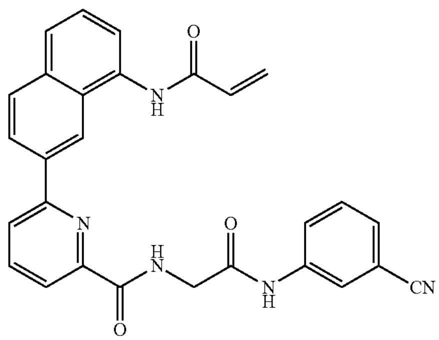 [SMILES: C=CC(=O)Nc1cccc2ccc(-c3cccc(C(=O)NCC(=O)Nc4cccc(C#N)c4)n3)cc12] | N-{7-[6-({[(3-cyanophenyl)carbamoyl]methyl}carbamoyl)pyridin-2-yl]naphthalen-1-yl}prop-2-enamide | 475.5 |
| 1165 | 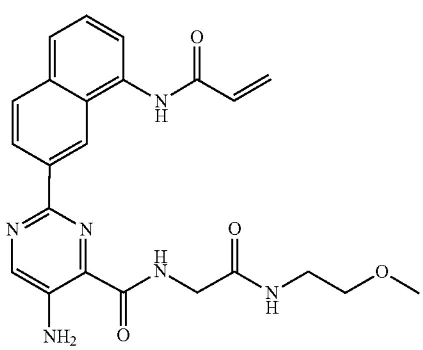 [SMILES: C=CC(=O)Nc1cccc2ccc(-c3ncc(N)c(C(=O)NCC(=O)NCCOC)n3)cc12] | N-{7-[5-amino-4-({[(2-methoxyethyl)carbamoyl]methyl}carbamoyl)pyrimidin-2-yl]naphthalen-1-yl}prop-2-enamide | 448.5 |
| 1166 | 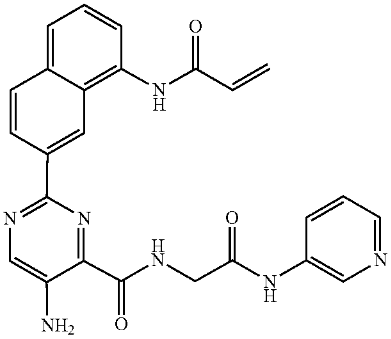 [SMILES: C=CC(=O)Nc1cccc2ccc(-c3ncc(N)c(C(=O)NCC(=O)Nc4cccnc4)n3)cc12] | N-{7-[5-amino-4-({[(pyridin-3-yl)carbamoyl]methyl}carbamoyl)pyrimidin-2-yl]naphthalen-1-yl}prop-2-enamide | 467.5 |

TABLE 16-continued

| Cpd No. | Structure | IUPAC | MW (g/mol) |
|---|---|---|---|
| 1167 | 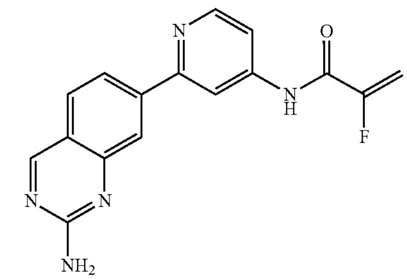 | N-[2-(2-aminoquinazolin-7-yl)pyridin-4-yl]-2-fluoroprop-2-enamide | 309.3 |
| 1168 | 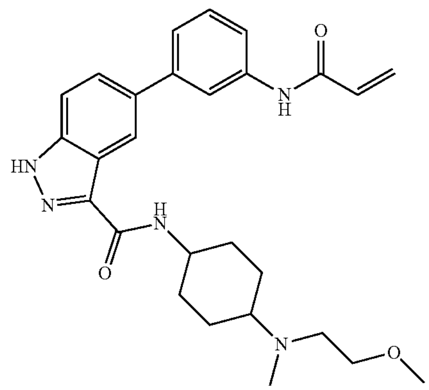 [SMILES: C=CC(=O)Nc1cccc(-c2ccc3[nH]nc(C(=O)NC4CCC(N(C)CCOC)CC4)c3c2)c1] | N-{4-[(2-methoxyethyl)(methyl)amino]cyclohexyl}-5-[3-(prop-2-enamido)phenyl]-1H-indazole-3-carboxamide | 475.6 |
| 1169 | 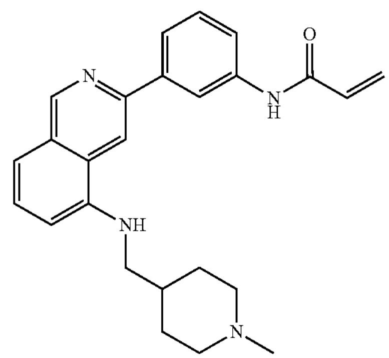 [SMILES: C=CC(=O)Nc1cccc(-c2cc3c(NCC4CCN(C)CC4)cccc3cn2)c1] | N-[3-(5-{[(1-methylpiperidin-4-yl)methyl]amino}isoquinolin-3-yl)phenyl]prop-2-enamide | 400.5 |
| 1170 | 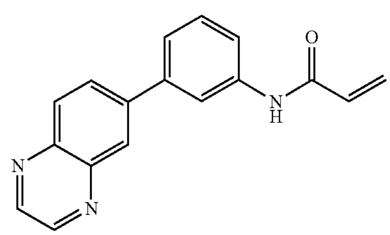 | N-[3-(quinoxalin-6-yl)phenyl]prop-2-enamide | 275.3 |
| 1171 | 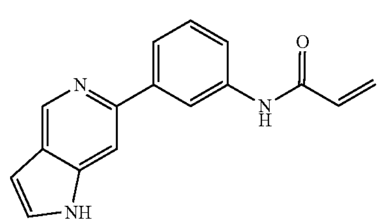 [SMILES: C=CC(=O)Nc1cccc(-c2cc3[nH]ccc3cn2)c1] | N-(3-{1H-pyrrolo[3,2-c]pyridin-6-yl}phenyl)prop-2-enamide | 263.3 |

TABLE 16-continued

| Cpd No. | Structure | IUPAC | MW (g/mol) |
|---|---|---|---|
| 1172 | 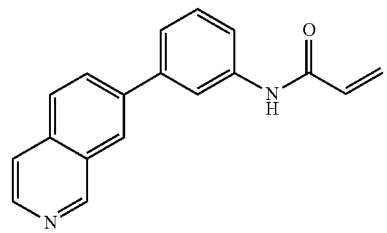 [SMILES: C=CC(=O)Nc1cccc(-c2ccc3ccncc3c2)c1] | N-[3-(isoquinolin-7-yl)phenyl]prop-2-enamide | 274.3 |
| 1173 | 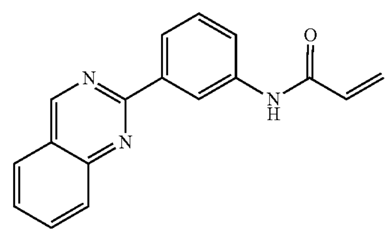 | N-[3-(quinazolin-2-yl)phenyl]prop-2-enamide | 275.3 |
| 1174 | 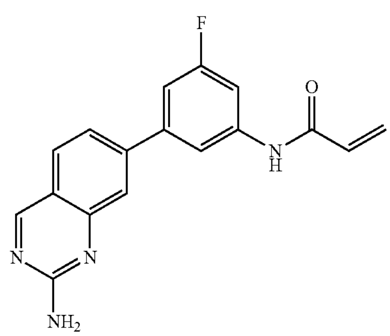 [SMILES: C=CC(=O)Nc1cc(F)cc(-c2ccc3cnc(N)nc3c2)c1] | N-[3-(2-aminoquinazolin-7-yl)-5-fluorophenyl]prop-2-enamide | 308.3 |
| 1175 | 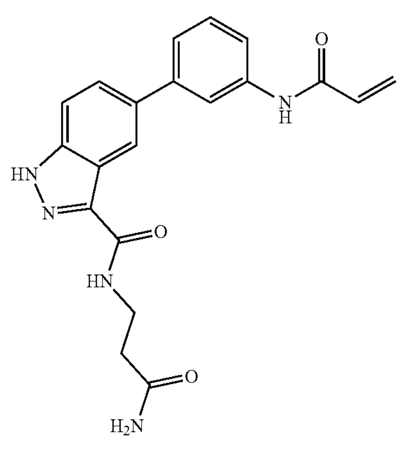 [SMILES: C=CC(=O)Nc1cccc(-c2ccc3[nH]nc(C(=O)NCCC(N)=O)c3c2)c1] | N-(3-{3-[(2-carbamoylethyl)carbamoyl]-1H-indazol-5-yl}phenyl)prop-2-enamide | 377.4 |

TABLE 16-continued

| Cpd No. | Structure | IUPAC | MW (g/mol) |
|---|---|---|---|
| 1176 | 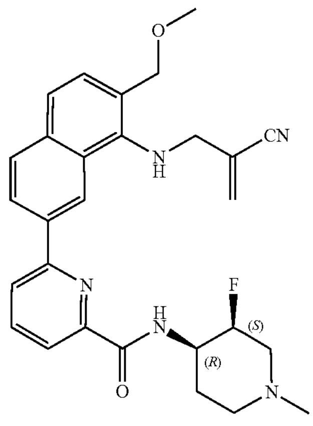 | 6-{8-[(2-cyano-2-methylideneethyl)amino]-7-(methoxymethyl)naphthalen-2-yl}-N-[(3S,4R)-3-fluoro-1-methylpiperidin-4-yl]pyridine-2-carboxamide | 487.6 |
| 1177 | 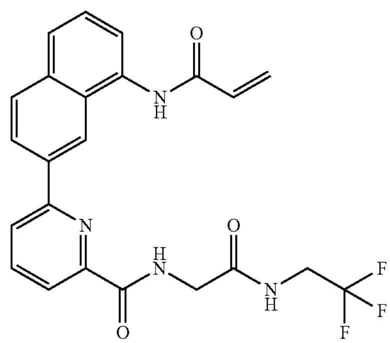 [SMILES: C=CC(=O)Nc1cccc2ccc(-c3cccc(C(=O)NCC(=O)NCC(F)(F)F)n3)cc12] | N-{7-[6-({[(2,2,2-trifluoroethyl)carbamoyl]methyl}carbamoyl)pyridin-2-yl]naphthalen-1-yl}prop-2-enamide | 456.4 |
| 1178 | 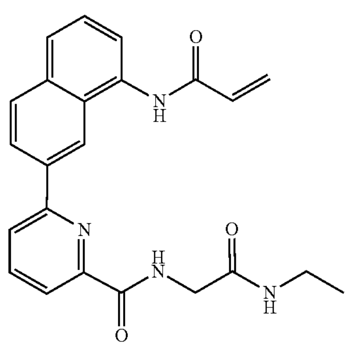 [SMILES: C=CC(=O)Nc1cccc2ccc(-c3cccc(C(=O)NCC(=O)NCC)n3)cc12] | N-[7-(6-{[(ethylcarbamoyl)methyl]carbamoyl}pyridin-2-yl)naphthalen-1-yl]prop-2-enamide | 402.5 |
| 1179 | 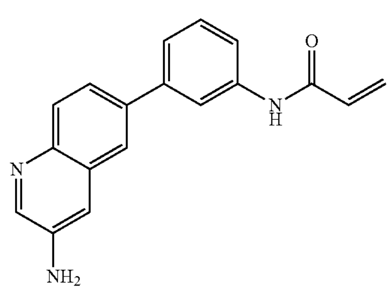 [SMILES: C=CC(=O)Nc1cccc(-c2ccc3ncc(N)cc3c2)c1] | N-[3-(3-aminoquinolin-6-yl)phenyl]prop-2-enamide | 289.3 |

TABLE 16-continued

| Cpd No. | Structure | IUPAC | MW (g/mol) |
|---|---|---|---|
| 1180 | 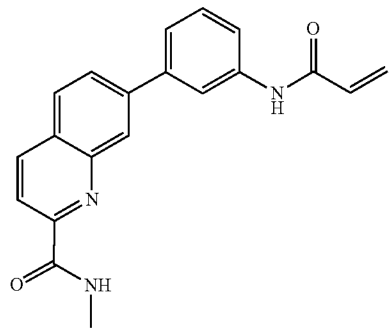 [SMILES: C=CC(=O)Nc1cccc(-c2ccc3ccc(C(=O)NC)nc3c2)c1] | N-methyl-7-[3-(prop-2-enamido)phenyl]quinoline-2-carboxamide | 331.4 |
| 1181 | 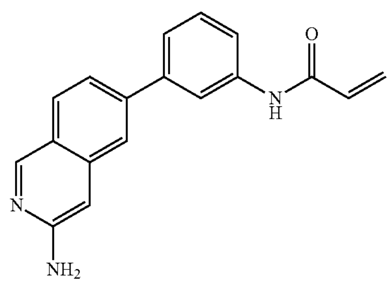 [SMILES: C=CC(=O)Nc1cccc(-c2ccc3cnc(N)cc3c2)c1] | N-[3-(3-aminoisoquinolin-6-yl)phenyl]prop-2-enamide | 289.3 |
| 1182 | 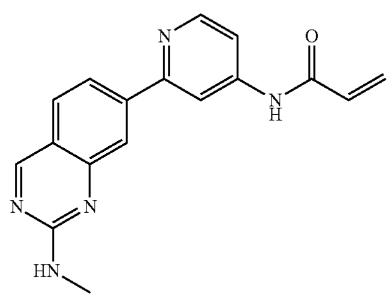 [SMILES: C=CC(=O)Nc1ccnc(-c2ccc3cnc(NC)nc3c2)c1] | N-{2-[2-(methylamino)quinazolin-7-yl]pyridin-4-yl}prop-2-enamide | 305.3 |
| 1183 | 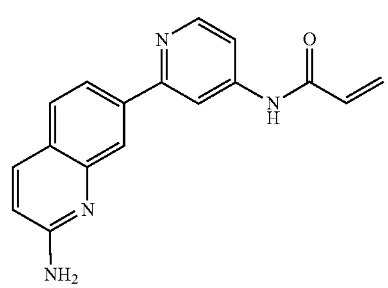 | N-[2-(2-aminoquinolin-7-yl)pyridin-4-yl]prop-2-enamide | 290.3 |
| 1184 | 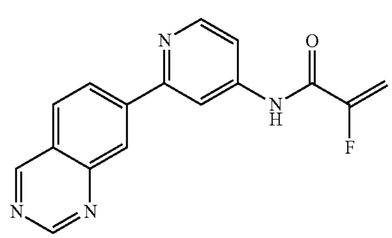 [SMILES: C=C(F)C(=O)Nc1ccnc(-c2ccc3cncnc3c2)c1] | 2-fluoro-N-[2-(quinazolin-7-yl)pyridin-4-yl]prop-2-enamide | 294.3 |

TABLE 16-continued
| Cpd No. | Structure | IUPAC | MW (g/mol) |
|---|---|---|---|
| 1185 | 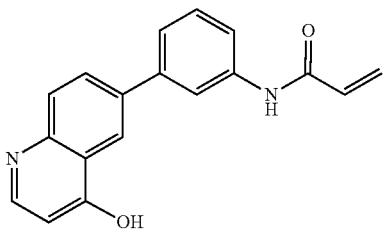 [SMILES: C=CC(=O)Nc1cccc(-c2ccc3nccc(O)c3c2)c1] | N-[3-(4-hydroxyquinolin-6-yl)phenyl]prop-2-enamide | 290.3 |
| 1186 | 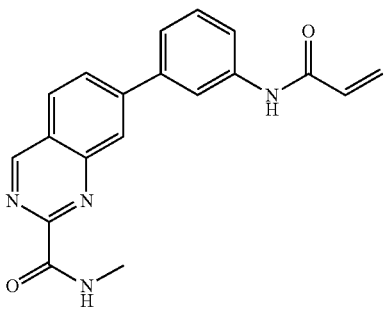 [SMILES: C=CC(=O)Nc1cccc(-c2ccc3cnc(C(=O)NC)nc3c2)c1] | N-methyl-7-[3-(prop-2-enamido)phenyl]quinazoline-2-carboxamide | 332.4 |
| 1187 | 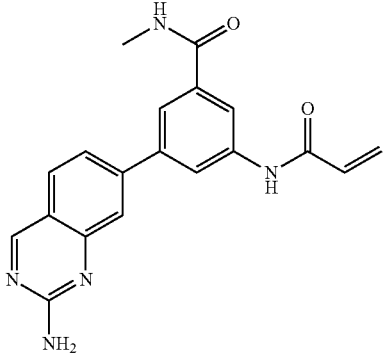 [SMILES: C=CC(=O)Nc1cc(C(=O)NC)cc(-c2ccc3cnc(N)nc3c2)c1] | 3-(2-aminoquinazolin-7-yl)-N-methyl-5-(prop-2-enamido)benzamide | 347.4 |
| 1188 | 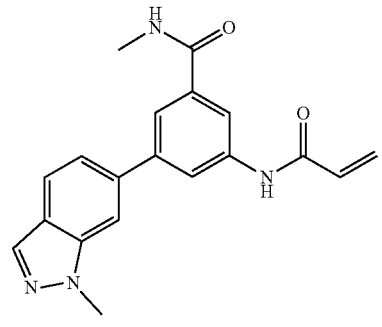 [SMILES: C=CC(=O)Nc1cc(C(=O)NC)cc(-c2ccc3cnn(C)c3c2)c1] | N-methyl-3-(1-methyl-1H-indazol-6-yl)-5-(prop-2-enamido)benzamide | 334.4 |
| 1189 | 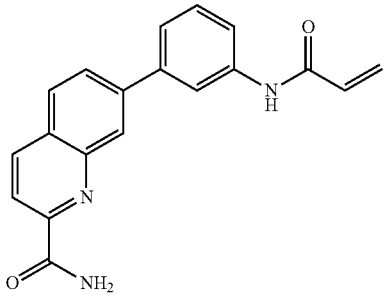 | 7-[3-(prop-2-enamido)phenyl]quinoline-2-carboxamide | 317.3 |

TABLE 16-continued

| Cpd No. | Structure | IUPAC | MW (g/mol) |
|---|---|---|---|
| 1190 | 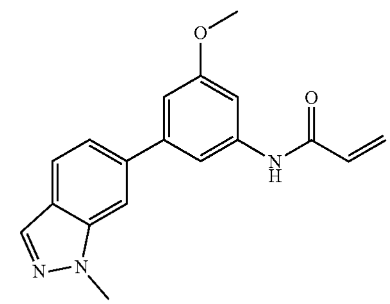 [SMILES: C=CC(=O)Nc1cc(OC)cc(-c2ccc3cnn(C)c3c2)c1] | N-[3-methoxy-5-(1-methyl-1H-indazol-6-yl)phenyl]prop-2-enamide | 307.4 |
| 1191 | 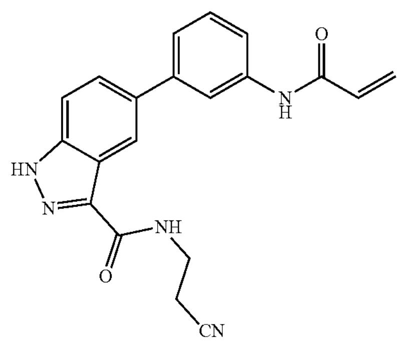 [SMILES: C=CC(=O)Nc1cccc(-c2ccc3[nH]nc(C(=O)NCCC#N)c3c2)c1] | N-(2-cyanoethyl)-5-[3-(prop-2-enamido)phenyl]-1H-indazole-3-carboxamide | 359.4 |
| 1192 | 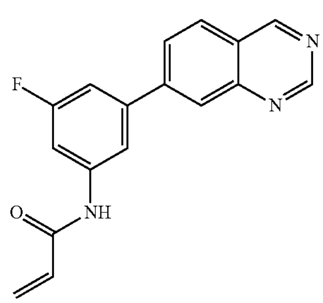 [SMILES: C=CC(=O)Nc1cc(F)cc(-c2ccc3cncnc3c2)c1] | N-[3-fluoro-5-(quinazolin-7-yl)phenyl]prop-2-enamide | 293.3 |
| 1193 | 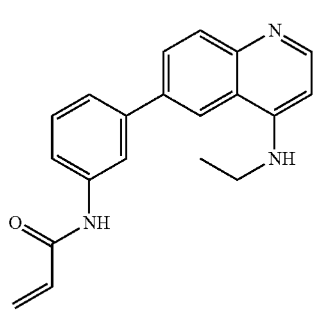 [SMILES: C=CC(=O)Nc1cccc(-c2ccc3nccc(NCC)c3c2)c1] | N-{3-[4-(ethylamino)quinolin-6-yl]phenyl}prop-2-enamide | 317.4 |

TABLE 16-continued

| Cpd No. | Structure | IUPAC | MW (g/mol) |
|---|---|---|---|
| 1194 | 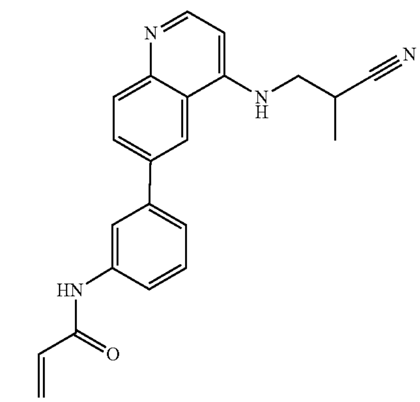 [SMILES: C=CC(=O)Nc1cccc(-c2ccc3nccc(NCC(C)C#N)c3c2)c1] | N-(3-{4-[(2-cyano-2-methylethyl)amino]quinolin-6-yl}phenyl)prop-2-enamide | 356.4 |
| 1195 | 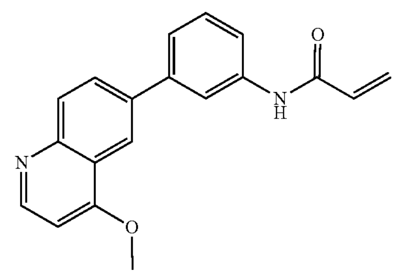 [SMILES: C=CC(=O)Nc1cccc(-c2ccc3nccc(OC)c3c2)c1] | N-[3-(4-methoxyquinolin-6-yl)phenyl]prop-2-enamide | 304.3 |
| 1196 | 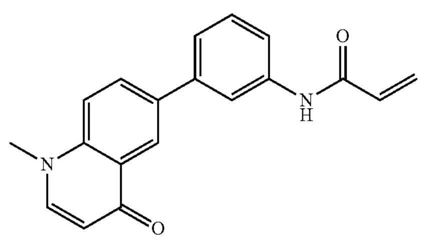 [SMILES: C=CC(=O)Nc1cccc(-c2ccc3c(c2)c(=O)ccn3C)c1] | N-[3-(1-methyl-4-oxo-1,4-dihydroquinolin-6-yl)phenyl]prop-2-enamide | 304.3 |
| 1197 | 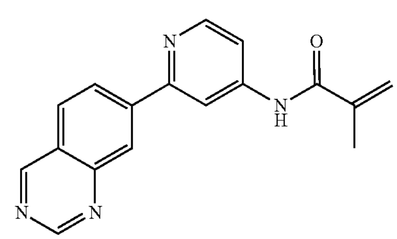 [SMILES: C=C(C)C(=O)Nc1ccnc(-c2ccc3cncnc3c2)c1] | 2-methyl-N-[2-(quinazolin-7-yl)pyridin-4-yl]prop-2-enamide | 290.3 |
| 1198 | 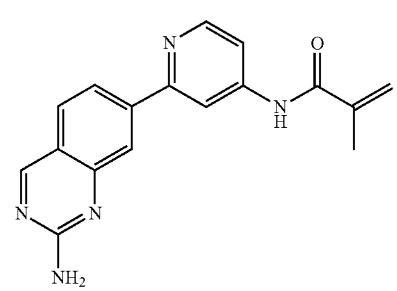 [SMILES: C=C(C)C(=O)Nc1ccnc(-c2ccc3cnc(N)nc3c2)c1] | N-[2-(2-aminoquinazolin-7-yl)pyridin-4-yl]-2-methylprop-2-enamide | 305.3 |

TABLE 16-continued

| Cpd No. | Structure | IUPAC | MW (g/mol) |
|---|---|---|---|
| 1199 | 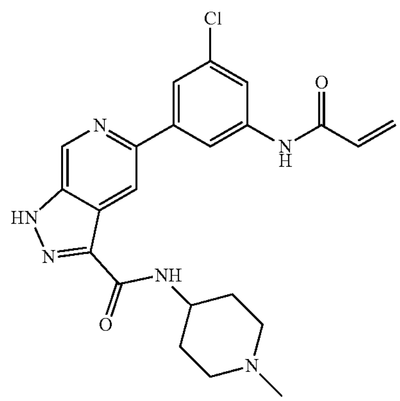 [SMILES: C=CC(=O)Nc1cc(Cl)cc(-c2cc3c(C(=O)NC4CCN(C)CC4)n[nH]c3cn2)c1] | 5-[3-chloro-5-(prop-2-enamido)phenyl]-N-(1-methylpiperidin-4-yl)-1H-pyrazolo[3,4-c]pyridine-3-carboxamide | 438.9 |
| 1200 | 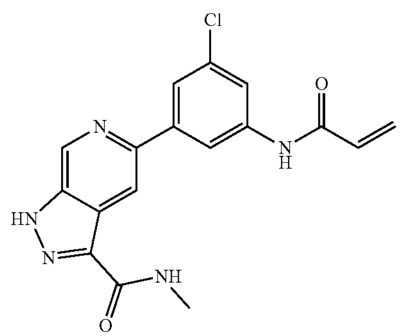 [SMILES: C=CC(=O)Nc1cc(Cl)cc(-c2cc3c(C(=O)NC)n[nH]c3cn2)c1] | 5-[3-chloro-5-(prop-2-enamido)phenyl]-N-methyl-1H-pyrazolo[3,4-c]pyridine-3-carboxamide | 355.8 |
| 1201 | 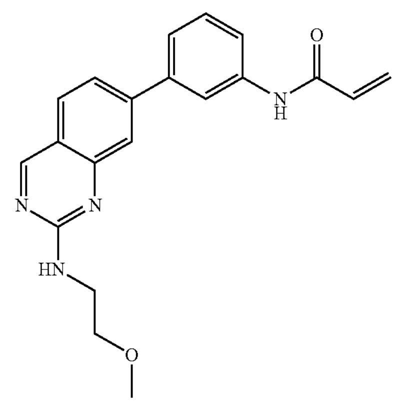 [SMILES: C=CC(=O)Nc1cccc(-c2ccc3cnc(NCCOC)nc3c2)c1] | N-(3-{2-[(2-methoxyethyl)amino]quinazolin-7-yl}phenyl)prop-2-enamide | 348.4 |
| 1202 | 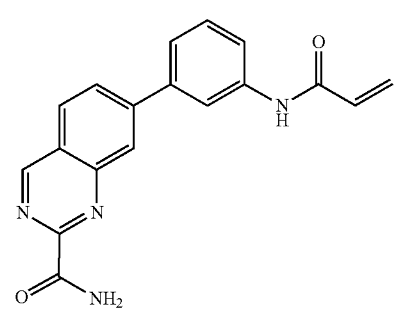 | 7-[3-(prop-2-enamido)phenyl]quinazoline-2-carboxamide | 318.3 |

TABLE 16-continued

| Cpd No. | Structure | IUPAC | MW (g/mol) |
|---|---|---|---|
| 1203 | 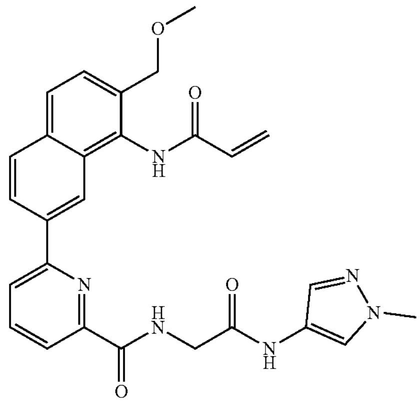 [SMILES: C=CC(=O)Nc1c(COC)ccc2ccc(-c3cccc(C(=O)NCC(=O)Nc4cnn(C)c4)n3)cc12] | N-[2-(methoxymethyl)-7-[6-({[(1-methyl-1H-pyrazol-4-yl)carbamoyl]methyl}carbamoyl)pyridin-2-yl]naphthalen-1-yl]prop-2-enamide | 498.5 |
| 1204 | 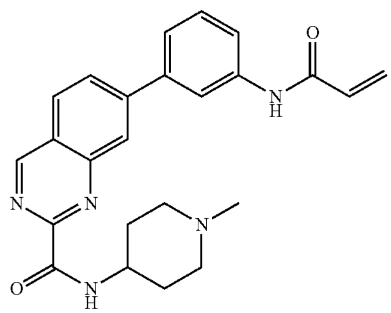 [SMILES: C=CC(=O)Nc1cccc(-c2ccc3cnc(C(=O)NC4CCN(C)CC4)nc3c2)c1] | N-(1-methylpiperidin-4-yl)-7-[3-(prop-2-enamido)phenyl]quinazoline-2-carboxamide | 415.5 |
| 1205 | 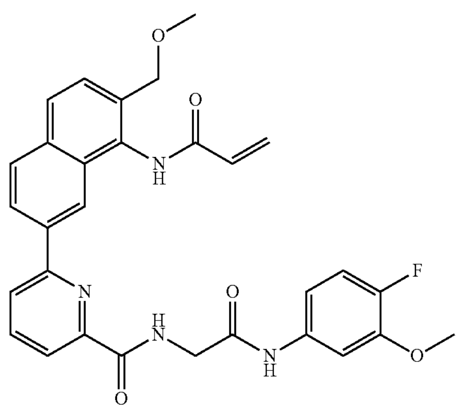 [SMILES: C=CC(=O)Nc1c(COC)ccc2ccc(-c3cccc(C(=O)NCC(=O)Nc4ccc(F)c(OC)c4)n3)cc12] | N-{7-[6-({[(4-fluoro-3-methoxyphenyl)carbamoyl]methyl}carbamoyl)pyridin-2-yl]-2-(methoxymethyl)naphthalen-1-yl}prop-2-enamide | 542.6 |
| 1206 | 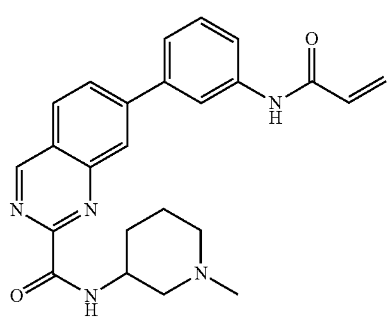 [SMILES: C=CC(=O)Nc1cccc(-c2ccc3cnc(C(=O)NC4CCCN(C)C4)nc3c2)c1] | N-(1-methylpiperidin-3-yl)-7-[3-(prop-2-enamido)phenyl]quinazoline-2-carboxamide | 415.5 |

TABLE 16-continued

| Cpd No. | Structure | IUPAC | MW (g/mol) |
|---|---|---|---|
| 1207 | 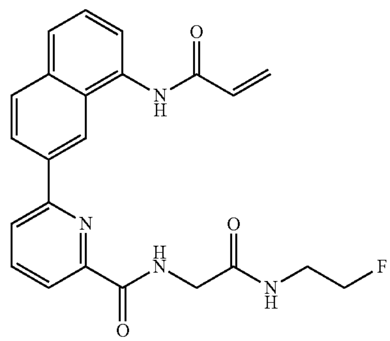 [SMILES: C=CC(=O)Nc1cccc2ccc(-c3cccc(C(=O)NCC(=O)NCCF)n3)cc12] | N-{7-[6-({[(2-fluoroethyl)carbamoyl]methyl}carbamoyl)pyridin-2-yl]naphthalen-1-yl}prop-2-enamide | 420.4 |
| 1208 | 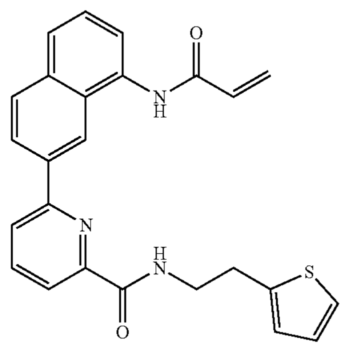 [SMILES: C=CC(=O)Nc1cccc2ccc(-c3cccc(C(=O)NCCc4cccs4)n3)cc12] | 6-[8-(prop-2-enamido)naphthalen-2-yl]-N-[2-(thiophen-2-yl)ethyl]pyridine-2-carboxamide | 427.5 |
| 1209 | 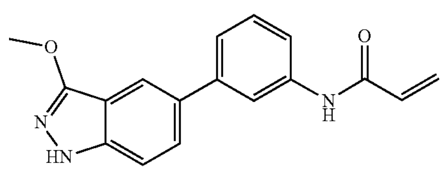 [SMILES: C=CC(=O)Nc1cccc(-c2ccc3[nH]nc(OC)c3c2)c1] | N-[3-(3-methoxy-1H-indazol-5-yl)phenyl]prop-2-enamide | 293.3 |
| 1210 | 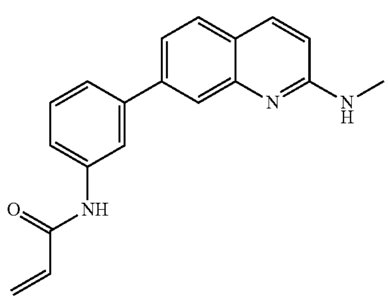 [SMILES: C=CC(=O)Nc1cccc(-c2ccc3ccc(NC)nc3c2)c1] | N-{3-[2-(methylamino)quinolin-7-yl]phenyl}prop-2-enamide | 303.4 |
| 1211 | 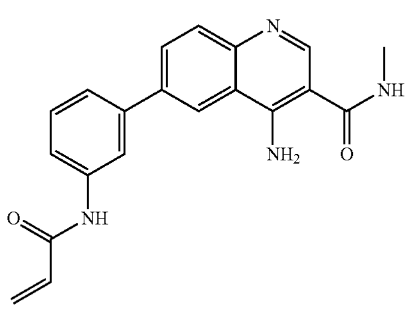 [SMILES: C=CC(=O)Nc1cccc(-c2ccc3ncc(C(=O)NC)c(N)c3c2)c1] | 4-amino-N-methyl-6-[3-(prop-2-enamido)phenyl]quinoline-3-carboxamide | 346.4 |

TABLE 16-continued

| Cpd No. | Structure | IUPAC | MW (g/mol) |
|---|---|---|---|
| 1212 | 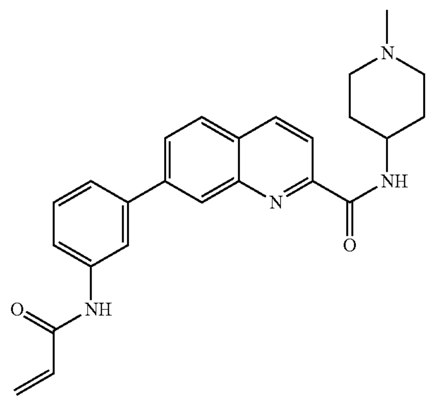 [SMILES: C=CC(=O)Nc1cccc(-c2ccc3ccc(C(=O)NC4CCN(C)CC4)nc3c2)c1] | N-(1-methylpiperidin-4-yl)-7-[3-(prop-2-enamido)phenyl]quinoline-2-carboxamide | 414.5 |
| 1213 | 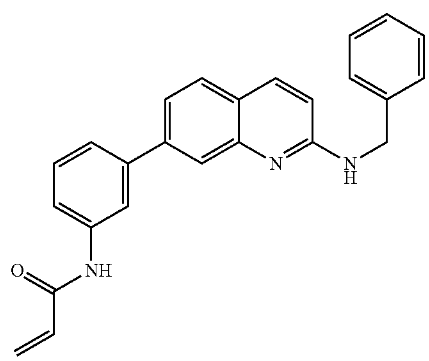 [SMILES: C=CC(=O)Nc1cccc(-c2ccc3ccc(NCc4ccccc4)nc3c2)c1] | N-{3-[2-(benzylamino)quinolin-7-yl]phenyl}prop-2-enamide | 379.5 |
| 1214 | 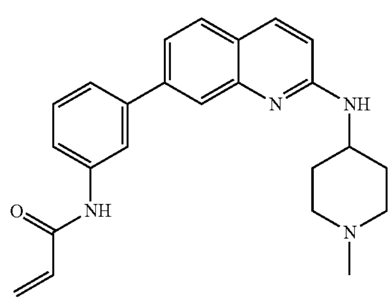 [SMILES: C=CC(=O)Nc1cccc(-c2ccc3ccc(NC4CCN(C)CC4)nc3c2)c1] | N-(3-{2-[(1-methylpiperidin-4-yl)amino]quinolin-7-yl}phenyl)prop-2-enamide | 386.5 |
| 1215 | 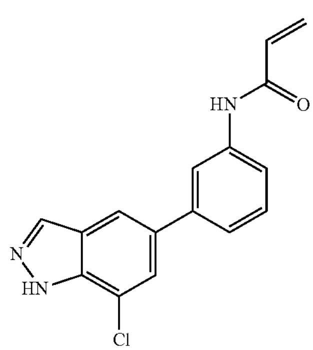 | N-[3-(7-chloro-1H-indazol-5-yl)phenyl]prop-2-enamide | 297.7 |

US 11,926,632 B2

TABLE 16-continued

| Cpd No. | Structure | IUPAC | MW (g/mol) |
|---|---|---|---|
| 1216 | 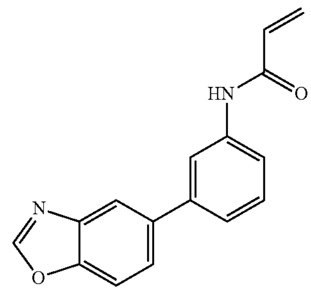 [SMILES: C=CC(=O)Nc1cccc(-c2ccc3ocnc3c2)c1] | N-[3-(1,3-benzoxazol-5-yl)phenyl]prop-2-enamide | 264.3 |
| 1217 | 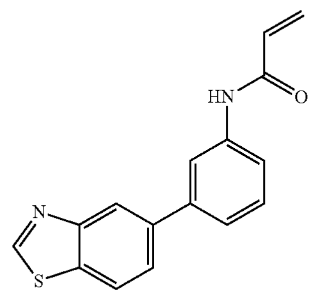 [SMILES: C=CC(=O)Nc1cccc(-c2ccc3scnc3c2)c1] | N-[3-(1,3-benzothiazol-5-yl)phenyl]prop-2-enamide | 280.4 |
| 1218 | 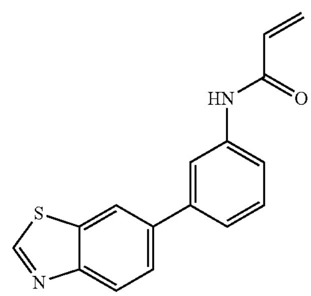 [SMILES: C=CC(=O)Nc1cccc(-c2ccc3ncsc3c2)c1] | N-[3-(1,3-benzothiazol-6-yl)phenyl]prop-2-enamide | 280.4 |
| 1219 | 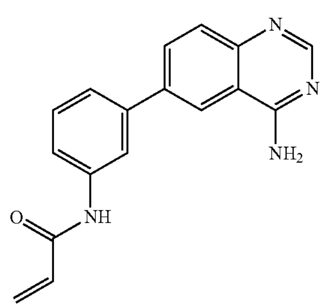 [SMILES: C=CC(=O)Nc1cccc(-c2ccc3ncnc(N)c3c2)c1] | N-[3-(4-aminoquinazolin-6-yl)phenyl]prop-2-enamide | 290.3 |
| 1220 | 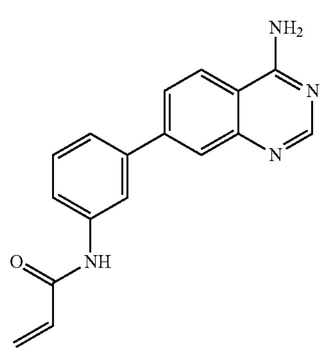 [SMILES: C=CC(=O)Nc1cccc(-c2ccc3c(N)ncnc3c2)c1] | N-[3-(4-aminoquinazolin-7-yl)phenyl]prop-2-enamide | 290.3 |

TABLE 16-continued

| Cpd No. | Structure | IUPAC | MW (g/mol) |
|---|---|---|---|
| 1221 | 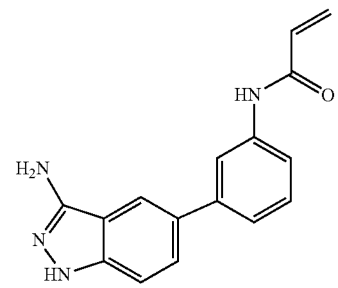 [SMILES: C=CC(=O)Nc1cccc(-c2ccc3[nH]nc(N)c3c2)c1] | N-[3-(3-amino-1H-indazol-5-yl)phenyl]prop-2-enamide | 278.3 |
| 1222 | 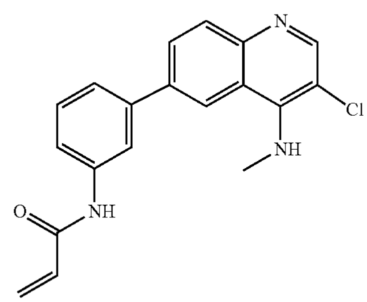 [SMILES: C=CC(=O)Nc1cccc(-c2ccc3ncc(Cl)c(NC)c3c2)c1] | N-{3-[3-chloro-4-(methylamino)quinolin-6-yl]phenyl}prop-2-enamide | 337.8 |
| 1223 | 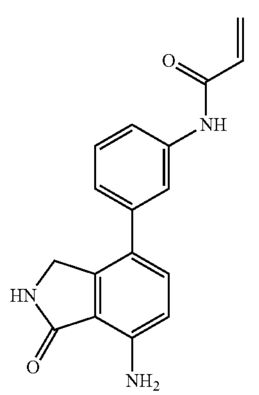 [SMILES: C=CC(=O)Nc1cccc(-c2ccc(N)c3c2CNC3=O)c1] | N-[3-(7-amino-1-oxo-2,3-dihydro-1H-isoindol-4-yl)phenyl]prop-2-enamide | 293.3 |
| 1224 | 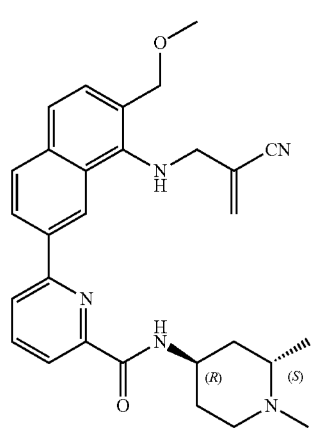 | 6-{8-[(2-cyano-2-methylideneethyl)amino]-7-(methoxymethyl)naphthalen-2-yl}-N-[(2S,4R)-1,2-dimethylpiperidin-4-yl]pyridine-2-carboxamide | 483.6 |

TABLE 16-continued

| Cpd No. | Structure | IUPAC | MW (g/mol) |
|---|---|---|---|
| 1225 | 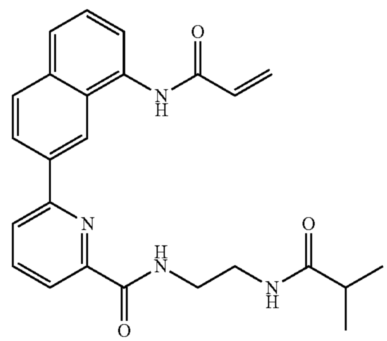 [SMILES: C=CC(=O)Nc1cccc2ccc(-c3cccc(C(=O)NCCNC(=O)C(C)C)n3)cc12] | N-[7-(6-{[2-(2-methylpropanamido)ethyl]carbamoyl}pyridin-2-yl)naphthalen-1-yl]prop-2-enamide | 430.5 |
| 1226 | 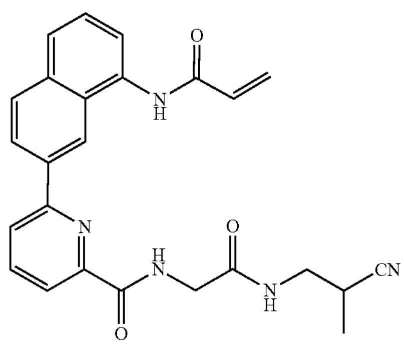 [SMILES: C=CC(=O)Nc1cccc2ccc(-c3cccc(C(=O)NCC(=O)NCC(C)C#N)n3)cc12] | N-{7-[6-({[(2-cyano-2-methylethyl)carbamoyl]methyl}carbamoyl)pyridin-2-yl]naphthalen-1-yl}prop-2-enamide | 441.5 |
| 1227 | 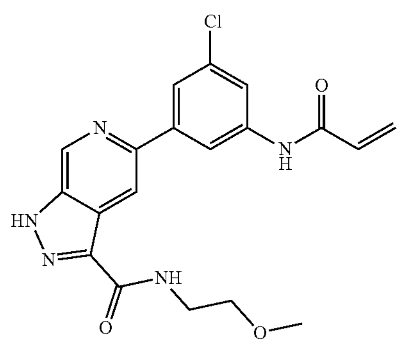 [SMILES: C=CC(=O)Nc1cc(Cl)cc(-c2cc3c(C(=O)NCCOC)n[nH]c3cn2)c1] | 5-[3-chloro-5-(prop-2-enamido)phenyl]-N-(2-methoxyethyl)-1H-pyrazolo[3,4-c]pyridine-3-carboxamide | 399.8 |
| 1228 | 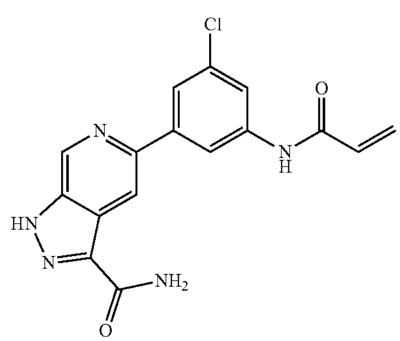 [SMILES: C=CC(=O)Nc1cc(Cl)cc(-c2cc3c(C(N)=O)n[nH]c3cn2)c1] | 5-{3-chloro-5-(prop-2-enamido)phenyl]-1H-pyrazolo[3,4-c]pyridine-3-carboxamide | 341.8 |

TABLE 16-continued

| Cpd No. | Structure | IUPAC | MW (g/mol) |
|---|---|---|---|
| 1229 | 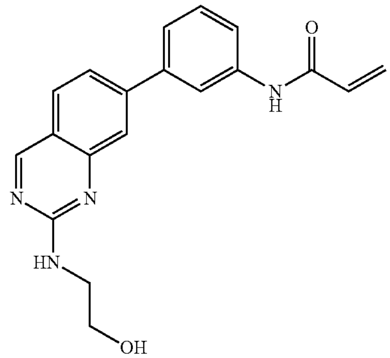 [SMILES: C=CC(=O)Nc1cccc(-c2ccc3cnc(NCCO)nc3c2)c1] | N-(3-{2-[(2-hydroxyethyl)amino]quinazolin-7-yl}phenyl)prop-2-enamide | 334.4 |
| 1230 | 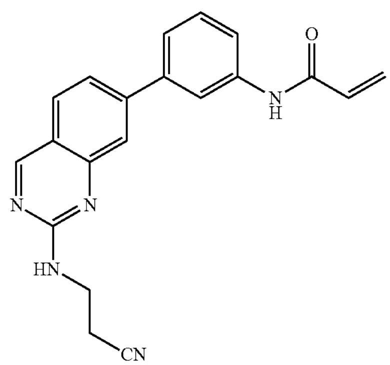 [SMILES: C=CC(=O)Nc1cccc(-c2ccc3cnc(NCCC#N)nc3c2)c1] | N-(3-{2-[(2-cyanoethyl)amino]quinazolin-7-yl}phenyl)prop-2-enamide | 343.4 |
| 1231 | 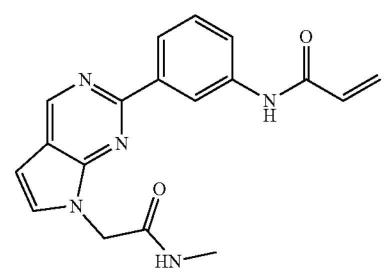 [SMILES: C=CC(=O)Nc1cccc(-c2ncc3ccn(CC(=O)NC)c3n2)c1] | N-(3-{7-[(methylcarbamoyl)methyl]-7H-pyrrolo[2,3-d]pyrimidin-2-yl}phenyl)prop-2-enamide | 335.4 |
| 1232 | 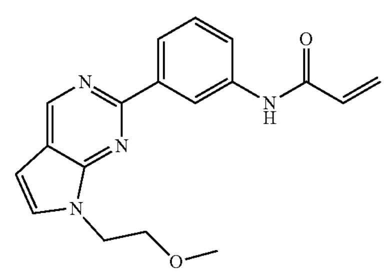 [SMILES: C=CC(=O)Nc1cccc(-c2ncc3ccn(CCOC)c3n2)c1] | N-{3-[7-(2-methoxyethyl)-7H-pyrrolo[2,3-d]pyrimidin-2-yl]phenyl}prop-2-enamide | 322.4 |

TABLE 16-continued

| Cpd No. | Structure | IUPAC | MW (g/mol) |
|---|---|---|---|
| 1233 | 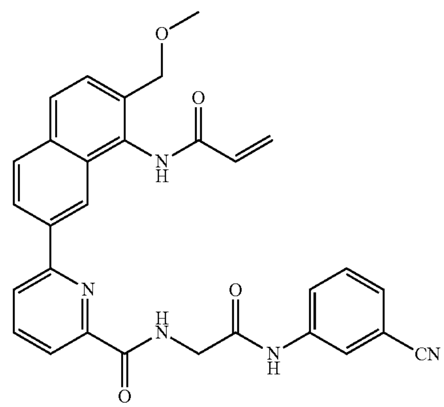 [SMILES: C=CC(=O)Nc1c(COC)ccc2ccc(-c3cccc(C(=O)NCC(=O)Nc4cccc(C#N)c4)n3)cc12] | N-{7-[6-({[(3-cyanophenyl)carbamoyl]methyl}carbamoyl)pyridin-2-yl]-2-(methoxymethyl)naphthalen-1-yl}prop-2-enamide | 519.6 |
| 1234 | 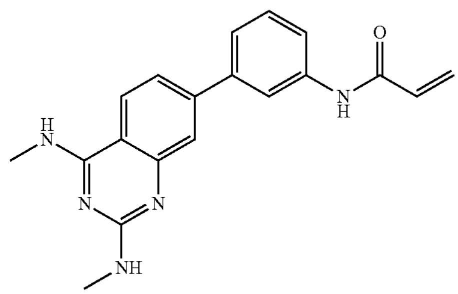 [SMILES: C=CC(=O)Nc1cccc(-c2ccc3c(NC)nc(NC)nc3c2)c1] | N-{3-[2,4-bis(methylamino)quinazolin-7-yl]phenyl}prop-2-enamide | 333.4 |
| 1235 | 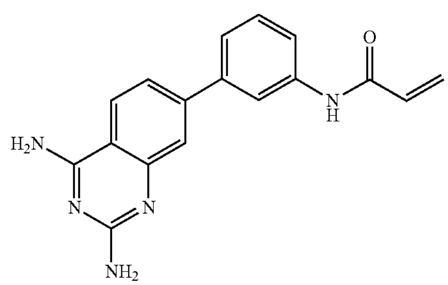 [SMILES: C=CC(=O)Nc1cccc(-c2ccc3c(N)nc(N)nc3c2)c1] | N-[3-(2,4-diaminoquinazolin-7-yl)phenyl]prop-2-enamide | 305.3 |
| 1236 | 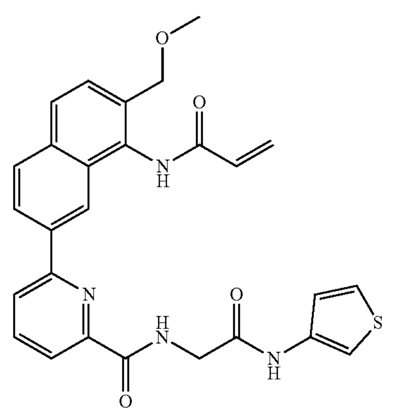 [SMILES: C=CC(=O)Nc1c(COC)ccc2ccc(-c3cccc(C(=O)NCC(=O)Nc4ccsc4)n3)cc12] | N-[2-(methoxymethyl)-7-[6-({[(thiophen-3-yl)carbamoyl]methyl}carbamoyl)pyridin-2-yl]naphthalen-1-yl]prop-2-enamide | 500.6 |

| Cpd No. | Structure | IUPAC | MW (g/mol) |
|---|---|---|---|
| 1237 | 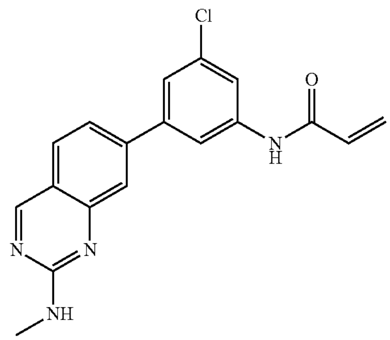 [SMILES: C=CC(=O)Nc1cc(Cl)cc(-c2ccc3cnc(NC)nc3c2)c1] | N-{3-chloro-5-[2-(methylamino)quinazolin-7-yl]phenyl}prop-2-enamide | 338.8 |
| 1238 | 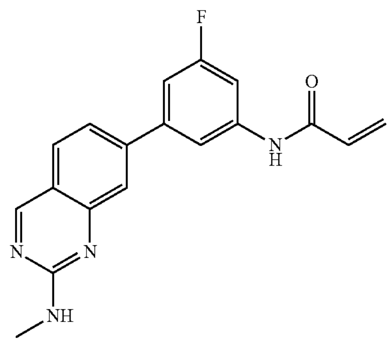 | N-{3-fluoro-5-[2-(methylamino)quinazolin-7-yl]phenyl}prop-2-enamide | 322.3 |
| 1239 | 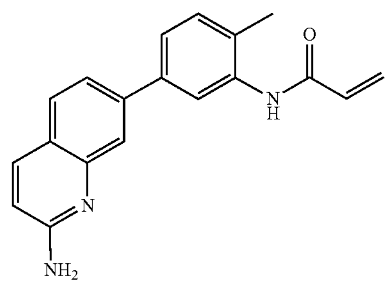 [SMILES: C=CC(=O)Nc1cc(-c2ccc3ccc(N)nc3c2)ccc1C] | N-[5-(2-aminoquinolin-7-yl)-2-methylphenyl]prop-2-enamide | 303.4 |
| 1240 | 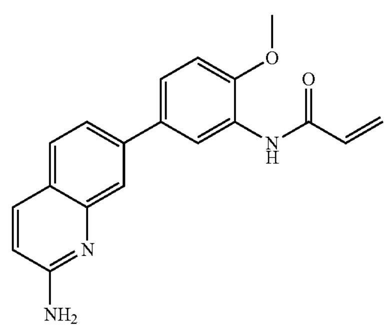 [SMILES: C=CC(=O)Nc1cc(-c2ccc3ccc(N)nc3c2)ccc1OC] | N-[5-(2-aminoquinolin-7-yl)-2-methoxyphenyl]prop-2-enamide | 319.4 |
| 1241 | 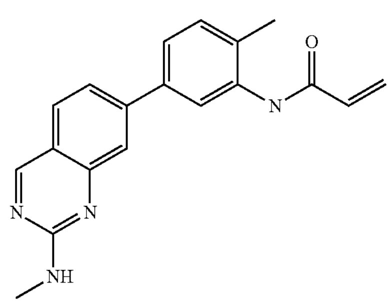 | N-{2-methyl-5-[2-(methylamino)quinazolin-7-yl]phenyl}prop-2-enamide | 318.4 |

TABLE 16-continued

| Cpd No. | Structure | IUPAC | MW (g/mol) |
|---|---|---|---|
| 1242 | 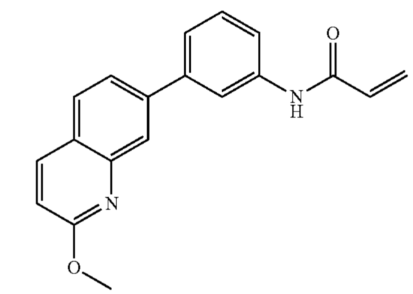 [SMILES: C=CC(=O)Nc1cccc(-c2ccc3ccc(OC)nc3c2)c1] | N-[3-(2-methoxyquinolin-7-yl)phenyl]prop-2-enamide | 304.3 |
| 1243 | 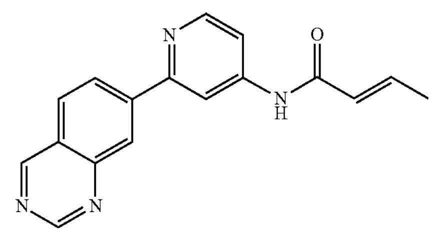 [SMILES: C/C=C/C(=O)Nc1ccnc(-c2ccc3cncnc3c2)c1] | (2E)-N-[2-(quinazolin-7-yl)pyridin-4-yl]but-2-enamide | 290.3 |
| 1244 | 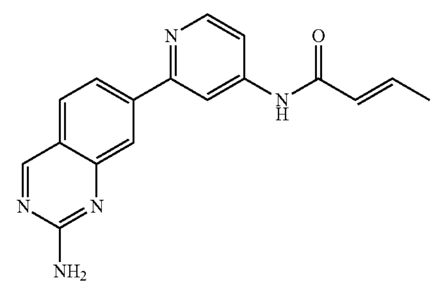 [SMILES: C/C=C/C(=O)Nc1ccnc(-c2ccc3cnc(N)nc3c2)c1] | (2E)-N-[2-(2-aminoquinazolin-7-yl)pyridin-4-yl]but-2-enamide | 305.3 |
| 1245 | 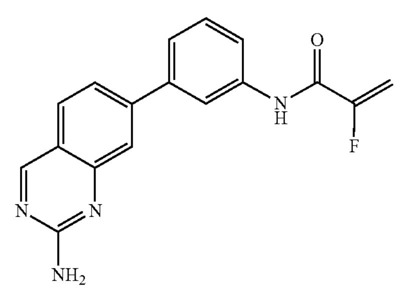 [SMILES: C=C(F)C(=O)Nc1cccc(-c2ccc3cnc(N)nc3c2)c1] | N-[3-(2-aminoquinazolin-7-yl)phenyl]-2-fluoroprop-2-enamide | 308.3 |
| 1246 | 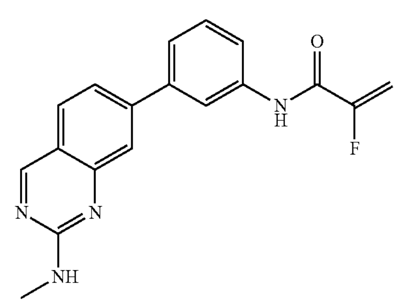 [SMILES: C=C(F)C(=O)Nc1cccc(-c2ccc3cnc(NC)nc3c2)c1] | 2-fluoro-N-{3-[2-(methylamino)quinazolin-7-yl]phenyl}prop-2-enamide | 322.3 |

TABLE 16-continued

| Cpd No. | Structure | IUPAC | MW (g/mol) |
|---|---|---|---|
| 1247 | 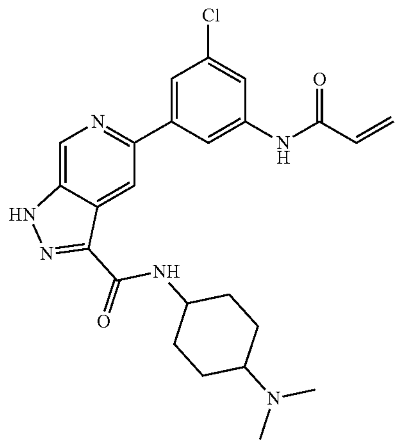 [SMILES: C=CC(=O)Nc1cc(Cl)cc(-c2cc3c(C(=O)NC4CCC(N(C)C)CC4)n[nH]c3cn2)c1] | 5-[3-chloro-5-(prop-2-enamido)phenyl]-N-[4-(dimethylamino)cyclohexyl]-1H-pyrazolo[3,4-c]pyridine-3-carboxamide | 467.0 |
| 1248 | 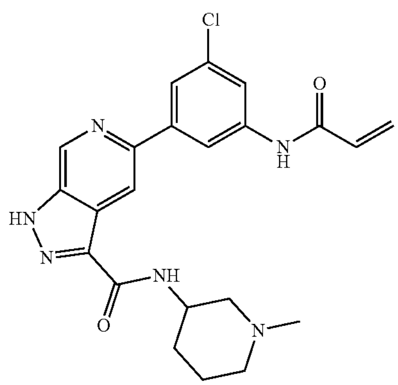 [SMILES: C=CC(=O)Nc1cc(Cl)cc(-c2cc3c(C(=O)NC4CCCN(C)C4)n[nH]c3cn2)c1] | 5-[3-chloro-5-(prop-2-enamido)phenyl]-N-(1-methylpiperidin-3-yl)-1H-pyrazolo[3,4-c]pyridine-3-carboxamide | 438.9 |
| 1249 | 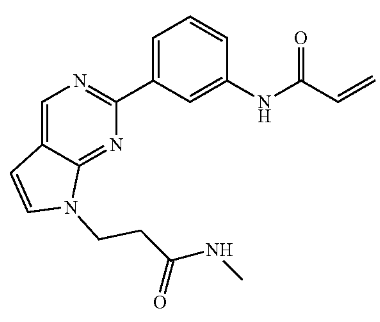 [SMILES: C=CC(=O)Nc1cccc(-c2ncc3ccn(CCC(=O)NC)c3n2)c1] | N-(3-{7-[2-(methylcarbamoypethyl]-7H-pyrrolo[2,3-d]pyrimidin-2-yl}phenyl)prop-2-enamide | 349.4 |
| 1250 | 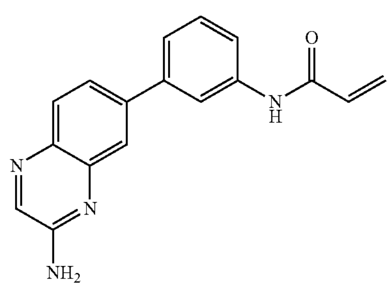 [SMILES: C=CC(=O)Nc1cccc(-c2ccc3ncc(N)nc3c2)c1] | N-[3-(3-aminoquinoxalin-6-yl)phenyl]prop-2-enamide | 290.3 |

TABLE 16-continued

| Cpd No. | Structure | IUPAC | MW (g/mol) |
|---|---|---|---|
| 1251 | 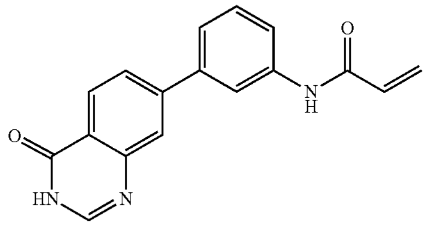 [SMILES: C=CC(=O)Nc1cccc(-c2ccc3c(=O)[nH]cnc3c2)c1] | N-[3-(4-oxo-3,4-dihydroquinazolin-7-yl)phenyl]prop-2-enamide | 291.3 |
| 1252 | 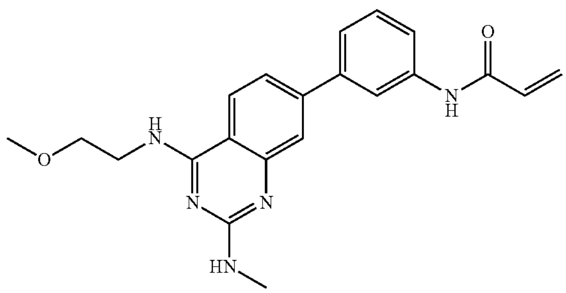 [SMILES: C=CC(=O)Nc1cccc(-c2ccc3c(NCCOC)nc(NC)nc3c2)c1] | N-(3-{4-[(2-methoxyethyl)amino]-2-(methylamino)quinazolin-7-yl}phenyl)prop-2-enamide | 377.4 |
| 1253 | 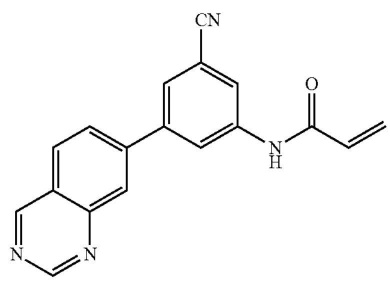 [SMILES: C=CC(=O)Nc1cc(C#N)cc(-c2ccc3cncnc3c2)c1] | N-[3-cyano-5-(quinazolin-7-yl)phenyl]prop-2-enamide | 300.3 |
| 1254 | 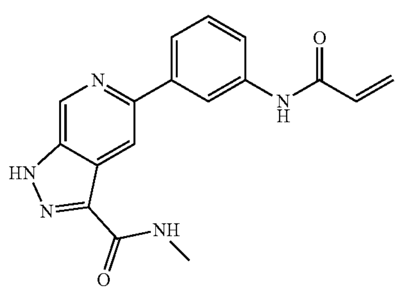 [SMILES: C=CC(=O)Nc1cccc(-c2cc3c(C(=O)NC)n[nH]c3cn2)c1] | N-methyl-5-[3-(prop-2-enamido)phenyl]-1H-pyrazolo[3,4-c]pyridine-3-carboxamide | 321.3 |
| 1255 | 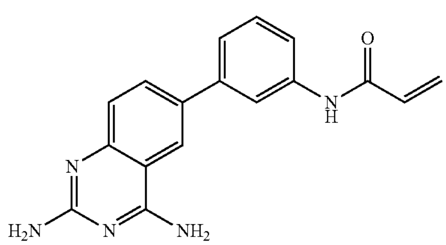 [SMILES: C=CC(=O)Nc1cccc(-c2ccc3nc(N)nc(N)c3c2)c1] | N-[3-(2,4-diaminoquinazolin-6-yl)phenyl]prop-2-enamide | 305.3 |

TABLE 16-continued

| Cpd No. | Structure | IUPAC | MW (g/mol) |
|---|---|---|---|
| 1256 | 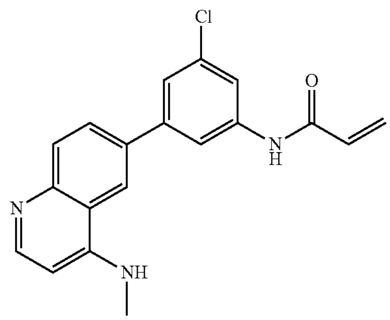 [SMILES: C=CC(=O)Nc1cc(Cl)cc(-c2ccc3nccc(NC)c3c2)c1] | N-{3-chloro-5-[4-(methylamino)quinolin-6-yl]phenyl}prop-2-enamide | 337.8 |
| 1257 | 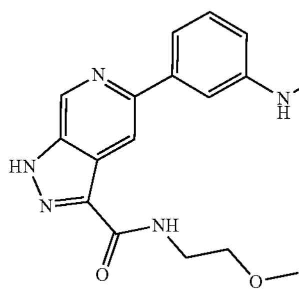 | N-(2-methoxyethyl)-5-[3-(prop-2-enamido)phenyl]-1H-pyrazolo[3,4-c]pyridine-3-carboxamide | 365.4 |
| 1258 | 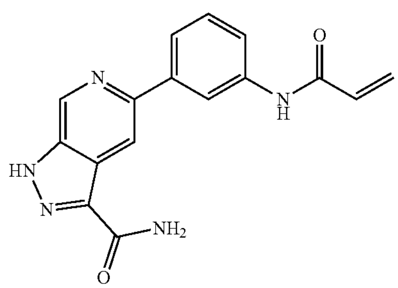 [SMILES: C=CC(=O)Nc1cccc(-c2cc3c(C(N)=O)n[nH]c3cn2)c1] | 5-[3-(prop-2-enamido)phenyl]-1H-pyrazolo[3,4-c]pyridine-3-carboxamide | 307.3 |
| 1259 | 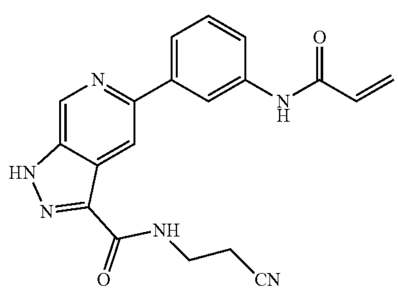 | N-(2-cyanoethyl)-5-[3-(prop-2-enamido)phenyl]-1H-pyrazolo[3,4-c]pyridine-3-carboxamide | 360.4 |
| 1260 | 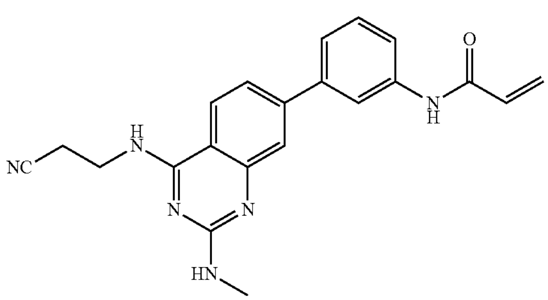 [SMILES: C=CC(=O)Nc1cccc(-c2ccc3c(NCCC#N)nc(NC)nc3c2)c1] | N-(3-{4-[(2-cyanoethyl)amino]-2-(methylamino)quinazolin-7-yl}phenyl)prop-2-enamide | 372.4 |

| Cpd No. | Structure | IUPAC | MW (g/mol) |
|---|---|---|---|
| 1261 | 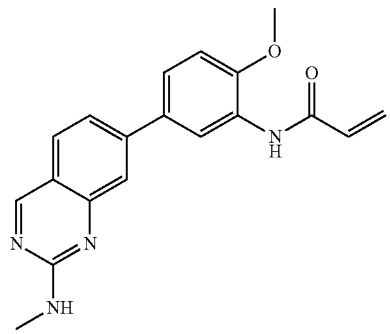 [SMILES: C=CC(=O)Nc1cc(-c2ccc3cnc(NC)nc3c2)ccc1OC] | N-{2-methoxy-5-[2-(methylamino)quinazolin-7-yl]phenyl}prop-2-enamide | 334.4 |
| 1262 | 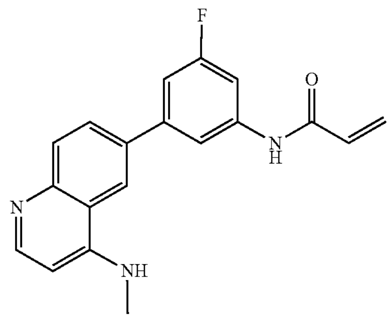 | N-{3-fluoro-5-[4-(methylamino)quinolin-6-yl]phenyl}prop-2-enamide | 321.4 |
| 1263 | 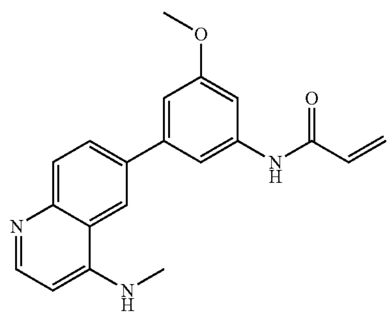 [SMILES: C=CC(=O)Nc1cc(OC)cc(-c2ccc3nccc(NC)c3c2)c1] | N-{3-methoxy-5-[4-(methylamino)quinolin-6-yl]phenyl}prop-2-enamide | 333.4 |
| 1264 | 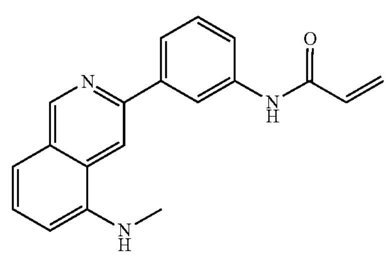 [SMILES: C=CC(=O)Nc1cccc(-c2cc3c(NC)cccc3cn2)c1] | N-{3-[5-(methylamino)isoquinolin-3-yl]phenyl}prop-2-enamide | 303.4 |
| 1265 | 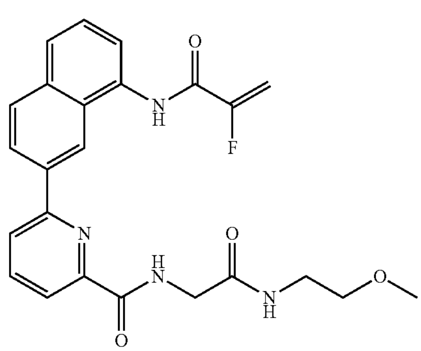 [SMILES: C=C(F)C(=O)Nc1cccc2ccc(-c3cccc(C(=O)NCC(=O)NCCOC)n3)cc12] | 2-fluoro-N-{7-[6-({[(2-methoxyethyl)carbamoyl]methyl}carbamoyl)pyridin-2-yl]naphthalen-1-yl}prop-2-enamide | 450.5 |

TABLE 16-continued

| Cpd No. | Structure | IUPAC | MW (g/mol) |
|---|---|---|---|
| 1266 | 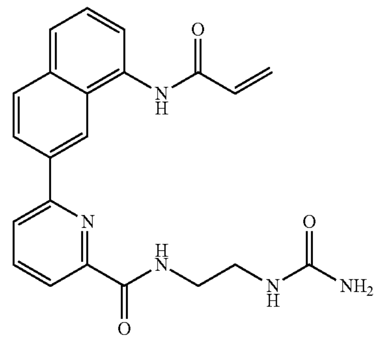 [SMILES: C=CC(=O)Nc1cccc2ccc(-c3cccc(C(=O)NCCNC(N)=O)n3)cc12] | N-[2-(carbamoylamino)ethyl]-6-[8-(prop-2-enamido)naphthalen-2-yl]pyridine-2-carboxamide | 403.4 |
| 1267 | 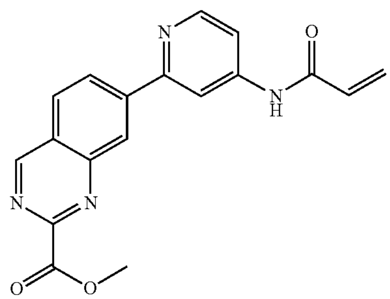 [SMILES: C=CC(=O)Nc1ccnc(-c2ccc3cnc(C(=O)OC)nc3c2)c1] | methyl 7-[4-(prop-2-enamido)pyridin-2-yl]quinazoline-2-carboxylate | 334.3 |
| 1268 | 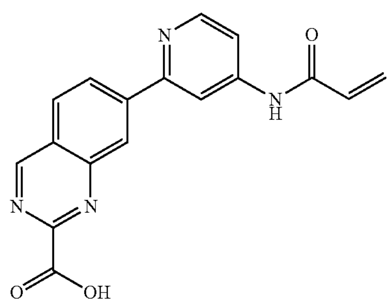 [SMILES: C=CC(=O)Nc1ccnc(-c2ccc3cnc(C(=O)O)nc3c2)c1] | 7-[4-(prop-2-enamido)pyridin-2-yl]quinazoline-2-carboxylic acid | 320.3 |
| 1269 | 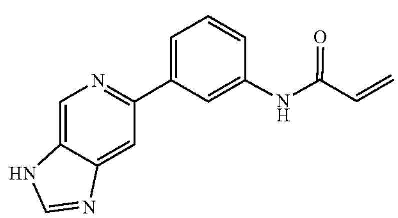 [SMILES: C=CC(=O)Nc1cccc(-c2cc3nc[nH]c3cn2)c1] | N-(3-{3H-imidazo[4,5-c]pyridin-6-yl}phenyl)prop-2-enamide | 264.3 |
| 1270 | 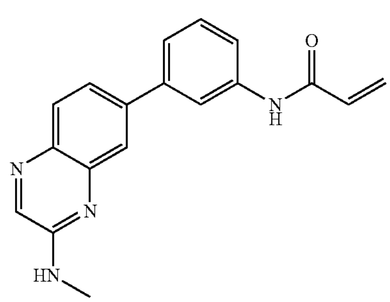 [SMILES: C=CC(=O)Nc1cccc(-c2ccc3ncc(NC)nc3c2)c1] | N-{3-[3-(methylamino)quinoxalin-6-yl]phenyl}prop-2-enamide | 304.4 |

| Cpd No. | Structure | IUPAC | MW (g/mol) |
|---|---|---|---|
| 1271 | 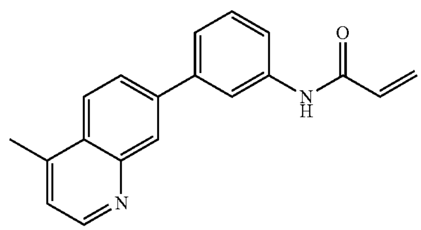 [SMILES: C=CC(=O)Nc1cccc(-c2ccc3c(C)ccnc3c2)c1] | N-[3-(4-methylquinolin-7-yl)phenyl]prop-2-enamide | 288.4 |
| 1272 | 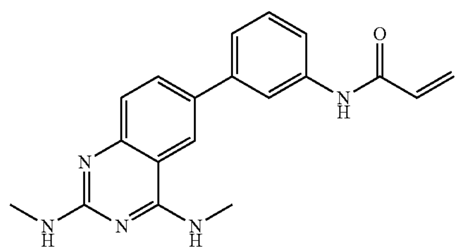 [SMILES: C=CC(=O)Nc1cccc(-c2ccc3nc(NC)nc(NC)c3c2)c1] | N-{3-[2,4-bis(methylamino)quinazolin-6-yl]phenyl}prop-2-enamide | 333.4 |
| 1273 | 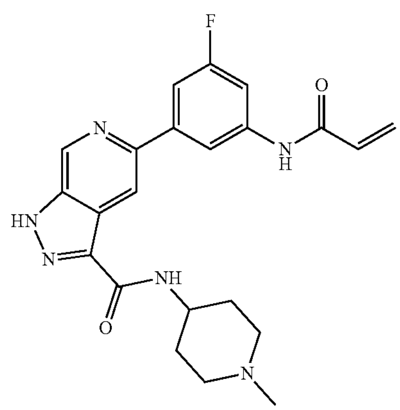 [SMILES: C=CC(=O)Nc1cc(F)cc(-c2cc3c(C(=O)NC4CCN(C)CC4)n[nH]c3cn2)c1] | 5-[3-fluoro-5-(prop-2-enamido)phenyl]-N-(1-methylpiperidin-4-yl)-1H-pyrazolo[3,4-c]pyridine-3-carboxamide | 422.5 |
| 1274 | 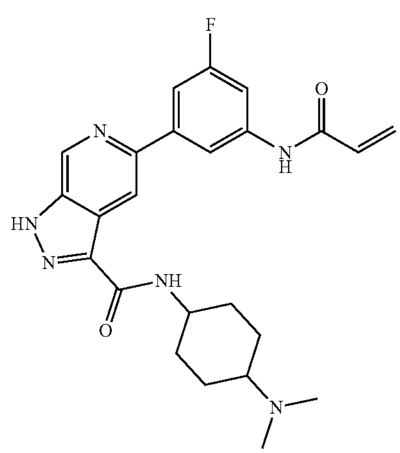 [SMILES: C=CC(=O)Nc1cc(F)cc(-c2cc3c(C(=O)NC4CCC(N(C)C)CC4)n[nH]c3cn2)c1] | N-[4-(dimethylamino)cyclohexyl]-5-[3-fluoro-5-(prop-2-enamido)phenyl]-1H-pyrazolo[3,4-c]pyridine-3-carboxamide | 450.5 |

TABLE 16-continued

| Cpd No. | Structure | IUPAC | MW (g/mol) |
|---|---|---|---|
| 1275 | 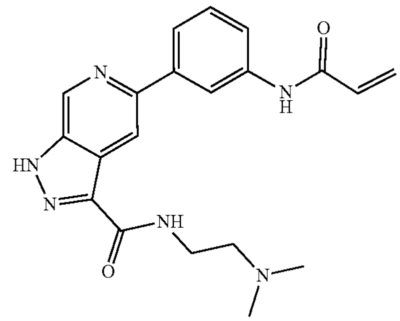 [SMILES: C=CC(=O)Nc1cccc(-c2cc3c(C(=O)NCCN(C)C)n[nH]c3cn2)c1] | N-[2-(dimethylamino)ethyl]-5-[3-(prop-2-enamido)phenyl]-1H-pyrazolo[3,4-c]pyridine-3-carboxamide | 378.4 |
| 1276 | 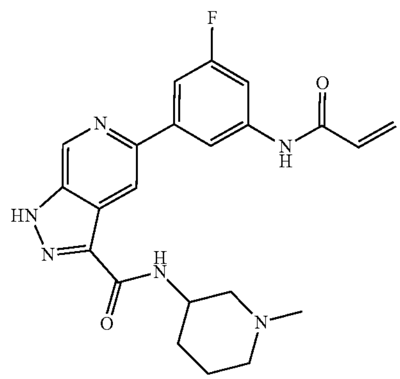 | 5-[3-fluoro-5-(prop-2-enamido)phenyl]-N-(1-methylpiperidin-3-yl)-1H-pyrazolo[3,4-c]pyridine-3-carboxamide | 422.5 |
| 1277 | 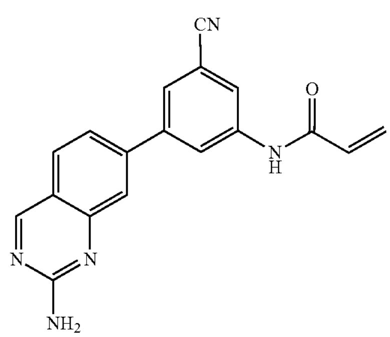 [SMILES: C=CC(=O)Nc1cc(C#N)cc(-c2ccc3cnc(N)nc3c2)c1] | N-[3-(2-aminoquinazolin-7-yl)-5-cyanophenyl]prop-2-enamide | 315.3 |
| 1278 | 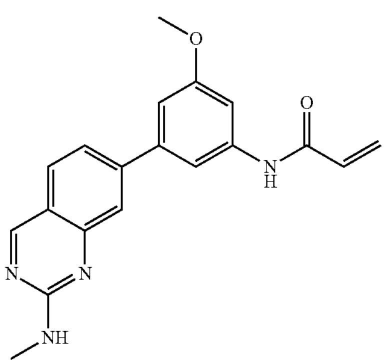 [SMILES: C=CC(=O)Nc1cc(OC)cc(-c2ccc3cnc(NC)nc3c2)c1] | N-{3-methoxy-5-[2-(methylamino)quinazolin-7-yl]phenyl}prop-2-enamide | 334.4 |

TABLE 16-continued

| Cpd No. | Structure | IUPAC | MW (g/mol) |
|---|---|---|---|
| 1279 | 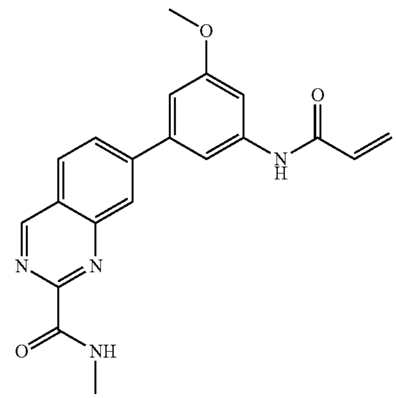 [SMILES: C=CC(=O)Nc1cc(OC)cc(-c2ccc3cnc(C(=O)NC)nc3c2)c1] | 7-[3-methoxy-5-(prop-2-enamido)phenyl]-N-methylquinazoline-2-carboxamide | 362.4 |
| 1280 | 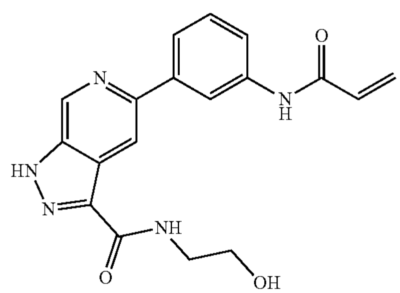 [SMILES: C=CC(=O)Nc1cccc(-c2cc3c(C(=O)NCCO)n[nH]c3cn2)c1] | N-(2-hydroxyethyl)-5-[3-(prop-2-enamido)phenyl]-1H-pyrazolo[3,4-c]pyridine-3-carboxamide | 351.4 |
| 1281 | 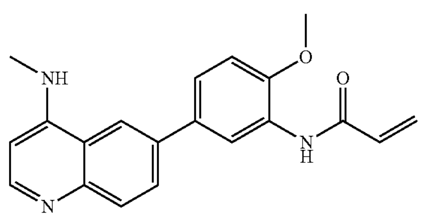 [SMILES: C=CC(=O)Nc1cc(-c2ccc3nccc(NC)c3c2)ccc1OC] | N-{2-methoxy-5-[4-(methylamino)quinolin-6-yl]phenyl}prop-2-enamide | 333.4 |
| 1282 | 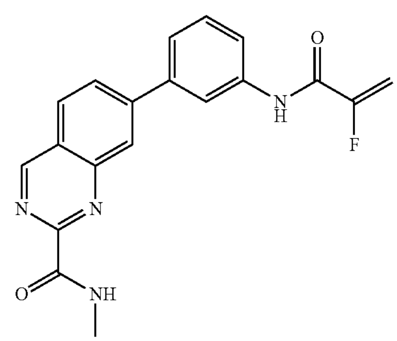 [SMILES: C=C(F)C(=O)Nc1cccc(-c2ccc3cnc(C(=O)NC)nc3c2)c1] | 7-[3-(2-fluoroprop-2-enamido)phenyl]-N-methylquinazoline-2-carboxamide | 350.4 |
| 1283 | 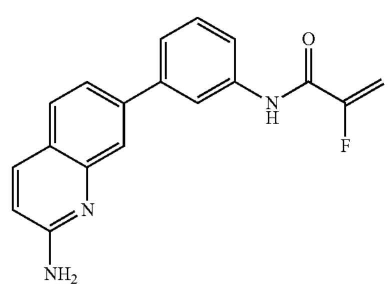 [SMILES: C=C(F)C(=O)Nc1cccc(-c2ccc3ccc(N)nc3c2)c1] | N-[3-(2-aminoquinolin-7-yl)phenyl]-2-fluoroprop-2-enamide | 307.3 |

TABLE 16-continued

| Cpd No. | Structure | IUPAC | MW (g/mol) |
|---|---|---|---|
| 1284 | 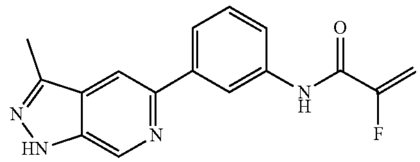 [SMILES: C=C(F)C(=O)Nc1cccc(-c2cc3c(C)n[nH]c3cn2)c1] | 2-fluoro-N-(3-{3-methyl-1H-pyrazolo[3,4-c]pyridin-5-yl}phenyl)prop-2-enamide | 296.3 |
| 1285 | 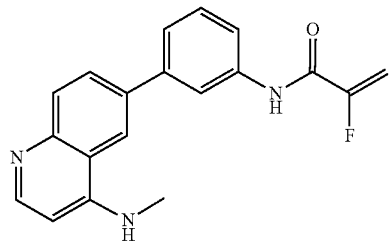 [SMILES: C=C(F)C(=O)Nc1cccc(-c2ccc3nccc(NC)c3c2)c1] | 2-fluoro-N-{3-[4-(methylamino)quinolin-6-yl]phenyl}prop-2-enamide | 321.4 |
| 1286 | 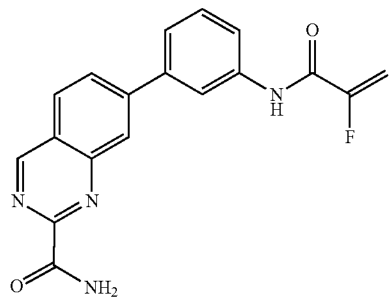 [SMILES: C=C(F)C(=O)Nc1cccc(-c2ccc3cnc(C(N)=O)nc3c2)c1] | 7-[3-(2-fluoroprop-2-enamido)phenyl]quinazoline-2-carboxamide | 336.3 |
| 1287 | 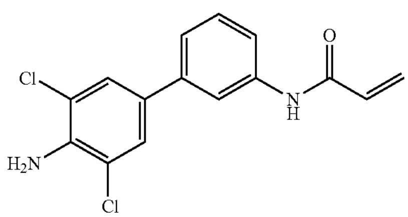 [SMILES: C=CC(=O)Nc1cccc(-c2cc(Cl)c(N)c(Cl)c2)c1] | N-{4'-amino-3',5'-dichloro-[1,1'-biphenyl]-3-yl}prop-2-enamide | 307.2 |
| 1288 | 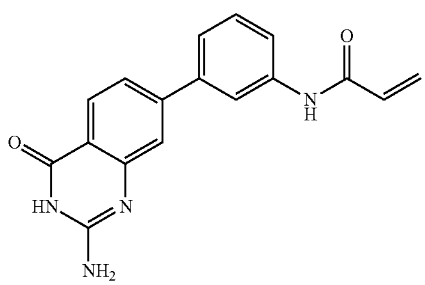 [SMILES: C=CC(=O)Nc1cccc(-c2ccc3c(=O)[nH]c(N)nc3c2)c1] | N-[3-(2-amino-4-oxo-3,4-dihydroquinazolin-7-yl)phenyl]prop-2-enamide | 306.3 |
| 1289 | 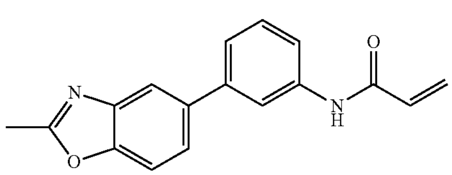 [SMILES: C=CC(=O)Nc1cccc(-c2ccc3oc(C)nc3c2)c1] | N-[3-(2-methyl-1,3-benzoxazol-5-yl)phenyl]prop-2-enamide | 278.3 |
| 1290 | 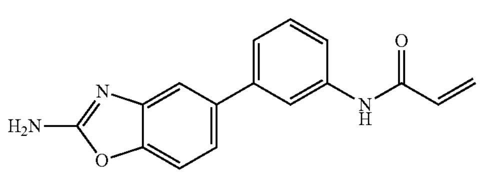 [SMILES: C=CC(=O)Nc1cccc(-c2ccc3oc(N)nc3c2)c1] | N-[3-(2-amino-1,3-benzoxazol-5-yl)phenyl]prop-2-enamide | 279.3 |

TABLE 16-continued

| Cpd No. | Structure | IUPAC | MW (g/mol) |
|---|---|---|---|
| 1291 | 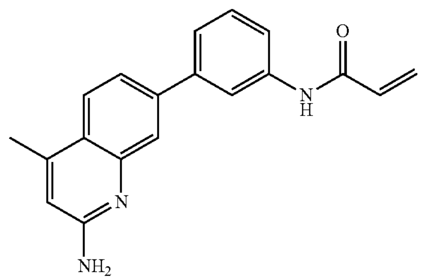 [SMILES: C=CC(=O)Nc1cccc(-c2ccc3c(C)cc(N)nc3c2)c1] | N-[3-(2-amino-4-methylquinolin-7-yl)phenyl]prop-2-enamide | 303.4 |
| 1292 | 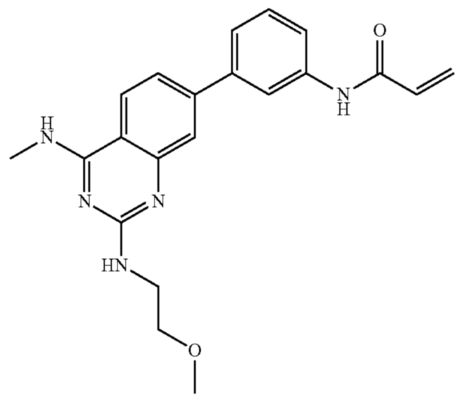 [SMILES: C=CC(=O)Nc1cccc(-c2ccc3c(NC)nc(NCCOC)nc3c2)c1] | N-(3-{2-[(2-methoxyethyl)amino]-4-(methylamino)quinazolin-7-yl}phenyl)prop-2-enamide | 377.4 |
| 1293 | 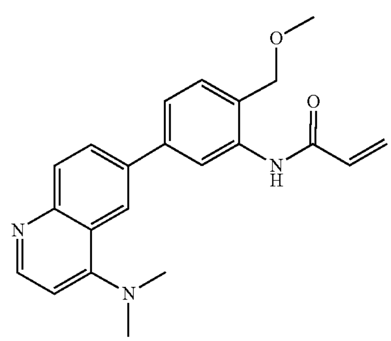 [SMILES: C=CC(=O)Nc1cc(-c2ccc3nccc(N(C)C)c3c2)ccc1COC] | N-{5-[4-(dimethylamino)quinolin-6-yl]-2-(methoxymethyl)phenyl}prop-2-enamide | 361.4 |
| 1294 | 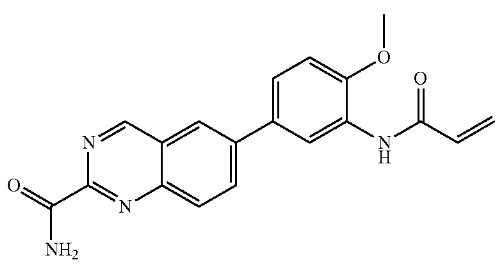 [SMILES: C=CC(=O)Nc1cc(-c2ccc3nc(C(N)=O)ncc3c2)ccc1OC] | 6-[4-methoxy-3-(prop-2-enamido)phenyl]quinazoline-2-carboxamide | 348.4 |
| 1295 | 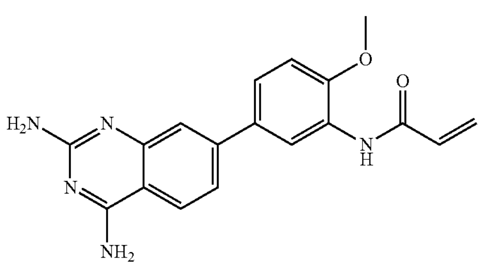 [SMILES: C=CC(=O)Nc1cc(-c2ccc3c(N)nc(N)nc3c2)ccc1OC] | N-[5-(2,4-diaminoquinazolin-7-yl)-2-methoxyphenyl]prop-2-enamide | 335.4 |

| Cpd No. | Structure | IUPAC | MW (g/mol) |
|---|---|---|---|
| 1296 | 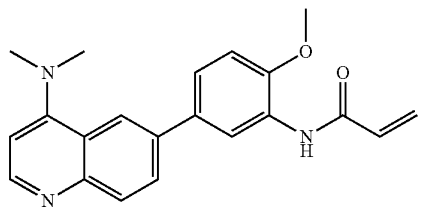 [SMILES: C=CC(=O)Nc1cc(-c2ccc3nccc(N(C)C)c3c2)ccc1OC] | N-{5-[4-(dimethylamino)quinolin-6-yl]-2-methoxyphenyl}prop-2-enamide | 347.4 |
| 1297 | 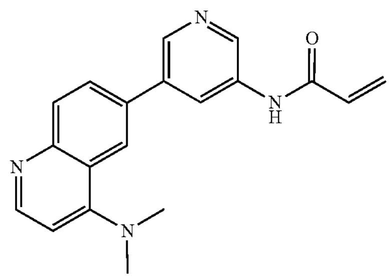 [SMILES: C=CC(=O)Nc1cncc(-c2ccc3nccc(N(C)C)c3c2)c1] | N-{5-[4-(dimethylamino)quinolin-6-yl]pyridin-3-yl}prop-2-enamide | 318.4 |
| 1298 | 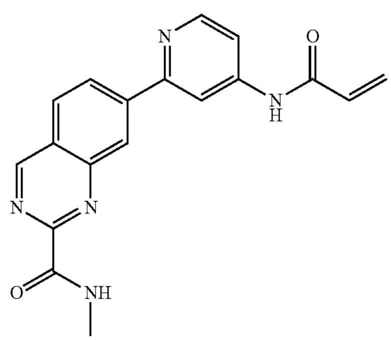 [SMILES: C=CC(=O)Nc1ccnc(-c2ccc3cnc(C(=O)NC)nc3c2)c1] | N-methyl-7-[4-(prop-2-enamido)pyridin-2-yl]quinazoline-2-carboxamide | 333.4 |
| 1299 | 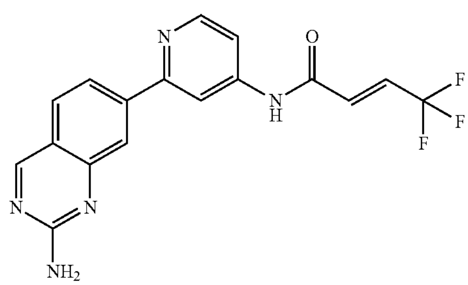 [SMILES: Nc1ncc2ccc(-c3cc(NC(=O)/C=C/C(F)(F)F)ccn3)cc2n1] | (2E)-N-[2-(2-aminoquinazolin-7-yl)pyridin-4-yl]-4,4,4-trifluorobut-2-enamide | 359.3 |
| 1300 | 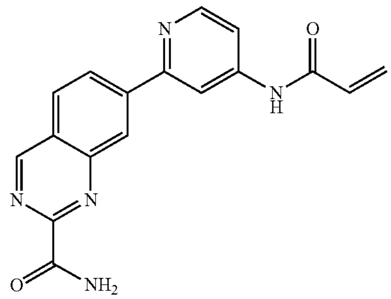 [SMILES: C=CC(=O)Nc1ccnc(-c2ccc3cnc(C(N)=O)nc3c2)c1] | 7-[4-(prop-2-enamido)pyridin-2-yl]quinazoline-2-carboxamide | 319.3 |

TABLE 16-continued

| Cpd No. | Structure | IUPAC | MW (g/mol) |
|---|---|---|---|
| 1301 | 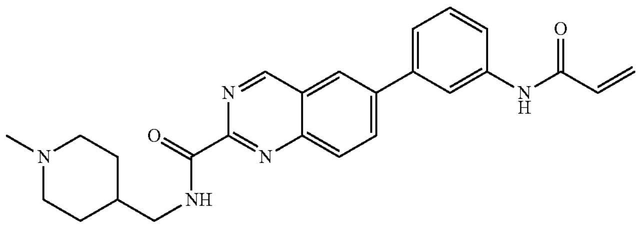 [SMILES: C=CC(=O)Nc1cccc(-c2ccc3nc(C(=O)NCC4CCN(C)CC4)ncc3c2)c1] | N-[(1-methylpiperidin-4-yl)methyl]-6-[3-(prop-2-enamido)phenyl]quinazoline-2-carboxamide | 429.5 |
| 1302 | 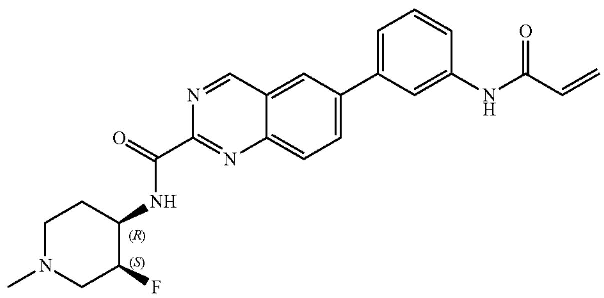 | N-[(3S,4R)-3-fluoro-1-methylpiperidin-4-yl]-6-[3-(prop-2-enamido)phenyl]quinazoline-2-carboxamide | 433.5 |
| 1303 | 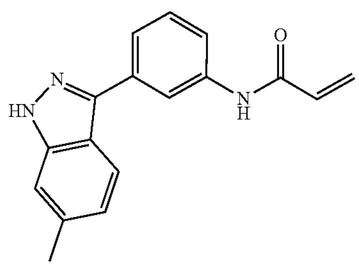 [SMILES: C=CC(=O)Nc1cccc(-c2n[nH]c3cc(C)ccc23)c1] | N-[3-(6-methyl-1H-indazol-3-yl)phenyl]prop-2-enamide | 277.3 |
| 1304 | 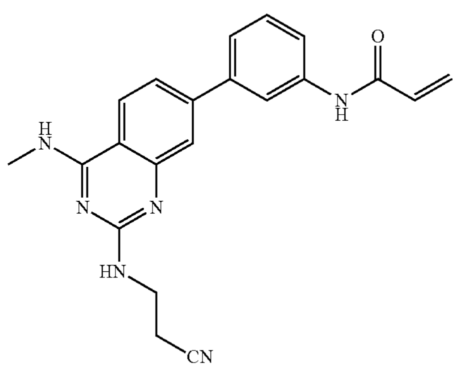 [SMILES: C=CC(=O)Nc1cccc(-c2ccc3c(NC)nc(NCCC#N)nc3c2)c1] | N-(3-{2-[(2-cyanoethyl)amino]-4-(methylamino)quinazolin-7-yl}phenyl)prop-2-enamide | 372.4 |
| 1305 | 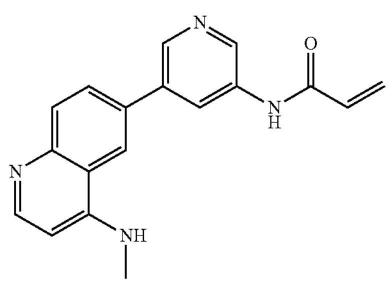 [SMILES: C=CC(=O)Nc1cncc(-c2ccc3nccc(NC)c3c2)c1] | N-{5-[4-(methylamino)quinolin-6-yl]pyridin-3-yl}prop-2-enamide | 304.4 |

TABLE 16-continued

| Cpd No. | Structure | IUPAC | MW (g/mol) |
|---|---|---|---|
| 1306 | 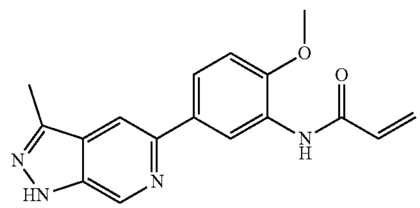 [SMILES: C=CC(=O)Nc1cc(-c2cc3c(C)n[nH]c3cn2)ccc1OC] | N-(2-methoxy-5-{3-methyl-1H-pyrazolo[3,4-c]pyridin-5-yl}phenyl)prop-2-enamide | 308.3 |
| 1307 | 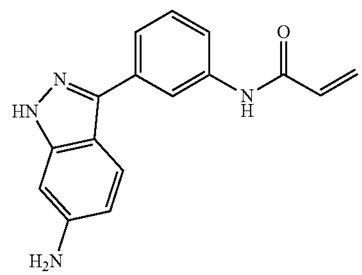 [SMILES: C=CC(=O)Nc1cccc(-c2n[nH]c3cc(N)ccc23)c1] | N-[3-(6-amino-1H-indazol-3-yl)phenyl]prop-2-enamide | 278.3 |
| 1308 | 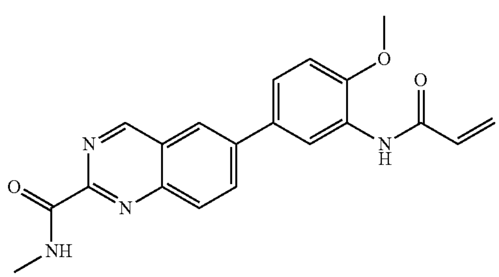 [SMILES: C=CC(=O)Nc1cc(-c2ccc3nc(C(=O)NC)ncc3c2)ccc1OC] | 6-[4-methoxy-3-(prop-2-enamido)phenyl]-N-methylquinazoline-2-carboxamide | 362.4 |
| 1309 | 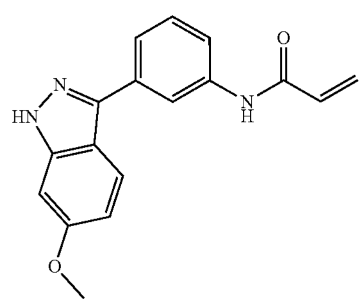 [SMILES: C=CC(=O)Nc1cccc(-c2n[nH]c3cc(OC)ccc23)c1] | N-[3-(6-methoxy-1H-indazol-3-yl)phenyl]prop-2-enamide | 293.3 |
| 1310 | 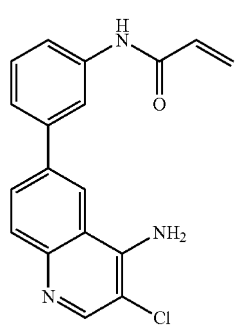 [SMILES: C=CC(=O)Nc1cccc(-c2ccc3ncc(Cl)c(N)c3c2)c1] | N-[3-(4-amino-3-chloroquinolin-6-yl)phenyl]prop-2-enamide | 323.8 |

TABLE 16-continued
| Cpd No. | Structure | IUPAC | MW (g/mol) |
|---|---|---|---|
| 1311 | 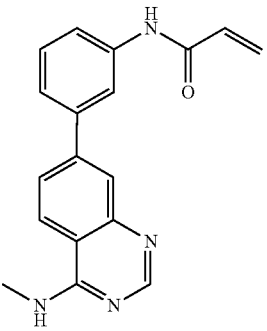 [SMILES: C=CC(=O)Nc1cccc(-c2ccc3c(NC)ncnc3c2)c1] | N-{3-[4-(methylamino)quinazolin-7-yl]phenyl}prop-2-enamide | 304.4 |
| 1312 | 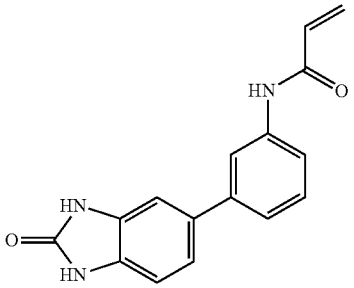 [SMILES: C=CC(=O)Nc1cccc(-c2ccc3[nH]c(=O)[nH]c3c2)c1] | N-[3-(2-oxo-2,3-dihydro-1H-1,3-benzodiazol-5-yl)phenyl]prop-2-enamide | 279.3 |
| 1313 | 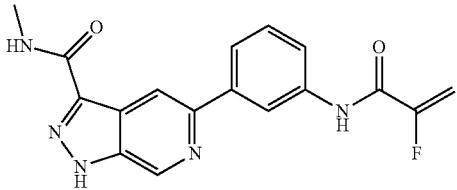 [SMILES: C=C(F)C(=O)Nc1cccc(-c2cc3c(C(=O)NC)n[nH]c3cn2)c1] | 5-[3-(2-fluoroprop-2-enamido)phenyl]-N-methyl-1H-pyrazolo[3,4-c]pyridine-3-carboxamide | 339.3 |
| 1314 | 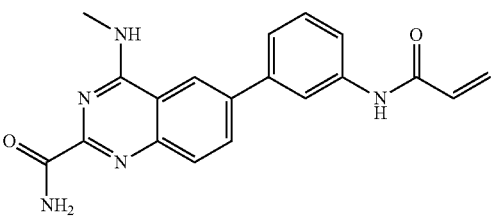 [SMILES: C=CC(=O)Nc1cccc(-c2ccc3nc(C(N)=O)nc(NC)c3c2)c1] | 4-(methylamino)-6-[3-(prop-2-enamido)phenyl]quinazoline-2-carboxamide | 347.4 |
| 1315 | 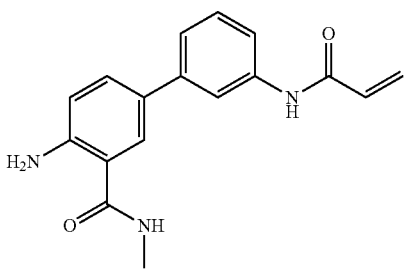 [SMILES: C=CC(=O)Nc1cccc(-c2ccc(N)c(C(=O)NC)c2)c1] | 4-amino-N-methyl-3'-(prop-2-enamido)-[1,1'-biphenyl]-3-carboxamide | 295.3 |

TABLE 16-continued
| Cpd No. | Structure | IUPAC | MW (g/mol) |
|---|---|---|---|
| 1316 | 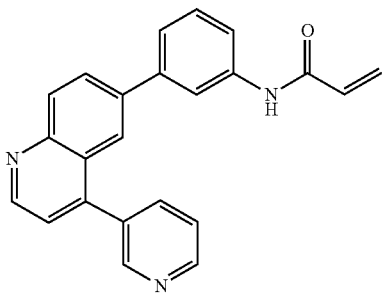 [SMILES: C=CC(=O)Nc1cccc(-c2ccc3nccc(-c4cccnc4)c3c2)c1] | N-{3-[4-(pyridin-3-yl)quinolin-6-yl]phenyl}prop-2-enamide | 351.4 |
| 1317 | 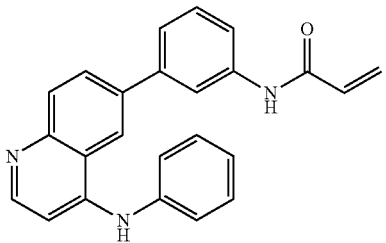 [SMILES: C=CC(=O)Nc1cccc(-c2ccc3nccc(Nc4ccccc4)c3c2)c1] | N-{3-[4-(phenylamino)quinolin-6-yl]phenyl}prop-2-enamide | 365.4 |
| 1318 | 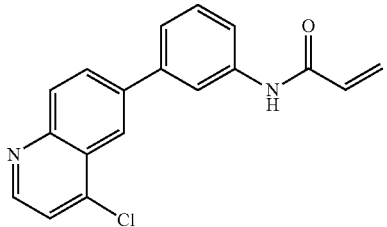 [SMILES: C=CC(=O)Nc1cccc(-c2ccc3nccc(Cl)c3c2)c1] | N-[3-(4-chloroquinolin-6-yl)phenyl]prop-2-enamide | 308.8 |
| 1319 | 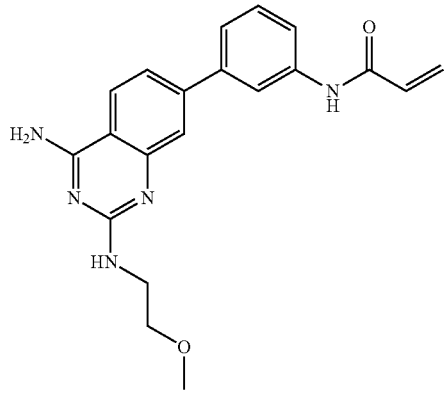 [SMILES: C=CC(=O)Nc1cccc(-c2ccc3c(N)nc(NCCOC)nc3c2)c1] | N-(3-{4-amino-2-[(2-methoxyethyl)amino]quinazolin-7-yl}phenyl)prop-2-enamide | 363.4 |
| 1320 | 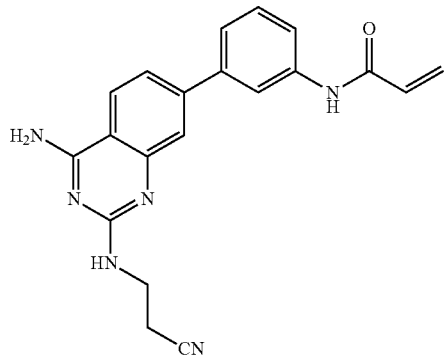 [SMILES: C=CC(=O)Nc1cccc(-c2ccc3c(N)nc(NCCC#N)nc3c2)c1] | N-(3-{4-amino-2-[(2-cyanoethyl)amino]quinazolin-7-yl}phenyl)prop-2-enamide | 358.4 |

TABLE 16-continued

| Cpd No. | Structure | IUPAC | MW (g/mol) |
|---|---|---|---|
| 1321 | 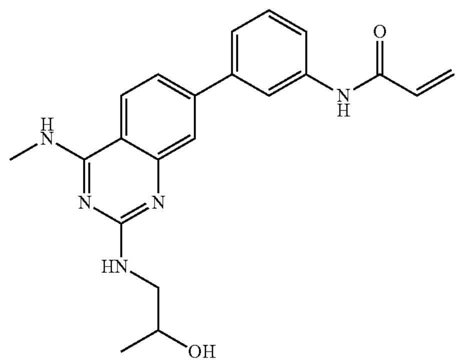 [SMILES: C=CC(=O)Nc1cccc(-c2ccc3c(NC)nc(NCC(C)O)nc3c2)c1] | N-(3-{2-[(2-hydroxypropyl)amino]-4-(methylamino)quinazolin-7-yl}phenyl)prop-2-enamide | 377.4 |
| 1322 | 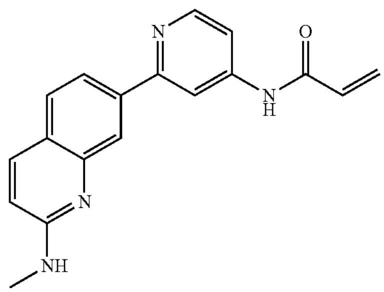 [SMILES: C=CC(=O)Nc1ccnc(-c2ccc3ccc(NC)nc3c2)c1] | N-{2-[2-(methylamino)quinolin-7-yl]pyridin-4-yl}prop-2-enamide | 304.4 |
| 1323 | 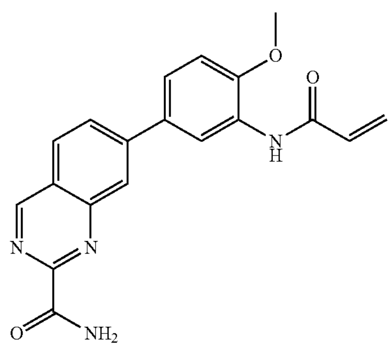 [SMILES: C=CC(=O)Nc1cc(-c2ccc3cnc(C(N)=O)nc3c2)ccc1OC] | 7-[4-methoxy-3-(prop-2-enamido)phenyl]quinazoline-2-carboxamide | 348.4 |
| 1324 | 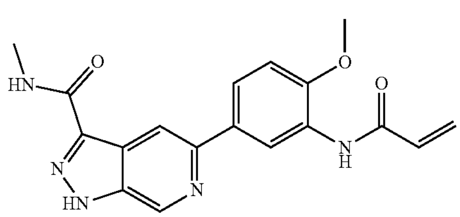 [SMILES: C=CC(=O)Nc1cc(-c2cc3c(C(=O)NC)n[nH]c3cn2)ccc1OC] | 5-[4-methoxy-3-(prop-2-enamido)phenyl]-N-methyl-1H-pyrazolo[3,4-c]pyridine-3-carboxamide | 351.4 |
| 1325 | 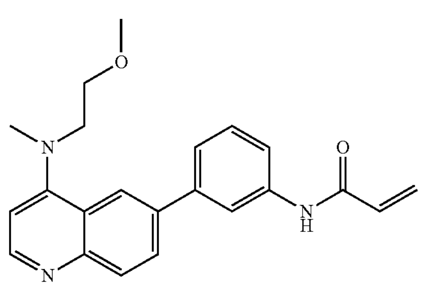 [SMILES: C=CC(=O)Nc1cccc(-c2ccc3nccc(N(C)CCOC)c3c2)c1] | N-(3-{4-[(2-methoxyethyl)(methyl)amino]quinolin-6-yl}phenyl)prop-2-enamide | 361.4 |

TABLE 16-continued

| Cpd No. | Structure | IUPAC | MW (g/mol) |
| --- | --- | --- | --- |
| 1326 | 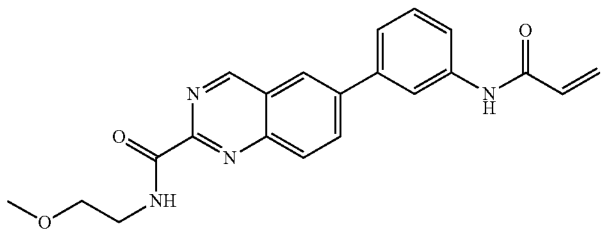 [SMILES: C=CC(=O)Nc1cccc(-c2ccc3nc(C(=O)NCCOC)ncc3c2)c1] | N-(2-methoxyethyl)-6-[3-(prop-2-enamido)phenyl]quinazoline-2-carboxamide | 376.4 |
| 1327 | 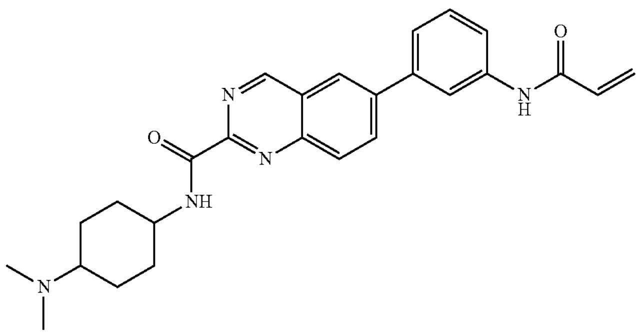 [SMILES: C=CC(=O)Nc1cccc(-c2ccc3nc(C(=O)NC4CCC(N(C)C)CC4)ncc3c2)c1] | N-[4-(dimethylamino)cyclohexyl]-6-[3-(prop-2-enamido)phenyl]quinazoline-2-carboxamide | 443.6 |
| 1328 | 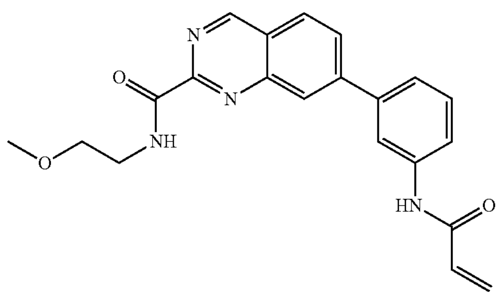 [SMILES: C=CC(=O)Nc1cccc(-c2ccc3cnc(C(=O)NCCOC)nc3c2)c1] | N-(2-methoxyethyl)-7-[3-(prop-2-enamido)phenyl]quinazoline-2-carboxamide | 376.4 |
| 1329 | 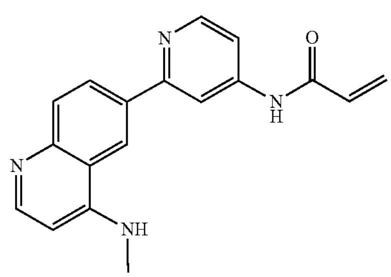 [SMILES: C=CC(=O)Nc1ccnc(-c2ccc3nccc(NC)c3c2)c1] | N-{2-[4-(methylamino)quinolin-6-yl]pyridin-4-yl}prop-2-enamide | 304.4 |
| 1330 | 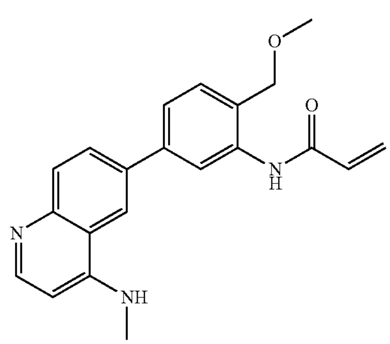 [SMILES: C=CC(=O)Nc1cc(-c2ccc3nccc(NC)c3c2)ccc1COC] | N-[2-(methoxymethyl)-5-[4-(methylamino)quinolin-6-yl]phenyl]prop-2-enamide | 347.4 |

TABLE 16-continued

| Cpd No. | Structure | IUPAC | MW (g/mol) |
|---|---|---|---|
| 1331 | 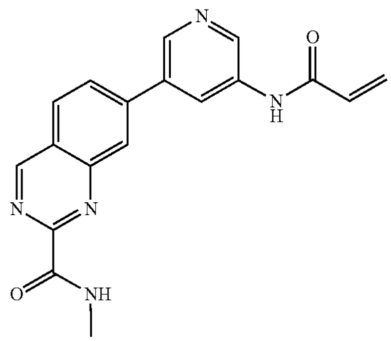 [SMILES: C=CC(=O)Nc1cncc(-c2ccc3cnc(C(=O)NC)nc3c2)c1] | N-methyl-7-[5-(prop-2-enamido)pyridin-3-yl]quinazoline-2-carboxamide | 333.4 |
| 1332 | 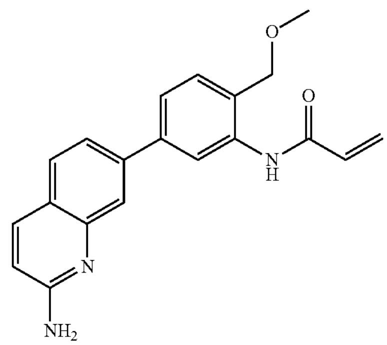 [SMILES: C=CC(=O)Nc1cc(-c2ccc3ccc(N)nc3c2)ccc1COC] | N-[5-(2-aminoquinolin-7-yl)-2-(methoxymethyl)phenyl]prop-2-enamide | 3314 |
| 1333 | 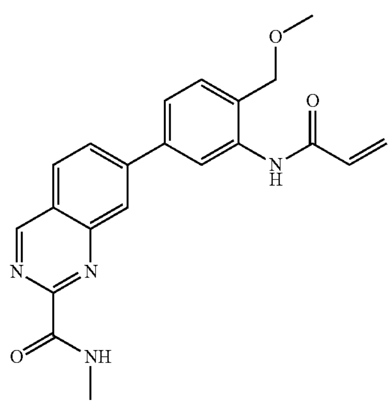 [SMILES: C=CC(=O)Nc1cc(-c2ccc3cnc(C(=O)NC)nc3c2)ccc1COC] | 7-[4-(methoxymethyl)-3-(prop-2-enamido)phenyl]-N-methylquinazoline-2-carboxamide | 376.4 |
| 1334 | 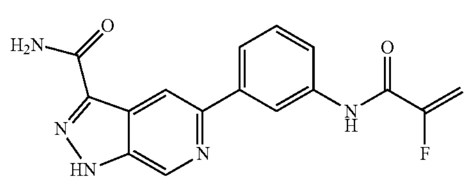 | 5-[3-(2-fluoroprop-2-enamido)phenyl]-1H-pyrazolo[3,4-c]pyridine-3-carboxamide | 325.3 |
| 1335 | 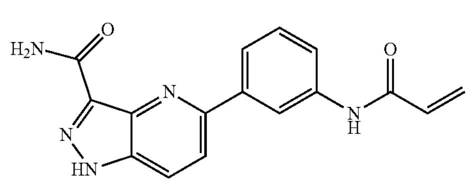 [SMILES: C=CC(=O)Nc1cccc(-c2ccc3[nH]nc(C(N)=O)c3n2)c1] | 5-[3-(prop-2-enamido)phenyl]-1H-pyrazolo[4,3-b]pyridine-3-carboxamide | 307.3 |

TABLE 16-continued

| Cpd No. | Structure | IUPAC | MW (g/mol) |
|---|---|---|---|
| 1336 | 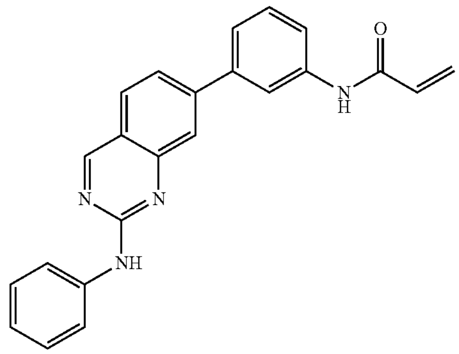 [SMILES: C=CC(=O)Nc1cccc(-c2ccc3cnc(Nc4ccccc4)nc3c2)c1] | N-{3-[2-(phenylamino)quinazolin-7-yl]phenyl}prop-2-enamide | 366.4 |
| 1337 | 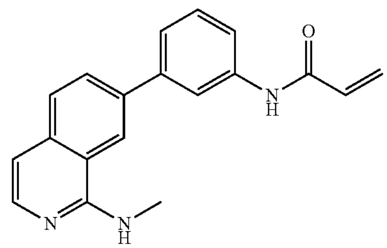 [SMILES: C=CC(=O)Nc1cccc(-c2ccc3ccnc(NC)c3c2)c1] | N-{3-[1-(methylamino)isoquinolin-7-yl]phenyl}prop-2-enamide | 303.4 |
| 1338 | 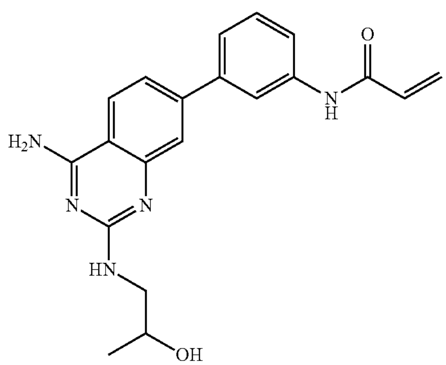 [SMILES: C=CC(=O)Nc1cccc(-c2ccc3c(N)nc(NCC(C)O)nc3c2)c1] | N-(3-{4-amino-2-[(2-hydroxypropyl)amino]quinazolin-7-yl}phenyl)prop-2-enamide | 363.4 |
| 1339 | 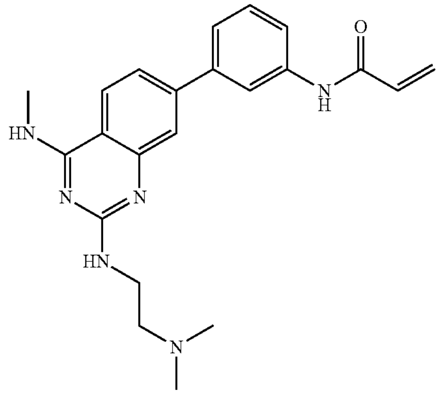 [SMILES: C=CC(=O)Nc1cccc(-c2ccc3c(NC)nc(NCCN(C)C)nc3c2)c1] | N-[3-(2-{[2-(dimethylamino)ethyl]amino}-4-(methylamino)quinazolin-7-yl)phenyl]prop-2-enamide | 390.5 |

TABLE 16-continued

| Cpd No. | Structure | IUPAC | MW (g/mol) |
|---|---|---|---|
| 1340 | 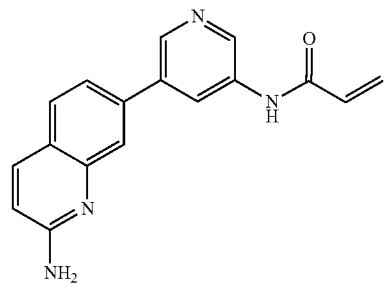 [SMILES: C=CC(=O)Nc1cncc(-c2ccc3ccc(N)nc3c2)c1] | N-[5-(2-aminoquinolin-7-yl)pyridin-3-yl]prop-2-enamide | 290.3 |
| 1341 | 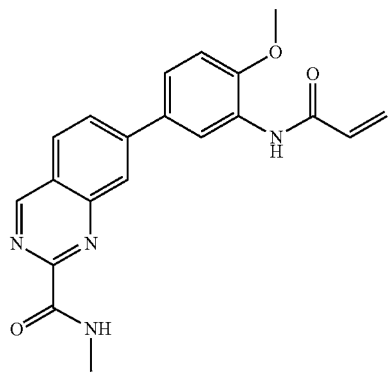 [SMILES: C=CC(=O)Nc1cc(-c2ccc3cnc(C(=O)NC)nc3c2)ccc1OC] | 7-[4-methoxy-3-(prop-2-enamido)phenyl]-N-methylquinazoline-2-carboxamide | 362.4 |
| 1342 | 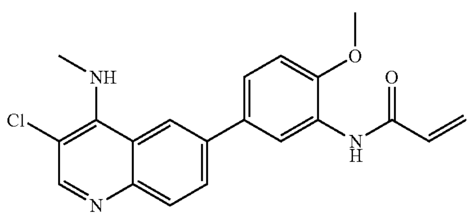 [SMILES: C=CC(=O)Nc1cc(-c2ccc3ncc(Cl)c(NC)c3c2)ccc1OC] | N-{5-[3-chloro-4-(methylamino)quinolin-6-yl]-2-methoxyphenyl}prop-2-enamide | 367.8 |
| 1343 | 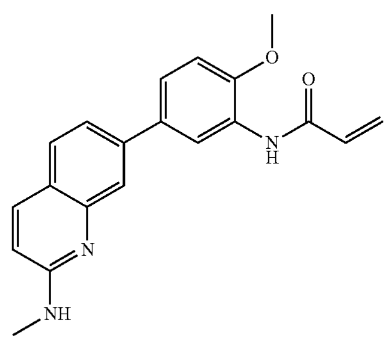 [SMILES: C=CC(=O)Nc1cc(-c2ccc3ccc(NC)nc3c2)ccc1OC] | N-{2-methoxy-5-[2-(methylamino)quinolin-7-yl]phenyl}prop-2-enamide | 333.4 |
| 1344 | 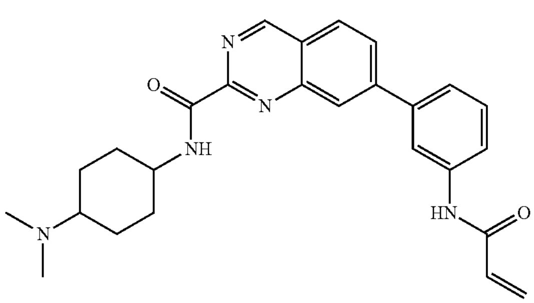 [SMILES: C=CC(=O)Nc1cccc(-c2ccc3cnc(C(=O)NC4CCC(N(C)C)CC4)nc3c2)c1] | N-[4-(dimethylamino)cyclohexyl]-7-[3-(prop-2-enamido)phenyl]quinazoline-2-carboxamide | 443.6 |

TABLE 16-continued

| Cpd No. | Structure | IUPAC | MW (g/mol) |
|---|---|---|---|
| 1345 | 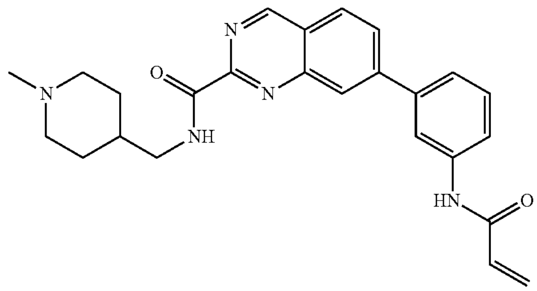 [SMILES: C=CC(=O)Nc1cccc(-c2ccc3cnc(C(=O)NCC4CCN(C)CC4)nc3c2)c1] | N-[(1-methylpiperidin-4-yl)methyl]-7-[3-(prop-2-enamido)phenyl]quinazoline-2-carboxamide | 429.5 |
| 1346 | 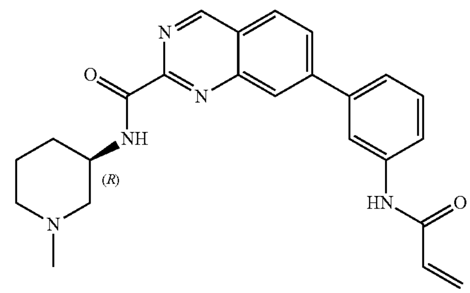 | N-[(3R)-1-methylpiperidin-3-yl]-7-[3-(prop-2-enamido)phenyl]quinazoline-2-carboxamide | 415.5 |
| 1347 | 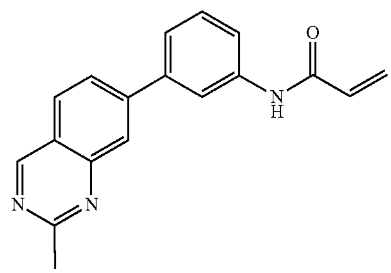 [SMILES: C=CC(=O)Nc1cccc(-c2ccc3cnc(C)nc3c2)c1] | N-[3-(2-methylquinazolin-7-yl)phenyl]prop-2-enamide | 289.3 |
| 1348 | 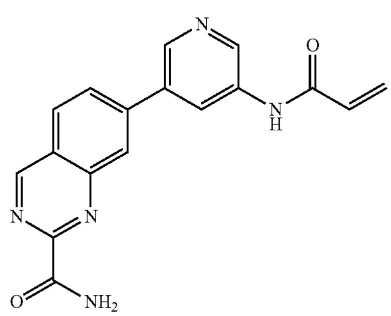 [SMILES: C=CC(=O)Nc1cncc(-c2ccc3cnc(C(N)=O)nc3c2)c1] | 7-[5-(prop-2-enamido)pyridin-3-yl]quinazoline-2-carboxamide | 319.3 |
| 1349 | 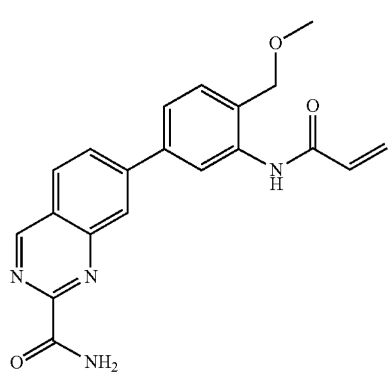 [SMILES: C=CC(=O)Nc1cc(-c2ccc3cnc(C(N)=O)nc3c2)ccc1COC] | 7-[4-(methoxymethyl)-3-(prop-2-enamido)phenyl]quinazoline-2-carboxamide | 362.4 |

TABLE 16-continued

| Cpd No. | Structure | IUPAC | MW (g/mol) |
|---|---|---|---|
| 1350 | 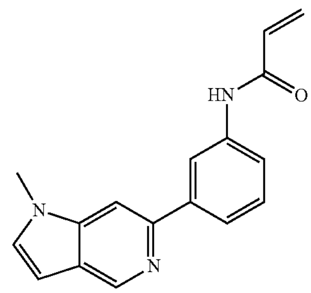 [SMILES: C=CC(=O)Nc1cccc(-c2cc3c(ccn3C)cn2)c1] | N-(3-{1-methyl-1H-pyrrolo[3,2-c]pyridin-6-yl}phenyl)prop-2-enamide | 277.3 |
| 1351 | 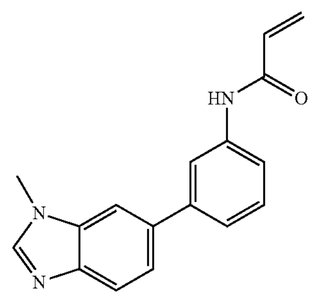 [SMILES: C=CC(=O)Nc1cccc(-c2ccc3ncn(C)c3c2)c1] | N-[3-(1-methyl-1H-1,3-benzodiazol-6-yl)phenyl]prop-2-enamide | 277.3 |
| 1352 | 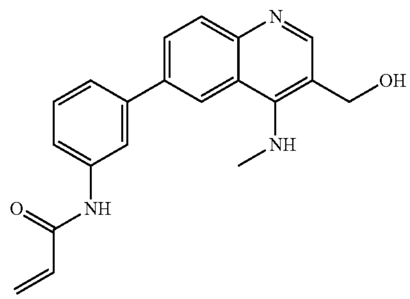 [SMILES: C=CC(=O)Nc1cccc(-c2ccc3ncc(CO)c(NC)c3c2)c1] | N-{3-[3-(hydroxymethyl)-4-(methylamino)quinolin-6-yl]phenyl}prop-2-enamide | 333.4 |
| 1353 | 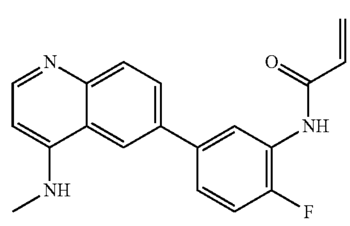 [SMILES: C=CC(=O)Nc1cc(-c2ccc3nccc(NC)c3c2)ccc1F] | N-{2-fluoro-5-[4-(methylamino)quinolin-6-yl]phenyl}prop-2-enamide | 321.4 |
| 1354 | 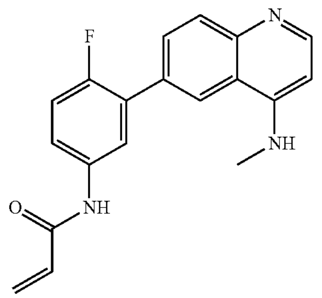 [SMILES: C=CC(=O)Nc1ccc(F)c(-c2ccc3nccc(NC)c3c2)c1] | N-{4-fluoro-3-[4-(methylamino)quinolin-6-yl]phenyl}prop-2-enamide | 321.4 |

TABLE 16-continued

| Cpd No. | Structure | IUPAC | MW (g/mol) |
|---|---|---|---|
| 1355 | 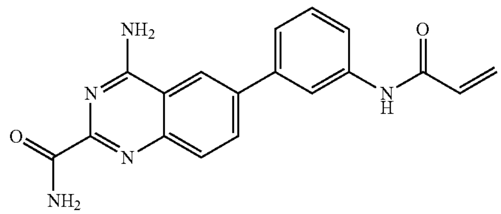 | 4-amino-6-[3-(prop-2-enamido)phenyl]quinazoline-2-carboxamide | 333.4 |
| 1356 | 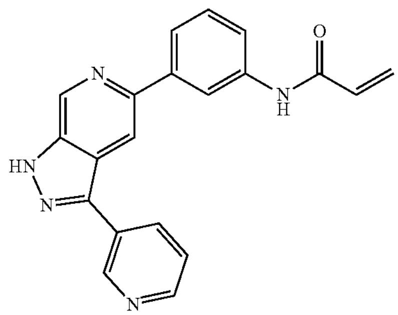 | N-{3-[3-(pyridin-3-yl)-1H-pyrazolo[3,4-c]pyridin-5-yl]phenyl}prop-2-enamide | 341.4 |
| 1357 | 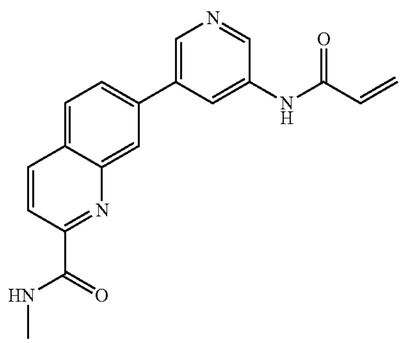 [SMILES: C=CC(=O)Nc1cncc(-c2ccc3ccc(C(=O)NC)nc3c2)c1] | N-methyl-7-[5-(prop-2-enamido)pyridin-3-yl]quinoline-2-carboxamide | 332.4 |
| 1358 | 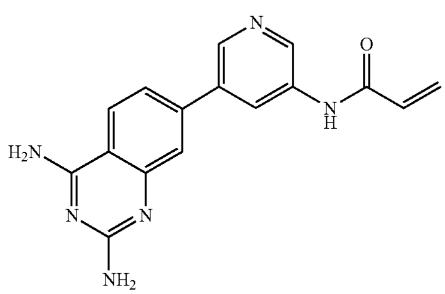 [SMILES: C=CC(=O)Nc1cncc(-c2ccc3c(N)nc(N)nc3c2)c1] | N-[5-(2,4-diaminoquinazolin-7-yl)pyridin-3-yl]prop-2-enamide | 306.3 |
| 1359 | 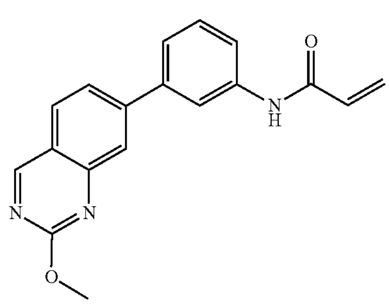 [SMILES: C=CC(=O)Nc1cccc(-c2ccc3cnc(OC)nc3c2)c1] | N-[3-(2-methoxyquinazolin-7-yl)phenyl]prop-2-enamide | 305.3 |

TABLE 16-continued

| Cpd No. | Structure | IUPAC | MW (g/mol) |
|---|---|---|---|
| 1360 | 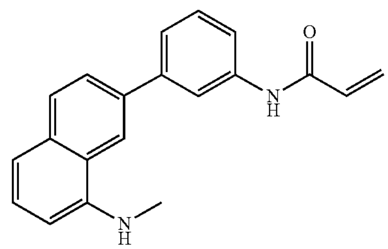 [SMILES: C=CC(=O)Nc1cccc(-c2ccc3cccc(NC)c3c2)c1] | N-{3-[8-(methylamino)naphthalen-2-yl]phenyl}prop-2-enamide | 302.4 |
| 1361 | 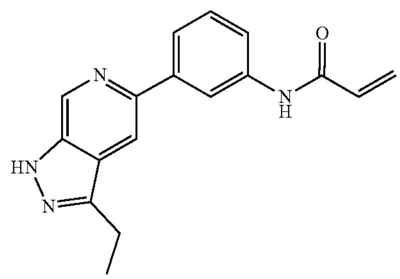 [SMILES: C=CC(=O)Nc1cccc(-c2cc3c(CC)n[nH]c3cn2)c1] | N-(3-{3-ethyl-1H-pyrazolo[3,4-c]pyridin-5-yl}phenyl)prop-2-enamide | 292.3 |
| 1362 | 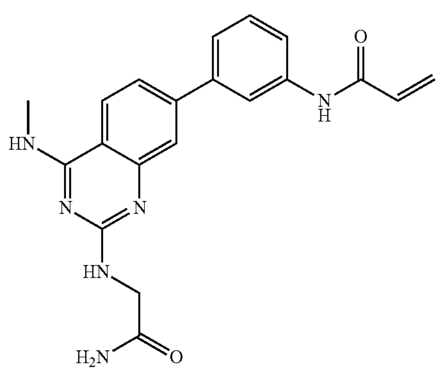 [SMILES: C=CC(=O)Nc1cccc(-c2ccc3c(NC)nc(NCC(N)=O)nc3c2)c1] | N-(3-{2-[(carbamoylmethyl)amino]-4-(methylamino)quinazolin-7-yl}phenyl)prop-2-enamide | 376.4 |
| 1363 | 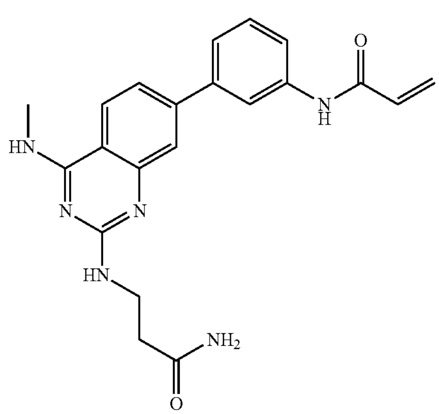 [SMILES: C=CC(=O)Nc1cccc(-c2ccc3c(NC)nc(NCCC(N)=O)nc3c2)c1] | N-(3-{2-[(2-carbamoylethyl)amino]-4-(methylamino)quinazolin-7-yl}phenyl)prop-2-enamide | 390.4 |

TABLE 16-continued

| Cpd No. | Structure | IUPAC | MW (g/mol) |
|---|---|---|---|
| 1364 | 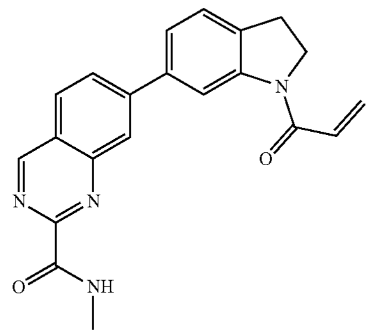 [SMILES: C=CC(=O)N1CCc2ccc(-c3ccc4cnc(C(=O)NC)nc4c3)cc21] | N-methyl-7-[1-(prop-2-enoyl)-2,3-dihydro-1H-indol-6-yl]quinazoline-2-carboxamide | 358.4 |
| 1365 | 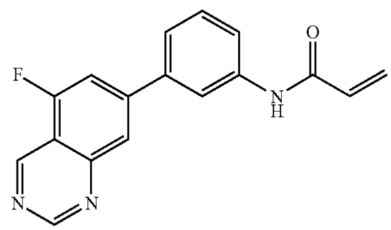 [SMILES: C=CC(=O)Nc1cccc(-c2cc(F)c3cncnc3c2)c1] | N-[3-(5-fluoroquinazolin-7-yl)phenyl]prop-2-enamide | 293.3 |
| 1366 | 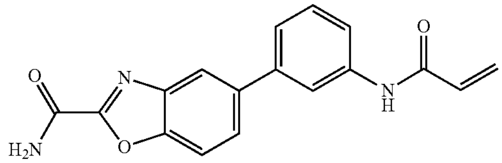 [SMILES: C=CC(=O)Nc1cccc(-c2ccc3oc(C(N)=O)nc3c2)c1] | 5-[3-(prop-2-enamido)phenyl]-1,3-benzoxazole-2-carboxamide | 307.3 |
| 1367 | 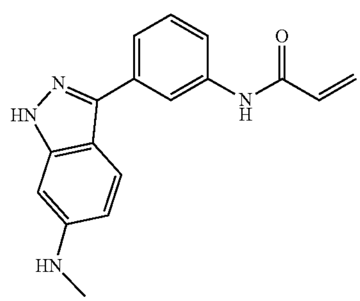 [SMILES: C=CC(=O)Nc1cccc(-c2n[nH]c3cc(NC)ccc23)c1] | N-{3-[6-(methylamino)-1H-indazol-3-yl]phenyl}prop-2-enamide | 292.3 |
| 1368 | 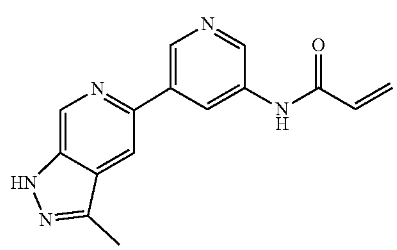 | N-(5-{3-methyl-1H-pyrazolo[3,4-c]pyridin-5-yl}pyridin-3-yl)prop-2-enamide | 279.3 |
| 1369 | 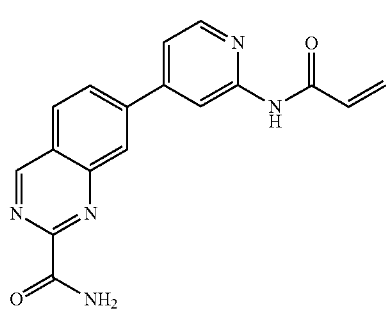 [SMILES: C=CC(=O)Nc1cc(-c2ccc3cnc(C(N)=O)nc3c2)ccn1] | 7-[2-(prop-2-enamido)pyridin-4-yl]quinazoline-2-carboxamide | 319.3 |

TABLE 16-continued

| Cpd No. | Structure | IUPAC | MW (g/mol) |
|---|---|---|---|
| 1370 | 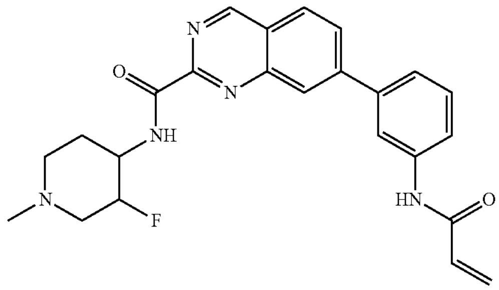 [SMILES: C=CC(=O)Nc1cccc(-c2ccc3cnc(C(=O)NC4CCN(C)CC4F)nc3c2)c1] | N-(3-fluoro-1-methylpiperidin-4-yl)-7-[3-(prop-2-enamido)phenyl]quinazoline-2-carboxamide | 433.5 |
| 1371 | 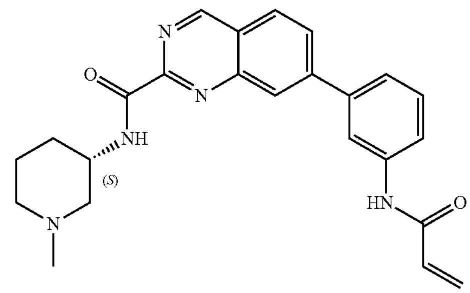 | N-[(3S)-1-methylpiperidin-3-yl]-7-[3-(prop-2-enamido)phenyl]quinazoline-2-carboxamide | 415.5 |
| 1372 | 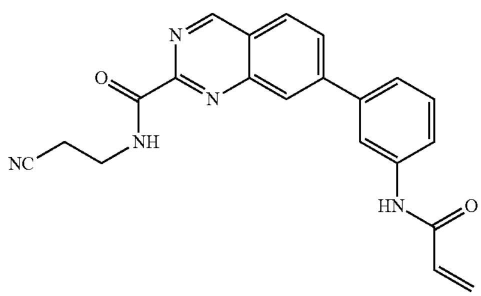 [SMILES: C=CC(=O)Nc1cccc(-c2ccc3cnc(C(=O)NCCC#N)nc3c2)c1] | N-(2-cyanoethyl)-7-[3-(prop-2-enamido)phenyl]quinazoline-2-carboxamide | 371.4 |

EMBODIMENTS

The following non-limiting embodiments provide illustrative examples of the invention, but do not limit the scope of the disclosure.

Embodiment 1. A compound of the formula:

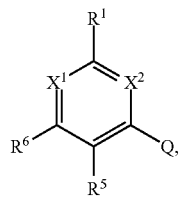

wherein:

$X^1$ is $CR^7$ or N;

$X^2$ is $CR^2$ or N;

each of $R^1$ and $R^2$ is independently alkyl, —$NR^8R^9$, —$C(O)NR^8R^9$, —$NR^8C(O)R^9$, —$OR^{10}$, —$SR^{11}$, —$C(O)R^{12}$, —$C(O)OR^{12}$, —$S(O)_2R^{13}$, CN, each of which is unsubstituted or substituted, or hydrogen or halogen;

Q is

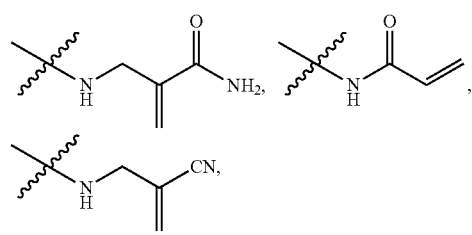

or $NR^3R^4$, wherein each of $R^3$ and $R^4$ is independently alkyl, cycloalkyl, alkenyl, —$C(O)R^{13}$, —$C(O)OR^{13}$, —$S(O)_2R^{13}$, —$S(O)_2R^{13}$, each of which is unsubstituted or substituted; or hydrogen, or $R^3$ and $R^4$ together with the nitrogen atom to which $R^3$ and $R^4$ are bound form a ring, wherein the ring is unsubstituted or substituted;

$R^7$ is alkyl, alkenyl, cycloalkyl, aryl, heteroaryl or heterocyclyl, each of which is unsubstituted or substituted, or hydrogen or halogen; each of $R^8$ and $R^9$ is alkyl, alkenyl, cycloalkyl, aryl, heteroaryl, heterocyclyl, each of which is unsubstituted or substituted, or hydrogen; or $R^8$ and $R^9$ together with the nitrogen atom to which $R^8$ and $R^9$ are bound form a ring, wherein the ring is unsubstituted or substituted;

each of $R^{10}$, $R^{11}$, $R^{12}$ and $R^{13}$ is independently is alkyl, alkenyl, cycloalkyl, aryl, heteroaryl or heterocyclyl, each of which is unsubstituted or substituted, or hydrogen or halogen.

Embodiment 2. The compound of embodiment 1, wherein:

when Q is

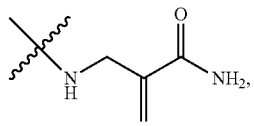

then each of $R^5$ and $R^6$ is independently aryl or heteroaryl, each of which is unsubstituted or substituted, or hydrogen or halogen; or $R^5$ and $R^6$ together with the carbon atoms to which $R^5$ and $R^6$ are bound form a ring, wherein the ring is unsubstituted or substituted.

Embodiment 3. The compound of embodiment 1 or embodiment 2, wherein when Q is

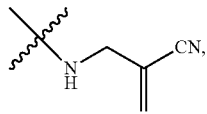 [SMILES: *NCC(=C)C#N]

then $R^5$ and $R^6$ together with the carbon atoms to which $R^5$ and $R^6$ are bound form the ring, wherein the ring is unsubstituted or substituted.

Embodiment 4. The compound of any one of embodiments 1-3, wherein when Q is

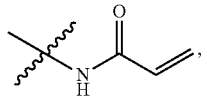

then $R^5$ is hydrogen or halogen, and $R^6$ is aryl or heteroaryl, which is unsubstituted or substituted.

Embodiment 5. The compound of any one of embodiments 1-4, wherein when Q is

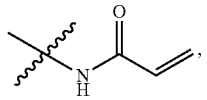 [SMILES: *NC(=O)C=C]

then $R^5$ and $R^6$ together with the carbon atoms to which $R^5$ and $R^6$ are bound form the ring, and the compound has the structure:

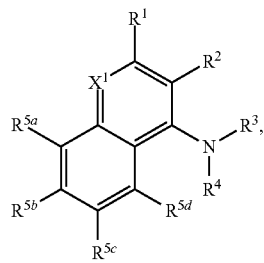

wherein $R^{5a}$, $R^{5b}$ and $R^{5d}$ are each independently aryl or heteroaryl, each of which is substituted or unsubstituted, or hydrogen or halogen, and $R^{5c}$ is

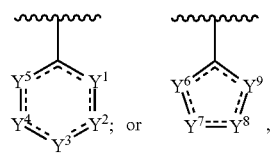

wherein each of ====== is independently a single bond or a double bond;

$Y^1$ is $CR^{6a}$, N, $NR^{6a}$, O or S;
$Y^2$ is $CR^{6b}$, N, $NR^{6b}$, O or S;
$Y^3$ is $CR^{6c}$, N, $NR^{6c}$, O or S;
$Y^4$ is $CR^{6d}$, N, $NR^{6d}$, O or S;
$Y^5$ is $CR^{6e}$, N, $NR^{6e}$, O or S;
$Y^6$ is $CR^{6f}$, N, $NR^{6f}$, O or S;
$Y^7$ is $CR^{6g}$, N, $NR^{6g}$, O or S;
$Y^8$ is $CR^{6h}$, N, $NR^{6h}$, O or S; and
$Y^9$ is $CR^{6i}$, N, $NR^{6i}$, O or S, wherein
each of $R^{6a}$, $R^{6b}$, $R^{6c}$, $R^{6d}$, $R^{6e}$, $R^{6f}$, $R^{6g}$, $R^{6h}$ and $R^{6i}$ is independently alkyl, cycloalkyl, $-N^{14}R^{15}$, $-OR^{16}$, $-SR^{17}$, $-C(O)NR^{14}R^{15}$, $-NHC(O)R^{14}R^{15}$, $-CN$, $-C(O)OR^{18}$, $-S(O)_2R^{19}$, $-NHS(O)_2R^{19}$, each of which is unsubstituted or substituted, or hydrogen or halogen; or $R^{6a}$ and $R^{6b}$ together with the carbon atoms to which $R^{6a}$ and $R^{6b}$ are bound form a ring, wherein the ring is unsubstituted or substituted, and each of $R^{6c}$, $R^{6d}$, $R^{6e}$, $R^{6f}$, $R^{6g}$, $R^{6h}$ and $R^{6i}$ is independently alkyl, cycloalkyl, $-N^{14}R^{15}$, $-OR^{16}$, $-SR^{17}$, $-C(O)NR^{14}R^{15}$, $-NHC(O)R^{14}R^{15}$, $-CN$, $-C(O)OR^{18}$, $-S(O)_2R^{19}$, $-NHS(O)_2R^{19}$, each of which is unsubstituted or substituted, or hydrogen or halogen; or $R^{6b}$ and $R^{6c}$ together with the carbon atoms to which $R^{6b}$ and $R^{6c}$ are bound form a ring, wherein the ring is unsubstituted or substituted, and each of $R^{6a}$, $R^{6d}$, $R^{6e}$, $R^{6f}$, $R^{6g}$, $R^{6h}$ and $R^{6i}$ is independently alkyl, cycloalkyl, $-N^{14}R^{15}$, $-OR^{16}$, $-SR^{17}$, $-C(O)NR^{14}R^{15}$, $-NHC(O)R^{14}R^{15}$, $-CN$, $-C(O)OR^{18}$, $-S(O)_2R^{19}$, $-NHS(O)_2R^{19}$, each of which is unsubstituted or substituted, or hydrogen or halogen; or $R^{6c}$ and $R^{6d}$ together with the carbon atoms to which $R^{6c}$ and $R^{6d}$ are bound form a ring, wherein the ring is unsubstituted or substituted, and each of $R^{6a}$, $R^{6b}$, $R^{6e}$, $R^{6f}$, $R^{6g}$, $R^{6h}$ and $R^{6i}$ is independently alkyl, cycloalkyl, $-N^{14}R^{15}$, $-OR^{16}$, $-SR^{17}$, $-C(O)NR^{14}R^{15}$, $-NHC(O)R^{14}R^{15}$, $-CN$, $-C(O)OR^{18}$, $-S(O)_2R^{19}$, $-NHS(O)_2R^{19}$, each of which is unsubstituted or substituted, or hydrogen or halogen; or $R^{6d}$ and $R^{6e}$ together with the carbon atoms to which $R^{6d}$ and $R^{6e}$ are bound form a ring, wherein the ring is unsubstituted or substituted, and each of $R^{6a}$, $R^{6b}$, $R^{6c}$, $R^{6f}$, $R^{6g}$, $R^{6h}$ and $R^{6i}$ is independently alkyl, cycloalkyl, $-N^{14}R^{15}$, $-OR^{16}$, $-SR^{17}$, $-C(O)NR^{14}R^{15}$, $-NHC(O)R^{14}R^{15}$, $-CN$, $-C(O)OR^{18}$, $-S(O)_2R^{19}$, $-NHS(O)_2R^{19}$, each of which is unsubstituted or substituted, or hydrogen or halogen; or $R^{6f}$ and $R^{6g}$ together with the carbon atoms to which $R^{6f}$ and $R^{6g}$ are bound form a ring, wherein the ring is unsubstituted or substituted, and each of $R^{6a}$, $R^{6b}$, $R^{6c}$, $R^{6d}$, $R^{6e}$, $R^{6h}$ and $R^{6i}$ is independently alkyl, cycloalkyl, $-N^{14}R^{15}$, $-OR^{16}$, $-SR^{17}$, $-C(O)NR^{14}R^{15}$, $-NHC(O)R^{14}R^{15}$, $-CN$, $-C(O)OR^{18}$, $-S(O)_2R^{19}$, $-NHS(O)_2R^{19}$, each of which is unsubstituted or substituted, or hydrogen or halogen; or $R^{6g}$ and $R^{6h}$ together with the carbon atoms to which $R^{6g}$ and $R^{6h}$ are bound form a ring, wherein the ring is unsubstituted or substituted, and each of $R^{6a}$, $R^{6b}$, $R^{6c}$, $R^{6d}$, $R^{6e}$, $R^{6f}$, and $R^{6i}$ is independently alkyl, cycloalkyl, $-N^{14}R^{15}$, $-OR^{16}$, $-SR^{17}$, $-C(O)NR^{14}R^{15}$, $-NHC(O)R^{14}R^{15}$, $-CN$, $-C(O)OR^{18}$, $-S(O)_2R^{19}$, $-NHS(O)_2R^{19}$, each of which is unsubstituted or substituted, or hydrogen or halogen; or $R^{6h}$ and $R^{6i}$ together with the carbon atoms to which $R^{6h}$ and $R^{6i}$ are bound form a ring, wherein the ring is unsubstituted or substituted, and each of $R^{6a}$, $R^{6b}$, $R^{6c}$, $R^{6d}$, $R^{6e}$, $R^{6f}$, and $R^{6g}$ is independently alkyl, cycloalkyl, $-N^{14}R^{15}$, $-OR^{16}$, $-SR^{17}$, $-C(O)NR^{14}R^{15}$, $-NHC(O)R^{14}R^{15}$, $-CN$, $-C(O)OR^{18}$, $-S(O)_2R^{19}$, $-NHS(O)_2R^{19}$, each of which is unsubstituted or substituted, or hydrogen or halogen.

Embodiment 6. The compound of any one of embodiments 1-5, provided that:
when Q is not

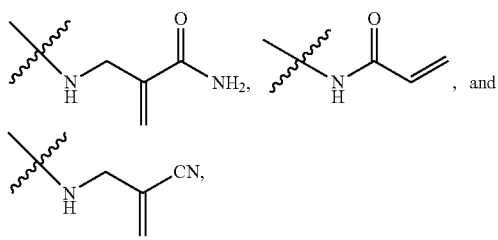

then $R^5$ and $R^6$ together with the carbon atoms to which $R^5$ and $R^6$ are bound form the ring, and compound has the structure:

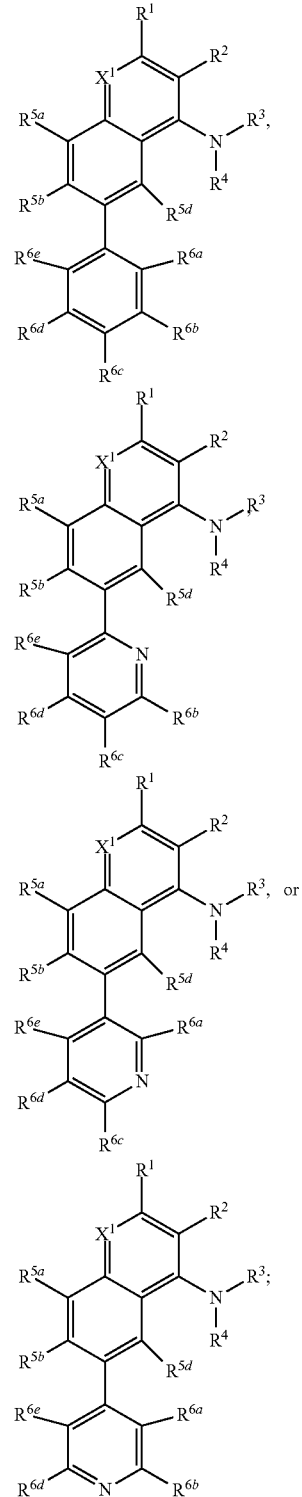

wherein:
$R^{5a}$, $R^{5b}$ and $R^{5d}$ are each independently aryl or heteroaryl, each of which is substituted or unsubstituted, or hydrogen or halogen; and
each of $R^{6a}$, $R^{6b}$, $R^{6c}$, $R^{6d}$, and $R^{6e}$ is independently alkyl, cycloalkyl, $-N^{14}R^{15}$, $-OR^{16}$, $-SR^{17}$, $-C(O)NR^{14}R^{15}$, $-NHC(O)R^{14}R^{15}$, $-CN$, $-C(O)OR^{18}$, $-S(O)_2R^{19}$, $-NHS(O)_2R^{19}$, each of which is unsubstituted or substituted, or hydrogen or halogen; wherein at least one of $R^{6a}$, $R^{6b}$, $R^{6c}$, $R^{6d}$, and $R^{6e}$ is —C(O)NR$^{14}$R$^{15}$, NR$^{14}$R$^{15}$, or NR$^{14}$C(O)R$^{15}$, and each of $R^{14}$ and $R^{15}$ is alkyl, alkenyl, cycloalkyl, aryl, heterocyclyl, or heteroaryl, each of which is unsubstituted or substituted, or hydrogen; or $R^{14}$ and $R^{15}$ together with the nitrogen atom to which $R^{14}$ and $R^{15}$ are bound form a ring, wherein the ring is unsubstituted or substituted; and each of $R^{16}$, $R^{17}$, $R^{18}$ and $R^{19}$ is independently is alkyl, alkenyl, cycloalkyl, aryl, heteroaryl or heterocyclyl, each of which is unsubstituted or substituted, or hydrogen or halogen;

or a pharmaceutically-acceptable salt thereof.

Embodiment 7. The compound of any one of embodiments 1-6, wherein $X^1$ is CR$^7$.

Embodiment 8. The compound of any one of embodiments 1-6, wherein $X^1$ is N.

Embodiment 9. The compound of any one of embodiments 1-8, wherein $R^1$ is H.

Embodiment 10. The compound of any one of embodiments 1-8, wherein $R^1$ is —C(O)NR$^8$R$^9$, —OR$^{10}$, or CN, each of which is unsubstituted or substituted.

Embodiment 11. The compound of any one of embodiments 1-10, wherein $X^2$ is CR$^2$ and $R^2$ is H.

Embodiment 12. The compound of any one of embodiments 1-10, wherein $X^2$ is CR$^2$ and $R^2$ is —OR$^{10}$.

Embodiment 13. The compound of any one of embodiments 1-10, wherein $X^2$ is CR$^2$ and $R^2$ is halogen.

Embodiment 14. The compound of any one of embodiments 1-10, wherein $X^2$ is CR$^2$ and $R^2$ is —C(O)NH$_2$.

Embodiment 15. The compound of embodiment 1, wherein Q is NR$^3$R$^4$, and wherein R$^3$ is hydrogen.

Embodiment 16, The compound of embodiment 1, wherein Q is NR$^3$R$^4$, and wherein one or both of R$^3$ and R$^4$ is

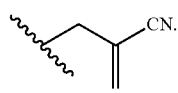

Embodiment 17. The compound of embodiment 1, wherein the compound has the formula:

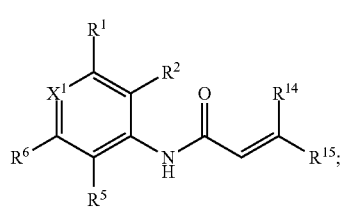

wherein each of $R^{14}$ and $R^{15}$ is independently alkyl, which is unsubstituted or substituted, or hydrogen.

Embodiment 18. The compound of embodiment 1 or 17, wherein the compound has the formula:

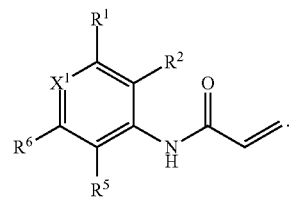

Embodiment 19. The compound of embodiment 1, wherein the compound has the formula:

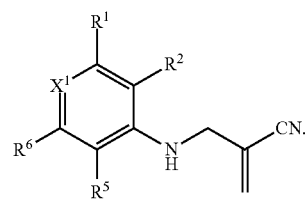

Embodiment 20. The compound of embodiment 1, wherein the compound has the formula:

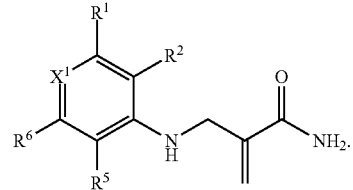

Embodiment 21. The compound of embodiment 1, wherein the compound has the formula:

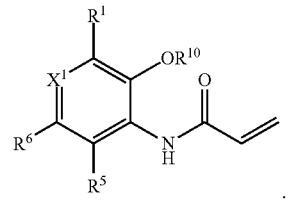

Embodiment 22. The compound of embodiment 1 or 19, wherein the compound has the formula:

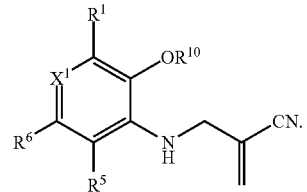

Embodiment 23. The compound of embodiment 1 or 20, wherein the compound has the formula:

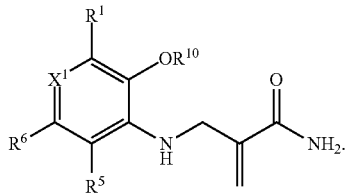

Embodiment 24. The compound of any one of embodiments 1, 3, or 5-23, wherein the compound has the formula:

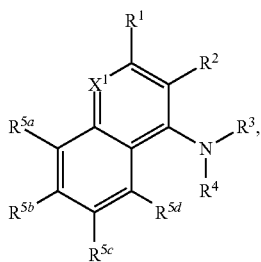

wherein
  $R^{5a}$, $R^{5b}$, $R^{5c}$, and $R^{5d}$ are each independently aryl or heteroaryl, each of which is substituted or unsubstituted, or hydrogen or halogen.

Embodiment 25. The compound of embodiment 24, wherein at least one of $R^{5a}$, $R^{5b}$, $R^{5c}$, and $R^{5d}$ is

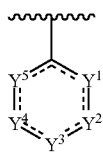

wherein
  each of ------ is independently a single bond or a double bond;
  $Y^1$ is $CR^{6a}$, N, $NR^{6a}$, O or S;
  $Y^2$ is $CR^{6b}$, N, $NR^{6b}$, O or S;
  $Y^3$ is $CR^{6c}$, N, $NR^{6c}$, O or S;
  $Y^4$ is $CR^{6d}$, N, $NR^{6d}$, O or S;
  $Y^5$ is $CR^{6e}$, N, $NR^{6e}$, O or S;
  wherein
    each of $R^{6a}$, $R^{6b}$, $R^{6c}$, $R^{6d}$, and $R^{6e}$ is independently alkyl, cycloalkyl, $-NR^{14}R^{15}$, $-OR^{16}$, $-SR^{17}$, $-C(O)NR^{14}R^{15}$, $-NHC(O)R^{14}R^{15}$, $-CN$, $-C(O)OR^{18}$, $-S(O)_2R^{19}$, $-NHS(O)_2R^{19}$, each of which is unsubstituted or substituted, or hydrogen or halogen; or
    $R^{6a}$ and $R^{6b}$ together with the carbon atoms to which $R^{6a}$ and $R^{6b}$ are bound form a ring, wherein the ring is unsubstituted or substituted, and each of $R^{6c}$, $R^{6d}$, and $R^{6e}$ is independently alkyl, cycloalkyl, $-NR^{14}R^{15}$, $-OR^{16}$, $-SR^{17}$, $-C(O)NR^{14}R^{15}$, $-NHC(O)R^{14}R^{15}$, $-CN$, $-C(O)OR^{18}$, $-S(O)_2R^{19}$, $-NHS(O)_2R^{19}$, each of which is unsubstituted or substituted, or hydrogen or halogen; or
    $R^{6b}$ and $R^{6c}$ together with the carbon atoms to which $R^{6b}$ and $R^{6c}$ are bound form a ring, wherein the ring is unsubstituted or substituted; and each of $R^{6a}$, $R^{6d}$, and $R^{6e}$ is independently alkyl, cycloalkyl, $-NR^{14}R^{15}$, $-OR^{16}$, $-SR^{17}$, $-C(O)NR^{14}R^{15}$, $-NHC(O)R^{14}R^{15}$, $-CN$, $-C(O)OR^{18}$, $-S(O)_2R^{19}$, $-NHS(O)_2R^{19}$, each of which is unsubstituted or substituted, or hydrogen or halogen; or
    $R^{6c}$ and $R^{6d}$ together with the carbon atoms to which $R^{6c}$ and $R^{6d}$ are bound form a ring, wherein the ring is unsubstituted or substituted, and each of $R^{6a}$, $R^{6b}$, and $R^{6e}$ is independently alkyl, cycloalkyl, $-NR^{14}R^{15}$, $-OR^{16}$, $-SR^{17}$, $-C(O)NR^{14}R^{15}$, $-NHC(O)R^{14}R^{15}$, $-CN$, $-C(O)OR^{18}$, $-S(O)_2R^{19}$, $-NHS(O)_2R^{19}$, each of which is unsubstituted or substituted, or hydrogen or halogen; or
    $R^{6d}$ and $R^{6e}$ together with the carbon atoms to which $R^{6d}$ and $R^{6e}$ are bound form a ring, wherein the ring is unsubstituted or substituted, and each of $R^{6a}$, $R^{6b}$, and $R^{6c}$ is independently alkyl, cycloalkyl, $-NR^{14}R^{15}$, $-OR^{16}$, $-SR^{17}$, $-C(O)NR^{14}R^{15}$, $-NHC(O)R^{14}R^{15}$, $-CN$, $-C(O)OR^{18}$, $-S(O)_2R^{19}$, $-NHS(O)_2R^{19}$, each of which is unsubstituted or substituted, or hydrogen or halogen.

Embodiment 26. The compound of embodiment 24, wherein at least one of $R^{5a}$, $R^{5b}$, $R^{5c}$, and $R^{5d}$ is

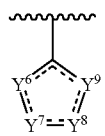

wherein
  each of ------ independently a single bond or a double bond;
  $Y^6$ is $CR^{6f}$, N, $NR^{6f}$, O or S;
  $Y^7$ is $CR^{6g}$, N, $NR^{6ga}$, O or S;
  $Y^8$ is $CR^{6h}$, N, $NR^{6h}$, O or S; and
  $Y^9$ is $CR^{6i}$, N, $NR^{6i}$, O or S;
  wherein
    each of $R^{6f}$, $R^{6g}$, $R^{6h}$, and $R^{6i}$ is independently alkyl, cycloalkyl, $-NR^{14}R^{15}$, $-OR^{16}$, $-SR^{17}$, $-C(O)NR^{14}R^{15}$, $-NHC(O)R^{14}R^{15}$, $-CN$, $-C(O)OR^{18}$, $-S(O)_2R^{19}$, $-NHS(O)_2R^{19}$, each of which is unsubstituted or substituted, or hydrogen or halogen; or
    $R^{6f}$ and $R^{6g}$ together with the carbon atoms to which $R^{6f}$ and $R^{6g}$ are bound form a ring, wherein the ring is unsubstituted or substituted, and each of $R^{6h}$ and $R^{6i}$ is independently alkyl, cycloalkyl, $-NR^{14}R^{15}$, $-OR^{16}$, $-SR^{17}$, $-C(O)NR^{14}R^{15}$, $-NHC(O)R^{14}R^{15}$, $-CN$, $-C(O)OR^{18}$, $-S(O)_2R^{19}$, $-NHS(O)_2R^{19}$, each of which is unsubstituted or substituted, or hydrogen or halogen; or
    $R^{6g}$ and $R^{6h}$ together with the carbon atoms to which $R^{6g}$ and $R^{6h}$ are bound form a ring, wherein the ring is unsubstituted or substituted, and each of $R^{6f}$ and $R^{6i}$ is independently alkyl, cycloalkyl, $-NR^{14}R^{15}$, $-OR^{16}$, $-SR^{17}$, $-C(O)NR^{14}R^{15}$, $-NHC(O)R^{14}R^{15}$, $-CN$, $-C(O)OR^{18}$, $-S(O)_2R^{19}$, $-NHS(O)_2R^{19}$, each of which is unsubstituted or substituted, or hydrogen or halogen; or R$^{6h}$ and R$^{6i}$ together with the carbon atoms to which R$^{6h}$ and R$^{6i}$ are bound form a ring, wherein the ring is unsubstituted or substituted, and each of R$^{6f}$, and R$^{6g}$ is independently alkyl, cycloalkyl, —NR$^{14}$R$^{15}$, —OR$^{16}$, —SR$^{17}$, —C(O)NR$^{14}$R$^{15}$, —NHC(O)R$^{14}$R$^{15}$, —CN, —C(O)OR$^{18}$, —S(O)$_2$R$^{19}$, —NHS(O)$_2$R$^{19}$, each of which is unsubstituted or substituted, or hydrogen or halogen.

Embodiment 27. The compound of embodiment 25, wherein the compound has the formula:

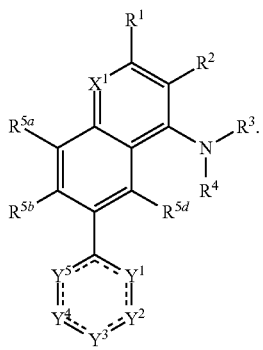

Embodiment 28. The compound of embodiment 25, wherein the compound has the formula:

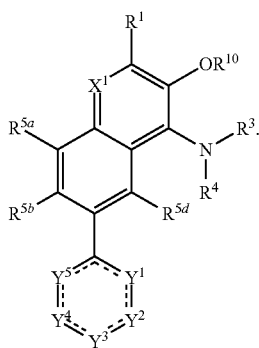

Embodiment 29. The compound of embodiment 25, wherein the compound has the formula:

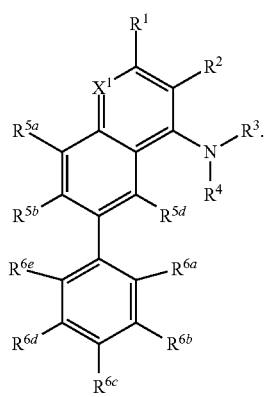

Embodiment 30. The compound of any one of embodiments 24-29, wherein at least one of R$^{6a}$, R$^{6b}$, R$^{6c}$, R$^{6d}$, and R$^{6e}$ is —C(O)NR$^{14}$R$^{15}$, —NR$^{14}$C(O)R$^{15}$, or —NR$^{14}$R$^{15}$.

Embodiment 31. The compound of embodiment 30, wherein R$^{6b}$ is —C(O)NR$^{14}$R$^{15}$.

Embodiment 32. The compound of embodiment 30, wherein R$^{6b}$ is —NR$^{14}$R$^{15}$.

Embodiment 33. The compound of embodiment 30, wherein R$^{6b}$ is —NR$^{14}$C(O)R$^{15}$.

Embodiment 34. The compound of any one of embodiments 30-33, wherein R$^{14}$ is hydrogen.

Embodiment 35. The compound of embodiment 25 or 26, wherein —NR$^{14}$C(O)R$^{15}$ is

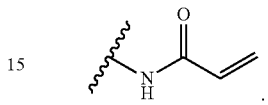

Embodiment 36. The compound of embodiment 25 or 26, wherein R$^{15}$ is cycloalkyl that is unsubstituted or substituted.

Embodiment 37. The compound of embodiment 36, wherein R$^{15}$ is cycloalkyl substituted by —C(O)NR$^{20}$R$^{21}$, —NR$^{20}$C(O)R$^{21}$, or —NR$^{20}$R$^{21}$, wherein each of R$^{20}$ and R$^{21}$ is alkyl, alkenyl, cycloalkyl, aryl, heterocyclyl, heteroaryl, each of which is unsubstituted or substituted, or hydrogen; or R$^{20}$ and R$^{21}$ together with the nitrogen atom to which R$^{20}$ and R$^{21}$ are bound form a ring, wherein the ring is unsubstituted or substituted.

Embodiment 38. The compound of embodiment 25 or 26, wherein R$^{15}$ is heteroaryl that is unsubstituted or substituted.

Embodiment 39. The compound of embodiment 38, wherein R$^{15}$ is heteroaryl substituted by —C(O)NR$^{20}$R$^{21}$, —NR$^{20}$C(O)R$^{21}$, or —NR$^{20}$R$^{21}$, wherein each of R$^{20}$ and R$^{21}$ is alkyl, alkenyl, cycloalkyl, aryl, heterocyclyl, heteroaryl, each of which is unsubstituted or substituted, or hydrogen; or R$^{20}$ and R$^{21}$ together with the nitrogen atom to which R$^{20}$ and R$^{21}$ are bound form a ring, wherein the ring is unsubstituted or substituted.

Embodiment 40. The compound of embodiment 25 or 26, wherein R$^{15}$ is heterocyclyl that is unsubstituted or substituted.

Embodiment 41. The compound of embodiment 40, wherein R$^{15}$ is heterocyclyl substituted by —C(O)NR$^{20}$R$^{21}$, —NR$^{20}$C(O)R$^{21}$, or —NR$^{20}$R$^{21}$, wherein each of R$^{20}$ and R$^{21}$ is alkyl, alkenyl, cycloalkyl, aryl, heterocyclyl, heteroaryl, each of which is unsubstituted or substituted, or hydrogen; or R$^{20}$ and R$^{21}$ together with the nitrogen atom to which R$^{20}$ and R$^{21}$ are bound form a ring, wherein the ring is unsubstituted or substituted.

Embodiment 42. The compound of embodiment 41, wherein R$^{15}$ is piperidinyl that is unsubstituted or substituted.

Embodiment 43. The compound of embodiment 41, wherein R$^{15}$ is

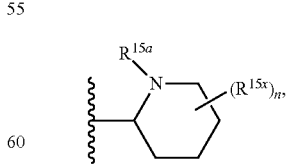

wherein
R$^{15a}$ is independently alkyl that is unsubstituted or substituted, or hydrogen or halogen;
each R$^{15x}$ is independently halogen or hydrogen; and
n is independently 0, 1, 2, 3, 4, 5, 6, 7, or 8.

Embodiment 44. The compound of embodiment 43, wherein $R^{15a}$ is methyl.

Embodiment 45. The compound of embodiment 41, wherein $R^{15}$ is

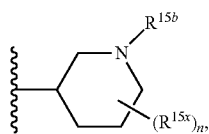

wherein each of $R^{15b}$ is independently alkyl that is unsubstituted or substituted, or hydrogen or halogen;

each $R^{15x}$ is independently halogen or hydrogen; and n is independently 0, 1, 2, 3, 4, 5, 6, 7, or 8.

Embodiment 46. The compound of embodiment 45, wherein $R^{15b}$ is methyl.

Embodiment 47. The compound of embodiment 41, wherein $R^{15}$ is

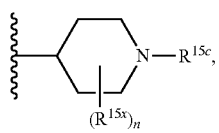

wherein each $R^{15c}$ is independently alkyl that is unsubstituted or substituted, or hydrogen or halogen;

each $R^{15x}$ is independently halogen or hydrogen; and n is independently 0, 1, 2, 3, 4, 5, 6, 7, or 8.

Embodiment 48. The compound of embodiment 47, wherein $R^{15c}$ is methyl.

Embodiment 49. The compound of embodiment 25 or 26, wherein $R^{15}$ is alkyl that is unsubstituted or substituted.

Embodiment 50. The compound of embodiment 49, wherein $R^{15}$ is alkyl that is substituted with a heterocyclyl group.

Embodiment 51. The compound of embodiment 50, wherein $R^{15}$ is alkyl that is substituted with a morpholinyl or piperidinyl group, each of which is substituted or unsubstituted.

Embodiment 52. The compound of embodiment 25 or 26, wherein $R^{15}$ is alkyl that is substituted with an unsubstituted or substituted heteroaryl group.

Embodiment 53. The compound of embodiment 52, wherein $R^{15}$ is alkyl that is substituted with an unsubstituted or substituted imidazolyl group.

Embodiment 54. The compound of embodiment 25, wherein the compound has the formula:

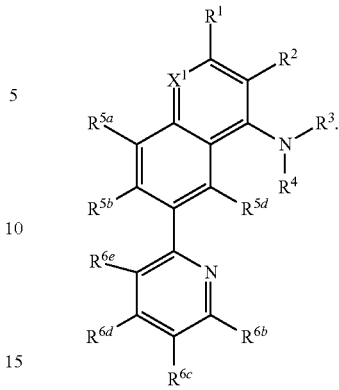

Embodiment 55. The compound of embodiment 54, wherein at least one of $R^{6b}$, $R^{6c}$, $R^{6d}$, and $R^{6e}$ is —C(O)NR$^{14}$R$^{15}$, —NR$^{14}$C(O)R$^{15}$, or —NR$^{14}$R$^{15}$.

Embodiment 56. The compound of embodiment 55, wherein $R^{6b}$ is —C(O)NR$^{14}$R$^{15}$.

Embodiment 57. The compound of embodiment 55, wherein $R^{6b}$ is —NR$^{14}$R$^{15}$.

Embodiment 58. The compound of embodiment 55, wherein $R^{6b}$ is —NR$^{14}$C(O)R$^{15}$.

Embodiment 59. The compound of embodiment 55, wherein $R^{14}$ is hydrogen.

Embodiment 60. The compound of embodiment 55 or 58, wherein —NR$^{14}$C(O)R$^{15}$ is

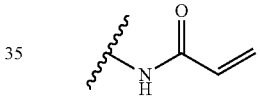

Embodiment 60a. The compound of embodiment 55, wherein $R^{15}$ is cycloalkyl that is unsubstituted or substituted.

Embodiment 61. The compound of embodiment 60a, wherein $R^{15}$ is cycloalkyl substituted by —C(O)NR$^{20}$R$^{21}$, —NR$^{20}$C(O)R$^{21}$, or —NR$^{20}$R$^{21}$, wherein each of $R^{20}$ and $R^{21}$ is alkyl, alkenyl, cycloalkyl, aryl, heterocyclyl, heteroaryl, each of which is unsubstituted or substituted, or hydrogen; or $R^{20}$ and $R^{21}$ together with the nitrogen atom to which $R^{20}$ and $R^{21}$ are bound form a ring, wherein the ring is unsubstituted or substituted.

Embodiment 62. The compound of embodiment 55, wherein $R^{15}$ is heteroaryl that is unsubstituted or substituted.

Embodiment 63. The compound of embodiment 55, wherein $R^{15}$ is heteroaryl substituted by —C(O)NR$^{20}$R$^{21}$, —NR$^{20}$C(O)R$^{21}$, or —NR$^{20}$R$^{21}$, wherein each of $R^{20}$ and $R^{21}$ is alkyl, alkenyl, cycloalkyl, aryl, heterocyclyl, heteroaryl, each of which is unsubstituted or substituted, or hydrogen; or $R^{20}$ and $R^{21}$ together with the nitrogen atom to which $R^{20}$ and $R^{21}$ are bound form a ring, wherein the ring is unsubstituted or substituted.

Embodiment 64. The compound of embodiment 55, wherein $R^{15}$ is heterocyclyl that is unsubstituted or substituted.

Embodiment 65. The compound of embodiment 64, wherein $R^{15}$ is heterocyclyl substituted by —C(O)NR$^{20}$R$^{21}$, —NR$^{20}$C(O)R$^{21}$, or —NR$^{20}$R$^{21}$, wherein each of $R^{20}$ and $R^{21}$ is alkyl, alkenyl, cycloalkyl, aryl, heterocyclyl, heteroaryl, each of which is unsubstituted or substituted, or hydrogen; or $R^{20}$ and $R^{21}$ together with the nitrogen atom to which $R^{20}$ and $R^{21}$ are bound form a ring, wherein the ring is unsubstituted or substituted.

Embodiment 66. The compound of embodiment 65, wherein $R^{15}$ is piperidinyl that is unsubstituted or substituted.

Embodiment 67. The compound of embodiment 66, wherein $R^{15}$ is

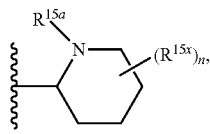

wherein
$R^{15a}$ is independently alkyl that is unsubstituted or substituted, or hydrogen or halogen;
each $R^{15x}$ is independently halogen or hydrogen; and
n is independently 0, 1, 2, 3, 4, 5, 6, 7, or 8.

Embodiment 68. The compound of embodiment 67, wherein $R^{15a}$ is methyl.

Embodiment 69. The compound of embodiment 66, wherein $R^{15}$ is

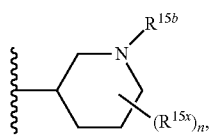

wherein
each of $R^{15b}$ is independently alkyl that is unsubstituted or substituted, or hydrogen or halogen;
each $R^{15x}$ is independently halogen or hydrogen; and
n is independently 0, 1, 2, 3, 4, 5, 6, 7, or 8.

Embodiment 70. The compound of embodiment 69, wherein $R^{15b}$ is methyl.

Embodiment 71. The compound of embodiment 66, wherein $R^{15}$ is

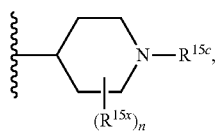

wherein
each $R^{15c}$ is independently alkyl that is unsubstituted or substituted, or hydrogen or halogen;
each $R^{15x}$ is independently halogen or hydrogen; and
n is independently 0, 1, 2, 3, 4, 5, 6, 7, or 8.

Embodiment 72. The compound of embodiment 71, wherein $R^{15c}$ is methyl.

Embodiment 73. The compound of embodiment 55, wherein $R^{15}$ is alkyl that is unsubstituted or substituted.

Embodiment 74. The compound of embodiment 73, wherein $R^{15}$ is alkyl that is substituted with a heterocyclyl group.

Embodiment 75. The compound of embodiment 55, wherein $R^{15}$ is alkyl that is substituted with a morpholinyl or piperidinyl group, each of which is substituted or unsubstituted.

Embodiment 76. The compound of embodiment 55, wherein $R^{15}$ is alkyl that is substituted with an unsubstituted or substituted heteroaryl group.

Embodiment 77. The compound of embodiment 55, wherein $R^{15}$ is alkyl that is substituted with an unsubstituted or substituted imidazolyl group.

Embodiment 78. The compound of embodiment 25, wherein the compound has the formula:

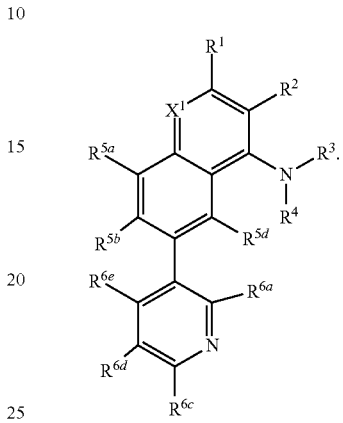

Embodiment 79. The compound of embodiment 78, wherein at least one of $R^{6a}$, $R^{6c}$, $R^{6d}$, and $R^{6e}$ is —C(O)NR$^{14}$R$^{15}$, —NR$^{14}$C(O)R$^{15}$, or —NR$^{14}$R$^{15}$.

Embodiment 80. The compound of embodiment 79, wherein $R^{6b}$ is —C(O)NR$^{14}$R$^{15}$.

Embodiment 81. The compound of embodiment 79, wherein $R^{6b}$ is —NR$^{14}$R$^{15}$.

Embodiment 82. The compound of embodiment 79, wherein $R^{6b}$ is —NR$^{14}$C(O)R$^{15}$.

Embodiment 83. The compound of embodiment 79, wherein $R^{14}$ is hydrogen.

Embodiment 84. The compound of embodiment 79, wherein —NR$^{14}$C(O)R$^{15}$ is

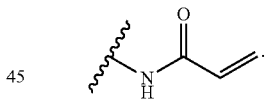

Embodiment 85. The compound of embodiment 79, wherein $R^{15}$ is cycloalkyl that is unsubstituted or substituted.

Embodiment 86. The compound of embodiment 85, wherein $R^{15}$ is cycloalkyl substituted by —C(O)NR$^{20}$R$^{21}$, —NR$^{20}$C(O)R$^{21}$, or —NR$^{20}$R$^{21}$, wherein each of $R^{20}$ and $R^{21}$ is alkyl, alkenyl, cycloalkyl, aryl, heterocyclyl, heteroaryl, each of which is unsubstituted or substituted, or hydrogen; or $R^{20}$ and $R^{21}$ together with the nitrogen atom to which $R^{20}$ and $R^{21}$ are bound form a ring, wherein the ring is unsubstituted or substituted.

Embodiment 87. The compound of embodiment 79, wherein $R^{15}$ is heteroaryl that is unsubstituted or substituted.

Embodiment 88. The compound of embodiment 87, wherein $R^{15}$ is heteroaryl substituted by —C(O)NR$^{20}$R$^{21}$, —NR$^{20}$C(O)R$^{21}$, or —NR$^{20}$R$^{21}$, wherein each of $R^{20}$ and $R^{21}$ is alkyl, alkenyl, cycloalkyl, aryl, heterocyclyl, heteroaryl, each of which is unsubstituted or substituted, or hydrogen; or $R^{20}$ and $R^{21}$ together with the nitrogen atom to which $R^{20}$ and $R^{21}$ are bound form a ring, wherein the ring is unsubstituted or substituted.

Embodiment 89. The compound of embodiment 79, wherein $R^{15}$ is heterocyclyl that is unsubstituted or substituted.

Embodiment 90. The compound of embodiment 89, wherein $R^{15}$ is heterocyclyl substituted by —C(O)NR$^{20}$R$^{21}$, —NR$^{20}$C(O)R$^{21}$, or —NR$^{20}$R$^{21}$, wherein each of $R^{20}$ and $R^{21}$ is alkyl, alkenyl, cycloalkyl, aryl, heterocyclyl, heteroaryl, each of which is unsubstituted or substituted, or hydrogen; or $R^{20}$ and $R^{21}$ together with the nitrogen atom to which $R^{20}$ and $R^{21}$ are bound form a ring, wherein the ring is unsubstituted or substituted.

Embodiment 91. The compound of embodiment 90, wherein $R^{15}$ is piperidinyl that is unsubstituted or substituted.

Embodiment 92. The compound of embodiment 91, wherein $R^{15}$ is

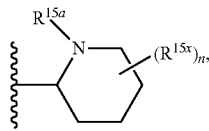

wherein
  $R^{15a}$ is independently alkyl that is unsubstituted or substituted, or hydrogen or halogen;
  each $R^{15x}$ is independently halogen or hydrogen; and
  n is independently 0, 1, 2, 3, 4, 5, 6, 7, or 8.

Embodiment 93. The compound of embodiment 92, wherein $R^{15a}$ is methyl.

Embodiment 94. The compound of embodiment 91, wherein $R^{15}$ is

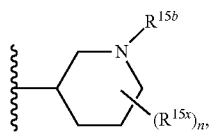

wherein
  each of $R^{15b}$ is independently alkyl that is unsubstituted or substituted, or hydrogen or halogen;
  each $R^{15x}$ is independently halogen or hydrogen; and
  n is independently 0, 1, 2, 3, 4, 5, 6, 7, or 8.

Embodiment 95. The compound of embodiment 94, wherein $R^{15b}$ is methyl.

Embodiment 96. The compound of embodiment 91, wherein $R^{15}$ is

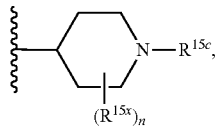

wherein
  each $R^{15c}$ is independently alkyl that is unsubstituted or substituted, or hydrogen or halogen;
  each $R^{15x}$ is independently halogen or hydrogen; and
  n is independently 0, 1, 2, 3, 4, 5, 6, 7, or 8.

Embodiment 97. The compound of embodiment 96, wherein $R^{15c}$ is methyl.

Embodiment 98. The compound of embodiment 79, wherein $R^{15}$ is alkyl that is unsubstituted or substituted.

Embodiment 99. The compound of embodiment 98, wherein $R^{15}$ is alkyl that is substituted with a heterocyclyl group.

Embodiment 100. The compound of embodiment 99, wherein $R^{15}$ is alkyl that is substituted with a morpholinyl or piperidinyl group, each of which is substituted or unsubstituted.

Embodiment 101. The compound of embodiment 79, wherein $R^{15}$ is alkyl that is substituted with an unsubstituted or substituted heteroaryl group.

Embodiment 102. The compound of embodiment 101, wherein $R^{15}$ is alkyl that is substituted with an unsubstituted or substituted imidazolyl group.

Embodiment 103. The compound of embodiment 25, wherein the compound has the formula:

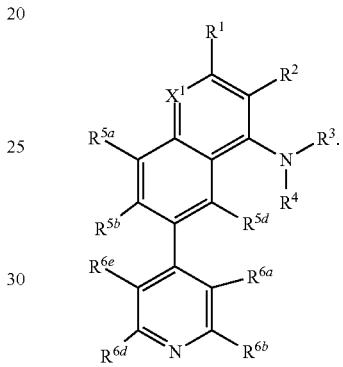

Embodiment 104. The compound of embodiment 103, wherein at least one of $R^{6a}$, $R^{6b}$, $R^{6d}$, and $R^{6e}$ is —C(O)NR$^{14}$R$^{15}$, —NR$^{14}$C(O)R$^{15}$, or —NR$^{14}$R$^{15}$.

Embodiment 105. The compound of embodiment 104, wherein $R^{6b}$ is —C(O)NR$^{14}$R$^{15}$.

Embodiment 106. The compound of embodiment 104, wherein $R^{6b}$ is —NR$^{14}$R$^{15}$.

Embodiment 107. The compound of embodiment 104, wherein $R^{6b}$ is —NR$^{14}$C(O)R$^{15}$.

Embodiment 108. The compound of embodiment 104, wherein $R^{14}$ is hydrogen.

Embodiment 109. The compound of embodiment 104, wherein —NR$^{14}$C(O)R$^{15}$ is

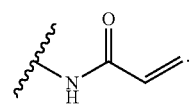

Embodiment 110. The compound of embodiment 104, wherein $R^{15}$ is cycloalkyl that is unsubstituted or substituted.

Embodiment 111. The compound of embodiment 104, wherein $R^{15}$ is cycloalkyl substituted by —C(O)NR$^{20}$R$^{21}$, —NR$^{20}$C(O)R$^{21}$, or —NR$^{20}$R$^{21}$, wherein each of $R^{20}$ and $R^{21}$ is alkyl, alkenyl, cycloalkyl, aryl, heterocyclyl, heteroaryl, each of which is unsubstituted or substituted, or hydrogen; or $R^{20}$ and $R^{21}$ together with the nitrogen atom to which $R^{20}$ and $R^{21}$ are bound form a ring, wherein the ring is unsubstituted or substituted.

Embodiment 112. The compound of embodiment 104, wherein $R^{15}$ is heteroaryl that is unsubstituted or substituted.

Embodiment 113. The compound of embodiment 112, wherein $R^{15}$ is heteroaryl substituted by —C(O)NR$^{20}$R$^{21}$, —NR$^{20}$C(O)R$^{21}$, or —NR$^{20}$R$^{21}$, wherein each of R$^{20}$ and R$^{21}$ is alkyl, alkenyl, cycloalkyl, aryl, heterocyclyl, heteroaryl, each of which is unsubstituted or substituted, or hydrogen; or R$^{20}$ and R$^{21}$ together with the nitrogen atom to which R$^{20}$ and R$^{21}$ are bound form a ring, wherein the ring is unsubstituted or substituted.

Embodiment 114. The compound of embodiment 104, wherein $R^{15}$ is heterocyclyl that is unsubstituted or substituted.

Embodiment 115. The compound of embodiment 114, wherein $R^{15}$ is heterocyclyl substituted by —C(O)NR$^{20}$R$^{21}$, —NR$^{20}$C(O)R$^{21}$, or —NR$^{20}$R$^{21}$, wherein each of R$^{20}$ and R$^{21}$ is alkyl, alkenyl, cycloalkyl, aryl, heterocyclyl, heteroaryl, each of which is unsubstituted or substituted, or hydrogen; or R$^{20}$ and R$^{21}$ together with the nitrogen atom to which R$^{20}$ and R$^{21}$ are bound form a ring, wherein the ring is unsubstituted or substituted.

Embodiment 116. The compound of embodiment 115, wherein $R^{15}$ is piperidinyl that is unsubstituted or substituted.

Embodiment 117. The compound of embodiment 116, wherein $R^{15}$ is

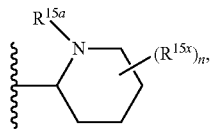

wherein
$R^{15a}$ is independently alkyl that is unsubstituted or substituted, or hydrogen or halogen;
each $R^{15x}$ is independently halogen or hydrogen; and
n is independently 0, 1, 2, 3, 4, 5, 6, 7, or 8.

Embodiment 118. The compound of embodiment 117, wherein $R^{15a}$ is methyl.

Embodiment 119. The compound of embodiment 116, wherein $R^{15}$ is

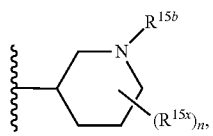

wherein
each of $R^{15b}$ is independently alkyl that is unsubstituted or substituted, or hydrogen or halogen;
each $R^{15x}$ is independently halogen or hydrogen; and
n is independently 0, 1, 2, 3, 4, 5, 6, 7, or 8.

Embodiment 120. The compound of embodiment 119, wherein $R^{15b}$ is methyl.

Embodiment 121. The compound of embodiment 116, wherein $R^{15}$ is

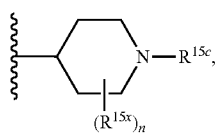

wherein
each $R^{15c}$ is independently alkyl that is unsubstituted or substituted, or hydrogen or halogen;
each $R^{15x}$ is independently halogen or hydrogen; and
n is independently 0, 1, 2, 3, 4, 5, 6, 7, or 8.

Embodiment 122. The compound of embodiment 121, wherein $R^{15c}$ is methyl.

Embodiment 123. The compound of embodiment 104, wherein $R^{15}$ is alkyl that is unsubstituted or substituted.

Embodiment 124. The compound of embodiment 123, wherein $R^{15}$ is alkyl that is substituted with a heterocyclyl group.

Embodiment 125. The compound of embodiment 124, wherein $R^{15}$ is alkyl that is substituted with a morpholinyl or piperidinyl group, each of which is substituted or unsubstituted.

Embodiment 126. The compound of embodiment 104, wherein $R^{15}$ is alkyl that is substituted with an unsubstituted or substituted heteroaryl group.

Embodiment 127. The compound of embodiment 126, wherein $R^{15}$ is alkyl that is substituted with an unsubstituted or substituted imidazolyl group.

Embodiment 128. The compound of embodiment 25, wherein the compound has the formula:

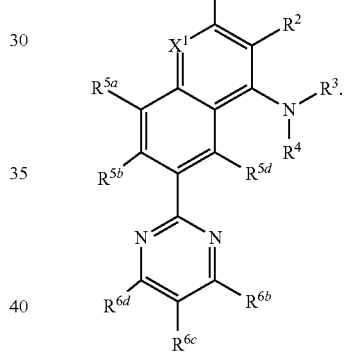

Embodiment 129. The compound of embodiment 128, wherein at least one of R$^{6b}$, R$^{6c}$, and R$^{6d}$ is —C(O)NR$^{14}$R$^{15}$, —NR$^{14}$C(O)R$^{15}$, or —NR$^{14}$R$^{15}$.

Embodiment 130. The compound of embodiment 129, wherein R$^{6b}$ is —C(O)NR$^{14}$R$^{15}$.

Embodiment 131. The compound of embodiment 129, wherein R$^{6b}$ is —NR$^{14}$R$^{15}$.

Embodiment 132. The compound of embodiment 129, wherein R$^{6b}$ is —NR$^{14}$C(O)R$^{15}$.

Embodiment 133. The compound of embodiment 129, wherein R$^{14}$ is hydrogen.

Embodiment 134. The compound of embodiment 129, wherein —NR$^{14}$C(O)R$^{15}$ is

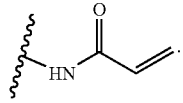

Embodiment 135. The compound of embodiment 129, wherein R$^{15}$ is cycloalkyl that is unsubstituted or substituted.

Embodiment 136. The compound of embodiment 135, wherein R$^{15}$ is cycloalkyl substituted by —C(O)NR$^{20}$R$^{21}$, —NR²⁰C(O)R²¹, or —NR²⁰R²¹, wherein each of R²⁰ and R²¹ is alkyl, alkenyl, cycloalkyl, aryl, heterocyclyl, heteroaryl, each of which is unsubstituted or substituted, or hydrogen; or R²⁰ and R²¹ together with the nitrogen atom to which R²⁰ and R²¹ are bound form a ring, wherein the ring is unsubstituted or substituted.

Embodiment 137. The compound of embodiment 129, wherein R¹⁵ is heteroaryl that is unsubstituted or substituted.

Embodiment 138. The compound of embodiment 137, wherein R¹⁵ is heteroaryl substituted by —C(O)NR²⁰R²¹, —NR²⁰C(O)R²¹, or —NR²⁰R²¹, wherein each of R²⁰ and R²¹ is alkyl, alkenyl, cycloalkyl, aryl, heterocyclyl, heteroaryl, each of which is unsubstituted or substituted, or hydrogen; or R²⁰ and R²¹ together with the nitrogen atom to which R²⁰ and R²¹ are bound form a ring, wherein the ring is unsubstituted or substituted.

Embodiment 139. The compound of embodiment 129, wherein R¹⁵ is heterocyclyl that is unsubstituted or substituted.

Embodiment 140. The compound of embodiment 139, wherein R¹⁵ is heterocyclyl substituted by —C(O)NR²⁰R²¹, —NR²⁰C(O)R²¹, or —NR²⁰R²¹, wherein each of R²⁰ and R²¹ is alkyl, alkenyl, cycloalkyl, aryl, heterocyclyl, heteroaryl, each of which is unsubstituted or substituted, or hydrogen; or R²⁰ and R²¹ together with the nitrogen atom to which R²⁰ and R²¹ are bound form a ring, wherein the ring is unsubstituted or substituted.

Embodiment 141. The compound of embodiment 140, wherein R¹⁵ is piperidinyl that is unsubstituted or substituted.

Embodiment 142. The compound of embodiment 141, wherein R¹⁵ is

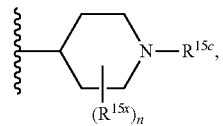

wherein
each of R¹⁵ᵃ is independently alkyl that is unsubstituted or substituted, or hydrogen or halogen;
each R¹⁵ˣ is independently halogen or hydrogen; and
n is independently 0, 1, 2, 3, 4, 5, 6, 7, or 8.

Embodiment 143. The compound of embodiment 142, wherein R¹⁵ᵃ is methyl.

Embodiment 144. The compound of embodiment 141, wherein R¹⁵ is

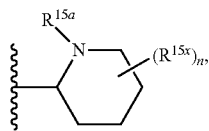

wherein
each of R¹⁵ᵇ is independently alkyl that is unsubstituted or substituted, or hydrogen or halogen;
each R¹⁵ˣ is independently halogen or hydrogen; and
n is independently 0, 1, 2, 3, 4, 5, 6, 7, or 8.

Embodiment 145. The compound of embodiment 144, wherein R¹⁵ᵇ is methyl.

Embodiment 146. The compound of embodiment 141, wherein R¹⁵ is

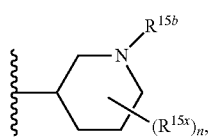

wherein
R¹⁵ᶜ is independently alkyl that is unsubstituted or substituted, or hydrogen or halogen;
each R¹⁵ˣ is independently halogen or hydrogen; and
n is independently 0, 1, 2, 3, 4, 5, 6, 7, or 8.

Embodiment 147. The compound of embodiment 146, wherein R¹⁵ᶜ is methyl.

Embodiment 148. The compound of embodiment 129, wherein R¹⁵ is alkyl that is unsubstituted or substituted.

Embodiment 149. The compound of embodiment 148, wherein R¹⁵ is alkyl that is substituted with a heterocyclyl.

Embodiment 150. The compound of embodiment 149, wherein R¹⁵ is alkyl that is substituted with a morpholinyl or piperidinyl, each of which is substituted or unsubstituted.

Embodiment 151. The compound of embodiment 129, wherein R¹⁵ is alkyl that is substituted with an unsubstituted or substituted heteroaryl group.

Embodiment 152. The compound of embodiment 141, wherein R¹⁵ is alkyl that is substituted with an unsubstituted or substituted imidazolyl group.

Embodiment 153. The compound of embodiment 25, wherein the compound has the formula:

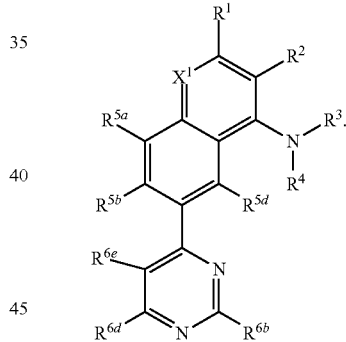

Embodiment 154. The compound of embodiment 153, wherein at least one of R⁶ᵇ, R⁶ᵈ, and R⁶ᵉ is —C(O)NR¹⁴R¹⁵, —NR¹⁴C(O)R¹⁵, or —NR¹⁴R¹⁵.

Embodiment 155. The compound of embodiment 154, wherein R⁶ᵇ is —C(O)NR¹⁴R¹⁵.

Embodiment 156. The compound of embodiment 154, wherein R⁶ᵇ is —NR¹⁴R¹⁵.

Embodiment 157. The compound of embodiment 154, wherein R⁶ᵇ is —NR¹⁴C(O)R¹⁵.

Embodiment 158. The compound of embodiment 154, wherein R¹⁴ is hydrogen.

Embodiment 159. The compound of embodiment 154, wherein —NR¹⁴C(O)R¹⁵ is

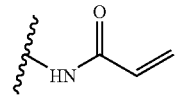

Embodiment 160. The compound of embodiment 154, wherein $R^{15}$ is cycloalkyl that is unsubstituted or substituted.

Embodiment 161. The compound of embodiment 160, wherein $R^{15}$ is cycloalkyl substituted by —C(O)NR$^{20}$R$^{21}$, —NR$^{20}$C(O)R$^{21}$, or —NR$^{20}$R$^{21}$, wherein each of R$^{20}$ and R$^{21}$ is alkyl, alkenyl, cycloalkyl, aryl, heterocyclyl, heteroaryl, each of which is unsubstituted or substituted, or hydrogen; or R$^{20}$ and R$^{21}$ together with the nitrogen atom to which R$^{20}$ and R$^{21}$ are bound form a ring, wherein the ring is unsubstituted or substituted.

Embodiment 162. The compound of embodiment 154, wherein $R^{15}$ is heteroaryl that is unsubstituted or substituted.

Embodiment 163. The compound of embodiment 162, wherein $R^{15}$ is heteroaryl substituted by —C(O)NR$^{20}$R$^{21}$, —NR$^{20}$C(O)R$^{21}$, or —NR$^{20}$R$^{21}$, wherein each of R$^{20}$ and R$^{21}$ is alkyl, alkenyl, cycloalkyl, aryl, heterocyclyl, heteroaryl, each of which is unsubstituted or substituted, or hydrogen; or R$^{20}$ and R$^{21}$ together with the nitrogen atom to which R$^{20}$ and R$^{21}$ are bound form a ring, wherein the ring is unsubstituted or substituted.

Embodiment 164. The compound of embodiment 154, wherein $R^{15}$ is heterocyclyl that is unsubstituted or substituted.

Embodiment 165. The compound of embodiment 164, wherein $R^{15}$ is heterocyclyl substituted by —C(O)NR$^{20}$R$^{21}$, —NR$^{20}$C(O)R$^{21}$, or —NR$^{20}$R$^{21}$, wherein each of R$^{20}$ and R$^{21}$ is alkyl, alkenyl, cycloalkyl, aryl, heterocyclyl, heteroaryl, each of which is unsubstituted or substituted, or hydrogen; or R$^{20}$ and R$^{21}$ together with the nitrogen atom to which R$^{20}$ and R$^{21}$ are bound form a ring, wherein the ring is unsubstituted or substituted.

Embodiment 166. The compound of embodiment 165, wherein $R^{15}$ is piperidinyl that is unsubstituted or substituted.

Embodiment 167. The compound of embodiment 166, wherein $R^{15}$ is

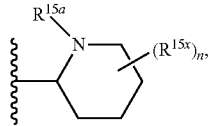

wherein
each of $R^{15a}$ is independently alkyl that is unsubstituted or substituted, or hydrogen or halogen;
each $R^{15x}$ is independently halogen or hydrogen; and
n is independently 0, 1, 2, 3, 4, 5, 6, 7, or 8.

Embodiment 168. The compound of embodiment 167, wherein $R^{15a}$ is methyl.

Embodiment 169. The compound of embodiment 166, wherein $R^{15}$ is

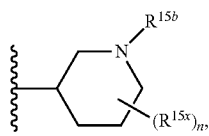

wherein
each of $R^{15b}$ is independently alkyl that is unsubstituted or substituted, or hydrogen or halogen;
each $R^{15x}$ is independently halogen or hydrogen; and
n is independently 0, 1, 2, 3, 4, 5, 6, 7, or 8.

Embodiment 170. The compound of embodiment 169, wherein $R^{15b}$ is methyl.

Embodiment 171. The compound of embodiment 166, wherein $R^{15}$ is

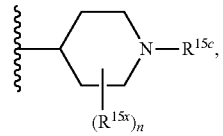

wherein
$R^{15c}$ is independently alkyl that is unsubstituted or substituted, or hydrogen or halogen;
each $R^{15x}$ is independently halogen or hydrogen; and
n is independently 0, 1, 2, 3, 4, 5, 6, 7, or 8.

Embodiment 172. The compound of embodiment 171, wherein $R^{15c}$ is methyl.

Embodiment 173. The compound of embodiment 154, wherein $R^{15}$ is alkyl that is unsubstituted or substituted.

Embodiment 174. The compound of embodiment 173, wherein $R^{15}$ is alkyl that is substituted with a heterocyclyl.

Embodiment 175. The compound of embodiment 173, wherein $R^{15}$ is alkyl that is substituted with a morpholinyl or piperidinyl, each of which is substituted or unsubstituted.

Embodiment 176. The compound of embodiment 173, wherein $R^{15}$ is alkyl that is substituted with an unsubstituted or substituted heteroaryl group.

Embodiment 177. The compound of embodiment 176, wherein $R^{15}$ is alkyl that is substituted with an unsubstituted or substituted imidazolyl group.

Embodiment 178. The compound of embodiment 25, wherein the compound has the formula:

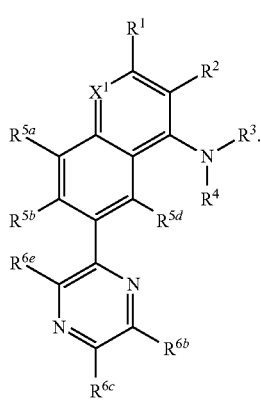

Embodiment 179. The compound of embodiment 178, wherein at least one of $R^{6b}$, $R^{6c}$, and $R^{6e}$ is —C(O)NR$^{14}$R$^{15}$, —NR$^{14}$C(O)R$^{15}$, or —NR$^{14}$R$^{15}$.

Embodiment 180. The compound of embodiment 179, wherein $R^{6b}$ is —C(O)NR$^{14}$R$^{15}$.

Embodiment 181. The compound of embodiment 179, wherein $R^{6b}$ is —NR$^{14}$R$^{15}$.

Embodiment 182. The compound of embodiment 179, wherein $R^{6b}$ is —NR$^{14}$C(O)R$^{15}$.

Embodiment 183. The compound of embodiment 179, wherein $R^{14}$ is hydrogen.

Embodiment 184. The compound of embodiment 179, wherein —NR$^{14}$C(O)R$^{15}$ is

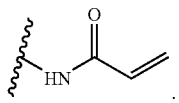

Embodiment 185. The compound of embodiment 179, wherein R$^{15}$ is cycloalkyl that is unsubstituted or substituted.

Embodiment 186. The compound of embodiment 185, wherein R$^{15}$ is cycloalkyl substituted by —C(O)NR$^{20}$R$^{21}$, —NR$^{20}$C(O)R$^{21}$, or —NR$^{20}$R$^{21}$, wherein each of R$^{20}$ and R$^{21}$ is alkyl, alkenyl, cycloalkyl, aryl, heterocyclyl, heteroaryl, each of which is unsubstituted or substituted, or hydrogen; or R$^{20}$ and R$^{21}$ together with the nitrogen atom to which R$^{20}$ and R$^{21}$ are bound form a ring, wherein the ring is unsubstituted or substituted.

Embodiment 187. The compound of embodiment 179, wherein R$^{15}$ is heteroaryl that is unsubstituted or substituted.

Embodiment 188. The compound of embodiment 187, wherein R$^{15}$ is heteroaryl substituted by —C(O)NR$^{20}$R$^{21}$, —NR$^{20}$C(O)R$^{21}$, or —NR$^{20}$R$^{21}$, wherein each of R$^{20}$ and R$^{21}$ is alkyl, alkenyl, cycloalkyl, aryl, heterocyclyl, heteroaryl, each of which is unsubstituted or substituted, or hydrogen; or R$^{20}$ and R$^{21}$ together with the nitrogen atom to which R$^{20}$ and R$^{21}$ are bound form a ring, wherein the ring is unsubstituted or substituted.

Embodiment 189. The compound of embodiment 179, wherein R$^{15}$ is heterocyclyl that is unsubstituted or substituted.

Embodiment 190. The compound of embodiment 189, wherein R$^{15}$ is heterocyclyl substituted by —C(O)NR$^{20}$R$^{21}$, —NR$^{20}$C(O)R$^{21}$, or —NR$^{20}$R$^{21}$, wherein each of R$^{20}$ and R$^{21}$ is alkyl, alkenyl, cycloalkyl, aryl, heterocyclyl, heteroaryl, each of which is unsubstituted or substituted, or hydrogen; or R$^{20}$ and R$^{21}$ together with the nitrogen atom to which R$^{20}$ and R$^{21}$ are bound form a ring, wherein the ring is unsubstituted or substituted.

Embodiment 191. The compound of embodiment 190, wherein R$^{15}$ is piperidinyl that is unsubstituted or substituted.

Embodiment 192. The compound of embodiment 191, wherein R$^{15}$ is

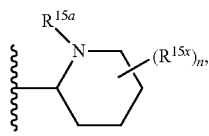

wherein
each of R$^{15a}$ is independently alkyl that is unsubstituted or substituted, or hydrogen or halogen;
each R$^{15x}$ is independently halogen or hydrogen; and
n is independently 0, 1, 2, 3, 4, 5, 6, 7, or 8.

Embodiment 193. The compound of embodiment 192, wherein R$^{15a}$ is methyl.

Embodiment 194. The compound of embodiment 191, wherein R$^{15}$ is

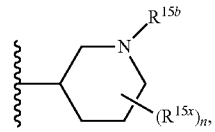

wherein
each of R$^{15b}$ is independently alkyl that is unsubstituted or substituted, or hydrogen or halogen;
each R$^{15x}$ is independently halogen or hydrogen; and
n is independently 0, 1, 2, 3, 4, 5, 6, 7, or 8.

Embodiment 195. The compound of embodiment 194, wherein R$^{15b}$ is methyl.

Embodiment 196. The compound of embodiment 191, wherein R$^{15}$ is

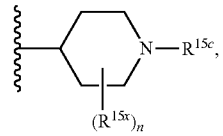

wherein
R$^{15c}$ is independently alkyl that is unsubstituted or substituted, or hydrogen or halogen;
each R$^{15x}$ is independently halogen or hydrogen; and
n is independently 0, 1, 2, 3, 4, 5, 6, 7, or 8.

Embodiment 197. The compound of embodiment 196, wherein R$^{15c}$ is methyl.

Embodiment 198. The compound of embodiment 179, wherein R$^{15}$ is alkyl that is unsubstituted or substituted.

Embodiment 199. The compound of embodiment 198, wherein R$^{15}$ is alkyl that is substituted with a heterocyclyl.

Embodiment 200. The compound of embodiment 198, wherein R$^{15}$ is alkyl that is substituted with a morpholinyl or piperidinyl, each of which is substituted or unsubstituted.

Embodiment 201. The compound of embodiment 198, wherein R$^{15}$ is alkyl that is substituted with an unsubstituted or substituted heteroaryl group.

Embodiment 202. The compound of embodiment 201, wherein R$^{15}$ is alkyl that is substituted with an unsubstituted or substituted imidazolyl group.

Embodiment 203. The compound of embodiment 25, wherein the compound has the formula:

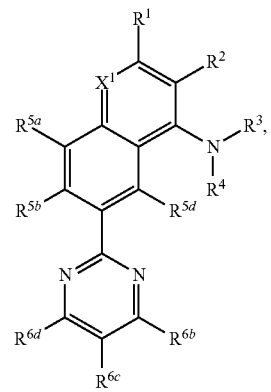

-continued

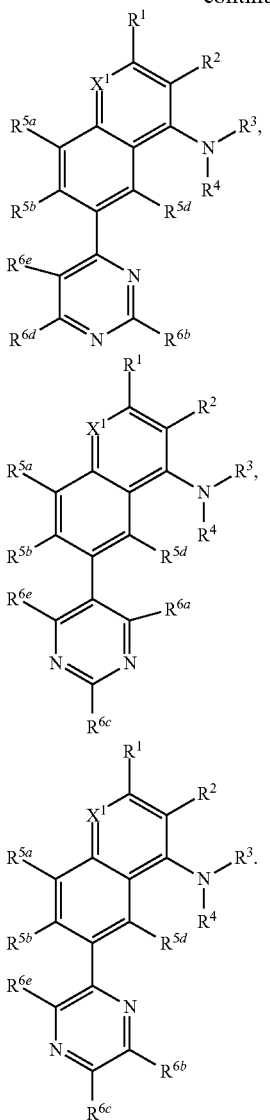

Embodiment 204. The compound of embodiment 203, wherein at least one of $R^{6a}$, $R^{6b}$, $R^{6c}$, $R^{6d}$, and $R^{6e}$ is —C(O)NR$^{14}$R$^{15}$, —NR$^{14}$C(O)R$^{15}$, or —NR$^{14}$R$^{15}$.

Embodiment 205. The compound of embodiment 204, wherein $R^{6b}$ is —C(O)NR$^{14}$R$^{15}$.

Embodiment 206. The compound of embodiment 204, wherein $R^{6b}$ is —NR$^{14}$R$^{15}$.

Embodiment 207. The compound of embodiment 204, wherein $R^{6b}$ is —NR$^{14}$C(O)R$^{15}$.

Embodiment 208. The compound of embodiment 204, wherein $R^{14}$ is hydrogen.

Embodiment 209. The compound of embodiment 204, wherein —NR$^{14}$C(O)R$^{15}$ is

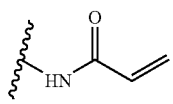

Embodiment 210. The compound of embodiment 204, wherein $R^{15}$ is cycloalkyl that is unsubstituted or substituted.

Embodiment 211. The compound of embodiment 210, wherein $R^{15}$ is cycloalkyl substituted by —C(O)NR$^{20}$R$^{21}$, —NR$^{20}$C(O)R$^{21}$, or —NR$^{20}$R$^{21}$, wherein each of $R^{20}$ and $R^{21}$ is alkyl, alkenyl, cycloalkyl, aryl, heterocyclyl, heteroaryl, each of which is unsubstituted or substituted, or hydrogen; or $R^{20}$ and $R^{21}$ together with the nitrogen atom to which $R^{20}$ and $R^{21}$ are bound form a ring, wherein the ring is unsubstituted or substituted.

Embodiment 212. The compound of embodiment 204, wherein $R^{15}$ is heteroaryl that is unsubstituted or substituted.

Embodiment 213. The compound of embodiment 212, wherein $R^{15}$ is heteroaryl substituted by —C(O)NR$^{20}$R$^{21}$, —NR$^{20}$C(O)R$^{21}$, or —NR$^{20}$R$^{21}$, wherein each of $R^{20}$ and $R^{21}$ is alkyl, alkenyl, cycloalkyl, aryl, heterocyclyl, heteroaryl, each of which is unsubstituted or substituted, or hydrogen; or $R^{20}$ and $R^{21}$ together with the nitrogen atom to which $R^{20}$ and $R^{21}$ are bound form a ring, wherein the ring is unsubstituted or substituted.

Embodiment 214. The compound of embodiment 204, wherein $R^{15}$ is heterocyclyl that is unsubstituted or substituted.

Embodiment 215. The compound of embodiment 214, wherein $R^{15}$ is heterocyclyl substituted by —C(O)NR$^{20}$R$^{21}$, —NR$^{20}$C(O)R$^{21}$, or —NR$^{20}$R$^{21}$, wherein each of $R^{20}$ and $R^{21}$ is alkyl, alkenyl, cycloalkyl, aryl, heterocyclyl, heteroaryl, each of which is unsubstituted or substituted, or hydrogen; or $R^{20}$ and $R^{21}$ together with the nitrogen atom to which $R^{20}$ and $R^{21}$ are bound form a ring, wherein the ring is unsubstituted or substituted.

Embodiment 216. The compound of embodiment 215, wherein $R^{15}$ is piperidinyl that is unsubstituted or substituted.

Embodiment 217. The compound of embodiment 216, wherein $R^{15}$ is

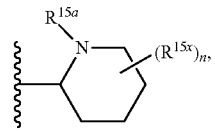

wherein
each of $R^{15a}$ is independently alkyl that is unsubstituted or substituted, or hydrogen or halogen;
each $R^{15x}$ is independently halogen or hydrogen; and
n is independently 0, 1, 2, 3, 4, 5, 6, 7, or 8.

Embodiment 218. The compound of embodiment 217, wherein $R^{15a}$ is methyl.

Embodiment 219. The compound of embodiment 216, wherein R is

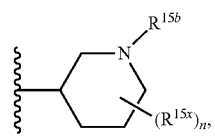

wherein
each of $R^{15b}$ is independently alkyl that is unsubstituted or substituted, or hydrogen or halogen;
each $R^{15x}$ is independently halogen or hydrogen; and
n is independently 0, 1, 2, 3, 4, 5, 6, 7, or 8.

Embodiment 220. The compound of embodiment 219, wherein $R^{15b}$ is methyl.

Embodiment 221. The compound of embodiment 216, wherein $R^{15}$ is

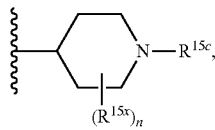

wherein
$R^{15c}$ is independently alkyl that is unsubstituted or substituted, or hydrogen or halogen;
each $R^{15x}$ is independently halogen or hydrogen; and
n is independently 0, 1, 2, 3, 4, 5, 6, 7, or 8.

Embodiment 222. The compound of embodiment 221, wherein $R^{15c}$ is methyl.

Embodiment 223. The compound of embodiment 204, wherein $R^{15}$ is alkyl that is unsubstituted or substituted.

Embodiment 224. The compound of embodiment 223, wherein $R^{15}$ is alkyl that is substituted with a heterocyclyl.

Embodiment 225. The compound of embodiment 224, wherein $R^{15}$ is alkyl that is substituted with a morpholinyl or piperidinyl, each of which is substituted or unsubstituted.

Embodiment 226. The compound of embodiment 223, wherein $R^{15}$ is alkyl that is substituted with an unsubstituted or substituted heteroaryl group.

Embodiment 227. The compound of embodiment 226, wherein $R^{15}$ is alkyl that is substituted with an unsubstituted or substituted imidazolyl group.

Embodiment 228. The compound of embodiment 25, wherein the compound has the formula:

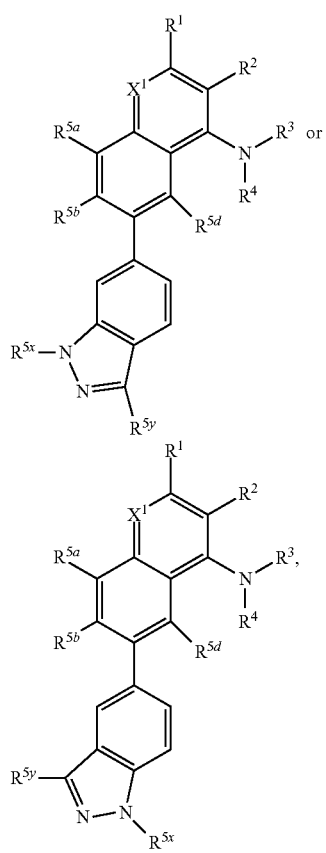

wherein each of $R^{5x}$ and $R^{5y}$ is each independently alkyl, cycloalkyl, $-NR^{14}R^{15}$, $-OR^{16}$, $-SR^{17}$, $-C(O)NR^{14}R^{15}$, $-NR^{14}C(O)R^{15}$, $-CN$, $-C(O)OR^{18}$, $-S(O)_2R^{19}$, $-NHS(O)_2R^{19}$, each of which is unsubstituted or substituted, or hydrogen or halogen.

Embodiment 229. The compound of embodiment 228, wherein $R^{5x}$ or $R^{5y}$ is $-C(O)NR^{14}R^{15}$.

Embodiment 230. The compound of embodiment 228, wherein $R^{5x}$ or $R^{5y}$ is $-NR^{14}R^{15}$.

Embodiment 231. The compound of embodiment 228, wherein $R^{5x}$ or $R^{5y}$ is $-NR^{14}C(O)R^{15}$.

Embodiment 232. The compound of embodiment 228, wherein $R^{14}$ is hydrogen.

Embodiment 233. The compound of embodiment 228, wherein $-NR^{14}C(O)R^{15}$ is

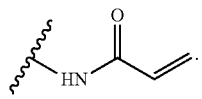 [SMILES: *NC(=O)C=C]

Embodiment 234. The compound of embodiment 228, wherein $R^{15}$ is cycloalkyl that is unsubstituted or substituted.

Embodiment 235. The compound of embodiment 234, wherein $R^{15}$ is cycloalkyl substituted by $-C(O)NR^{20}R^{21}$, $-NR^{20}C(O)R^{21}$, or $-NR^{20}R^{21}$, wherein each of $R^{20}$ and $R^{21}$ is alkyl, alkenyl, cycloalkyl, aryl, heterocyclyl, heteroaryl, each of which is unsubstituted or substituted, or hydrogen; or $R^{20}$ and $R^{21}$ together with the nitrogen atom to which $R^{20}$ and $R^{21}$ are bound form a ring, wherein the ring is unsubstituted or substituted.

Embodiment 236. The compound of embodiment 234, wherein $R^{15}$ is heteroaryl that is unsubstituted or substituted.

Embodiment 237. The compound of embodiment 236, wherein $R^{15}$ is heteroaryl substituted by $-C(O)NR^{20}R^{21}$, $-NR^{20}C(O)R^{21}$, or $-NR^{20}R^{21}$, wherein each of $R^{20}$ and $R^{21}$ is alkyl, alkenyl, cycloalkyl, aryl, heterocyclyl, heteroaryl, each of which is unsubstituted or substituted, or hydrogen; or $R^{20}$ and $R^{21}$ together with the nitrogen atom to which $R^{20}$ and $R^{21}$ are bound form a ring, wherein the ring is unsubstituted or substituted.

Embodiment 238. The compound of embodiment 234, wherein $R^{15}$ is heterocyclyl that is unsubstituted or substituted.

Embodiment 239. The compound of embodiment 238, wherein $R^{15}$ is heterocyclyl substituted by $-C(O)NR^{20}R^{21}$, $-NR^{20}C(O)R^{21}$, or $-NR^{20}R^{21}$, wherein each of $R^{20}$ and $R^{21}$ is alkyl, alkenyl, cycloalkyl, aryl, heterocyclyl, heteroaryl, each of which is unsubstituted or substituted, or hydrogen; or $R^{20}$ and $R^{21}$ together with the nitrogen atom to which $R^{20}$ and $R^{21}$ are bound form a ring, wherein the ring is unsubstituted or substituted.

Embodiment 240. The compound of embodiment 239, wherein $R^{15}$ is piperidinyl that is unsubstituted or substituted.

Embodiment 241. The compound of embodiment 240, wherein $R^{15}$ is

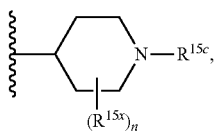

wherein

R$^{15c}$ is independently alkyl that is unsubstituted or substituted, or hydrogen or halogen;

each of R$^{15x}$ is independently halogen or hydrogen; and n is independently 0, 1, 2, 3, 4, 5, 6, 7, or 8.

Embodiment 242. The compound of embodiment 241, wherein R$^{15c}$ is methyl.

Embodiment 243. The compound of embodiment 240, wherein R$^{15}$ is

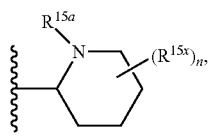

wherein

R$^{15a}$ is independently alkyl that is unsubstituted or substituted, or hydrogen or halogen;

each of R$^{15x}$ is independently halogen or hydrogen; and n is independently 0, 1, 2, 3, 4, 5, 6, 7, or 8.

Embodiment 244. The compound of embodiment 243, wherein R$^{15a}$ is methyl.

Embodiment 245. The compound of embodiment 240, wherein R$^{15}$ is

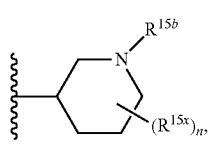

wherein

R$^{15b}$ is independently alkyl that is unsubstituted or substituted, or hydrogen or halogen;

each of R$^{15x}$ is independently halogen or hydrogen; and n is independently 0, 1, 2, 3, 4, 5, 6, 7, or 8.

Embodiment 246. The compound of embodiment 245, wherein R$^{15b}$ is methyl.

Embodiment 247. The compound of embodiment 228, wherein R$^{15}$ is alkyl that is unsubstituted or substituted.

Embodiment 248. The compound of embodiment 247, wherein R$^{15}$ is alkyl that is substituted with a heterocyclyl group.

Embodiment 249. The compound of embodiment 248, wherein R$^{15}$ is alkyl that is substituted with a morpholinyl or piperidinyl group, each of which is substituted or unsubstituted.

Embodiment 250. The compound of embodiment 247, wherein R$^{15}$ is alkyl that is substituted with an unsubstituted or substituted heteroaryl group.

Embodiment 251. The compound of embodiment 250, wherein R$^{15}$ is alkyl that is substituted with an unsubstituted or substituted imidazolyl group.

Embodiment 252. The compound of embodiment 26, which has the structure:

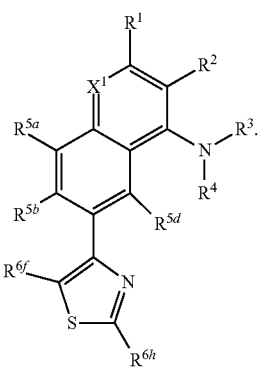

Embodiment 253. The compound of embodiment 26 which has the structure:

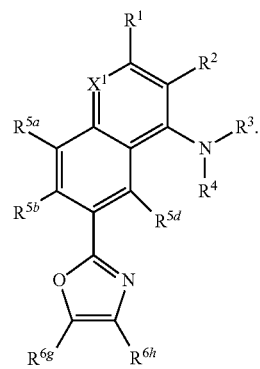

Embodiment 254. The compound of embodiment 1, which has the formula:

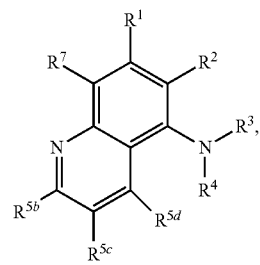

wherein R$^{5b}$, R$^{5c}$, and R$^{5d}$ are each independently aryl, heteroaryl, each of which is substituted or unsubstituted, or hydrogen or halogen3

Embodiment 255. The compound of embodiment 1, wherein the compound has the formula:

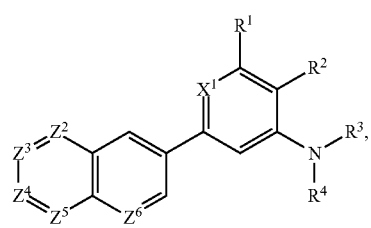

wherein
Z² is N or CH;
Z³ is N or CR²²;
Z⁴ is N or CR²³;
Z⁵ is N or CR²⁴; and
Z⁶ is N or CR²⁵,
wherein each of $R^{22}$, $R^{23}$, $R^{24}$, and $R^{25}$ is independently, alkyl, heteroaryl, —NR¹⁴R¹⁵, —C(O)NR¹⁴R¹⁵, —NR¹⁴C(O)R¹⁵, —OR¹⁶, —SR¹⁷, —C(O)R¹⁸, —C(O)OR¹⁸, —S(O)₂R¹⁹, or —CN, each of which is unsubstituted or substituted, or hydrogen or halogen.

Embodiment 256. The compound of embodiment 255, wherein Z⁶ is CR²⁵, wherein R²⁵ is —C(O)NR¹⁴R¹⁵, —NR¹⁴C(O)R¹⁵, or —NR¹⁴R¹⁵.

Embodiment 257. The compound of embodiment 255, wherein Z² is CR²¹, wherein R²¹ is —C(O)NR¹⁴R¹⁵, —NR¹⁴C(O)R¹⁵, or —NR¹⁴R¹⁵.

Embodiment 258. The compound of embodiment 255, wherein Z³ is CR²², wherein R²² is —C(O)NR¹⁴R¹⁵, —NR¹⁴C(O)R¹⁵, or —NR¹⁴R¹⁵.

Embodiment 259. The compound of embodiment 255, wherein Z⁴ is CR²³, wherein R²³ is —C(O)NR¹⁴R¹⁵, —NR¹⁴C(O)R¹⁵, or —NR¹⁴R¹⁵.

Embodiment 260. The compound of embodiment 255, wherein Z⁵ is CR²⁴, wherein R²⁴ is —C(O)NR¹⁴R¹⁵, —NR¹⁴C(O)R¹⁵, or —NR¹⁴R¹⁵.

Embodiment 261. The compound of embodiment 255 wherein Z⁶ is CH.

Embodiment 262. The compound of embodiment 1, wherein the compound has the formula:

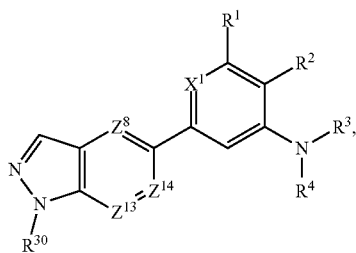

wherein Z⁸ is N or CR²⁷; Z¹³ is N or CR³²; and Z¹⁴ is N or CR³³, wherein each of R²⁷, R³⁰, R³², and R³³ is independently, alkyl, heteroaryl, —NR¹⁴R¹⁵, —C(O)NR¹⁴R¹⁵, —NR¹⁴C(O)R¹⁵, —OR¹⁶, —SR¹⁷, —C(O)R¹⁸, —C(O)OR¹⁸, —S(O)₂R¹⁹, or —CN, each of which is unsubstituted or substituted, or hydrogen or halogen.

Embodiment 263. The compound of embodiment 262, wherein R²⁷, R²⁹, R³⁰, R³², or R³³ is —C(O)NR¹⁴R¹⁵.

Embodiment 264. The compound of embodiment 262, wherein R²⁷, R²⁹, R³⁰, R³², or R³³ is —NR¹⁴R¹⁵.

Embodiment 265. The compound of embodiment 262, wherein R²⁷, R²⁹, R³⁰, R³², or R³³ is —NR¹⁴C(O)R¹⁵.

Embodiment 266. The compound of embodiment 262, wherein Z⁸ is CR²⁷; Z¹³ is CR³²; and Z¹⁴ is CR³³.

Embodiment 267. The compound of embodiment 262, wherein Z⁸ is N; Z¹³ is CR³²; and Z¹⁴ is CR³³.

Embodiment 268. The compound of embodiment 262, wherein Z⁸ is CR²⁷; Z¹³ is N; and Z¹⁴ is CR³³.

Embodiment 269. The compound of embodiment 262, wherein Z⁸ is CR²⁷; Z¹³ is CR³²; and Z¹⁴ is N.

Embodiment 270. The compound of embodiment 262, wherein X¹ is CH.

Embodiment 271. The compound of embodiment 261, wherein X¹ is N.

Embodiment 272. The compound of embodiment 1, wherein the compound has the formula:

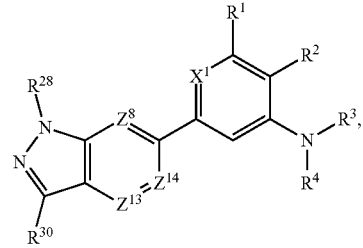

wherein Z⁸ is N or CR²⁷; Z¹³ is N or CR³²; and Z¹⁴ is N or CR³³, wherein each of R²⁷, R²⁸, R³⁰, R³², and R³³ is independently, alkyl, heteroaryl, —NR¹⁴R¹⁵, —C(O)NR¹⁴R¹⁵, —NR¹⁴C(O)R¹⁵, —OR¹⁶, —SR¹⁷, —C(O)R¹⁸, —C(O)OR¹⁸, —S(O)₂R¹⁹, or —CN, each of which is unsubstituted or substituted, or hydrogen or halogen.

Embodiment 273. The compound of embodiment 272, wherein R²⁷, R²⁸, R²⁹, R³⁰, R³², or R³³ is —C(O)NR¹⁴R¹⁵.

Embodiment 274. The compound of embodiment 272, wherein R²⁷, R²⁸, R²⁹, R³⁰, R³², or R³³ is —NR¹⁴R¹⁵.

Embodiment 275. The compound of embodiment 272, wherein R²⁷, R²⁸, R²⁹, R³⁰, R³², or R³³ is —NR¹⁴C(O)R¹⁵.

Embodiment 276. The compound of embodiment 272, wherein Z⁸ is N; Z¹³ is CR³²; and Z¹⁴ is CR³³.

Embodiment 277. The compound of embodiment 272, wherein Z⁸ is CR²⁷; Z¹³ is N; and Z¹⁴ is CR³³.

Embodiment 278. The compound of embodiment 272, wherein Z⁸ is CR²⁷; Z¹³ is CR³²; and Z¹⁴ is N.

Embodiment 279. The compound of embodiment 272, wherein X¹ is CH.

Embodiment 280. The compound of embodiment 272, wherein X¹ is N.

Embodiment 281. The compound of embodiment 1, wherein the compound has the formula:

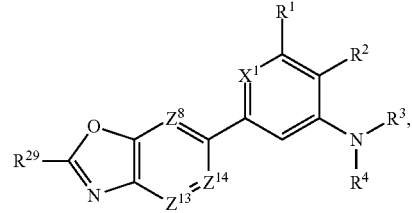

wherein Z⁸ is N or CR²⁷; Z¹³ is N or CR³²; and Z¹⁴ is N or CR³³, wherein each R²⁷, R²⁹, R³², and R³³ is independently alkyl, heteroaryl, —NR¹⁴R¹⁵, —C(O)NR¹⁴R¹⁵, —NR¹⁴C(O)R¹⁵, —OR¹⁶, —SR¹⁷, —C(O)R¹⁸, —C(O)OR¹⁸, —S(O)₂R¹⁹, or —CN, each of which is unsubstituted or substituted, or hydrogen or halogen.

Embodiment 282. The compound of embodiment 281, wherein R²⁷, R³², or R³³ is —C(O)NR¹⁴R¹⁵.

Embodiment 283. The compound of embodiment 281, wherein R²⁷, R³², or R³³ is —NR¹⁴R¹⁵.

Embodiment 284. The compound of embodiment 281, wherein R²⁷, R³², or R³³ is —NR¹⁴C(O)R¹⁵.

Embodiment 285. The compound of embodiment 281, wherein $Z^8$ is N; $Z^{13}$ is $CR^{32}$; and $Z^{14}$ is $CR^{33}$.

Embodiment 286. The compound of embodiment 281, wherein $Z^8$ is $CR^{27}$; $Z^{13}$ is N; and $Z^{14}$ is $CR^{33}$.

Embodiment 287. The compound of embodiment 281, wherein $Z^8$ is $CR^{27}$; $Z^{13}$ is $CR^{32}$; and $Z^{14}$ is N.

Embodiment 288. The compound of embodiment 281, wherein $X^1$ is CH.

Embodiment 289. The compound of embodiment 281, wherein $X^1$ is N.

Embodiment 290. The compound of embodiment 1, wherein the compound has the formula:

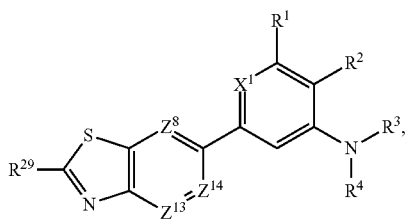

wherein $Z^8$ is N or $CR^{27}$; $Z^{13}$ is N or $CR^{32}$; and $Z^{14}$ is N or $CR^{33}$, wherein each $R^{27}$, $R^{29}$, $R^{32}$, and $R^{33}$ is independently alkyl, heteroaryl, $-NR^{14}R^{15}$, $-C(O)NR^{14}R^{15}$, $-NR^{14}C(O)R^{15}$, $-OR^{16}$, $-SR^{17}$, $-C(O)R^{18}$, $-C(O)OR^{18}$, $-S(O)_2R^{19}$, or $-CN$, each of which is unsubstituted or substituted, or hydrogen or halogen.

Embodiment 291. The compound of embodiment 290, wherein $R^{27}$, $R^{32}$, or $R^{33}$ is $-C(O)NR^{14}R^{15}$.

Embodiment 292. The compound of embodiment 290, wherein $R^{27}$, $R^{32}$, or $R^{33}$ is $-NR^{14}R^{15}$.

Embodiment 293. The compound of embodiment 290, wherein $R^{27}$, $R^{32}$, or $R^{33}$ is $-NR^{14}C(O)R^{15}$.

Embodiment 294. The compound of embodiment 290, wherein $Z^8$ is N; $Z^{13}$ is $CR^{32}$; and $Z^{14}$ is $CR^{33}$.

Embodiment 295. The compound of embodiment 290, wherein $Z^8$ is $CR^{27}$; $Z^{13}$ is N; and $Z^{14}$ is $CR^{33}$.

Embodiment 296. The compound of embodiment 290, wherein $Z^8$ is $CR^{27}$; $Z^{13}$ is $CR^{32}$; and $Z^{14}$ is N.

Embodiment 297. The compound of embodiment 290, wherein $X^1$ is CH.

Embodiment 298. The compound of embodiment 290, wherein $X^1$ is N.

Embodiment 299. The compound of embodiment 1, wherein the compound has the formula:

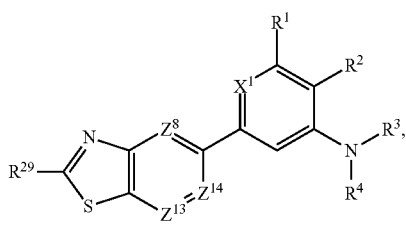

wherein $Z^8$ is N or $CR^{27}$; $Z^{13}$ is N or $CR^{32}$; and $Z^{14}$ is N or $CR^{33}$, wherein each $R^{27}$, $R^{29}$, $R^{32}$, and $R^{33}$ is independently alkyl, heteroaryl, $-NR^{14}R^{15}$, $-C(O)NR^{14}R^{15}$, $-NR^{14}C(O)R^{15}$, $-OR^{16}$, $-SR^{17}$, $-C(O)R^{18}$, $-C(O)OR^{18}$, $-S(O)_2R^{19}$, or $-CN$, each of which is unsubstituted or substituted, or hydrogen or halogen.

Embodiment 300. The compound of embodiment 299, wherein $R^{27}$, $R^{32}$, or $R^{33}$ is $-C(O)NR^{14}R^{15}$.

Embodiment 301. The compound of embodiment 299, wherein $R^{27}$, $R^{32}$, or $R^{33}$ is $-NR^{14}R^{15}$.

Embodiment 302. The compound of embodiment 299, wherein $R^{27}$, $R^{32}$, or $R^{33}$ is $-NR^{14}C(O)R^{15}$.

Embodiment 303. The compound of embodiment 299, wherein $Z^8$ is N; $Z^{13}$ is $CR^{32}$; and $Z^{14}$ is $CR^{33}$.

Embodiment 304. The compound of embodiment 299, wherein $Z^8$ is $CR^{27}$; $Z^{13}$ is N; and $Z^{14}$ is $CR^{33}$.

Embodiment 305. The compound of embodiment 299, wherein $Z^8$ is $CR^{27}$; $Z^{13}$ is $CR^{32}$; and $Z^{14}$ is N.

Embodiment 306. The compound of embodiment 299, wherein $X^1$ is CH.

Embodiment 307. The compound of embodiment 299, wherein $X^1$ is N.

Embodiment 308. The compound of embodiment 1, wherein the compound has the formula:

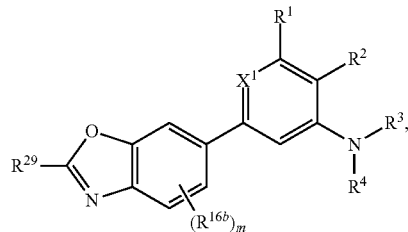

wherein
each $R^{16b}$ is independently alkyl that is unsubstituted or substituted, or hydrogen or halogen;
$R^{29}$ is alkyl, $-NR^{14}R^{15}$, $-C(O)NR^{14}R^{15}$, $-NR^{14}C(O)R^{15}$, or $-OR^{16}$, each of which is unsubstituted or substituted, or hydrogen or halogen; and
m is 0, 1, 2, or 3.

Embodiment 309. The compound of embodiment 308, wherein $R^{29}$ is $-C(O)NR^{14}R^{15}$.

Embodiment 310. The compound of embodiment 308, wherein $R^{29}$ is $-NR^{14}R^{15}$.

Embodiment 311. The compound of embodiment 308, wherein $R^{29}$ is $-NR^{14}C(O)R^{15}$.

Embodiment 312. The compound of embodiment 308, wherein $X^1$ is CH.

Embodiment 313. The compound of embodiment 308, wherein $X^1$ is N.

Embodiment 314. The compound of embodiment 1, wherein the compound has the formula:

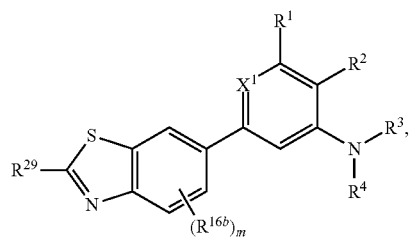

wherein
each $R^{16b}$ is independently alkyl that is unsubstituted or substituted, or hydrogen or halogen;
$R^{29}$ is alkyl, $-NR^{14}R^{15}$, $-C(O)NR^{14}R^{15}$, $-NR^{14}C(O)R^{15}$, or $-OR^{16}$, each of which is unsubstituted or substituted, or hydrogen or halogen; and
m is 0, 1, 2, or 3.

Embodiment 315. The compound of embodiment 314, wherein $R^{29}$ is —C(O)NR$^{14}$R$^{15}$.

Embodiment 316. The compound of embodiment 314, wherein $R^{29}$ is —NR$^{14}$R$^{15}$.

Embodiment 317. The compound of embodiment 314, wherein $R^{29}$ is —NR$^{14}$C(O)R$^{15}$.

Embodiment 318. The compound of embodiment 314, wherein $X^1$ is CH.

Embodiment 319. The compound of embodiment 314, wherein $X^1$ is N.

Embodiment 320. The compound of embodiment 1, wherein the compound has the formula:

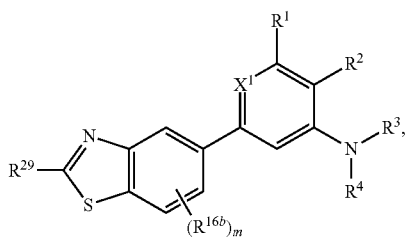

wherein
each $R^{16b}$ is independently alkyl that is unsubstituted or substituted, or hydrogen or halogen;
$R^{29}$ is alkyl, —NR$^{14}$R$^{15}$, —C(O)NR$^{14}$R$^{15}$, —NR$^{14}$C(O)R$^{15}$, or —OR$^{16}$, each of which is unsubstituted or substituted, or hydrogen or halogen; and
m is 0, 1, 2, or 3.

Embodiment 321. The compound of embodiment 320, wherein $R^{29}$ is —C(O)NR$^{14}$R$^{15}$.

Embodiment 322. The compound of embodiment 320, wherein $R^{29}$ is —NR$^{14}$R$^{15}$.

Embodiment 323. The compound of embodiment 320, wherein $R^{29}$ is —NR$^{14}$C(O)R$^{15}$.

Embodiment 324. The compound of embodiment 320, wherein $X^1$ is CH.

Embodiment 325. The compound of embodiment 320, wherein $X^1$ is N.

Embodiment 326. The compound of embodiment 1, which has the formula:

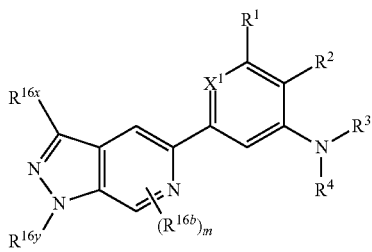

wherein
each $R^{16b}$ is independently alkyl that is unsubstituted or substituted, or hydrogen or halogen;
each of $R^{16x}$ and $R^{16y}$ is independently alkyl, —NR$^{14}$R$^{15}$, —C(O)NR$^{14}$R$^{15}$, —NR$^{14}$C(O)R$^{15}$, or —R$^{16}$, each of which is unsubstituted or substituted, or hydrogen or halogen; and
m is 0, 1, or 2.

Embodiment 327. The compound of embodiment 326, wherein $R^x$ or $R^y$ is —C(O)NR$^{14}$R$^{15}$.

Embodiment 328. The compound of embodiment 326, wherein $R^x$ or $R^y$ is —NR$^{14}$R$^{15}$.

Embodiment 329. The compound of embodiment 326, wherein $R^x$ or $R^y$ is —NR$^{14}$C(O)R$^{15}$.

Embodiment 330. The compound of embodiment 326, wherein $X^1$ is CH.

Embodiment 331. The compound of embodiment 326, wherein $X^1$ is N.

Embodiment 332. The compound of embodiment 1, which has the formula:

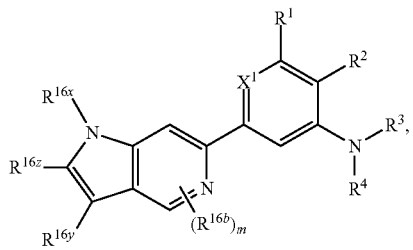

wherein
each $R^{16b}$ is independently alkyl that is unsubstituted or substituted, or hydrogen or halogen;
each of $R^{16x}$, $R^{16y}$, and $R^{16z}$ is independently alkyl, —NR$^{14}$R$^{15}$, —C(O)NR$^{14}$R$^{15}$, —NR$^{14}$C(O)R$^{15}$, —OR$^{16}$, each of which is unsubstituted or substituted, or hydrogen or halogen; and
m is 0, 1, or 2.

Embodiment 333. The compound of embodiment 332, wherein $R^{16x}$, $R^{16y}$, or $R^{16z}$ is —C(O)NR$^{14}$R$^{15}$.

Embodiment 334. The compound of embodiment 332, wherein $R^{16x}$, $R^{16y}$, or $R^{16z}$ is —NR$^{14}$R$^{15}$.

Embodiment 335. The compound of embodiment 332, wherein $R^{16x}$, $R^{16y}$, or $R^{16z}$ is —NR$^{14}$C(O)R$^{15}$.

Embodiment 336. The compound of embodiment 332, wherein $X^1$ is CH.

Embodiment 337. The compound of embodiment 332, wherein $X^1$ is N.

Embodiment 338. The compound of embodiment 1, which has the formula:

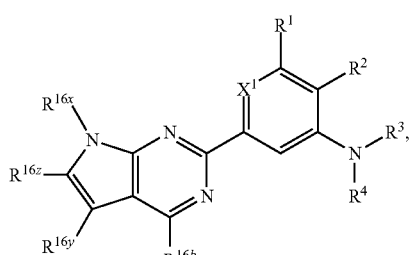

wherein
$R^{16b}$ is alkyl that is unsubstituted or substituted, or hydrogen or halogen; and
each of $R^{16x}$ $R^{16y}$, and $R^{16z}$ is independently alkyl, —NR$^{14}$R$^{15}$, —C(O)NR$^{14}$R$^{15}$, —NR$^{14}$C(O)R$^{15}$, or —OR$^{16}$, each of which is unsubstituted or substituted, or hydrogen or halogen.

Embodiment 339. The compound of embodiment 338, wherein $R^{16x}$, $R^{16y}$, or $R^{16z}$ is —C(O)NR$^{14}$R$^{15}$.

Embodiment 340. The compound of embodiment 338, wherein $R^{16x}$, $R^{16y}$, or $R^{16z}$ is —NR$^{14}$R$^{15}$.

The compound of embodiment 334, wherein $R^{16x}$, $R^{16y}$, or $R^{16z}$ is —$NR^{14}C(O)R^{15}$.

Embodiment 341. The compound of embodiment 338, wherein $X^1$ is CH.

Embodiment 342. The compound of embodiment 338, wherein $X^1$ is N.

Embodiment 343. The compound of embodiment 1, which has the formula:

wherein
- each $R^{16b}$ is independently alkyl that is unsubstituted or substituted, or hydrogen or halogen;
- each of $R^{16x}$ and $R^{16y}$ is each independently alkyl, —$NR^{14}R^{15}$, —$C(O)NR^{14}R^{15}$, —$NR^{14}C(O)R^{15}$, —$OR^{16}$, each of which is unsubstituted or substituted, or hydrogen or halogen; and
- n is independently 0, 1, 2, or 3.

Embodiment 344. The compound of embodiment 343, wherein $R^x$ or $R^y$ is —$C(O)NR^{14}R^{15}$.

Embodiment 345. The compound of embodiment 343, wherein $R^x$ or $R^y$ is —$NR^{14}R^{15}$.

Embodiment 346. The compound of embodiment 343, wherein $R^x$ or $R^y$ is —$NR^{14}C(O)R^{15}$.

Embodiment 347. The compound of embodiment 343, wherein $X^1$ is CH.

Embodiment 348. The compound of embodiment 343, wherein $X^1$ is N.

Embodiment 349. The compound of embodiment 1, which has the formula:

wherein
- each $R^{16a}$ is independently alkyl that is unsubstituted or substituted, or hydrogen or halogen;
- $R^{16x}$ is each independently alkyl, —$NR^{14}R^{15}$, —$C(O)NR^{14}R^{15}$, —$NR^{14}C(O)R^{15}$, —$OR^{16}$, each of which is unsubstituted or substituted, or hydrogen or halogen; and
- n is independently 0, 1, 2, or 3.

Embodiment 350. The compound of embodiment 349, wherein $R^x$ or $R^y$ is —$C(O)NR^{14}R^{15}$.

Embodiment 351. The compound of embodiment 349, wherein $R^x$ or $R^y$ is —$NR^{14}R^{15}$.

Embodiment 352. The compound of embodiment 349, wherein $R^x$ or $R^y$ is —$NR^{14}C(O)R^{15}$.

Embodiment 353. The compound of embodiment 349, wherein $X^1$ is CH.

Embodiment 354. The compound of embodiment 349, wherein $X^1$ is N.

Embodiment 355. A pharmaceutical composition comprising a compound of any one of embodiments 1-355 and a pharmaceutically-acceptable excipient.

Embodiment 356. A method of inducing apoptosis in a cell, the method comprising contacting the cell with a therapeutically-effective amount of a compound of any one of embodiments 1-355.

Embodiment 357. The method of embodiment 356, wherein the compound increases an ability of a mutant p53 protein to bind DNA.

Embodiment 358. The method of embodiment 356 or 357, wherein the cell expresses a mutant p53 protein.

Embodiment 359. The method of any one of embodiments 356-358, wherein the mutant p53 protein has a mutation at amino acid R248.

Embodiment 360. The method of embodiment 359, wherein the mutant p53 protein is p53 R248Q.

Embodiment 361. The method of embodiment 359, wherein the mutant p53 protein is p53 R248W.

Embodiment 362. The method of any one of embodiments 356-361, wherein the mutant p53 protein has a mutation at amino acid R273.

Embodiment 363. The method of embodiment 362, wherein the mutant p53 protein is p53 R273C.

Embodiment 364. The method of embodiment 362, wherein the mutant p53 protein is p53 R273H.

Embodiment 365. The method of any one of embodiments 356-364, wherein the compound selectively binds the mutant p53 protein as compared to a wild type p53 protein.

Embodiment 366. The method of any one of embodiments 356-365, wherein the therapeutically-effective amount is from about 50 mg to about 3,000 mg.

Embodiment 367. The method of any one of embodiments 356-366, wherein the therapeutically-effective amount is about 600 mg.

Embodiment 368. The method of any one of embodiments 356-366, wherein the therapeutically-effective amount is about 1,200 mg.

Embodiment 369. A method of treating a condition, the method comprising administering to a subject in need thereof a therapeutically-effective amount of a compound of any one of embodiments 1-355.

Embodiment 370. The method of embodiment 369, wherein the condition is a cancer.

Embodiment 371. The method of embodiment 370, wherein the cancer is ovarian cancer.

Embodiment 372. The method of embodiment 370, wherein the cancer is breast cancer.

Embodiment 373. The method of embodiment 370, wherein the cancer is lung cancer.

Embodiment 374. The method of embodiment 370, wherein the cancer is pancreatic cancer.

Embodiment 375. The method of any one of embodiments 369-374, wherein the administering is oral.

Embodiment 376. The method of any one of embodiments 369-374, wherein the administering is intravenous.

Embodiment 377. The method of any one of embodiments 369-374, wherein the administering is subcutaneous.

Embodiment 378. The method of any one of embodiments 369-374, wherein the administering is topical.

Embodiment 379. The method of any one of embodiments 369-378, wherein the subject is human.

Embodiment 380. The method of any one of embodiments 369-379, wherein the therapeutically-effective amount is from about 50 mg to about 3,000 mg.

Embodiment 381. The method of any one of embodiments 369-380, wherein the therapeutically-effective amount is about 600 mg.

Embodiment 382. The method of any one of embodiments 369-380, wherein the therapeutically-effective amount is about 1,200 mg.

Embodiment 383. The method of any one of embodiments 369-382, wherein the compound increases a stability of a biologically-active conformation of a p53 mutant relative to a stability of the biologically-active conformation of the p53 mutant in an absence of the compound.

Embodiment 384. The method of any one of embodiments 369-383, wherein the compound selectively binds a mutant p53 protein as compared to a wild type p53 protein.

Embodiment 385. The method of any one of embodiments 369-384, wherein the compound increases an ability of a mutant p53 protein to bind DNA.

Embodiment 386. The method of any one of embodiments 369-385, wherein the mutant p53 protein has a mutation at amino acid R248.

Embodiment 387. The method of embodiment 386, wherein the mutant p53 protein is p53 R248Q.

Embodiment 388. The method of embodiment 385, wherein the mutant p53 protein is p53 R248W.

Embodiment 389. The method of any one of embodiments 369-385, wherein the mutant p53 protein has a mutation at amino acid R273.

Embodiment 390. The method of embodiment 389, wherein the mutant p53 protein is p53 R273C.

Embodiment 391. The method of embodiment 389, wherein the mutant p53 protein is p53 R273H.

What is claimed is:

1. A compound of formula:

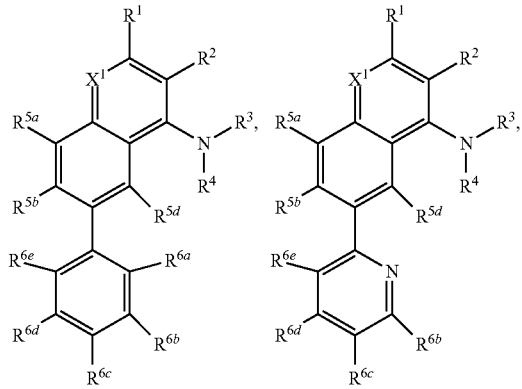

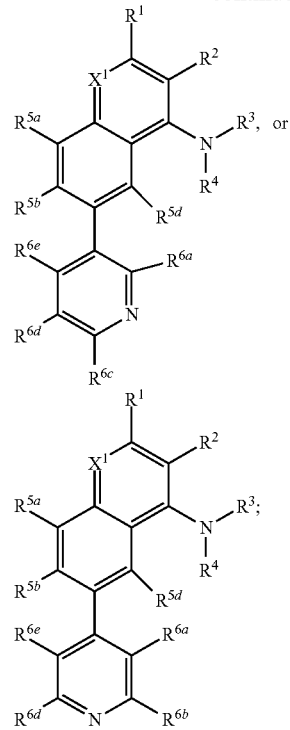

wherein:

$X^1$ is $CR^7$ or N;

$R^1$ is alkyl that is unsubstituted or substituted, or —$NR^8R^9$, —$C(O)NR^8R^9$, —$NR^8C(O)R^9$, —$OR^{10}$, —$SR^{11}$, —$C(O)R^{12}$, —$C(O)OR^{12}$, —$S(O)_2R^{13}$, —CN, hydrogen, or halogen;

$R^2$ is —$OR^{10}$;

$R^3$ is hydrogen;

$R^4$ is alkyl, cycloalkyl, or straight or branched alkenyl, each of which is unsubstituted or substituted, or —$C(O)R^{13}$, —$C(O)OR^{13}$, —$S(O)_2R^{13}$, or hydrogen;

$R^{5a}$, $R^{5b}$, and $R^{5d}$ are each independently hydrogen or halogen;

each of $R^{6a}$, $R^{6b}$, $R^{6c}$, $R^{6d}$, and $R^{6e}$ is independently alkyl or cycloalkyl, each of which is unsubstituted or substituted, or —$NR^{14}R^{15}$, —$OR^{16}$, —$SR^{17}$, —$C(O)NR^{14}R^{15}$, —$NR^{14}C(O)R^{15}$, —CN, —$C(O)OR^{18}$, —$S(O)_2R^{19}$, —$NHS(O)_2R^{19}$, hydrogen, or halogen; or $R^{6a}$ and $R^{6b}$ together with the carbon atoms to which $R^{6a}$ and $R^{6b}$ are bound form a ring, wherein the ring is unsubstituted or substituted, and each of $R^{6c}$, $R^{6d}$, and $R^{6e}$ is independently alkyl or cycloalkyl, each of which is unsubstituted or substituted, or —$NR^{14}R^{15}$, —$OR^{16}$, —$SR^{17}$, —$C(O)NR^{14}R^{15}$, —$NR^{14}C(O)R^{15}$, —CN, —$C(O)OR^{18}$, —$S(O)_2R^{19}$, —$NHS(O)_2R^{19}$, hydrogen, or halogen; or —$R^{6b}$ and $R^{6c}$ together with the carbon atoms to which $R^{6b}$ and $R^{6c}$ are bound form a ring, wherein the ring is unsubstituted or substituted, and each of Ra $R^{6b}$, and $R^{6e}$ is independently alkyl or cycloalkyl, each of which is unsubstituted or substituted, or —$NR^{14}R^{15}$, —$OR^{16}$, —$SR^{17}$, —$C(O)NR^{14}R^{15}$, —$NR^{14}C(O)R^{15}$, —CN, —$C(O)OR^{18}$, —$S(O)_2R^{19}$, —$NHS(O)_2R^{19}$, hydrogen, or halogen; or $R^{6c}$ and $R^{6d}$ together with the carbon atoms to which $R^{6c}$ and $R^{6d}$ are bound form a ring, wherein the ring is unsubstituted or substituted, and each of $R^{6a}$, $R^{6b}$, and $R^{6e}$ is independently alkyl or cycloalkyl, each of which is unsubstituted or substituted, or —$NR^{14}R^5$, —$OR^{16}$, —$SR^{17}$, —$C(O)NR^{14}R^{15}$, —$NR^{14}C(O)R^{15}$, —CN, —$C(O)OR^{18}$, —$S(O)_2R^{19}$, —$NHS(O)_2R^{19}$, hydrogen, or halogen; or $R^{6d}$ and $R^{6e}$ together with the carbon atoms to which $R^{6d}$ and $R^{6e}$ are bound form a ring, wherein the ring is unsubstituted or substituted, and each of $R^{6a}$, $R^{6b}$, and $R^{6c}$ is independently alkyl or cycloalkyl, each of which is unsubstituted or substituted, or —$NR^{14}R^{15}$, —$OR^{16}$, —$SR^{17}$, —$C(O)NR^{14}R^{15}$, —$NR^{14}C(O)R^{15}$, —CN, —$C(O)OR^{18}$, —$S(O)_2R^{19}$, —$NHS(O)_2R^{19}$, hydrogen, or halogen;

$R^7$ is alkyl, alkenyl, cycloalkyl, aryl, heteroaryl or heterocyclyl, each of which is unsubstituted or substituted, or hydrogen or halogen;

each of $R^8$ and $R^9$ is alkyl, alkenyl, cycloalkyl, aryl, heterocyclyl, or heteroaryl, each of which is unsubstituted or substituted, or hydrogen; or $R^8$ and $R^9$ together with the atom(s) to which $R^8$ and $R^9$ are bound form a ring, wherein the ring is unsubstituted or substituted;

each of $R^{10}$, $R^{11}$, $R^{12}$, and $R^{13}$ is independently alkyl, alkenyl, cycloalkyl, aryl, heteroaryl or heterocyclyl, each of which is unsubstituted or substituted, or hydrogen or halogen;

each of $R^{14}$ and $R^{15}$ is independently alkyl, alkenyl, cycloalkyl, aryl, heterocyclyl, or heteroaryl, each of which is unsubstituted or substituted, or hydrogen; and each of $R^{16}$, $R^{17}$, $R^{18}$, and $R^{19}$ is independently alkyl, alkenyl, cycloalkyl, aryl, heteroaryl or heterocyclyl, each of which is unsubstituted or substituted, or hydrogen or halogen, or a pharmaceutically-acceptable salt thereof.

2. The compound of claim 1, wherein $X^1$ is $CR^7$.

3. The compound of claim 1, wherein $X^1$ is N.

4. The compound of claim 1, wherein $R^1$ is H.

5. The compound of claim 1, wherein $R^1$ is —$C(O)NR^8R^9$, —$OR^{10}$, or CN.

6. The compound of claim 1, wherein at least one of $R^{6a}$, $R^{6b}$, $R^{6c}$, $R^{6d}$ and $R^{6e}$ is —$C(O)NR^{14}R^{15}$, —$NR^{14}C(O)R^{15}$, or —$NR^{14}R^{15}$.

7. The compound of claim 1, wherein $R^{6b}$ is —$C(O)NR^{14}R^{15}$.

8. The compound of claim 1, wherein $R^{6b}$ is —$NR^{14}R^{15}$.

9. The compound of claim 1, wherein $R^{6b}$ is —$NR^{14}C(O)R^{15}$.

10. The compound of claim 1, wherein $R^7$ is H.

11. The compound of claim 1, wherein $NR^3R^4$ is

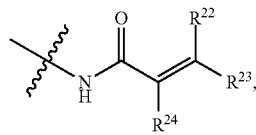

wherein each of $R^{22}$, $R^{23}$, and $R^{24}$ is independently alkyl, which is unsubstituted or substituted, or hydrogen, or halogen.

12. The compound of claim 1, wherein $NR^3R^4$ is

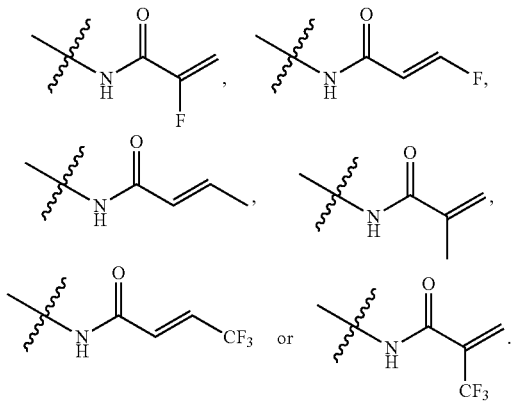

* * * * *

UNITED STATES PATENT AND TRADEMARK OFFICE
CERTIFICATE OF CORRECTION

PATENT NO. : 11,926,632 B2
APPLICATION NO. : 17/353199
DATED : March 12, 2024
INVENTOR(S) : Vu et al.

It is certified that error appears in the above-identified patent and that said Letters Patent is hereby corrected as shown below:

In the Claims

Claim 1; Column 1234; Line 55:
Delete: "—S(O)R$^{19}$"
And replace with: -- —S(O)$_2$R$^{19}$--

Claim 1; Column 1234; Line 59:
Delete: "Ra R$^{66}$"
And replace with: --R$^{6a}$, R$^{6d}$--

Claim 1; Column 1234; Line 64:
Delete: "halogen:"
And replace with: --halogen;--

Claim 1; Column 1234; Line 67:
Delete: "R$^{6c}$"
And replace with: --R$^{6e}$--

Claim 1; Column 1235; Line 2:
Delete: "—NR$^{14}$R$^{5}$"
And replace with: -- —NR$^{14}$R$^{15}$--

Claim 5; Column 1235; Line 38:
Delete: "CN"
And replace with: -- —CN--

Signed and Sealed this
Twenty-fifth Day of June, 2024

Katherine Kelly Vidal
*Director of the United States Patent and Trademark Office*